US009700502B2

(12) United States Patent
Cotsarelis et al.

(10) Patent No.: US 9,700,502 B2
(45) **Date of Patent: *Jul. 11, 2017**

(54) METHODS FOR GENERATING NEW HAIR FOLLICLES, TREATING BALDNESS, AND HAIR REMOVAL

(75) Inventors: George Cotsarelis, Berwyn, PA (US); Mayumi Ito, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 234 days.

This patent is subject to a terminal disclaimer.

(21) Appl. No.: 12/904,822

(22) Filed: Oct. 14, 2010

(65) Prior Publication Data

US 2011/0152746 A1 Jun. 23, 2011

Related U.S. Application Data

(63) Continuation of application No. 11/887,104, filed as application No. PCT/US2006/011319 on Mar. 28, 2006, now abandoned.

(60) Provisional application No. 60/665,857, filed on Mar. 29, 2005, provisional application No. 60/683,293, filed on May 23, 2005.

(51) Int. Cl.

| | |
|---|---|
| ***A61Q 7/00*** | (2006.01) |
| ***A61K 8/49*** | (2006.01) |
| ***A61K 9/00*** | (2006.01) |
| ***A61B 8/00*** | (2006.01) |
| ***A61K 8/65*** | (2006.01) |
| ***A61Q 5/00*** | (2006.01) |
| ***A61Q 5/10*** | (2006.01) |
| ***A61K 31/506*** | (2006.01) |
| ***A61K 31/517*** | (2006.01) |
| ***A61K 31/65*** | (2006.01) |
| ***A61K 35/36*** | (2015.01) |
| ***A61K 38/18*** | (2006.01) |
| ***A61M 37/00*** | (2006.01) |
| *A61B 17/00* | (2006.01) |
| *A61B 18/00* | (2006.01) |

(52) U.S. Cl.

CPC .............. *A61K 8/4953* (2013.01); *A61K 8/65* (2013.01); *A61K 9/0014* (2013.01); *A61K 31/506* (2013.01); *A61K 31/517* (2013.01); *A61K 31/65* (2013.01); *A61K 35/36* (2013.01); *A61K 38/1825* (2013.01); *A61M 37/00* (2013.01); *A61Q 5/00* (2013.01); *A61Q 5/10* (2013.01); *A61Q 7/00* (2013.01); *A61B 2017/00765* (2013.01); *A61B 2018/00452* (2013.01); *A61K 2800/74* (2013.01); *A61K 2800/805* (2013.01); *A61M 2037/0007* (2013.01)

(58) Field of Classification Search

CPC ...... A61N 5/0617; A61Q 7/00; A61B 18/203; A61B 2018/00452; A61B 2018/00476

See application file for complete search history.

(56) References Cited

U.S. PATENT DOCUMENTS

| | | | |
|---|---|---|---|
| 4,490,365 | A | 12/1984 | Panaretto et al. |
| 4,919,664 | A | 4/1990 | Oliver et al. |
| 5,466,695 | A | 11/1995 | Poulos et al. |
| 6,075,005 | A | 6/2000 | Lurie |
| 6,159,950 | A | 12/2000 | Crystal et al. |
| 6,867,179 | B1 | 3/2005 | Gilchrest et al. |
| 6,936,044 | B2 | 8/2005 | McDaniel |
| 8,252,749 | B2 | 8/2012 | Steinberg et al. |
| 8,431,400 | B2 | 4/2013 | Hoffmann et al. |
| 2002/0065314 | A1 | 5/2002 | Nielsen et al. |
| 2002/0114772 | A1 | 8/2002 | Morgan et al. |
| 2002/0132792 | A1 | 9/2002 | Prien et al. |
| 2003/0007941 | A1 | 1/2003 | Cornelius et al. |
| 2004/0153131 | A1 | 8/2004 | Yorke |
| 2005/0049625 | A1 | 3/2005 | Shaya et al. |
| 2006/0008505 | A1 | 1/2006 | Brandon et al. |
| 2006/0073117 | A1 | 4/2006 | Li |
| 2006/0241696 | A1 | 10/2006 | Krco |
| 2006/0287385 | A1 | 12/2006 | Baxter et al. |
| 2007/0190075 | A1 | 8/2007 | Suzuki et al. |
| 2008/0182859 | A1 | 7/2008 | Brunton et al. |
| 2008/0193423 | A1 | 8/2008 | Brunton et al. |
| 2011/0086007 | A1 | 4/2011 | Kemp et al. |

FOREIGN PATENT DOCUMENTS

| | | | |
|---|---|---|---|
| EP | 1634874 | A1 | 3/2006 |
| JP | 2003-081866 | A | 3/2003 |
| WO | WO 99/01034 | | 1/1999 |
| WO | WO 00/31134 | | 6/2000 |
| WO | WO 00/45736 | A1 | 8/2000 |
| WO | WO 01/32840 | | 5/2001 |

(Continued)

OTHER PUBLICATIONS

Kawano et al., J. Invest Dermatol 124:877-885, 2005.*
Suzuki et al., J. Invest Dermatol 114;456-463, 2000.*
Blanpain et al., Cell, 118 (2004), pp. 635-648.*
Kimura-Ueki J Invest Dermatol. May 2012;132(5):1338-1345.*
Argyris et al., "Factors affecting the stimulation of hair growth during wound healing", Anatomical Record, vol. 142, No. 2, 1962, pp. 139-145.
Breedis et al., "Regeneration of hair follicles and sebaceous glands from the epithelium of scars in the rabbit", Cancer Research, vol. 14, No. 8, 1954, p. 17.

(Continued)

*Primary Examiner* — Daniel C Gamett
(74) *Attorney, Agent, or Firm* — Mark S. Cohen; Pearl Cohen Zedek Latzer Baratz LLP

(57) ABSTRACT

The present invention provides methods of treating baldness in a subject and generating new hair follicles, comprising epidermal disruption and administration of a compound that promotes a differentiation of an uncommitted epidermal cell into a hair follicle cell. The present invention also provides methods for hair removal and inducing hair pigmentation.

17 Claims, 43 Drawing Sheets

(56) References Cited

FOREIGN PATENT DOCUMENTS

| | | |
|---|---|---|
| WO | WO 01/58413 | 8/2001 |
| WO | WO 01/74164 | 10/2001 |
| WO | WO 02/060396 | 8/2002 |
| WO | WO 02/092771 | 11/2002 |
| WO | WO 03/039478 | 5/2003 |
| WO | WO 03/061362 A2 | 7/2003 |
| WO | WO 03/068248 | 8/2003 |
| WO | WO 2004/043415 | 5/2004 |
| WO | WO 2004/060488 A1 | 7/2004 |
| WO | WO 2005/017107 | 2/2005 |
| WO | WO 2010/056759 | 5/2010 |

OTHER PUBLICATIONS

Li Y et al. "Early epidermal destruction with subsequent epidermal hyperplasia is a unique feature of the papilloma-independent squamous cell carcinoma phenotype in PKCepsilon overexpressing transgenic mice" Toxicol Pathol ;33(6):684-94, (2005).
Ley et al. "Hair growth induction by ultraviolet radiation in the marsupial Monodelphis domestica" Arch Dermatol. ;123(8):1032-5, Aug. 1987.
Argyirs T. "Kinetics of epidermal production during epidermal regeneration following abrasion in mice" Am J Pathol. 83(2):329-40, May 1976.
Du Cros. "Fibroblast Growth Factor and Epidermal Growth Factor in Hair Development" Journal Invest Dermatol., vol. 101, pp. 106S-113S, (1993).
Lo Celso et al. "Transient activation of beta-catenin signalling in adult mouse epidermis is sufficient to induce new hair follicles but continuous activation is required to maintain hair follicle tumours" Development, vol. 131, pp. 1787-1799, (2004).
Mater et al., Transient Activation of β-Catenin Signaling in Cutaneous Keratinocites is Sufficient to Trigger the Active Growth Phase of the Hair Cycle in Mice, Genes and Development, 2003, vol. 17, pp. 1219-1224.
Botchkarev VA et al. "Edar signaling in the control of hair follicle development" J Investig Dermatol Symp Proc. ;10(3):247-51, Dec. 2005.
Fuchs E et al. "Stem cells A new lease on life" Cell. 7;100(1):143-55, Jan. 2000.
Joerg Huelsken et al. "β-Catenin Controls Hair Follicle Morphogenesis and Stem Cell Differentiation in the Skin" Cell, vol. 105, Issue 4, 533-545, May 18, 2001.
Moore et al. "Epidermal Hyperplasia and wool follicle Repression in sheep Infused with Epidermal growth factor" The Journal of Investigation Dermatology, 84:172-175, (1985).
Millar et al. "Molecular Mechanisms Regulating Hair follicle Development" The Journal of Investigation Dermatology 118:216-225, (2002).
International Search Report for International Application No. PCT/US06/11319 Date of Mailing May 28, 2008.
Hallmans et al., Regeneration of Hair Follicles from Experimental Wounds on the Rabbit Ear, Scandinavian Journal of Plastic and Reconstructive Surgery, 1974, vol. 8. No. 3, pp. 207-210.
Jahoda et al., Cellular and Extracelluar Involvement in the Regeneration of the Rat Lower Vibrissa Follicle, Development, 1992, vol. 114, pp. 887-897.
Mattar et al., Inhibition of Epidermal Growth Factor Receptor Tyrosine Kinase Activity by Leflunomide, Federation of European Biochemical Societies, Nov. 1993, vol. 334, No. 2, pp. 161-164.
Mak et al., Epidermal Growth Factor as a Biological Switch in Hair Growth Cycle, The Journal of Biological Chemistry, Jul. 11, 2003, vol. 278, No. 28, pp. 26120-26126.
Danilenko et al., Keratinocyte Growth Factor is an Important Endogenous Mediator of Hair Follicle Growth, Development, and Differentiation, Normalization of the nu/nu Follicular Differentiation Defect and Amelioration of Chemotherapy-Induced Alopecia, American Journal of Pathology, Jul. 1, 1995, vol. 147, No. 147, pp. 145-154.
Srivastava et al., Ectodysplasin-A1 is Sufficient to Rescue Both Hair Growth and Sweat Glands in Tabby Mice, Human Molecular Genetics, 2001, vol. 10, No. 26, pp. 2973-2981.
Han et al., Effect of Minoxidil on Proliferation and Apoptosis in Dermal Papilla Cells of Human Hair Follicle, Journal of Dermatological Science, 2004, vol. 34, pp. 91-98.
Botchkarev et al., Noggin is a Mesenchymally Derived Stimulator of Hair-Follicle Induction, Nature Cell Biology, Jul. 1999, vol. 1, pp. 158-164.
Botchkarev et al., Noggin is Required for Induction of the Hair Follicle Growth Phase in Postnatal Skin, FASEB Journal, 2001, vol. 15., pp. 2205-2214.
Ota et al., Fibroblast Growth Factor 5 Inhibits Hair Growth by Blocking Dermal Papilla Cell Activation, Biochemical and Biophysical Research Communications, 2002, vol. 290, pp. 169-176.
Kashiwagi et al., Specific Inhibition of Hair Follicle Formation by Epidermal Growth Factor in an Organ Culture of Developing Mouse Skin, Developmental Biology, 1997, vol. 189, pp. 22-32.
Mitsuyuki et al., Recent Studies on Mechanism of Hair Loss/Hair Growth and Developing Trend of Hair Growth Drug, 2003, Fragrance Journal, vol. 31, No. 2, pp. 33-40. (English abstract.)
Katsuyuki, Effects of Epidermal Growth Factor and Transforming Growth Factor on Cultured Hair Follicle Cells from Human Scalp, Skin, 1994, vol. 36, No. 2, pp. 125-133. (English abstract.).
Tanabe et al., Basic Technology Meeting of the Japanese Orthopedic Association, Program & Abstract, 2003, vol. 12, p. 118. (English abstract.)
Pestana, A et al. "Effect of ultraviolet light on topical minoxidil-induced hair growth in advanced male pattern baldness". Journal of the American Academy of Dermatology, 1987.vol. 16(5): pp. 971-976.
Argyris et al., "On the mechanism of hair growth stimulation in wound healing", Develop. Biol. 9:230-254, 1964.
Johnson et al., "The effect of plucking hairs during different phases of the follicular cycle", J. Embryol. Exp. Morph. 12: 465-474, 1964.
Kligman et al., "Neogenesis of human hair follicles", Ann. NY. Acad. Sci. 83: 507-511, 1959.
Mahe et al., "Pro-inflammatory cytokine cascade in human plucked hair", Skin Pharmacol. 9: 366-375, 1996.
Muller et al., "Hair Neogenesis", J. Invest. Dermatol. 56:1-9, 1971.
Reynolds et al., "Inductive properties of hair follicle cells", Ann. NY Acad. Sci. 642: 226-242, 1991.
Buckland et al. "Effect of scalp burns on common male pattern baldness", British Meidcal Joruna, vol. 293, pp. 20-27, Dec. 1986.
Ito et al. "hair follicle stem cells in the lower bulge form the secondary germ, a biochmically distinct but functionally equivalent progenitor cell population, at the termination of catagen", Differentiation (2004) 72:548-557.
McElwee et al. "Cultured Peribulbar Dermal Sheath Cells Can Induce Hair Follicle Development and Contribute to the Dermal Sheath and Dermal Papilla", The Journal of Investigative Dermatology, vol. 121, No. 6, Dec. 2003.
Argyris "The growth-promoting effects of wounds on hair follicles already stimulated by plucking", Anat Rec. Jul. 1962;143:183-8.
European Search Report for European Application No. 15165807.7 dated Oct. 21, 2015.
Kligman et al. "The formation of vellus hair follicles from human adult epidermis", J Invest Dermatol. Jul. 1956;27(1):19-23.
Messenger et al. "Minoxidil: mechanisms of action on hair growth", Br J Dermatol. Feb. 2004;150(2):186-94.
Mimura et al., Functional Cosmetics II, 1996, Chapter 9, Mechanism of hair loss and application of hair growing agent, pp. 124-130.

* cited by examiner

K 17 immuno-stain

Alkaline Phosphatase

FIG. 22A

| probe set | SEQ ID No | bs-line mean | bs-line SE | expt mean | expt SE | fold change | lower bound:FC | upper bound:FC | diff. of mean |
|---|---|---|---|---|---|---|---|---|---|
| 160841_at | 1 | -4.59 | 7.45 | 117.99 | 26.88 | 117.99 | 8.2 | 100000000 | 122.57 |
| 103589_at | 2 | -1.28 | 6.58 | 112.41 | 43.53 | 112.41 | 7.13 | 100000000 | 113.68 |
| 103562_f_at | 3 | 23.45 | 12.4 | 220.55 | 110.78 | 9.4 | 1.52 | 75.74 | 197.1 |
| 97527_at | 4 | 27.15 | 14.75 | 173.81 | 24.11 | 6.4 | 3.2 | 60.38 | 146.66 |
| 160909_at | 5 | 115.74 | 46.42 | 706.06 | 192.98 | 6.1 | 2.8 | 18.81 | 590.32 |
| 93285_at | 6 | 132.73 | 53.69 | 782.45 | 138.65 | 5.89 | 3.17 | 17.98 | 649.72 |
| 98988_at | 7 | 119.09 | 33.93 | 650.75 | 97.47 | 5.46 | 3.38 | 10.62 | 531.65 |
| 161903_f_at | 8 | 33.82 | 7.85 | 183.08 | 42.87 | 5.41 | 3.03 | 9.65 | 149.26 |
| 97542_at | 9 | 199 | 149.69 | 1009.76 | 317.31 | 5.07 | 1.71 | 100000000 | 810.76 |
| 104701_at | 10 | 181.01 | 54.87 | 893.77 | 110.08 | 4.94 | 3.1 | 10.04 | 712.76 |
| 94057_g_at | 11 | 194.15 | 36.67 | 895.05 | 169.8 | 4.61 | 2.91 | 7.29 | 700.89 |
| 160092_at | 12 | 142.8 | 67.19 | 637.32 | 153.3 | 4.46 | 2.08 | 20.18 | 494.52 |
| 93527_at | 13 | 55.64 | 18 | 246.09 | 25.21 | 4.42 | 2.77 | 9.57 | 190.46 |
| 92978_s_at | 14 | 208.74 | 82.76 | 904.6 | 260.29 | 4.33 | 1.93 | 13.15 | 695.86 |
| 93985_at | 15 | 117.48 | 43.72 | 505.43 | 102.78 | 4.3 | 2.29 | 11.47 | 387.95 |
| 97197_r_at | 16 | 238.01 | 60.95 | 975.35 | 226.41 | 4.1 | 2.27 | 7.7 | 737.34 |
| 160606_r_at | 17 | 105.16 | 32.48 | 420.67 | 154.57 | 4 | 1.47 | 9.32 | 315.51 |
| 92925_at | 18 | 257.38 | 102.47 | 1023.17 | 152.45 | 3.98 | 2.22 | 11.7 | 765.8 |
| 99849_at | 19 | 611.78 | 159.55 | 2401.77 | 484.37 | 3.93 | 2.29 | 7.33 | 1790 |
| 96295_at | 20 | 147.89 | 44.65 | 548.52 | 112.75 | 3.71 | 2.08 | 7.76 | 400.63 |
| 101554_at | 21 | 561.24 | 162.46 | 1994.33 | 289.7 | 3.55 | 2.2 | 6.99 | 1433.09 |
| 101964_at | 22 | 136.06 | 40.77 | 481.38 | 53.63 | 3.54 | 2.25 | 7.09 | 345.33 |
| 93974_at | 23 | 129.04 | 15.59 | 454.75 | 88.15 | 3.52 | 2.31 | 5.03 | 325.71 |
| 93573_at | 24 | 705.68 | 193.8 | 2449.83 | 87.02 | 3.47 | 2.38 | 6.34 | 1744.15 |
| 162206_f_at | 25 | 283.3 | 111.46 | 948.01 | 188.26 | 3.35 | 1.77 | 9.75 | 664.71 |
| 94056_at | 26 | 380.59 | 72.3 | 1264.27 | 225.61 | 3.32 | 2.14 | 5.22 | 883.68 |
| 101019_at | 27 | 50.97 | 13.15 | 169.04 | 59.25 | 3.32 | 1.32 | 6.77 | 118.07 |
| 160894_at | 28 | 234.87 | 60.8 | 773.72 | 130.11 | 3.29 | 2.04 | 6.01 | 538.85 |
| 102363_r_at | 29 | 483.67 | 195.98 | 1579.93 | 198.13 | 3.27 | 1.86 | 9.9 | 1096.27 |
| 104156_r_at | 30 | 461.52 | 147.14 | 1505.8 | 282.6 | 3.26 | 1.86 | 7.14 | 1044.27 |
| 98083_at | 31 | 265.71 | 64.72 | 829.49 | 157.14 | 3.12 | 1.89 | 5.55 | 563.79 |
| 98589_at | 32 | 237.6 | 42.69 | 733.9 | 54.22 | 3.09 | 2.31 | 4.46 | 496.3 |

FIG. 22A (continued)

| | | | | | | | | | |
|---|---|---|---|---|---|---|---|---|---|
| 101410_at | 33 | 77.22 | 17.11 | 236.17 | 12.53 | 3.06 | 2.21 | 4.84 | 158.95 |
| 102362_i_at | 34 | 590.2 | 219.11 | 1763.85 | 203.43 | 2.99 | 1.77 | 7.76 | 1173.65 |
| 102955_at | 35 | 126.89 | 27.41 | 378.95 | 95.38 | 2.99 | 1.62 | 5.21 | 252.05 |
| 96657_at | 36 | 202.33 | 31.51 | 593.78 | 96.07 | 2.93 | 2 | 4.28 | 391.45 |
| 92232_at | 37 | 318.7 | 94.52 | 932.68 | 64.57 | 2.93 | 1.93 | 5.75 | 613.99 |
| 99457_at | 38 | 70.6 | 9.12 | 200.86 | 50.21 | 2.85 | 1.63 | 4.33 | 130.26 |
| 103665_at | 39 | 137.79 | 18.28 | 391.39 | 104.78 | 2.84 | 1.55 | 4.42 | 253.6 |
| 104149_at | 40 | 593.93 | 166.71 | 1682.3 | 182.25 | 2.83 | 1.84 | 5.36 | 1088.37 |
| 92730_at | 41 | 221.49 | 83.2 | 627.03 | 101.25 | 2.83 | 1.59 | 7.57 | 405.54 |
| 93346_at | 42 | 149.96 | 31.14 | 421.18 | 85.61 | 2.81 | 1.7 | 4.66 | 271.23 |
| 95439_at | 43 | 88.13 | 19 | 245.95 | 59.22 | 2.79 | 1.56 | 4.83 | 157.82 |
| 102049_at | 44 | 94.74 | 20.76 | 262.21 | 46.03 | 2.77 | 1.75 | 4.61 | 167.47 |
| 97909_at | 45 | 249.59 | 47.89 | 689.01 | 94.06 | 2.76 | 1.9 | 4.23 | 439.41 |
| 97546_at | 46 | 133.71 | 39.2 | 365.48 | 46.12 | 2.73 | 1.73 | 5.4 | 231.77 |
| 98829_at | 47 | 470.98 | 294.77 | 1272.68 | 140.61 | 2.7 | 1.29 | 100000000 | 801.7 |
| 160834_at | 48 | 141.39 | 33.56 | 380.2 | 57.73 | 2.69 | 1.74 | 4.61 | 238.81 |
| 99076_at | 49 | 76.48 | 15.08 | 204.33 | 17.28 | 2.67 | 1.94 | 4.03 | 127.85 |
| 102791_at | 50 | 103.99 | 28.25 | 276.51 | 56.18 | 2.66 | 1.54 | 5.11 | 172.52 |
| 99548_at | 51 | 304.99 | 77.26 | 808.21 | 116.83 | 2.65 | 1.7 | 4.71 | 503.23 |
| 160273_at | 52 | 666.44 | 103.7 | 1761.34 | 209.34 | 2.64 | 1.93 | 3.73 | 1094.9 |
| 101487_f_at | 53 | 394.46 | 67.78 | 1039.29 | 199.81 | 2.63 | 1.68 | 4.05 | 644.83 |
| 104712_at | 54 | 163.95 | 30.93 | 426.88 | 44.04 | 2.6 | 1.87 | 3.89 | 262.93 |
| 98469_at | 55 | 68.51 | 16.59 | 178.35 | 23.69 | 2.6 | 1.71 | 4.47 | 109.84 |
| 93058_at | 56 | 79.66 | 9.53 | 206.19 | 32.24 | 2.59 | 1.83 | 3.55 | 126.53 |
| 95348_at | 57 | 113.11 | 26.29 | 291.76 | 31.62 | 2.58 | 1.76 | 4.28 | 178.65 |
| 98627_at | 58 | 75.74 | 13.15 | 192.98 | 18.48 | 2.55 | 1.88 | 3.67 | 117.24 |
| 103905_at | 59 | 85.15 | 18.59 | 216.11 | 31.03 | 2.54 | 1.69 | 4.14 | 130.96 |
| 96704_at | 60 | 1004.68 | 292.32 | 2541.06 | 64.9 | 2.53 | 1.71 | 4.86 | 1536.38 |
| 96841_at | 61 | 148.26 | 37.17 | 373.77 | 37.64 | 2.52 | 1.7 | 4.37 | 225.51 |
| 93528_s_at | 62 | 325.47 | 42.91 | 814.6 | 94.75 | 2.5 | 1.87 | 3.38 | 489.14 |
| 103995_at | 63 | 99.71 | 18.04 | 245.79 | 64.04 | 2.47 | 1.34 | 4.07 | 146.08 |
| 93619_at | 64 | 211.26 | 36.62 | 518.24 | 59.87 | 2.45 | 1.77 | 3.57 | 306.98 |
| 99603_g_at | 65 | 189.95 | 54.67 | 464.45 | 56.46 | 2.45 | 1.56 | 4.74 | 274.5 |

FIG. 22A (continued)

| | | | | | | | | | |
|---|---|---|---|---|---|---|---|---|---|
| 97241_at | 66 | 76.34 | 20.54 | 185.14 | 28.15 | 2.43 | 1.52 | 4.51 | 108.8 |
| 93975_at | 67 | 318.9 | 42.47 | 771.29 | 153.37 | 2.42 | 1.56 | 3.52 | 452.39 |
| 92830_s_at | 68 | 951.79 | 313.65 | 2304.83 | 151.2 | 2.42 | 1.54 | 5.31 | 1353.04 |
| 160359_at | 69 | 125.24 | 14.57 | 301.36 | 29.27 | 2.41 | 1.88 | 3.12 | 176.12 |
| 93250_r_at | 70 | 315.77 | 42.86 | 755.99 | 65.92 | 2.39 | 1.86 | 3.18 | 440.23 |
| 101561_at | 71 | 1691.83 | 299.29 | 3988.08 | 129.84 | 2.36 | 1.81 | 3.34 | 2296.25 |
| 160463_at | 72 | 240.25 | 84.32 | 557.92 | 63.82 | 2.32 | 1.4 | 5.56 | 317.68 |
| 94881_at | 73 | 246.87 | 52.18 | 570.73 | 72.1 | 2.31 | 1.58 | 3.68 | 323.86 |
| 162234_f_at | 74 | 104.55 | 14.78 | 240.86 | 33.15 | 2.3 | 1.66 | 3.22 | 136.31 |
| 92777_at | 75 | 354.22 | 125.82 | 815.02 | 57.76 | 2.3 | 1.43 | 5.56 | 460.8 |
| 97413_at | 76 | 186.46 | 42.02 | 426.43 | 57.65 | 2.29 | 1.53 | 3.78 | 239.97 |
| 93290_at | 77 | 220.69 | 54.35 | 506.12 | 81.35 | 2.29 | 1.45 | 4.04 | 285.43 |
| 93193_at | 78 | 106.8 | 15.31 | 243.51 | 20.34 | 2.28 | 1.76 | 3.07 | 136.71 |
| 160369_at | 79 | 171.88 | 14.05 | 391.54 | 74.72 | 2.28 | 1.53 | 3.11 | 219.66 |
| 102788_s_at | 80 | 202.74 | 39.62 | 459.62 | 105.41 | 2.27 | 1.31 | 3.74 | 256.88 |
| 92862_f_at | 81 | 707.54 | 191.58 | 1602.3 | 269.42 | 2.26 | 1.39 | 4.26 | 894.76 |
| 161666_f_at | 82 | 159.92 | 55.82 | 361.44 | 63.64 | 2.26 | 1.28 | 5.47 | 201.53 |
| 100612_at | 83 | 109.28 | 13.06 | 244.41 | 39.49 | 2.24 | 1.57 | 3.09 | 135.13 |
| 100144_at | 84 | 766.09 | 156.62 | 1706.03 | 266.57 | 2.23 | 1.47 | 3.55 | 939.93 |
| 101065_at | 85 | 328.05 | 58.88 | 730.71 | 145.44 | 2.23 | 1.39 | 3.49 | 402.66 |
| 101876_s_at | 86 | 155.5 | 38.86 | 346.44 | 59.57 | 2.23 | 1.38 | 3.98 | 190.94 |
| 92202_g_at | 87 | 330.57 | 53.31 | 733.66 | 40.66 | 2.22 | 1.72 | 3.05 | 403.09 |
| 102371_at | 88 | 1213.29 | 329.9 | 2695.65 | 108.01 | 2.22 | 1.52 | 4.03 | 1482.37 |
| 103846_at | 89 | 1321.78 | 263.93 | 2925.01 | 471.95 | 2.21 | 1.46 | 3.51 | 1603.23 |
| 94375_at | 90 | 146.6 | 20.7 | 321.94 | 52.11 | 2.2 | 1.51 | 3.13 | 175.34 |
| 101995_at | 91 | 98.55 | 18.7 | 215.04 | 21.12 | 2.18 | 1.58 | 3.26 | 116.49 |
| 100156_at | 92 | 99.29 | 9.58 | 216.55 | 45.69 | 2.18 | 1.39 | 3.08 | 117.26 |
| 94452_g_at | 93 | 120.03 | 28.17 | 261.62 | 55.25 | 2.18 | 1.28 | 3.85 | 141.58 |
| 94805_f_at | 94 | 694.87 | 148.44 | 1505.05 | 159.22 | 2.17 | 1.51 | 3.43 | 810.19 |
| 94011_at | 95 | 512.81 | 134.05 | 1106.93 | 232.4 | 2.16 | 1.24 | 4.05 | 594.13 |
| 102381_at | 96 | 135.96 | 23.62 | 291.09 | 59.57 | 2.14 | 1.33 | 3.34 | 155.12 |
| 160617_at | 97 | 202.28 | 37.36 | 430.01 | 58.22 | 2.13 | 1.47 | 3.21 | 227.74 |
| 94246_at | 98 | 466.99 | 78.37 | 985.61 | 170.81 | 2.11 | 1.4 | 3.17 | 518.61 |

FIG. 22A (continued)

| | | | | | | | | | |
|---|---|---|---|---|---|---|---|---|---|
| 101658_f_at | 99 | 285.59 | 88.76 | 603.43 | 91.07 | 2.11 | 1.28 | 4.44 | 317.83 |
| 160651_at | 100 | 451.96 | 149.58 | 951.74 | 153.08 | 2.11 | 1.23 | 4.75 | 499.78 |
| 99835_at | 101 | 126.74 | 16.43 | 265.21 | 28.87 | 2.09 | 1.59 | 2.8 | 138.46 |
| 94384_at | 102 | 744.33 | 121.74 | 1547.75 | 85.27 | 2.08 | 1.61 | 2.88 | 803.42 |
| 99602_at | 103 | 331.17 | 83.9 | 684.41 | 59.53 | 2.07 | 1.41 | 3.59 | 353.24 |
| 93970_at | 104 | 107.79 | 18.66 | 223.33 | 41.74 | 2.07 | 1.33 | 3.18 | 115.53 |
| 94325_at | 105 | 345.93 | 53.16 | 716.7 | 145.74 | 2.07 | 1.3 | 3.12 | 370.77 |
| 102161_f_at | 106 | 714.47 | 196.16 | 1476.07 | 225.27 | 2.07 | 1.29 | 3.9 | 761.6 |
| 99378_f_at | 107 | 649.9 | 166.98 | 1346.61 | 258.64 | 2.07 | 1.23 | 3.81 | 696.72 |
| 100633_at | 108 | 203.48 | 33.65 | 416.96 | 46.25 | 2.05 | 1.5 | 2.93 | 213.48 |
| 92205_at | 109 | 187.34 | 23.61 | 383.05 | 29.19 | 2.04 | 1.62 | 2.65 | 195.7 |
| 98507_at | 110 | 210.52 | 28.44 | 427.41 | 62.39 | 2.03 | 1.45 | 2.82 | 216.88 |
| 94967_at | 111 | 105.62 | 17.9 | 214.5 | 28.22 | 2.03 | 1.44 | 2.97 | 108.88 |
| 160237_at | 112 | 135.67 | 34.39 | 275.02 | 38.2 | 2.03 | 1.31 | 3.6 | 139.35 |
| 98446_s_at | 113 | 141.88 | 41.45 | 287.07 | 41.58 | 2.02 | 1.25 | 4.01 | 145.19 |
| 96926_at | 114 | 144.45 | 27.93 | 290.46 | 15.29 | 2.01 | 1.5 | 2.97 | 146.01 |
| 92845_at | 115 | 170.95 | 17.73 | 342.33 | 49.39 | 2 | 1.47 | 2.66 | 171.38 |
| 100581_at | 116 | 705.51 | 57.45 | 1408.65 | 224.5 | 2 | 1.44 | 2.63 | 703.14 |
| 104480_at | 117 | 184.72 | 13.66 | 369.2 | 61.29 | 2 | 1.43 | 2.63 | 184.47 |
| 96634_at | 118 | 103.53 | 13.51 | 205.16 | 16.27 | 1.98 | 1.56 | 2.6 | 101.63 |
| 94276_at | 119 | 197.58 | 26.99 | 391.41 | 48.86 | 1.98 | 1.46 | 2.71 | 193.84 |
| 95731_at | 120 | 220.03 | 43.23 | 436.14 | 48.05 | 1.98 | 1.4 | 3.02 | 216.12 |
| 98946_at | 121 | 162.82 | 41.36 | 321.71 | 43.79 | 1.98 | 1.28 | 3.51 | 158.89 |
| 92855_at | 122 | 584.64 | 123.66 | 1154.24 | 120.73 | 1.97 | 1.38 | 3.11 | 569.6 |
| 98545_at | 123 | 237.76 | 53.22 | 464.91 | 55.5 | 1.96 | 1.33 | 3.19 | 227.15 |
| 92625_at | 124 | 397.13 | 83.29 | 780.25 | 118.82 | 1.96 | 1.3 | 3.16 | 383.12 |
| 100618_f_at | 125 | 737.43 | 221.94 | 1443.15 | 153.88 | 1.96 | 1.25 | 3.93 | 705.72 |
| 97826_at | 126 | 831.97 | 82.48 | 1620.67 | 288.56 | 1.95 | 1.34 | 2.67 | 788.7 |
| 96592_at | 127 | 190.99 | 39.76 | 373.19 | 46.44 | 1.95 | 1.34 | 3.08 | 182.19 |
| 95446_at | 128 | 345.12 | 51.28 | 672.7 | 111.59 | 1.95 | 1.33 | 2.82 | 327.59 |
| 93728_at | 129 | 165.51 | 34.39 | 321.77 | 28.72 | 1.94 | 1.39 | 3.01 | 156.26 |
| 103035_at | 130 | 212.61 | 41.86 | 413.17 | 40.37 | 1.94 | 1.39 | 2.95 | 200.56 |
| 102821_s_at | 131 | 332.53 | 54.89 | 646.41 | 115.67 | 1.94 | 1.28 | 2.92 | 313.89 |

FIG. 22A (continued)

| | | | | | | | | | |
|---|---|---|---|---|---|---|---|---|---|
| 94485_at | 132 | 174.54 | 18.63 | 337.38 | 17.63 | 1.93 | 1.61 | 2.38 | 162.84 |
| 96041_at | 133 | 581.54 | 85.07 | 1124.91 | 148.43 | 1.93 | 1.4 | 2.71 | 543.37 |
| 94526_at | 134 | 119.03 | 10.37 | 229.15 | 35.02 | 1.93 | 1.4 | 2.53 | 110.12 |
| 102121_f_at | 135 | 203.34 | 36.01 | 393.38 | 52.67 | 1.93 | 1.35 | 2.87 | 190.03 |
| 101502_at | 136 | 227.82 | 30.05 | 439.1 | 70.68 | 1.93 | 1.34 | 2.71 | 211.29 |
| 160253_at | 137 | 559.17 | 112.52 | 1080.53 | 208.1 | 1.93 | 1.2 | 3.14 | 521.36 |
| 93833_s_at | 138 | 118.76 | 25.65 | 228.26 | 30.94 | 1.92 | 1.29 | 3.11 | 109.51 |
| 97890_at | 139 | 886.59 | 114.32 | 1689.19 | 208.5 | 1.91 | 1.42 | 2.57 | 802.6 |
| 92578_at | 140 | 167.52 | 26.78 | 319.95 | 49.6 | 1.91 | 1.31 | 2.79 | 152.43 |
| 96357_at | 141 | 208.53 | 27.17 | 398.66 | 67.01 | 1.91 | 1.31 | 2.69 | 190.13 |
| 95514_at | 142 | 164.5 | 28.56 | 311.09 | 31.76 | 1.89 | 1.38 | 2.73 | 146.59 |
| 93738_at | 143 | 135.63 | 16.76 | 256.05 | 38.57 | 1.89 | 1.35 | 2.59 | 120.42 |
| 92848_at | 144 | 329.18 | 59.95 | 621.01 | 79.59 | 1.89 | 1.32 | 2.82 | 291.83 |
| 97819_at | 145 | 417.76 | 74.71 | 789.92 | 105.09 | 1.89 | 1.32 | 2.82 | 372.16 |
| 103736_at | 146 | 124.32 | 15.56 | 234.82 | 40.52 | 1.89 | 1.29 | 2.65 | 110.49 |
| 103015_at | 147 | 302.46 | 28.21 | 568.15 | 94.81 | 1.88 | 1.32 | 2.52 | 265.69 |
| 101954_at | 148 | 499.7 | 65.21 | 941.2 | 170.98 | 1.88 | 1.26 | 2.69 | 441.5 |
| 97914_at | 149 | 239.83 | 28.01 | 448.44 | 80.3 | 1.87 | 1.27 | 2.62 | 208.61 |
| 103990_at | 150 | 1427.05 | 431.41 | 2668.76 | 224.52 | 1.87 | 1.21 | 3.76 | 1241.72 |
| 94448_at | 151 | 235 | 27.61 | 436.14 | 53.8 | 1.86 | 1.39 | 2.46 | 201.14 |
| 101589_at | 152 | 314.4 | 38.1 | 582.39 | 71.53 | 1.85 | 1.39 | 2.47 | 267.99 |
| 93844_at | 153 | 321.51 | 64.32 | 596.1 | 69.34 | 1.85 | 1.3 | 2.86 | 274.59 |
| 94837_at | 154 | 388.4 | 69.03 | 718.72 | 96.69 | 1.85 | 1.29 | 2.75 | 330.32 |
| 160415_at | 155 | 424.11 | 58.34 | 778.3 | 86.16 | 1.84 | 1.38 | 2.49 | 354.18 |
| 93581_at | 156 | 203.54 | 51.74 | 373.94 | 25.84 | 1.84 | 1.27 | 3.19 | 170.4 |
| 96866_at | 157 | 176.53 | 22.06 | 323.63 | 37.09 | 1.83 | 1.39 | 2.44 | 147.1 |
| 97456_at | 158 | 213.02 | 29.46 | 390.07 | 48.64 | 1.83 | 1.35 | 2.52 | 177.05 |
| 95518_at | 159 | 339.31 | 32.71 | 620.19 | 93.36 | 1.83 | 1.33 | 2.42 | 280.88 |
| 99109_at | 160 | 1264.78 | 364.09 | 2315.1 | 123.26 | 1.83 | 1.23 | 3.49 | 1050.32 |
| 92861_i_at | 161 | 752.97 | 134.96 | 1369.66 | 155.42 | 1.82 | 1.31 | 2.68 | 616.69 |
| 98608_at | 162 | 220.94 | 24.33 | 399.97 | 47.71 | 1.81 | 1.38 | 2.37 | 179.03 |
| 93119_at | 163 | 411.82 | 64.25 | 746.17 | 89.81 | 1.81 | 1.32 | 2.56 | 334.36 |
| 104155_f_at | 164 | 1737.95 | 437.64 | 3138.54 | 128.49 | 1.81 | 1.27 | 3.09 | 1400.59 |

FIG. 22A (continued)

| | | | | | | | | | |
|---|---|---|---|---|---|---|---|---|---|
| 160321_at | 165 | 218.41 | 25.78 | 395.96 | 64.49 | 1.81 | 1.27 | 2.5 | 177.55 |
| 100617_at | 166 | 1161.14 | 143.75 | 2096.53 | 335.8 | 1.81 | 1.26 | 2.5 | 935.39 |
| 103980_at | 167 | 140.65 | 23.54 | 253.19 | 23.59 | 1.8 | 1.34 | 2.56 | 112.54 |
| 94789_r_at | 168 | 601.41 | 109.67 | 1080.26 | 78.55 | 1.8 | 1.34 | 2.61 | 478.85 |
| 99643_f_at | 169 | 319 | 24.89 | 569.9 | 65.84 | 1.79 | 1.4 | 2.23 | 250.9 |
| 99133_at | 170 | 590.99 | 89.73 | 1055.14 | 72.4 | 1.79 | 1.39 | 2.42 | 464.15 |
| 93309_at | 171 | 233.93 | 36.64 | 418.52 | 42.99 | 1.79 | 1.33 | 2.5 | 184.59 |
| 92523_at | 172 | 250.73 | 25.34 | 449.69 | 71.54 | 1.79 | 1.28 | 2.41 | 198.96 |
| 100332_s_at | 173 | 208.03 | 48.17 | 371.64 | 18.02 | 1.79 | 1.28 | 2.9 | 163.61 |
| 160832_at | 174 | 308.34 | 41.38 | 551.8 | 80.83 | 1.79 | 1.27 | 2.49 | 243.46 |
| 103715_at | 175 | 173.45 | 25.07 | 308.76 | 42.06 | 1.78 | 1.28 | 2.49 | 135.31 |
| 93865_s_at | 176 | 169.23 | 21.49 | 299.7 | 39.44 | 1.77 | 1.3 | 2.4 | 130.47 |
| 100557_g_at | 177 | 383.54 | 88.02 | 679.22 | 63.17 | 1.77 | 1.23 | 2.9 | 295.69 |
| 93753_at | 178 | 360.92 | 31.33 | 633.75 | 85.9 | 1.76 | 1.32 | 2.26 | 272.82 |
| 92562_at | 179 | 207.67 | 23.98 | 366.25 | 58.35 | 1.76 | 1.24 | 2.41 | 158.58 |
| 92829_at | 180 | 489.72 | 42 | 854.63 | 124.19 | 1.75 | 1.29 | 2.27 | 364.91 |
| 104410_at | 181 | 246.52 | 31.44 | 430.65 | 61.19 | 1.75 | 1.26 | 2.39 | 184.13 |
| 99106_at | 182 | 144.13 | 12.82 | 252.81 | 42.37 | 1.75 | 1.24 | 2.35 | 108.68 |
| 98059_s_at | 183 | 1207.59 | 325.93 | 2116.17 | 106.63 | 1.75 | 1.2 | 3.16 | 908.58 |
| 160383_at | 184 | 362.28 | 56 | 631.49 | 47.87 | 1.74 | 1.34 | 2.39 | 269.21 |
| 92986_g_at | 185 | 166.57 | 14.19 | 290.15 | 37.21 | 1.74 | 1.33 | 2.22 | 123.57 |
| 93104_at | 186 | 542.76 | 93.36 | 945.49 | 92.87 | 1.74 | 1.28 | 2.5 | 402.74 |
| 95697_at | 187 | 635.08 | 135.07 | 1103.54 | 97.58 | 1.74 | 1.24 | 2.72 | 468.47 |
| 96258_at | 188 | 211.85 | 36.09 | 365.74 | 32.96 | 1.73 | 1.28 | 2.46 | 153.89 |
| 94806_at | 189 | 218.46 | 32.82 | 378.12 | 46.11 | 1.73 | 1.26 | 2.42 | 159.66 |
| 96899_at | 190 | 178.06 | 30.62 | 308.09 | 36.14 | 1.73 | 1.24 | 2.52 | 130.03 |
| 97751_f_at | 191 | 658.6 | 107.19 | 1141.8 | 151.91 | 1.73 | 1.23 | 2.5 | 483.2 |
| 93277_at | 192 | 505.99 | 44.71 | 874.53 | 145.9 | 1.73 | 1.22 | 2.31 | 368.54 |
| 101214_f_at | 193 | 685.55 | 109.92 | 1182.57 | 109.46 | 1.72 | 1.29 | 2.41 | 497.02 |
| 100595_at | 194 | 237.36 | 25.26 | 407.84 | 55.12 | 1.72 | 1.28 | 2.27 | 170.47 |
| 98472_at | 195 | 651.55 | 118.79 | 1119.49 | 134.47 | 1.72 | 1.22 | 2.56 | 467.94 |
| 101989_at | 196 | 570.91 | 114.95 | 974.97 | 77.6 | 1.71 | 1.24 | 2.6 | 404.06 |
| 93029_at | 197 | 187.78 | 36.47 | 321.07 | 37.75 | 1.71 | 1.2 | 2.61 | 133.29 |

FIG. 22A (continued)

| | | | | | | | | | |
|---|---|---|---|---|---|---|---|---|---|
| 96353_at | 198 | 171.48 | 29.57 | 291.99 | 26.09 | 1.7 | 1.27 | 2.44 | 120.52 |
| 99642_i_at | 199 | 290.17 | 36.11 | 492.69 | 65.91 | 1.7 | 1.25 | 2.3 | 202.52 |
| 98505_i_at | 200 | 276.98 | 10.47 | 471.34 | 7(FIG. | 7 | 1.22 | 2.19 | 194.37 |
| 93818_g_at | 201 | 365.43 | 53.8 | 615.41 | 50.44 | 1.68 | 1.3 | 2.28 | 249.98 |
| 94489_at | 202 | 678.41 | 80.48 | 1140.47 | 120.27 | 1.68 | 1.3 | 2.2 | 462.07 |
| 98447_at | 203 | 474.58 | 68.17 | 797.13 | 65.87 | 1.68 | 1.3 | 2.26 | 322.55 |
| 101906_at | 204 | 195.27 | 13.72 | 328.07 | 43.2 | 1.68 | 1.29 | 2.12 | 132.79 |
| 100599_at | 205 | 590.8 | 50.09 | 988.25 | 112.1 | 1.67 | 1.31 | 2.1 | 397.45 |
| 94062_at | 206 | 293.1 | 32.58 | 485.75 | 61.45 | 1.66 | 1.24 | 2.19 | 192.66 |
| 97386_at | 207 | 281.32 | 33.9 | 464.62 | 46.81 | 1.65 | 1.28 | 2.16 | 183.3 |
| 100578_at | 208 | 359.42 | 48.01 | 592.91 | 61.72 | 1.65 | 1.25 | 2.21 | 233.49 |
| 98438_f_at | 209 | 1400 | 229.84 | 2305.65 | 172.46 | 1.65 | 1.25 | 2.3 | 905.65 |
| 103612_at | 210 | 586.37 | 64.7 | 961.03 | 78.44 | 1.64 | 1.31 | 2.08 | 374.66 |
| 160246_at | 211 | 218.98 | 23.47 | 358.79 | 45.78 | 1.64 | 1.23 | 2.15 | 139.81 |
| 92958_at | 212 | 197.31 | 18.13 | 321.1 | 12.53 | 1.63 | 1.39 | 1.94 | 123.79 |
| 93023_f_at | 213 | 1289.41 | 185.86 | 2104.73 | 90.02 | 1.63 | 1.3 | 2.16 | 815.32 |
| 160568_at | 214 | 312.65 | 31.22 | 508.7 | 70.08 | 1.63 | 1.21 | 2.14 | 196.06 |
| 92816_r_at | 215 | 461.32 | 64.04 | 752.55 | 93.39 | 1.63 | 1.2 | 2.24 | 291.23 |
| 98937_at | 216 | 195.45 | 27 | 317.11 | 20.14 | 1.62 | 1.28 | 2.14 | 121.67 |
| 160451_at | 217 | 210.95 | 25.47 | 341.15 | 38.6 | 1.62 | 1.23 | 2.14 | 130.2 |
| 93714_f_at | 218 | 1503.18 | 228.1 | 2418.85 | 193.58 | 1.61 | 1.24 | 2.2 | 915.67 |
| 160090_f_at | 219 | 680.13 | 60.49 | 1097.27 | 134.99 | 1.61 | 1.24 | 2.06 | 417.13 |
| 96755_at | 220 | 262.5 | 36.34 | 420.8 | 38.88 | 1.6 | 1.23 | 2.15 | 158.3 |
| 93354_at | 221 | 674.48 | 86.44 | 1059.32 | 74.23 | 1.57 | 1.25 | 2.04 | 384.83 |
| 93071_at | 222 | 434.6 | 69 | 682.99 | 36.08 | 1.57 | 1.22 | 2.15 | 248.4 |
| 93264_at | 223 | 431.59 | 34.88 | 673.83 | 41.04 | 1.56 | 1.33 | 1.85 | 242.23 |
| 100128_at | 224 | 247.99 | 29.26 | 385.76 | 26.99 | 1.56 | 1.25 | 1.98 | 137.77 |
| 93057_at | 225 | 612.72 | 56.09 | 945.97 | 107.03 | 1.54 | 1.2 | 1.96 | 333.24 |
| 103416_at | 226 | 297.37 | 17.14 | 454.06 | 55.15 | 1.53 | 1.2 | 1.88 | 156.69 |
| 95069_at | 227 | 204.72 | 17.73 | 310.68 | 31.68 | 1.52 | 1.21 | 1.89 | 105.96 |
| 93274_at | 228 | 455.45 | 34.85 | 687.58 | 68.3 | 1.51 | 1.22 | 1.85 | 232.13 |
| 101112_g_at | 229 | 316.94 | 39.38 | 479.63 | 30.55 | 1.51 | 1.22 | 1.94 | 162.69 |
| 96416_f_at | 230 | 1047.69 | 154.71 | 1580.26 | 36.04 | 1.51 | 1.21 | 2 | 532.57 |

FIG. 22A (continued)

| | | | | | | | | | |
|---|---|---|---|---|---|---|---|---|---|
| 96115_at | 231 | 882.18 | 67.27 | 1307.78 | 68.28 | 1.48 | 1.28 | 1.73 | 425.6 |
| 162358_i_at | 232 | 260.46 | 28.47 | 382.39 | 11.42 | 1.47 | 1.23 | 1.8 | 121.92 |

FIG. 22B

| SEQ ID No | A1- High | A2- ctrl | A3- ctrl | A4- ctrl | High-dep A1 | High_dep A2 | High-dep A4 |
|---|---|---|---|---|---|---|---|
| 1 | -5.63 | -17.67 | -5.17 | 6.77 | 83.12 | 169.99 | 100.58 |
| 2 | -2.54 | -14.06 | 0.94 | 10.82 | 87.42 | 54.4 | 195.99 |
| 3 | 23.31 | 8.36 | 7.01 | 53.96 | 38.68 | 206.2 | 417.26 |
| 4 | 19.77 | 2.26 | 24.49 | 58.97 | 205.62 | 127.45 | 188.14 |
| 5 | 139.28 | 52.41 | 114.17 | 154.8 | 635.16 | 417.84 | 1060.26 |
| 6 | 39.56 | 63.62 | 152.7 | 275.17 | 1060.5 | 629.24 | 658.28 |
| 7 | 110.88 | 59.72 | 89.21 | 214.03 | 726.78 | 468.04 | 764.58 |
| 8 | 32.41 | 21.49 | 24.37 | 54.71 | 255 | 107.37 | 188.45 |
| 9 | 331.43 | -167.33 | 163.29 | 469.3 | 481.09 | 1002.95 | 1554.39 |
| 10 | 116.76 | 108.93 | 156.49 | 342 | 1063.9 | 692.84 | 928.59 |
| 11 | 283.17 | 121.9 | 170.16 | 205.78 | 1011.81 | 567.07 | 1110.23 |
| 12 | 74.97 | 22.58 | 143.49 | 331.85 | 942.05 | 448.77 | 522.72 |
| 13 | 42.96 | 17.71 | 59.52 | 96.43 | 288.14 | 207.6 | 245.94 |
| 14 | 444.42 | 87.63 | 119.71 | 180.16 | 943.76 | 445.53 | 1329.18 |
| 15 | 78.04 | 27.45 | 130.69 | 228.96 | 704.54 | 360.25 | 453.08 |
| 16 | 221.31 | 82.68 | 273.71 | 375.27 | 720.98 | 786.45 | 1419.72 |
| 17 | 68.92 | 41.02 | 121.74 | 188.95 | 730.1 | 262.37 | 269.51 |
| 18 | 129.38 | 43.78 | 378.11 | 479.44 | 1325.48 | 831.71 | 919.9 |
| 19 | 418.78 | 404.48 | 559.46 | 1077.69 | 2507.7 | 1533.6 | 3167.77 |
| 20 | 256.89 | 60.48 | 111.55 | 157.48 | 478.62 | 401.72 | 765.65 |
| 21 | 442.7 | 254.33 | 526.58 | 1016.59 | 2409.26 | 1449.07 | 2138.65 |
| 22 | 114.71 | 44.84 | 149.01 | 227.39 | 581.81 | 403.71 | 464.3 |
| 23 | 140.81 | 93.38 | 119.51 | 155.72 | 371.38 | 380.48 | 623.48 |
| 24 | 720.51 | 156.21 | 941.53 | 1000.88 | 2478.16 | 2355.04 | 2547.28 |
| 25 | 192.27 | 92.36 | 240.88 | 605.76 | 1169.42 | 577.85 | 1099.93 |
| 26 | 580.94 | 313.16 | 283.46 | 347.07 | 1341.64 | 851.31 | 1604.33 |
| 27 | 84.02 | 29.36 | 36.55 | 53.49 | 134.3 | 91.56 | 282.49 |
| 28 | 143.01 | 123.84 | 298.75 | 373.89 | 1005.66 | 557.55 | 761.95 |
| 29 | 320.38 | 113.16 | 481.11 | 1025.22 | 1437.46 | 1952.41 | 1354.26 |
| 30 | 296.03 | 137.39 | 718.51 | 695.82 | 2067.83 | 1311.65 | 1152.53 |
| 31 | 214.27 | 126.62 | 314.52 | 408.07 | 1145.61 | 689.57 | 663.78 |
| 32 | 206.21 | 153.91 | 280.51 | 297.21 | 837.74 | 706.2 | 660.62 |
| 33 | 81.04 | 51.06 | 75.14 | 98.1 | 233.5 | 241.15 | 234.39 |
| 34 | 395.98 | 128.67 | 700.46 | 1145.39 | 1809.54 | 2080.32 | 1412.16 |
| 35 | 65.85 | 99.89 | 157.89 | 185.62 | 569.39 | 266.39 | 301.91 |
| 36 | 263.18 | 139.8 | 182.15 | 218.92 | 598.64 | 431.27 | 753.7 |
| 37 | 177.42 | 150.27 | 399.45 | 540.28 | 983.19 | 832.33 | 997.4 |
| 38 | 74.75 | 74.97 | 48.84 | 82.72 | 182.41 | 128.43 | 293.82 |
| 39 | 150.84 | 95.39 | 167.23 | 138.08 | 392.12 | 214.37 | 570.07 |
| 40 | 540.31 | 300.82 | 465.12 | 1073.48 | 1938.91 | 1348.09 | 1771.76 |
| 41 | 132.57 | 108.3 | 176.91 | 468.34 | 826.57 | 495.76 | 559.84 |
| 42 | 202.76 | 65.77 | 160.86 | 161.92 | 501.64 | 253.72 | 509.75 |
| 43 | 70.65 | 48.97 | 117.21 | 117.12 | 212.32 | 168.69 | 357.86 |
| 44 | 59.89 | 73.74 | 89.86 | 151.61 | 354.26 | 227.02 | 207.74 |
| 45 | 262.7 | 140.08 | 223.83 | 362.92 | 768 | 506.51 | 792.68 |
| 46 | 203.13 | 24.19 | 141.14 | 166.52 | 396.35 | 278.68 | 423.13 |
| 47 | 1249.11 | -163.61 | 288.35 | 509.86 | 1213.24 | 1064.64 | 1540.1 |
| 48 | 112.44 | 70.65 | 156.69 | 225.29 | 470.4 | 278.49 | 398.79 |
| 49 | 78.27 | 43.65 | 67.66 | 114.57 | 215.12 | 174.03 | 225.14 |

FIG. 22B(continued)

| | | | | | | | |
|---|---|---|---|---|---|---|---|
| 50 | 132.5 | 26.28 | 122.03 | 135.16 | 277.18 | 181.31 | 371.58 |
| 51 | 262.43 | 112.26 | 371.84 | 470.08 | 711.07 | 681.81 | 1033.8 |
| 52 | 536.76 | 461.17 | 769.77 | 889.81 | 1975.05 | 1352.89 | 1960.32 |
| 53 | 438.88 | 225 | 382.84 | 525.6 | 835.86 | 857.62 | 1428.27 |
| 54 | 141.38 | 90.71 | 202.04 | 223.88 | 495.75 | 346.79 | 438.26 |
| 55 | 74.76 | 50.42 | 52.47 | 86.4 | 192.43 | 139.97 | 206.83 |
| 56 | 79.05 | 66.18 | 67.55 | 103.4 | 264.65 | 154.74 | 201.21 |
| 57 | 80.07 | 90.7 | 102.4 | 176.88 | 281.97 | 349.67 | 243.8 |
| 58 | 68.4 | 106.51 | 76.63 | 59.14 | 167.01 | 225.34 | 186.51 |
| 59 | 83.86 | 39.01 | 93.03 | 123.08 | 222.12 | 160.9 | 264.71 |
| 60 | 1296.17 | 167.7 | 1103.2 | 1462.67 | 2516.18 | 2486.75 | 2606.4 |
| 61 | 149.99 | 61.1 | 151.09 | 218.82 | 346.11 | 438.58 | 339.9 |
| 62 | 215.58 | 309.49 | 355.1 | 416.34 | 941.89 | 641.57 | 866.1 |
| 63 | 137.69 | 69.83 | 69.95 | 117.25 | 233.19 | 145.75 | 360.25 |
| 64 | 176.23 | 129.22 | 287.4 | 244.63 | 611.3 | 538.23 | 410.26 |
| 65 | 135.04 | 70.48 | 243.79 | 312.9 | 563.01 | 370.79 | 457.06 |
| 66 | 65.19 | 25.39 | 94.18 | 120.53 | 218.57 | 131.58 | 207.17 |
| 67 | 356.76 | 227.22 | 367.73 | 327.65 | 715.66 | 626.94 | 1034.2 |
| 68 | 643.68 | 299.61 | 1106.73 | 1751.38 | 2438.92 | 2465.26 | 2012.95 |
| 69 | 119.23 | 94.41 | 135.34 | 146.07 | 349.59 | 254.82 | 301.39 |
| 70 | 360.47 | 304.94 | 200.13 | 397.18 | 812.63 | 626.76 | 826.71 |
| 71 | 1701.31 | 921.16 | 1800.76 | 2328.77 | 4084.28 | 3803.84 | 4121.35 |
| 72 | 101 | 107.87 | 287.29 | 454.65 | 684.09 | 490.91 | 508.17 |
| 73 | 346.1 | 105.04 | 264.96 | 271.03 | 707.56 | 464.44 | 544.27 |
| 74 | 85.55 | 89.81 | 95.56 | 146.28 | 262.05 | 181.42 | 283.51 |
| 75 | 182.89 | 96.32 | 560.09 | 578.66 | 860.12 | 883.46 | 701.98 |
| 76 | 115.65 | 123.07 | 243.02 | 261.83 | 523.34 | 333.37 | 432.41 |
| 77 | 198.8 | 93.34 | 229.65 | 356.53 | 561.03 | 352.4 | 609.09 |
| 78 | 93.9 | 77.62 | 124.29 | 133.58 | 283.15 | 228.24 | 224.33 |
| 79 | 149.09 | 174.43 | 183.43 | 179 | 525.24 | 268.7 | 384.89 |
| 80 | 163.12 | 123.1 | 266.84 | 253.62 | 470.88 | 274.31 | 633.27 |
| 81 | 511.47 | 273.07 | 950.77 | 1091.08 | 1547.45 | 1179.77 | 2083.79 |
| 82 | 131.81 | 52.72 | 137.49 | 317.72 | 382.99 | 247.01 | 456.6 |
| 83 | 119.97 | 78 | 102.46 | 124.31 | 250.65 | 174.67 | 308.27 |
| 84 | 946.19 | 351.71 | 705.88 | 1059.06 | 1534.13 | 1361.23 | 2222.82 |
| 85 | 298.4 | 248.35 | 262.8 | 500.23 | 730.02 | 490.82 | 977.92 |
| 86 | 126.17 | 60.47 | 225.06 | 210.49 | 298.85 | 278.49 | 462.49 |
| 87 | 204.53 | 399.01 | 430.57 | 291 | 748.26 | 669.68 | 788.41 |
| 88 | 897.74 | 464 | 1566.84 | 1913.81 | 2787.91 | 2754.92 | 2592.71 |
| 89 | 1876.3 | 682.31 | 1158.85 | 1527.08 | 3819.6 | 2224.18 | 2746.01 |
| 90 | 109.7 | 130.79 | 142.04 | 203.42 | 416.8 | 240.51 | 313.38 |
| 91 | 70.83 | 65.03 | 116.01 | 137.3 | 243.19 | 178.45 | 227.11 |
| 92 | 104.22 | 80.52 | 100.91 | 111.37 | 166.84 | 178.35 | 305.19 |
| 93 | 160.76 | 41.21 | 121.95 | 155.07 | 261.42 | 168.61 | 355.69 |
| 94 | 1002.21 | 376.59 | 623.8 | 798.55 | 1496.07 | 1240.29 | 1771.65 |
| 95 | 565.29 | 155.67 | 524.23 | 804.82 | 1036.06 | 747.86 | 1536.56 |
| 96 | 83.36 | 127.14 | 137.58 | 196.8 | 262.3 | 209.25 | 402.22 |
| 97 | 170.87 | 118.9 | 283.84 | 230 | 370.12 | 379.44 | 542.27 |
| 98 | 510.11 | 255.73 | 467.06 | 628.25 | 1295.4 | 706.07 | 958.06 |
| 99 | 460.1 | 53.41 | 304.69 | 327.47 | 443.97 | 628.87 | 737.78 |

FIG. 22B(continued)

| | | | | | | | |
|---|---|---|---|---|---|---|---|
| 100 | 863.6 | 207.42 | 306.15 | 435.08 | 951.34 | 699.25 | 1208.97 |
| 101 | 115.92 | 128.12 | 128.12 | 137.12 | 321.41 | 245.54 | 230.42 |
| 102 | 609.66 | 500.34 | 785.38 | 1034.85 | 1585.94 | 1451 | 1624.77 |
| 103 | 264.25 | 164.9 | 333.89 | 561.29 | 779.16 | 607.88 | 694.78 |
| 104 | 123.78 | 64.66 | 93.68 | 149.27 | 251.83 | 142.53 | 276.23 |
| 105 | 448.92 | 217.48 | 316.74 | 404.21 | 792.91 | 438.86 | 920.02 |
| 106 | 872.5 | 136.08 | 872.47 | 976.55 | 1308.91 | 1211.31 | 1907.24 |
| 107 | 782.84 | 160.15 | 782.21 | 875.83 | 1103.1 | 1100.16 | 1844.59 |
| 108 | 183.5 | 120.8 | 230.11 | 274.68 | 502.11 | 346.62 | 406.3 |
| 109 | 145.22 | 154.75 | 215.32 | 223.86 | 402.89 | 331.79 | 416.36 |
| 110 | 242.68 | 131.21 | 227.3 | 239.68 | 545.7 | 407.72 | 334.91 |
| 111 | 152.64 | 73.67 | 94.27 | 97.84 | 216.43 | 168.83 | 260.02 |
| 112 | 137.9 | 40.27 | 191.51 | 171.58 | 349.08 | 223.32 | 253.36 |
| 113 | 231.99 | 37.75 | 125.33 | 172.57 | 318.72 | 207 | 336.68 |
| 114 | 129.7 | 79.03 | 166.88 | 193.5 | 277.7 | 286.34 | 305.25 |
| 115 | 151.91 | 143.6 | 165.79 | 218.92 | 406.76 | 248.28 | 374.11 |
| 116 | 688 | 569.04 | 732.38 | 823.68 | 1470.55 | 998.09 | 1757.45 |
| 117 | 177.77 | 181.58 | 163.05 | 216.72 | 349.95 | 275.4 | 480.9 |
| 118 | 67.73 | 111.6 | 121.41 | 116 | 229.84 | 178.33 | 208.33 |
| 119 | 186.4 | 143.44 | 190.67 | 266.45 | 474.16 | 308.84 | 393.31 |
| 120 | 213.57 | 102.11 | 277.63 | 286.81 | 395.79 | 387.24 | 526.05 |
| 121 | 153.49 | 76.2 | 145.61 | 274.72 | 403.36 | 255.75 | 309.24 |
| 122 | 511.99 | 296.95 | 641.95 | 887.33 | 1370.99 | 960.71 | 1133.77 |
| 123 | 255.48 | 96.57 | 246.27 | 353.38 | 455.98 | 376.23 | 562.17 |
| 124 | 519.52 | 161.83 | 403.43 | 502.64 | 902.52 | 546.05 | 893.71 |
| 125 | 1059.81 | 121.89 | 723.62 | 1035.98 | 1346.69 | 1263.28 | 1730.1 |
| 126 | 794.58 | 646.29 | 894.06 | 979.75 | 1585.26 | 1153.91 | 2124.6 |
| 127 | 182.15 | 100.35 | 187.18 | 293.39 | 300.2 | 373.46 | 449.27 |
| 128 | 310.84 | 246.38 | 333.32 | 488.12 | 876.51 | 493.78 | 651.77 |
| 129 | 152.43 | 89.76 | 166.79 | 251.84 | 357.65 | 267 | 340.43 |
| 130 | 207.57 | 100.38 | 282.81 | 259.08 | 456.54 | 335.38 | 446.38 |
| 131 | 455.54 | 202.21 | 301.47 | 370.84 | 756.41 | 417.26 | 766.51 |
| 132 | 145.05 | 144.44 | 187.68 | 216.41 | 338.95 | 310.57 | 362.17 |
| 133 | 554.11 | 402.15 | 567.63 | 809.76 | 1292.17 | 844.8 | 1249.13 |
| 134 | 130.24 | 103.48 | 113.49 | 126.1 | 297.16 | 184.92 | 204.95 |
| 135 | 186.7 | 119.75 | 289.61 | 216.49 | 446.72 | 288.14 | 445.05 |
| 136 | 189.47 | 168.95 | 262.02 | 293.93 | 548.58 | 309.28 | 462.05 |
| 137 | 638.29 | 239.8 | 626.95 | 717.65 | 999.55 | 774.33 | 1465.56 |
| 138 | 124.73 | 52.62 | 119.62 | 177.26 | 234.37 | 175.19 | 275.85 |
| 139 | 829.09 | 706.34 | 788.34 | 1218.18 | 1732 | 1318.01 | 2016.68 |
| 140 | 196.56 | 96.26 | 168.71 | 211.3 | 409.32 | 239.57 | 313.52 |
| 141 | 194.4 | 142.96 | 233.73 | 262.23 | 436.12 | 272.78 | 488.44 |
| 142 | 144.74 | 96.33 | 183.54 | 226.73 | 338.13 | 260.1 | 343.18 |
| 143 | 132.94 | 103.91 | 170.64 | 131.81 | 328.78 | 200.99 | 237.08 |
| 144 | 385.59 | 190.9 | 277.34 | 461.73 | 691.3 | 466.96 | 705.79 |
| 145 | 479.58 | 201.87 | 479.86 | 510.07 | 855.6 | 589.24 | 927.23 |
| 146 | 82.02 | 125.19 | 133.96 | 156.08 | 293.82 | 157.63 | 253.33 |
| 147 | 242.78 | 269.89 | 348.84 | 344.92 | 707.32 | 393.24 | 610.03 |
| 148 | 565.1 | 394.93 | 387.65 | 642.06 | 946.42 | 655.01 | 1228.65 |
| 149 | 275.94 | 169.57 | 227.25 | 286.38 | 493.91 | 297.39 | 557.13 |

FIG. 22B(continued)

| | | | | | | | |
|---|---|---|---|---|---|---|---|
| 150 | 781.55 | 580.02 | 2127.05 | 2208.06 | 3043.92 | 2702.29 | 2282.46 |
| 151 | 261.4 | 158.9 | 250.2 | 264.02 | 505.64 | 334.83 | 472.08 |
| 152 | 372.91 | 232.5 | 286.71 | 377.42 | 687.16 | 450.09 | 612.82 |
| 153 | 410.42 | 131.97 | 369.05 | 367.78 | 720.73 | 484.99 | 582.85 |
| 154 | 461.07 | 191.03 | 424.7 | 468.61 | 797.92 | 532.2 | 829.45 |
| 155 | 546.5 | 268.31 | 446.34 | 433.67 | 794.32 | 630 | 915.07 |
| 156 | 282.84 | 57.22 | 211.67 | 257.88 | 396.65 | 328.24 | 398.79 |
| 157 | 201.46 | 120.48 | 177.34 | 191.62 | 357.2 | 254.61 | 361.88 |
| 158 | 232.31 | 128.28 | 247.88 | 241.71 | 440.6 | 294.47 | 435.39 |
| 159 | 334.05 | 275.32 | 324.52 | 425.52 | 772.86 | 454.43 | 637.76 |
| 160 | 1051.89 | 397.67 | 1479.38 | 2126.13 | 2268.38 | 2529.2 | 2169.17 |
| 161 | 798.21 | 399.8 | 899.89 | 912.54 | 1287.69 | 1165.36 | 1655.86 |
| 162 | 244.32 | 157.06 | 225.73 | 253.07 | 427.09 | 313.85 | 463.56 |
| 163 | 438.76 | 226.89 | 457.14 | 513.87 | 898.95 | 594.47 | 745.37 |
| 164 | 1352.95 | 718.09 | 2236.02 | 2654.99 | 3278.78 | 3093.26 | 3118.24 |
| 165 | 214.2 | 173.96 | 194.94 | 287.47 | 464.04 | 272.6 | 455.63 |
| 166 | 1255.16 | 786.4 | 1150.85 | 1467.91 | 2159.71 | 1497.04 | 2635.45 |
| 167 | 126.6 | 89.26 | 180.85 | 154.61 | 268.42 | 225.32 | 276.81 |
| 168 | 771.24 | 305.25 | 587.97 | 728 | 1144.4 | 942.94 | 1161.59 |
| 169 | 263.57 | 319.12 | 316.73 | 380.47 | 669.63 | 447.63 | 593.13 |
| 170 | 590.2 | 359.6 | 608.4 | 795.03 | 1151.48 | 940.65 | 1093.9 |
| 171 | 240.81 | 133.89 | 251.93 | 307.57 | 489.86 | 345.71 | 424.47 |
| 172 | 261.55 | 218.92 | 220.14 | 275.29 | 400.11 | 375.64 | 584.55 |
| 173 | 293.62 | 82.87 | 186.43 | 269.33 | 379.84 | 345.41 | 394.6 |
| 174 | 317.27 | 208 | 305.44 | 404.98 | 669.86 | 404.54 | 588.74 |
| 175 | 210.83 | 108.43 | 178.61 | 189.73 | 297.39 | 249.07 | 382.93 |
| 176 | 148.52 | 120.38 | 201.64 | 203.61 | 293.01 | 238.39 | 369.71 |
| 177 | 389.88 | 142.96 | 438.38 | 556.24 | 611.53 | 633.48 | 795.43 |
| 178 | 351.77 | 286.84 | 364.72 | 436.79 | 792.97 | 498.19 | 611.18 |
| 179 | 189.25 | 165.89 | 196.05 | 273.16 | 411.47 | 252.37 | 435.01 |
| 180 | 549.81 | 444.28 | 396.42 | 562.95 | 980.17 | 611.93 | 973.6 |
| 181 | 256.18 | 158.27 | 285.46 | 278.17 | 552.75 | 386.78 | 362.56 |
| 182 | 158.87 | 122.18 | 130.52 | 158.92 | 323.99 | 182.08 | 258.41 |
| 183 | 1266.87 | 291.34 | 1465.85 | 1809.88 | 1981.71 | 2056.61 | 2286.62 |
| 184 | 441.84 | 217.7 | 330.57 | 455.9 | 703.49 | 549.05 | 646.54 |
| 185 | 189.38 | 134.13 | 158.87 | 184.24 | 293.44 | 226.46 | 351.53 |
| 186 | 682.11 | 281.63 | 567.42 | 645.45 | 1043.8 | 769.32 | 1024.99 |
| 187 | 863.99 | 258.52 | 643.98 | 775.24 | 1117.04 | 935.31 | 1259.67 |
| 188 | 250.42 | 107.62 | 249.84 | 237.46 | 404.92 | 391.03 | 300.92 |
| 189 | 268.86 | 131.02 | 211.1 | 263.99 | 412.1 | 289.7 | 433.76 |
| 190 | 202.48 | 88.45 | 208.4 | 211.97 | 366.42 | 245.63 | 315.38 |
| 191 | 763.84 | 372.77 | 638.07 | 864.79 | 1250.89 | 844.06 | 1330.22 |
| 192 | 579.01 | 403.81 | 461.65 | 580.39 | 930.22 | 604.38 | 1090.47 |
| 193 | 759.99 | 385.43 | 693.65 | 904.07 | 1217.27 | 982.86 | 1345.6 |
| 194 | 218.54 | 189.34 | 293.62 | 244.62 | 464.88 | 302.69 | 459.29 |
| 195 | 548.82 | 366.81 | 834.12 | 848.12 | 1219.9 | 862.27 | 1278.38 |
| 196 | 680.15 | 231.09 | 644.14 | 722.42 | 1096.65 | 839.03 | 998.56 |
| 197 | 200.26 | 89.81 | 194.73 | 265.83 | 363.25 | 250.69 | 353.76 |
| 198 | 195.2 | 85.23 | 185.31 | 214.94 | 331.76 | 248.9 | 298.72 |
| 199 | 212 | 250.08 | 339.99 | 361.59 | 598.36 | 376.5 | 508.79 |

FIG. 22B(continued)

| | | | | | | | |
|---|---|---|---|---|---|---|---|
| 200 | 267.45 | 277.85 | 265.49 | 300.01 | 535.99 | 315.33 | 563.39 |
| 201 | 414.1 | 209.26 | 389.63 | 447.03 | 704.17 | 533.38 | 606.64 |
| 202 | 702.54 | 622.66 | 506.76 | 887.7 | 1280.35 | 902.88 | 1236.37 |
| 203 | 562.75 | 314.93 | 512.53 | 482.74 | 699.39 | 791.42 | 899.59 |
| 204 | 176.32 | 180.1 | 192.77 | 232.45 | 379.17 | 247.14 | 362.22 |
| 205 | 629.29 | 458.8 | 613.35 | 651.07 | 1183.61 | 987.06 | 799.55 |
| 206 | 342.38 | 206.66 | 284.15 | 335.68 | 601.51 | 395.73 | 459.67 |
| 207 | 271.67 | 202.61 | 343.8 | 307.21 | 558.1 | 415.73 | 421.02 |
| 208 | 430 | 247.26 | 315.46 | 443.18 | 686.4 | 481.82 | 615.21 |
| 209 | 1559.47 | 729.14 | 1615.57 | 1698.99 | 2185.57 | 2100.15 | 2626.25 |
| 210 | 662.81 | 397.68 | 634.11 | 643.3 | 1107.81 | 940.38 | 839.18 |
| 211 | 222.23 | 162.57 | 220.06 | 269.77 | 416.59 | 274.84 | 388.42 |
| 212 | 198.65 | 151.97 | 226.1 | 213.29 | 320.21 | 308.37 | 336.35 |
| 213 | 1380.47 | 792.07 | 1290.47 | 1682.72 | 2232.77 | 1953.77 | 2136.47 |
| 214 | 372.07 | 247.11 | 335.34 | 290.23 | 459.08 | 423.98 | 642.32 |
| 215 | 566.12 | 321.59 | 390.04 | 561 | 789.62 | 590.84 | 888.3 |
| 216 | 200.62 | 121.34 | 232.22 | 226.78 | 326.33 | 286.45 | 343.48 |
| 217 | 246.19 | 144.99 | 211.15 | 234.88 | 314.82 | 301.03 | 411.93 |
| 218 | 1721.33 | 840.27 | 1669.65 | 1755.13 | 2306.27 | 2166.06 | 2773.47 |
| 219 | 704.75 | 519.05 | 747.7 | 748.74 | 1333.75 | 871.82 | 1091.69 |
| 220 | 259 | 166.63 | 282.19 | 337.55 | 408.79 | 375.26 | 479.62 |
| 221 | 762.24 | 437.4 | 762.93 | 712.17 | 1160.49 | 930.78 | 1073.37 |
| 222 | 421.07 | 252.08 | 477.89 | 578.49 | 728.91 | 622.27 | 701.27 |
| 223 | 436.26 | 347.21 | 430.15 | 487.11 | 692.96 | 626.57 | 710.07 |
| 224 | 255.08 | 191.63 | 252.08 | 299.78 | 352.3 | 389.18 | 420.82 |
| 225 | 643.97 | 457.99 | 643.94 | 704.09 | 1101.19 | 747.64 | 992.5 |
| 226 | 274.58 | 299.77 | 293.16 | 323.11 | 563.29 | 405.68 | 409.07 |
| 227 | 186.13 | 172.79 | 219.76 | 232.07 | 339.35 | 262.31 | 339.85 |
| 228 | 457.34 | 362.32 | 508.79 | 494.57 | 785.83 | 563.9 | 719.97 |
| 229 | 297.86 | 227.4 | 320.96 | 414 | 512.8 | 427.09 | 503.93 |
| 230 | 1134.57 | 717.69 | 898.31 | 1436.2 | 1584.96 | 1523.99 | 1635.62 |
| 231 | 853.21 | 716.93 | 927.26 | 1001.4 | 1324.43 | 1206.98 | 1396.24 |
| 232 | 298.82 | 186.1 | 288.38 | 265.88 | 378.11 | 395.22 | 375.85 |

FIG. 22C

| SEQ ID | common name | description |
|---|---|---|
| 1 | Sphingosine kinase 2 | UI-M-BH1-ame-a-08-0-UI.s1 NIH_BMAP_M_S2 Mus musculus cDNA clone UI-M-BH1-ame-a-08-0-UI 3', mRNA sequence. |
| 2 | Krt1-16 | intermediate filament protein |
| 3 | 1300007C21Rik | truncated; Mouse endogenous retrovirus truncated gag protein, complete cds, clone del env-1 3.1. |
| 4 | RIKEN cDNA 1110038L14 | vr45a06.s1 Knowles Solter mouse 2 cell Mus musculus cDNA clone IMAGE:1123570 5' similar to gb:X54942 CDK |
| 5 | Sprr1a | MSPRR1A; similar to mSPRR1A encoded by GenBank Accession Number M19888; Mus musculus SPRR 1A (Sprr1a) gene |
| 6 | RIKEN cDNA 1300019I03 | UI-M-AQ1-adx-c-06-0-UI.s1 NIH_BMAP_MHI_N Mus musculus cDNA clone UI-M-AQ1-adx-c-06-0-UI 3', mRNA sequence. |
| 7 | Mail-pending | vo32e09.r1 Barstead mouse irradiated colon MPLRB7 Mus musculus cDNA clone IMAGE:1051624 5', mRNA sequence. |
| 8 | MAIL | AV374591 RIKEN full-length enriched, adult male cecum Mus musculus cDNA clone 9130013H11 3', mRNA sequence. |
| 9 | Myln | Mus musculus non-muscle myosin light chain 3 (MLC3nm) mRNA, partial cds. |
| 10 | Stimulated by retinoic acid 14 | M.musculus mRNA for basic-helix-loop-helix protein. |
| 11 | ab, SCD, Scd-1 | stearoyl-CoA desaturase; Mouse stearoyl-CoA desaturase gene, exon 6. |
| 12 | Interferon-related regulator 1 | reading frame interferon beta-2; Messenger RNA fragment for mouse interferon beta (type 2) coding for the C-terminal part. |
| 13 | | Mus musculus mRNA for BTEB-1 transcription factor. |
| 14 | Ser (or cys) proteinase inhib | Mouse RNA for plasminogen activator inhibitor 2. |
| 15 | Expressed sequence AW558171 | UI-M-BH2.3-aoa-g-07-0-UI.s1 NIH_BMAP_M_S3.3 Mus musculus cDNA clone UI-M-BH2.3-aoa-g-07-0-UI 3', mRNA seq |
| 16 | | C78850 Mouse 3.5-dpc blastocyst cDNA Mus musculus cDNA clone J0056C12 3' similar to mouse proviral retroviral insertion |
| 17 | ADAMTS-1 | putative; Mouse mRNA for secretory protein containing thrombospondin motifs, complete cds. |
| 18 | C/EBP, beta | Mouse alpha-1-acid glycoprotein (AGP/EBP) mRNA, complete cds. |
| 19 | | C85523 Mouse fertilized one-cell-embryo cDNA Mus musculus cDNA clone J0209F01 3', mRNA sequence. |
| 20 | DNA segment, Chr 8 ERATO Doi 814, expressed | UI-M-BH2.2-aoo-b-05-0-UI.s1 NIH_BMAP_M_S3.2 Mus musculus cDNA clone UI-M-BH2.2-aoo-b-05-0-UI 3', mRNA seq |
| 21 | Nfkbi | Mus musculus I kappa B alpha gene, exons 2-6, partial cds. |
| 22 | Transketolase | Mus musculus LAF1 transketolase mRNA, complete cds. |
| 23 | RIKEN cDNA 1300002F13 gene | uo89c05.x1 NCI_CGAP_Mam3 Mus musculus cDNA clone IMAGE:2649704 3', mRNA sequence. |
| 24 | MT-I, Mt-1 | Mouse gene for Metallothionein-I (three exons). |
| 25 | Cytokine ind SH2-cont protein 3 | AV374868 RIKEN full-length enriched, adult male cecum Mus musculus cDNA clone 9130017A09 3' similar to U88328 |
| 26 | ab, SCD, Scd-1 | stearoyl-CoA desaturase; Mouse stearoyl-CoA desaturase gene, exon 6. |
| 27 | Ctsc | Cathepsin C |
| 28 | C/EBP, delta | M.musculus mRNA for C/EBP delta. |
| 29 | Jun-B oncogene | Mus musculus transcription factor junB (junB) gene, 5' region and complete cds. |
| 30 | Atf3 | leucine zipper protein; Mus musculus transcription factor LRG-21 mRNA, complete cds. |
| 31 | Immediate early response, erythropoietin 1 | UI-M-BH1-amp-g-08-0-UI.s1 NIH_BMAP_M_S2 Mus musculus cDNA clone UI-M-BH1-amp-g-08-0-UI 3', mRNA sequence. |
| 32 | ADFP | Mouse adipose differentiation related protein (ADFP) mRNA, complete cds. |
| 33 | mCPE-R | Mus musculus mCPE-R mRNA for CPE-receptor, complete cds. |
| 34 | Jun-B oncogene | Mus musculus transcription factor junB (junB) gene, 5' region and complete cds. |
| 35 | Nfil3 | Mus musculus NFIL3/E4BP4 transcription factor mRNA, complete cds. |
| 36 | Sat | putative; Mouse spermidine/spermine N1-acetyltransferase (SSAT) mRNA, complete cds. |
| 37 | Cish3 | Mus musculus suppressor of cytokine signalling-3 (SOCS-3) mRNA, complete cds. |
| 38 | Antigen identified by mAb Ki 67 | M.musculus mRNA for Ki-67. |
| 39 | Expressed sequence C77826 | UI-M-BH2.2-aox-b-05-0-UI.s1 NIH_BMAP_M_S3.2 Mus musculus cDNA clone UI-M-BH2.2-aox-b-05-0-UI 3', mRNA seq |
| 40 | Nuclear factor of kappa light chain gene enhancer in B-cells inhibitor, alpha | ub75b05.x1 Soares_mammary_gland_NMLMG Mus musculus cDNA clone IMAGE:1383537 3' similar to gb:M69043. |

FIG. 22C (continued)

| | | |
|---|---|---|
| 41 | HB-EGF | Mus musculus (clone lambda mouse 1) heparin-binding EGF-like growth factor precursor mRNA, complete cds. |
| 42 | pgk1 | X-linked; Mus musculus X chromosome-linked phosphoglycerate kinase (pgk-1) mRNA, complete cds. |
| 43 | RIKEN cDNA 5033417E09 gene | ud61f11.x1 Sugano mouse liver mlia Mus musculus cDNA clone IMAGE:1450413 3' similar to gb:L32179 |
| 44 | Pyruvate dehydrogenase kinase 4 | Mus musculus mRNA for pyruvate dehydrogenase kinase-like protein. |
| 45 | Leukemia-associated gene | UI-M-AL0-abv-e-12-0-UI.s1 NIH_BMAP_MCO Mus musculus cDNA clone UI-M-AL0-abv-e-12-0-UI 3', mRNA sequence. |
| 46 | Claudin 1 | integral membrane protein localizing at tight junctions; Mus musculus claudin-1 mRNA, complete cds. |
| 47 | Potassium inwardly-rectifying channel, subfamily J, member 12 | M.musculus MB-IRK2 mRNA. |
| 48 | RIKEN cDNA 1110032C13 gene | UI-M-AP1-agn-a-04-0-UI.s1 NIH_BMAP_MST_N Mus musculus cDNA clone UI-M-AP1-agn-a-04-0-UI 3', mRNA sequence. |
| 49 | Thyroid hormone receptor alpha | Mus musculus orphan nuclear receptor Rev-Erb-beta mRNA, partial cds. |
| 50 | Proteosome (prosome, macropain) subunit, beta type 8 (large | Lmp7k, s, f allele; Mus musculus 20S proteasome subunit Lmp7 (Lmp7k, s, f allele) mRNA, complete cds. multifunctional protease 7) |
| 51 | aldh3 | Mus musculus aldehyde dehydrogenase 3 (aldh3) gene, partial cds. |
| 52 | Butyrate response factor 2 | vw64d05.s1 Soares_mammary_gland_NMLMG Mus musculus cDNA clone IMAGE:1248585 3', mRNA sequence. |
| 53 | TSA-1 | Mus musculus thymic shared antigen-1 (TSA-1) gene, complete cds. |
| 54 | c-myc | Mouse c-myc gene exon 3. |
| 55 | MMSTK1 | putative serine/threonine kinase; Mouse mRNA for STK-1 (serine/threonine kinase), complete cds. |
| 56 | EIF 1A | translation initiation factor; Mus musculus eIF-1A (eIF-1A) mRNA, complete cds. |
| 57 | GRO1 oncogene | secretory protein KC precursor; Mouse platelet-derived growth factor-inducible KC protein mRNA, complete cds. |
| 58 | IGF binding protein 2 | M.musculus mRNA for insulin-like growth factor binding protein-2. |
| 59 | Expressed sequence AI314958 | uj34f07.x1 Sugano mouse kidney mkia Mus musculus cDNA clone IMAGE:1921861 3', mRNA sequence. |
| 60 | Mkrn3 | Mus musculus 14-3-3 protein sigma mRNA, complete cds. |
| 61 | | UI-M-BH1-ald-c-09-0-UI.s1 NIH_BMAP_M_S2 Mus musculus cDNA clone UI-M-BH1-ald-c-09-0-UI 3', mRNA sequence. |
| 62 | Kruppel-like factor 9 | UI-M-AH1-agp-g-10-0-UI.s1 NIH_BMAP_MCE_N Mus musculus cDNA clone UI-M-AH1-agp-g-10-0-UI 3', mRNA sequence. |
| 63 | FGF binding protein 1 | heparin and fibroblast growth factor binding; similar to Homo sapiens HBp17 protein encoded by seq in AN M60047; FGFBP-1 |
| 64 | Period homolog (Drosophila) | circadian pacemaker protein; Mus musculus Rigui mRNA, complete cds. |
| 65 | TGFB induc. early growth resp. | zinc finger protein; Mus musculus transcription factor GIF mRNA, complete cds. |
| 66 | RIKEN cDNA 4930455J02 gene | ul21f04.y1 Sugano mouse embryo mewa Mus musculus cDNA clone IMAGE:2088223 5' sim to SW:Y33K_HUMAN Q04323 |
| 67 | RIKEN cDNA 1300002F13 gene | UI-M-BH0-ajd-f-01-0-UI.s1 NIH_BMAP_M_S1 Mus musculus cDNA clone UI-M-BH0-ajd-f-01-0-UI 3', mRNA sequence. |
| 68 | Zinc finger protein 36 | TIS11 (AA 1 - 183); Mouse TPA-induced TIS11 mRNA. |
| 69 | RIKEN cDNA 1190002H23 gene | UI-M-BG1-aic-e-02-0-UI.s1 NIH_BMAP_MSC_N Mus musculus cDNA clone UI-M-BG1-aic-e-02-0-UI 3', mRNA sequence. |
| 70 | High mobility group box 2 | M.musculus mRNA for high mobility group 2 protein. |
| 71 | Metallothionein 2 | metallothionien II; Mouse metallothionein II (MT-II) gene. |
| 72 | Myd116 | MyD116 protein (AA 1-657); Mouse myeloid differentiation primary response mRNA encoding MyD116 protein. |
| 73 | CDK inhibitor 1A (P21) | UI-M-BH1-amo-d-08-0-UI.s1 NIH_BMAP_M_S2 Mus musculus cDNA clone UI-M-BH1-amo-d-08-0-UI 3', mRNA sequence. |
| 74 | Stromal cell derived factor 1 | AV139913 Mus musculus C57BL/6J 10-11 day embryo Mus musculus cDNA clone 2810055D15, mRNA sequence. |
| 75 | Cyr61 | Cyr61 product; Mouse Cyr61 mRNA, complete cds. |
| 76 | RIKEN cDNA 1600029D21 gene | uc30b06.r1 Soares_mammary_gland_NbMMG Mus musculus cDNA clone IMAGE:1399475 5', mRNA sequence. |
| 77 | Purine-nucleoside phosphorylase | Mus musculus purine nucleoside phosphorylase (Np-b) mRNA, complete cds. |
| 78 | BAR, B2AR, ADRBR, ADRB2R | Mouse gene for beta-2-adrenergic receptor. |
| 79 | RIKEN cDNA 2310076D10 gene | UI-M-AH1-agw-h-03-0-UI.s1 NIH_BMAP_MCE_N Mus musculus cDNA clone UI-M-AH1-agw-h-03-0-UI 3', mRNA sequence. |
| 80 | Paired-like homeodomain TF 2 | bicoid-related homeodomain protein; murine homolog of Rieger syndrome; mouse bicoid-rel homeodomain prot solurshin (Rgs) |
| 81 | Keratin complex 1, acidic, gene 17 | epidermal keratin type I; Mouse type I epidermal keratin mRNA, clone pkSCC-50, 3' end. |

FIG. 22C (continued)

| | | |
|---|---|---|
| 82 | Growth arrest and DNA-damage-inducible 45 beta | AV138783 Mus musculus C57BL/6J 10-11 day embryo Mus musculus cDNA clone 2810046L02, mRNA sequence. |
| 83 | Rrm1 | ribonucleotide reductase subunit M1; Mouse ribonucleotide reductase subunit M1 mRNA, complete cds. |
| 84 | Ncl | Mouse nucleolin gene. |
| 85 | PCNA | Murine PCNA gene for proliferating cell nuclear antigen (DNA polymerase delta auxiliary protein). |
| 86 | H-2T17 | MHC H2-TL-T17-c; Mouse MHC class I H2-TL-T17-c mRNA (d haplotype), complete cds. |
| 87 | Expressed sequence AI467657 | vf37g06.y1 Soares mouse NbMH Mus musculus cDNA clone IMAGE:846010 5' similar to SW:PLZF_HUMAN Q05516 |
| 88 | Nr4a1 | Mouse N10 gene for a nuclear hormonal binding receptor. |
| 89 | Lectin, galactose binding, sol 7 | Mus musculus galectin-7 mRNA, complete cds. |
| 90 | HKII | Mus musculus gene for hexokinase II, exon 1 (and joined CDS). |
| 91 | Sequestosome 1 | similar to D. melanogaster Ref(2)Pp protein; Mus musculus oxidative stress-induced protein mRNA, complete cds. |
| 92 | Mcm5, Cdc46, mCD46 | put. mouse homolog of yeast CDC46; Mouse mRNA for mCDC46 protein, complete cds. |
| 93 | DNA segment, Chr 13, WSU 123, e | ul20f06.y1 Sugano mouse embryo mewa Mus musculus cDNA clone IMAGE:2088131 5' similar to SW:YBC4_YEAST P38205 |
| 94 | | Mouse histone H2A.1 gene, complete cds. |
| 95 | RIKEN cDNA 3100004P22 gene | UI-M-BG0-aht-a-11-0-UI.s1 NIH_BMAP_MSC Mus musculus cDNA clone UI-M-BG0-aht-a-11-0-UI 3', mRNA sequence. |
| 96 | Expressed sequence AU018108 | vo73e09.r1 Barstead mouse myotubes MPLRB5 Mus musculus cDNA clone IMAGE:1064776 5', mRNA sequence. |
| 97 | Kruppel-like factor 13 | UI-M-BH2.2-aql-f-08-0-UI.s1 NIH_BMAP_M_S3.2 Mus musculus cDNA clone UI-M-BH2.2-aql-f-08-0-UI 3', mRNA sequence. |
| 98 | E26 avian leuk oncogen 2, 3' dom | ets2 protein; Mouse erythroblastosis virus oncogene homolog 2 (ets-2) mRNA, complete cds. |
| 99 | H2-Q8 | Mouse Q8/9d gene. |
| 100 | TACSTD 2 | vz06h06.x1 Soares_mammary_gland_NbMMG Mus musculus cDNA clone IMAGE:1314971 3' similar to gb:J04152_rna1 |
| 101 | Fosl1 | Fra-1; B-Zip transcription factor; subunit of AP-1 member of the Fos family; Mus musculus fos-related antigen 1 (fra-1) gene |
| 102 | Immediate early response 3 | M.musculus gly96 mRNA. |
| 103 | TGFB inducible early growth resp | zinc finger protein; Mus musculus transcription factor GIF mRNA, complete cds. |
| 104 | RIKEN cDNA 5730403B10 gene | UI-M-AK1-aes-b-10-0-UI.s1 NIH_BMAP_MHY_N Mus musculus cDNA clone UI-M-AK1-aes-b-10-0-UI 3', mRNA sequence. |
| 105 | Pre B-cell leukemia TF 1 | UI-M-BH2.1-apu-g-09-0-UI.s1 NIH_BMAP_M_S3.1 Mus musculus cDNA clone UI-M-BH2.1-apu-g-09-0-UI 3', mRNA seq |
| 106 | MHC Q2-k | Mouse MHC (Qa) Q2-k gene for class I antigen, exons 1-3. |
| 107 | | MHC beta-2-microglobulin; Mouse MHC class I Q4 beta-2-microglobulin (Qb-1) gene, complete cds. |
| 108 | RIKEN cDNA 2810484M10 gene | UI-M-BH2.1-aph-h-08-0-UI.s1 NIH_BMAP_M_S3.1 Mus musculus cDNA clone UI-M-BH2.1-aph-h-08-0-UI 3', mRNA seq |
| 109 | Irs2 | IRS-2; Mus musculus insulin receptor substrate-2 (Irs2) gene, partial cds. |
| 110 | Thra | UI-M-AM1-afw-b-05-0-UI.s1 NIH_BMAP_MAM_N Mus musculus cDNA clone UI-M-AM1-afw-b-05-0-UI 3', mRNA seq |
| 111 | DNA segment, Chr 19, ERATO Doi 410, expressed | UI-M-BH0-akh-e-08-0-UI.s1 NIH_BMAP_M_S1 Mus musculus cDNA clone UI-M-BH0-akh-e-08-0-UI 3', mRNA sequence. |
| 112 | RIKEN cDNA 2700038D15 gene | UI-M-BH1-ame-a-04-0-UI.s1 NIH_BMAP_M_S2 Mus musculus cDNA clone UI-M-BH1-ame-a-04-0-UI 3', mRNA sequence. |
| 113 | Eph receptor B4 | Mus musculus Balb/c eph-related receptor protein tyrosine kinase mRNA, complete cds. |
| 114 | Secreted modular calcium-binding p | ua31a05.r1 Soares_mammary_gland_NbMMG Mus musculus cDNA clone IMAGE:1348304 5', mRNA sequence. |
| 115 | RIKEN cDNA 2610008O03 gene | UI-M-AK1-aet-h-03-0-UI.s1 NIH_BMAP_MHY_N Mus musculus cDNA clone UI-M-AK1-aet-h-03-0-UI 3', mRNA sequence. |
| 116 | Cystatin B | also known as stefin B; Mus musculus cystatin B (Stfb) gene, complete cds. |
| 117 | Expressed sequence AA408168 | ud93d03.r1 Soares_NMPu Mus musculus cDNA clone IMAGE:1478405 5', mRNA sequence. |
| 118 | RIKEN cDNA 5730469M10 gene | UI-M-BG0-aia-g-01-0-UI.s1 NIH_BMAP_MSC Mus musculus cDNA clone UI-M-BG0-aia-g-01-0-UI 3', mRNA sequence. |
| 119 | Hydroxysteroid (17-beta) dehyd 12 | Mus musculus putative steroid dehydrogenase (KIK-I) mRNA, complete cds. |
| 120 | Expressed sequence AU044290 | UI-M-AK1-aes-e-01-0-UI.s1 NIH_BMAP_MHY_N Mus musculus cDNA clone UI-M-AK1-aes-e-01-0-UI 3', mRNA sequence. |
| 121 | WSB-1 | Mus musculus WSB-1 mRNA, complete cds. |

FIG. 22C (continued)

| | | |
|---|---|---|
| 122 | Supp of initiator codon mutations, related sequence 1 (S. cerevisiae) | homolog of human sui1iso1, yeast sui1 and rice gos2; M.musculus mRNA for Sui1. |
| 123 | B-cell receptor-associated prot 37 | M.musculus mRNA for B-cell receptor associated protein (BAP) 37. |
| 124 | NM 2 protein (NM23B) (nucleoside diphosphate kinase) | M.musculus mRNA for nucleoside diphoshate kinase B. |
| 125 | Solute carrier family 25 (mitochondrial carrier; ANT), member 5 | mj83h01.r1 Soares mouse p3NMF19.5 Mus musculus cDNA clone IMAGE:482737 5' similar to gb:J02683 ADP,ATP CARRIER PROTEIN, FIBROBLAST ISOFORM (HUMAN); gb:X70847 M.musculus mRNA for adenine nucleotide translocase |
| 126 | | vw19g10.y1 Soares_mammary_gland_NbMMG Mus musculus cDNA clone IMAGE:1244322 5' sim to SW:ZAN_PIG Q28983 |
| 127 | Pik3r1 | PI3K regulatory subunit; Mus musculus phosphoinositide 3-kinase regulatory subunit p85alpha mRNA, complete cds. |
| 128 | RIKEN cDNA 6330577E15 gene | UI-M-BH1-ami-f-05-0-UI.s2 NIH_BMAP_M_S2 Mus musculus cDNA clone UI-M-BH1-ami-f-05-0-UI 3', mRNA sequence. |
| 129 | TGF beta 1 induced transcript 4 | M.musculus TSC-22 mRNA. |
| 130 | ABS, sub-family B (MDR/TAP), member 2 | Mus musculus antigen processing-associated transporter TAP1-g7 mRNA, complete cds. |
| 131 | Ran | Mouse (clone M2) GTPase (Ran) mRNA, complete cds. |
| 132 | Peroxisomal delta3, delta2-ECI | UI-M-AH0-acu-e-04-0-UI.s1 NIH_BMAP_MCE Mus musculus cDNA clone UI-M-AH0-acu-e-04-0-UI 3', mRNA sequence. |
| 133 | rbm3 | Mus musculus rbm3 mRNA, complete cds. |
| 134 | DNA segment, Chr 10, ERATO Doi 214, expressed | UI-M-AH1-ags-f-11-0-UI.s1 NIH_BMAP_MCE_N Mus musculus cDNA clone UI-M-AH1-ags-f-11-0-UI 3', mRNA sequence. |
| 135 | Keratin complex 1, acidic, gen 19 | AU040563 Mouse four-cell-embryo cDNA Mus musculus cDNA clone J0812H07 3', mRNA sequence. |
| 136 | TG interacting factor | M.musculus mRNA for mTGIF protein. |
| 137 | RIKEN cDNA 1110004C05 gene | UI-M-BH2.3-aqh-c-06-0-UI.s1 NIH_BMAP_M_S3.3 Mus musculus cDNA clone UI-M-BH2.3-aqh-c-06-0-UI 3', mRNA seq |
| 138 | | histone H2B-291A (AA 1 - 126); histone H2A-291A (AA 1 - 135); Mouse H2B and H2A histone genes (291A). |
| 139 | SGK | UI-M-BH1-akw-d-06-0-UI.s1 NIH_BMAP_M_S2 Mus musculus cDNA clone UI-M-BH1-akw-d-06-0-UI 3', mRNA sequence. |
| 140 | EMAP 2 | Mus musculus endothelial-monocyte activating polypeptide II mRNA, complete cds. |
| 141 | Actin related protein 2/3 complex, subunit 1B (41 kDa) | uo66e09.x1 NCI_CGAP_Mam1 Mus musculus cDNA clone IMAGE:2647528 3', mRNA sequence. |
| 142 | Expressed sequence AA536646 | UI-M-AK1-aez-g-04-0-UI.s1 NIH_BMAP_MHY_N Mus musculus cDNA clone UI-M-AK1-aez-g-04-0-UI 3', mRNA sequence. |
| 143 | Solute carrier family 2 (GLUT), mem | facilitated glucose transporter; Mouse facilitated glucose transport protein mRNA, complete cds. |
| 144 | Ornithine aminotransferase | M.musculus Oat mRNA for ornithine aminotransferase. |
| 145 | GST omega 1 | UI-M-AK1-aes-f-05-0-UI.s1 NIH_BMAP_MHY_N Mus musculus cDNA clone UI-M-AK1-aes-f-05-0-UI 3', mRNA sequence. |
| 146 | | UI-M-AK0-adl-e-02-0-UI.s1 NIH_BMAP_MHY Mus musculus cDNA clone UI-M-AK0-adl-e-02-0-UI 3', mRNA sequence. |
| 147 | B-cell leukemia/lymphoma 6 | homolog of human oncogene, BCL-6; Mus musculus BCL-6 mRNA, complete cds. |
| 148 | H2A histone family, member Z | histone H2A.Z; Mus musculus histone H2A.Z (H2A.Z) mRNA, complete cds. |
| 149 | mot2, Hsc74, Hsp74, Hsp74a, mortalin | Mouse gene for mitochondrial stress-70 protein (PBP74/CSA), exon 14,15,16 and 17. |
| 150 | Fosb | fosB protein (AA 1-338); Mouse fosB mRNA. |
| 151 | B-cell leukemia/lymphoma 10 | Mus musculus mRNA for bcl-10 protein. |
| 152 | HMG nucleosomal binding dom 2 | HMG-17 protein (AA 1 - 90); Mouse mRNA for HMG-17 chromosomal protein. |
| 153 | RIKEN cDNA 1500040F11 gene | UI-M-BH1-anw-c-09-0-UI.s1 NIH_BMAP_M_S2 Mus musculus cDNA clone UI-M-BH1-anw-c-09-0-UI 3', mRNA sequence. |
| 154 | EIF 3, subunit 8 (110 kDa) | similar to yeast NIP1 nuclear import protein; transmembrane protein; contains several potential phosphorylation sites for PKC and casein kinase II; Mus musculus NIPI-like protein (NIPIL(A3)) mRNA, complete cds. |
| 155 | Claudin 1 | vv68a06.x1 Stratagene mouse skin (#937313) Mus musculus cDNA clone IMAGE:1227538 3', mRNA sequence. |
| 156 | RIKEN cDNA 2900010I05 gene | UI-M-BG0-ahs-b-12-0-UI.s1 NIH_BMAP_MSC Mus musculus cDNA clone UI-M-BG0-ahs-b-12-0-UI 3', mRNA sequence. |

FIG. 22C (continued)

| | | |
|---|---|---|
| 157 | RIKEN cDNA 2310008N12 gene | UI-M-BH1-alk-c-09-0-UI.s1 NIH_BMAP_M_S2 Mus musculus cDNA clone UI-M-BH1-alk-c-09-0-UI 3', mRNA sequence. |
| 158 | Fatty acid Coenzyme A ligase, long chain 5 | UI-M-AP0-abl-g-11-0-UI.s1 NIH_BMAP_MST Mus musculus cDNA clone UI-M-AP0-abl-g-11-0-UI 3', mRNA sequence. |
| 159 | RIKEN cDNA 1810015C04 gene | UI-M-BH2.1-apa-d-07-0-UI.s1 NIH_BMAP_M_S3.1 Mus musculus cDNA clone UI-M-BH2.1-apa-d-07-0-UI 3', mRNA seq |
| 160 | Ier2 | Mouse growth factor-inducible protein (pip92) mRNA, complete cds. |
| 161 | Keratin complex 1, acidic, gene 17 | epidermal keratin type I; Mouse type I epidermal keratin mRNA, clone pkSCC-50, 3' end. |
| 162 | DNA segment, Chr 6, ERATO Doi 109, expressed | UI-M-AO1-aeg-h-09-0-UI.s1 NIH_BMAP_MPG_N Mus musculus cDNA clone UI-M-AO1-aeg-h-09-0-UI 3', mRNA sequence. |
| 163 | Cytochr c oxidase, subunit Vb | cytochrome c oxidase subunit Vb precursor; Mouse mRNA for mitochondrial cytochrome c oxidase subunit Vb. |
| 164 | Atf3 | leucine zipper protein; Mus musculus transcription factor LRG-21 mRNA, complete cds. |
| 165 | Zinc finger protein 216 | Mus musculus zinc finger protein ZNF216 mRNA, complete cds. |
| 166 | Solute carrier family 25 (mitochondrial carrier; ANT), member 5 | Mus musculus adenine nucleotide translocase mRNA, complete cds. |
| 167 | Epha2 | similar to human eck gene product, Swiss-Prot Accession Number P29317; Mus musculus receptor-protein tyrosine kinase (eck) |
| 168 | Tubb5 | beta-tubulin [AA 1-444] (79 is 1st base in codon); Mouse mRNA for beta-tubulin (isotype Mbeta 5). |
| 169 | Carboxypeptidase E | Mouse mRNA for carboxypeptidase H. |
| 170 | Solute carrier family 3 (activators of dibasic and neutral AA transport), member 2 | 4F2 heavy chain (AA 1-526); Murine mRNA for 4F2 antigen heavy chain. |
| 171 | FGF inducible 14 | Mus musculus fibroblast growth factor inducible gene 14 (FIN14) mRNA, complete cds. |
| 172 | Kcnj6 | Mus musculus G-protein coupled inwardly rectifying K+ channel (Girk2C) mRNA, complete cds. |
| 173 | Peroxiredoxin 5, related seq 3 | CP-2; Mus musculus 1-Cys peroxiredoxin protein 2 gene, complete cds. |
| 174 | Ldlr | Low density lipoprotein receptor |
| 175 | Scin | gelsolin-like protein; Mus musculus ADSEVERIN mRNA, complete cds. |
| 176 | H-2T10 | MHC H2-TL-T10-129; Mouse MHC class I H2-TL-T10-129 mRNA (b haplotype), complete cds. |
| 177 | Expressed sequence C85189 | UI-M-BH2.3-aoj-d-12-0-UI.s1 NIH_BMAP_M_S3.3 Mus musculus cDNA clone UI-M-BH2.3-aoj-d-12-0-UI 3', mRNA sequence. |
| 178 | LPS-induced TNF-alpha factor | UI-M-BH0-aiu-f-10-0-UI.s1 NIH_BMAP_M_S1 Mus musculus cDNA clone UI-M-BH0-aiu-f-10-0-UI 3', mRNA sequence. |
| 179 | NRF2 | CNC basic leucine zipper DNA binding protein; Mus musculus p45 NF-E2 related factor 2 (NRF2) gene |
| 180 | HS 10 kDa protein 1 (chaperonin 10 | heat shock protein 10, HSP10; Mus musculus chaperonin 10 mRNA, complete cds. |
| 181 | Midnolin | UI-M-BH2.1-aqa-h-06-0-UI.s1 NIH_BMAP_M_S3.1 Mus musculus cDNA clone UI-M-BH2.1-aqa-h-06-0-UI 3', mRNA sequence. |
| 182 | Cops6 | similar to human Vpr interacting protein (hVIP) ; 34 kDa human MOV34 isologue; subunit 6 is a 36 kDa component of the COP9 complex which contains a total of 8 distinct subunits, similar to the JAB1-containing signalosome; mouse COPS6 mRNA |
| 183 | | |
| 184 | Silica-induced gene 81 | partial homology to cytochrome C oxidase subunit VII; M.musculus mRNA for cytochrome C oxidase subunit VII homologue. |
| 185 | PTP, receptor type, J | Mus musculus mRNA, one isoform of PTP-RL9. |
| 186 | Btg1 | M.musculus btg1 mRNA. |
| 187 | EIF factor 5a | UI-M-AH0-acw-e-01-0-UI.s1 NIH_BMAP_MCE Mus musculus cDNA clone UI-M-AH0-acw-e-01-0-UI 3', mRNA sequence. |
| 188 | RIKEN cDNA 2010306B17 gene | UI-M-AQ1-aec-e-01-0-UI.s1 NIH_BMAP_MHI_N Mus musculus cDNA clone UI-M-AQ1-aec-e-01-0-UI 3', mRNA sequence. |
| 189 | RIKEN cDNA 2610103L06 gene | UI-M-BH2.1-apy-g-01-0-UI.s1 NIH_BMAP_M_S3.1 Mus musculus cDNA clone UI-M-BH2.1-apy-g-01-0-UI 3', mRNA sequence. |
| 190 | RIKEN cDNA 0610010M09 gene | UI-M-BH2.1-apm-e-09-0-UI.s1 NIH_BMAP_M_S3.1 Mus musculus cDNA clone UI-M-BH2.1-apm-e-09-0-UI 3', mRNA sequence. |
| 191 | | UI-M-AI0-aaq-a-05-0-UI.s1 NIH_BMAP_MBS Mus musculus cDNA clone UI-M-AI0-aaq-a-05-0-UI 3', mRNA sequence. |
| 192 | Heat shock protein, 60 kDa | HSP60 protein (555 AA); Mouse mRNA for HSP60 protein (clones 3T3-7, -9, and -M1). |
| 193 | Gapd | glyceraldehyde-3-phosphate dehydrogenase; Mouse glyceraldehyde-3-phosphate dehydrogenase mRNA, complete cds. |
| 194 | Protein tyrosine phosphatase 4a2 | potentially prenylated protein tyrosine phosphatase; Mus musculus potentially prenylated protein tyrosine phosphatase mPRL-2 |

FIG. 22C (continued)

| | | |
|---|---|---|
| 195 | gene 37 | Murine gene 37 for pot. membrane bound protein. |
| 196 | RIKEN cDNA 1110032G10 gene | UI-M-BH2.3-aqh-b-06-0-UI.s1 NIH_BMAP_M_S3.3 Mus musculus cDNA clone UI-M-BH2.3-aqh-b-06-0-UI 3', mRNA sequence. |
| 197 | Isocitrate dehydrogenase 3 (NAD+), gamma | Mus musculus NAD(H)-specific isocitrate dehydrogenase gamma subunit precursor, mRNA, complete cds. |
| 198 | RIKEN cDNA 1110021D01 gene | UI-M-BH2.1-apy-h-02-0-UI.s1 NIH_BMAP_M_S3.1 Mus musculus cDNA clone UI-M-BH2.1-apy-h-02-0-UI 3', mRNA sequence. |
| 199 | Carboxypeptidase E | Mouse mRNA for carboxypeptidase H. |
| 200 | Cpo | Mouse mRNA for coproporphyrinogen oxidase, complete cds. |
| 201 | Sid394 | Mus musculus mRNA for Sid394p, complete cds. |
| 202 | Protein tyrosine phosphatase 4a1 | Mus musculus protein tyrosine phosphatase (PRL-1) mRNA, complete cds. |
| 203 | mc/EPB | Mouse CCAAT/enhancer binding protein gene, complete cds. |
| 204 | Zinc finger protein 36 | MTA.G11.085.A MTA adult mouse thymus library Mus musculus cDNA clone MTA.G11.085 5' end similar to xenopus XCAP-C |
| 205 | mATF4 | murine homolog of TAXREB67/ATF4; M.musculus mATF4 (mTR67) mRNA, complete cds. |
| 206 | NADH dehydrogenase (ubiquinone) flavoprotein 2 | UI-M-AP1-agg-c-11-0-UI.s1 NIH_BMAP_MST_N Mus musculus cDNA clone UI-M-AP1-agg-c-11-0-UI 3', mRNA sequence. |
| 207 | Expressed sequence AI430822 | UI-M-BH0-ajl-f-03-0-UI.s1 NIH_BMAP_M_S1 Mus musculus cDNA clone UI-M-BH0-ajl-f-03-0-UI 3', mRNA sequence. |
| 208 | Inosine 5'-phosphate dehydrog 2 | IMP dehydrogenase (EC 1.2.1.14); Mouse IMP dehydrogenase mRNA, complete cds. |
| 209 | | MHC Q4 class I antigen (31 AA) (119 is 2nd base in codon); Protein sequence is in conflict with the conceptual translation; Mouse Q4 class I MHC gene (exon 5). |
| 210 | Aquaporin 2 | va26c10.x1 GuayWoodford Beier mouse kidney day 7 Mus musculus cDNA clone IMAGE:732498 3', mRNA sequence. |
| 211 | Expressed sequence AA987150 | UI-M-AO0-ach-a-08-0-UI.s1 NIH_BMAP_MPG Mus musculus cDNA clone UI-M-AO0-ach-a-08-0-UI 3', mRNA sequence. |
| 212 | Expressed sequence C76856 | UI-M-AJ1-agy-b-09-0-UI.s1 NIH_BMAP_MOB_N Mus musculus cDNA clone UI-M-AJ1-agy-b-09-0-UI 3', mRNA sequence. |
| 213 | Hist4 | Mouse histone H3 (H3.2-221) gene, complete cds. |
| 214 | Enolase 1, alpha non-neuron | UI-M-AM0-adv-h-04-0-UI.s1 NIH_BMAP_MAM Mus musculus cDNA clone UI-M-AM0-adv-h-04-0-UI 3', mRNA sequence. |
| 215 | Eif4 | unidentified reading frame; put. eIF-4A (aa 1-390); put. altern. eIF-4A (aa 1-370); Mouse mRNA for initiation factor eIF-4AI. |
| 216 | TGF beta regulated gene 1 | UI-M-BH1-anm-f-07-0-UI.s1 NIH_BMAP_M_S2 Mus musculus cDNA clone UI-M-BH1-anm-f-07-0-UI 3', mRNA sequence. |
| 217 | D6Ertd109e | Mus musculus mRNA for eRF1, partial cds. |
| 218 | Histocompatibility 2, L region | ub83g12.r1 Soares_thymus_2NbMT Mus musculus cDNA clone IMAGE:1395142 5' similar to gb:K01762_rna1 |
| 219 | Aldolase 1, A isoform | aldolase A; Mouse mRNA for aldolase A. |
| 220 | | vr30d10.r1 Barstead mouse myotubes MPLRB5 Mus musculus cDNA clone IMAGE:1122163 5', mRNA sequence. |
| 221 | Apoc1 | Source: M.musculus Apoc1 gene, exons 1 to 3 and complete CDS. |
| 222 | Tripartite motif protein 28 | M.musculus mRNA for TIF1 beta protein. |
| 223 | Ethanol induced 6 | UI-M-AK1-aeu-f-09-0-UI.s1 NIH_BMAP_MHY_N Mus musculus cDNA clone UI-M-AK1-aeu-f-09-0-UI 3', mRNA sequence. |
| 224 | CDC 2 homolog A (S. pombe) | Mouse cell cycle protein (p34 CDC2) mRNA, complete cds. |
| 225 | Basic transcription factor 3 | UI-M-BH2.1-apb-b-08-0-UI.s1 NIH_BMAP_M_S3.1 Mus musculus cDNA clone UI-M-BH2.1-apb-b-08-0-UI 3', mRNA sequence. |
| 226 | MAP kinase 6 | UI-M-AH1-agx-b-06-0-UI.s1 NIH_BMAP_MCE_N Mus musculus cDNA clone UI-M-AH1-agx-b-06-0-UI 3', mRNA sequence. |
| 227 | Expressed sequence C81323 | vz48h05.r1 Soares_thymus_2NbMT Mus musculus cDNA clone IMAGE:1329753 5' similar to SW:SSRP_MOUSE Q08943 |
| 228 | Clk | Mouse serine threonine tyrosine kinase (STY) mRNA, complete cds. |
| 229 | Arha2 | RHOA; Mus musculus Rho family GTPase (ArhA) mRNA, complete cds. |
| 230 | Histone gene complex 1 | M.domesticus (CD-1) mRNA for histone H3 (partial). |
| 231 | Dp1 | Mus musculus GP106 mRNA, complete cds. |
| 232 | RIKEN cDNA 1300019P08 gene | AV218217 RIKEN full-length enriched, adult male hippocampus Mus musculus cDNA clone 2900087J21 3' similar to L12016 |

SEQUENCE LISTING

<160> NUMBER OF SEQ ID NOS: 273

<210> SEQ ID NO 1
<211> LENGTH: 321
<212> TYPE: RNA
<213> ORGANISM: Homo sapiens

<400> SEQUENCE: 1
uuuuuuuuuu uuuuuuucuu aaaaauauaa auguauuugu cugcaucaug acguucuucg 60
ggcaccuagc uggccagacc acuggccaug ggacaaggag gaagucaggu guaagucuga 120
gcaaggaaca ggacucugcc cuggcagggu ggagguggcc ucacaguguc ccaugcuggg 180
ccugguagcg ugaaagcaca gcacgguagu gggacagcuc cugccgcaca gccaccaccu 240
ccugccgcaa cagggcguuu uccuucucca ggaaggcagc ccgcacagau auccgguucu 300
ccuugagucu ucuugcaucu c 321

<210> SEQ ID NO 2
<211> LENGTH: 1580
<212> TYPE: RNA
<213> ORGANISM: Homo sapiens

<400> SEQUENCE: 2
caguuccuca gcauggccac cugcagccgc caguucaccu ccuccagcuc caugaagggc 60 uccugugggca ucgguggugg cucuagccgc auguccucca uccuggcugg aggauccugc 120
cgggcuccca gcaccugcgg gggcauguca guuaccuccu cucgcuucuc cucuggggga 180
gucuguggga uuggaggugg cuaugguggg agcuucagca gcagcaguuu ugguggagga 240
cuugguagug gauuuggugg ucgauuugau ggauuuggug gugguuuugg ugcuggucuu 300
gguggugguc uuggcggugg uauuggugau gggcuccugg ugggcaguga gaaagugacc 360
augcagaacc ucaaugaccg ccuggccacc uaccuggaca aggugcgugc ccuggaagag 420
gccaacagag accuggaggu gaagauccgg gacugguacc agaggcagcg gcccacugag 480
aucaaagacu acagccccua cuucaagacc auugaggacc ugaagagcaa gaucauuauu 540
gccacccagg agaaugcaca guucacuuug cagauugaca augccaggcu ggcagcugau 600
gacuucagga ccaaguacga gaaugagcug uucuugcggc aguccgugga gggugacauc 660
aauggccugc gcaaggugcu agaugagcug acccugucca gagcugaccu ggaaaugcag 720
auugaaaacc ucagagaaga gcuggccuuc cugaagaaga accaugagga ggagaugcuu 780
gccuugaggg gucagacugg uggggacguc aauguggaga uggacgcagc ccccggugug 840
gaccucagcc gcauucugaa ugagaugagg gaccaguaug agcagauggc agagaagaac 900
cgcagagaug uggaggccug guuccugaga aagacugagg agcugaacaa agagguggcc 960
ucuaacagug aucuaaucca gagcaaccgc agcgaggugg cugagcuccg cagggguguc 1020
cagggccugg agauugaacu gcagucccag cucagcauga aagcauccuu ggagaacagc 1080
cuagaagaga ccaaaggcag auacuguaug cagcuguccc agauccaggg uuugaucagc 1140
aguguggagg agcagcuggc ucagcuucgc ugcgagaugg agcagcagag ccaggaguac 1200
aacaucuugu uggaugugaa gacaaggcug gagcaggaga ucgccaccua ccgccgucug 1260
cuggauggcg agaauaucca cuccuccuca cagcacuccu cuggacaguc cuauucuucu 1320
cgagaagucu ucuccucauc cucccgccag ccccggucca uccucaagga gcaagguuca 1380
accagcuuca gccagagcca aagucagagu uccagggacu aauguuuugc cuagagccuc 1440
cucacccaca acugccucuc aagcugaggg cuuggggcag gacccuguuu ucuuugcgca 1500
uuccccaucu gucuccccua cccucucaug gugguaggcu aauaaagcuu uuugguugau 1560
gcaaaaaaaa aaaaaaaaaa 1580

<210> SEQ ID NO 3
<211> LENGTH: 1357
<212> TYPE: RNA
<213> ORGANISM: Homo sapiens

<400> SEQUENCE: 3
gcgccagucc uccgauagac ugagucgccc ggguacccgu guucucaaua aagccucuug 60
cuguuugcau ccgaaucgug gucucgcugg uccuugagag ggucuccuca gauugauuga 120
cuacccacgu cgggggucuu ucauuuggag gccccagcga gauuuggaga ccccugccca 180
gggaccaccg accccccguc gggagguaag cuggccagcg gucguuucgu gucugucucu 240
gucuucgugc guguuugugc cggcauuuaa uguuugcgcc ugcgucugua cuaguuagcu 300
aacuagaucu guaucuggcg guuccgcgga agaacugacg aguucguauu cccggccgca 360
gccccuggga gacgucccag cggccucggg ggcccguuuu guggcccauu cuguaucagu 420
aaccacccga gucggacuuu uuggagcucc gccacuguac guggcuuugu ugggggacga 480
gagacagaga cacuucccgc ccccgucuga auuuuugcuu ucgguuuuac gccgaaaccg 540
cgccgcgcgu cugauuuguu uguuguucuu uuguucuucg uuaguuuucu ucugucuuua 600
aguguuuuuc gagaucaugg gacagaccgu aacuaccccu cugaguuuaa ccuugcagca 660
cuggggagau guccagcgca uugcauccaa ccagucugug gaugucaaga agaggcgcug 720
gauuaccuuc uguuccgcug aauggccaac uuucaaugug ggauggccuc aggaugguac 780
uuucaauuua aguauuaucu cucagguuaa gucuagagug uuuuguccug guccccacgg 840
acacccggau cagguuccau auaucgucac cugggaggca cuugccuaug acccccccucc 900 gugggucaaa ccguuugugu cuccuaaacu uccucccucg ccgacagcuc ccguccuccc 960
gcccgguccu ucugcgcaac cuccgucccg aucugcccuu uacccugccc uuaccccccuc 1020 uauaaagucc aaaccuccua agccccaggu ucucccugau agcggcggac cccucauuga 1080
ccuucucaca gaggaccucc cgccguacgg agcacaaccu uccuccucug ccagagagaa 1140
cgauaaagaa gaggcggcca ccaccuccga gguuuccccc ccuucuccca uggugucucg 1200
acugcgggga aggagagacc cuccccgcagc ggacuccauc aucucccagg cauucccacu 1260
ccgcaugggg ggagauggcc agcuucagua cuggccguuu uccuccucug auuuaacccu 1320
uccuuuucug aagauccagg uaaauugacg gccuuga 1357

<210> SEQ ID NO 4
<211> LENGTH: 463
<212> TYPE: RNA
<213> ORGANISM: Homo sapiens

<400> SEQUENCE: 4
gacguagagc cccuugcgcc cgguuuccug aucccgcuua cuccucugcg cgccggcagg 60
auggcccaca agcagaucua cuacucagac aaguacuucg augagcacua cgaguaccgg 120
caugucaugu uacccagaga acucucuaaa caaguaccca aaacucaucu gauguccgaa 180
gaggagugga ggagacuugg uguccaacag agucuaggau ggguucauua caugauucau 240
gagccagaac cgcauauucu ucucuuuaga cgaccucuuc caaaagaaca acaaaaauga 300
agugcagcug ggaucaucua aucuuuuuca aauuuaaugu auauguguau auaagguagu 360

-continued

```
auucagugaa uacuugaaaa guguacaaac cuuucaucca uaccugugca ugcgcuguau    420

ucuucacagc aacagagcuc agucaaaugc aacugcaagu agg                      463


<210> SEQ ID NO 5
<211> LENGTH: 1973
<212> TYPE: RNA
<213> ORGANISM: Homo sapiens
<220> FEATURE:
<221> NAME/KEY: misc_feature
<222> LOCATION: (558)..(558)
<223> OTHER INFORMATION: n is a, c, g, or u
<220> FEATURE:
<221> NAME/KEY: misc_feature
<222> LOCATION: (569)..(569)
<223> OTHER INFORMATION: n is a, c, g, or u

<400> SEQUENCE: 5

auuaaaaagc cagcugccca augccugcac acagaaucca caccaacaga gaaccugcuc     60

uucucugagu auuagguaag ucucugcuug caacugauuu gaaauucuug cuuauuuuuu    120

uacuaugaaa aacuguucaa agccaacucu auuacagagu ugaugugggg ugcugccuac    180

aguuagugaa caguagcauu guuugcuuaa auuauagcac auuuugggguc uaggaacuug    240

agaggugauu caguugguca cuguaguaga cagccuugga aucagagauu aaggcaaaag    300

gaaaccucca uucaaauauu cauggaaguu cacagcugga gacagguuaa ggcuucaguc    360

cagauagcuu ucagaauuau ugcaguucuu acugauaggc auaucaauag cgaaauuuaa    420

uuuauuagag gaaucuacua aaguaaauuu uuaggccaau auagaacaua ccauacuugu    480

agucuggcag agaaggugac auaugaaauu gaaaugcgau ucauagacag ugguagugaa    540

agaaauaaug guggggangg gcugugcang ggaggcaugg cucaaggaca gcacuuagug    600

guagcacaca ccaugaacua ugauggaaaa gcauuugaua ggcagagaca gaaauguagg    660

aaauguguag ggauccauga gagcauaaac uaaaagggca aaagcauaug agcauggacu    720

aacaugcagc cacucugcaa guuauacuau gaucuauuuc acaaggaggu ugguaugcug    780

cugucuuugg gugacaccgc uuucccagau guccuggugu guagguucac aagccucuca    840

gaagccauac uuuauugcuu uuuaagacgu auuauuaaua uuuuggcuag cauaugguuu    900

agugugagag uuuuauaugc auaugucauu auacuuugcu cauuuauguc uuggaacuuc    960

uucaacuagg uagaaaacau gaccagggag aaugagagua aggaaagaac ccacugagac   1020

agacaagagc aaaccauacu ucugcuaauc auguuuaaaa guccagaaau gaucauacca   1080

uauuuuauuu ucaagugugg aagucagcau ggagaggggc ucuuuuucuc uaaaggggcc   1140

ugaaauuaaa uugacuugau guugagguua ccuucucuuu caaugaauca cuaaauuguc   1200

uuuucuguuu cccaggaccc aagugcuauc uaaccaugag uucccaccag cagaagcagc   1260

ccugcacugu accuccucag cugcaccagc agcaggugaa gcagccuugc cagccaccac   1320

cccaggaacc uugugccccc aaaaccaagg aucccugcca cccuguuccu gagcccugca   1380

accccaaggg gccagagccc ugccacccca aggcacccga gcccugccac cccaaggcac   1440

cugagcccug caaccccaag gugccagagc ccugccagcc uaaggugcca gagcccugcc   1500

agccuaaggu gccagagccc ugcaacccca aggugccaga gcccugccaa ccuaaggcac   1560

cagagccuug ccaccccaag gcgccugagc ccugccaccc uguuguuccc gagcccugcc   1620

ccucaacugu cacuccauca ccauaccagc agaagacaaa gcagaaguaa uauuguccag   1680

agccaugccu gaagaccuga ucaccagaug cugaggcugc ugucuauccu gcuuaugagu   1740

cccauugccu ugugcuacca augcugugac cuucagucuu aaucccucuc uccuugcacc   1800
```

accuaaaaag uugacucuca uccucaucuu caagggcucc ugagccucuu aacauugccc 1860
aaagucauau ugaauggcua cacuuuucau ggcucaggau ucaucugaag ggggugagga 1920
gugagacaag uguaugguca auauuuuccc cccauuaaau gccauuuaac ucc 1973

<210> SEQ ID NO 6
<211> LENGTH: 254
<212> TYPE: RNA
<213> ORGANISM: Homo sapiens

<400> SEQUENCE: 6
uuuuuuuuuu uuuuuuuagc caaaauaguu auuuauuaau aauuuaaggu uuuacauucu 60
uauaauaaau uccagcucaa aacuuuacac cacgaacauc auggagcaag uuaauucucc 120
cuuccucuca accuguugca uccaccaaau gggcgcucau acucgcacac auacacacac 180
uuccaguuuc guauuuuuuu uuaaaaggaa agaaaccaac ccaaaguauu gcauuugagg 240
ugacacuccc ugaa 254

<210> SEQ ID NO 7
<211> LENGTH: 137
<212> TYPE: RNA
<213> ORGANISM: Homo sapiens

<400> SEQUENCE: 7
aagaugcccu uuggauugga uuggauugau cauguuuaac ucagcguauu uuauggauga 60
aagcuaaaua cagauauuug gcaucucuaa gguggaauga gcccacucca cacacugaua 120
aaauucaugc auaguuu 137

<210> SEQ ID NO 8
<211> LENGTH: 622
<212> TYPE: RNA
<213> ORGANISM: Homo sapiens
<220> FEATURE:
<221> NAME/KEY: misc_feature
<222> LOCATION: (27)..(27)
<223> OTHER INFORMATION: n is a, c, g, or u
<220> FEATURE:
<221> NAME/KEY: misc_feature
<222> LOCATION: (30)..(30)
<223> OTHER INFORMATION: n is a, c, g, or u
<220> FEATURE:
<221> NAME/KEY: misc_feature
<222> LOCATION: (133)..(133)
<223> OTHER INFORMATION: n is a, c, g, or u

<400> SEQUENCE: 8
aaccaaaugg gaauggggucc cccaacnuun cugugguacc agccggguuu cucuugcauu 60
ggaaacaaac accuuuguag gcauuugcgu auucgugaag agacuguuuu augaaucacc 120
ucuuagauuu aunuaauuaa ccuaaguugu ugaaguuucu guuucuccuu aagagaaauu 180
acaaaaauuc aacauugaag cauaguuucu uguuuucugu ugucaaauag uaauaaugug 240
cugugauguu uaugcuuauu cauaaagaug uuuuacuuuu uaguguaaug uuaguucuuu 300
uuaacauuau uuugcuuaaa uuugauaaug cccgacaaga auauauuuug cuuugauuua 360
uacacugauu cuuugugaca aauaugaccc auuaaaaaug ccuuuuaaua gacuaacuua 420
ccuuuuguag cuagguacuc auguucuuuu uuaaaagaug cccuuuggau uggauuggau 480
ugaucauguu uaacucagcg uauuuuaugg augaaagcua aauacagaua uuuggcaucu 540
cuaaggugga augagcccac uccacacacu gauaaaaauc augcauaguu uuaaaugaac 600

-continued

```
auuaauaaac ucauguuguc uu                                             622


<210> SEQ ID NO 9
<211> LENGTH: 613
<212> TYPE: RNA
<213> ORGANISM: Homo sapiens

<400> SEQUENCE: 9

gaauucaagg aggcuuucca gcuguuugac cgaacaggug auggcaagau ccuguacagc      60

cagugugggg augugaugcg ggcccugggc cagaacccua ccaacgccga ggugcucaag     120

guucuaggaa cccccaagag ugaugagaug aaugugaagg uacuggacuu ugagcacuuc     180

cugcccaugc ugcagaccgu ggcgaagaac aaggcccagg gaaccuacga ggauuauguu     240

gaaggccuuc guguguuuga caaggaagga aauggcaccg ucaugggugc ugaaauccgu     300

cauguccuag ucacacuggg cgagaagaug acagaggaag aaguagagau gcuaguggca     360

gggcaugagg acagcaaugg uugcaucaac uaugaagcau uugugaggca uauccugucg     420

gggugacggg cccgaugggg cggagcucgu ccggauggug cugaauggcu gagacauucu     480

guaucccgag ucuguucccu gcccagugug auuucugugu ggcuccagac gcuccccugu     540

cacagcaccu ugucccauuu gguuucuuug gaugauguuu gccuucacca aauaaaauuu     600

gcucucuuug ccc                                                       613


<210> SEQ ID NO 10
<211> LENGTH: 1508
<212> TYPE: RNA
<213> ORGANISM: Homo sapiens

<400> SEQUENCE: 10

caaccaccuc cuaccugccu gcccaaagcu ccagggcugg agcacggaga ccugucaggg      60

auggauuuug cccacaugua ccaaguguac aaguccaggc ggggaauaaa acggagcgaa     120

gacagcaagg aaacuuacaa acugccgcac cggcugauug agaaaaagag acgugaccgg     180

auuaacgagu gcauugccca gcugaaggau cuccuacccg aacaucucaa acuuacuacu     240

uugggucacu uggaaaaagc agugguucug gagcuuacgu ugaagcacgu gaaagcauug     300

acaaaucuaa uugaucagca gcagcagaaa aucauugccc ugcagagcgg uuuacaagcu     360

ggugauuugu cgggaagaaa ucucgaggca gggcaagaaa uguucugcuc agguuuccag     420

acuugugccc gugagguacu ucaguaccug gcgaagcaug agaacacucg ggaccugaaa     480

ucuucccagc ucgucacuca ucuccaucgu guggucucgg agcugcugca ggguggugcu     540

uccaggaaac cauuggacuc ggcucccaaa gccgucgacu ugaaagagaa gcccagcuuc     600

cuagccaagg gaucagaagg cccagggaaa aacugugugc cagucaucca gcggacuuuu     660

gcucccucgg guggggagca gagcggcagu gacacggaca cagacagugg cuauggaggu     720

gaauuggaga aaggggacuu gcgcagugaa cagccguacu ucaaaagcga ccauggacgc     780

agguucgccg ugggagaacg ugucagcaca auuaagcaag aauccgaaga gcccccccacc     840

acaaagagcc gaaugcagcu cucagaagag gaaggccacu ucgcgggcag ugaucugaug     900

gguuccccau uucuugggcc acacccacau cagccuccuu uuugccuucc cuucuaucuc     960

aucccaccau cggccacugc cuaccugccu augcuggaga aaugcuggua ccccaccucu    1020

gugccagugu uauacccagg ccucaacacc ucagcugcag cccucuccag cuucaugaac    1080

ccagacaaga uaccgacucc cuugcuucug ccccagagac ucccuucucc uuuggcacau    1140

ucgucccuug acucuucggc cuugcuccag gcuuugaagc agaucccucc uuuaaacuua    1200
```

gaaaccaaag acuaaacucu ggagggaucu ccugcugccu ugcuuucuuu ccucccuaau 1260
uccaaaaacc acgaagguuu cccugagugc agagagauca gcccacccug cagacccaca 1320
gagaagauuc agagugugug ugagagugag ugagugugcg ugcgugcgug cuuguaugua 1380
uguuuguaua uguaggacaa uaaguuccuu cugacacaag ggagacacga gaaggauagc 1440
cugacaucag augacagacu ggaggacugu agcacaucuc ugggcguuuc ccuacccaga 1500
gaagagcc 1508

<210> SEQ ID NO 11
<211> LENGTH: 3660
<212> TYPE: RNA
<213> ORGANISM: Homo sapiens

<400> SEQUENCE: 11
uugcaggcga gggcuuccac aacuaccacc acaccuuccc cuucgacuac ucugccagug 60
aguaccgcug gcacaucaac uucaccacgu ucuucaucga cugcauggcu gcccugggcc 120
uggcuuacga ccggaagaaa guuucuaagg cuacugucuu agccaggauu aagagaacug 180
gagacgggag ucacaagagu agcugagcuu ugggcuucug aguuccuguu ucaaacguuu 240
ucuggcagag auuuaauauu cuguugauua acuaacaacu ggauauugcu aucggggugu 300
uaaugaugca uuuaaccuau uccgguacag uauucuuaua aaaugagaaa gcuuugauca 360
cguuuugagg uaauaaauau uuuauuuagc uaggauuaac caugccacaa gacauuauau 420
auuucuaagc acacaugaua aaugcauaua caauuuugca caacagcuuu aaaauaauaac 480 aauaaauuug aacauucuau acagagagga ucaaagccaa ggaacaugcu guuuugaugc 540
uagggugagc auggugcuca gucccuguuu guuugcaugg uguccagcuu uguuucuucu 600
cugucaucac caccuucagg caaauaguug accaaccacu ggccugugug uguccacccu 660
ccaaagccca ggccaccuuu cuguuuucug aaauacugau ccuuccuccu gaauacaucc 720
cuccuuguuc cuagcuucaa gacugcugcc ucaaauaggg auagagcaag uccccgcugc 780
agguugugcu agaugggaug gagaaauuau cuucauuuga uacagagcaa guagauuguc 840
ucgagagaaa aguuagcaug cgugguauga uuuguaagua aagauggaag agagagagag 900
agagagagag agagagagag agagagagag agagguagcc auaucuaaca gccuacuuac 960
caaagacccc aggccucucu gcuuggcaug ccuccuuucu guccauccuc ugaaccccag 1020
agauuaguga gauuugaaua auuaaaucau uuucagagug aagggggguua augcaggguc 1080 ugugcuaggg gaggguuuua gcuuuuggua acugaagauu uuuucaugga aaaagucuuc 1140
guguucaaug ugccuagaac ugauaacuaa acagcugaca uuugucgggg acagauaugg 1200
ugugaaacua ugaaaauaua agcaaaaucu ucacuuggaa caugaaacua uuucacuuag 1260
aaaauaaucg aaggacccga gguguugccu ggguugccag uuucuuucgu ggcugggcag 1320
gaacuaguga gguugagggg cagugucugu aaguagcugc uaagaggugc auuuccagau 1380
gaagcccuug gggaacaucu gccagggauc cgcauggugu uggcuccauc cauugcuuua 1440
guuuccuccu uggauugugu agaaacuugg cuucccaugg uuuugaaccu uccaugccuu 1500
cuuugcuuug uggccaccca gccugccuag ugcugccuag gaagcucuua cccaccugau 1560
uucuucugac auuucuuucu uuggccuuuu uuucuuucuc cggacaugca gcuaguugcc 1620
ugaguguauc aagagcaccc aggacuugcu gcuguccagg ccuguuccuc ccccaguauc 1680
cgugggugug gaagagcugu guagcuucag gaagcagagc caggugccac cuuucugugg 1740

-continued

```
cuuccagauc cucccuaccu ccaacucaug ugccucuguc acagugauuu caggaaagcu   1800
ugguagaccc ucuagcaaca ucucgguuca gaaagucucu cugguuugug aguuaacagc   1860
ucagcuaagu gcuguuuugu cucagugagu uaaccacuga augcgagggu ugguuguuga   1920
ucugucucgg ugugugucgg aguagacagc auaugcacuu cucccugugc gcuuugcaag   1980
guaauguggc uuuggcugau ccaugcaggc agguaguggu acagugcugc ugaaaggaag   2040
aaguucccca uuuuaucugu uaaaacacca gagacauggg caagugcuaa uggaccucac   2100
uucaggaaga gggucugcuu ccugaagcca gugugugaug aaaagugacu gagaccugau   2160
aucuaaggug agaccugaua ccuaacacuc ugucacacag uccagggcca acagugcuau   2220
aggaaagucu agaagaaaac aucacaucag uauuuuagaa ccaucaacca ucucuugucc   2280
cuauagccca auccagaggc cugguuuuua gaacuggcug uguaaggugc caaacacuca   2340
guucacuugu agaaucagag ccuuuuuucc ccccuauguu aauugaacac gcgcucugag   2400
cuguuuuguu gaaguagaaa aucucauaga aaaaucacug uagaucuacu gaccuauagc   2460
ccucuggaaa ugccuuugag augguuuuac uuuucuaggu cauagaugcc ugauuauaaa   2520
gaugaacaau aaaaucagcu uucuuucuuu cucuucugau cuuauucccc agaucugauu   2580
caggccaugu uccaaagcaa ggcuacauug agguccuggu gucuuuaagu aaaggacauc   2640
uuucagaucc ucucaaagaa ggauuuauaa caguuuccag augaauguac uaauagcuuu   2700
gggugccuua ucucuuuccu aaucuguagu gccugugagc ucagucucac uccuucccuu   2760
agcccggaga ccccuuagau cgagugggaa uagucaagag gcuggcugga gagucaucag   2820
uacauugguu ugcagaaauc uuuuacaggc uacauuuugg aauuuuuuuu uuuuuaguaa   2880
gugaucaaau uuggugggaa guaauucgag uguauucgau uguauuugcg uccucguuau   2940
cauugucaaa cauguuauag acggcaguug gcacuggggc ugcuaaucuc ugggguguagu   3000
cucugaaacu guagcuccag ugaggugug ugaaagguua gcaaagccac caucugcugg   3060
ugcuccagcc aaggugccuc uuagccacug aauugcuaug uuauccuuuc ucuuguaaca   3120
aacccacccc agagauaaag ccuuuaauca acccaagaaa cuccugggcu aaguaucuga   3180
cagucucaca ucucaacagu gugaauuaag uguccauagc aucagcucag gaggacacuc   3240
ugggagagug cugacaaaaa aggguuauua auacugaccu acuacuucaa gggcaguucu   3300
gaggugauua gagcuuuuuu uaaaaaccaa guauuugggg auccucagca gagguauuca   3360
uacagacucc caaagaacua uauauguucc ugagaccauc guuuagucua cauugcucuu   3420
cccagagacu gacagauaug accagucaaa gugcaagacu accuacccac ugccaugaaa   3480
accauugcag gaaaccuuuc ccuuccugaa ugagauuuuu uuuuucccuu uuuauguggg   3540
guaauuauuu gugacccaag uguaauuugg augauuucca uuaauaucaa cucuugaagc   3600
cuacuuguac ugauugagau uguauuuguu ccuaauaaaa guggaucugg uuguacuguc   3660
```

<210> SEQ ID NO 12
<211> LENGTH: 429
<212> TYPE: RNA
<213> ORGANISM: Homo sapiens

<400> SEQUENCE: 12

```
accacuugca gacaaaugaa uuccuucgaa auguauuuga gguuggaccc ccugugaugc     60
uugaugcugc aacacuuaaa accaugaaga uuucucguuu ugaaaggcau uuauauaacu    120
cugcagcuuu caaagcucga acaaaagcuc gaagcaaaug ccgagauaag agagcagaug    180
uuggagaauu cuuguagaug ucugaauuug auggcuguuu ucuaaucucu uccuuuauua    240
```

uuauuuuugc uacuucuaau guauauaagc uuuuagagac aguuuuuuau cuuggucaac 300
uuaaauaauu uuugauguag gggugggguug uauuuuaauu uaauguacag uguuacaaau 360
uaaugaguuc uuuauucucu guaaaaauaa cugguaacca caaauaaagu guuugugaug 420
uuuggucgu 429

<210> SEQ ID NO 13
<211> LENGTH: 1639
<212> TYPE: RNA
<213> ORGANISM: Homo sapiens
<220> FEATURE:
<221> NAME/KEY: misc_feature
<222> LOCATION: (1003)..(1003)
<223> OTHER INFORMATION: n is a, c, g, or u
<220> FEATURE:
<221> NAME/KEY: misc_feature
<222> LOCATION: (1098)..(1099)
<223> OTHER INFORMATION: n is a, c, g, or u
<220> FEATURE:
<221> NAME/KEY: misc_feature
<222> LOCATION: (1106)..(1106)
<223> OTHER INFORMATION: n is a, c, g, or u
<220> FEATURE:
<221> NAME/KEY: misc_feature
<222> LOCATION: (1112)..(1112)
<223> OTHER INFORMATION: n is a, c, g, or u
<220> FEATURE:
<221> NAME/KEY: misc_feature
<222> LOCATION: (1158)..(1158)
<223> OTHER INFORMATION: n is a, c, g, or u
<220> FEATURE:
<221> NAME/KEY: misc_feature
<222> LOCATION: (1161)..(1161)
<223> OTHER INFORMATION: n is a, c, g, or u
<220> FEATURE:
<221> NAME/KEY: misc_feature
<222> LOCATION: (1171)..(1171)
<223> OTHER INFORMATION: n is a, c, g, or u
<220> FEATURE:
<221> NAME/KEY: misc_feature
<222> LOCATION: (1182)..(1182)
<223> OTHER INFORMATION: n is a, c, g, or u
<220> FEATURE:
<221> NAME/KEY: misc_feature
<222> LOCATION: (1245)..(1245)
<223> OTHER INFORMATION: n is a, c, g, or u
<220> FEATURE:
<221> NAME/KEY: misc_feature
<222> LOCATION: (1436)..(1436)
<223> OTHER INFORMATION: n is a, c, g, or u
<220> FEATURE:
<221> NAME/KEY: misc_feature
<222> LOCATION: (1472)..(1473)
<223> OTHER INFORMATION: n is a, c, g, or u

<400> SEQUENCE: 13
auguccgcgg ccgccuacau ggacuucgug gcugcccagu gucugguuuc caucuccaac 60
cgcgccgccg ugccggagca cgggggcgcu ccggaagccg agcggcugcg acuaccugag 120
cgcgagguga ccaaggaaca cggugacccg ggggacaccu ggaaggauua uugcacgcug 180
gucacuaucg ccaagagcuu guuggaccuc aacaaauacc gacccaucca gaccccccucg 240 gugugcagcg acagucugga gagucccgau gaggauauag gauccgacag cgacgugacc 300
accgaaucug ggucgagucc uucccacagc ccggaggaga gacaggauuc uggcagcgcg 360
cccagcccac ucucccuccu ccacucugga guggcuucga aggggaaaca cgccuccgaa 420
aagaggcaca agugccccua caguggcugu gggaaagucu auggaaaauc cucccaucuu 480
aaagcccauu acagagugca uacaggugaa cggcccuuuc ccugcacgug gccagacugc 540

-continued cuuaaaaagu ucucgcgcuc ggaugagcug acccgccacu accggaccca cacuggggaa 600
aagcaguucc guugcccacu gugugagaag agauucauga ggagugacca ucucaccaag 660
caugcccggc gucacaccgu guuccauccc agcaugauca agagaucaaa aaaggcucuu 720
gccugccccu ugugaggugc uccccauggc agccaggcag agaugggucc ccggaaggac 780
agagcuccca ggaaacagac ugacacaugg aaaucugcca cagcagaggc gcgcuggcca 840
caggagguca cugcuucuuu ggccaauauu cugauaucuc ccugcacugu uuccaaaaag 900
cacaugguag cccuaagguc aaagucaaca uuugguccc uugcagaggc aacucugaac 960
cgucucugac ugaagauuca gacugguggu guacauacgu cunacugggu gaguugaccc 1020
cuggccuccc acagugcaga accacucucu ugaaucacau uaacuuuuga gauuuaaaaa 1080
aaacccaaac ccaacccnnc aaaacnccag anacaccgaa acucuggauc cucgaugcuu 1140
gcugacucuc agaauugnuu nuucuucuca nuuaugcaag cnagagcaca ccuacuccag 1200
caugauuugu caucuaaaga cuugaaaaca aaacaacaac aacanaaagu uacuuuauagu 1260 caauggauaa gcagaguccg aauuuacacu aaucaagaca gaccuucgag ggguucacgau 1320 aaguccggaa cuuucaaacc uugcuucgua ugaauuguac uaucugaaca uaaacugcac 1380
uuuuauuuuc uaauaccgag ggugaauacg guaaauacau gcuuugaggg uagaanccga 1440
cggucuguuu ggcaccacgu uauaaucugc unnuuuuaac gaguaccacc uuggagggca 1500
ggcaaauaaa ugcuuuuggg uauuuucucc uuuguuuuug acaaaugcug cggaaugggg 1560
aucgggaucg gaggggagug cuuuuaaaga uaauaaaaaa ugagguaaau aauuuuaacu 1620
uaugaauuug uuugaauuc 1639

<210> SEQ ID NO 14
<211> LENGTH: 1929
<212> TYPE: RNA
<213> ORGANISM: Homo sapiens

<400> SEQUENCE: 14
gagauugaaa caauggaaga acuuuccaug gcaaacacca uguuugcccu caaucuccuu 60
aagcagauag aaaaaucaaa cucuacccag aacaucuuua ucucuccaug gagcaucuca 120
ucaacauugg ccauaguucu ccucggugcu gggguaaca cugaacagca gauggccaaa 180
gugcugcagu uuaaugaaau uggcaguuau gguaucacca caagaaaccc agagaacuuc 240
aguggcugug auuucgcaca acagauacag aaggaaaauu auccuagugc uauuuuacag 300
gcacaagcag gagauaaaau ccauucagcc uucuccucuc ucagcucaac aaucaacaca 360
ccacaggggg auuauuuguu agaaagugca aacaagcugu uuggagagaa gucugcaaga 420
uucaaagaag aauacaucca acucucuaag aaauauuacu caacagaacc agaagcagug 480
gacuuccuug aaugugcuga agaagcuagg gaaaagauua auucuugggu caagacucaa 540
accaaaggug aaaucccaaa ccugcuaccc gaagguucug uagaugaaga caccaagaug 600
gugcugguga augcugucua cuucaaagga aaguggaaaa cuccauuuga gaagaaacuu 660
aaugggcuuu auccuuuccg ugugaacucg caugagagca uaccugucca gaugauguuc 720
cuccaugcaa agcugaacau uggauacaua aaggaccuga agacucagau ccuagaacuu 780
ccgcauacug gaaacaucag caugcuccug uugcuucccg augagauuga ggacgcaucc 840
acuggcuugg aauugcugga aagugaaaua aacuuugcca acuucaacaa guggaucagc 900
aaagacacac uggaugaaga ugauguugug gucuacauuc ccaaguucaa acuggcacaa 960
agcuacgaac ucaaguccau ucuucaaagc augggcaugg aggaugccuu caacaagggc 1020
aaggccaacu ucucaggaau gucugagagg aaugaccuuu uucuuucuga gguguuccau 1080
caagccagcg uggaugucac cgaggagggc acuguggcag cuggugggac uggggcaguu 1140
augacaggaa gaacuggcca ugguggccca caguuugugg ccgaucaucc cuuucuuuuc 1200
uuuaucaugg acaaaauuac ccacacgaua cuauuuguug guagauucuc cucacccuaa 1260
aaggggaaga ccuauuucca caugagguuu uguagcauga acuauaagcc ucagaauugc 1320
aucuucaagu gccaaaaguu uaaauacuuu cuuacacauu uuuauacuuc ugcuauacac 1380
uaaauauaac cuaaaagcaa uuguauagca gucuucagug cuuacaguau aacucuauua 1440
augauuuugu uuccuaaagu cagaugaugu cuauuuaguu cauccuuauu acugcuuugu 1500
cuuuauaacu uuaguuuuua caguguuauu uauuguuuau auaaugguug uuuuacaaau 1560
uguuguccuc uguuuaauga aacuguaaca cuacagaagc agaaaauuag auaauuuucu 1620
auuuaaagaa aaucagccau uuaauuuaau aaugaaggaa aaauaugagu cuuccauacu 1680
uucccaugau auucacccag aaaaaaugua cuuaacaaaa gacauguuau aucucuauca 1740
uuauauauca uauguacgua ucugcaacuc aucuauaauu aggacuacau cauaaguaag 1800
caugcuuacu uacacacugc uaucuguugu auaaaacuua gcaauccuua uuuguuaguu 1860
aucuuucuau cacuguaaca aaauaccuga gauaauaaag uucaaagauu uauuuugaaa 1920
aaaaaaaaa 1929

<210> SEQ ID NO 15
<211> LENGTH: 284
<212> TYPE: RNA
<213> ORGANISM: Homo sapiens
<220> FEATURE:
<221> NAME/KEY: misc_feature
<222> LOCATION: (16)..(16)
<223> OTHER INFORMATION: n is a, c, g, or u

<400> SEQUENCE: 15
uuuuuuuuuu uuuuunuaag aauuaacuuu uauuuuugcu uaguuuuauu aaaaaaauaa 60
auaugucaua aagcuuuugu uuccuuuagg gagaaaaaaa aggaacaagu uccauaaaau 120
caaacaagca augguaacau gucuuaacuu gaaaacaacu ggggucacug guuuacaagu 180
uauaacugaa ugaaugacug ccacaguugc ccauuuccuc cugccaaugg cagcaaacaa 240
caggaucaac uagggcaaaa uaaauaauug uguggaagcc cuga 284

<210> SEQ ID NO 16
<211> LENGTH: 219
<212> TYPE: RNA
<213> ORGANISM: Homo sapiens
<220> FEATURE:
<221> NAME/KEY: misc_feature
<222> LOCATION: (70)..(70)
<223> OTHER INFORMATION: n is a, c, g, or u
<220> FEATURE:
<221> NAME/KEY: misc_feature
<222> LOCATION: (88)..(88)
<223> OTHER INFORMATION: n is a, c, g, or u
<220> FEATURE:
<221> NAME/KEY: misc_feature
<222> LOCATION: (132)..(132)
<223> OTHER INFORMATION: n is a, c, g, or u
<220> FEATURE:
<221> NAME/KEY: misc_feature
<222> LOCATION: (205)..(205)
<223> OTHER INFORMATION: n is a, c, g, or u

<400> SEQUENCE: 16
aacuaaacuu ccuuguaacu uuugagaacu cagcucuggu acuuuuucau gccuugcaaa 60
auggcguuan ugcagcuagc uugcuaancc uuauggugg gucuuucauu ccccccucuu 120
ucuggaaacu gnauaaaauc auuuauucac gugauucuau uucuucugga ucuauugauu 180
ugaguuggug auacuguugg gucanaacca gggccuguu 219

<210> SEQ ID NO 17
<211> LENGTH: 4179
<212> TYPE: RNA
<213> ORGANISM: Homo sapiens

<400> SEQUENCE: 17
cagcuccgag cuaggugcua ucgcaaggcc agagcgcaca gcccggcgga gagagcagau 60
ccuugcucag aucgagucaa aucgggccaa ggcggaggac gaagagucca ggcuccuauu 120
cuggacuugu uccccagcuc cgggggcgcu ucuagguccu gcagcagcca gcagugcgga 180
gccaccaacu cggugcugga augaaaaaau ucccgcgcgc cagugcagaa ucuuucuaag 240
ugacccggag cuucgggugc uagcucugca cgaacuuucc caucaaagug aucgugaauu 300
uuaagcauca ggagcaggcc agcgaagcuc uacgcgucua aacgucuauc cagaccaaga 360
guucucugcg gugcagggug cggugccaug cagccaaaag ucccuuuugg ggucacgcaa 420
gcagaagccc ugcuccgaca ugggggacgu ccagcgggca gcgagaucuc ggggcucucu 480
guccgcacac augcuguugc ugcuccucgc uuccauaaca augcugcuau gugcgcgggg 540
cgcacacggg cgccccacgg aggaagauga ggagcugguc cugcccucgc uggagcgcgc 600
cccgggccac gauuccacca ccacacgccu ucgucuggac gccuuuggcc agcagcuaca 660
ucugaaguug cagccggaca gcgguuucuu ggcgccuggc uucacccugc agacuguggg 720
gcgcaguccc ggguccgagg cacaacaucu ggaccccacc ggggaccugg cucacugcuu 780
cuacucuggc acggugaacg gugaucccgg cucugccgca gcccucagcc ucugugaagg 840
ugugcguggu gccuucuacc uacaaggaga ggaguucuuc auucagccag cgccuggagu 900
ggccaccgag cgccuggccc cugccgugcc cgaggaggag ucauccgcac ggccgcaguu 960
ccacauccug aggcgaaggc ggcggggcag uggcggcgcc aagugcggcg ucauggacga 1020
cgagacccug ccaaccagcg acucgcgacc cgagagccag aacacccgga accaguggcc 1080
ugugcgggac ccccacgccuc aggacgcggg aaagccauca ggaccaggaa gcauaaggaa 1140
gaagcgauuu guguccagcc cccguuaugu ggaaaccaug cucguagcug accaguccau 1200
ggccgacuuc cacggcagcg gucuaaagca uuaccuucua acccuguucu cgguggcagc 1260
cagguuuuac aagcauccca gcauuaggaa uucaauuagc cugguggugg ugaagaucuu 1320
ggucauauac gaggagcaga agggaccaga aguuaccucc aaugcagcuc ucacccuucg 1380
gaauuucugc agcuggcaga aacaacacaa cagccccagu gaccgggauc cagagcacua 1440
ugacacugca auucuguuca ccagacagga uuuauguggc ucccacacgu gugacacucu 1500
cggaauggca gauguuggaa ccguauguga ccccagcagg agcugcucag ucauagaaga 1560
ugaugguuug caagccgccu ucaccacagc ccaugaauug ggccaugugu uuaacaugcc 1620
gcacgaugau gcuaagcacu gugccagcuu gaauggugug aguggcgauu cucaucugau 1680
ggccucgaug cucuccagcu uagaccauag ccagcccugg ucaccuugca gugccuacau 1740
ggucacgucc uuccuagaua auggacacgg ggaauguuug auggacaagc cccagaaucc 1800
aaucaagcuc ccuucugauc uucccgguac cuuguacgau gccaaccgcc agugucaguu 1860
uacauucgga gaggaaucca agcacugccc ugaugcagcc agcacaugua cuacccugug 1920

```
gugcacuggc accuccggug gcuuacuggu gugccaaaca aaacacuucc cuugggcaga   1980
uggcaccagc uguggagaag ggaagugug ugucaguggc aagugcguga acaagacaga    2040
caugaagcau uuugcuacuc cuguucaugg aagcugggga ccaugggac cguggggaga    2100
cugcucaaga accuguggug guggaguuca auacacaaug agagaaugug acaacccagu   2160
cccaaagaac ggagggaagu acugugaagg caaacgaguc cgcuacaggu ccuguaacau   2220
cgaggacugu ccagacaaua acggaaaaac guucagagag gagcagugcg aggcgcacaa   2280
ugaguuuucc aaagcuuccu uugggaauga gcccacugua gaguggacac ccaaguacgc   2340
cggcgucucg ccaaaggaca ggugcaagcu caccugugaa gccaaaggca uuggcuacuu   2400
uuucgucuua cagcccaagg uuguagaugg cacucccugu aguccagacu cuaccucugu   2460
cugugugcaa gggcagugug ugaaagcugg cugugaucgc aucauagacu ccaaaaagaa   2520
guuugauaag uguggcguuu guggaggaaa cgguuccaca ugcaagaaga ugucaggaau   2580
agucacuagu acaagaccug gguaucauga cauugucaca auuccugcug gagccaccaa   2640
cauugaagug aaacaucgga aucaaagggg guccagaaac aauggcagcu uucuggcuau   2700
uagagccgcu gaugguaccu auauucugaa uggaaacuuc acucugucca cacuagagca   2760
agaccucacc uacaaaggua cugucuuaag guacagugu ucccucggcug cgcuggaaag   2820
aauccgcagc uuuaguccac ucaaagaacc cuuaaccauc cagguucuua ugguaggcca   2880
ugcucuccga cccaaaauua aauucaccua cuuuaugaag aagaagacag agucauucaa   2940
cgccauuccc acauuuucug agugggugau ugaagagugg ggggagugcu ccaagacaug   3000
cggcucaggu uggcagagaa gaguagugca gugcagagac auuaacggac acccugcuuc   3060
cgaaugugca aaggaaguga agccagccag uaccagaccu ugugcagacc uuccuugccc   3120
acacuggcag guggggauu ggucaccaug uuccaaaacu ugcgggaagg guuacaagaa    3180
gagaaccuug aaaugugugu cccacgaugg gggcguguua ucaaaugaga gcugugaucc   3240
uuugaagaag ccaaagcauu acauugacuu uugcacacug acacagugca guuaagaggc   3300
guuagaggac aagguagcgu ggggaggggc ugauacacug agugcaagag uacuggaggg   3360
auccagugag ucaaaccagu aagcagugag guguggcaag gaggugugug uaggggauac   3420
auagcaaagg agguagauca ggacacuacc cugccaguua cauucugaua agguaguuaa   3480
ugaggcacag uagcaucuga aagaccauac agagcacuaa ggagccccaa agcacuauua   3540
guaucucuuu ucuuauaucu aucgcccaaa uaauuuucag agucuggcag aagcccuguu   3600
gcacuguacu aacuagauac uucuuaucac aaagauuggg aaaggcaaag cagaaagaug   3660
guaagacugg guuucaaaca aggcuugguu ucaaucacug gaggcaagga ggaggggaca   3720
aacaagauca uuauucgaag ucgcugguug cugugguuuu acggaagguu gaugcaucau   3780
uccuaucaac agugaaaagu ucagcuuguu caacgugaca gaaaggcuca ucuccgugaa   3840
agagcuccug auuucuucuu acaccaucuc aguucuuaac uauaguucau guugagguag   3900
aaacaauuca ucuauuuaua aaauguacau uggaaaaaaa aagugaaguu uaugagguac   3960
acauaaaaac ugaaggaaac aaugagcaac augccuccug cuuugcuucc uccugaggua   4020
aaccugccug gggauugagg uuguuuaaga uuauccaugg cucacaagag gcaguaaaau   4080
aauacauguu gugccagagu uagaaugggg uauagagauc agggucccau gagaugggga   4140
acauggugau cacucaucuc acaugggagg cugcugcag                          4179
```

<210> SEQ ID NO 18

<211> LENGTH: 1416
<212> TYPE: RNA
<213> ORGANISM: Homo sapiens

<400> SEQUENCE: 18
ccgcgggccc gcguucaugc accgccugcu ggccugggac gcagcaugcc ucccgccgcc 60
gcccgccgcc uuuagaccca uggaaguggc caacuucuac uacgagcccg acugccuggc 120
cuacggggcc aaggcggccc gcgccgcgcc gcgcgccccc gccgccgagc cggccauugg 180
cgagcacgag cgcgccaucg acuucagccc cuaccuggag ccgcucgcgc ccgccgcgga 240
cuucgccgcg cccgcgcccg cgcaccacga cuuccucucc gaccucuucg ccgacgacua 300
cggcgccaag ccgagcaaga agccggccga cuacgguuac gugagccucg gccgcgcggg 360
cgccaaggcc gcgccgcccg ccugcuuucc gccgccgccu cccgccgcgc ucaaggcgga 420
gccgggcuuc gaacccgcgg acugcaagcg cgcggacgac gcgcccgcca uggcggccgg 480
uuucccguuc gcccugcgcg ccuaccuggg cuaccaggcg acgccgagcg gcagcagcgg 540
cagccugucc acgucgucgu cguccagccc gcccggcacg ccgagccccg ccgacgccaa 600
ggccgcgccc gccgccugcu ucgcggggcc gccggccgcg cccgccaagg ccaaggccaa 660
gaagacggug gacaagcuga gcgacgagua caagaugcgg cgcgagcgca acaacaucgc 720
ggugcgcaag agccgcgaca aggccaagau gcgcaaccug gagacgcagc acaaggugcu 780
ggagcugacg gcggagaacg agcggcugca gaagaaggug gagcagcugu cgcgagagcu 840
cagcacccug cggaacuugu ucaagcagcu gccccgagccg cugcuggccu cggcgggcca 900
cugcuagcgc ggcgcggugg cgugggggc gccgcggcca ccgugcgccc ugccccgcgc 960
gcuccggccc cgcgcgcgcg cccggaccac cgugcgugcc cugcgcgcac cugcaccugc 1020
accgagggga caccgcgggc acaccgcggg cacgcgcggc gcacgcaccu gcacagcgca 1080
ccggguuucg ggacuugaug caauccggau caaacguggc ugagcgcgug uggacacggg 1140
acuacgcaac acacguguaa cugucuagcc gggcccugag uaaucaccuu aaagauguuc 1200
cugcgggguu guugauguuu uugguuuugu uuuuguuuuu uguuuuguuu uguuuuuuuu 1260
uuuggucuua uuauuuuuuu uguauuauau aaaaaaguuc uauuucuaug agaaaagagg 1320
cguauguaua uuuugagaac cuuuuccguu ucgagcauua aagugaagac auuuuaauaa 1380
acuuuuuugg agaauguuua aaagccaaaa aaaaaa 1416

<210> SEQ ID NO 19
<211> LENGTH: 566
<212> TYPE: RNA
<213> ORGANISM: Homo sapiens
<220> FEATURE:
<221> NAME/KEY: misc_feature
<222> LOCATION: (154)..(154)
<223> OTHER INFORMATION: n is a, c, g, or u
<220> FEATURE:
<221> NAME/KEY: misc_feature
<222> LOCATION: (254)..(254)
<223> OTHER INFORMATION: n is a, c, g, or u
<220> FEATURE:
<221> NAME/KEY: misc_feature
<222> LOCATION: (262)..(262)
<223> OTHER INFORMATION: n is a, c, g, or u
<220> FEATURE:
<221> NAME/KEY: misc_feature
<222> LOCATION: (287)..(287)
<223> OTHER INFORMATION: n is a, c, g, or u
<220> FEATURE:
<221> NAME/KEY: misc_feature
<222> LOCATION: (305)..(305)
<223> OTHER INFORMATION: n is a, c, g, or u
<220> FEATURE:
<221> NAME/KEY: misc_feature
<222> LOCATION: (354)..(354)
<223> OTHER INFORMATION: n is a, c, g, or u
<220> FEATURE:
<221> NAME/KEY: misc_feature
<222> LOCATION: (378)..(378)
<223> OTHER INFORMATION: n is a, c, g, or u
<220> FEATURE:
<221> NAME/KEY: misc_feature
<222> LOCATION: (419)..(419)
<223> OTHER INFORMATION: n is a, c, g, or u
<220> FEATURE:
<221> NAME/KEY: misc_feature
<222> LOCATION: (449)..(449)
<223> OTHER INFORMATION: n is a, c, g, or u
<220> FEATURE:
<221> NAME/KEY: misc_feature
<222> LOCATION: (492)..(493)
<223> OTHER INFORMATION: n is a, c, g, or u
<220> FEATURE:
<221> NAME/KEY: misc_feature
<222> LOCATION: (521)..(521)
<223> OTHER INFORMATION: n is a, c, g, or u
<220> FEATURE:
<221> NAME/KEY: misc_feature
<222> LOCATION: (550)..(550)
<223> OTHER INFORMATION: n is a, c, g, or u

<400> SEQUENCE: 19
aaaauguaga aggcaagauu uaauaaggca gcaacaugaa agcacacaga ccagagcucu 60
ggggucgaaa uaaagcagca acauggaagc acacagagcu cuggggucga aacucauaca 120
ccuuagcaca ggguagagga gucucgacgg ucanccagaa uuuuucacag gcuuauauag 180
uaaaacucaa agggggagaa cugggcaggg aaaguacaag uuuacaucac uagggaguuc 240
ugccaaagga caangggguuc unucagagga aucuacguaa cuaaggnguc auguccuauc 300
aaggnaucua cguaacuaag gagucauguc cuaucauuug gcaauguacc cggnucuuuu 360
gagguuguuc cggagggncu uauucucaaa auguuuuuca gauuggaagg ggugggguunc 420 cgguaaaaag uucuguuuuc aaagaggcng uaauuuucua uucuucauuc cccauucucc 480
uguaaguauu cnnaucuuag aauuucagaa guccauauuc ncuauguggg gaauaacugg 540
cuuuaacccn aucuuuaaaa uggggg 566

<210> SEQ ID NO 20
<211> LENGTH: 358
<212> TYPE: RNA
<213> ORGANISM: Homo sapiens
<220> FEATURE:
<221> NAME/KEY: misc_feature
<222> LOCATION: (269)..(269)
<223> OTHER INFORMATION: n is a, c, g, or u

<400> SEQUENCE: 20
uuuuuuuuuu uuuuuuuaug aaacaguuuu guucagccca ugacuuugug caugacuguc 60
guccguucua gucaccugug cucuccaucu acugccuuuu aaagcugcgu caugagaagg 120
aucuacacgu uccaccauga cucucguuuc uugccacaag uagaagaaau gguugauucu 180
uugcuuuucg guuaggccgu uaaacaaaac ucagucacac cccugccuuc cacccucaaa 240
cugugaucac guggcuguuc uuguaguuna accagggcaa cacuauauau uccaggucua 300
uacauugcug aggucuuuuu cugguuguuc auguaucagu guuuucaacc ucgugccg 358

<210> SEQ ID NO 21
<211> LENGTH: 2149
<212> TYPE: RNA

<213> ORGANISM: Homo sapiens

<400> SEQUENCE: 21
gcggccgcgg cuccagaccc cggccuugcg cacccucccc ccaccuccag cccgcgccuc 60
cccccccccc acgcauggcu caccaccccu cggguuuccc ugucaucccu cagguuccug 120
cacuuggcaa ucauccacga agagaagccg cugaccaugg aagucauugg ucaggugaag 180
ggagaccugg ccuuccucaa cuuccagaac aaccugcagc aggugcgcug cuugcuugcc 240
ccgcggugcc ccucuuugac ccccuuggugg agucagaugu agcacggucg cccccaaagc 300
guuucuaaau uaauagucac uuaguucuua ucugccuugg cuuuuuugca uucaaaucag 360
ccaacgucuu agaaccagaa gaaaaauccc uugguuuuag ugaggucuuu augacccacc 420
uagggccucc uguuugccug aucuccuaag agacaaaugg gaggaucaga uuccauagcg 480
ggagguguicu gggguucagg aaacucaaga cuauggguuu gcuccauggc uuaucccuuu 540
cuguuuccuc uuccauuugu agacuccacu ccacuuggcu gugaucacca accagccagg 600
aauugcugag gcacuucuga aagcuggcug ugauccugag cuccgagacu uucgaggaaa 660
uaccccucua caucuugccu gugagcaggg cugccuggcc aguguagcag ucuugacgca 720
gaccugcaca ccccagcauc uccacuccgu ccugcaggcc accaacuaca augguagguc 780
ugccagucca uccaaggaug cagaggaggg agagagaugg ggccacuuga gucuuaaacu 840
ccgaacguau acaaaguuca gacacuguga ucuuuuuaaa aaguuuucuc cucgaugccu 900
auaugauauu cacucagaac ccagauucug aguucuucaa aacugaugau guuugugguu 960
guccucaaga caauagacau gaguugugug aggauugaaa cacguaguac aguuuuuguc 1020
uuccuccucc aggccacacg ugucugcacc uagccucuac ucacggcuac cuggccaucg 1080
uggagcacuu ggugacuuug ggugcugaug ucaacgcuca ggugaguaca ucucccuucc 1140
accuaaucuc uguugggcug gcucugaugg ugagcagguu uccagaugca gccguaaacu 1200
aacgccugau ugcuuuuggu uucaggagcc cugcaauggc cggacagccc uccaccuugc 1260
gguggaccug cagaauccug accugguuuc gcucuuguug aaaugugggg cugaugucaa 1320
caggguaacc uaccaaggcu acucccccua ccagcuuacc uggggccgcc caaguacccg 1380
gauacagcag cagcugggcc agcugacccu ggaaaaucuc cagaugcuac ccgagagcga 1440
ggaugaggag agcuaugaca cggagucaga auucacagag gaugagguga guguuccucc 1500
ccucagcacg cugacggcug uucuagggcu gcuuuggauc agagggauuu caguuguuua 1560
acuucucaga cucggcuugc aaagcaggau cccaagaauu ugucucuggu uuguuuuaag 1620
agcuuacccu uuugguugag gaaugaggga auucuagaaa uugaacccag gccuuagcac 1680
auggugauaa gcacacguuc aaccauuaag cuccaccccc ucaauagcuu agacuuuuuu 1740
uuuuuuuaag gaaagaauag guaagggaaa cuccuacagc cuggugcccu uguucuauuu 1800
ggguuaagga gaaaaagagc ccaagaauag gaguuauuuc agcagcagcu cuccccuuau 1860
cccaaugucu uggugaaguu cuaggaauuu aauaugucuu uuuccccucu cuuguuuuag 1920
cugcccuaug augacugugu guuuggaggc cagcgucuga cauuauaagu ggaaaguggc 1980
aaaaaagaau guggacuugu auauuuguac aaauagaguu uuauuuuucu aaaaaaaaaa 2040
aaaaaaaaaa aaaaaaaaaa aaaaaguaua cuuagcacca caccacacag cgccuagacc 2100
caggcauuuu acuggggguga uucggcuguu gucuuuguga aauccgggg 2149

<210> SEQ ID NO 22
<211> LENGTH: 2062

```
<212> TYPE: RNA
<213> ORGANISM: Homo sapiens

<400> SEQUENCE: 22

cucucgguca cugccggucg cuuccugagc cgcugcuggc ucugugucuc uguccucagc      60

guucucuucc ucguccucgu ccuaccacgc cauggaaggu uaccauaagc cagaucagca     120

gaagcuccag gcccugaagg acacagccaa ucgccugcgc aucagcucca uccaggccac     180

caccgcggca ggcucaggcc accccacauc augcugcagc gcugccgaga ucauggcugu     240

ccuguuuuuc cauaccaugc gcuacaaggc ccuggauccc cgaaacccuc acaaugaucg     300

cuuugugcuc ucuaagggcc augcagcucc cauuuuauau gcagucuggg cugaagcugg     360

cuuccugccc gaggccgagc ugcugaaccu gaggaagauc agcucugacu uggacgggca     420

uccugucccg aaacaagccu ucaccgaugu ggccacuggc ucccugggcc agggccuggg     480

agcugcuugc gggauggcau acacaggcaa auacuuugac aaagccagcu accgagucua     540

uugcaugcug ggagacgggg aggucuccga gggcuccguc ugggaggcca uggccuuugc     600

uggaauuuac aagcuggaca accucguugc cauuuuugac aucaaccgcc ugggccagag     660

cgacccagcc ccgcugcagc accaggugga caucuaccag aagcgcugug aggccuuugg     720

cuggcacacc aucaucgugg acggacacag cguggaggag cugugcaagg ccuuugguca     780

ggccaagcac caaccaacag ccaucaucgc caagaccuuc aagggccgag ggaucacagg     840

gauugaagac aaggaggcgu ggcacgggaa gccccucccc aaaaacaugg ccgagcagau     900

uauccaggag auuuacagcc agguucagag caaaaagaag auccuggcca cgcccccuca     960

ggaggaugcc ccauccgugg acauugcuaa cauccgaaug ccuacgccac ccagcuacaa    1020

agugggggac aagauagcca cccggaaggc cuauggacug gcccucgcua agcugggcca    1080

cgccagugac cguaucauug cccuggaugg agacaccaag aauuccaccu ucucggagcu    1140

cuucaaaaag gagcacccag accgguucau ugagugcuac auugccgagc aaaacauggu    1200

gagcauugcc gugggcugug ccacacguga ccggacagug cccuucugca guacuuucgc    1260

ggccuucuuc acacgggccu ucgaccagau ucgcauggcc gccaucucug agagcaacau    1320

caaccucugu ggcucccacu guggugugucc cauuggggaa gacgggcccu cucagauggc    1380

ccucgaagac cuggccaugu uccggucagu ccccaugucc accgucuuuu acccaagcga    1440

uggaguugca acagagaagg caguggaguu agcagccaac acaaagggca uuugcuucau    1500

ccggaccagc cgcccagaga augccauuau uuauagcaac aaugaggauu uccaggucgg    1560

ccaagccaag guggguccuga agagcaagga ugaccaagug acagugaucg gggcuggugu    1620

aacucugcau gaggccuugg cugcugcaga gagucuaaag aaagauaaga ucagcauccg    1680

ggugcuggau cccuucacua ucaagccccu ggacaggaaa cucauccuag acucugcccg    1740

agcaaccaaa ggcaggaucc ucaccgugga ggaccacuac uacgaaggug gcauaggaga    1800

ggcagugucu gcugccguag ugggugaacc uggagugacg gucacucgcc uggcugucag    1860

ccaaguacca cgaaguggca agccagcuga gcuacugaag auguucggua uugacaagga    1920

cgccauugug caagcuguga aaggccuugu caccaagggc uagggagggc augggaugcu    1980

gggugggguga acuacacauu ccagggaggu ucuggcagag guggcgaagg uguacugagu    2040

ggggagguaa auauauguuu ug                                             2062

<210> SEQ ID NO 23
<211> LENGTH: 230
<212> TYPE: RNA
```

<213> ORGANISM: Homo sapiens

<400> SEQUENCE: 23
uuaacggugu cauaaauaag uaauauaacu uuauuaaaau gaaaagacaa uauucaaaau 60
aaugcaacaa aaugaauaaa uccuuugucc aauacuguac acacagugcg gagaucagug 120
cauuuuucua aagcauguuu uaaccuucau uuaguucaua cuaaaguaag cuuuaaauag 180
cucaaauaau gucauucagc aguuuaaacu gaacagcuug uugggacaug 230

<210> SEQ ID NO 24
<211> LENGTH: 1560
<212> TYPE: RNA
<213> ORGANISM: Homo sapiens

<400> SEQUENCE: 24
ugaguucucg uaaacuccag agcagcgaua ggccguaaua ucggggaaag cacuauaggg 60
acaugauguu ccacacguca caugggucgu ccuauccgag ccagucgugc caaaggggcg 120
gucccgcugu gcacacuggc gcuccaggga gcucugcacu ccgcccgaaa agugcgcucg 180
gcucugccag gacgcggggc gcgugacuau gcgugggcug gagcaaccgc cugcugggug 240
caaacccuuu gcgcccggac ucguccaacg acuauaaaga gggcaggcug uccucuaagc 300
gucaccacga cuucaacguc cugaguaccu ucuccucacu uacuccguag cuccagcuuc 360
accagaucuc ggaauggacc ccaacugcuc cugcuccacc gguaagacuc ccgauccuug 420
gucuuuagaa uaccaaguug ggaccgcaga gcggaauccc cgaguuguag aggcuuggcg 480
ggaauaggca ccuuuaguug gcgauucauu ccgguucuuu cuagaauccg cucuugcaaa 540
agccuucauu aguuacgagu auugucgaac ggguccuuug gcgggguugg ggcuaggauu 600
uagacgcgca aauguccggu uccugaucac ccaguuagug gggacaucug gguugagucc 660
caggcauuac uaaacuuacu gugaauugcu ugaauuaaga aagaggugaa ggaccuuuau 720
gucuugggac ucaaagacau aaucccugac uuaaccugug aggagaaaag uggggcuagg 780
cucccugcag cuccgaggag gacuuaguga acugagccgg gacucguggu guuggccacu 840
gcuguaaugc ugccucccuc augcugucuu cuuucuccuc ccaggcggcu ccugcacuug 900
caccagcucc ugcgccugca agaacugcaa gugcaccucc ugcaagaaga gugaguuggg 960
acaccuuggg uggcggcuaa ggcuaggggc ggggaacucc uacaaaacug gcucugagaa 1020
auguccuuug cuucccggag gccauuguau ugucucgggg acagaacuau acagagaacu 1080
auuuaaaaaa accgaggucu ucucuguugg ggacaggaag cagaggucuu cagccaggcu 1140
gccucuuccu ccuucuucua ggcugcugcu ccugcugucc cgugggcugc uccaaaugug 1200
cccagggcug ugucugcaaa ggcgccgcgg acaagugcac gugcugugcc ugaugugacg 1260
aacagcgcug ccaccacgug uaaauaguau cggaccaacc cagcgucuuc cuauacaguu 1320
ccacccuguu uacuaaaccc ccguuuucua ccgaguacgu uaauaauaaa agccuguuug 1380
agucuaacuc ugguuucuug guguguuug gcaauaagaa acugggguga cuugauaguc 1440
uggggaucug guuuuggacc cccucgugcc uuuaccuccg cccucuggcc cucacagagg 1500
gguaaugucu uuggguaaag ccaagcuaua ucccauaagc uuccucaugg aaaacagcug 1560

<210> SEQ ID NO 25
<211> LENGTH: 253
<212> TYPE: RNA
<213> ORGANISM: Homo sapiens

<400> SEQUENCE: 25

-continued gcggcacgau gugucuucgg guggcuuuuu uuuuuuuguu uugaauaaug uuuacaauuu 60
cccucaauca cuuuuauaga aauccaccuc caggcccccc ccuuucccca cuuaggccuu 120
cgaggcuguc ugaagaugcu ugagaaacuc aaccaaaucc caguucaauu cagacuuugc 180
acauauauuu auauuuauaa ucagaaaaga aacauuucag uaauuuauaa uaaaagagca 240
cuauuuuuua acg 253

<210> SEQ ID NO 26
<211> LENGTH: 3660
<212> TYPE: RNA
<213> ORGANISM: Homo sapiens

<400> SEQUENCE: 26
uugcaggcga gggcuuccac aacuaccacc acaccuuccc cuucgacuac ucugccagug 60
aguaccgcug gcacaucaac uucaccacgu ucuucaucga cugcauggcu gcccugggcc 120
uggcuuacga ccggaagaaa guuucuaagg cuacugucuu agccaggauu aagagaacug 180
gagacgggag ucacaagagu agcugagcuu ugggcuucug aguuccuguu ucaaacguuu 240
ucuggcagag auuuaauauu cuguugauua acuaacaacu ggauauugcu aucgggggugu 300 uaaugaugca uuuaaccuau uccgguacag uauucuuaua aaaugagaaa gcuuugauca 360
cguuuugagg uaauaaauau uuuauuuagc uaggauuaac caugccacaa gacauuauau 420
auuucuaagc acacaugaua aaugcauaua caauuuugca caacagcuuu aaauaauaac 480
aauaaauuug aacauucuau acagagagga ucaaagccaa ggaacaugcu guuuugaugc 540
uagggugagc auggugcuca gucccuguuu guuugcaugg uguccagcuu uguuucuucu 600
cugucaucac caccuucagg caaauaguug accaaccacu ggccugugucu uguccacccu 660 ccaaagccca ggccaccuuu cuguuuucug aaauacugau ccuuccuccu gaauacaucc 720
cuccuuguuc cuagcuucaa gacugcugcc ucaaauaggg auagagcaag ucccccgcugc 780 agguugugcu agaugggaug gagaaauuau cuucauuuga uacagagcaa guagauuguc 840
ucgagagaaa aguuagcaug cgugguauga uuuguaagua aagauggaag agagagagag 900
agagagagag agagagagag agagagagag agagguagcc auaucuaaca gccuacuuac 960
caaagacccc aggccucucu gcuuggcaug ccuccuuucu guccauccuc ugaaccccag 1020
agauuaguga gauuugaaua auuaaaucau uuucagagug aaggggguua augcaggguc 1080
ugugcuaggg gaggguuuua gcuuuuggua acugaagauu uuuucaugga aaaagucuuc 1140
guguucaaug ugccuagaac ugauaacuaa acagcugaca uuugucgggg acagauaugg 1200
ugugaaacua ugaaaauaua agcaaaaucu ucacuuggaa caugaaacua uuucacuuag 1260
aaaauaaucg aaggacccga gguguugccu ggguugccag uuucuuucgu ggcugggcag 1320
gaacuaguga gguugagggg cagugucugu aaguagcugc uaagaggugc auuuccagau 1380
gaagcccuug gggaacaucu gccagggauc cgcauggugu uggcuccauc cauugcuuua 1440
guuuccuccu uggauugugu agaaacuugg cuucccaugg uuuugaaccu uccaugccuu 1500
cuuugcuuug uggccaccca gccugccuag ugcugccuag gaagcucuua cccaccugau 1560
uucuucugac auuucuuucu uuggccuuuu uuucuuucuc cggacaugca gcuaguugcc 1620
ugaguguauc aagagcaccc aggacuugcu gcuguccagg ccuguuccuc ccccaguauc 1680
cguggguguG gaagagcugu guagcuucag gaagcagagc caggugccac cuuucugugg 1740
cuuccagauc cucccuaccu ccaacucaug ugccucuguc acagugauuu caggaaagcu 1800

-continued ugguagaccc ucuagcaaca ucucgguuca gaaagucucu cugguuugug aguuaacagc 1860
ucagcuaagu gcuguuuugu cucagugagu uaaccacuga augcgagggu ugguuguuga 1920
ucugucucgg ugugugucgg aguagacagc auaugcacuu cucccugugc gcuuugcaag 1980
guaauguggc uuuggcugau ccaugcaggc agguaguggu acagugcugc ugaaaggaag 2040
aaguucccca uuuuaucugu uaaaacacca gagacauggg caagugcuaa uggaccucac 2100
uucaggaaga gggucugcuu ccugaagcca gugugugaug aaaagugacu gagaccugau 2160
aucuaaggug agaccugaua ccuaacacuc ugucacacag uccagggcca acagugcuau 2220
aggaaagucu agaagaaaac aucacaucag uauuuuagaa ccaucaacca ucucuugucc 2280
cuauagccca auccagaggc cugguuuuua gaacuggcug uguaaggugc caaacacuca 2340
guucacuugu agaaucagag ccuuuuuucc ccccuauguu aauugaacac gcgcucugag 2400
cuguuuuguu gaaguagaaa aucucauaga aaaaucacug uagaucuacu gaccuauagc 2460
ccucuggaaa ugccuuugag augguuuuac uuuucuaggu cauagaugcc ugauuauaaa 2520
gaugaacaau aaaaucagcu uucuuucuuu cucuucugau cuuauucccc agaucugauu 2580
caggccaugu uccaaagcaa ggcuacauug agguccuggu gucuuuaagu aaaggacauc 2640
uuucagaucc ucucaaagaa ggauuuauaa caguuuccag augaauguac uaauagcuuu 2700
gggugccuua ucucuuuccu aaucuguagu gccugugagc ucagucucac uccuucccuu 2760
agcccggaga ccccuuagau cgaguggaa uagucaagag gcuggcugga gagucaucag 2820
uacauugguu ugcagaaauc uuuuacaggc uacauuuugg aauuuuuuuu uuuuuaguaa 2880
gugaucaaau uugguggaa guaauucgag uguauucgau uguauugucg uccucguuau 2940
cauugucaaa cauguuauag acggcaguug gcacuggggc ugcuaaucuc ugggguguagu 3000 cucugaaacu guagcuccag ugagguggug ugaaagguua gcaaagccac caucugcugg 3060
ugcuccagcc aaggugccuc uuagccacug aauugcuaug uuauccuuuc ucuuguaaca 3120
aacccacccc agagauaaag ccuuuaauca acccaagaaa cuccugggcu aaguaucuga 3180
cagucucaca ucucaacagu gugaauuaag uguccauagc aucagcucag gaggacacuc 3240
ugggagagug cugacaaaaa aggguuauua auacugaccu acuacuucaa gggcaguucu 3300
gaggugauua gagcuuuuuu uaaaaaccaa guauuugggg auccucagca gagguauuca 3360
uacagacucc caaagaacua uauauguucc ugagaccauc guuuagucua cauugcucuu 3420
cccagagacu gacagauaug accagucaaa gugcaagacu accuacccac ugccaugaaa 3480
accauugcag gaaaccuuuc ccuuccugaa ugagauuuuu uuuuucccuu uuuauguggg 3540
guaauuauuu gugacccaag uguaauuugg augauuucca uuaauaucaa cucuugaagc 3600
cuacuuguac ugauugagau uguauuuguu ccuaauaaaa guggaucugg uuguacuguc 3660

<210> SEQ ID NO 27
<211> LENGTH: 1969
<212> TYPE: RNA
<213> ORGANISM: Homo sapiens

<400> SEQUENCE: 27
acugccaucg aguggguguuc caguugaacu ugcucucucu gccaucugcu ccgcgggcgc 60
cgucagcaug ggucccugga cccacuccuu gcgcgccguc cugcugcugg ugcuuuuggg 120
agucugcacc gugcgcuccg acacuccugc caacugcacc uacccugauc ugcugggcac 180
cuggguguuc caggugggcc cuagaaguuc ccgaagcgac auuaacugcu cggugaugga 240
agcaacagaa gaaaagguag ugguacaccu uaagaaguug gauacugccu acgacgagcu 300
gggcaauucc gggcauuuua cccucauuua caaccaaggc uucgagauug uguugaauga 360
cuacaaaugg uuugcguuuu ucaaguauga agucagaggc cacacagcua ucaguuacug 420
ccaugagacc augacugggu ggguccauga ugugcugggc cggaacuggg cuugcuuugu 480
uggcaagaag guggaaaguc acauugagaa gguuaauaug aaugcagcac aucuuggagg 540
ucuccaggaa agauauucug aaagacucua cacucacaac cacaacuuug ugaaggccau 600
caauaccguu cagaagucuu ggacugcaac ugcauauaag gaauaugaga aaaugagccu 660
gcgagaucug auaaggagaa guggccacag ccaaaggauc ccaaggccca aaccugcccc 720
gaugacugau gaaauacagc aacaaauuuu aaauuugcca gaaucuuggg acuggagaaa 780
cguccaaggc gucaauuaug uuagcccugu ucgaaaccaa gaaucuugug gaagcugcua 840
cucauuugcc ucuaugggua ugcuagaagc aagaauucgu auauuaacca acaauucuca 900
gacaccaauc cugaguccuc aggagguugu aucuugcagc cccuaugccc aagguuguga 960
ugguggauuc ccauaccuca uugcagggaa guaugcccaa gauuuugggg ugguggaaga 1020
aagcugcuuu cccuacacag ccaaagauuc uccaugcaaa ccaagggaga auugccuccg 1080
uuacuauucu ucugacuacu acuauguggg ugguuucuau gguggcugca augaagcccu 1140
gaugaagcuu gagcugguca aacauggacc cauggcaguu gccuuugaag uccacgauga 1200
cuuccuacac uaccacagug gaaucuauca ccacacuggg cugagugacc cuuucaaccc 1260
cuucgagcug acaaaucaug cuguuuugcu ugugggcuau ggaagagauc caguuacugg 1320
gauagaauac uggauuauaa agaacagcug ggcucuaac ugggggggaga guggcuacuu 1380 ccguauccgc agaggaacug augaaugugc aauugagagu auagccgugg cggccauacc 1440
gauuccuaaa uuauaggaca uagcucccag uguuacauac gggucuuuau cacucacaga 1500
gugauuuagu cacaugcuga agacuuuuuc agagcaauau cagaagcuua ccacuaagca 1560
ucuuuaaaga auuuugucuu ugaacuuaaa accauccuug auuuuuuucu uuuaauaucu 1620 ucccaucaa cuacugaacu acuuuucuuu uuaaaguacu ugguuaagua auacuuuuau 1680
gagcaguggu ucaguugucc aauauuuuuu gcaggucauc uacaaugcaa ccagauguuu 1740
caguucuaaa aaucuaugua aaaguacaag cucguuuuua aauuauguaa gucacaugaa 1800
aacauggcaa aaaaauuagu uaaauuuuuu acaaagaguu uuaaauaaau guuuauguaa 1860
ucaguaccau agucuuucua ugugugguuua caagaauuuu ugucaccuac uucuucccuu 1920
agaagcauuu augcuccaug gacguacuuc uuuauggaga aaaaaaaaa 1969

<210> SEQ ID NO 28
<211> LENGTH: 1478
<212> TYPE: RNA
<213> ORGANISM: Homo sapiens

<400> SEQUENCE: 28
gagcucgauc ccuguuccgc cuuugcuaug ucugaaggcg uccugcuuug cgcgugucgg 60
ggccaaaucc agauuuucau uucgcuccag gcuuggacgg cuaaguaggu ccaaaccgca 120
caaacaggaa ggagggaagg caaggagugc gggcagaggg cgggucguuc ccagcagcac 180
cccagucccu ccccgcuccg ucuccgaccc acuggggccg gggcgggcgu gcgcgucagc 240
uggggcuaga aaaggcggcg guccggcccg gcgaggugac agccaacuug gacgccaggu 300
ccggccgacg ccgccaugag cgccgcgcuu uucagccugg acagcccggu gcgcggcaca 360
cccuggccca cagaacccgc ggccuucuac gagccaggca ggguggacaa gcccggccga 420

-continued gggcccgagc caggggaacu gggggagcug ggcuccacga cuccugccau guacgacgac 480
gagagcgcca ucgacuucag cgccuacauu gacuccaugg ccgccgugcc cacccuagag 540
cugugccacg acgaacucuu cgccgaccuc uucaacagca accacaaagc ggccggcgcg 600
ggcggccugg agcugcugca gggcggcccu acgcgacccc cgggugaggg gucugucgcu 660
agggggccgc ucaagcgcga acccgacugg ggcgacggcg acgcgccggg cucccugcug 720
ccggcgcaag uggcggugug cgcgcagaca guggugagcu uggcggccgc ggcucagccc 780
acuccaccca cuucgccgga gccuccucga ggcagcccgg ggccgagccu cgcgcccggc 840
acaguccgag aaaagggcgc gggcaagagg gguccggacc gcggcagccc ggaguaccgg 900
cagcggcgcg agcgcaacaa caucgcugug cgcaagagcc gcgacaaggc caagcgccgc 960
aaccaggaga ugcagcagaa gcugguggag uugucggccg agaacgagaa gcugcaucag 1020
cgcguggagc agcucacccg ggaccuggcu ggccuccggc aguucuucaa aaaacugccc 1080
agcccgccuu uccugccgcc caccggcgcc gacugccggu aacgcgcggc gugggccuuu 1140
gagacucuga acgaccuaua ccucagaccc cgacagcggg gagcagacgc cgcccgaauc 1200
gcuaguuucu uugggaccug cgagcgacag gaagcugcag cuugggcacu ggacugcgag 1260
agaagcuaua uuaaucuuuc cccuuaaauu auuuuuuaua augguagcau uuucuacguc 1320
uuauuaccau ugcagcuaag guacauuugu agaaaagaca uuuccgacag acuuuuguag 1380
auaagaggaa gagacugcgc augcuuuuua uauucauuuu uacaguauuu guaagaauaa 1440
gaauaagaau aaagaagcau uuaaaucgca aaaaaaaa 1478

<210> SEQ ID NO 29
<211> LENGTH: 1786
<212> TYPE: RNA
<213> ORGANISM: Homo sapiens

<400> SEQUENCE: 29
uugagggugg ccaggccagc guaggaggcc agcguaggau ccugcuggga gcggggaacu 60
gagggaagcg acgccgagaa agcaggcgua ccacggaggg agagaaaagc uccggaagcc 120
cagcagcgcc uuuacgcaca gcugccaacu ggccgcugcc gaccgucucc agcucccgag 180
gacgcgcgac cggacaccgg guccugccac agccgaggac agcucgccgc ucgccgcagc 240
gagcccgggg cggcccuuca gggggaccuu ucccagaucg cccaggccgc ccggaugugc 300
acgaaaaugg aacagccuuu cuaucacgac gacucuuacg cagcggcggg auacggucgg 360
agcccuggca gccugucucu acacgacuac aaacuccuga aacccaccuu ggcgcucaac 420
cuggcggauc ccuaucgggg ucucaagggu ccuggggcgc ggggguccagg cccggagggc 480 aguggggcag gcagcuacuu uucgggucag ggaucagaca caggcgcauc ucugaagcua 540
gccuccacgg aacuggagcg cuugaucguc cccaacagca acggcgugau cacgacgacg 600
cccacgccuc cgggacagua cuuuuacccc cgugggggug gcagcggugg agguacaggg 660
ggcggcguca ccgaggagca ggagggcuuu gcggacgguu uugucaaagc ccuggacgac 720
cugcacaaga ugaaccacgu gacgcccccc aacgugucc ugggcgccag cgggggucccc 780 caggccggcc cagggggcgu cuaugcuggu ccggagccgc cucccgucua caccaaccuc 840
agcaguuacu cuccagccuc ugcacccucu ggaggcuccg ggaccgccgu gcggacuggg 900
agcucauacc cgacggccac caucagcuac cucccacaug caccacccuu ugcgggcggc 960
cacccggcac agcuggguuu gagucguggc gcuuccgccu uuaaagagga accgcagacc 1020
guaccggagg cacgcagccg cgacgccacg ccgccugugu cccccaucaa cauggaagac 1080
caggagcgca ucaaagugga gcgaaagcgg cugcggaaca ggcuggcggc caccaagugc 1140
cggaagcgga agcuggagcg caucgcgcgc cuggaggaca aggugaagac acucaaggcu 1200
gagaacgcgg ggcugucgag ugcugccggu cuccuaaggg agcaaguggc gcagcucaag 1260
cagaagguca ugacccaugu cagcaacggc ugccaguugc ugcuaggggu caagggacac 1320
gccuucugag agccucccuu gccccauacg gacaccccca gccuugaagg cugggcgccu 1380 gcccccacu ggggugaggg gggcaggcga ugggcacccg ccaaaaggcc uggggcgcag 1440
cucacacacu ggacuccggc ccgcccgccu gcgcccaguc cuuccaccuc gagguuuaca 1500
uggcccccuu ccagcguauu uuguauguuu uuuuuuucug caaagagacu gaauucauau 1560
ugaauauaau auauuugugu auuuaacagg agggagaagg gggcugucgc ggcggagcug 1620
gccgccgcuu gguacucagc ugcgggggaua cuagggaggg accuccgccc ccugcccucc 1680
cccucugcau aguacugugg agaagaaaca cgacuucgug ucuaaagucu auuuuaagau 1740
guguuugugu gugugugguuu gacuuuuuau ugaaucuauu uaagua 1786

<210> SEQ ID NO 30
<211> LENGTH: 1897
<212> TYPE: RNA
<213> ORGANISM: Homo sapiens

<400> SEQUENCE: 30
gaauucggca cgagcagcga gacgccgcgc acggugcuuc cccaguggag ccaaucggcu 60
aacccgcgcu ccggcagagu ccuuggcgcu cgcccgccgg cgggacagac cacccgccuc 120
uggccgcucu cuggacccug gccgccccga gcgaagacug gagcaaaaug augcuucaac 180
auccaggcca ggucucugcc ucagaaguca gugcgaccgc cauuguccccc ugccucucac 240 cuccuggguc acugguauuu gaggauuuug cuaaccugac acccuuuguc aaggaagagc 300
ugagauucgc cauccagaau aaacaccucu gccaucggau guccucugcg cuggagucag 360
uuaccgucaa caacagaccc cuggagaugu cagucaccaa gucugaggcg gccccugaag 420
aagaugagag gaaaaggagg cggcgagaaa gaaauaaaau ugcugcugcc aagugucgaa 480
acaagaaaaa ggagaagaca gagugccugc agaaagaguc agagaaacug gagaguguga 540
augcugagcu gaaggcccag auugaggagc ugaagaauga gaaacagcau uugauauaca 600
ugcucaaccu gcaccggccc accuguaucg uccgggcuca gaauggacgg acaccggaag 660
acgagaggaa ccucuuuauc caacagauaa aagaaggaac auugcagagc uaagcagagg 720
uggcacggag gcaauugggg aguucuuacu gaauccuccu uuuccacccc acacccugaa 780
gccauuggaa aacuggcuuc cugugcacuu cuagaauccc agcagccaag agccguuggg 840
gcaggagggc cugugguguac cuacugcauu gacccacucu gccccccgagu gaaccgugga 900 gcaggcagga gcauccuuug ucucaccaau uccaggauuu aggccuuauc aucccggcca 960
gucucagaug accuagcugg ccccaggcug ggguccuaug caaagcagga ucccacuaau 1020
gggauucagg cagaaguguc uaccuugaua ggugggggugg gaccacaucc uccacugugg 1080
cugacaacgc ccuuccaagg gaauauggaa ugagaacauu cauuauugag guuguccaau 1140
ggccagggua ugcuuucuag aaaauaugcu guucuguccc agaaugacug ugcauagggu 1200
auccguuuca gagccuggug uugugcuauu uagauguuug ucuugcacaa cauuggcaug 1260
auuuuuccgg gaguuucauc agaucugauu ucugagaguc uggggaucug ccauggugga 1320
aagugccccu caaaagcauu uguguggcca caugaacugg cuggcaccag gggagugaaa 1380
cuggcugaug accagcugag ccacuuugug ccaacagagg auggacgaca ccuuucccug 1440
uacccacugc agaggaagaa cccugggcac agcagcuuug uccuuggcua caaacuguua 1500
caacgucaca caaugaaggc acaaagucca acuuucaaag gguguaggac uccauacuca 1560
gugacagggc aggaagagcc aaagauaacc acagccacag ccuguggaga ccaggguugg 1620
aagccaggug cagggccagg caucugcauu gugggauguu aauggcacuu uugucuugua 1680
gcuauuuuga gauguggucc agagcauuuc agcugggaga ucucccucug gccaccagga 1740
cucuggcuac uguuaaaauc cugauguuuc uguggaaucc ucaguguuua aucccacuca 1800
auaguaucau uacaguuuuc uguaagagaa aauauuacuu auuuauccca guauuccuag 1860
ccugucaaca uaauaaauau cggaacaaaa ccuggua 1897

<210> SEQ ID NO 31
<211> LENGTH: 473
<212> TYPE: RNA
<213> ORGANISM: Homo sapiens

<400> SEQUENCE: 31
uuuuuuuuuu uuuuuuugcu gauaagaauu cuuuuuaugu uauucgaaua aaaaauacau 60
ucauacagaa auauaacaau cucgcaaaaa acaauuucaa auaaaaucuu guaaaacaaa 120
auuuuacaaa aaucuuacaa agauucuuua gauaacaggg ugcuucaaaa aaaaagaaau 180
aaagaaauuu cacuaauaga aauuuuuuuu uuuaauuuca agcaaaaguu ccugcuugau 240
ugaggcucag uugucaccug accagaaugg acugcuuagu auuaaaguua cagcaucgac 300
acggacggca cccagcccca gccaguccag caacgucgcu guguuucaua agugagacgc 360
gccagcacaa guuuccucuc ucuucuguuu accuucuuac uuaauggaau ugcuauggau 420
aagcacacag cagggccaaa aaaggaguuu uccaaaaucc agcaaaucaa gug 473

<210> SEQ ID NO 32
<211> LENGTH: 1680
<212> TYPE: RNA
<213> ORGANISM: Homo sapiens

<400> SEQUENCE: 32
uaguggugau cuggaccgug cggacuugcu cgucccucag cucuccuguu aggcgucucu 60
uuucuccagg aggaaaaaau ggcagcagca guaguggauc cgcaacagag cgugguguaug 120 agaguggcca accugcccuu ggugagcucu accuacgacc uuguguccuc cgcuuauguc 180
aguacaaagg aucaguaccc guauuugaga uccgugugug agauggccga gaagggcgug 240
aagaccguga ccucugcggc caugacaagu gcccugccca ucauccagaa gcuggagcca 300
caaauugcgg uugccaauac cuaugccugc aaggggcuag acaggaugga ggaaagacug 360
ccuauucuga accagccaac guccgagauu guugccagug ccagaggugc cguaacuggg 420
gcgaaggaug uggugacgac uaccauggcu ggagccaagg auucuguagc cagcacaguc 480
ucaggggugg uggauaagac caaaggagca gugacuggca gcguggaaag gaccaagucu 540
guggucaaug gcagcaucaa uacaguuuug gggauggugc aguucaugaa caguggagua 600
gauaaugcca ucaccaaguc ggagaugcug guagaccagu acuucccucu cacucaggag 660
gagcuggaga uggaagcaaa aaaggugggaa ggauuugaua ugguucagaa gccgagcaac 720
uaugaacggc uggagucccu gucuaccaag cucugcucuc gggcuuauca ccaggcucuc 780
agcaggguua aagaggccaa acaaaagagc caggagacca uuucucagcu ccacuccacu 840
guccaccuga uugaauucgc caggaagaau augcacagug ccaaccagaa aauucagggu 900
gcucaggaua agcucuaugu cucgugggug gaguggaaga gaagcaucgg cuacgacgac 960
accgaugagu cccacugugu ugagcacauc gagucacgua cucuggcuau cgcccgcaac 1020
cugacccagc agcuccagac uacaugccag acuguccugg ucaacgccca aggguuacca 1080
cagaacauuc aagaucaggc caaacacuug gggugauggg caggcgacau cuacuccgua 1140
uuccgcaaug cugccuccuu uaaggaagug uccgauggcg uccucacauc uagcaagggg 1200
cagcugcaga aaaugaagga auccuuagau gaaguuaugg auuacuuugu uaacaacacg 1260
ccucucaacu ggcugguagg ucccuuuuau ccucagucua ccgaggugaa caaggccagc 1320
cugaaggucc agcagucuga ggucaaagcu caguaaaccc cuccuuguca ccagagcaug 1380
auguugcugg ccagaugacc ccuuuugcug uauugaaauu aacuugguag auggcuuuag 1440
cuuagaaaag cagcuucuua gaaccaaggg ccucauuaug gucacucaca gcucaguuau 1500
ggucuugccc cagcuggccc uggcacagga guucucuuac cuggcuggug aguggccugu 1560
guuagucuug ugaggaccug gaggaaccua aaagcucaga ugcacuuaca gucuugucug 1620
uggccuuugu auuguuauug gcuguaaacg ucugucugga ccgaauaaag auucacguga 1680

<210> SEQ ID NO 33
<211> LENGTH: 1783
<212> TYPE: RNA
<213> ORGANISM: Homo sapiens

<400> SEQUENCE: 33
ggcacgaggg agcugcagug uucgcgcuug guagcuggug caucggacuc agcuggcuuu 60
gugucccuga ggcucaccga aaaacacuuu cucagcccuc ugacuccaga gagagagaga 120
gagagguacu uuuuguggu accgacuuug accccugcag aggcugagcg auggcgucua 180
ugggacuaca gguccuggga aucuccuugg caguccuggg cuggcugggg aucauccuga 240
guugugcgcu ccccaugugg cgggugaccg ccuucaucgg cagcaacauc gucacggcac 300
agaccagcug ggagggccuc uggaugaacu gcgugguca gagcacaggu cagaugcagu 360
gcaagaugua cgacucgaug cucgcccugc cgcaggaccu gcaggccgcc cgagcccuua 420
uggucaucag caucaucgug ggugcucugg ggaugcuucu cucaguggua gggggcaagu 480
gcaccaacug cauggaggac gagaccguca aggccaagau caugaucacc gccggagccg 540
uguucaucgu ggcaagcaug cugauuaugg ugcccguguc cuggaccgcu cacaacguca 600
uccgcgacuu cuacaacccu augguggcuu ccgggcagaa gagggaaaug ggggccucgc 660
uuuacgucgg cugggcggcc uccgggcugc ugcuccuggg aggaggccuc cucugcugca 720
guugcccacc ucguagcaac gacaagcccu acucggccaa guacuccgcc gcccgcucug 780
uccccgccag caacuaugug uaaggugggc cacucugucc acauugccuu uguuauuuuu 840
uuucggauug agcucauaac agccuguggc cccucacauu cuccaggacc ugcccugcua 900
ugggccacua acugcuugcu ggggacaggc aaacccggac ugugcaaagu uacuagcccg 960
uagcucuugg gcugcuccac auggcuccuu acggccggca agaauggaug uaaaaaauac 1020
uugcugcuua cauccaaauu gcgguggaua ugggcugaag gcagaagcag cugggaaggg 1080
caguagaggc gcaagcuggg uccugcuggc cgggguagcu cagcugugac uuuggacucg 1140
gaguggaugu ccucauguua gcaaacgucc acuguccuuu cucuaucccc cucacucagc 1200
cuacacguua cuccagcgcu acucuugcca uuacgccccg uguuuccgag cacagcuggu 1260
ccuaccccaa gucauggugu gcugagugac ugaugagggg ccauugagag ccggugggcu 1320

-continued

```
cugccaugga acccuuccgu ugauuagcaa ugacugugcu ugacccaccc accuacccua   1380

cuaaugaauu ucuguagagu ggauggacgg guuugaggga agaagggugg agguggauua   1440

aacugguuug gggagggcug gggaccuaga agcagcccag ugugucccca ccccuuuucc   1500

gcacugucuu gcuaauguuc ugaucacugu gcgccccccuc ccucuucaga aggacccugg   1560

gccucuugag uuggccccuc ugaguucccu cccuuugccc auuucaagga caccggccag   1620

ucugcggaag gaagguacgg gggggggggg gggggugau ggcauuguac cagggagucu   1680

ccuggacucc ccugccuucu cugugguuuc uuguuuugua auuaaggucu guucacagcu   1740

guaauuauua uuauuuucua caauaaaugg caccugcaua cag                    1783
```

<210> SEQ ID NO 34
<211> LENGTH: 1786
<212> TYPE: RNA
<213> ORGANISM: Homo sapiens

<400> SEQUENCE: 34

```
uugagggugg ccaggccagc guaggaggcc agcguaggau ccugcuggga gcggggaacu     60

gagggaagcg acgccgagaa agcaggcgua ccacggaggg agagaaaagc uccggaagcc    120

cagcagcgcc uuuacgcaca gcugccaacu ggccgcugcc gaccgucucc agcucccgag    180

gacgcgcgac cggacaccgg guccugccac agccgaggac agcucgccgc ucgccgcagc    240

gagcccgggg cggcccuuca gggggaccuu ucccagaucg cccaggccgc ccggaugugc    300

acgaaaaugg aacagccuuu cuaucacgac gacucuuacg cagcggcggg auacggucgg    360

agcccuggca gccugucucu acacgacuac aaacuccuga aacccaccuu ggcgcucaac    420

cuggcggauc ccuaucgggg ucucaagggu ccuggggcgc ggggguccagg cccggagggc    480

aguggggcag gcagcuacuu uucgggucag ggaucagaca caggcgcauc ucugaagcua    540

gccuccacgg aacuggagcg cuugaucguc cccaacagca acggcgugau cacgacgacg    600

cccacgccuc cgggacagua cuuuuacccc cgugggggug gcagcggugg agguacaggg    660

ggcggcguca ccgaggagca ggagggcuuu gcggacgguu uugucaaagc ccuggacgac    720

cugcacaaga ugaaccacgu gacgcccccc aacgugucccc ugggcgccag cgggggguccc    780

caggccggcc cagggggcgu cuaugcuggu ccggagccgc cucccgucua caccaaccuc    840

agcaguuacu cuccagccuc ugcacccucu ggaggcuccg ggaccgccgu gcggacuggg    900

agcucauacc cgacggccac caucagcuac cucccacaug caccacccuu ugcgggcggc    960

cacccggcac agcuggguuu gagucguggc gcuuccgccu uuaaagagga accgcagacc   1020

guaccggagg cacgcagccg cgacgccacg ccgccugugu cccccaucaa cauggaagac   1080

caggagcgca ucaaagugga gcgaaagcgg cugcggaaca ggcuggcggc caccaagugc   1140

cggaagcgga agcuggagcg caucgcgcgc cuggaggaca aggugaagac acucaaggcu   1200

gagaacgcgg ggcugucgag ugcugccggu cuccuaaggg agcaaguggc gcagcucaag   1260

cagaagguca ugacccaugu cagcaacggc ugccaguugc ugcuaggggu caagggacac   1320

gccuucugag agccucccuu gccccauacg gacaccccca gccuugaagg cugggcgccu   1380

gcccccccacu gggggugaggg gggcaggcga ugggcacccg ccaaaaggcc uggggcgcag   1440

cucacacacu ggacuccggc ccgcccgccu gcgcccaguc cuuccaccuc gagguuuaca   1500

uggcccccuu ccagcguauu uuguauguuu uuuuuuucug caaagagacu gaauucauau   1560

ugaauauaau auauuugugu auuuaacagg agggagaagg gggcugucgc ggcggagcug   1620

gccgccgcuu gguacucagc ugcggggaua cuagggaggg accuccgccc ccugcccucc   1680
```

cccucugcau aguacugugg agaagaaaca cgacuucgug ucuaaagucu auuuuaagau 1740
guguuugugu gugugugguuu gacuuuuuau ugaaucuauu uaagua 1786

<210> SEQ ID NO 35
<211> LENGTH: 1389
<212> TYPE: RNA
<213> ORGANISM: Homo sapiens

<400> SEQUENCE: 35
augcagcuga gaaaaaugca gaccaucaaa aaggagcccg caccccuaga uccuaccagc 60
agcucagaca agaugcugcu gcugaacucu gccuuagcug agguggccga ggaccuagcc 120
ucaggugaag auuugcuccu gaacgaaggg agcaugggga aaaacaaauc cucggcgugu 180
cggagaaaac gggaauucau uccggacgag aagaaagacg ccauguauug ggagaaacgg 240
cggaaaaaca acgaagcugc caaaagaucu cgggagaagc gccgccucaa ugaccugguu 300
uuggagaaca agcugauugc ccugggagaa gaaaaugcca cuuuaaaagc ugagcugcuc 360
ucccugaaau uaaaguuugg uuuaauuagc uccacggcgu augcccaaga aauccagaaa 420
cucaguaauu ccacagcugu cuacuuucag gacuaccaga cauccaaggc ugccgugagc 480
ucuuuugugg acgagcauga gccugcgaug guagccggaa guugcaucuc agucaucaag 540
cacucucccc agagcucgcu cuccgaugug ucagaggugu ccucggugga gcacacucag 600
gaaagccccg cacagggagg cugccggagc ccugagaaca aguucccugu gaucaagcag 660
gagcccgugg aguuggagag cuuugccagg gaggccaggg aggagcgggg cacguauucc 720
accuccaucu accagagcua caugggaagc ucuuucucca cuuacuccca cuccccaccc 780
cucuugcagg uccaugggguc cacuagcaac uccccaagaa ccucagaggc cgaugagggu 840 guaguggggca agucuucuga uggggaagac gaacaacagg ucccuaaggg ccccauccau 900
ucuccagugg agcugcaacg gguucacgcc acggugguga agguuccgga agugaacccu 960
ucugccuuac cgcacaagcu ucggauuaaa gccaaggcca ugcaggucaa aguggaggcu 1020
uuggacagcg aguuugaagg caugcagaaa cucucuucac ccgccgaugc gaucgccaaa 1080
agacauuuug accuggagaa acauggaacc ucggguaugg cccauuccuc ccucccuccu 1140
uucucagugc aggugacgaa cauucaagau ugguccccuca aaucggaaca cuggcaucac 1200
aaagaacuga gcagcaaaac ucagaguagc uucaaaacag guguggugga agucaaagac 1260
gguggcuaua agguuuccga agcugagaau uuguauuuga agcagggaau agcaaacuua 1320
ucugcagagg uggucucgcu caagagauuc auagccacac aaccgaucuc ggcuucggac 1380
uccagguaa 1389

<210> SEQ ID NO 36
<211> LENGTH: 961
<212> TYPE: RNA
<213> ORGANISM: Homo sapiens

<400> SEQUENCE: 36
gcucccggga aacgaaugag gaaccaccuc cuccugcugu ucaaguacag gggccuggug 60
cgcaaaggga agaaaagcaa aagacgaaaa uggcuaaauu uaagauccgu ccagccacug 120
ccucugacug cagugacauc cugcgacuga ucaaggaacu ggcuaaauau gaauacaugg 180
aagaucaagu cauuuuaacu gagaaagauc uccaagagga uggcuuugga gaacaccccu 240
ucuaccacug ccugguugca gaagugccua aagagcacug gaccccugaa ggacauagca 300

-continued

```
uuguuggguu cgccauguac uauuuuaccu augacccaug gauuggcaag uugcuguauc    360
uugaagacuu cuucgugaug agugauuaca gaggcuuugg uauaggauca gaaauuuuga    420
agaaucuaag ccagguugcc augaagugc gcugcagcag uaugcacuuc uugguagcag    480
aauggaauga accaucuauc aacuucuaca aaagaagagg ugcuucggau cuguccagug    540
aagagggaug gaggcucuuc aagauugaca aagaguacuu gcuaaaaaug gcagcagagg    600
agugaggcgu gccgguguag acaaugacaa ccuccauugu gcuuuagaau aauucucagc    660
uucccuugcu uucuaucuug uguguaguga aauaauagag cgagcaccca uuccaaagcu    720
uuauuaccag ugacguuguu gcauguuuga aauucggucu guuuaaagug gcagucaugu    780
auguggguug gaggcagaau ucuugaacau cuuuugauga agaacaaggu gguaugaucu    840
uacuauauaa gaaaaacaaa acuucauucu ugugagucau uuaaaugugu acaauguaca    900
cacugguacu uagaguuucu guuuugauuc uuuuuuuuua aauaaacucg cucuuugauu    960
u                                                                    961
```

<210> SEQ ID NO 37
<211> LENGTH: 2187
<212> TYPE: RNA
<213> ORGANISM: Homo sapiens

<400> SEQUENCE: 37

```
cgcuggcucc gugcgccaug gucacccaca gcaaguuucc cgccgccggg augagccgcc     60
cccuggacac cagccugcgc cucaagaccu ucagcuccaa aagcgaguac cagcuggugg    120
ugaacgccgu gcgcaagcug caggagagcg gauucuacug gagcgccgug accggcggcg    180
aggcgaaccu gcugcucagc gccgagcccg cgggcaccuu ucuuauccgc gacagcucgg    240
accagcgcca cuucuucacg uugagcguca agacccaguc ggggaccaag aaccuacgca    300
uccagugga ggggggcagc uuuucgcugc agagugaccc ccgaagcacg cagccaguuc    360
cccgcuucga cuguguacuc aagcuggugc accacuacau gccgccucca gggacccccu    420
ccuuuucuuu gccacccacg gaacccucgu ccgaaguucc ggagcagcca ccugcccagg    480
cacuccccgg gaguaccccc aagagagcuu acuacaucua uucugggggc gagaagauuc    540
cgcugguacu gagccgaccu cucuccucca acguggccac ccuccagcau cuuugucgga    600
agacugucaa cggccaccug gacuccuaug agaaagugac ccagcugccu ggacccauuc    660
gggaguuccu ggaucaguau gaugcuccac uuuaaggagc aaaaggguca gaggggggcc    720
ugggucgguc ggucgccucu ccuccgaggc acauggcaca agcacaaaaa uccagcccca    780
acggucggua gcucccagug agccaggggc agauuggcuu cuuccucagg cccuccacuc    840
ccgcagagua gagcuggcag gaccuggaau ucgucugagg ggagggggag cugccaccug    900
cuuuccccc ucccccagcu ccagcuucuu ucaaguggag ccagccggcc uggccuggug    960
ggacaauacc uuugacaagc ggacucuccc cuccccuucc uccacacccc cucugcuucc   1020
caagggaggu ggggacaccu ccaaguguug aacuuagaac ugcaagggga aucuucaaac   1080
uuucccgcug gaacuuguuu gcgcuuugau uugguuugau caagagcagg caccuggggg   1140
aaggauggaa gagaaaaggg ugugugaagg guuuuuaugc uggccaaaga aauaaccacu   1200
cccacugccc aaccuaggug aggaguggug gcuccuggcu cuggggagag uggcaagggg   1260
ugaccugaag agagcuauac uggugccagg cuccucucca uggggcagcu aaugaaaccu   1320
cgcagauccc uugcacccca gaacccuccc cguugugaag aggcaguagc auuuagaagg   1380
gagacagaug aggcugguga gcuggccgcc uuuuccaaca ccgaagggag gcagaucaac   1440
```

agaugagcca ucuuggagcc cagguuuccc cuggagcaga uggaggguuc ugcuuugucu 1500
cuccuaugug gggcuaggag acucgccuua aaugcccucu gucccaggga uggggauugg 1560
cacacaagga gccaaacaca gccaauaggc agagaguuga gggauucacc cagguggcua 1620
caggccaggg gaaguggcug caggggagag acccagucac uccaggagac uccugaguua 1680
acacugggaa gacauuggcc aguccuaguc aucucucggu caguaggucc gagagcuucc 1740
aggcccugca cagcccuccu uucucaccug gggggaggca ggaggugaug gagaagccuu 1800
cccaugccgc ucacaggggc cucacgggaa ugcagcagcc augcaauuac cuggaacugg 1860
uccuguguug gggagaaaca aguuucuga agucagguau ggggcugggu ggggcagcug 1920
uguguugggg uggcuuuuuu cucucuguuu ugaauaaugu uuacaauuug ccucaaucac 1980
uuuuauaaaa auccaccucc agcccgcccc ucuccccacu caggccuucg aggcugucug 2040
aagaugcuug aaaaacucaa ccaaauccca guucaacuca gacuuugcac auauauuuau 2100
auuuauacuc agaaaagaaa cauuucagua auuuauaaua aaagagcacu auuuuuuaau 2160
gaaaaaaaaa aaaaaaaaaa aaaaaaa 2187

<210> SEQ ID NO 38
<211> LENGTH: 2046
<212> TYPE: RNA
<213> ORGANISM: Homo sapiens

<400> SEQUENCE: 38
aaggaaucuu caguacagaa acaagaccca aguguaaguu uaacuggcag gaggaaccaa 60
ccaaggacag uuaaggagaa aacccaaccc uuagaagaac ucaccaguuu ccaagaggaa 120
acugccaaaa gaauaucuuc caaaucucca caaccggaag agaaggaaac cuuagcaggu 180
uuaaagaggc agcucagaau acaacuaauc aacgauggug uaaaagaaga gcccacagca 240
cagagaaagc aaccauccag ggaaaccagg aacacacuca aagagccugu agguggacagu 300 auaaaauguug aagagguuaa gaagucuaca aagcagaaaa uugauccagu agcaagugug 360
ccugucagca agaggccacg gaggguaccc aaggaaaagg cacaggcccu agaauuggcu 420
ggucucaaag gaccaaucca aacccuaggc cacacugaug aaucagcaag ugauaaagga 480
cccacacaga ugcccuguaa uucucuacaa ccagagcaag uugacagcuu ccaaagcuca 540
ccaaggcgac ccaggacaag acgugggaaa guagaggcag augaagagcc uucagcagua 600
agaaagacag uaucaacauc aaggcaaacu augcgauccc gcaaggucccc ugaaauuggu 660 aacaauggua cccaaguuuc aaaggccucc auaaagcaga cauuagauac aguagccaaa 720
guaacuggca gcaggaggca gcuaaggaca cauaaaggau gggguucaac ccucuugaag 780
uuguuaggug acuccaaaga aauaacccaa auaucagauc acucugagaa acuagcacau 840
gacaccagua uccuuaagag cacucaacag caaaagccag acucaguaaa accucugaga 900
acaugcagaa gagugcugag ggccucuaaa gagguccccca aggaagu guu gguggacacc 960 agagaccaug caacauuaca aagcaaaagc aacccuuugc uguccccgaa gaggaagucu 1020
gcaagagaug gaagcauugu gagaaccagg gcuuugcgcu cuuuagcacc aaagcaggaa 1080
gcaacagaug agaagccugu accugagaaa aaaagggcug cuuccagcaa gagguaugua 1140
ucaccugagc cugugaagau gaaacaccug aaaaucgugu caaacaaacu ugaaucugug 1200
gaagagcagg uuagcacugu uaugaaaaca gaagaaaugg aagccaaaag agaaaauccu 1260
gucacuccag aucagaacuc uagguaccga aagaaaacca auguaaaaca gccaaggccc 1320
aaguuugaug caucugcaga gaaugucggg auaaagaaaa acgagaagac uaugaagacu 1380
gccucccagg agacagagcu gcagaaucca gaugauggag ccaagaaauc uacaucucgg 1440
ggccaaguca gugggaaaag aacaugcuug aggucuagag gaacgacuga gaugccccag 1500
ccuugugaag cagaagagaa aacaagcaaa ccagcugcag aaaucuugau aaagccucag 1560
gaagagaaag gagucucugg agagucugau guuaggugu ugagguccag aaaaacuaga 1620
gucgcuuugg acagugaacc uaagccaagg guaacucgug gaaccaagaa agaugcaaaa 1680
acucugaagg aggaugaaga cauuguaugc accaagaagu uaagaacaag aaguuaagaa 1740
caagaaguua ccagaaaagu gaaacuaugu agcaaagaca uuuaagaagg aaaaguaaau 1800
uugacuuagu gauaaguucc agugugguuu ucaccuccag uguaaagaug aacuguaaau 1860
acuacugcua cugccugagu uuaaggaagg aagcuuugag cuuuccuggu cauacucucu 1920
ucagacgcca auggagguca ugaggaagau caccagggau cucagcgcaa uuacaguuua 1980
ggggugagca ggcagaaaug uggcccucug uccuauccaa uaaagcucug aaauucgcug 2040
ccaaaa 2046

<210> SEQ ID NO 39
<211> LENGTH: 423
<212> TYPE: RNA
<213> ORGANISM: Homo sapiens

<400> SEQUENCE: 39
uuuuuuuuuu uuuuuuuaaa ucaaaaguua ugaugacuuu auuuuaaauc uuaauacacc 60
aaaaauauuu uucaauguug ugagauaagc acuugaaaau aagaauucca acacugcugu 120
gauuucgcug ugaggcuuga uagugaauuu ucccucugaa uauggguuua gggccuagga 180
agcagaaugc cagucauuuu ccaaguagca gugagcuaag cccagcccgg ucaugcucag 240
acccacacuu aacugaaaua uucacacuag gaggcggcac caccaggcaa caccuugauc 300
aaccaggaga acaaaagucu gaagugccac caagcauugg ggaaaugaua uuguuuagau 360
gcuagugagu cagguucuuu caaauguguc cuaacugggu ugcaaacaua guugcauccu 420
uau 423

<210> SEQ ID NO 40
<211> LENGTH: 434
<212> TYPE: RNA
<213> ORGANISM: Homo sapiens

<400> SEQUENCE: 40
gucuguaaaa aucuguuuaa uaaauauaca ucuuagaagu accaaaauaa uuaccaacaa 60
aauacaacau auacaacauu uacaagaagg cgacacagac cuuaguuggg ggcgacuuuu 120
aagcacaugc cacugaacac cuggcucuua caugggagga cacacugggc ucacuuacua 180
ggucuauggu gguucaauca aaagcacaau aaauaaaacg ugguccuuuc auuagguucu 240
ggaaaaucac cuccccccccc cccaaaaaaa aucccacaaa caugaaccuu aagagacauu 300
uucuuugaau uucagugauc uguuuccccg gauuucacaa agacaacagc cgaaucaccc 360
caguaaaaug ccugggucua ggcgcugugu ggugugggugc uaaguauacc cuuucucauu 420
uuuuuucuuu uucu 434

<210> SEQ ID NO 41
<211> LENGTH: 1000
<212> TYPE: RNA
<213> ORGANISM: Homo sapiens

<400> SEQUENCE: 41
cggccgccag accuucaagg gcuggagugg acgcgcggac cgacucugaa cagacagacg 60
aaccgcggcc gcaagguucc cagacaggau cucacccaga ggcaggcagc ggacagugcc 120
uuaguggaac cucgcugucc uccaccgccu ggccccggug caggcgucca guggccgccg 180
cauccaaagu gaucgcugcc ucccccgucuc cgccagcucg ggaccaugaa gcugcugccg 240
ucggugaugc ugaagcucuu ucuggccgca guguuguccg cguuggugac cggugagagu 300
cuggagcggc uucggagagg ucuggcggca gcaaccagca acccugaccc ucccacugga 360
uccacaaacc agcugcuacc cacgggaggu gaucgugcuc agggggucca ggacuuggaa 420
gggacagauc ugaaccuuuu caaaguugcu uucuccucca agccacaagg ccuggccacc 480
ccaagcaaag aaaggaaugg gaaaaagaag aagaaaggaa aggggguuagg gaagaagaga 540 gacccaugcc ucaggaaaua caaggacuac ugcauccacg gggagugcag auaccugcag 600
gaguuccgua cucccucuug caaaugccuc ccugguuacc acggacacag gugucauggg 660
cugacucuac caguggagaa uccccuauac acauaugacc acacuacagu cuuggcugug 720
guggcuguag uacugucguc cgucugucuu cuugucaucg ugggacuucu cauguuuagg 780
uaccacagga gaggagguua ugacuuggaa agugaagaga aagugaaguu gggcguggcu 840
agcucccacu gaggaggacc ugagcuauag gaaccuucag aggcuacuuc ugagacagug 900
guucguuaca cguucuacau agaggagaaa uauuucacca gcagccauga aaacgucuuc 960
auucauuucc aguugcuacc cugacugggc cuccuguaau 1000

<210> SEQ ID NO 42
<211> LENGTH: 1653
<212> TYPE: RNA
<213> ORGANISM: Homo sapiens

<400> SEQUENCE: 42
ucgaccucac ggucuugcca aaaugucgcu uuccaacaag cugacuuugg acaagcugga 60
cgugaagggg aagcgggucg ugaugagggu ggacuucaac guuccuauga agaacaacca 120
gauaacaaac aaccaaagga ucaaggcugc uguuccaagc aucaaauucu gcuuggacaa 180
uggagccaac uccguugucc uuaugagcca ccugggccgg ccugauggug uucccaugcc 240
ugacaaguac ucccuuagagc caguugcugc ugaacucaaa ucucugcugg gcaaggaugu 300
ucuguucuug aaggauugug ugggcccaga agucgagaau gccugugcca acccagcggc 360
ugggacuguc auccugcugg aaaaccuccg cuuucaugua gaggaagaag ggaagggaaa 420
agaugcuucu gggaacaagg uuaaagcuga gccggccaaa auugaugcuu uccgagccuc 480
acuguccaaa cuaggagaug ucuaugucaa ugaugcuuuu gggacugcac accgagccca 540
uagcuccaug gugggguguga aucugccaca gaaggcuggu ggauuuuuga ugaagaagga 600
gcugaacuac uuugccaagg cuuuggagag uccugagcga cccuuccugg cuaucuuggg 660
aggcgcuaaa guugcagaca agauccagcu gaucaauaau augcuagaca aagucaauga 720
gaugaucauu ggugguggaa uggccuuuac cuuccuuaag guccucaaca acauggagau 780
uggcacaucu cuguaugaug aagaaggagc caagauuguc aaagaucuca uguccaaagc 840
ugagaaaaau ggugugaaga uuaccuugcc uguugacuuu gucacugcug acaaauuuga 900
ugagaaugcc aagacuggcc aagcuacugu ggccucuggu auaccugcug gcuggauggg 960
cuuggacugu gguacugaga gcagcaagaa auaugccgag gcugugggguc gagcuaagca 1020 gauuguuugg aauggucug uugggguauu ugaaugggaa gccuuugcca ggggaaccaa 1080
gucacucaug gaugaggugg ugaaagccac uucuaggggu ugcaucacua ucauaggugg 1140
uggagacacu gccacuugcu gugccaaaug gaacacagag gauaaaguca gccaugugag 1200 cacuggggggc ggugccaguc uagagcuccu ggaagguaaa guccuuccug ggguggaugc 1260
ucucagcaau guuuaguauu uucuuuccug ccuuugguuc cugugcuccu aagcuaaccu 1320
gcuguuuucc acaucuccau uugguguuag cgcaagauuc agcuaguggc ugagaugugg 1380
cacagaccuu aacagugcaa gcaucucagc ucgucuuacu gcaucagaug cugguucuuc 1440
aagaucccau uuaaauuccu uagugacuaa aaccauugug cauuguagag ggcgucuauu 1500
uauauucugc cugagaaagg aagugagcug uaaaggcuga gcucucucuc ugacguaugu 1560
agccucuggu uagcuucguc acucacuguu cuugacucag cauggcaauc ugaugaaauu 1620
cccagcugua agucugcaga aauuuccgaa uuc 1653

<210> SEQ ID NO 43
<211> LENGTH: 485
<212> TYPE: RNA
<213> ORGANISM: Homo sapiens

<400> SEQUENCE: 43
uuuuuuuuuu uuuuuucaug uuuaauaguu uauuucuuau uuuguugcuu auaucuucaa 60
uaaaucauuu ugcagguuuu guuacagauu uuugauaagc caacucaagu acugauuuuu 120
cauccucucu gaaaguuuua aaccaggaaa ggaaaacguu ccauggaauc caucuuccac 180
auggugauga gucacaugaa cuccaacauu cugaagccgc uugacauaca ugaguccauc 240
aucucuuagg acaucauacu ggcaagugau gauauagguc uuagguaaau gaugcaauau 300
auugucauug gccaacagag ggcaugccuu cacaucuaug aacccuggau acuuuugagc 360
cagcucagaa cuaccaggag ugggauuuuu guaaacggga cuuuucuugu aucucucagg 420
gagcaaggaa cuccaauuca caaacuguaa caaguggcua gauuccaugg guacauguug 480
guuga 485

<210> SEQ ID NO 44
<211> LENGTH: 3449
<212> TYPE: RNA
<213> ORGANISM: Homo sapiens

<400> SEQUENCE: 44
gagcacccgg gacccuggga ccacaacgca cuugcucccu cucgaccgcg cuccugaccc 60
gcagcccucg ccaacccuac ggauccuaac caccgccagc cuaggugggc gucaggauga 120
aggcagcccg cuucgugaug cgcagcgcca gcucgcugag cagcgccagc cugguccca 180 gggaggucga gcuguucucc cgcuacagcc cguccccgcu guccaugaag cagcugcugg 240
acuuugguuc agaaaaugcc ugugaaagaa cguccuuugc uuuucugcgg caagagcugc 300
ccguccgccu ggccaauauc cugaaggaga uugacauccu gccugaccgc uuagugaaca 360
cuccuucggu gcagcuggug aagagcuggu auauccagag ccugauggau uugguggagu 420
uccaugagaa gagcccagaa gaccagaaag cccugucaga guuuguagac acgcugguca 480
aaguucgaaa cagacaucau aauguggucc cuacaauggc ucaaggcauc cuggaguaua 540
aagacaccug cacaguggac cccguuacca aucaaaaucu ucaguauuuu uuagaccggu 600
uuuacaugaa ccgcauuucu acucggaugc ucaugaauca gcacauccuc auauucagug 660
acucaaagac gggaaaccca agccacauug gaaguaucga cccaaacugu gauguguag 720

-continued caguagucca agaugccuuu gagugugcaa agaugcucug cgaccaguau uaucuaacau 780
cgccagaauu aaaccucaca caagucaaug gaaaauuucc aggccaacca auccacauug 840
uguacguucc uucacaccuu caccacaugc ucuucgaacu cuucaagaau gccaugaggg 900
ccacggucga gcaucaagaa aaccguccuu ccuugacccc aguagaggcc acugucgucu 960
ugggaaaaga agaccuuaca aucaagauuu cugaccgagg aggcggguguu ccucugagga 1020 uuacugaccg ccucuuuagu uacacguacu ccacugcucc aacaccugug auggacaauu 1080
cccggaaugc cccuuuggcu gguuuugguu auggcuugcc aauuucucgu cucuacgcca 1140
aguauuuuca aggagaucug aaucucuacu cuaugucagg uuaugggaca gacgcuauca 1200
ucuacuuaaa ggcuuuaucu ucugagucug uagaaaagcu cccagucuuu aacaagucag 1260
ccuucaaaca uuaucagaug agcuccgaag cugaugacug guguaucccca agcagggaac 1320 cgaagaaccu ggcgaaggag aagcuggcag ugugaagcgg augacgccug acauuuuacg 1380
ggaucaaagu gggucugugg cauugcugcu ucgugaaugu guguggacuc uaguuuccgc 1440
aaaacaacgc aacacaaaac caagcaagca aaacacaaac acgaguacaa accuugaccu 1500
gaugagggac agagcuuggu uggaugaccc gggagaaguc agggcagggc uccaggggau 1560 aacaggugguc cugcuucucc uuuggcaaug caaaaugacu ccugacuguu ccaaauacug 1620
aaaagaaguc ugccucugag uuacagcucu uucucaacaa guacagaguu ugaggcuugc 1680
aguugcaaca gcuggauguu ugguguucu ugcugccagc caaauaaauu gguguuuagu 1740
gaacauuuuc aguguuuccc cgccaugcaa agcuuggcgc cuugggagaa augugguaa 1800 auguacauug uauagguauu agugugcucu agaaaggaca ggauggaagg aaucaaagca 1860
cuuuaucgag cuuguggcug agcauugcag ccuaugugca aacccagagg aaaaguaucu 1920
cugucaagac agcuccagua ucaugcagcu uuuuauguuu gcacucaaaa agccagugcc 1980
uucuggcugg ugccgaggcu ugggugaaau guuaaauaug cacugaccuc agaaagucga 2040
guucaaaagg gagauaaaau ugccaaagug auccaaggau ugugcauguu gggaaaccca 2100
uaugagagaa aggauucuca uacuuagaac uuuccuauga agaaauggug guaaacuuuc 2160
ucuaccuaga aguaguggaa auuucaaggu caucuuaaaa aagaugugcg uuguauauuu 2220
uaacuacauu cucuacacuc uaacauuaac auaucuauuc aaauuugucu aguugccaau 2280
ugucuucaga gugugaaaau uuaaauccuu cuugaaguau cuuucgugag aguaguaugg 2340
aaguaaaacg uucucauauc aggaggaugu cauuugugaa gcauggggac aucaugaacu 2400
agugaugugc gugaggcuug ggaggcugaa ggguaaggau cagcgggagg ccauccaugu 2460
aggagagaga auuaaaacga ggagcgaggg aagcaaugga gagagggaag caagaaagga 2520
accagaaggc uggcaucauc cuauuuccca caggcuaacc caagggaugc ucugugccuu 2580
uccuggggag ggaagggggu gaacugguag auuugaaagc aguauggcuu cuucuguggg 2640
ucucccucuu acuagacaag gugaaaugau aauucguguc aaauuaaugu gaaauuuuuu 2700
uccugcauug uaauauuaug aggccugagu cgcaguugag uuugaaauuu guauuuaauu 2760
ucacagugac cuagagcuaa ggugcucccg guuguggcaa uaggagccac aaguauuuuc 2820
uuucuuucuu ucguucuuuc uuucuuucuu ucuuucuuuc uuucuuucuu ucuuucuuuc 2880
cuuccuuccu uccuuccuuc cuuccuuccu uccuuccuuc cuucuuccuu uccuuuucuu 2940
uucucuucuc uucuuuucuu uuuucuguuu cuuuuucuuu uuuugcauug uagauguugu 3000
ccuuaaaaga ucagggcagu gacuuucaca gcaggacuuu gacucccaca uugguugauc 3060

-continued acacaaaacu gucagcauuu ggguaaucug auguauaguu guuuuguugc ugauguuucc 3120
auugaaauuu cagcucugag uuugugcaca ugaauacuua cuuguguuua ccaaaggucu 3180
aaggcauuug guuacuuaac ccaaauaucc ugaacugugc guaaaguaau agagaaaagc 3240
uuuagggucu caauaguguc accuguguaa aucaaaucaa aauagccuuc ccuauuauuu 3300
augaacccau gggagacuuu aaacucuugu agauagaugc uaaaugccca ggcccacuua 3360
acuuauuaau gugugaauua cauuuauguu uuuaguuuau augcaaagaa uugugauaau 3420
uuuauaauaa auauuuuuau uauaaauagu 3449

<210> SEQ ID NO 45
<211> LENGTH: 226
<212> TYPE: RNA
<213> ORGANISM: Homo sapiens

<400> SEQUENCE: 45
uuuucuuuuu uuuuuuucuu cucuuuuuuc ugccaccaac agcacugugc aguuuauuaa 60
ccauucaugu acaguagcca ucuggggaga uugggacaga auugggaucg caaaguggau 120
agauauucag caucuaaugg guuggcagaa gccgccauau acucuucaca aauaucuucc 180
acagucaaua cagaacuagc cauuauccca gcacaccgau uugugc 226

<210> SEQ ID NO 46
<211> LENGTH: 952
<212> TYPE: RNA
<213> ORGANISM: Homo sapiens

<400> SEQUENCE: 46
agccaggagc cucgccccgc agcugcacag agagcaaggg uauaggcacu aacuuguuug 60
cagagacccc aucaccuucg ggagcucagg ugcgcaccuu gcaaacucca cuuucugcau 120
cugccacuga gcccgcggga gccucggaaa gagccauggc caacgcgggg cugcagcugc 180
uggguuucau ccuggcuucu cugggaugga ucggcuccau cgucagcacu gcccugcccc 240
aguggaagau uuacuccuau gcuggggaca acaucgugac cgcucaggcc aucuacgagg 300
gacuguggau guccugcguu ucgcaaagca ccgggcagau acagugcaaa gucuucgacu 360
ccuugcugaa ucugaacagu acuuugcagg caacccgagc cuugauggua auuggcaucc 420
ugcuggggcu gaucgcaauc uuugugucca ccauuggcau gaagugcaug aggugccugg 480
aagaugauga ggugcagaag auguggaugg cugucauugg gggcauaaua uuuuuaauuu 540
caggucuggc gacauuagug gccacagcau gguauggaaa cagaauuguu caagaauucu 600
augaccccuu gacccccauc aaugccaggu augaauuugg ccaggcccuc uuuacuggcu 660
gggccgcugc cucccucugc cuucugggag guguccuacu uuccugcucc uguccccgga 720
aaacaaccuc uuacccaaca ccacggccuu aucccaagcc aacaccuucu agugggaaag 780
acuaugugug acagaggcaa aggaagagau cuuccuggag caaauacaaa auggacauug 840
aaccuaggau ugacauuaac gccuuagacu guugaugaug guuaucggaa cugugguaga 900
acagaaggaa gcauauuuuu auacaucccc auggcuaugc aggccuuggc ug 952

<210> SEQ ID NO 47
<211> LENGTH: 1777
<212> TYPE: RNA
<213> ORGANISM: Homo sapiens

<400> SEQUENCE: 47
cggcacgagc ggccacugac cgagaagugc ccccgccugg agucagccug ggggcaggcc 60 agggucccacc agaccccggg augaccgcag ccagucgggc caaccccuac agcaucguau 120
caucagagga ggacgggcug caccugguua ccaugucagg cgccaacggu uuuggcaaug 180
gcaaggugca uacacggcgc cggugccgca accgcuucgu caagaagaac ggucagugca 240
acauugaauu cgccaacaug gacgagaagu cacaacgcua ccuggcugac auguuuacca 300
cgugugugga cauccgcugg cgcuacaugc ugcucaucuu cucucuggcc uuucuugccu 360
ccugguuguu guuuggcauc aucuucuggg ucauugcugu cgcccacggg gaccuggagc 420
cagccgaggg ccguggccgu acacccugug ugcugcaggu ccacggcuuc auggcagccu 480
uucucuucuc cauugagaca cagaccacca uuggcuacgg gcuacgcugu gugacugaag 540
agugcccggu ggcugucuuc augguggugg cgcaguccau ugugggcugc aucauugacu 600
ccuucaugaa uggugccauc auggccaaga uggcacggcc caagaagcgc gcacagacuc 660
ugcuuuucag ccauaaugcc gugguggcuc ugcgugacgg caagcucugc cucauguggc 720
gcgugggcaa ccugcguaag agucacaucg uggaggccca ugugcgggcc cagcucauca 780
agcccagggu cacagaggag ggugaguaca ucccacugga ccagauugac aucgaugucg 840
gcuuugacaa gggccuagac cguaucuucc ugguaucacc caucaccauc uugcacgaga 900
uugaugaggc cagcccacug uuuggcauua gccgucagga ccuugagaca gacgacuuug 960
agauuguggu cauccuggag ggcaugguag aggccacagc caugaccaca caggcucgca 1020
guuccuaccu ggcuaacgag auccuguggg gccaccgcuu ugagccagug cucuucgaag 1080
agaagaacca guacaagauu gacuauucac acuuccacaa gaccuacgag gugccaucua 1140
caccccgcug cagcgccaag gaccuggugg agaacaaguu ccuccugccc agcgccaacu 1200
cuuucugcua ugagaacgag cuggccuucc ugaucagaga ugaggaggac gaggugucua 1260
ccgaccggga uguccgcacc ccucagcccg agcaugacuu ugacagacug caggccagca 1320
gcgcugcccu ugugcggccc uacagacggg agucggagau uugaaugccc uuggcuuaga 1380
ugcagcacca cccugaccac aauaggucccc augucccuug ggggccugcg uuugagcaga 1440
gcaggccgaa agccucgggu cacagacuca guagcaucuu agucuuuuuc auguuuuuuc 1500
gcaguagcuu gggaaaguug gcgggagcgu ggauggccca aaugacuggc ucacggccuc 1560
ggaggcugau guauacccau gggcaaggag gugacuucuu gggguagggu ugcucaggag 1620
uuagggacuc ugcuggaggc cuuaggugca ggucccaacc ccggugggag gaggcugugu 1680
auguacacuu cauugguuuu uaacuugggc aagacuguuu acaaaccaaa acaaacaaac 1740
aaacaaucca aaaaaaaaaa aaaaaaaaaa aaaaaaa 1777

<210> SEQ ID NO 48
<211> LENGTH: 175
<212> TYPE: RNA
<213> ORGANISM: Homo sapiens

<400> SEQUENCE: 48
uuuuuuuuuu uuuuguuccu uuuuuggaau ucccaaagcu gguuuuaauu ucaaaaaauu 60
augaggucuc uucccacacu ggggauaaug ggaugggaua gcccaaacua uuaucccagu 120
ucaaccccag ccugguccaa acaccauuac ugucacuggg cccugucauu ucacc 175

<210> SEQ ID NO 49
<211> LENGTH: 1629
<212> TYPE: RNA
<213> ORGANISM: Homo sapiens

<400> SEQUENCE: 49
uccucguccu cgucuguucc aucuucucca aauagcucua acugugaugc caacggcaau 60
cccaagaacg cugauaucuc uagcaucgau gguguucuga agagugaccg cacagauugu 120
ccugugaaaa caggcaaaac cagugcuccu ggcaugacua agagucacag uggaaugaca 180
aaauuuagug gcaugguucu acuguguaaa gucuguggg auguggcauc aggauuccac 240
uauggaguuc augcuuguga aggcuguaag gguuucuuuc ggaggagcau ucagcaaaac 300
auccaguaua agaagugccu gaagaaugag aacuguucca ucaugaggau gaacaggaac 360
cggugccagc agugccgcuu uaagaagugu cugucugugg ggaugucacg agaugcuguu 420
cgauuuggcc gaauuccuaa gcgugaaaaa cagagaaugc uaauugaaau gcaaagugca 480
augaagacca ugaugaacac ccaguucagu ggccaccugc agaaugacac cuuagcagaa 540
cagcaugauc agucagcacu accagcucag gaacagcugc ggcccaaguc ccagcuggag 600
caagaaaaca ucaaaaacac uccuucugau uuugcaaagg aggaagugau ugguauggug 660
accagagccc acaaggauac cuuucuguau aaucaggaac aucgagaaaa cucaucugag 720
agcaugccac cucagagagg agaacggauu cccaggaaca uggagcaaua uaauuuaaau 780
caagaccauc guggcagugg gauucacaac cacuuccccu guagugagag gcagcaacau 840
cucaguggac aguacaaagg gaggaacaua augcauuacc caaacggcca ugccguuugu 900
auugcaaaug gacacuguau gaacuucucc agugcuuaua cucaaagagu cugugauaga 960
auuccaguag guggauguuc ucagacugag aacagaaaua guuaccugug caacacugga 1020
gggaggaugc aucuggugug uccuaugagc aagucuccau auguggaccc ucagaagucu 1080
ggacaugaaa ucugggaaga auuuucaaug aguuuuaccc cagcaguaaa agagguggug 1140
gaauuugcaa agaggauucc uggcuuccga gaucugucuc agcaugauca ggucaaucug 1200
uuaaaagcug ggacuuuuga gguuuuaaug guacgauuug cuucauuauu ugaugcaaag 1260
gaacggaccg ucaccuuucu aagugguaag aaguacagug uggaugaccu gcacucaaug 1320
ggagcagggg aucugcucag cucuauguuu gaguucagug agaagcugaa ugcccuccag 1380
cucagugaug aggaaaugag cuuguucaca gcaguuguuc ugguaucugc agaucgaucu 1440
ggaauugaaa augucaacuc aguggaggcu uugcaggaaa cacucauccg ugcacuaagg 1500
accuuaauaa ugaaaaacca uccaaaugag gccuccauuu uuacaaaauu acuucuaaag 1560
uugccagauc uucgaucuuu aaacaacaug cacucugagg aacucuuggc cuuuaaaguu 1620
cauccuuaa 1629

<210> SEQ ID NO 50
<211> LENGTH: 831
<212> TYPE: RNA
<213> ORGANISM: Homo sapiens

<400> SEQUENCE: 50
auggcguuac uggaucugug cggugccgcu cgggggcagc ggcccgagug ggcugcccug 60
gaugcgggaa gcgggggucg cucggacccg ggacacuaca guuucuccgc gcaagcuccg 120
gagcucgcac uuccccgggg aaugcagccc accgcauucc ugagguccuu ugguggugac 180
caggaaagga auguucaaau ugagauggcc cacggcacaa ccacacucgc cuucaaguuc 240
cagcauggcg ucaucguggc uguggacucc agggccacug cagggaguua cauuagcucc 300
uuaaggauga acaaagugau cgagauuaac ccuuaccugc uuggcaccau gucugguugu 360
gcagccgacu gccaguacug ggagaggcug uuggccaagg agugcagguu guauuaucuu 420
cggaaugggg aacgcaucuc cgugucugca gcauccaagc ugcuuuccaa caugaugcug 480
caguaccggg ggaugggccu cuccaugggc agcaugaucu guggcuggga caagaaggga 540
ccaggacuuu acuacguaga ugacaauggg acucggcucu cgggacagau guuuuccacu 600
ggcagcggga acaccuaugc cuacggggug auggacagug guuaccggca ggaccucagu 660
ccugaagagg ccuacgaccu uggccgcaga gcuauugcuu augcuaccca cagagacaac 720
uauucuggag gagucgucaa cauguaccac augaaggaag acgguugggu gaaaguggag 780
aguuccgaug ucagugaccu gcuguacaag uaccgagagg ccgcucugug a 831

<210> SEQ ID NO 51
<211> LENGTH: 3601
<212> TYPE: RNA
<213> ORGANISM: Homo sapiens

<400> SEQUENCE: 51
auuccaggag uuccagcugc uggagaggac uguguagaag guaaccuacc ccaucucucu 60
uacuucgucu cuagauggga gcagacaagu acauauagcc ugcuuggagc gaggacuuug 120
aaaggcugag acuugcgucc acucugaggg caacuagucc agacucugac aggucagcau 180
uuccugacug ggugcacuga augccaagca ccagaggucu gucaccuucc gacauuggac 240
caagagaguc ccagagaccc ucaaagacac aggaacagag guguccuuug ggugagagac 300
cugugcccug ccaagccucu cagccccuag aaaggcggca gggcugagua gcugagugug 360
ugcaacuugg gagcagccug auuucagugc uugucaccug ugagggcaaa ggcagcaugc 420
uuaaugccau caguccuacu cuucucaccc guggaacaga cgcauaacug accuuuuuuc 480
gugaccacua uuagggugca uuuaaaaauc aaucucucuc uuuucugcuc cucuuucucc 540
accuucccuc augugugugu cugugugugu guguuucugu gugugugugc gugcaccaua 600
cagguauaug ugccaugaca ugugugcagg ucaguagaca gccuugguug ucagucccug 660
ccuucuacuu uguucaaggc agggucuauu cuuuauuauu gacugcuauc cagguacacc 720
aagacaguug gccugugagg uuccagggag ucuccugucu cuggcccccca ucuuauagca 780 ggaguuguga gauuucagaa augugcaccc acaucuagcu uuauuuggca ucuuggcacc 840
caaacuuggg uucucaugcu uuccaagcaa ggacuucacc cacugaacca ucucaccagc 900
uccacuaugg cgguuuucug aaacugaagg gaguggggag aaggcgcuga gugugaacgg 960
gucuggaagg cggguauaac cuuuaaggcu ggcugguucu gagagaggaa agccggcuug 1020
ugucccauuc aggugccagg ugcagcauca aauguggcuc cacccaacgg ucaguaacuc 1080
cgcagacagc accgugguua acugccucac agagggggcc cagggaccua guuccuuaaa 1140
gcccacuuag uuuugagaga cgacauggag gggcaagccc agcccugucc agcugcauuc 1200
acacgaggcc cuucuccucc gaggacccua ccuuuguguu uaguggcuga ggcugugugg 1260
cucugcuuga agcucuggcu aucaggaagg accuggccca ccggcuggca ggacaaacug 1320
gcccagugaa ggcacugucc ggucuccugg uggaucacaa ggaaaggggc guggcauguc 1380
cagauuugaa cccuggaugc cucuucccag gguaggaagu cuaaggguca acaugaauag 1440
gugagggugg ugguggaaag aaucugcaug caaaaucagg cacucauguc ugacaucguc 1500
aaacacuaua uuuauguaga uuuauauggg ggugaggcuu ggggagcacu uguauuuuug 1560
ugugcaauug caagagcuuc cuccacauug caguguuaaa uaucauaugg ugcuggacca 1620
accaucucug gaacgagggu gaggguuugg uacccgugac uaugguucuc uguguaguag 1680

-continued

```
aaacggcuuc uugggaagag agaggaagug cuuugaaaug cauccucucu uguuucauuc   1740

ugcaucaugg ccagguuucu cugcacaaag augcaauaga cauucaggaa aauaagcgca   1800

uugcaagaug ucaaaaguca ugaaaaauga aaagcaaggu cacugcagcu ggggugu agu   1860

guggcuguag aagcacguuu augauguaca gguuccggga gagggaggaa gagagaggga   1920

gggaaggagg aauggaggaa gagagggaga gggagcaaga gaggggggag ggagggaggg   1980

gagaagggag agagagagag aagaaagaga gggagggaag aaggaaugga ggaagagaga   2040

gaaagagggg aagaaagaga gggagggaag gaggggugga ggaagagaga ggugugaggg   2100

auggagggac agagagggag ggaaggagaa auggaggaag agagaaacag agagauggag   2160

gaagagagaa aagucaccaa uuauuuuucu ccccagucgc ccccugcccu cacaccaagg   2220

guacccccac uuuucuuuca cucaugcaca cacacuacac ccaauguuua gguaacacau   2280

guagggcagg cagagccuuu gugaaugugc uugguaguuu ucugccuuac uucuaaauaa   2340

ccaaucacac ggaugccaca ggguuccuuu agacugucca gggcuccggg gcucuuagac   2400

uguucccaau gugggugucA caugcaaaca guaagcaccu ucuuguuugu ggugcccagg   2460

augcugcagg uacuagaaau uccugcacag accuuugcua cuucuacaca gacuuacccu   2520

uuaaaacauu uaauuauaug uuuuuuucag cauaaagauc uauuuugauu auuuuuaguu   2580

gcguguaugg gugugugccu gugugugauu guguaauugu cuguauggga guguaagugc   2640

cuacagaggc aucggauccc cuggagcugc cguuacaagu aagggacugg gacucagacc   2700

ugagugguuu ggaugagcag ugaaugagcg uggugagcca ucccaccaug cccuauaaac   2760

acuuucaaga ggacuuugcu ggguaugguc aaguuguccc ccugcgacag ccaccccaac   2820

uugccauccu cauuuacugu acuggaagca gcaaccaccu cugcaauuuu gcacaagaac   2880

cugagagucu gaaagacuuu uguuggcacu ggccuguguu ccacuggggu ggacacauua   2940

aucuaaaagc uaagaagcuc acuucagcuu ugccaggcaa ccagcacguu ugagcacaac   3000

gguguagcca ggaagggugu gugggaauuu ugaugcuagu uuuucuuuaa uuagguugag   3060

agugaaauca uggucuguau gcauccaaca acuuaaucca aaaaguuggu ugcacggcuc   3120

cuggaagguu uaccggcaag gaaccugucc cauuuuguaa guagguggga cuggagaguu   3180

gccaagaagc cccccucccu gcccccuucc uccuggcaga uucugcuuaa aaugagugug   3240

guucacugca gaauaguguc accugucuuc agaugucuaa agacauaaga aaggccuagc   3300

cagcuaaguc agaaaagggg acuuuccggu gggaaugcau uuuccagucu cuaggagaag   3360

ucuuuaucca aauaaaauua gcauaguggu ggagucacug ccagggcgcu ggugcggaag   3420

cacagcccag agccgaggac guggccaucc uccuuccucu gaugcaaagu guucucuauc   3480

cccaguuacc augagcaaua ucaguagcau cgugaaccgg gcccgugaug ccuuuaacuc   3540

aggcaagacu cgaccgcugc aguuccgggu ugagcagcug gaggcguugc agcgcaugau   3600

c                                                                   3601
```

<210> SEQ ID NO 52
<211> LENGTH: 329
<212> TYPE: RNA
<213> ORGANISM: Homo sapiens

<400> SEQUENCE: 52

```
uuuuuuuuuc caaaaaauuu uauuggggga aacuacaaaa cauuuacagu acaauguuua     60

cagucacaau uuguagugaa cugauucccc aaaauauauu acaacucaag uugacuuaau    120

cuuguuacau ucaaaaaccu acuucuguca aaguagucca gagugcacac gcggugcucc    180
```

aacuguaccu acauacaaac uaaacaacug cucauuuauc ugccauccag gaaagccgga 240
gacauuccug ccucuuuaca uugaaaaaua auaguacaag uuuuuggacu gucauugaac 300
aaggcauauu cauguaccac caacauuuc 329

<210> SEQ ID NO 53
<211> LENGTH: 3671
<212> TYPE: RNA
<213> ORGANISM: Homo sapiens

<400> SEQUENCE: 53
ggugauccuc caggaccuaa gguuucggua uuaucuucgg ggccucuuca cccggaggug 60
agucugcuga gcccgaccuc agguguucac ucgucacgcg agggccuggc cacggcgggg 120
aagcacuggg agagagcggg aggccuugac cgcagcgugu aggaucuggg gucccggcgc 180
ucugcucccg ggugcagagu gguuggagca ugcgaggccc ucugcagcgu gcucuguucc 240
uaccaucacc ccaccccac cccaguccuu ccugcacguu ucuggagagg caaaggcccc 300
ugcugagccu ucacugggua ccccuaucuc gacuccacuu gucugcuugg gaucuccaaa 360
gggggauaca cccucguaaa cuagagcagg aggcuggggg guggggguag ggguaggguc 420
ugaccaguua gauugaggcu ggacccuccc cagagugagg agcgggaagc ucuuugucuu 480
auccaggauu uugcauauca augcugaggu ucuggugauu aaguaggguc ccuggcuagc 540
ggggguaacc ugaacaaccu uccuccgcug gccgcuagcc aauagacacc uggcuuccgc 600
ggaugagccc uuugaguuug uggaggugu ccucaggucc ccagggcccu gccccguugc 660
cugcagaugu guggacagac aaaacauugg acucguuuuc caaccacuuc accccuuccu 720
ucgcuagucc uccgguggac gaugggaugc cucauugacu uguuuguggc ugugcaugcc 780
agagcuuccu agcagacagc ucagggcucc aucguuccua aaucccacug uguaacgaaa 840
aaaaaaaaaa caaaaacaac aacaacaaca acaacaaaaa caaaaccaga aaugaggaca 900
ggcccagcug ggcuuggcac ugaacuuggc caccuggagc uuuggcuacc cacuacaaga 960
ugucagcaag ucucaggaua gaagaggccu aaggccaguc cuggaagaua ccaaaacuuc 1020
accuccucua uaccccguuc cucuaggaga acuguaagcc accuuugucu cugggacgcc 1080
ccucucccac ucaacagaug gcaccaguca ucuuccuccu caagaggcca gugguauuca 1140
aaauaggaua uugaaaccaa gcaagcuggu ccucuccucu acccuaugcc aaagacuucu 1200
gcccaaaggg cccagaaaag ucccauagcc aucuggcugg cuagugugcu gacugcuaca 1260
ggugucagug uccccagcga gcagguagug gaguggaggu gucuucuugu ggaaaugggu 1320
ccugagccuc uaccuuguac agaaaggaau uagugaagcc cagaggccuc cagcccgugu 1380
cucugccaca agagagaggg gguggggggug gggcuguauu ugguucccag ggcucaggga 1440
agguuuucgg uucaugcaug cucauuuauc ugaccacugu cuuaacccca ggacaaccac 1500
uuaacugucc acuuccauau cagaguucuu gguuccccuu uacuucgucu auggagcccc 1560
ugaguuuggg aagggguauu aacugaaagg uaccauuaga ugaacuugga gaaagauuug 1620
uaggugccac gggagauuuc agguaaaagc ucuuuuaaua auuggcuaca auagcagcag 1680
gaggaggcca ggaauucuga gguagagauu ugauuagcag cacguggagc aaaggagacu 1740
ucugacuccu acagguuuca gaaagugggg agaggcucuc agaugaaugg cuuggacugu 1800
gagguaagug uuaguguagc acgagacuag cuuaaggcug uacaaauugu ccgucugauu 1860
ggugcauugg gccagguaga cacuagauaa gcaauugggc cuuaacucga guugucuuaa 1920

-continued uggcuacccc cagggcagca gggagucaau acugcucucc ugucuggggc cugaaugcug 1980
aaaccaucua caaaggggac auaaggcaua uuggggaggu guagaguggg ccaggcccag 2040
ggucugcugg uaucuaugcc aggauccuga gugguguggg cguagccugu cuuuuaacca 2100
acugccucuc ucacaguagg cuucuuuggc uugcgaaccu ucagcagaug ucugccacuu 2160
ccaacaugag agucuuccug ccugugcugu uggcagcccu ucugggcaug gagcaaggua 2220
uggagcucug agauaacccu gcagccuggu ccuccuccug aucucucauu cuuucuccug 2280
aguagaugcc cagggcuccu ccugagccag cccuccuagg aacgucuggc cuucccaccu 2340
ccuacucucu agccaacuga ccuaguuccc cugaugcugu gcuggcccag cuacaccuuu 2400
gucaccucgu guugacuuua gccacuccag uaccaaaguc ugaagucagu ugucauuggc 2460
uggcuuuuuu cccugaccca gggcugagca ugcuguugcu ucuugucagu ggguugggga 2520
ucaagggccc cacuggaaag ucaccuuacc cuggaaggcu uccccaggca auaggcaggu 2580
gucaccuaca gcauuguccc uuuugcaguu cauucccuga ugugcuucuc auguaccgau 2640
cagaagaaca auauaaacug ccuguggcca guuucaugcc aggagaaaga ccauuacugu 2700
aucacguuau cugccgcugc gggcuuuggu gaguagcugc cuguuucccu agccagggcc 2760
agggaccugc ggggcuuucc ccauuuccug cuacccuguc ugucuguccc cucauccuca 2820
cuuuccaugc agggaauguc aaccuuggcu acacccugaa caagggcugc uccccgaucu 2880
gccccaguga aaaugucaau cucaaucucg guguggcguc cgugaacagc uacugcugcc 2940
aaagcuccuu cugcaacuuc agcgcagcug gccucggacu ucgugccagu aucccacuac 3000
ugggccuugg acuccugcuu agcuuguugg cucugcugca gcugagcccc ugaccauccc 3060
ccauguguuc uccauauccc cccagcucag gaaaagccca gcuccuuuua ggucccaggg 3120
gacccuagga accuucagcu ccuccugggu gugucuaguu cccccuccac acucucucaa 3180
cgucagggcu aaguaccaaa cucacccaua ccugcucugu ugaaguggua cuggcuaccc 3240
uugcuuccag agccaauccu auaaccuccc uuggggaacc agcgaagggg ugaagaucuc 3300
cuuggagucu caagaguacc agagucagcg ccgaaucuug uggacacacu gacaaggaug 3360
ucuaauccaa auagauguau aucugugugc ucaguguauc ccugugugaa ugaagccacu 3420
uggauucugg ggugggcaaa gaagaccuga aaagauucua cagcagaagg ccugugucgc 3480
caccaaaacc ccucccccug guaucauugu acccaccuug uacucuguuc aggaggcugc 3540
ccauggagga cugccacccc uccagaugaa ggcucccacu acccgaugca guugaguccc 3600
auccugcccu cucugcccac acuggcuucc ugcugcuauu cuagugccuc aaauaaaccg 3660
uucacacccu u 3671

<210> SEQ ID NO 54
<211> LENGTH: 951
<212> TYPE: RNA
<213> ORGANISM: Homo sapiens

<400> SEQUENCE: 54
cuuccucccu cuacagaaga agagcaagaa gaugaggaag aaauugaugu ggugucugug 60
gagaagaggc aaaccccugc caagaggucg gagucgggcu caucuccauu ccgaggccac 120
agcaagccuc cgcacagccc acugguccuc aagaggugcc acgucuccac ucaccagcac 180
aacuacgccg caccccccuc cacaaggaag gacuauccag cugccaagag ggccaaguug 240
gacaguggca ggguccugaa gcagaucagc aacaaccgca agugcuccag ccccaggucc 300
ucagacacgg aggaaaacga caagaggcgg acacacaacg ucuuggaacg ucagaggagg 360

```
aacgagcuga agcgcagcuu uuuugcccug cgugaccaga ucccugaauu ggaaaacaac    420
gaaaaggccc ccaagguagu gauccucaaa aaagccaccg ccuacauccu guccauucaa    480
gcagacgagc acaagcucac cucugaaaag gacuuauuga ggaaacgacg agaacaguug    540
aaacacaaac ucgaacagcu ucgaaacucu ggugcauaaa cugaccuaac ucgaggagga    600
gcuggaaucu cucgugagag cuaaggagaa cgguuccuuc ugacagaacu gaugcgcugg    660
aauuaaaaug caugccaaag ccuaaccuca caaccuuggc uggggcuuug ggacuguaag    720
cuucagccau aauuuuaacu gcucaacuaa auaguauaaa agaacuuuuu uuuaugcuuc    780
ccacucuuuu uucuuuuucc uuuuaacaga uuuguauuua auuguuuuuu uaaaaaaucg    840
uuaaaaucua uccaauuuuc cauguaaaua gggccuugaa auguaaacaa cuuuaauaaa    900
acguuuauaa caguuacaaa agauuuuaag acauguacca uaauuuuuuu u             951
```

<210> SEQ ID NO 55
<211> LENGTH: 1822
<212> TYPE: RNA
<213> ORGANISM: Homo sapiens

<400> SEQUENCE: 55

```
gugggacggg ccccccucga ggucgaccca cgcguccggg aguacccccg accuuggcug     60
cgugcugacu cgcuuccuuc ugccugccca ggcuugcacu ccccggggau cugccucugc    120
aucucuugcc uucgcuguug uuucccucuc uguccagcuc cccucccgcu cucgcccugg    180
agaauggcuc agaaggagaa cgccuacccg uggcccuacg gcucaaagac gucucagucu    240
ggccugaaca cguuguccca gagaguccua cggaaggagc cugccacgac aucugcgcuu    300
gcucucguga acugguccaa cagccagucc acagcugccc cuggccagaa guuggcugag    360
aacaagaguc agggcuccac ugccucgcaa ggaucccaga acaagcagcc uuucacuauu    420
gacaacuuug agauugggcg uccuuugggc aaaggcaaau uuggaaacgu guacuuggcu    480
cgggagaaga agagccguuu caucguggca cucaagaucc ucuucaaguc ucagauugag    540
aaggaggggg uagagcacca gcuucgccga gagaucgaaa uccaggcgca ccugaaacau    600
cccaacaucc uucaacucua caacuacuuc uacgaccagc agaggaucua cuuaauccug    660
gaauacgccc cucgcgggga acucuacaag gaacugcaga agagucggac cuucgaugag    720
cagcggacug ccacgaucau ggaggaacug ucagaugccc ugaccuacug ccacaagaag    780
aagguaauuc acagagacau aaagccggag aaccugcugu uaggucugca gggagaacug    840
aagauugcag acuuuggcug gucggugcau gccccauccc ugaggaggaa gaccaugugc    900
ggcacgcugg acuaucugcc cccagagaug auugaggggc gcaugcauaa ugaaauggua    960
gaucuauggu gcaucggggu gcucugcuau gaacugaugg uggggaaccc cccuucgag    1020
agcccuagcc acagugagac guaucgucgg auugucaagg uggaccugaa guuccccucu   1080
ucugugccuu cgggcgccca ggaccucauc uccaagcugc ucaaacauaa ccccuggcaa   1140
cggcugcccc uggcggaggu ugcagcucac ccuugggucc gggccaacuc aaggaggguu   1200
cugccucccu cugcccuuua gccugcuccu ugguuuuuug ucccugucau uuuucagugu   1260
ucuuuguaug ucuguguaug uguucugaga aggggurggga acuggaaacu auuccuagcu   1320
ccaguucuag ggaucugau cucucuucug accucuacag gcaaaauuag gcaccccugu   1380
ggugcacaua uaugcacgcc aaacacauga aguuacaaac aaacaacaaa cacacagaua   1440
gugcuggaga gauggcucgg caguuaaaag cacuggcugc ucuucccagg aaccuagaac   1500
```

ucaauucuag cacuacaugg ugcucacggc cacugucugu aacacccagu ccuggggaau 1560
cuggggccuu cgagccucug caggcacuag gcauggaugu gguauacaug uaugcaggca 1620
aaacacccau gcacugacuu uuaagaaacc cucuagucug auuccuuuca auuugucaaa 1680
uguugaaugu uauuuuuaaa auauuauaag ccauuuaaua caauuuuucu uugaaacaug 1740
guauagccua gucugucuua aauucagaaa aauuaugaag aacaacauuu uauaauaaag 1800
ucuuaaaugu uucauguuuu ug 1822

<210> SEQ ID NO 56
<211> LENGTH: 2663
<212> TYPE: RNA
<213> ORGANISM: Homo sapiens

<400> SEQUENCE: 56
uugccuagga agggcgcguc gucucucugc ucguccggcu gugacgggga agggucccgc 60
ugcguuuugg ucacugugag uaccaaguuu gggggauccc cgagggacuc ucgagagcuc 120
auuuuaggga ugcaggggcu acuccccggu gguagagagc uuucuaguug gcaggagguu 180
ucguaugugg aggaggccag cuuaggcaga aagcacaugu ucucagagau gaggacaaga 240
cuaagaccgu cuaaucccug aucuuuaccu uccggcccgc ugaccugggc cuggaugcua 300
aagcccucug cuuucgucua aacagcgcua aauaguaaac aguauugccu aagauaaaug 360
cggauuauua cccgauucag ugucgggaaa aggcagcuag gagagagcgg cuggcacgug 420
guaagcacac gguaaguuuc gguuaaauua aaacaaccau ccguugagca ucucuuagca 480
agcuccuucc acccuucaaa caaucaguga uagugcgucu guuucacuga uuagggagcu 540
aaggcuccaa cagcagcaaa ggaacuaauc cgccucugau caacauggcg uuucuuacag 600
ggcauuccuu auacgcuuuc ccacgugcgu aacaggaauc gggguguuccc ggguuuuguu 660 uuguuguugu uguuuuuguu uuguuuucuu agugaaagag gcaggguggg cuccaggccg 720
cugaggauua auaaagagau ucuaugagga ggaaauaaca ggcagguggu augaucgagg 780
caaggcccug aggaaggcuu ggguggggug aguagaacca gagccggaag uccacucagc 840
agccuggggc acuuaaagcu ucugcugggg caaaugguaa ggcggcguaa ggucacauuc 900
cuuucauuuc uuccagacuc aggaggagac cacaccuucc ggagaaccag gccugaaccg 960
agguacuauu uuguagcucu cagaagccag gacucugcaa cacuguuugc ugccugugga 1020
ucuucuauau ucacaguguc ccaguugcuu cugaucuacc acuguuagau acuucugcca 1080
cccauccuaa gaguauaguu guucuuggaa aggagucuca gcugcuguca gcaggagucc 1140
cucauucgac uccugugguu gcccuuucca ccaugccaaa gaauaaaggc aaaggaggca 1200
aaaacaggcg cagagguaaa aaugaaaaug aaucugagaa aagagaguug guguuuaaag 1260
aggaugggca ggaguaugcu caggugauca aaaugcuggg aaauggacgg uuggaagcaa 1320
ugugcuuuga cggugugagg aggcugugcc auauaaagagg gaagcugaga aagaagguuu 1380
ggauaaauac cucggacauu auauugauug gucuacgaga cuaucaagau aacaaagcug 1440
auguaaucuu aaaguauaau gcagaugaag caagaagucu gaaggccuau ggagaacuuc 1500
cagaacaugc caaaaucaau gaaacggaca cauuugguccc uggggaugau gaugaaaucc 1560
aauuugauga uauuggagau gaugaugaag acauugauga caucuagccu gaccuaagca 1620
ugcuaccuuc caaguucucu gaagauagcu ccacacagug gcaucuugac cuucaucugu 1680
uaaguaaaac uucauggcau guguaugacu uguuaaugca agcuaaugaa uuuuauuuuu 1740
ugaaguacua uauuucuuug aaaaccaaag auguugaguu aucaucuuaa gugacauguu 1800

-continued aacacuuugu gcuuuugaau auaaauugaac cuagcgcaca gcagugagca cuguuaagag 1860
acugccuuuc cauuuguagc uucauuucug gcacgggagu guuuuguguc agcaguucug 1920
ccagguggcc aucgaugagc ugaaguaagu ccuaguccag cacaucugcu ucaggccuuu 1980
guacucuagu caucuggcug cguucgagac uucucagcag aacuuauaga uguguacggc 2040
ugcacuugga gucagacaag auauggcuac uuuuguacuu auggagccau gccauuuuau 2100
acuuucacgu uguauacauu cguuugaccc uuuaaguugu ugccacccau aaaaaggcau 2160
cuuacagugc aguuuuuaaa uuacaugggu agcaauuuug aguuuuaaaa auuagucauu 2220
gcagaaauua aauacuuaga ggagauaauc cauuaucuug auuuuaggaa uauaauaguu 2280
gacaauguuu auauauaauu uuacuucucu aaggcauacc caaaaauaga aaaugaaaaa 2340
gagcagugag ucuguucuga ugcuugcauu gcauagagaa guuuuccaac aaagcagcug 2400
uuaauaacac auaaaaauaug uuuuacuuug caaaguaggu uguguuaagu cauuuucaaa 2460
aaguuaccua cuauaucgag gcucuggaua auuacuaugu guugauuaaa guuaguuaca 2520
gaauuguaca agcuaaguuu uccuuaaacu aagcuuaggu uaaagggaga ggagccacag 2580
cucaaugaaa acacgguucc uguuuucuaa auggaggcgc ccagaaacac aauaaaacau 2640
guugguacaa aaaaaaaaaa aaa 2663

<210> SEQ ID NO 57
<211> LENGTH: 884
<212> TYPE: RNA
<213> ORGANISM: Homo sapiens

<400> SEQUENCE: 57
caugauccca gccacccgcu cgcuucucug ugcagcgcug cugcugcugg ccaccagccg 60
ccuggccaca ggggcgccua ucgccaauga gcugcgcugu cagugccugc agaccauggc 120
ugggauucac cucaagaaca uccagagcuu gaagguguug cccucagggc cccacugcac 180
ccaaaccgaa gucauagcca cacucaagaa uggucgcgag gcuugccuug acccugaagc 240
ucccuugguu cagaaaauug uccaaaagau gcuaaaaggu guccccaagu aacggagaaa 300
gaagacagac ugcucugaug gcaccgucug gugaacgcug gcuucugaca acacuauaca 360
auuucuuuug agggucuau uuauuuaugu auuuauuuau uccacaaagu gugugguuuu 420
uauuuuacau uaauauuuaa caguguggau acauuucauc gaugguaguu caguucugcu 480
uguucaguuu aaagauggua ggcuuaaaau auuucauuaa aacuaauauu uauugggaga 540
ccacuaagug ucaaccacug ugcuaguaga agggguguug gcgaaaagaa gugcagagag 600
auagaguuua guauuauguu uuguauguau uagggugagg acaugugugg gaggcugugu 660
uuguaugucu ugaaaagaau gucaguuauu uauugaaagu cgucuuucau auuguauggu 720
caacacgcac guguugacgc uucccuugga cauuuugugu cuaguuggua gcccauaaug 780
ggcuuuuaca uucuuuaacc cuguuucucc uggucucguc ucgcucggga cagagacguu 840
caaaggacug uuacaaauga aguaaaaaua aaaguuuuau uaag 884

<210> SEQ ID NO 58
<211> LENGTH: 1310
<212> TYPE: RNA
<213> ORGANISM: Homo sapiens

<400> SEQUENCE: 58
cgucucccgc auucgucugg gccgugcacc ugcccgcuag cucgcugcac uaccguugcc 60

```
cacaagccaa caugcugccg agauugggcg gccccgcgcu gccgcugcuc cugccgucgu    120

ugcucuugcu gcugcucuug ggcgcgggcg gcugcggccc cggggugcgc gccgaggugc    180

uguuccgcug cccacccugc acgcccgagg cucuggccgc uugcgggccc ccacccgacg    240

cgcccugcgc cgagcuggug cgagagcccg gcugcggcug cugcuccgug ugcgcacggc    300

aggagggcga agcaugcggc gucuacaucc cgcgcugcgc ccagacgcua cgcugcuauc    360

ccaacccggg cuccgagcug ccccugaagg cgcuugucac aggcgcgggu accugugaaa    420

agagacgcgu gggcaccacc ccacagcagg uugcagacag ugaugacgac cacucugagg    480

gaggccuggu ggagaaccac guggauggga ccaugaacau guugggaggu gguagcagug    540

cuggccggaa gccccucaag ucaggcauga aggagcuggc uguguuccgg gagaagguca    600

augaacagca ccggcagaug ggcaagggug ccaaacaccu cagucuggag gagcccaaga    660

aguugcgccc gccucccgcc aggaccccuu gccagcagga guuggaccag guccuggagc    720

ggaucuccac caugcgccuu ccggaugauc ggggcccccu ggaacaucuc uacucccugc    780

acaucccaa cugugacaag cauggccggu acaaccuuaa gcagugcaag augucucuga    840

acggacagcg cggggagugc ugguguguga accccaauac cgggaagccc auccagggag    900

cucccaccau ccggggagac cccgagugcc aucucuucua caacgagcag caggagacug    960

guggggccca ugcccaaagu gugcaguaaa ccccagccag ucggugccug gcuuccccau   1020

cccgaacacc agcagaaaug gagggcguca gggugacggg uguggaggag uucccaguuu   1080

ugacacaugu auuuauauug gaaagagacc aacacugagc ucagaagccc cccucugacc   1140

ccccccagcg gcuguuaacu gaaccucccu ugcuucuguu agagagggga aggguggua    1200

ggagggcacu ggguacaggc cugggaaugg ggaaagaaau uuuuauuuuu gaaucccugu   1260

gucucuuuua cuuaagauua aaggaaggaa aaauaaaaaa aaaaaaaaaa              1310
```

<210> SEQ ID NO 59
<211> LENGTH: 487
<212> TYPE: RNA
<213> ORGANISM: Homo sapiens

<400> SEQUENCE: 59

```
gaugugaaaa acguuuuuau uauaaucucu uaaacuuuca guguauauuu ucauuacaau     60

cauugguaca auaaaauaugg aaaugcugag cagacaauua ucacaguggc cuaugggcug   120

agggacaggg acccaggaau acuguuaccc uggauacuuc cucagggcca aucaggaggu    180

cuucaaagag uauugagagg gagagggaua gaaauauuau uaagacuguc agugcagcaa    240

cuuuuagaau gucuauuaaa gccauggaua caggauuuac gauaacagaa gauggauacu    300

aaaaaagaac agagacucaa guucuccugu aagaggcaga agaaacauug cagaagccag    360

ugccuuccuc ggguccccag ugugugcccc cauccaccca cgcauugugu uggucaucuc    420

caccugcccu gugcccagcc cugugcccac ccagguucuc cuaggcaccc accuugcacc    480

ucgcacg                                                              487
```

<210> SEQ ID NO 60
<211> LENGTH: 1430
<212> TYPE: RNA
<213> ORGANISM: Homo sapiens

<400> SEQUENCE: 60

```
gaauucugcg cgguuuugca uuuuuugggu cagauuggcu uuuuacauga uuacgaagcu     60

ccaacgacua gaccacaggg accgucgccu uggcggccga gcagucguau ccaacuugga    120
```

gacagccagu ucgccgugug ucugucuguc cuucaucgca gucauggaga gagccagucu 180
gauccagaag gccaaguugg cugaacaggc cgaacgguau gaagacaugg cagcuuucau 240
gaagagcgcc guggaaaagg gcgaggagcu cuccugcgag gagcgaaacc ugcuuuccgu 300
agccuacaag aacguggugg gcggccagag agcggccugg agggguccugu ccagcaucga 360 gcagaagagc aacgaggagg ggucagaaga gaagggcccc gaggugaaag aguaccggga 420
gaagguagag accgagcuca gaggugugug cgacaccgua cucggccugc uggacucgca 480
ccucaucaaa ggggcuggag augcagagag ccgcgucuuc uaccugaaga ugaaggguga 540
cuacuaccgc uaccuagccg agguggccac uggcgaugac aagaagcgca ucaucgauuc 600
ugcccgguca gccuaccagg aggccaugga caucagcaag aaggagaugc cgccuaccaa 660
ccccauccgc cugggccugg cccugaacuu uucagucuuc cacuacgaga uagccaacag 720
ccccgaggag gccaucucgc uggccaagac caccuucgac gaggccaugg ccgaccugca 780
cacccucagu gaggacuccu acaaggacag cacccucauc augcagcucc ugagagacaa 840
ccugacgcug uggacagccg acagugcugg ggaagagggu ggugaggcuc cggaugaccc 900
ccacaucuga agcagcggaa aaacaacccg gguuggcuug gccuuccagu ccccagccug 960
gcauagagga uuaaaaggga gugggauuuu gccuuuccca aacccugaau guucagcaac 1020
accuugggaa ggucuuucga agggggcgca gccaagcuga agccaccagg gcagggaauu 1080
uaauuuuucg uguagcuguu uggguggggug uuucccaaaa ccaucccacc ccuguuuuuu 1140
gaacccccuc cccaauucuu cccccugagc cucccucggg caccuguugc uuuuggaucc 1200
gaauaaucca ggagguuccc cacccugugg cugagaaaug gacuguggca agggcugugu 1260
gugugugaga gagagggaaa cucugugugu guguguguga gagagagaga gagagugaau 1320
gagagggaaa aaguuugcug ggugugacca ugguaccaau caauaaaguu gcccugugag 1380
acucaaaaaa aaaaaaaaaa aaaaaaaaaa aaaaaaaaaa aaaaaaaaaa 1430

<210> SEQ ID NO 61
<211> LENGTH: 268
<212> TYPE: RNA
<213> ORGANISM: Homo sapiens

<400> SEQUENCE: 61
uuuuuuuuuu uuuuuuuaaa uaccaaaaca uuuaauugaa auaccuguau aaaaaauaug 60
aucuucagac auuucacacu uuugaacuua uacaacccca ccccugaugc uuagucacac 120
cagggucaca gaaacacagc ugcuaaaaua aauuaagggc uugagacucu guccccccaac 180 cccagcuuuc agagccagca agcagacugu acaaggucaa uaauuuaaac cccuccccag 240
cgcagagugc ucagggugac agggucuc 268

<210> SEQ ID NO 62
<211> LENGTH: 377
<212> TYPE: RNA
<213> ORGANISM: Homo sapiens

<400> SEQUENCE: 62
uuuuuuuuuu uuuuuuuaau guaacgaccg gugugcuuca guuuguuuag cagaaccacu 60
cucuugaauc acauuaacuu uugagauuua aaaaaaacaa aacaaaaaaa aaaaaaaaca 120
acaaaaaaaa aaccaacccu ccauagcaca gcugucuuuu augcaagcaa gagcacaccu 180
acuccagcau gauuugucau cuaaagacuu gaaaacaaaa caacaacaac aaaaaguuac 240
uuauagucaa uggauaagca gaguccgaau uuacacuaau caagacagac cuucgagggg 300
ucacgauaag uccggaacuu ucaaaccuug cuucguauga auuguacuau cugaacauaa 360
acugcacuuu uauuuuc 377

<210> SEQ ID NO 63
<211> LENGTH: 756
<212> TYPE: RNA
<213> ORGANISM: Homo sapiens

<400> SEQUENCE: 63
augagacucc acagccucau ccugcucucc uuccuucucc uggcuacuca ggcguucuca 60
gaaaagguca gaaagagagc caagaacgca ccacacagca cagcggagga gggggguagag 120 gguucagcuc ccucguuagg gaaggcccag aauaagcaga gaagcaggac aucuaaaucu 180
cugacgcaug gcaaguuugu caccaaagac caagccacau gcagaugggc ugugacugag 240
gaggagcagg gcaucagccu gaagguccag ugcacacaag ccgaucagga guuuucuugu 300
guuuuugcug gugacccaac ugacugccuu aaacacgaca aagaccagau cuacuggaaa 360
cagguugccc gcacgcugcg caaacagaaa aauaucugca ggaacgccaa gagugucuug 420
aagaccagag ugugcagaaa gagauuucca gagucuaacc ucaagcuggu gaaccccaac 480
gcacguggaa acacgaagcc caggaaggag aaagcagagg ucuccgcaag ggagcacaac 540
aagguccaag aagcugucuc cacggagcca aacaggguca aagaagacau cacacucaau 600
ccagcugcga cccagaccau ggccauuaga gauccagagu gucuagagga uccagaugug 660
cucaaccaga ggaagaccgc ccuggaguuc ugugggggaau cuuggagcuc cauuugcaca 720
uucuuccuca acauguuaca ggcgacauca ugcuaa 756

<210> SEQ ID NO 64
<211> LENGTH: 4701
<212> TYPE: RNA
<213> ORGANISM: Homo sapiens

<400> SEQUENCE: 64
cgggucgacc cacgcguccg cccacgcguc cggcggagcu ucuggguugc gggccgaaac 60
ggcaagcgga uggagggcgc ucgaacggcc aggugucgug auuaaauuag ucagccccuca 120 gagacaggcg uccuaccucc uuuauccaga ccucaaaagc cccguugugc acccguggug 180
gcuucuucac cuucccuguu ucguccucca cuguauggcc cagacaugag ugguccccua 240
gaaggggccg augggggagg agaccccagg cccggagaac cuuuuugucc uggaggaguc 300 ccaucccccug gggccccgca gcaccggccu uguccaggcc ccagccuggc ugaugacacu 360
gaugcaaaca gcaauggcuc aaguggcaau gaguccaacg gacccgaguc caggggcgca 420
ucucagcgga guucucauag uuccucuucu ggcaauggca aggacucagc ucugcuggag 480
accacugaga gcagcaagag uacaaacuca cagagcccau ccccacccag cagcuccauu 540
gccuacagcc uccugagugc gagcucagag caggacaacc caucuaccag uggcugcagc 600
agugaacagu cagcucgagc caggacccag aaagaacuca ugacugcacu ucgggagcuc 660
aaacuucgac ugccaccaga gcgucggggc aagggccgcu cugggaccuu ggccacacug 720
caguacgcuc uggccugugu caagcagguu caggcuaacc aggaauauua ccagcagugg 780
agucuggagg agggugagcc uugugccaug gacaugucua cuuacacccu ggaggaauug 840
gagcauauca cauccgaaua cacacuucga aaccaggaca ccuucucugu ggcuguguccc 900 uuccugacag gccggauugu cuauauuucg gagcaggcag guguccugcu gcguugcaaa 960

-continued

```
cgggaugugu uucggggugc ccgcuucuca gagcuccugg cuccccagga ugugggugucc   1020
uucuauggcu cuacuacacc aucucgacug cccaccuggg gcacuggcac cucugcaggu   1080
ucaggucuca aggacuucac ccaggaaaag ucugucuucu gccgaaucag aggagguccu   1140
gaccgggauc cagggccucg guaccagcca uuccgccuaa ccccauaugu gaccaagauu   1200
cgggucucag auggagcccc ugcacagccg ugcugccuac ucauugccga gcgcauccac   1260
ucugguuaug aagcuccccg gaucccuccu gacaagagga ucuucaccac ccgacacaca   1320
ccaagcugcc ucuuccagga uguagaugaa agggcugccc cacugcuggg uuaccuuccc   1380
caggaucucc ugggggcucc aguacuucuc uuucuacauc cugaggaccg accccucaug   1440
cuggccauuc auaagaagau acugcagcug gcaggccagc ccuuugacca uuccccuauu   1500
cgcuucugug cucggaacgg ggaauauguc accauggaca ccagcugggc cgguuuugug   1560
caccccugga gccgcaaggu ggcuuucgug uugggucgcc auaaagugcg cacggcaccc   1620
cugaaugagg acgucuucac ucccccagcc cccagcccag cuccgucccu ggacucugau   1680
auccaggagc ucucagagca gauccaucga uugcugcugc agccugugca cagcuccagc   1740
cccacggggc ucuguggagu uggcccucug augucccug guccucuaca cagcccuggc   1800
uccuccagug auagcaaugg gggggacgcu gaggggccug ggccuccugc uccagugacu   1860
uuccagcaga ucuguaagga ugugcaucug guaaagcacc agggacaaca gcucuucauu   1920
gaaucucggg ccaagccccc accccggccc cgccuccuug cuacagguac auucaaagcc   1980
aaaguccuuc ccugccaguc cccaaacccc gaacuggagg uggccccagu uccugaccaa   2040
gccucguuag ccuuggcccc ugaggagcca gagaggaaag aaaccucugg cuguuccuac   2100
cagcagauca acugccugga cagcauccuc agguauuugg agagcugcaa cauucccagu   2160
acaaccaagc guaaaugugc cuccuccucc uccuacacug ccucuucagc cucugaugau   2220
gacaagcaga gggcaggucc aguuccugug gggggccaaga aagauccguc gucagcaaug   2280
cugucugggg agggggcaac uccucggaag gagccagugg ugggaggcac ccugagcccg   2340
cucgcccugg ccaauaaggc agagagcgug guguccguca ccagucagug uagcuucagc   2400
uccaccaucg uccauguggg agacaagaag cccccggagu cggacaucau caugauggaa   2460
gaccugccug gccuggcccc uggcccagcc cccaguccgg cccccagccc cacaguagcc   2520
ccugacccaa ccccagaugc uuaucgccca gugggucuga ccaaggccgu gcuguccug   2580
cacacacaga aggaagagca agccuuccuc aaccgcuuca gagaucuugg caggcuucgu   2640
ggacuugaca ccucuucugu ggcccccuca gccccuggcu gccaccaugg ccccauuccc   2700
ccuggucgcc gacaccacug ccgaucuaaa gcaaagcguu cccgccacca ccaccaccag   2760
acccccggc ccgaaacucc cugcuauguc ucccauccuu caccugugcc cucuucugga   2820
cccuggccac ccccaccagc cacgaccccc uucccagcaa ugguccagcc cuacccacuc   2880
ccaguauucu ccccucgagg aggaccccag ccccuucccc cugccccuac aucugugucc   2940
ccugcuaccu ucccuucucc cuuagugacc ccaauggugg ccuuggugcu cccuaacuau   3000
cuauucccua ccccaccuag uuauccauau ggggugucccc aggccccugu ugaggggcca   3060
cccacgccug cuucccacuc gcccucucca ucccugcccc caccaccucu cagcccccc   3120
caccgcccag acuccccacu guucaacucg agaugcagcu ccccacucca gcucaaucug   3180
cugcagcuug aggagucccc ccgcacggag gggggcgcug cugcaggagg cccaggaagc   3240
agugcugggc cccugccucc cagugaggag acugcugagc cagaggccag auugguggag   3300
```

-continued

```
guuacugagu cguccaauca ggaugcacuu ucaggcucca gcgaccugcu ggagcuacug   3360

cuccaagaag acucucgcuc gggcacaggc uccgcagccu caggcucccu gggcucuggc   3420

cugggcucug ggucugguuc aggaucccac gaagggggaa gcaccucagc cagcaucacc   3480

cgcagcaguc agagcagcca uacaagcaag uacuuuggca gcaucgacuc uuccgaggcu   3540

gaagcugggg cugcucgggc caggacugag ccuggggacc aggucauuaa gugugugcuc   3600

caggacccca ucuggcugcu cauggccaau gccgaccagc gugucaugau gacauaccag   3660

gugccgucca gggaugcagc cucugugcug aagcaagacc gggagaggcu ccgggccaug   3720

cagaaacagc agccacgguu cucagaggac cagaggcggg aacugggugc ugugcacucc   3780

ugggucogga agggccagcu gccucgggcc cuugauguga uggcgugugu ggacuguggc   3840

agcagcguuc aagauccugg ccacucugau gacccgcucu ucucagaacu ggauggauug   3900

gggcuggagc ccauggaaga ggguggaggc gaggguggug ggugugggugu uggcggugu   3960

gggggugaug gugguggagga ggcccagacc caaauugggg cuaaggguuc aagcucucag   4020

gacucugcca uggaggaaga agagcaaggu gggggcucau ccagcccagc uuuaccugca   4080

gaagaaaaca gcaccagcua gauccauuuu ggggccgcuu acagcagucu aaugagaggc   4140

uuccuuucga ccauguuggg guucuuauaa cucaagauac agcuggacca accaauagga   4200

aacugcccca gcuucuccca acauaggggg cuggaccccc auuaccagcc caggcacagg   4260

agcugccucu agcuucuuag cagaguggaa guucucagcc ccauuuggag gauuguccac   4320

gcccguccca cugaggagac gggcgggucu ucgguuaagg uugcugacaa gcugcugaag   4380

uggucugucc aaaucccagc ugagccugag ucccagucgc aggguugggg cugcacuuau   4440

uuauuuggga gagacagcuc acucucccac cucaccccaa gaugggagga ggggaaccug   4500

ggaucugugu aggauccagg uccgugaacc ccuagcugcu ccagggugggg ggagguuggu   4560

ggaccaugga gucccuggug cugccccuca ggugggaccc aggguguucuc agcucuaccc   4620

ucuaccaaug acauuugugu uuuugauauu gugucuguua uuuuuuuuuu aauacaaaau   4680

gacaaaauga aaaaccaaaa a                                             4701
```

<210> SEQ ID NO 65
<211> LENGTH: 3036
<212> TYPE: RNA
<213> ORGANISM: Homo sapiens

<400> SEQUENCE: 65

```
gacagcggag cgcgguggcg ucgacgucua gugucucagu gcucccgucu guggcuaacu     60

aagcagccag cagccaggca gcucgcgacc ugcggccagg cagccaacca ugcucaacuu    120

cggcgcuucu cuccagcaag cuucggaggg gaaaauggaa cuaauuucug aaaagcccag    180

agaggggaug caucccuggg acaaagcuga gcagagugac uuugaagcgg uggaagcgcu    240

cauguccaug agcugcgacu ggaagucuca uuucaagaaa uaccuugaaa acaggccugu    300

cacaccagug ucugauaccu ccgaggauga cagcuugcuu ccagggacgc cugaccuuca    360

gacaguccca gcauuuuguu uaacgccacc uuacagcccc ucugacuucg aacccuccca    420

agggucaaau cugacugcau cagcgccauc uacuggccac uucaaaucuu ucuccgaugc    480

ugccaagccu ccaggcgcca cuccuuucaa agaggaggaa aagaauccuu uagcugcccc    540

uccucuuccu aaggcucaag ccaccagugu cauccgucac acagcugaug cccaacugug    600

caaccaccag uccugccccg ugaaagcagc uagcauccuc aacuaucagg acaauucuuu    660

ccggagaaga acccacggaa auguugaggc uacucgaaag aacauacccu gugcugcagu    720
```

-continued

```
gucaccaaac agauccaagc cugagcccag cacaguguce gauggugaug agaaggcggg    780
cgcugcacua uaugacuuug cugugccuuc cucagagaca guaauuugua ggucucagcc    840
agcuccuucg uccccagugc agaagucagu acuggugucu ucaccuacag uauccacugg    900
gggagugcca ccccugccug ucaucugcca gaugguuccc cuuccugcca acaacucucu    960
uguuagcaca guuguccoca gcacuccucc uagccagcca ccagcugucu gcucaccugu   1020
guuguucaug ggcacucagg ugccugaggg caccgucgug uuugugguac cccagcccgu   1080
ugugcagagc ccaaggccuc caguggugag ccccaguggc accagacugu cucccauugc   1140
cccugcuccu ggauucucuc cuucagcagc aagggucacu ccucagauug acucguccag   1200
aguaagaagu cacaucugua gccacccagg guguggcaag acuuacuuua aaaguuccca   1260
ucugaaggcc cacgugagga cacacacagg ggaaaaaccu uucagcugca gcuggaaagg   1320
cugugaaagg agguuugcuc gcuccgauga acuguccaga caccggcgga cacacacagg   1380
ugagaagaag uuugccuguc ccauguguga ccgucgguuu augaggagcg accauuuaac   1440
caagcaugcc cgacgccacc uaucagccaa gaagcugcca aacuggcaaa uggaaguuag   1500
caaguuaaau gacauugcuc ugccuccgac cccugcuucc gcacagugac ggccagaaga   1560
uggagacgca gaauaaacuu uggucagagu caggagccag ugauggugue aagugcuucu   1620
gcaaggcugu ggcccuccaa aagggccuaa aguagaagcc cuggccuggg ggaggccccg   1680
ccugggugaa augacaagaa gugcuucagc cacaggcagg ucacagagga cagggcucag   1740
uucuuaccac agagagagag gagaacccuu uuauuccucc cuuauuuuag ucuggaaagu   1800
uucggcugag gugagcgcag cacagguuuu gaaucacaua cacauugggg acuuuguuuu   1860
ugccauuuau acuugagacc agcuuugcag ugugauucuu ucaaaggauu gguuucaaga   1920
auauagaggc uggaaauuac gguacagaaa uggagcuaga aaaugaguuu guguuacaca   1980
gagaugucau cuucuccuag aguuaucuug uuucuuauuc cuagucuuuc cagucaaauc   2040
cguggaugua gcuaaguaua ucuaaaacuc auuuuuccac uauuguuggu auuugaaguu   2100
gaacagcugu acauugcugu gggggagcca aaggauugga acccucauua auuuaauugc   2160
uuggaaaugc agcuaaaauu cuucuuuggc auuuuguuuu gaaaguuuag gcauuuuacu   2220
cuacuuuaga uuuuaguuug cuugcaguuu uuuguguaga uuugaaaauu guauaccaau   2280
guguuuucug uaggcuuaaa auacacugca cuuuguuuag aaaaaaaucu ggagaugaaa   2340
auauguauua uaaagaagag augucaagaa uuugagauaa cuccuugaga aaguuggcuu   2400
uaugucauca gcaaaggaca cuuaacguca agcauacacu gugguuuuuu uguuuuuuug   2460
uuuuuuuuuu ucaaauuaga aaguuuaaug accguuacag auggacagug ucuuuuuauu   2520
uauaggaguu uuucaggaug ucagaguaga uagguaggaa aauuguuauu agaacauucg   2580
cuucuaccuu gaaaaggaug uuaauguggu cauguucuua gcaccacagu gucugggcau   2640
cugggaaacu ccgagacuuu uuuaaagugu caugauguga ucacaccugc aguuuggggc   2700
aucgaaucca gggccuugca ugucuucugu aagagcucuc aucgcugacc uguauccccc   2760
gcaagagcaa ugacuuuugc uaacaguauu ucuuuucugu uguaaagugg acagaugaua   2820
cacuuggucg caaagguaaa uuauucaaaa uccacaguga aaccucacc acacuuuccc    2880
auuuaaacua uuuccauauc ucagagguuu cugacaugca aacuugaacc cuugaaagaa   2940
gaguuuucuu aaaaauuaua aaaaaucacg aguuacaauu ugcacaauau uuuuuguuga   3000
acuuuauacc uuguuuacaa uaaagacuuu ucuuug                             3036
```

<210> SEQ ID NO 66
<211> LENGTH: 526
<212> TYPE: RNA
<213> ORGANISM: Homo sapiens
<220> FEATURE:
<221> NAME/KEY: misc_feature
<222> LOCATION: (7)..(7)
<223> OTHER INFORMATION: n is a, c, g, or u

<400> SEQUENCE: 66
uugucanuug cacgacagaa acugcaggaa gaugagaugc gccgggcugc ggaggagcgc 60
aggaggguaa aggcugaaga guuagcugcc agacaaaggg uucuagaaaa aauugaaagg 120
gacaaagcag agagagccaa gaaguauggu gguagugugg guucucgguc auccccacca 180
gcaacagacc cagguccugu uccuucuucu cccagccagg agcccccuac uaagcgggag 240
uaugaccagu gucguauaca gguuaggcug ccugauggga cuucacugac ccagacuuuc 300
cgggcccggg aacagcuggc agcugugagg cucuacgugg agcuucaccg uggggaggag 360
ccuggacagg accaggaccc ugugcaguug cucaguggcu uccccagacg ggcuuucuca 420
gaggcugaua uggaacggcc ucugcaggaa cugggacucg ugccuucugc uguccucauu 480
guggccaaga agugucccag cugaggguuc uccaucccac caucuc 526

<210> SEQ ID NO 67
<211> LENGTH: 425
<212> TYPE: RNA
<213> ORGANISM: Homo sapiens

<400> SEQUENCE: 67
uuuuuuuuuu uuuuuuucac aaauaaguaa uauaacuuua uuaaaaugaa aagacaauau 60
ucaaaauaau gcaacaaaau gaauaaaucc uuuguccaau acuguacaca cagugcggag 120
aucagugcau uuuucuaaag cauguuuuaa ccuucauuua guucauacua aaguaagcuu 180
uaaauagcuc aaauaauguc auucagcagu uuaaacugaa cagcuuguug ggacauggca 240
gcaguguccc ugcuagcaag caccuucucu uuguguuuau cugcacaaga uaaacaauca 300
gaggauguaa aaacugaaca caaacugcgu gucucacuga aucucagggc agugaagcag 360
ccagcgugag uuuucaaagc aggaagaugc ugaagugacc ucuggcauua agacguucug 420
ugcua 425

<210> SEQ ID NO 68
<211> LENGTH: 2282
<212> TYPE: RNA
<213> ORGANISM: Homo sapiens

<400> SEQUENCE: 68
uucauuggaa agcacauugc ucuucucagu aauuucuuua guaucuucau gaauuuuuuc 60
cuuuugcguc guuauuucag caauucuauc ugcagaucau aaagguagua uugacagaug 120
ugauucuuuu ucuuaaacau uucauuucca ggguaaggaa cucaauggcu auguuuuucu 180
cucccucuag ugcauccuuc uccuuuucua ccauuuucac ucuauuuaac uucaucaugu 240
ucagucuggc cuuuggguuu caucauagca aucuguucaa cuucacccug caagauuaaa 300
aaucgauuau ggucuaaguc aaugccaugg cuucuaagga gauuuccaac aucuuuaaac 360
gucuucuucu ucccacuuau gugguagaca gaagugcuau cucuguaggc gguucuggau 420
acauagaagu ugcuguuagg aaggacuucg uaaucaucuc cuuccuuauc aauuaucuuu 480
ugaaaaugaa cuucuacagu acaacucuga auauccuugu guucaucaga auuauguauc 540

```
aguaccgaua gcuuuuuaga ccuuauuuuu ugugcucgau agccaaacac aaaaagcaug    600

gaaucaauaa cauuggauuu uccacugcca uuuggucaa uaauacagga aaagcgcuua    660

uggaaagguc ccacaaguuu cucuccagca uaggacuuga aguuuugguu uacaauauga    720

guuaucauga gacgaggagc uccagcuuca cuggccaugg cuggaggugg ggguggaggg    780

auacuauuca aaaucuccuc uaaacuucug uuauccagcu ccucaccugg aggcuuugcg    840

ggugcagcgc uccccucacc uacuucgccu acugcaacuc ccaccaccuc cucucgauac    900

aagaccgagc ucugucggac cuacucagaa agcgggcguu gucgcuacgg ggccaagugc    960

caguuugcuc acggccuggg ugaacuucgc caagccaauc gccaccccaa guacaaaacg   1020

gaacucugcc acaaguucua ccuccagggc cgcugccccu auggcucucg augccacuuc   1080

auccacaacc ccaccgagga ccuagcucuc ccuggccagc cccaugugcu gcgacaaagc   1140

aucagcuucu ccggcuugcc ucaggccgca gaagcucgcc gccaccucca ggcuuuucug   1200

gcccuucccu guccucuugu uccuuuucgc cuuccagcuc cccaccgccc ccugggga uc   1260

uuccacuuuc cccuucugcc uucucugcug ccccugggac cccugugacu cgaagagacc   1320

cuaaccaggc cuguugcccc uccugccgaa ggucuacuac ccccagcacc aucugggggc   1380

ccuugggugg ccuggcucgg agcccaucug cccacucucu gggauccgau ccugaugacu   1440

acgccagcag cggcagcagc cugggggggu cagacucacc ugucuuugag gcagggggugu   1500

uugggccucc ccagaccccu gcacccccaa ggcgucuccc caucuucaau cguaucucug   1560

ucucugagug acaagugccu accuacccag uauggaucag cuagaucuca aagagagggc   1620

agggacugcu cauugcugug gggaccuggg gcacuccucu aaguuaauaa gucccaucuu   1680

cuggacauuc caagaugcaa uaacccauuu cccuggugcu gggcuggggc agguccccuag   1740

uuugcaaauu caguguuugg guggauccgu uccuagggua ccuaagaugu uugagggaga   1800

caguugacag uuggucuucc aggccccaag ucuucuguug uuuuugagau aggagcuuau   1860

uaugguaccc caggcuggcu uugaacucaa uauaauccug ccuuagccuu uuccaaguuc   1920

uggggguuaca gguaugcacc agccccucug caacucuggu cuccuggaau cuuaagugcu   1980

gugaagagcc ggcucccaca auacuauccu aauuuuuacu agacccugaa guucaguguc   2040

cgguggucga agccucuccu gagaauccug gugcucaaau uucccuccua aagcaaauag   2100

ccaaagccau ugccaaaucc cuucuccccc aaccaguggg cccuuuauuu augacgacuu   2160

uauuuauugu auuaagauuu uauaguauuu auauauauug ggucgucuac uccguuuuuc   2220

uuuuuguaau guuaaaacug auacuguauu aaguauaugc uauaauauau uaauauauug   2280

cu                                                                  2282
```

<210> SEQ ID NO 69
<211> LENGTH: 364
<212> TYPE: RNA
<213> ORGANISM: Homo sapiens

<400> SEQUENCE: 69

```
cggacgcugc agaccugacc gacgugcugu gcgaguucga cgcggugcug gccgacuucg     60

cgucgcccuu ccacgagcgc acuuccacua ugaggagcac cuagagcgca ugaagcggcg    120

cagcagcgcc agcgucagcg acagcagcgg cuucagcgac ucggagagug cagacucagu    180

guacagggac agcuucaccu ucagugauga gaagcugaau ucuccaacca acuccucucc    240

agcucuccug cccuccgcug ucacuccucg gaaagccaaa uuaggugaca cuaaagagcu    300
```

cgaagacuuc auugccgauc uggacaggac cuuagcaugu augugaagca aggaguuugg 360
gguc 364

<210> SEQ ID NO 70
<211> LENGTH: 847
<212> TYPE: RNA
<213> ORGANISM: Homo sapiens

<400> SEQUENCE: 70
ccgggccgag gagaagucug caaaacaaga ggcuggggau ugccuuagcg agaaaucagu 60
ucucuuagga gguuagggaa ggaagucuuu cucuggaggu cugagggaag cgcucguguc 120
agaugccggg uugucauggg uaagggugac cccaucaagc cgcugggcaa aauguccucu 180
uacgccuuuu uugugcagac cugccgggag gagcacaaga agaagcaucc caauucgucg 240
gucaacuucg ccgagaucuc caagaaaugc uccaagagau ggaagaccau gucugcaaag 300
gaaaacucga aguuugaaga uuuggccaag agcgacaaag cuuguuauua cagggagaug 360
aagaacuaug uuucucccaa aggugauaag aaaggaaaga aaaaagaucc aaaugcuccg 420
aagagaccac cgucugccuu cugccuguuu ugcucugaaa aucgcccaaa gaucaaaauu 480
gaauacccgg gccugucuau uggagauacu gcgaagaaac ugggugagau guggucugag 540
cagucugcca aagagaaaca accguaugag cagaaagcag cuaaacuaaa ggagaaguau 600
gaaaaggauu uugcugcaua ccgugucaag ggcaaaagug aagcaggaaa gaagggucccu 660 gguaggccag caggcucaaa gaagaaugac ucagaagaug aggaagaaga agaggaggaa 720
gaugaagagg gggaagaaga ggaugaagaa uaaguggcua uccuaaagug uggaguauau 780
gugcucaggc aguuauuuug cuaagaaugu aaauucaagc gcagcucaac auuagcucca 840
guaggaa 847

<210> SEQ ID NO 71
<211> LENGTH: 779
<212> TYPE: RNA
<213> ORGANISM: Homo sapiens

<400> SEQUENCE: 71
aucacgcucc uagaacucuu caaaccgauc ucucgucgau cuucaaccgc cgccuccacu 60
cgccauggac cccaacugcu ccugugccuc cgguaagggg gacugcugac gggauuucug 120
ggagagcuag acaggcuuuu uggccccucc uuuaguaauu acuuuaaggg uacgaccggc 180
uaccccuucc gaaugaauuc ugaagcacuc cugcuccuuu aaacuagucc uugagauagu 240
ggcucgccua cccgggugau uugccucacc uuccuaggag aacagcguuc agguacuccc 300
gggucccacu caaccgcgcu cacugacugc cuucuacuuu uagauggauc cugcuccugc 360
gcuggcgccu gcaaaugcaa acaaugcaaa uguacuuccu gcaagaaaag uaaguuggau 420
cuucucugcc auuuccccgu cacucuccug ggucccuag cccgccgcgc cgcgccuucc 480
cucccgggag cguucaggug gugugccucu gacaagguuu cucgcucacg uucaacucuu 540
cucuccccac aggcugcugc uccugcugcc ccgugggcug ugcgaagugc ucccagggcu 600
gcaucugcaa agaggcuucc gacaagugca gcugcugugc cugaaggggg gcggaggggu 660
ccccacaucu guguaaauag accauguaga agccuagccu uuuuuguaca acccugacuc 720
guucuccaua acuuuuucua uaaagcaugu aacugacaau aaaagccguu gacuugauu 779

<210> SEQ ID NO 72
<211> LENGTH: 2275

-continued

<212> TYPE: RNA
<213> ORGANISM: Homo sapiens

<400> SEQUENCE: 72
gcucugaguu uguggaagau uacaugcgau aucccgcgcg accccgcauc ccuuugccgg 60
ccgggacagc cuuugcuaca gccugugaaa cauugcgucc ccgagcccca cgccugaggg 120
cgacaugaac ccgcuggcuu cgcgagcagu ccggacccac gaucgcuuuu ggcaaccaga 180
accggcgcuu cagcccccgg ggugacgugc agcccgccgc ccagacacau ggccccgagc 240
ccaagacccc agcauguccu gcacuggagg gacgcccaca acuucuaucu ccugucccca 300
cugaugggcu ugcucagucg ggccuggagc cgccugaggg gcccagaagu cccagaggca 360
uggcuggcaa aaacaguaac aggagcagau cagauagaag cugcggcucu gcugacaccu 420
accccugucu cugguaaccu ccucccucau ggggagacug aagaaagugg aucuccugaa 480
cagagucaag cagcccagag gcucugccuu guggaagcug aaaguucccc uccugaaacu 540
uggggacuuu caaauguuga ugaguacaau gcaaagccag gacaagauga ccuuagagag 600
aaggaaaugg aacgcacagc uggcaaggcc acacuacagc ccgcuggccu gcaaggggcu 660
gauaagaggc uuggggaggu gguggcuaga gaagagggag uggcugagcc cgcuuauccc 720
acaucacagc uggagggugg uccagcugag aaugaagagg auggagaaac agugaagacu 780
uaccaagcuu cugcugcuuc cauagcuccg ggauacaaac ccagcacccc ugugccuuuc 840
uugggggagg cagaacauca agccacggaa gaaaaaggaa cagaaaacaa ggcugacccc 900
uccaacucuc cuucuucagg cucccacucc agagccuggg aguacuacuc uagagagaag 960
ccuaagcagg agggagaagc caagguagag gcacacaggg cagggcaggg ucacccuugu 1020
cggaaugcug aggcugagga aggaggaccu gagacaacuu uugucuguac uggaaaugcc 1080
uuccugaagg ccugggugua ucgcccagga gaggacacag aggaagaaga caacagcgau 1140
ucggauucag cugaggaaga cacagcucag accggugcca ccccccauac aagugccuuc 1200
cugaaggccu ggguguaucg cccaggagag gacacagagg aagaagacag cgauucggau 1260
ucagcugagg aagacacagc ucagaccggu gccacccccc auacaagugc cuuccugaag 1320
gccugggugu aucgcccagg agaggacaca gaggaagaaa acagcgauuu ggauucagcu 1380
gaggaagaca cagcucagac cggugccacc ccccauacaa gugccuuccu gaaggccugg 1440
guguaucgcc caggagagga cacagaggaa gaaaacagcg auuuggauuc agcugaggaa 1500
gacacagcuc agaccggugc caccccacau acaagucccu uccugaaggc cuggguguau 1560
cgcccaggag aggacacaga agaugacaca gaagaggaag aggacaguga gaauguggcc 1620
ccaggugacu cagaaacagc ugacucaagc cagagucccu gccuucagcc ccagcguugu 1680
cuaccaggag agaagaccaa gggacguggg gaagagcccc cucucuucca gguggccuuc 1740
uauuuacccg gagagaagcc agaaucaccu ugggcugcac cuaagcugcc ccuucgacug 1800
cagaggcggc ucagauuguu caaagccccc acccgggauc aggaccccga gauuccucua 1860
aaagcucgga agguacacuu cgcugagaaa gucacagucc auuuccuugc ugucugggca 1920
ggaccagccc aagcugcccg ucgaggaccc ugggagcagu uugcacgaga ucgaagccgc 1980
uuugcucgac gcauugccca ggcagaggag aagcuggguc ccuaccuuac ccccugauucc 2040 agggccagag caugggcacg ccuuagaaac ccaucucuuc cacaguccga gccucgcucu 2100
uccucugagg ccacucccuu gacccaagau gugaccacac ccucuccccu ucccagugaa 2160
accccuucgc ccagccugua cuugggaggg aggcggggcu aagccugagu aguuuccuau 2220
uauuuauuua uuuauuuauu ugaauaagaa auaaagccuu uuaauuugua gugau 2275

<210> SEQ ID NO 73
<211> LENGTH: 355
<212> TYPE: RNA
<213> ORGANISM: Homo sapiens

<400> SEQUENCE: 73
uuuuuuuuuu uuuuuuuaau caucgagaag uauuuauuga gcaccagcuu uggggucggg 60
ugugaggacu cgggacaaug cagggugcug ucccuucucg ugagacgcuu acaaucugag 120
uggagacagg gagggagcca caauacaugu ucuuggggug cgggcuaagg guagacaguc 180
cagaccagga uguuacagaa acagggaugu uuggggcugg agucagaccc acuaagugcu 240
uugacaccca cgguauucaa cacugagaaa ggaucagcca uugcucagug uccugugagc 300
ucccuuagcc cccaagacac caucuuggcc uggcuccuug uacaacugcu acuaa 355

<210> SEQ ID NO 74
<211> LENGTH: 289
<212> TYPE: RNA
<213> ORGANISM: Homo sapiens

<400> SEQUENCE: 74
cccaaaaccc auucagcaaa guucccaacc ucgacgggcu agcaguauuu aaccagugau 60
ggguucacug uuguauuugg ugaauacugu auuuuguuuc aguucuuucu cccagauaau 120
uugaaaacgu uccaggagaa ggcagcuucc uauaugcagc gugugcuuuc uuauucuuuu 180
uuuuaauaua ugacaguuau uugagaaccc auuucuacuu ugaauucauu uucguugaaa 240
gugauguuuc uucaccuacc auuuuccuau uaaaguucug uauucaaau 289

<210> SEQ ID NO 75
<211> LENGTH: 2018
<212> TYPE: RNA
<213> ORGANISM: Homo sapiens

<400> SEQUENCE: 75
agaccgugag cgagagcgcc ccagagaagc gccugcaauc ucugcgccuc cuccgccagc 60
accucgagag aaggacaccc gccgccucgg cccucgccuc accgcacucc gggcgcauuu 120
gaucccgcug cucgccggcu uguugguucu gugucgccgc gcucgccccg guuccuccug 180
cgcgccacaa ugagcuccag caccuucagg acgcucgcug ucgccgucac ccuucuccac 240
uugaccagac uggcgcucuc caccugcccc gccgccugcc acugcccucu ggaggcaccc 300
aagugcgccc cgggagucgg guugguccgg gacggcugcg gcugcuguaa ggucugcgcu 360
aaacaacuca acgaggacug cagcaaaacu cagcccugcg accacaccaa gggguuggaa 420
ugcaauuucg gcgccagcuc caccgcucug aaagggaucu gcagagcuca gucagaaggc 480
agacccugug aauauaacuc cagaaucuac caaaacgggg aaagcuucca gcccaacugu 540
aaacaccagu gcacauguau ugauggcgcc gugggcugca uuccucugug uccccaagaa 600
cugucucucc ccaaucuggg cugucccaac ccccggcugg ugaaagucag cgggcagugc 660
ugugaagagu ggguuuguga ugaagacagc auuaaggacu cccuggacga ccaggaugac 720
cuccucggac ucgaugccuc ggagguggag uuaacgagaa acaaugaguu aaucgcaauu 780
ggaaaaggca gcucacugaa gaggcuuccu gucuuuggca ccgaaccgcg aguucuuuuc 840
aacccucugc acgcccaugg ccagaaaugc aucguucaga ccacgucuug gucccagugc 900
uccaagagcu gcggaacugg caucuccaca cgaguuacca augacaaccc agagugccgc 960
cuggugaaag agacccggau cugugaagug cguccuugug gacaaccagu guacagcagc 1020
cuaaaaaagg gcaagaaaug cagcaagacc aagaaauccc cagaaccagu cagauuuacu 1080
uaugcaggau gcuccagugu caagaaauac cggcccaaau acugcggcuc cugcguagau 1140
ggccggugcu gcacaccucu gcagaccaga acugugaaga ugcgguuccg augcgaagau 1200
ggagagaugu uuuccaagaa ugucaugaug auccaguccu gcaaauguaa cuacaacugc 1260
ccgcauccca acgaggcauc guuccgacug uacagccuau ucaaugacau ccacaaguuc 1320
agggacuaag ugccuccagg guuccuagug ugggcuggac agaggagaag cgcaagcauc 1380
auggagacgu gggugggcgg aggaugaaug gugccuugcu cauucuugag uagcauuagg 1440
guauuucaaa acugccaagg ggcugaugug gacggacagc agcgcagccg caguuggaga 1500
augccaaggg gcugaugugg acggacagca gcgcagccgc aguuggagaa gacuucgcuu 1560
cauaguacug gagcgggcau uauugcucca uauuggagca uguuuacgga ugacguucug 1620
uuuucuguuu guaaauuauu ugcuaagugu auuuuuuugc uccagacccc ccccccccuuu 1680 cuugguucua caauuguaau agagacaaaa uaagauuagu ugggccaagu gaaagcccug 1740
cuuguccuuu gacagaagua aaugaaagcg ccucucauuc cuucccgagc ggagggggac 1800
acucugugag uguccuuggg gcagcuaccu gcacucuaaa acugcaaaca gaaaccaggu 1860
guuuuaagau ugaauguuuu uuuauuuauc aaaguguagc uuuuggggag ggaggggaaa 1920
uguaauacug gaauaauuug uaaaugauuu uaauuuuaua ucagugaaga gaauuuauuu 1980
auaaaauuaa ucauuuaaua aagaaauauu uaccuaaa 2018

<210> SEQ ID NO 76
<211> LENGTH: 358
<212> TYPE: RNA
<213> ORGANISM: Homo sapiens

<400> SEQUENCE: 76
ccaauaccac agccgugacc acagccaaga ccacagccaa aagccuggcc auccgcacuc 60
ucggcagccc ccuggcagug cccuccauau ccugcuuguu uuucucauua guaaacuccu 120
cuucuaaaga aaacugggga agcagaucuc caaccuccag gucauccucc cgagcucauu 180
ucaggccagu gcuuaaacau acccgaauga agguuuuaug uccucagucc gcagcuccac 240
caccuuggac cacagaccug caacacuagu gcacuugagg gauacaaaug cuugccugga 300
ucuuucaggg cacaaauucc gcuucuugua aauacuuagu ccauccaucc ugcgugua 358

<210> SEQ ID NO 77
<211> LENGTH: 870
<212> TYPE: RNA
<213> ORGANISM: Homo sapiens

<400> SEQUENCE: 77
auggagaacg aguucacaua cgaagauuau gagaccacug ccaaguggcu ucugcaacac 60
acugaauauc gaccucaagu ggcagugauc ugugguuccg gcuuaggagg gcugacugcu 120
cacuuaaagg aggcucagau cuuugacuac aaugagauac ccaacuuucc ccaaagcaca 180
gugcaagguc acgcaggccg acugguguuu ggauugcuga auggcagaug cugugugaug 240
augcaaggcc gguuccauau guaugaagga uacucacugu caaaggugac auucccagug 300
agaguuuucc aucuucuggg uguggaaacu uuggugguca ccaaugcugc uggaggacuc 360
aaccccaauu uugaaguugg agauauuaug cugauccgug aucacaucaa ccuaccuggu 420
uucuguggcc agaacccucu ccggggcccc aacgaugaaa gguuuggagu ucguuuuccu 480
gccaugucug augcuuauga ccgggauaug aggcagaagg cuuucagugc cuggaaacaa 540
augggggagc aacgaaagcu acaagaaggc accuacguga uguuggcagg ccccaacuuu 600
gagacugugg cagagagucg ucugcuaaag augcuggggg cagaugcugu uggcaugagc 660
acagucccag aaguuaucgu cgcaaggcac ugugggcucc gugucuuugg uuucucacuc 720
auuacgaaca agguugucau ggauuaugag aacuuggaga aggccaauca cauggaaguu 780
cuggaugccg ggaaagcagc ugcacagaca uuggaaaggu uugucuccau ucuuauggag 840
agcauuccac ucccggaucg uggcagcuga 870

<210> SEQ ID NO 78
<211> LENGTH: 4928
<212> TYPE: RNA
<213> ORGANISM: Homo sapiens

<400> SEQUENCE: 78
uuccaggaca gcuggggcuc cacgagagaa acccugccuc ccccccaaaa auggcccaaa 60
guucacugac aaacucacau uugucugaua uuuagcuaug uaacagcacu uacgguagca 120
auagaauuug auucucacuc aucacaauga aaauggcugg cgcucucucu cucccucucu 180
ccccauuuca aaucugcaag cacaccccuu agagauggag agaauuugau ccauuggaga 240
aucgagcuaa aaauaccacc auggaauugu gggaaggauu aaaugcaaua augcacaaaa 300
ggcacauagc agaaugugcc cuaaauguca gccauuguua ugguauuaug uaaucuacaa 360
aguauguuug cuuacuccgu gugaaagacu uucagucuau caaacauaau acaugugaaa 420
ucaaaccuug aaaauuaauu uuuuucccaa cagucaagac auuugccagc ugcagagauu 480
agcauuucau gaaucuuagu cuugucugau uuuuuuaaug ggaaggaaca acuauccuca 540
acuauccuuu uuuuuuuucu guaguuuuaa aaugaacucc acaaaacaug uuuuuaauau 600
agggaauuau augaaauugu ggggugggca gcgagguuaa aggcagaaau agcccaaugg 660
uggcacauuc acugacacag ccuaaaagau uagcaaauua cccagccaac acauacaauu 720
aauacaauua auauuuuuau aguuaaaaca gaguuacuaa agaaauuguu ugaaaagaaa 780
auuaugaaga cuggaaagac ggcucagugc uuaagagcuu uggcuagucu uccagagaac 840
cagggucauc cagcacucac aaggcagcuu gugagcugau acuaucugua uauucagucc 900
uagggaaucu gaugcuuugu ccugaccucc aaaacaggca caaauguggu gcacaggcaa 960
auguagagau aagacuccca ugcacagaac auaaauaacg uaguuuaauu uuuuaaauug 1020
uaaaacugaa aaugguugca cuugcauuuu uauuuucagc acauccccag auauccgcca 1080
uauaacaaga aaaugaugcc acacucccaa gaauuaagaa uuacaccucc caacccuacc 1140
caaaugugua uacucuaggu cuaaagaaau gcaaaggaug aaguuacugc cuugugcggu 1200
ucucaaggag ggaggaugcc aaaaaaauau uuuuucacaa agugugcuga gaaacucugu 1260
agcuguugga gucaucuccu gugcucuugc caaauaacug aaaggggaua cacuggaugu 1320
cugugaaugg ggugucacuu augagugcua gaagcgggua ccuggaugug gacacggugu 1380
cugagugguc cgcacuccau gucuccacag gagcgcuuau guguguuucu uuccuccugc 1440
uucugggugu uccuggguuu guuuacagcc accucucugu uggaccagga gacagcuguc 1500
gucuccagaa ugagcgggca cgggugugc ucgguggcug uggcuguggu ucggcauaag 1560
ucugagcaug uccuggucgu cagggugcgu uugugcugug ugugcguguc cgggugagcu 1620
ugcucuuucu guuccuaaaa gaaaaugcac ccugcgcuac cggcguccag agacucucag 1680

-continued

```
cccgcagagg ugaccugaac ggacagguag caccuccaga cagcgccugg uuggcggguu   1740
gcacagcagc cccagauuuc ucucucuggu gccccagcua ggguagcugg aagggagcgg   1800
uggccuggcc uccggggagc cgcugggccc cgccgggcua acccaggagg aggccggcua   1860
ggcugggagg guuagcccuu ggugcccuac gccugcccgg gccagucgcg gccgccggcc   1920
auuggcccaa agaauuguug cacgucacug gcaauucccc uagaagucug ugcacauaac   1980
gggcagggcg cacugcaagg cugcuucucc cgcauuuagg cugcggcugc aggcaccgcg   2040
agcccggagc acccacgagc uuagugugca ggacgcaccc cagcacagcc accuacggcc   2100
gcugaaugaa gcuuccagga guccgccccc ggccgucgcc ccgucggagg ugcacccgcu   2160
gagagcgccu ggaccgaaag gccggugcgc ucaccugcua accugccagc cauggggcca   2220
cacgggaacg acagcgacuu cuugcuggca cccaacggaa gccgagcgcc acaccacgac   2280
gucacucagg aacgggacga agcgugggu gugggcaugg ccauccucau gucgguuauc   2340
guccuggcca ucguguuugg caacgugcug gucaucacag ccauugccaa guucgagcga   2400
cuacaaaccg ucaccaacua cuucauaauc uccuuggcgu gugcugaucu agucaugggc   2460
cuagcggugg ugccguuugg ggccagucac accucuauga aaauguggaa uuuuggcaac   2520
uucuggugcg aguucuggac uuccauugau guguugugcg ucacagccag caucgagacc   2580
cugugcguga uugcagugga ucgcuauguu gcuaucacau cgcccuucaa guaccagagc   2640
cugcugacca agaauaaggc ccgagugguc auccugaugg uauggauugu aucuggccuu   2700
accuccuuuu ugccuaucca gaugcacugg uaccgugcca cccacaagaa agcuaucgau   2760
uguuacaccg aggagacuug cugugacuuc uucacgaacc aggccuacgc caucgcgucc   2820
ucgauugugu cuuucuacgu gccccuggug gugaugg ucu uugucuauuc ccgggucuuc   2880
cagguggcca aaaggcagcu gcagaagaua gacaaaucug aaggaagauu ccacgcccaa   2940
aaccucagcc agguggagca ggaugggcgg acgggccacg gacuccgaag guccuccaag   3000
uucugcuuga aagagcacaa agcccucaag acuuuaggca ucaucauggg cacauucacc   3060
cucugcuggc ugcccuucuu cauugucaau aucgugcacg uuaucaggga caaccucauc   3120
ccuaaggaag uuuacauucu ccuuaacugg uugggcuacg ucaacucugc cuucaauccu   3180
cuuaucuacu gucggagucc agauuucagg auugccuuuc aagagcuucu gugccuucgc   3240
aggucuuccu ucgaaaccua ugggaacggc uacucuagca auagcaacgg cagaacggac   3300
uacacagggg agccaaacac uugucagcug gggcaggaga gagaacagga acugcugugu   3360
gaggaucccc caggcaugga aggcuuugug aacugucaag guacugugcc uagccuuagc   3420
guugacuccc aaggaaggaa cuguaguaca aaugacucgc cacuguaaua caggcuuucu   3480
acucucuaag accccuccuu gacaggacac uaaccagacu auuuaacuug aguguaauaa   3540
cuuuagaaua aaauuguaua gagauuugca gaaggggggg cacauccuuc ucgccuuuuu   3600
uuaauuuuua uuuuauuuuu uagcugcaaa caagagagag aacuguauuu gagugcuuau   3660
uguucuugua uaguucaguu ccucuuguau ggaacuuaaa gguuucuguc ugaagagugu   3720
ugguucugag gacugagucu gucugucugu cugucugucu gucugucugg augauguuuu   3780
cauguaucua ccucacuggu caaguauuaa gaaugauaua uauugcugcu ggaaauccau   3840
aucuaaagga gagaguuuuc uuccuguacc cuuggacuug aaauauccug ugucuuggac   3900
cuuucugcug ugacaauggg cccuuucucu cucacuccac uuauuuacuc aaauggauuc   3960
gaggcaggga uuugagggac aacacuaguu guuuuguuuu uguuuuuguu uuuuuguuug   4020
```

-continued uuugguucgu uuuugguuug uuguuguuuu uuggggguuug uuuuuguuuu uguuuuuuug 4080
gguuuuuuuu uuuugcugag aaaagucuaa aguuuacagu aaauaaauug uuuaaccaug 4140
acuucauugc acccguuucu ucaaaaccuc uugacucugg aguguccuug ucucucccac 4200
uggaaaccac agguaaacua ugugucguga ccgaugagug gcuuaaugug uaagaguacc 4260
agaauggcau gcuugcaugc accgugccua gcccuuccgu gugugucuuc agagcuccag 4320
augcaaaccu gugccuuccc uaacuucacu cgugucccaa agcaguccug ccuguucaca 4380
gcauaaccca guauguccua caguugcucu ucugugcugu cacuccagaa acccugacuc 4440
acggaaacag aguuauggac auauguuuuu guccccauau gcucugacac caccuucagc 4500
cuuacuugcu uaauaacugu guauauuuac aucacugcgu cucuuacagu agugccuuug 4560
uacugcauca gggcuuggug uguucaggau gaggaagaug uucuguguaa uagcuguuca 4620
agcaucuaga aauucugagg gaaaucaaag gccucgguca gagagagaga gagagagcaa 4680
agcuuuaaaa aacauagcug gugaaugcuu cacgcccuuc agccucuccu cgcuccgucu 4740
gcugucccgu gucuucuguu cccaauucuc ugcacuucug uguaaaccag gcuucccaug 4800
ucuggcauuc cgugcauuau augauauuug gcggcacguc uguaccagua aauucuggua 4860
gcacccccua guuacaauaa uugcagacac ucagcgcgua cgacccccua guuacauaug 4920
cagacacu 4928

<210> SEQ ID NO 79
<211> LENGTH: 374
<212> TYPE: RNA
<213> ORGANISM: Homo sapiens

<400> SEQUENCE: 79
uuuuuuuuuu uuuuuuuaag cguccaggcu guacuuuauu uuacacaagu gguggcccca 60
gaaccacagg gacaugaccu ggagaguagg cacagugccu gaggcugcaa gagccaaaua 120
cagggauuca ugccuucucc uuggucccca ugaccaaauu aaaaaaaaaa aaaacaacaa 180
aucacacagc acacaucgcc acacccaucc ccuccuuccu uucagcaaca gccaauucag 240
cuuucuagcc aaagacagug gcuacaacug aauuuacaga gaaccaugca gccaagaaac 300
cagagccacg gaggggagag gcuugcguug acuucccaca ugugcugucc cauagcagcu 360
gagugacccc acca 374

<210> SEQ ID NO 80
<211> LENGTH: 1285
<212> TYPE: RNA
<213> ORGANISM: Homo sapiens

<400> SEQUENCE: 80
agaaagauaa gggccagcaa ggaaagaaug aggauguggg cgccgaggac ccguccaaga 60
agaagcggca acgccggcag aggacucauu ucacuagcca gcagcugcag gagcuggaag 120
ccacuuucca gagaaaccgc uacccagaca uguccacucg cgaagaaauc gccgugugga 180
ccaaccuuac ggaagcccga guccggguuu gguucaagaa ucgccgggcc aaauggagaa 240
agcgggaacg caaccagcag gccgagcugu gcaagaaugg cuuugggccg caguucaacg 300
ggcucaugca gcccuacgau gacauguacc ccggcuauuc guacaacaau ugggcugcca 360
agggccucac gucagcgucu cuguccacca agagcuuccc cuucuucaac uccaugaacg 420
ucaauccccu guccucucag aguauguuuu ccccgcccaa cuccaucuca ucuaugagua 480
ugucguccag cauggugccc uccgcgguga ccggcguccc gggcuccagc cucaauagcc 540

-continued ugaauaacuu gaacaaccug agcagcccgu cgcugaauuc cgcggugccc acgcccgccu 600
guccuuacgc gccgccgacu ccuccguacg uuuauaggga cacauguaac ucgagccugg 660
ccagccugag acugaaagca aagcagcacu ccagcuucgg cuacgccagc gugcagaacc 720
cggccuccaa ccugagugcu ugccaguaug cagucgaccg gccgguguga accgcgccca 780
gggcgcgggg auccgaggac ugucggagug ggcaacucug ccccagaaag acugagaauu 840
gugcuagaag uucgugcgca cuaugggaag gaagaggggg gaaaaaagau cagaggaaaa 900
gaaaccacug aauucaaaga gagagcgccu uugauuucaa aggaaugucc ccaagugucu 960
acgucuuucg cuaagaguau ucccaacagu uggaggacgc guacgcccac aaauguuuga 1020
cuggauauga cauuuuaaca uuacuauaag cuuguuauuu uuuaaguuua gcauuguuaa 1080
cauuaaaaug acugaaagga uguauauaua ucgaaauguc aaauuaauuu uauaaaagca 1140
guuguuagua cuaucacuac aguguuuuua aaggcuaggc uuuaaaauaa agcauguuau 1200
acagaaucag uuaggauuuu ucgcuugcga gcaaaggaau guauauacua aaugccacac 1260
uguauguuuc uaacauauua uuauu 1285

<210> SEQ ID NO 81
<211> LENGTH: 801
<212> TYPE: RNA
<213> ORGANISM: Homo sapiens

<400> SEQUENCE: 81
cugagaggcc aggugggcgg cgaaaucaac guggagaugg augccgcucc cggugugga c 60 cugagccgca uccugucaga gaugcgugau caguacgaga agauggcgga gaagaaccgc 120
aaggaugccg aagacugguu cuucagcaag accgaggagc ugaaccgcga ggugccacc 180 aacagcgagc uggugcagag cggcaagagc gagaucuccg agcucaggcg caccaugcag 240
gcccuggaga uugagcugca gucccagcuc agcaugaaag caucucugga gggcagccug 300
gcagagacag agaaccgcua cugcgugcag cugucucaga uccaggggcu gaucggcagu 360
guggaggagc agcuggcuca gcugcgcugc gagauggagc agcagaacca ggaguacaag 420
auccugcugg augugaagac aaggcuggag caggagaucg ccaccuaccg ccgucugcug 480
gagggagagg augcccaccu gacucaguac aagccaaaag aaccugugac cacccgccag 540
gugcgcacca uuguggaaga aguucaggau ggcaagguca ucucaucccg ggaacaggug 600
caccagacca cccguuaagg acucagcucc uuccgcccag uuccccgagg cugcagagag 660
gcagcuuccc ucuccgcucc ggcaucaccc uccugcuaca gccucucccc agcauuccua 720
ugcuugagac cauuaaagcu ugcugaccug aagugaacug uggccuuugu ucugaacacu 780
gaaauaaaug accaugguga c 801

<210> SEQ ID NO 82
<211> LENGTH: 216
<212> TYPE: RNA
<213> ORGANISM: Homo sapiens

<400> SEQUENCE: 82
ccccaggggu gaaaugagga uucccccacc cugcggaaca gugaaaugug uauaauuaag 60
aggagggcga cgacccuugc cgcgggaccc gggacucgag cccgggacuu cgcagcuaca 120
gcaaaucuau uuuuaauauu gugcugagca agacagaucg cuugcauauu uuuaaaaauu 180
uuuacuacag agacauucca auaaauucgu uaagcc 216

<210> SEQ ID NO 83
<211> LENGTH: 2901
<212> TYPE: RNA
<213> ORGANISM: Homo sapiens

<400> SEQUENCE: 83
cugacagucg ucucuguccc uucuucgccu cggagcugcu aacuggucuc gaaccucuca 60
gcacuucagc uucuagcggc gaugcaugug aucaagcgag auggccgcca agagcgaguu 120
auguuugaca aaauuacauc acgaauccag aaacucuguu auggacucaa cauggacuuu 180
guugauccug cucagaucac caugaaagua auccaaggcc uauauagugg ggucaccaca 240
guggaacugg acacccuggc ugcugagaca gccgcgaccu ugaccacgaa gcacccugac 300
uaugccaucc uggcagcaag gauagccguc ucuaacuugc acaaagaaac aaagaaagug 360
uucagugaug ugauggagga ucucuacaac uacauaaauc cgcacaacgg cagacacucu 420 cccaugguggcc agcucaac acucgacauu guuauggcca auaaggaucg ccugaauucu 480
gccauuaucu augaccgaga uuucucuuau aacuacuuug gcuuuaagac acuggaacgg 540
ucauauuugu ugaagaucaa ugguaaagug gcugaaagac cacagcauau guugaugagg 600
guuucugugg ggauucacaa agaagauauu gaugcugcaa uugaaaccua caaccuacuu 660
ucugagaagu gguucacuca ugccccuccu acucucuuca augcugggac caaccgccca 720
cagcugucua gcuguuuccu cuugaguaug aaagaugaca gcauugaagg aauuuaugau 780
acucugaagc agugugccuu gauuucuaag uccgcugggg gaauuggugu ugcugugagu 840
uguauucggg ccacugguag cuacaucgcu gggacuaaug gcaauucuaa uggccuugug 900
ccaaugcuga gaguauauaa caacacagcu cgcuaugugg aucaaggugg aaacaagcgc 960
ccaggcgcgu uugcuauuua ccuggagccu uggcacuuag acaucuuuga guuccuugac 1020
uugaagaaga acacaggcaa ggaagaacag cgagcacgcg aucucuucuu ugcacuuugg 1080
aucccagauc ucuucaugaa gcgaguggag acuaaccagg acuggucauu gaugugcccc 1140
aaugaguguc cuggucugga cgaggucugg ggagaggagu uugagaaguu auaugaaagu 1200
uacgagaagc agggucgugu ccgaaaaguu guaaaagcuc agcagcuuug guaugccauc 1260
auugaguccc agacggagac cgguacccca uacaugcucu acaaagauuc cuguaaccgg 1320
aagagcaacc agcagaaccu gggaaccauc aaaugcagca accuguguac agaaauagua 1380
gaguacacca guaaagauga gguugcaguu uguaacuugg cuucucuggc ucugaauaug 1440
uaugucacac cggaacauac guaugacuuu gagaaacugg cagaagucac uaaagucauu 1500
guccgaaauc ugaauaaaau aauugauaua aacuacuacc cuauuccaga ggcacacuua 1560
ucaaacaaac gccaucggcc cauuggaauu gggguacaag guuuagcaga ugcuuucauc 1620
cugaugagau accccuuuga gagcccagaa gcccaguuau uaaauaagca gaucuuugaa 1680
accauuuacu auggagcccu ggaagccagc ugugaacuag ccaaggagua uggccccuau 1740
gaaacguaug agggaucucc agucagcaag gguauucuuc aguaugacau guggaauguu 1800
gcuccuacag accuguggga cuggaagccu cucaaggaga agauugcaaa guaugguaua 1860
aggaacaguu uacuuauugc ccaaugccu acugcuucaa cugcccagau ucuggggaau 1920
aaugagucca uugagccuua uaccaguaac aucuacacuc gaagagucuu gucaggggaa 1980
uuucagauug ugaauccuca cuuacugaaa gaucuuacug agcggggcuu guggaaugag 2040
agaugaaaaa ucagauuauu gcaugcaaug gcuccauuca gagcauacca gaaauuccug 2100
augaccugaa gcaacucuau aagaccgugu gggaaaucuc ucagaagacu guucucaaga 2160
uggcagccga gagaggugcu uucaucgauc agagccaguc uuuaaacauc cauauugcug 2220
agcccaacua uggcaaacuc acuaguaugc acuucuacgg uuggaagcag gguuuaaaga 2280
cuggaaugua uuacuuaagg acgaggccug ccgcuaaucc aauccaguuc acucugaaca 2340
aggaaaaacu gaaagauaag gaaaaggcac ugaaggagga ggaggagaag gagaggaaca 2400
cagcagccau ggugugcucu uuggagaaca gagaggagug ccugaugugu ggauccugag 2460
aaaagcgggg ccugggagac gcagcgggcu cuccugcccg agaggcagac gauuugagca 2520
uagauaggau agugggguug cuugguuauc agcagcucug cuuggacgug ccugccagga 2580
cagggagcca cgacuuacag uacuguuucu acacagugua aauaucauuu uuaacaaaca 2640
gaaaaccaaa gccagcuuug auauuaggaa ucaagguaga ggcuuuggga auacuaaaga 2700
gccuuccugc aaauagugag gagacuuagg aagucucguc ucuccagcuu ucccugccug 2760
gccauucuca guuugggcaa agagauuuag uuugauuuga cugauugccu agaaguaaaa 2820
ucaagcaauu acucaucagc uaaagaccuu ugucuagaca aacuucuaua agucauuuug 2880
aaauaaacau uucuaaguga u 2901

<210> SEQ ID NO 84
<211> LENGTH: 8752
<212> TYPE: RNA
<213> ORGANISM: Homo sapiens

<400> SEQUENCE: 84
uugccucaga cgcuagcugu agcuggcagg cgguuguacg ugcuccagag ucgucgguac 60
ccgcuacugc agucgcuuuc guguggcuuc cgcugagcuc uuccgagcug cucgcucucc 120
acacgcgccg ccgccguaau ccgccaccau ggugaagcuc gcaaagguaa gaggccuugg 180
cgcgccgacg cggacgacua ggccccugcu uucggaggga cgcgcgcgcg cccgcccguc 240
cgucgcggag gggaggaggg cuugcgcgca aucccgggcg cguucgaggg cgccaugcug 300
ggggggaaag ucucgcgcga cuagcgggag gucucgcggu gcuugcccuc ugacuuaggg 360
ggaugagaag agcggaggca gguuuccggg agggcgauau cgaggguucg gauguagcgg 420
gcgggagggg acggugugag gagagaucgg aggagcugag agcggauagg ggcacggcgu 480
gggaagagag ggccaaccuu aggcggcgag cggucccggg gccccgccuc cccgcgcacg 540
ugcucuggug cgcgcccgcc acgugcucug cggagccccg cacgugucgc gcgacccggg 600
gcaguggggg agugucugua guaccccgga aagggggacg gcagcguggg gauggauggg 660
uggcccggcg aucugcuguc ucugccggug accgggaugg acacguggug gaccccugag 720
guggcggcgu ggugacucca cguggugggg cuggaagcga gagaaagugg gaagcaguug 780
gguuacgugg ugcugcuuua agaggugauu ucgagauacc cccuucccca gcaaauaacu 840
uaaagggauc ccuuuaacug gguuuuuuuu uuuuuuuuuu uuuuuuuuuu uguggaagau 900
gccagaaaau agauggccag gauuaggaga cuuuauaacc uguggcuguu ucuuggugua 960
gaguucuguc ugcucaguua ucugugagaa ggaaaaaaaa auuaugcgcg guucgcagaa 1020
aaaacugcca ggagaaugcc augccuggcc aagaagaagu cuuuaugcuu guguccuuua 1080
guaagaaaaa ggugguggcc aaaggcaaag ugacugaaaa ugcgugcaau uuuugugugc 1140
guuuguaggc uggcaaaacc cacggugagg ccaagaaaau ggcuccuccu ccaaaggagg 1200
uggaagagga uagugaagau gaagaaaugu cagaagauga agaugacagc aguggagaag 1260
aggagguaag aagcuauuug cagcgaauua aaccggugga auugaauguc uggaagucuu 1320

-continued

```
agaaauacag gauauguagu aaaugguuga auggcaagcc ccuuccuccc ucccucccuc   1380
ccucccuccc ucccucccuc ccucccuucc uuccuuccuu ccuuccuucc uuccuuccuu   1440
cugcaagaca gucggcaaaa caggggacag aaacaggcag aauuuugagu uccaggcaag   1500
cagggaguag uacauaguga aaccuugucu caagaccguu guuaugguca ugcucaauca   1560
gauuucuuag aaaagcucag gugcugaguc caguuuuuuu uuuuuuaaag uauugaaagc   1620
caugucuccu uauuucaggg uuuaauguuu aucuuugugu gugcgcgcac ccauuaagca   1680
ugcuugguac ccucauacua gaauguacuu ggaucccug gaacuggagu uaaagccaca   1740
ugugaauguu acauguuaca agaguaacac augugcuuaa cuuuugaguc aucucuccag   1800
uucuugguug uuuguuuuuu uuuuuuuaag ccuaucuaau guccauuuuc uugugcucaa   1860
aguuagucuc uuaauguagc auuggguaua aaggaaugcu uaugauuugu uugcuuucaa   1920
gguugucauc ccucagaaaa aaggcaaaaa ggcuaccaca accccagcaa agaaggugguu   1980
uguuucacaa acaaaaaagg cugcaguucc cacaccagcu aagaaagcag cugugacccc   2040
aggcaaaaag gcaguagcca caccagcuaa gaaaaacauu acaccagcca aagucauucc   2100
aacaccgggu aagaagggag cugcacaagc aaaagcguug guaccaacuc cugguaaaaa   2160
gggagcugcc acuccagcua agggggcuaa gaacgguaag aaugccaaga aggaagacag   2220
ugaugaggau gaagaugaag aggaugaaga ugauagcgau gaggaugaag augaugagga   2280
agaggaugag uuugagccac caauaguaaa aggagugaag ccagcaaaag cagcuccugc   2340
ugcuccugcc ucagaggaug aggaagauga ugaggaugaa gaugaugagg aagaugauga   2400
ugaagaggag gaagauggug aguuagaucu uaggauauuu aggguacugc auguacauuc   2460
ccucacuguu ucauuagauu aaaaacucau uuugugcucu uaguucuuuc cauaacuuaa   2520
uagguuuuca uuugcuaagu aguuuuuguu uuuuuuaagu auuuguagca uuuaucuugu   2580
cuggauuggu agguagcaaa uacauuugcc ugauuugcca ucuuucuucc agacucugag   2640
gaagaaguua uggagaucac aacagccaaa ggaaagaaaa cuccugcaaa aguuguuccu   2700
augaaagcca agagugugge ugaggaggag gaugaugagg aagaggauga agaugacgag   2760
gaugaggaug augaggaaga ggaugacgaa gaugaugaug aggaagaaga ggaggaaggu   2820
aaccauauua acuuuuaaag uaugcugacc uaaguaaggc uuacuggcua ugcuaaagug   2880
ucugcuuacu caugaauggc auuuuaaaac aucuagaacc uguuaaagca gcaccuggaa   2940
aacggaagaa ggagaugacc aagcagaaag aagccccuga agccaagaaa cagaaaguag   3000
aagguaagcc ugcaaaacug ggaaacaga ucagaguagc acuagcacaa gugaugagug   3060
acaaagggac uuaauacuga accaugggu ugaaaugaaa uaugcugaug ugcuuuauag   3120
uuuaugauga aauuuguugu gugcuuaagu gggcugaaag uucauuuuuu gugugugcag   3180
gcucagaacc aacuacaccu uucaaucugu ucauuggaaa ccuuaaucca aacaagucug   3240
uuaaugaauu aaaauuugcc aucagugaac uuuuugcuaa aaaugaucuu gcuguugugg   3300
augucagaac ugguacaaau agguaaguuu uaauugaaug uuacaugugu aucagcuaga   3360
auuuuuaguu uccaguugua uucuucccug ccuuuaaaca uggggcuaua ucuaacuaug   3420
uuaguaaaag ucaguugucu ccucucgugg ccuuaaguac aguuaaggag cugcaguaag   3480
aaagacuaua guauugaacu aaaugaucga gucauagggc cugcaauuug aaguuccugu   3540
guuugacuug auaaagauaa aauaaaauuu aaagaagaaa agauauuaaa cacauaaaau   3600
uuugugcagu aucuacaacu auggaucugc auagucauau gcuuuuagcu aaaaguauuc   3660
ucuguacuuu uagcggggguc caugcuagcu acugcuguua guuacaauau acugaaugaa   3720
```

-continued

```
gaaaucgagg ugaauuuguu guaaugucuu gguacaugga cuuguuuugu uuuuuguuuu   3780
uuuuucuuua agauuuguuu auguauauga gcacacugua gcuguccaga ugguuuugag   3840
ccuucaugug guuguuggga auugaauuuu uaggaucuca gcucgcucug cucucagucc   3900
uugcuugcuc uggcccaaag auuuauuugu uguuauacau aaguacacug uagcugacuu   3960
aagaugcauc agaagagggc auuaggucuc auuaugggug gugguugagcc accauguggu   4020
ugcugggauu ugaacucagg accuucagaa gagcagucaa ugugcuuacc cgcugagcca   4080
ucucuccagc cuuuggacuu gguuuuaugg aagauaaggg ugaucuaguu uuauuuuugu   4140
uagugcugua gaugcucugu gugugugcca caugguauaa gugcagauca ccuucucaua   4200
ccuguaaucu uguuuuuucc aucuucaagg aaauuugguu auguggacuu ugagucugcu   4260
gaagaccuag aaaaggccuu ggagcucacu gguuuaaaag uguuuggcaa ugaaauuaaa   4320
cuagaaaaac caaaaggaag agauaguaag aaagguaugu aagggggucu gggugacugg   4380
auacuaacag acuuaggcag ucuggugccu cuuccuuagu uucauccuca uugugaacca   4440
augagauguc auaggucaug ugcuuguuga cagguuugau uccugggaua uauaauguca   4500
gggcugacag gaggaauagc uuagugagua aagaugcuug cugcaaaaug uuugaucucu   4560
agaagccaca ugaagagaga agaaccuuua aucccagcau uugggagaca gaggcaggca   4620
gauuucagag uucgaggcca gccuggucua cagagugagu uccaggacau ccagggcuac   4680
acagagaaac ccugucucgg aaaaaaaguu uuagcuuauc cucugaccac auguguaucg   4740
ugacaugcuu gaagcuuacc uaucucuuaa augaauucuu gaucccuaua uuuugaguuu   4800
cagaauuugg auuuuaagug uuuguuucuu aguugugcug aaaauugaac gugggcuuuu   4860
cacaugcuag gcaaauuugu uggguuuuuu uguuuguuuu uuucucaaga cagggguuuuu   4920
cuguguagcc cuggcugucc uggagaccaa gcuagccuug aacucagaaa ucugccugcc   4980
ucccaagugc ugggauuaaa ggcgugaguc accacugccc ugcuaggcaa ucacucuuaa   5040
aacugcuaca uauccucugu ccccuuuugc ucauuuuaca agguugcugu gugcucaauc   5100
ugcagucuau guuauaugcu uacuggaucu aggcuuuuga uguagaauga accauaugag   5160
ugaugaggua ucuuagagau ggaaacuaag ucuaaauaga cuuguuccau auacaacuua   5220
auacauaugg ucuaaggaac augauauaca uguaaacaag uaggaaggag auaagucugg   5280
uguccaggga agccaggaga gccucaucug aaacuggaca gggguuugug agucaucagg   5340
ugacaauuga acauggguac ucuucaugca aaugguuagu aaccauugag ccaccucucc   5400
aucccuuuau accauuuuuu uuuuuagcau auauccuugu acuuuauagg aauuauuugc   5460
uuuauucucu ugugacuugu aaauugaugu acuuaauuaa aucuuuuucc aacauaguuc   5520
gagcugcaag aacacuucua gccaaaaacc ucucuuucaa caucacugag gaugaauuaa   5580
aggaaguguu ugaagacgcc auggagauca gauuagucag ccaggauggg aaaaguaaag   5640
gguaguuuug ugucuuugag uguuaaaguu uuauuaaguu uagugucuuc uuccccucuc   5700
cuuguccuug acagucucua gucugcugcu ucaaacuuaa cuucauaacc agaaaauuga   5760
auaucugguc cucuggccuc uaccucccaa guucugacau uaaaaaugcu caacugaugg   5820
guuuugaagg ugugaucaau uuuacaggcu caauccaaau uggcaucuuu ugccacaagu   5880
acuauccuuc ccuauuuuau gagagaaaug ugauucuagg caguucaguc uauuguguug   5940
gcucuuuuuc cuccucacca guuuaaagga ugaagaugag cuaauacaua guaaaagaac   6000
aguaaaagca caugugacua aguccuucau gucugaugcu ugaguaauau uuucucuaac   6060
```

-continued

```
guaguaacug aauugucuug uacucuuuca ggauugcuua uauugaauuu aagucugaag   6120
cugaugcaga gaaaaauuug gaagaaaagc agggggcaga aauugaugga cgaucuguuu   6180
cacucuacua uacuggagag aaaggucaaa ggcaagagag aacuggaaag accagcacuu   6240
ggaguggu aa guuaaagggu uuauugugua gugggaacag gaaucauuug uaucuuugua   6300
uuuuaaguaa uugguuaccu acaauuaguu caccuuuguu cauauagcug auguuuaguc   6360
uucaugagug aaagcuauuu gaaaucauuu ccuuuggagu auaguaggca aauaaagcuu   6420
uuuguugggu auguuuugua cuuuaaaugg cuuaaacuau uuuagaaaau aguguaagac   6480
aacaaagaac aguuaucuaa uuagaaugaa aaugaaagga gcaaagaagg cauuacugua   6540
uauaauggau auacacuggu gguucuagaa uuaugguaua ugguacaugg uugaagugcc   6600
auuguuucag uuaacauucc aguaaccuug uggauuaggu uggagacaug cuuuauaggu   6660
gacccacuua cugaguguuu aaauauacac agacauacuc uaacauaccu ugcuaaugug   6720
uuaucuuugu auuugcaggu gaaucaaaga cuuugguuuu aaguaaccuu uccuacagug   6780
caacaaaaga aacucuugag gaaguauuug agaaagcaac uuuuaucaaa gugccccaga   6840
acccacaugg caaaccuaaa ggguaaaaua auuuuuacgu uagaugugggg cuggacauac   6900
auacucuuac guauaagagu aagacugucc uguuagcuua aaaaaaaacu aaaguuuuag   6960
cuauacaaag ggcaguaaau auugauagua aauuacaugc ugaugccaag uguuucuaag   7020
cuuuauucug agaacugacu uucaaccuuc agguaugcau uuauagaauu ugcuucauuu   7080
gaagaugcua aagaagcuuu aaauuccugu aauaaaaugg aaauugaggg cagaacaauc   7140
aggcuggagu ugcaaggauc caauucgaga agucguaagu ccuuugacau gauaugacuu   7200
gguuggguga uuuuuuuuuu uauuuuuaug ugccuauaug cucauuuggg gcugucuuua   7260
uguuguugcu gagaaaauga caacuggaua ugaugacuga uuaccugaga aauaauugau   7320
gaaaucucaa gaaaauuccu cuagauaguc aaguucugau ccagcuaugu caacucaaag   7380
cagcaaccuu gauugcccuc ugaguacgcu uuuuuuuuga uccaguguag ucuuuuuuuu   7440
uuuaaccuua auuucuugug uuaauugcuu uuucugguaa aagggggaaa aaaagacaua   7500
acaaaaucag uguaaggaa ggcucagugg uugagcacug agaggaccug gguucaaauc   7560
ccagcacuca cauggcaccu aucgagacag gauuucucug uguaguccug ccugucgugg   7620
aacucacucu guagaccagg cuggccucaa acucagaaau cugccugccu cugccuccua   7680
ggugcuggga uuaaaggugu gcgccaccac ugcccaaccc ugucuguaac ucuuaagauc   7740
ugacauagau ugcagacaaa acacuaaugc acauaaaaaa auuuuuuuuu uuaaaaaagg   7800
aaucuacuuc agcugaaugu ggcaguaugg caguauucac caaggguuca uagugaaaca   7860
ggaauuuuuc ucuuccagaa ccauccaaaa cucuguuugu caaaggucug ucugaggaua   7920
ccacugaaga gaccuuaaaa gaaucauuug agggcucugu ucgugcaaga auagucacug   7980
aucgggaaac ugguucuucc aaaggguaag aaggcguagu aguguugcug cuuuuuagug   8040
aauucugcau ggagaacuug ggucugcagu aucuucucau ugagcuccuu ucuguccauc   8100
agugauagau uauggauucg cacgagaaga agagagaauu cacagaacug gcacuuaucu   8160
ucuguuuuug cagaaguaua uuuggcuguu gugugagaca uuaugagaua cuggcgauuu   8220
ucucgaccug aagaguacuu uggucacucu acuuggguga cuugguacuu auuguguuac   8280
uuuaaaaugu guuuacuuaa ugggugaggu uuuuuuguuu uucuuuucug uuuuagguuu   8340
gguuuuguag acuuuaauag ugaggaagau gccaaagcug ccaaggaggc cauggaagau   8400
ggagaaauug acggaaacaa aguuaccuug gacugggcca aaccuaaggg ugaagguggc   8460
```

uuuggugguc gagguggagg cagaggaggu uucggaggca gagguggagg cagaggugga 8520
agagguggau uuggaggaag aggccgggga ggcuuuggag guaaggaagg gaaaggaacu 8580
ggaaacggau uccuaaaccu guguccuaac caaccaccuu aaaugggaag gucaguccua 8640
auuguaucac ccuuugaugu uuuuccuucc uauagguaga ggaggcuucc gaggcggcag 8700
aggaggaggg ggagacuuca agccacaagg aaagaagacg aaguuugaau ag 8752

<210> SEQ ID NO 85
<211> LENGTH: 3889
<212> TYPE: RNA
<213> ORGANISM: Homo sapiens

<400> SEQUENCE: 85
uuagacgguu gcgcgcgcag aggguuggua guugucgcug uaggccuucg cugccgcuuc 60
ugcaucguga aucgggggac cuuggcagcc agaccucguu ccucuuagag uagcucucau 120
cuagucgcca caacuccgcc accauguuug aggcacgccu gauccagggc uccauccuga 180
agaaggugcu ggaggcucuc aaagaccuca ucaaugaggc cugcugggac gucagcucgg 240
gcggcgugaa ccugcagagc auggacucgu cucacgucuc cuugguacag cuuacucugc 300
gcuccgaagg cuucgacaca uaccgcugcg accgcaaccu agccaugggc gugaaccuca 360
ccaggugagc ggguggcggg agcggggccc cacucuuccc gcuuccgcuc uuggcggggc 420
ugugacucug cacgcucauu ggcuggcuug gccauccgcg cuuucugauu ggucuauggu 480
gucgggggca gcccucacca aagcgcgcgg uuccgaaaag cccgcgcugg caguggcgcc 540
cacucuguuu ccgcgccaaa gccacaaagc gggaguccgc gggaaaauga gugcuccgga 600
gcugugcuca uuaaaugccu gcagcuuuga guggcugguc uuagcgccua auaaacgagu 660
cuuagugcaa auguaauguc gacuuagagu gacaauagac cuuuucuuga cuuccagagu 720
cucacugcgc aucauggauu ugaggggaaa ucugucaguu uuagcuuuua acuuugcuac 780
agcuaccuag guuagugccu ccuguauacg uguucaagga caguguguga cuuauuuuag 840
uacagauaca uggauuagug ccacuuguau acauuuugaa agauuuacga aaaggccaga 900
cgugaugggg cacauucucc aguacacuag aaaccaagga caccccgcuc aaaaagaugc 960
uuucucgaau guuggcuuuu agugcauuuu acuaagucgg uuuuaagaau cacauauacc 1020
cgguaauuug cuucaccccu gagagaguuu gggguacccu uagccccuuu aacaguucuc 1080
caaccgugag ugugaaaugg uacaacuugu aauugcuuuu uaaaauauag auguggauua 1140
cauguugaua aagccugucu uuuuuuuuuu ggggggguagc auguccaaaa uucuaaaaug 1200
ugcugguaau gaagacauca uuacauuaag ggcugaagau aaugcagaca ccuuagcacu 1260
aguauucgaa gcaccaagua aguuaaacac cuuuaaaacu cggaguuacg uguuguuucu 1320
guuucucaaa accaaaaaaa auauuaacaa uauuguaaau uccaucauag auaggaccgu 1380
guggugugcu ugguaacauu uuccuucuuu ugguagauca agagaaaguu ucagacuaug 1440
aaaugaaguu aauggacuua gauguggagc aacuuggaau cccagugagu uaccuuguuu 1500
cugauugugu guuacccugc ugugauacca gcugaugcgu guucugagug gagugguggu 1560
auuggggaug aauggcacac ugccauuuca cuaaaccaca gcagucuaaa guugauugag 1620
uuuuaaagaa accagaaguc uugcauucug aguucugguu aagaugcuaa aucuugagaa 1680
caugaagcug agccuucccc cuuuucuaga cugaccuuua acuugugggu uuacaggaac 1740
aggaguacag cuguguaaua aagaugccgu cgggugaauu ugcacguaua ugccgagacc 1800
uuagccacau uggagaugcu guugugauau ccugugcaaa gaaugggggug aaguuuucug 1860 caaguggaga gcuuggcaau gggaacauua aguugucaca aacaaguaau guggauaaag 1920
aagaggaggc ggugaguagu aagggggcgu ccaguuaggu gucugaagca gggauggagc 1980
cucggcuuuu guuuuuauuu auucauucau uuugagaugg agucuugagu agaccaagcu 2040
aucuuagagc ucagagacga cuccauaagc uuuuacaggu agcauuugga aagcuaagug 2100
uacagccuuu ugcuuccugg aaauacucuu ggcaaauaag ugaggguugg caagugagca 2160
aaagaaaaug guuggggggug uauguagcuu uauguguugc agguucaaga guauuugcag 2220
ucccaaggga aauaagaaag acuucacaaa auguggaaag aguuguauua aaugcucuug 2280
acaguuacau ccauagagaa agcugggcau gaugucucaa acccacaacu gauguacuca 2340
aagcuacagc aggaagauuc ucagcuuaaa gucaaccugg cagaaaaucu agcucaaaaa 2400
gaaugaggaa gaaauuggga aggcaaagga agauguucuc cgaguccucc ucauucaagu 2460
agaacauacu aggccucuuu aauuucuaag uaucccugaa ucgaggcuuu uucucaggaa 2520
uccaauguau auuucauggc uacacuuuuu uuuuucuuuu uuaaguuuug cuagcuagcc 2580
ugagcaucag aauuacacac agaagucuga acuaaauagg auuuuuaggg uuuaguauag 2640
ugaaauucag agugcuucug caaguauuua agguaaauau aagguguuac uuggccucug 2700
caugaauuua aaguaaauga aaguguaaga auucgaacau agauaaacac acaacccaag 2760
aacuaguucu uaaccuuaau cugcugaauu auuucuacuu ccauaucaac uucagcuccu 2820
caguucucaa auacugacau guaauucauc aguauuuguc ugaugugcaa gcauuuccac 2880
aacaaaagaa auuaaggaau uuuucaguau ccacauguuc aaggauuggg aauugaauaa 2940
aauugauaau cauacaauga agacugguuu acugucccuu agcuugcauu cagcuguugg 3000
uucuuguuuu uggaaguggu uauguguuau cuuccucucu ucaugcauuc uuugcaagag 3060
aaguauguac aaucugaaua ggaacaacuu ucuccuuugu uuugauugcu uggggugugg 3120
cucuacagga ugggcaagcu agacuuuuuu cuucuuuagu caagguuuuc aucaacccuu 3180
ccaaaaugau aacuauuugu uuugcuuugu gguauaaauac cgugaucuaa uagugugagu 3240
uucugauguc uacagugagc cuguuuucuc cucuagguaa ccauagagau gaaugagccu 3300
guucaccuaa cguuugcucu gagguaccug aacuuuuuca caaaagccac uccacugucu 3360
ccuacaguaa cacucaguau gucugcagau gugccccuug guaagaugau aaguuugaac 3420
auuguuuugu aaugugguau uuauaguauu cgguggguuua auuuuuccug ucuuucaguu 3480
guagaguaua aaauugcuga caugggacac uuaaaguauu auuuggcucc caagauugaa 3540
gaugaggaag caucuuaggc auugcuagaa auugagaaaa cuaaaccuuu gaagauugcu 3600
ccugagaugc cagcguguccc ugaggucuuu ucugucacca aguuuguacc ugaguauucu 3660
uaaauauuaa aauaaaauau guagauaucu ucuguaaaua accuacuuuc uuuucucucc 3720
auucuccaua auuugcuuaa agaauaagcu ccaaaguaaa aacuaguuuu guuaacauga 3780
auguuucugc uuuacaaaua cuggugauuu uccaucaaug aucuugacgc uaaaugcagu 3840
uuuaagaaau auuguucaau uuaaauaaag uuaacaauuu gaaaaguca 3889

<210> SEQ ID NO 86
<211> LENGTH: 1720
<212> TYPE: RNA
<213> ORGANISM: Homo sapiens

<400> SEQUENCE: 86
ggugcaggau guaggccugc agaauuguca gacccagugg cggcuuuugc cacuggaaga 60

-continued

```
auuuccaaca uaaaacagau gaucaguuug ggacaaucga uucugcgacc agagguagug    120
ucauuugguu acuuuuaaaa uucagauugu cuggguguuu ccaaucacuc gcgacuguaa    180
uuugaaguug gguucugaga uaauacaauc gcugucgcuc uaguuuauaa agcuguccaa    240
gaucugccca gucccagaug uccugggucc ucagggccgc uguggucugc caacuucugc    300
agcuggaugc cagaccaucc uggacucgga ucccuuuggg uauuucuaca ccgcuguguc    360
ccggccuggc cuuggggagc ccugguucau aaucgucggc uauguggacg acaugcaggu    420
ccugcgcuuc agcagcaagg aggagacucc gaggauggca cccuggcugg agcaggagga    480
agcaggugac ugggagcagc agacucguau agucacaauu caaggacagc ugucugaaag    540
gaaucugaug acccugguuc auuuuuacaa caagagcaug gacgacucuc acacacuaca    600
guggcugcaa ggcugcgaug uggagccaga ucggcaccug ugucucuggu acaaccagcu    660
cgccuaugau agcgaggauc ucccccaccu gaacgaaaac ccaaguuccu guacaguggg    720
aaacagcacu guaccucaca ucucucagga ccugaagagc cacugcucag aucugcugca    780
gaaauaccug gaaaaaggga aggagaggcu gcugcguuca gacccuccaa aggcacaugu    840
gacccgucac cccagaccug aaggugaugu cacccugagg uguugggccc ugggcuucua    900
cccugcugac aucacccuga ccuggcaguu gaauggggag gagcugaccc aggacaugga    960
gcuuguggag accaggccug caggggaugg aaccuuccag aagugggcag cugugguggu   1020
gccucuuggg aaagagcaga guuacacaug ccauguguac caugaggggc ugccugagcc   1080
ccucauccug agaugggagc cugcauggua ccaaaagccu uggauuugga uuguugccau   1140
gguuuucauu uuguucauca uuugucucug ugugguuugc auaugcauga agaagaaugc   1200
aggugggaga ggaaggcgug acacccaaga agcaggcaga gacaguccc aagacucuag   1260
caagacuguu guggaugaug aggagauggg gguuugcuuu uggaagauua aguccuguaa   1320
aacuugucua ggccacuccc caggaacuuc aguuggcgag ucuuuacugu caccuugacu   1380
ggauuuagga ucaucuggga gaugccccuu ugaguggcug ggcugugagg acagcaggcc   1440
aguucuugcc acccuggaca gaaacacauc ucaccuuucu ggcucaagga ucugaacacc   1500
ugucucuugc cuacucggcu ucuagucagg cauuuuguca ccuugucaag ggucccaggg   1560
acacaaagcu cccuccucuc acccacagca cucuggguccc uacccucagu gcuucaggga   1620
cauuuaauca ggucaaauug ggaucaaugg cuuugaugca gaaaagaacu guggacuaau   1680
agagauaggg uuuaauuaaa aaauauaucu uuuuaauuuu                         1720
```

<210> SEQ ID NO 87
<211> LENGTH: 367
<212> TYPE: RNA
<213> ORGANISM: Homo sapiens

<400> SEQUENCE: 87

```
cuggcacgga cauggcuguc uucugucugc uguguggga acgcuuucag gcacaaagcg     60
cacuccagca gcacauggag guccacgcag gcgugcgcag cuauauuugc agugagugca    120
accgcaccuu ccccagccac acggcucuca agcgccaccu ucgcucacau acagguuuuu    180
uucuccaugu gucaccaagu gaaguuugug ccuucuauag caaagagaau auuuuuuaca    240
uccuacuaac aguagauuuu uuuguaguga acauuuuuug uauuuuuauu uauaagucuc    300
auaagaaaaa uagcgauguu caguuguaua ccuugaaucu gcaguuagaa gagaauaaag    360
uuaacuc                                                              367
```

<210> SEQ ID NO 88
<211> LENGTH: 7879
<212> TYPE: RNA
<213> ORGANISM: Homo sapiens
<220> FEATURE:
<221> NAME/KEY: misc_feature
<222> LOCATION: (4457)..(4460)
<223> OTHER INFORMATION: n is a, c, g, or u
<220> FEATURE:
<221> NAME/KEY: misc_feature
<222> LOCATION: (4471)..(4471)
<223> OTHER INFORMATION: n is a, c, g, or u

<400> SEQUENCE: 88
ggagccccag ugcaggaggc ugcgaaaguu gggggagugu gcuagaagga cugcggagcg 60
gagcgcacgc gggaccaggc ugcgacuggg ucgcuggucc cggccacagg gaguggggagc 120 cggcugggua gguaccccgc agggagcgug uuucuguuuc uagggacagu gcaugaaaga 180
gauggggugu acgcgcgggc gaaaaggaag gguguuuucg ggucggcuua cgaggagggg 240
uguguagggu gcauuuuugg uauuaaagga uagcucuugg aguagggugga gccagggcuu 300 gaaguuuagg aagcgggcga agggucugca aggugcuugg uuuugguagg uagugggcgc 360
uuguuuagga gguuuccccg cuaggaucuc cagugugagg cacucuguac ucuggguuug 420 ggguguugauu gccggguagg ggguugucug agcauggacu gggaaaaggu acucagagcu 480
ucggcguugc uggggaucca uccaaguaca aguaagauug gauuuccacg ggucuccuuc 540
ccggcucuca gcccccuuuc ccaguguuua cuuaauacuu cauaggcugu acuuagauuu 600
ucugauuccc uuaccgaacu uucuuucuga accgugcugg aagaccuggg gguugcugaa 660
ggaaauggcc agcuagguug gcuggguaau gguuguguua gacuaaguug ucagaguauc 720
uagaaaccua ggagcuguag ccuggugcag cuacugaaag ccgcacgugg agccugggug 780
gaaguugcuc acgauagagu cucgauguag uacugacuag gggggagacc ccuucuguca 840
ucagacagac uuguauaccc caguggucuu uugaaucugu uagguagggu gcagccugcg 900
ggcuugguca ccuaacaggu guugccagga ccugccccaa gccggauucu cccacucccu 960
cuuucaaccc cgccucuucc uccuccuuga gacaccccca cccccucagg aggcuagaug 1020
cagaucugua ucuuguguug cugacuaucg gccugaagcu ggguagauug guggggguug 1080
auccggaugu aggaugucca aguggagaaa caggauuuga auggagcugg aacaaacgcc 1140
caguccugac ugcugccacc cuucuucccuc cacccccaac ccaucccuuc ccaggcuucu 1200
ugcaaacaga ggcagaagug gccauauuuc uuucuuucuc ccaggugcug uaugcccuag 1260
ggacuugaca cggggcaggc ggggugggaa cugguugggg ggggacgugc uguuuuaugg 1320
gaagucguau gccuagccag cgguggagcu guccuggcua ggcacccagg ggugguguggg 1380 ggaaugggag aaauacuggg acuagagggu cucaagggcc agcaggugggu gauagucuuu 1440 uucuccaccc cacccucugc uccaccaccc cucugccuca gcaccccucu gcccucagca 1500
ccccucugcc ucagcacccu cugccuccag ccacccucug ccucagcacc cucugccuca 1560
gcacccucug ccucagcacc cucugccuca gcacccucug ccucaguguu ccugugugac 1620
cugucuuuuc aacuagaaag ucuagaacug uacagacccc agaguuggag guggaaaggg 1680
acacuagguc cuggagccuc cucugugggc uuuuuugacc agaugagaac guaagggccu 1740
ccuccagcua ucccugguca uucaggugcu ucagguuugu gaccuuugcu gagacccugg 1800
augcugcagc aaacagacau cugcuuuagc agagggacag cuugucucug ugcauccgcu 1860
gguaggaucc uccacucugu ccaauuagcu ugcgcugcug cuggguucug aguguucucu 1920

-continued

```
uacaaaauga caagguuagg gggcuggaga gauggcucag gggcuaagag cacccaugug   1980
gcaguuugca acugucugua acuccuguuc caggggggau cugacacccu cacacggaca   2040
aacaugcagg caaaacaccu auuggcaugg aaaaugaaaa uaaaugaccg gguuagcuga   2100
gaaauuccuu uugagaguug ucuuuucucc aguccaggac ugcucucugg aucuuccugc   2160
ucaguuccuc gccucccuuc cauauauggu auuuaagguu uuacuuuuuu uugcguuuuc   2220
aauuguuuuu aauuguauuu auaugugucu cugugugugc acaugagcau ggguguccua   2280
caaggcuaga gacaucagau guccuggagc uagaguuaca gaugguugug agccaccuga   2340
uguaguugcu gggaacugga uuuaguuccu guggaagagc agugcaugcu cuuaaccacu   2400
gagcaacuuc uccacgcggc cccccccag uauacgguau uuaaaacucu auagcaaugc   2460
uacccaaccc auuguggagc uggggauggu gagguggccu aguucccccc aacuccugga   2520
aacaugucag aaaguacaga gugggugccu gugggaucag caugcggggg gugguggugg   2580
ugaggugugg ggcugcuuuc ucccgaggcu accgugauag acaguuguac cuugcuggca   2640
gccucuaccc cauuuccagg augucagucu cugcagacgu augggggacg gugggggaagg   2700
gguauacaga gccaugggug ugccugggaa uguacuccca ggaagugacu gguugaaaag   2760
ucagcagauc uccuggggga uagaggggug ggcugaagcu cuguggguug ccucucucag   2820
cccugaccug ugaacaggga ggcugggggu uggaggaaca cagcuucccc cuguuccugg   2880
ggggacaugc uggacagccu uuccuagcuc ccccggccca cuggggugug gcuggucguc   2940
ggacugagcu cuuuuggacc uggucucugc cugugagcuu ugugacucgu ugagauagca   3000
uuugggcuga gggauuggga gucuucuguu cuuuggcccu gacacccgcu uccuugucua   3060
ggccugccac cuggcucccc ccacccccu ccccggccua ccaaguuucu ugcuucccuu   3120
acugaccccu ccuccucccu ccuuugugucc uccucccucu ccagagaugc ccuguauuca   3180
agcucaauau ggaacaccag caacgagccc aggaccgcgu gaccaccuga ccggugaucc   3240
ccuggcccuu gaguucggca agccuaccau ggaccuggcc agccccgaga cagcaccugc   3300
cgcaccugcu acacugccca gcuucagcac cuucauggac ggguacaccg gagaguuuga   3360
caccuuccuc uaccagcugc cggggacgac ccagccgugc uccucagcuu guuccucugc   3420
cuccuccacg ucuucuuccu cauccucggc caccucccccc gcuucggcgu ccuucaaguu   3480
ugaggacuuc cagguguacg gcugcuaccc gggcacccug agcggcccau uagaugagac   3540
ccuauccucc agcggcucug aguacuaugg caguccccugc ucagcccccu cgccaucuac   3600
acccaacuuc cagccguccc agcuuucucc cugggacggc ucauuuggcc acuucucccc   3660
gagccagacu uaugaaggcc ucugggcaug gacagagcag uugccuaagg cuucuucagg   3720
gccuccgcca ccuccaaccu ucuucuccuu caguccuccc acuggcccca gccccagccu   3780
ggcccagagu ucucugaaau uguucccacc accagccacc caccagcuug gggaggggga   3840
gagcuauucc augccagcag cuuuccccgg cuuggcaccc accucuccga accgugacac   3900
uuccggcauu cuggacgcac ccgugaccuc caccaagucc cggagcgggg cuucaggugg   3960
cagcgagggc cgcugugcag ucugugguga caaugcuucg ugucagcacu augggguccg   4020
caccugugag ggcugcaagg gcuucuucaa gguauuuugu ugguucuggg ggacgaugau   4080
aucauguugg aggugggggu ggagugggguc auccguuggg aucuguagug accucuccug   4140
agguuucuuc ccagcugguu cuguccugca ggacgaggga caggugugug ccaucuuaga   4200
ggcugggacu uuuuauucag cagggcacac aucucucuag ggcugcagaa agcuggggaa   4260
```

-continued gggggcagaa ggugugugug uguguggccu gcaguggugc ucagaaacag aaaaccuagu 4320
gggcagccuc ugguucucca cagaacuugu guuucuggca cuggaugaaa ggacacaggc 4380
agaggguuug guucuugcug ggggugggacu ugggaacagg cuguguguuu gucccagugc 4440
uggggugccug cuuggcnnnn cccaccucca nccccuuagu ccucuccucu gcgccaggaa 4500
aagggcaggu ggacacaugc agacaccugu uagaacaggu gucuggacgg ccgugggagu 4560
uccuagaccc uggucuuggg uucugggauc uucccuguga gguugaaacc uucuccagua 4620
ucucccagac uccucucugc gcucuggccc uccguuucuc ccucccccua cauccaaaug 4680
uuaggaaaau agcuaugaac agagggcgcu uuugucugcg ucggccacag gaucuggacg 4740
guccccuccc cugggcucuc cacccccccc ccaaacccca ugcucugaca gccuguuccg 4800
uguccccccu uccuccagcg cacaguacag aaaagcgcca aguacaucug ccuggcaaac 4860
aaggauugcc cuguggacaa gaggcggcgg aaccgcugcc aguucugccg cuuccagaag 4920
ugccuggcug ugggcauggu gaaggaaggu ggguggcaag auggugcccu cggcauaggc 4980
gaccugaugg ggugggacag ccgggcucac caggaucugc accuaauucc cacucccacu 5040
ucuagauucc agccccuaaa ugcaggugua gcuuccaccu gcuuucugga aagggugggg 5100
ugaggagggc cuuguggggu ccccaucaug gucugaguuc ucugucucug acuucucaga 5160
agugggggugu auagugugcc cugaagaccc uccuucucca ggucuccuuu cucaauacug 5220
cccgucucuc ugcaguugua cggacagaca gccuaaaagg gcggcggggc cggcuaccuu 5280
caaaacccaa gcagccucca gaugccuccc cuaccaaucu ucucacuucc cucauccggg 5340
cacacuugga cuccgggccu agcacugcca aauuggacua uuccaaggug aggucuugcc 5400
cgcccaucug cccugcccug agaacauaug caaugccuuu gugccuguua ggaaaggcuc 5460
ucccuccagg gcaacaucag gaaacaagca uccucuaugu acuggcuagu uggagaaaug 5520
cauugggaug gguguggggu cggggagcca guuacaaaca gcugccguag cccuguuuuc 5580
cugugggaau ugacaagcac augggcccag aauagggcuc uuuugcacgc cuggaucugg 5640
ugucccagug caugagagcu cuguaaugca gcuuguguag gcuuugcugu ggacccaaug 5700
caggacacag cugugugaug caggccuugc uguggagcca gugcgugaca cagcugugug 5760
gugcaggccc ucauguggaa cuuaccugcg uuccuuucag uuccaggaac uggugcugcc 5820
ccgcuucggg aaggaagaug ccggugacgu gcaacaauuu uaugacuugc ucucugguuc 5880
ccuggacguu auccgaaagu gggcagaaaa aaucccuggc uucauugagc uuugcccagg 5940
agaccaagac cuguugcuag agucugccuu ccuggaacuc uucauccucc gccuggcaua 6000
ccgguaagcu gcccaccauc cuccuagccc uggccccagc ccugcggccc cggccugccu 6060
ggacccugag uccugacugu ucucugccuu cugccagauc uaaacccggu gaggggaagc 6120
ucaucuucug cucaggccug guacuacacc agcugcagug ugcccguggc uuuggugauu 6180
ggauugacaa cauccuggcc uucucacggu cccugcacag cuugggguguu gauguucccg 6240
ccuuugccug ccuguccgcu cugguccuca ucacugguga guggcagaaa cuagacuggg 6300
cccaaggguu gcaggaccau uggguaggua gcaucuaaca cuuuggggac cccuagagug 6360
ccugcaacau ugggauguua ggaccugcaa agggacuuag cucuauucgc cccuaaagcu 6420
uaaaucagcc uccgaaugac cccggacucc ucagguacga cuguaggcgc ugggcaucua 6480
gcuuagggau ucuguuuguu uaaaaaccua gcugucaacc ucacaagaca caggaacgug 6540
cacacaugaa uuuuucacau ucugcgcuug gauagcuauc gccauggucc agaaacagga 6600
ccuacuucag cucuguuggg cucccuccuu auugucucug uaagagguaa ccacucugcc 6660
agccucagug gcauuccugu cauggauuuu acugugcgua ucacagggua uggacucuag 6720
uguuaaaugu agagguuucu gggucccuuc ucguuccgcu cccauuucca cuuaaauuuc 6780
uuaggggauc cuccugagua gaucaagacc aggagcugga ucuugaaagg guagggagug 6840
auaucuacac ccagcucagu ccuuagucug uccugcgaga cuccaggauu uuagaacagu 6900
guggagccug gaccuccaga aaaccuggau uaggcuuuug ccuuggccag ccauucagug 6960
guuucaaaua uugaccaguc uggacagugg gcuccugugg gacgugcuag agggcugggg 7020
aagcuuguca gggagaaggc gucaacugag cggggcugac ucuaccuucc cugcugcaga 7080
ucgacacggg cuccaggacc cucgucgggu ggaagagcug cagaaucgca uugcuagcug 7140
ucugaaggag cacauggcua ccguggcagg agacccacag ccggccagcu gccugucacg 7200
ucugcugggc aaacugccug agcuucggac ccugugcacu caaggccugc agcgcaucuu 7260
uugccucaag uuggaggacu ugguaccccc uccaccuauu guggacaaga ucuuuaugga 7320
cacauugucu uucugacccc ugcccugaac augugugcgc acacgugcgu gcucuucugu 7380
cacccaugug ccuuuaagcc uauagcccac ggaccccag accacccuac ccccagccug 7440
guuuugagcu aagacugacg uaccuccuca cuccagaaga uggacagaga acucaagacc 7500
ugggggaggg uguguauuca cgggggugac cccacuauuu gucuuauccc uccagcucag 7560
uccuggccuu cguguguuuu uguaagauaa accauuuuua acacauacca cucuguugua 7620
aauaagcuga cgcuacugua aauacagaaa ggaagagguu gagauggggg uugggaggaa 7680 ggggugggc ucccaccagc ugggcgagcc uccaacucga gaucucuucc gcucuccuuc 7740
cauguguaca uaacugucac ucaagaaggu gauugacaga uucugauuua uauuugugua 7800
uuuuccugga uuuauaggau gugacuuuuc ugauuaauau auuuaauaua uugaauaaaa 7860
aauagacaug uaguugaaa 7879

<210> SEQ ID NO 89
<211> LENGTH: 586
<212> TYPE: RNA
<213> ORGANISM: Homo sapiens

<400> SEQUENCE: 89
ggcacgaggc ugugcccgcc augucugcua cccaucacaa gaccucccug ccucagggcg 60
uccgcguggg cacugucaug agaauucgag gcuugguccc ugaccaggcu ggcagguucc 120
auguaaaccu gcuaugcggu gaggagcaag gagcagaugc cgccuugcac uuuaacccga 180
ggcuggacac uuccgagguu gucuucaaca ccaaacaaca aggcaaaugg ggccgugagg 240
agcgaggcac cggcaucccc uuccagcgug ggcagcccuu ugaagugcuc cucaucgcca 300
cagaggaagg cuucaaggcu gugguucgggg augacgaaua ucuccacuuc caccaccggc 360
ugccgcccgc ccgcguucgc uugguggaag ugggcggaga cgugcagcug cauucauuga 420
auaucuucua agcaaaggac ccaagggccu uugcccgguu acggguuggg gguuuuuuga 480
ucccacaaga aagguuuugg aucggccaau aacauuuuuc uguuguucug aaaaauuaaa 540
aaaaaaaaaa aaaaaaaaaa aaaaaaaaaa aaaaaaaaaa aaaaaa 586

<210> SEQ ID NO 90
<211> LENGTH: 540
<212> TYPE: RNA
<213> ORGANISM: Homo sapiens

<400> SEQUENCE: 90

-continued gccacauugu ugcaccaacu ccagugcugg agucucagga caccacaggc uacccggagu 60
uguucugcuu uggagauccg agggcaggag caucacgcca gugacucuga uaggugcgau 120
cgccggauug gaacagaacu gucauuuuuu uccgaaguug agccuuagug acccagugag 180
ugaaguuagc gacgggacgc uaagcagcua gaccggucgg caggagugag acuuagggua 240
ccuucuagua guugugauua aaaaaauuga aaaaaagaaa aaaaaaaacc cuguuucugg 300
aaacuugagg cccucagcug gugagccauc gugguuaagc uucuuugugu ggcuccugga 360
gucuucgauc ccagccggac acccgggccu gguuucaaag cggucggaca gcgcugccug 420
cuccaucggu agcgcucgag ccucgguuuc ucuauuuggc cccgacucgc cgcaacaaga 480
ugaucgccuc gcauaugauc gccugcuuau ucacggagcu caaccaaaac caagugcaga 540

<210> SEQ ID NO 91
<211> LENGTH: 2000
<212> TYPE: RNA
<213> ORGANISM: Homo sapiens

<400> SEQUENCE: 91
cccagcuguu ucguccguac cuagaccgcg guuauggcgu cguucacggu gaaggccuau 60
cuucugggca aggaggaggc gacccgcgag auccgccgcu ucagcuucug cuucagcccg 120
gagccggagg cggaagccca agccgcggcc ggcccggggc ccugcgagag gcugcugagc 180
cgaguggcug ugcuguuccc cacgcugagg ccuggcggcu uccaggcgca cuaccgcgau 240
gaggaugggg acuugguugc cuuuuccagu gaugaggagc ugacaauggc uauguccuau 300
gugaaagaug acaucuuccg caucuacauu aaagagaaga aggagugccg gcgggaacau 360
cgcccaccau gugcucagga ggcaccccga aacauggugc accccaaugu gaucugugau 420
gguugcaacg ggccuguggu gggaacucgc uauaagugca gugugugccc agacuacgac 480
cugugcagcg ugugcgaggg gaagggccug cacagggaac acagcaagcu caucuuuccc 540
aaccccuuug gccaccucuc ugauagcuuc ucucauagcc gcuggcuucg gaagcugaaa 600
cauggacacu uuggcuggcc uggcugggag augggcccac cggggaacug gagcccacgu 660
ccuccucgug caggggaugg ccgcccuugc ccuacagcug agucagcuuc ugcuccacca 720
gaagauccca augucaauuu ccugaagaau gugggggaga guguggcagc ugcccucagc 780
ccucuaggca uugagguuga cauugaugug gaacauggag ggaagagaag ccgccugaca 840
cccacuaccc cagaaaguuc cagcacaggc acagaagaca agaguaacac ucagccaagc 900
agcugcucuu cggaagucag caaaccugac ggggcugggg agggcccugc ucagucucug 960
acagagcaaa ugaaaaagau agccuuggag ucggugggac agccagagga acagauggag 1020
ucgggaaacu gcucaggagg agacgaugac uggacacauu ugucuucaaa agaaguggac 1080
ccaucuacag gugaacucca gucucuacag augccagaau cggaagggcc aagcucucua 1140
gaccccucac aggaaggacc cacagggcug aaggaagcug cccuauaccc acaucuccca 1200
ccagaggcug aucccccggcu gauugagucc cucucccaga ugcuguccau ggguuucucg 1260
gaugaaggcg gcuggcucac caggcuccua cagaccaaga auuacgacau cggggcugcu 1320
cuggacacga uccaguauuc gaagcacccu ccaccauugu gauagugcug uggccaagcc 1380
ccacccccuu ugucuuguag uugcaucacg uagagcagca gggcuucuau agauaggccc 1440
agugucuugg cauucuugua gaaucuucag gugggaaugu gugaugccuu uucaggcaau 1500
aggaaagugc augaggagag uuuugaaugu gcauaugcug acgccugaga acagacccag 1560
guacccgugg cugagcugag cuuccucugc uuccccuagg ccuggccucu gcagggaacu 1620
gcagcacaca cugcacuccc accugcucuu gccgccagca uugcaccagc aguccagaau 1680
uccugccuga caacccgugu uuccuuuauu aaaagugauu aguacaacug cuaguuauuu 1740
ucaacaaaua aagccauuau guuaagaggg gacuguccau agugagugaa agguggcagg 1800
caggggccua cagcuccuag ggaauggaga auucauguga agccgaauga aggaucuuau 1860
cuuauacugu cccccuuucu aauggccacu cuuuaguguu ugugucuaau guuaaugcuu 1920
aaagcacagg acccccaugu agcuuccucu gacuugguuu guaaguaacc uguaauaaaa 1980
ugccauaugc acuuuaacca 2000

<210> SEQ ID NO 92
<211> LENGTH: 2649
<212> TYPE: RNA
<213> ORGANISM: Homo sapiens

<400> SEQUENCE: 92
gagggaauug cgggaccccg ucuggggaag cucccgccgc cccggggugc ucagcucucu 60
gucucccuug acccagguac agucaugucg ggcuucgacg acccgggcau uuucuacagc 120
gacagcuucg guggcgaccc cggugcggaa gagggccagg cccgcaaguc gcaacugcag 180
aggcgauuca aggaguuccu gagacaguac cgagugggca ccgaucgcac gggcuucacc 240
uucaaguaca gagaugaacu caagcggcau uacaaccugg gugaauacug gaucgaggug 300
gagauggagg accuggccag uuuugacgag gaacuggcug accacuugca uaaacagccg 360
gccgagcacu uacagcugcu ugaggaagcu gccaaggagg uggcagauga ggugacccgg 420
ccccggccag cuggagauga gcugcuccaa gacauccagg ucaugcucaa gucagaugcc 480
agcccgucga gcauucggau ucugaaguca gacaugaugu cacaccuggu gaagaucccu 540
ggcaucauca uuucagccuc ugcaguccgu gccaaggcua cucguaucuc cauucagugc 600
cgcagcugcc acaacacccu caccaauauc gccaugccca ggccuagagg gcuaugccuu 660
cccaggaagu gcaauaugga ucaggcuggg cgcccaaagu gcccacugga uccauacuuc 720
aucaugccug acaagugcaa gugugugac uuccagacuc ugaaacugca ggagcugccu 780
gaugcagucc cucauggug a gaugcccagg cacaugcagc uuuauuguga cagguaccug 840
ugugacaagg uuguuccugg gaacaggguc accaucaugg gcauuuauuc caucaagaag 900
uuuggcuuga accccagcaa gggccgggac aggguaggug ugggcauccg gagcucguac 960
auccgagugc ugggcaucca gguggacaca gauggcucug gccgaagcuu ugcugggucu 1020
gucagcccac aggaagagga ggaauuucgu cgccuggcug cccuccccaa cauauaugag 1080
cucaucucca agagcauuuc cccucccauc uuugggggca uggauaugaa gaaggccauu 1140
gccugccugc uuuuuggggg uucccggaag aggcucccag auggacucac ucgccgaggu 1200
gauaucaacu ugcugauguu gggagacccu gguacagcca agucucagcu ucugaaguuu 1260
guggagaagu gcucucccau uggggguguac acaucuggga aagguagcag ugcugcaggc 1320
uugacugccu cagugauacg ggaccccuca ucucgaaacu ucaucaugga agguggagcc 1380
augguucugg ccgauggugg gguugucugu auugaugagu uugacaagau gcgggaagau 1440
gaccguguug caauccauga ggcuauggag cagcagacca ucuccauugc uaaagcuggg 1500
aucacuacca ccuugaacuc ucgcugcucu guucuggcug cagccaacuc aguguuuggc 1560
cgaugggaug agacaaaagg ggaggacaau auugacuuca ugccuaccau cuugucccga 1620
uuugauauga ucuucaucgu caaagaugag cacaaugagg agagggacau gaugcuagcc 1680
aaacauguga ugacucugca ugugagugca cugacacaga cacaggcugu ggagggugag 1740
aucgaccugg ccaagaugaa gaaguucauu gccuacugcc gagcgaggug uggaccucgg 1800
cuaucagcag aggcagcaga gaagcugaag aaccgcuaca ucaucaugcg gaguggggcu 1860
cgucagcaug agagggacag ugaccggcgu uccagcaucc ccaucacugu gcggcagcug 1920
gaggcuauug ugcgcauugc ugaggcccuc aguaagauga aacugcagcc cuuugccacu 1980
gaggcugaug uagaggaggc auugagacug uuccaggugu ccacacugga ugcugcuuug 2040
ucuggcaauc ugucgggggu ggagggcuuc acuacccagg aggaccagga gaugcugagc 2100
cgcauugaga agcaacucaa gcgccguuuu gccauuggcu cucaggugucc ugaacacagc 2160 auuguccagg acuucaccaa acagaaauau ccagagcacg cuauccgaaa ggugcugcag 2220
cucaugcuac gcaggggguga gauccaacac cguaugcagc gcaaggugcu cuaucgccuc 2280
aagugagccc auugcccauc aacccucaag ccugaaaugc ugccaccacc cuaucuccca 2340
gucagugcuc caaaccuccu uuugcccugc cucuccaccu cagacugcug ucugcagcac 2400
aucugcagcc ccuggaaaug uacuuugguc uguuggcuca uacuguguuu gagugucuga 2460
ggacucucug cucugggugu cuauccccug ucaugccuuc ucaacaagau gagucuggag 2520
caggaacagg cccuggaaug uagaugggc uguauauugg cucccgggcc acucacugcc 2580
aagcuucuuu guauguacag agguaauaaa gcaauugagu cccuggcugc uaaggucagu 2640
ggacccagu 2649

<210> SEQ ID NO 93
<211> LENGTH: 450
<212> TYPE: RNA
<213> ORGANISM: Homo sapiens
<220> FEATURE:
<221> NAME/KEY: misc_feature
<222> LOCATION: (389)..(389)
<223> OTHER INFORMATION: n is a, c, g, or u

<400> SEQUENCE: 93
ggaugcagcc ggaagugcag cgugcgugcg guuuggug gg ucgcugugug cgcuccgcgu 60
gugcagccgc gugggccaug gggcggcggg cgcggggccg gcgguuccag cagccgccgc 120
agccugaggg cgaggaagac gccagcgacg gcggcagaaa gcgaggccag gcgggcuggg 180 aaggugg cua ucccgagauc guaaaggaga acaagcucuu cgagcacuac uaucaggaac 240
ucaagaucgu gccagaggga gaaugggacc aauucaugga gucacuccga gaaccucucc 300
cagccacacu gagaaucacu ggguacaaaa gccaugccaa agagauucuc cauugcuuga 360
agaacaagua cuuuaaggag uuggaggan c cugaaguaga uggacagaaa guugaguucc 420
acaaccacua agcugguacc cugaagaacu 450

<210> SEQ ID NO 94
<211> LENGTH: 929
<212> TYPE: RNA
<213> ORGANISM: Homo sapiens

<400> SEQUENCE: 94
gagcucaaau ucuggcuuuc uauugg guac gauauauuaa ccaaugggag aaacacaaac 60
agaauaccuc caguuaguau aaaugcuugc uguucaguug cagaauuuac uauauauucu 120
uuuccuuucu cugcuuugcc uuuacugaua cuuaaacgca uacaugucug gacgcggaaa 180
gcaagggugc aaggcccgcg cuaaggccaa gacccgcucc ucccgggccg gccugcaguu 240
ccccgugggc cgcgugcacc ggcugcuccg caagggcaac uacucggagc gcgugggcgc 300
cggcgccccg guguaccugg cggcugugcu ggaguaccug acggccgaga uccuggagcu 360
ggcgggcaau gcggcccgcg acaacaagaa gacgcgcauc aucccgcgcc accugcagcu 420
ggccauccgc aacgacgagg agcucaacaa gcugcugggc cgcgugacca ucgcgcaggg 480
cggcguccug cccaacaucc aggccgugcu gcugcccaag aagaccgaga gccaccacaa 540
ggccaagggg aaguaaucug gcgauugucu guacugccca guugaaaguu aaccaaaaca 600
aaggcucuuu ucagagccac ccacaucuuu ccauaaaaug agcugccacc ucgugaaacg 660
uucuuccacu acaguuuuua uacuacauau gaaaaaguua cgaaguagcu uucaaucuua 720
guaaauugau uuuaauacug uuagucccug cgauaaaucu uacgaccuuc cuuaguuuga 780
gucaaaagug uguaagagau gaaaccuuua gaacauacua uaaauuuuua guagaaauuu 840
ggcacccagg uuugucauuc acgucacgau ugucuagagc auaaugguag uaagggcuaa 900
gggccauuaa aucccacuuc cauaguuuc 929

<210> SEQ ID NO 95
<211> LENGTH: 325
<212> TYPE: RNA
<213> ORGANISM: Homo sapiens

<400> SEQUENCE: 95
uuuuuuuuuu uuuuuuugga aaugaaggua auuuauugaa acugguuuug ggacaggcga 60
guggacaacu guugaaagga gcuagcgcac agccgggugg gagcgggugc uuagccacag 120
auccuaucug aggcccaacu uuuucuuuuc cuucugcuuc uuacggacca cauccagguu 180
ccgguccuuc cacaugcuuu ugcgaagcuu gaugggggcgu gagcccacau acuucccauu 240
caucucucgc auggcgcgca cauagucacu ggggucuuug aagcugacaa agccauagcc 300
cuugguuuug ccugugcgcu uguca 325

<210> SEQ ID NO 96
<211> LENGTH: 367
<212> TYPE: RNA
<213> ORGANISM: Homo sapiens

<400> SEQUENCE: 96
uucggauccu ugccaauaua uguaucccau uuggaauggu gaucuuaaaa ugugagugca 60
ugcauacuau cuuauuuaag auacuugcac ccccacccacu cccaucuccc gaagcuggaa 120
cacugccaac uagguccuua agaaucacgc aauuaacaca agguuggggug cugcuaauuc 180 uucaugaaaa uccaaacacg uuaagggacc agggagaugc cacugccccc cugaauuuuc 240
aucaaaaaua gacacguuua uguaaacaga acuauuuucc auauucauag ugacuuuuua 300
aguauuugag ccuaaagauu uugaucucca uuuuuauaac uauuuaaauu guucacaauu 360
auuacau 367

<210> SEQ ID NO 97
<211> LENGTH: 418
<212> TYPE: RNA
<213> ORGANISM: Homo sapiens

<400> SEQUENCE: 97
cggccgccgc cgcccccaca cugccccgcg uugacgagcg ccgcgacggc aaggacagcg 60
ccucgcuuuu cgugguggcu cggauccuag cggaccucaa ccagcaggcg ccggcgcccg 120
cccccgcgga acgcagagaa ggggccgcug cgcgcaaggc gaggaccccc ugccgccugc 180
cgccugcgcc cccugcgccg ccacccggcc cagagcccgc cuccccggga caagcaggcg 240
cgccggccgc gccccccagc cccgcgugga gcgagccgga ggcggcauug gagcaggagc 300
ccggccccgc ggggagcggc gagccuggcc ucagacaaag gggucgggga ggccggagcc 360
gcgcggaccu cgaguccccg cagaggaagc acaagugcca cuacgcgggc ugcgagaa 418

<210> SEQ ID NO 98
<211> LENGTH: 1552
<212> TYPE: RNA
<213> ORGANISM: Homo sapiens

<400> SEQUENCE: 98
cgucaguccc cgccaccucc ccggccccgc gcgcccggau cggcccuacg gccucgucuc 60
gcccggccuu gcgcgccggg accgccgcga ucuccucucc ccgccgcccu ccggcuggcc 120
cugccugcug cggcgcgaug aaugacuuug gaaucaagaa cauggaccaa guggccccug 180
ucgccaacag uuuucguggg acacucaagc gccagccagc cuuugacacc uucgauggcu 240
cucuguuugc ugugcucccu ucucucagug aagaucagac acuccaagaa gugcccacgg 300
gccuggauuc ugucucccau gacucggcca gcugcgagcu gccuuugcuc acucccugca 360
gcaaggcagu gaugagccaa gccuuaaaag ccaccuucag uggcuuccaa aaggagcaac 420
gacgucuugg caucccaaa aaccccuggc uguggagcga gcagcaggug ugccaguggc 480
uucucugggc caccaacgag uucagccugg ugaaugugaa ccugcaccag uuuggcauga 540
acggccagau gcuguguaac cucggcaagg agcgcuuccu ggagcuggcg ccugacuuug 600
ugggugacau ccucugggaa caucuagagc agaugaucaa agagaaccaa gaaaagacag 660
aagaccaaua ugaggaaaac ucucaccuca acgcgguucc ucauuggauc aacagcaaua 720
cauuaggcuu cagcauggaa caggcuccau auggaaugca ggcaccaaac uaccccaaag 780
acaaucuccu ggacagcaug ugcccgccau cggccacgcc ugcagcucug ggcucugagc 840
uccagauguu gcccaagucu cggcucaaca ccgucaaugu caauuacugu uccaucagcc 900
aggacuuccc cagcagcaac gugaauuugc ucaacaacaa uucuggaaaa cccaaggacc 960
acgacucucc agagaacggu ggggacagcu ucgagagcuc cgacucgcug cugaggaccu 1020
ggaacagcca gucgucccua cuggauguac agcggguacc uuccuucgag agcuuugagg 1080
aggacuguag ccagucucug ugccucagua agcugaccau guccuucaag gacuacaucc 1140
aagagaggag cgacccaguc gagcaaggca aaccaguuau uccugcagca guacuggcug 1200
gcuucacugg aagcggacca auccaguugu ggcaguuucu ucuggagcua cucucugaca 1260
aguccuguca aucuuucauc agcuggacgg gggauggaug ggaguucaag cuugcugacc 1320
ccgaugaggu ugcccgccgg ugggggaaga ggaaaaauaa accaaagaug aacuacgaga 1380
agcugagccg gggcuuacgu uacuacuacg acaagaacau cauccacaag acuucgggca 1440
agcgcuacgu guaccguuuc guaugugacc ugcagaacuu gcugggcuuc acuccggagg 1500
aacugcaugc cauccugggc guccagccug auacagaaga cugagggccu ca 1552

<210> SEQ ID NO 99
<211> LENGTH: 4043
<212> TYPE: RNA
<213> ORGANISM: Homo sapiens

<400> SEQUENCE: 99
auggcucuaa caacgcugcu cuuggugug gcggccgccc ugacccugau cgagacccgc 60
gcgggugagu gcggggucgg gagggaaaca gccccugugc cgcguccccg cuucgcccac 120

-continued

```
cggaccuccg ccccuucucc acccgagccc cgagcccugc uccacucccg gcccgcguac    180
ccgaccgggg ucccgggagg aggucggggu cucaccgcgc gccgccccca ggcccacacu    240
cgcugcggua uuuccacacc gcuguguccc ggcccggacu cggggagccc cgguucauca    300
ucgucggcua cguggacgac acgcaguucg ugcgcuucga cagagacgcg gaaaauccga    360
ggauggagcc gcgggcgcgg uggauggagc aggaggggcc ggaguauugg gagcgggaga    420
cacagaucgc caagggccau gagcagaguu uccaagggag ccugaggacu gcacagagcu    480
acuacaacca gagcaagggc ggugagugac cccgggucgg aggucacuac cucuccacgu    540
cccgaaacag aggccgguga gguccegggu gcaaaguccg agguucagga gcagaacuga    600
cccaggacug gauucccuuu caguuuggag gaguccgcgg ugggggggug ggggggggggc    660
ggaggaggga cugaccacug ggucccgcag gcucucacac acuccagugg auguauggcu    720
gugacauggg guccgacggg cgccuccucc gcggguaccu gcaguucgcc uaugaaggcc    780
gcgauuacau cgcccugaac gaagaccuga aaacguggac ggcggcggac auggaggcac    840
agaucacccg acgcaagugg gagcaggcug guauugcaga gagagaccgg gccuaccugg    900
aggucgcgug aggcuccgca gauaccugca gcucgggaag gagacgcugc ugcgcacagg    960
ugcaggggcc gcgggcagcu ccucccucug cccucaggcu ggggcucagu ccuggggaag   1020
aagaaacccu cagcuggggu ggugccccug gcucagaggg gagagaguga cccugggucu   1080
ccugaucccu caucacagug acugcacuga cucucccagg gcucagccuu cucccuggac   1140
agugcccagg cugucucagg agggaaggag agaauuuccc ugagguaaca acagcugcuc   1200
ccuucaguuc cccuguagcc ucugucagcc auggccucuc ccaggccagg guucucagcc   1260
uacacccacu gucuguagac acugacuccu guccugcuga gugugucagc ccuuacaccu   1320
caugaccuga agucuccuuu acccgauggg agacauggac aucuacacua ggcugguucc   1380
cccaguuucu agaacuuucc aaagaauaca gucuaccaga uccuucccug ucuguggggu   1440
uugcauccuu ugacacccaa uucuaucuau uccugcaaug gugaauaguc acaugagcca   1500
uuaugggua cccuaaacaa auacuuuucu uguguuuuuc cccucucguu uucuuuuuau   1560
cuuuacuuuu uuuuuaaggg uauuauguug cuuauaaucg guuuuucuuc ggcacuggaa   1620
ugauauugcu cucucucccc accauacccc cacccccgcc uauaucauuu guaucaguag   1680
cccuggcugu cguggaacuc acucuguaga ccaggcuggc cuugaacuca gaaaucagcc   1740
ugccucuguc ucugccucug ccucccaagu gcugggauua aaggcuuggg ccaccaccac   1800
ugggcagaag aaagguuccu gugagcuuaa aauguuuucu ggcagaauua accauccaga   1860
ucacuccuga uaucccugug ccccaccaag uuacagugcu cccccuggug aaucagaacu   1920
uggacucuga gagacagggu cuucugcaau ccaggccuga gugagaggga agaccacaca   1980
cccugugagc ccacuguguu ccagugagug cugcacuggg guccacagca cauuccaggg   2040
auccugugug acacaucugu accuuguccc ccagagucag gggcugggag ucauuuucuc   2100
uggcugagug ucagagguuc accacauuuc ugcuacacac ucccugaugg cuguuuacuu   2160
ggacugacag uuaauguugg ucagcaagau gaccacagug guuuagucuc aauggugucaa  2220
cucuuccagu agcauauggu ccugauuucu aauuuagaua cgaacucaaa cacauaugaa   2280
auuucuuauu uuccauucca ucuuccauua uauagcuacc uaucucgugc uauugaacau   2340
cacauaagga ugaccauguu gacccacugg cucaugugga uucccucuua gcuucugagu   2400
ccccucagga aaaugugcag uccugugcug agggggccag cucugccugc aggucacuag   2460
```

-continued

```
ugccaugaca guuaaagugu ucauacagac acauaguuca uuguaauuac ugauuuagcg   2520
uugucuuggc aguuuucagu uugcaugcau uuauuuauuu auuuauuuau uuauuuauuu   2580
auuuaaugca uggaaguaca cuguugcugu acugaugguu guuugccuuu gugugguugu   2640
ugggaauuga auuuuuuuuu uuaggaccuc ucuuugcucu ggucgacccu gcucacuccg   2700
gucaacuccu augggucaac ucugcucauu cagucccugc uuguucuggc ccaaagauuu   2760
auuuauuauu uauuauacau aaauacacug uagcugacuu cagaugcacc agaagagggc   2820
gucagaucuc auuacagaug guugugagcc accauguggu ugcuggaguu ugaacucagg   2880
accuucaaaa gagcagucag ugcucuuacc cucugagcca ucuccccagu ccucaguuug   2940
ucuucuuaau ugugcgauuu cuugaaucuu ccaaacagau cccccaaaga cacaugugac   3000
ccaucacccc auaucuuaug augcugucac ccugaggugc ugggcccugg gcuucuaccc   3060
uguugacauc acccugacuu ggcaguugaa uggggaggag cugacccagg acacggagcu   3120
uguggagacc aggccugcag gggauggaac cuuccagaag ugggcagcug ugauggugcc   3180
uuuuggggag gagcagaauu acacaugcca ugugcaccau gaggggcugc cugagccccu   3240
cacccugaga ugggguaagg agggugugg ugcagagcug uggucaggga aagcuggagc   3300
auucugcaga cucugagcug gucagggcug agagcuggga ucaugacccu caccuucauu   3360
uccuguaccu guccuuccca gagccuccuc cauacacugu cuccaacaug gcgaccauug   3420
cuauuguggu ugaccuugga gcuguggcca ucauuggagc ugugguggcu uuugugauga   3480
auaggaggug aaacacaggu aggaaagggc agggucugag uucucucuca gucuccuuua   3540
gaagugugcu cuaaucauua augggaaacc caucuacacc ccacauugcu accuucucca   3600
acuggguccu cugucaguuc ugggaacuuc caagaucuuc cuugaacucu cacagcuuuc   3660
cuucucacag guggacaagg aggggacugu gcuccagcuc cagguuagug uggggacagg   3720
auuguccugu ggacauugca gugaagcugg agauguuggg gagcucuggg aacccauagu   3780
aacucuucca gagaaaucuu ccagggccgc aguuguccaa uaugaauaca uauauguaca   3840
uaugcauaua cauuuuuuac ccuuggcagg gacagcuccu agagcucuga uagaucucuc   3900
ccagguggua aaggugacac ucugggaccu gauuggggag gggcaaugug gauaugauug   3960
gguuucaggg acuccacgaa uccccucuga gugaguggug gguuguugga auguugucuu   4020
cacagugaug ggucgugucc cuc                                            4043
```

<210> SEQ ID NO 100
<211> LENGTH: 211
<212> TYPE: RNA
<213> ORGANISM: Homo sapiens

<400> SEQUENCE: 100

```
uuaaaucugg agggauuuuu cacacagccu aucuuuuuag gugugccuuu cccauauuuu     60
auuaaacucg aguuguuguu uuaaaaaaac agcagcauua ucaaagacac aucuguacaa    120
acauuuuaca aaagagaacu cucuaggauc agcuacauca aggacaagca gaaaaauaga    180
ugcaguccaa caaagacauu gaaaaugacu u                                   211
```

<210> SEQ ID NO 101
<211> LENGTH: 8252
<212> TYPE: RNA
<213> ORGANISM: Homo sapiens

<400> SEQUENCE: 101

```
ggucgcuuuc ugucuguaga ggcggcuugc cacccgagca gagggucgug aaguuccgac     60
```

-continued

```
cggaccgguc cacagagguu caucuggaga ggugggaccc cuccgaggug aaaggcgccg    120
cugagaaacg cccccacccc ccgugguuca agugguucag cccaagaacu uuucauucau    180
aaaaaagacc agacuccgag aggcgcgagu gagucagaac cgcagccgcc aacgcggacc    240
cuaccgaaca uccagcccag ggcauguacc gagacuacgg ggaaccggga ccgagcuccg    300
gggcuggcag cccguacggu cgccccgcgc agcccccgca agcucaggca cagaccgccc    360
agcagcaggu gagacuggcc gaaucgucgg gggggggggg accugaguuu ggacagcauc    420
agggaugcug ggauuagucu aguuugcucc gggauuugga cuggggcccc gagcagcauc    480
ugacucuggu ggucgcgacc gaggauccug cacguucugu guggucgggg aaccuaugua    540
cccgguggcc aaggggacga gcgcagcggg aagcgcgaau aucugcgaau uccccuucuc    600
gcucgcccgu aucucccuag cugacugucu uucugccccu ccgucuccgu uacggucuua    660
cauuuccucc uaucugcccc uaauacgcug ucccucuaaa uaccugcccc aucccugccu    720
ggacaggauc agagguguuc uccaucucca guuaauaacu gggaccuggg gucugggcac    780
auagagacgg gguccaucag aacucagccg ggacagagaa uucuuagcag ccuguccgag    840
gcuguccgug uguugcucug guuguccgug ucccuuuauc cggucaaguc cucaucucuu    900
ugugcgcagu auagagccca ugggccccag gcagugguuc cgaggggguuc cuggagacca    960
cgaaguguug ggaugugcgc ggggucaccu gcccggccac acucgcgcuc cacauucucg   1020
gcacccgacg ucucucacug cuggauaggg gcacuugaga gguugcaggu guccauuucc   1080
ugucgagggg ccgcgagcac gugucgccag gggagggaag gagcugcguc cguuucgccg   1140
agucacagcg ggccgaguca cugaggcuga gucacccugg gugccccucc cuuccuggcc   1200
ccaaacggcc ccuaaggacc gacgaccugg gagcgagaga ugccccuggc agugcuucua   1260
gcccagaacg ggggucacug agaugcuggg ucccccagua uugggcuggg gacauagcug   1320
uccagacuug ccuaagcaug ugaggugcuu ccuggacugg agggccccca cauccuuagc   1380
ucacagagcu ugaacccagu uuucucuccc agaacgcuga gcccccaccc ccaccgacac   1440
ucaaucccaa cacaugccuc agauuucugc aagaaaagga aggaaaggau gccagacccc   1500
uuauaggagg cuuuuacucu cuucacuuua uuucauggac uuaaaaaacc ccaucaauuu   1560
ugaacuuuca aguuuuuaag ucgacagcua ggcaugcauu uaaucccagc auucaggagg   1620
cagaggcagg cagaucucug ggaguuugaa gccaauuugg ucuacaaagu gacuuccagg   1680
ucagcuagag cuacauaaua gagauccugu cucaaaacuu aaaaaauaaa aaacaaaaac   1740
aaaagccgau uaaaacucug auuucugagc uaugagagcu ggcuucucaa cagcaaugga   1800
acguugaaug auguuaauaa cagggaaacu gagacuaaau aacaugcccc agucucaaag   1860
cccaucaaug gccaagcucc aagcugaugc uggacuccca agcucuggug cuacaugucu   1920
auagucuugg ugccugggag guagaggcag aggaaucgug aguuuagguc uagccugagc   1980
uaugugagau ccugcccacc ccacccccgg cccccaaaca acaaauucuc auccugauuc   2040
ucagaauugc cuugggagcu agaagcugaa aguaugccca ucugugagga cugggucuca   2100
aaucuuaguu ucuacuuacu agcugugggu cuaugggcaa cugcucuccu gucugaaaac   2160
aggauuaugg cagcugugug agucacuauu uguuaaauag uuggaacagu guuacgcagu   2220
ccauacuuga uuuaaaacaa aaaaccaaac uaucucuggu ggggaaacag acagacgaag   2280
agagacauuu ugugaccugc ccaaaaucac acagcuccug aacaaguaag uuucugguug   2340
ccaaauguug cuccuugugg ucucccaaaa cugguaucua cacugaggug aagggagaca   2400
```

-continued

```
gaaguccagc cucugucccc gggaagcccc ucaguccaca cagaccuuau cauuucccuu   2460
cuuaucucuc agaaguucca ccuugugcca agcaucgaca gcagcagcca ggaacugcac   2520
uggauggugc agccucauuu ccugggaccc acuggcuauc cccgaccucu ggccuauccc   2580
caguacaguc cccucagcc ccggccagga gucauacgag cccuagggcc accuccgggg   2640
gugcgucgca ggcccugcga gcagguaaga aacagcgaug uuucacuuuc cauagcccgu   2700
agggguccua cuagacaggg acaggaucuu gcuacgaggg aauuucuuau ucagcauuga   2760
aguuccugag aggccaagaa ggagguaaaa ggucaccuuu gagucaagga aggcuuccug   2820
gagaaggcua cacguuaacc uaaaccacgg auaggauuug cguauggaag cugaaaagaa   2880
ucuucuggga ggaggguugg aggcacagaa uugaggugaa ggggacagag uguuaaguga   2940
gcaugucucc acugucugac gugcacaggg uggaaggaag ccugaugcug gcuuuguacc   3000
ucggggugac ucuucuuuuc aacagucacg gaaucucagc cuauuucuuu uaauuaucac   3060
aaaaagugag ugggcagugg uggcucacac cuuaaauuuc agcacugggg aggcagaggc   3120
agguggaucu cuggguucaa ggccagccug guuuacagag ugaguuccag gacagccaag   3180
gcuacagaga aacccugucu caagaaaggg aaaaaaaaag ugaaugggaa auguauuuca   3240
auuuuuccau cuuccaucag aggaagugaa gcauagaggg guacucacuu guccagauuc   3300
auacaaaugu gaguaaugag acaggacugg uccuggccug aggucuacuc aacucccaaa   3360
gucagagcuu aaugagccac ugucucaaug ggagcucaca gaagccugca gagggaguga   3420
gcugagaacu uuugccuccc ugaaugccuu ucuaaaauaa agaagggugu guuuugguug   3480
guuuguagag gugggggucuu gagagccucc ugccuuccca agugcuagga guauaggugu   3540
augcuagaua cccgacaggg augacggauc uuuuaggcca uagcacuuuc uuuccucucc   3600
cugaaguacu gagacugagu cuagugcagg gaggccucca uacuaaaaag cugggguguac   3660
ccguaauccc agaacucgga aaaucaagac aggaggagcc auucaaguca cgcucagaaa   3720
cauggagagu uuaaggucag ccugggauau auaaacccua ucuccgauaa ccaaacaaca   3780
aucaaagcaa accugacuua aguguuaagu aggaaagaau augcuguaag ucaucagccu   3840
ggcuggggga cugaccgccu cugagggacu gaagaaccug cuucaagccc ggagcccugc   3900
acucaacccc uaguggaugc acacacagau ccuugccaug auggcucgaa gagggauggc   3960
aagacccugg gagauaugug agauuggcca gagaagagcc agcaacaggc uucccagcaa   4020
gggaacagcu uaccucugug aucagcuggg gcgugagcaa gaggcaagcc cagggugaau   4080
ccuuccuuua gcccuguccu gaggagacac cuuuugacca cggguacuag uggguuggag   4140
cugugagcug uggguaggug gcuuccccuc ggugugcucu ggaacuugaa caaaucacuc   4200
auccuuccug agcuuccuca caugugagug ugcagagauc uggaugggug acucagcagc   4260
ggcucuggcu gcuccuuaga ggauccgggu uccaaucuca gcacccacgu ggcaacucac   4320
uguccacaac guccccccaaa gguucugaug cccucuucug gccuccacca gcacugaaug   4380
cacaaggugc ucauacaaac acacaggcaa aauacucaga gguaaauuug uucuuuuuuu   4440
ucuuuugaga caggguuucu cuguauagcc cuggcugucc uagaacucac ucuacagacc   4500
aggcuggccu caaacucaca gaggcaucug ccugccuccc aaguguuggg accaaagaug   4560
uaugccauca cuauaagccu uuuuuuuuuu uguaaauuuu auuuaugaau gagugcuucc   4620
auguauaccu ucaugccagg agagggcauc agauccuauu auaggugguu gugagccacc   4680
guguguggcu gggauuugaa cucaggaccu cugaaagagg agcucuuaac ugcuaaaaca   4740
ucucucuagc cccagucuac auauuuuaaa ucuuuuuuua agauugauuu auuuauuaua   4800
```

cauaaguaca uuguagcugu cuucagacac uccagaagag ggcgucagau cuuguuaugg 4860
augauuguga gccaccaugu gguugcuggg auuugaacuc aggaccuuug gaagaguagu 4920
caaugcucuu acccgcugag ccaucucacc agccccuuuu uuaaucuuua aaaaaaaaag 4980 gggggggcc uggagagaug gcucagccgu uaagagcacu gaaugcuuuu ccagaggucc 5040
ugaguucaau ucccaacaac cacaugguag cucacaacca ucuguaaugg gauccaaugc 5100
ccucuucugg uguaucugaa gacagcaagg gucuacucac auauguuaaa uaaauaaaua 5160
aaaauuuaaa agccaggugg uguugguuca gacagcagau cucuguuuaa ggccagccug 5220
gucugaucua caaaccaagu uccaggacag ccagggcuac acagagaaac ccucuaaaaa 5280
accaaucuau guaggggggug cuggugaaau ggcuccgugg guaaagguac uugcugcgaa 5340
auuaaugacc ugaguucaau ccuugaaauc cacacaguag aaggagagaa ccaaccucca 5400
agggugcuau gacacacaca cacacacaca cacacacaca cacacacaca cacacacaca 5460
cacgacuaua uauaugaaua uaugacucua gccaggcaua guguggcaca ugccuuuaau 5520
cacaguacuu gggaggcaga ggcaggugaa guuugaggcc agccuacaga gugaauucca 5580
ugacagcuag aacuaugaag augaacccug ucuuuaaaaa caacagcaac auaaagaauc 5640
uauguaggga agcuggaagg gaugcugaua cagucugcaa ucccuauuacu cuagaggugg 5700 aagccaaaga aucagggguu ucaggccggu cuugccuaua cacugagcua aaggccagcc 5760
ugggacacau gagacuuugu cucuuuuaaa aagacaaaac aagggggguug guuagauggc 5820 ucagugggua agagcaccca acugcucuuc ugcagguccg aaguucaaau cccagcaacc 5880 acauggugc ucacaaccau cuguaacgaa aucugagucc cucuucugga gugucugaaa 5940
acaacuacag uguacuuaca uauaauaaaa auaaauaaau cuuaaaaaaa aaaaaaaaag 6000
acaaaacaag ccagaugagg ucugugaguu ccaggccagc cuggucuaua aaucaaguuc 6060
aaggccaggc agggcuacuc agagauucug ucuaaaauac aaagaaacaa aacuacaaaa 6120
agcagaaaaa ggaaucuacg aaagggcugg ugaaggggug uaacucagug guagagcauu 6180
ugccgagcua gcauguacca agccaugggu uugaucccua gcacuaagca aaagaaaagu 6240
ccuacaaagg gcuuuguugg cauaguagau ugauucccag uagcuuuugg cacucaagag 6300
caccuucuac aauucacagc uccuggggga agaaaauccca ucuuccacag augaggaggc 6360
ugagaguccu gugaaaagag auaaucaugu cucauacacu caggagagaa ggcuacuucu 6420
gccugagaaa ugaaaaggcu uccuggggguc ccaacaucuu aguccagucc uaagaugcgg 6480
aagggaggaa gaucaaaguu uacagagagg gaaagcauuu caggaaagaa accagcagua 6540
aagcuaggug ugugugagcu ggaaauguca ccaaugagau gacaagcguc cgguacagag 6600
aagcaacugu ggaguguugg gugguggcac cuagacuaca gacugaagga aagcuggaug 6660
accagcucag ggcagcuggu ggcucagagu cagccucauu gucucccuuc uucuauccca 6720
accuagauca gcccagagga ggaagagcgc cgcagggguga gacgcgagcg gaacaagcua 6780
gcagcugcua agugcagaaa ccgaagaaag gagcugacag acuuccugca ggcggugagc 6840
aucaucccca ggcccggacc cacagagccc caagaggggu cucggcuccc aagaacacaa 6900
aagacccaaa auuacuccuc aggacucugu cauccucccu gccuguggggg aaguccugga 6960 aaaaggauaa gggaaagugg cuuaaaauauu guuugucggg cuucgaggca gagucgaaga 7020
ugguaggcag caauucuccu aagaugcccc cgucugaugg gagucauggc cauuuucucc 7080
cagaggcuca cgggagggag uugcagucca gacuuguugg ggaugacagg cacaguccccu 7140

-continued acuccagccu gaggcuuggg gaucuuuagc cuucauuuuc cuaucuuucu gcuaauccug 7200
uaaaggagac cgacaaauug gaggaugaga aaucggggcu gcagcgagag auugaagagc 7260
ugcagaagca gaaggaacgc cuugagcugg ugcuggaagc ccaucgcccc aucugcaaaa 7320
ucccagaagg agacaagaag gacccaggug guucuggcag caccagcggu gcuagcagcc 7380
caccagcccc cggccgccca gugccuugca ucucccuuuc uccaggaccc guacuugaac 7440
cggaagcacu gcauacccc acgcucauga ccacacccuc ucugacuccu uuuacuccga 7500
gucugguuuu caccuauccu agcacaccag aaccuugcuc cuccgcucac cgaaagagua 7560
gcagcagcag uggcgacccc uccuccgacc cccugggcuc uccuacacuc cuggcuuugu 7620
gaggcaccca gccacauccc uugcuggugc uacuccaagc cauccccuuu cucccauuga 7680
uccagcaggc cuggaccaua cccuugcccc aaaccagcag aucuuuuauc ucuuccgacu 7740
agaacaaaca cauuaugcuu ugauguagag ccagcuugga ggggaucccc aaagcugcuc 7800
acuguuuuuc uagagcuggc cuaucauaau uugcacaaaa uuagaggaaa auauguuccc 7860
ucugccagag aacgccuggc agcccagacu uuguagaucc ccaggggucc uuugacaccc 7920
uuaccccuug cagaccacuu ucccacacca cgucacuuuc uucauguuau ccagccuacu 7980
cuacaccuag acagaaggug cccuuugacu agccuagaac acuaacucac acagcaucaa 8040
cagccagcag caccggacau ccugcaggcu ccuccugaau ggcacaacgc aggaggcgcc 8100
aggggcuucu gugaggagcg gagcugcacu cccuagcucu gagaagcgcu uagcuucagg 8160
guauccgagc cuccaccgca agggcagcug cuauuuauuu uccuaaagag acuauuuuua 8220
uacaaaccuu ccaaaaugga auaaaaggcu ug 8252

<210> SEQ ID NO 102
<211> LENGTH: 1938
<212> TYPE: RNA
<213> ORGANISM: Homo sapiens

<400> SEQUENCE: 102 ccgugggguuc cuaauggugc uauugacgac gggcacaaag ucucauaauu uuagaaacuu 60
cacuuauuuu gugacccacc uaguaugggg caaaggcagg agcuucggac uuccugucuu 120
cccucuaucc cuuugaauag cgucucggga guguccuaa guaaccauug caguuuugug 180
uccgugugcu cuguugaaau cucugugaug uguguauggu uuucacguga acggaggcag 240
gcagagcccg gucugugggu ucuagugugu ucuuuaucuu cuuggaaguu ugugcaauga 300
cuucccuccu guuuccugcg cauaccucca aguaaguacg ugaauguguu uucugugguc 360
ccuugaucuu gcuggacuuc acuaaggagg guggcuggac caucugcuac gugucugaga 420
gccccucucu agcuaccuca uguccggacg ugagcuuacu cccaauguuu uuacccacaa 480
gcauucacua cucccaggaa agaacgugca cuggggcacc uagagaauaa ccaaucaacg 540
cuccgccuac auuuugcuuc cuccuuggaa uuuccagccc cuugcagcca acugcucccc 600
agcugcgaag ggcggaguuc cccccggccc ggccccuucu uuggcucuau aaguagcucu 660
gcuuugcggg ggauuugcac uccucuacac ucucugcaca acgucuaaau uaugugccac 720
ucgcgcaacc aucuccacac caugacuggc cugagggccc cuucuccagc ucccuccacc 780
ggcccggaac uccggcgggg cucuggucccc gaaauuuuca ccuucgaccc ucuccccggag 840 cgggccgugg uguccaccgc gcguuugaac acuucucgcg ggcaccgaaa acgcagccga 900
agggugcucu acccucgagu ggugaguauc gcccgagugg gcaucaggag gucgcgucgc 960
ccuggaacuu guagguaaca acuaggagca gggaccuucg aucugacguu ucccucuuuu 1020

-continued

```
aucugcucag guccggcgcc agcuaccaac cgaggaaccc aacauugcca agaggguccu   1080

cuuucuccug uucgccauca ucuucugcca gauuuugaug gcugaagagg gugugucgca   1140

gccccuggcu ccggaggaug cuaccagcgc cgugacaccu gagcccauuu cugcgcccau   1200

uacugcgccc ccgguccucg agccuuugaa ccugaccucg gaguccucgg acuaugcgcu   1260

ggaucuuaaa gcuuuucucu agcaacaucc ggcggccuuc uaaacgcgau gggucacagu   1320

ccgaagaaac aaaggcacca uggaugggua ccuggugcga gagaacguau cccaaacugg   1380

gauuucuaag gcaacgcuaa cucagaacac uaccgccaag agacaccgcg gguccuggcu   1440

aggcccacug gggacggaca gagacuuucu ccgugucuaa uuaauauuua uguauuuaug   1500

uauauccucc uaggugaagg aggggugcau guaauauuua uucuaacuua ugcaggggug   1560

cgagauaugc cucccugcug uaacacagau auuuauuacg auuuauaggg ucgguaagac   1620

agaguugugg gagggaggac ccggguggua ggacucccag cuuggggauu agucuggggg   1680

gggugcaaua agauuagggg uaacacuccg ucuuccagca cuucaacucu guagucuguu   1740

guaaggcuuu ggaagacccu ugggaauccg gccuuugaug ucuucugguu gcuucucagg   1800

ggcagcugca ggagucuugg guccauggau ugucagaggg cggcugucug gggucgccua   1860

guauguaugu ucugugaaca cgaauaaacu ugauuugccu gucauuauua ucugcaguuc   1920

ucgaagugua ucauucag                                                  1938
```

<210> SEQ ID NO 103
<211> LENGTH: 3036
<212> TYPE: RNA
<213> ORGANISM: Homo sapiens

<400> SEQUENCE: 103

```
gacagcggag cgcgguggcg ucgacgucua gugucucagu gcucccgucu guggcuaacu     60

aagcagccag cagccaggca gcucgcgacc ugcggccagg cagccaacca ugcucaacuu    120

cggcgcuucu cuccagcaag cuucggaggg gaaaauggaa cuaauuucug aaaagcccag    180

agaggggaug caucccuggg acaaagcuga gcagagugac uuugaagcgg uggaagcgcu    240

cauguccaug agcugcgacu ggaagucuca uuucaagaaa uaccuugaaa acaggccugu    300

cacaccagug ucugauaccu ccgaggauga cagcuugcuu ccagggacgc cugaccuuca    360

gacaguccca gcauuuuguu uaacgccacc uuacagcccc ucugacuucg aacccuccca    420

agggucaaau cugacugcau cagcgccauc uacuggccac uucaaaucuu ucuccgaugc    480

ugccaagccu ccaggcgcca cuccuuucaa agaggaggaa aagaauccuu uagcugcccc    540

uccucuuccu aaggcucaag ccaccagugu cauccgucac acagcugaug cccaacugug    600

caaccaccag uccugccccg ugaaagcagc uagcauccuc aacuaucagg acaauucuuu    660

ccggagaaga acccacggaa auguugaggc uacucgaaag aacauacccu gugcugcagu    720

gucaccaaac agauccaagc cugagcccag cacaguguccc gauggugaug agaaggcggg    780

cgcugcacua uaugacuuug cugugccuuc cucagagaca guaauuugua ggucucagcc    840

agcuccuucg uccccagugc agaagucagu acuggugucu ucaccuacag uauccacugg    900

gggagugcca ccccugccug ucaucugcca gaugguuccc cuuccugcca acaacucucu    960

uguuagcaca guugucccca gcacuccucc uagccagcca ccagcugucu gcucaccugu   1020

guuguucaug ggcacucagg ugccugaggg caccgucgug uuugugguac cccagcccgu   1080

ugugcagagc ccaaggccuc caguggugag ccccaguggc accagacugu cucccauugc   1140
```

cccugcuccu ggauucucuc cuucagcagc aagggucacu ccucagauug acucguccag 1200
aguaagaagu cacaucugua gccacccagg guguggcaag acuuacuuua aaaguuccca 1260
ucugaaggcc cacgugagga cacacacagg ggaaaaaccu uucagcugca gcuggaaagg 1320
cugugaaagg agguuugcuc gcuccgauga acuguccaga caccggcgga cacacacagg 1380
ugagaagaag uuugccuguc ccauguguga ccgucgguuu augaggagcg accauuuaac 1440
caagcaugcc cgacgccacc uaucagccaa gaagcugcca aacuggcaaa uggaaguuag 1500
caaguuaaau gacauugcuc ugccuccgac cccugcuucc gcacagugac ggccagaaga 1560
uggagacgca gaauaaacuu uggucagagu caggagccag ugaugguguc aagugcuucu 1620
gcaaggcugu ggcccuccaa aagggccuaa aguagaagcc cuggccuggg ggaggccccg 1680
ccugggugaa augacaagaa gugcuucagc cacaggcagg ucacagagga cagggcucag 1740
uucuuaccac agagagagag gagaacccuu uuauuccucc cuuauuuuag ucuggaaagu 1800
uucggcugag gugagcgcag cacagguuuu gaaucacaua cacauugggg acuuuguuuu 1860
ugccauuuau acuugagacc agcuuugcag ugugauucuu ucaaaggauu gguuucaaga 1920
auauagaggc uggaaauuac gguacagaaa uggagcuaga aaaugaguuu guguuacaca 1980
gagaugucau cuucuccuag aguuaucuug uuucuuauuc cuagucuuuc cagucaaauc 2040
cguggaugua gcuaaguaua ucuaaaacuc auuuuuccac uauuguuggu auuugaaguu 2100
gaacagcugu acauugcugu gggggagcca aaggauugga acccucauua auuuaauugc 2160
uuggaaaugc agcuaaaauu cuucuuuggc auuuuguuuu gaaaguuuag gcauuuuacu 2220
cuacuuuaga uuuuaguuug cuugcaguuu uuuguguaga uuugaaaauu guauaccaau 2280
guguuuucug uaggcuuaaa auacacugca cuuuguuuag aaaaaaaucu ggagaugaaa 2340
auauguauua uaaagaagag augucaagaa uuugagauaa cuccuugaga aaguuggcuu 2400
uaugucauca gcaaaggaca cuuaacguca agcauacacu gugguuuuuu uguuuuuuug 2460
uuuuuuuuuu ucaaauuaga aaguuuaaug accguuacag auggacagug ucuuuuuauu 2520
uauaggaguu uuucaggaug ucagaguaga uagguaggaa aauuguuauu agaacauucg 2580
cuucuaccuu gaaaaggaug uuaaugugu cauguucuua gcaccacagu gucugggcau 2640
cugggaaacu ccgagacuuu uuuaaagugu caugauguga ucacaccugc aguuuggggc 2700
aucgaaucca gggccuugca ugucuucugu aagagcucuc aucgcugacc uguaucccc 2760 gcaagagcaa ugacuuuugc uaacaguauu ucuuuucugu uguaaagugg acagaugaua 2820
cacuuggucg caaagguaaa uuauucaaaa uccacaguga aaaccucacc acacuuuccc 2880
auuuaaacua uuuccauauc ucagagguuu cugacaugca aacuugaacc cuugaaagaa 2940
gaguuuucuu aaaaauuaua aaaaaucacg aguuacaauu ugcacaauau uuuuuguuga 3000
acuuuauacc uuguuuacaa uaaagacuuu ucuuug 3036

<210> SEQ ID NO 104
<211> LENGTH: 279
<212> TYPE: RNA
<213> ORGANISM: Homo sapiens

<400> SEQUENCE: 104
uuuuuuuuuu uuuuuuuaaa uugccgaauu aaguucuuuu aauagauugc auauauagau 60
guuuagccau acucuagauc aacucuuuaa gaguagaauu uuauauccaa uuuacaugcu 120
ucagauauca ccucuguuug uuacauaagg ucuuguaucc aaauguccac uuguacacug 180
agagcuuuag gaacaaaaaa ggacacagag agaguugcca uuuuuagcag caaugaaaca 240
ucacuaaccc cuuuuuacau accgaauuca agucacuac 279

<210> SEQ ID NO 105
<211> LENGTH: 143
<212> TYPE: RNA
<213> ORGANISM: Homo sapiens

<400> SEQUENCE: 105
cggccgccgg uauuuuuuug caaguauuga gaguucugua uguuuugaaa agaguaauuu 60
uaacguuugg gugccaagaa gugggguuuuc ucagagucca uugccggcaa ugggcaagcc 120
uggcgguacu ccucgugccg aau 143

<210> SEQ ID NO 106
<211> LENGTH: 989
<212> TYPE: RNA
<213> ORGANISM: Homo sapiens

<400> SEQUENCE: 106
auggcgcugg gaacgcugcu ccugcugcug gcggccgccc uggcccggac ccagaaccga 60
gccggugagu gcagggucgg gagggaaaca gaacuuucca aacagucugc ggggaggggc 120
gggugcggca ccggggaagc cgcgugcccg cgucgcccac cagacccucc gucucuuuac 180
ccgcgucccu agccccgcgc ccugcucccc uccugucccg cgcauccgcc cggggucccg 240
ggagaagguc ggggucucac cgcgcgccgc ccccaggcuc acacucgaug cgguauuucg 300
agaccgucgu gucccggccg ggccucgggg agccccggua cgucucuguc ggcuacgugg 360
acgacacgga guucgugcgc uucgacagcg acgcggagaa accgagguau gagccgcggg 420
cgcgguggau ggagcaggag gggccggagu auugggagcg gaucacgcag aucgccaagg 480
gccaugagca gugguuccga gugagccuga ggaaacugcu aggcuacuac aaccagagcg 540
cgggcgguga gugaccccgg gucggagguc aggccccucc acuucccgac acagggacgc 600
ugacguccug guucccaagu cugagguucg ggaacagaac ggacccggga ccgguuuccc 660
uuucaguuug gaggaguccg cgggugggcg gggcugaccg cggggucccg cagguucuca 720
cacacuccag gagauguaug gcugugaugu gggaucggac gggcgccucc uccgcgggua 780
ccggcagucc gccuaugaug gcugcgauua cauugcccug aacgaagacc ugaaaaccug 840
gacugcgaag gauguggcag cgcugaucac cagacgcaag ugggagcagg auggugcugc 900
agaguauuac aaggcuuaca uggagggcga gugcgugcag ucgcuccgca gauaccugga 960
gcucgggaag gagacgcugc ugcgcacag 989

<210> SEQ ID NO 107
<211> LENGTH: 4484
<212> TYPE: RNA
<213> ORGANISM: Homo sapiens

<400> SEQUENCE: 107
auggcgucaa caaugcugcu ucugcuggug gcagucgccc agacccugau cgagauccgc 60
gcgggugagu accggguccg gagggaaaug gccucugagg aaaggggagg gggcggcacg 120
ggggaagccg cgucccggcg ucgcccaccu gacccuccgc cccuucucca cccuagcccc 180
gcgcccugcu ccccucccgg cccgcucacc cgcggggguc ccggaaggag uucggggucu 240
caccgcgccc ugccuccagg cccacacuug cugaguuauu ucuacaccuc cgugucccgg 300
ccgggccuug gggagccccg guucaucucu gucgguuacg uggacaacac ggaguucgug 360

-continued

```
cgcuucgaca gcgacgcgga gaauccgaga uaugagccgc gggcaccgug gauggagcag    420
gaggggccgg aguauuggga gcgggaaaca cagaaagcca agggcaauga gcagauuuuc    480
cgagugaacc ugaggacccu gcucagcuac uacaaccaga gcgcgggcgg ugagugaccc    540
cggaucggag gucacgaccc cuccacgucc caaaacaggg gcccgagacg ucccgggccc    600
caaguucgag guucugagca gaacggacgc gggacugguu ucccuuucag uuuggaggag    660
ccgcgggugg gcggggccgg ggcgugugggg cggggcugac cgcggggucc cgcaggcucu   720
cacacuauuc aggugaucuc uggcugugaa gugggguccg acgggcgccu ccuccgcggg    780
uaccagcagu ucgccuacga cggccgcgau uacaucgccc ugaacgaaga ccugaaaacg    840
uggacggcgg cggacauggc ggcacagauc acccgacgca agugggagca ggcugguggcu   900
acagagaaaa gcaaggccua ccuggagggc gcgugcgugc agucccuccg cagauaccug    960
gagcucggga aggagacgcu gcugcgcaca ggugcagggg ccgcgggcag cuccucccuc   1020
ugcccucggg cuggggcuca guccugggga agaagaaacc cucagcuggg gugaugcccc   1080
ugucucagag ggagagagug acccuggucu ccugaucccu caucacagug acugcacuga   1140
cucucccagg gcucagccuu cucccuggac agugcccagg cugucucagg agggaaggag   1200
agaauuuccc ugagguaaca acagcugcuc ccuucaguuc cccuguagcc ucugucagcc   1260
auggccucuc ccaggccggg uucucagccc acugucugua gacacugacu ccuguccugc   1320
ugagugugc agcccuuaca ccucaggacc agaagucgcc uuuaacugau cggagacaug     1380
gacuacccua cacuaggcug auugccucag uuuccugaau uuucaaaaga auacauucuc   1440
ccagaucccu cccugucugu gggguuucca ccccuucgac aaccuaauuc ucucuauucc   1500
uauaguggug gucacaucag cccuuauggg guacccugga ggaauaucaa uaguggaauu   1560
ucuucuucuu cuucuucuuc uucuucuucu ucuucuucuu cuucuucuuc uucuucuucu   1620
ucuucuucuu cuucuucuuc uucuucuucu uccuucucuc ucucucucuc ucucucucuc   1680
ucucucucuc ucucucucuc ucucucucuc ucucucucuu cuucaguuuu ugagauaggg   1740
uuucucugua ugcccuggcu guccuggaac ucacuuguag accaggaugg ccucgaccuc   1800
agaaauccgc cugccucugc cucccagugc ugggauuaaa ggcguguggc caccuugccc   1860
agccuuucuu auuuucuuua cuuuuuuuuu uuuuuuugga gggguaauu uuguuucuag     1920
ucaucuuuug ucuuuugucu gcacuggagu gauccuguuu cucccugccc uuauauuauc   1980
auguguauca gucuccacag gugccaggga aguuaagaca aguuaaauca ggguucucuu   2040
uaaaggagag auuccuguga acuuagacug uuuccuguca gaacuaaaca uccagaagcc   2100
uccugcucuu ccucugaccc acaaguuaca gugcuccccc ccccccccca gugaaucugg   2160
acuuggacuc ugagagacag ggucuucugc aauccagggc uggagugaga gggaagacca   2220
cacacccugu gagcccacug uguugcagug agugcugcac uggggucccac agcauacucc  2280
agggauccug ugugacacac cuguaccuug ucccccagag ucaggggcug gaagucauuu   2340
ucucuggcug agugucagag guugacacca uuucugcuac acacucugug auggcugcuc   2400
acuuggacug gcgguuaugc uaguuagcaa gaugaacaca gugguuuacg ucucaguugu   2460
cacacccuuc caguggcaua uggcucuaau uucuacuuuu gauacgaacu caaacacuua   2520
uuaaauuagu uaguuuccau uccaucuucc auucuagucc auucaugcua aagaacauca   2580
cauaaggacu gccaggauga cccacuggcu cauguggauu cccucuuagc uucugagucc   2640
cccagaaaaa ugugcagcug aggaaaccag cucugccugc aggucaccag ugccaugaca   2700
guugaagugu caaacagaca cauuguucag ugucaucagu gauuuaacug ugccuugugu   2760
```

-continued agauuucaga gggucuuguu aauuguggua cuuuuuuuug uuuuuuguuu uuuuuuuuuu 2820
uuguuuuguu uucaagacag gauuuuucug uauagcccug gcuguccugg aacucacauu 2880
guggaccagg cugaccacga acucagaaau cugccugccu cugccucccg agugcuggga 2940
uuaaaggcgu gugccaccac caaccagcua aucgugagau uucuuucuuu uuucuuuucu 3000
uuucuucuuu uuuuuuuuuu uuuuguuguu guuguuuugu uuuuugagac aggguucucu 3060
guguaucccu ggcuguccuu gaacucacuu uguagaccag gcuggccuug aacuuagaaa 3120
uuugccugcc ucugcuccgg agugcuggga uuaaaggcau gugccacuac caaccagcua 3180
auugugggau uucuuaaauc uuccacacag auccuccaaa ggcacaugug acaugucacc 3240
acagaucuga cggugauguc acccugaggu gcugggcccu gggcuucuac ccugcuaaca 3300
ucauccugac cuggcaguug aauggggagg agcugaccca ggacauggag cuuguggaga 3360
ccaggccuuc aggggaugga accuuccaga agugggcauc ugugguggug ccucuuggga 3420
aggagcagaa uuacacaugc caugugcacc augaggggcu gccugagccc cucacccuga 3480
gaugggguaa ggagggugug ggugcagagc uggggucagg gaaagcugga gccuuuugca 3540
gacccugagc ugcucagggc ugagagcugg ggucaugacc ucaccuucau uuccuguacc 3600
uguccuuccc agagccuccu ccauccacug ucuccaacau ggcgaacgua gcuguucugg 3660
uuguccuugg agcuuggcca ucauugcagc uguggugggcu uuugugauga agagaaggag 3720
acacacaggu aggaaagggc agagucugag uuuucucuca gccuccuuua gagugugcuc 3780
ugcucaucaa uggggaacac aggcacaccc cacauugcua cugucuguaa cugugucugc 3840
ucucaguucu gggaacuucc uagugucaag cucuuccuug aacucucaca gcuuuccuuc 3900
ucacaggugg acaaggaggg gacuaugcuc uggcuccagg uuagugugggg ggacagaguu 3960 guccugaggu cauuggagug aagcuggagu uguugggugc ucugggaacc cauaauagcu 4020
ucucuguugu aauccucugg uggccugugu cagaucuugc uauagauaua ucuuuguaua 4080
uauuuuuccc uaggcaggga cagcucccag agcucugaua uguuucucuc aagauuguaa 4140
aggugacauu cuauggccug auugcagagg ggcacugugg acaugguugu guuucaggga 4200
cucccacaau ccccugugag uggugggguug uugggauauu gucuucauug uggugguucc 4260
ugacccucau ucucuaucau gaagacagcu gccuggagug gacuuaguga cagccagugu 4320
gaccuugggu cuucauuuuu cuuuagagaa cagcgccuga uguucccugu gagccuaugg 4380
gcucaaugug aagaauugug gagcccagcc uucgccuaca caccaggacc ugucucuugc 4440
auugcccugu guucccuucc accgccaacc uuccgggucu gcag 4484

<210> SEQ ID NO 108
<211> LENGTH: 385
<212> TYPE: RNA
<213> ORGANISM: Homo sapiens

<400> SEQUENCE: 108
uuuuuuuuuu uuuuuuucag aauaauugca gacaaauucc auuuauuuuu cuaaaaaccu 60
cauuaucuaa aauuuauaca gccucacauu ccuaaaccac cucuggcacu uuucuugaau 120
uaagucaagg cguacacagc uccgaaagaa aaauagagau ccgguuccag gaagauggcc 180
augaggacuc gcagauaugu cuccucggac cuggaagcgu gucagccaug ggauccacua 240
auccaccauc cgguacacag ggucacccac ucucaggcuc ccaagcuucu ccaccgagaa 300
auacauccca aaaaguggag augacuggua uauacucuuc acagaaggau cacacaggcg 360

-continued

```
auagcucuuc agggucucca guggc                                          385


<210> SEQ ID NO 109
<211> LENGTH: 2247
<212> TYPE: RNA
<213> ORGANISM: Homo sapiens

<400> SEQUENCE: 109

cucuagauga auacacucuc augagggcca ccuucucugg uaguucaggu cgccucugcc     60

cauccuuccc ugcguccucu cccaaagugg ccuacaaccc uuacccagag gacuauggag    120

acauugagau ugguucucac aagaguucca gcaguaaccu gggggcagau gauggcuaca    180

ugcccaugac cccuggggca gcccuuagga gugguggucc caauagcugc aagagcgaug    240

acuacaugcc caugagcccc acaagcgugu cugcucccaa gcagauccug cagccacgcu    300

uggcagcggc cuugccccu uccggagcag ccgugccagc acccccuuca ggggugggca     360

ggaccuuccc aguaaacgga ggugggcuaca aagccagcuc cccagcggag agcuccccag    420

aagacagugg guacaugcga auguggugug gcuccaagcu gucuauggag aacccagacc    480

cuaagcuacu ccccaacggg gacuaccuca acaugucccc cagcgaggca ggcacugcag    540

ggacccccacc ugacuucuca gcagcuuugc guggaggcag ugaaggccuc aaaggcaucc   600

cgggccacug cuacagcucu uugccccgcu cuuauaaggc ucccuguucc ugcagcggag    660

acaaugacca guaugugcuc augagcuccc cugugggccg gaucuuggaa gaggagagac    720

uggagcccca ggccacccca ggggcuggca ccuuuggggc agcugguggu agucauaccc    780

agccucauca cucagcagug ccuuccucca ugaggccgag ugccaucggu ggccgcccug    840

agggcuuccu gggccagcga ugucgggcag ugcggccuac acgccuaucg cuagagggac    900

ugcagacccu ucccagcaug caagaguacc cucuacccac agagcccaag agcccuggcg    960

aguacaucaa cauugacuuu ggugaggcag guacccgucu gucuccgccu gccccccccac  1020

uacuggcauc cgcggccuca ucuucuucac ugcucucagc uaguaguccu gcuucauccc   1080

uggguucagg aaccccaggc accagcagcg acagccggca gcgcucucca cucucugacu   1140

auaugaaccu ggacuucagu ucucccaagu cccccaagcc uagcacccgc aguggggaca   1200

caguaggcuc cauggauggc cuucucucuc cagaggcuuc aucccccauac ccaccacugc  1260

ccccacgucc uuccacuucc ccuuccuccu uacagcagcc ucugccaccu gccccgggag   1320

accuauaccg ccugccucca gcaucagcug ccacuuccca ggguccacu gcuggcuccu    1380

caauguccuc cgagccuggg gauaauggug acuauaccga gauggccuuu ggugugggcug  1440

caaccccgcc acaaccuauc guggcaccuc caaagccaga aggugcccga guggccaguc   1500

ccacaucggg cuugaagcgg cuaagucuca uggaucaggu aucuggggug gaggcuuucc   1560

uucaagucag ccagcccccu gacccccacc ggggugcuaa ggucauccgu gcagacccac   1620

agggggggacg ucgucgccac aguucagaga ccuuuuccuc uaccaccacc gucaccccag  1680

uguccccauc cuuugcccac aauuccaagc gccacaauuc ggccucugug gaaaaugucu   1740

cacucaggaa aagcagugaa ggcagcagua cccugggagg aggugaugag ccgcccacau   1800

ccccaggaca ggcacagccc uuggugggcug ugcccccagu gccacaggcu aggccgugga  1860

accccgguca gcccggagcu uugauuggcu guccuggagg cagcaguucu cccaugcgca   1920

gagagaccuc cgugggguuuc cagaacggcc ucaacuauau cgccaucgau gugagaggcg  1980

agcaggggguc cuuggcgcag ucucagccgc agccaggaga caagaacucc uggagccgga  2040

cccguagccu uggggggcuc cucggcaccg ucggaggcuc uggcgccagc ggagugugug   2100
```

gggguccagg cacuggagcu uugcccucug ccagcaccua ugcaagcauc gacuuccugu 2160
cccaucacuu gaaggaagcc acagucguga aaggugaggc ccuuugaccu ugaggauggg 2220
ggagggagag uggaguauug gguggcu 2247

<210> SEQ ID NO 110
<211> LENGTH: 315
<212> TYPE: RNA
<213> ORGANISM: Homo sapiens

<400> SEQUENCE: 110
uuuuuuuuuu uuuuuuucag cugugaacua uuggauuuga gacaggaaca gaacaaaucg 60
acgggccaga ggagggugga gagagcacga gugguuuaaa uaggggagga ugggagcaug 120 gcggugggggg ugggggaaga guuauuuaca agaaggcuca gggggccaga ggcucaucuu 180
ggaauauuuu auaacaauau auauaagauu cugguuugcu uuuccuuuuc gucucguaaa 240
ggagagagaa uugcauaguu cgauucuguc caagggggca gcugcauaug gucggccggg 300
cgggucacug gucgu 315

<210> SEQ ID NO 111
<211> LENGTH: 481
<212> TYPE: RNA
<213> ORGANISM: Homo sapiens

<400> SEQUENCE: 111
uuuuuuuuuu uuuuuuuaag ugucaccacu ugugacaguc agcauguuac uaucagcucc 60
agccgcagcg uuuuuaaggc guuauagauu aggcaggcaa uacaaggaac acgauuaaga 120
aacugacacg uaccacacga gcaauuucca gaggcuccuc uucugcggug cacacguaac 180
agugcucuug uugacauuca gacaguucug agggccacuc ugagaggcgc cuuccuguuc 240
ucaccugaca aggauauugu uugguuuggu uugguuuggu uuugccuuac uauggcuuuu 300
cuuucaacua cauuuugugu caugcuuguu agcuaacuca aauuuugucu uuguauauuu 360
acuacuguaa aauuagaaua auuuacuguu caucucaucc ucugucacug auggaaccua 420
gagacgccac aagagccacu gccgugacau accucacaag cuacaucccu guccucaaaa 480
u 481

<210> SEQ ID NO 112
<211> LENGTH: 379
<212> TYPE: RNA
<213> ORGANISM: Homo sapiens

<400> SEQUENCE: 112
cggccgcggc caccggccug cgccaagcug cugcugcggc agccaguacc ucggugaagc 60
ccauuuucag ucgcgaccug aacgaggcca agcggagggu gcgcgagcuc uaccgcgcuu 120
gguaucggga gcgugccgaa caccgugcac uuaaugcagc uggauaucac ggugaaacaa 180
ggacgggaua aaguccgaga aauguucaug aagaaugccc augucacaga ccccagagug 240
guugaucugc uggucauuaa gggaaagaug gagcuccagg aaaccaucaa aguauggaag 300
cagcggacac acguuaugcg guuuuuccau gaaacagaaa caccaaggcc aaaggauuuc 360
uuauccaagu ucuauaugg 379

<210> SEQ ID NO 113
<211> LENGTH: 3733
<212> TYPE: RNA

<213> ORGANISM: Homo sapiens

<400> SEQUENCE: 113
gcaccugagc gcgggugccu ggcgcgcccg augggaucgu ugagaggccc ucgacggaaa 60
gucccaaacu cggaucgcau ucagccaaag ugaggcggcg ccauggagcu ccgagcgcug 120
cugugcuggg cuucccucgc cacugcuuua gaagagaccc uguugaacac aaaacuggaa 180
acggcggauc ugaaaugggu gacuuacccu caggcagagg gccaguggga ggagcuaagc 240
ggccuggaug aggaacagca cagcguccgc accuaugagg ugugcgacau gaagcgucca 300
gggggccagg cucacuggcu gcgcacuggc ugggucccaa ggcgaggugc uguccacgug 360
uaugccacga uacgcuucac caugauggaa ugccuguccc ugccgagggc cagucgcucc 420
ugcaaggaga cauucacugu cuucuauuac gagagcgaac gugauacggc cacggcccau 480
acgcccgccu ggauggagaa ccccuacauc aagguggaca caguggccgc agaacaucug 540
acucggaagc gcccuggagc ugaagccaca gggaaaguua auaucaagac gcugcgccug 600
gguccucuca gcaaagcugg cuucuaccug gcuuuccagg accaaggagc cugcauggcu 660
cugcucuccc ugcaucucuu uuacaagaag ugcuccuggc ugaucacgaa cuugaccuac 720
uuccccgaga cggugccucg ggagcucgug gugccggugg cagguagcug cguggccaac 780
gcggucccua ccgccaaccc cagccccagc cucuacugcc gggaagaugg ucaaugggcu 840
gagcagcagg ucacgggcug cagcugcgcg ccaggguacg aggcugcgga aagcaacaaa 900
guaugcagag ccuguggcca gggaaccuuc aagccccaaa uaggagacga guccugccug 960
ccgugcccag ccaacagcca cucgaauaac auugggucuc cugucugccu gugucgaauu 1020
ggguauuacc gggcccgcuc agacccccgg aguucaccuu gcacuacccc acccucugcu 1080
ccaagaagcg ugguucacca uuugaauggu uccacccugc gccuggagug gagugcuccc 1140
cuugaguccg gaaggccgag agaccucacu uaugcuguuc gcugccgaga gugccguccu 1200
gggggguucc gcuugcccug ugggggcgac augaccuucg accccggucc ucgagaccug 1260
guugagcgcu ggguggcaau ccgagggcug cguccugaug ucaccuauac cuuugagguu 1320
gcugcuuuga augguguguc uaccuuagcc acuggaccac cuccuuuuga gccugucaau 1380
gucaccacug accgugaggu gccuccugca gugucugaca uccgagugac ucggucguca 1440
cccagcagcu ugauccuguc augggcuauc cccagagcac ccaguggggc cgugcuggac 1500
uacgagguca aguaucauga gaagggcgca gagggcccca gcaguguucg uuuccugaag 1560
acaucagaaa accgagcuga gcuccggggg cugaagcggg gagccagcua ucugguccag 1620
guacgcgcac gguccgaggc uggcuacggu cccuucggcc aggagcauca cagucagacu 1680
caacuggaug agagcgagag cuggcgggag cagcuggccc ugauugcagg cacugcgguu 1740
gugggugugg uccugguccu gguggucguc aucauugcag uucucugccu caggaagcag 1800
agcaauggga gggaaguuga guacucggau aagcaugggc aguaucucau cgggcacggu 1860
accaaggucu acauugaucc uuuuacuuac gaagacccua augaggcagu gagggaauuu 1920
gccaaagaga ucgaugucuc cuaugucaag auugaagagg uaauuggugc aggugaguuc 1980
ggcgaggugu gccggggucg gcugaaggca ccagggaaaa aggagagcug uguggccauc 2040
aagacucuga aggguggcua caccgagcgc cagagggcug aguuccugag cgaggccucc 2100
aucaugggcc aguucgagca ucccaacauc auccgccucg agggcguggu caccaacagu 2160
gugccgguua ugauccucac ggaauucaug gagaacggag cccuggacuc cuuccugcgg 2220
cugaacgacg ggcaguucac agucauccag cuggugggca ugcugagggg caucgccucg 2280
ggcaugcggu accuggcuga aaugagcuau guccaccgag accuggcugc ucggaacauc 2340
uuggucaaca guaaccuggu cugcaaggug uccgacuuug gccucuccag auucuuggag 2400
gagaacuccu cugaucccac cuacacaagu ucccugggag gcaagauucc cauccgaugg 2460
accgccccug aagccauugc cuucaggaag uucaccucug ccagugaugc cuggcgcuau 2520
gggaucguca ugugggaggu caugucuuuu ggggaacggc cauacuggga caugagcaac 2580
caggauguga ucaaugccau ugaacaggac uaccggcugc cuccuccucc agacugcccc 2640
accucccucc accagcucau gcuggacugu uggcagaagg accggaaugc ccggccccgc 2700
uuuccccagg uggucagcgc ucuggacaag augauccgga aucccgcuag ccucaaaauc 2760
guggccaggg agaauggcgg ggccucacau ccacucuugg accaacggca gccucacuac 2820
ucugcuuucg guucuguggu cgaguggcuu cgagccauca agaugggaag auacgaggaa 2880
aguuuugcag cggcuggauu cggcuccuuu gagaugguca gucagaucuc ugccgaggac 2940
cuucuccgaa uuggagucac ucuggcagga caccagaaga aaaucuuggc cagugugcag 3000
cauaugaagu gggaagcuaa gccaggagcc ccugguggga caggggggacc agcccagcag 3060 uucugaccuc caaggacuca ccaccguggc agauucuucu uuccgggagg cagaguuggg 3120
uggggacuca caagaugagc cccuccccccu cgucacagcc uucccauugg auugcacuuu 3180
gaacagaggg ggucggagac acagauuugg ggaaccgugc cauaugggau cauacaugug 3240
cccuccaggc ggggaacccc aaacucagag ugagucuuuc ccucaagacu gggcaaagaa 3300
acaucccuac gucucuaacc ucccaucuuc ccagaggcuc ucuccccaag cgccuuccac 3360
cucaacgggc augucccugc agaccaaaga gaaagggguga ccagccugcc aacuugggag 3420
uggaaaaugc cgucccagga ggcaggaagg ggcugucagg acccggugau guaaucauug 3480
gguuuugaug uccugacuug cugucaccac caaaggcaau cauuuuuccc uuguaaaugc 3540 cccucccccuc aucugccuuc auauugaagg uucugaaguu uuacuguuuu uuauuuuguu 3600
aauuuuuucc uccuuccccc cucccucccc uucuugucca gauuuugugu guuaaagggc 3660
accugguucc acuaucuccu guugggaaca aggacccauc gauauguucu agaacagugc 3720
cuuggaaaug cca 3733

<210> SEQ ID NO 114
<211> LENGTH: 560
<212> TYPE: RNA
<213> ORGANISM: Homo sapiens
<220> FEATURE:
<221> NAME/KEY: misc_feature
<222> LOCATION: (107)..(107)
<223> OTHER INFORMATION: n is a, c, g, or u

<400> SEQUENCE: 114
ggcagcgaga cgagcucacg gucgaggaua cgggugaagc gggacaggag caggagccgg 60
agccgggcca aagcagaagg ugcaggucgg cgccggcggu ugggcangac ccagucaagc 120
cggacaguga ggagcggaug cagacggcac gaccauggcc acgauggugc uuccucgaga 180
ggagaagcug agucaggacg agauagugcu gggcaccaag gcggugaucc aggguuuaga 240
gacccugaga ggggagcauc gugcccugcu agcuccccua gcuucucaug aagcaggcga 300
ggcugagcgg gcucacagga gcgcugccuc cuccugcgcc gcucccugga ggccaucgag 360
cuggggcuug gggaggcuca ggugauccug gcauuaucaa gccaucuggg ggcuguggag 420
ucagagaagc agaagcugcg ggcucaggug cggcccuggu acaagagaac aguggguugcg 480 ugaggagcug gcagggacac agcagaagcu cagcgcagug aacaggcggu ggcucagcug 540
gagaagagag cagcacaucu 560

<210> SEQ ID NO 115
<211> LENGTH: 560
<212> TYPE: RNA
<213> ORGANISM: Homo sapiens
<220> FEATURE:
<221> NAME/KEY: misc_feature
<222> LOCATION: (107)..(107)
<223> OTHER INFORMATION: n is a, c, g, or u

<400> SEQUENCE: 115
ggcagcgaga cgagcucacg gucgaggaua cgggugaagc gggacaggag caggagccgg 60
agccgggcca aagcagaagg ugcaggucgg cgccggcggu ugggcangac ccagucaagc 120
cggacaguga ggagcggaug cagacggcac gaccauggcc acgauggugc uuccucgaga 180
ggagaagcug agucaggacg agauagugcu gggcaccaag gcggugaucc aggguuuaga 240
gacccugaga ggggagcauc gugcccugcu agcuccccua gcuucucaug aagcaggcga 300
ggcugagcgg gcucacagga gcgcugccuc cuccugcgcc gcucccugga ggccaucgag 360
cuggggcuug gggaggcuca ggugauccug gcauuaucaa gccaucuggg ggcuguggag 420
ucagagaagc agaagcugcg ggcucaggug cggcccuggu acaagagaac agugguugcg 480
ugaggagcug gcagggacac agcagaagcu cagcgcagug aacaggcggu ggcucagcug 540
gagaagagag cagcacaucu 560

<210> SEQ ID NO 116
<211> LENGTH: 1649
<212> TYPE: RNA
<213> ORGANISM: Homo sapiens

<400> SEQUENCE: 116
augaugugug gcgcgccauc ugccacaaug ccagccacgg ccgagacgca ggaggucgcc 60
gaccagguga ggcugggccc aggucaggcc agucugagcc aggccugcgg agacccggcg 120
gccucaggga ccggccugcc cagacugguc agguccugca gcggguuucc ggggcggcca 180
caagugugac ugggagcugg gggcucugga ucugguugga agauucaggg ccgggaacug 240
gggcgagucu ucugccgcuu gcauacaaga gggccacuca ccuauuaggg aacuagcccc 300
gggaucggug gagggauccg guggucccag agaauucagg aaggcagugu uagaaccuag 360
acggcaccuu uuugacuuac acccaggccu aaacaagaga aagccagacu gggcuacugu 420
gcuugucucc ucaaaagaaa gagcuaggac uguuuagcuc aguggcagga auucaacuga 480
uaccaccacc accaucacca acaccgcccc ucagggaaaa aaaaaaggau caaaaccaga 540
aguuguagaa cuugcuugug ccuagucuga aacgaggggg uggaccuugg gccugggcug 600
cccuuccugu gacuguuagc agagcagaga uucaguacaa gguagggggga gguucagggu 660 auuagcaaga gaagaaaagu uaaacaaauc cucucuucag cucuccugcc acgccccaag 720
cccaggaccc uguccacuaa gccuagcuga ucuugggagg uguuugcucu gaacugaagu 780
ggccaagaag gaagugaguc agcuccauga gacccuagaa augaggaaau guuacagaca 840
cacuggccag gcaagggaac cuuggccacg ugccacauca gcacucagga ggcagagaca 900
ggcgagucuc ucugaauuug aagccagccc aguuugcuua guuccaugcc agccauagcu 960
acauagugag acccuguccc cccccccccc aaaaaaaagg agcuguguug uucuuuauca 1020
guggggccaa caguuuacca uguccccccgg aaugaggagu auugaaggcu ggcagugugu 1080
gugugugggg gcaccugugc augaaucuaa guccuuccuu cucacccacc auccaggugal 1140 agucccagcu ugaaucgaaa gaaaaucaga aguuugaugu cuuuaaagcc auauccuuca 1200
agagacagau aguggcuggc accaaccucu ucaucaaggu ggguacugau aguagcuugc 1260
caugaacugg ggacauaguc ucagaguaga gcagaguguc cugcaacuuc cugcagagaa 1320
ccccuuaagg ggacauguac auguucugag aggaugaauu uggggguuua ggguucccgg 1380
ccuuaaagga ggagacaagg guuaucacug gcuaaguuag uggcuggugg ccuguucugg 1440
cucaguuucu aaggcugggu uaagccugga acuggaaccu uaccuuucac ucacaugucu 1500
gucugucugu cuuccuccag guugauguug guggagauaa augcgugcac uugagggugu 1560
uucaaccccu cccccaugaa aacaagccuu ugacccuguc uuccuaucag accaacaaag 1620
aaaggcacga ugagcucucc uacuucuga 1649

<210> SEQ ID NO 117
<211> LENGTH: 334
<212> TYPE: RNA
<213> ORGANISM: Homo sapiens

<400> SEQUENCE: 117
gaaaauguua agagccauca aauuucugga uauuuugcua ggaaaaugaa auucuacacu 60
uauuuuuugu agacuuuuuu uaaaugcugu uuacaugaau uguauuuugg aaaaaauauu 120
auacugugca cccugugaug caugaaguga uuuuauguau ggucugcuau gugggcagag 180
gucaccuuau uccuaugauc uggaauuguu uacuuucuac aaaguaagcu uuguggggau 240
uuugcuuuca uuuucuuugu agcugauguu auuuuaccag gugugcagca ggaauuacac 300
cacugugugg aauuauaaau acaucccaug ugca 334

<210> SEQ ID NO 118
<211> LENGTH: 481
<212> TYPE: RNA
<213> ORGANISM: Homo sapiens

<400> SEQUENCE: 118
uuuuuuuuuu uuuuuuuccu ggugaauauu uuuauuagag gugacaguuu cccaggugac 60
aguuuuuccc aaggaagcaa aucucugcgu cuauaaggga agaccacaga accuucacuu 120
uguaauuuac cuguguaauu uauccaagaa cacagcacag caauugcuuu augugguacu 180
cugaccuuaa guaacaaguu guuaacagaa aacacaucaa acaaaaggau aauucucuaa 240
uuaucaaguc agccaucagc uuuucuuagg agagagagag agagugugug ugugugugug 300
ugugugugug ugugugugc ugucugucug ucugucuggg uaucccacuu agggccaugu 360
gcauguuagg uaaaugcucc accacugagc uguuucuuag ccgcacuuuu cucagauuuc 420
agguuuguuu guuuguuugu uuguuuuuua acuaggcaug aaaauaaacu ucacuucaaa 480
u 481

<210> SEQ ID NO 119
<211> LENGTH: 481
<212> TYPE: RNA
<213> ORGANISM: Homo sapiens

<400> SEQUENCE: 119
uuuuuuuuuu uuuuuuuccu ggugaauauu uuuauuagag gugacaguuu cccaggugac 60
aguuuuuccc aaggaagcaa aucucugcgu cuauaaggga agaccacaga accuucacuu 120

-continued

```
uguaauuuac cuguguaauu uauccaagaa cacagcacag caauugcuuu augugguacu    180

cugaccuuaa guaacaaguu guuaacagaa aacacaucaa acaaaaggau aauucucuaa    240

uuaucaaguc agccaucagc uuuucuuagg agagagagag agagugugug ugugugugug    300

ugugugugug ugugugugug ugucugucug ucugucuggg uaucccacuu agggccaugu    360

gcauguuagg uaaaugcucc accacugagc uguuucuuag ccgcacuuuu cucagauuuc    420

agguuuguuu guuuguuugu uuguuuuuua acuaggcaug aaaauaaacu ucacuucaaa    480

u                                                                    481
```

<210> SEQ ID NO 120
<211> LENGTH: 302
<212> TYPE: RNA
<213> ORGANISM: Homo sapiens

<400> SEQUENCE: 120

```
uuuuuuuuuu uuuuuuugug gaaauuacuc uuuauugaaa aauaccagua auacugacag     60

acuucaaaau caauuuacgg uuccagaaua caaaguacuu aauacauuuu uuuccaaacc    120

uguuuguauc ucaaaguuag cauuuuugua aaucaagaua caaauaugau aacuucacua    180

aaauauuuuc cagcuuuauu cuuuaaggag cuguauaacc uucaaaguca ggguccccgag   240

gucagcaggg caugggggcag aaugcaccug gcacucccug ugcagcagac ugcaaccaca   300

uu                                                                   302
```

<210> SEQ ID NO 121
<211> LENGTH: 1266
<212> TYPE: RNA
<213> ORGANISM: Homo sapiens

<400> SEQUENCE: 121

```
auggccagcu uuccccccgag gguuaacgag aaagagaucg ugagaucacg uacuauaggg    60

gaacucuugg cuccagcagc uccuuuugac aagaaaugug guggugagaa cuggacgguu   120

gcuuuugcuc cugaugguuc cuacuuugcg uggucacaag gauaucgcau agugaagcuu   180

gucccguggu cccagugccg uaagaacuuu cuuuugcaug guuccaaaaa uguuaccaau   240

ucaagcuguc uaaaaauuggc aagacaaaac aguaauggug gucagaaaaa caagccuccu  300

gagcacguua uagacugugg agacauaguc uggagucuug cuuuugggguc uucaguucca 360

gaaaaacaga gucguugcgu uaauauagaa uggcaucggu uccgauuugg acaggaucag   420

cuacuccuug ccacaggauu aaacaauggu cgcaucaaaa ucugggaugu auauacagga   480

aaacuccucc uuaauuuggu agaccacauu gaaaugguua gagauuuaac uuuugcucca   540

gaugggagcu uacuccuugu aucagcuuca agagacaaaa cucuaagagu gugggaccug   600

aaagaugaug gaaacauggu gaaaguauug cgggcacauc agaauugggu guacaguugu   660

gcauucucuc ccgacuguuc uaugcugugu ucaguuggcg ccaguaaagc aguuuuccuu   720

uggaauaugg auaaauacac caugauuagg aagcuggaag gucaucacca ugauguugua   780

gcuugugacu uuucuccuga uggagcauug cuagcuacug cauccuauga cacucgugug   840

uaugucuggg auccacacaa uggagaccuu cugauggagu uugggcaccu guuucccucg   900

cccacuccaa uauuugcugg aggagcaaau gaccgauggg ugagagcugu gucuuucagu   960

caugauggac ugcauguugc cagccuugcu gaugauaaaa uggugagguu cuggagaauc  1020

gaugaggauu guccgguaca aguugcaccu uugagcaaug gucuuugcug ugccuuuucu  1080

acugauggca guguuuuagc ugcugggaca caugauggaa guguguauuu uugggccacu  1140
```

ccaaggcaag ucccuagccu ucaacauaua ugucgcaugu caauccgaag agugaugucc 1200
acccaagaag uccaaaaacu gccuguuccu uccaaaauau uggcguuucu cuccuaccgc 1260
gguuag 1266

<210> SEQ ID NO 122
<211> LENGTH: 1266
<212> TYPE: RNA
<213> ORGANISM: Homo sapiens

<400> SEQUENCE: 122
auggccagcu uucccccgag gguuaacgag aaagagaucg ugagaucacg uacuauaggg 60
gaacucuugg cuccagcagc uccuuuugac aagaaaugug guggugagaa cuggacgguu 120
gcuuuugcuc cugaugguuc cuacuuugcg uggucacaag gauaucgcau agugaagcuu 180
gucccguggu cccagugccg uaagaacuuu cuuuugcaug guuccaaaaa uguuaccaau 240
ucaagcuguc uaaaauuggc aagacaaaac aguaauggug gucagaaaaa caagccuccu 300
gagcacguua uagacugugg agacauaguc uggagucuug cuuuugggtc uucaguucca 360
gaaaaacaga gucguugcgu uaauauagaa uggcaucggu uccgauuugg acaggaucag 420
cuacuccuug ccacaggauu aaacaauggu cgcaucaaaa ucugggaugu auauacagga 480
aaacuccucc uuaauuuggu agaccacauu gaaaugguua gagauuuaac uuuugcucca 540
gaugggagcu uacuccuugu aucagcuuca agagacaaaa cucuaagagu gugggaccug 600
aaagaugaug gaaacauggu gaaaguauug cgggcacauc agaauugggu guacaguugu 660
gcauucucuc ccgacuguuc uaugcugugu ucaguuggcg ccaguaaagc aguuuuccuu 720
uggaauaugg auaaauacac caugauuagg aagcuggaag gucaucacca ugauguugua 780
gcuugugacu uuucuccuga uggagcauug cuagcuacug cauccuauga cacucgugug 840
uaugucuggg auccacacaa uggagaccuu cugauggagu uugggcaccu guuucccucg 900
cccacuccaa uauuugcugg aggagcaaau gaccgauggg ugagagcugu gucuuucagu 960
caugauggac ugcauguugc cagccuugcu gaugauaaaa uggugagguu cuggagaauc 1020
gaugaggauu guccgguaca aguugcaccu uugagcaaug gucuuugcug ugccuuuucu 1080
acugauggca guguuuuagc ugcugggaca caugauggaa guguguauuu uugggccacu 1140
ccaaggcaag ucccuagccu ucaacauaua ugucgcaugu caauccgaag agugaugucc 1200
acccaagaag uccaaaaacu gccuguuccu uccaaaauau uggcguuucu cuccuaccgc 1260
gguuag 1266

<210> SEQ ID NO 123
<211> LENGTH: 1287
<212> TYPE: RNA
<213> ORGANISM: Homo sapiens

<400> SEQUENCE: 123
gaauuccgug ugcaaggcga ggucuguaag cuggagcggg gcagaggcug gcgggcaccc 60
cuuccugacc gcuggugccg ccgccgccgc cuucgggagg aucagacaug gcccagaacu 120
ugaaggacuu agcuggacgc cugcccgccg ggccucgggg caugggcacg gcgcugaagc 180
ugcugcuggg ggccggggcg guggccuacg gcguccgcga auccguguuc accguggaag 240
gcggucauag agccaucuuu uuuaaucgua uugguggcgu gcagcaggac acgauccugg 300
ccgaauuuca cuucaggauc cccugguucc aguaccccau caucuaugac auucgggcca 360
gaccucggaa aaucuccucc cccacaggcu ccaaagaccu gcagauggug aacaucuccc 420
ugcgugugcu gucccgaccc aaugcccagg agcuccccag cauguaccag cgucuagggc 480
uggacuauga ggagcgagug cugccgucca uuguuaauga ggugcucaag agugugggug 540
ccaaguucaa ugccucgcag cugaucaccc agcgggcuca ggugucccug uugauccgaa 600
gagagcugac agagcgcgcc aaggacuuca gccucauccu ggaugaugua gcuaucacag 660
agcugagcuu cagccgagag uacacagcug cuguagaagc caagcaagug gcccagcagg 720
aagcccagcg ggcccaguuu uugguggaga aagcgaagca ggaacagcga cagaagauug 780
ugcaggcuga gggggaggcg gaggcugcca agaugcuugg agaagcacug agcaagaauc 840
cuggcuauau caagcuccga aagauccggg ccgcccagaa caucucuaaa acgaucgcca 900
caucacagaa ccgaaucuau cucacagcug acaaccuugu gcugaaucua caggaugaaa 960
guuuuacucg gggaagugac agccucauua aggguaagaa augagugugg acaucaagaa 1020
ccccaccacc agagaaguug gcacacuugu ccagcuugga ggagccagcu cggggucaag 1080
cacagcccac ccugccccag gcaucaugug auggacuuuu cuguaucugc ccucuuggau 1140
uaaggaagac ugagaccagc ccuuucagag gcuuuccucc uuccuguguu ggcugggaag 1200 cggggguggac aaugugauuu cuccgugauu uccuacagcc uugagccucu cccagagugg 1260
gggagauaac caccaugcca ggaauuc 1287

<210> SEQ ID NO 124
<211> LENGTH: 612
<212> TYPE: RNA
<213> ORGANISM: Homo sapiens

<400> SEQUENCE: 124
acccaccggc uuucggacca uggccaaccu cgagcguacc uucauugcca ucaagccaga 60
uggcgugcag cgcggccugg ugggcgagau caucaaacgg uucgagcaga agggguuccg 120
ccugguggcc augaaguucc uucgggccuc ugaagaacac cugaagcagc auuacaucga 180
ccugaaagac cguccuuucu ucccggggcu ggugaaguac augaacucgg ggcccguggu 240
ggccaugguc ugggaggggc ucaauguggu gaaaacgggc cgagugaugc ugggggagac 300
caauccagcu gauucaaaac caggcaccau ccguggggau uucugcauuc aaguuggcag 360
gaacaucauu cauggcagug auucagugga gagugcugag aaagagaucc aucugugguu 420
uaagcccgaa gaacugaucg acuacaaguc uugugcccau gacugggugu acgaguagac 480
augaagaaac cagaauccuu uucagcacua cugaugggu ucuggacaga gcucuucauc 540
ccacugacag gauggaucau cuuuucuaaa acaauaaaga cuuuggaacu gaaaaaaaaa 600
aaaaaaaaaa aa 612

<210> SEQ ID NO 125
<211> LENGTH: 529
<212> TYPE: RNA
<213> ORGANISM: Homo sapiens

<400> SEQUENCE: 125
uuuugcuuuc aacaugacag augccgcugu guccuucgcc aaggacuucu uggccggugg 60
aguggccgca gcaucuccaa gacagcgguc acaccaucga gagggucaag cugcugcugc 120
aggugcacau gccagcaagc aaaucacggc agauaagcaa uacaagggca ucauagacug 180
cgugguucgu auccccaagg aacagggagu gcucuggucc uuugggcgug ggaaccgggc 240
caaugucauc agauacuucc ccaccaaggc ucucaacuug gccuucaaag uuaauuccaa 300
gcagaucuuu cugggguggug uugacaagag gacccaguuc uggcgcuacu uuugcaggga 360
accuggcauc aggugguugc cgcuggggcu acauccuugg gcuuugugua cccucuugau 420
uuuugccggu accgucuagc agcugaugug ggcaagcugg agcuaaaggg aauucaaggg 480
ccuugggacu gccugguaag acuucaaucu gaugggauaa gggcuguac 529

<210> SEQ ID NO 126
<211> LENGTH: 291
<212> TYPE: RNA
<213> ORGANISM: Homo sapiens

<400> SEQUENCE: 126
auccgggacc cccacggccc cuuugcagcu ugccacaagg uucugagccc cuuggaauac 60
uuccgccaau guguguauga caugugugcc cauaagggug acaaagccua ucucugccgu 120
agccuggcug cuuauacugc agccugucag gcagcugggg cagcagugaa gcccuggagg 180
acagacagcg ucugcccucu ccaguguccu gcccacagcc acuacuccau cugcacccgc 240
uccugccagg gcuuccugug cugcucucuc uggccucacu ggcugcacca c 291

<210> SEQ ID NO 127
<211> LENGTH: 3454
<212> TYPE: RNA
<213> ORGANISM: Homo sapiens

<400> SEQUENCE: 127
ggcacgagcc gaguuggagg aagcagcggc agcggcagcg gcagcgguag cggugaggac 60
ggcugugcag ccaaggaacc gggacagcga agcgacggca ggucgcagcu ggaucgcagg 120
agccugggag cugggagcuu cagaggccgc ugaagcccag gcugggcaga ggaaggaagc 180
gagccgaccc ggaggugaag cugagagugg agcguggcag uaaaaucaga cgacagaugg 240
acagugugac aggaacguca gagaggauug ggccucgcug cgagagucag ccuggaguca 300
agguguugac aaguugcuga gaaggacacg ugggaggacg guggcgcgcg gagggagagc 360
ccugucuuca gucaccccgu ugauggagga cagauggaca gcagccggac ggccagucac 420
cucucuuaaa ccuuuggaua gugguccuuu gugcucugcu ggacaccugu uggggauuuu 480
agcccauucu cugaacucac uuucucuuaa aacguaaacu cggacggcag ugugcgagcc 540
agcuccucug uggcagggca cuagagcugc agacaugagu gcagagggcu accaguacag 600
agcacuguac gacuacaaga aggagcgaga ggaagacauu gaccuacacc ugggggacau 660
acugacugug aauaaaggcu ccuuaguggc acuuggauuc agugauggcc aggaagcccg 720
gccugaagau auuggcuggu uaaauggcua caaugaaacc acuggggaga ggggagacuu 780
uccaggaacu uacguugaau acauuggaag gaaaagaauu ucacccccua cucccaagcc 840
ucggcccccu cgaccgcuuc cuguugcucc ggguucuuca aaaacugaag cugacacgga 900
gcagcaagcg uugccccuuc cugaccuggc cgagcaguuu gccccuccug auguugcccc 960
gccucuccuu auaaagcucc uggaagccau ugagaagaaa ggacuggaau guucgacucu 1020
auacagaaca caaagcucca gcaacccugc agaauuacga cagcuucuug auugugaugc 1080
cgcgucagug gacuuggaga ugaucgacgu acacgucuua gcagaugcuu ucaaacgcua 1140
ucucgccgac uuaccaaauc cugucauucc uguagcuguu uacaaugaga ugaugucuuu 1200
agcccaagaa cuacagagcc cugaagacug cauccagcug uugaagaagc ucauuagauu 1260
gccuaauaua ccucaucagu guuggcuuac gcuucaguau uugcucaagc auuuuuucaa 1320
gcucucucaa gccuccagca aaaaccuuuu gaaugcaaga guccucucug agauuuucag 1380
ccccgugcuu uucagauuuc cagccgccag cucugauaau acugaacacc ucauaaaagc 1440
gauagagauu uuaaucucaa cggaauggaa ugagagacag ccagcaccag cacugccccc 1500
caaaccaccc aagcccacua cuguagccaa caacagcaug aacaacaaua uguccuugca 1560
ggaugcugaa ugguacuggg gagacaucuc aagggaagaa gugaaugaaa aacuccgaga 1620
cacugcugau gggaccuuuu ugguacgaga cgcaucuacu aaaaugcacg gcgauuacac 1680
ucuuacaccu aggaaaggag gaaauaacaa auuaaucaaa aucuuucacc gugauggaaa 1740
auauggcuuc ucugauccau uaaccuucaa cucugugguu gaguuaauaa accacuaccg 1800
gaaugagucu uuagcucagu acaaccccaa gcuggaugug aaguugcucu acccaguguc 1860
caaauaccag caggaucaag uugucaaaga agauaauauu gaagcuguag ggaaaaaauu 1920
acaugaauau aauacucaau uucaagaaaa aagucgggaa uaugauagau uauaugagga 1980
guacacccgu acuucccagg aaauccaaau gaaaagaacg gcuaucgaag cauuuaauga 2040
aaccauaaaa auauuugaag aacaaugcca aacccaggag cgguacagca aagaauacau 2100
agagaaguuu aaacgcgaag gcaacgagaa agaaauucaa aggauuaugc auaaccauga 2160
uaagcugaag ucgcguauca gugagaucau ugacaguagg aggagguugg aagaagacuu 2220
gaagaagcag gcagcugagu accgagagau cgacaaacgc augaacagua uuaagccgga 2280
ccucauccag uugagaaaga caagagacca auacuugaug uggcugacgc agaaaggugu 2340
gcggcagaag aagcugaacg aguggcuggg gaaugaaaau accgaagauc aauacucccu 2400
gguagaagau gaugaggauu ugccccacca ugacgagaag acguggaaug ucgggagcag 2460
caaccgaaac aaagcggaga accuauugcg agggaagcga gacggcacuu uccuuguccg 2520
ggagagcagu aagcagggcu gcuaugccug cuccguagug guagacggcg aagucaagca 2580
uugcgucauu aacaagacug ccaccggcua uggcuuugcc gagcccuaca accuguacag 2640
cucccugaag gagcuggugc uacauuauca acacaccucc cucgugcagc acaaugacuc 2700
ccucaauguc acacuagcau acccaguaua ugcacaacag aggcgaugaa gcgcugcccu 2760
cggauccagu uccucaccuu caagccaccc aaggccucug agaagcaaag ggcuccucuc 2820
cagcccgacc ugugaacuga gcugcagaaa ugaagccggc ugucugcaca ugggacuaga 2880
gcuuucuugg acaaaaagaa gucggggaag acacgcagcc ucggacuguu ggaugaccag 2940
acguuucuaa ccuuauccuc uuucuuucuu ucuuucuuuc uuucuuucuu ucuuucuuuc 3000
uuucuuucuu ucuuucuuuc uuucuaauuu aaagccacaa cacacaacca acacacagag 3060
agaaagaaau gcaaaaaucu cuccgugcag ggacaaagag gccuuuaacc auggugcuug 3120
uuaacgcuuu cugaagcuuu accagcuaca aguugggacu uuggagacca gaagguagac 3180
agggccgaag agccugcgcc ugggggccgcu ugguccagcc ugguguagcc ugggugucgc 3240 ugggugugggu gaacccagac acaucacacu guggauuauu uccuuuuuaa aagagcgaau 3300
gauauguauc agagagccgc gucugcucac gcaggacacu uugagagaac auugaugcag 3360
ucuguucgga ggaaaaauga aacaccagaa aacguuuuug uuuaaacuua ucaagucagc 3420
aaccaacaac ccaccaacag aaaaaaaaaa aaaa 3454

<210> SEQ ID NO 128
<211> LENGTH: 199
<212> TYPE: RNA
<213> ORGANISM: Homo sapiens
<220> FEATURE:
<221> NAME/KEY: misc_feature
<222> LOCATION: (136)..(136)
<223> OTHER INFORMATION: n is a, c, g, or u

<400> SEQUENCE: 128
uuuuuuuuuu uuguuuuaau uuggcuccaa ugaucgcauu cucaaacucc uuugggaggg 60
cauuagauga cccaguaucc gacgacuuag auucacacgu guuuuucucc ucugagcucu 120
uuucuccagg cucacngucu uuguuuuuca agcuuucuug ggccuuugaa caauuuucuu 180
ccuuugaaga uucuccugg 199

<210> SEQ ID NO 129
<211> LENGTH: 1706
<212> TYPE: RNA
<213> ORGANISM: Homo sapiens

<400> SEQUENCE: 129
agccgaguag gaccgagcug cugcagacgc gccgggucac ucgagccagc accaccguuc 60
ucacgcccug agcugcagac agcuaggcgg uuuuaucuag uuugaaccag gcugcuggag 120
cuugcucccu cccgcccucu cucuuuuuuu uccacggggc uguuuuuuua auuuggcugc 180
aauugcauga aaucccaaug guguagacca guggcgaugg aucuaggagu uuaccaacug 240
agacauuuuu ccauuucuuu cuugucgucu uugcugggaa ccgaaaacgc uuccgugaga 300
cuugacaaua gcucuggugc aaguguggua gcuaucgaca acaaaauaga gcaagcuaug 360
gaucugguga aaagccauuu gauguaugcg gugagggagg aaguggaagu ucugaaggag 420
cagaucaaag aacuaauaga gaaaaacucc cagcuggagc aggagaacaa ucugcugaag 480
acgcuggcca guccggagca gcucgcccag uuucaggccc agcugcagac uggcuccccu 540
ccggccacca cgcagccaca ggggaccaca cagcccccug cacagccagc aucccagggc 600
ucaggaucaa ccgcauagcc uccuaggccc caacagaacu ggcugcugcu gcugcugucu 660
gaacugaaca gaccgaagag augugcuaga gagaagccgc cuccacaguc acccauuuca 720
uugcugucua cgaaagagac gugagacuca cacgcuguuc ucgcuuucuc cccaguauua 780
agcacucaua agcuuuuggc uugaagaaau guacuaguug agugaauuaa agguuaauca 840
gagagugagc agggaugugc ccugugcaac guggcagaug ucugaggaau gguuuaauug 900
accccgagga gcucugugcc uuuucaaccc uccccagccg cccacccugc uucugagagc 960
ucgggcggcu cgccuucgug gggcucgccu gcguggggguu cgaaaguggg cugcuccugg 1020
auucugcgcu cucuucuccu ucccuucaaa gaacucggag aggccagaaa caagacugca 1080
auggggggcg gggggaggga ugaugcaguc cuuauacaaa accgacaacu gucaccaaag 1140
cuuauaaaac acgauaguac ugucccucuu uucugaacca ucagaagaca caaaacuguu 1200
agugacacaa cggugacagg uagcugggac cuaggcuauc uuauuaugaa gguuguuuug 1260
cuuguuguau auuuguguau guaguguaac gaauuuguac cauagaggac uguccguaac 1320
uacuguuuag cuucuacaca uugaaaugua gauguuucau uggcugucug aaaaggugug 1380
gcuuguccuu ccuagagaga ucuacuuaaa aacugcuuug uggcaaaaac cacaccugaa 1440
gaaauuuuaa gaauuuggcc caguuaguca cucuguguaa ucccggaauc uagcugcuga 1500
agucuugcga aguaaacucc ccgugaccga ugucaguuaa gcuggugaua ccuggagaag 1560
uggucaguug cuaaggaagu ggauuuccca guaggggguuu cugcaccuca ccuguauagu 1620
cguucugcgc augucccca cacaguccccc accuguauuu accuguucua cuugucaccu 1680
uucaauaaag cauaucaaau guugau 1706

<210> SEQ ID NO 130
<211> LENGTH: 2175
<212> TYPE: RNA
<213> ORGANISM: Homo sapiens

<400> SEQUENCE: 130
auggcugcgc acgucuggcu ggcggccgcc cugcuccuuc ugguggacug gcugcugcug 60
cggcccaugc ucccgggaau cuucuccug uugguucccg aggugccgcu gcuccggguc 120
uggguggugg gccugagucg cugggccauc cuaggacuag ggguccgcgg gguccucggg 180
gucaccgcag gagcccaugg cuggcuggcu gcuuugcagc cgcugguggc cgcacugagu 240
uuggcccugc cuggacuugc cuuguuccga gagcuggccg ccuggggaac acuccgggag 300
ggugacagcg cuggauuacu guacuggaac agucguccag augccuucgc uaucaguuau 360
guggcagcau ugcccgcagc cgcccugugg cacaaguugg ggagccucug ggcgcccagc 420
ggcaacaggg acgcuggaga caugcugugu cggaugcugg gcuuccuggg cccuaagaag 480
agacgucucu accugguucu gguucucuug auucucucuu ggcuuggga aauggccauu 540 cccuucuuca cgggccgcau cacugacugg auucuucagg auaagacagu uccuagcuuc 600
acccgcaaca uauggcucau guccauucuc accauagcca gcacagcgcu ggaguuugca 660
agugauggaa ucuacaacau caccauggga cacaugcacg gccgugugca cagagaggug 720
uuucgggccg uccuucgcca ggagacaggg uuuuuccuga agaacccagc agguuccauc 780
acaucucggg ugacugagga cacagccaac gugugcgagu ccauuaguga cacgcugagc 840
cugcugcugu gguaccuggg gcgagcccug ugucucuugg uguucauguu uugggggguca 900 ccguaccuca cucuggucac ccugaucaau cugccccugc uuuuucuuuu gccuaagaag 960
cugggaaaag ugcaccaguc acuggcagug aaggugcagg agucucuagc aaaguccacg 1020
cagguggccc uugaggccuu aucggcgaug ccuaccgugc ggagcuuugc caacgaggag 1080
ggugaggccc agaaguucag gcagaaguug gaagaaauga agacgcuaaa caagaaggag 1140
gccuuggcuu acgucgcuga agucuggacc acgagugucu cgggaaugcu gcugaaggug 1200
ggaauucugu accugggcgg gcagcuggug aucagaggga cugucagcag cggcaaccuu 1260
gucucauucg uucucuacca gcuucaguuc acccaggcug uucagguccu gcucucccuc 1320
uaccccucca ugcagaaggc ugugggcucc ucagagaaaa uauucgaaua cuuggaccgg 1380
acuccuugcu cuccacucag uggcucguug gcacccucaa acaugaaagg ccuuguggag 1440
uuccaagaug ucucuuuugc cuacccaaac cagcccaaag uccaggugcu ucaggggcug 1500
acguucaccc ugcauccugg aacggugaca gcguuggugg gacccaaugg aucagggaag 1560
agcaccgugg cugcccugcu gcagaaccug uaccagccca ccgggggcca gcugcugcug 1620
gauggccagc gccugguccca guaugaucac cauuaccugc acacucaggu ggccgcagug 1680
ggacaagagc cgcugcuauu uggaagaagu uuucgagaaa auauugcgua uggccugaac 1740
cggacuccaa ccauggagga aaucacagcu guggccgugg agucuggagc ccacgauuuc 1800
aucucugggu ucccucaggg cuaugacaca gagguaggug agacugggaa ccagcuguca 1860
ggaggucagc gacaggcagu ggccuuggcc cgagccuuga uccggaagcc acuccugcuu 1920
aucuuggaug augccaccag ugcccuggau gcuggcaacc agcuacgggu ccagcggcuc 1980
cuguaugaga gccccaagcg ggcuucucgg acgguucuuc uuaucaccca gcagcucagc 2040
cuggcagagc aggcccacca cauccucuuu cucagagaag gcucugucgg cgagcagggc 2100
acccaccugc agcucaugaa gagaggaggg ugcuaccggg ccaugguaga ggcucuugcg 2160
gcuccugcag acuga 2175

<210> SEQ ID NO 131
<211> LENGTH: 970
<212> TYPE: RNA
<213> ORGANISM: Homo sapiens

<400> SEQUENCE: 131
gaauuccggg gccgcucucu ccggcaggau cgccgcgaug gccgcccagg gagagccgca 60
gguccaguuc aaggucgucc uggugggcga cggcggcacc ggaaagacga cauucaugaa 120
gcgccacuug accggagagu uugagaagga guauguagcc acccugggcg uggaggugca 180
cacauuaguc uuccauacca acagaggacc uaucaaguuc aauguguggg acacagccgg 240
ucaggagaag uucgggggc ugcgcgaugg cuacuacauc caagcccagu gugccauuau 300
aauguuugac guaacaucaa gaguuacuua caagaaugug ccuagcuggc auaaagaucu 360
agugcgugug ugugaaaaca uccccauugu auuguguggc aacaaagugg auguuaaaga 420
caugaaagug aaggcaaaac cuauucucuu ccaccgaaag aagaaucuuc aguacuauga 480
cauuucugcc agaaguaacu acaacuuuga aaagccuuuc uucuggcuug ccagaaagcu 540
cauuggagau ccuaacuugg aguucguugc caugccugcu cuugccccac cugagguagu 600
cauggaccca gcuuuggcag cacaguacga gcaugauuua gagguugcuc agacgacugc 660
ucucccagau gaggaagaug accugugaga aagugaagcu ggagcccugc gucagaaguc 720
uauuuuaggc aacuguccug ugaugccagc cagcggugca gugugugugc caccuuauuu 780
agcuaaagga gaucgugcaa uucauuggga ugcugaagga gaugaauggg cuucggagug 840
aauguggcag uuaaaauaca ccuucauuuu uuuggacuug cguauuuagc ccccuggaac 900
agaguuguuc uggauuucaa agauaagacu gcuaccguag caucacaaua gucagguggug 960 accggaauuc 970

<210> SEQ ID NO 132
<211> LENGTH: 356
<212> TYPE: RNA
<213> ORGANISM: Homo sapiens

<400> SEQUENCE: 132
uuuuuuuuuu uuuuuuugau uuaugaaaag uuuuauuuau caguacugug aagaauucuc 60
aucauaauug cuacguuaau caaggaaaag gcacagagaa gcaugugucg uuugaguccu 120
cgauacugga ccucccagcc caugcucccu augaggaguc uagcugcugu gguggucuuc 180
acagcuuugg uuuucuggag acgaagcuca ugauugcguu caugcacucc ucugacagcc 240
accuugcuug cagaguagug cacucuucag cguugacugc guagagcuuu ucuuucucau 300
uuuuucugau uaacucuuug gaaauucuca uuggguuugg cgggagcuuc gcauau 356

<210> SEQ ID NO 133
<211> LENGTH: 626
<212> TYPE: RNA
<213> ORGANISM: Homo sapiens

<400> SEQUENCE: 133
ucgggaaucg auugagagac cgcgaaccug uaaacggaug auaccgaguc gggcaggcgu 60
uaugccagcc caacucggga ccucgcauca uguccgcggc uaccuuagag uguuucggga 120
augauuugcg guggaugaac gaaaccccgg uacguccugu gccaaggagc auaugucagg 180

-continued

```
acggacgcuc guuaaugccu caguggaggg gcaacguucg cucucuaucu auacgacucu    240

cgacaaugga uaucucggcu cucgcaucga ugaagaacgu agcgaaaugc gauacuuggu    300

gugaauugca gaauccugug aaccaucgag ucuuugaacg caaguugcgc ccgaggccuu    360

ucgguugagg gcacgccugc cugggcguca cgccuuguuu ugcucugugc ccgugcucuu    420

ucgggggcgg ucauggaugc ggagauuggc ccuccgugcc ucgugugcgg cgggcuuaag    480

cgcggggugu cggcgucggg aagggcacga cgaguggugg acggagcacc agcaggaugu    540

ugugguCCCC cgucaccuua aggggcucaa gagacccgga cuaggcgagc cgcgcuucgu    600

aagaggaggg cgagcugucu cgcaau                                          626
```

<210> SEQ ID NO 134
<211> LENGTH: 495
<212> TYPE: RNA
<213> ORGANISM: Homo sapiens
<220> FEATURE:
<221> NAME/KEY: misc_feature
<222> LOCATION: (485)..(485)
<223> OTHER INFORMATION: n is a, c, g, or u

<400> SEQUENCE: 134

```
uuuuuuuuuu uuuuuuugaa guugcugccc cuuuauuggu gacccgggca aguuuaagga     60

gaacaacauu aaagcacaca aaguguaucc augucaccag cucaaccagg aggagugagg    120

gucacggcag gguucuccca ugguguaaga aaucaacgca auuucaucac accccguuac    180

uuuccaaguu aacgaaccga uaagaaaaga uucucccuua aacugacaag uacaauguac    240

auguacauga uuuuggaaua auuuaauacu uuaaccucaa gauacaacua uauucuaaga    300

ccauuauuuu aaaggaacgg auccuuacaa aaccaaaaua acccauauag cacgagguug    360

guuuagccuu ucuucuucuu ucaacaaacg ugcaccacau guuucaguag caaggccgau    420

gccauggaua ugagagcugu gauuugcagg gaccaaccac aucuagaacc ggggaggcca    480

aucanacggu ggguu                                                      495
```

<210> SEQ ID NO 135
<211> LENGTH: 257
<212> TYPE: RNA
<213> ORGANISM: Homo sapiens
<220> FEATURE:
<221> NAME/KEY: misc_feature
<222> LOCATION: (254)..(254)
<223> OTHER INFORMATION: n is a, c, g, or u

<400> SEQUENCE: 135

```
cccuuggagg auaguuuuau ugacaagucg aguuagguuu uagaguaaac uuuuaucacc     60

ccagucaggc cccuucccag gggaggcucg cugguagcuc agauggccuu ggugguggggc   120

agauuguugu aguugucuuc cuggcccucc agcaggcuuc gggagguggc uaucuccugc    180

uccagccugg acuugauguc caguagcugc uuauacuccg gguucuggcg cucuaugugc    240

ggcacgcagg ugcngcg                                                    257
```

<210> SEQ ID NO 136
<211> LENGTH: 1186
<212> TYPE: RNA
<213> ORGANISM: Homo sapiens

<400> SEQUENCE: 136

```
ggacugacuc cuugggcaga uugccucucc uccuucucau gccagaggcu gcugaugagg     60

aaagguccag gggacugucc augcugucuu cauccucaga gucacugccu gaugcugcaa    120
```

caagacccuu cuuguuuagc aauaguggau ggaacacucu cuuguaaguu accggagcac 180
uaguauagga ggaggaucau cgacuacccu cccgccacuc cacggcugcu ggcuccuaga 240
aaccccagcu ucaccucuca cugggacucg aguuccagaa ugaaaagcaa gaagggucuu 300
guugcagcau caggcaguga cucugaggau gaagacagca uggacagucc ccuggaccuu 360
uccucaucag cagccucugg caugagaagg aggagaggca aucugcccaa ggagucaguc 420
cagauucugc gagacuggcu guaugaacac agauacaacg ccuaucccuc agagcaagag 480
aaagcacugc ugucccagca gacacaccug uccacacuac aggucuguaa cugguucauc 540
aacgcccgcc gcaggcuccu uccugacaug cugagaaagg auggcaaaga uccaaaucag 600
uucacgauuu cccgccgugg ggccaagauu ucagaagcua gcucuauuga agcugcaaug 660
gguaucaaaa acuucaugcc aacucuagaa gagagcccau uucauuccug cguaguugga 720
cccaacccaa cccuagggag accagugucu cccaaaccuc ccucccccagg auccauuuug 780 gcucgcccgu cagugaucug ccauaccacu gugacugcau ugaaggaugg gccuuucucu 840
cucugucagc cgauuggugu gggacagagu acagauguac cgcaaauagc acccagcaac 900
uuuacagaca ccucucucgu guacccagag gacacuugca aaucuggacc caguccaaac 960
ccucagagug gucuuuucaa cacuccuccc ccuacuccac cagaccucaa ccaggauuuu 1020
aguggauucc agcuucuagu ggauguugca cucaaacgag cggcagagau ggagcuucag 1080
gccaaacuca cagcuuaacc guuuuuucaa acaaaacagu ucuccaaaau acgguccuga 1140
uugccggggg ugauggcaag agaugcauua uuuuauauau uuuuuc 1186

<210> SEQ ID NO 137
<211> LENGTH: 455
<212> TYPE: RNA
<213> ORGANISM: Homo sapiens

<400> SEQUENCE: 137
uuuuuuuuuu uuuuuuuggu gguuaucaag ugcacuuuau ugaauccacu guggauagau 60
aaaugagugu uacaccugcg uguagggagg ggcaaggagg gacgcagcug cggagggguga 120 agcacuucag gaccggaagu cggaauccuc uauuaagugu gaagguuuug agcguuaaga 180
acaaugauga ugacacuaac aauggugaua acaaccauca ggaugcugag gaccaaggug 240
cugauguuca ggcacuuagc aguggaggcg uaggccuggg cuccagucac aucacccacc 300
aucuuccgau cccuagacuu cacggaguag gcauaggcua ugaagcccag gcagcagaag 360
uucaugaaga guguauugaa cagggaccag accacauggu caggcaccga caccucucug 420
ggcauguuga ucacaguagu ucugacagaa gccga 455

<210> SEQ ID NO 138
<211> LENGTH: 1797
<212> TYPE: RNA
<213> ORGANISM: Homo sapiens

<400> SEQUENCE: 138
aagcuucagg auacagugca cacucguaaa uaaaaacuac aggcugcugc gaauuauauu 60
ucaacugacc ggagaggcaa agccugacug uccauuaacc cuuaacuucc aaacgcaaac 120
ugcuuacugc aucuuuuggc auuuuaccuu augccuuguu agguccaagg caagagaagc 180
gucaucaaua accacgcaug ugcaacagcu uuuccagagg aaaggugugg guggcucuua 240
aaagagccuu ugaguuagga gugugaguua aacgagcuca cuuggagcug guguacuugg 300

-continued ugacugccuu ggugcccucc gacaccgcgu gcuuggccag cuccccgggc agcagcaggc 360
gcacggccgu cuggaucucc cgggacguga uggucgagcg cuuguuguaa ugcgccaggc 420
gggaagccuc gcucgcgaug cgcucgaaga ugucguucac gaacgaguuc augaugccca 480
uggccuugga ggagaugccg gugucggggu gcacuugcuu cagcaccuug uacacguaca 540
ccgaguagcu cuccuugcgg cugcgcuugc gcuucuugcc guccuucuuc ugggccuugg 600
ugacggccuu cuuggagccc uucuucgggg cgggagcgga cuuggcgggc ucaggcauac 660
ugagaggaug aagugaacua aguugaaaaa ggauaacuaa aaguuaauga cuguucuggc 720
ugcaauuuua aacaaacuua cggcuauggc aaccugaauc accauacguc auguacuaac 780
aguccaauca aaacaaggga uuuucaaacc agggcgccau ugguaaccaa uguguaacca 840
augaaaucuc uccguuuucg cguccagccu ugacuauaua uacuaugcgu auacguuuuu 900
gcuucuuacu gcggugguua ucuacagcug aguuaugucu ggacguggca agcaaggacg 960
uggcaagcaa ggaggcaagg cccgcgccaa ggccaagacg cgcuccuccc gggccggccu 1020
gcaguucccc gugggccgcg ugcaccggcu gcuccgcaag ggcaacuacu cggagcgcgu 1080
gggcgccggc gccccggugu accuggcggc cgugcuggag uaccugacgg ccgagauccu 1140
ggagcuggcg ggcaacgcgg cccgcgacaa caagaagacg cgcaucaucc cgcgccaccu 1200
gcagcuggcc auccgcaacg acgaggagcu caacaagcug cugggccgcg ugaccaucgc 1260
gcagggcggc guccugccca acauccaggc cgugcugcug cccaagaaga ccgagagcca 1320
ccacaaggcc aaggggaagu gaaaccaaac auuacgaauc accaaggcuc uuuucagagc 1380
cacucacuuu cucaaagaga ccuaacacua cugggauagu gcauuguggg aaauacgugu 1440
auuaaccuuc cuccuauuuu cccugcuugu gguuaguuca accccuaagc cuuaggcuaa 1500
gaguauauug guuuuuggaa ggcaggcacc caaccucgga ccuaguacau aaaacagaca 1560
caucuugaac uccaggccag ccuacucugc aggacgaguu ccaggacaga ccggacugca 1620
caaagaauug ucuugaaaug uuccuuuauc agcacauaug cugauaaaca acuaaucacu 1680
guacaaucaa uccucacuug aauccuguuu auguggcaug auugacaagu ccugccauuu 1740
ggcaaaguca aaaucagcaa aggauguuaa agcauuuggu gguaucacag cuaaaac 1797

<210> SEQ ID NO 139
<211> LENGTH: 376
<212> TYPE: RNA
<213> ORGANISM: Homo sapiens

<400> SEQUENCE: 139
uuuuuuuuuu uuuuuaugca aauaguuuuc aagauuuuau ugcaaaccaa aauugguuua 60
ucgcacacaa aaaaaguugu gugguaagga ggaggaauug uacaggauua uaacccaugu 120
uaauuacagu acauuaaaau gaugguuuac aaauaagccu guaaguuuaa auaucuagug 180
uuauaaccca auguacagac uuccuuuaca cgauacauac aauaaucagg aaugcaaaag 240
aauaugaaca aagggaaaaa aaacauaaau aaugcccguu uuauagguga cauuuuaaac 300
aauugaaaac accaaccggc uuugacugac aacuggggca uugguccaua aaaacccuuu 360
cuaaaaauag aaauau 376

<210> SEQ ID NO 140
<211> LENGTH: 1068
<212> TYPE: RNA
<213> ORGANISM: Homo sapiens

<400> SEQUENCE: 140
gaggcugcuc aagagcugcg guugggucac cgcuucaugu uucucugccg auucugggga 60
aagauggcaa cgaaugaugc uguucugaag aggcuggagc agaagggugc agaggcggau 120
cagaucaucg aauaucucaa gcagcagguu gcucuucuua aggagaaagc aauuuugcag 180
gcaacaauga gagaagaaaa gaaacuucga guugaaaaug cuaaacugaa aaaagaaaua 240
gaagagcuaa agcaagagcu gauucuggca gaaauucaua acggagugga gcaagugcgu 300
guucgauuga guacuccacu gcagacgaac uguacugcuu cugaaagugu ggugcagucu 360
ccaucaguag caaccaccgc cucuccugcu acaaaagagc agaucaaagc gggagaagaa 420
aagaagguga aagagaagac ugaaaagaaa ggagagaaaa aggagaagca gcagucggca 480
gcagcaagua cugacuccaa gccuaucgac gcaucgcguc uggaucuucg aauugguugu 540
auuguuacug ccaagaagca cccugaugca gauucacugu auguggagga aguagaugug 600
ggagaagcag ccccgcgcac ggucgucagc gggcugguga aucauguucc ucuagaacag 660
augcaaaauc guaugguggu uuuacucugu aaucugaagc cugcaaagau gcggggaguu 720
cugucucaag ccauggugau gugugccagu ucaccagaga aaguggagau ucuggccccu 780
cccaacgggu ccguuccugg ggacagaauu acuuuugaug cuuuuccugg agagccugac 840
aaggagcuaa acccuaagaa gaagaucugg gagcagaucc agccugaccu gcacaccaau 900
gcugagugug uggccacaua caaaggagcu cccuuugagg ugaaggggaa gggaguuugc 960
agagcccaaa ccauggccaa uaguggaauu aaauaagugc ucuguaacug aaagacauug 1020
gcgaaaacuu aauaacaaua aagagaagug uguuuaucac uuacauau 1068

<210> SEQ ID NO 141
<211> LENGTH: 165
<212> TYPE: RNA
<213> ORGANISM: Homo sapiens

<400> SEQUENCE: 141
ggccuuguuu uugguuugca auaaagagua uuucuuuaaa aggcacauuu uguuaaauag 60
gcaguucccc uccugccucu uccuuuguag caguguacug cauccuagaa acauuuagca 120
aagcagcccu uagccucccc gacccccuuu cccucccucc cagca 165

<210> SEQ ID NO 142
<211> LENGTH: 324
<212> TYPE: RNA
<213> ORGANISM: Homo sapiens

<400> SEQUENCE: 142
uuuuuuuuuu uuuuuuuaaa caaugacgcc guuuauuuaa aauguuuacu cccagaaaua 60
uagauauaaa aaaaaaaaua agacaauuaa cagcacuaaa ccaggcaccu ucaaccgaau 120
cccaccaucc ucguuaacuc ccuuccuguu acccuuugua gaugaccaga agauuucagg 180
agccccugga cagccagagu gguuccugcc cagggcuucc cgccuuccuc cuguccuaga 240
gcuucccgug ggaaagcuug ggugagaauu uuagccuaaa gggagggggc uguggccggg 300
cacuuugcgc ucauccacug cagg 324

<210> SEQ ID NO 143
<211> LENGTH: 2473
<212> TYPE: RNA
<213> ORGANISM: Homo sapiens

<400> SEQUENCE: 143

-continued

```
acaggguaca guugugcguc agggcgugga ggucuggcgg gagacgcaua guuacagcgc      60
guccguucuc cgucucgcag ccggcacagc uagagcuucg agcgcagcgc ggccauggau     120
cccagcagca agaaggugac gggccgccuc auguuggcug ugggaggagc agugcucgga     180
ucacugcagu ucggcuauaa cacuggugu c aucaacgccc cccagaaggu uauugaggag     240
uucuacaauc aaacauggaa ccaccgcuac ggagagccca ucccauccac cacacucacc     300
acgcuuuggu cucucuccgu ggccaucuuc ucugucgggg gcaugauugg uuccuucucu     360
gucggccucu uuguuaaucg cuuuggcagg cggaacucca ugcugaugau gaaccuguug     420
gccuuugugg cugcugugcu uaugggcuuc uccaaacugg gcaaguccuu ugagaugcug     480
auccugggcc gcuucaucau cggguguguac ugcggccuga cuacuggcuu ugugcccaug     540
uauguggggag agguguacacc uacagcucua cguggagccc uaggcacacu gcaccagcug     600
ggaaucgucg uuggcauccu uauugcccag guguuuggcu uagacuccau caugggcaau     660
gcagacuugu ggccucugcu gcucagug uc aucuucaucc cagcccugcu acaguguauc     720
cuguugcccu ucugccccga gagcccccgc uuccugcuca ucaaucguaa cgaggagaac     780
cgggccaaga gugugcugaa gaagcuucga gggacagccg augugacccg agaccugcag     840
gagaugaaag aagagggucg gcagaugaug cgggagaaga aggucaccau cuuggagcug     900
uuccgcucac ccgccuaccg ccagcccauc cucaucgcug uggugcugca gcugucccag     960
cagcugucgg guaucaaugc uguguucuac uacucaacga gcaucuucga gaaggcaggu    1020
gugcagcagc cuguguacgc caccaucggc uccgguaucg ucaacacggc cuucacugug    1080
gugucgcugu uuguuguaga gcgagcugga cgacggaccc ugcaccucau uggccuggcu    1140
ggcauggcag gcugugcugu gcucaugacc aucgcccugg ccuugcugga acggcugccu    1200
uggaugucuu aucugagcau cguggccauc uuuggcuuug uggccuucuu ugaaguaggc    1260
ccugguccua uuccaugguu cauuguggcc gagcuguuca gccaggggcc ccguccugcu    1320
gcuauugcug uggcuggcuu cuccaacugg accucaaacu ucauuguggg caugugcuuc    1380
caguaugugg agcaacugug cggcccccuac gucuucauca ucuucacggu gcuccucgug    1440
cucuucuuca ucuucaccua cuucaaaguc ccugagacca aaggccgaac cuucgaugag    1500
aucgcuuccg gcuuccggca gggggggugcc agccaaagug acaagacacc cgaggagcuc    1560
uuccacccuc ugggggcgga cucccaagug ugaggagccc cacacccagc ccggccugcu    1620
cccugcagcc caaggaucuc ucuggagcac aggcagcuag augagaccuc uuccgaaccg    1680
acagaucucg ggcaagccgg gccugggcgc cuuuccucag ccagcaguga aguccaggag    1740
gauauucagg acuuugaugg cuccagaauu uuuaaugaaa gcaagacugc ugcucagauc    1800
uauucagaua agcagcaggu uuuauaauuu uuuuauuacu gauuuuguua uuuuuuuuuu    1860
uuaucagcca cucuccuauc uccacacugu agucuucacc uugauuggcc cagugccuga    1920
gggugggggac cacgcccugu ccagacacuu gccuucuuug ccaagcuaau cuguagggcu    1980
ggaccuaugg ccaaggacac acuaauaccg aacucugagc uaggaggcuu uacgcuggag    2040
gcgguagcug ccacccacuu ccgcaggccu ggaccucggc accauagggg uccggacucc    2100
auuuuaggau ucgcccauuc cugucucuuc cuacccaacc acucaauuaa ucuuuccuug    2160
ccugagacca guuggaagca cuggagugca gggaggagag ggaagggcca ggcugggcug    2220
ccagguucua gucuccugug cacugagggc cacacaaaca ccaugagaag gaccucggag    2280
gcugagaacu uaacugcuga agacacggac acuccugccc ugcuguguau agauggaaga    2340
uauuuauaua uuuuuugguu gucaauauua aauacagaca cuaaguuaua guauaucugg    2400
```

acaaacccac uuguaaauac accaacaaac uccuguaacu uuaccuaagc agauauaaau 2460
ggcugguuuu uag 2473

<210> SEQ ID NO 144
<211> LENGTH: 2125
<212> TYPE: RNA
<213> ORGANISM: Homo sapiens

<400> SEQUENCE: 144
gcuuucuaaa cuagcaagca ucgugugggu ccuucaggag ugggagugca gacagaccug 60
acagcguccg cuaagcgaca cugacuguac uuccacuccu gaaggaccca cacgaugcuu 120
ucuaaacuag caagucugca gaccauugcu gcucugcgcc gaggagucca caccucaguc 180
gccucugcca cgucuguugc cacaaagaag acagagcaag gcccaccauc cuccgaguac 240
auuuuugaac gggaaucuaa auauggugca cacaauuacc auccuuugcc uguagcccug 300
gagagaggaa aaggcauuua uauguggau guggaaggca ggcaguacuu cgauuuccug 360
agugcuuaug gugcugucag ccaaggacac ugccacccaa agaucauaga ugccaugaag 420
agucaggugg acaagcugac auuaacaucu cgggcuuucu auaacaaugu ccuuggugaa 480
uacgaggagu acaucaccaa gcuuuucaac uacaacaaag uucucccuau gaauacagga 540
guggaggcug gagagacugc auguaagcuc gcucgucguu ggggcuacac cgugaaaggc 600
auccagaaau acaaagcaaa gauuguuuuu gcugauggga acuuuugggg ucgaacacua 660
ucugcaaucu ccaguuccac agauccgacc aguuaugaug gcuuuggacc cuucaugcca 720
ggcuuugaaa ccaucccaua uaacgaucug cccgcacugg agcgugcucu ucaggaucca 780
aauguugcug ccuucauggu ggagcccauc cagggugaag caggcguuau cguuccggau 840
ccaggauacc ugacaggagu ucgggaacuc ugcaccaggc accaggaccu guuuauugcu 900
gaugaaauac agacaggauu ggccagaacu gguagauggc uggcugugga ucaugagaau 960
gucagaccug auaugguucu ucuugggaag gcccuuucug gcgguuuaua cccugugucu 1020
gcagugcugu gugacgauga gauaaugcug accauuaaac caggcgagca cggcuccaca 1080
uacggcggaa acccacuagg cugccgaauu gccauugcgg cucuugaggu uuuagaagag 1140
gagaaucuug cugagaaugc agacaagaug ggcgcuaucc ugaggaagga gcucaugaag 1200 cugccccucug acguugugac cucagugaga gggaaagggu ugcuaaaugc cauugucauc 1260
agagaaacca aagacuguga ugcuuggaag gugugccugc gacuucgaga uaacgggcuu 1320
cuggccaagc caacccacgg ugauaucauc aggcuugccc cuccccuugu gaucaaggag 1380
gaugagaucc gggaguccgu ggagaucauc aacaagacua ucuuguccuu cugagaguag 1440
gaacucuggg gagccaucuu cagacagggc ucuugugaaa cucugcuugc aguggccaga 1500
gccugucucc ugaaaggcau auauuucagu ugaugcauaa uagagugaca ccuaggaacc 1560
ugcagguggc ugcgugacag aaaagugaga gcgagaggcg aggcgucucu uuguugaggu 1620
uugacugugu gggaacuuuc uaaggagaaa cggacccauc ugcguacagc cugcagaugg 1680
aggccugcag ucauuuacgu gcgucuuuac aguuuccuug cugaugugaa ugguuuguau 1740
uuagaaguua uuucugagau acuacagaac aguuaaauca uuauaaucaa ugaauguuaa 1800
guugauugaa gguuaagcau auguaaaaua cuaguuuaaa guaaacuuuu cauuggccaa 1860
caccagaaug uauuauauag auucugagaa uucauuacua aauuacacuu ugcuugauug 1920
caauuuguaa aacauuuauu uucaguauuu cuuugaauaa agcuuaaugu uucuuuuuac 1980
gccaacagag uauuuuguau uuccauuuug guaauaauca guguauuauu ucauccugau 2040
gacuggcauu ucaucaccua uugagaucac ugggugugu ucaggccuuu uauucuaaau 2100
aaagcuauga ccaguuucug ucugu 2125

<210> SEQ ID NO 145
<211> LENGTH: 199
<212> TYPE: RNA
<213> ORGANISM: Homo sapiens

<400> SEQUENCE: 145
uuuuuuuuuu uucuuuuccg acgcccacaa gaggaauaag agauuuaaug auggaaagua 60
uggggaaauc acaguuuuca gacaugagua aucaaaaacu ugacauuuuu cuugauaucc 120
aaaucuagau gucuguauca aaccagaggu gauggccuug gggauggcag ugaagacugu 180
uaggaccauu agaucagau 199

<210> SEQ ID NO 146
<211> LENGTH: 412
<212> TYPE: RNA
<213> ORGANISM: Homo sapiens

<400> SEQUENCE: 146
uuuuuuuuuu uuuuuuuaca guuuuaaaac aauacacagc uuucucgggc ugaagcaauu 60
gcaagaacgu auugguauug guauauuaca gcuacauaca agguuuauga auagcaaugg 120
agaaaaauaa guuauuuaaa uauugacuuc auaaagagaa agugcaaugu uguuaguugu 180
cauaucacuu gcuugacagu uuguggguu ucuucccuau caauuuuaac aaucaagaua 240
acauggacuc aagacagaau uuuucgggaa ccucacucag uccucacaca gcagugacuu 300
gggaaucuac guguguucca ccgcaguugu gaaacacacu acuccguguc caggacucau 360
uucucagaga agaaucaauu cgaguuccau ccacaccugg ggucgggaca ca 412

<210> SEQ ID NO 147
<211> LENGTH: 2373
<212> TYPE: RNA
<213> ORGANISM: Homo sapiens

<400> SEQUENCE: 147
ccgggcucga auucucuaga cucgaguuua gagaauucga gcucucccag uuuuaaagca 60
aaauuuugga cugugaagca aggcacuggg caaacacaac auggccuccc cggcugacag 120
cuguauccag uuuacccggc acgcuaguga uguucuucuc aaccuuaauc gccuccggag 180
ucgggacauc uugacggacg uugucaucgu ggugagccgu gagcaguuua gagcccauaa 240
gacagugcuc auggccugca gcggccuguu cuacaguauc uucacugacc aguugaaaug 300
caaccuuagu guaaucaauc uagauccuga aaucagcccu gaggggguuu gcauccuccu 360
ggacuucaug uacacaucua ggcucaaccu gagggaaggc aauaucaugg cggugaugac 420
cacagccaug uaccugcaga uggagcaugu ugucgacaca ugcaggaagu ucaucaaggc 480
cagugaagca gaaauggccc cugcacuuaa accuccccgu gaagaguucc ugaacagccg 540
gaugcugaug ccccaugaca ucauggccua ccgagguucgu gaggucgugg agaacaauau 600
gccacugaga aauacucccg ggugugagag cagagcuuuu gcuccuccuc uguacagugg 660
ccugucaaca ccaccagccu cuuaucccau guacagccau cucccgcuca gcaccuuccu 720
cuucucugau gaggagcucc gagaugcccc ccgaaugccu guggccaacc cuuuucccaa 780
ggagcgugcc cuccccugcg acagugccag gcaagucccu aaugaguaua gcaggccagc 840
cauggaggug ucccccaguu ugugucacag caacaucuac ucgcccaagg aggcaguccc 900
agaggaggcu cggagugaca uacacuacag ugugccugag ggccccaagc cugcuguccc 960
uucugcucgg aaugcuccau acuuccccug ugacaaagcc agcaaagaag aagagagacc 1020
uucuucggag gaugagauug cccugcauuu cgagcccccc aaugcacccu ugaaccggaa 1080
gggucugguu aguccccaga guccccagaa auccgacugc cagcccaacu cacccacaga 1140
guccugcagc agcaagaacg ccugcauccu ucaggccucu ggcucuccgc cagccaagag 1200
ccccacugac ccgaaagccu gcaacuggaa gaaguauaag uucaucguuc ucaacagccu 1260
caaucagaau gccaaacccg agggcucuga gcaggcagag cugggucgcc ucucccccucg 1320 agccuacccu gcaccgcccg cuugccagcc gccuauggag cccgcgaacc uugaucucca 1380
guccccgacc aagcucagug ccaguggga ggacucuacc aucccccaag ccagccggcu 1440
caauaaucuc gugaacaggu cccugggagg cucccccga agcagcagug agagucacuc 1500
accacucuac augcaccccc caaagugcac auccugcggc ucucaguccc cacagcauac 1560
agagaugugc cuccauacug cugggcccac guucccggag gagaugggg aaacccaguc 1620 agaguauucg gauucuagcu gugagaaugg gaccuucuuc ugcaacgaau gugacugccg 1680
uuucucugag gaggccucgc ucaagaggca cacgcugcag acgcacagug acaaaccaua 1740
caaaugugau cgcugccagg ccuccuuccg cuacaagggc aaccucgcca gccacaagac 1800
uguccacacg ggugagaaac ccuaucgcug uaacauuugu ggagcgcagu ucaaucggcc 1860
agccaaccug aagacccaca cucgaauuca cucuggagaa aagcccuaca aaugugaaac 1920 cugugggcc agguuuguuc agguggccca ccuccgugcc cacgugcuca uccacacugg 1980
agagaagccg uaccccugug aaaucugugg cacucgcuuc cggcaccuuc agacucugaa 2040
gagccaucug cgcauccaca caggagagaa accuuaccau ugugagaagu guaaccugca 2100
cuuucgucac aaaagccaac ugcgacuuca uuugcgccag aagcacggcg ccaucaccaa 2160
caccaaggug caauaccgcg ugucggccgc ugaccugccu ccggagcucc ccaaagccug 2220
cugaaugaag cauggagugu uccucgcccu uuccucucca gccccuucuc agaaucuacc 2280
caaaggaugc uguaacacuu uauacaaagg ucaucccaug auguagugcc ucucucaucc 2340
acuagugcaa aucauaguug ggguggggu ggg 2373

<210> SEQ ID NO 148
<211> LENGTH: 989
<212> TYPE: RNA
<213> ORGANISM: Homo sapiens

<400> SEQUENCE: 148
ucgcgguccg acggaggagu gggcgcuggg aucucgcuga gcguccgccu ggccucgucu 60
cuuccucgcu cgucggagcu ucagcacggu ccgagauggc uggcgguaag gcuggaaagg 120
acuccggaaa ggccaagaca aaggcgguuu cccgcucgca gcgagccggc uugcaguucc 180
cugugggccg uauucaucga caccugaaau cuaggacaac cagccacgga cgugugggcg 240
cgaccgccgc uguguacagc gcagccaucc uggaguaccu caccgcagag guacuugagu 300
uggcaggaaa ugcgucaaaa gacuuaaagg uaaagcguau caccccucgu cacuugcagc 360
uugcuauacg uggagaugaa gaauuggauu cucugaucaa agcuaccauu gcugguggug 420
gugucauccc acacauccac aaaucgcuga ucgggaagaa aggacaacag aagacuguuu 480
aaggaugccu ggauuccuua uuaucucagg acucuaaaua uuccuaacag cuguccagug 540
uuggugauuc caguggacug uaucucugug aaaaacacaa uuuugccuuu uuguaauucu 600
auuugagcaa guuggaggcu uaauuagccu uccaaccaac caaauuucug cauucgaguc 660
uuaaccauau uuaaguguua cuguggcuuc aaagaagcua uugauucuga aguagugggu 720
uuugauugag uugacuguuu uuaaaaaacu guuuggauuu uaauugugau gcagaaguua 780
uaguaacaag cauuugguuu uguacagaca uuguuuccac ucugguggau aagcucaaua 840
aaggucauau cccaaacuag cuuuaaacuu gcuuaauaau cggguucuuac cuuagaucuc 900 acucagcaac aaguacauuc ucugcuuacu aauuaaacag ugcaucugua gucauaaaaa 960
aaaaaaaaaa aaaaaaaaaa aaaaaaaaa 989

<210> SEQ ID NO 149
<211> LENGTH: 6342
<212> TYPE: RNA
<213> ORGANISM: Homo sapiens
<220> FEATURE:
<221> NAME/KEY: misc_feature
<222> LOCATION: (439)..(538)
<223> OTHER INFORMATION: n is a, c, g, or u
<220> FEATURE:
<221> NAME/KEY: misc_feature
<222> LOCATION: (1133)..(1232)
<223> OTHER INFORMATION: n is a, c, g, or u
<220> FEATURE:
<221> NAME/KEY: misc_feature
<222> LOCATION: (1698)..(1797)
<223> OTHER INFORMATION: n is a, c, g, or u
<220> FEATURE:
<221> NAME/KEY: misc_feature
<222> LOCATION: (2105)..(2204)
<223> OTHER INFORMATION: n is a, c, g, or u
<220> FEATURE:
<221> NAME/KEY: misc_feature
<222> LOCATION: (2861)..(2960)
<223> OTHER INFORMATION: n is a, c, g, or u
<220> FEATURE:
<221> NAME/KEY: misc_feature
<222> LOCATION: (3546)..(3645)
<223> OTHER INFORMATION: n is a, c, g, or u
<220> FEATURE:
<221> NAME/KEY: misc_feature
<222> LOCATION: (4057)..(4156)
<223> OTHER INFORMATION: n is a, c, g, or u
<220> FEATURE:
<221> NAME/KEY: misc_feature
<222> LOCATION: (4736)..(4835)
<223> OTHER INFORMATION: n is a, c, g, or u
<220> FEATURE:
<221> NAME/KEY: misc_feature
<222> LOCATION: (5487)..(5586)
<223> OTHER INFORMATION: n is a, c, g, or u

<400> SEQUENCE: 149
caccaccgug cacgcagcuc cgggcccgug ggguguuggu ucuugcccuc guaacccccu 60
cuguccagcc accaugauaa gcgccagcag agccgcggcc gcgcgucucg ugggcaccgc 120
ugcgucccgg agccccgcag ccgcccgucc ccaggugaga agcugccaug ccuuccggug 180
ggggcuccag gcccggacuc gagugaggca ggccuugccu ucgggucaga cucuaggaaa 240
aauccggagc gaagggaugu aacggaccuu cugugggcau uguuggccuu cuugcagggc 300
uuuagcuucg aacugugcug agucacaauc cuuggcguuc cuaagucuuu accccgcuaa 360
uugagacguc uguccccccu cuaaccugug cgcuuugaau gugccuggac uuaggcagug 420
gacguaguuu acuggaaann nnnnnnnnnn nnnnnnnnnn nnnnnnnnnn nnnnnnnnnn 480
nnnnnnnnnn nnnnnnnnnn nnnnnnnnnn nnnnnnnnnn nnnnnnnnnn nnnnnnnnuu 540
uuacauacua aggacuaaag cuugcaugug uuccucagaa uaugaaaagc ccaaguucuu 600

-continued

```
guguaguuga uggcugaugc aacuuuuuuc cccccaggau ggcuggaaug gccuuagcca    660
ugaggcuuuu agauuuguuu caagaagaga uuaugcguaa guacaaccuc aguuucucug    720
agaaaaaaaa aaaacacuua uugaaccuca aagcuuggau ggguuggg ug cguuauacau    780
uuguacuugu aguuuauuca auaugccacu gguaacacca acauaaaaca caguucuucg    840
uauuggagac cacuguucag augaccaugg aauuucauuu cuuacagauc agaagcaauc    900
aagggugcag ugguugguau ugauuugggu acuacuaacu ccuguguggc uguuauggag    960
ggcaaacaag caaaggugag caugauugga aaccugaggu cacuuagaua cccagucugg   1020
cauuaaguac auaggaaugc ugagucggag cccagguuag uggugggcac uuuaauccua   1080
guaaaggcag agggaucucu gaguucagga ccagccuaga guacaaagug agnnnnnnnn   1140
nnnnnnnnnn nnnnnnnnnn nnnnnnnnnn nnnnnnnnnn nnnnnnnnnn nnnnnnnnnn   1200
nnnnnnnnnn nnnnnnnnnn nnnnnnnnnn nnacuuuaau cagugucuuu gggaauuuua   1260
gguccuggag aaugcugaag gugccagaac uaccccuucu gugguugccu uuacagcaga   1320
uggagaacga cuuguuggua ugccagcaaa acggcaagcu gucaccaauc caaacaauac   1380
cuucuaugcu acuaagcguc uuauuggacg acgauaugau gacccugaag uacagaaaga   1440
cacgugagua auaggaaaau caguccagaa gacuggugcu uugaucaaag uucuguggau   1500
accuugaguu cuguggauca ccuuggauca cuuuuucauu auuucugcuu gggaagaaau   1560
cacaccacca ucagaggcau auagguuuuu uuuuuguuau uucuuuguug uuguuguuuu   1620
ccuauuuauu uguuuguuug uuugggggg gguuucuuug uguauuuucc uggaacucau   1680
ucuguagacc aggcuggnnn nnnnnnnnnn nnnnnnnnnn nnnnnnnnnn nnnnnnnnnn   1740
nnnnnnnnnn nnnnnnnnnn nnnnnnnnnn nnnnnnnnnn nnnnnnnnnn nnnnnnnuca   1800
ugugauauau gaugaacuua gagugguuaa guuucacagg gauaguuuac uuacauaauc   1860
uuucugucuu uaaguaagaa uguuccuuuu aaaauugucc gugccuccaa uggugaugcu   1920
uggguugagg cucauggaaa acucuauucu ccaagucaga uuggagcauu uguguugaug   1980
aagaugaaag agacugcagg uaaguggauu uauuucacau uuaggaaaau uggaaugugc   2040
uguuuauuuc ucugcauuaa uacugauuaa cuucauauuc uguagauaau ggagucugaa   2100
gcuunnnnnn nnnnnnnnnn nnnnnnnnnn nnnnnnnnnn nnnnnnnnnn nnnnnnnnnn   2160
nnnnnnnnnn nnnnnnnnnn nnnnnnnnnn nnnnnnnnnn nnnngaauuc augcuccucc   2220
ugcugccucc ugggugcuaa guugcaaggu gauagcucag guacucacuc uagugucuuu   2280
cuuggggugc ucuuuuccaa ggccucucua cauauuaagc cacaaaggag ucuguugccc   2340
cucaagagga ugagaugugg aauauuaggc uacaguuuug uugccuuuuu uuuauuuucc   2400
uaacauggua ccacaauuga auuuuauucu uuguuuccca gaaaauuacu ugggccacac   2460
agcaaaaaau gcugugauca caguccccugc uuauuucaau gauucacagc gacagguaaa   2520
auuagaucuc uuguuugcug ggaguggagg ugggguaccu gaguuaaagg auggaaagau   2580
agauuuauuu cuacuuucuc uaggccacua aggaugcugg ccagauaucu gggcuaaaug   2640
ugcuucgagu gaucaaugag ccuacagcug cugcucuagc uuacggucug gacaaaucug   2700
aagauaaagu guaaguuggu cagaugacgu agcauuaccu gcauuuacag ggguugugug   2760
ugugugugug uguguguaau uuuacuacaa uuugugu ggg uccgugugu u gugguacauu   2820
uguacauuug uacauggcau ggauauggau gucaaagauu nnnnnnnnnn nnnnnnnnnn   2880
nnnnnnnnnn nnnnnnnnnn nnnnnnnnnn nnnnnnnnnn nnnnnnnnnn nnnnnnnnnn   2940
```

-continued

```
nnnnnnnnnn nnnnnnnnnn aaaccaguag uuggugugu u acuaauuuua cuuguuucug   3000
uaugacaugc uuauaugaua cguuaacagg caugccacuu agguugauaa cuacauucag   3060
uuauuaagua uuucaggaaa uaucauaguu aauaauuaaa cuuuuggucu uuuaauucgu   3120
uccuuuguuu uguuccuugg aacuuaacuu acuuauuuau uuuuuagcau ugcuguguau   3180
gauuuaggug guggaaccuu ugacauuucu auccuggaaa uucagaaagg aguguuugag   3240
gugaaaucua ccaaugggga cacuuucuua ggaggggaag acuuugacca agcuuuguug   3300
cggcacauug ucaaggaguu caagagagag guuaguuacc acugcuuagu caccacuggu   3360
uaaggugug gcguugggu u guugagaauu uuuguuuguu ugcauugcuu uuagcuuugu   3420
uaauagcuuu uuuauacuaa gguaacuaac uauacuucag auucaugggu aaacuaaacc   3480
aguuuaguua uauaaucuua gauugggaac aaaagaccaa gugacagugu uauaguaggg   3540
agaagnnnnn nnnnnnnnnn nnnnnnnnnn nnnnnnnnnn nnnnnnnnnn nnnnnnnnnn   3600
nnnnnnnnnn nnnnnnnnnn nnnnnnnnnn nnnnnnnnnn nnnnnacuac ucucucgcag   3660
ucuauauaug ucuccuaauc cuauuuauag acaggggguug auuugaccaa agacaacaug   3720
gcgcuucaga ggguucggga agcugcugag aaggcuaaau gugaacuuuc cucaucugug   3780
caggugaggg auggaaaaau cccaguacug agcauauuug aauaguguau ucuaauuuac   3840
cuaaugucag uguagcucuu uacaguuuuc uguuggcuga aaacuugggg caugagcaaa   3900
ggaacaacuu gaugaucagu ucuuuucauu ugaaugaaug aaguagauuu auggaugugu   3960
guaucuuuug ccugcaugug ugucuguacu acauuugugc uugguuucug uggcggccag   4020
aagaggguau cagaacugac augucagugu uggggannnn nnnnnnnnnn nnnnnnnnnn   4080
nnnnnnnnnn nnnnnnnnnn nnnnnnnnnn nnnnnnnnnn nnnnnnnnnn nnnnnnnnnn   4140
nnnnnnnnnn nnnnnncaca cugagucuaa auucugauca ugucuuucag ucguguuaug   4200
uuacuuugag ugaguaucaa agaucacguc ucccaucuga cguguggucc ugugcagacu   4260
gacaucaacu ugccauaccu uaccauggau gcuucuggac caaagcauuu gaauaugaag   4320
cugacucgag cucaguuuga aggcauuguc acagaucuaa ucaagagaac uauugcuccg   4380
ugucagaaag cuaugcagga ugcagaaguc agcaagagug acauaggaga agugauucug   4440
guuggugca ugacaaggau gcccaaggua uggacucaug guauuucucc uagaggaaaa   4500
aaauaacaau gcauucuuga ggcaaauggc uuguguugug uguggaaaca aaugugaucc   4560
auucuucuag uguucuuuaa agaguggug a gaccagacuc accaaaaagu gcuuuuaguc   4620
gccugugaug gcucauguag gaggauggcc uugaguucug gguaagaugc agcuacagaa   4680
uucuaccuug cacacacacu uaaacccagu cugguaaaga gaaguuguua agcuunnnnn   4740
nnnnnnnnnn nnnnnnnnnn nnnnnnnnnn nnnnnnnnnn nnnnnnnnnn nnnnnnnnnn   4800
nnnnnnnnnn nnnnnnnnnn nnnnnnnnnn nnnnncagau guaaaauuga uaauacuucu   4860
uccuaagauu gggcgauugu guagaauaug agaacuguau uuuauaaccc cuugucaugu   4920
gccuucuauu ucaaaugaua ucccucuggga agcuagauaa uuaaauucuu cucucauuua   4980
aguggacagu ggaugagaug cucugaaguu gucaaauaca aacaagucug cagucuugga   5040
uaugaaucuc ucugacuugc ugucuggcag gcguauucug uuuggcucca ucagucgccc   5100
ugggguguugg cuaacagguu cuuucucccu gaugcuuagg uucagcagac uguacaagau   5160
cuuuuuggca gagccccgag uaaagcuguu aauccugaug aggcuguagc caucggagcu   5220
gccauccagg gagguguguu ggcuggugac guuacagacg ugcugcuccu ggaugucacu   5280
ccccucucuc uggguauuga gacucuggga ggcgucuuua ccaaacuuau uaauaggaac   5340
```

accacuauuc caaccaaaaa gagccaggua agagccauuc uuuuuuccug ccuauuaaca 5400
gucccaaguu guacaagugc uguuuacaau cacuuuauga acucuuuaaa acuuuguuuc 5460
uaagacuaua cuaacuggac ugggugnnnn nnnnnnnnnn nnnnnnnnnn nnnnnnnnnn 5520
nnnnnnnnnn nnnnnnnnnn nnnnnnnnnn nnnnnnnnnn nnnnnnnnnn nnnnnnnnnn 5580
nnnnnnccua gguguuuucu acugcugcug auggacaaac ucaaguagag auuaaagugu 5640
gucaggggga acgagagaug gcuggagaca acaaacuucu aggacaguuc acuuugguaa 5700
guguuuuuga gucugaguau caugcuuuug gggucuauag cuugcaaagc uccaaacugc 5760
ugacauuaca ggcauauugu guuauuuuuu aaaaagaacg uuauguacau gaguuaugaa 5820
acccaugauu uuaguuuuuu accuaaagug cuuuguguuu ucagaauuug aaauuuucaa 5880
agccugggaa auguucagac ucagaagcaa ugcuaacuca gaaguuaguu uuauccugau 5940
uacucauuuu aaaaaacuua auagcuacug guucugguca gcauugcuac aguagagaag 6000
uuuauuugcu guaaauucug ggcacauaua accaucaugg uuauuaacuu cuugaagccc 6060
agugauuuca gaaagcacua aaacuaccac caucacuuaa aaucucaagg uuuugaacau 6120
ucagugaaga uacuuguuuu aggaaacaag ugguuaguug gccugauuug gaaaugagaa 6180
uacaugggcc uuucaaagga gcucacucug gauauuuauu uuagauugga auuccccag 6240 ccccucgugg agugccccag auugaaguua cauuugacau ugaugccaau gggauugugc 6300
acguuucugc caaagauaaa ggcacugguc gugagcaaca ga 6342

<210> SEQ ID NO 150
<211> LENGTH: 4145
<212> TYPE: RNA
<213> ORGANISM: Homo sapiens
<220> FEATURE:
<221> NAME/KEY: misc_feature
<222> LOCATION: (4045)..(4045)
<223> OTHER INFORMATION: n is a, c, g, or u

<400> SEQUENCE: 150 auaaaauucuu auuuugacac ucaccaaaau agucaccugg aaaacccgcu uuuugugaca 60
aaguacagaa ggcuugguca cauuuaaauc acugagaacu agagagaaau acuaucgcaa 120
acuguaauag acauuacauc cauaaaaguu uccccagucc uuauuguaau auugcacagu 180
gcaauugcua cauggcaaac uaguguagca uagaagucaa agcaaaaaca aaccaaagaa 240
aggagccaca agaguaaaac uguucaacag uuaauaguuc aaacuaagcc auugaaucua 300
ucauugggau cguuaaaaug aaucuuccua caccuugcag uguaugauuu aacuuuuaca 360
gaacacaagc caaguuuaaa aucagcagua gagauauuaa aaugaaaagg uuugcuaaua 420
gaguaacauu aaauacccug aaggaaaaaa aaccuaaaua ucaaaauaac ugauuaaaau 480
ucacuugcaa auuagcacac gaauaugcaa cuuggaaauc augcaguguu uuauuuaaga 540
aaacauaaaa caaaacuauu aaaauaguuu uagaggggu aaaauccagg uccucugcca 600
ggaugcuaaa auuagacuuc aggggaauuu ugaagucuuc aauuuugaaa ccuauuaaaa 660
agcccaugau uacaguuaau uaagagcagu gcacgcaaca gugacacgcc uuuagagagc 720
auuacugugu augaacaugu uggcugcuac cagccacagu caauuuaaca aggcugcuca 780
gucaugaacu uaauacagag agagcacgcc uaggcagcaa gcacagcuug cugggccacu 840
uuccucccug ucgugacaca aucaauccgu guacuuggug uaucugaagc gcacgcugca 900
ccgcggcacu gcccggcggg uuucugggcg gggagcgauc cccgcgucgc cccccgugaa 960

-continued

```
accgacagag ccuggacuuu caggagguac agcggcgguc ugaaggggau cugggaucuu   1020
gcagagggaa cuugcaucga aacuugggca guucuccgaa ccggagacua agcuuccccg   1080
agcagcgcac uuuggagacg uguccggucu acuccggacu cgcaucucau uccacucggc   1140
cauagccuug gcuucccggc gaccucagcg uggucacagg ggccccccug ugcccaggga   1200
aauguuucaa gcuuuucccg gagacuacga cuccggcucc cgguguagcu caucacccuc   1260
cgccgagucu caguaccugu cuucggugga cuccuucggc aguccaccca ccgccgccgc   1320
cucccaggag ugcgccgguc ucggggaaau gcccggcucc uucgugccaa cggucaccgc   1380
aaucacaacc agccaggauc uucaguggcu cgugcaaccc acccucaucu cuuccauggc   1440
ccagucccag gggcagccac uggccuccca gccuccagcu guugacccuu augacaugcc   1500
aggaaccagc uacucaaccc caggccugag ugccuacagc acuggcgggg caagcggaag   1560
ugguggggccu ucaaccagca caaccaccag uggaccugug ucugcccguc cagccagagc   1620
caggccuaga agaccccgag aagagacacu uaccccagaa gaagaagaaa agcgaagggu   1680
ucgcagagag cggaacaagc uggcugcagc uaagugcagg aaccgucgga gggagcugac   1740
agaucgacuu caggcggaaa cugaucagcu ugaagaggaa aaggcagagc uggagucgga   1800
gaucgccgag cugcaaaaag agaaggaacg ccuggaguuu guccuggugg cccacaaacc   1860
gggcugcaag auccccuacg aagaggggcc ggggccaggc ccgcuggccg aggugagaga   1920
uuugccaggg ucaacauccg cuaaggaaga cggcuucggc uggcugcugc cgccccccucc   1980
accacccccc cugcccuucc agagcagccg agacgcaccc cccaaccuga cggcuucucu   2040
cuuuacacac agugaaguuc aaguccucgg cgaccccuuc cccguuguua gcccuucgua   2100
cacuuccucg uuuguccuca ccugcccgga ggucuccgcg uucgccggcg cccaacgcac   2160
cagcggcagc gagcagccgu ccgacccgcu gaacucgccc ucccuucuug cucuguaaac   2220
ucuuuagaca aacaaaacaa acaaacccgc aaggaacaag gaggaggaag augaggagga   2280
gaggggagga agcaguccgg gggugugugu guggacccuu ugacucuucu gucugaccac   2340
cugccgccuc ugccaucgga caugacggaa ggaccuccuu uguguuuugu gcuccgucuc   2400
ugguuuucug ugccccggcg agaccggaga gcuggugacu uuggggacag ggggugggggc   2460
ggggauggac accccuccug cauaucuuug uccuguuacu ucaacccaac uucuggggau   2520
agauggcugg cugggugggu agggugggggu gcaacgccca ccuuuggcgu cuugcgugag   2580
gcuggagggg aaagggugcu gagugugggg ugcagggugg guugaggucg agcuggcaug   2640
caccuccaga gagacccaac gaggaaauga cagcaccguc cuguccuucu uuucccccac   2700
ccacccaucc acccucaagg gugcagggug accaagauag cucuguuuug cucccucggg   2760
ccuuagcuga uuaacuuaac auuuccaaga gguuacaacc uccuccugga cgaauugagc   2820
ccccgacuga gggaagucga ugcccccuuu gggagucugc uaaccccacu ucccgcugau   2880
uccaaaaugu gaaccccuau cugacugcuc agucuuuccc uccugggaaa acuggcucag   2940
guuggauuuu uuuccucguc ugcuacagag cccccuccca acucaggccc gcucccaccc   3000
cugugcagua uuaugcuaug ucccucucac ccucaccccc accccaggcg cccuuggccg   3060
uccucguugg gccuuacugg uuuugggcag cagggggcgc ugcgacgccc aucuugcugg   3120
agcgcuuuau acugugaaug agugguucgga uugcugggug cgccggaugg gauugacccc   3180
cagcccucca aaacuuuccc ugggccuccc cuucuuccac uugcuuccuc ccucccccuug   3240
acagggaguu agacucgaaa ggaugaccac gacgcauccc gguggccuuc uugcucaggc   3300
cccagacuuu uucucuuuaa guccuucgcc uuccccagcc uaggacgcca acuucucccc   3360
```

-continued acccugggag ccccgcaucc ucucacagag gucgaggcaa uuuucagaga aguuuucagg 3420
gcugaggcuu uggcuccccu auccucgaua uuugaauccc caaauauuuu uggacuagca 3480
uacuuaagag ggggcugagu ucccacuauc ccacuccauc caauuccuuc agucccaaag 3540
acgaguucug ucccuucccu ccagcuuuca ccucgugaga aucccacgag ucagauuucu 3600
auuuuuuaau auuggggaga ugggcccuac cgcccguccc ccgugcugca uggaacauuc 3660
cauacccugu ccugggcccu agguuccaaa ccuaauccca aaccccaccc ccagcuauuu 3720
aucccuuucc ugguucccaa aaagcacuua uaucuauuau guauaaauaa auauauuaua 3780
uaugagugug cgugugugug cgugugcgug cgugcgugcg ugcgugcgag cuuccuuguu 3840
uucaagugug cuguggaguu caaaaucgcu ucuggggauu ugagucagac uuucuggcug 3900
ucccuuuuug ucaccuuuuu guuguugucu cggcuccucu ggcuguugga gacagucccg 3960
gccucucccu uuauccuuuc ucaagucugu cucgcucaga ccacuuccaa caugucucca 4020
cucucaauga cucugaucuc cggunugucu guuaauucug gauuugucgg ggacaugcaa 4080
uuuuacuucu guaaguaagu gugacugggu gguagauuuu uuacaaucua uaucguugag 4140
aauuc 4145

<210> SEQ ID NO 151
<211> LENGTH: 1756
<212> TYPE: RNA
<213> ORGANISM: Homo sapiens

<400> SEQUENCE: 151
caccugauuc ccggaggccc gagcccuuag ucugggcggg guggcgcggg ccggaaggac 60
gccaucccgg ccugggccau ggaggcuccc gcaccguccc ucacggagga ggauuugacu 120
gaagugaaga aggacgcuuu agagaauuua cguguuuacc ugugugagaa aaucauagcu 180
gagagacauu uugaucaucu acgugcaaaa aaaauacuaa guagagaaga cacugaagaa 240
auuucuugcc gaacuucaag uagaaaacgg gcugggaagu uguuagacua cuuacaggag 300
aaccccaggg gccuggacac ccugguggaa uccauccgca gggagaaaac acagagcuuc 360
cugauucaga agauaacgga ugaggugcua aagcuucgga auauaaaacu ggagcaccuc 420
aaaggccuga agugcagcag cugugagccc uuugcagccg gagccaccaa caaccucucu 480
aggugcaauu ccgaugagag caaucucucu gagaaacaga gagcauccac ugucauguac 540
cacccggagg gagaguccag cacggcuccc uucuucucua uggcgucguc ccugaacuug 600
ccaguccugg aaguuggcag gacugaaaac agcagcuucu cuucagccac ucuuccucga 660
ccuggggacc cuggggcucc cccuuugccc ccagaccuuc gguuggaaga gggggggaagu 720 uguggaaacu caagugagau guuucucccc uuacggucac gggcucuuuc acgccaauga 780
uacaucaccg ccuaguuguu uuacuaguga ugcaaaaugc ugugaaggag gccaucuuuc 840
uauacaaacc acggugacag gucacucaca uucgaugcgu gccuuuaaaa ucaguguaca 900
cauucucugu aaauaggauu uguuagggua aagaagcgcu cuggggcggc gugguguaau 960 caugguggucc gugacuuuuc cauaaugucc uuucuuuuuu auuauuuuua gguguuugcg 1020
uauuuugaac uuuucauaag auuaauuuua ucggaauauu ucucaauuug agaaaacaac 1080
uuguggauug ggaauaaugu uuuuagcaca uuuaugcuac aaauuuucag ucugauuguu 1140
uuucccacug aucuggcagu auauuuuagc aguaagcugu ugugugucag gaaagcugga 1200
cacgggaaag cugccgacac acucagcagu gucccacucc uuaguucuga gaagccgucg 1260 ggucucugagg agacaccugg uggcacugag ccuggugacc ucagugggcc aaaauuuguu 1320
uuauacucac ccugccagcg ugagugucuu acuuucacag gccuuguguc cucagucuua 1380
ucuuaaagga uguuaucuug gcagggcauc acuuguaauu aauggaugau acuuguaauu 1440
gacuaaaguc cucgcucuga gccguuuguu cuggcuccga gagcgcugac augugaagca 1500
uggugagcag cgagggaacu gacaggaugu ggccguggcc aguguggcuu uaguguuugc 1560
aucaggcagc caccagcucc auccguguuc uuacugcuuu acaaaguuug acuaacuuua 1620
cacauuuuaa aaaugcugau ugucuucguu uaaauuauaa uuuuaccuau uucuugacau 1680
cuaacuccua uuuauuucua uuauuuaaaa auuaagaaau gaaaauuugc uauuaacaau 1740
aaaguuuuuu uaaugu 1756

<210> SEQ ID NO 152
<211> LENGTH: 1113
<212> TYPE: RNA
<213> ORGANISM: Homo sapiens

<400> SEQUENCE: 152
gggggggggg ggucagcgcc gacguccccu gccgccacca ugcccaaaag aaaggcugaa 60
ggggaugcua aaggagacaa aaccaaggug aaggacgagc cacagagaag aucugcaagg 120
uugucugcua aaccugcucc uccaaagcca gagcccaaac cuaaaaaggc cccugcgaag 180
aagggagaga agguacccaa ggggaagaag gggaaagcug acgccgggaa ggaugcgaau 240
aauccugcag aaaauggaga ugccaaaaca gaccaggcac agaaagcuga aggugcugga 300
gaugccaagu gaugugugug cauuuuugau aacuguguac uucuggugac uguacaguuu 360
gaaauacuau uuuuuaucaa guuuuauaaa aaugcagaau uucguuuuac uuuuuuuuuu 420
uuuuuaagcu auauuguuag cacacagaac acuucauuac uggguggggg aaggaucaug 480
ugucaguaac aaaaucucuc ccaagcugga uugaggacag aaaaccucuu ucccugauaa 540
uuuuggaagg cuccuguugg cucccaggag agagauccug gucuugaccu agguggccac 600
caaggcacaa caaugccuug uggucuggga aaacuauaaa uucacuuuua uauccucuuc 660
ccccuguacu aucaacauag acuuaauucc cuuaaaaacc agagaccugu uggaaccugg 720
cccccaaaau ugguuuccca guccauugag ugauggggac uuugcaguga cuucauugag 780
uguucucaaa agagcacugg uuccuuuuau aaaagauugu ggaucuucag auugauaauu 840
cugccuaaaa gucagggucg gcuugugaaa aguuguuaaa acaacauccu uaaugugaaa 900
ugucaacccu cacucuaagc uacuuccccc uuuucaaagc auugaaugaa gacuucauug 960
gguuuuauag uggcuuucug auuuugguag ucauaucaga agggaauuug gaaguucuug 1020
uauauuguug cauugucugc ccauguccug ccugaauacc augauuguuu augaaagaau 1080
cuuaauaaag cugguuacag uuaggcugga aaa 1113

<210> SEQ ID NO 153
<211> LENGTH: 321
<212> TYPE: RNA
<213> ORGANISM: Homo sapiens

<400> SEQUENCE: 153
uuuuuuuuuu uuuuuuugga aguccauaag uaguuuauug ucuucaagac uacagugugg 60
auuccucucc cagagaaggg ucuuucagag gcaggggacu gucacccagg ugcaggccgu 120
cuacuuguca uuuucauaca uggcuggauu cuuccuuuuc gacugcucaa acuccugguu 180
gccccaugug uagaucaggu agaccacuac aaacggcggc gccacgcgca ggaugcgcuc 240
gcgagugcgg cgcaacacgu uggggaugcc uuugcugaaa uagcuuggga aggcgcgcug 300
cucaaagggc gacaagcugu a 321

<210> SEQ ID NO 154
<211> LENGTH: 1720
<212> TYPE: RNA
<213> ORGANISM: Homo sapiens
<220> FEATURE:
<221> NAME/KEY: misc_feature
<222> LOCATION: (952)..(952)
<223> OTHER INFORMATION: n is a, c, g, or u

<400> SEQUENCE: 154
caugaagcca gagaugugga agaugugucu agacugcauc aaugaacuga uggauacguu 60
ggaugcacau uccaacaucu cugucggaga gaacauuuug gcagagagug agaacuuaca 120
caacuuugau caguucacuc cguguacgac gcugcauccu aacuuuggug gagcgaaugg 180
augaagaauu uaccaaaaua augcaaaaua cugauccuca cucccaagag uauguggagc 240
accugaagga ugaggcacaa gugugugcau cauugagcga gugcagcgcu accuggagga 300
gaaagguacc acugaggaga ucugccagau cuacuuaagg cgcauccugc acacguacua 360
caaguuugac uacaaggccc aucagcggca cguuacuccu ccugaaggau ccucaaaguc 420
ugagcaagac caggcagaaa augaggguga ggacucagcu gugcuaaugg aaagacugug 480
caaguacauc uaugccaagg accguacaga ccggauccgu accugugcca ucccucugcca 540 uaucuaccau caugcgcucc acucccgcug guaucaggcc cgugaccuca ugcucaugag 600
ccaccuacag gacaacauuc agcacgcaga cccgccggug cagauccugu auaaccguac 660
uauggugcaa cugggcaucu gugcuuuccg ccaaggccug acaaaggaug cacacaaugg 720
cacuucugga uauucaguca agugguggug ccaaggagcu ucuaggucag gguuugcugc 780
ugcgcgcuug caggagcgaa aucaggaaca ggaaaaggua gagcgacgcc ggcaggugcc 840
cuuucaccug cacaucaacc uggagcugcu ggagugugc uaucuggugu cagcuaugcu 900
ccuggagauc cccuacaugg cugcccauga gagcgaugcc cgccgacgca unaucagcaa 960
gcaguuccac caccaacugc gggugggcga gcggcacgcc cugcuagguc cucccgaguc 1020
aaugagggag cauguggucg cugccuccaa ggccaugaag augggcgacu ggaagaccug 1080
ccacaguuuc aucauuaaug aaaagaugaa ugggaaagug ugggaccuuu ucccugaggc 1140
ugacaaaguu cgcaccaugc uaguucggaa gauccaggaa gagucucuga ggaccuaccu 1200
uuuuaccuac agcagugucu augacucaau caguauggag acacuaucag auauguuuga 1260
gcuggaucua cccacuguuc acuccaucau cagcaagaug aucauuaacg aagaauugau 1320
ggcuucccug gaccagccga cacagacugu ggugaugcac cguacugagc ccucugccca 1380
gcaagaaacu uggcucugca agcuggcuga gaaaacuugg cacccuagug gagaauaaug 1440
gacggguguu ugaccaaaaa cagggaaccu augguggcua uuuccgagac cccaagggug 1500
gcuaccggaa aaauggaggc uaaaugcccc gugguggcua cccccagcaa cagucucaga 1560
caaccuccug aguuccccac uucagucacc cuguggacag accaucuaac cuuuuucucc 1620
uaacucaccc caaucauuaa agaucuuuug aggaauuaaa aaaaaagaaa gaaaaaaaaa 1680
aaaaaaaaaa aaaaaaaaaa aaaaaaaaaa aaaaaaaaaa 1720

<210> SEQ ID NO 155
<211> LENGTH: 453
<212> TYPE: RNA

<213> ORGANISM: Homo sapiens

<400> SEQUENCE: 155
uuauuaauua aaaaacaauu uauugaaaaa gaguagugcu uuguacaaau ucccauugca 60
gcccccagau aucaacugau cucuuuccag cuuugguagu aggguauaaa aauaucaaaa 120
cuagguaagu ucugauguaa gauuucuaug ggauuauuuu agaauauaua gauuugugua 180
guuuggcaag uaucauuucu augcauuuac auuacauauu aagcacagau ucuguggcaa 240
aacaucuuug caugauuacu uuacacacac aaauauagua aaacuuacau aguacaaauu 300
cacauaagac uccauucugu cuauaacuuc auccaugugg uuuuaccaug aauuauaauu 360
cuuaaccucu ccuauaacug ucagcuucca uuuaauuuug aaaguaucac uucacaaaga 420
gcacuucauu ugcuuuuaga guauacauag acu 453

<210> SEQ ID NO 156
<211> LENGTH: 361
<212> TYPE: RNA
<213> ORGANISM: Homo sapiens
<220> FEATURE:
<221> NAME/KEY: misc_feature
<222> LOCATION: (230)..(230)
<223> OTHER INFORMATION: n is a, c, g, or u

<400> SEQUENCE: 156
cggccgccaa gaaguauaac augcgagugg aagacuacga gccauacccc gaugauggca 60 uggggguaugg cgacuacccg augcuccccca accgaucaca gcaugagagg gauccguggu 120
aucaguggga ccacucagaa cucaggauga acugggguga accgauacac ugggaccuag 180
acauguacau caggaaucgu guggacacgu caccuacccc uguguccugn gaugucaugu 240
guaaacaucu cuucggcuuu guggcuuuca ugguuuucau guucugggua gggcacgugu 300
ucccuuccua ccagccugug gguccgaagc aguacccuua caaaaaucug uaccuggagc 360
g 361

<210> SEQ ID NO 157
<211> LENGTH: 452
<212> TYPE: RNA
<213> ORGANISM: Homo sapiens

<400> SEQUENCE: 157
uuuuuuuuuu uuuuuuugau gcaaaugucu uuauuuucca cuuaaacaag uuucccuuuu 60
gcacuggccu guggcacaaa acagauggcu ggguggugac auuaacuguc aaguuaguga 120
gaugcagaga uggugagaca cugcauuuga gugcauaaua cuuuuauucc agaggaacgc 180
caugcagccc aguuacaccu uuaggucaga aaggcugaug cgugaccagc cucuauugcc 240
ucccuuggua agaaggaccc acaagugcag aguccaacag augcuggcuc ugagcugaac 300
ucagggcauu ccaauuacca cuuucuucuu caccuacaca gggccugcuc agauguccuu 360
uuuacaacuc cauaagcccu uuggccaaag ucccugcagu guuuggggag gaccuuccca 420
cccuucacca gucagugucu gaucuggugg ag 452

<210> SEQ ID NO 158
<211> LENGTH: 392
<212> TYPE: RNA
<213> ORGANISM: Homo sapiens

<400> SEQUENCE: 158
uuuuuuuuuu uuuuuuuaau aucuguaaua guuuauuuca aagauuugac auuuacaagu 60
agaggcacca caugcuaucu gacaguaaaa uacugcaggg acugaaggcc aaggagagag 120
auccacagaa gacaggccug uagugcaggc auugcaucga ccuugcccac agugcuuugu 180
ucccaacuca ggacaguacu uuagugcuug cuucauuuac uggaaaaguu cacuggacau 240
aguuuccacu ucuuccccca cagcuuccag cucagcaaac uuaagcuacu acuccucgau 300
gcucucauag aggcucuuga uuugugucug gaagaacuug gcaagcucua cucguuuggc 360
uuucaguguc ggugucagaa guccguuuuc aa 392

<210> SEQ ID NO 159
<211> LENGTH: 217
<212> TYPE: RNA
<213> ORGANISM: Homo sapiens

<400> SEQUENCE: 159
uuuuuuuuuu uuuuuuucug agguauuaaa auaucuagac ugaauuuugc caaauguaag 60
agggagaaag uuccugaaga cucugacuac uugcuuauuu uugauugacc uucuaugcuu 120
augucauuac ugccucacaa cguguuugau guccuuuaau gauacaaagu gagccugugc 180
cuucauuuuc uugcccauuu ugguaccccu cgugccg 217

<210> SEQ ID NO 160
<211> LENGTH: 1515
<212> TYPE: RNA
<213> ORGANISM: Homo sapiens

<400> SEQUENCE: 160
gcgcccgaac gucuagcaga guaccugcug cuguaagcuu gucgucuggg cugcaccgcc 60
cgucuuaacc cauucucgac uuaacuacuc ucgucgaaca agcauggaag uacagaaaga 120
agcgcagcgc aucaugacuc ugucgguaug gaagauguac cacucucgca ugcagcgagg 180
uggcuugcga cuccaccgga gucugcagcu aucccucguu augcgcagcg cucgagagcu 240
cuaccucuca gccaagguag aagcccacca gcccgaguuc ccgccauccc gcagggcucu 300
ugacccucgc cugcacccgc cgcgggaagc cgaaguugca guggaaguag cguccccoga 360 agccgugcag ccuccggagc ccauggauac gcaagaggaa gugcugcgag uccaggagac 420
cccugcgcuc ugugacccgc cccccgcuag agucagccgc aagcgccgga gcagcagcga 480
uuugagcgac aguagugaug ccggacuggu accaagcaag aaggcccguc uagaagaggu 540 ggaggggggag gcgacgucgg agguucccga ucgccugcag cuuccuccgg cacaaagcga 600
aggugccuuc ccuaaccucg cccgcguccu ccaaaggcgc uucuccaguc uccugaacug 660
uggacccgcc gugcccccgc cgacgccccc cacgugcgag gccaagccag ccugccgccc 720
ggccgacaau augcucaacg ugcuggugcg agcuguggug gccuucugag agcucuggug 780
gcuucuuucg agcggcgcca ccggagcgga gaacgcacac ccgaggcgaa ggccggcggg 840
ggccgugaag aagagccgcg gcccgagcug ccgagaggcc agggcaagga cugaggagcg 900
aggggcgcgg gcgccuucuc ccagacgugc guccauaggu gcuauuaaag gacugucccu 960
uccuuggcuu ggagaaggga caccuagauc uugaaucuca gggucgaacu cucuaggggc 1020
caggcugccc uuucaaggcc guuucacuac cauucgcguu ucggccccua caagugggca 1080
cgcuugugca agcggucaga guugcgucau gggacagacg cgggugcuuc cuguugccuu 1140
gcgugggugu ggggccuggg aggaggccag ggguguggacc cgcccuaggg acugggaagu 1200
gacuugaguc accucgcccc cacaggcugc ugugggugag ccugaacuga accaaucaaa 1260
ucugcgcaga guugaagugg cuggagaccc cgggacuggu caaccuagau gaucgccugg 1320
cguggaccac cgcgggacgg gugggccgcu ggucguaguu gcugccguag acacagcuuc 1380
uucgggcagg aaagaaaauu uuuuuuuuac cagcguguuu aagaaagucu guuuacuuuu 1440
cccacggugg guuguuuaau uagcaacuac cuggaguuuu acaaugucag cuaggaaaau 1500
aaagaccauc ggugu 1515

<210> SEQ ID NO 161
<211> LENGTH: 801
<212> TYPE: RNA
<213> ORGANISM: Homo sapiens

<400> SEQUENCE: 161
cugagaggcc aggugggcgg cgaaaucaac guggagaugg augccgcucc cggugugac 60 cugagccgca uccugucaga gaugcgugau caguacgaga agauggcgga gaagaaccgc 120
aaggaugccg aagacugguu cuucagcaag accgaggagc ugaaccgcga gguggccacc 180
aacagcgagc uggugcagag cggcaagagc gagaucuccg agcucaggcg caccaugcag 240
gcccuggaga uugagcugca gucccagcuc agcaugaaag caucucugga gggcagccug 300
gcagagacag agaaccgcua cugcgugcag cugucucaga uccaggggcu gaucggcagu 360
guggaggagc agcuggcuca gcugcgcugc gagauggagc agcagaacca ggaguacaag 420
auccugcugg augugaagac aaggcuggag caggagaucg ccaccuaccg ccgucugcug 480
gagggagagg augcccaccu gacucaguac aagccaaaag aaccugugac cacccgccag 540
gugcgcacca uuguggaaga aguucaggau ggcaagguca ucucaucccg ggaacaggug 600
caccagacca cccguuaagg acucagcucc uuccgcccag uuccccgagg cugcagagag 660
gcagcuuccc ucuccgcucc ggcaucaccc uccugcuaca gccucucccc agcauuccua 720
ugcuugagac cauuaaagcu ugcugaccug aagugaacug uggccuuugu ucugaacacu 780
gaaauaaaug accaugguga c 801

<210> SEQ ID NO 162
<211> LENGTH: 447
<212> TYPE: RNA
<213> ORGANISM: Homo sapiens

<400> SEQUENCE: 162
uuuuuuuuuu uuuuuuuggu uccacuuaag uugcauguuu uauuucuccc aaucccagca 60
auagcacaga agcccaucau guccauccca gacugguuuc uaguaggcug agaugacagg 120
gagccucagu aacgcuaaug gcacagaggg cucccaaaug ccaggcacaa cugugccucc 180
acacugguga cugcccagag ugcccuggcc ccaguguguu ggcacucagu cugacuuuac 240
aacgcaaccu gcaccuuuga aagggacagu cugggagugg ggagugugag ggagugaagc 300
ucaaacugcc uccugucagc ucacccuuuc aacauuaaac agagaccaag agagaaacag 360
uuccaauauu ucacauauau uucuucuugu gcagucuaag ccgagaaugc cauguaaaug 420
ggucacugcg aaaugcagca auuuagu 447

<210> SEQ ID NO 163
<211> LENGTH: 475
<212> TYPE: RNA
<213> ORGANISM: Homo sapiens

<400> SEQUENCE: 163
gucucgggcg agauggcuuc aagguuacuu cgcggagugg gcgcuuuggc ggcgcaggcc 60
cugaggcgca cggcccgugg cgcggccgug acccgcucca uggcuucugg agguggugu c 120 cccacugaug aggagcaggc uacugggcug gagagggaga ucaugauagc agcacagaag 180
ggacuggacc cauacaauau gcuaccucca aaggcagcuu caggcaccaa ggaagacccu 240
aaucuagucc cguccaucag caacaagaga auagugggcu gcaucuguga agaggacaac 300
uguacuguca ucugguuuug gcugcacaaa ggcgagaguc agcgaugccc caacugugga 360
acccauuaca agcuggugcc ccaccaaaug gcccacugag ccccuguguu aucuuuucag 420
aauguaaaga aaaacuucuc ucuaauaaag acuagccauu gcaccugcuc cuccc 475

<210> SEQ ID NO 164
<211> LENGTH: 1897
<212> TYPE: RNA
<213> ORGANISM: Homo sapiens

<400> SEQUENCE: 164
gaauucggca cgagcagcga gacgccgcgc acggugcuuc cccaguggag ccaaucggcu 60
aacccgcgcu ccggcagagu ccuuggcgcu cgcccgccgg cgggacagac cacccgccuc 120
uggccgcucu cuggacccug gccgccccga gcgaagacug gagcaaaaug augcuucaac 180
auccaggcca ggucucugcc ucagaaguca gugcgaccgc cauugucccc ugccucucac 240 cuccugggu c acugguauuu gaggauuuug cuaaccugac acccuuuguc aaggaagagc 300
ugagauucgc cauccagaau aaacaccucu gccaucggau guccucugcg cuggagucag 360
uuaccgucaa caacagaccc cuggagaugu cagucaccaa gucugaggcg gccccugaag 420
aagaugagag gaaaaggagg cggcgagaaa gaaauaaaau ugcugcugcc aagugucgaa 480
acaagaaaaa ggagaagaca gagugccugc agaaagaguc agagaaacug gagaguguga 540
augcugagcu gaaggcccag auugaggagc ugaagaauga gaaacagcau uugauauaca 600
ugcucaaccu gcaccggccc accuguaucg uccgggcuca gaauggacgg acaccggaag 660
acgagaggaa ccucuuuauc caacagauaa aagaaggaac auugcagagc uaagcagagg 720
uggcacggag gcaauugggg aguucuuacu gaauccuccu uuuccacccc acacccugaa 780
gccauuggaa aacuggcuuc cugugcacuu cuagaauccc agcagccaag agccguuggg 840
gcaggagggc cugugguga c cuacugcauu gacccacucu gcccccgagu gaaccgugga 900
gcaggcagga gcauccuuug ucucaccaau uccaggauuu aggccuuauc aucccggcca 960
gucucagaug accuagcugg ccccaggcug ggguccuaug caaagcagga ucccacuaau 1020
gggauucagg cagaagug uc uaccuugaua gguggggugg gaccacaucc uccacugugg 1080
cugacaacgc ccuuccaagg gaauauggaa ugagaacauu cauuauugag guuguccaau 1140
ggccagggua ugcuuucuag aaaauaugcu guucugu ccc agaaugacug ugcauagggu 1200
auccguuuca gagccuggug uugugcuauu uagauguuug ucuugcacaa cauuggcaug 1260
auuuuuccgg gaguuucauc agaucugauu ucugagaguc uggggaucug ccauggugga 1320
aagugccccu caaaagcauu uguguggcca caugaacugg cuggcaccag gggagugaaa 1380
cuggcugaug accagcugag ccacuuugug ccaacagagg auggacgaca ccuuucccug 1440
uacccacugc agaggaagaa cccugggcac agcagcuuug uccuuggcua caaacuguua 1500
caacgucaca caaugaaggc acaaagucca acuuucaaag gguguaggac uccauacuca 1560
gugacagggc aggaagagcc aaagauaacc acagccacag ccuguggaga ccaggguugg 1620
aagccaggug cagggccagg caucugcauu gugggauguu aauggcacuu uugucuugua 1680

-continued

```
gcuauuuuga gauguggucc agagcauuuc agcugggaga ucucccucug gccaccagga   1740

cucuggcuac uguuaaaauc cugauguuuc uguggaaucc ucaguguuua aucccacuca   1800

auaguaucau uacaguuuuc uguaagagaa aauauuacuu auuuauccca guauuccuag   1860

ccugucaaca uaauaaauau cggaacaaaa ccuggua                            1897
```

<210> SEQ ID NO 165
<211> LENGTH: 2167
<212> TYPE: RNA
<213> ORGANISM: Homo sapiens

<400> SEQUENCE: 165

```
gcgcaccgcc ygyguygcgc gscagcgucg ucuaggugca ucgcgggccc ccgcagrwag     60

aaaaauaugg cucaggagac uaaccagacc ccagggccca ugcuguguag uacaggaugu    120

ggcuuuuaug ggaauccuag gacaaaugga auguguucug uuugcuacaa agaacaucuu    180

cagagacagc agaauagugg cagaaugagc ccaaugggga cagcuagugg uuccaacagu    240

ccuaccucag auucugcauc uguacagaga gcagaugcug guuuaaacaa cugugaaggu    300

gcugcuggca gcacaucuga aaaaucaaga aaugugccug uggcugccuu gccuguaacu    360

caacaaauga cagaaaugag cauuucaaga gaggacaaaa uaacuacccc gaaaacagag    420

gugucagagc caguugucac ucagcccagu ccaucaguuu cucagcccag uucuucucaa    480

agugaagaaa aagcuccuga guugcccaaa ccaaagaaga acagauguuu uaugugua ga    540

aagaaaguug gccuuacagg guuugacugc cgauguggaa auuuguuuug uggacuucac    600

cguuacucug acaagcacaa cuguccauau gauuacaaag cagaagcugc agcaaaaauc    660

agaaaagaaa auccaguugu uguggcugaa aaaauccaga gaauauaaaa uuacuacaug    720

ugaagagacu gaaacuuugu uuuuauuuua auauaucgua ggaaaacauu aaagagcaga    780

ugcauggcca uuuuccuuug auguucucca gaguuuugcu uuauacuugu cugucauaua    840

auugaucuuu uaggauguuu ggguguuugu uacaggcaga auuggauaga uacagcccua    900

caaauguaua ugcccucccc ucaguaaaau uggacaaaaa uaugcacaac aaauugaaau    960

acacauauac uaggaacaaa auuuaguucc acgugccaaa cuaaaggaau gaaaucucug   1020

cauguuugca gcauaucugc cuuuugggaa uguaaucaag guauaaucuu uggcuagugu   1080

uaugugccug uacuuaaaaa aaaaaaaaug guacaccaga aaaggacugg cagucuacua   1140

ccauagucaa acuucaccuu aauuucgaca ugacuuuugg aagcaggaag aaagcuacaa   1200

aacugguauu ugguaccaug ugugagccug guuaaauugg ucuucuaaaa gcugucaauu   1260

aggacauucu gcgaaaggua acaucacaac ugguucuaag ucaaaccauc aagucaacag   1320

cagggugccu gagauaaucu uggaagcuua uugugcuggc cugcaccaga agauaucugc   1380

auucucauua cuaaaauugu agcacagaac ugcacuagga uuuguuuaca aggagaaauu   1440

aaacucuguu ugguuuucac auauagcagc ucuguuaaau aacaugcauc ugaauuuuaa   1500

guugcaaagg uaucugaaca guuaauuuuu caugugcauc uuuuguugaa uguuuugguu   1560

caagaaagaa uguuuaaagc uuuuuaaaga cuucaguucu uaauguaacu guacccuucu   1620

gcauggaaaa ucauaaccaa cauggcugca guagacuucu uuaguggua u ccagcaccac   1680

uugcagaggg cugcuuuauc auauuguacu ugggguguagg acucuagugu ucuugggugu   1740

auugcauggg cugcauuauc uacagcauug uacaauaaca acuagaaaag gcgguauacu   1800

ucacugaugc uugucuggua auaucacuuc uguguuaaaa uggaagguuu uuugugaugu   1860

augaaacuug uguuuuuuau auauaaauga guauaguuag auuaguguug ugguaaugcc   1920
```

uguuuucauc uguaaauagu uaaguaugua cacaacaagg cacuacuucu gauuuuugca 1980
guguucaguc cuaguuuuuc uuuauuaaaa cauugaguuu ugcuucaauu uuauguaccu 2040
uaguucuaag uuagauuugc agauguguac agauaguuca uauuuaugua uugcacauaa 2100
ucaugcuauu cagcauugau gcuauauugu auuauguaaa uaauaaaagc aguguacaga 2160
gggaaaa 2167

<210> SEQ ID NO 166
<211> LENGTH: 897
<212> TYPE: RNA
<213> ORGANISM: Homo sapiens

<400> SEQUENCE: 166
augacagaug ccgcuguguc cuucgccaag gacuucuugg ccgguggagu ggccgcagcc 60
aucuccaaga cagcgguagc acccaucgag agggucaagc ugcugcugca ggugcagcau 120
gccagcaagc aaaucacggc agauaagcaa uacaagggca ucauagacug cgugguucgu 180
auccccaagg aacagggagu ccuguccuuc uggcguggga accuggccaa ugucaucaga 240
uacuucccca cccaggcucu caacuuugcc uucaaagaua aauacaagca gaucuuucug 300
gguggugugg acaagaggac ccaguucugg cgcuacuuug cagggaaccu ggcaucaggu 360
ggugccgcug ggcuacauc cuugugcuuu guguacccuc uugauuuugc ccguacccgu 420
cuagcagcug augugggcaa agcuggagcu gaaagggaau ucaaaggccu uggugacugc 480
cugguuaaga ucuacaaauc ugaugggauu aagggccugu accaaggcuu uaauguguca 540
guacagggca uuaucaucua ccgagcugcc uacuuuggua ucuaugacac ugcaaaggga 600
augcucccag aucccaagaa uacucacauc uucaucagcu ggaugauugc acagucuguc 660
acugcugucg cuggccugac uuccuauccu uuugacacgg uucgccgucg uaugaugaug 720
cagucuggac gcaaaggaac ugauaucaug uacacaggca cgcuugacug cuggcggaag 780
aucgcgcgcg augaagggag caaggcuuuu uucaagggcg cauggcucaa cguucucaga 840
ggcaugggug gcgccuuugu gcuugucuug uaugaugaga ucaagaaaua cacauaa 897

<210> SEQ ID NO 167
<211> LENGTH: 3873
<212> TYPE: RNA
<213> ORGANISM: Homo sapiens

<400> SEQUENCE: 167
cguagaaguu gucucugucg gcgggcgggc gggcaggauu ggggcaccga gaccggcgug 60
cggacagcag ggaucgcggg gagcgagggg ugcggcaugg agcuccgggc agucgguuuc 120
ugccuggcgc ugcugugggg uugcgcgcug gcggccgcgg cggcacaggg aaaggaaguu 180
guuuuguugg acuucgcagc aaugaaggga gagcucggcu ggcucacgca ccccuauggc 240 aaagggu ggg accugaugca gaacaucaug gacgacaugc cuaucuacau guacucggug 300
ugcaacgugg uauccggcga ccaggacaac uggcuccgca ccaacugggu guaccgggag 360
gaggccgagc gcaucuuuau ugagcucaag uucacggugc gagacuguaa cagcuucccg 420
gguggcgccc augccugcaa agagaccuuc aaccucuacu augcagaguc agauguggac 480
uauggcacca acuuccagaa gcgccaguuc accaagauug acaccaucgc cccugacgag 540
aucacgguca gcagugacuu cgaggcucgc aacgucaagc ugaacguaga ggagcgcaug 600
guggggcccc uuacccggaa gggcuucuac cuggccuucc aggacaucgg cgccugcgug 660

-continued

```
cggcugcucu ccguucgcgu cuacuacaag aagugucccg agaugcugca gagcuuggcc    720
ugcuuccccg agaccauugc ugucgcuguu uccgauacac aaccccuggc cacgguggcc    780
gguaccugcg uggaccaugc cguggugccu uaugggggcg agggggcucu caugcacugc    840
acgguggaug gcgaguggcu ggugccaucc gagugccugu gccaggaagg cuacgagaag    900
gucgaggaug ccugccgagc cuguucucca ggauucuuca agucugaggc aucugagagc    960
ccuucccugg aguguccaga gcauacccug ccauccacag agggugccac cuccugccag   1020
ugugaagaag gcuauuucag ggcaccugag gacccacugu ccaugucuug cacacgucca   1080
cccucugccc cuaacuaccu cacggcaugc augggugcca aaguagaacu gcguuggaca   1140
gcucccaagg acacuggugg ccgccaggac auugucuaca gugucacuug ugaacagugc   1200
ugcgcagagu cuggcgagug ugggcccugu gaggccacgg ugcgcuauuc agaaccuccu   1260
cacgcccuga cccgcacgag ugugacaguc agugaccugg agccccacau gaacuauacc   1320
uucgcugucg aagcacgcaa uggcgucuca ggccugguga cuagccgaag cuuccggacu   1380
gccagcguca guauuaacca aacagagccc cccaaaguga ggcuggagga ccgaagcacc   1440
accucccuga gugucaccag gagcaucccg gugucacagc agagccgugu guggaaguac   1500
gaagucaccu accgcaagaa gggggaugcc aacagcuaua auggccgccg cacggaaggc   1560
uucuccguga cccuggauga ccuugcuccg gauaccacgu accuggugca ggugcaggca   1620
uggacgcagg agggccaagg agccggcagc aaagugcacg aguuccagac gcuguccacg   1680
gaaggaucuc gcaacauggc ggugaucggc gguguggcug uagguguugu uuugcuucug   1740
guacuggcag gaguuggccu cuucauccau cgaaggagga ggaaccugcg ggcucgccag   1800
uccucugagg auguccguuu uuccaaguca gaacaacuaa agccccugaa gaccuaugug   1860
gauccucaca cuuacgaaga ccccaaccag gcuguacuca aguuuaccac cgagauccac   1920
ccauccugug uggcaaggca gaaggucauu ggagcaggag aguuuggaga ggucuauaaa   1980
gggacgcuga aggcauccuc ggggaagaag gagauaccgg uggccaucaa gacacugaaa   2040
gcgggcuaca cugagaagca gcggguggac uuccugagcg aggccagcau caugggccag   2100
uuuagccacc acaauaucau ccgccuggag gcgguggucu cuaaauacaa acccaugaug   2160
auuaucacag aguacaugga gaauggagcg cuagacaagu uccuuaggga gaaggauggu   2220
gaguucagcg uacuucaguu gguggcaug cugaggggua ucgcauccgg caugaaguac   2280
cuggccaaca ugaacuacgu gcacagagac cuggcugccc gcaacauccu cgucaacagc   2340
aaccuggugu gcaaggugu cgauuuuggc cugucgcgug ugcuggagga ugaccccgag   2400
gccaccuaca ccacaagugg cggcaagauc ccuauucgau ggacagcccc agaggccauu   2460
uccuaccgca aguucaccuc agccagcgau guguggagcu acggcauugu cauguggaa   2520
gugaugacuu auggcgaacg gcccuuacug gaacugucaa accacgaggu caugaaagcc   2580
aucaacgacg gcuuccggcu ccccacgccc auggacugcc cuucagccau uuaccagcuc   2640
augaugcagu gcuggcagca agagcgcucc cgccggccca aguuugccga caucguuagc   2700
auccuggaca agcucauccg acgccccgac ucccucaaga cgcuggcuga cuucgauccc   2760
cgagugucca uccggcugcc cagcaccagc ggcucggagg gaguccccuu ccguacggug   2820
uccgaguggc uggagagcau caagaucgaa caguacacgg aacacuucau gguggcuggc   2880
uacacggcca ucgagaaggu gguacagaug uccaacgaag acaucaaaag gaucggagug   2940
cgucuuccug gccaccagaa gcgcauugcc uacagccugc ugggacucaa ggaccagguc   3000
aacacagugg ggauuccuau cugaguccau uggggcuguc acacaauacu ugaagagcca   3060
```

-continued caguggucuc ccugccgauc uggugcuggc ccacuggaac uuuauuuauu ucuguuuccu 3120
cgucuaugcc ucccuaggac ucugcagggg cuuuuugaau gacaccugcc ugagccuggg 3180
aaacuuggau ugcuggucag ggcucucuuu ccccugaaaa ggacccagcu aagaacuuag 3240
caguuugcca uggccuuccc agcauccccu gaggcuaaag uuccaccaag agucgauauc 3300
gacgagggac auuuccaaac ggaccucccc aucuucauuu ggccuccuga gaagccacuc 3360
uggagcugag gcuaagcacu aagcccagga ccauaugacu agcacuguac cgcccgcccc 3420
uaguuagagg guagguuuug gacuuggcug gguuguggucc acaagcaauc ucccagugcc 3480
uuuuacagac cccagucugc ccuccccgucg agggccagcu ucuugcuuuc cuagggcccu 3540
cucaggaugc uuggcugugc ugagguuuuu auuaaaauaua uauuuuauac uugcggaaag 3600
aaugagugug uggcagggac uugccagggc uggagacaga ggauccccug caacaagaca 3660
uucccgggcu gggggcuggc ggaccugcag gagacuuucc gccaccaccc cgucuccagc 3720
cccuuuggac aaaugucgcu gucaguguua cagauuucuu uuauuggguu guuuuuuugu 3780
uguauuuuuu ugaaccuuaa cuuauuauuu uuuuuauauu uauuguuaga aaaugacuua 3840
uuucugcucu ggaauaaagu ugcagauggu uca 3873

<210> SEQ ID NO 168
<211> LENGTH: 1591
<212> TYPE: RNA
<213> ORGANISM: Homo sapiens

<400> SEQUENCE: 168
ccaaaaaccu uaauuuucuu ucuuguucgg uaccuacauu ggaaccacca aaaacaauua 60
uuucaguaaa ccguagccau gagggaaauc gugcacaucc aggccggaca guguggcaac 120
cagaucggug cuaaguucug ggaggucaua agcgaugaac auggcaucga ccccaccggu 180
accuaccacg gugacagcga ccugcagcug gaccgaaucu cuguguacua uaaugaagcc 240
acagguggca aguauguccc ucgagcuauc uugguggauc uagaaccugg gacuauggac 300
uccguucgcu cagguccuuu uggccagauc uucagaccag acaacuucgu uuucggucag 360
ucuggggcag gcaacaacug ggcuaaaggc cacuacacag agggagcuga guugguugac 420
ucugucuugg auguggugcg gaaggaggcg gagagcugug auugccugca aggcuuucag 480
cugacccacu cacugggugg aggcacuggc ucuggcaugg gcacccugcu caucagcaag 540
auccgggaag aauauccuga ccguaucaug aauaccuuca guguggugcc cucgcccaaa 600
gucucugaua ccguggucga gcccuacaau gccacccugu cuguccauca guugguugag 660
aacacggaug agaccuacug caucgacaac gaggcccucu acgacaucug cuuccguacc 720
cucaagcuca ccacgccaac cuacggagac cugaaccauc ucgucucggc caccaugagc 780
ggcgucacca ccugccuccg uuucccgggc cagcuuaaug cugaccuucg aaagcuggcu 840
gucaacaugg ugccauuccc acgucuccac uucuucaugc cuggcuuugc cccucucacc 900
agccguggaa gccagcagua ccgggcccuc acugugccug aacuuaccca gcaggucuuc 960
gaugccaaga acaugauggc cgccugcgac ccgcgccacg gccgguaccu cacaguugcc 1020
gccgucuucc guggacggau guccaugaag gagguggaug agcagaugcu caacgugcag 1080
aacaagaaua gcagcuacuu cguggaaugg aucccccaaca augucaagac agcugucugu 1140
gacaucccac cgcguggccu caagauggca gucaccuuca uuggaaacag cacagccauc 1200
caggagcugu ucaagcgcau cucugagcag uuuacggcua uguuccgccg gaaggcuuuc 1260

-continued cuccacuggu acacggguga gggcauggac gagauggagu ucaccgaggc ugagagcaac 1320
augaacgacc uggugucuga guaccagcag uaccaggaug ccaccgcgga agaggaagag 1380
gauuucggag aggaggcaga agaggaggcc uaacggcaga gagcccugca ucagcucagg 1440
cugcuuagau cccucagccu uucuccaacu gcccuuuguc cuccaguuuc uuucugcugc 1500
cucugucuug uauuuguuuu gcuucuguuu ucucauuggg gguaaauggu gccuggcaca 1560
uggcaggcac ucaauaaaua uuuguuugug g 1591

<210> SEQ ID NO 169
<211> LENGTH: 1992
<212> TYPE: RNA
<213> ORGANISM: Homo sapiens

<400> SEQUENCE: 169
ggcagacaaa agaggccggc agugcagcuc gcgggacgca uggccgggcg cggaggacgg 60
gugcugcugg cgcugugugc cgcgcuggug gccggcgggu ggcugcugac gcgugaagcc 120
caggagcccg gggcgccagc ggcuggcaug aggcgccgcc ggcggcucca gcaagaggac 180
ggcaucuccu ucgaguacca ccgcuaucca gagcugcgcg aggcgcuggu gucgguaugg 240
cugcagugca ccgccaucag cagaaucuac acagugggcg ccagcuucga gggccgggag 300
cuccugguca ucgagcuguc ugacaacccc ggggguccaug agccggguga accugaauuu 360
aaauacaucg ggaacaugca uggcaaugag gcgguuggac gggaauugcu cauuuucuug 420
gcccaguacc uguguaacga guaccagaaa ggcaaugaga caauugucaa ccugauccac 480
agcacccgaa uucauaucau gcccuccuug aaccccgacg gcuuugagaa agccgcaugg 540
cagcccgggc agcugaagga cugguuugug ggccgcagca acgcccaggg aauagaucug 600
aaccguaacu ucccagaccu ggacaggauc guauauguua augagaaaga aggcgguccc 660
aacaaccacc ugcugaagaa ucugaagaaa auuguggacc aaaauucaaa gcuugccccc 720
gagaccaagg cugucauuca cuggaucaug gacauuccau uugugcuuuc ugccaaucug 780
cacggaggag accuugugg c uaauuaccca uaugaugaga cacggagcgg uacugcucac 840
gaauacaguu ccugcccuga ugacgcaauu uuccaaagcu uggcucgcgc guacucuucu 900
uucaacccag ucaugucuga ccccaaucga ccucccugcu gcaagaauga cgaugacagc 960
agcuuugaug auggaacgac caaugguggu gcaugguaca gcguccccgg uggaaugcaa 1020
gacuucaauu accugagcag cagcaacugc uuugagauca cuguggagcu uacgugugag 1080
aaguucccac cugaagagac ucucaaaagc uacugggaag auaacaaaaa cucccucauc 1140
aacuaccugg agcagauaca ccgaggugu u aaaggguuug uccgugaccu ucaggguaac 1200
ccgaaugcca acgcaaccau cucuguggau gggauagacc augaugucac cucggcuaag 1260 gaugggggauu acuggcgauu gcuugcuccu ggaaacuaua aacuuacagc cuccgauccu 1320
ggcuaccugg caaucacaaa gaaagugggca guuccuuuua gcccugcugu uggggguggac 1380 uuugagcuug agucuuucuc ugaaaggaag gaggaggaga aggaagaauu gauggagugg 1440
uggaaaauga ugucagaaac uuugaauuuu uaagaaaggc uucuaacuaa uugcuuucau 1500
cuaucuauag acuguaguaa gaugcaaugu ggcucuuuuc uuuuagguug ugugcaguug 1560
auauuuaaca uugauuuauu uuugaucauu aaguaauagu uacuaaucac guaaauacac 1620
ccggacagaa auauaaugcu ggacaucuuc auucuacauc aacauucgcu uaaaucauuc 1680
gaagccucuu uuaacguaau gggugacaau gucacuugac agaugcauga gagucacgau 1740
auagcugacu gugacccugc acugcaauca cauaguucca uauaaguugu ccuuagucuc 1800
uugugcugau ucacuguaua agcaugaucc ugguaaugca cuuuggaugg gaagaaaaug 1860
uacgugcuuu ucagaggggc ucugaacaga augaaaaccu aguucuugcg uguacuuuga 1920
agaauggaau uguauuaguc agcuguuaau gccacuucag aaguuugggg uuuugucuug 1980
auuguagauu gg 1992

<210> SEQ ID NO 170
<211> LENGTH: 1828
<212> TYPE: RNA
<213> ORGANISM: Homo sapiens

<400> SEQUENCE: 170
gccacggacg ccucucugaa cggggaucca ggcaggauua gagcugccuc acugacuaca 60
ggccgugucg ugucaccguu ucugcaggca ccaugagcca ggacaccgaa guggacauga 120
aagaugugga gcugaacgag cuagaaccgg agaagcagcc caugaaugca gcggacgggg 180
cggcggccgg ggagaagaac ggucugguga agaucaaggu ggcggaggac gagacggagg 240
ccggggucaa guucaccggc uuauccaagg aggagcuacu gaagguagcg ggcagcccug 300
gcugggugcg cacccgcugg gcgcugcugc ugcucuucug gcucgguugg cugggcaugc 360
uggcgggcgc cgugguuauc aucguucggg cgccgcgcug ccgugagcug ccuguacaga 420
gguggugcca caagggcgcc cucuaccgca ucggcgaccu ucaggccuuu guaggccggg 480
augcgggagg cauagcuggu cugaagagcc aucuggagua cuugagcacc cugaagguga 540
agggccuggu guuaggccca auucacaaga accagaagga ugaaaucaau gaaaccgacc 600
ugaaacagau uaaucccacu uugggcuccc aggaagauuu uaaagaccuu cuacaaagug 660
ccaagaaaaa gagcauucac aucauuuugg accucacucc caacuaccag ggccagaaug 720
cgugguuccu cccugcucag gcugacauug uagccaccaa aaugaaggaa gcucugaguu 780
cuuggcugca ggacggugug gaugguuucc aauuccggga ugugggaaag cugaugaaug 840
cacccuugua cuuggcugag uggcagaaua ucaccaagaa cuuaagugag gacaggcuuu 900
ugauugcagg gacugagucc ucugaccugc agcaaauugu caacauacuu gaauccacca 960
gcgaccugcu guugaccagc uccuaccugu caaauuccac uuucacuggg gagcguacug 1020
aaucccuagu cacuagguuu uugaaugcca cuggcagcca auggugcagc uggagugugu 1080
cgcaagcagg acuccucgca gacuuuauac cggaccaucu ucuccgacuc uaccagcugc 1140
ugcucuucac ucugccaggg acuccuguuu uuagcuacgg ggaugagcuu ggccuucagg 1200
gugcccuucc uggacagccu gcgaaggccc cacucaugcc guggaaugag uccagcaucu 1260
uucacauccc aagaccugua agccucaaca ugacagugaa gggccagaau gaagacccug 1320
gcucccuccu uacccaguuc cggcggcuga gugaccuucg ggguaaggag cgcucucugu 1380
ugcacgguga cuuccaugca cugucuuccu caccugaccu cuucuccuac auacgacacu 1440
gggaccagaa ugagcguuac cugguggugc ucaacuuccg agauucgggc cggucagcca 1500
ggcuaggggc cuccaaccuc ccugcuggca uaagccugcc agccagcgcu aaacuuuugc 1560
uuaguaccga cagugcccgg caaagccgug aggaggacac cucccugaag cuggaaaacc 1620
ugagccugaa uccuuaugag ggcuugcugu uacaguuccc cuuuguggcc ugauccuucc 1680
uaugcagaac cuaccacccu ccuuuguucu ccccaggccu uuuggauucu agucuuccuc 1740
uccuuguuuu uaaacuuuug cagauuacau acgaauucuu auacugggug uuuuugucuu 1800
caaauaaaaa caucaccccu gccucaug 1828

-continued

<210> SEQ ID NO 171
<211> LENGTH: 2610
<212> TYPE: RNA
<213> ORGANISM: Homo sapiens
<220> FEATURE:
<221> NAME/KEY: misc_feature
<222> LOCATION: (2)..(2)
<223> OTHER INFORMATION: n is a, c, g, or u
<220> FEATURE:
<221> NAME/KEY: misc_feature
<222> LOCATION: (11)..(11)
<223> OTHER INFORMATION: n is a, c, g, or u
<220> FEATURE:
<221> NAME/KEY: misc_feature
<222> LOCATION: (26)..(26)
<223> OTHER INFORMATION: n is a, c, g, or u
<220> FEATURE:
<221> NAME/KEY: misc_feature
<222> LOCATION: (41)..(41)
<223> OTHER INFORMATION: n is a, c, g, or u
<220> FEATURE:
<221> NAME/KEY: misc_feature
<222> LOCATION: (45)..(45)
<223> OTHER INFORMATION: n is a, c, g, or u
<220> FEATURE:
<221> NAME/KEY: misc_feature
<222> LOCATION: (56)..(56)
<223> OTHER INFORMATION: n is a, c, g, or u
<220> FEATURE:
<221> NAME/KEY: misc_feature
<222> LOCATION: (70)..(70)
<223> OTHER INFORMATION: n is a, c, g, or u
<220> FEATURE:
<221> NAME/KEY: misc_feature
<222> LOCATION: (2262)..(2262)
<223> OTHER INFORMATION: n is a, c, g, or u
<220> FEATURE:
<221> NAME/KEY: misc_feature
<222> LOCATION: (2276)..(2276)
<223> OTHER INFORMATION: n is a, c, g, or u
<220> FEATURE:
<221> NAME/KEY: misc_feature
<222> LOCATION: (2288)..(2288)
<223> OTHER INFORMATION: n is a, c, g, or u
<220> FEATURE:
<221> NAME/KEY: misc_feature
<222> LOCATION: (2290)..(2290)
<223> OTHER INFORMATION: n is a, c, g, or u
<220> FEATURE:
<221> NAME/KEY: misc_feature
<222> LOCATION: (2298)..(2298)
<223> OTHER INFORMATION: n is a, c, g, or u
<220> FEATURE:
<221> NAME/KEY: misc_feature
<222> LOCATION: (2309)..(2309)
<223> OTHER INFORMATION: n is a, c, g, or u
<220> FEATURE:
<221> NAME/KEY: misc_feature
<222> LOCATION: (2311)..(2311)
<223> OTHER INFORMATION: n is a, c, g, or u
<220> FEATURE:
<221> NAME/KEY: misc_feature
<222> LOCATION: (2324)..(2324)
<223> OTHER INFORMATION: n is a, c, g, or u
<220> FEATURE:
<221> NAME/KEY: misc_feature
<222> LOCATION: (2333)..(2333)
<223> OTHER INFORMATION: n is a, c, g, or u
<220> FEATURE:
<221> NAME/KEY: misc_feature
<222> LOCATION: (2335)..(2335)
<223> OTHER INFORMATION: n is a, c, g, or u
<220> FEATURE:
<221> NAME/KEY: misc_feature
<222> LOCATION: (2412)..(2412)
<223> OTHER INFORMATION: n is a, c, g, or u
<220> FEATURE:
<221> NAME/KEY: misc_feature
<222> LOCATION: (2418)..(2418)
<223> OTHER INFORMATION: n is a, c, g, or u
<220> FEATURE:
<221> NAME/KEY: misc_feature
<222> LOCATION: (2435)..(2435)
<223> OTHER INFORMATION: n is a, c, g, or u
<220> FEATURE:
<221> NAME/KEY: misc_feature
<222> LOCATION: (2447)..(2447)
<223> OTHER INFORMATION: n is a, c, g, or u
<220> FEATURE:
<221> NAME/KEY: misc_feature
<222> LOCATION: (2462)..(2462)
<223> OTHER INFORMATION: n is a, c, g, or u
<220> FEATURE:
<221> NAME/KEY: misc_feature
<222> LOCATION: (2475)..(2475)
<223> OTHER INFORMATION: n is a, c, g, or u
<220> FEATURE:
<221> NAME/KEY: misc_feature
<222> LOCATION: (2483)..(2483)
<223> OTHER INFORMATION: n is a, c, g, or u
<220> FEATURE:
<221> NAME/KEY: misc_feature
<222> LOCATION: (2493)..(2493)
<223> OTHER INFORMATION: n is a, c, g, or u
<220> FEATURE:
<221> NAME/KEY: misc_feature
<222> LOCATION: (2513)..(2513)
<223> OTHER INFORMATION: n is a, c, g, or u
<220> FEATURE:
<221> NAME/KEY: misc_feature
<222> LOCATION: (2523)..(2523)
<223> OTHER INFORMATION: n is a, c, g, or u
<220> FEATURE:
<221> NAME/KEY: misc_feature
<222> LOCATION: (2535)..(2535)
<223> OTHER INFORMATION: n is a, c, g, or u
<220> FEATURE:
<221> NAME/KEY: misc_feature
<222> LOCATION: (2552)..(2552)
<223> OTHER INFORMATION: n is a, c, g, or u
<220> FEATURE:
<221> NAME/KEY: misc_feature
<222> LOCATION: (2555)..(2555)
<223> OTHER INFORMATION: n is a, c, g, or u
<220> FEATURE:
<221> NAME/KEY: misc_feature
<222> LOCATION: (2566)..(2566)
<223> OTHER INFORMATION: n is a, c, g, or u
<220> FEATURE:
<221> NAME/KEY: misc_feature
<222> LOCATION: (2590)..(2590)
<223> OTHER INFORMATION: n is a, c, g, or u

<400> SEQUENCE: 171
gncuuaagcc ncguuuauuu ugaugnccug uuggcucagu naugnccaag augccnauug 60
uuuuugcccn aaauaaauuu acugaacuug ggcuaaaacc aaaccuuggc acacaggugu 120
gauacaacuu aacaggaauc aucgauucau ccauaaauaa uauaaggaaa aacucaagug 180
guagccuguc uuaaggcuuu ugauacuugc agauugggga aaaacaaaca acaaacgucu 240
ugaagcauau uaauggaauu aguuucuaau guggcaaacu guauuaaguu aaaaguucug 300
auuugcucac ucuauccugg auagguauuu agaaccugau aauagucuuu aaacaagcca 360
uuccagucau gaugagguga uguauggaua caugcauaca uucaaagcac uguucucaaa 420
guuaaugcaa guaaauacag caauuccucu uucaauguuu aggcagaucg uuaacuauga 480
gcuagccaaa ugugggcaug uuauuacagg gaaaguuuaa aggucugaua acuugaaaua 540
gguuuaggag aauucaucua cuuagacuuu uuaaaugccu gccauaaaaa auugaaaugg 600
uagaauggcu gaccacagca augaccagcc cucaccuagg gcucuggaug auuuuugguc 660
uaauaacgca ugcuaguguu gauguuuuuu ggucaagaug ggaaugaaca ggaagaauua 720
ugcagcaggc uuuauuuuaa augccgauuc acauuacucu guucaagcug cguugagaug 780
uuaaacuggc uuacuauaga cuuuguaaaa aaaaaaaaaa ccaaacaaau ggcuccagaa 840
gaguaacaaa cugaaaucug agaucacaca gguuggaaau auguacauaa cugaacaagg 900
ugucaauucu gcucuacagu gcaguuuagu caguuuuagu ugcauagguu uccauuguuu 960
uuauagucug uuuaugcuaa aucuggccaa agaugagcau uguccaccac uaaaaugccu 1020
augccacugg gaauucuggg uuaauuuugu gaccagaaug cagugaucaa aauguucaau 1080
cuuuuuacag uggcauagga agauggcaaa aauuuccuaa agugcaauag auuuucaagu 1140
guauugugcc uuguucuaaa acuuuuauua aguaggugca cuugacagua uugaggucau 1200
uuguuauggu gcuauuucaa uuagucuagg uuuaggcccu uguacauuug gcccauaacu 1260
uuuuacaaag uacuucuuuu auugcacauu cagagaauuu uauauauaug ucuugugugc 1320
guguccuuaa acuuccaauc uuauuuuguc ucuuggagau uguugaacgc agcuugucua 1380
ggaaagggau gggacuagau ucuaaaauuu auuugggacc augggaauga uaguugggaa 1440
gaaacuuugc acacgacaga uuucuagaua cuuuuugcug cuaguuuuau guaauauuua 1500
uugaacauuu ugacaaauau uuauuuuugu aagccuaaaa gugauucuuu gaaaguuuaa 1560
agaaacuuga ccaaaagaca guacaaaaac acuggcacuu gaauguugaa ugucaccgua 1620
ugcgugaaau uauauauuuc gggguagugu gagcuuuuaa uguuaaguca uaauaaacuc 1680
uuaagucaaa uuaagcagac ccggcauugg cguguagcca uaacuuucug auguuaguaa 1740
aaacaaaauu ggcgacuuga aacuaaauca ugccaagguu ugauacacuu gucuugagau 1800
auuaacgaaa cacuuccaaa cacugauaca aaguguccag auucucagau guuuguugug 1860
ugaguuuugu uuaguuguau uuuuuuuuca gugaaugucu ggcacauugc aauccucaaa 1920
cauguggcua ucuuuguugu auuggcauau ucagugacuu guacauucag caauagcauu 1980
ugagcaaguu uuaucagcaa gcaauauuuu caguuauguu uccaaauuaa gaauggguuu 2040
aaacuugcug aauguaaaga uugacccuca agucacugua gcuuuaguag uugcuuauug 2100
uauuaguuua gaugcuagca cugcaugugc ugugcauauu cugguuuuau uaaaauaaaa 2160
aguugaacug cacagucucc uuuguuguug ucaauugugg uuuacuuuua gaggugaaaa 2220
uaaaguugug cucuugccuc gugccaauau guacauaacu gnacaaggug ucaauncugc 2280
ucuacagngn aguuuagnca guuuuagung nauagguucc caunguuuuu aungncuguu 2340
uaugcuaaau cuggccaaag augagcauug cccaccacua aaaugccuau gccacuggga 2400
auccuggguu anuuuggnga ccagaaugaa gugancaaaa uguccanucu uuuuacagug 2460
gnauaggaag auggnaaaaa uunccuaaag ugnaauagau uuccaagugu uungugccug 2520
guncuaaaac uuuunuuaag uagggugcac unganaguau ugaggncauu gguuauggug 2580
cuauuuccan uuagucuagg uuuaggcccu 2610

<210> SEQ ID NO 172
<211> LENGTH: 3657
<212> TYPE: RNA
<213> ORGANISM: Homo sapiens

<400> SEQUENCE: 172
cucggucucc aagauggugg cuaacaaaac gugaggccua gagguugauc cuaggucacu 60
ggaagcaugu ccuugaagag gacuaugggc aucuggguuc uuccucuucu acuuggccac 120
gagguaaccg gcuucuugua ccacgugugc ucaccucuac aaucugugcg gauucagacu 180

-continued

```
ccaagcaacu aggcuaccca gugacaggcu aaaaacuaca gcucuaacgu cuuggaaggc    240
gauuccaugg accaggaugu ggaaagccca guggccauuc accagccaaa guugccuaag    300
caggccaggg acgaccugcc gagacacauc agccgagaca ggaccaaaag gaaaauccag    360
agguacguga ggaaggaugg gaagugcaac guucaccacg gcaaugugcg ggagacguac    420
cgauaccuga cggacaucuu caccacccug guggaccuga aguggagauu caaccuguug    480
aucuuuguca uggucuacac agugacgugg cuuuucuuug ggaugaucug guggcugauu    540
gcguacaucc ggggagauau ggaccacaua gaggaccccu cguggacucc uugugucacc    600
aaccucaacg gguuugucuc ugcuuuuuua uucuccauag agacagaaac caccaucggu    660
uauggcuacc gggucaucac ggacaagugc ccugagggga uuauucuccu cuuaauccag    720
uccguguugg gguccauugu caacgccuuc augguaggau guauguuugu gaaaaauauccc    780
caacccaaga agagggcaga gacccugguc uuuuccaccc acgcggugau cuccaugcgg    840
gaugggaaac ugugcuugau guuccgggug ggggacuuga ggaauucuca cauuguggag    900
gcauccauca gagccaaguu gaucaagucc aaacagacuu cagaggggga guuuauuccc    960
cucaaccaga cugauaucaa cgugggguac uacacagggg acgaccggcu cuuucuggug   1020
ucaccauuga uuauuagcca ugaaauuaac caacagaguc ccuucuggga gaucuccaaa   1080
gcgcagcugc cuaaagagga acuggagauu guggucaucc uggagggaau gguggaagcc   1140
acagggcagu ucugaaaucg aaaucaagca gaggucuaua agaacacccu ggagaccccc   1200
augcugcugg aucuugggguc caugaacugc uuuuauuugc ugcaaucaaa aaugcuaguc   1260
gcugaucuga uaggagagga aacgagacuc agagccugaa ggauaacacg cugagggcug   1320
auuucauaca cucuucccgg cuggaucauc ccagccccca cagcguccag gcuuaguuuc   1380
uuccuuuguu uuaacaaucu auacuucuc cagccugggc gagcuaguau acccagaguu   1440
ugguuuuguu ucuuuucaga gcuguaagcc cagugcccag ugaccucauc ugggaggaga   1500
guuaagcaau aagaccugaa augcuaaacu cuggggguaga aaaccucugc agagacagcg   1560
ucucugggaa gucucuacag agacagagua gggaagucuc acgaagguca gagucuuacu   1620
uccauaccug gagaaauccg cccguccguu cagugccggu uucaacuccu cugccaaaga   1680
cuucuuucca agacacuggu aucagcuauc ccagcaguaa cuuuggcagu auauaaauca   1740
auggcacugc cccauaaaac ccccguugagu aaaaccuaug gucuucaaca gcuggggagc   1800
cuguagccca gcuccugugu gaggcuaagg cuguggagac caugccugcu caccuccucg   1860
uugaaaagca aaacacugua agaaaccuaa caugacuuuu uccaacauuu cucaggcugg   1920
ggagaagacu ugguccacaa agagcuugag gucuugaucu ggaucccuag cauccaugga   1980
agaaggugggg caugaucacc cacacuccuc aucccauagc ucugaaugag guaggcagau   2040
uccuggggcu caccagcuca uccuaacagc cagguccccaa ugagggacug ucuacaaaag   2100
aacaagaggu ggauccugag aagcgacacc caagcuugac cucuagcccc uguacacacc   2160
uguuaagcac cugggcaucg ggacacacac ucgcaauuug caaacaaggc aaauucucac   2220
acuucagaag gcacugagag aaucccauaa gcucaaaaag uuaggagcca agauugacca   2280
uuaaugacuu ggguugaaaa gacuaaacca cuggauagaa uguuucauua cuaaaacacc   2340
uuaccugaaa aguauuacug cucuucuuuc ugcaacugga ccaugcagag auccacaaag   2400
agaugcccag agauuauuag ugauggucau augauauaca caauguggac ucuaagccaa   2460
ggccccauca acucagaucc agaggcugac agugugcuua ucuuagagau accacagugg   2520
```

cugccuaauc accacguccu uaagucaggg gaguuugauu auuuccuaug aacaccgagu 2580
ggggacagcg gauuaccaau gaagcaaucc aaccugacaa uccuaaccac ccagaagagg 2640
aucgcugggg gaaagcauga auuauuuacg ugucaacaug ugcacacucc ggccacgcag 2700
cucaacagcc aggagugcuu cuccacuuag cccugcccug gcauccauuu augaucucgu 2760
cuguuguguu aauuacccag cuagcuuuuu ucucaaaaau aauaucuccc agccauagac 2820
cuacucaucu guguccucuu uaauuucaac ccacaguuac aucauucacu ggcuugcuca 2880
guuucuucaa cucugaaaug ggaaugauga ugaugaugcc ucuuccccca agccaccauc 2940 cuccccgug accuuccuag guacagacuc aaaccaggga agauuauuuc cuucucauag 3000
gccacagggu gaaaugcaau aaagaacaaa gccuuguagg gaggcagagg gaaagaccag 3060
uccucacaag aggcuccauu guuuccaggg acuuugaagc uuggacagaa ugucagauga 3120
uccccuuuga aggugcucca aagagucaau gugaaaaaua uugacugaug ugugcccguc 3180
cacaagccaa ggugccucug cccuggucac cuaccaugaa uuauaaacug augauauuug 3240
aaauaauaag gaacacugga gccggccaga aaggauucug cagucccaua aauagcaaca 3300
uucaucacua caaugccugc caacggguggc cgugaaugua gauuaccccc ggcucuucug 3360
aggccacuga ggacagggca aacuaccucu gagaauggag gcucacuguu cugcauccca 3420
cuucuaaaug uuccaugaau uuuuugagac aucucccaua ucccuguuag aaagauucaa 3480
ccuugugcua uuaaccaaau cauuuugaau uccauaaacc ucuacucuaa aguauacacu 3540
uaauucuaca auacagacaa caaauaugac uuuuuccuau gaaagaguga uaaagauacu 3600
guaucagucu gcuuugacuc aaaaaaaaaa aaaaaaaaaa aaaaaaaaaa aaaaaaa 3657

<210> SEQ ID NO 173
<211> LENGTH: 2267
<212> TYPE: RNA
<213> ORGANISM: Homo sapiens

<400> SEQUENCE: 173
uggaaugggu gcuaggugaa ggcuuuguug aaucaggaug cugagcuggu guuuuuacag 60
guccagauau gaugagcugg aguuuuggua ggcccaggua ccuccuccaa aauugaccac 120
auaauugguc acaaaucagg ccuccacaga uacaaaaaua uugaaauuau cccaugcauc 180
cugucugauc accacagacu aaggcugauc uucaauaaca acauaaaaau agaaagccag 240
guucacugcu gcggcugcgc cuccuuguuc ucagcgucac cacugccgcc augcccggag 300
gguugcuucu cggggacgaa gcccccaacu uugaggccaa uaccaccauc ggccgcaucc 360
gcuuccacga uuuccuggga gauucauggg gcauucucuu uucccaccca cgggacuuua 420
ccccagugug caccacagaa cuuggcagag cugcaaagcu ggcgccagag uucgccaaga 480
ggaauguuaa guugauugcu cuuucaauag acaguguuga ggaucaucuu gccuggagca 540
aggacaucaa ugcuuacaau ggugaaacac ccacggaaaa guugccauuu cccaucauug 600
augauaaggg cagggaccuu gccauccuuu ugggcauguu ggauccaguc gagaaggacg 660
auaacaacau gccugugacg gcccgugugg uguucauuuu uggcccugac aagaaacuga 720
agcugucuau ccucuacccu gccaccacga gcaggaacuu ugaugagauu cucagagugg 780
uugacucucu ccagcugaca ggcacaaagc cgguugccac cccaguugac uggaagaagg 840
gagagagcgu gaugguaguc cccacccucu ccgaagagga agccaaacaa uguuucccua 900
aaggagucuu caccaaagag cucccgucug gcaaaaaaua ccuccguuau acaccccagc 960
cuuaagucuu ugcggaaauu ggggcugcau cugcacgucc agcacugggg ccugaggacg 1020
ucagccggca gccgugggu c cuugcagcag guccguagaa agaucguggc augaucacag 1080
ccgguccugu agaucgcucg cuauacuacu gggucauuaa auggaaaugg caccaaaacc 1140
uucucgggau ucuuuacucu gugccuucgc cagcauucug ccccucugcc ugucacagug 1200
cccuacugac uggcucucuu ugaaacgaau uauguauuga agauuccuua ggucucugca 1260
gggucuuuga ucagcaagca agguaguguc agugugggcu cugugcuaga augaugaaac 1320
accuuuugua gcuuuccgaa cggaaucuuc uguuacccau uuuggagagc acugacaugg 1380
ggagaagcuu ucaauucugu auuuuuagua aauaaagugg ggacagccgg gagaauucuu 1440
acagggaauc uauuguaagu uucuaucgaa gugggcucag aaagccuuuc gccucccaag 1500
agugcgcaug uaccuccuag aguuuccaca ucugcucucu ggugaugucu gccugugaac 1560
gcaccuuaua aaagacgggc ggugacagug uuuuaccacu caguguccua guagugggug 1620
gccauuucug aauucugcuu uuugagguuc aacaaauaaa auccugauca gaaaaaaaaa 1680
aaaauagaaa gccaacauuc auguggaaac ugaacaacac uacucaauga uuccuugguc 1740
agagaugaaa uaaagaaaga aauuaaagac uuuuuagagu uuaaugaaaa ugaagccaca 1800
acauacccaa acuuauggga cacaaugaag gcauuucuaa gaggaaaacu cauagcccug 1860
agugcaucca aaggaaaaaa aaaaaaaccu agagagagug uacacuagca gccugacugc 1920
acacuuagaa gcucugcaaa aaaaggaauc aaauucaccc aagaggaaua gacagcagga 1980
aauaaucaaa cuuagggcug aaaucaacca aauggaaaca aaaagaacua uucaaagagu 2040
gggccaaacc aggagcuagu ucuuugagaa aaucaacaag auagauaaac ccuuagccag 2100
acucacuaga gggcacaggg acagcauccu aauuaacaaa aucagaacug aaaagggaga 2160
cauaacaaca gauccugaag aaauccaaaa caccaccaga uccucuacaa aaggcuauac 2220
ucaacaaaac uggaaaaccu ggaugaaagg aaaagcuucu agacaga 2267

<210> SEQ ID NO 174
<211> LENGTH: 2834
<212> TYPE: RNA
<213> ORGANISM: Homo sapiens

<400> SEQUENCE: 174
augagcaccg cggaucugau gcgucgcugg gucaucgccc ugcuccuugc ugcugccgga 60
guugcaguag aagacucagg cagcaggaac gaguuccagu guagagacgg aaaaugcauc 120
gcuagcaagu gggugugcga uggcagcccc gagugcccgg auggcuccga ugaguccccca 180 aagacaugca ugucugucac cugucagucc aaucaauuca gcuguggagg ccgugucagc 240
cgaugcauuc cugacuccug gagaugugau ggacagguag acugugaaaa ugacucagac 300
gaacaaggcu gucccccccaa gacgugcucc caggaugacu uccgaugcca ggauggcaag 360
ugcaucuccc cgcaguuugu gugugaugga gaccgagauu gccuagaugg cucugaugag 420
gcccacugcc cagccaccac uuguggcccc gcccacuucc gcugcaaauc auccauaugc 480
auccccaguc uuugggccug cgacggggau gucgacugug uugacggcuc ccaugagugg 540
ccacagaacu gccaggccga agacacggcc uccaaaggcg uuagcagccc cugcuccucc 600
cuggaguucc acugugguag cagugagugu auccaucgca gcugggucug ugacggcgag 660
gcagacugca aggacaaguc agaugaggag cacugcgcgg uggccaccug ccgaccugau 720
gaauuccagu gugcagaugg cuccugcauu cacgguagcc gccagugugga ccgugaacau 780 gacugcaagg acaugagcga cgagcucggc ugcgucaaug ugacacagug ugauggcccc 840

-continued aacaaguuca agugucacag uggggagugc aucagcuugg acaaggugug cgacuccgcc 900
cgcgacugcc aggacugguc ggaugagccc aucaaggagu gcaagaccaa cgaguguuug 960
gacaacaaug guggcuguuc ccacaucugc aaggaccuca agauuggcuc ugagugccug 1020
ugucccagcg gcuuccgguu gguggaccuc cacaggugug aagauauuga cgagugucag 1080
gagccagaca ccugcagcca gcucugugug aaccuggaag gcagcuacaa gugugagugc 1140
caggccggcu uccacaugga cccacacacc agggucugca aggcuguggg cuccauaggc 1200
uaucugcucu ucaccaaccg ccacgagguc cggaagauga cccuggaccg cagcgaguac 1260
accagucugc uccccaaccu gaagaaugug guggcucucg acacggaggu gaccaacaau 1320
agaaucuacu gguccgaccu gucccaaaaa aagaucuaca gcgcccugau ggaccaggcc 1380
ccuaacuugu ccuacgacac caucaucagu gaggaccugc augccccuga cgggcuggcg 1440
guagacugga uccaccgcaa caucuacugg acagauucag ucccaggcag cguaucugug 1500
gcugacacca agggcguaaa gaggaggaca cuguuccaag aggcaggguc cagacccaga 1560
gccaucguag uggacccugu gcauggcuuc auguacugga cagauugggg aacacccgcc 1620
aagaucaaga aaggggguuu gaauggugug gacauccacu cacuggugac cgaaaacauc 1680
caguggccaa auggcaucac acuagaucuu uccaguggcc gucucuauug gguugauucc 1740
aaacuccacu cuaucuccag caucgauguc aaugggggca aucggaaaac cauuuuggag 1800
gaugagaacc ggcuggccca ccccuucucc uuggccaucu augaggacaa aguguauugg 1860
acagauguca uaaacgaagc cauuuucagu gccaaucgac ucacggguuc agaugugaau 1920
uugguggcug aaaaccucuu guccccggag gacauugucc uguuccacaa ggucacacag 1980
ccuagagggg ugaacuggug ugagacaaca gcccuccucc ccaauggugg uugccaguac 2040
cugugccugc ccgccccaca gaucgguccc cacucgccca aauucaccug cgccugcccu 2100
gauggcaugc ugcuggccaa ggacaugcgg agcugccuca cagaagucga cacuguacug 2160
accacccagg ggacauccgc cguccggccu guggucaccg caucagcuac caggccaccg 2220
aagcacagug aggaucucuc agcucccagu acuccuaggc agccugugga caccccaggg 2280
cucagcacag uggcgucagu gacagugucc caccaagucc agggugacau ggcuggcaga 2340
gggaaugagg agcagccaca ugguaugagg uuccugucca ucuucuuccc uauugcacug 2400 guugccccucc uuguccuugg ggccguccug cuguggagga acuggcggcu gaagaacauc 2460
acaaucaaca gcauaaacuu ugacaaccca gucuaccaga agaccacaga ggacgagcuc 2520
cacauuugcc gaagccagga uggcuauacc uaccccucaa gacagauggu cagccuggag 2580
gacgaugugg caugagcagc cgggagagcc gucucuuucc gggauccauu gccaagcuua 2640
ggcagaaaag acacucucuc cagaccuccc cauccagcac ugguccugcc accucccugg 2700
gucuguguug cucaaagcaa gauagagcaa agcugggcug gggggccaag cucagcuucc 2760
ugucugcccc agguucuguu uuauauauuu auugucuggg acagaaaagg cuacuggcug 2820
ugcuugaaau ucga 2834

<210> SEQ ID NO 175
<211> LENGTH: 2940
<212> TYPE: RNA
<213> ORGANISM: Homo sapiens

<400> SEQUENCE: 175
accggucauc gggcucuucc uugggcucag ggcacggauc aaguccucgg cucgcucggc 60
cagcaccgcg gcaccauggc gcaggagcug cagcaccccg aguucgcgcg cgcaggccag 120

-continued

```
caggcugggc ugcaggugug gagggucgag aagcuggaac ugguaccggu gccccagggu    180
gccuauggug acuuuuacgu cggagagccc uaccuggugc ugcacaccac caaguccagc    240
aggggcuucu ccuaccgccu gcauuucugg cugggaaagg aguguuccca ggaugagagc    300
acagcggcug ccaucuuuac gguccagaug gacgacuauu ugggugcaa gccaguccag     360
agcagagagc uucaaggcua ugagucgacu gauuuugugg gcuauuucaa aggcggucug    420
aaguacaagg cuggaggugu ggcuucugga cuaaaccaug ucccucacca ugaucugacu    480
gcgaaaagac uucugcacgu gaagggucgg agagugguca gagccacuga aguuccccuc    540
agcugggaga gcuucaacaa gggcgacugc uucaucauug accuuggcac cgaaauuuac    600
caguggugug guuccuccug caacaaauau gagcgucuga aagcaagcca gguggccauu    660
ggcauccggg acaaugagag gaaaggaaga ucucaacuca uuguggugga agaaggaagu    720
gaaccaucag agcucaugaa gguuuuaggg agaaagccug agcuuccaga uggggacaau    780
gaugacgaug ucguagcaga cauaaguaac aggaagaugg cgaagcucua caugguuuca    840
gaugcaagug gguccaugaa aguaacacug guggcugaag aaaacccguu cuccauggga    900
auguugcuuu cugaagaaug cuucauuuug gaccauggug cugcaaaaca aauuuuugua    960
uggaaaggua aaaaugcuaa cccacaggag aggaagacug ccaugaagac agcugaggag   1020
uuuuuacaga aaaugaagua uucuacuaau acucaaauuc agguucuucc ggaaggcggu   1080
gaaacaccaa uuuucaaaca guucuuuaag gacuggaagg auaaagacca gagugauggc   1140
uuugggaagg uguacaucac ggagaaagug gcucagauaa agcagauucc guuugaugcc   1200
ucaaaacugc acaguucucc gcagauggca gcccagcaca acauggugga cgauggcucu   1260
ggcgggggugg agaucuggcg uguagagaac agugguagag uccagauuga cccaagcucc  1320
uauggcgagu ucuauggcgg ugacugcuac auuauccucu acacuuaucc cagaggacag   1380
aucaucuaca cauggcaagg agcaaaugcu accagagaug aacugaccau guccgcguuu   1440
cugacugucc aguuggaccg gucccuugga gggcaggcug ugcagguccg ugucucucaa   1500
ggcaaagagc cugcucaccu gcugaguuug uucaaagaca aaccacucau uauuuuauaag  1560
aaugggacau ccaagaaaga agggcaggca ccggcucccc cuacacgccu uuuucaaguc   1620
cggaggaacc uggcaucuau caccagaauu guggagguug acguugaugc aaauucauua   1680
aauucuaaug acacuuuugu ccuaaaacug ccacgaaaca auggcuucau cuggauagga   1740
aaaggugcua gccaggagga ggagaaagga gcagaguaug uggcugaugu ccucaagugc   1800
aaagcuucaa gaauucaaga aggcaaggaa ccagaggaau ucuggaacuc ucuuggaggg   1860
aggggagacu accagacuuc accauugcua gaaacucggg cugaagacca uccaccucgg   1920
cuuuaugguu gcuccaacaa aacuggaaga uucauuauug aagaaguucc gggagaguuc   1980
acccaggaug accuggcaga agaugauguc augcuacuug augcguggga acagaucuuu   2040
auuuggauug gcaaagaugc caaugaaguu gagaaaaagg aaucagugaa gucugccaaa   2100
auguaccugg agacagaccc uucuggaaga gacaagagga caccgauugu caucaucaag   2160
caagggcacg agcccccac auucacaggc ugguuucugg gcugggacuc cagcaggugg    2220
uaaaaccagc aacuauccug gcugcauugg ggcagcugcc acuuuguugu uggggaauug   2280
uuuacuuuuu guuauuggcu uuugaagaua aacuccugcc aaauggauau auaucuauau   2340
cuauaucuau aucuauaucu auaucuauau cuauaucuau aucuauaucu aucuauaucu   2400
aaucuauauc uaucuaucua ucuaucuauc uaucuaucua ucuaucuauc uaucuauaug   2460
```

-continued cuccucuuuu ccuucucuuu caaagggaau ugcuguaugu uacuauacug aaauaaccua 2520
aagcaaccau uuguuuucga gcaauuuugc aaucugggga ccucugagga aguaauuuug 2580
ucauucagcc acugcuagcc aaacuugucu uuucccauag agaggaagga gagccacagu 2640
gcuucuaagc auuuccccgu cugcuacucu guuugcagug agcuuuacuu uauguauggc 2700
uuuaacaaug ccuugcuguu ucccaucuca agucaaugcc acuuggaugc cauucacucc 2760
caaguguccu uacauaggau gaacuucuuu agcuuuuuua gaaaacuaaa aucaugucuu 2820
uuaugauaaa acacauuuua uuucuauaag uuuaacuuua uauauuugau agcacaugcu 2880
caauagcaua aagaauaugc auugaaugau guuuuucaua auuaaaauau auccuuuugg 2940

<210> SEQ ID NO 176
<211> LENGTH: 1714
<212> TYPE: RNA
<213> ORGANISM: Homo sapiens

<400> SEQUENCE: 176 cagguugag agcaagaagg ugcaggaugu aggccagcag aauuaucaga cccaguggcg 60
gcuucugcca cuggaagaau uuccaacaua aaacagauga ucaguuuggg acaaucgauu 120
cugcgaccag agguagugc aucugguuac uuuuaaaauu cagauugucu gguguuuucc 180
aaucacucgc gacuguaauu ugaaguugga uucugagaua auacaaucgc ugucgcucua 240
guuuauaaag cuguccaaga ucugcccagu cccagauguc cugggucuc agggcggcug 300 uggucugcgc ccuucuccug cagcuggaug ccagaccauc cuggacucgg aucccuuugg 360
guucacacuc gcuuagguau uucuacaccg cuguguccg gccuggccuu ggggagcccu 420
gguucauaau cgucggcuau guggacgaca ugcagguccu gcgcuucagc agcaaggagg 480
agacuccgag gauggcaccc uggcuggagc aggaggaagc agaugacugg gaacagcaga 540
cucauauagu cacaauucaa ggacagcugu cugaaaggaa ucugaugacc cugguucauu 600
uuuacaacaa gagcauggac gacucucaca cacuacagug gcugcaggac ugcgaugugg 660
agccagaucg gcaccugugu cucugguaca accagcucgc cuaugauagc gaggaucucc 720
ccacccugag cgaaaaccca aguuccugua caguggggaaa cagcacugua ccucagaucu 780
cucagcaccu ggagggccac ugcucagaug ugcugcagaa auaccuggaa aaagggaagg 840
agaggcugcu gcguucagac ccccaaagg cacaugugac ccgucacccc agaccugaag 900
gugaugucac ccugaggugc ugggcccugg guuucuaccc ugcugacauc acccugaccu 960
ggcagaagga uggggaggag cugacccaag auguggaguu uguggagacc aggccugcag 1020
gggauggaac cuuccagaag ugggcagcug ugguggugcc ucuuggaaag gugcagaguu 1080
acacgugcca uguggaccau gaggggcugc cugagccccu cacccugaga ugggagccug 1140
caugguacca aaagccuugg auuuggauug uugccacggu uuuuuccauu uugcucauuu 1200
gucucugugu ggcucgcaga cccaugaaga agaaugcagg ugggagagga aggcgugaca 1260
cccaagaagc aggcagagac aguccccaag acucuagcaa gacuguugug gaugaugagg 1320
agaugggggu uugcuuuugg aagauuaagu ccuguaaaac uugucuaggc cacuccccag 1380
gaacuucagg aucaucuggg agaugccccu uugaguggcu gggcugugag gacagcaggc 1440
caguucuugc cacccuggac agaaacacau cucaccuuuc uggcucgagg aucugaacac 1500
cugucucuug ccuacucggc uucuagucag gcauuuuguc accuugucaa ggguucccagg 1560 gacacaaagc ucccuccucu cacccacagc acucuggguc cuacccccaa ugcuucaggg 1620
acauuuaauc aggucaaauu gggaucaaug gcuuugaugc agaaaagaac uguggacuaa 1680
uagagauagg guuuaauaaa aaaaauaucu uuuu 1714

<210> SEQ ID NO 177
<211> LENGTH: 467
<212> TYPE: RNA
<213> ORGANISM: Homo sapiens

<400> SEQUENCE: 177
uuuuuuuuuu uuuuuuucaa cuuuaaagac uggauuugag guucagucug ggucucuggg 60
ggggaccucu gucaucacgc cuauaaucau cccgagagua gucaucccug gagcuccacg 120
accgaucauc ccgucuguca uagcggucuu cauagcgguc cccaccuccu cuguagucau 180
caucucuccg guacccacuu ccaaaugccc uucugccacu gccuauccug gagucauagc 240
cucggucaua gucucugcug ccucggucau cauagcgauc ccggccccca uagcggucca 300
ugucucugcg ugggccgucc cgauauccgu cccuauaccc aucccgauac cggucugaau 360
cguaacgauc ucgauacuug ucuccaaagc uaucaucgcc ucuucuaggu ggguagucau 420
cacaacuguc uguggugggga cgggcccucc agucuguguc uguuuug 467

<210> SEQ ID NO 178
<211> LENGTH: 346
<212> TYPE: RNA
<213> ORGANISM: Homo sapiens

<400> SEQUENCE: 178
uuuuuuuuuu uuuuuuuggc ccccaggcuc ugucucaagg augggaauag aucaagccaa 60
acagugaaaa auaaggcaaa ucguggcuuc gggguuugag acuggcacca auggcaaauc 120
agcagaggag augcaaaugg gguaacaauc acaguuagug ggguaacaug agcaggcagg 180
aaacccuuga gacaacaccc aagguccacg ucuucgcaug ugcagggcac aacuccagca 240
gcaguuucug ggcuuggagg cuuguuacuc uuccuaccuu ucccaccccc uaaaagacac 300
caagauggag cccacgaaga gauuacauca agcucuucug gcuggg 346

<210> SEQ ID NO 179
<211> LENGTH: 4902
<212> TYPE: RNA
<213> ORGANISM: Homo sapiens

<400> SEQUENCE: 179
ucuaggacag ccagggcuac acagagaaac ccugucucaa cuaaaacaaa gcaaaccccc 60
cgaauauugu uuuuuauuug cggaugucug uuuauugaga cggggguucau ggcagacaug 120 agugucucag ugcauuugcu auccucucuu cuaaaggggc gggggggggg gugcgcugga 180
gagguggcuc agcaguuaag agcacugacu ucucuuccag agguccugag uucaauuccc 240
agcaaccaca ugguggcuua uaaccaucua uagugagauc ugaugccuuc uucuugccug 300
uaggcagacc acuguauaca uaauaaauaa aucuuaaaag gggggggaag guguggagcu 360
aaaaguaugg caauaugcau aaguuuagcu auuucuguug uuuugcaguc aucagugagc 420
caaacuaauu cgaaugggua gcuagaucuu guugcuuuua gcgaauauau auugagugaa 480
uggaauugac agucuucugu auucucauuc aguuuguuug uguucuuccc caucagugau 540
aacauguagu gaacuaaccc guguggacca ucuuaaccau ggcuucuccu uccuuuucug 600
uuuuaaacau aggacaugga uuugauugac auccuuugga ggcaagacau agaucuugga 660
guaagucgag aaguguuuga cuuuagucag cgacagaagg acuaugagcu ggaaaaacag 720

-continued

```
aaaaaacucg aaaaggaaag acaagagcaa cuccagaagg aacaggagaa ggccuuuuuc    780
gcucaguuuc aacuggauga agaaacagga gaauucccucc caauucagcc ggcccagcau    840
auccagacag acaccagugg auccgccagc uacucccagg uacacucguc guggugggag    900
cuaaggaaaa cucuagugag aaagcagacu cucuggaguu gaguucuugg ucugccauuu    960
acugugucuu uugugaggag gagaaguucu caaacuucgc uucuugauaa ucaggacaca   1020
gaucacaggg aggacuuugu gaguucagaa acauccucug uggugaugaa acagcggcag   1080
aaauacuguu gggaguaaaa gaaguaggca uugcucauug ugguaggcag ggcccugauu   1140
guaugguaa cugacuuaac uguguuaagu augauuccca uuuuauauuc ccaugucuaa   1200
acaacuaaag cauuugccca gaacacucag aaagaaauga agggagguua uugccuagca   1260
cagagcccug guucaguccc ccacgcuguu cguuaaaggg gagggacuaa uaauuugaac   1320
acaaucuggu uugaaucuau gcaaaucgau uucugaaaug agaccauagg uuauuuuaug   1380
aacaagucuu auugcucguu gugacccugu gcuuagaaca uuucauaaau gaugcucucu   1440
gugccuuucc ccuuccucca gguugcccac auucccaaac aagaugccuu guacuuugaa   1500
gacuguaugc agcuuuuggc agagacauuc ccauuuguag augaccauga gguauaaaaa   1560
uguuuguuua acagcaaaac ucccuuaucu gauauuaguu ccuuucaugu gucuccaauu   1620
aagagaagaa aagaaaauuu uagaaggaaa aaauugauca aagaaauugu caaguaaacu   1680
guaugagagc uauauaaugc uuaaaaauaa gaccuguaug ggcugguaag auggcucagu   1740
ugguaagagu acccgacugc ucuuccgaag guccagaguu caaaucccag caaccacaag   1800
guggcucaca acauccauaa caagaucuga cucccucuuc uggagugucu gaagacagcu   1860
acaguguacu uacauauaau aaauaaauaa aucuuuaaaa aaaaaaaaua aggccuguaa   1920
acuacaaguc cauuuuacug uauagcugga aacaggaauc agaauaauuu ucccuggaaa   1980
cuggauauag auauauaaaa uauuuugacu aguaaagaac aacuauuaau cagcauuugg   2040
auuaaaaaau cuuaaucugu uguuugaagc auucugcuag auauuauggg uacagauuaa   2100
guccuaauga auguuuuuau ccauuuugaa gucugccuuu aaauacaugg agugaaauaa   2160
ccuaggagug uauuaauaug gagucacugg gaggaggaaa uguuucauuu uauaaaagca   2220
gccugagagc uguaggcccu gcugcugucu guucuucaug ccuuggcucu cacucacaug   2280
aaucaauguc acgucaaucu uggcuuucuu cacuugcauu ucagucgcuu gcccuggaua   2340
uccccagcca cgcugaaagu ucagucuuca cugccccuca ucaggcccag ucccucaaua   2400
gcucucugga ggcagccaug acugauuuaa gcagcauaga gcaggacaug gagcaaguuu   2460
ggcaggagcu auuuuccauu cccgaauuac agguaagaga gcucuaggag ugugcuguuu   2520
ucugcgggcc cuuuuaaauu agucauccua guuauuuauu auuuacaugc uaccuccuca   2580
aaggaagaaa uugauggugu auuuaaauua cucaugagag cuucccagac ucacuuaaca   2640
cacauaguuu uuagguaauc agacugaaua uuucuggaua aauucauuca aagacugaaa   2700
gcuaauuuag aguucugaca aagauaaaau acuuaucuau ugaaaaaugg gaguugaagg   2760
aauuauugaa aagaacaccu uggauuuggg gguagggaau ugaucuaaaa ugcacuuagc   2820
cucugcucau acaaugugac cuucuuuccu agugucuuaa uaccgaaaac aagcagcugg   2880
cugauacuac cgcuguuccc agcccagaag ccacacugac agaaauggac agcaauuacc   2940
auuuuuacuc aucgaucucc ucgcuggaaa aagaaguggg caacuguggu ccacauuucc   3000
uucaugguuu ugaggauucu uucagcagca uccucuccac ugaugaugcc agccagcuga   3060
ccuccuuaga cucaaauccc accuuaaaca cagauuuugg cgaugaauuu uauucugcuu   3120
```

```
ucauagcaga gcccagugac gguggcagca ugccuuccuc cgcugccauc agucagucac   3180

ucucugaacu ccuggacggg acuauugaag gcugugaccu gucacugugu aaagcuuuca   3240

acccgaagca cgcugaaggc acaauggaau ucaaugacuc ugacucuggc auuucacuga   3300

acacaagucc cagccgagcg uccccagagc acuccgugga gucuuccauu uacggagacc   3360

caccgccugg guucagugac ucggaaaugg aggagcuaga uagugccccu ggaaguguca   3420

aacagaacgg cccuaaagca cagccagcac auucuccugg agacacagua cagccucugu   3480

caccagcuca agggcacagu gcuccuaugc gugaauccca augugaaaau acaacaaaaa   3540

aagaaguucc cgugaguccu ggucaucaaa aagccccauu cacaaaagac aaacauucaa   3600

gccgcuuaga ggcucaucuc acacgagaug agcuuagggc aaaagcucuc cauauuccau   3660

ucccugucga aaaaaucauu aaccucccug uugaugacuu caaugaaaug auguccaagg   3720

agcaauucaa ugaagcucag cucgcauuga uccgagauau acgcaggaga gguaagaaua   3780

aagucgccgc ccagaacugu aggaaaaagga agcuggagaa cauugucgag cuggagcaag   3840

acuugggcca cuuaaaagac gagagagaaa aacuacucag agaaaaggga gaaaacgaca   3900

gaaaccucca ucuacugaaa aggcggcuca gcaccuugua ucuugaaguc uucagcaugu   3960

uacgugauga ggauggaaag ccuuacucuc ccagugaaua cucucugcag caaaccagag   4020

auggcaaugu guuccuuguu cccaaaagca agaagccaga uacaaagaaa aacuagguuc   4080

gggaggaugg agccuuuucu gagcuagugu uuguuuugua cugcuaaaac uuccuacugu   4140

gaugugaaau gcagaaacac uuuauaagua acuaugcaga auuauagcca aagcuaguau   4200

agcaauaaua ugaaacuuua caaagcauua aagucucaau guugaaucag uuucauuuua   4260

acucucaagu uaauuucuua ggcaccauuu gggagaguuu cuguuuaagu guaaauacua   4320

cagaacuuau uuauacuauu cucacuuguu acagucauag acuuauauga caucuggcua   4380

aaagcaaacu auugaaaacu aaccagacca cuauacuuuu uuauauacug uaugaacagg   4440

aaaugacauu uuuauauuaa auuguuuagc ucauaaaaau uaaaaggagc uagcacuaau   4500

aaaagaauau caugacuuaa acuacuuugg acuuuuugaa uuuauucaca cuauuuucca   4560

uaggacaauc acucauuuac cacauuuggu uauuuuacau uuucaaaaug gguuugaaaa   4620

uacagaggca uuuuauagcc augugugca guccaugauu uuuuauuccc gacauucagg   4680

aggcagaagc aggcagaucc cugggcucca ggacggccaa ggcuacauga gagccugucu   4740

caagaaagac aaacccuuuc uauacuaaac guuagcuagg auugucaagg agaugguaua   4800

uauccacaau gguaugccug cuguacagua cuguggcaca gagaacaaaa ccuguaaccu   4860

ccuguguucu uagaaguggc auucuaagaa gggcuaggaa ga                       4902
```

<210> SEQ ID NO 180
<211> LENGTH: 462
<212> TYPE: RNA
<213> ORGANISM: Homo sapiens

<400> SEQUENCE: 180

```
ggccagcagg acucuccuug cagcagcggc ccgaguucag aguccggagc ugcgguggug     60

gcggcgaagg cgagagucau ggcuggacaa gcuuuuagga aguuucuucc gcucuuugac    120

agaguauugg uugaaaggag ugccgccgaa acuguaacca aagguggcau uaugcuucca    180

gaaaagucuc aaggaaaagu guugcaagca acggucgugg cuguggggguc aggagggaaa    240

ggaaagagug gagagauuga accugucagu gugaaaguug gagauaaagu ucuucuccca    300
```

gaauauggag gcaccaaagu aguucuagau gacaaggauu auuucuuauu uagagauagu 360
gacauucuug gaaaguaugu cgacugaaau cacuguugaa augguguacac gugaagcugc 420 cauuccacug augucugaac uauuucauca uguaaauaau uu 462

<210> SEQ ID NO 181
<211> LENGTH: 417
<212> TYPE: RNA
<213> ORGANISM: Homo sapiens

<400> SEQUENCE: 181
uuuuuuuuuu uuuuuuucag gucucauuuu cguuuauuug aaauucggug cucguguaag 60
uuuuuucucu uccccucaaa uuuuauuuca guaaaaggag acuugggcga gguggauacc 120
ccacagccgg auucuucccc cccugccccc cagggguggcu aaugcuaucu ggggaagucg 180
ucauagggaa gagaacuaug ggugggcucc ugccugaggc cuccaaucuc agcccagugg 240
acauaucaca ggcagcuuaa aaaaaaaacc cuaaaaaaaa caccccaaaa cacacauuua 300
aauagguauu caagacagcu uuaaaaaaug cacccacuca cacccccuc ccuuuucuuu 360 uuggaaaaaa aaauaggaaa aaaaaaaaaa ccaaaccgaa uucucgcuug gccucua 417

<210> SEQ ID NO 182
<211> LENGTH: 1160
<212> TYPE: RNA
<213> ORGANISM: Homo sapiens

<400> SEQUENCE: 182
auuuggcucc gaggccaaga auucggaucc aaggcgggcg cggggaaaau ggcggcggca 60
gcugcggcgg gggcgaaugg gagcggaggc agcagcggca uggaagugga ugcagcaguc 120
cccagcguga uggccuccgg agugacuggg aguguuuccg ucgcucuuca uccccuuguc 180
auccuuaaca ucucagacca uuggauccgc augcgcuccc aggaggggcg gccuaugcag 240
gugauugggg cucugaucgg gaagcaggag gggcgaaaua ucgaagugau gaacuccuuu 300
gagcugcugu cccacaccgu ggaagagaag auuaucauug acaaagaaua uuauuacacc 360
aaggaggagc aguuuaaaca gguuuucaag gagcuggagu uucuggguug guauaccaca 420
ggggggccac cugaccccuc agacauccac guccauaagc agguguguga gauaauugag 480
aguccgcucu uucugaaguu gaacccuaug accaagcaca cagaucuucc ugucagcguu 540
uuugagucug ucaucgauau aaucaaugga gaggccacaa ugcuguuugc ugagcucacu 600
uacacucugg ccacugagga agcugaacgg aucgguguag accacguggc ccggaugaca 660
gcaacaggca guggggagaa cuccacugug gcugaacacc ugauagcuca gcauagugcc 720
aucaagaugc ugcacagccg ugugaagcuc auuuuagaau augucaaggc cucugaagca 780
ggagagguuc ccuucaacca ugagauccug cgggaggccu augcccuaug ucacugucuc 840
ccaguucuca gcacugacaa guucaagaca gacuuuuaug aucaaugcaa ugacguggggg 900 cucauggccu accucggcac caucaccaaa acgugcaaca caaugaacca guuugugaac 960
aaguucaacg ucccucuacga ccgacaaggc auuggccggc gaaugcgggg acuguuuuuc 1020
ugaugauggu ucuggaaggg auggugugug ggcucagac agcuguucca uggaccugag 1080
uaccacauuc ccuuuagaga aacucauuaa uaaaagagca gccccuuaaa aaaaaaaaaa 1140
aaaaaaaaaa aaaaaaaaaa 1160

<210> SEQ ID NO 183
<211> LENGTH: 8322

<212> TYPE: RNA
<213> ORGANISM: Homo sapiens
<220> FEATURE:
<221> NAME/KEY: misc_feature
<222> LOCATION: (1298)..(1397)
<223> OTHER INFORMATION: n is a, c, g, or u
<220> FEATURE:
<221> NAME/KEY: misc_feature
<222> LOCATION: (2040)..(2139)
<223> OTHER INFORMATION: n is a, c, g, or u
<220> FEATURE:
<221> NAME/KEY: misc_feature
<222> LOCATION: (2495)..(2594)
<223> OTHER INFORMATION: n is a, c, g, or u
<220> FEATURE:
<221> NAME/KEY: misc_feature
<222> LOCATION: (3800)..(3899)
<223> OTHER INFORMATION: n is a, c, g, or u
<220> FEATURE:
<221> NAME/KEY: misc_feature
<222> LOCATION: (4897)..(4897)
<223> OTHER INFORMATION: n is a, c, g, or u
<220> FEATURE:
<221> NAME/KEY: misc_feature
<222> LOCATION: (4909)..(4909)
<223> OTHER INFORMATION: n is a, c, g, or u

<400> SEQUENCE: 183
aaaacccaau guuugguuuu aaagccaaaa auauaaggga agugcauagg uuuggguuuu 60
guuuuuuguu uuuuccccgag guccuugauc uuugcccca aauuugaggg cauaaaguaa 120
ucccucaguu accuaaaaac acagccauuc cuuugccauu ccacucuccu ggauuggccg 180
cuucugugcg cgggggagag gugacucacu auuacuacug aggaaagggg agccaguggu 240
ggaagugggg ugagucacug augggcagca gcuucagccc uccccccaac uuccuuggcu 300
cucuggggau gccugauccu cucccucacu uugcaccuac uuccccuggu cccucaccac 360
uacccuuugc ccacccacuc aaauucuuug gcucugcucu uuacuccaga aggccaaagg 420
caagcuuaga guugaguagg caggaaccaa cauugugaag ccccaggcca gaaaggggug 480
uucugcagag ugaggguugg caugcuggcu ccuccucacc auaccugccc ccgccccuuu 540
ggguacagga uggcuccuuu aagagcagug gauccacccc cuguagagga gggccuauua 600
gagccucugc cuggcuguca gugacucagu guucgcggga acgcugccuc agccucaaca 660
ccagccaacc cagaucccga ggugcgccag cgcccagccc agaucuccac gccugccagg 720
agcgagcuuc gccggcucgc uguccccug agcagccucu guccuucugu ccaaguccg 780 cgcccuucuc gggaccccug cccagcgggc agcacuguca cccugccggc cauggagacc 840
ccgucacagc ggcgcgccac ccgcaguggg gcgcaggcca gcucuacccc acugucgccc 900
acucggauca cccggcugca ggagaaggag gaccugcagg agcucaauga ccgccuggcc 960
guguacaucg aucgcgugcg uucccuggag accgagaacg cggggcugcg ccuucgcauc 1020
acugagucug aagagguggu cagccgagag guguccggca ucaaggcggc cuacgaggcc 1080
gagcuggggg augcccgcaa gacccuugau ucuguggcca aggagcgcgc ccgccuccag 1140
cuagagcuga gcaaagugcg ugaggaguuc aaggagcuga aggcucggug agugaggccc 1200
ggccggccgg caccagggag gcagcagucg ccuguaacug gccaucuagu ccccucccuc 1260
cccggaacug ccucccgcgg gugacuggca gugccaannn nnnnnnnnnn nnnnnnnnnn 1320
nnnnnnnnnn nnnnnnnnnn nnnnnnnnnn nnnnnnnnnn nnnnnnnnnn nnnnnnnnnn 1380
nnnnnnnnnn nnnnnnngcu aggccagaua uagaaagcuu ucuguauuua auacacagua 1440
caugcaucau ucaugucuac auaauuaaga uaaaggaagc ugcauuguua augggaaaaa 1500

-continued

```
aaauagggucugggaaugua gugugccuag cauuuacgaa cuucgggguu uggguuugau 1560
cccagcaucu cacaaaccac guguaauccc agcacuugga agguagaggc cggaggaucc 1620
gaaguuuaag gucauucuug acuacuuagc aaauucgggg cacccuagga uaccugagac 1680
ccugucauga auaaaaauaa auaauaaaua aaccaauaug ggucuagguu gagcagcagc 1740
uugggcaggg uagggccgga aguuagccag guagaggguu gcagucccag gaggacccug 1800
gcugggagca gcaccucagu ccccugccca accacagggg gccaccgggu cuuuccggaa 1860
cuccugaggg cgcaaggccu ugcucucucu ggcccagcca uggggaacgc ggagggccgg 1920
ugaggcaggc ggcaggcggg cgggcggggc gcgggccguc auccccuccu gcuccuuauu 1980
uuuagcccag uguagagucu gggccgccug ucccuccccc aggacagggg gaggaaauun 2040
nnnnnnnnnn nnnnnnnnnn nnnnnnnnnn nnnnnnnnnn nnnnnnnnnn nnnnnnnnnn 2100
nnnnnnnnnn nnnnnnnnnn nnnnnnnnnn nnnnnnnnng augccaacaa uccuaaugua 2160
augaugcccu cuucugacag cugcggggac cgcagagagg ucccauccca gaugcacucc 2220
ugaaaccugc uuuucuuuuu cuagcaacac caagaaggag ggggacuugu uggcugcgca 2280
ggcccggcuc aaggaccucg aggcucuucu caacuccaag gaagcugccc ugagcacugc 2340
ucucagugag aagcgcacau uggagggcga gcuccaugac cugcgggggc agguagccaa 2400
gguaggccgc uguccuguga ccccagugac cccaccuggu ccgacauauc auucgguccc 2460
auuugccugc ucaccuucac uucuccaguc uagannnnnn nnnnnnnnnn nnnnnnnnnn 2520
nnnnnnnnnn nnnnnnnnnn nnnnnnnnnn nnnnnnnnnn nnnnnnnnnn nnnnnnnnnn 2580
nnnnnnnnnn nnnnucuaga uggggacagc caucaccucu ccuuuggcau uuccugaacc 2640
cccucccacc ucuccaugaa cuuggcuuuc ucccucucag cuugaggcgg cccugggaga 2700
ggcuaagaag cagcuucagg augagaugcu gaggcgagug gaugcugaga acaggcuaca 2760
gacgcugaag gaggagcuug acuuccagaa gaacauuuac agcgagguaa gcgucccgcu 2820
guacaggucu uucuuacugu ggacagcugg gaggggucac cuaauaaugc caggcuaagc 2880
gagggcugcc cgugccuggc cgguggaguu acgacuucug gucucagcuu cuaaggaacc 2940
auugcgaugu ucuaaucuaa gugucucccc uuaaccuuuc aggaacugcg ugagaccaag 3000
cgccggcaug agacgcggcu uguggagauc gauaacggga agcagcgaga guuugagagc 3060
cggcuggcag augcccugca ggagcugcgg gcucagcaug aggaccaggu ggaacaguau 3120
aagaaggagc uagaaaagac auacuccgcc aaggugcugg ccucauccug uccucucccu 3180
ggugcugccc uggggacggg uggguggugg caggggggcca gggaugccuu ccucaggccc 3240
ccagcuccag guuccugcuc ucauaacugu gugcucccug cagcuggaua augccaggca 3300
gucugcugag aggaacagca accucguggg ggcugcccau gaggaacugc agcagucucg 3360
aauccgcauu gacagccucu cggcccagcu cagccagcuc caaaagcagg ugacccucag 3420
uuuaccccuc ccaccuuggc ucuggucuaa gcagauacug cagaagccca cugagaaggg 3480
gguggggggag ggacuccagg accacaugcu augguucuga aucugaugcc ugucuggcuu 3540
uccagggcuc uccuuuagcu agcccugauc cucagagccu cuauuuuacu gugcaugaag 3600
gguuuuucau guuucuucug ugccugccgg agacugaacc agaggccucu ugcuugguag 3660
auaggugcuu ucucacugag uuacaaaccc agccgcauuc ccuacuugga gauagagcuu 3720
cccuuggacu ggacauguag cucaguuggu acagugcuug cuuauuauac acgauggccu 3780
ggcuucuauc cccaggaccn nnnnnnnnnn nnnnnnnnnn nnnnnnnnnn nnnnnnnnnn 3840
nnnnnnnnnn nnnnnnnnnn nnnnnnnnnn nnnnnnnnnn nnnnnnnnnn nnnnnnnnnu 3900
```

cuagagagag ccuacagauc cugagugucc cucugccugc cccugugccc cucccucuuc 3960
aucgacauca gcccuuggga gcucaucaga cccuuugucu uccccgcccc aguuggcagc 4020
caaggaggca aagcugcgug accuggagga cucgcuggcc cgugagcgcg auaccagccg 4080
gcgccugcug gcugagaaag agcgagagau ggcggagaug cgggcgagga ugcagcagca 4140
gcuggacgag uaccaggagc ugcuggacau caagcuggcc cuggacaugg agauccaugc 4200
cuaucgaaag cugcuggagg gcgaggagga gaggugaacu aggaggggguc uacagaacuu 4260
gucaggggcc ucuggccgca acuaccauga cuaaccccgc accgugucuc caccuucccc 4320
aggcugcgcc ugucccccag cccuaccucg cagcgcagcc guggccgcgc cuccucccac 4380
ucaucccagu cucagggugg aggcagcguc accaaaaagc gcaagcugga gucuuccgag 4440
agccggagca gcuucucgca gcaugcucgc acuagcgggc guguggcggu agaggaaguc 4500
gaugaagagg gaaaguucgu gcggcugcgc aacaagucca acgaggugggg ccugugaacc 4560
agggugggucu uuucaguggc ugggaguucu ugguucucgu ggagcaucug ucucccuauc 4620
ugagaauuug gagugugugg uaguccuguc aucuuuaaau uguugggaag augcaugaua 4680
uagggauggg ugacccuuga gccaauaguc uagguuugau gccagaggua gugguggaag 4740
ccugucuuuc uuuucuuuuu cuuuuucuuu uucuuuuucu uuuucucuuu cuucucucuu 4800
uuuuuuuuuu ccgauggggu cuugcccagg uuggcuuuga ucucccuagu uaagcuguuc 4860
cccugccuca gccuccauag uagcuggaac ugcaggngca cacuggcgnc cagccuaccu 4920
aagcuccuga gugagauaau ccaagagucg guugaacucc cuguccuccu uccuccuucc 4980
uccuuccucc acccuacuuc aggaccaguc caugggcaac uggcagauca ggcgucagaa 5040
uggugacgau ccuuugauga ccuaucgcuu cccaccgaag uucacccuaa aggcugggca 5100
ggugguggacg gugaguggaa gggcacuugg gacucuggcu ggaguggaga aguuggccuc 5160
aggacaggag cauuaaaaau aagcacaucu cuuaaaccau cuuuucccag aucugggcuu 5220
caggagcugg ggccacccau agcccccccua cugacuuggu guggaaggcg cagaacaccu 5280
ggggcugugg gagcagccuu cgcaccgcuc ucaucaacuc cacuggagaa gugaguaugu 5340
ugcagccggu agcuugcugg acaaggcucc cccgggugac cauaauggga acuagcuacc 5400
uccaacccaa gggaaccugc cuuggguuua ggaucgcuuu ccugagccca agucccaccc 5460
aguaagcaag ccagaagucu ccccaguaga auaaugggug gaagucagcc agugaguguu 5520
aauagcagac uccagcuuac agagcaccga gcucucaguu guguccuuuu ugcgcgugcg 5580
ugcgcgcgug ugcacaugug cauguguuua uccuuagucc ccagcaucag agguuggaca 5640
agguuguaua aaggcccggg acaguucuaa gugguuacua uggguagaca ggcugcacag 5700
cccucacccc cugacucuug ggccugggcu uaugucccca caggaagugg ccaugcgcaa 5760
gcuggugcgc ucacugacca ugguugagga caaugaggau gacgacgagg auggagaaga 5820
gcuccuccau caccaccgug ugaguggcag ccgccgcuga ggcccagccc acaaggguag 5880
cccugccagc cuagggcagc ucucccaccu ccaugccaaa gucuuuucau uaaagaaugu 5940
uuuggaaugc cacuugcugc ccuggccuuu cuucucucuc cucccucuac cuugaacagg 6000
gaacccaggu gucugguaag gaagggagug gggacuugcu gaugccaugg auacuccacg 6060
gugggcagugg acaggguucu ggauuugugu ccugggaagg ggcugggagg acagaggugg 6120
ccccagcccu gccucucuuc cucacuccca uugcaugcac acuucucucc ucucuccuuc 6180
cacccuauug caugcuucuc cucagauuuc ccugcaacaa uguucucuuu ccuuccuguc 6240

```
cccucacaaa uuaagucucu ccaucuuugc ucuuccucuu gauugcccca uaagugucua   6300
agauucagga gagaguuaaa gccacagcuc uuuauuucga aggcuuccug gcuauuuccc   6360
ccaucaugcc cuuccuccca gccacagguc ucccaagucc ccaucacuug guugucuggg   6420
uacagacaga ggucaccuuc cugcccaaug gccaggaagc uccaagagcc cacagccuag   6480
gugccggucc uaagaaguca gucccaaacu cgcugucccu ccugagccuu gucucccuuc   6540
ccaggguucc cacugcagcg gcucgggga ccccgcugag uacaaccugc gcucacgcac   6600
cgugcugugc gggacgugug ggcagccugc ugacaaggcu gccgguggag cgggagccca   6660
ggugggcgga uccaucuccu cuggcucuuc ugccuccagu gucacaguca cucgaagcuu   6720
ccgcagugug gggggcagug ggggugcag cuucggggac aaccuaguca cccgcuccua   6780
ccuccugggc aacuccaguc cccggagcca ggugagucau cucugcccua cagcaggaca   6840
cugcucacug agcagcaggg cagggcagcc caagggagug ggguccccccu ccuugcaguc   6900
ccucuugcau ccugccccuc cugucugaac cccagacucg aggucagggc aaggcccaga   6960
gugugagggu uggggagaca accccuuugg ggucagggag ggagaggaag ggccagccac   7020
ugcugcucac accucugccu ucucuucucu cuuagagcuc ccagaacugc agcaucaugu   7080
aaucugggac cugccaggca gggcuggggg cagaggccac cugcuccccc cucaccacau   7140
gccaccuccu gucugcuccu uaggagagca ggccugaagc caaagaaaaa uuuaucccccu   7200
gccuuugguu uuuuuuuuc uucuauuuuu uuuucuuuuu cuaagagaag uuauuuucua   7260
caguggguuuu auacugaagg aaaaacucaa gcaaaaaaaa aaaucuuuau cucaauccua   7320
aguccuuccc cuuucuuucc uuguaucugc cuuaaaacca aagggcuucu cuaggagccc   7380
agggaaagga cugcuuuuua uagagucuag auuuuugucc ugcugccuug gcuuuacccu   7440
caucccagga cccugugaca auggugccug agaggcaggc auggaguucu cuucaccagc   7500
cuccuccaac agcuggccca cugccacgcc agcugcagag aaauggggcg cagagaggau   7560
gacugagaag gucaagcccc ucccggcac uacacgaggc cgaggcuccu cugccugccu   7620
uaccuucuuc cugcccuucc cuagccuggg gcgaguggau ucccagaggc aaaucugccg   7680
ugcuugcuuu uucuauauuu uauuuagaca agagauggga augacgggga aggagaaggg   7740
aagaucaguu ugagccuacc uuuucccagc uucugagccu ggugggcucu gucucaauga   7800
uggagggcaa ugucaagugg gauacaggga agagugggggg acgaaggcuc ccagagaugg   7860
ggagaaccug cuggggcugg ugagaagucu agaggugcgg cgauuggugg cuacagcaaa   7920
cacuaaggaa cccuucaccc cauuucccau cugcaccucu gcucuccccu ccaaaucaau   7980
acacuaguug uuuccauccc agaugcugug gugucucuuu guugggugug augugguuuu   8040
ucaggggcag acacaugcac acagaggugc cacacauuca cuauauauuc acuacccagc   8100
uauaaaggug uguaugaggg agacuucuag aaaggucagc auaugugggg ugagcgaggg   8160
guguccuucc uaucccucau ccauccagca ccuuuuaaaa ggggccagca auccacaugu   8220
gcaucagaca caggagcaca gagagacgga ggguagagua gggcagagua gcagagcuuc   8280
cuugcugccc uguagucgca ggcucuugau cgugugaucg cu                      8322
```

<210> SEQ ID NO 184
<211> LENGTH: 1054
<212> TYPE: RNA
<213> ORGANISM: Homo sapiens

<400> SEQUENCE: 184

```
gcggugcgaa gcgggccucc gccaacaugu acuacaaguu uagcaguuuc acgcagaagu     60
```

uggcuggagc uugggcuucg gaagccuaca ccccgcaggg guuaaagcca guuuccacag 120
aagcaccacc uaucauauuu gccacaccaa ccaaacugac cuccagugug acagcauaug 180
auuauucugg gaagaacaaa guuccagagc ugcagaaguu uuuccagaag gcugaugguu 240
uccaccugaa acgaggccuu ccagaccaaa ugcuuuaccg gaccaccaug gcucugacac 300
ugggagggac caucuacugc cugaucgccc ucuacauggc cucgcagccc agaaacaaau 360
gagcuugccu guggaggacu gguucacuuu guggcacaaa cccuuugaau ccucacguuu 420
cauguuuucc acuuggauag ucuacuuaac auuuugcaaa caaaggaaaa gauaagaaua 480
cauuguuuug auuuguuuau ggugugcaga uggccuguca gaugucagag cugguuugac 540
aguuaaaacu auuguuuaag gaaaugucac ugagccauca cugagcugug cuucugcucc 600
ugauuucccu ggaguucugc aggaaaguug cucuccagcu cauucguggc cagccgugcu 660
cagggccucg ggacucaggc ggugucugag cgggaagcga acgcggaagc cuuuuggagu 720
guagguguga uugaggaagg aaaacaaaag ccagcggaca gguggugaag ugagggcuga 780
guuagccacc cuagggauuc guccgccuug cagaaaacau ugagaggaau gauagcaacc 840
ugccucuauu ugugggcagu ugguuucaaa ggguugugug ucucgcccag aaccuaggga 900 aaugggguguu uguuccaucg ugggaggagc accugucagu gcugcacauu agacagcugu 960
gucaggacuu cuccuuuaau aaugcugugg cuuuacguua ugauugaccg gacugcggaa 1020
uaaacacugg aaucaaaaaa aaaaaaaaaa aaaa 1054

<210> SEQ ID NO 185
<211> LENGTH: 4208
<212> TYPE: RNA
<213> ORGANISM: Homo sapiens

<400> SEQUENCE: 185
cugagacaga acgaaacguc cgcagauaac uacccguucu ggcucuuguu aguucuaugu 60
guauggauaa ugucuuggga gguuuugaaa ugccacaagc cuugcuggcc cagggugcag 120
cugccucugc cguucagacc ucagauuaua aggacagaac acagcacgga agugggggga 180
ucagaaccau gggagaucca ggacgaaggg uccugugcgc aggugcggca ccgaauccua 240
uauuugacau ugaagcuguc gucagcccaa cuagugugu auuaacaugg aagcacaaug 300
acucaggcgc uucagaaugu agaauagaga auaagaugga gagcaaucug acguuuccug 360
uuaaaaacca gacaucaugu aacauuacag gcuuaagccc agguacuucg uauacauucu 420
ccaucaucuc uguaacaacc aaugagaccu ugaacaaaac uaucacaaca gagcccuggc 480
cagugucuga ucuccauguc accucugugg gugugacaca ggcucgucuc accuggagca 540
augcaaaugg cacugccucc uaccggaugc ugauugaaga guugaccaca cauuccucag 600
ucaauauuuc aggucugaag ccggggacca auaauacguu cgcuuuccca gaaucaaaug 660
agacacaggc ugacuuugca guugcagagg aggucccgga ugccaauggu accaagagaa 720
ucccagugac caaccuaucc caaccacaca agaauucucu ugccucugug gacccacccu 780
cuggccagga ucccucccuc acagagaucu ugcuuacuga ccuaaagccu gauacucagu 840
acaaugccac caucuauucu caagcagcaa auggcacuga aggacagccc aggaacaaag 900
uguuuaaaac aaauuccacc cagguuucug acguccgagc uaugaacauc agugccucaa 960
gcaugacccu gaccuggaaa agcaauuacg augggucccg uacuucaauu gucuacaaaa 1020
uacacguggc ugggggggac cacuccguca accaaacugu caauaagacu gaggccauca 1080

-continued

```
uccucggacu cagcuccagc accuuguaca acaucacagu ucauccuuuc cugggucaga   1140

cggagggcac accaggcuuc cuccaagugu acacuucccc cgaucagguc ucugacuucc   1200

gagugacaaa ugucagcaca agggcaauug guuuggcuug gaggagcaau gacuccaagu   1260

ccuucgagau uuucaucaag caggacggag gugagaagca ucgaaaugcu ucgacgggaa   1320

accagagcua uaugguugaa gauuuaaagc cuggaaccag uuaccauuuu gagauaaauc   1380

cacgaggacc agacgggaca gaagggcugu ccaguacagu gaaugggagc acugacccca   1440

gugccgugac ugacauccgg guggucaaca uuagcaccac ugaaaugcag uuggaguggc   1500

agaauacgga cgaugccucu ggauacacuu accauuuagu ucuagagucu aaaaguggcu   1560

ccaucaucag gaccaacagu ucucagaagu ggaucacagu agggagccuc accccaggca   1620

ccuuauacaa ugucacaauc uuuccagaag uggaccagau ccagggaauc uccaacucca   1680

uuacccagua cacacggccc agcagugugu cccacauuga aguaaacacc accaccacca   1740

cggcagccau ccgauggaag aacgaggaca cagccucugc uuccuaugcc uacuccgucc   1800

uuaucuugaa gacuggagau ggcagcaaug uaaccagcaa cuucacaaaa gacccuucua   1860

uucuaauccc ugaguuaauc ccuggcgucu cuuacacagu gaagauccuu acacaaguug   1920

gggaugguac aacaucacug guaccugguu ggaagcuguu cuguacggaa ccugaaucag   1980

ugaccuccuu ccacugugaa gugguccoua aggagccagc auugguucuc aagugggccu   2040

gccccuuugg cauguacaca ggcuucgagc ugggggucag gagugauucc ugggacaaua   2100

ugacacgccu agagaacugc acaucggaug augacacaga gugcaggacg gaagucgccu   2160

auuugaauuu uucuaccucg uacaacauca gcaucgccac cuugucaugu gggaagaugg   2220

cgcuucccgc ccagaacauc ugcaccacug gcaucacaga cccaccuacu ccggauggau   2280

ccccuaauau uacaucgguc agucacaauu caguaaaggu uaaguucagc ggguuugaag   2340

ccagccacgg accuaucaaa gccuaugcug ucauccucac caccggggaa gcugcccaac   2400

cuucugcaga uguuuugaag uacacguaug aggauuucaa aaggggagcc ucggauacuu   2460

augucacaua ccucauaaga auagaagaga agggacaguc ucagggcuug ucugaagucu   2520

ugaacuauga aauugaugug gggaaccaau ccacuacccu cggcuacuac aacgggaggc   2580

uggagccucu gggcuccuac cgggauugug uugcuggcuu uaccaauauu accuacaacc   2640

uucagaauga cggccucauc aaugggggaug agagcuaugu gucuuucagu ccauauucag   2700

aggccguguu cuugccccag gauccaggug ucaucugcgg agcaguguuu ggauguaucu   2760

uuggugcccu ggccaucaca gcugugggag gcuucaucuu cuggagaaag aaaaggacag   2820

augccaagaa uaaugaagug uccuuuucuc aaauuaaacc uaaaaaaucc aaguuaaucc   2880

gaguggagaa uuuugaggcc uacuuuaaga aacagcaagc ugacucuaac uguggguuug   2940

cagaggaaua ugaggaccug aagcugauug ggauaaguuu accuaaauac acagcugaga   3000

uagccgagaa cagagggaag aaccgcuaca acaauguucu gcccuaugau auuucucgag   3060

ucaaacuuuc aguccagacc cauucgacag augacuacau caaugccaac uauaugccug   3120

gcuaccauuc caagaaagau uucauugcca cacaaggacc uuuacccaac acuuugaaag   3180

auuucuggcg uaugguuugg gagaaaaacg uauaugccau uguuauguug accaaaugcg   3240

uggagcaggg aaggaccaaa ugugaggagu acuggccuuc caagcaggcu caggacuacg   3300

gggacauaac uguggcgaug acaucagaag ucguucuucc agaauggacc aucagagauu   3360

uuguggugaa aaauaugcag aauagcgaga gccauccucu gcggcaguuc cauuucaccu   3420

ccuggccuga ccacgguguu ccugacacca cugaccugcu caucaacuuu cgguaccugg   3480
```

uccgggauua caugaagcag auacccccg agucaccaau ucuggugcau ugcagugcug 3540
ggguuggaag gacgggcacu uucaucgcca ucgaucgccu gaucuaucag auagagaaug 3600
agaacaccgu ggacguguau gggauugucu augaccuucg gaugcacagg ccucugaugg 3660
ugcagacaga ggaccaguau guuuuccuca aucagugugu uuuggauauu aucagagccc 3720
agaaagacuc aaaaguugau cucaucuauc agaacacaac ggcaaugaca aucuaugaaa 3780
accucgagcc aaguuccuug aaugugacua uguugcuuca uccacagcug aacgauuuug 3840
gauguugggu ucuagguccu ggcuguugcu ggucugcuag gauccagggc cuuguugaca 3900
ucugggaaga uguaaauugu cccgcugaag gccgcaguuu uagauguggc cacuagaugg 3960
agccagagca cugguaugaa ggagcaccag ggccguguaa ggcaaaagag gacccagaaa 4020
aagaaacuua acuuguucac uccugagaaa ccugcaaguc aacaagccaa ggaagugccu 4080
uugcaugcau uugguagccu uuccaauccc gcuuauuaca uaauauguuc auguucaugg 4140
caaaaaaaaa aaaaauaaaa uaaaauaaau aaaaaaggaa aacaaaauaa aaaaaaucuu 4200
agaacauu 4208

<210> SEQ ID NO 186
<211> LENGTH: 249
<212> TYPE: RNA
<213> ORGANISM: Homo sapiens

<400> SEQUENCE: 186
gcccccucaa gggcauccug ggcuacacug agcaccaggu ggucuccucu gacuucaaca 60
gcgacaccca cuccuccacc ugacgcuggg gcuggcauug cccucaacga ccacuuuguc 120
aagcucauuu ccugguauga caacgaauuu gcuacagcaa cagggugugg accucauggc 180
ccacauggcc uccaagguaa gccccuggac caccagcccc agcaaggcac aagaggaagg 240
agagacccu 249

<210> SEQ ID NO 187
<211> LENGTH: 410
<212> TYPE: RNA
<213> ORGANISM: Homo sapiens

<400> SEQUENCE: 187
uuuuuuuuuu uuuuuuucau auuaaacuug uaguuuuauu cagguuugau uuuuaacaaa 60
ugugucaggg agagagccca caggaaaggg uaaagcccgu gggggcaagg ccuucccaga 120
ugccugagga gggaucgugu ccccuccccc ccuccucuuc ucaccacccc uacaggggguu 180 ugggaagaga cacaggcagg gaaggggcug guccccaguc uguacagugg ugcuuggggg 240
ugaaggacua uggagaacag gggaccagau cggggaugag uaggauaaag ggcacaagac 300
cauuuaccag aauccagcuu ucugauucca aauugaauua aaaagaaaaa aaggagaggg 360
gaaccuaaac cacaagcagu acccaacucc cuuuccccca ucagggcugc 410

<210> SEQ ID NO 188
<211> LENGTH: 382
<212> TYPE: RNA
<213> ORGANISM: Homo sapiens

<400> SEQUENCE: 188
uuuuuuuuuu uuuuuuuagg gaagaggcug augccagaua aguuuuuauu auauuaaaaa 60
aaaaaaaaaa accagugcaa cuggaaauca gggugagucg cuggagguga gugagagucg 120

-continued gaaggcccuc cacaccucag ugguggcagg aucuggaccc guagccuaag ccuggucuga 180
uccagccgag augcuggaaa gcagagcaca cgguggugcc caucagggca aagagggcaa 240
gagagcccac ggcuccucca uaccgcuugc uagggucucc uguguaguag ccauaugcgu 300
aaaggacucg cccaauaauc caggccaggc ccaggccaga agcuaugcgc gggugguaaa 360
caccucccac cguuaggaaa aa 382

<210> SEQ ID NO 189
<211> LENGTH: 253
<212> TYPE: RNA
<213> ORGANISM: Homo sapiens
<220> FEATURE:
<221> NAME/KEY: misc_feature
<222> LOCATION: (32)..(32)
<223> OTHER INFORMATION: n is a, c, g, or u
<220> FEATURE:
<221> NAME/KEY: misc_feature
<222> LOCATION: (41)..(41)
<223> OTHER INFORMATION: n is a, c, g, or u

<400> SEQUENCE: 189
cggccgcgug aguuuugacu gagcuucugc angaaguuca naugcaacuc cauacaucag 60
uucauuuucu agcauuacca cuggguuauu aucacgaaug gccgauuuaa uaaguccuuu 120
ugcauccucg gaauuccagg ggcugaccac uuuuaaaccu gggcagugcc cauaccaugc 180
agcaaagcau ugcgagugcu gagcagcuac accugcugag gcgccauugg gcccccugaa 240
uacuaugggc aca 253

<210> SEQ ID NO 190
<211> LENGTH: 371
<212> TYPE: RNA
<213> ORGANISM: Homo sapiens

<400> SEQUENCE: 190
uuuuuuuuuu uuuuuuugaa gggccauugg aguuuauuua cagacaaccu uaggugaggc 60
cuuuuccucu aggaucuaca ugcuuuugaa guuacuuggu uucaggcuuc uugucuccag 120
cuucgagcuu gagacucuca ggaggcuggc gauaggcagg gaaagccucc caggggcugu 180
ucaggucaaa cuugcggaau ucuugugcca gcuccacugg uucagccacu acccgcuuua 240
ccucaucguc guaacgaagc ucaacauagc cagugagggg aaagucuuuc cggaaaggau 300
gucccucgaa gccauaaucu gucaggaucc uucuuaaauc agggugguua aaaaaaaaaa 360
aaaaaaaaaa a 371

<210> SEQ ID NO 191
<211> LENGTH: 324
<212> TYPE: RNA
<213> ORGANISM: Homo sapiens

<400> SEQUENCE: 191
uuuuuuuuuu uuuuuuuggg gggcagcgaa cuuuauugau gguauucaaa aaaauaggga 60
gggcucccua ggccccccu guuauuaugg gggucuggga uggaaauuuu gagggaaaug 120
cucaauuuug ggggcccauu ugggaaaagg ccccccuugc ccaauguccu ugcuggggug 180 gguggucaa gguuucuuac uccuuggagg ccauuuuggc caagaggucc accacccugu 240
ugcuguagcc guauucauug ucaaaccaag aaaugagcuu gacaaauuug ucauugaaaa 300
aaaugccaac cccggaauca aagg 324

<210> SEQ ID NO 192
<211> LENGTH: 2110
<212> TYPE: RNA
<213> ORGANISM: Homo sapiens

<400> SEQUENCE: 192
gcuccucauc ucacucgggc cuaugccaaa gauguaaaau uuggugcgga ugcucgagcc 60
uuaaugcuuc aaggguguaga ccuuuuagcc gaugcuguag cuguuacaau ggggccaaag 120
ggaagaacag ugauuauuga acagaguugg ggaaguccca aaguaacaaa agauggggc 180 acuguugcaa agucaauuga uuuaaaggau aaauacaaaa auaucggagc uaagcuuguu 240
caggauguug ccaauaacac aaaugaagag gcuggggaug gcaccaccac ugccacuguu 300
cuggcacggu cuauugccaa ggagggcuuu gagaagauca gcaaaggggc uaauccagug 360
gaaauccgga gaggugugau guuggcugug gaugcuguaa uugcugaacu uaagaaacag 420
ucuaaaccug ugacaacccc ugaagaaauu gcucagguug cuacaauuuc ugcaaacgga 480
gacaaagaca uugggaacau cauuucugau gcaaugaaga agguuggaag aaagggugucc 540 aucacaguga aggauggaaa aacccugaau gaugagcuag aaauuauuga aggcaugaag 600
uuugauagag gauauauuuc cccauauuuu auuaacacau caaaagguca aaaaugugaa 660
uuccaagaug ccuauguuuu guugagugaa aagaaauuuu ccaguguuca guccauuguc 720
ccugcucuug aaauugcuaa ugcucaucgg aagccauugg ucauaaaucgc cgaagauguu 780 gacggagaag cucuaagcac gcugguuuug aacaggcuaa aaguuggucu ucagguugua 840
gcagucaaag cuccaggguu uggggacaac aggaagaacc agcuuaaaga uauggcuauc 900
gcuacuggug gugcgguguu uggagaagag gguuugaauc uaaaucuuga agauguucaa 960
gcucaugauu uagggaaagu uggagagguc aucgucacca aagaugaugc caugcuuuug 1020
aaaggaaaag gugacaaagc ucacauugaa aaacguauuc aagaaaucac ugagcagcua 1080
gacaucacaa cuagugaaua ugaaaaagaa aagcugaacg agcgacuugc uaaacuuuca 1140
gauggaguag cuguguugaa gguuggagga acaagugaug uugaagugaa ugagaagaaa 1200
gacagaguua cugaugcucu caaugcuaca agagcagcug uugaagaagg cauuguucua 1260
ggagggggcu gcgcucugcu ucggugcauc ccagccuugg auucauuaaa gccugcuaau 1320
gaagaccaga aaauagguau agaaauuauu aaaagagcac uuaaaauucc ugcaaugacg 1380
auugcuaaga augcaggugu ugaaggaucu uugauaguug agaaaauucu gcagaguucc 1440
ucagaaguug guuaugacgc caugcuugga gauuuuguga acauggugga aaaagggauc 1500
auugauccaa caaagguugu gagaacugcc uuacuggaug cugcuggggu ggccuccuug 1560
cuaacuacag ccgaagcugu agugacagaa auuccuaaag aagagaagga cccuggaaug 1620
ggugcaaugg guggcauggg agggggguaug ggaggcggca uguucuaacu ccuagaguag 1680
ugcuuugccc uuaucaauga acugugacag gaagcucaag gcagguuccu caccaauaac 1740
uucagagaag ucaccuggag aaaaugacug aagagaaggc uggcugacca cuguaaucau 1800
caguuacugg uuuccuuuga cgauauauaa ugguuuacug cugucauugu ccaugccuac 1860
agauaauuua uuuuguauuu uugaauaaag aacauuugua cauuccugau gcugguugca 1920
agagccauau accagugucc ugcuuucaac uuaaaucacu gaggcaucuc uacucuucug 1980
ugagucauca ggacuguagc gcugugucaa caaaacauag agaguucaga agacagccuu 2040
ucuguggaag ggugggaaug auuguguaca aaguagagaa guauccaauu augugacaac 2100
cuuuguguaa 2110

<210> SEQ ID NO 193
<211> LENGTH: 1228
<212> TYPE: RNA
<213> ORGANISM: Homo sapiens

<400> SEQUENCE: 193
acagccgcau cuucuugugc agugccagcc ucguccccgua gacaaaaugg ugaaggucgg 60
ugugaacgga uuuggccgua uugggcgccu ggucaccagg gcugccauuu gcaguggcaa 120
aguggagauu guugccauca acgaccccuu cauugaccuc aacuacaugg ucuacauguu 180
ccaguaugac uccacucacg gcaaauucaa cggcacaguc aaggccgaga augggaagcu 240
ugucaucaac gggaagccca ucaccaucuu ccaggagcga gaccccacua acaucaaaug 300
gggugaggcc ggugcugagu augucgugga gucuacuggu gucuucacca ccauggagaa 360
ggccggggcc cacuugaagg guggagccaa acgggucauc aucuccgccc cuucugccga 420 ugccccccaug uuugugaugg gugugaacca cgagaaauau gacaacucac ucaagauugu 480
cagcaaugca uccugcacca ccaacugcuu agcccccccug gccaagguca uccaugacaa 540
cuuuggcauu guggaagggc ucaugaccac aguccaugcc aucacugcca cccagaagac 600
uguggauggc cccucuggaa agcuguggcg ugauggccgu ggggcugccc agaacaucau 660
cccugcaucc acuggugcug ccaaggcugu gggcaagguc aucccagagc ugaacgggaa 720
gcucacuggc auggccuucc guguuccuac ccccaaugug uccgucgugg aucugacgug 780
ccgccuggag aaaccugcca aguaugauga caucaagaag guggugaagc aggcaucuga 840
gggcccacug aagggcaucu ugggcuacac ugaggaccag guugucuccu gcgacuucaa 900
cagcaacucc cacucuucca ccuucgaugc cggggcuggc auugcucuca augacaacuu 960
ugucaagcuc auuuccuggu augacaauga auacggcuac agcaacaggg ugguggaccu 1020
cauggccuac auggccucca aggaguaaga aacccuggac cacccacccc agcaaggaca 1080
cugagcaaga gaggcccuau cccaacucgg cccccaacac ugagcaucuc ccucacaauu 1140
uccaucccag acccccauaa uaacaggagg ggccuaggga gcccucccua cucucuugaa 1200
uaccaucaau aaaguucgcu gcacccac 1228

<210> SEQ ID NO 194
<211> LENGTH: 723
<212> TYPE: RNA
<213> ORGANISM: Homo sapiens

<400> SEQUENCE: 194
agaagcuucc uaaggaacaa gcaaguugaa uagagaaaau agugaucaau aauaggcauu 60
uuaguggucu uuuuaauguu uucugcugcg gaacauuuca agauuuauug auuuccuccu 120
ccccccauuu uuuucccacc acacucacac acgcacgcuc acacuuuuua uuugccauaa 180
ugaaccgucc agccccugug gagaucucuu augagaacau gcguuuucug auaacucaca 240
accccaccaa ugcgacucuc aacaaguuca cagaggaacu uaagaaguac ggagugacaa 300
cuuugguucg aguuugugau gcuacauaug auaaagcucc aguugaaaaa gaaggaaucc 360
acguucuaga uuggccguuu gaugauggag cuccaccccc uaaucagaua guagaugauu 420
ggcuaaaccu guuaaaaacc aaauuucgug aagagccagg cuguugugu gcagugcauu 480 guguugcagg auugggaagg gcuccugugc uaguugcgcu ugcauugauu gaaugcggaa 540
ugaaguauga agaugcuguu caauuuauaa gacaaaaaag aagaggagca uucaauucca 600
aacagcugcu uuacuuggag aaguaccgac cuaagaugcg guuacgcuuc agagauacca 660
augggcacug cuguguucag uagaaguaga agcaggcugg cuggaucgug gcauuagagg 720
gaa 723

<210> SEQ ID NO 195
<211> LENGTH: 2690
<212> TYPE: RNA
<213> ORGANISM: Homo sapiens

<400> SEQUENCE: 195
auucagguuc cucacagacc caggggguga ggauguugcu uuuugcccac uugcuucagc 60
ugcuggucag cgccacaguc ccgacccaga guaguaagug aggggagggg ugaggggagg 120
gguugggagc gaaaaagacu cugugaggaa aagcgggagg gugguggugg cggaggugca 180
gcaccccaag uuccgccgcc cuguccuagu cccuccccg ccuuuaccug ggaccuugag 240
ccugggggag gucggggucu caccgcgcgc cgcccccagg cccacacucg cugcgguauu 300
ucaccaccgc cgugucccgg cccggccucg gggagccccg guucaucauu gucggcuacg 360
uggacgacac gcaguucgug cgcuucgaca gcgacgcgga aaauccgagg auggagccuc 420
gggcgcggug gauugagcag gaggggccgg aguauuggga gcgggagacu uggaaagcca 480
gggacauggg gaggaacuuc agaguaaacc ugaggacccu gcucggcuac uacaaucaga 540
guaacgacgg ugagugcggc ugggaucaca gcuaugauca cucccauguсс ccugagacgg 600 gccuggguca ucuugacccg cugagacaaa guuucaucca aacgccuacc cagaaccuca 660
gacaaaaaag cccccgcaga guucugcuua gguuuggggu uguacuuuug uuucucuuuu 720
guuuugagau aucuacuaac auugggcaaa guggccacag guggcgcuca ucagcguauc 780
ccuuccagaa ucucacacgc ugcaguggau guacggcugc gacgugggc ccgaugggcg 840 ccugcuccgc ggguauuguc aggaggccua cgauggccag gauuacaucu cccugaacga 900
ggaccugcgu uccuggaccg cgaaugacau agccucacag aucucuaagc acaagucaga 960
ggcagucgau gaggcccacc aacagagggc auaccugcaa gguccuugcg uggaguggcu 1020
ccauagauac cuacggcugg gaaaugagac acugcagcgc ucaggugccc uggagagcuc 1080
uccucacuuu uccucugcgg uuuggggaa auccuugagg uauaaccuca ggggcagaac 1140
gcuguucagc gggcacagcg cggaggagga gggagaggga cucccaaaac ugcuuuuccc 1200
cuguagggau ucuaauccuu aacaaaagca gaucaggcuc gacaauggcc cuggacccau 1260 gggggaggg ggcucuuucu caggccuccc uccuugcccu acucaguguc ucuauaguca 1320
gacuccagcu uuucucaauc ucuuggcccu cauccagcuc aggaccagaa gcccuuccca 1380
ugagucugca gagaccugga gccuccuguc cauguugucc ugcucacauc cuaaggcauc 1440
ccuaagagca gauccuccca ggugcaggug cucuagcugg ugucuagaug auggacacca 1500
uaaucccacc gcaguccucc uguccacccc aggacgguca caugaacacu gcugaguccc 1560
cagaagaaag caagaugccu cauccuuuca acucucuccc ucagacccuc caaaggcaca 1620
ugugacccau cacccuagau cugaagauga agucacccug aggugcuggg cccugggcuu 1680
cuacccugcu gacaucaccc ugaccuggca guugaauggg gaggagcuga cccaggacau 1740
ggagcuugug gagaccaggc cugcagggga uggaaccuuc cagaaguggg cagcugucgu 1800
ggugccucuu gggaaggagc aguauuacac augccaugug uaccaugagg ggcugccuga 1860
gccccucacc cugagauggg guaaggaggg ugugggugcu gaacuggggu cagggaaagc 1920
uggagccuuc ugcagacccu gaguugguca uggcucagag cugggaucau aacccucacc 1980

-continued uucauuuccu guaccugucc uucccagagc cucccuccauc cacugucucc aacaugguaa 2040
ucauagcugu ucugguuguc cuuggagcug ugaucauccu uggagcugug guggcuuuug 2100
ugaugaagag gaggagacac auagguagga aagggcaggg ucugaguuuu cucucagccu 2160
ccuuuugcag ugugcucugc uccuuaaugg gaaacauagc cacacccaca uugcugcagu 2220
cuccaacugg gucagcuguc aguuccggga acucccuagg gcugguguuu cucuggucuc 2280
ucauggcuuu ucuucucaca gguguaaaag gaugcuaugc ucauguucua gguaagugcg 2340
agagaggggc aggggacacc cuuguccug aggcucucag gauggagcug ggauuuguuc 2400
cagcccauaa ucuccucuug ccacauccuc ucugucuccu cugugugccu uguuaucucu 2460
ucuacugcag gcagcaagag cuuccagacc ucugacuggc cucagaaggc augaaaaucc 2520 cuggggggc uggugagaug gcucaguggg uaagagcacu gacugcucuu cugaagguce 2580 agaguucaaa ucccagcaac cacauggugg cucacaacca uccguaacga gaucugacuc 2640
ccucuucugg agugucugaa gacagcuaca auguacuuac auauaauaaa 2690

<210> SEQ ID NO 196
<211> LENGTH: 269
<212> TYPE: RNA
<213> ORGANISM: Homo sapiens

<400> SEQUENCE: 196
uuuuuuuuuu uguucccuug aaagccagau guuccaaaaa guagccugcu ccauuguucu 60
ucucagucuc auagcgacug ccagcgucaa uccacacucc caccgugcag guagcaugcg 120
aggacugcuc cgaggccaca cgcagcccgu uguccaagau gcugaccugg gucuccggca 180
cgcucuggag ggccugggcg aagguugcgg uaccccgcaa ggcagguaac cucagcaggg 240
ccggcgagcg gcgggugcgc cucgugccg 269

<210> SEQ ID NO 197
<211> LENGTH: 1335
<212> TYPE: RNA
<213> ORGANISM: Homo sapiens

<400> SEQUENCE: 197
ggugcuuaau guuuugaccu guagaggucc ucacuuuucg ucauggcgcu gaagguggcg 60
auagcugcug gcggugcugc aaaggcaaug cucaagccaa cucuccucug ccguccuugg 120
gagguucugg cugcccaugu ggcccccga aggagcauuu ccucacaaca aacaauuccu 180
ccaucugcua aguauggugg gcggcauaca gugacuauga ucccagggga uggcaucggc 240
ccagagcuca uguugcaugu uaagucugua uucaggcaug caugugugcc gguggacuuu 300
gaagaggugc auguaagcuc caacgcugau gaggaggaca uccgcaaugc caucauggcc 360
auccgccgga accguguggc ccugaagggc aacauugaaa caaaucauaa ccugccacca 420
ucccacaaau cucgaaacaa cauccuucgc accagccuag accucuaugc caacgucauc 480
cacuguaaga gccugccagg aguggugacc cggcacaagg acauagacau ccucauugua 540
cgggaaaaca cagaaggcga guacagcagc cuggagcaug agagcguagc aggagguggug 600 gagagcuuga agauuaucac caaagccaag ucccugcgca uugcugaaua ugcuuucaag 660
cuggcccagg agaguggggcg uaagaaagug acggcugugc acaaggccaa caucaugaaa 720
cugggugaug gacucuuccu ccagugcugc agggaaguag cagcccacua cccucagauc 780
accuuugaca gcaugauugu agacaacaca acaaugcagc ugguaucccg gccucagcag 840
uuugauguca uggugaugcc uaaucucuau gguaacauug ucaacaacgu cugugcaggg 900

-continued cuaguuggag gcccaggccu uguggcuggg gccaacuaug gccaugugua ugcaguauuc 960
gagacagcua caaggaacac aggcaaaagu auugccaaua agaacauugc uaacccgacu 1020
gccacacugc uagcaagcug caugaugcua gaccaccuca agcuccacuc cuaugccacu 1080
uccauccgca aagcugucuu agcauccaug gacaaugaaa auaugcauac cccagauauu 1140
ggaggccagg gcaccacauc ccaagccauc caggacauca uucgucauau ccgcaucauu 1200
aauggacggg cuguggaggc uuagcuaucc cuacaguuuu gcucagcuug ucuguaggac 1260
ucucuucuca cuuuagcacu ccagcuagcu ugggggacag gacccagaau aaagccacuu 1320
cuguuccaga aaaaa 1335

<210> SEQ ID NO 198
<211> LENGTH: 382
<212> TYPE: RNA
<213> ORGANISM: Homo sapiens

<400> SEQUENCE: 198
uuuuuuuuuu uuuuuuuguu cuuaauagaa aacuuuauuu ucacugauaa ugucacugua 60
acauaauuuc auagcagacc ugugcaaaag aucccacauc accaaugucu ccaagagauu 120
ucacacacuu cugggcagga cgcacagcuc ugccccccacc cccguguuga cagucaacau 180
uuuacccccg cuaugaguac agaaaggcga ggcaucauaa cgaagccgcc ugaaggcagc 240
gugagcugaa gucggacgcu ugccaccucu gaaugaaugg ucaccacagc aacagcacau 300
gguugccuca gugugcucag ggugggucuu ugaaaaaacg ucccacuaug uaaauaugcu 360
gcacuuaucc cuucaacauu gu 382

<210> SEQ ID NO 199
<211> LENGTH: 1992
<212> TYPE: RNA
<213> ORGANISM: Homo sapiens

<400> SEQUENCE: 199
ggcagacaaa agaggccggc agugcagcuc gcgggacgca uggccgggcg cggaggacgg 60
gugcugcugg cgcugugugc cgcgcuggug gccggcgggu ggcugcugac gcgugaagcc 120
caggagcccg gggcgccagc ggcuggcaug aggcgccgcc ggcggcucca gcaagaggac 180
ggcaucuccu ucgaguacca ccgcuaucca gagcugcgcg aggcgcuggu gucgguaugg 240
cugcagugca ccgccaucag cagaaucuac acagugggcg ccagcuucga gggccgggag 300
cuccugguca ucgagcuguc ugacaacccc ggggguccaug agccgggugaa accugaauuu 360 aaauacaucg ggaacaugca uggcaaugag gcgguuggac gggaauugcu cauuuucuug 420
gcccaguacc uguguaacga guaccagaaa ggcaaugaga caauugucaa ccugauccac 480
agcacccgaa uucauaucau gcccuccuug aaccccgacg gcuuugagaa agccgcaugg 540
cagcccgggc agcugaagga cugguuugug ggccgcagca acgcccaggg aauagaucug 600
aaccguaacu ucccagaccu ggacaggauc guauauguua augagaaaga aggcgguccc 660
aacaaccacc ugcugaagaa ucugaagaaa auuguggacc aaaauucaaa gcuugccccc 720
gagaccaagg cugucauuca cuggaucaug gacauuccau uugugcuuuc ugccaaucug 780
cacggaggag accuuguggc uaauuaccca uaugaugaga cacggagcgg uacugcucac 840
gaauacaguu ccugcccuga ugacgcaauu uuccaaagcu uggcucgcgc guacucuucu 900
uucaacccag ucaugucuga ccccaaucga ccucccugcu gcaagaauga cgaugacagc 960

-continued agcuuugaug auggaacgac caaugguggu gcaugguaca gcguccccgg uggaaugcaa 1020
gacuucaauu accugagcag cagcaacugc uuugagauca cuguggagcu uacgugugag 1080
aaguucccac cugaagagac ucucaaaagc uacugggaag auaacaaaaa cuccccucauc 1140 aacuaccugg agcagauaca ccgaggguguu aaagggguuug uccgugaccu ucaggguaac 1200
ccgaaugcca acgcaaccau cucugguggau gggauagacc augaugucac cucggcuaag 1260
gauggggauu acuggcgauu gcuugcuccu ggaaacuaua aacuuacagc cucccgaucu 1320
ggcuaccugg caaucacaaa gaaaguggca guuccuuuua gcccugcugu uggggguggac 1380 uuugagcuug agucuuucuc ugaaaggaag gaggaggaga aggaagaauu gauggagugg 1440
uggaaaauga ugucagaaac uuugaauuuu uaagaaaggc uucuaacuaa uugcuuucau 1500
cuaucuauag acuguaguaa gaugcaaugu ggcucuuuuc uuuuagguug ugugcaguug 1560
auauuuaaca uugauuuauu uuugaucauu aaguaauagu uacuaaucac guaaauacac 1620
ccggacagaa auauaaaugcu ggacaucuuc auucuacauc aacauucgcu uaaaucauuc 1680
gaagccucuu uuaacguaau gggugacaau gucacuugac agaugcauga gagucacgau 1740
auagcugacu gugacccugc acugcaauca cauaguucca uauaaguugu ccuuagucuc 1800
uugugcugau ucacuguaua agcaugaucc ugguaaugca cuuuggaugg gaagaaaaug 1860
uacgugcuuu ucagaggggc ucugaacaga augaaaaccu aguucuugcg uguacuuuga 1920
agaauggaau uguauuaguc agcuguuaau gccacuucag aaguuugggg uuuugucuug 1980
auuguagauu gg 1992

<210> SEQ ID NO 200
<211> LENGTH: 210
<212> TYPE: RNA
<213> ORGANISM: Homo sapiens
<220> FEATURE:
<221> NAME/KEY: misc_feature
<222> LOCATION: (118)..(121)
<223> OTHER INFORMATION: n is a, c, g, or u

<400> SEQUENCE: 200
gauccuguau augugguuuu ugggggagcu augauaaguu uuauggcaaa cgguugguau 60
uguuaacuuu uuauugucau caaaaguuca uaaaaguccu auuaaucccc auauucunnn 120
ncugcccuua acucugguau acaccaaaaa gaaaucuuua cuuuccuugu uuuaucauua 180
uaaaaauaaa guauuuugcu aguauggaaa 210

<210> SEQ ID NO 201
<211> LENGTH: 677
<212> TYPE: RNA
<213> ORGANISM: Homo sapiens

<400> SEQUENCE: 201
aguccgcguc ccggcgucgg cccguccccgc accaugguga cgcucgccga gcugcuggcg 60
cugcuggccg cgcugcuggc cacggccucg ggcuacuuug ucagcaucga cgcgcacgcc 120
gaggagugcu ucuucgagcg ggucaccucc ggcaccaaga ugggccucau cuucgaggug 180
gcggagggcg gcuuccugga caucgacgug gagaucacag gaccagauaa uaaaggaauc 240
uauaaaggag accgggaguc cagcgggaag uacacauuug cagcccacau ggaugggaca 300
uacaaguucu gcuuuagcaa uaggaugucc acuaugacuc caaagauagu aauguucacc 360
auugacauug gggaggcucc caaaggacaa gacauggaga cagaagcuca ucagaacaag 420
cuagaagaaa ugauuaauga gcuggcagug gcaaugacag ccguaaagca cgaacaggag 480

-continued uacauggaag uccgggagag aauacacaga gccaucaaug acaacacaaa cagcagagug 540
guccuuuggu ccuucuucga agcucuuguu cuaguugcca ugacauuggg acagaucuac 600
uaccugaaga gauuuuuuga aguccggagg guuguuuaaa aggccuuuuc cuguugaucc 660
caaauucaug auuuacu 677

<210> SEQ ID NO 202
<211> LENGTH: 2849
<212> TYPE: RNA
<213> ORGANISM: Homo sapiens
<220> FEATURE:
<221> NAME/KEY: misc_feature
<222> LOCATION: (2158)..(2158)
<223> OTHER INFORMATION: n is a, c, g, or u

<400> SEQUENCE: 202
gcauuggcuc ugggcugcgg ccggcucggc gacgcuccuc gggcagcuca cugcaugguc 60
gucuggugcc cccgccgccu gcauccccgc cgccgccccg cgacgcccac cgccgccugc 120
ccugccgccg ccgccugcgc cgccucggga ccggcuguau gauuaggcca caaucuucaa 180
ugaguagaca uauuccucag uucuguggug uucucgguca cacauuuaug gaguuucuga 240
agggcagugg agauuacugc caggcacagc acgaccucua ugcagacaag ugaacuguag 300
aaauucauua cuacuccacc aagaaacccc cauaagagug gauaaccugg acacaggcgu 360
guugaauuga aaucugcaca gcauuugaga agagcucaga ccuggauggg guaaaccuca 420
gugccacuuc cuuuguauug ccucuaguau uacugggauu gaagagucac ugcuucuugu 480
uuaggagguu cauuucauug gcccguuucu cccaauuuca uacucaagca cugagaauuu 540
caaguggagu auaucgaaua ucgaaguaga cuucagguug uuuuuugguu uuguuuuguu 600
uuuuuuuugu uuugguuuuu uuuuuuuuuu ucuguuuugg uuuaaaucau uucuguauuc 660
aauuuuuuaa uucuuucaua acccuauugg guguuuuuuu aaacuaaauu aacauggcuc 720
gaaugaaccg cccugcuccu guggaaguca cauacaagaa caugcgauuu cuuauuacac 780
acaauccaac caaugcgacc uuaaacaaau uuauagagga acuuaagaag uauggaguua 840
ccacaauagu aagaguaugu gaagcaacuu acgacacuac ucuuguggag aaagaaggca 900
uucauguucu ugacuggccu uuugaugaug gugcaccacc auccaaccag auugucgaug 960
acuggcuaag ucuugugaag auuaaguuuc gugaagaacc ugguugcugu auugcugucc 1020
auugugucgc aggccuuggc agagcuccgg ugcuuguugc ccuagcauua auugaaggug 1080
gaaugaaaua ugaagaugca guacaauuca uaagacaaaa gcggcgugga gcuuuuaaca 1140
gcaagcaacu uuuguaucug gagaaguacc guccgaaaau gcggcuccgc uucaaggauu 1200
ccaaugguca uagaaacaac uguuguauuc aauaaaacug gggugccuga ugccauugcc 1260
uuggaagugg aacuucagau gggaccugau uugucaugca uauuacccaa ugugucggcu 1320
uacugaauaa gucuacugca gcuccacagg aauacugaaa aaccagucuu accaggccac 1380
aaguuugaca gaauugcaac cucuauauuu gggcuaugau caacauguuu ggacacuuag 1440
caaaagauuu uugcuguuca gcauuuaaaa ugugcuuauu auuuguacca auugaccuuu 1500
ccuaaaauaa gguauugagu uaugucauua aauguacucc ugugccagaa uauuauuagu 1560
cuauaaggaa uuuagaagga uuaggugcca aaauacccag cacaauacuu guauauuuuu 1620
agcaucauac agaaccaaaa uugcaggaac ugagaacucu cagaccaucc auggugu auu 1680 ccuucaguca uuucaaacac ugcagggcuc cucucguuau cugccugcuc acucuguuua 1740
caucucccac acuuaugcca gaauacguca gguuugcuua gccauccuuu auuuuuuuua 1800
uuuuuuuuuu uaacuaaguc uugcgcugau uauuuaauau gucugucuca uuuuguuuug 1860
uuuugggaaa ccucugucug aaaaaucaac uuuguuacag aagcacauau cuucaacaau 1920
gucuccagac aaaaagccuu auaguuaauu uaauguuugc acucagaagu gcaaccuaac 1980
agggagggcc ugaaaaagaa acgagaggag gcuauuaaau auuuuuagua auauguugcc 2040
uuugucaugu gcagaacaug uagaguaugc ucuuaauuua guaaauauuu uuaagacaua 2100
gagauacaug uguagcuaac ccauucuuau ucaaaauucu ggaauuuugu guuuuccnau 2160
accuaucagg aaguuuccag cuuguuugaa uuauggcuuu ccucuuccca aucucuugca 2220
aaaaagacaa agugggauga aucugcuagu gaacugagca gaaauguuuu auaacgccuu 2280
uugagcuaug uaacuuaaua auuggauacu ugaucauuug uuuuauuaug uaaucggaua 2340
aaauggugau guguauuaaa guuaguucaa ccauauauuu auacugucug ggaaugugug 2400
guuauaguuc ugugggagaa auaguuuguc aguguucacc agcuuguaaa aacuuaguau 2460
gagagcuuca acauuuaaau aaaugaugaa ccgcauucgu cacugaggac acuuuugccu 2520
aaaauuaacu uaauuuguag aaaacaaugg auucaguuaa uaucauuuca auuuauggaa 2580
aaaauuguua ggguugccaa gugcuuuuua uuaaaaguuu cucuuuaaag gucuagauaa 2640
uugugaauca guugaauguu gggcaccgag gggaaacagu uuguaauaga ugaucuagau 2700
uuuucaguuc aguuccauca gucacuugua gcucugcaau uuccagacca guuuucucau 2760
uuuuaaguuc auuacaugcc uguauauauu uugaaauuaa cuugaaccug aguauuuggc 2820
acaugauggc uuaauaaauu uuaacuuuc 2849

<210> SEQ ID NO 203
<211> LENGTH: 3023
<212> TYPE: RNA
<213> ORGANISM: Homo sapiens

<400> SEQUENCE: 203
acgcucccca accuccaccu ccccucgcuc ggccucuaua ugcucccggg cucccuagug 60
uuggcuggaa gugggugacu uagaggcuua aaggaggggc gccuaaccac ggaccacgug 120
ugugcggggg cgacagcgcc gccgggggugg ggcugagcgc ugcaagccgg guucgccuug 180
cagcgcagga gucagugggc guugcgccac gaucucucuc cacuagcacu augcuccccgc 240 cccacucacc gccuuggaaa gucacaggag aaggcgggcu cuaagaccca gcaggcacca 300
uccuacuggc gccuucgauc cgagacccgu uuggacacca gggggcgaug ccgacccucu 360
auaaaagcgg ucccccgcgcg ggccuggcca uucgcgaccc gaagcugcgc gggcgcgagc 420
caguuggggc acuggguggg cggcggcgac agcggcgcca cgcgcaggcu ggaggccgcc 480
gaggcucgcc augccgggag aacucuaacu cccccaugga gucggccgac uucuacgagg 540
uggagccgcg gcccccgaug agcagucacc uccagagccc cccgcacgcg cccagcaacg 600
cccgccuuug gcuuuccccg gggcgcgggc ccccgcgccgc ccccagcccc accugccgcc 660
ccggagccgc ugggcggauc ugcgagcacg agacgucuau agacaucagc gccuacaucg 720
acccggccgc cuucaacgac gaguuccugg ccgaccucuu ccagcacagc cgacagcagg 780
agaaggccaa ggcggcggcg ggccccgcgg guggcggcgg ugacuuugac uacccgggag 840
ccccggcggg ccccggcggc gcggucaugu ccgcgggggc gcacgggccc ccucccggcu 900
acggcugugc ggcggccggc uaccuggacg gcaggcugga gccccuguac gagcgcgucg 960
gggcgcccgc gcuacggccg cugguggauca aacaagagcc ccgcgaggag gacgaggcga 1020

-continued agcagcuggc gcuggccggc cucuuccccu accagccacc gccgccaccg ccaccgccgc 1080
acccgcacgc gucucccgcg caccuggccg ccccccacuu gcaguuccag aucgcgcacu 1140
gcggccagac caccaugcac cuacagccug gccaccccac accgccgccc acgcccgugc 1200
ccagcccgca cgcugcgccc gccuugggug cugcgggccu gccuggcccc gggagcgcgc 1260
ucaagggcuu ggccggugcg caccccgacc uccgcacggg aggcggcggc gguggcagcg 1320
gugccggugc gggcaaagcc aagaagucgg uggacaagaa cagcaacgag uaccggguac 1380
ggcgggaacg caacaacauc gcggugcgca agagccgaga uaaagccaaa caacgcaacg 1440
uggagacgca acagaaggug cuggaguuga ccagugacaa ugaccgccug cgcaagcggg 1500
uggaacagcu gagccgugaa cuggacacgc ugcggggcau cuuccgccag cugccugaga 1560
gcuccuuggu caaggccaug gcaacugcgc gugaggcgcg cggcugcggg accgccuugg 1620
gccggccccc uggcuggaga cccagaggau gguuucgggu cgcuggaucu cuaggcugcc 1680
cgggccgcgc aagccaggac uaggagauuc cggugugggcc ugaaagccug gccugcuccg 1740
cguguccccu cccuuccucu gagccggacu cggugcgucu aagaugaggg agucaggccg 1800
uggugguuuc uccuugagac cgagagacuu uuccgcggag cugagcuggg ggcccggcag 1860
uacuaguauu aaggaaguaa ccuugugccu uggauacuca aaacucgcuc cuuuuccuac 1920
cgaguagggg gagcaaaaau gugccuugau auuuuauuug gaggauuccu gcuuccucuc 1980
gggccucagc uggcccccgu gagaaaaaug aagggugcag gcccagggca ggaggaagau 2040
acaggaagcu gagaucccgg cagugcccug agcugccccu cagucccugu cuuuagaggg 2100
gagggacuua gguguugggg auuugagucu guguccucac ccccagcuac agggaggugg 2160
agggcuccua aucccuugcu uuuugcaccu ccaccuacau cccccccccc ccacucagcu 2220
uacaacaggc cagguuuccu gggugaguuc auggagaaug ggggcaccac ccccagucag 2280
acagaaagcu gaguugugag uuagccaugu gguaggagac agagaccuag guuucugggc 2340
uuuguggggu gggggauagg aggacacggg gaccauuagc cuugugugua cuguaugucg 2400
ccagccgcug uugcugaagg aacuugaagc acaaucgauc caucccagag ggacuggagu 2460
uaugacaagc uucccaaaua uuuugcuuua ucauccgaua ucaacacuug uaucuggucu 2520 cugugucccca gcggugccuu gugcaauggc agugugcacg ucuaugcuaa accaccauuu 2580
uauuuggucu uuuguuuugu uuugguuuug cucugauucu ugccaaacug agacucuuca 2640
cuaacggcug ggggaaggag cugagugagg cucucauucu uuuugguuua gggauguuug 2700
gguuuuuucg ucugccuccc agaggaccaa ugaaaugaag ugggcuuccc ccucuccccu 2760
aguuguccaa ggguguaugu aguagugggu cuuagcuucc uccggcuaag acuuaggcuu 2820
ccccacccac ccaaccccau ccccaacggc ccuggcucug ggucuggaaa gaaggccacc 2880
uccagccagu ucauacacac accccugugg cugggagcag ggcuggaccg cuuccuucuc 2940
uucuuuuuuu gggggggggg acacaaaguu ucaugcuaga ugucguaugu auuauaucua 3000
uaauauaaac auaucaaacu caa 3023

<210> SEQ ID NO 204
<211> LENGTH: 380
<212> TYPE: RNA
<213> ORGANISM: Homo sapiens
<220> FEATURE:
<221> NAME/KEY: misc_feature
<222> LOCATION: (76)..(76)
<223> OTHER INFORMATION: n is a, c, g, or u

<400> SEQUENCE: 204
gaagcucagu gucgugaaau ggaaaccaaa ccuuggagcc aucgcugagu auaaaaaaaa 60
ggaagauuua uauucngcaa agaguagccg aacuggacaa aauuacuucu gaaagagaua 120
auuuuagaca agcauaugaa gaucuucgaa aacaaaggcu gaaugaauuu auggcugguu 180
uuuacguaau aacaaauaaa cuaaaagaaa acuaccagau gcucacauug ggaggagaug 240
cugaacugga gcuuguggac aguuuagauc cuuuuucuga aggaaucaug uucaguguuc 300
ggccaccuaa gaaaaguugg aagaagaucu uuaaccucuc aggaggcgag aaaacccuua 360
guuccuggcc uuaguguuug 380

<210> SEQ ID NO 205
<211> LENGTH: 1391
<212> TYPE: RNA
<213> ORGANISM: Homo sapiens

<400> SEQUENCE: 205
gccgguuuga guugugcgcu cgggfugucccc uuuccucuuc cccucccgca gggcuugcgg 60
ccaccauggc guauuagagg cagcagugcc ugcggcagcg uuggccuuug cagcggcggc 120
agcagcacca ggcucugcag cggcaacccc caccggccua agccauggcg cucuucacga 180
aauccagcag caguguugcu guaacggaca aagauaccuu cgaguuaagc acauuccugg 240
aauccagcaa agccccacaa caugaccgag augagcuucc ugaacagcga aguguuggcg 300
ggggacuuga uguccccccuu cgaccagucg gguuuggggg cugaagaaag ccuaggucuc 360
uuagaugacu aucuggaggu ggccaagcac uugaaaccuc augguucuc cagcgacaag 420 gcgggcuccu cggaauggcc ggcuauggau gauggcuugg ccagugccuc agacaccggc 480
aaggaggaug ccuuuuccgg gacagauugg auguuggaga aaauggaucu gaaagaguuu 540
gacuucgaug cucuguuucg aauggaugac cuggaaacca ugccagauga gcucuugacc 600
acguuggaug acacauguga ucuuuuugcc ccucuagucc aagagacuaa uaaggagccc 660
ccucagacag ugaacccaau uggccaucuc ccagaaaguu uaauaaaagu cgaccagguu 720
gcccccuuua cauucuugca gccuuucccc uguuccccag ggguucuguc uuccacucca 780
gagcauuccu uuaguuuaga gcuaggcagu gaaguugaua ucucugaagg agacaggaag 840
ccugacucug cugcuuacau uacucuaauc ccuccaugug uaaaggagga agacacuccc 900
ucugacaaug acaguggcau cuguaugagc ccggaguccu accugggcuc uccccagcau 960
agccccucca ccuccagggc ccccaccagac aaucugccuu cuccaggugg uucccguggg 1020
ucuccucggc ccaaaccuua ugacccaccu ggaguuaguu ugacagcuaa agugaagacu 1080
gagaaauugg auaagaagcu gaaaaagaug gagcaaaaca agacagcagc cacuagguac 1140
cgccagaaga agcgggcuga gcaggaggcc cucacuggcg aguguaagga gcuagaaaaa 1200
aagaaugagg cucugaaaga gaaggcagau ucucuggcca aggagaucca guaucugaaa 1260
gaccugauag aagagguccg uaaggcaagg gggaagaaga gaguuccgua auaggguagu 1320
caggugcuuu gugcuuguac auagucuugu guugcugugu uugcuguaau aaauuauuuu 1380
guagugaaag u 1391

<210> SEQ ID NO 206
<211> LENGTH: 356
<212> TYPE: RNA
<213> ORGANISM: Homo sapiens

<400> SEQUENCE: 206
uuuuuuuuuu uuuuuaugua gggaaguuca uauuuuauuu guccagugac auuuuuuaca 60
guugaauaca aguuaaaggc cugcuugcac accaaagcca gguccuuugg gugguucagu 120
caaagaagua aggccuccag cuggcucaca acagaagcgg ccacuccuug gcccugguuu 180
gggaacuuuu ccagcuuuga guucaucaau aaucucuuca auauccuugg gugucagauc 240
cucauaguag uugucauuua uuugaaccau cggugcauuu acacaggccc cuaaacauuc 300
cacuucuaua agagugaaaa guuugucagg uguagucucu ccaaccuuua uuccaa 356

<210> SEQ ID NO 207
<211> LENGTH: 413
<212> TYPE: RNA
<213> ORGANISM: Homo sapiens

<400> SEQUENCE: 207
uuuuuuuuuu uuuuuuuggg gugaauauag ccaaguauuc cauuuauuaa caaaauaguc 60
uuagcaaggg agagcucugu ucaccccaca agaggccccg cagccgaggc cggcccgaag 120
ccccagcgcu gcugcguaag accgggaggg agggaaggug uuggggagaa gacuuguauu 180
aagucuuuaa uccuagccac cgcaggaacc cacggaaacc uaaugccagc uuuggcgauu 240
gcuggcucag gucugggaca uggcgaaggg agugcucuga uccuagggcu cccugagucc 300
ccagccugcc cccaacagag cuccuaaagu ugucuggucu gcugacuuga ggacugguaa 360
gcuuuggagg gauccaucaa ggauuccccg accccacccc uaucgccagg gga 413

<210> SEQ ID NO 208
<211> LENGTH: 1707
<212> TYPE: RNA
<213> ORGANISM: Homo sapiens

<400> SEQUENCE: 208
ccucugcggc gcgguccucg gagcggcgcg guucucggag ccacgcgucu gucuuccucc 60
guggucaugg cggacuaccu gauuagcgga ggcaccucuu acgugccgga cgacgggcuc 120
acagcgcagc agcucuucaa cugcggggac ggccucaccu acaaugauuu ucucauucuu 180
ccuggguaua ucgacuucac ugcagaucag guggacuuga cgucugcucu aacuaagaag 240
auuacacuaa agaccccauu gguuuccuca cccauggaca cugucacaga ggcuggaaug 300
gccaucgcga uggcgcuuac aggagguauu gguuucaucc accacaacug cacaccugaa 360
uuccaggcca augaaguucg gaaagugaag aaauacgaac agggauucau cacugacccc 420
gugguccuua gccccaagga ucguguacgc gauguuuuug aggccaaagc caggcauggc 480 uucugguggua uccccaucac agauacaggc cggaugggga gucgauuggu gggcaucauc 540
uccucaaggg acauugauuu ccucaaggag gaagagcaug accgguucuu ggaagagauc 600
augacuaaga gggaagauuu gguggucgcc ccugccggcg ucacucugaa agaggcaaau 660
gagauucugc agcgaaguaa aaagggaaag uugcccauug ugaaugaaaa ugaugagcug 720
guagccauca uugcccggac agaccuaaag aagaaucgug auuacccccu ggccuccaaa 780
gaugccaaga agcaacugcu gugugggggca gccauuggca cucaugagga ugacaaguau 840
aggcuggacu uacuggcccu ugcuggugug gauguagugg uuuuggacuc uucccaggga 900
aacuccaucu uccaaaucaa uaugaucaaa uacaucaagg agaaguaucc cagucuacag 960
gucauuggag gcaauguagu cacugcugcg caagccaaga accucauaga ugcaggugua 1020
gaugcuuugc gagucggcau gggaaguggu uccaucugca ucacccagga aguguuggcc 1080

-continued ugugggcggc cccaagccac agcaguguac aaggucucug aguaugcccg ucgcuuuggu 1140
guuccuguua uugcugaugg aggaauccaa aaugugggc auauugccaa agcuuuggcu 1200
cuuggggcuu ccacagucau gaugggcucc cuccuggcug ccaccacuga ggccccuggc 1260
gaguacuucu ucucagaugg gauccggcug aagaaauacc gagguauggg uucucuugau 1320
gccauggaca aacaucucag cagccagaac cgauacuuca gugaagcuga caaaaucaaa 1380
guggcccaag gaguuucagg ggcagugcag gacaaggggu cuauccacaa guucguuccu 1440
uaccugauug cuggcaucca gcauuccugu caagacauug gugccaagag uuuaacccaa 1500
gucagagcca ugacguacuc gggggagcuu aaauuugaga agaggacauc cucugcucag 1560
guggaaggug gcguccacag ccuccauucg uacgagaaac ggcuuuucug aaaacagauc 1620
caguauaugc cuugaauuuu ucaauaaaag uuugggaaaa aaaaagugaa aaaaaaaaaa 1680
aaaaaaaaaa aaaaaaaaaa aaaaaaa 1707

<210> SEQ ID NO 209
<211> LENGTH: 261
<212> TYPE: RNA
<213> ORGANISM: Homo sapiens

<400> SEQUENCE: 209
gugugggugc agagcugggg ucagggaaag cuggagccuu uugcagaccc ugagcugcuc 60
acggcugaga gcuggggguca uuacccucac cuucauuucc uguaccuguc cuucccagag 120
ccuccuccau ccacugucuc caacauggcg aacguagcug uucugguugu ccuuggagcu 180
uggccaucau ugcagcugug guggcuuuug ugaugaagag aaggagacac acagguagga 240
aagggcagag ucugaguuuu u 261

<210> SEQ ID NO 210
<211> LENGTH: 173
<212> TYPE: RNA
<213> ORGANISM: Homo sapiens

<400> SEQUENCE: 210
acaggagggg aaggccaaag caagaaugaa aguccccgc cccguaucac cacgggcacu 60
cggggucacc cucaggaaca ugcagucucu gcacgugagg aaagaaacac gcagagaugg 120
acgagcacuu uuacacccua auaaaauuag augcacuaac cacagacccc ccu 173

<210> SEQ ID NO 211
<211> LENGTH: 494
<212> TYPE: RNA
<213> ORGANISM: Homo sapiens

<400> SEQUENCE: 211
uuuuuuuuuu uuuuuuuaaa aaaaaaaaug gcaucuuuua uucaucaauc ccuguuacac 60
acugaaauac augcaucuuu cuuauguuac uuagcaacgu ccuuucuauc cuuucaccca 120
uaaaucaguc ugaugaauuc aucuuuaaau ucaagaaguu uuucuuuuug aaacgcuacu 180
uacauuuuau ugucucaaua ucaaagccaa ucuagagauu uauucuuccu acaggugaaa 240
uagauguuaa uacgggaaca gucaguacau guucaagaug acaucaaagu uaugcccuaa 300
gcagauauuu caaggcaaua ucaugccacu agcucugaga cucuaaguau cacugauagu 360
acuaaaaggu agaagucagc uucaaaaaca cacucuugca auggacacug cucaugaugu 420
cuaagauugu ucacucccac agucaugauu ucagaugcac aguuuuuuuu gcuuuccuga 480
gcauucgguu ugac 494

<210> SEQ ID NO 212
<211> LENGTH: 384
<212> TYPE: RNA
<213> ORGANISM: Homo sapiens

<400> SEQUENCE: 212
uuuuuuuuuu uuuuuuuaag agugucacca aagcuuuauu uacaugcguc aucaucucuu 60
uuacaaacua gauuaugguu uuaaauggaa uacacaggca auaucuacaa acgccacggg 120
aaguacgcac cuccauucca ccgggaaggg gcagauuccc aaaucaaacu gguuuugauc 180
cuugagaaga aaggcggcag agcuaacuca cggcagcgua ugguuagaca agguccucag 240
uacccagaau gcagcaggau ugcgucugcc ucaaaccaga cgaccaacug cugcaggugu 300
uuaaacaugg ccacgcgcca cacgaaauuc uaguuugugu gggguagaag caagaaaaaa 360
aaaaaaccau ggcgccucgu gccg 384

<210> SEQ ID NO 213
<211> LENGTH: 982
<212> TYPE: RNA
<213> ORGANISM: Homo sapiens

<400> SEQUENCE: 213
gguccggaua guaaacugcu cccuuacauc uccuuaaaua uaaaguaagg aaaaagaaaa 60
aacucaguuc ggguaaccaa guucaacaag uaauccuugg ggccgcugug guaucgccaa 120
aaucuacaua guaucucuua uuaaaauguu uugacgaaaa uguaacaauu acgguacuua 180
augguaacaa uguggcugag gaagcaauag uuaacaaaga ggagcuaagc uaugcaacaa 240
accagauuuc uauuggucac aaauuugaag uugagaccug uuauccaauu accaaguacu 300
uccgcauaca ucaucauagg cauuugaaga uuucaaccaa ucaggagcau guuccuucua 360
uaaaggaacc cagaaccuaa ccucugcauu uccuauuucu uuguagaaau ggcucguacg 420
aagcagaccg cucgcaaguc cacuggcggc aaggccccgc gcaagcagcu ggccaccaag 480
gccgcccgca agagcgcccc ggccaccggc ggcgugaaga aaccucaccg cuaccguccc 540
ggcaccgugg cgcugcgcga gauccggcgc uaccagaagu cgaccgagcu gcugauccgc 600
aagcugccgu uccagcgccu ggugcgcgag aucgcgcagg acuucaagac cgaccugcgc 660
uuccagagcu cggccgucau ggcucugcag gaggcgagcg aggccuaccu ugugggucug 720
uuugaggaca ccaaccugug cgccauccac gccaagcgug ucaccaucau gcccaaggac 780
auccagcugg cccgccguau ccgcggcgag cgggcuuaau aggcacgcuu ucuacacugg 840
cacguaaacc aaaacggcuc uuuuaagagc caccuccauu auccaccaaa gaugcuugaa 900
guacaaguug ugagaguuuu cuaggguuuc cuauuauagc cuuucuugac aaugugagca 960
ccacccgacg aagcagucug ag 982

<210> SEQ ID NO 214
<211> LENGTH: 424
<212> TYPE: RNA
<213> ORGANISM: Homo sapiens

<400> SEQUENCE: 214
uuuuuuuuuu uuuuuuugga cuucugcggc uuuuauuuuu gcauguaaac cacugggggg 60
agggggaucu ugaugguggg cacccuagag auuacacugg aguuccgagg gcuccagaca 120
cuagcuggga agucagguga cagaaacaau gauucagacc aaucacauga uugcaaaacu 180

-continued gggucuccag cagggauucu gguggucagg uguggaugcc uaaggaagca gugacauggg 240
aggggcacgc acugggcugg ccuugagcug cugggaugac aucagggaua gaggaccuag 300
cagcuggugg cuccagggau cuccggucca ugcuuuauuu ggccaggggg uuccugaagg 360
accugccagc aaacuuggcu uugcugccca gcucuuccuc aauucugagg aucugauugu 420
acuu 424

<210> SEQ ID NO 215
<211> LENGTH: 1407
<212> TYPE: RNA
<213> ORGANISM: Homo sapiens

<400> SEQUENCE: 215
auucuaagga ucaugucugc gagucaggau ucucgaucca gagacaaugg ccccgacggg 60
auggagccgg aaggcgucau cgagaguaac uggaacgaga uuguggauag cuuugaugac 120
augaaucucu cagaguccu ccuccguggu auuuaugccu augguuuuga gaagcccucu 180
gccauccagc agcgagcuau ucuuccuugu aucaagggu augaugugau ugcucaagcc 240
cagucuggga cugggaaaac agcuacauuu gccauaucaa uucugcagca gauugaauua 300
gaucuaaagg ccacucaggc uuugguucug gcacccacac gugaauuggc ucagcagaua 360
caaaaggugg uuauggcauu aggagacuac augggugccu cuugucaugc cugcauuggg 420
ggcaccaaug ugcgugcuga ggugcagaag cugcagaugg aagcucccca uaucaucgug 480
gguaccccug gccggguguu ugacaugcuu aaccggagau accuguccc caaauacauc 540 aagauguucg uacuggauga agcagaugaa auguuaagcc gaggguucaa ggaucagauc 600
uaugacauau uccagaagcu caacagcaac acacagguag uuuuguuguc ugcuacaaug 660
ccuucugaug uccuugaggu gaccaagaaa uuuaugagag acccuauucg gauucuuguc 720
aagaaggaag aauugacccu ggaggguauc cgccaauucu acaucaaugu ggaacgagag 780
gaguggaagc uugacacauu gugugacuug uaugagacgc ugaccaucac ccaggcaguc 840
aucuuuauca acaccagaag gaagguggac uggcucaccg agaagaugca ugcccgagau 900
uucacuguuu cugccaugca cggagauaug gaccaaaagg aacgagaugu gaucaugagg 960
gaguuccggu cuggcucuag cagaguauua auuaccacug accuguuggc cagaggcauu 1020
gaugugcagc aggucuccuu agucaucaac uaugaccuuc ccaccaacag ggaaaacuac 1080
auccacagaa ucggucgagg uggucgguuu ggucguaagg guguggcuau uaacauggug 1140
accgaagaag acaagaggac ucuucgagac auugagacuu ucuacaacac cuccauugaa 1200
gagaugcccc ucaacguugc ugaccucauu ugaggggcug uccugcgacc uggcccuagc 1260
ccaggguuca guccuggggu ggggcuaagg aagagcugga ggggggaggg gagggagcca 1320
agggauggac aucuuguuuu uguuuuggcu uuuuuuuuuu uuuguuucag uuuuuuuucu 1380
cuaugaauaa augucacuuu uugaggc 1407

<210> SEQ ID NO 216
<211> LENGTH: 562
<212> TYPE: RNA
<213> ORGANISM: Homo sapiens

<400> SEQUENCE: 216
uuuuuuuuuu uuuuuuugcc aggauauauu uauuacugaa aguacaagca acugagguuu 60
acccugggaa cacccacaau gaaacgugua ucuucccugu uucucagaug cugccuccuu 120
ccacagagug aguuucguu uaaaacucau aaugaggaga aggcaggggg cuccaccccu 180
uuccuguuca aucugaagac ugaauugggc uacacuggga uggagauuuc aggugcugca 240
ggucagugus aaccaagggu ucguguguca ggaacucugg cugguaagau gacacaaagg 300
cuucaugcug aagcucaggg agguccaggg agccuggcag aauggaauca ucauggucau 360
caucaaacgu cugugucugg aaggcuucaa ggcucauaau ugcaucauuc ucuggcaguu 420
ccugagagag cugccccuuc cuggguuugc acgcaucaaa uuucacccac ugguaauuga 480
cacaguuuug agcuucggga caacucuuaa ucagguugug gaugguugga ugagaaaacc 540
caaagaaguc ggcaccgcau ga 562

<210> SEQ ID NO 217
<211> LENGTH: 1238
<212> TYPE: RNA
<213> ORGANISM: Homo sapiens

<400> SEQUENCE: 217
auuguaacag aagaaggaaa ggaaaagaaa guuaacauug acuuugaacc uuucaaacca 60
auuaauacau cauuguauuu gugcgacaau aaguuucaua cagaggcucu uacagcguua 120
cuuucagaug acagcaaguu ugguuuuauu guaauagacg gaaguggugc ucuuuuuggc 180
acgcuccaag gaaacaccag agaaguccug cacaaauuca cuguggaucu cccaaagaaa 240
cacggcagag gaggucaauc agccuugcgu uuugcccguu uaagaaugga aaagagacau 300
aacuauguuc ggaaaguagc cgagacugcu gugcagcugu uuauuucugg agaccaagug 360
aauguggcug guuugguuuu agcuggauca gcugacuuua aaacugaacu aagucaaucu 420
gacauguuug accagagguu gcaaucuaaa guuuuaaaau uaguugauau auccuauggu 480
ggugaaaaug gauucaacca agcuauugaa uuaucuacug aaguucucuc caacgugaag 540
uucauucaag agaagaaauu aauaggacga uauuuugaug aaauuagcca ggacacaggc 600
aaguacuguu uuggaguuga agauacacua aaggcuuugg aaaugggagc uguacaaauu 660
cuaauagucu augaaaaucu ggauauaaug agauacguuc uucauugcca aggcacagaa 720
gaggagaaaa uucucuauuu aacuccagaa caagagaagg auaaaucuca cuucacagac 780
aaagagacug gacaggaaca cgaacugaua gaaagcaugc cucucuugga augguuugcu 840
aacaacuaua aaaaauuugg agcuacacua gaaauuguca cagauaaguc acaagaagga 900
ucacaguuug ugaaaggauu ugguggaauu ggagguaucu ugcgguaccg aguagauuuc 960
cagggaaugg aguaccaagg aggagaugau gaauuuuuug accuugauga cuacuaggua 1020
gucgacaugg guccggcaac cgugccucac ccuccagcau ucaacccaag gagcauaccc 1080
gugguggagu ccaacagauc ccugccuuac aauuggagca uuuccagaac uuaauccgug 1140
agcauuggau acugaaaaga aaagugaaac aaaaccagac ccaacccuac acuuugguuu 1200
gucguggugu cagcgcagca gccgacaacu aagucucu 1238

<210> SEQ ID NO 218
<211> LENGTH: 464
<212> TYPE: RNA
<213> ORGANISM: Homo sapiens

<400> SEQUENCE: 218
cagaggaguc auuguugcug ugguggcuuu ugugaugaag aggaggagaa acacagcgua 60
agccagcugc cuggagugga cuaagugaca gacaaugucu ucacacaucu ccugugacau 120
ccagagcccu caguuucuu uagucaagua ucugauguuc ccugugagcc uaugggucaa 180

-continued agugaagaac ugugcagccc agccugcccu gcacacagaa cccugucccu gcacugcccu 240
ggguucccuu ccacagccaa ccuugcugcu ccagccaaac acugggcgac aucugcaucc 300
ugccagcucc augcugcccu gagcugcagc uccucacuuc cacacugaga guaagaaucu 360
gaaugggacc uugauucuua acauccugac cgaggguuga uuucuuguua auuucaugga 420
uugagaauac uuagaguuuu gguuugucuu gauuuuuuuu caag 464

<210> SEQ ID NO 219
<211> LENGTH: 841
<212> TYPE: RNA
<213> ORGANISM: Homo sapiens

<400> SEQUENCE: 219
ugaauaaaaa cgaggagccg aagauucuag ggggcuacag cugcgcuuuu gcagcacuga 60
acaugguucc ggguacucaa gauauugcgu uuguguuugg agagguguag auuguagauu 120
ccagccgaga agaccaggaa aagauaagga uaaagaaugu cauauaucuc aggagcuaga 180
ucacuucccg augaacaagu aagaauugcc ucaacaaaaa uggauggaau uggaccgaaa 240
aaagccauuc agcuucguua ucgauuaggu aucaguggga acaucaagau gaaugaguua 300
acuaaguauc agaucgacca aauugaacaa augauagcuc aagaucaugu uguucauugg 360
gaauugaaga ggggagaacg agcagacauc gaacgauuaa uuucuauuuc ucguuaucgu 420
ggaauucguc aucaagaugg aucgcccuua cgcggucaac gaacucauac uaaugcaagg 480
acugcucgca agcaaauucg gaaaugaaag aaggcuaccg aaagaacaag caacggauuu 540
cgcgcucauc ccuugcuaaa gcgcauacgu uuucuugcuc cuugguacuu gucugaucaa 600
ucacacuguu cauuaguuca cuugauuuuu cguucgaugu cuugaaccgc uuacuaauca 660
cguauacgua uaguaggccc ccuucgccac uccacgucug gcccgucuug gucucgcuca 720
cuucgcccgc cuaucguauc ggcucggcuu cguccgucaa gcgacagcuu cugccucuga 780
cggcuucacu aucgcucaug acugguagua cucuauguag uagucggccu uuguuaagcu 840
u 841

<210> SEQ ID NO 220
<211> LENGTH: 136
<212> TYPE: RNA
<213> ORGANISM: Homo sapiens

<400> SEQUENCE: 220
uauaaccaug uuagaagcgg aaguuggccu gaaaaccuga ggcuuaggcu ucauagcugg 60
gcuguagauu ggauuuaaac ccaguuggag ugcaaaguca uggugugcuc aaggugauga 120
cagugaacag aguaug 136

<210> SEQ ID NO 221
<211> LENGTH: 752
<212> TYPE: RNA
<213> ORGANISM: Homo sapiens

<400> SEQUENCE: 221
caugggccuc cugagagauc cuuagaucca gguuagugca uaggaaagug ucccccccacu 60 accuacagcu aagggauugg gguggugggga ucauggugga gggccguggu gaauacuagc 120 gaugucccccc gcuacccgug cgucugccuc cagggugccc cuccaaccag gaugaggcuc 180
uucaucgcuc uuccuguccu gauuguggguc guagccauga ccuuggaagg uaagaaagag 240
ccuuggaagg uaagaaagau gcuuggaagu gugaaguugg ccuugugccu gcggcccagg 300
cuuagaagac ccucgaggag ggcucugagg ucccuuucug ugucaucauu ccacuaccgc 360
ccucccaucg ucccccaucc caccugccag gugccuuauu uuugugucaa agugggugcu 420
gaaggaggca acucugucca gaaaagacgc aguaaccaau gaccuaggau accacccuuu 480
ggaauuggcu aaucuuccua gaaggggcgg acgguaaaaa caaggaggug agaggugcag 540
uaaaaucaag uguccaauac ccucccccau gcuaaugagu uugcucgcaa cccucucgcg 600
gcaggcccag cccccgccca ggcggccccg gauuuguccg gaacauugga gagcauaccg 660
gauaaacuga aggaguuugg gaacacuuug gaagacaagg cccgggcagc cauugaacau 720
aucaaacaga aggaaauuuu gaccaagacc cg 752

<210> SEQ ID NO 222
<211> LENGTH: 2858
<212> TYPE: RNA
<213> ORGANISM: Homo sapiens

<400> SEQUENCE: 222
cagcgccugg ggcgcggcgg gcgucggccc aggagacgcg uggcggcgcu cggccucgcg 60
gcaucggcgg cugccuggcc guuggcggcg agcgcacuug cgccugcgca gcggggguccg 120 ugccccuccu ccccugggcg gcccccccac ccccccggcg gcgugugaau ggcggccucg 180
gcggcagcga cugcagcggc cucggccgcg acggccgccu cggcggccuc ugguagccca 240
gggucgggcg agggcucggc gggcggugag aagcguccgg cugcuuccuc agccgcggcg 300
gccucugcag ccgcgucguc cccugcgggg ggcgguggcg aggcgcagga gcuucuggag 360
cacugcggcg ugugucgcga gcgccugcgg cccgagcggg auccucggcu gcugcccugu 420
cuacauucgg ccugcagugc cugccugggc cccgcuacac ccgccgcagc gaauaauucg 480
ggggauggcg gcucggcggg cgacggcgcu augguggauu guccagugug caaacagcag 540
ugcuacucca aagacaucgu ggagaauuau uuuaugcgug auaguggcag uaaggccucu 600
ucugauuccc aggaugcuaa ccagugcugc acuagcugug aagauaaugc cccagccacu 660
agcuauugug uggagugcuc ugaaccacuu ugugagaccu guguggaggc ucaccagcgg 720
gugaaauaca ccaaggacca cacugugcgc uccacaggac cugcuaagac ucgagaugga 780
gagcgaacag ucuacuguaa ugugcacaag caugagcccc ucgugcuguu cugugagagc 840
ugugacacac ucaccugccg cgacugccag cucaacgcuc acaaggacca ucaguaccag 900
uuuuuggaag augcagugag gaaccaacgu aaacucuugg cuucacuggu gaaacgucuu 960
ggggacaaac augccacacu ucagaaaaac accaaggagg uucgaagcuc gauccgccag 1020
gugucugaug ugcagaagcg agugcagguu gaugucaaga uggccauucu gcagaucaug 1080
aaggagcuga auaagcgggg ucgaguucug gucaaugaug cccagaaggu gaccgagggu 1140
cagcaggaac gucuggagcg ccagcacugg accaugacca aaauucagaa gcaccaggaa 1200
cacauuuugc guuuugccuc uugggcucug gagagugaua acaauacagc ucucuugcuc 1260
ucuaagaagc ugaucuauuu ccagcugcau cgggcccuca aaaugauugu ggauccugug 1320
gagccucaug gugagaugaa guuucagugg gaucucaaug ccuggaccaa gagugcugaa 1380
gccuuuggca agauuguggc ugagcguccu gguacgaacu ccacaggucc ugggcccaug 1440
gcuccuccaa gagccccagg cccucuaagc aagcaagguu cuggcaguag ccagcccaug 1500
gaaguacaag agggauaugg cuuuggguca gaugaucccu auucaagugc agagccgcau 1560
guaucaggca ugaagcgguc ccgcucuggu gagggagagg uaaguggccu cuuaaggaag 1620
gugccacgug ugagccuuga acgccuggau cuggaccuca ccucugacag ccagccacca 1680
gucuucaagg ucuuuccugg aagcacuacu gaggacuaca aucugauugu uauugagcgu 1740
ggugcugcug cagcagcugc uggucaggcu gggacugugc caccaggagc cccuggugcc 1800
ccaccccuuc cuggcauggc cauugucaag gaagaagaga cagaagcugc uauuggagcu 1860
cccccggcug cccccgaggg uccugaaacc aagccugugu ugaugccucu gacugaaggu 1920
ccuggugccg agggaccucg ucuagcuuca ccuaguggca guaccagcuc aggcuuggag 1980
gugguggcuc cugagguuac uucagcccca guaagugggc cagguauccu ggaugacagu 2040
gccacuaucu gccgagucug ccagaaacca ggugaccugg ucauguguaa ccagugcgaa 2100
uuuugcuucc accuggauug ccaccucccu gcccugcagg auguuccagg ggaggaaugg 2160
aguugcucac ucugccacgu gcucccugac cuaaaggagg aagauggaag ccucagccug 2220
gauggagcag auagcacugg ugugguagcu aaacucucac cagccaacca gcggaaaugu 2280
gagcguguuc uccuggcccu guucugccau gaaccaugcc gucccuugca ucagcuggcu 2340
accgacucua cauucuccau ggagcagccu ggugguaccc uagaccugac cuugauucgu 2400
gcucgccucc aagagaagcu gucaccuccu uauagcuccc cccaggaguu ugcucaagau 2460
gugggccgca uguucaaaca guucaacaag cugacugagg acaaggcaga uguucagucc 2520
aucaucggcu ugcagcgcuu cuuugagaca cgcaugaaug augccuuugg ugacaccaag 2580
uuuucugcug ugcugguaga accaccacca uugaaccuuc ccagugcugg ccuaaguucu 2640
caggagcucu cuggcccugg ugauggcccc ugaagcuggg gcucuugugg ucagcccagu 2700
ccagcucugg ucucuguauu uucaccccau acccuguccu uugguggccu gacuccuguu 2760
cuugcuggcc ccaucguccc cucagucccu cuucacaaaa ugguuuuuac uucuguggau 2820
uuaauaaaaa cuucacugag ucaguuaaaa aaaaaaaa 2858

<210> SEQ ID NO 223
<211> LENGTH: 420
<212> TYPE: RNA
<213> ORGANISM: Homo sapiens

<400> SEQUENCE: 223
uuuuuuuuuu uuuuuuuaaa aauaauuuca uuuuuuaaua uucuguacaa aauuucucaa 60
ccuaugaaaa uaaaguuugc aaaagucaaa guaguacaug ggccugcccu ggagccaggc 120
ccagccggau cuacacuaug uacaggucuc ccagggugag ccucagcuag ggaaaagcca 180
cuaaggugcc uacagagcaa gagggugcca ucgggccagu gcagccucug caauuuccag 240
aucugccacu agaggucggc augguccuga uugcuuguca ggcucacccu cuggaagacc 300
acagccaaug acaaagaucc ucaagggaaa gcuuuggggu cuagcuggaa gugacggugg 360
guccgccgcc caggcgcagg agcaucugcu ggcaguccag caguaaccgg ugaucgccaa 420

<210> SEQ ID NO 224
<211> LENGTH: 963
<212> TYPE: RNA
<213> ORGANISM: Homo sapiens

<400> SEQUENCE: 224
uccgucguaa ccuguugagu aacuauggaa gacuauauca aaauagagaa aauuggagaa 60
gguacuuacg guguggugua uaaggguaga cacagaguca cuggccagau aguggccaug 120
aagaagauca gacuugaaag cgaggaagaa ggagugccca guacugcaau ucgggaaauc 180
ucucuauuaa aagaacuucg acauccaaau auagucagcc ugcaggaugu gcucaugcag 240
gacuccaggc uguaucucau cuuugaguuc cuguccaugg accucaagaa guaccuggac 300
uccaucccuc cugggcaguu cauggauucu ucacucguua agaguuacuu acaccaaauc 360
cuccagggaa uuguguuuug ccacucccgg cgaguucuuc acagagacuu gaaaccucaa 420
aaucuauuga uugaugacaa aggaacaauc aaacuggcug auuucggccu ugccagagcg 480
uuuggaauac cgauacgagu guacacacac gagguaguga cgcuguggua ccgaucucca 540
gaaguguugc ugggcucggc ucguuacucc acuccgguug acaucuggag uauagggacc 600
auauuugcag aacuggccac caagaagccg cuuuuccacg gcgacucaga gauugaccag 660
cucuucagga ucuucagagc ucugggcacu ccuaacaacg aaguguggcc agaagucgag 720
ucccugcagg acuacaagaa caccuuuccc aaguggaagc cggggagccu cgcaucccac 780
gucaagaacc uggacgagaa cggcuuggau uugcucucaa aaaugcuagu cuaugauccu 840
gccaaacgaa ucucuggcaa aauggcccug aagcacccgu acuuugauga cuuggacaau 900
cagauuaaga agauguagcc cucuggaugg augucccugu cugcuggucg uaggggaaga 960
ucg 963

<210> SEQ ID NO 225
<211> LENGTH: 479
<212> TYPE: RNA
<213> ORGANISM: Homo sapiens

<400> SEQUENCE: 225
uuuuuuuuuu uuuuuuuacu aggcaaagaa uuuuauuaac ccuuuccaaa cuuuauuccc 60
aggcuucuuc agcuuuauuu gccgcaaaga augaauuagg uauagcgaaa acugaaaaga 120
gcugcagugu ccgggggcuu gggcuuaaaa auauuagaga ucuagauuuu aucagaucca 180
uaauaaacaa aaaaauuuua aaaagcaguc augauauaaa auagcagcuc cuguaauuuc 240
ugcaaguauc accuucuuca gaaguugcuu caauucaguu ugccucauuc uuagaagccu 300
caucaaaauu cuccaccaga ucuggaacuu caucaucauc auccucucca guagcaaggg 360
gugcuuuucc auccacagau uguuugggca gagcuucagc cagucuccuu aaacuaguca 420
ggcugucugc accaagcugg uugaggaugc ugggaagcau uucugucagc ugcuuuguc 479

<210> SEQ ID NO 226
<211> LENGTH: 520
<212> TYPE: RNA
<213> ORGANISM: Homo sapiens

<400> SEQUENCE: 226
uuuuuuuuuu uuuuuuuauu caugcuugcc uagggauggg gaauagauca uucaauaaaa 60
acauacagua aaaacagggg guggggaggg ggaaggcuua ucauguacaa uguuuaaacu 120
acaauaguga uguaccuuaa uuacuuccau gcacacaagu cuaacauuac aaguuuuuaa 180
aaaauaaaca ccauuaagac uucuaggagc auuuuauaau aaauuccuaa uuuuuucuuu 240
guagauagau caagcaccuc caaaauacag auuccuauac acagugagca cuuuacuuaa 300
cguacaugga cagccucagg acgagcugac gucucggauc agcucggcag gcaacaaacc 360
auagugccaa auggaaagaa gggcaguugc aaauaaacuu aaaacuaagu uaacuuuuau 420
aauuaaauac agaaaauaua cugauuugcu aaaaauaaau aagaugugau guauuuaaca 480
cuucacuaua aagaaugaac accaugacau ccucgugccg 520

<210> SEQ ID NO 227

<211> LENGTH: 468
<212> TYPE: RNA
<213> ORGANISM: Homo sapiens

<400> SEQUENCE: 227
agaagaagga ggagugggac cgcaagcaug aggaugcuag uagggaguau gagaaaggca 60
ugaaagagua ugaaggagga agaggggacu caucuaaaag ggacaagucu aagaagaaaa 120
agaaaguaaa agcaaagaug gaaaaaaagu ccacuccuuc ccggggcucg ucauccaagu 180
cuucauccag gcaguugagu gacagcuuca agagcaaaga guuugugucc agugaugaga 240
gcucuucagg cgagaacaag agcaaaaaga agaggaggcg gacgaggacu cugaagagga 300
gcuagccagu accccuccaa gcucagagga cucugccucg ggaucugaug aauaaaggag 360
ggaauuccca ccccgucaca gcuccagucu cucacauagu ccuuggauuc ugugccaucu 420
gaguaacugc ucuugguggc uuccacugcc cugaggcuuu gagggaag 468

<210> SEQ ID NO 228
<211> LENGTH: 1740
<212> TYPE: RNA
<213> ORGANISM: Homo sapiens

<400> SEQUENCE: 228
aucgucguaa ucguuugcag acuucucgcc gucgccuugu aagcuuuguc uucgccuugc 60
aagcuuuguc uucaggguug gaaagaugag acauucaaag agaacuuacu guccugacug 120
ggaugaaaga gacugggauu auggaacaug gagaagcagc agcagucaca aaagaaagaa 180
gagaucacau agcagcgccc gugagcaaaa gcgcugcagg uacgaucacu ccaaaacgac 240
agacagcuau uaucuggaaa gcagauccau aaaugagaaa gcuuaucaua gucgacgcua 300
uguugaugaa uacaggaaug acuacauggg cuacgagcca gggcaucccu auggagaacc 360
uggaagcaga uaccagaugc auaguagcaa guccucuggu aggaguggaa gaagcaguua 420
caaaaguaaa cacaggaguc gccaccacac aucgcagcac cauucacacg ggaagaguca 480
ccgaaggaaa agaucgagga guguagagga ugaugaggag ggucaccuga ucugucagag 540
uggagacgua cuaagugcaa gauaugaaau uguugauacu uuaggugaag gugcuuucgg 600
aaaaguggug gaaugcaucg aucauaaagu gggagguaga cguguagcag uaaaaauagu 660
uaaaaaugug gauagauacu gugaagcugc ucaaucggaa auacaaguuu uggaacacuu 720
gaauacaaca gacccccaua guacuuuccg uuguguccag auguuggagu gguuugagca 780
ucgaggucac auuugcauug uguuugaacu ucuggggcuu aguacuuaug auuucauuaa 840
ggaaaacagu uuucugccgu uucgaaugga ucauaucagg aagauggcau aucaaauaug 900
caaaucugua aacuuuuugc auaguaauaa auugacucau acagacuuga agccugaaaa 960
caucuuauuu gugaagucug acuacacaga ggcuuauaau cccaaaauga aacgugauga 1020
acguacuaua guaaauccag auauuaaagu gguggacuuu ggaagugcaa cauaugauga 1080
ugaacaccac agcacauugg uaucuacaag acauuauaga gcaccggaag uuauuuuagc 1140
ccucgggugg ucacagccau gugaugucug gagcauagga uguauucuua ucgaguauua 1200
ucuuggauuu acaguuuuuu cgacucauga uagcagggaa cauuuagcaa ugauggaaag 1260
gauucuugga ccacuaccaa agcacaugau acagaaaacc aggaaacgca gauauuucca 1320
ucaugaucga uuagauuggg augaacacag uucugcuggc agauauguuu cucggcgcug 1380
uaaaccucug aaggaguuua ugcuaucuca ggaugccgaa caugagcuuc ucuuugaccu 1440
cauugggaaa auguuggagu augaucccgc caaaagaauu acucucaaag aagcccuaaa 1500
gcauccuuuc uuuuacccac uuaaaaagca uacgugauuu auaaacacag ugcucugaaa 1560
ggaaucuuac agacuguauc agucuagcuu uuaauuaagu uauuuuguau agcuuaauuu 1620
guaaaacauu uuauguuuuu uagaugcuuu auuaaauaca uggccaaacc aaauaacauc 1680
uuucaguaau uauagaauga uuuauuugga auaaaauuug ugcuuaugaa uguaaaaaaa 1740

<210> SEQ ID NO 229
<211> LENGTH: 815
<212> TYPE: RNA
<213> ORGANISM: Homo sapiens

<400> SEQUENCE: 229
ggacucgcga caagcguccu cagcgcgaag aggcggacuc ggaguccucg ccuugagccu 60
ugcaucugag aaguuccagg uacuuuguac aacugcaucc cagaaccugu guguuuucag 120
caccuuuaua agugauggcu gccaucagga agaaacuggu gauuguuggu gauggagcuu 180
gugguaagac augcuugcuc auagucuuca gcaaggacca guucccagag gucuaugugc 240 ccacggugu ugaaaacuau guggcggaua ucgaggugga ugggaagcag guagaguugg 300
cuuuauggga cacagcugga caggaagauu augacugccu gaggccucuc ucuuauccag 360
acaccgaugu uauauugaug uguuuuucca uugacagccc ugauaguuua gaaaacaucc 420
cagaaaaaug gacuccagaa gucaagcauu ucuguccaaa ugugcccauc auccugguug 480
ggaacaagaa ggaccuucgg aaugacgagc acacgagacg ggaguuggcc aaaaugaagc 540
aggagccggu aaaaccugaa gaaggcagag auauggcaaa caggauuggc gcuuuugggu 600
acauggagug uucagcaaag accaaagaug gagugagaga gguuuuugag auggccacga 660
gagcugcucu gcaagcuaga cgugggaaga aaaagucugg gugccucauc uugugaagcc 720
uugugaacgc agccucaugc gguuaauuug aagugcuguu uauuaaucuu aguguaugau 780
uacuggccuu ucauuuaucu auaauuuacc uaaga 815

<210> SEQ ID NO 230
<211> LENGTH: 287
<212> TYPE: RNA
<213> ORGANISM: Homo sapiens

<400> SEQUENCE: 230
uucaagaccg accugcgcuu ccagagcucg gccgucaugg cucugcagga ggcgagcgag 60
gccuaccucg ugggucuguu ugaggacacc aaccugugcg ccauccacgc caagcguguc 120
accaucaugc ccaaggacau ccagcuggcc cgucgcauuc guggggagag ggcguaaauu 180
aggguaguga gugaauuugg accccaaagg cucuuuucag agccacccac auuuucuaua 240
aaaggcugua uaucgauaag cuuuuauaaa ccccacucag caacucc 287

<210> SEQ ID NO 231
<211> LENGTH: 945
<212> TYPE: RNA
<213> ORGANISM: Homo sapiens

<400> SEQUENCE: 231
uuaugugaua aaaaaauuca acuugguauu aacuuaacua agggccuugg ugcuggugcu 60
uugccugaug uugguaaagg ugcagcagaa gaaucaauug augaaauuau ggagcauaua 120
aaagauagcc auaugcucuu uaucacagca gggaugggug gugguacugg aacaggugcu 180
gcaccgguaa uugcaaaagc agccagagaa gcaagagcgg uaguuaaaga uaaaggagca 240

```
aaagaaaaaa agauacugac uguuggaguu guaacuaagc cguucgguuu ugaaggugug    300

cgacguaugc gcauugcaga gcuuggacuu gaagaguugc aaaaauacgu agauacacuu    360

auugucauuc ccaaucaaaa uuuauuuaga auugcuaacg agaaaacuac auuugcugac    420

gcauuucaac ucgccgauaa uguucugcau auuggcauaa gaggaguaac ugauuugaug    480

aucaugccag gacugauuaa ucuugauuuu gcugauauag aaacaguaau gagugagaug    540

gguaaggcaa ugauugguac uggagaagca gaaggagaag auagggcaau uagugcugca    600

gaggcugcga uaucuaaucc auugcuugac aauguaucaa ugaaaggugc gcaaggaaua    660

uugauuaaua uuacuggugg uggagacaug acucuauuug aaguugauuc ugcagccaau    720

agagugcgug aagaagugga ugaaaaugca aauauaauau uuggugccac uuuugaucag    780

gcgauggagg gaagaguuag aguuucuguu cuugcaacug gcauugauag cuguaacgac    840

aauucaucug uuaaucaaaa caagauccca gcagaggaaa aaaauuuuaa auggccuuau    900

aaucaaauuc caacauuaga aacaaaagaa uaugcuucaa cugag                     945
```

```
<210> SEQ ID NO 232
<211> LENGTH: 238
<212> TYPE: RNA
<213> ORGANISM: Homo sapiens

<400> SEQUENCE: 232

ugaucagguc acauuccggu gccuuccacc cccuauggca cgggcgcccc gccuugccau     60

accacagcuc ccuccaggcu uagaccuggc uucaccgcau uucaggugcu auacccccccc    120

cugcuuuucc ccccauugcc cuuaaaugcc ccucggcccc uccauccccc cggaacaggg    180

uggcacuugc cacucucagg accaccuugc caaggagaau aaaccgaauc cuguugcu      238
```

```
<210> SEQ ID NO 233
<211> LENGTH: 341
<212> TYPE: RNA
<213> ORGANISM: Homo sapiens

<400> SEQUENCE: 233

uuuuuuuuuu uuuuuuucac ucaucacguu uauucagaag agaauacacc caauccucuc     60

aucucuggaa aguuuuguuc cuagccauca uuaagaucag gaccccuguu cuccccuuaa    120

ccccaggaga ggaagcuuau agucuuugua gauauucuga accucugauc acaaaggguu    180

auaaaaauagu gaaggggguuu ggacuaggaa aggcacagac ugaaaggaau cugccagggg    240

acugaggcca cagcuccccc aggagucaga ggaaggggga agucacguau uuuauagaag    300

gccaagggcc ucagagcaag aguauuccuu ugaagagcuc a                         341
```

```
<210> SEQ ID NO 234
<211> LENGTH: 495
<212> TYPE: RNA
<213> ORGANISM: Homo sapiens

<400> SEQUENCE: 234

ugguggagca ggucucagga aucucuucgc uucagcuuca aucauggccu gugguucuggu    60

cgccagcaac cugaaucuca aaccugggga augucucaaa guucggggag agguggccuc    120

ggacgccaag agcuuugugc ugaaccuggg aaaagacagc aacaaccugu gccuacacuu    180

caauccucgc uucaaugccc auggagacgc caacaccauu guguguaaca ccaaggaaga    240

ugggaccugg ggaaccgaac accgggaacc ugccuucccc uuccagcccg ggagcaucac    300

agaggugugc aucaccuuug accaggcuga ccugaccauc aagcugccag acggacauga    360
```

auucaaguuc cccaaccgcc ucaacaugga ggccaucaac uacauggcgg cggauggaga 420
cuucaagauu aagugcgugg ccuuugagug aagccagcca gccuguagcc cucaauaaag 480
gcagcugccu cugcu 495

<210> SEQ ID NO 235
<211> LENGTH: 861
<212> TYPE: RNA
<213> ORGANISM: Homo sapiens

<400> SEQUENCE: 235
gugguucuuc ggcgccaggu ucgcccgcuu cugcccuuag guaacauucu cuaaacugcg 60
uuucucuccc aaucuuuugc aggcauuugg ggacuuuuuc uuuucuuuuu acuuucucuu 120
uuucuuuugc acaagaagaa gucuacaaga ucuuuuaaga cuuuuguuau cagccauuuc 180
accaggagaa cacguugaau ggaccuuuuu aaaaagaaag cggaaggaaa acuaaggaug 240
aucgucuugc ccaggugucu uguucuccgg ccuggacugu gauaccguua uuuaugagag 300
acuuucagug cccuuucuac aguuggaagg uuuucuuuau auacuauucc caccaugggg 360
agcgaaaagg uuaaaaaaaa gaaaaaaauc acaaggaauu gcccaaugua agcagacuuu 420
gccuuuucac aaagguggag cgugaauucc aggaggaccc aguauucggu uacuuaaaug 480
aagucuucgg ucagaaaugg ccuuuuugac acgagccuac ugaaugcugu guauauauuu 540
auauauaaau auauauauau ugagugaacc uuguggacuc uuuaauuaga guuuucuugu 600
auaguggcag aaauaaccua uuucugcauu aaaauguaau gacguacuua ugcuaaacuu 660
uuuauaaaag uuuaguugua aacuuaaccc uuuuauacaa aauaaaucaa guguguuuau 720
ugaauguuga uugcuugcuu uauuucagac aaccagugcu uugauuuuuu uuuaugcuau 780
guuauaacug aacccaaaua aauaccaguu caaauuuaug uagacuguau uaagauuaua 840
auaaaaugug ucugacauca a 861

<210> SEQ ID NO 236
<211> LENGTH: 830
<212> TYPE: RNA
<213> ORGANISM: Homo sapiens

<400> SEQUENCE: 236
cgaugaaggc ggugagcccg gugcgccccu cgggccgcaa ggcgccgucg ggcugcggcg 60
gcggggagcu ggcgcuacgc ugccuggcgg agcacggcca cagccugggu ggcucggcag 120
ccgccgccgc cgcugcggcg gccgcgcgcu gcaaggcggc cgaggcggcg gccgaugagc 180
cggcgcugug ccugcagugc gauaugaacg acugcuacag ucgccugcgg aggcucgugc 240
cuaccauccc gcccaacaag aaagucagca aaguggagau ccugcagcac guuaucgacu 300
acauccugga ccugcagcug gcgcuggaga cucacccugc uuugcugaga cagccgccac 360
cgcccgcgcc accucuccac ccggccgggg cuuguccggu cgcgccgccg cggaccccac 420
ucaccgcgcu caacacugac ccggugagaa gccuuggcgg gcacccuggg caucgcggga 480
aagguggcgg ggcggcgaga uacgggugguu cuugcuccuc ucagggaaug acagccgcuu 540 cuccccgucuc caccgagagc cgccugcugg gcuuggugau ccacuggucc cugagccgag 600
ggcgguuggg cuuggagccc ugcgucuccg gagugucccu ugcaucacag gaggcuuccc 660
cagcuucggg cucgggguggg gacucugcuc accugccuag uuuuccagga cgucuccugg 720
gugguggcga cacugugaua ugcgcacucu aaccgcuuuu ccccuuggug uuggguugcu 780
guuccaggcc ggcgccguga acaagcaggg ugacagcauu cucugccgcu 830

<210> SEQ ID NO 237
<211> LENGTH: 5560
<212> TYPE: RNA
<213> ORGANISM: Homo sapiens

<400> SEQUENCE: 237
acuagucucg accauguacc aucacggaga cgacaccaac agugacauga acagugacga 60
cgacaugagc cgaaguggga gagaaacccc acccccucga ccaucucaug cuuuuggcag 120
ugagcgagac cuggagcgca ggggcagaag cagagaugug gagccucgag accgcuggcc 180
auacaccagg aaucccagaa gcaggcugcc ucaacgggau cuuucucuuc cugugauguc 240
aagaccacau uuuggacugg acagagauga ugacagacgu uccauggauu augagucucg 300
aucccaggau gccgagucau accagaaugu uguggaacuc aaagaggaca agaagccuca 360
gaauccaauu caggacaacc uggagaacua cagaaagcug cucucgcugg gaguccagcu 420
ugccgaagau gaccgacacu cucacaugac acaaggccac ucaucgaggu ccaagagagc 480
ugccuaccca agcaccagcc gaggucucaa acccaugccu gaggccaaaa agccauccca 540
caggcguggg aucugugagg acgagucuuc ucauggagug auaauggaaa aauucaucaa 600
ggauguggcu cgcaacccca aauccggaag agcaagggag cugaacgagc guccuccucc 660
aagguucccc aggccuaaug auaacuggaa ggacaguucc uccagcagaa gagagucagu 720
gauccaggag aggggguuaug aagggagcgc auuuaggggc ggcuuccggu ucaacgcaga 780
ccuggcuucc agaagcagag cucuagaaag gaagaggcgu uaccacuuug auucugauga 840
gcgggguucg ggccaugagc auaaaagcug ugugaggaag aagccuuuug aguguggugc 900
ugagaugaga caggcuauga gcaugggcaa ccugaacagc ccuuccuucu cugagucgca 960
gucaaucgau uuuggggcca acccauacgu gugugaugag ugcgggaggc aguucagugu 1020
caucucugag uuuguugagc accagaucau gcacacuagg gagaaccucu augaauaugg 1080
agaguccuuu auucauagcg uggcugucaa ugaggugcaa agaagucagg guggggggaa 1140
acgcuuugag uguaaggaau guggagaaac cuucaguagg agugcugccc uggcagagca 1200
ccgccaaauc caugcuagag aauaucuugc agaauguaga gaucaggagg augaggagac 1260
caucaugccu agcccgaccu uuagugagcu gcagaagaug uauggcaaag auaaguucua 1320
ugagugcaag gugugcaagg agaccuuucu gcacaguucc gcccugauug agcaccagaa 1380
aauccauggu agaggcaacu cagaugacag agauaaugag cgugaacgcg aacgugaucg 1440
ucuacgugca cgugcacgag agcagcguga gcgcgaacgu gaacgggagc gugagcguga 1500
gcuuggggaa cccuuucuga ccuguccaaa cuucaaugag uuucggaaga uguacaggaa 1560
agacaaaauc uaugagugca aagugugugg ggagagcuuu cuucaucucu caucccugag 1620
ggagcaucag aaaauccaua cuagaggaaa cccauuugaa aauaagagca ggaugugcga 1680
ggagaccuuu gucccuaguc agucucuccg acggcgccag aaaacuuaca gagagaagcu 1740
guucgacuuu aacaaugcca gggaugcacu gaugggaaac ucagacucca gcgagcauca 1800
gaaaaaccgu ucccgaagga acuucuuuga gggcagagga uuugagaaac ccuucguuga 1860
aucucagaag agucauacua uaacaagacc accugaaaac aaagacgaug acaagccguu 1920
cacaaucagu gucaacccua augacaagcu gaaacucccc aucauggaaa auggcuccca 1980
gggcaaaucc ugugagaggu cuguuauuca uagcuugggc uccgcagaag cucagaagag 2040
ucauggugga cuggggguuca guaaaccaag accaguggca gagucuagca cccagagcuc 2100
aagcagcauu uacuacccca gagcacacuc uggaggcaac accuaugaag gaaaagaaua 2160
caaggacucu aucauccaua gcuugccagc uccucgaccu cugaaacguc auagagcaaa 2220
ugaccauauu caaugugaug aggggggaga auccuccauu uauaucccag auauuauuaa 2280
uaagggaagg aagauuccug ccagagaaga ugcuuaugaa ggaaguagca gcagcaacua 2340
ccacacacca aauguauccc gugcugagcc uccaagucuu ucuggagagu cccaugacuc 2400
uaagcaggau gucacguuuu caguucccag cucaaguguu cgugaacacc agaaagcucg 2460
ugccaaaaag aaguacauug agcccaggaa caacgagacc ucuguuaucc acucccuacc 2520
uuuuggugag uugcuugcag gucaccguag ggcaaaguuc uuugaguguc aggaaugcgg 2580
ggaggccuuu gcucguaggu cugagcucau ugagcaccag aagauucaug auagagaaag 2640
accuucugga agccgacauu augagcgcuc ugucauccgc agccuugcgc ccagugaccc 2700
ucagaccagu uaugcccaag aacguuucau ccaagaacaa gugcguaaau ucagagcguu 2760
uggacaacgc ucaacuacca gcaacaaccu caguguacag aaaaucuaug cccaagagac 2820
auuuaaugcc gaggagcccc augauaaaga aacucauggu caaaaaauuc augacaaaga 2880
gccauauggu aaggagccca guggcaagga gccccauggu gaugagcccc aggacaaaga 2940
accccuuguu caggagaugc gcagugaaga gccccaugau gauaagcccc auggccagga 3000
gccccaugau gauaagcccc auggccagga gccccaugau gauaagcccc auggccagga 3060
gccccacggu gaugagcccc auggccagga gccccacggu gaugagcccc augacaagga 3120
acccauugau caggagaugc gcagugaaga gccccacagu gaagagucuc auggugauga 3180
gccccauggu gaagaguccc auggccagga gaaaguugaa gaugcuacca uucaggccuc 3240
aguuucugaa gagcaucaga aagaugacgc uggugaugca aucuaugaau gccaggacug 3300
ugggcugggc uuuacugauc ucaaugaccu cacaagccac caggacaccc auagcagaaa 3360
ggcucugguu gacagucgug aauaugcaca uucugaaguu caugcccacu ccgucagcga 3420
auuugagaaa aaaugcucug gagagaaacu auaugaaugu ccaaaaugug gggagucuuu 3480
cauucacagc ucguuacuuu ucgagcacca gagaguucac gaacaagacc agcuguauuc 3540
cguaaaggcc uguuaugacg cuuucaucgc ucuguugccc guuagaccaa ggagaaauug 3600
cacuguugaa aggaauccug ccguuucugg gucagccauu cgaugccguc aguguggaca 3660
aggcuucauu cacaguucug cccuaaauga gcacaugaga cagcacagag auaaugaaau 3720
aauggaacag agugagcuuu cagaugagau uuucauucaa ggccuagccc ucacugagua 3780
ucagggggagu gaaacagaag agaagcuuuu cgagugcaca aucuguggggg aaugcuucuu 3840
cacugccaaa cagcucgggg accaccacac caaaguucac aaggaugagc ccuaugagua 3900
ugggcccucc uacacccaug ccuccuuucu caccgagccc cucaggaagc acaucccacu 3960
guacgaaugc aaagauugcg gccaguccuu ccuagacgac acugucaucg cugagcgcau 4020
gguguuucau ccugagcgag aaggugggguc agaaauagua gcugccacug cccaagaggu 4080
cgaagccaau guccucaucc cacaagaagu acugcgaauc caggggucaa augcagaagc 4140
ugcugagccc gaaguggagg cugcagagcc cgagguggag gcugcagagc cugaggugga 4200
ggcugcagag ccuauuggag aggcugaagg gccagaugga gaagcugcug agccugaugg 4260
cgaggcugag cagcccaaug gagaggcuga acagccaaac ggugaugcug acgagccaga 4320
cggagccggg aucgaagacc cagaagagag agcugacgag ccugaggaag acgucgaaga 4380
gccagaggga gaugcagaug agcccgaugg ugcagacauu gaagacccag aagaggaagg 4440

-continued agaagaucaa gagauugagg uugaagaacc auacuacaac ugucaugaau gcgcagaaac 4500
guucgcuucc agcucagccu uuggcgagca ucugaaaagu cacgccagug ugaucaucuu 4560
cgagccggcc aaugcuccug gagagugcuc uggcuacauu gaacgggcca gcaccagugc 4620
agguggugcg gagcaggcag acgacaagua cuucaaaugu gaugugugcg ggcaacucuu 4680
caacgaccgc cucucccuug ccagacacca gaauucucac acugguugag uaaccaggcu 4740
gaagaaaaga agagcaaagc caaaccuucu ucccagaacc agacccuuaa uaaaucacaa 4800
agagagccua aaccaaccca uaaugucuau aagaaauuca ccuuccugua uacauaccgg 4860
acuucacauc aaagacuuuc acucucauca cagacugaaa aaagaaaaga cauugaacgc 4920
agggacucuu ucaguuuuag cuguucccua uggaacauca guguauauuu gggaaagcua 4980
gagugaacau cuacaucuuc cauuucaucu aaguaacuag auugagggaa accuagugac 5040
aauuccagac cacagagguu gccccagucg acuguaaaug auaccccuuu cauacccuau 5100
acauaaugau uccugccaug uauauaaaug agcaaaucag ugauacauau auuuggauuu 5160
agugugcuau agaauuuaca guuuacucua cagagcuacc uagccuggua cucugauuuu 5220
uucccugagg aggaagagag caacaauuua gcauauauuu guaaguauug uccaugcaga 5280
agcuuuucug ugcaucauuu gaaccccauu aguauccuuu ccaguaaugg aguguucugu 5340
ccccuaccuc uuagauaguc cugugaaggu gugggugua aagaucgugu gucuuugaau 5400
ccuggcugug uggaaacagg cauuuuagcu ucuacagcca uuuggugugc acccagaccc 5460
cuugagacug auuguguaac ccuuuacaau auauggauuu gucucuguga cccaaaucaa 5520
cccaucccua cauuuauaua ccuuacagug guuuucuugc 5560

<210> SEQ ID NO 238
<211> LENGTH: 416
<212> TYPE: RNA
<213> ORGANISM: Homo sapiens

<400> SEQUENCE: 238
uuuuuuuuuu uuuuuuuacc guucuuuauu uaaaaaaaua aaauaggagu ccguagggug 60
cacccucccc ccuccugagu gaaggagggc acggugcagu ccggaccugg gagaggggaa 120
agcccggcag gcaggcgaga ccgcuucaca caguggucuc gccaugccgg cuguuggua 180 gacgagugua gaacuuccuc cacgagugca gugucuugcc ggaccagauc cagaagcccg 240
acgugaugcc cacgaugagc gucaugaggu auuugaucau guagacugug aagucgggcg 300
acaugcgggg cguguagugg gccgggcagg ggauggcuag gcucuugcag ugcuggcuua 360
cccaggagcg cucccagugc ucgcggaagg ccugcucaua gaaguagcag gcgaug 416

<210> SEQ ID NO 239
<211> LENGTH: 2380
<212> TYPE: RNA
<213> ORGANISM: Homo sapiens

<400> SEQUENCE: 239
ggccgcgucg acgccucucc agcugcucug uggcagccca gcuaccgguc gugaccagau 60
ccagcuugca gcucagcuuu guucauucga auugggcggc ggccagcgcg gaacaaacau 120
gcagcggcuc gggggguauuu ugcuguguac acugcuggcg gcggcggucc ccacugcucc 180
ugcuccuucc ccgacgguca cuuggacucc ggcggagccg ggcccagcuc ucaacuaccc 240
ucaggaggaa gcuacgcuca augagauguu ucgagaggug gaggagcuga uggaagacac 300
ucagcacaaa cugcgcagug ccguggagga gauggaggcg gaagaagcag cugcuaaaac 360
guccucugag gugaaccugg caagcuuacc ucccaacuau cacaaugaga ccagcacgga 420
gaccagggug ggaaauaaca caguccaugu gcaccaggaa guucacaaga uaaccaacaa 480
ccagagugga cagguggucu uuucugagac agucauuaca ucuguagggg augaagaagg 540
caagaggagc caugaaugua ucauugauga agacuguggg cccaccaggu acugccaguu 600
cuccagcuuc aaguacaccu gccagccaug ccgggaccag cagaugcuau gcacccgaga 660
cagugagugc uguggagacc agcugugugc cuggggucac ugcacccaaa aggccaccaa 720
agguggcaau gggaccaucu gugacaacca gagggauugc cagccuggcc uguguugugc 780
cuuccaaaga ggccugcugu uccccgugug cacaccccug cccguggagg gagagcucug 840
ccaugacccc accagccagc ugcuggaucu caucaccugg gaacuggagc cugaaggagc 900
uuuggaccga ugccccugcg ccaguggccu ccuaugccag ccacacagcc acagucuggu 960
guacaugugc aagccagccu ucgugggcag ccaugaccac agugaggaga gccagcugcc 1020
cagggaggcc ccggaugagu acgaagaugu uggcuucaua ggggaagugc gccaggagcu 1080
ggaagaccug gagcggagcc uagcccagga gauggcauuu gaggggccug ccccugugga 1140
gucacuaggc ggagaggagg agauuuaggc ccagacccag cugagucacu gguagaugug 1200
caauagaaau ggcuaauuua uuuucccagg agugucccca aguguggaau ggccgcagcu 1260
ccuucccagu agcuuuuccu cuggcuugac aagguacagu gcaguacauu ucuuccagcc 1320
gcccugcuuc ucuggcuugg gaaagacagg cauggcgggu aagggcagcg gugagucguc 1380
ccucgcuguu gcuagaaacg cugucuuguu cuucauggau ggaagauuug uuugaaggga 1440
gaggauggga aggggugaag ucugcucaug auggauuugg gggauacagg gaggaggaug 1500
ccugccuugc agacguggac uuggcaaaau guaaccuuug cuuuugucuu gcgccgcucc 1560
caugggcuga ggcaguggcu acacaagagc uaugcugcuc uguggccucc cacauauuca 1620
ucccuguguu ucagcuccua ccucacuguc agcacagccc uucauagcca cgcccccucu 1680
ugcucaccac agccuaggag gggaccagag gggacuucuc ucagagcccc augcucucuc 1740
ucucaacccc auaccagccu cugugccagc gacagcccuu ccaaauggag ggagugaaau 1800
ccuuugguuu uauuauuuuc uccuucaagg cacgccugcc acuaagguca ggcugacuug 1860
caugucccuc uaacguucgu agcagugugg uggacacugu cuuccaccga cugcuucaau 1920
accucugaaa gccagugcuc ggagugcagu ucguguaaau uaauuugcag gaaguauacu 1980
uggcuaauug uagggcuagg auugugaaug aaauuugcaa agucgcuuag caacaaugga 2040
aagccuuucu cagucacacc gagaagucac aaccaagcca gguuguguag aguacagcug 2100
ugacauacag acagaagaag gcugggcugg augucaggcc ucagaugacg guuucaggug 2160
ccaggaacua uuaccauucu guaucuaucc agaguuauua aaauugaaag uugcacacau 2220
uuguauaagc augccuuucu ccugaguuuu aaauuauaug uauacacaaa cauguggccc 2280
ucaaagauca ugcacaaacc acuacucuuu gcuaauucuu ggacuuuucu cuuugauuuu 2340
caauaaauac aaauccccuu caugcaaaaa aaaaaaaaaa 2380

<210> SEQ ID NO 240
<211> LENGTH: 2659
<212> TYPE: RNA
<213> ORGANISM: Homo sapiens
<220> FEATURE:
<221> NAME/KEY: misc_feature
<222> LOCATION: (1274)..(1274)
<223> OTHER INFORMATION: n is a, c, g, or u
<220> FEATURE:

-continued

<221> NAME/KEY: misc_feature
<222> LOCATION: (1358)..(1358)
<223> OTHER INFORMATION: n is a, c, g, or u
<220> FEATURE:
<221> NAME/KEY: misc_feature
<222> LOCATION: (1507)..(1508)
<223> OTHER INFORMATION: n is a, c, g, or u

<400> SEQUENCE: 240
gcacgagcag cccgcagccc gccgcgccug ugcgagccgg gacagcacuc ggccccgcgc 60
gcuccccgcc ccgcgccagc cccgccgcgg cgaccugcug cagcggagga ccccaucgau 120
cggagacccg gggagcagcg cgcagcccgc gagccgacgg gccccgacug cgucuuuguc 180
cccggaggcu ccgggaaguu ugcagcggga cgcgcgcgug aaggcagcgu gggcagcccc 240
gacgucgccg agcaacaugg gcgucgggcg cagcgcgcgg ggucgcggcg gggccgccuc 300
gggagugcug cuggcguugg ccgccgcucu gcuggccgcg gguucggcca gcgaguacga 360
cuacgugagc uuccaguccg acaucggcuc guaucagagc gggcgcuucu acaccaagcc 420
cccgcagugc guggacaucc cgguggaccu gaggcugugc cacaacgugg gcuacaagaa 480
gauggugcug cccaaccugc uggagcacga gaccauggca gaggugaagc agcaggccag 540
cagcugggug ccgcugcuca acaagaacug ccacaugggc acccaggucu uccucuguuc 600
gcucuucgcg cccgucuguc uggaccggcc caucuacccg ugucgcuggc ucugcgaggc 660
cgugcgcgac ucgugcgagc cggucaugca guucuucggc uucuacuggc ccgagaugcu 720
caaaugugac aaguuccccg agggcgacgu cugcaucgcc augaccccgc ccaauaccac 780
ggaagccucu aagccccaag guacaaccgu guguccucca ugcgacaacg aguugaaguc 840
agaggccauc auugaacauc ucugugcaag cgaguuugca cugaggauga aaaucaaaga 900
agugaagaag gaaaacggug acaagaagau uguccccaag aagaagaaac ccuugaagcu 960
ggggcccauc aagaagaagg agcugaaggc gcuugugcug uuccugaaga acggugccga 1020
cugucccugc caccagcugg acaaccucag ccacaacuuu cucaucaugg gccgcaaggu 1080
gaagagccag uaccugcuga cagccauuca caagugggac aagaaaaaca aggaguucaa 1140
aaacuucaug aagagaauga aaaaccacga gugucccacc uuccagucug uuuuuaagug 1200
auacuggggc ggacugggga aggggagugu ggcuuggggu gagggugggg gcgcguggau 1260
gacccuggcu cuunggggcu cacauauugc ucucacccau acaguugugg cuuuugcauu 1320
gcaccuggcu cuguuccuac agcgaacccu cucccuuncc uccauagcca cauccagcua 1380
aggccacggc cuuuagauua ggaaggcuuu uuuuuuuuua agggcugcag cagggccagc 1440
agcgacgugc aaaaggagag gcagaauccu uucacugagc cuggggcaca aaaaacagaa 1500
aauguunncc gguuuggaaa aacaaaacaa aacggauugu aaagaacugc agacggacag 1560
cugcucagcu caacguuguu cgggacauca uuaccaauug cuuguggagu cuaagccucu 1620
acagguagaa gagucugauc auugccaagc caggcugcuu ucaguuuauu auuaaucccc 1680
cucuuucugc cuuagauaga ccaucgccac cuucaaaaca cacacacaca cacacacaca 1740
cacacacaca cacacacaca cacacacaca cacuucugaa aguagccagg guaucccagu 1800
auagaacggg auagcuaagg guuugggugg gaggccacug cuacucuacc uucagcuuuu 1860
gaacuggcca ccuuugauag gaaacugagg ucucagaugg acacuucuac caguccaucg 1920
ggauacaagg augccaggca agggucugcu uuugucugaa ggagguacgu gggcaugaag 1980
agacaugagg cauuucaggc ugagaagcaa cagcuacuag uuuucaacaa uagaguggaa 2040
gaaaugagca aagguagaaa ugucaagcag gucacaaguc agggugauug ggggaauccu 2100
gugccaacag ccucacuuug uaauuccauc ugucacuuuc aaaagaacag cagcauaaga 2160
cagggauaaa agcccacaua cccuccaagg cuugaguaaa aguccacacu cagcauuuca 2220
aagacuaacg ucguugacug cccaaggcug cccucuuaau acaccgccua ugcaugugcu 2280
guggaaggca acucugugca ugugcugugg aggagauggg ccucauggcu gugcuggcug 2340
cccggaauca guauagcgug gaaggagaca guauccauag acucugcuuu ucugcaagga 2400
aagcccuuuu ccuuauacau gauugccuau aauucagaca aauuuaaaau cgcugccugc 2460
cugagcccuc caccuuuacu uuugcauucu ccggucauau ucuuuugagg cuaaagugcc 2520
cuauccgagg agaugguuuc aaaggcuaac uaaucugcag cuuucccaag ugcccagagg 2580
uauuucucaa aguugguaug cuuaauaagu gauguaaaua uuccaguucu cuuaggcagc 2640
cuuacuccug uugucccug 2659

<210> SEQ ID NO 241
<211> LENGTH: 3347
<212> TYPE: RNA
<213> ORGANISM: Homo sapiens

<400> SEQUENCE: 241
aauuccgagu ggccgcgcgg cuauuuaagu ggcguuacuc cgcguccucg gcgcugcagc 60
cuugaggcuu cgggcgcggg ggaagucaug cuggcuccac agaagcacua gcuaguccgu 120
guacuuugug gguucugucc uuuugagacc ugcccgccgg ggauuggcug guaucaguga 180
cugucuacug cuggauuuuc ugcuugccuu cccgucaugu cuaacgaagu agaaacaagc 240
acaaccaaug gccagccuga ccaacaggcu gccccgaaag cgccaucaaa gaaggagaag 300
aagaaagguu cugaaaagac agacgaguac uuguuggcca gguucaaagg ugauggguu 360 aaauacaagg ccaagcuaau cgguauugau gaugugccug augcucgagg agacaaaaug 420
agucaggauu cuaugaugaa acucaaggga auggcagcag cuggucgcuc ucagggacaa 480
cacaagcaaa gaaucugggu caacauuucc uugucuggca uaaaaaucau ugaugagaaa 540 acuggggua uugaacauga acauccagua aauaagauuu ccuucauugc ucgugaugug 600
acagacaaca gagcauuugg uuaugugugu ggaggugaag gccagcauca auuuuuugcu 660
auaaaaacag ggcaacaggc ugagccauua gucgucgauc uuaaagaccu uuuucaaguu 720
aucuauaaug uaaagaaaaa ggaagaagau aagaaaaagg uugaagaagc caacaaagca 780
gaagagaaug gaagugaggc ccuaaugacc cuugaugauc aagcuaacaa auugaagcug 840
gguguugacc agauggauuu guuuggggac augucuacac cuccugaccu aaauagucca 900
acagaaagca aagauauccu guuaguggau cuaaacucug aaaucgacac caaucagaac 960
ucuuuaagag aaaauccauu cuuaacaaau ggagucaccu ccuguucucu cccucgacca 1020
aagccucagg cauccuucuu gccugagaac gccuuuucug ccaaucucaa cuucuuuccc 1080
accccuaacc cugauccuuu ccgugaugau cccuuugcac agccagacca aucggcaccc 1140
ucuucguucg auucucucac aucuccagau cagaagaaag cgagucugag uagcucgucu 1200
acuccacaga guaaagggcc ccugaacguc gauacugauu acuuugguca gcaauuugac 1260
cagcucucua accggacugg caaaccggaa gcucagggag gcccguggcc cuacccaagu 1320
ucgcagaccc agcaagcagu gagaacucaa aaugggguau cugaaagaga acagaacggc 1380
uuccauauca aaucuucccc gaacccuuuu gugggaagcc cucccaaagg acuaucggua 1440
ccgaauggcg uaaagcagga cuuggaaagu ucuguccagu ccucagcaca ugacuccaua 1500

-continued gccauuaucc caccuccaca aaguaccaaa ccaggaagag gcagaaggac ugcuaagucu 1560
ucagcaaacg acuugccugc uucagacauc uuugccucag aaccuccagg ccagaugucc 1620
cccacaggac aaccugcagu cccgcagucg aacuuccugg aucucuucaa aggcaaugcu 1680
ccucccccag uggggccccu uguaggucua gguacggucc caguaacacc cccccaagca 1740
ggacccugga cgccuguugu cuacaguccu ucgacaacug uggucccagg agccauaaua 1800
aguggccagc cucccaguuu ucgccagcca cucguuuuug guacaacccc agcaguacaa 1860
gucuggaauc agucuccauc auuugcaacc ccagcuuccc cuccaccccc cacaguuugg 1920
uguccuacca caucuguggc gcccaacgcu uggucaucca caagcccucu ggggaauccu 1980
uuucagagua auaauaucuu uccaccuccc accaugucca cucaguccuc uccucagccu 2040
augaugaccu cuguucuggc cacaccgccu caaccaccuc cccgaaaugg cccacuaaag 2100
gacauuccca gugacgcuuu cacuggcuua gacccccuug gggauaaaga ggucaaggaa 2160
gugaaagaaa uguuuaagga cuuccagcug cggcagccac cucuuguucc cucaaggaag 2220
ggggagacgc cucccucugg gacuucaagc gccuucucca guuacuucaa caauaaaguu 2280
ggcauuccuc aggagcaugu agaccaugau gauuuugaug ccaaucaacu guugaacaag 2340
auuaaugaac caccaaagcc agccccgaga caaggugucc ucuugggguac caagucugcu 2400 gacaauucac ucgagaaccc uuucuccaaa ggguucagcu caucaaaccc cucugugguu 2460
ucucagccug caucuucuga uccccacagg agcccuuucg gaaauccuuu ugccuagcuu 2520
cugaaguugu aaugaugacu auccagauga gcaaaagacu ggcuuugguc aagaaugaag 2580
cagacagcca gaaacauguu gaccucuguc cucgcuccag cuuugacgua uuaucuguua 2640
cccuauuugu uuuggccucu uguacuugua aaaugccuuu cauuuuccug ucuaggcuaa 2700
agcuaaacuu aaacuauggc uuuacguaaa uuaagcuccu aaacucucua gcuccaauau 2760
aaaugaagua gcuucccuau caaaucccug ucuguugugc ccccuugaaa cuuccagaau 2820
auucuccauu cuacccucca uuugggagga gcggcuaccu uuacccuuaa uaucacacug 2880
ccuugaguca auguccaaau acucauagcu cucaaaguca uuuggggguuc cuggugugcg 2940 gccuaaaccu aaagcauccu auuaauaggg aaguaagaca ccuugcuucc uauguccacu 3000
cagggagaau uuuauuuaau aaaaugaaag caagacuaac uucucaaauc cacccaagga 3060
ccauuuugag auggucguuu cucagcuaac ugcaccauuu accaauccug ccccaagugg 3120
ugcuuacauu ugacuugaag aagagaaaga gcuaacucaa aacacaaggc auuauucaaa 3180
gcuaauaaaa caauuucucc cuggggcccc acauuguuuu cauuccagau acguugcagc 3240
uguuugaccc ugaugacauu augcccuaca uuuuccuuga agauccugau uuuauuucau 3300
gugauuuuug uuucucaaua aagaugauua uugugugcac ggaauuc 3347

<210> SEQ ID NO 242
<211> LENGTH: 555
<212> TYPE: RNA
<213> ORGANISM: Homo sapiens

<400> SEQUENCE: 242
augaaucgca ccgcauacac ugugggagcg uugcuucucc uccuggggac ccuacugcca 60
acagcugagg ggaaaaagaa agguucccaa ggagccauuc cgccuccuga caaggcucag 120
cacaaugacu cugagcagac ccaguccccca ccacaaccug gcuccaggac ccgggggcgg 180
ggccaggggc ggggcaccgc caugccugga gaggaggugc uugaguccag ccaagaggcc 240
cugcacguga cagagcgcaa guaucugaag cgagauuggu gcaaaacuca gccccugaag 300
cagaccaucc acgaggaggg cugcaacagc cgcacuauca ucaaccgcuu cuguuauggc 360
cagugcaacu ccuucuacau ccccaggcac auccgaaagg aggaagggUC cuuucagucu 420
ugcuccuucu gcaagcccaa gaaguucacc accaugaugg ucacacucaa cuguccugag 480
cuacagccac ccaccaagaa gaaaagggUC acacgcguga agcagugccg uugcauaucc 540
aucgacuugg auuaa 555

<210> SEQ ID NO 243
<211> LENGTH: 2526
<212> TYPE: RNA
<213> ORGANISM: Homo sapiens

<400> SEQUENCE: 243
guggaauauc cauggaggua cggagccuug uuaccaaccu uuaaccgcag aacugggaug 60
uggggcugga agugccuccu cuucugggcu gugcugguca cagccacucu cugcacugcc 120
aggccagccc caaccuugcc cgaacaagcu cagcccuggg gagucccugu ggaaguggag 180
ucucuccugg uccacccugg cgaccugcua cagcuucgcu gucggcuucg cgaugaugug 240
cagagcauca acuggcugcg ggaugggug cagcuggugg agagcaaccg uacccgcauc 300
acaggggagg agguggaggu gcgggacucc aucccccgcug acucuggccu cuacgcuugc 360
gugaccagca gccccucugg cagcgauacc accuacuucu ccgucaaugu cucagaugca 420 cucccaucu cggaagauga ugacgacgac gaugacuccu ccucggagga gaaagagacg 480
gacaacacca aaccaaaccg uaggccugua gcucccuacu ggacaucccc agagaaaaug 540
gagaagaaac ugcaugcggu gcccgcugcc aagacgguga aguucaagug cccgucgagu 600
gggacaccca accccacucu gcgcugguug aaaaauggca aagaguuuaa gccugaccac 660
cgaauuggag gcuacaaggu ucgcuaugcc accuggagca ucauaaugga uucuguggug 720
ccuucugaca agggcaacua caccugcauc guggagaaug aguaugggag caucaaccac 780
accuaccagc uugacgucgu ggaacgaucu ccgcaccgac ccauccuuca ggcagggcug 840
ccugccaacg agacaguggc ccugggcagc aauguggagu ucauguguaa gguguacagc 900
gauccgcagc cucacauuca guggcugaag cacaucgagg ugaacgggag uaagaucggg 960
ccagacaacu ugccguaugu ccagauccug aagacugcug gaguuaauac caccgacaag 1020
gaaauggagg ugcuucaucu acggaauguc uccuuugagg augcggggga guauacgugc 1080
uuggcgggua acucuaucgg acucucccau cacucugcau gguugaccgu ucuggaagcc 1140
cuggaagaga gaccagcugu gaugaccuca ccgcucuacc uggagaucau uaucuacugc 1200
accggggccu uccugaucuc cugcauguug ggcucuguca ucaucuauaa gaugaagagc 1260
ggcaccaaga agagcgacuu ccauagccag auggcugugc acaagcuggc caagagcauc 1320
ccucugcgca gacagguaac agugucagcu gacuccagug cauccaugaa cucugggguu 1380
cuccugguuc ggcccucacg gcucuccucc agcgggaccc ccaugccggc uggagucucc 1440
gaauaugagc ucccugagga ucccccgcugg gagcugccac gagacagacu ggucuuaggc 1500
aaaccacuug gcgagggcug cuucgggcag gugguguugg cugaggccau cgggcuggau 1560
aaggacaaac ccaaccgugu gaccaaagug gccgugaaga uguugaaguc cgacgcaacg 1620
gagaaggacc ugucggaucu gaucucggag auggagauga ugaaaaugau ugggaagcac 1680
aagaauauca ucaaccuucu gggagcgugc acacaggaug guccucuuua ugucauugug 1740
gaguacgccu ccaaaggcaa ccuccgggag uaucuacagg cccggaggcc uccugggcug 1800

-continued

```
gaguacugcu auaaccccag ccacaacccc gaggaacagc ugucuuccaa agaucuggua   1860

uccugugccu aucagguggc ucggggcaug gaguaucuug ccucuaagaa guguauacac   1920

cgagaccugg cugcuaggaa cguccuggug accgaggaua acguaaugaa gaucgcagac   1980

uuuggcuuag cucgagacau ucaucauauc gacuacuaca agaaaaccac caacggccgg   2040

cugccuguga aguggauggc cccugaggcg uuguuugacc ggaucuacac acaccagagc   2100

gaugugugu cuuuuggagu gcucuugugg gagaucuuca cucugggugg cuccccauac   2160

cccggugugc cuguggagga acuuuucaag cugcugaagg agggucaucg aauggacaag   2220

cccaguaacu guaccaauga gcuguacaug augaugcggg acugcuggca ugcagugccc   2280

ucucagagac cuacguucaa gcaguuggug gaagaccugg accgcauugu ggccuugacc   2340

uccagccagg aguaucugga ccuguccaua ccgcuggacc aguacucacc cagcuuuccc   2400

gacacacgga gcuccaccug cuccucaggg gaggacucug ucuucucuca ugagccguua   2460

ccugaggagc ccugucugcc ucgacacccc acccagcuug ccaacagugg acucaaacgg   2520

cgcuga                                                              2526
```

<210> SEQ ID NO 244
<211> LENGTH: 468
<212> TYPE: RNA
<213> ORGANISM: Homo sapiens

<400> SEQUENCE: 244

```
auggcugaag gggagaucac aaccuucgca gcccugaccg agagguucaa ccugccucua     60

ggaaacuaca aaaagcccaa acugcucuac ugcagcaacg gggccacuu cuugaggauc    120

cuuccugaug gcaccgugga ugggacaagg gacaggagcg accagcacau ucagcugcag    180

cucagugcgg aaagugcggg cgaaguguau auaaagggua cggagaccgg ccaguacuug    240

gccauggaca ccgaagggcu uuuauacggc ucgcagacac caaaugagga augucuguuc    300

cuggaaaggc uggaagaaaa ccauuauaac acuuacaccu ccaagaagca ugcggagaag    360

aacugguuug ugggccucaa gaagaacggg agcuguaagc gcgguccucg gacucacuau    420

ggccagaaag ccaucuuguu ucugccccuc ccggugucuu cugacuag                468
```

<210> SEQ ID NO 245
<211> LENGTH: 3115
<212> TYPE: RNA
<213> ORGANISM: Homo sapiens

<400> SEQUENCE: 245

```
auggacaccu ccugcgucca caugcuccug uccuugcugg cgcugcugca guugguggcc     60

gccggcagcu caccgggacc agaugcgaua ccgcggggcu gcccaucaca cugucacugu    120

gagcuggaug gcaggaugcu gcucagggug gacugcucgg accuggggcu cucggagcug    180

cccuccaacc ucagcgucuu caccuccuac cuggaccuca guaugaacaa caucagucag    240

cuacccgcca gucuccuaca ucgccucugc uuccuagaag aguuacgucu ugcuggaaau    300

gcuuugacac acauucccaa gggagcguuc acgggccuuc acagccucaa agugcuuaug    360

cugcagaaca accagcugag aaagguuccg gaggaagcgc uacagaauuu gagaagccuu    420

caaucccugc gccuagaugc caaccacauc agcuacgugc cacccagcug uuucagcggc    480

cugcacuccc ugaggcaccu guggcuagau gacaaugcuc ucacagacgu cccuguccag    540

gcuuucagaa guuuaucagc ccugcaagcc augaccuugg cccugaacaa aauacaccac    600

auagcagacu acgccuuugg aaaccucucc agccucgugg uucugcaucu ccauaauaau    660
```

-continued

```
agaauccacu cccugggaaa gaaaugcuuu gauggacucc acagccugga gacuuuagau    720
uuaaauuaua auaaccuuga ugaauucccc acugcaauca agacacucuc caaccuuaag    780
gaacuaggau uccacagcaa caacaucagg ucaauaccgg agcgagcguu cguaggcaac    840
ccuucucuua ucacaauaca cuucuaugac aaccccaucc aauuuguugg aguaucugcu    900
uuucagcauu ugccugaacu aagaacacug acuuugaaug gugccucgca cauuacugaa    960
uuuccucacu ugacaggaac ugccacccug gagagucuga cuuuaacugg agcaaagauc   1020
ucaucucuuc cccaggccgu cugugaucag uuaccuaauc uccaagugcu agauuugucu   1080
uacaaccuac ucgaagacuu acccaguuug ucaggcugcc aaaaacuuca gaaaauugac   1140
cugaggcaua acgagaucua ugaaauuaag ggcagcacuu uucagcaguu guuuaaccuc   1200
cgaucucuga acuuagcaug gaauaaaauu gcuaucauuc accccaaugc guuuucuacg   1260
uugccgucuc uaauaaaguu ggaccuauca uccaaucucc ugucguccuu cccugugacu   1320
ggguuacaug guuuaacuca cuuaaaauua acagggaacc gagccuuaca gagccugaua   1380
ccaucugcaa acuucccaga gcucaagauu auagaaaugc caucugcuua ccaguguugu   1440
gcauuugggg ggugugagaa ugucuauaaa auuucuaacc aauggaauaa agacgacggc   1500
aacagugugg acgaccuuca uaagaaagac gcuggguuau uucaaguuca agaugagcgg   1560
gaccuugaag auuuccuacu ugacuuugag gaagaccuga augcccuuca cucggugcag   1620
ugcucgccuu ccccaggucc cuucaagccc ugugagcacc uauuugguag cuggcugauc   1680
cgaaucgggg uguggaccac ggcaguacug acgcuuuccu gcaaugccuu gguggcuuug   1740
accguguuca gaacuccccu guacaucucu uccauaaagc ugcuaauugg gguaaucgcg   1800
guaguggaca uucucauggg ggucuccagu gcugugcugg cugccgugga ugcauucacu   1860
uuuggccguu uugcucagca cggugcgugg ugggaagacg gaaucggcug ccaaaucguu   1920
ggcuuccugu ccauuuuugc uuccgaaucg ucgaucuucc ugcucacucu ggcagcgcug   1980
gaacgagguu uuucugucaa gugcucuucg aaguuugaag ugaaagcucc ccuuuuuagc   2040
cugagagcga ucguuuugcu augugucug uuggcccuga ccauugccac aaucccccuug   2100
cuaggaggca guaaguacaa ugccucuccc cucugccugc ccuugcccuu uggggagccc   2160
agcaccacgg gcuacauggu ggcucucgug uugcucaacu cucucuguuu ccucauaaug   2220
accauugccu acacaaagcu cuacugcagu uuggagaaag gagagcugga gaaucuuugg   2280
gauuguucga uggugaagca cauugcucug uugcucuucg ccaacugcau ccuuuacugc   2340
cccguggcuu ucuuauccuu cuccucuuug cuaaaccuca ccuuuaucag uccugacguc   2400
auuaaauuua uacuucucgu gaucguccca cuuccuuccu gucucaaccc acuucucuac   2460
auugucuuca auccccauuu uaaggaggau augggcagcc ugggaaagca uacccguuuc   2520
uggaugagau caaaacacgc gagucugcug uccauuaacu cggacgaugu ugagaaacgg   2580
uccugugagu caacccaagc cuuaguaucc uuuacccacg ccagcauagc cuaugacuug   2640
ccuuccacuu ccggggcauc accagcuuac cccaugacug aaagcuguca ucucucuuca   2700
guugcauuug ucccaugucu cuagugacua ugagagagga acguuuuuaa gaguuggaaa   2760
ccugaaaagu gauuucuauc agagcaguag cuaagaaaag cugagcuaaa aaccuaccuu   2820
aaaacccaag caaacaucuc uaaauuggug uggaaacagu ggugccuuag agcaggagag   2880
caucauuaaa caccgcuugu aucauuuguu cagcuaagaa ggaaagccau caagucacuu   2940
aggugaaccc agaugagaaa agcagccuga aaugcucuuc gcauuguagu cucuucugac   3000
```

-continued ucaccagcau agucucccau agugagaaga cucguuggau gacucaaugg guguauuuaa 3060
auccacaaau uccuuguuua aaagguuaga guuuuaagaa aaaaaaaaaa aaaaa 3115

<210> SEQ ID NO 246
<211> LENGTH: 5561
<212> TYPE: RNA
<213> ORGANISM: Homo sapiens
<220> FEATURE:
<221> NAME/KEY: misc_feature
<222> LOCATION: (4879)..(4879)
<223> OTHER INFORMATION: n is a, c, g, or u
<220> FEATURE:
<221> NAME/KEY: misc_feature
<222> LOCATION: (5116)..(5116)
<223> OTHER INFORMATION: n is a, c, g, or u

<400> SEQUENCE: 246
uuuuuuuucu ucaccuccuc ccuuuucaag gccuccaagc uaauuauuuc uguugcuuug 60
gagugagcaa uucugugguu cucuccacca ccaccccaa uucugacccg aucccgccug 120 ggggguuucua cggucuccgc ucacucugcg ugcaccuggc gcgccucuuu uuuucacccc 180
caaccuguug caagucuuua auccucgcaa uugggacuug cgugcaggca ccugaauccu 240
ccuugccuca uauuuugcaa guguuugggg gagagcaccu gcucuaccug caagagauuu 300
aaaaggaaaa aaaucuccag gcucccucuu ucuccacaca cucucgcucu ccugccccgc 360
cccgagguaa agccagacuc cgagaaaaug gugaucagcg ugguccuccu gcugcuggcc 420
gccuaugccg uaccggcuca aggccugggu ucuuucgugc auugugaacc cugcgacgag 480
aaagcucugu ccauguguccc ccccagcccu cugggcugug agcuggucaa agagcccggc 540
uguggcugcu gcaugacuug cgcccuggcg gagggacagu cguguggugu cuacacagag 600
cgcugcgccc aggguuugcg cugccucccc cggcaggaug aggagaagcc gcugcacgcc 660
cugcugcacg gccgcggggu uugccucaac gaaaagagcu acggcgagca aaccaagaua 720
gagagagacu cucgggaaca cgaggaaccc accaccuccg agauggcuga agagaccuac 780
ucccccaagg ucuuccggcc caagcacacu cgcauuuccg agcugaaggc ugaggcugug 840
aagaaggacc gcagaaagaa gcugacccag uccaaguuug uggggggugc agagaacacu 900
gcccacccca gagucauccc ugcaccugag augagacagg aauccgaaca aggccccugc 960
cgcagacaca uggaagcuuc ccuccaggag uucaaagcca gcccacgcau ggugccccgu 1020
gcuguguacc ugcccaacug ugaccgcaaa ggauucuaca agagaaagca guguaagccc 1080
ucccguggcc gcaaacgugg caucugcugg uguguggaca aguacggaau gaagcugccg 1140
ggcauggagu acguggaugg ggacuuucag ugccacgccu ucgacagcag uaacguugag 1200
ugacgcgucc ccucccuucc ucccccuauc cuacccccccc agccccaacu ccagccagcg 1260
ccucccucca ccccaggacg ucacucauuu caucucauuu aggggaaaua uauauacaua 1320
uauauuugag gaaacugagg accucggaau cucuagcaag ggcuaaggag acacucccca 1380
ccaugacccc ggaaauguau uccuuuuuga agcaaguuga acggacagag aagggaagga 1440
gagaagaagc aagagggagc gagagaugga aagaaagcaa agcguuggaa uagaggaaaa 1500
gagggaagga cagauaggau uagagagaga agagagaaac agcaaggcag aaaggacucc 1560
acaaccaagg cugaaucugc ccuuuugcuu ucagcucuag ccuggggguca gaaaaagugu 1620 ggcauucagu gacacccagu uuagauuggu caaggggaga aaagaaacaa ggugugucag 1680
ugccucucgg gucuguccccc uccugcagcc agcagugugg auggcuagac cccucacccu 1740
ccucuccucu uacccaagug cagggugauu ucauccccaa auuuacaaag acuaaaaugc 1800

-continued

```
auuccauccc ucugaaaaua aacaaaagug agugauugaa gauagguuuu cccccagcag   1860
acaagugaac ucagaaugug ugcaaauuuu acucuuguua aagauuuuuu uaagaaguca   1920
guacgcaccc ccaacacugg aaagacuuga uucuccaggg ugacaagcaa uucagaagcg   1980
cguggcuucg gcccuugauu ucacuagacu caaagcuggc ccggcagccu cuguggagga   2040
ggaugagagg uggagaaaac caaggggcuu guacucaccc acaagacucc auguagacuu   2100
uauaggcaua uaaaucuauu uucuuuaccu uuuuuucccu uucccuuucu uucgaaguuu   2160
ugcauuaccu cuuuaaagua guuuuuuuua ggacacugaa gaucuuccuc auucugggaa   2220
aaauccauau uucacaaaua caacccagaa cgccagcuug gccugcgucc aggcagccuu   2280
ucucgugagc uacaagugug gcucuuuugu ggggcaccga uuuggaucuu cucaugauuc   2340
caaacgugug uugaagugaa uccaccaagc cagguaacug ccagcaccca agggugcauc   2400
aagugcauag cccaggucac cccauuucag ccuuccaacc cgcagaaagu aacugucuca   2460
caccacacca cauaaaccug ccagauccau cuguaaccca cuggccugcc cagaccuuuu   2520
uuucccaucu gcauuuuuuu uuuugaacug cauuuugaaa gccucccuca gaugccaggc   2580
ugacagauca gagagaaacu aacaugagag augacagagg aggaggaagu ggaggguggg   2640
ggcagagacu uccacagaga gacauagaag auggagcaga ggucuggggg uggggaggac   2700
aagaaagaga cagagagagg aaaauaccaa uagaauuuuc cuuggugucu cccaucuaau   2760
caacucucug agauuugaga ggaaaaagaa ggcaggggaa gaacuugagg uagaaaugag   2820
gucaguucaa gucacagggc ccagauggug gguaacugag gcaggaucca gacuugagac   2880
acacgguugg aaacaaggcu gguuagccug acuggguauu gaagggugaa gaggaugccu   2940
uggaaagaca gcacaacuuc aguucaacuu caggccccca aggaggaacu gaggccaaag   3000
aauccuucaa gugcuucaug agucuccucu gcccgacuca aacauccuuc ccugugaugg   3060
aggaugguag aaagcccagg acaacucagg cccggaucuu cacgacuguu gucauuugcc   3120
agccugauuu ugauccaaga gaagcaucuc auugcccacu ggcuucuuca acaaagaggu   3180
gcuuaacaaa aggcucagga cuaucuuuga agacugaaga uaaccuucca ggagaggaga   3240
cucggacauu gguacaggag gccccuuuug gcgggggaca cagcucuuug cgcucucuug   3300
auggcauggc auaguagagg cccccuccaa cccggaacau ggagcaacac aaagggagag   3360
caaagaaacu gacgugcguc gacucauagg acaugggugg cugcgggcac agaaagggau   3420
gccuccuguu gccuggacag gacaguuggc ugggaaggaa agagaaaauu gaucuucaua   3480
agacaaaggg ccugauggga uggcaauaga aggacuuacc agaccugcag ggucaguaua   3540
cccaucaccc cgcacaacau ccccagcccc caacucaaac uucaauauau cuuaggccag   3600
uauccuagac cuaagucucu ccuuucugcc auuauuucuc cgcaucuuga gcagucaucu   3660
gacugagauu ugccaagugg auacuggggu accacugccc cccaagaaaa gacugagcca   3720
ggaacugccu acucgcuccc ccucccgagc cuggagcuaa cuccugugag ggugcucuc    3780
uucaccccac aacuuacuag accuugagug agccucuguc ccuuaugugg gcucuucgcu   3840
gugagccaca gauggagguc auuguauaga caguuagccu uccccagguc agccuaccuc   3900
ccccaaacuu gugagucucc ccgcugcuca uauggagagg caugucuaag acagcaaguc   3960
uucuagagga agcuugccuu uaacagacag auggaacuaa accuuccaaa ugggagaucu   4020
ggcugaaccc aggauacaga gaccauggac auggaugggg ucaucaagag aagagggaug   4080
uccuucucca gguuagggag agagaaggca aguuugcaac gaucccauca ugcccugagc   4140
```

-continued

```
aagaagcuuu uggcccaggc uagccuuuaa cuccauuaga ggccucucug uuggguuuau   4200
ccacagcagu aggcccaagu auggccuguc cccaccucua cuaucccgug gaagguuucu   4260
ucccacccu uuuugacaaa ugccucacuc gagcagugga aagauagcuc ucuuccccu   4320
cuucugccag guaacaaaga gaccuaacca ggaccuauuc uccaccccag ccagucuuga   4380
ccagccagaa caaagcaggg aaccuggaga auaaaagacu cuacguuccu cugacaaaga   4440
cucuacguuu cucugacggc caggccuaaa cagacaaggc uugggaacau cugccccaca   4500
ggauacggag gaggucagcu gugcucacuc cucuucuccu uccaagaccc ucuuccgacc   4560
augacuuauc uccaugguaa cauccucacc aucauucucc cacuaccaag gguugccaug   4620
gcaaccuccc aaccaccugc ccaucccagg caggcagcug uccuucugcu cagaacccua   4680
gaggacucua ggugaaauuu uacagcuuaa gagaggagug agccaaggag aagagacccu   4740
guaguccucu ggcuuucaag agaaagaagg cuaugauuua aaacacagua gaagggaaag   4800
aggucucguc gaggucgacc ucuccccgggg agcuuagggg uuguacuguc uuuauuuuuu   4860
aaaccacuaa agugcaaunu uuccugcacu cuuguuaccc cgccucucuu cccuguuagg   4920
uuuucauuuc cuugagcaga cuuucuuggu uuuuuaaugg aguauagacu uucaccacuu   4980
cacagacucu ggccuccucu ccaagucucu cuggaugggg aaaaggaagg uagaggguca   5040
gaggggaagg gguccucgu caccccgcau ccauucaccc ccacuucucu ggucccuagu   5100
caccggcuuc accccnaucu ccgacaccau cacugucaca caguagccug ucacacggau   5160
aguacaguuc agacaagacu ccuucagauu ccgagacgcc uaccgguugu uuuugguuuu   5220
uguuuuguuu ucuuuuguuu guuuguuugu uuguuuuuua caacagcaau aaccacauca   5280
cauauuacug uagcucucua uaguguuacg uucagacacc guagcucugu ccucucuuau   5340
uuuguugguu uugacuuaaa aaaaaauacu uaugcuuuuu acuggugaaa cagauugaaa   5400
aaaaaauuga acaacaaacc aguuugugaa aaaaaaaaaa aaugugaaaa aaaaucaccc   5460
cgauguggaa gagcucggcu ccucuuuagc auuuuguacu uaaggaaaua aaaaagaaaa   5520
accuggaaga ucucacauuu uauuacaaag ugaaaaaaaa a                        5561
```

<210> SEQ ID NO 247
<211> LENGTH: 1113
<212> TYPE: RNA
<213> ORGANISM: Homo sapiens

<400> SEQUENCE: 247

```
guccagucug cagucuguau ucggaagaca uagauacuaa auacauggca acucuuuuuu     60
uuguuuguuu uaauucauca ggauguggag cgcuagucug gguaggagag ccagucaccc    120
ugaggacagc ugaaacaauc gcuggcaagu auggagugug gaugagagac cccaagccca    180
cccaccccua cacccaggaa agcacaugga ggauugacac gguuggcaca gagauccgcc    240
aggguguuga guacagucag auaagccagu ucgagcaggg cuauccuucc aagguccaug    300
ugcucccucg ggcacuggag agcacgggug cuguggugua ugcggggagc cucuauuucc    360
agggggcuga guccagaacu guggucaggu augagcuaga cacggagacc gugaaggcag    420
agaaggaaau uccuggagcu ggcuaccacg gacacuuccc guacgcgugg ggcggcuaca    480
cagacauuga cuuagcugug gaugagagcg gccucugggu caucuacagc acggaggaag    540
ccaagggggc cauaguccuc uccaaauuga acccagcgaa ccuggaacuu gagcguaccu    600
gggagacuaa cauccguaag cagucugugg ccaaugccuu uguuaucugu ggcaucuugu    660
acacggugag cagcuacucu ucagcccaug caaccgucaa cuucgccuac gacacuaaaa    720
```

cggggaccag uaagacccug accaucccau ucacgaaucg cuacaaguac agcaguauga 780
uugacuacaa cccccuggag aggaagcugu uugccuggga caacuucaac auggucaccu 840
augauaucaa gcucuuggag augugaggag ccucuaugcc uaccagcaaa ggccagaaaa 900
ggugaaguuc cgggcucccg ggugaagcag cugucagcag aggcagccag augcauggag 960
uuucuccucc ugcuaaagau uuuguuuauc cgggucaaug uacagcuagc uccccucuga 1020
cugacacguc cuccaggcuu guauagucgc auagacucug uucucuucug ucagcuuuca 1080
aagggcuguu ccucuuuuaa aaaucacaua gug 1113

<210> SEQ ID NO 248
<211> LENGTH: 1635
<212> TYPE: RNA
<213> ORGANISM: Homo sapiens

<400> SEQUENCE: 248
gggagaccug agcucgcugc ugccugugga agacugggag aggagacacu aagugcugcu 60
caagcaagcg cgauccucuc cucuuucaac cugcagccca agauacugau ucgagccgcg 120
ccuuaccgcg cagcccgaag auucaccaug gugaagaucg ccuucaacac cccuacggcg 180
gugcaaaagg aggaggcgcg gcaagauaua gaggcgcucg ucagucgcac uguccgagcu 240
caaauccuga cuggcaagga gcucagaguu gucccgcagg agaaagaugg cucaucuggg 300
agaugcaugc uuacucuccu aggccucuca uucaucuugg caggacugau uguuggugga 360
gccugcauuu acaaguacuu caugcccaag agcaccauuu accaugguga gaugugcuuc 420
uuugauucug aggauccugu caauuccauu ccuggaggag agccauacuu ucugccugug 480
acugaggagg cugauauccg ugaggaugac aacauugcca ucauugaugu gccugugccc 540
aguuucucug auagcgaucc ggcggcaauu auucacgacu uugagaaggg aaugacugcu 600
uaccuggacu ugcuuuuggg aaacuguuau cugaugcccc ucaauacuuc cauuguuaug 660
acuccaaaga aucuggugga acuuuuugga aaacuggcaa guggcaagua uuugccucau 720
acuuaugugg uucgugaaga ccugguugcu guggaagaaa uucgugaugu uaguaaccuu 780
gguauuuuua uuuaccaacu uugcaacaac cgaaaauccu uccgccuuag acgcagagac 840
cuucugcugg guuucaacaa gcgugccauu gacaaaugcu ggaagauuag acacuucccc 900
aaugaauuua ucguugaaac caagaucugu caggagugaa augugacaga uaaagaguau 960
ccuugauaau aagaagucag gaacuuaccg ucugacuugg aaaauugaaa uugaugggau 1020
acucaugcua uuuacucaua cauuuacucu auugcuuaua cuggaaaagg aaagggaaag 1080
gggggagaaa acuacuaacc acugcaagcg auuguccaau ucuacuuuaa uugacauugc 1140
uugcuguuuu caacaaguca aaugauuauc uuuucucuug aauuuauagg guuuagauuu 1200
cugaaagcag caugaaugug ucaucuuacc auccugacaa uaaagcccau ccucugguuu 1260
uauuuaaagc aagcucuuuc caacaucacu uggcuagagc augcuuuaaa uuuaaaauau 1320
uugaaauuug uuuuugacau uuuuuugugu gaaacauguc aaaucucuua ccauucuuug 1380
guuuucuucu uuauuauguu caacucuccu gauuucagaa guuacauuuu ugcauuucua 1440
ucaggugcug uguaacgaau cugacugaua ugugaacaau cuucaugagg aagcaauuuu 1500
uuacucaugu aaugauucuu ucucacugau aucuguauug ugaaauccac agaacuguac 1560
aggugcugaa ugcuguaagg aguucugguu guaugaauuc uacaacccua uaauaaaguu 1620
uaccguauuc aauca 1635

<210> SEQ ID NO 249
<211> LENGTH: 3550
<212> TYPE: RNA
<213> ORGANISM: Homo sapiens

<400> SEQUENCE: 249
ggccauuacc aaucgcgacc cgcgcacaca cggcccgggc ggcgggcgaa gcgggcuccc 60
ggggcgcugg gcgcagggcg cggggcaagc cccagcagcg ugucugcaac ggggcgcggc 120
gggcgcucca gcuccgggau cuuucucccu cggucaccuc ccucgcgucu agggaggucg 180
uggcacuccc ugaggagcgc ggcugcucgg agggcggauc cuagaacaga ggcgugagag 240
ccggcaugaa uggucauaug ucuaaccgcu ccagugggua uggagucuac ccuucucaac 300
ugaaugguua cggaucuuca ccacccuauu cccagaugga cagagaacac agcucaagaa 360
caagugcaaa ggcccuuuau gaacaaagga agaacuaugc ccgagacagu gucagcagug 420
ugucggacgu gucccaguac cgcguggaac acuugaccac cuucgugcug gaucggaaag 480
augcaaugau cacugucgag gacggaauaa gaaagcugaa guugcuggau gccaagggca 540
aaguguggac ucaagauaug auucuccaag uggaugaccg agcugugagc cugauugacu 600
uagagucaaa gaaugaauug gagaauuuuc cucuaaacac aaucucgcau ugucaagcag 660
uggugcaugc augcagcuau gacuccauuc ucgccuuggu augcaaagag ccaacgcaga 720
gcaagccaga ccuucaccuu uuccagugug augagguuaa ggcaaaccua auuagugaag 780
auaucgaaag ugcaaucagu gacaguaaag gugggaaaca gaagaggcgg ccggaggccc 840
ugaggaugau ugccaaagca gauccuggca ucccuccucc ucccagagcu ccugccccug 900
ugccaccggg gacugucaca cagguggacg uuaggagucg cguagcagcc uggucugccu 960
gggcagcuga ccagggugac uucgagaagc cccggcagua ccacgagcaa gaagagacgc 1020
ccgagaugau ggcagcccgg aucgacaggg augugcaaau cuuaaaccau auuuuggaug 1080
acauugaauu uuuuaucacc aaacuccaaa aagccgccga agcguuuucu gagcuuucua 1140
aaaggaagaa aaguaagaaa aguaaaaagga aaggaccugg agagggcguu uuaacacuga 1200
gggcaaaacc gccaccuccu gacgaguuug uugacuguuu ccagaaguuu aaacauggau 1260
ucaaccuucu ggccaaguug aagucccaua uccagaaccc gagugcuuca gaucugguuc 1320
auuuuuuguu uacuccacua aauauggugg uccaggcaac agguggcccu gaacuggcca 1380
guucgguacu cagcccacug uugacaaaag acacaguuga uuucuuaaac uacacagcca 1440
cugcggagga acggaagcug uggaugucac ugggagauag uugggugaaa gugagagcag 1500
aguggccgaa agaacaguuc aucccaccuu acgucccgag guuccgcaac ggcugggagc 1560
ccccgaugcu gaacuucaug ggcgcgccca cagagcaaga cauguaucaa cuggccgagu 1620
ccguggccaa cgcagaacac cagcgcaaac aggacagcaa gaggcugucc acagagcauu 1680 ccaaugugucc cgacuauccu ccagccgacg gauaugcgua caguagcagc auguaccaca 1740
gaggaccaca ugcagaccac ggggaggcug ccaugccuuu caagucaacu ccuaaucacc 1800
aaguagauag gaauuaugac gcagucaaaa cacaacccaa gaaauacgcc aaauccaagu 1860
acgacuuugu ggcgaggaac agcagcgagc ucucgguuau gaaagaugau gucuuagaga 1920
uacucgacga ucgaaggcag ugguggaaag uccggaaugc caguggagac ucuggguuug 1980
ugccaaauaa cauucuggau aucaugagaa cuccagaauc uggagugggg cgcgcugacc 2040
ccccauacac acauaccaua cagaaacaaa ggacggaaua cggccugaga ucagcugaca 2100
cuccuucugc ccaucaccc ccuccaacgc cagcacccgu uccggucccc cuuccaccuu 2160
cuguaccagc acccguuucu gugcccaagg uuccagcaga ugucacccgc cagaacagca 2220
gcuccaguga caguggggc agcauugugc gggacagcca gagauacaaa caacucccag 2280
uggaccgaag gaagucccag auggaagagg uucaggauga gcucuuccag aggcugacca 2340
ucgggcgcag ugcugcgcag aggaaguucc acgugccacg gcagaacguu ccagugauca 2400
auaucacuua ugacuccuca ccggaagaag uaaagacuug gcugcaguca aagggauuca 2460
aucccgugac ugucaauagc cucgggugu ugaacggagc acaacucuuu ucucucaaca 2520
aagacgaacu gaggucuguc ugcccggaag gugccagagu cuuuaaccaa aucacuguuc 2580
agaaagcugc uuuggaggac aguaauggaa gcuccgaguu acaagagauc augcggagac 2640
ggcaggagaa gaucagcgcc gcugcgagcg acucgggagu ggagucuuuu gaugaaggga 2700
gcagccacug aguccaugaa cuuccuuauu cuuggugugg ucguugaaca gugauggaca 2760
ugcuuuguuu uaagaagccu ugaagggaau gucaaagcug ucgucuuggu auauguaauu 2820
uaucgccaua uaaggaaaca guauaugccu gaguaagcag aggacccgcu gcuucugugc 2880
acauuaguuu gauuaaaacu gagaagcggg uaggugagau ggcucagcaa guaaaggugc 2940
uugcugccaa gcccaaugac ccaaguucga gucccugggu cuacauggua ggagagagcu 3000
ggcuucugca aguuguccuc ugaccaccac acauaaauaa auaacaaaug uaauuuacaa 3060
acuuuuaaaa gaaaauguaa uuuaaaaaac cagacguucu agacuguucu gggcuuggga 3120
aauauuuuuu ucacuuuccu aagguguacu uucccuuugcu acauuaauua uugcagccuu 3180
guucgaugau cuaagugggg auauuugaca auggcagauu uauucauugc aacaaggaaa 3240
gacacagcca uugaugaaaa aaaaaagaaa gucucagcuu ucagugacug ggauaccugc 3300
uguccaggga ggaggcucag uuagacuacc cucugcuuac uugaggucug acaugcccaa 3360
ugagagugua uuuagcuuua uuuaaaguuc uuaaugccaa caguuuuaaa aaucacauuu 3420
aaaugaacug uacaagguag ccagaccuug aauguaugaa uagacuauau aauaugucc 3480 gagaaacuuu guuacucuca gcucuguuga uugcgaaauc uugcauagau uaugcuuuga 3540
uuuaguuucu 3550

<210> SEQ ID NO 250
<211> LENGTH: 2299
<212> TYPE: RNA
<213> ORGANISM: Homo sapiens

<400> SEQUENCE: 250
ccugggcccc gccgcggacg cgcggagccg ccugggccgc gccggaggag ggcggggaga 60
ggaccaugug aaugugcucc ggagcugagc gccaagccaa gcaguguuug aaaggaacag 120
gaugcugauc uaaucguggc aaaaagucag uccgaccgcu gguuucgaag acauguggug 180
uauauaaagu uugugauagu ugguggaaau uugggagcuu ggauaauggg cugugugcaa 240
uguaaggaua aagaagcagc gaaacugaca gaggagaggg acggcagccu gaaccagagc 300
ucuggguacc gcuauggcac agaccccacc ccucagcacu accccagcuu cggcgugacc 360
uccaucccga acuacaacaa cuuccacgca gcugggggcc agggacucac cgucuuuggg 420
ggugugaacu ccuccucuca cacugggacc cuacgcacga gaggagggac aggagugaca 480
cuguuugugg cgcuuuauga cuaugaagca cggacggaag augaccugag uuucacaaa 540 ggagaaaaau uucaaauauu gaacagcucg gaaggagauu ggugggaagc ccgcuccuug 600
acaaccgggg aaacugguua cauucccagc aauuacgugg cuccaguuga cuccauccag 660
gcagaagagu gguacuuugg aaaacuuggc cgcaaagaug cugagagaca gcuccugucc 720
uuuggaaacc caagagguac cuuucuuauc cgcgagagcc aaaccaccaa aggugccuac 780
ucacuuucca uccgugauug ggaugauaug aaaggggacc acgucaaaca uuauaaaauc 840
cgcaagcuug acaauggugg auacuauauc acaacgcggg cccaguuuga aacacuucag 900
caacugguac agcauuacuc agagaaagcu gaugguuugu guuuuaacuu aacuguggun 960
ucaucaaguu guaccccaca aacuucugga uuggcuaaag augcuuggga aguugcacgu 1020
gacucguugu uucuggagaa gaagcugggg caggggguguu ucgcugaagu guggcuuggu 1080
accuggaaug gaaauacaaa aguagccaua aagacccuua agccaggcac caugucuccg 1140
gaguccuucc uggaggaggc gcagaucaug aagaagcuga agcaugacaa gcuggugcag 1200
cucuacgcgg ucgugucuga ggagcccauu uacaucguca cggaguacau gagcaaagga 1260
aguuugcuug acuucuuaaa agauggugaa ggaagagcuc ugaaguugcc aaaccuugug 1320
gacauggcgg cacagguugc ugcaggaaug gcuuacaucg agcgcaugaa uuauauccac 1380
agagaucugc gaucagcaaa cauucuagug gggaauggac uaauuugcaa gauugcugac 1440
uuuggauugg cucgguugau ugaagacaau gaauacacag caagacaagg ugcgaaguuu 1500
cccauuaagu ggacagcccc cgaagcggcc cuguauggaa gguucacaau caagucugac 1560
guauggucuu uuggaaucuu acucacagag cuggucacca aaggaagagu gccauaccca 1620
ggcaugaaca accgggaggu gcuggagcag guggagagag gcuauaggau gcccugccca 1680
caggacugcc cgaucucccu gcacgagcuc augauccacu gcuggaaaaa ggauccggaa 1740
gagcgcccga ccuucgagua cuugcagggc uuccuggagg acuacuuuac ggccacagag 1800
ccccaguauc agcccgguga aaaccuguga gagccugcgc uucagacgcc ucuucccgag 1860
gccucccuac cccuccccau uagcuuccaa uucuguagcc agcugcccca gagcaggaga 1920
accguccagg aucagauugc augugacucu ugaagcugaa cuuccacggc ccucauuaau 1980
gacacuuguc ccccaguccg aaccuccucu gugaaccauc ugagacagaa gcguguuauu 2040
ucucagacuu ggaaaugcau uguaucgaug uuaugucaaa ggccaaaccu cuguucagug 2100
uaaauagcug cuccugugcc aacaauccca gugcuuuccu uuuuuaaaaa agaaaaagca 2160
aauccuaugu gauuuuaacu cugauuucac cugauucaac uaaaaaaaaa aaaguauuau 2220
uuuccaaaag uggccucuuu gucuaaaaca auaaaauuuu uuuucauguu uuaacaaaaa 2280
aaaaaaaaaa aaaaaaaaa 2299

<210> SEQ ID NO 251
<211> LENGTH: 3991
<212> TYPE: RNA
<213> ORGANISM: Homo sapiens

<400> SEQUENCE: 251
cccucccugg cucucuccuc agcucugggc ucugacugca gcaagcagag acaaccucuc 60
acucugccuu ucccagcgcc cacccugacc cuggcccaca uuugacggug acucgcaggc 120
cagccagaaa caugaggcug gcccacgcuc ugcugccccu gcugcuacaa gccugcuggg 180
uggccacaca ggacauccag ggcuccaaag cgauugccuu ccaagacugc ccuguggauc 240
uauucuucgu gcucgacacc ucggagagug uggccuugag gcugaaaccu uaugggggccu 300 ugguggacaa ggugaagucc uucacuaagc gcuucauuga caaccugaga gacagguacu 360 accggugug ccgcaaccug guuuggaaug cgggugcgcu gcacuacagu gacgaggugg 420
agaucauccg agggcucacg cgcaugccca guggccgcga ugagcucaag gccagcgugg 480

-continued

```
augcggucaa guacuucggg aaaggcaccu acaccgacug cgccauuaag aaggggcugg    540
aggagcugcu cauagggggc ucccaccuga aggagaacaa guacuugauc guggugaccg    600
acgggcaucc ucuagagggc uacaaggaac caugcggggg ucuggaagau gcaguaaaug    660
aggccaaaca ccugggcauc aaggucuuuu cuguggccau cacaccugac caccuggagc    720
cacgucuaag uaucauugcc acagaccaca cauaccggcg caauuucacg gcagcugacu    780
gggggcauag ccgcgaugca gaagagguca ucagccagac cauugacacc auuguggaca    840
ugauuaaaaa uaacguggaa caaguguguu guucuuuuga gugccaggcu gccagaggac    900
cuccagggcc ccgaggcgac ccuggguaug agggggagcg aggaaagcca ggucuuccgg    960
gagagaaggg agaagcugga gacccuggac gaccugggga ucuuggacca gucggguacc   1020
aggguaugaa gggagaaaag gggagccgug gagagaaggg uuccagagga ccgaaagguu   1080
acaagggcga gaaaggcaag cgcggaaucg acggggucga cggcaugaag ggagagacgg   1140
gguacccagg acuaccgggc ugcaagggcu ccccaggauu ugauggcauu caaggacccc   1200
cgggucccaa gggugaugcu ggugccuuug ggaugaaggg agaaaagggu gaagcuggag   1260
cagacgguga ggcugggaga ccagggaacu cagggucacc uggagaugag ggugauccug   1320
gagagccugg ucccccggga gaaaaaggag aggccgguga ugaaggaaau gcuggcccag   1380
acggugcccc uggagagagg gguggcccug gugaaagagg accucggggg accccuggug   1440
ugagaggacc aaggggagac ccgggugaag cuggaccaca gggugaccaa ggaagagagg   1500
ggcccgucgg caucccugga gacucgggug aggcuggccc cauuggaccu aaaggauacc   1560
gaggugauga ggguccucca gguccugagg gccucagagg agccccagga ccuguugguc   1620
cuccuggaga ccccggacug augggugaga gaggugagga uggaccacca ggaaacggca   1680
cggaagguuu ccccggcuuc ccuggguauc caggcaacag aggcccuccu gggcuaaaug   1740
gcacaaaagg cuacccuggc cucaaggggg augaggguga agugggagac ccaggagagg   1800
auaacaacga cauuucaccc cgugggguca aaggggcaaa gggauaccga ggcccagaag   1860
gaccccaggg accuccagga caugugggac caccugggcc agaugagugu gagauccugg   1920
auaucaucau gaaaaugugc uccugcugug agugcacaug uggacccauu gacauccucu   1980
ucgugcugga cagcucggag agcauuggcc uacagaacuu ugagauugcc aaggacuuca   2040
ucaucaaggu cauugaccgg uugagcaagg augagcuggu caaauuugag ccagggcagu   2100
cucacgcggg cgugguacag uacagccaca accagaugca agagcacgug gacaugcgga   2160
gccccaacgu ccgcaacgcc caggacuuca aagaagcugu caagaagcua caauggaugg   2220
cugguggcac auucaccgga gaagcgcugc aguacacccg ggaccggcua cucccaccca   2280
cacagaacaa ccgaauugcc cuggucauua cggauggacg uucugacacu caacgggaca   2340
cgacaccucu cagugugcuc uguggugcag acauucaggu aguuucugug ggaaucaagg   2400
auguguuugg cuuuguggcg ggcuccgacc agcucaaugu cauuuccugc caaggcuuau   2460
cgcaaggucg uccagguauc ucccugguga aggagaacua ugcagagcuu cucgaugacg   2520
gcuuucugaa gaacauaaca gcccagaucu guauagauaa gaaguguccg gauuauaccu   2580
guccaaucac auucuccucc ccggcugaca ucaccauccu gcuagacagc ucagccagug   2640
ucggcagcca caacuucgaa accaccaagg ucuucgccaa gcgccuagcu gagcgauucc   2700
ugucagcagg cagggcggau ccuucccagg augugcgggu ggccguggua caguauagug   2760
gccaggggca gcaacagcca ggucgggcgg cucuucaguu cuuacagaau uacacagugc   2820
```

-continued uggccagcuc uguggacagc auggauuuca ucaacgacgc cacagacguc aacgaugcuc 2880
ugagcuacgu gacucguuuc uaccgggaag ccucgucagg ugccaccaag aagagagugc 2940
uguuguuuuc agacggcaac ucucaggggg ccacagcaga ggccauugag aaggcugugc 3000
aggaggccca gcgugcaggc auugagaucu uuguggugga ggugggaccc caggugaacg 3060
agccccacau ccgugugcuu gucacuggca agacugcaga guacgacgug gccuuuggcg 3120
agcgccaccu auuccgugua ccaaacuacc aggcccugcu acguggcgua cucuaccaga 3180
cagucuccag gaagguggca cugggcuaga gggccacaca cguggcugga cacacauggc 3240
auggagacac auuucaacag gccuuccccgc ccuucccacu gacaaaacag gaauaggaaa 3300
ugugacccaa cuggucaacu caacugucuu aaagggaacg cugagaugca cacucuuugc 3360
uuuguguaau guccccugug gcucaccuga gcuccuaucu agaucccgcc cuugguuugu 3420
acaucauggu ggccaucuug cugaccccuc ccccaucugg gacuggaucc agccaucucg 3480
ucuuccuccu cacugccccu aaccuauccg uggugucuuc acaccaucac ugcaguuucc 3540
gucuguguuc ugucuuccau gcucaacaug aagcagaccu ucucaugagu ucagcuugcu 3600
ggauuauggc uuuuaggaaa uugaacacag gaggaguucc aaacacaaac uuggaggaga 3660
ccccuccucu ucaucaggug cuugucagug accuacaugc aucuuggucu gguccuuagu 3720
ggcuaguccu uccacucuga aagcaaaggu gcuaucuauc uguaagggcu cucucuacac 3780
acccagaggc uuagcuugga caguucacac ucaagugucc ugucagaauc aauccagagc 3840
uuucucccuc aaaauaguga cuugucuccc ccuggucccc aaaggcuccc cuuuaguuag 3900
uuucuucaug gcucccccac auuccccgua aucugaucca agccagcuau cucugcuaau 3960
aaagguuucc auuuuucaaa aaaaaaaaaa a 3991

<210> SEQ ID NO 252
<211> LENGTH: 235
<212> TYPE: RNA
<213> ORGANISM: Homo sapiens

<400> SEQUENCE: 252
accccaugcc ccaccccca c cuucgauguu uugaacauuu cuaacaacug aagccaguaa 60
agucauauuc uuuaaauuuc caggacauuc auauuauuca cauaaucaug gucaugguga 120
ugauggaaac ugaggacuuu aaaagagauu uucccuuccc aaacguuucu ggacaguacc 180
ugauuguauu uuuuuuguuu uguuuuguuu uuuaauaaaa gcacaguacu uuucc 235

<210> SEQ ID NO 253
<211> LENGTH: 2005
<212> TYPE: RNA
<213> ORGANISM: Homo sapiens

<400> SEQUENCE: 253
gucugcccug ccguuucucu acuucccagc cuucucaucu ccaggaacca ugucuaccaa 60
aaccaccauc aaaagucaaa ccagccaccg uggcuacagu gccagcucag ccagagugcu 120
uggacucaac cgcucgggcu ucagcagugu guccgugugc cgcucccggg gcagcggugg 180
cuccagugca augugugggag gagcuggcuu uggcagcagg agccucuaug gugugggggag 240 cuccaagagg aucuccaucg gagggggcag cuguggcauu ggaggaggcu auggcagccg 300
auucggagga agcuucggca uuggugguggg agcugguagu ggcuuuggcu ucggugguggg 360 agcuggcuuu ggugguggcu augggggagc uggcuucccg gugugcccac uuggaggcau 420
ccaagagguc accaucaacc agagccuccu cacaccccug aaccugcaaa uugaccccac 480
cauccagcgg gucaggacug aggagaggga gcagaucaag acccucaaua acaaguuugc 540
cuccuucauc gacaaggugc gguucaugga gcagcagaac aaggucaugg acaccaagug 600
ggcccugcug caagagcagg acaccaagac cgugaggcag aacauggagc ccauguuuga 660
gcaguacauc agcaaccucc gcagacagcu ggacagcauc auuggagaga ggggucgcau 720
gaacucagag cugaggaaca ugcaggaacu cguagaagaa cuacggaaca aauaugaaga 780
ugaaaucaac aagcgcacag acgcagagaa ugaauucgug acccugaaga aggauguaga 840
ugcugccuac augaacaaag uugaacugca agccaaggca gacagucuaa cagaugauau 900
caacuucuug agagcucucu augaagcaga acugucucag augcaaacuc acaucucaga 960
cacaucugug guccucucca uggucaacaa ccguagccuc guccuagaca gcaucaucgc 1020
ugaggucaag gcccaguuug aggucauagc ucagagaagu cgggcugaag cugagucauu 1080
guaccagacu aaauaugagg agcugcaggu cacagcuggc agacaugggg acgaccugcg 1140
caacaccaag caggagauug cugagaucaa ccgcaugauc cagaggcuga gaucugagau 1200
cgaccacguu aagaagcagu gugccaaccu gcaagcugcu auugcugaug cugagcaacg 1260
uggggagaug gcccugaagg augcaagggg caagcuggaa gggcuggagg augcccugca 1320
gaaggccaaa caggacaugg ccaugcugcu gaaggaguac caugaacuca ugaaugucaa 1380
gcuggcccuu gauguggaaa uugccaccua caggaagcug cuggaaggag aggagugcag 1440
guugaauggu gaagguguug gaccagucaa caucucugug gugcagucca ccguguccag 1500
cggcuauggc agugccgggg gugccagcag cagcuuaggc augggugggag gcagcagcua 1560 cuccuauagc agcagccaug gccuuggagg uggcuucagu gcuggcagug gcagagccau 1620
cggagguggc cucagcucuu cugguggccu cagcucuucu accaucaaau acaccaccac 1680
cuccuccagc aagaagagcu acaggcagug aauucuguca ccaagagcuu gucucugguc 1740
ccagauguca uggcugcagc ugaaccacau gcuuugguuc ccggaaggga acgaauccca 1800
accucuggcc uccccauggc ucaguucuac auuuguguug cacgucagca ccuauacaug 1860
uucuuuggug acccagaccc caaaauguug cagaauguag accuccaaga cgaaacccca 1920
aacccuaccc agaauaccca ccuaaauucu gucaugguuc ugacuuccuc cagagucugu 1980
aaaauaaaau gcccccacaa caaac 2005

<210> SEQ ID NO 254
<211> LENGTH: 357
<212> TYPE: RNA
<213> ORGANISM: Homo sapiens

<400> SEQUENCE: 254
uuuuuuuuuu uuuuuuugau uuuaauuaca aacuuuauuu guccuccagu ucacaguuua 60
uacgugguac aucccaccau gucagcuucc agaacggcua uucaggagau ggguggagcu 120
uucuuuguaa aggaacccga cauuuuaaaa uuuugguuag aaucuucaua gguuuauaaa 180
aguacucucu gcaagcgaac uggauauauu uacauuuaua gcuuaaauuc aaauuuugga 240
aaauaggaau cuuuuugugu uuuuaaacau ccuggguuua ugucuuaaga cuuuacucug 300
aaugccacau gaucacguaa gcccaagccu cccccagaag ggaaaaauca guuuugc 357

<210> SEQ ID NO 255
<211> LENGTH: 271
<212> TYPE: RNA
<213> ORGANISM: Homo sapiens

<400> SEQUENCE: 255
uuuuuuuuuu uuuuuuuggg ugccaugcca cagcaagggg ccuuuauuag auguucaggg 60
cacagacagg uggaugcuag augguguagc acaccuucuc aggguggagu ggugccugga 120
uguccaguuu gcgggucuug cuguccuuau caaugaucuc cagucgcaau guagguggac 180
gcuucucagc cuggggugag ggcagcucac ggcucuugag gaggugcuug uccgaauccu 240
ccacagugau acccagggug caaccccug g 271

<210> SEQ ID NO 256
<211> LENGTH: 255
<212> TYPE: RNA
<213> ORGANISM: Homo sapiens

<400> SEQUENCE: 256
uuuuuuuuuu uuuuucugac acaguaguaa uccuuccaga cuccuuacac aauauuacaa 60
cucccccagu acauaaaugu uccuauacca ugcacacagc aacauggggu ccacugaugu 120
cgcaggcgac uuuucuaaug guggaacaua gcaccucaag uucugccauc uacacaguga 180
agggacguga uggucggggc uccagaguga cagcaaacug ccucuugggu gacacgcuug 240
uggcgaagug ccucc 255

<210> SEQ ID NO 257
<211> LENGTH: 4031
<212> TYPE: RNA
<213> ORGANISM: Homo sapiens

<400> SEQUENCE: 257
gagaauguug cugaggaggu ggggcugcug cagcuccuug gagaccccccu accugagaag 60 aucucacaaa ucgaugaccc ucacgucggg ccggccuaca ucuuuggacc agacuccaac 120
aguggccagg uggcccagua ucauuuccca aaacucuucu uccgggacuu uucgcugcug 180
uuucaugucc ggccagccac agaggcagca ggggugcuau uugccaucac agaugcugcc 240 cagguggguag ucucacuggg cgugaagcuc ucagaggucc gagauggaca gcaaaacauc 300
ucauugcucu acacggagcc uggggccagc cagacccaga cgggagccag cuuccgccua 360
ccugcauuug uugggcagug gacacacuuc gcgcucagcg ucgacggagg cucuguggcu 420
cucuacguag acugugaaga auuccagagg gugccauuug cucgggccuc gcagggacug 480
gagcuagagc guggcgcugg ccucuuugug ggucaggcug gaacagcaga cccugacaag 540
uuccagggga ugaucucaga gcugaaggua cgcaaaaccc cccgggugag cccugugcac 600
ugucuggaug aagaagauga ugaugaagac cgggcaucug gagauuuugg aaguggcuuu 660
gaagaaagca gcaagucaca caaggaggau acaucucuac uaccugggcu cccucagcca 720
ccuccuguca cuuccccacc ccuggcugga ggcagcacca cagaagaucc uagaacagaa 780
gaaacggagg aagacgccgc gguagauucu auaggagcug agacccuucc uggcacaggu 840
ucaagcggug caugggauga ggcuauccag aaccccggaa ggggcuugau aaagggaggu 900
augaaaggac aaaagggaga accaggugcc cagggcccac cuggcccagc uggcccccag 960
gguccugccg guccaguggu ccagagcccc aacucacaac cugucccugg agcacaagga 1020
cccccgggac cucaggggcc accagggaag gauggcacuc caggaaggga uggugaaccg 1080
ggugacccug gugaagaugg gagaccgggu gacacuggac cucaaggcuu uccagggacc 1140
ccaggagaug ugggcccuaa gggcgagaag ggagauccug guauugggcc ccgaggaccu 1200
ccagggccuc cagggccacc aggacccucc uucagacaag acaagcugac cuucauugac 1260
auggagggau ccgguuucag cggagacaua gagagccuua gaggcccacg aggcuucccu 1320 ggcccccegg ggcccccugg ugucccagga cuuccuggug agccaggacg cuuugggauc 1380
aaugguuccu augcaccagg accugcaggc cuuccuggug uaccugggaa ggaaggaccc 1440
cccgguuuuc caggucccce gggaccucca gguccuccag gcaaagaggg cccaccagga 1500
guggccggcc agaaaggcag uguuggugau gugggcaucc caggacccaa ggggagcaaa 1560
ggagaccuug ggcccaucgg uaugccuggc aagucuggcu uggcuggauc cccugggcca 1620
guuggacccc caggaccucc agggccucca gggccaccag gaccaggauu ugcugcugga 1680
uucgaugaua uggaaggcuc uggaauaccc cucuggacaa cagcccgaag cucugauggg 1740
cugcagggac cucccggguc gccgggacuc aagggggauc cuggaguggc aggccuaccu 1800
ggagccaagg gagaaguugg agcagaugga gcccagggca ucccuggucc cccaggaaga 1860
gaaggugcag cuggaucucc ggggccaaaa ggagagaagg ggaugccggg agaaaaggga 1920
aacccaggaa aagauggagu gggccggccg ggccuccug ggccuccagg accuccaggg 1980
cuggugaucu augugucaag ugaggauaaa gcaauaguga gcacgccagg accugagggc 2040
aagccagggu acgcaggcuu uccuggaccu gcuggaccga agggugaccu ggguuccaaa 2100
ggcgagcagg gucuucccggg guuuaagggu gagaagggag agccaggcac uaucuuuagu 2160
ccugauggca gacgucuggg ccaucccag aagggagcca agggagagcc aggcuuucga 2220 ggaccccegg guccuuaugg acgaccuggg cacaagggug aaauuggcuu cccuggacgg 2280
ccgggucgac cuggaacgaa uggcuuaaag ggagagaagg gagagccugg agaugccagc 2340
cuuggguuca gcaugagggg auugccuggc ccccuggge cuccaggacc cccagguccu 2400
ccugggaugc ccaucuauga cagcaaugca uuuguggagu cuggccgacc uggacuacca 2460
ggacagcagg gugugcaggg gccuucagga ccaaagggug acaaaggaga gguggggcca 2520
ccugggccac cagggcaauu ccccauugac cucuuccacc uggaagcgga aaugaagggg 2580
gacaagggag accgagggga ugcuggacag aaaggagaga ggggagaacc uggggcuccu 2640 gguggugga u ucuucagcuc aaguguaccu ggcccacccg gcccaccugg auacccugga 2700
auuccggguc caaagggaga gagcauccgg gggccaccug gcccuccugg cccgcaggga 2760
ccuccuggca uuggcuauga gggucgccag gguccccag gaccuccagg accuccagga 2820
ccucccuccu ucccuggccc ucacagacag acugucagug uuccuggucc uccgggccca 2880
ccugguccuc cagguccccc aggagccaug ggugccucug cugggcaggu gaggaucugg 2940
gccacauacc agaccaugcu ggacaagauc cgggaggugc cggagggcug gcucaucuuu 3000
guggccgaga gggaagagcu cuauguacgc guuagaaaug gcuuccggaa ggugcugcug 3060
gaggcccgga cagcccuccu gagaggcacg ggcaaugagg uggcugcuuu ccagcccca 3120 uugguccagc uucaugaggg caguccauac acccggaggg aguacuccua uuccacggca 3180
cgacccuggc gagcagauga cauccuggcc aacccaccgc gccugccaga ccgccagccu 3240
uacccuggag uuccacauca ccacaguucc uaugugcacc ugccgccagc ccgcccacc 3300 cucucacuug cucauacuca ucaggacuuu cagccagugc uccaccuggu ggcacugaac 3360
accccccugu cuggaggcau gcgugguauc cguggagcag auuuccagug cuuccagcaa 3420
gcccgagccg uggggcuguc gggcaccuuc cgggcuuucc uguccucuag gcugcaggau 3480
cucuauagca ucgugcgccg ugcugaccgg gggucugugc ccaucgucaa ccugaaggac 3540
gaggugcuau cucccagcug ggacuccug uuuucuggcu cccaggguca agugcaaccc 3600

-continued ggggcccgca ucuuuucuuu ugacggcaga gauguccuga gacacccagc cuggccgcag 3660
aagagcguau ggcacggcuc ggaccccagu gggcggaggc ugauggagag uuacugugag 3720
acauggcgaa cugaaacuac uggggcuaca ggucaggccu ccucccugcu gucaggcagg 3780
cuccuggaac agaaagcugc gagcugccac aacagcuaca ucguccugug cauugagaau 3840
agcuucauga ccucuuucuc caaauaggcc ucugccagcu agggugggcag acagaggcca 3900 ugcagaacuu ugacacagcg cagggagcau ucagucagca cccagggcuc uggcugggau 3960
acaacuccug uauaguuccc auuuuuaugu aauccucaag aaauaaaagg aagccaaaga 4020
guaaaaaaaa a 4031

<210> SEQ ID NO 258
<211> LENGTH: 1503
<212> TYPE: RNA
<213> ORGANISM: Homo sapiens

<400> SEQUENCE: 258
aacugccuuc gagaagcguu agccuagaga uccgagccuc uucuccauac cauaguuggu 60
ucaggugguu uccucuucaa accuugcguc ugcggauaau ccgcgcggcc gggcguuaag 120
cuccaggucc cugucgcucc gucgaggugg caagccaugg ccggcugcug cuguuugucu 180
gcggaggaga aagagucuca gcgcaucagc gcggagaucg agcggcacgu ucgccgcgac 240
aagaaggacg cgcgccggga gcucaagcug cuguugcugg gaaccgguga gagugggaaa 300
agcaccuuua ucaagcagau gaggauaauc caugggucug gcuacaguga ugaagauaga 360
aagggcuuca cgaagcuggu uuaccaaaac auauucacgg ccaugcaagc caugaucaga 420
gcaauggaua cccugaggau acaauacaug ugugagcaga auaaggaaaa ugcccagauc 480
aucagggaag uggaaguaga caaggucacu gcacucucua gagaccaggu ggcagccauc 540
aagcagcugu ggcuggaucc cggaauccag gaguguuacg acaggaggag ggaguaccag 600
cugucagacu cugccaaaua uuaccugacg gacauugagc guaucgccau gcccucuuuc 660
gugccaacac aacaggaugu gcuucguguu agagugccca ccacuggcau cauagaauau 720
ccauucgacc uggaaaacau caucuuccga augguggaug uuggguggcca gcgaucugaa 780 cgacggaaau ggauucacug cuuugagagu gucaccucca ucauuuucuu gguugcucug 840
agugaauaug accagguucu ggcugagugu gacaaugaga accgcaugga ggagagcaaa 900
gcccuguuua gaaccaucau caccuacccc ugguuucuga acuccuccgu gauucuguuc 960
uuaaacaaga aggaucuucu agaggagaaa aucauguacu cucaucuaau uagcuacuuc 1020
ccagaguaca caggaccaaa gcaagauguc aaagcggcca gggacuuuau ccugaagcug 1080
uaucaagacc agaauccuga caaagagaag guuaucuauu cucacuucac uugugcuaca 1140
gacaccgaga auauccgcuu uguguuugcu gcugucaaag acacaauccu acagcuaaac 1200
cuacgggagu ucaacuuggu guaaauggag ggccuacucc uccgagacag agggugaucu 1260
gagcccuucc ugccugaucu acaagugcuu cuggaccagg accuaaggac auuauguagc 1320
ccacaggaca gagaugggua gugcaaugug aaaaauacuu caccaacccu uuuaaguguc 1380
uuuaauucuu cacugucuaa cucuuuucuc gccuuuuggu ugaacgauua gguaucauuu 1440 uugaguggguu cccccucucc uauuuuuuua aacuaguguu caacaguuau uaaaaaauca 1500
ugc 1503

<210> SEQ ID NO 259
<211> LENGTH: 876

<212> TYPE: RNA
<213> ORGANISM: Homo sapiens

<400> SEQUENCE: 259
gaauucccug caaccuuguc ugagaggaag caaggacugg ugugaggagg gagcugugag 60
guuuuaucug ugcagcccuu cucugaggau ggacacuucu cacacuacaa aguccuguuu 120
gcugauucuu cuuguggccc uacugugugc agaaagagcu cagggacugg aguguuacca 180
gugcuaugga gucccauuug agacuucuug cccaucaauu accugccccu acccugaugg 240
agucuguguu acucaggagg cagcaguuau ugugggguucu caaacaagga aaguaaagaa 300
caaucuuugc uuacccaucu gcccuccuaa uauugaaagu auggagaucc ugggguacuaa 360 ggucaaugug aagacuuccu guugccagga agaccucugc aaugcagcag uucccaaugg 420
aggcagcacc uggaccaugg caggggugcu ucuguucagc cugagcucag uccuccugca 480
gaccuugcuc ugauggguccu cccaaugacc uccacccuug uccuuuuauc cucaugugca 540
acaauucuuc cuggagcccu cuagugauga auuaugaguu auagaagcuc caaggguggga 600 guagugugug aaauaccaug uuuugccuuu auagcccugc uggguaggua ggugcucuaa 660
uccucucuag ggcuuucaag ucuguacuuc cuagaauguc auuuuguugu ggauugcugc 720
ucaugacccu ggaggcacac agccagcaca gugaagaggc agaauuccaa gguauuaugc 780
uaucaccauc cacacauaag uaucuggggu ccugcaaugu ucccacaugu auccugaaug 840
ucccccuguu gaguccaaua aacccuuugu ucuccc 876

<210> SEQ ID NO 260
<211> LENGTH: 6929
<212> TYPE: RNA
<213> ORGANISM: Homo sapiens
<220> FEATURE:
<221> NAME/KEY: misc_feature
<222> LOCATION: (2080)..(2080)
<223> OTHER INFORMATION: n is a, c, g, or u
<220> FEATURE:
<221> NAME/KEY: misc_feature
<222> LOCATION: (2082)..(2082)
<223> OTHER INFORMATION: n is a, c, g, or u
<220> FEATURE:
<221> NAME/KEY: misc_feature
<222> LOCATION: (4019)..(4019)
<223> OTHER INFORMATION: n is a, c, g, or u
<220> FEATURE:
<221> NAME/KEY: misc_feature
<222> LOCATION: (4119)..(4119)
<223> OTHER INFORMATION: n is a, c, g, or u
<220> FEATURE:
<221> NAME/KEY: misc_feature
<222> LOCATION: (5039)..(5039)
<223> OTHER INFORMATION: n is a, c, g, or u
<220> FEATURE:
<221> NAME/KEY: misc_feature
<222> LOCATION: (5048)..(5048)
<223> OTHER INFORMATION: n is a, c, g, or u
<220> FEATURE:
<221> NAME/KEY: misc_feature
<222> LOCATION: (5054)..(5054)
<223> OTHER INFORMATION: n is a, c, g, or u
<220> FEATURE:
<221> NAME/KEY: misc_feature
<222> LOCATION: (5079)..(5079)
<223> OTHER INFORMATION: n is a, c, g, or u
<220> FEATURE:
<221> NAME/KEY: misc_feature
<222> LOCATION: (5131)..(5131)
<223> OTHER INFORMATION: n is a, c, g, or u

<400> SEQUENCE: 260

-continued

```
ggaagaaaga gagggaggga aaagagaagg aaggaguaga ugugagaggg uggugcugag      60
ggugggaagg caagagcgcg aggccuggcc cggaagcuag gugaguucgg cauccgagcu     120
gagagacccc agccuaagac gccugcgcug caacccagcc ugaguaucug gucuccgucc     180
cugaugggau ucucgucuaa accgucuugg agccugcagc gauccagucu cuggcccucg     240
accagguuca uugcagcuuu cuagaggucc ccagaagcag cugcuggcga gcccgcuucu     300
gcaggaacca auggugagca gggcaaccug gagaggggcg cuauucugag gauucgaggu     360
gcacccguag uagaagcugg ggauggggcu caggcuguaa ccgaggcaaa aguuggccua     420
uuccuccuuc cuucuccaac aguguuggag gugggaugau ggaggcuaaa aggcaccucc     480
auauauguua cugcgucuau caaccuacuu uagggaggug cgggccagga gaggcgggaa     540
ggagagaagg ccuuggaaga gaggucauug ggaagaacug ugggguuugg uggguuugcu     600
uccacuuaga cuauaagagu gggagaggag ggagucaacu cuaaguuuca acaccagugg     660
gggacugagg acugcuucau uaggagagag aaccuagcca gagcuagcuu ugcaaaagag     720
gcuguagucc ugcuuugcuc uaaagcgcga cccgggauag agaggcuucc uugagcgggg     780
ugucaccuaa ucuuguccccc aacgcacccc cucccagccc cugagagcua gcgaacugua     840
gguacacaac ucgcucccau cuccaggagc uauuuucuua gacaugggca cccaugauuc     900
ugccuucugg uacucucccc ucccugggaa aggggugua a gguuccgacg gaaccguggc     960
caggaugccg aaaggcuacc ugugcggguc uucugccaug cugugucugu gcggacaugc    1020
cagcagggcu aaugaggagc uugcgauacu ccaaaggguu cgggaauugc gggguccuua    1080
cacgcagugg aguugggccc cuuuuacuca gaagguuucc gccacggcuu ugguugauag    1140
uuuuuuuagu auccugguuu augaacugaa gguuuuguga gauguugaau cacuagcagg    1200
gucauauuug gcaaaccgag gcuacuauua aauuuugguu uuagaagaag auucugggga    1260
gaaagugaag gguaacugcc uccaggagcu guaucaaccc cauuaagaaa aaaaaaaaua    1320
ccaggagaug aaaauuuacu uugaucugua uuuuuuaauu aaaaaaaauc agggaagaaa    1380
ggagugauua gaaagggauc cugagcgucg gcgguuccac ggugcccucg cuccgcgugc    1440
gccagucgcu agcauaucgc caucucuuuc ccccuuaaaa gcaaauaaac aaaucaacaa    1500
uaagcccuuu gcccuuucca gcgcuuuccc aguuauuccc agcggcgacg cgugucgggg    1560
aauagagaaa ucgucucaga aagcugcgcu gaugguggug agagcggacu gucgcucagg    1620
ggcgcccgcg gucucugcac ccagggcagc agugugggau ggcgcugggc agccaccgcc    1680
gccaggaagg acgugacucu ccauccuuua cacuucuuuc ucaaagguuu cccgaaagug    1740
ccccccgccu cgaaaacugg ggccggugcg gggggggggga gagguuaggu ugaaaaccag    1800
cuggacacgu cgaguuccua agugaggcaa agaggcgggg uggagcgggc ucuggagcgg    1860
gggaguccug ggacucgguc cucggaugga ccccgugcaa agaccuguug gaacaagagu    1920
ugcgcuuccg agguuagaac aggccaggca ucuuaggaua gucaggucac cccccccccc    1980
aaccccaccc gaguuguguu ggugaauuuc uuggaggaau cuuagccgcg auucuguagc    2040
uggugcaaaa ggaggaaagg gguggggggaa ggaaguggcn gngcgggggu ggcggugggg    2100
guggaggugg uuuaaaaagu aagccaagcc agagggagag gucgagugca ggccgaaagc    2160
uguucucggg uuuguagacg cuugggaucg cgcuuggggu cuccuuucgu gccggguagg    2220
aguuguaaag ccuuugcaac ucugagaucg uaaaaaaaau gugaugcgcu cuuucuuugg    2280
cgacgccugu uuuggaaucu guccggaguu agaagcucag acguccaccc cccaccccccc    2340
gcccaccccc ucugccuuga auggcaccgc cgaccgguuu cugaaggauc ugcuuggcug    2400
```

-continued

```
gagcggacgc ugagguuggc agacacggug uggggacucu ggcggggcua cuagacagua   2460
cuucagaagc cgcuccuucu aacuuuccca caccgcucaa accccgacac ccccgcggcg   2520
gacugaguug gcgacggggu cagagucuuc uggcugaaag uuagauccgc uaggggucgg   2580
cugccugucg cuagaagcau uauuuggccu cucggagacc cguguggagg aagugcugga   2640
gugugcgagu guguuugcgu gugugugugu gugugugugu gugugugugu gugugugugu   2700
gugcgcgcgc ccuuggaggg ucccuaugcg cuuuccuuuu cauggaacgc ugucgugagg   2760
cuuugguaaa cugucuuuuc gguuccucuc ucggcugcac uuaagcuuug ucggcgcugu   2820
aaagagacgc gucuucaagu gcacccugau ccucaggcuu cagauaaccc guccccgaac   2880
cuggccagau gcauugcacu gcgcgccgca gguagagacg ugccccacgu ccccugcgug   2940
cagcgacuac gaccgagagc cgcgccagug uggugucccg ccgagaguuc cucagagcag   3000
gcggggacaa cucccagacg gcuggggcuc cagcugcggg cgcggagguu ggccucgcuc   3060
gcaggggcug gacccagccg gggugggagg auggaggagg ggcgggcggg cucuucggug   3120
aguggggcgg ggccucuggg uccacgugac uccuaggggc uggaagaaaa acagagccug   3180
ucugcuccag agucucauua uaucaaauau cauuuuagga gccauuccgu agugccauuc   3240
ggagcgacgc acugccgcag cuucucugag ccuuuccagc aaguuuguuc aagauuggcu   3300
cccaagaauc auggacuguu auuaugccuu guuuucuguc agugaguaga caccucuucu   3360
uucccuucuu gggauuucac ucuguccucc caucccugac cacugucugu cccucccguc   3420
ggacuuccau uucagugccc cgcgcccuac ucucaggcag cgcuaugguu cucuuucugg   3480
ucccugcaag gccagacacu cgaaauguac gggcuccuuu uaaagcgcuc ccacuguuuu   3540
cucugauccg cugcguugca agaaagaggg agcgcgaggg accaaauaga ugaaaggucc   3600
ucagguuggg gcugucccuu gaagggcuaa ccacucccuu accagucccg auauauccac   3660
uagccuggga aggccaguuc cuugccucau aaaaaaaaaa aaaaaaacaa aaaacaaaca   3720
gucguuuggg aacaagacuc uuuagugagc auuuucaacg cagcgaccac aaugaaauaa   3780
aucacaaagu cacuggggca gccccuugac uccuuuuccc agucacugga ccuugcugcc   3840
cgguccaagc ccugccggca cagcucuguu cuccccuccu ccuguucuua accagcugga   3900
aguuguggaa auugggcugg agggcggagg aagggcgggg gugggggggu ggagaaggug   3960
gggggggggg aggcugaagg uccgaaguga agagcgaugg cauuuuaauu cucccuccnc   4020
cuccccccuu uaccuccuca auguuaacug uuuauccuug aagaagccac gcugagauca   4080
uggcucagau agccguuggg acaggaugga ggcuaucuna uuuggggcuua uuugagugua   4140
aacaaguuag accaaguaau uacagggcga uucuuacuuu cgggccgugc auggcugcag   4200
cuggugugug ugugugguagg gugugaggga gaaaacacaa acuugaucuu ucggaccugu   4260
uuuacaucuu gaccgucggu ugcuaccccu auaugcauau gcagagacau cucuauuucu   4320
cgcuauugau cgguguuuau uuauucuuua accuuccacc ccaaccccu ccccagagac   4380
accaugauuc cugguaaccg aaugcugaug gucguuuuau uaugccaagu ccugcuagga   4440
ggcgcgagcc augcuaguuu gauaccugag accgggaaga aaaaagucgc cgagauucag   4500
ggccacgcgg gaggacgccg cucagggcag agccaugagc uccugcggga cuucgaggcg   4560
acacuucuac agauguuugg gcugcgccgc cguccgcagc cuagcaagag cgccgucauu   4620
ccggauuaca ugagggaucu uuaccggcuc cagucugggg aggaggagga ggaagagcag   4680
agccagggaa ccgggcuuga guacccggag cgucccgcca gccgagccaa cacugugagg   4740
```

-continued

```
aguuuccauc acgaagguca guuucugcuc uuaguccugg cgguguaggg ugggguagag   4800

crccggggca gagggugggg ggugggcagc uggcagggca agcugaaggg guuguggaag   4860

cccccgggga agaagaguuc auguuacauc aaagcuccga guccuggaga cuguggaaca   4920

gggccucuua ccuucaacuu uccagagcug ccucugaggg uacuuucugg agaccaagua   4980

guggugguga ugggggaggg gguuacuuug ggagaagcgg acugacacca cucagacunc   5040

ugcuaccncc cagngggugu ucuuuagcua uaccaaagnc agggauucug cccguuuugu   5100

uccaaagcac cuacugaauu uaauauuaca ncugugugu ugucagguuu aucaauaggg   5160

gccuuguaau acgaucugaa uguuuccuag cggauguuuc uuuuccaaag uaaaucugag   5220

uuauuaaucc uccagcauca uuacuguguu ggaauuuauu uucccuucug uaacaugauc   5280

aacaaggcgu gcucuguguu ucuaggaucg cuggggaaau guuugguaac auacucaaaa   5340

guggagaggg agagagggug gccccucuuu uucuuuacaa ccacuuguaa agaaaacugu   5400

acacaaagcc aagagggggc uuuaaaaggg gaguccaagg gugguggagu aaaagaguug   5460

acacauggaa auuauuaggc auauaaagga gguugggaga uacuuucugu cuuuggugu   5520

ugacaaaugu gagcuaaguu uugcugguuu gcuagcugcu ccacaacucu gcuccuucaa   5580

auuaaaaggc acaguaauuu ccuccccuua gguuucuacu auauaagcag aauucaacca   5640

auucugcuau uuuuuguuuu uguuucuugu uuuuguuuug uuugguuuuu uuuuuuuuuu   5700

uuuuuuuuuu gucucagaaa agcucauggg ccuuuucuuu uccccuuuca acugugccua   5760

gaacaucugg agaacauccc agggaccagu gagagcucug cuuuucguuu ccucuucaac   5820

cucagcagca ucccagaaaa ugaggugauc uccucggcag agcuccggcu cuuucgggag   5880

cagguggacc agggcccuga cugggaacag ggcuuccacc guauaaacau uuaugagguu   5940

augaagcccc cagcagaaau gguuccugga caccucauca cacgacuacu ggacaccaga   6000

cuaguccauc acaaugugac acggugggaa acuuucgaug ugagcccugc aguccuucgc   6060

uggacccggg aaaagcaacc caauuauggg cuggccauug aggugacuca ccuccaccag   6120

acacggaccc accagggcca gcaugucaga aucagccgau cguuaccuca agggagugga   6180

gauugggccc aacuccgccc ccuccugguc acuuuuggcc augauggccg gggccauacc   6240

uugacccgca ggagggccaa acguaguccc aagcaucacc cacagcgguc caggaagaag   6300

aauaagaacu gccgucgcca uucacuauac guggacuuca gugacguggg cuggaaugau   6360

uggauugugg ccccacccgg cuaccaggcc uucuacugcc augggggacug ucccuuucca   6420

cuggcugauc accucaacuc aaccaaccau gccauugugc agacccuagu caacucuguu   6480

aauucuagua ucccuaaggc cuguugugu cccacugaac ugagugccau uuccauguug   6540

uaccuggaug aguaugacaa ggugguguug aaaaauuauc aggagauggu gguagagggg   6600

uguggaugcc gcugagauca gacaguccgg agggcggaca cacacacaca cacacacaca   6660

cacacacaca cacacacaca cacguuccca uucaaccacc uacacauacc acacaaacug   6720

cuucccuaua gcuggacuuu uaucuuaaaa aaaaaaaaaa gaaagaaaga aagaaagaaa   6780

gaaaaaaaau gaaagacaga aaagaaaaaa aaaacccuaa acaacucacc uugaccuuau   6840

uuaugacuuu acgugcaaau guuuugacca uauugaucau auuugacaa auauauuuau   6900

aacuacauau uaaaagaaaa uaaaaugag                                     6929
```

<210> SEQ ID NO 261
<211> LENGTH: 277
<212> TYPE: RNA
<213> ORGANISM: Homo sapiens

<400> SEQUENCE: 261
gaaucccacu uacaugcgag caucucuaua uacauccuca aucuaucccc ucgaauccac 60
ggacuuauca gucaaucaau acuacaguca aagaauuuuu uucuacguua uccuggagca 120
uugcgcuggc accucuuuuu cuaaucaucu ugguuguggg gccaauaugg augcgcagac 180
gguguaaacg cagggcugga aagacauaug gacugaccaa gcuacggacu gacaaccagg 240
acuucccuuc cagcccaaac uaaauaaagg aaaugaa 277

<210> SEQ ID NO 262
<211> LENGTH: 2810
<212> TYPE: RNA
<213> ORGANISM: Homo sapiens

<400> SEQUENCE: 262
gaauucaugu cuuacgguca aggcagaggg cccagcgcca cugcagccgc gccaccuccc 60
agggccgggc cagcccaggc guccgcgcuc ucggggugga cuccccccgc ugcgcgcuca 120
agccggcgau ggcuccucuc ggauaccucu uagugcucug cagccugaag caggcucugg 180
gcagcuaccc gaucuggugg uccuuggcug ugggacccca guacuccucu cugagcacuc 240
agcccauucu cugugccagc aucccaggcc ugguaccgaa gcagcugcgc uucugcagga 300
acuacgugga gaucaugccc agcguggcug agggugucaa agcgggcauc caggagugcc 360
agcaccaguu ccgaggccgg cguuggaacu gcaccaccgu cagcaacagc cuggccaucu 420
uuggcccugu ucuggacaaa gccacccggg agucagccuu uguccaugcc aucgccuccg 480
cuggaguagc uuucgcagug acacgcuccu gugcagaggg aucagcugcu aucuguggguu 540 gcagcagccg ccuccagggc uccccaggcg agggcuggaa gugggggcggc uguagugagg 600 acauugaauu uggaggaaug gucucucggg aguuugccga ugccagggag aaccggccgg 660
augcccgcuc ugccaugaac cgucacaaca augaggcugg gcgccaggcc aucgccaguc 720
acaugcaccu caagugcaaa ugccacgggc uaucuggcag cugugaagug aagaccugcu 780
gguggucgca gccggacuuc cgcaccaucg gggauuuccu caaggacaag uaugacagug 840
ccucggagau gguggguagag aaacaccgag agucucgugg cuggguggag acccugaggc 900
cacguuacac guacuucaag gugccgacag aacgcgaccu ggucuacuac gaggccucac 960
ccaacuucug cgaaccuaac ccgaaaccg gcuccuucgg gacgcgugac cgcaccugca 1020
augugagcuc gcauggcaua gaugggugcg accuguugug cugcgggcgc gggcauaacg 1080
cgcgcacuga gcgacggagg gagaaaugcc acuguguuuu ccauuggugc ugcuacguca 1140
gcugccagga gugcacacgu gucuaugacg ugcacaccug caaguaggag agcuccuaac 1200
acgggagcag gguucauucc gaggggcaag guuccuaccu gggggcgggg uuccuacuug 1260
gaggggucuc uuacuugggg acucgguucu uacuugaggg cggagauccu accugugagg 1320
gucucauacc uaaggacccg guuucugccu ucagccuggg cuccuauuug ggaucugggu 1380
uccuuuuuag gggagaagcu ccugucuggg auacggguuu cugcccgagg gugggggcucc 1440 acuuggggau ggaauuccaa uuugggccgg aaguccuacc ucaauggcuu ggacuccucu 1500
cuugacccga cagggcucaa auggagacag guaagcuacu cccucaacua gguggggguuc 1560 gugcggaugg gugggagggg agagauuagg gucccuccuc ccagaggcac ugcucuaucu 1620
agauacauga gagggugcuu caggguggggc ccuauuuggg cuugaggauc ccguggggggc 1680 ggggcuucac cccgacuggg uggaacuuuu ggagaccccc uuccacuggg gcaaggcuuc 1740
acugaagacu caugggaugg agcuccacgg aaggaggagu uccugagcga gccugggcuc 1800
ugagcaggcc auccagcucc caucuggccc cuuuccaguc cuggug uaag guucaaccug 1860 caagccucau cugcgcagag caggaucucc uggcagaaug aggcauggag aagaacucag 1920
gggugauacc aagaccuaac aaaccccgug ccuggguacc ucuuuuaaag cucugcaccc 1980
cuucuucaag ggcuuuccua gucuccuugg cagagcuuuc cugaggaaga uuugcagucc 2040
cccagaguuc aagugaacac ccauagaaca gaacagacuc uauccugagu agagaggguu 2100
cucuaggaau cucuaugggg acugcuagga aggauccugg gcaugacagc cucguaugau 2160
agccugcauc cgcucugaca cuuaauacuc agaucucccg ggaaacccag cucauccggu 2220
ccgugauguc caugccccaa augccucaga gauguugccu cacuuugagu uguaugaacu 2280
ucggagacau ggggacacag ucaagccgca gagccagggu uguuucagga cccaucugau 2340
uccccagagc cugcuguuga ggcaaugguc accagauccg uuggccacca cccugucccg 2400
agcuucucua gugucugucu ggccuggaag ugaggugcua cauacagccc aucugccaca 2460
agagcuuccu gauugguacc acugugaacc gucccucccc cuccagacag gggaggggau 2520
guggccauac aggagugugc ccggagagcg cggaaagagg aagagaggcu gcacacgcgu 2580
ggugacugac ugucuucugc cuggaacuuu gcguucgcgc uuguaacuuu auuuucaaug 2640
cugcuauauc cacccaccac uggauuuaga caaaagugau uuucuuuuuu uuuuuuucuu 2700
uucuuucuau gaaagaaauu auuuuaguuu auaguauguu uguuucaaau aaugggg aaa 2760 guaaaaagag agaaaaaaaa aaaaaaaaaa aaaaaaaaaa aaaaaaaaaa 2810

<210> SEQ ID NO 263
<211> LENGTH: 2948
<212> TYPE: RNA
<213> ORGANISM: Homo sapiens

<400> SEQUENCE: 263
cgcaccggag guccacacug ccgcguggac uccagcgaug gcgcugcgcu aggcuagcgg 60
gugccaggau cccucucugc guccugugcg cgggaagagc ucuggagaac cagaguugca 120
uucuggaguu gaagacucau ggcacagacu guuagagaau gcucauuggc acuucuuuuu 180
uuguucaugu ggcugcugau uaaagcaaau auagaugugu gcaagcuugg cacugugacc 240
guccagccug ccccugugau ucccucuugg ucagcugcca auauuuccug cuccuugaau 300
cccaagcaag gcuguucaca uuaucccagu ucuaacgaau uaauccucuu aaaguuuguc 360
aaugaugucc uuguugaaaa ucuccauggc aagaaagucc augaccacac uggucacucc 420
uccacuuuuc aagucaccaa ccugucccuu gguaugaccu uguuugucug caagcuaaac 480
uguagcaacu cucaaaagaa gccaccaguc ccaguaugug ggguggagau cucaguuggu 540
guugcuccag agccaccuca aaacauauca uguguccagg aaggagaaaa uggaacugug 600
gccuguuccu ggaacucugg aaaaguuacu uaucugaaaa ccaauuacac uuuacaguua 660
aguggaccaa acaaucugac cugucagaaa caauguuuuu cugacaaucg ucagaauugc 720
aaucgccugg aucuugggau caaucuaagc ccugauuuag cugaauccag guucauaguc 780
cguguuacug ccaucaacga ucuuggaaau ucuucuucac uuccgcauac guucacguuc 840
uuggacauag ugaucccucu ucccuccgugg gacaucagaa ucaacuuucu aaaugcuucu 900
gggagcagag guacacugca gugggaagau gaggggcaag ugguacucaa ucaacucaga 960
uaucagccuc uuaacagcac guccuggaac auggucaaug cuacaaaugc caaaggaaaa 1020
uaugaccugc gagaucugag accguuuaca gaauaugaau uucaaaucuc cucuaagcua 1080
caucucucug gaggaaguug gaguaauugg agugagucac ugagaacacg aacaccagag 1140
gaagagccug uugggauauu agacaucugg uacaugaaac aagacaucga cuaugacaga 1200
cagcagaucu cucuuuucug gaagagucug aauccaucag aggcaagggg gaagauccuc 1260
cacuaucagg ugacguuaca agaggugaca aagaaaacaa cacugcagaa uacuacaaga 1320
cacaccuccu ggaccagggu cauccccega acuggggcuu ggacggcauc agugucugca 1380
gccaacucaa aaggcgcuuc ugcacccacu cacauuaaca uaguggaccu auguggcacu 1440
ggguugcugg cuccucacca ggucucugca aagucggaga acauggacaa cauucuagug 1500
accuggcagc cuccuaagaa agcugauucu gcuguucggg aguacauagu ggaauggaga 1560
gcucuccaac cagggagcau cacgaaguuu cccccacacu ggcugcggau ccccccggac 1620
aacaugucug cucugauuuc agagaacaua aagcccuaua ucuguuauga aaucagggug 1680
caugcacugu cagagagcca aggagggugc agcuccaucc ggggugacuc caagcacaaa 1740
gcaccaguga guggcccuca cauuacugcc aucacagaga aaaaggaacg ccuuuucauu 1800
uccuggaccc acauuccauu cccggagcaa aggggcugca uccuccauua cagaauauac 1860
uggaaagaac gagacucgac agcacaaccu gagcucugcg aaauucagua ccgacgcucu 1920
caaaacucac auccaauaag cagccuacag cccagggcuga cauaugucu auggaugaca 1980 gcugugacag cugcugguga aaguccccaa ggaaaugaaa gggaauuuug uccacagggc 2040
aaagccaacu ggaaagcauu cgugauauca agcauuugca ucgcuaucau cacggugggc 2100
acguucucaa uucguuacuu ccggcaaaag gcauuuacuc uccugucuac ucucaaaccu 2160
caaugguaua gcagaaccau uccagaucca gcaaacagca cuuggguaaa gaaguauccc 2220
auucuggagg agaagaucca gcuaccuacg gauaaucucc ugauggcaug gcccacuccu 2280
gaagagccug agccccugau cauccaugaa guccucuacc acaugauccc aguugucaga 2340
caaccauauu acuucaaaag aggccaagga uuccaaggcu acucuaccuc caagcaagau 2400
gcaauguaua uugccaaucc acaagcuaca ggaacucuca cagcugagac cagacaacua 2460
gugaaccuau acaaggugcu agaaagcaga gacccugacu caaaacuggc caaccugacc 2520
agccccuuga cagucacccc agugaacuac cuuccuagcc augaaggcua uuuacccucc 2580
aacauagaag aucugucacc acaugaggcu gacccaacug auucuuuuga ccuggagcau 2640
caacauauuu cucuuuccau uuuugcauca aguucucucc gcccacucau cuucggugguu 2700 gagcggcuga cucuagaucg guuaaagaug ggcuaugacu cccucaugag uaaugaggcu 2760
ugauacuaga aagccaacgu accucauuuu aucugcccag uuccuacucc aaaggucugu 2820
gacagugaag acaagccagc ugucucugga uaaaguuagc uucaccauag guacuuaagu 2880
cuuauggaua agguggcaau acaccaacac ugauaucaua uagaaaggac cccaagauag 2940
ucaugcuc 2948

<210> SEQ ID NO 264
<211> LENGTH: 2487
<212> TYPE: RNA
<213> ORGANISM: Homo sapiens

<400> SEQUENCE: 264
ggcacgaguu cacccucugc augcguuccc cucccccuc uccagcaaac acggcgcgcc 60
aguccaaagc ggacucagug gccucgggga cgggagcaug ccaccuccug uggugacguc 120
acuuggggua gaacccuuag acacuacaug gggggggggg guacagaacu cccgagccag 180

-continued

```
gacagucacu cacucuucag gcggugggc ugggccagac aguaccgccc ccaccgcgcc    240
cgccucgcac acccucggaa gcgcaggcuc gcagcgcggc gcuggggugg gggguugcgc    300
cccagaacuu cggccuccag uccccagccc gcugcaccuc cuuacccucu agaggccccc    360
ucccccuuac ccucuagagg caccaggagu ugucgcaagg ggcccuuggg aaauucccug    420
gaccccugug ccaggaggug cccgguucgc ccgcucccca uccaccccc cgagggcggu    480
gcccgggggc gcugccccau ggagcgggga ggcgggcgcc gucugcugcg ggagcuguga    540
ccugaguagg agcugugugu cgcagccgcc ccaccccugc cgaucaugcg ccggcgaccc    600
ugguucgcca gucccacugg gcugugagcc ccccacuccu ggccugucac ggcccgcgcg    660
ccaugggcag cgcccacccu cgccccuggc ugcggcuccc acaagggccc cagccgcggc    720
cugaguucug ggcgcuccug uucuuccuac ugcugcuggc ugccgcugug cccaggucag    780
cacccaacga cauccugggc cuccgccuac ccccagagcc cgugcucaac gccaacacag    840
ugugccugac auugcccggc cugagccggc ggcagaugga ggugugugug cgucacccug    900
acguggccgc cucugcuauc cagggcaucc agaucgccau ccaugagugc cagcaucagu    960
uccgggacca gcgcuggaac ugcuccagcc uggagacucg gaacaaaguc cccuacgaga   1020
gccccaucuu cagccgaggu uuucgagaga gugcuuucgc cuacgccaua gcagcugccg   1080
gggugguca cgcaguguccc aacgcgugcg cucuggguaa acugaaggcu ugcgguugcg   1140
acgccuccag acguggggac gaagaagcuu uccgucggaa gcugcaccgc uugcagcugg   1200
acgcgcugca gcgcggaaag ggcuugagcc acggggu ccc ugaacacccg gccauacuuc   1260
cugccagccc aggucugcag gacuccuggg agugggugg cugcaguccg gaugugggcu   1320
ucggagaacg cuucucuaag gacuuucugg acucccgaga gccucacaga gacauccaug   1380
cucgaaugag acuccacaac aaccgugugg gccggcaggc ggugauggag aacaugcggc   1440
guaagugcaa augccacggc accucaggca gcugccagcu caagaccugc uggcaggua   1500
cgccugaguu ccgcacagua ggggcgcugc ugcgcaaccg cuuccaccgc gccacgcuca   1560
uccggccgca caaccgcaac gguggccagc uggagcccgg ccccgcggga gcacccucgc   1620
cagcaccggg cacuccaggg cugcgccgca gggccagcca cuccgaccug gucuacuuug   1680
agaaaucucc cgacuucugu gagcgcgagc cgcgccugga cucggcaggc acugugggcc   1740
gccugugcaa uaagagcagc acgggucccg auggcugcgg cagcaugugc uguggccgcg   1800
gccacaacau ucugcgccag acgcgcagcg agcgcugcca cugccgguuc cacuggugcu   1860
gcuucguggu cugcgaagaa ugccgcauca ccgaguggu cagcgucugc aagugagcag   1920
acccaagcuc cucuggucu caagaauggu uguccucuug gugccuggcu ucugccgcua   1980
gcggaucuga gccaggcagc aagcagcagc cuuggcuccu gagagaggug guuggcucuu   2040
acagccccga gggucuacaa ucaccagaca guccagaucu gauugacauu ccuccgcuca   2100
ccucuguagg uuccccucuu ucuguuccua gcucagacag cuggggguga uaguggagac   2160
uguuccacac ccuaggacag gucaccaaag cagcccagcc uggcaugccu accuccuguc   2220
aucucuucuu cccuucccca ggagugauag gcaaugcacu gaagcugaug ggcaccgggg   2280
aagaaaacua aaaggcagaa auggccguca ucgggcugaa gugacucuaa gggcuccaga   2340
ccucugcucc ugucuuucac uuaacagaua uuuauuuuug cgcucucuuu gagacacucu   2400
cuggggaaaa agaagcuccg gagucuacag gcugauuaag ggacauggac aauaaaccag   2460
uaaacacaca aaaaaaaaaa aaaaaaa                                       2487
```

<210> SEQ ID NO 265
<211> LENGTH: 2093
<212> TYPE: RNA
<213> ORGANISM: Homo sapiens

<400> SEQUENCE: 265
gaauuccggg ccgcuugcac uuggcgacua gucugcggcg gacgugacgc caaggccacg 60
ggcagcgcgg guccccuguc agaggugucc cucgcgcagg aaugggcccg caggcggcag 120
cuggcaggau gauucugcug gugguccuga ugcugucugc gaaggucggg aguggagcuu 180
ugacgagcac cgaggauccu gagccucccu cggugccugu accgacgaau guucuaauua 240
agucuuauaa cuugaacccu gucguaugcu gggaauacca gaacauguca cagacuccua 300
uuuuuacugu acagguaaag guguauucgg guuccuggac ugauuccugc accaacauuu 360
cugaucauug uuguaauauc uaugaacaaa uuauguaucc ugauguaucu gccugggcca 420
gaguuaaagc uaagguugga caaaaagaau cugacuaugc acggucaaaa gaguuccuua 480
ugugccuaaa gggaaagguc gggcccccug gccuggagau caggaggaag aaggaagaac 540
agcucuccgu ccucguauuu cacccugaag ucguugugaa uggagagagc cagggaacca 600
uguuugguga cgggagcacc uguuacacau ucgacuauac uguguaugug gagcauaacc 660 ggaguggga gauccuacau acgaaacaua cggucgaaaa agaagagugu aaugagacuc 720
ugugugaguu aaacaucuca guauccacac uggauuccag auauuguauu ucaguagacg 780
gaaucucauc uuucuggcaa guuagaacag aaaaaucgaa agacgucugu aucccuccuu 840
uccaugauga cagaaaggau ucaauuugga uucugguggu ugcuccucuu accgucuuua 900
caguaguuau ccugguauuu gcguauuggu auacuaagaa gaauucauuc aagagaaaaa 960
gcauaauguu accuaagucc uugcucucug ugguaaaaag ugccacguua gagacaaaac 1020
cugaaucgaa guauucacuu gucacaccgc accagccagc uguccuagag agugagacgg 1080
ugaucuguga agagccccug uccacaguga cagcuccaga cagccccgaa gcagcagaac 1140
aggaagaacu uucaaaagaa acaaaggcuc uggaggcugg aggaagcacg ucugccauga 1200
ccccagacag cccuccaacu ccgacacaaa gacgcagcuu uucccuguua aguaguaacc 1260
agucaggccc uuguagccuc accgccuauc acucccgaaa cggcucugac aguggccucg 1320
ugggaucggg cagcuccaua ucggacuugg aaucucuccc aaacaacaac ucagaaacaa 1380
agauggcaga gcacgacccu ccacccguga gaaaggcccc cauggccucc gguuaugaca 1440
aaccgcacau guugguggac gugcuugugg auguuggggg gaaggagucu cucaugggu 1500 auagacucac aggagaggcc caggagcugu ccuaagguca cccgaggccu gcugguggua 1560
aagaaacuga ccuuuuaggc aguuuuucug cauugauuuc augaaagaag cuauacauua 1620
gcuaauacua accacauaga auaucagacu uagauacgug aauaaggauc cugugggcac 1680
ugcugggucc acucugcaaa ugccaagacu aucaaaggaa cguauugucg cuucuggcuc 1740
cuucccaggu gggcuagcau cugugaguuu gccucggcua gccuugcuuc cuacagccgc 1800
cacugcuccu ccacccugau caucucacag gacagggugg accggguuuu uuuuuuuuuu 1860
ucacacaccu uuguauaugu aaguucaugu auauaauaug uuuacauguu ucacuuugaa 1920
cugaaagcua cucaaagcca gccguaaguc uaugguagaa ugugauggaa cauguuggug 1980
gaagcuugua caauagaaca cauugguggg agcuuguaca uacuuuuuua uggagcauua 2040
cuuacgauuu uuuaaguaaa auguuuugaa accaaaaaaa aaaaaaggaa uuc 2093

<210> SEQ ID NO 266

-continued

<211> LENGTH: 756
<212> TYPE: RNA
<213> ORGANISM: Homo sapiens

<400> SEQUENCE: 266
augagacucc acagccucau ccugcucucc uuccuucucc uggcuacuca ggcguucuca 60
gaaaagguca gaaagagagc caagaacgca ccacacagca cagcggagga gggggguagag 120 gguucagcuc ccucguuagg gaaggcccag aauaagcaga gaagcaggac aucuaaaucu 180
cugacgcaug gcaaguuugu caccaaagac caagccacau gcagaugggc ugugacugag 240
gaggagcagg gcaucagccu gaagguccag ugcacacaag ccgaucagga guuuucuugu 300
guuuuugcug gugacccaac ugacugccuu aaacacgaca aagaccagau cuacuggaaa 360
cagguugccc gcacgcugcg caaacagaaa aauaucugca ggaacgccaa gagugucuug 420
aagaccagag ugugcagaaa gagauuucca gagucuaacc ucaagcuggu gaaccccaac 480
gcacguggaa acacgaagcc caggaaggag aaagcagagg ucuccgcaag ggagcacaac 540
aagguccaag aagcugucuc cacggagcca aacaggguca aagaagacau cacacucaau 600
ccagcugcga cccagaccau ggccauuaga gauccagagu gucuagagga uccagaugug 660
cucaaccaga ggaagaccgc ccuggaguuc uguggggaau cuuggagcuc cauuugcaca 720
uucuuccuca acauguuaca ggcgacauca ugcuaa 756

<210> SEQ ID NO 267
<211> LENGTH: 181
<212> TYPE: RNA
<213> ORGANISM: Homo sapiens

<400> SEQUENCE: 267
aauucgucga caugcgccgu uccagugcau ggugugccaa cgcagcuucu cccgcuccga 60
ccaccucgcg cugcacauga agcgccacca gaacugagcg agcgagcgcu gccccacccg 120
ccugacgccu ugcaguccgc ucugccaucc uuuaaaccgc agaccuaacu ucauaaaaag 180
a 181

<210> SEQ ID NO 268
<211> LENGTH: 2056
<212> TYPE: RNA
<213> ORGANISM: Homo sapiens
<220> FEATURE:
<221> NAME/KEY: misc_feature
<222> LOCATION: (1942)..(1943)
<223> OTHER INFORMATION: n is a, c, g, or u

<400> SEQUENCE: 268
gcuaaacuau cccgcaaaga uuuuucuuuc cucccuaaac ccuccuuuuu gcucuccuuu 60
ucuauacccu uaacugcaaa caaaccauua aacgaccccu cuccugggcc uccgacggca 120
ggaguccgcg gaccucccag gccgacagcc cucccucuac ccgcgagguu ccgggccggg 180
cgagagggcg cgagcacagc cgaggacaug gaggugacug cggaccagcc gcgcugggug 240
agccaccauc accccgcggu ccucaacggu cagcacccag acacgcacca cccgggccuc 300
ggccauucgu acauggaagc ucaguauccg cugacggaag agguggacgu acuuuuuaac 360
aucgaugguc aaggcaacca cgucccgucc uacuacggaa acuccgucag ggcuacggug 420
cagagguauc cuccgaccca ccacgggagc cagguaugcc gcccgccucu gcugcacgga 480
ucucugcccu ggcuggaugg cggcaaagcc cugagcagcc accacaccgc cucgcccugg 540
aaccucagcc ccuucuccaa gacguccauc caccacggcu cuccggggcc ucuguccguu 600
uacccuccgg cuucauccuc uucucuggcg gccggccacu ccaguccuca ucucuucacc 660
uucccgccca ccccgccgaa agacgucucc ccagacccgu cgcuguccac cccgggaucc 720
gccgggucgg ccaggcaaga ugagaaagag ugccucaagu aucaggugca gcugccagau 780
agcaugaagc uggagacguc ucacucucga ggcagcauga ccacccuggg uggggccuca 840
uccucagccc accaccccau uaccaccuau ccgcccuaug ugcccgagua cagcucugga 900
cucuucccac ccagcagccu gcugggagga ucccccuaccg gguucggaug uaagucgagg 960
cccaaggcac gauccagcac agaaggcagg gaguguguga acugcggggc aaccucuacc 1020
ccacuguggc ggcgagaugg uaccgggcac uaccuuugca augccugcgg acucuaccau 1080
aaaaugaaug ggcagaaccg gccccuuauc aagcccaagc gaaggcuguc ggcagcaagg 1140
agagcaggga cauccugcgc gaacugucag accaccacca ccacccucug gaggaggaac 1200
gcuaaugggg acccggucug caaugccugu gggcuguacu acaagcuuca uaauauuaac 1260
agaccccuga cuaugaagaa agaaggcauc cagacccgaa accggaagau gucuagcaaa 1320
ucgaaaaagu gcaaaaaggu gcaugacgcg cuggaggacu uccccaagag cagcuccuuc 1380
aacccggccg cucucuccag acacauguca ucccugagcc acaucucucc cuucagccac 1440
uccagccaca ugcugaccac accgacgccc augcauccgc ccuccggccu cuccuucgga 1500
ccucaccacc cuuccagcau ggucaccgcc augggguuaga gaggcagagc ccugcuccac 1560
augcgugagg agucuccaag ugugcgaaga guuccuccga ccccuucuac uugcguuuuu 1620
cgcaggagca guaucaugaa gcccgaaagc gacagaucug uguuuuugaa ggcagaaagc 1680
aaaauguuug cuucuuuuuu caaaggagcu cgagguggug ucugcauucc aaccacugaa 1740
uccggauccc auuugugaau aagccauuca gacucauauu cccuauuuaa cagggucucu 1800
agugcuguga aaaaaauauu gcugaacauu gcauauaacu uauauuguaa gaaauacugu 1860
acauuugagg aagacuuuau uguaccugga uagcuguaag aaaggcauga aggacgccaa 1920
gaguuuuaag gaauauaggg gnnuuaaagu auggagauac agaagaaacc acuaagucug 1980
auguccaaau gggcacacug ucaguuuugu uucccuucag uuguuugaug cauuuaaaaa 2040
aaaaaaaaag aaagaa 2056

<210> SEQ ID NO 269
<211> LENGTH: 1508
<212> TYPE: RNA
<213> ORGANISM: Homo sapiens

<400> SEQUENCE: 269
caaccaccuc cuaccugccu gcccaaagcu ccagggcugg agcacggaga ccugucaggg 60
auggauuuug cccacaugua ccaaguguac aaguccaggc ggggaauaaa acggagcgaa 120
gacagcaagg aaacuuacaa acugccgcac cggcugauug agaaaaagag acgugaccgg 180
auuaacgagu gcauugccca gcugaaggau cuccuacccg aacaucucaa acuuacuacu 240
uugggucacu uggaaaaagc agugguucug gagcuuacgu ugaagcacgu gaaagcauug 300
acaaaucuaa uugaucagca gcagcagaaa aucauugccc ugcagagcgg uuuacaagcu 360
ggugauuugu cgggaagaaa ucucgaggca gggcaagaaa uguucugcuc agguuuccag 420
acuugugccc gugagguacu ucaguaccug gcgaagcaug agaacacucg ggaccugaaa 480
ucuucccagc ucgucacuca ucuccaucgu guggucucgg agcugcugca ggguggugcu 540
uccaggaaac cauuggacuc ggcucccaaa gccgucgacu ugaaagagaa gcccagcuuc 600
cuagccaagg gaucagaagg cccagggaaa aacugugugc cagucaucca gcggacuuuu 660
gcucccucgg gugggggagca gagcggcagu gacacggaca cagacagugg cuauggaggu 720
gaauuggaga aaggggacuu gcgcagugaa cagccguacu ucaaaagcga ccauggacgc 780
agguucgccg ugggagaacg ugucagcaca auuaagcaag aauccgaaga gcccccccacc 840 acaaagagcc gaaugcagcu cucagaagag gaaggccacu ucgcgggcag ugaucugaug 900
gguuccccau uucuugggcc acacccacau cagccuccuu uuugccuucc cuucuaucuc 960
aucccaccau cggccacugc cuaccugccu augcuggaga aaugcuggua ccccaccucu 1020
gugccagugu uauacccagg ccucaacacc ucagcugcag cccucuccag cuucaugaac 1080
ccagacaaga uaccgacucc cuugcuucug ccccagagac ucccuucucc uuuggcacau 1140 ucguccccuug acucuucggc cuugcuccag gcuuugaagc agaucccucc uuuaaacuua 1200
gaaaccaaag acuaaacucu ggagggaucu ccugcugccu ugcuuucuuu ccucccuaau 1260
uccaaaaacc acgaagguuu cccugagugc agagagauca gcccacccug cagacccaca 1320
gagaagauuc agagugugug ugagagugag ugagugugcg ugcgugcgug cuuguaugua 1380
uguuuguaua uguaggacaa uaaguuccuu cugacacaag ggagacacga gaaggauagc 1440
cugacaucag augacagacu ggaggacugu agcacaucuc ugggcguuuc ccuacccaga 1500
gaagagcc 1508

<210> SEQ ID NO 270
<211> LENGTH: 9471
<212> TYPE: RNA
<213> ORGANISM: Homo sapiens
<220> FEATURE:
<221> NAME/KEY: misc_feature
<222> LOCATION: (121)..(121)
<223> OTHER INFORMATION: n is a, c, g, or u

<400> SEQUENCE: 270
agucaccgac guuguauaac gacggccagu gaauuguaau acgacucacu auagggcgaa 60
uuggguaccg gccccccccu cgaggucgac gguaucgaua agcuugauau cgaauucucg 120
nccgcgugcg ggucuggucg gggcggagcg aaggccgcgg guggccgugg ucgguccucc 180
gcggcuaagg agccgagggc uccgacgcgg gcugcgcccg gugagcggcg gccagagcua 240
acuugcgcug acuggaccag cugaggagcg gcccggcggg gcgacugcga gcuucaccga 300
gaggcuucuc cgcccugguc cgcagucccg acggccgggc ggaccauggc guccucggcu 360
caccugguca ccaucaagcg gagcggcgau gacggcgcac acuucccgcu gagccucagc 420
uccugccugu uuggaaggag uauugaaugu gacauucgua uccagcugcc uguagugucu 480
caaagacauu gcccaauugu aguccaagag caagaggcga uauuauauaa uuucaguucu 540
accaauccaa cucaaguaaa cggggguuacu auagaugagc cugugaggcu gagacaugga 600
gacauaauaa ccaucauuga ccgcuccuuu agguaugaag auggaaauca ugaggaugga 660
agcaaaccaa cagaauuucc aggaaagucc cuuggaaagg aaccaucaag gcgagccuca 720
agagauagcu ucugugcuga cccugauggg gaaggucaag auaccaaagc uucaaaaaug 780
acugcuucaa gaagaucuuu uguguaugcc aagggccuuu cugcagauag cccugccuca 840
gauggcucaa agaacagugu uagccaagac ucaucaggc auguagaaca gcacacuggc 900
agaaacauag uagagcccac uucuggggga ucucuuuuaa gaaguccagg ucuacaggga 960
gcaguuacag ggaaccgaag ucuucuuccu acacagagcc uuagcaauag caacgaaaag 1020
gaaucucccu uugagaaacu uuaucaauca augaaggaag aguuggaugu aaaaucccag 1080

-continued aaaucuugua ggaaaucaga accccaaccu gaccgugcag cagaggaauc gcgggagaca 1140
cagcuauugg ugucaggcag ggcaagagca aagucuagug gaagcacccc uguuacugca 1200
gccucuucac ccaaaguagg aaagaucugg acugagagau ggcgcggugg aauggugccu 1260
guccagacuu ccacagagac agcuaaaaug aagaccccug ugcggcauuc acagcaacuu 1320
aaggaugaag acucucgugu uacuggcaga cgacauucug ugaaucugga ugaaggugga 1380
agugcccagg caguccauaa aacagucacu ccugggaaac uggcgacuag aaaccaaacu 1440
ccgguggagg cuggggaugu uggcagcccc gcugauacac cagaacauuc cucuuccccc 1500
cagagaagua uuccugcaaa gguagaggcu ccaucugcag agacacaaaa ucggcucucu 1560
uuaacucagc gccuuguucc aggugaaaag aaaacuccca aggguuccuu cagcaagccu 1620
gagaaacugg ccacagccgc cgaacagacu ugcucuggcc uaccuggucu uaguuccguu 1680
gauaucagca acuuugguga uuccauuaac aagagugagg gaaugccuau gaagagaaga 1740
cguguauccu uugguggaca ucuaagaccu gaauuauuug augaaaacuu gccuccuaau 1800
acaccacuga aaagaggaga aacgccaacc aagaggaagu cucuuggcac ucacagccca 1860
gcuguccuca agacaaucau caaggaacgg ccccagucuc cagggaaaca agagucuccu 1920
gggauaacgc caccgaggac aaaugaucaa agacgcagau caggcaggac uuccagugga 1980
agcaauuucu uaugugagac agacauuccc aagaaagcag gcaggaagag cgguaaccug 2040
ccugcgaaga gagcauccau cagccggagu cagcauggca uucuacagau gauuugcucc 2100
aaaaggcgaa guggagcuuc ugaagccaac uugauuguug caaaaucaug ggcugauguu 2160
guaaaacuug gcgugaaaca aacacaaacg aaaguugcga aacaugaccc uccaaagcag 2220
acgagcaaga gacaaagaag acccagcacu ccaaagaaac ccacaagcaa ucuucacaau 2280
caauuuacua caggccaugc aaacucuccc uguaccauug uaguagguag agcgcagauu 2340
gaaaaaguaa gugugccugc ccgacccuac aaaaugcuga auaacuugau gcuaaaccga 2400
aaaguggacu ucagugaaga ucugucagga cuaacugaaa uguucaagac uccagugaag 2460
gagaagcagc agcagaugag ugauacaggc uccguacuuu ccaauucagc gaauuugucu 2520
gaaagacaau ugcaaguaac uaauucagga gacauaccug agcccaucac cacagagauu 2580
uugggagaaa aagugcuauc caguacucgg aaugcagcaa agcagcaguc ugauagauau 2640
ucugcaaguc cuaccuuaag acggcggagc aucaaacaug aaaacacagu gcaaacuccu 2700
aagaaugucc auaacauuac ugaccuugag aagaagacuc cggucucuga gacagagccc 2760
cugaagacug caucgagugu gagcaaguua agaagaucua gagagcucag acauacccuu 2820
guggaaacua ugaaugaaaa aacagaagca guccuugcug agaacaccac agcaagacau 2880
uuaaggggga cauuucgaga acaaaaagua gaucaacagg ugcaggacaa ugaaaacgcu 2940
ccucaaagau gcaaggaaag uggugaauua agugaaggu ucagaaaagac aucagcuagg 3000 agaucaagug ccaggaagca gaagccgaca aaagacuuac uaggaaguca gauggucacc 3060
caaacagcag acuaugcuga ggaacuacuu agucaaggac aaggaaccau acaaaaccua 3120
gaggaaucca ugcacaugca aaacacauca auaagugagg aucaaggaau uacagaaaag 3180
aaagugaaca uaauaguaua ugcaaccaaa gagaagcacu cgccaaagac cccuggcaaa 3240
aaggcacaac cucuagaagg gccagcuggu cucaaggaac acuuugaaac accaaacccc 3300
aaagauaaac cuauaacgga agacagaacu agaguccuuu gcaaaucacc acaagucaca 3360
acagagaaua ucacaacaaa cacaaagcca cagacuagca caucugggaa gaaaguagac 3420

-continued

```
augaaggaag aaagcucugc cuugacaaaa cguauacaua ugccagggga auccaggcau   3480
aaucccaaaa uuuuaaaacu ugagugugag gauaucaaag cuuugaagca aucugaaaau   3540
gaaaugcuga ccucaacagu aaauggaagc aagaggacuu uaggaaaauc uaaaaaaaag   3600
gcucagcccc uggaagaccu gacuuguuuc caggaacucu uuauaucacc aguuccuacu   3660
aacauaauca aaaaaauucc cagcaaaucu ccacacacac aaccagucag aaccccagcg   3720
agcacaaaga gacucuccaa gacaggucuc aguaaagugg augugagaca agaaccuuca   3780
acacuuggga aaagaacgaa gucaccaggc agagccccag gcacaccagc accagugcag   3840
gaagaaaaug acugcacagc cuacauggaa acuccaaagc agaaacugga gucuauagaa   3900
aauuuaacag ggcuuaggaa acaguccaga acaccuaaag acaucacugg uuuccaggau   3960
aguuuccaaa uaccagauca ugcuaauggc ccauuagugg uugucaaaac caaaaaaaug   4020
uucuuuaauu cuccacaacc agaaagugcc auaacccgaa agagcagaga gagacagucu   4080
agggcaagua uaaguaaaau agauguuaaa gaagaacuuu uagaaucaga ggaacaccua   4140
caauuaggag aagguguaga cacauuucag guauccacca acaaagucau uagaucaucu   4200
aggaaaccug caaagcguaa acuggauuca acagcuggua ugccuaacag caagaggaug   4260
cgcuguucuu caaaggauaa cacaccaugc cuagaagacc ugaauggcuu ccaagagcuc   4320
uuccaaaugc caggcuaugc uaaugacucu uugaccacug gaaucucaac aaugcuugcu   4380
agaucaccac aauuaggacc aguuagaacc caaaucaaca aaaagagucu gcccaagauc   4440
aucuugagaa aaauggaugu gacagaagaa auuucagguc ucuggaagca gucacugggc   4500
agaguccaca ccacacaaga gcaggaggau aaugcaauca aagcaauuau ggagauucca   4560
aaggaaacac ugcagacugc agcagaugga acuaggcuua ccagacagcc acaaacaccu   4620
aaggaaaaag uucaaccgcu ggaagaucac agugucuucc aagaacucuu ccaaacauca   4680
cgcuacuguu cugauccauu aauugguaac aaacaaacaa gaauguccuu gagaucucca   4740
caaccaggau uuguuagaac uccacgaacc ucaaagagac uggcuaagac aaguguuggg   4800
aauauugcug ugagagaaaa gaucucucca gugagucugc cacagugugc uacaggggag   4860
guuguacaca uacccauagg gccagaagau gacacagaga acaaaggugu gaaggaaucc   4920
acaccucaga cacuggacuc aucagcaagu cgaacuguca gcaagaggca gcaaggggca   4980
caugaggaaa ggccucaguu cucaggagac uuauuucauc cccaagagcu cuuucaaaca   5040
ccagccagug gcaaagaccc aguaacuguu gaugaaacua caaaaauagc ucugcagucu   5100
ccacaaccag gacauaucau aaacccagca agcaugaaga gacaguccaa caugagucuc   5160
aggaaagaca ugagagaauu uuccauacuu gaaaaacaaa cacagucacg aggcagagac   5220
gcaggcacac cagcaccaau gcaggaagaa aauggcacca cagccauuau ggaaacacca   5280
aagcagaaac uggauuucau aggaaauuca acaggacaua agaggaggcc ucggacaccc   5340
aaaaacaggg cucagccccu agaagaccug gauggcuucc aagaacucuu ucaaacacca   5400
gcuggugcca gugacccugu gaguguugaa gaaagugcaa agauaucuuu ggcaucuuca   5460
caagcagaac cagucagaac cccagcaagu acaaagagac gcuccaagac aggucucagu   5520
aaaguggaug ugagacaaga accuucaaca cuugggaaaa gaaugaaguc acuaggcaga   5580
gccccaggca caccagcacc agugcaggaa gaaaaugaca gcacagccuu cauggaaacu   5640
ccaaagcaga aacuggauuu cacaggaaau ucaucaggac auaagaggag gccacagaca   5700
ccuaagauca gggcucagcc ccuagaagac cuggauggcu uccaagaacu cuuccaaaca   5760
ccagcuggug ccaaugacuc agugacuguu gaggaaagug uaaagauguc uuuggaaucu   5820
```

ucacaagcag aaccagucaa aaccccggca agcacaaaga gacucuccaa gacaggucuc 5880
aguaaggugg augugagaga agacccuuca auacuugaga aaaaaacaaa gucaccaggc 5940
acaccagcac cagugcagga agaaaaugac ugcacagccu ucauggaaac uccaaagcag 6000
aaacuggauu ucacaggaaa uucaucagga cauaagagga ggccacggac accuaagauc 6060
agagcucagc cccuagaaga ccuggauggc uuccaagaac ucuuccaaac accagcuggu 6120
gcuagugacu cagugacugu ugaggaaagu gcaaagaugu cuuuggaauc uucacaagca 6180
aaaccaguca aaaccccggc aagcacaaag agacucucca agacaggucu caguaaggug 6240
gaugugagag aagacccuuc aacacuuggg aaaaaaacaa agucaccagg cagagcccca 6300
ggcacaccag caccagugca ggaagaaaau gacagcacag ccuucaugga aacuccaaag 6360
cagaaacugg auuuugcaga gaauucauca gggaguaaga gaaggucacg aacaucuaag 6420
aacaggucuc agccccuaga agaccuggau ggcuuccaag aacucuucca aacaccagcu 6480
ggugccagua acccugugag uguugaagaa agugcaaaga uaucuuugga aucuucacaa 6540
gcagaaccag ucagaacccg ggcaagcaca aagagacuuu ccaagacagg ucucaauaag 6600
auggauguga gagaagggca cucuccgcuc aguaagucaa gcugugcauc acagaaaguc 6660
augcaaaccc ucacacuugg agaagaucau ggcagagaga ccaaagaugg gaagguauug 6720
uuagcucaga aauuggaacc agcaauauau guuacucgug gcaagaggca gcaaagguca 6780
uguaagaaaa ggucccaguc cccagaagac cucucuggug uucaggaggu cuuccaaaca 6840
ucaggccaua acaaggauuc agugacagug gacaaucuug caaaacugcc cagcucgucu 6900
ccaccacuag agccaacaga cacuucagua accucacgga gacaggccag aacuggucug 6960
aggaaaguuc acgugaaaaa ugaacuuuca ggaggcauaa ugcauccaca aauaucaggg 7020
gaaauugugg acuuaccuag agaaccagaa ggugaaggca aagucauuaa aacaaggaag 7080
caaucuguaa aacggaaauu ggacacagaa gucaaugugc cucgcaguaa gaggcaaaga 7140
auuacaagag cagaaaagac ccuagaggau cugccuggcu uccaagagcu cugccaagcu 7200
ccaagcuugg uaauggacuc aguuauuguu gagaaaaccc caaagaugcc cgacaaaucu 7260
ccagaaccug uggauacaac uucagagaca caggcaagaa gaagacucag gagacugguu 7320
guuacugaag agcccauacc acaaagaaag acuacaagag uuguaaggca aaccagaaac 7380
acacagaaag agcccauaag ugacaaucaa gguauggaag aguuuaagga aucuucagua 7440
cagaaacaag acccaagugu aaguuuaacu ggcaggagga accaaccaag gacaguuaag 7500
gagaaaaccc aacccuuaga agaacucacc aguuuccaag aggaaacugc caaaagaaua 7560
ucuuccaaau cuccacaacc ggaagagaag gaaaccuuag cagguuuaaa gaggcagcuc 7620
agaauacaac uaaucaacga ugguguaaaa gaagagccca cagcacagag aaagcaacca 7680
uccagggaaa ccaggaacac acucaaagag ccuguaggug acaguauaaa uguugaagag 7740
guuaagaagu cuacaaagca gaaaauugau ccaguagcaa gugugccugu cagcaagagg 7800
ccacggaggg uacccaagga aaaggcacag gcccuagaau uggcuggucu caaaggacca 7860
auccaaaccc uaggccacac ugaugaauca gcaagugaua aaggacccac acagaugccc 7920
uguaauucuc uacaaccaga gcaaguugac agcuuccaaa gcucaccaag gcgacccagg 7980
acaagacgug ggaaaguaga ggcagaugaa gagccuucag caguaagaaa gacaguauca 8040
acaucaaggc aaacuaugcg aucccgcaag gucccugaaa uugguaacaa ugguacccaa 8100
guuucaaagg ccuccauaaa gcagacauua gauacaguag ccaaaguaac uggcagcagg 8160
aggcagcuaa ggacacauaa aggaugggggu ucaacccucu ugaaguuguu aggugacucc 8220
aaagaaauaa cccaaauauc agaucacucu gagaaacuag cacaugacac caguauccuu 8280
aagagcacuc aacagcaaaa gccagacuca guaaaaccuc ugagaacaug cagaagagug 8340
cugagggccu cuaaagaggu ccccaaggaa guguuggugg acaccagaga ccaugcaaca 8400
uuacaaagca aaagcaaccc uuugcugucc ccgaagagga agucugcaag agauggaagc 8460
auugugagaa ccagggcuuu gcgcucuuua gcaccaaagc aggaagcaac agaugagaag 8520
ccuguaccug agaaaaaaag ggcugcuucc agcaagaggu auguaucacc ugagccugug 8580
aagaugaaac accugaaaau cgugucaaac aaacuugaau cuguggaaga gcagguuagc 8640
acuguuauga aaacagaaga aauggaagcc aaaagagaaa auccugucac uccagaucag 8700
aacucuaggu accgaaagaa aaccaaugua aaacagccaa ggcccaaguu ugaugcaucu 8760
gcagagaaug ucgggauaaa gaaaaacgag aagacuauga agacugccuc ccaggagaca 8820
gagcugcaga auccagauga uggagccaag aaaucuacau cucggggcca agucaguggg 8880
aaaagaacau gcuugagguc uagaggaacg acugagaugc cccagccuug ugaagcagaa 8940
gagaaaacaa gcaaaccagc ugcagaaauc uugauaaagc cucaggaaga gaaaggaguc 9000
ucuggagagu cugauguuag guguuugagg uccagaaaaa cuagagucgc uuuggacagu 9060
gaaccuaagc caaggguaac ucguggaacc aagaaagaug caaaaacucu gaaggaggau 9120
gaagacauug uaugcaccaa gaaguuaaga acaagaaguu aagaacaaga aguuaccaga 9180
aaagugaaac uauguagcaa agacauuuaa gaaggaaaag uaaauuugac uuagugauaa 9240
guuccagugu gguuuucacc uccaguguaa agaugaacug uaaauacuac ugcuacugcc 9300
ugaguuuaag gaaggaagcu uugagcuuuc cuggucauac ucucuucaga cgccaaugga 9360
ggucaugagg aagaucacca gggaucucag cgcaauuaca guuuaggggu gagcaggcag 9420
aaauguggcc cucuguccua uccaauaaag cucugaaauu cgcugccaaa a 9471

<210> SEQ ID NO 271
<211> LENGTH: 463
<212> TYPE: RNA
<213> ORGANISM: Homo sapiens

<400> SEQUENCE: 271
gacguagagc cccuugcgcc cgguuuccug aucccgcuua cuccucugcg cgccggcagg 60
auggcccaca agcagaucua cuacucagac aaguacuucg augagcacua cgaguaccgg 120
caugucaugu uacccagaga acucucuaaa caaguaccca aaacucaucu gauguccgaa 180
gaggagugga ggagacuugg uguccaacag agucuaggau ggguucauua caugauucau 240
gagccagaac cgcauauucu ucucuuuaga cgaccucuuc caaaagaaca acaaaaauga 300
agugcagcug ggaucaucua aucuuuuuca aauuuaaugu auauguguau auaagguagu 360
auucagugaa uacuugaaaa guguacaaac cuuucaucca uaccugugca ugcgcuguau 420
ucuucacagc aacagagcuc agucaaaugc aacugcaagu agg 463

<210> SEQ ID NO 272
<211> LENGTH: 1280
<212> TYPE: RNA
<213> ORGANISM: Homo sapiens

<400> SEQUENCE: 272
cuacccuaga caaucacggc uuagccggcg cgcggagucg aucgucucgg ucgcuagagc 60
uguccugagc ucgaacgguc cgacgccccc gccgcgccgg uccgugacgc cggggccgac 120

-continued

```
acgaugaagg auuuggggggc caagcacuug gcagguggcg aaggggguuca gcuuuucgga    180

uuguugaacu ucuaccugga acaagaacag agauaccaac cucgggaaaa agggcugauc    240

uugauggagg cuaccccgga gaaugauaac acuuuguguu caagacugag aaaugccaaa    300

guggaagauu uaagaaguuu aacuaacuuc uuuggaucug gcacugaaac uuucguucug    360

gcugucaaua uuuuggauag auucuuggcc cuuaugaagg ugaaaccgaa acaccugucc    420

ugcauuggcg ucugcugcuu uuugcuggcc gccaggcugg cggaagaaga aggugacguu    480

ccccccacgc acgacgugau ccgcaucagu caguguaaau gcacagcguc ugacauuaaa    540

cgcauggaga aaaucaucuc agagaaacug cacuaugagc uggaagcuac cacugccuua    600

aacuuuuugc acuuguacca cgcgauugua uuuugucaca cuucagaaag gaaggagauu    660

cucagccucg auaaacucga agcgcagcug aaagcuugca acugccgagu ugucuucucc    720

aaagcaagac caucuguauu agcucugugc cuucucaauu uggaaauaga aacgauaaaa    780

uccguggaac ugcuggaaau ucucuugcuu guuaaaaaac auuugaagcu cagcgacacu    840

gaauucuuuu acuggaggga acugguuucu aaaugucuag cagaguauuc uucgccucgc    900

ugcugcaagc cugaucugaa gaagcuggua uggauuguuu cgcgacgcac ugcgcagaac    960

cuccacagca gcuacuacag uguuccugag cugcccacua ucccagaggg ggguugcuuu   1020

gacggaagug aaagugagga cucuggugaa gacaugaguu guggagagga gagucucagc   1080

agcuccccac ccagcgauca ggagugcacc uucuucuuug acuuccaagu ggcucagaca   1140

cugugcuuuc caccauagag gaaucugaca uuguucugug ucagggaauu uauaagugug   1200

uguaccuagg uuucaaagca auaaacuugg ggguugaaua ggguaguuuu ccuagguuuc   1260

cagcccccccg ucuagucagg                                             1280
```

<210> SEQ ID NO 273
<211> LENGTH: 291
<212> TYPE: RNA
<213> ORGANISM: Homo sapiens

<400> SEQUENCE: 273

```
aacuaccuug ggcagguucu auuaacugca ccuaacucag acgugaguag gacagaagga     60

agcuguccccg ggcgaacuga ggucacaaag acuugcuuuu gauucaagag agaccuuaaa    120

ggcuaguuau gauaguuaag uacaaguuuu aacaucuggu agcuaacuuu uuuucucuac    180

cccguaauuc uacuaugacu gcucuucuag agguccugag uucaaauccc agcaaccaca    240

ugguggcuca caaccaucua uaaugggauc ugaugcccuc uucuggugug c             291
```

METHODS FOR GENERATING NEW HAIR FOLLICLES, TREATING BALDNESS, AND HAIR REMOVAL

CROSS-REFERENCE TO RELATED APPLICATIONS

This application is a continuation of U.S. patent application Ser. No. 11/887,104, filed Sep. 25, 2007, now abandoned which is a National Phase Application of PCT International Application No. PCT/US06/11319, filed Mar. 28, 2006, claiming priority to U.S. Provisional Patent Applications 60/665,857 and 60/683,293, filed 29 Mar. 2005 and 23 May 2005, respectively, all which are incorporated by reference herein in their entirety.

FIELD OF INVENTION

The present invention provides methods of treating baldness in a subject and generating new hair follicles, comprising epidermal disruption and administration of a compound that promotes a differentiation of an uncommitted epidermal cell into a hair follicle cell. The present invention also provides methods for hair removal and inducing hair pigmentation.

BACKGROUND OF THE INVENTION

Follicular neogenesis is defined as the generation of new hair follicles (HF) after birth. Humans are born with a full complement of HF, which can change in size and growth characteristics as in early baldness or can ultimately degenerate and disappear as in late stages of baldness or in permanent scarring (cicatricial) alopecias. Therefore, the generation of new HF is desirable in the treatment of common baldness as well as less common hair loss conditions, such as discoid lupus erythematosis, congenital hypotrichosis, lichen planopilaris and other scarring alopecias.

SUMMARY OF THE INVENTION

The present invention provides methods of treating baldness in a subject and generating new hair follicles (HF), comprising epidermal disruption and administration of a compound that promotes a differentiation of an uncommitted epidermal cell into a hair follicle cell. The present invention also provides methods for hair removal and inducing hair pigmentation.

In one embodiment, the present invention provides a method for generating a hair follicle in a scalp, eyebrow, or scarred region of a subject, comprising the steps of (a) disrupting the epidermis of the scalp, eyebrow, or scarred region; and (b) contacting the scalp, eyebrow, or scarred region with a compound that promotes a differentiation of an uncommitted epidermal cell into a hair follicle cell, thereby generating a hair follicle in a scalp, eyebrow, or scarred region of a subject.

In another embodiment, the present invention provides a method for generating a hair follicle in a scalp, eyebrow, or scarred region of a subject, comprising the steps of: (a) disrupting the epidermis of the scalp, eyebrow, or scarred region; and (b) contacting the scalp, eyebrow, or scarred region with a factor that promotes a differentiation of an uncommitted epidermal cell into a hair follicle cell, thereby generating a hair follicle in a scalp, eyebrow, or scarred region of a subject.

In another embodiment, the present invention provides a method for treating baldness in a scalp, eyebrow, or scarred region, comprising the steps of (a) disrupting the epidermis of the scalp, eyebrow, or scarred region; and (b), contacting the scalp, eyebrow, or scarred region with a compound that promotes a differentiation of an uncommitted epidermal cell into a hair follicle (HF) cell, thereby treating baldness in a scalp, eyebrow, or scarred region.

In another embodiment, the present invention provides a method for treating baldness in a scalp, eyebrow, or scarred region, comprising the steps of: (a) disrupting the epidermis of the scalp, eyebrow, or scarred region; and (b) contacting the scalp, eyebrow, or scarred region with a factor that promotes a differentiation of an uncommitted epidermal cell into a HF cell, thereby treating baldness in a scalp, eyebrow, or scarred region. In another embodiment, the baldness is an androgenetic alopecia (AGA)-induced baldness. Each possibility represents a separate embodiment of the present invention.

In another embodiment, the present invention provides a method for removal of an HF from a skin or scalp of a subject, comprising the steps of: (a) disrupting an epidermis of the skin or scalp; and (b) contacting the skin or scalp with either: (i) an EGF protein; (ii) an EGF receptor; (iii) a nucleotide encoding an EGF protein or EGF receptor; or (iv) a compound or factor that activates a EGF protein or EGF receptor, thereby removing an HF from a skin or scalp of a subject.

In another embodiment, the present invention provides a method for increasing a size of a hair follicle in a scalp, eyebrow, or scarred region of a subject, the method comprising the steps of: (a) disrupting an epidermis of the scalp, eyebrow, or scarred region; and (b) contacting the scalp, eyebrow, or scarred region with a compound or factor that promotes a differentiation of an uncommitted epidermal cell into a hair follicle cell, thereby increasing a size of a hair follicle in a scalp, eyebrow, or scarred region of a subject.

In another embodiment, the present invention provides a method for generating a hair follicle in a scalp, eyebrow, or scarred region of a subject, comprising the steps of: (a) disrupting an epidermis of said scalp, eyebrow, or scarred region; and (b) contacting said scalp, eyebrow, or scarred region with a cell selected from (a) a precursor cell that is capable of differentiation into a hair follicle cell; (b) an inductive cell that is capable of inducing differentiation of an uncommitted epidermal cell into a hair follicle cell; or (c) a hair follicle or portion thereof, thereby generating a hair follicle in a scalp, eyebrow, or scarred region of a subject. In another embodiment, step (b) is performed 3-12 days after step (a). Each possibility represents a separate embodiment of the present invention.

In another embodiment, the present invention provides a method for treating an AGA in a scalp, comprising the steps of: (a) disrupting an epidermis of said scalp; and (b) contacting said scalp with a cell selected from (a) a precursor cell that is capable of differentiation into a hair follicle cell; (b) an inductive cell that is capable of inducing differentiation of an uncommitted epidermal cell into a hair follicle cell; or (c) a hair follicle or portion thereof, thereby treating an AGA in a scalp. In another embodiment, step (b) is performed 3-12 days after step (a). Each possibility represents a separate embodiment of the present invention.

BRIEF DESCRIPTION OF THE FIGURES

FIG. 22. Transcripts up-regulated at least 2-fold in activated HF cells, as assessed by dChip analysis. (A). Mean values and standard errors of the up-regulated transcripts in non-activated ("bs-line") and activated ("expt") samples and fold-changes and differences between non-activated and activated values are depicted. (B). Raw data for up-regulated transcripts in non-activated and activated cells. "Ctrl" denotes non-activated and "High-dep" denotes activated cells. (C). Additional information about up-regulated transcripts.

DETAILED DESCRIPTION OF THE INVENTION

Figure 1:
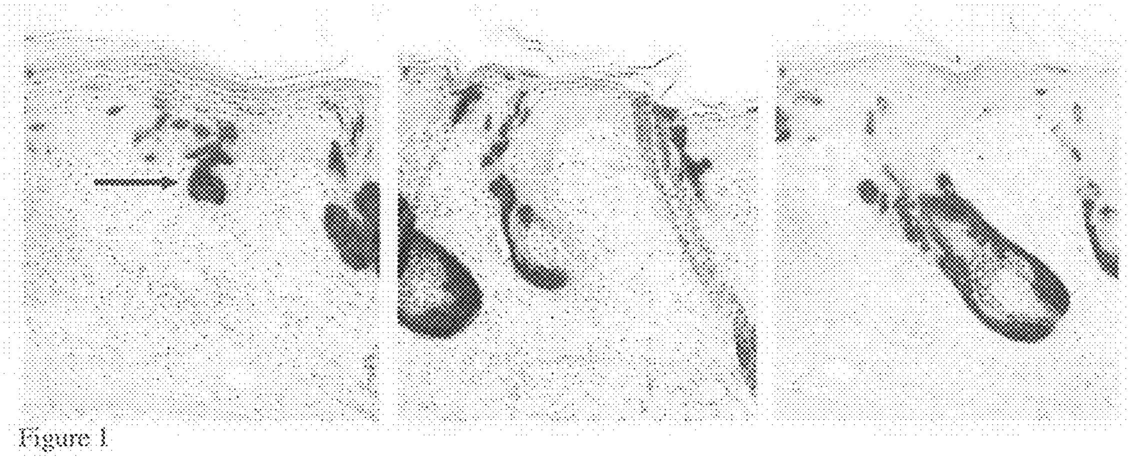
FIG. 1: Epidermal abrasion results in de novo hair follicle (HF) formation. HF at progressive stages of development are depicted in the left, center, and right panels. The arrow in the left panel indicates a hair germ. The dark stained cells are progeny of HF stem cells in the bulge.

The present invention provides methods of treating baldness in a subject and generating new HF, comprising epidermal disruption and administration of a compound that promotes a differentiation of an uncommitted epidermal cell into a hair follicle cell. The present invention also provides methods for hair removal and inducing hair pigmentation.

In one embodiment, the present invention provides a method for generating a hair follicle (HF) in a scalp, eyebrow, or scarred region of a subject, comprising the steps of: (a) disrupting an epidermis of the scalp, eyebrow, or scarred region; and (b) contacting the scalp, eyebrow, or scarred region with a compound that promotes a differentiation of an uncommitted epidermal cell into an HF cell, thereby generating an HF in a scalp, eyebrow, or scarred region of a subject.

In another embodiment, the present invention provides a method for generating an HF in a scalp, eyebrow, or scarred region of a subject, comprising the steps of (a) disrupting an epidermis of the scalp, eyebrow, or scarred region; and (b) contacting the scalp, eyebrow, or scarred region with a factor that promotes a differentiation of an uncommitted epidermal cell into an HF cell, thereby generating an HF in a scalp, eyebrow, or scarred region of a subject.

In another embodiment, the present invention provides a method for generating a new HF in a scalp, eyebrow, or scarred region of a subject, comprising the steps of: (a) disrupting an epidermis of the scalp, eyebrow, or scarred region; and (b) contacting the scalp, eyebrow, or scarred region with a compound or factor that promotes a differentiation of an uncommitted epidermal cell into a hair follicle cell, thereby generating a new HF in a scalp, eyebrow, or scarred region of a subject.

In another embodiment, the present invention provides a method for increasing the number of HF in a scalp, eyebrow, or scarred region of a subject, comprising the steps of: (a) disrupting an epidermis of the scalp, eyebrow, or scarred region; and (b) contacting the scalp, eyebrow, or scarred region with a compound or factor that promotes a differentiation of an uncommitted epidermal cell into an HF cell, thereby increasing the number of HF in a scalp, eyebrow, or scarred region of a subject.

In another embodiment, the present invention provides a use of a compound or factor that promotes a differentiation of an uncommitted epidermal cell into an HF cell, for the preparation of a pharmaceutical composition for use in a method for generating a hair follicle in a scalp, eyebrow, or scarred region of a subject, the method comprising the steps of: (a) disrupting an epidermis of the scalp, eyebrow, or scarred region; and (b) contacting the scalp, eyebrow, or scarred region with the compound or factor.

In another embodiment, the present invention provides a use of a compound or factor that promotes a differentiation of an uncommitted epidermal cell into an HF cell, for the preparation of a pharmaceutical composition for use in a method for treating baldness in a scalp, eyebrow, or scarred region of a subject, the method comprising the steps of: (a) disrupting an epidermis of the scalp, eyebrow, or scarred region; and (b) contacting the scalp, eyebrow, or scarred region with the compound or factor.

In another embodiment, the present invention provides a use of a compound or factor that promotes a differentiation of an uncommitted epidermal cell into an HF cell, for the preparation of a pharmaceutical composition for use in a method for treating AGA in a scalp of a subject, the method comprising the steps of: (a) disrupting an epidermis of the scalp, eyebrow, or scarred region; and (b) contacting the scalp with the compound or factor.

In another embodiment, the present invention provides a method for increasing a size of a hair follicle in a scalp, eyebrow, or scarred region of a subject, the method comprising the steps of: (a) disrupting an epidermis of the scalp, eyebrow, or scarred region; and (b) contacting the scalp, eyebrow, or scarred region with a compound or factor that promotes a differentiation of an uncommitted epidermal cell into an HF cell, thereby increasing a size of a hair follicle in a scalp, eyebrow, or scarred region of a subject. In another embodiment, the factor is an inhibitor of an EGF protein or an EGFR. In another embodiment, the factor is a Hedgehog protein, a nucleotide encoding same or an activator of same. In another embodiment, the factor is an androgen antagonist. In another embodiment, the factor is any other compound or factor that promotes a differentiation of an uncommitted epidermal cell into an HF cell. Each possibility represents a separate embodiment of the present invention.

In another embodiment, the present invention provides a method for generating a hair follicle in a scalp, eyebrow, or scarred region of a subject, comprising the steps of: (a) disrupting an epidermis of said scalp, eyebrow, or scarred region; and (b) contacting said scalp, eyebrow, or scarred region with a cell selected from (a) a precursor cell that is capable of differentiation into a hair follicle cell; (b) an inductive cell that is capable of inducing differentiation of an uncommitted epidermal cell into a hair follicle cell; or (c) a hair follicle or portion thereof, thereby generating a hair follicle in a scalp, eyebrow, or scarred region of a subject. In another embodiment, step (b) is performed 3-12 days after step (a). Each possibility represents a separate embodiment of the present invention.

The precursor cell of methods and compositions of the present invention, is, in another embodiment, a HF stem cell. In another embodiment, the precursor cell is an epidermal cell. In another embodiment, the precursor cell is a dermal papilla cell. In another embodiment, the precursor cell is a connective tissue sheath cell. In another embodiment, the precursor cell is any other type of cell known in the art that is capable of differentiation into a hair follicle cell. Each possibility represents a separate embodiment of the present invention.

In another embodiment, the present invention provides a method for generating a hair follicle in a scalp, eyebrow, or scarred region of a subject, comprising the steps of: (a) disrupting an epidermis of said scalp, eyebrow, or scarred region; and (b) contacting said scalp, eyebrow, or scarred region with a precursor cell that is capable of differentiation into a hair follicle cell, thereby generating a hair follicle in a scalp, eyebrow, or scarred region of a subject.

In another embodiment, the present invention provides a method for treating an AGA in a scalp, comprising the steps of: (a) disrupting an epidermis of said scalp; and (b) contacting said scalp with a cell selected from (a) a precursor cell that is capable of differentiation into a hair follicle cell; (b) an inductive cell that is capable of inducing differentiation of an uncommitted epidermal cell into a hair follicle cell; or (c) a hair follicle or portion thereof, thereby treating an AGA in a scalp. In another embodiment, step (b) is performed 3-12 days after step (a). Each possibility represents a separate embodiment of the present invention.

In another embodiment, the present invention provides a method for treating an AGA in a scalp, comprising the steps of: (a) disrupting an epidermis of said scalp; and (b) contacting said scalp with a precursor cell that is capable of differentiation into a hair follicle cell, thereby treating an AGA in a scalp.

In another embodiment, the inductive cell is a mesenchymal cell. In another embodiment, the inductive cell is any other type of inductive cell enumerated herein. In another embodiment, the inductive cell is any other type of inductive cell known in the art. Each possibility represents a separate embodiment of the present invention.

"Contacting" as used herein refers, in another embodiment, to bringing the scalp, eyebrow, etc, into to contact with the compound, factor, cell, etc. In another embodiment, the term refers to embedding the compound, factor, cell, etc into the scalp, eyebrow, etc. In another embodiment, the term refers to injecting the compound, factor, cell, etc into the scalp, eyebrow, etc. In another embodiment, term refers to any other type of contacting known in the art. Each possibility represents a separate embodiment of the present invention.

"Promotes a differentiation" refers, in another embodiment, to the act of increasing the percentage of cells that will differentiate as indicated. In another embodiment, the term refers to increasing the number of cells per unit area of skin that will differentiate. In another embodiment, the promoter of differentiation is active in the milieu of the skin. Each possibility represents a separate embodiment of the present invention.

"Uncommitted epidermal cell" refers, in another embodiment, to an epidermal stem cell. In another embodiment, the epidermal cell is a bulge cell. In another embodiment, the epidermal cell is a bulge-derived cell. In another embodiment, the epidermal cell is any other type of cell known in the art that can be induced to differentiate into an HF cell.

The "HF cell" that results from the diffentiation is, in another embodiment, an HF stem cell. In another embodiment, the HF cell is a dermal papilla cell. In another embodiment, the HF cell is a bulb cell. In another embodiment, the HF cell is a matrix cell. In another embodiment, the HF cell is a hair shaft cell. In another embodiment, the HF cell is an inner root sheath cell. In another embodiment, the HF cell is an outer root sheath cell. In another embodiment, the HF cell is a melanocyte stem cell. In another embodiment, the HF cell is a melanocyte. Each type of uncommitted epidermal cell and HF cell represents a separate embodiment of the present invention.

In another embodiment, the present invention provides a method for treating baldness in a scalp, eyebrow, or scarred region, comprising the steps of: (a) disrupting an epidermis of the scalp, eyebrow, or scarred region; and (b) contacting the scalp, eyebrow, or scarred region with a compound that promotes a differentiation of an uncommitted epidermal cell into a hair follicle (HF) cell, thereby treating baldness in a scalp, eyebrow, or scarred region. In another embodiment, the baldness is an androgenetic alopecia (AGA)-induced baldness. Each possibility represents a separate embodiment of the present invention.

In another embodiment, the present invention provides a method for treating baldness in a scalp, eyebrow, or scarred region, comprising the steps of: (a) disrupting an epidermis of the scalp, eyebrow, or scarred region; and (b) contacting the scalp, eyebrow, or scarred region with a factor that promotes a differentiation of an uncommitted epidermal cell into a HF cell, thereby treating baldness in a scalp, eyebrow, or scarred region. In another embodiment, the baldness is an androgenetic alopecia (AGA)-induced baldness. Each possibility represents a separate embodiment of the present invention.

In another embodiment, the compound or factor that promotes a differentiation of an uncommitted epidermal cell into a HF cell is administered in a solution. In another embodiment, the compound or factor is administered in a cream. In another embodiment, the compound or factor is administered in an ointment. In another embodiment, the compound or factor is administered in a slow release formulation. In another embodiment, the compound or factor is administered in a liposome encapsulated formulation. In another embodiment, the compound or factor is directly injected. In another embodiment, the compound or factor is administered by any other method known in the art. Each possibility represents a separate embodiment of the present invention.

The compound or factor that promotes a differentiation of an uncommitted epidermal cell into a HF cell is, in another embodiment, an inhibitor of an Epidermal Growth Factor (EGF). In another embodiment, the compound or factor is an inhibitor of an EGF receptor. Each possibility represents a separate embodiment of the present invention.

As provided herein (Example 11), activating one or more pathways in which EGF is involved (by injection of EGF) blocks the formation of HF. Thus, antagonizing the pathway increases HF formation, as demonstrated in Example 12.

In another embodiment, the inhibitor of an EGF or an EGF receptor is panitumumab. In another embodiment, the inhibitor is AG1478. In another embodiment, the inhibitor is nimotuzumab. In another embodiment, the inhibitor is an antibody that binds EGF or EGFR. In another embodiment, the inhibitor is HuMax-EGFR® (Genmab, Copenhagen, Denmark). In another embodiment, the inhibitor is cetuximab. In another embodiment, the inhibitor is IMC 11F8. In another embodiment, the inhibitor is matuzumab. In another embodiment, the inhibitor is SC 100. In another embodiment, the inhibitor is ALT 110. In another embodiment, the inhibitor is PX 1032. In another embodiment, the inhibitor is BMS 599626. In another embodiment, the inhibitor is MDX 214. In another embodiment, the inhibitor is PX 1041. In another embodiment, the inhibitor is any other inhibitor of an EGF or an EGF receptor known in the art. Each possibility represents a separate embodiment of the present invention.

In another embodiment, the compound or factor that promotes a differentiation of an uncommitted epidermal cell into a HF cell is an inhibitor of a tyrosine kinase activity of an EGF receptor. In another embodiment, the inhibitor is gefitinib. In another embodiment, the inhibitor is erlotinib. In another embodiment, the inhibitor is canertinib. In another embodiment, the inhibitor is leflunomide. In another embodiment, the inhibitor is A77 1726. In another embodiment, the inhibitor is pelitinib. In another embodiment, the inhibitor is ZD 1839. In another embodiment, the inhibitor is CL 387785. In another embodiment, the inhibitor is EKI 785. In another embodiment, the inhibitor is vandetanib. In another embodiment, the inhibitor is any other inhibitor of a tyrosine kinase activity of an EGF receptor known in the art. Each possibility represents a separate embodiment of the present invention.

In another embodiment, the EGF or EGFR antagonist is a carboxypeptidase inhibitor from potato (PCI) protein or a homologue, fragment or mimetic thereof. In another embodiment, the EGF or EGFR antagonist is a sprouty protein or a homologue, fragment or mimetic thereof. In another embodiment, the EGF or EGFR antagonist is an Argos protein or a homologue, fragment or mimetic thereof. In another embodiment, the EGF or EGFR antagonist is a lefty protein or a homologue, fragment or mimetic thereof. In another embodiment, the EGF or EGFR antagonist is an antibody that recognizes EGF or EGFR, or a fragment or mimetic thereof. In another embodiment, the EGF or EGFR antagonist is small molecule inhibitor that binds and reduces the activity of EGF or EGFR. In another embodiment, the EGF or EGFR antagonist is CRM197. In another embodiment, the EGF or EGFR antagonist is IMC-C225 (ImClone Systems, New York, N.Y.). In another embodiment, the EGF or EGFR antagonist is any other antagonist of EGF or EGFR known in the art. Each possibility represents a separate embodiment of the present invention.

In another embodiment, the present invention provides a use of an inhibitor of an EGF protein or an EGF receptor for the preparation of a pharmaceutical composition for use in a method for generating a hair follicle in a scalp, eyebrow, or scarred region of a subject, the method comprising the steps of: (a) disrupting an epidermis of the scalp, eyebrow, or scarred region; and (b) contacting the scalp, eyebrow, or scarred region with the inhibitor of an EGF protein or an EGF receptor.

In another embodiment, the present invention provides a use of an inhibitor of an EGF protein or an EGF receptor for the preparation of a pharmaceutical composition for use in a method for treating baldness in a scalp, eyebrow, or scarred region of a subject, the method comprising the steps of: (a) disrupting an epidermis of the scalp, eyebrow, or scarred region; and (b) contacting the scalp, eyebrow, or scarred region with the inhibitor of an EGF protein or an EGF receptor.

In another embodiment, the present invention provides a use of an inhibitor of an EGF protein or an EGF receptor for the preparation of a pharmaceutical composition for use in a method for treating AGA in a scalp of a subject, the method comprising the steps of: (a) disrupting an epidermis of the scalp, eyebrow, or scarred region; and (b) contacting the scalp with the inhibitor of an EGF protein or an EGF receptor.

In another embodiment, the compound or factor that promotes a differentiation of an uncommitted epidermal cell into a HF cell is a β-catenin protein. In another embodiment, the compound or factor is a nucleotide that encodes a β-catenin protein. In another embodiment, the compound or factor is an activator of a β-catenin protein. In another embodiment, the compound or factor is an inhibitor of a protein that suppresses an activity of the β-catenin protein. Each possibility represents a separate embodiment of the present invention.

In another embodiment, the present invention provides a use of (a) a β-catenin protein; (b) a nucleotide encoding a β-catenin protein; or (c) a compound or factor that activates a β-catenin protein, for the preparation of a pharmaceutical composition for use in a method for generating a hair follicle in a scalp, eyebrow, or scarred region of a subject, the method comprising the steps of: (a) disrupting an epidermis of the scalp, eyebrow, or scarred region; and (b) contacting the scalp, eyebrow, or scarred region with the β-catenin protein, nucleotide, compound or factor.

In another embodiment, the present invention provides a use of (a) a β-catenin protein; (b) a nucleotide encoding a β-catenin protein; or (c) a compound or factor that activates a β-catenin protein, for the preparation of a pharmaceutical composition for use in a method for treating baldness in a scalp, eyebrow, or scarred region of a subject, the method comprising the steps of: (a) disrupting an epidermis of the scalp, eyebrow, or scarred region; and (b) contacting the scalp, eyebrow, or scarred region with the β-catenin protein, nucleotide, compound or factor.

In another embodiment, the present invention provides a use of (a) a β-catenin protein; (b) a nucleotide encoding a β-catenin protein; or (c) a compound or factor that activates a β-catenin protein, for the preparation of a pharmaceutical composition for use in a method for treating AGA in a scalp of a subject, the method comprising the steps of: (a) disrupting an epidermis of the scalp, eyebrow, or scarred region; and (b) contacting the scalp with the β-catenin protein, nucleotide, compound or factor.

In another embodiment, the compound or factor that promotes a differentiation of an uncommitted epidermal cell into a HF cell is a fibroblast growth factor (FGF) protein. In another embodiment, the compound or factor is a nucleotide that encodes an FGF protein. In another embodiment, the compound or factor is an FGF receptor. In another embodiment, the compound or factor is a nucleotide that encodes an FGF receptor. In another embodiment, the compound or factor is an activator of an FGF protein. In another embodiment, the compound or factor is an activator of FGF receptor. In another embodiment, the compound or factor is an inhibitor of a protein that suppresses an activity of the FGF protein or FGF receptor. In another embodiment, the protein that is inhibited is an FGF binding protein. In another embodiment, the protein that is inhibited is FGF-bp1. Each possibility represents a separate embodiment of the present invention.

Is provided herein, FGF and its receptor are upregulated, under the conditions utilized herein, upon HF stem cell differentiation (Example 9). Moreover, FGF-bp1 is down-regulated, under the conditions utilized herein, upon HF stem cell differentiation. Thus, FGF and its receptor promote differentiation of uncommitted epidermal cells into HF cells.

In another embodiment, the compound or factor that promotes a differentiation of an uncommitted epidermal cell into a HF cell is an ectodysplasin protein (referred to, in another embodiment, as "eda"; in another embodiment, as "ectodermodysplasin protein.") In another embodiment, the ectodysplasin protein is Eda-A1. In another embodiment, the compound or factor is an ectodysplasin receptor (referred to, in another embodiment, as "edar"). In another embodiment, the compound or factor is an activator of an ectodysplasin protein. In another embodiment, the compound or factor is an activator of an ectodysplasin receptor. In another embodiment, the compound or factor is an inhibitor of a protein that suppresses an activity of the ectodysplasin protein or ectodysplasin receptor. Each possibility represents a separate embodiment of the present invention.

In another embodiment, the eda protein of methods and compositions of the present invention has the sequence:
MGYPEVERRELLPAAAPRERGSQGCGCGGAPAR-
AGEGNSCLLFLGFFGLSLALHLLTLCC YLELRSELR-
RERGAESRLGGSGTPGTSGTLSSLGGLDPDSPITSHL-
GQPSPKQQPLEPGEAAL
HSDSQDGHQMALLNFFFPDEKPYSEEESRRVR-
RNKRSKSNEGADGPVKNKKKGKKAGPP GPNGPPG-
PPGPPGPQGPPGIPGIPGIPGTTVMGPPGPPGPPGPQG-
PPGLQGPSGAADKAGTR
ENQPAVVHLQGQGSAIQVKNDLSGGVLNDWSRITM-
NPKVFKLHPRSGELEVLVDGTYFIY SQVEVYYIN-
FTDFASYEVVVDEKCPFLQCTRSIETGKTNYNT-
CYTAGVCLLKARQKIAVKM
VHADISINMSKHTTFFGAIRLGEAPAS (GenBank Accession No: NM_001399; SEQ ID No: 274). In another embodiment, the eda protein has a sequence selected from the sequences set forth in GenBank entries NM_001005609, NM_001005610, NM_001005611, NM_001005612, NM_001005613, NM_001005614, NM_001005615, AF040628, AF061194, AF061193, AF061192, AF061191, AF061190, AF061189, and AF060999. In another embodiment, the eda protein is encoded by a nucleic acid molecule having a sequence set forth in the one of the above GenBank entries. In another embodiment, a biologically active fragment of an Eda protein is utilized in a method of the present invention. Each possibility represents a separate embodiment of the present invention.

In another embodiment, the edar protein of methods and compositions of the present invention has the sequence:

MAHVGDCTQTPWLPVLVVSLMCSARAEYSNC-GENEYYNQTTGLCQECPPCGPGEEPYLS CGYGTKD-EDYGCVPCPAEKFSKGGYQICRRHKDCEGFFRATV-LTPGDMENDAECGPCLP GYYMLENRPRNIYGMVCYSCLLAPPNTKECVGATS-GASANFPGTSGSSTLSPFQHAHKELS GQGHLATALI-IAMSTIFIMAIAIVLIIMFYILKTKPSAPACCTSHPGKS-VEAQVSKDEEKKEAP DNVVMFSEKDEFEKLTATPAKPTKSENDASS-ENEQLLSRSVDSDEEPAPDKQGSPELCLLS LVHLAREKSATSNKSAGIQSRRKKILDVYANVCGV-VEGLSPTELPFDCLEKTSRMLSSTYN SEKCAVVKT-WRHLAESFGLKRDEIGGMTDGMQLFDRISTAGYSIP-ELLTKLVQIERLDAVES LCADILEWAGVVPPASQPHAAS (GenBank Accession No: BC093872; SEQ ID No: 275). In another embodiment, the edar protein has a sequence selected from the sequences set forth in GenBank entries BC093870; BC034919; NM_021783; NM_022336; AY152724; AF298812; AH008077; AF130996; AF130988. In another embodiment, the edar protein is encoded by a nucleic acid molecule having a sequence set forth in the one of the above GenBank entries. In another embodiment, a biologically active fragment of an Edar protein is utilized in a method of the present invention. Each possibility represents a separate embodiment of the present invention.

In another embodiment, the compound or factor that promotes a differentiation of an uncommitted epidermal cell into a HF cell is a Noggin protein. In another embodiment, the compound or factor is a nucleotide encoding a Noggin protein. In another embodiment, the compound or factor is an activator of a Noggin protein. In another embodiment, the compound or factor is an inhibitor of a protein that suppresses an activity of the Noggin protein. Each possibility represents a separate embodiment of the present invention.

In another embodiment, the Noggin protein of methods and compositions of the present invention has the sequence: MERCPSLGVTLYALVVVLGLRATPAGGQHYLHIRP-APSDNLPLVDLIEHPDPIFDPKEKDLNE TLLRSLLG-GHYDPGFMATSPPEDRPGGGGGAAGGAEDLAEL-DQLLRQRPSGAMPSEIKGLE FSEGLAQGKKQRLSKKLRRKLQMWLWSQTFCPV-LYAWNDLGSRFWPRYVKVGSCFSKRS CSVPEGM-VCKPSKSVHLTVLRWRCQRRGGQRCGWIPIQYPI-ISECKCSC (GenBank Accession No: NM_005450; SEQ ID No: 276). In another embodiment, the Noggin protein has a sequence selected from the sequences set forth in GenBank entries BC034027 and U31202. In another embodiment, the Noggin protein is encoded by a nucleic acid molecule having a sequence set forth in the one of the above GenBank entries. In another embodiment, a biologically active fragment of a Noggin protein is utilized in a method of the present invention. Each possibility represents a separate embodiment of the present invention.

In another embodiment, the compound or factor that promotes a differentiation of an uncommitted epidermal cell into a HF cell is a Hedgehog protein. In another embodiment, the compound or factor is a nucleotide encoding a Hedgehog protein. In another embodiment, the compound or factor is an activator of a Hedgehog protein. In another embodiment, the compound or factor is a sonic Hedgehog protein. In another embodiment, the compound or factor is a nucleotide encoding a sonic Hedgehog protein. In another embodiment, the compound or factor is an activator of a sonic Hedgehog protein. Each possibility represents a separate embodiment of the present invention.

In another embodiment, the Hedgehog protein of methods and compositions of the present invention has the sequence set forth in GenBank Accession No. NM_000193. In another embodiment, the Hedgehog protein has a sequence selected from those set forth in GenBank entries L38518 and NP_000184. In another embodiment, the Hedgehog protein has any other Hedgehog sequence known in the art. In another embodiment, the Hedgehog protein has any other sonic Hedgehog sequence known in the art. Each possibility represents a separate embodiment of the present invention.

In another embodiment, the compound or factor that promotes a differentiation of an uncommitted epidermal cell into a HF cell is a Transforming Growth Factor (TGF)-beta1 protein. In another embodiment, the compound or factor is a nucleotide encoding a TGF-beta1 protein. In another embodiment, the compound or factor is an activator of a TGF-beta1 protein. In another embodiment, the compound or factor is a TGF-beta3 protein. In another embodiment, the compound or factor is a nucleotide encoding a TGF-beta3 protein. In another embodiment, the compound or factor is an activator of a TGF-beta3 protein. In another embodiment, the compound or factor is an antagonist of a TGF-beta1 protein. In another embodiment, the compound or factor is an antagonist of a TGF-beta3 protein. Each possibility represents a separate embodiment of the present invention.

In another embodiment, the TGF-beta1 protein of methods and compositions of the present invention has the sequence set forth in GenBank Accession No. BC000125. In another embodiment, the Hedgehog protein has a sequence selected from those set forth in GenBank entries BC001180, BC022242, and NM_000660. In another embodiment, the TGF-beta1 protein has any other TGF-beta1 sequence known in the art. Each possibility represents a separate embodiment of the present invention.

In another embodiment, the TGF-beta3 protein of methods and compositions of the present invention has the sequence set forth in GenBank Accession No. J03241. In another embodiment, the Hedgehog protein has a sequence selected from those set forth in GenBank entries NM_003239, BC018503, BT007287 and X14149. In another embodiment, the TGF-beta3 protein has any other TGF-beta3 sequence known in the art. Each possibility represents a separate embodiment of the present invention.

In another embodiment, the compound or factor that promotes a differentiation of an uncommitted epidermal cell into a HF cell acts directly on the uncommitted epidermal cell. In another embodiment, the compound or factor acts on the uncommitted epidermal cell via a mesenchymal cell. Each possibility represents a separate embodiment of the present invention.

In another embodiment, the mesenchymal cell is a dermal condensate cell. In another embodiment, the mesenchymal cell is a DP cell. In another embodiment, the mesenchymal cell is another cell type or differentiation stage in the dermal condensate-DP lineage. In another embodiment, the mesenchymal cell is any other type of mesenchymal cell known in the art. Each possibility represents a separate embodiment of the present invention.

The EGFR of methods and compositions of the present invention has, in another embodiment, the sequence: MRPSGTAGAALLALLAALCPASRALEEKKVC-QGTSNKLTQLGTFEDHFLSLQRMFNNCEV VLGNLE-ITYVQRNYDLSFLKTIQEVAGYVLIALNTVERIPLEN-LQIIRGNMYYENSYALAVL SNYDANKTGLKELPMRNLQEILHGAVRFSNNPALCN-VESIQWRDIVSSDFLSNMSMDFQN HLGSCQKCDP-SCPNGSCWGAGEENCQKLTKIICAQQCSGRCRGK- SPSDCCHNQCAAGCTG PRESDCLVCRKFRDEATCKDTCPPLMLYNPTTYQMD-VNPEGKYSFGATCVKKCPRNYVV TDHGSCVRAC-GADSYEMEEDGVRKCKKCEGPCRKVCNGI-GIGEFKDSLSINATNIKHFKN CTSISGDLHILPVAFRGDSFTHTPPLDPQELDILKT-VKEITGFLLIQAWPENRTDLHAFENLEII RGRTKQH-GQFSLAVVSLNITSLGLRSLKCEISDGDVIISGNKNL-CYANTINWKKLFGTSGQKT KIISNRGENSCKATGQVCHALCSPEGCWGPEPRD-CVSCRNVSRGRECVDKCNLLEGEPREF VENSECI-QCHPECLPQAMNITCTGRGPDNCIQCAHYIDGPH-CVKTCPAGVMGENNTLVWK YADAGHVCHLCHPNCTYGCTGPGLEGCPTNGPKIP-SIATGMVGALLLLLVVALGIGLFMR RRHIVRKCRTL-RRLLQERELVEPLTPSGEAPNQALLRILKETEFKKIKV-LGSGAFGTVYKGLW IPEGEKVKIPVAIKELREATSPKANKEILDEAYVMAS-VDNPHVCRLLGICLTSTVQLITQLMP FGCLLDYVRE-HKDNIGSQYLLNWCVQIAKGMNYLEDRRLVHRD-LAARNVLVKTPQHVKI TDFGLAKLLGAEEKEYHAEGGKVPIKWMALE-SILHRIYTHQSDVWSYGVTVWELMTFGS KPYDGIPA-SEISSILEKGERLPQPPICTIDVYMIMVKCWMIDAD-SRPKFRELIIEFSKMARDPQ RYLVIQGDERMHLPSPTDSNFYRALMDEEDMDDV-VDADEYLIPQQGFFSSPSTSRTPLLSS LSATSNNST-VACIDRNGLQSCPIKEDSFLQRYSSDPTGALTEDSID-DTFLPVPEYINQSVPKR PAGSVQNPVYHNQPLNPAPSRDPHYQDPHSTAVGN-PEYLNTVQPTCVNSTFDSPAHWAQ KGSHQISLDN-PDYQQDFFPKEAKPNGIFKGSTAENAEYLRVAPQSSE-FIGA (GenBank Accession No: NM_005228; SEQ ID No: 277). In another embodiment, the EGFR has a sequence selected from the sequences set forth in GenBank entries NM_201282, NM_201283, NM_201284, BC094761, AF288738, AY588246, AY573061, X17054, AF125253, U48722, K03193, and AY698024. In another embodiment, the EGFR is encoded by a nucleic acid molecule having a sequence set forth in the one of the above GenBank entries. In another embodiment, a biologically active fragment of an EGFR is utilized in a method of the present invention. Each possibility represents a separate embodiment of the present invention.

The EGF of methods and compositions of the present invention has, in another embodiment, the sequence: MLLTLIILLPVVSKFSFVSLSAPQHWSCPEGTLA-GNGNSTCVGPAPFLIFSHGNSIFRIDTEGTN YEQLV-VDAGVSVIMDFHYNEKRIYWVDLERQLLQRVFLNG-SRQERVCNIEKNVSGMAINW INEEVIWSNQQEGIITVTDMKGNNSHILLSALKYPAN-VAVDPVERFIFWSSEVAGSLYRADL DGVGVKALLET-SEKITAVSLDVLDKRLFWIQYNREGSNSLICSCDY-DGGSVHISKHPTQHNL FAMSLFGDRIFYSTWKMKTIWIANKHTGKDMVRIN-LHSSFVPLGELKVVHPLAQPKAEDDT WEPEQKLCK-LRKGNCSSTVCGQDLQSHLCMCAEG-YALSRDRKYCEDVNECAFWNHGCTL GCKNTPGSYYCTCPVGFVLLPDGKRCHQLVSCPRN-VSECSHDCVLTSEGPLCFCPEGSVLER DGKTCSGC-SSPDNGGCSQLCVPLSPVSWECDCFPGY-DLQLDEKSCAASGPQPFLLFANSQDI RHMHFDGTDYGTLLSQQMGMVYALDHDPVENKIY-FAHTALKWIERANMDGSQRERLIEE GVD-VPEGLAVDWIGRRFYWTDRGKSLIGRSDLNG-KRSKIITKENISQPRGIAVHPMAKRLFW TDTGINPRIESSSLQGLGRLVIASSDLIWPSGITIDFLT- DKLYWCDAKQSVIEMANLDGSKRRR LTQNDVGHP-FAVAVFEDYVWFSDWAMPSVIRVNKRTGKDRVR-LQGSMLKPSSLVVVHPL AKPGADPCLYQNGGCEHICKKRLGTAWCSCREGFM-KASDGKTCLALDGHQLLAGGEVDL KNQVTPLDIL-SKTRVSEDNITESQHMLVAEIMVSDQDDCAPVGCSM-YARCISEGEDATCQC LKGFAGDGKLCSDIDECEMGVPVCPPASSKCINTEG-GYVCRCSEGYQGDGIHCLDIDECQLG VHSCGENA-SCTNTEGGYTCMCAGRLSEPGLICPDSTPPPHLRED-DHHYSVRNSDSECPLSHD GYCLHDGVCMYIEALDKYACNCVVGYIGERC-QYRDLKWWELRHAGHGQQQKVIVVAVC VVV-LVMLLLLSLWGAHYYRTQKLLSKNPKNPYEESSRD-VRSRRPADTEDGMSSCPQPWFV VIKEHQDLKNG-GQPVAGEDGQAADGSMQPTSWRQEPQLCGMGTE-QGCWIPVSSDKGSCP QVMERSFHMPSYGTQTLEG-GVEKPHSLLSANPLWQQRALDPPHQMELTQ (GenBank Accession No: NM_001963; SEQ ID No: 278). In another embodiment, the EGF has a sequence selected from the sequences set forth in GenBank entries BC093731, AY548762, and X04571. In another embodiment, the EGF is encoded by a nucleic acid molecule having a sequence set forth in the one of the above GenBank entries. In another embodiment, a biologically active fragment of an EGF is utilized in a method of the present invention. Each possibility represents a separate embodiment of the present invention.

The beta-catenin protein of methods and compositions of the present invention has, in another embodiment, the sequence: MATQADLMELDMAMEPDRKAAVSHWQQQSYLDS-GIHSGATTTAPSLSGKGNPEEEDVDT SQVLY-EWEQGFSQSFTQEQVADIDGQYAMTRAQRVRAAMF-PETLDEGMQIPSTQFDAAHP TNVQRLAEPSQMLKHAVVNLINYQDDAELATRAI-PELTKLLNDEDQVVVNKAAVMVHQLS KKEAS-RHAIMRSPQMVSAIVRTMQNTND-VETARCTAGTLHNLSHHREGLLAIFKSGGIPAL VKMLGSPVDSVLFYAITTLHNLLLHQEGAKMAVR-LAGGLQKMVALLNKTNVKFLAITTDC LQILAYGN-QESKLIILASGGPQALVNIMRTYTYEKLLWTTSRVLK-VLSVCSSNKPAIVEAGG MQALGLHLTDPSQRLVQNCLWTLRNLSDAATKQEG-MEGLLGTLVQLLGSDDINVVTCAAG ILSNLTCN-NYKNKMMVCQVGGIEALVRTVLRAGDREDITEPA-ICALRHLTSRHQEAEMAQN AVRLHYGLPVVVKLLHPPSHWPLIKATVGLIRNLAL-CPANHAPLREQGAIPRLVQLLVRAHQ DTQRRTSMG-GTQQQFVEGVRMEEIVEGCTGALHILARDVHNRIV-IRGLNTIPLFVQLLYSHE NIQRVAAGVLCELAQDKEAAEAIEAEGATAPL-TELLHSRNEGVATYAAAVLFRMSEDKPQD YKKRLS-VELTSSLFRTEPMAWNETADLGLDIGAQGE-PLGYRQDDPSYRSFHSGGYGQDALG MDPMMEHEMGGHHPGADYPVDGLPDLGHAQDLM-DGLPPGDSNQLAWFDTDL (GenBank Accession No: NM_001904; SEQ ID No: 279). In another embodiment, the beta-catenin protein has a sequence selected from the sequences set forth in GenBank entries BC058926, X87838, AF130085, AB062292, Z19054, and NP_001895. In another embodiment, the beta-catenin protein is encoded by a nucleic acid molecule having a sequence set forth in the one of the above GenBank entries. In another embodiment, a biologically active fragment of a beta-catenin protein is utilized in a method of the present invention. Each possibility represents a separate embodiment of the present invention.

The Wnt protein of methods and compositions of the present invention has, in another embodiment, the sequence: MNRKARRCLGHLFLSLGMVYLRIGGFSSVVALGASIICNKTGLAPRQRAICQSRPDAIIVIGE GSQMGLDECQFQFRNGRWNCSALGERTVFGKELKVGSREAAFTYAIIAAGVAHAITAACT QGNLSDCGCDKEKQGQYHRDEGWKWGGCSADIRYGIGFAKVFVDAREIKQNARTLMNLH NNEAGRKILEENMKLECKCHGVSGSCTTKTCWTTLPQFRELGYVLKDKYNEAVHVEPVRA SRNKRPTFLKIKKPLSYRKPMDTDLVYIEKSPNYCEEDPVTGSVGTQGRACNKTAPQASGC DLMCCGRGYNTHQYARVWQCNCKFHWCCYVKCNTCSERTEMYTCK (GenBank Accession No: BC008811; SEQ ID No: 280). In another embodiment, the Wnt protein has a sequence selected from the sequences set forth in GenBank entries NM_004625, D83175, U53476, and NP_004616. In another embodiment, the Wnt protein is a Wnt7 protein. In another embodiment, the Wnt protein is a Wnt7a protein. In another embodiment, the Wnt protein is Wnt1 protein. In another embodiment, the Wnt protein is a Wnt3 protein. In another embodiment, the Wnt protein is a Wnt3a protein. In another embodiment, the Wnt protein is a Wnt10 protein. In another embodiment, the Wnt protein is a Wnt10a protein. In another embodiment, the Wnt protein is a Wnt10b protein. In another embodiment, the Wnt protein is encoded by a nucleic acid molecule having a sequence set forth in the one of the above GenBank entries. In another embodiment, a biologically active fragment of a Wnt protein is utilized in a method of the present invention. In another embodiment, a biologically active fragment of a Wnt7 protein is utilized in a method of the present invention. In another embodiment, a biologically active fragment of a Wnt7a protein is utilized in a method of the present invention. Each possibility represents a separate embodiment of the present invention.

In another embodiment, the compound or factor that promotes a differentiation of an uncommitted epidermal cell into a HF cell is a protein encoded by a ribonucleic acid (RNA) molecule having a sequence selected from the sequences set forth in SEQ ID No: 1-232. In another embodiment, the compound or factor is an RNA molecule having a sequence selected from SEQ ID No: 1-232. In another embodiment, the RNA molecule is homologous to a sequence selected from SEQ ID No: 1-232. In another embodiment, the RNA molecule is an isoform of a sequence selected from SEQ ID No: 1-232. In another embodiment, the compound or factor increases an activity of a protein encoded by an RNA molecule having a sequence selected from SEQ ID No: 1-232. In another embodiment, the compound or factor increases an expression or level of a protein encoded by an RNA molecule having a sequence selected from SEQ ID No: 1-232. Each possibility represents a separate embodiment of the present invention.

As provided herein, the transcripts depicted in Table 3 (Example 8; SEQ ID No: 1-232), the proteins they encode, and the pathways in which the proteins participate contribute significantly to HF stem cell activation. Accordingly, under the conditions utilized herein, anagen can be induced by activation of these transcripts, proteins, and pathways. Activation of the transcripts, proteins, and pathways depicted in Table 3 is thus a method for enhancing EDIHN. In another embodiment, activation of these transcripts, proteins, and pathways represents a method for enhancing hair growth in a subject.

In another embodiment, the compound or factor that promotes a differentiation of an uncommitted epidermal cell into a HF cell is a protein encoded by an RNA molecule having a sequence selected from the sequences set forth in SEQ ID No: 233-257. In another embodiment, the compound or factor is an RNA molecule having a sequence selected from SEQ ID No: 233-257. In another embodiment, the RNA molecule is homologous to a sequence selected from SEQ ID No: 233-257. In another embodiment, the RNA molecule is an isoform of a sequence selected from SEQ ID No: 233-257. In another embodiment, the compound or factor increases an activity of a protein encoded by an RNA molecule having a sequence selected from SEQ ID No: 233-257. In another embodiment, the compound or factor increases an expression or level of a protein encoded by an RNA molecule having a sequence selected from SEQ ID No: 233-257. Each possibility represents a separate embodiment of the present invention.

As provided herein, the transcripts depicted in Table 4 (Example 9; SEQ ID No: 233-257), the proteins they encode, and the pathways in which the proteins participate, contribute significantly, under the conditions utilized herein, to induction of epidermal cells to differentiate into HF stem cells. Activation of the transcripts, proteins, and pathways depicted in Table 4 is thus a method for enhancing EDIHN. In another embodiment, activation of these transcripts, proteins, and pathways represents a method for enhancing hair growth in a subject.

In another embodiment, the compound or factor that promotes a differentiation of an uncommitted epidermal cell into a HF cell is a compound or factor that decreases an activity of a protein encoded by an RNA molecule having a sequence selected from the sequences set forth in SEQ ID No: 258-273. In another embodiment, the compound or factor decreases an expression or level of a protein encoded by an RNA molecule having a sequence selected from SEQ ID No: 258-273. Each possibility represents a separate embodiment of the present invention.

As demonstrated by findings of the present invention, the transcripts depicted in Table 5 (Example 9; SEQ ID No: 258-273), the proteins they encode, and the pathways in which the proteins participate, contribute significantly, under the conditions utilized herein, to preventing induction of epidermal cells to differentiate into HF stem cells. Inhibition of the transcripts, proteins, and pathways depicted in Table 5 is thus a method for enhancing EDIHN. In another embodiment, inhibition of these transcripts, proteins, and pathways represents a method for induction of hair growth in a subject.

In one embodiment, the compound that modulates a protein encoded by an RNA molecule having a sequence selected from the sequences set forth in SEQ ID No: 233-273 or the nucleic acid encoding same is administered before the compound that modulates a protein encoded by an RNA molecule having a sequence selected from the sequences set forth in SEQ ID No: 1-232 or the nucleic acid encoding same. In another embodiment, the two compounds are administered simultaneously. Each possibility represents a separate embodiment of the present invention.

In one embodiment, a protein encoded by an RNA sequence selected from SEQ ID No: 1-273, or a compound that modulates the protein, is administered before other proteins encoded by same or compounds that modulate them, in order to further enhance their effect in generating an HF or stimulating hair growth. In another embodiment, the wnt pathway is stimulated before the hedgehog pathway. In another embodiment, the two pathways are stimulated in an overlapping fashion. In another embodiment, the two pathways are stimulated simultaneously. Each possibility represents a separate embodiment of the present invention.

In another embodiment, activating or decreasing expression of an RNA transcript in methods of the present invention occurs via a transcription mechanism (e.g. activation of expression of the RNA). In another embodiment, activating or decreasing expression of the RNA transcript occurs via a translational mechanism. In another embodiment, activating or decreasing expression of the RNA transcript occurs via a post-translational mechanism. Each possibility represents a separate embodiment of the present invention.

In another embodiment, the nucleic acid molecule utilized in methods of the present invention is a deoxyribonucleic acid (DNA) molecule that encodes an RNA molecule having a sequence selected from the sequences set forth in the present invention.

In one embodiment, an RNA molecule of the present invention encodes a protein that plays a role in HF regeneration. In another embodiment, the RNA molecule is itself catalytically active, e.g., a ribozyme, etc. Each possibility represents a separate embodiment of the present invention.

In another embodiment, the compound or factor that promotes a differentiation of an uncommitted epidermal cell into a HF cell is a compound or factor that promotes placodal cell fate. As provided herein, factors that promote placodal cell fate enhance EDIHN, as exemplified in the Examples herein. In another embodiment, the compound or factor acts at the placode stage of HF development.

In another embodiment, the compound or factor inhibits a biological factor that inhibits a differentiation of an uncommitted epithelial cell into an HF cell.

In another embodiment of methods and compositions of the present invention, a composition comprising one of the above compounds or factors is administered. Each of the above types of compounds, factors, and compositions represents a separate embodiment of the present invention.

In one embodiment, the present invention provides a method for generating an HF in a scalp, eyebrow, or scarred region of a subject, comprising the steps of: (a) disrupting an epidermis of the scalp, eyebrow, or scarred region; and (b) contacting the scalp, eyebrow, or scarred region with minoxidil, thereby generating an HF in a scalp, eyebrow, or scarred region of a subject.

In one embodiment, the present invention provides a method for treating baldness in a scalp, eyebrow, or scarred region of a subject, comprising the steps of (a) disrupting an epidermis of the scalp, eyebrow, or scarred region; and (b) contacting the scalp, eyebrow, or scarred region with minoxidil, thereby treating baldness in a scalp, eyebrow, or scarred region of a subject.

In another embodiment, the present invention provides a use of minoxidil for the preparation of a pharmaceutical composition for use in a method for an HF in a scalp, eyebrow, or scarred region of a subject, the method comprising the steps of: (a) disrupting an epidermis of the scalp, eyebrow, or scarred region; and (b) contacting the scalp, eyebrow, or scarred region with the minoxidil.

In another embodiment, the present invention provides a use of minoxidil for the preparation of a pharmaceutical composition for use in a method for treating baldness in a scalp, eyebrow, or scarred region of a subject, the method comprising the steps of: (a) disrupting an epidermis of the scalp, eyebrow, or scarred region; and (b) contacting the scalp, eyebrow, or scarred region with the minoxidil.

In another embodiment, the present invention provides a method for removal of an HF from a skin or scalp of a subject, comprising the steps of: (a) disrupting an epidermis of the skin or scalp; and (b) contacting the skin or scalp with either: (i) an EGF protein; (ii) an EGF receptor; (iii) a nucleotide encoding an EGF protein or EGF receptor; or (iv) a compound or factor that activates a EGF protein or EGF receptor, thereby removing an HF from a skin or scalp of a subject.

In another embodiment, the present invention provides a method for hair removal from a skin or scalp of a subject, comprising the steps of (a) disrupting an epidermis of the skin or scalp; and (b) contacting the skin or scalp with either: (i) an EGF protein; (ii) an EGF receptor; (iii) a nucleotide encoding an EGF protein or EGF receptor; or (iv) a compound or factor that activates a EGF protein or EGF receptor, thereby removing hair from a skin or scalp of a subject. In another embodiment, the epidermal disruption is light dermabrasion. In another embodiment, the epidermal disruption is a non-scarring method. In another embodiment, administration of the EGF protein, EGF receptor, nucleotide, compound, or factor suppresses HF formation. In another embodiment, the EGF protein, EGF receptor, nucleotide, compound, or factor is administered within several days of healing. In another embodiment, the EGF protein, EGF receptor, nucleotide, compound, or factor is administered within about 1 day of healing. In another embodiment, the EGF protein, EGF receptor, nucleotide, compound, or factor is administered according to any of the timing embodiments enumerated herein for Dkk1 protein. Each possibility represents a separate embodiment of the present invention.

In another embodiment, the present invention provides a use of either: (i) an EGF protein; (ii) an EGF receptor; (iii) a nucleotide encoding an EGF protein or EGF receptor; or (iv) a compound or factor that activates a EGF protein or EGF receptor, for the preparation of a pharmaceutical composition for use in a method for removal of an HF from a skin or scalp of a subject, the method comprising the steps of: (a) disrupting an epidermis of the scalp, eyebrow, or scarred region; and (b) contacting the scalp, eyebrow, or scarred region with the EGF protein, EGF receptor, nucleotide, compound, or factor.

In another embodiment, a composition or method of the present invention is utilized on human skin. In another embodiment, the composition or method is utilized on an area of unwanted hair growth. In another embodiment, the area is the face. In another embodiment, the area is the bikini area. In another embodiment, the area is the legs. In another embodiment, the area is the arms. In another embodiment, the area is the chest.

An "inhibitor" utilized in methods and compositions of the present invention is, in another embodiment, an antibody that binds the protein or biological factor that is the target of the inhibitor. In another embodiment, the inhibitor is a pharmacologic inhibitor. In another embodiment, the inhibitor is any other type of inhibitor known in the art. Each possibility represents a separate embodiment of the present invention.

The step of disrupting the epidermis in methods of the present invention is performed, in another embodiment, by abrading the scalp, eyebrow, or scarred region. In another embodiment, the term "abrading" refers to an act of creating an abrasion. In another embodiment, "abrading" refers to rubbing. In another embodiment, "abrading" refers to wearing away by friction. As provided herein (Example 1), epidermal abrasion causes, under the conditions utilized herein, de novo HF neo-genesis. In another embodiment, the epidermal layer is disrupted.

In one embodiment, "abrasion" has the same meaning as "abrading." In another embodiment, "abrasion" refers to an area of the scalp or skin from which the epidermis is removed. In another embodiment, "abrasion" refers to an area of the scalp or skin from which the epidermis and dermis are removed. Each definition of "abrading" and "abrasion" represents a separate embodiment of the present invention.

As provided herein, under the conditions utilized, epidermal disruption by a method of the present invention converts the skin back, in another embodiment, to an embryonic-like state, in which the follicle regenerates. In another embodiment, a subsequent window of opportunity is created, during which the number and size of new HF in the skin can be manipulated. In another embodiment, the administration of a compound or factor that promotes a differentiation of an uncommitted epidermal cell into a HF cell during this window causes regeneration of larger and more numerous HF. The morphology of HF in abraded skin is similar to that of embryonic HF (Example 1-2 and subsequent Examples), and the markers expressed are similar as well.

In another embodiment, the present invention provides a method of stimulating hair growth in a scalp, eyebrow, or scarred region of a subject, comprising performing a method of present invention, thereby stimulating hair growth in a scalp, eyebrow, or scarred region of a subject. As demonstrated in Example 3, EDIHN-induced HF are capable of generating hairs. Thus, methods of the present invention can be used to stimulate hair growth.

"EDIHN," in another embodiment, refers to HF neogenesis induced by disruption of the epithelial layer. In another embodiment, the term refers to HF neogenesis induced by abrasion. In another embodiment, the term refers to HF neogenesis induced by wounding. In another embodiment, the term refers to HF neogenesis induced by disruption of the epithelial layer, followed by administration of a compound or factor that promotes a differentiation of an uncommitted epidermal cell into a HF cell. Each possibility represents a separate embodiment of the present invention.

In another embodiment, the present invention provides a method of testing an ability of a compound to modulate HF generation in vivo, comprising (a) disrupting an epithelial layer of a first scalp, eyebrow, or scarred region, whereby the first scalp, eyebrow, or scarred region has been contacted with the compound; (b) measuring a first HF generation in the first scalp, eyebrow, or scarred region; (c) disrupting an epithelial layer of a second scalp, eyebrow, or scarred region, wherein the second scalp, eyebrow, or scarred region is a scalp, eyebrow, or scarred region of the first subject or a second subject, whereby the second scalp, eyebrow, or scarred region has not been contacted with the compound; (d) measuring a second HF generation in the second scalp, eyebrow, or scarred region; and (e) comparing the first HF generation to the second HF generation, whereby a difference between the first HF generation and the second HF generation indicates that the compound modulates an HF generation in vivo (Examples).

In another embodiment, the present invention provides a method of testing an ability of a compound to stimulate hair growth in vivo, comprising disrupting an epithelial layer of a first scalp, eyebrow, or scarred region, whereby the first scalp, eyebrow, or scarred region has been contacted with the compound; measuring a first HF generation in the first scalp, eyebrow, or scarred region; disrupting an epithelial layer of a second scalp, eyebrow, or scarred region, whereby the second scalp, eyebrow, or scarred region has not been contacted with the compound; measuring a second HF generation in the second scalp, eyebrow, or scarred region; and comparing the first HF generation to the second HF generation, whereby a difference between the first HF generation and the second HF generation indicates that the compound stimulates a hair growth in vivo.

In one embodiment, the methods of the present invention of testing a compound are repeated using a plurality of subjects, until a statistically significant sample has been tested.

In another embodiment of methods for testing compounds of the present invention, the first scalp, eyebrow, or scarred region is a scalp, eyebrow, or scarred region of a first subject. In another embodiment, the subject is a subject in need of generation of a new HF. The second scalp, eyebrow, or scarred region, in another embodiment, is a scalp, eyebrow, or scarred region of the first subject. In another embodiment, the second scalp, eyebrow, or scarred region is a scalp, eyebrow, or scarred region of a second subject. Each possibility represents a separate embodiment of the present invention.

In another embodiment, the excisional wounds of methods of the present invention are created using a surgical tool. In one embodiment, the surgical tool is a dermal biopsy punch (Example 2). In another embodiment, the excisional wounds are induced by freezing or cryoinjury. The use of freezing or cryoinjury is well known in the art, and is used, for example by dermatologists to injure skin. In one embodiment, the freezing or cryoinjury results in a blister. In another embodiment, the blister is used as a "chamber" to introduce drugs and or cells into the reepithelialized area. Each possibility represents a separate embodiment of the present invention.

In another embodiment, the excisional wounds of methods of the present invention are not surgically closed. In another embodiment, the excisional wounds are not contacted with a bandage or dressing before they heal or during a period of time after wound induction. In another embodiment, the excisional wounds are not contacted with an ointment before they heal or during a period of time after wound induction. In another embodiment, the excisional wounds are allowed to heal by secondary intention. Each possibility represents a separate embodiment of the present invention.

The subject of methods of the present invention, is, in another embodiment, a human. As provided herein (Example 7) human skin responds to EDIHN in the same manner as mouse skin. In another embodiment, the subject is a male. In another embodiment, the subject is a female. In another embodiment, the subject is any other type of subject known in the art. Each possibility represents a separate embodiment of the present invention.

In another embodiment, the subject is an adult. In one embodiment, "adult" refers to an age greater than about 18 years. In another embodiment, "adult" refers to an age greater than about 20 years. In another embodiment, "adult" refers to an age greater than about 25 years. In another embodiment, "adult" refers to an age greater than about 30 years. In another embodiment, "adult" refers to an age greater than about 35 years. In another embodiment, "adult" refers to an age greater than about 40 years. In another embodiment, "adult" refers to an age greater than about 45 years.

In another embodiment, the subject is elderly. In one embodiment, "elderly" refers to an age greater than about 45 years. In another embodiment, "elderly" refers to an age greater than about 50 years. In another embodiment, "elderly" refers to an age greater than about 55 years. In another embodiment, "elderly" refers to an age greater than about 60 years. In another embodiment, "elderly" refers to an age greater than about 65 years. In another embodiment, "elderly" refers to an age greater than about 70 years.

In another embodiment, the first subject, or, where applicable, both the first subject and the second subject, is a laboratory animal. In another embodiment, the subject(s) is/are mice. In another embodiment, the subject(s) is/are rats. In another embodiment, the subject(s) is/are gerbils. In another embodiment, the subject(s) is/are hamsters. In another embodiment, the subject(s) is/are guinea pigs. In another embodiment, the subject(s) is/are rabbits. In another embodiment, the subject(s) is/are pigs. In another embodiment, the subject(s) is/are dogs. In another embodiment, the subject(s) is/are cats. In another embodiment, the subject(s) is/are primates. In another embodiment, the subject(s) is/are any other laboratory animal known in the art. Each possibility represents a separate embodiment of the present invention.

In another embodiment, the subject(s) has a disease or disorder comprising balding. In another embodiment, the subject(s) does not have a disease or disorder comprising balding. In another embodiment, the disease or disorder is androgenetic alopecia (AGA). In another embodiment, the disease or disorder is male pattern baldness. In another embodiment, the disease or disorder is female pattern baldness. In another embodiment, the disease or disorder is a discoid lupus erythematosis. In another embodiment, the disease or disorder is a congenital hypotrichosis. In another embodiment, the disease or disorder is a lichen planopilaris. In another embodiment, the disease or disorder is a scarring alopecia. In another embodiment, the disease or disorder is any other disease or disorder comprising balding known in the art.

In another embodiment, the scalp, eyebrow, or scarred region(s) has a majority of HF in the telogen stage of the hair cycle. The findings of Examples 5-6 show that (a) EDIHN can restore hair growth to the scalp, eyebrow, or scarred region at the telogen stage; and (b) the efficiency of EDIHN at the telogen stage can be enhanced by depilation prior to abrasion or wound induction. In another embodiment, the scalp, eyebrow, or scarred region(s) has more than about 60% of HF in the telogen stage of the hair cycle. In another embodiment, the scalp, eyebrow, or scarred region(s) has more than about 70% of HF in the telogen stage of the hair cycle. In another embodiment, the scalp, eyebrow, or scarred region(s) has more than about 80% of HF in the telogen stage of the hair cycle. In another embodiment, the scalp, eyebrow, or scarred region(s) has more than about 90% of HF in the telogen stage of the hair cycle. In another embodiment, the scalp, eyebrow, or scarred region(s) does not have a majority of HF in the telogen stage of the hair cycle. Each possibility represents a separate embodiment of the present invention.

In another embodiment of methods and compositions of the present invention, the first step (e.g. epithelial disruption) is performed 3-12 days prior to the second step (e.g. addition of an active compound, factor, cell, etc). In another embodiment, the interval is 4-12 days. In another embodiment, the interval is 5-12 days. In another embodiment, the interval is 4-11 days. In another embodiment, the interval is 6-11 days. In another embodiment, the interval is 6-10 days. In another embodiment, the interval is 6-9 days. In another embodiment, the interval is 6-8 days. In another embodiment, the interval is 7-8 days. In another embodiment, the interval is 5-11 days. In another embodiment, the interval is 5-10 days. In another embodiment, the interval is 7-10 days. In another embodiment, the interval is about 1 week. Each possibility represents a separate embodiment of the present invention.

In another embodiment, a method of the present invention further comprises the step of suppressing an activity or expression of a Wnt protein in the scalp, eyebrow, or scarred region. As provided herein, suppressing Wnt activity induces pigmentation in HF generated by methods of the present invention. In another embodiment, the step of suppressing Wnt activity or expression is performed within about 10 days of epidermal disruption. In another embodiment, the step of suppressing Wnt activity or expression is performed prior to the second step (e.g prior to addition of a compound or factor that promotes HF cell differentiation. Each possibility represents a separate embodiment of the present invention.

In another embodiment, the present invention provides a method for inducing pigmentation of a hair, comprising suppressing expression of a Wnt protein in a follicle of the hair. In another embodiment, the Wnt protein is Wnt1. In another embodiment, the Wnt protein is a Wnt7. In another embodiment, the Wnt protein is a Wnt7a. In another embodiment, the Wnt protein is a Wnt3. In another embodiment, the Wnt protein is a Wnt3a. In another embodiment, the Wnt protein is a Wnt10. In another embodiment, the Wnt protein is a Wnt10a. In another embodiment, the Wnt protein is any other Wnt protein known in the art. Each possibility represents a separate embodiment of the present invention.

In another embodiment, the present invention provides a method for inducing growth of a pigmented scalp hair or eyebrow of a subject, comprising generating a hair follicle in the scalp, eyebrow, or scarred region according to a method of the present invention and suppressing expression of a Wnt protein in the hair follicle, thereby inducing a growth of a pigmented scalp hair or eyebrow of a subject.

In another embodiment, the step of suppressing expression of a Wnt protein comprises inducing an expression of a Dkk1 protein. In another embodiment, the step of suppressing expression of a Wnt protein comprises inducing an expression of any other Wnt inhibitor known in the art. In another embodiment, the step of suppressing expression of a Wnt protein is performed immediately or shortly after epidermal disruption. In another embodiment, the step of inducing expression of a Dkk1 protein is performed immediately or shortly after epidermal disruption. In another embodiment, the step of suppressing expression of a Wnt protein is performed at the time of epidermal disruption. In another embodiment, the step of inducing expression of a Dkk1 protein is performed at the time of epidermal disruption. In another embodiment, the step of suppressing expression of a Wnt protein is performed several days before generation of the follicle. In another embodiment, the step of inducing expression of a Dkk1 protein several days before generation of the follicle. Each possibility represents a separate embodiment of the present invention.

In another embodiment, the step of suppressing expression of a Wnt protein is performed for about 8 days. In another embodiment, the step of inducing expression of a Dkk1 protein is performed for about 8 days. In another embodiment, the step of suppressing expression of a Wnt protein is performed for about 9 days. In another embodiment, the step of inducing expression of a Dkk1 protein is performed for about 9 days. In another embodiment, the step of suppressing expression of a Wnt protein is performed for about 10 days. In another embodiment, the step of inducing expression of a Dkk1 protein is performed for about 10 days. In another embodiment, the step of suppressing expression of a Wnt protein is performed for about 12 days. In another embodiment, the step of inducing expression of a Dkk1 protein is performed for about 12 days. In another embodiment, the step of suppressing expression of a Wnt protein is performed during the period of re-epithelialization. In another embodiment, the step of inducing expression of a Dkk1 protein is performed during the period of re-epithelialization. In another embodiment, expression of a Dkk1 protein is halted after several days. In another embodiment, halting expression of Dkk1 protein after several days induces, or enables induction of Wnt protein expression. In another embodiment, the expression of a Wnt protein is induced about 9 days after the abrating or wounding. In another embodiment, the expression of a Wnt protein is induced following the period of re-epithelialization. In another embodiment, induction of Wnt protein expression is necessary for formation of new HF. Each possibility represents a separate embodiment of the present invention.

In another embodiment, “several” refers to about 1 day. In another embodiment, “several” refers to about 2 days. In another embodiment, “several” refers to about 3 days. In another embodiment, “several” refers to about 5 days. In another embodiment, “several” refers to about 7 days. In another embodiment, “several” refers to about 10 days. In another embodiment, “several” refers to about 12 days. Each possibility represents a separate embodiment of the present invention.

In another embodiment, the step of contacting in methods of the present invention comprises directly contacting the scalp, eyebrow, or scarred region with the compound, RNA, protein, etc. In another embodiment, the step of contacting comprises indirectly contacting the scalp, eyebrow, or scarred region via contacting another site or tissue of the subject, after which the compound, RNA, or protein is transported to the scalp, eyebrow, or scarred region by a biological process; e.g, diffusion, active transport, or circulation in a fluid such as the blood, lymph, interstitial fluid, etc. Each possibility represents a separate embodiment of the present invention.

In another embodiment, the epidermal disruption in methods of the present invention further removes dermal, tissue from the scalp, eyebrow, or scarred region. In another embodiment, the epidermal disruption does not remove dermal tissue from the scalp, eyebrow, or scarred region. Each possibility represents a separate embodiment of the present invention.

“Disrupting” an epidermis or epidermal layer refers, in another embodiment, to removing part of the epidermis or epidermal layer. In another embodiment, the term refers to disturbing the intactness of the epidermis or epidermal layer. In another embodiment, the term refers to perforating the epidermis or epidermal layer. In another embodiment, only part of the epidermal layer need be removed. In another embodiment, the entire epidermal layer is removed. In another embodiment, the term refers to abrading the epidermis or epidermal layer (Examples). In another embodiment, the term refers to wounding the epidermis or epidermal layer (Examples). Each possibility represents a separate embodiment of the present invention.

In another embodiment, the epidermal disruption is performed with a tool that comprises sandpaper. In another embodiment, the epidermal disruption is performed with a laser. In another embodiment, the laser is a Fraxel laser. In another embodiment, the laser is a $CO_2$ laser. In another embodiment, the laser is an excimer laser. In another embodiment, the laser is any other type of laser capable of inducing trans-epithelial injury. In another embodiment, the epidermal disruption is performed with a felt wheel. In another embodiment, the epidermal disruption is performed with a surgical tool. In another embodiment, the epidermal disruption is performed with any other tool known in the art that is capable of epidermal disruption. In another embodiment, the epidermal disruption comprises use of a microdermabrasion device. In another embodiment, the epidermal disruption comprises a burn treatment.

In another embodiment, the epidermal disruption comprises a disruption of a follicle of said epidermis and a disruption of an interfollicular region of said epidermis. In another embodiment, the epidermal disruption comprises a disruption of a follicle of said epidermis and does not comprise a disruption of an interfollicular region of said epidermis. Each possibility represents a separate embodiment of the present invention.

In another embodiment, the epidermal disruption comprises a light-based method. In another embodiment, the epidermal disruption comprises irradiation with visible light. In another embodiment, the epidermal disruption comprises irradiation with infrared light. In another embodiment, the epidermal disruption comprises irradiation with ultraviolet radiation. In another embodiment, the epidermal disruption comprises orthovoltage irradiation. In another embodiment, the epidermal disruption comprises X-ray irradiation. In another embodiment, the epidermal disruption comprises any other type of irradiation known in the art.

In another embodiment, the epidermal disruption is performed by mechanical means. In another embodiment, “mechanical means” refers to abrading. In another embodiment, the term refers to wounding. In another embodiment, the term refers to ultrasound. In another embodiment, the term refers to radio-frequency. In another embodiment, the term refers to ab electrical process or the use of an electrical current. In another embodiment, the term refers to electoporation. In another embodiment, the term refers to exision. In another embodiment, the term refers to tape-stripping. In another embodiment, the term refers to microdermabrasion. In another embodiment, the term refers to the use of peels. In another embodiment, the term refers to any other type of mechanical means known in the art. Each possibility represents a separate embodiment of the present invention.

In another embodiment, the epidermal disruption comprises chemical treatment. In another embodiment, the chemical is phenol. In another embodiment, the chemical is trichloracetic acid. In another embodiment, the chemical is ascorbic acid. In another embodiment, the chemical is any other chemical capable of epidermal disruption that is known in the art.

Each method or type of method of epidermal disruption represents a separate embodiment of the present invention.

In another embodiment, epidermal trauma is utilized in a method of the present invention.

Each type of epidermal abrasion and epidermal trauma represents a separate embodiment of the present invention.

In another embodiment, the epidermal disruption of methods of the present invention creates an abrasion at least about 1-1.5 centimeters (cm) in width. In another embodiment, the abrasion is at least about 1 cm in width. In another embodiment, the abrasion is at least about 1.5 cm in width. In another embodiment, the abrasion is at least about 2 cm in width. Each type of abrasion represents a separate embodiment of the present invention.

In another embodiment, the scalp, eyebrow, or scarred region is not contacted with a bandage or dressing following the epidermal disruption. In another embodiment, the scalp, eyebrow, or scarred region is not contacted with an ointment following the epidermal disruption. In another embodiment, the scalp, eyebrow, or scarred region is allowed to heal for a period of time without being contacted by any substance, device, ointment, etc., that is ordinarily administered to an abrasion or wound to facilitate healing. In another embodiment, the scalp, eyebrow, or scarred region is allowed to heal for a period of time without being contacted by any substance, device, ointment, etc., that is ordinarily administered to an abrasion or wound to prevent infection. In another embodiment, the period of time is the time it takes the epidermal disruption to heal. In another embodiment, the period of time is any time or range of times between 2 days and 3 weeks. Each possibility represents a separate embodiment of the present invention.

In one embodiment, "following" refers to a period of time of about 2 days. In another embodiment, "following" refers to a period of time of about 3 days. In another embodiment, "following" refers to a period of time of about 4 days. In another embodiment, "following" refers to a period of time of about 5 days. In another embodiment, "following" refers to a period of time of about 7 days. In another embodiment, "following" refers to a period of time of about 10 days. In another embodiment, "following" refers to a period of time of about 2 weeks. In another embodiment, "following" refers to a period of time of about 3 weeks. Each possibility represents a separate embodiment of the present invention.

In another embodiment, a method of the present invention further comprises the step of depilating the scalp, eyebrow, or scarred region. As provided herein, the findings of Example 6 show that the efficiency of EDIHN can be enhanced by depilation prior to abrasion or wound induction.

In another embodiment, the depilation is epilation. In another embodiment, the depilation comprises the step of waxing. In another embodiment, the depilation comprises the step of plucking. In another embodiment, the depilation comprises the use of an abrasive material. In another embodiment, the depilation comprises the use of a laser. In another embodiment, the depilation comprises the use of electrolysis. In another embodiment, the depilation comprises the use of a mechanical device. In another embodiment, the depilation comprises the use of thioglycolic acid. In another embodiment, the depilation comprises the use of any other method of depilation or epilation known in the art. Each possibility represents a separate embodiment of the present invention.

In another embodiment, a method of the present invention further comprises the step of administering a topical retinoid to the scalp, eyebrow, or scarred region. In one embodiment, the topical retinoid induces resting (telogen) HF in the scalp, eyebrow, or scarred region to enter anagen. Each possibility represents a separate embodiment of the present invention.

In another embodiment, the additional step (depilation or administration of a retinoid) is performed prior to the step of disrupting the epidermis. In another embodiment, the additional step is performed following the step of disrupting the epidermis, but prior to the addition of the compound or factor that promotes a differentiation of an uncommitted epidermal cell into a HF cell. In another embodiment, the additional step is performed concurrently with the addition of the differentiation-promoting compound or factor. In another embodiment, the additional step is performed following the addition of the differentiation-promoting compound or factor. Each possibility represents a separate embodiment of the present invention.

In another embodiment, the additional step is performed between about two days and about three weeks before the step of abrading. In another embodiment, the additional step is performed about two days before the step of abrading. In another embodiment, the additional step is performed about three days before the step of abrading. In another embodiment, the additional step is performed about four days before the step of abrading. In another embodiment, the additional step is performed about one week before the step of abrading. In another embodiment, the additional step is performed about ten days before the step of abrading. In another embodiment, the additional step is performed about two weeks before the step of abrading. In another embodiment, the additional step is performed about three weeks before the step of abrading. Each possibility represents a separate embodiment of the present invention.

In another embodiment, the methods of the present invention further comprise the step of contacting the scalp, eyebrow, or scarred region with an inductive cell capable of inducing an epidermal cell to differentiate into an HF cell. In another embodiment, the HF cell is an HF stem cell. Each possibility represents a separate embodiment of the present invention.

In another embodiment, the inductive cell is a dermal papilla cell. In another embodiment, the inductive cell is a follicular papilla cell. In another embodiment, the inductive cell is a dermal sheath cell. In another embodiment, the inductive cell is a cell that has been genetically modified; for example, with a gene encoding a factor that activates one of the proteins or pathways shown in the present invention to be up-regulated in HF stem cells. In one embodiment, the factor is hedgehog. In another embodiment, the factor is a DP cell protein. In another embodiment, the factor is wingless/int (wnt). In another embodiment, the factor is a Noggin protein. In another embodiment, the factor is a bone morphogenic protein (BMP). In another embodiment, the factor is a fibroblast growth factor (FGF). In another embodiment, the factor is a transforming growth factor beta (TGF-beta) protein. In another embodiment, the factor is sonic hedgehog protein. In another embodiment, the factor is a neurotropin. In another embodiment, the factor is any other factor known in the art that can contribute to induction of an epidermal cell to differentiate into an HF cell. Each possibility represents a separate embodiment of the present invention.

In another embodiment, the inductive cell has been genetically modified with a gene encoding a factor that represses one of the proteins or pathways shown in the present invention to be down-regulated in HF stem cells. In another embodiment, the inductive cell has been genetically modified with a gene encoding a factor that activates one of the proteins or pathways shown in the present invention to be up-regulated in HF stem cells upon their activation.

In another embodiment, the inductive cell is an autologous cell. In another embodiment, the inductive cell is an allogenic cell.

In another embodiment, the inductive cell is derived from a mesenchymal stem cell. In another embodiment, the inductive cell is derived from a mesodermal progenitor cell. In another embodiment, the inductive cell is derived from a hematopoietic stem cell. In another embodiment, the inductive cell is derived from an embryonic stem cell. In another embodiment, the inductive cell is derived from an embryonic carcinoma cell. In another embodiment, the inductive cell is one of the cell types disclosed in United States Patent Application No. 2003/0201815. In another embodiment, the inductive cell is any other type of cell known in the art with inductive properties for an epidermal cell. Each type of inductive cell represents a separate embodiment of the present invention.

In another embodiment, the epidermal cell (e.g. the epidermal cell that is induced to differentiate into an HF cell) is an epidermal stem cell. In another embodiment, the epidermal cell is a bulge cell. In another embodiment, the epidermal cell is any other type of cell known in the art that can be induced to differentiate into an HF stem cell. Each possibility represents a separate embodiment of the present invention.

In another embodiment, a method of the present invention further comprises the step of contacting the scalp, eyebrow, or scarred region with an anti-androgen compound. In one embodiment, the anti-androgen compound is finasteride. In another embodiment, the anti-androgen compound is Fluridil®. In another embodiment, the anti-androgen compound is dutasteride. In another embodiment, the anti-androgen compound is spironolactone. In another embodiment, the anti-androgen compound is cyproterone acetate. In another embodiment, the anti-androgen compound is bicalutamide. In another embodiment, the anti-androgen compound is flutamide. In another embodiment, the anti-androgen compound is nilutamide. In another embodiment, the anti-androgen compound is an inhibitor of an androgen receptor. In another embodiment, the anti-androgen compound is any other anti-androgen compound known in the art. Each possibility represents a separate embodiment of the present invention.

In another embodiment, a method of the present invention further comprises the step of contacting the scalp, eyebrow, or scarred region with an estrogen compound. In another embodiment, a method of the present invention further comprises the step of contacting the scalp, eyebrow, or scarred region with an estrogen receptor agonist. In another embodiment, a method of the present invention further comprises the step of contacting the scalp, eyebrow, or scarred region with an estrogen analogue. In one embodiment, the estrogen analogue is estradiol. In another embodiment, the estrogen analogue is 17 beta-estradiol. In another embodiment, the estrogen analogue is 17 alpha-estradiol. In another embodiment, the estrogen analogue is ZYC3. In another embodiment, the estrogen compound, estrogen receptor agonist, or estrogen analogue is any other estrogen compound, estrogen receptor agonist, or estrogen analogue known in the art. Each possibility represents a separate embodiment of the present invention.

In another embodiment, a method of the present invention further comprises the step of contacting the scalp, eyebrow, or scarred region with an inhibitor of an EGF protein. In another embodiment, a method of the present invention further comprises the step of contacting the scalp, eyebrow, or scarred region with an inhibitor of an EGFR. In another embodiment, a method of the present invention further comprises the step of contacting the scalp, eyebrow, or scarred region with a compound that reduces an expression of an EGF protein or an EGFR. Each possibility represents a separate embodiment of the present invention.

In another embodiment, a method of the present invention further comprises the step of contacting the scalp, eyebrow, or scarred region with a Hedgehog protein. In another embodiment, a method of the present invention further comprises the step of contacting the scalp, eyebrow, or scarred region with a nucleotide encoding a Hedgehog protein. In another embodiment, a method of the present invention further comprises the step of contacting the scalp, eyebrow, or scarred region with an activator of a Hedgehog protein. Each possibility represents a separate embodiment of the present invention.

In one embodiment, a scalp is treated by a method of the present invention. In another embodiment, an eyebrow is treated. In another embodiment, any other hair-bearing area or region of the skin is treated. Each possibility represents a separate embodiment of the present invention.

In another embodiment, a method of the present invention further comprises the step of contacting the scalp, eyebrow, or scarred region with a lithium compound. In one embodiment, the lithium compound contains a lithium ion. In another embodiment, the lithium compound contains a lithium atom.

In another embodiment, a method of the present invention further comprises the step of contacting the scalp, eyebrow, or scarred region with (2'Z,3'E)-6-bromoindirubin-3'-oxime (BIO). In another embodiment, a method of the present invention further comprises the step of contacting the scalp, eyebrow, or scarred region with any other compound known in the art that is capable of inducing an epidermal cell to differentiate into an HF stem cell. Each compound represents a separate embodiment of the present invention.

In one embodiment, the compound administered as part of methods of the present invention is administered systemically. In another embodiment, the compound is administered topically. In another embodiment, the compound is administered to the site of the abrasion. In another embodiment, the compound is administered to the site of the wound induction. In another embodiment, the compound is administered to the site of the depilation. In another embodiment, the compound is administered during wound healing. In another embodiment, the compound is administered prior to HF neo-genesis. In another embodiment, the compound is administered during HF neo-genesis. Each possibility represents a separate embodiment of the present invention.

In another embodiment, the present invention provides a method of inducing formation of an HF stem cell, comprising performing a method of the present invention. In another embodiment, the present invention provides a method of inducing formation of a DP cell, comprising performing a method of the present invention. Each possibility represents a separate embodiment of the present invention.

In another embodiment, homologues and variants of transcripts and proteins of the present invention are administered in methods of the present invention. In another embodiment, homologues and variants of transcripts and proteins of the present invention are targeted in methods of the present invention. Each possibility represents a separate embodiment of the present invention.

The terms "homology," "homologous," etc, when in reference to any protein or peptide, refer in one embodiment, to a percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art.

In another embodiment, the term "homology," when in reference to any nucleic acid sequence similarly indicates a percentage of nucleotides in a candidate sequence that are identical with the nucleotides of a corresponding native nucleic acid sequence.

In another embodiment, "homology" refers to identity of greater than 70%. In another embodiment, "homology"

refers to identity of greater than 75%. In another embodiment, "homology" refers to identity of greater than 80%. In another embodiment, "homology" refers to identity of greater than 82%. In another embodiment, "homology" refers to identity of greater than 85%. In another embodiment, "homology" refers to identity of greater than 87%. In another embodiment, "homology" refers to identity of greater than 90%. In another embodiment, "homology" refers to identity of greater than 92%. In another embodiment, "homology" refers to identity of greater than 95%. In another embodiment, "homology" refers to identity of greater than 97%. In another embodiment, "homology" refers to identity of greater than 98%. In another embodiment, "homology" refers to identity of greater than 99%. In another embodiment, "homology" refers to identity of 100%.

Protein and/or peptide homology for any amino acid sequence listed herein is determined, in one embodiment, by methods well described in the art, including immunoblot analysis, or via computer algorithm analysis of amino acid sequences, utilizing any of a number of software packages available, via established methods. Some of these packages may include the FASTA, BLAST, MPsrch or Scanps packages, and may employ the use of the Smith and Waterman algorithms, and/or global/local or BLOCKS alignments for analysis, for example. Each method of determining homology represents a separate embodiment of the present invention.

In another embodiment, the present invention provides a kit, comprising a tools and/or a compound suitable for performing a method of the present invention.

In another embodiment, the present invention provides a device, comprising a tool suitable for epidermal disruption and a means of delivering a compound or factor that promotes a differentiation of an uncommitted epidermal cell into a HF cell.

In other embodiments, the present invention provides a method of treating any disease, disorder, or symptom associated with balding. In other embodiments, the present invention provides a method of treating any disease, disorder, or symptom associated with balding. In other embodiments, the present invention provides a method of treating any disease, disorder, or symptom associated with balding. Each disease, disorder, or symptom represents a separate embodiment of the present invention.

Pharmaceutical Compositions

In another embodiment, methods of the present invention comprise administering a pharmaceutical composition comprising the HF stem cell-inducing or -activating compound and/or its analog, derivative, isomer, metabolite, pharmaceutically acceptable salt, pharmaceutical product, hydrate, N-oxide, or any combination thereof; and a pharmaceutically acceptable carrier. Each possibility represents a separate embodiment of the present invention.

The pharmaceutical compositions containing the HF stem cell-inducing or -activating compound can, in another embodiment, be administered to a subject by any method known to a person skilled in the art, such as topically, parenterally, paracancerally, transmucosally, transdermally, intramuscularly, intravenously, intradermally, subcutaneously, intraperitonealy, intraventricularly, intracranially, intravaginally or intratumorally. Each possibility represents a separate embodiment of the present invention.

In another embodiment, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In one embodiment of the present invention, the HF stem cell-inducing or -activating compounds are formulated in a capsule. In another embodiment, the compositions of the present invention comprise, in addition to the HF stem cell-inducing or -activating compound active compound and the inert carrier or diluent, a hard gelating capsule.

In another embodiment, the pharmaceutical compositions are administered topically to body surfaces and are thus formulated in a form suitable for topical administration. Suitable topical formulations include gels, ointments, creams, lotions, drops and the like. For topical administration, the HF stem cell-inducing or -activating compound or its physiologically tolerated derivatives such as salts, esters, N-oxides, and the like are prepared and applied as solutions, suspensions, or emulsions in a physiologically acceptable diluent with or without a pharmaceutical carrier.

In another embodiment, the pharmaceutical compositions are administered by subcutaneous implantation of a pellet. In another embodiment, the pellet provides for controlled release of HF stem cell-inducing or -activating compound agent over a period of time.

For liquid formulations, pharmaceutically acceptable carriers are, in another embodiment, aqueous or non-aqueous solutions, suspensions, emulsions or oils. Examples of non-aqueous solvents are propylene glycol, polyethylene glycol, and injectable organic esters such as ethyl oleate. Aqueous carriers include, in another embodiment, water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

In one embodiment, the pharmaceutical compositions are controlled-release compositions, i.e. compositions in which the HF stem cell-inducing or -activating compound is released over a period of time after administration. Controlled- or sustained-release compositions include, in another embodiment, formulation in lipophilic depots (e.g. fatty acids, waxes, oils). In another embodiment, the composition is an immediate-release composition, i.e. a composition in which all the HF stem cell-inducing or -activating compound is released immediately after administration.

EXPERIMENTAL DETAILS SECTION

Example 1

Depilation and Epidermal Abrasion Causes De Novo Hair Follicle Formation

Materials and Experimental Methods

Depilation and Epidermal Abrasion

Mice were anesthetized with an injection of sodium pentobarbital before the hair on the back was clipped and depilated with Nair (Carter-Wallace, New York, N.Y.), then epidermis was removed using a rotating felt wheel as described by Argyris T, J Invest Dermatol, 75: 360-362, 1980). After scrubbing with 70% ethanol and drying under an incandescent lamp, the basal and supra-basal layers in an area of $(1.5\ cm)^2$ cm of the inter-follicular epidermis were removed by careful abrasion with a felt wheel mounted on a Dremel Moto-tool (Racine, Wis.). After abrasion, the skin was shiny and smooth, and there was no blood. One day later, the abraded area was covered by a fibrin crust, which fell off after 3-7 days, exposing the newly regenerated epidermis. A group of control mice was sacrificed immediately after abrasion to confirm microscopically the complete removal of the interfollicular epidermis.

Immunohistochemistry

Skin samples were fixed in PBS-buffered 10% formalin. Six-micron thick paraffin sections were cut and stained, where applicable, with antibodies.

BrdU Labeling

The protocol described by Bickenbach and colleagues (Bickenbach et al, Cell Tiss Kinet 19: 325-333, 1986; Bickenbach et al, Exp Cell Res 244, 184-195, 1998) was used. Mice were injected with 50 milligrams per kilogram (mg/kg) bodyweight 5-bromo-2'-deoxyuridine (BrdU) every 12 hours for a total of four injections.

Results

Figure 2:
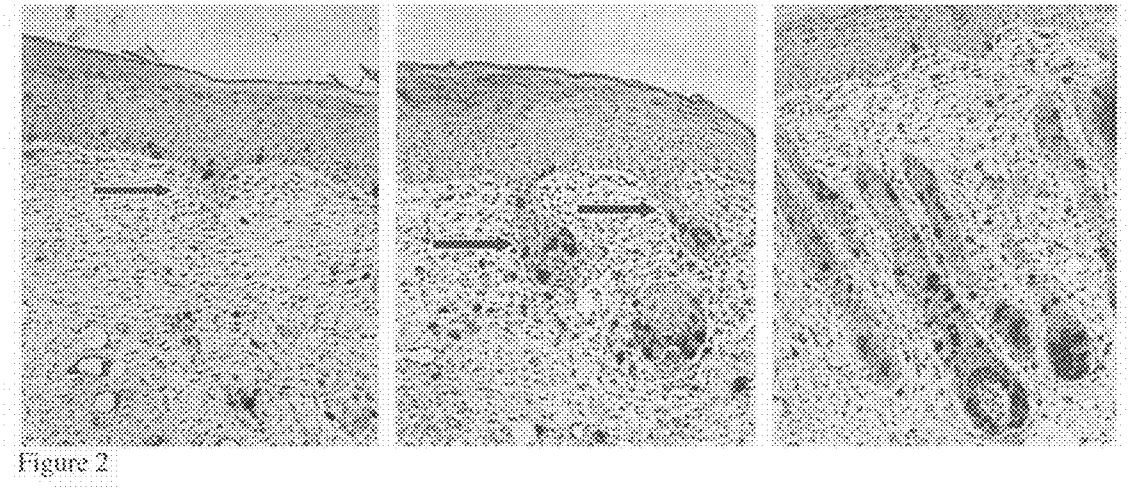
FIG. 2: BrdU labeling of HF following epidermal abrasion. HF at progressive stages of development are depicted in the left, center, and right panels.

An area of the backs of 50-day old mice was subjected to depilation and removal of the epidermis using a rotating felt wheel. Fifteen days later, HF placodes, hair germs and other signs of follicle neogenesis were present (FIG. 1; arrow indicates a hair germ). Morphology of the follicles was similar to embryonic follicle development. To further characterize proliferation in the new follicles, the skin was labeled with BrdU 60 minutes before sacrifice. As depicted in FIG. 2, the proliferation pattern was similar to developing follicles in the embryo.

These findings demonstrate that (a) disruption of the epidermis causes generation of new HF, and that this generation of new HF can occur (b) in adult subjects and (c) during telogen (50-day-old mice are in the second telogen stage of the hair cycle).

Example 2

Induction of a Large Excisional Wound, but not a Small Punch Wound, Causes De Novo Hair Follicle Formation Materials and Experimental Methods Punch Wound and Excisional Wound Induction The backs of 21-day-old mice were depilated as described for Example 1 and sterilized with alcohol, followed by 1% iodine solution. Punch wounds, 4 mm in diameter, were induced using a dermal biopsy punch, down to, but not through, the muscle fascia. Excisional wounds were full thickness and 1 cm in diameter; skin and panniculus carnosus was excised using fine surgical scissors.

Results

Figure 3:
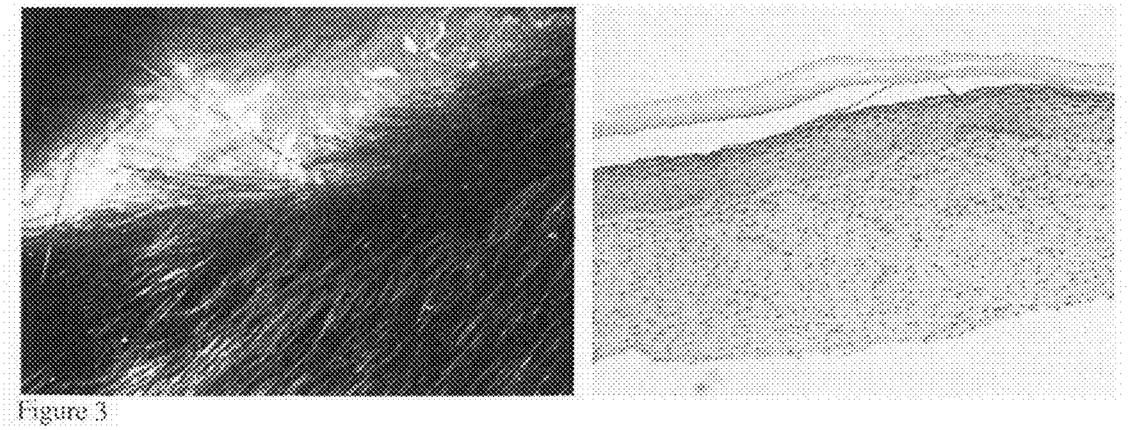
FIG. 3. The wound site did not contain HF immediately after re-epithelialization. Top view (left panel) and tissue section (right panel) of the site 10 days after wound induction.
Figure 4:
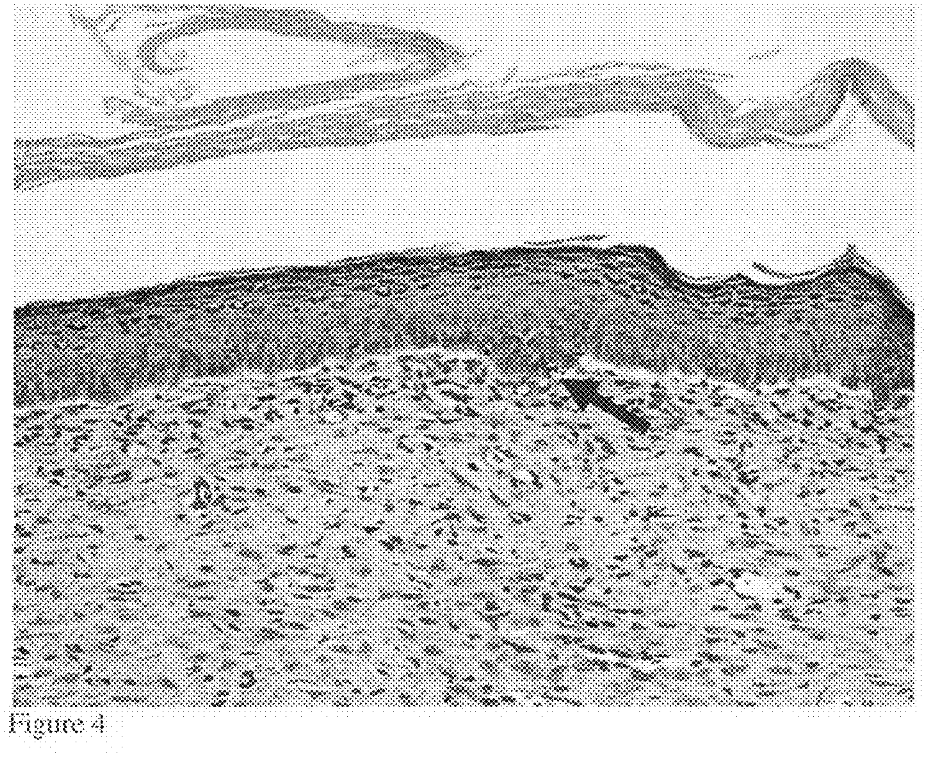
FIG. 4. Appearance of hair germs 12 days after wound induction. Arrow indicates hair germ.
Figure 5:
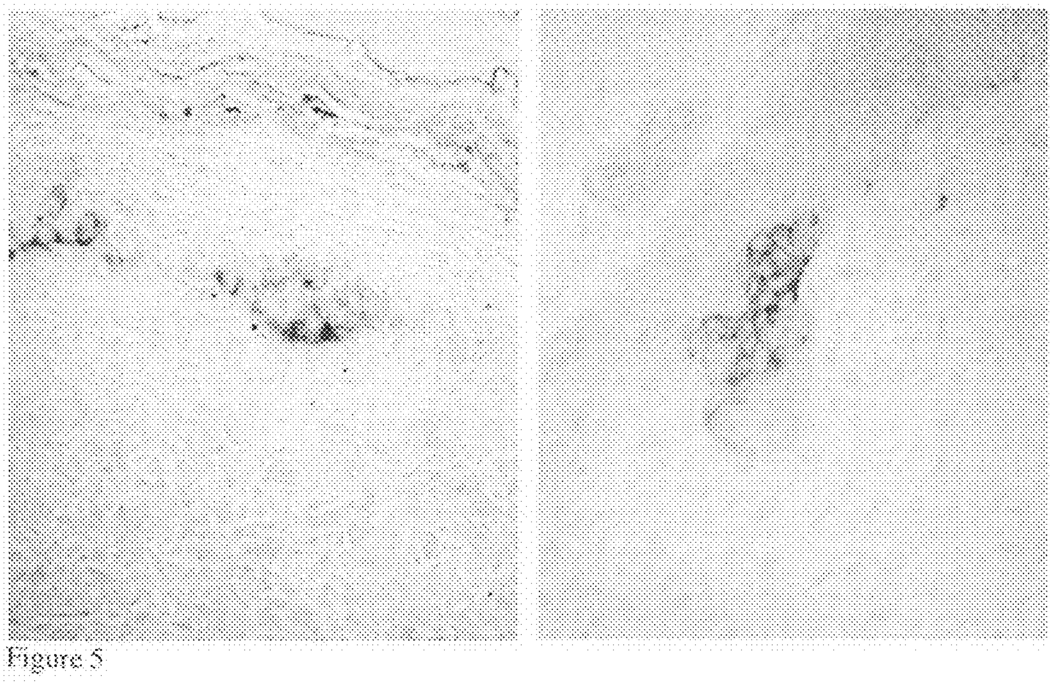
FIG. 5. Epidermal Disruption-Induced HF neogenesis (EDIHN)-induced hair germs express K17. Two different hair germs are depicted in the left and right panels.
Figure 6:
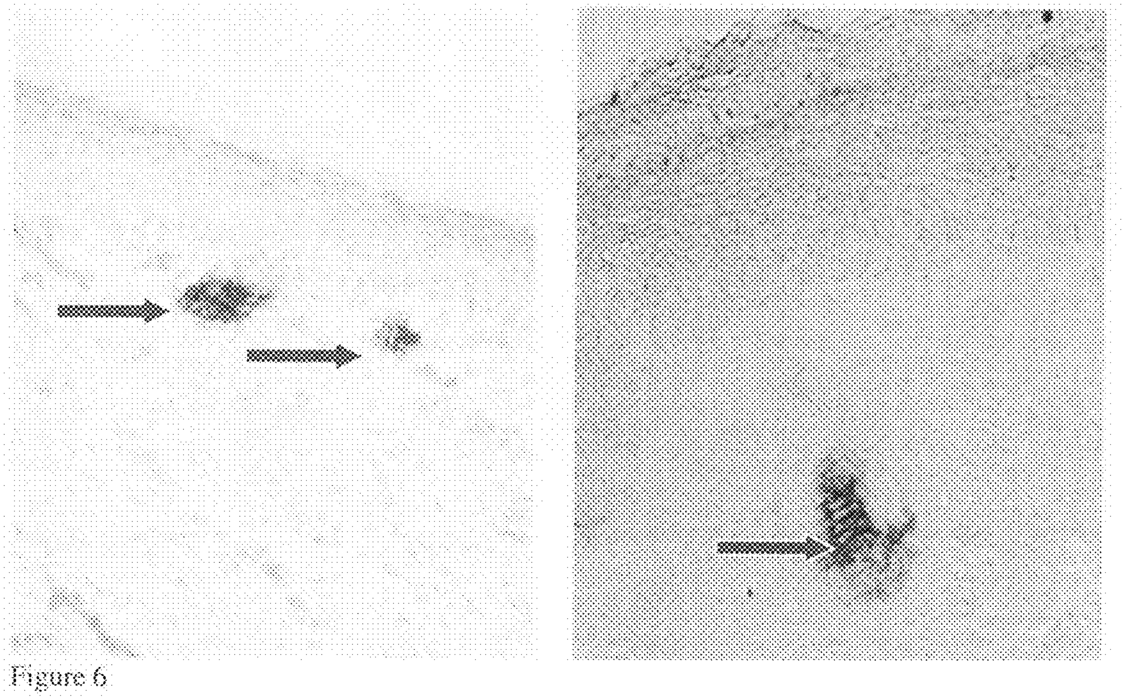
FIG. 6. EDIHN-induced hair germs contain dermal papilla (DP) cells, as evidenced by alkaline phosphatase (AP) staining. Arrows indicate DP cells. Left panel: hair germs. Right panel: HF at a further developmental stage.

To test whether wounding could induce HF formation, punch wounds or excisional wounds were induced in mice. Both types of wounds exhibited contraction and re-epithelialization following wound induction; however, unlike the mice receiving punch wounds, the mice receiving excisional wounds also exhibited scar formation within 10 days of wound induction (FIG. 3, left panel). No follicles were evident at this time point (FIG. 3, right panel). 12 days after wound induction, hair germs, with similar morphology to fetal hair germs, were observed in the wound site, following BrdU pulse labeling (FIG. 4). Several markers were used to verify that the observed structures were HF. The structures exhibited staining with anti-keratin 17 (K 17), an HF marker (FIG. 5), and staining with anti-alkaline phosphatase at the 12 day time point verified that the structures had dermal papilli containing fibroblasts, as expected for HF (FIG. 6; HF at earlier and later stages are depicted in the left and right panels, respectively).

Figure 7:
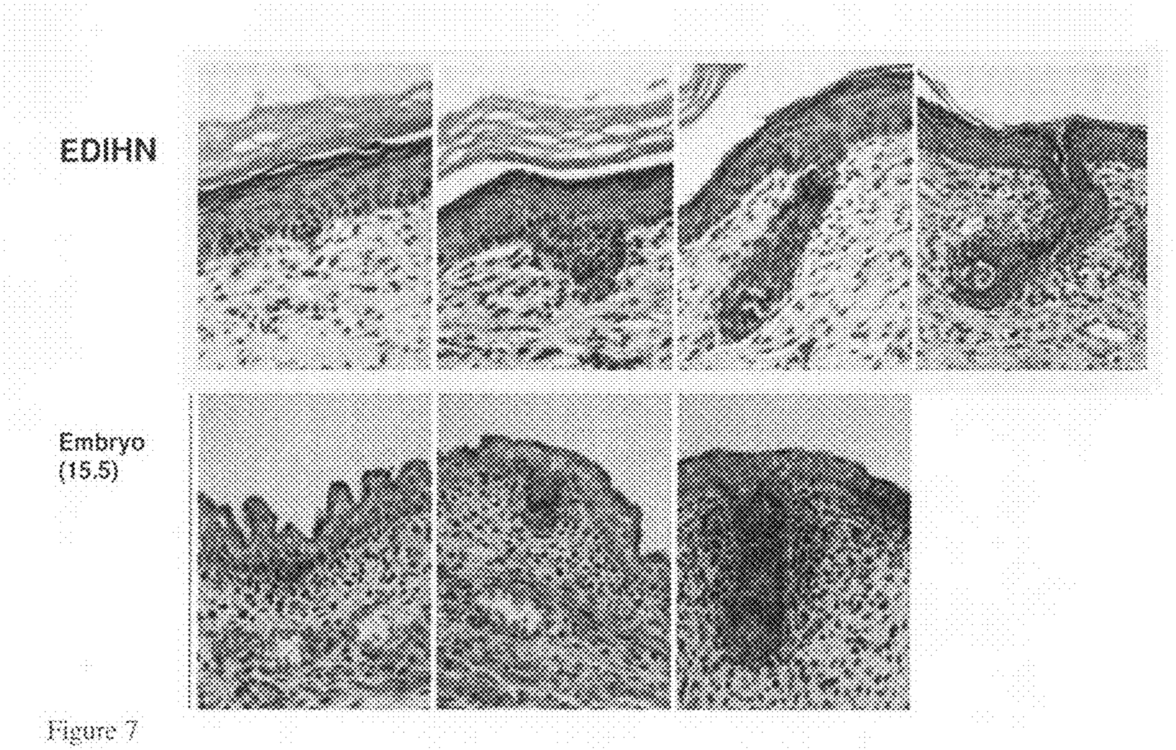
FIG. 7. Histological comparison between EDIHN-induced and embryonic HF. Top left, second from left, third from left, and right panels: Progressive stages of EDIHN-induced HF development. Bottom left, center, and right panels: Progressive stages of and embryonic HF development.
Figure 8:
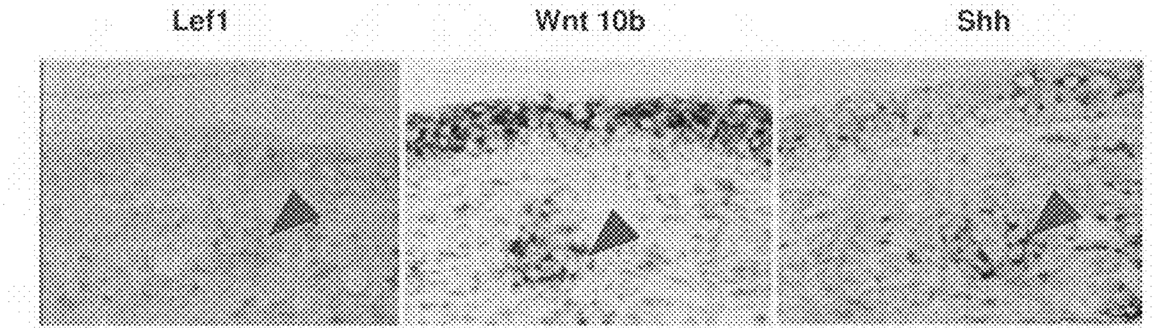
FIG. 8. Induction of several markers of embryonic HF development, Lef1 (left panel), wingless/int (Wnt) 10b (center panel), and sonic hedgehog (Shh; right panel), by EDIHN. HF structures are indicated by arrowheads.
Figure 9:
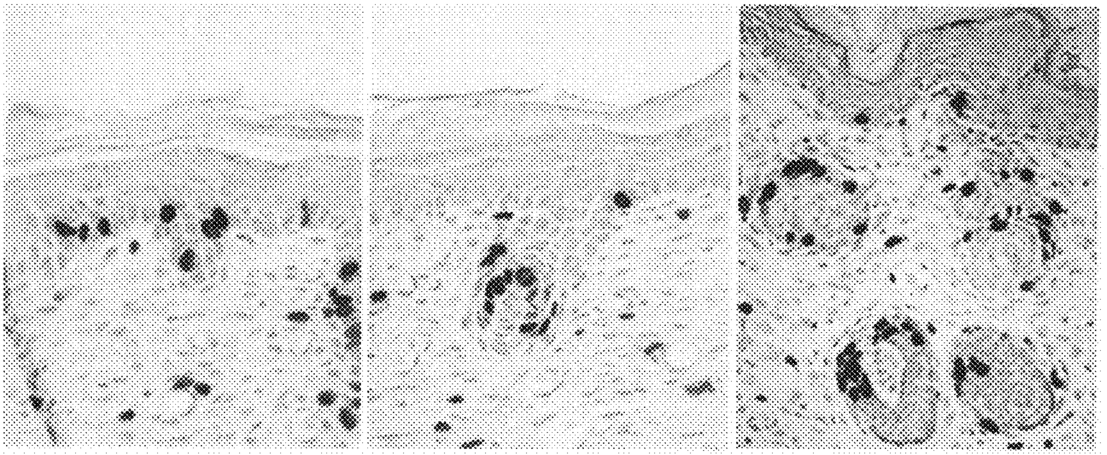
FIG. 9. Proliferative activity during EDIHN, as evidenced by BrdU pulse-labeling. Progressive stages of HF development are depicted in the left, center, and right panels.
Figure 10:
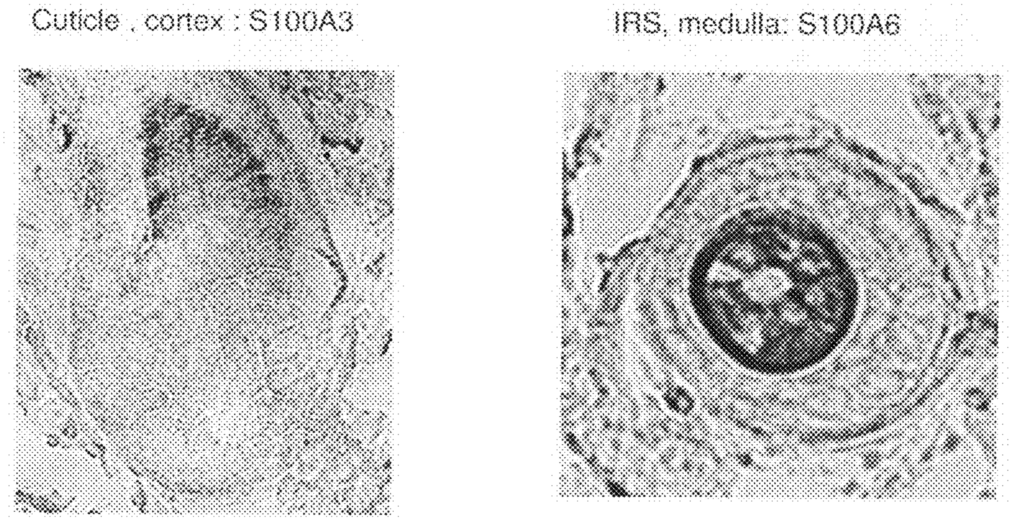
FIG. 10. Induction of HF markers S100A3 (left panel; tissue section parallel to HF axis) and S100A6 (right panel; cross-sectional view of follicle) by EDIHN.

The HF generated by wound induction were further characterized by morphological comparison to embryonic HF, following BrdU staining; a clear correspondence in morphology was observed at various stages (FIG. 7). In addition, several markers of embryonic HF development, namely Lef1, wingless/int (Wnt) 10b, and sonic hedgehog (Shh), were also induced in the epidermal disruption-induced HF neogenesis (EDIHN) (FIG. 8). Additional BrdU staining (FIG. 9) and staining for HF markers S100A3 and S100A6 (FIG. 10; left panel: tissue section parallel to HF axis; right panel: cross-sectional view of follicle) provided further verification that the development of the EDIHN follicles closely paralleled embryonic HF development.

These findings provide further evidence that disruption of the epidermis causes generation of new HF, and that this generation of new HF can occur (b) in adult subjects and (c) during telogen (21-day-old mice are in the first telogen stage of the hair cycle).

Example 3

EDIHN-Induced Hair Follicles Generate Hairs

Figure 11:
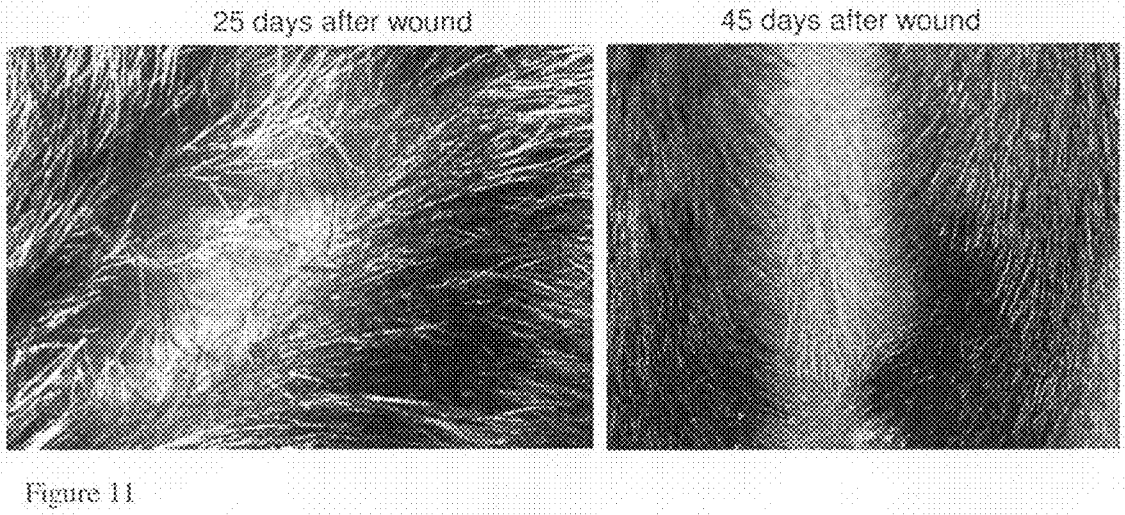
FIG. 11. New hair growth 25 days (left panel) and 45 days (right panel) after wound induction.

At 25 and 45 days after wound induction, wound sites contained new hairs (FIG. 11, left and right panels, respectively). New hairs appeared to lack pigmentation, except when the wnt pathway was inhibited, using Dkk-1 (Dickkopf-1) during the first nine days after wounding (see Example 10).

These findings indicate that EDIHN-induced HF function normally; i.e. are capable of generating hairs.

Example 4

EDIHN Hair Follicles Retain the Ability to Enter into Cyclical Hair Growth

Materials and Experimental Methods

BrdU Labeling 50 mg/kg bodyweight BrdU (Sigma) was injected twice per day for 3 days beginning 20 days after wounding. BrdU was detected 40 days after wounding (17 day chase).

Whole Mounting and Immunofluorescence

Figure 12:
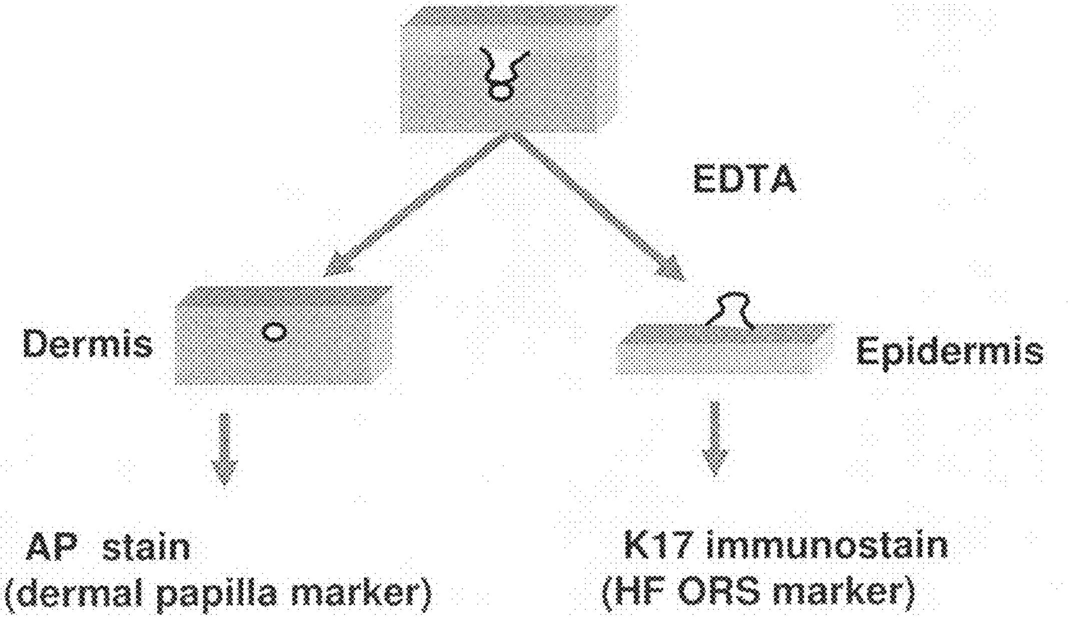
FIG. 12. Schematic of whole-mount EDIHN assay.

HF whole mounts were obtained by incubating fresh skin with EDTA (20 mM in PBS) at 37° C. overnight, then separating the epidermis and dermis. Epidermis was then fixed in 10% formalin for 10 min, room temperature (RT). Dennis was fixed in acetone overnight, RT. After rinsing with PBS, whole mounts were stained with antibodies for immunohistochemistry (schematically depicted in FIG. 12) and were imaged using a Leica confocal microscope.

Results

Figure 13:
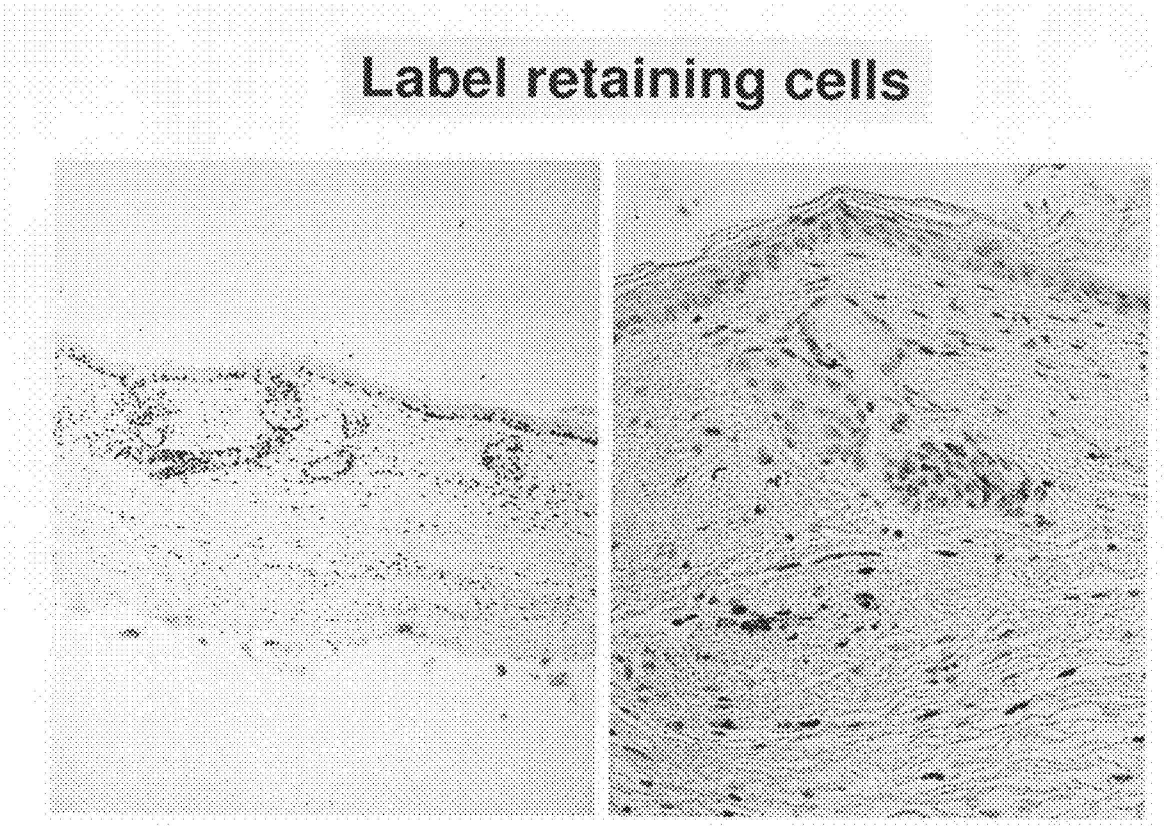
FIG. 13. Repopulation of stem cells in the bulge of EDIHN-induced HF, as evidenced by retention of BrdU label following a chase period. Left panel: lower magnification: 50×. Right panel: higher magnification: 400×.
Figure 14A:
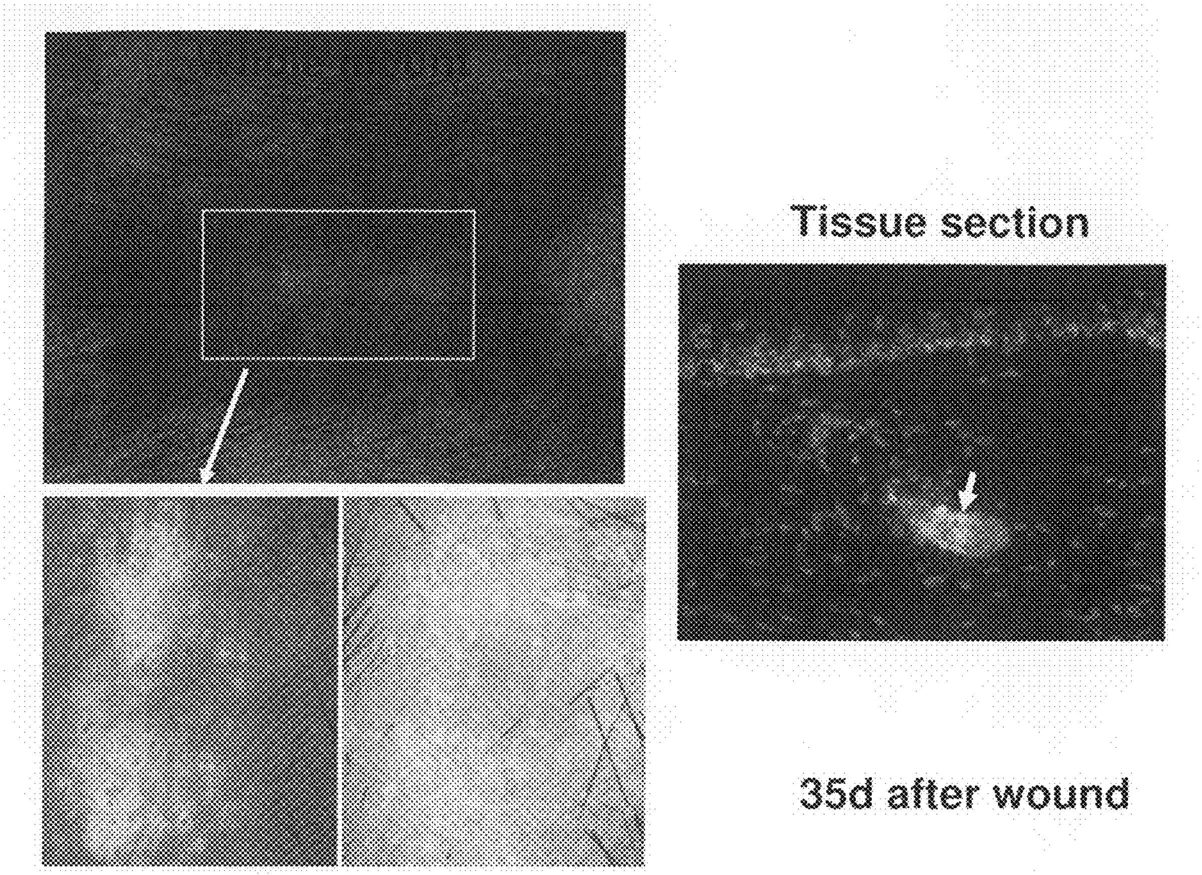
FIG. 14. A. Stem cells in EDIHN-induced HF express K15. Left top panel: Top view of wound site. Bottom, far left panel: epidermis whole mount; bottom, second from left panel: same as [bottom, far left] panel but viewed under white light; right panel: tissue sections. B. Neogenesis HF proceed to next hair cycle.

To determine whether EDIHN-induced HF contain normal levels of HF stem cells, mouse skin was examined for the presence of label-retaining cells at 21 days after wound induction. Retention of BrdU during a long chase period is, under these conditions, one of the hallmarks of HF stem cells. Normal numbers and placement of label-retaining cells (in the bulge of the HF) were observed (FIG. 13). To verify that the label-retaining cells were HF stem cells, K15-eGFP mice were utilized. In these mice, eGFP (enhanced green fluorescent protein) is expressed from the K15 promoter; thus, expression of eGFP identifies HF stem cells. As depicted in FIG. 14A, eGFP-expressing cells were observed in tissue sections (right side) of newly formed hair follicles 35 days following wound induction. eGFP-expressing cells were also seen in the epidermis whole mounts (bottom, far left panel) indicating the conversion of epidermal cells into cells with hair follicle stem cell characteristics. ([bottom, second from left] panel is same as [bottom, far left] panel but viewed under white light) This finding shows that the observed label-retaining cells exhibited HF stem cell properties.

Figure 14B:

To determine whether EDIHN-induced HF cycle normally, mounts were prepared from additional mice at 35, 38 and 45 days after wounding. As depicted in FIG. 14B, the EDIHN-induced HF entered the resting phase, telogen, and then re-entered a new anagen stage.

Figure 15:
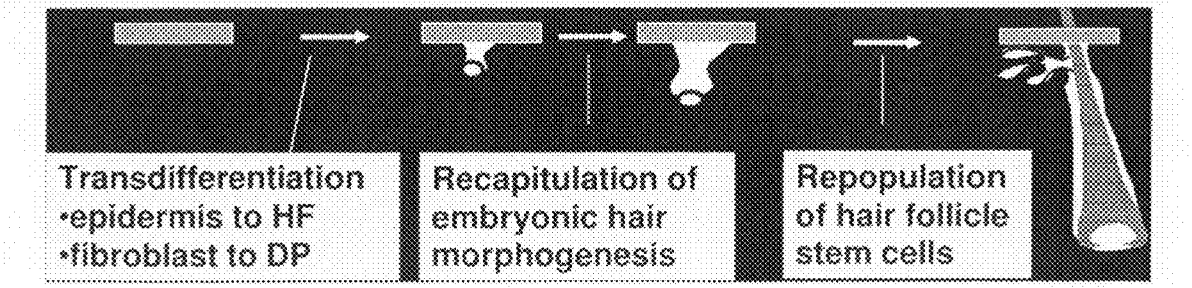
FIG. 15. Schematic of creation of new HF by EDIHN.

In summary, the findings of this Example show that EDIHN-induced HF contain HF stem cells, as do embryonically generated HF. The presence of the HF stem cells shows that EDIHN-induced HF retain the ability to enter into cyclical hair growth in the same manner as embryonically generated HF. The findings also show that wounding induces epidermal cells to assume a hair follicle stem cell state (expressing K15-eGFP). This model is shown schematically in FIG. 15. The findings of Examples 2, 3, and 4 show that EDIHN-induced HF are fully functional and thus able to restore hair growth to a subject in need.

Example 5

Figure 16:
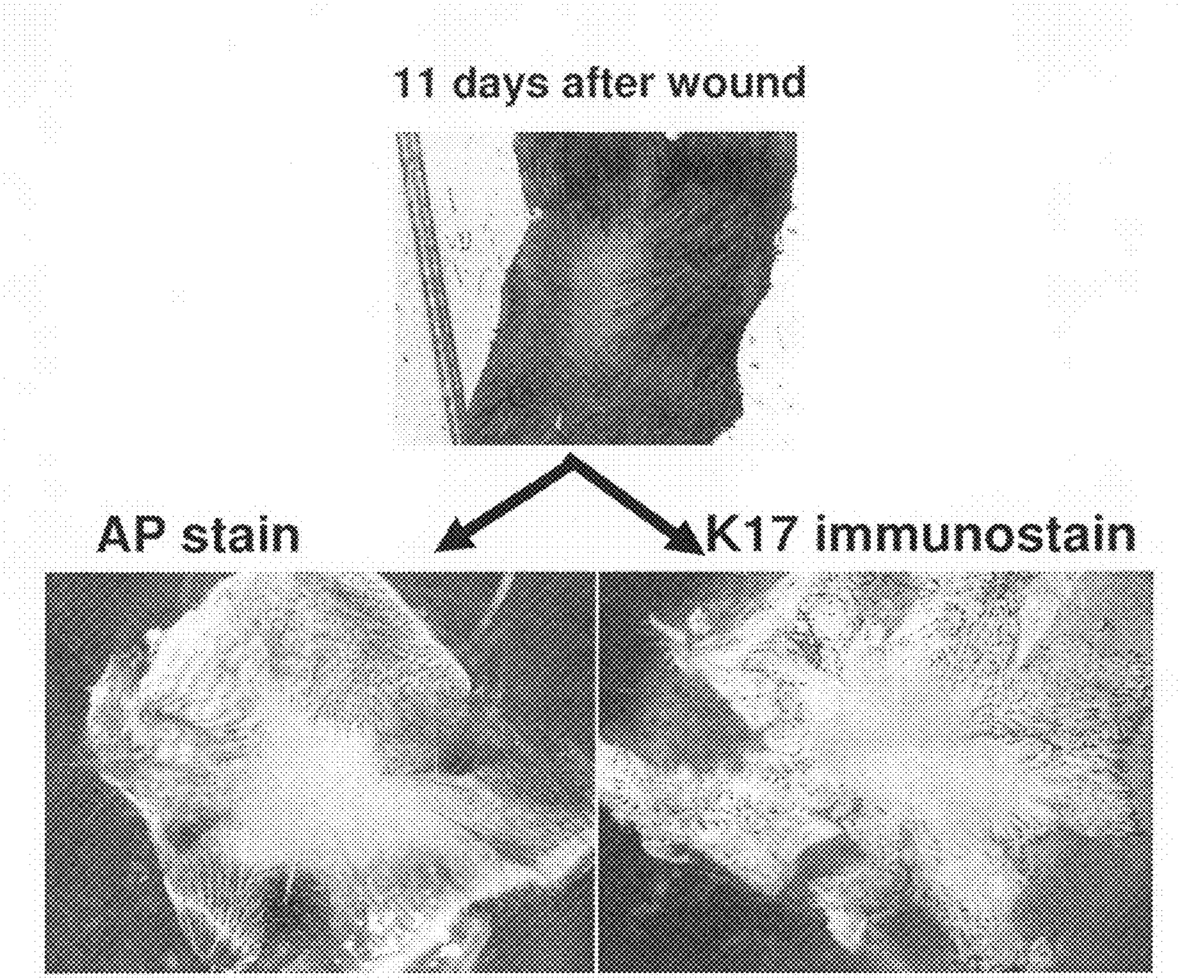
FIG. 16. No new HF are evident 11 days after wound induction in 21-day-old mice. Top panel: macroscopic examination; bottom left panel: AP staining of the dermis; bottom right panel: K17 staining of the epidermis.
Figure 17:
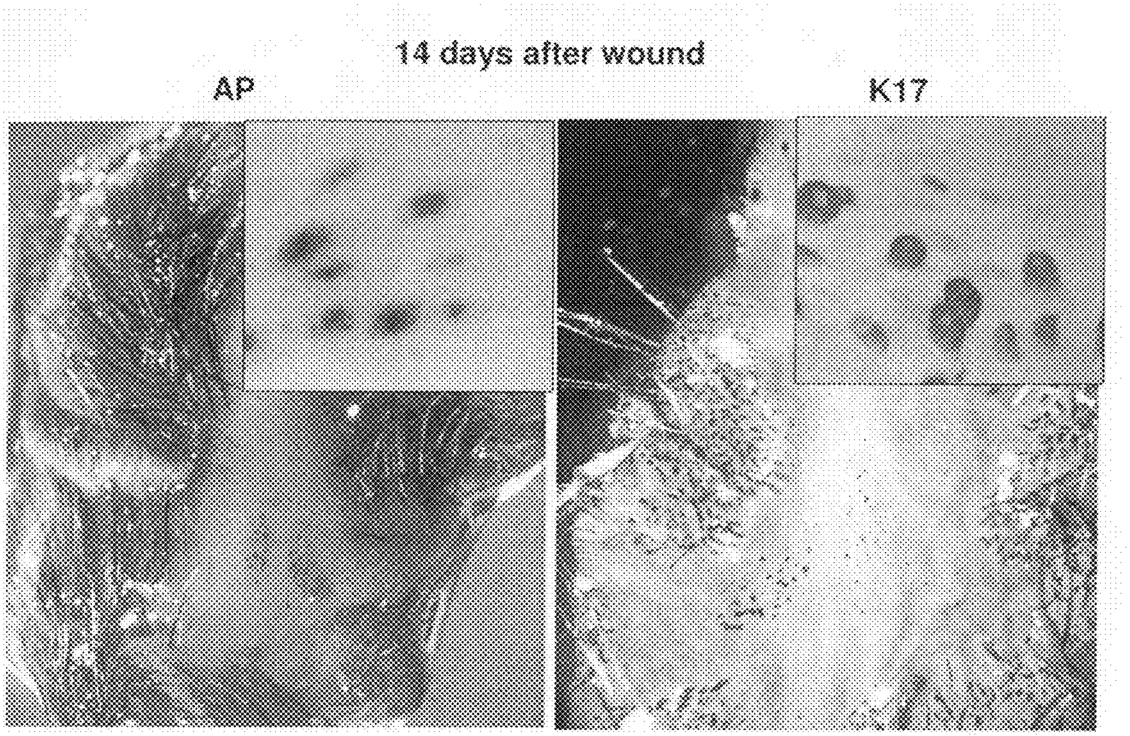
FIG. 17. 14 days after wound induction, new HF have begun to form as evidenced by AP staining of the dermis (left panel) and K17 staining of the epidermis (right panel). Main panels: 10× magnification. Inserts: 80× magnification.
Figure 18:
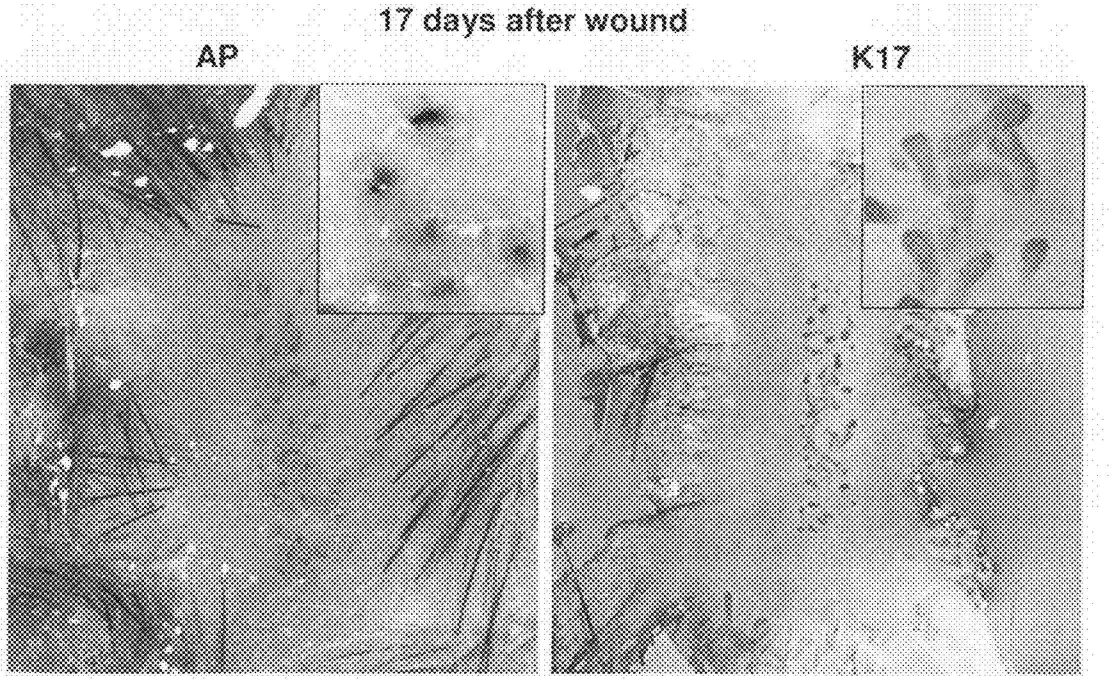
FIG. 18. 17 days after wound induction, new HF are more developed. Left panel: AP staining of the dermis; right panel: K17 staining of the epidermis. Main panels: 10× magnification. Inserts: 80× magnification.

EDIHN-Induces New Hair Follicles in Mice at the Telogen Stage of the Hair Cycle To determine whether EDIHN was induced new hair follicles in mice wounded at the telogen stage of the hair cycle, 21-day-old mice were subjected to EDIHN using a 1-cm excisional wound, as described in Example 2. Skin was then examined by whole-mount assay for indications of new HF. As depicted in FIG. 16, after 11 days, new HF were not evident by macroscopic examination (top panel), AP staining of the dermis (bottom left panel), or K17 staining of the epidermis (bottom right panel). After 14 days, as depicted in FIG. 17, dermal papilla cells were detected in the dermis (left panel) and HF stem cells in the epidermis (right panel), demonstrating that new follicles were being formed. After 17 days, the new follicles were more developed, as shown by examination of the dermis and epidermis (FIG. 18, left and right panels, respectively). This method induced formation of an average of 49 new follicles in the wound, a number that was consistent over three separate experiments, as depicted in Table 1.

TABLE 1

Results of three separate experiments performed on 21-day-old mice.

| Sample | Expt 1 | Expt 2 | Expt 3 | Avg of expts | Std dev of expts |
|---|---|---|---|---|---|
| 1 | 24 | 70 | 55 | | |
| 2 | 29 | 52 | 25 | | |
| 3 | 27 | 85 | 53 | | |
| 4 | 102 | 25 | 80 | | |
| 5 | 53 | 27 | 23 | | |
| Average | 47 | 51.8 | 47.2 | 48.67 | 2.71 |
| Std dev | 32.8 | 26.3 | 23.7 | | |

The findings of this Example demonstrate that EDIHN is capable of inducing formation of new HF in mice at the telogen stage of the hair cycle, despite that fact that these mice do not contain HF at the anagen stage during wounding.

Example 6

In Adult Mice, Induction of Anagen Increases the Efficiency of EDIHN

The experiment described in Example 5 was repeated with mice of different ages, and therefore at different stages of the hair cycle. To ensure that wound scarring occurred, larger wounds were in induced in the older mice. As depicted in Table 2, adult mice at telogen, such as 8-week-old mice, exhibited lower efficiencies of HF formation by EDIHN.

TABLE 2

Efficiency of HF formation by EDIHN in adult mice at various stages of the hair cycle.

| Age | Wound size | Days after wound | Mice exhibiting EDIHN | Hair cycle |
|---|---|---|---|---|
| 3 wk | 1 cm | 20 | 25/25 (100%) | Telogen |
| 4 wk | 1 cm | 20 | 5/5 (100%) | Early anagen |
| 5 wk | 1 cm | 20 | 1/2 (50%) | Anagen |
| 8 wk | 1.5 cm | 30 | 16/35 (46%) | Telogen |
| 14 wk | 1.5 cm | 30 | 1/2 (50%) | N/A* |
| 20 wk | 1.5 cm | 30 | 2/2 (100%) | N/A* |

*The second telogen lasts approximately 40 days in mice. Thus, 14-week-old and 20-week-old mice contained a mixture of telogen and anagen HF.

Figure 19:
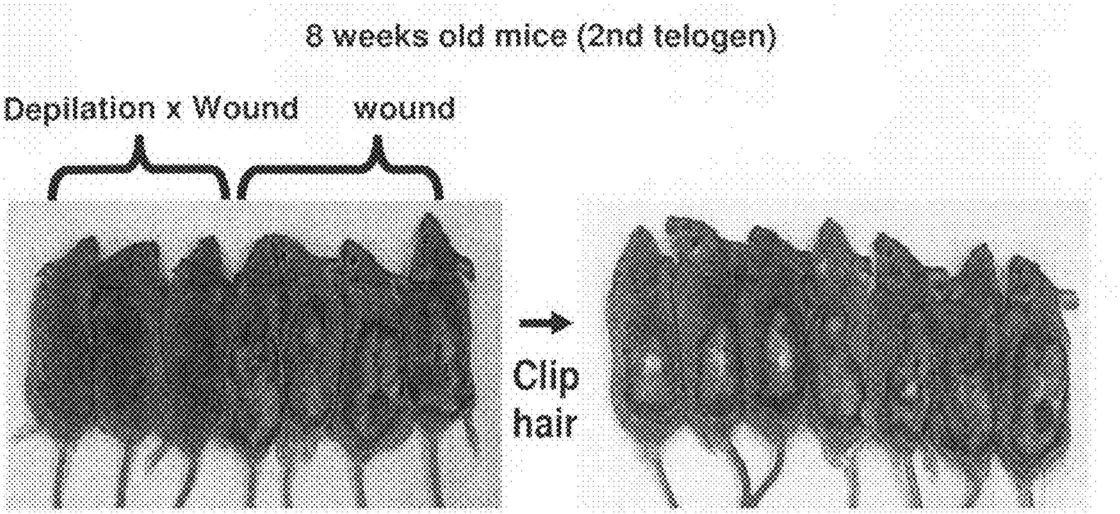
FIG. 19. Wounds closed similar in mice subjected to depilation, then wounding (left 3 mice in each panel) vs. wounding alone (right 4 mice in each panel). Left panel: immediately following wounding. Right panel: 10 days following wounding.
Figure 20:
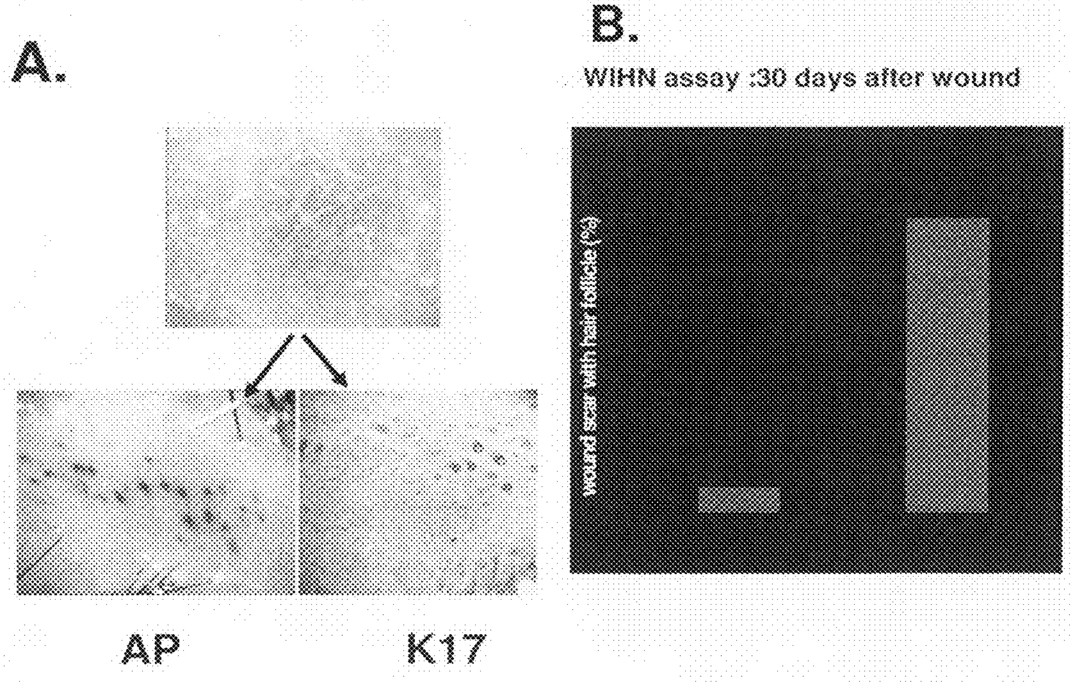
FIG. 20. Anagen induction by depilation prior to wounding enhances the efficiency of EDIHN. A. Top panel: lower left panel AP staining of the dermis; lower right panel: K17 staining of the epidermis. B. Graphical representation of enhancement of EDIHN by depilation.

To determine whether experimental induction of anagen increased the efficiency of EDIHN, 8-week-old mice were depilated several days prior to wound induction. As depicted in FIG. 19, the wounds closed similarly whether or not they were preceded by depilation. As depicted in FIG. 20A-B, the depilated mice exhibited enhanced EDIHN relative to the non-depilated mice depicted in the previous Example by a factor of 11-fold.

The findings of this Example demonstrate that anagen induction enhances EDIHN. In addition, these findings show that EDIHN is capable of not only forming new HF, but also of activating anagen in pre-existing HF in the telogen stage.

Example 7

EDIHN-Induces New Hair Follicles in Human Skin

Materials and Experimental Methods

Grafting

Discarded human adult scalp from the preauricular area obtained from plastic surgery was grafted onto immunodeficient (scid) mice. The graft was bandaged and allowed to heal, then was used in the wound healing study 3 months after grafting.

Results

Figure 21A:
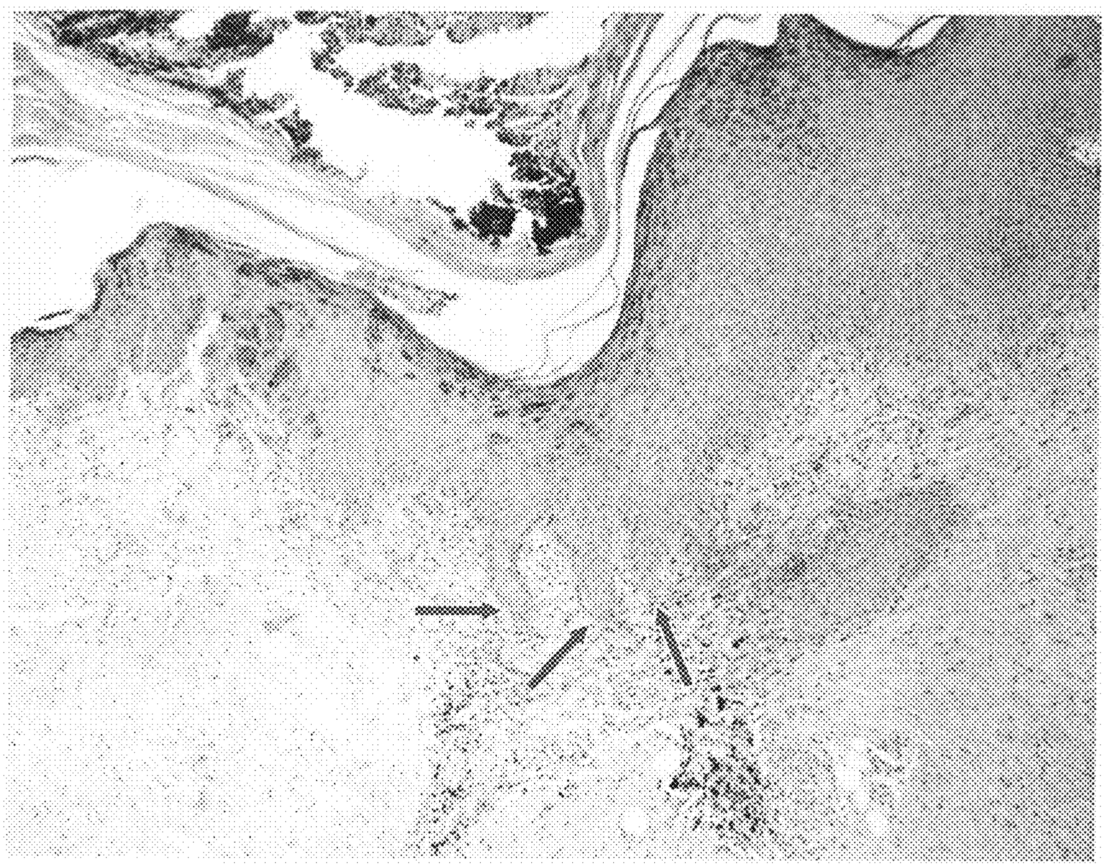
FIG. 21. A. EDIHN in human skin grafted to immunodeficient (scid) mice, seven days after induction of an excisional wound. Arrows indicate new HF. B. Dermal abrasion of human skin grafts results in EDIHN. Human adult skin (W) was grafted onto mice, abraded, and examined seven days later, by staining for S100A6 (first, second, and fourth rows) or S100A4 (third row). Hair germs (HG) and dermal papilla (DP) are indicated. Human fetal skin (F) with normal developing hair follicles is shown for comparison. Mouse skin 17 d post wounding was included as a control (top left panel).

To determine whether human skin responded to EDIHN as did mouse skin, human skin was grafted onto SCID (immuno-deficient) mice and subjected to depilation by plucking and wound induction three days later. Seven days following wound induction, formation of new HF was observed in the human skin (FIG. 21A; arrows indicate new HF) by hematoxylin and eosin staining of paraffin embedded tissue sections.

Figure 21B:
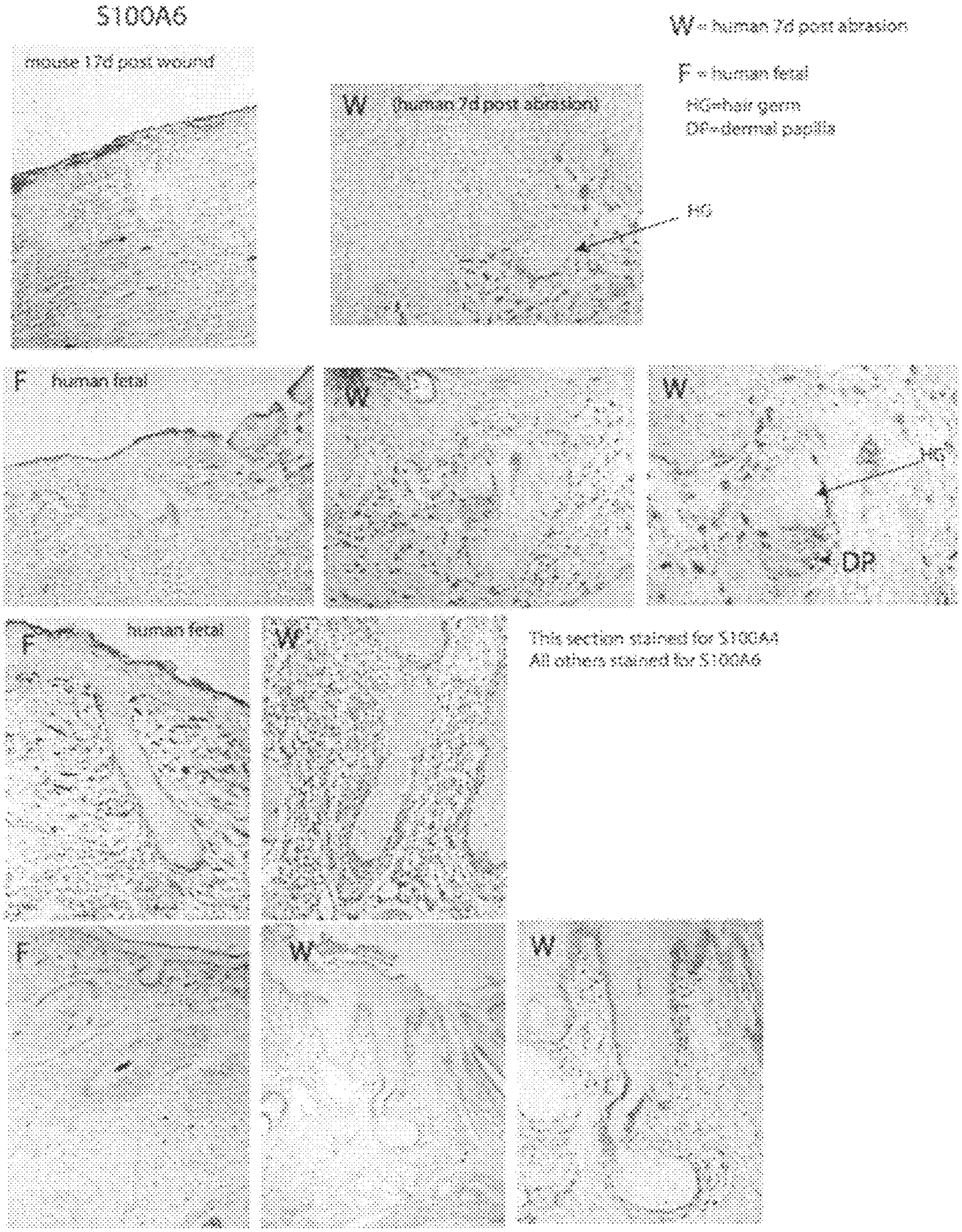

In additional experiments, adult human skin was grafted onto mice, abraded, and examined at 7 days post-abrasion. New HF were generated in the human skin, which mimicked normal hair follicle formation during fetal development, as evidenced by staining for S100A6 or S100A4 (FIG. 21B).

The results of this Example show that EDIHN can be used to generate hair growth in human skin as for mouse skin.

Example 8

Molecular Pathways Activated During HF Stem Cell Activation

Materials and Experimental Methods

Isolation and Activation of HF Stem Cells

K15-eGFP mice were depliated in order to induce formation of new HF. Activated hair follicle stem cells were isolated from K15-eGFP mice using fluorescence-activated cell sorting (FACS) two days after depilation and 5 μg (micrograms) total RNA from the cell population was isolated, reverse-transcribed and hybridized to an Affymetrix (Santa Clara, Calif.) array MG_U74v2 chip. Scanned chip images were analyzed using Affymetrix Microarray Suite 5.0 and GeneSpring software (Silicon Genetics) to detect fold-change differences between activated HF stem cells (HFSCs) and non-activated (telogen) HFSCs. Values were normalized before computing fold-changes and differences between non-activated "bs-line" and activated ("expt") samples.

Results

To identify molecular pathways up-regulated during HF stem cell activation, activated HF stem cells were isolated, and the gene expression patterns of the cells were analyzed to detect up-regulated transcripts. The transcripts depicted in Table 3 were up-regulated at least 2-fold in the activated HF stem cells relative to the cells prior to activation. In some cases, the sequence in Table 3 is a genomic sequence that contains the sequence of the transcript. Data pertaining to the up-regulation of the transcripts and further information about them is provided in FIG. 22.

TABLE 3

RNA transcripts up-regulated during HF stem cell activation.

| SEQ ID No: | Access. # | Sequence |
|---|---|---|
| 1 | AW047343 | uuuuuuuuuuuuuuuuucuuaaaaauauaaauguauuugucugcaucaugacguucuucg<br>ggcaccuagcuggccagaccacuggccaugggacaaggaggaagucagguguaagucugagc<br>aaggaacaggacucugcccuggcaggguggagguggccucacagugucccaugcugggccug<br>guagcgugaaagcacagcacgguagugggacagcuccugccgcacagccaccaccuccugccg<br>caacagggcguuuuccuucuccaggaaggcagcccgcacagauauccgguucuccuugaguc<br>uucuugcaucuc |
| 2 | AF053235 | Sequence below.<br>caguuccucagcauggccaccugcagccgccaguucaccuccuccagcuccaugaagggcuccuguggcaucgguggugg cu<br>cuagccgcauguccuccauccuggcuggaggauccugccgggcucccagcaccugcgggggcaugucaguuaccuccucucg<br>cuucuccucugggggagucugugggauuggagguggcuauggugggagcuucagcagcagcaguuuugguggaggacuug<br>guaguggauuugguggucgauuugauggauuuggugugguuuuggugcuggucuugguggugguc uuggcgguggua<br>uuggugaugggcuccuggugggcagugagaaagugaccaugcagaaccucaaugaccgccuggccaccuaccuggacaaggu<br>gcgugcccuggaagaggccaacagagaccuggaggugaagauccgggacugguaccagaggcagcggcccacugagaucaaa<br>gacuacagccccuacuucaagaccauugaggaccugaagagcaagaucauuauugccacccaggagaaugcacaguucacuu<br>ugcagauugacaaugccaggcuggcagcugaugacuucaggaccaaguacgagaaugagcuguucuugcggcaguccgugg<br>agggugacaucaauggccugcgcaaggugcuagaugagcugacccuguccagagcugaccuggaaaugcagauugaaaaccu<br>cagagaagagcuggccuuccugaagaagaaccaugaggaggagaugcuugccuugaggggucagacugguggggacgucaa<br>uguggagauggacgcagcccccgguguggaccucagccgcauucugaaugagaugagggaccaguaugagcagauggcaga<br>gaagaaccgcagagauguggaggccugguuccugagaaagacugaggagcugaacaaagagguggccucuaacagugaucua<br>auccagagcaaccgcagcgagguggcugagcuccgcaggguguuccagggccuggagauugaacugcagucccagcucagca<br>ugaaagcauccuuggagaacagccuagaagagaccaaaggcagauacuguaugcagcugucccagauccagguuugaucag<br>cagugugga ggagcagcuggcucagcuucgcugcgagauggagcagcagagccaggaguacaacaucuuguuggaugugaa<br>gacaaggcuggagcaggagaucgccaccuaccgccgucugcuggauggcgagaauauccacuccuccucacagcacuccucu<br>ggacaguccuauucuucucgagaagucuucuccucauccucccgccagccccgguccauccucaaggagcaagguucaacca<br>gcuucagccagagccaaagucagaguuccagggacuaauguuuugccuagagccuccucacccacaacugccucucaagcug<br>agggcuuggggcaggacccuguuuucuuugcgcauuccccaucugucuccccuacccucucaugguggu aggcuaauaaag<br>cuuuugguugaugcaaaaaaaaaaaaaaaaaa |
| 3 | M26005 | gcgccaguccuccgauagacugagucgcccggguacccguguucucaauaaagccucuug<br>cuguuugcauccgaaucguggucucgcugguccuugagaggucuccucagauugauugac<br>uacccacgucgggggucuuucauuuggaggccccagcgagauuuggagaccccugcccaggg<br>accaccgacccccgucgggagguaagcuggccagcggucguuucgugucugucucugucuu<br>cgugcguguuugugccggcauuuaauguuugcgccugcgucuguacuaguuagcuaacuag<br>aucuguaucuggcgguuccgcggaagaacugacgaguucguauucccggccgcagccccugg<br>gagacgucccagcggccucgggggcccguuuuguggcccauucuguaucaguaaccacccga<br>gucggacuuuuuggagcuccgccacuguacguggcuuuguuggggga cgagagacagagac<br>acuucccgcccccgucugaauuuuugcuuucgguuuuacgccgaaaccgcgccgcgcgucug<br>auuuguuuguuguucuuuuguucuucguuaguuuucuucugucuuuaaguguuuuucgag<br>aucaugggacagaccguaacuaccccucugaguuuaaccuugcagcacuggggagaugucca<br>gcgcauugcauccaaccagucuguggaugucaagaagaggcgcuggauuaccuucuguuccg<br>cugaauggccaacuuucaauguggauggccucaggaugguacuuucaauuuaaguauuau<br>cucucagguuaagucuagaguguuuuguccugguccccacggacacccggaucagguccca u<br>auaucgucaccugggaggcacuugccuaugacccccuccgugggucaaaccguuugugucu<br>ccuaaacuuccucccucgccgacagcucccguccucccgcccgguccuucugcgcaaccuccg<br>ucccgaucugcccuuuacccugcccuuaccccucuauaaaguccaaaccuccuaagccccag<br>guucucccugauagcggcggaccccucauugaccuucucacagaggaccucccgccguacgg<br>agcacaaccuuccuccucugccagagagaacgauaaagaagaggcggccaccaccuccgaggu<br>uucccccccuucucccauggugucucgacugcggggaaggagagacccucccgcagcggacu<br>ccaucaucucccaggcauucccacuccgcauggggggagauggccagcuucaguacuggccg<br>uuuuccuccucugauuuaacccuuccuuuucugaagauccagguaaauugacggccuuga |

TABLE 3-continued

RNA transcripts up-regulated during HF stem cell activation.

| SEQ ID No: | Access. # | Sequence |
|---|---|---|
| 4 | AA681998 | gacguagagccccuugcgcccgguuuccugaucccgcuuacuccucugcgcgccggcaggau<br>ggcccacaagcagaucuacuacucagacaaguacuucgaugagcacuacgaguaccggcaugu<br>cauguuacccagagaacucucuaaacaaguacccaaaacucaucugauguccgaagaggagug<br>gaggagacuugguguccaacagagucuaggaugguucauuacaugauucaugagccagaac<br>cgcauauucuucucuuuagacgaccucuuccaaaagaacaacaaaaaugaagugcagcuggga<br>ucaucuaaucuuuuucaaauuuaauguauauguguauauaagguaguauucagugaauacu<br>ugaaaaguguacaaaccuuucauccauaccugugcaugcgcuguauucuucacagcaacaga<br>gcucagucaaaugcaacugcaaguagg |
| 5 | AF057156 | atuaaaaagccagcugcccaaugccugcacacagaauccacaccaacagagaaccugcucuucu<br>cugaguauuagguaagucucugcuugcaacugauuugaaauucuugcuuauuuuuuuacua<br>ugaaaaacuguucaaagccaacucuauuacagaguugaugugggugcugccuacaguuagu<br>gaacaguagcauuguuugcuuaaauuauagcacauuuuggucuaggaacuugagagguga<br>uucaguuggucacuguaguagacagccuuggaaucagagauuaaggcaaaaggaaaccucca<br>uucaaauauucauggaaguucacagcuggagacagguuaaggcuucaguccagauagcuuuc<br>agaauuauugcaguucuuacugauaggcauaucaauagcgaaauuuaauuuauuagaggaau<br>cuacuaaaguaaauuuuuaggccaauauagaacauaccauacuuguagucuggcagagaagg<br>ugacauaugaaauugaaaugcgauucauagacagugguagugaaagaaauaaugguggggan<br>gggcugugcangggaggcauggcucaaggacagcacuuagugguagcacacaccaugaacua<br>ugauggaaaagcauuugauaggcagagacagaaauguaggaaauguguagggauccaugaga<br>gcauaaacuaaaagggcaaaagcauaugagcauggacuaacaugcagccacucugcaaguuau<br>acuaugaucuauuucacaaggagguugguaugcugcugucuuuggguggacaccgcuuuccc<br>agauguccugguguguagguucacaagccucucagaagccauacuuuauugcuuuuuaaga<br>cguauuauuaauauuuuggcuagcauaugguuuagugugagaguuuuauaugcauauguca<br>uuauacuuugcucauuuaugucuuggaacuucuucaacuagguagaaaacaugaccagggag<br>aaugagaguaaggaaagaacccacugagacagacaagagcaaaccauacuucugcuaaucaug<br>uuuaaaaguccagaaaugaucauaccauauuuuauuuucaagugugggaagucagcauggaga<br>ggggcucuuuuucucuaaaggggccugaaauuaaauugacuugauguugagguuaccuucu<br>cuuucaaugaaucacuaaauugucuuuucuguuucccaggacccaagugcuaucuaaccaug<br>aguucccaccagcagaagcagcccugcacuguaccuccucagcugcaccagcagcaggugaag<br>cagccuugccagccaccaccccaggaaccuugugcccccaaaccaaggaucccugccacccu<br>guuccugagcccugcaaccccaaggggccagagcccugccaccccaaggcacccgagcccugc<br>caccccaaggcaccugagcccugcaaccccaaggugccagagcccugccagccuaaggugcca<br>gagcccugccagccuaaggugccagagcccugcaaccccaaggugccagagcccugccaaccu<br>aaggcaccagagccuugccaccccaaggcgccugagcccugccacccuguuguucccgagccc<br>ugccccucaacugucacuccaucaccauaccagcagaagacaaagcagaaguaauauugucca<br>gagccaugccugaagaccugaucaccagaugcugaggcugcugucuauccugcuuaugaguc<br>ccauugccuugugcuaccaaugcugugaccuucagucuuaaucccucucuccuugcaccacc<br>uaaaaaguugacucucauccucaucuucaagggcuccugagccucuuaacauugcccaaagu<br>cauauugaauggcuacacuuuucauggcucaggauucaucugaagggggugaggagugaga<br>caaguguauggucaauauuuucccccauuaaaugccauuuaacucc |
| 6 | AI845584 | uuuuuuuuuuuuuuuuuuagccaaaauaguuauuuauuaauaauuuaagguuuuacauucu<br>uauaauaaauuccagcucaaaacuuuacaccacgaacaucauggagcaaguuaauucucccuu<br>ccucucaaccuguugcauccaccaaaugggcgcucauacucgcacacauacacacacuuccag<br>uuucguauuuuuuuuuaaaaggaaagaaaccaacccaaaguauugcauuugaggugacacuc<br>ccugaa |
| 7 | AA614971 | aagaugcccuuuggauuggauuggauugaucauguuuaacucagcguauuuuauggaugaa<br>agcuaaauacagauauuuggcaucucuaagguggaaugagcccacuccacacacugauaaaau<br>ucaugcauaguuu |
| 8 | AV374591 | aaccaaaugggaauggggucccaacnuuncugugguaccagccggguuucucuugcauug<br>gaaacaaacaccuuuguaggcauuugcguauucgugaagagacuguuuuaugaaucaccucu<br>uagauuuaunuaauuaaccuaaguuguugaaguuucuguuucuccuuaagagaaauuacaa<br>aaauucaacauugaagcauaguuucuuguuuucuguugucaaauaguaauaaugugcugug<br>auguuuaugcuuauucauaaagauguuuuacuuuuuaguguaauguuaguucuuuuuaaca<br>uuauuuugcuuaaauuugauaaugcccgacaagaauauauuuugcuuugauuuauacacug<br>auucuuugugacaaauaugacccauuaaaaaugccuuuuaauagacuaacuuaccuuuugua<br>gcuagguacucauguucuuuuuuaaaagaugcccuuuggauuggauuggauugaucauguu<br>uaacucagcguauuuuauggaugaaagcuaaauacagauauuuggcaucucuaagguggaau<br>gagcccacuccacacacugauaaaauucaugcauaguuuaaaugaacauuaauaaacucaug<br>uugucuu |
| 9 | U04443 | gaauucaaggaggcuuuccagcuguuugaccgaacaggugauggcaagauccuguacagcca<br>gugugggaugugaugcgggcccugggccagaacccuaccaacgccgaggugcucaagguuc<br>uaggaacccccaagagugaugagaugaaugugaagguacuggacuuugagcacuuccugccc<br>augcugcagaccguggcgaagaacaaggcccagggaaccuacgaggauuauguugaaggccu<br>ucgugugguuugacaaggaaggaaauggcaccgucaugggugcugaaauccgucauguccua<br>gucacacugggcgagaagaugacagaggaagaaguagagaugcuaguggcagggcaugagga<br>cagcaaugguugcaucaacuaugaagcauuugugaggcauauccugucggggugacgggccc<br>gauggggcggagcucguccggauggugcugaauggcugagacauucuguaucccgagucug<br>uucccugcccagugugauuucuguguggcuccagacgcuccccugucacagcaccuugucccc<br>auuugguuucuuuggaugauguuugccuucaccaaauaaaauuugcucucuuugccc |

TABLE 3-continued

RNA transcripts up-regulated during HF stem cell activation.

| SEQ ID No: | Access. # | Sequence |
|---|---|---|
| 10 | Y07836 | caaccaccuccuaccugccugcccaaagcuccagggcuggagcacggagaccugucaggg<br>auggauuuugcccacauguaccaaguguacaaguccaggcggggaauaaaacggagcgaa<br>gacagcaaggaaacuuacaaacugccgcaccggcugauugagaaaaagagacgugaccgg<br>auuaacgagugcauugcccagcugaaggaucuccuacccgaacaucucaaacuuacuacu<br>uugggucacuuggaaaaagcagugguucuggagcuuacguugaagcacgugaaagcauuga<br>caaaucuaauugaucagcagcagcagaaaaucauugcccugcagagcgguuuacaagcuggu<br>gauuugucgggaagaaaucucgaggcagggcaagaaauguucugcucagguuuccagacuu<br>gugcccgugagguacuucaguaccuggcgaagcaugagaacacucgggaccugaaaucuucc<br>cagcucgucacucaucuccaucgugugguucucggagcugcugcaggguggugcuuccagga<br>aaccauuggacucggcucccaaagccgucgacuugaaagagaagcccagcuuccuagccaagg<br>gaucagaaggcccagggaaaaacugugugccagucauccagcggacuuuugcuccccucgggu<br>ggggagcagagcggcagugacacggacacagacaguggcuauggaggugaauuggagaaagg<br>ggacuugcgcagugaacagccguacuucaaaagcgaccauggacgcagguucgccgugggag<br>aacgugucagcacaauuaagcaagaauccgaagagcccccccaccacaaagagccgaaugcagc<br>ucucagaagaggaaggccacuucgcgggcagugaucugaugggguuccccauuucuugggcca<br>cacccacaucagccuccuuuuugccuucccuucuaucucaucccaccaucggccacugccuac<br>cugccuaugcuggagaaaugcugguaccccaccucugugccaguguuauacccaggccucaa<br>caccucagcugcagcccucuccagcuucaugaacccagacaagauaccgacucccuugcuucu<br>gccccagagacucccuucucuccuuuggcacauucguccccuugacucuucggccuugcuccagg<br>cuuugaagcagaucccuccuuuaaacuuagaaaccaaagacuaaacucuggagggaucuccu<br>gcugccuugcuuucuuucucccuaauuccaaaaaccacgaagguuucccugagugcagaga<br>gaucagcccacccugcagacccacagagaagauucagagugugugugagagugagugagugu<br>gcgugcgugcgugcuuguauguauguuuguauauguaggacaauaaguuccuucugacaca<br>agggagacacgagaaggauagccugacaucagaugacagacuggaggacuguagcacaucuc<br>ugggcguuucccuacccagagaagagcc |
| 11 | M21285 | Sequence below. |

uugcaggcgagggcuuccacaacuaccaccacaccuuccccuucgacuacucugccagugaguaccgcuggcacaucaacuuc
accacguucuucaucgacugcauggcugcccugggccuggcuuacgaccggaagaaaguuucuaaggcuacugucuuagcca
ggauuaagagaacuggagacgggagucacaagaguagcugagcuuugggcuucugaguuccuguuucaaacguuucuggc
agagauuuaauauucuguugauuaacuaacaacuggauauugcuaucgggguguuaaugaugcauuuaaccuauuccggua
caguauucuuauaaaaugagaaagcuuugaucacguuuugagguaauaaauauuuuauuuagcuaggauuaaccaugccac
aagacauuauauauuucuaagcacacaugauaaaugcauauacaauuuugcacaacagcuuuaauaauaacaauaaauuug
aacauucuauacagagaggaucaaagccaaggaacaugcuguuuugaugcuaggugagcauggugcucagucccuguuug
uuugcaugguguccagcuuuguuucuucucugucaucaccaccuucaggcaaauaguugaccaaccacuggccugugucug
uccacccuccaaagcccaggccaccuuucuguuuucugaaauacugauccuuccuccugaauacaucccuccuuguuccuag
cuucaagacugcugccucaaauagggauagagcaaguccccgcugcagguugugcuagaugggauggagaaauuaucuuca
uuugauacagagcaaguagauugucucgagagaaaaguuagcaugcgugguaugauuuguaaguaaagauggaagagagag
agagagagagagagagagagagagagagagagagagagguagccauaucuaacagccuacuuaccaaagaccccaggccucuc
ugcuuggcaugccuccuuucuguccauccucugaaccccagagauuagugagauuugaauaauuaaaucauuuucagagug
aagggguuaaugcagggucugugcuaggggaggguuuuagcuuuugguaacugaagauuuuuucauggaaaagucuuc
guguucaaugugccuagaacugauaacuaaacagcugacauuugucggggacagauauggugugaaacuaugaaaauauaa
gcaaaaucuucacuuggaacaugaaacuauuucacuuagaaaauaaucgaaggacccgagguguugccugguugccaguuu
cuuucguggcugggcaggaacuagugagguugaggggcagugucuguaaguagcugcuaagaggugcauuuccagaugaa
gcccuuggggaacaucugccagggauccgcaugguguuggcuccauccauugcuuuaguuuccuccuuggauuguguagaa
acuuggcuucccaugguuuugaaccuuccaugccuucuuugcuuuguggccacccagccugccuagugcugccuaggaagc
ucuuacccaccugauuucuucugacauuucuuucuuuggccuuuuuuucuuucuccggacaugcagcuaguugccugagu
guaucaagagcacccaggacuugcugcuguccaggccuguuccucccccaguauccguggguguggaagagcuguguagcu
ucaggaagcagagccaggugccaccuuucuguggcuuccagauccucccuaccuccaacucaugugccucugucacagugau
uucaggaaagcuugguagacccucuagcaacaucucgguucagaaagucucucugguuugugaguuaacagcucagcuaag
ugcuguuuugucucagugaguuaaccacugaaugcgagguugguuguugaucugucucggugugugucggaguagacag
cauaugcacuucucccugugcgcuuugcaagguaauguggcuuuggcugauccaugcaggcagguagugguacagugcugc
ugaaaggaagaaguuccccauuuuaucuguuaaaacaccagagacaugggcaagugcuaauggaccucacuucaggaagagg
gucugcuuccugaagccagugugugaugaaaagugacugagaccugauaucuaaggugagaccugauaccuaacacucugu
cacacaguccagggccaacagugcuauaggaaagucuagaagaaaacaucacaucaguauuuuagaaccaucaaccaucucuu
gucccuauagcccaauccagaggccugguuuuuagaacuggcuguguaaggugccaaacacucaguucacuuguagaaucag
agccuuuuuucccccc uauguuaauugaacacgcgcucugagcuguuuuguugaaguagaaaaucucauagaaaaaucacu
guagaucuacugaccuauagcccucuggaaaugccuuugagaugguuuuacuuuucuaggucauagaugccugauuauaaa
gaugaacaauaaaaucagcuuucuuucuuucucuucugaucuuauuccccagaucugauucaggccauguuccaaagcaagg
cuacauugagguccuggugucuuuaaguaaaggacaucuuucagauccucucaaagaaggauuuauaacaguuuccagaug
aauguacuaauagcuuugggugccuuaucucuuuccuaaucuguagugccugugagcucagucucacuccuucccuuagcc
cggagaccccuuagaucgagugggaaugaucaagaggcuggcuggagagucaucaguacauugguuugcagaaaucuuuua
caggcuacauuuuggaauuuuuuuuuuuuuaguaagugaucaaauuuggugggaaguaauucgaguguauucgauuguau
ugucguccucguuaucauugucaaacauguuauagacggcaguuggcacuggggcugcuaaucucuggguguagucucuga
aacuguagcuccagugagguggugugaaagguuagcaaagccaccaucugcuggugcuccagccaaggugccucuuagccac
ugaauugcuauguuauccuuucucuuguaacaaacccaccccagagauaaagccuuuaaucaacccaagaaacuccugggcu
aaguaucugacagucucacaucucaacagugugaauuaaguguccauagcaucagcucaggaggacacucugggagagugcu
gacaaaaaaggguuauuaauacugaccuacuacuucaagggcaguucugaggugauuagagcuuuuuuuaaaaaccaaguau
uuggggauccucagcagagguauucauacagacucccaaagaacuauauauguuccugagaccaucguuuagucuacauugc
ucuucccagagacugacagauaugaccagucaaagugcaagacuaccuacccacugccaugaaaaccauugcaggaaaccuuu
cccuuccugaaugagauuuuuuuuuucccuuuuuauguggguaauuauuugugacccaaguguaauuuggaugauuucc
auuaauaucaacucuugaagccuacuuguacugauugagauuguauuuguuccuaauaaaaguggaucugguuguacuguc TABLE 3-continued RNA transcripts up-regulated during HF stem cell activation.

| SEQ ID No: | Access. # | Sequence |
|---|---|---|
| 12 | V00756 | accacuugcagacaaaugaauuccuucgaaauguauuugagguuggaccccugugaugcuu<br>gaugcugcaacacuuaaaaccaugaagauuucucguuuugaaaggcauuuauauaacucugc<br>agcuuucaaagcucgaacaaaagcucgaagcaaaugccgagauaagagagcagauguuggaga<br>auucuuguagaugucugaauuugauggcuguuuucuaaucucuuccuuuauuauuauuuu<br>ugcuacuucuaauguauauaagcuuuuagagacaguuuuuuaucuuggucaacuuaaauaa<br>uuuuugauguaggggugguuguauuuuaauuuaauguacaguguuacaaauuaaugagu<br>ucuuuauucucuguaaaaauaacugguaaccacaaauaaaguguuugugauguuuggucgu |
| 13 | Y14296 | auguccgcggccgccuacauggacuucguggcugcccagugucugguuuccaucuccaaccg<br>cgccgccgugccggagcacgggggcgcuccggaagccgagcggcugcgacuaccugagcgcg<br>aggugaccaaggaacacggugacccgggggacaccuggaaggauuauugcacgcuggucacu<br>aucgccaagagcuuguuggaccucaacaaauaccgacccauccagacccccucggugugcagc<br>gacagucuggagagucccgaugaggauauaggauccgacagcgacgugaccaccgaaucugg<br>gucgaguccuucccacagcccggaggagagacaggauucuggcagcgcgcccagcccacucuc<br>ccuccuccacucuggaguggcuucgaaggggaaacacgccuccgaaaagaggcacaagugccc<br>cuacaguggcugugggaaagucuauggaaaauccucccaucuuaaagcccauuacagagugc<br>auacaggugaacggcccuuucccugcacguggccagacugccuuaaaaaguucucgcgcucg<br>gaugagcugacccgccacuaccggacccacacuggggaaaagcaguuccguugcccacugug<br>ugagaagagauucaugaggagugaccaucucaccaagcaugcccggcgucacaccguguucc<br>aucccagcaugaucaagagaucaaaaaaggcucuugccugccccuugugaggugcuccccau<br>ggcagccaggcagagaugggucccggaaggacagagcucccaggaaacagacugacacaugg<br>aaaucugccacagcagaggcgcgcuggccacaggaggucacugcuucuuuggccaauauucu<br>gauaucucccugcacuguuuccaaaaagcacaugguagcccuaaggucaaagucaacauuug<br>guccccuugcagaggcaacucugaaccgucucugacugaagauucagacuggugguguacau<br>acgucunacugggugaguugaccccuggccucccacagugcagaaccacucucuugaaucac<br>auuaacuuuugagauuuaaaaaaaacccaaacccaacccnncaaaacnccaganacaccgaaac<br>ucuggauccucgaugcuugcugacucucagaauugnuunuucuucucanuuaugcaagcna<br>gagcacaccuacuccagcaugauuugucaucuaaagacuugaaaacaaaacaacaacaacana<br>aaguuacuuauagucaauggauaagcagaguccgaauuuacacuaaucaagacagaccuucg<br>aggggucacgauaaguccggaacuuucaaaccuugcuucguaugaauuguacuaucugaaca<br>uaaacugcacuuuuauuuucuaauaccgagggugaauacgguaaauacaugcuuugagggu<br>agaanccgacggucuguuuggcaccacguuauaaucugcunnuuuuaacgaguaccaccuug<br>gagggcaggcaaauaaaugcuuuugguauuuucuccuuuguuuuugacaaaugcugcgga<br>ugggggaucgggaucggaggggagugcuuuuaaagauaauaaaaaaugagguaaauaauuu<br>uaacuuaugaauuuguuugaauuc |
| 14 | X16490 | gagauugaaacaauggaagaacuuuccauggcaaacaccauguuugcccucaaucuccuu<br>aagcagauagaaaaaucaaacucuacccagaacaucuuuaucucuccauggagcaucuca<br>ucaacauuggccauaguucuccucggugcugggguaacacugaacagcagauggccaaa<br>gugcugcaguuuaaugaaauuggcaguuaugguaucaccacaagaaacccagagaacuuc<br>aguggcugugauuucgcacaacagauacagaaggaaaauuauccuagugcuauuuuacaggc<br>acaagcaggagauaaaauccauucagccuucucccucucucagcucaacaaucaacaca<br>ccacaggggggauuauuuguuagaaagugcaaacaagcuguuuggagagaagucugcaagauu<br>caaagaagaauacauccaacucucuaagaaauauuacucaacagaaccagaagcagug<br>gacuuccuugaaugugcugaagaagcuagggaaaagauuaauucuugggucaagacucaaac<br>caaaggugaaaucccaaaccugcuacccgaagguucuguagaugaagacaccaagauggugc<br>uggugaaugcugucuacuucaaaggaaaguggaaaacuccauuugagaagaaacuuaauggg<br>cuuuauccuuuccgugugaacucgcaugagagcauaccuguccagaugauguuccuccaugc<br>aaagcugaacauuggauacauaaaggaccugaagacucagauccuagaacuuccgcauacugg<br>aaacaucagcaugcuccuguugcuucccgaugagauugaggacgcauccacuggcuuggaau<br>ugcuggaaagugaaauaaacuuugccaacuucaacaaguggaucagcaaagacacacuggau<br>gaagaugauguuguggucuacauucccaaguucaaacuggcacaaagcuacgaacucaaguc<br>cauucuucaaagcaugggcauggaggaugccuucaacaagggcaaggccaacuucucaggaa<br>ugucugagaggaaugaccuuuuucuuucugagguguuccaucaagccagcguggaugucac<br>cgaggagggcacuguggcagcugguggacuggggcaguuaugacaggaagaacuggccau<br>gguggcccacaguuuguggccgaucaucccuuucuuuucuuuaucauggacaaaauuaccca<br>cacgauacuauuuguugguagauucuccucacccuaaaggggaagaccuauuuccacauga<br>gguuuuguagcaugaacuauaagccucagaauugcaucuucaagugccaaaaguuuaaauac<br>uuucuuacacauuuuuauacuucugcuauacacuaaauauaaccuaaaagcaauuguauagc<br>agucuucagugcuuacaguauaacucuauuaaugauuuuguuuccuaaagucagaugaugu<br>cuauuuaguucauccuuauuacugcuuugucuuuauaacuuuaguuuuuacaguguuauu<br>uauuguuuauauaaugguuguuuuacaaauuguuguccucuguuuaaugaaacuguaacac<br>uacagaagcagaaaauuagauaauuuucuauuuaaagaaaaucagccauuuaauuuaauaau<br>gaaggaaaaauaugagucuuccauacuuucccaugauauucacccagaaaaaauguacuuaac<br>aaaagacauguuauaucucuaucauuauauaucauauguacguaucugcaacucaucuauaa<br>uuaggacuacaucauaaguaagcaugcuuacuuacacacugcuaucuguuguauaaaacuua<br>gcaauccuuauuuguuaguuaucuuucuaucacuguaacaaaauaccugagauaauaaaguu<br>caaagauuuauuuugaaaaaaaaaaaa |
| 15 | AW120868 | uuuuuuuuuuuuuuunuaagaauuaacuuuuauuuuugcuuaguuuuauuaaaaaaaauaa<br>auaugucauaaagcuuuuguuuccuuuagggagaaaaaaaaggaacaaguuccauaaaauca<br>aacaagcaaugguaacaugucuuaacuugaaaacaacuggggucacugguuuacaaguuaua<br>acugaaugaaugacugccacaguugcccauuuccuccugccaauggcagcaaacaacaggauc<br>aacuagggcaaaauaaauaauuguguggaagcccuga |

TABLE 3-continued

RNA transcripts up-regulated during HF stem cell activation.

| SEQ ID No: | Access. # | Sequence |
|---|---|---|
| 16 | C78850 | aacuaaacuuccuuguaacuuuugagaacucagcucugguacuuuuucaugccuugcaaaau<br>ggcguuanugcagcuagcuugcuaanccuuaugguggggucuuucauucccccucuuucu<br>ggaaacugnauaaaaucauuuauucacgugauucuauuucuucuggaucuauugauuugag<br>uuggugauacuguugggucanaaccagggccuguu |
| 17 | D67076 | Sequence below. |

gcagcuccgagcuaggugcuaucgcaaggccagagcgcacagcccggcggagagagcagauccuugcucagaucgagucaaa
ucgggccaaggcggaggacgaagaguccaggcuccuauucuggacuuguuccccagcuccgggggcgcuucuagguccugc
agcagccagcagugcggagccaccaacucggugcuggaaugaaaaaauucccgcgcgccagugcagaaucuuucuaagugac
ccggagcuucgggugcuagcucugcacgaacuuucccaucaaagugaucgugaauuuuaagcaucaggagcaggccagcgaa
gcucuacgcgucuaaacgucuauccagaccaagaguucucugcggugcagggugcggugccaugcagccaaaagucccuuuu
ggggucacgcaagcagaagcccugcuccgacauggggacguccagcgggcagcgagaucucggggcucucuguccgcacac
augcuguugcugcuccucgcuuccauaacaaugcugcuaugugcgcggggcgcacacgggcgccccacggaggaagaugagg
agcugguccugcccucgcuggagcgcgccccgggccacgauuccaccaccacacgccuucgucuggacgccuuuggccagca
gcuacaucugaaguugcagccggacagcgguuucuuggcgccuggcuucacccugcagacuguggggcgcagucccggguc
cgaggcacaacaucuggaccccaccggggaccuggcucacugcuucuacucuggcacggugaacggugaucccggcucugcc
gcagcccucagccucugugaaggugugcguggugccuucuaccuacaaggagaggaguucuucauucagccagcgccugga
guggccaccgagcgccuggccccugccgugcccgaggaggagucauccgcacggccgcaguuccacauccugaggcgaaggc
ggcggggcaguggcggcgccaagugcggcgucauggacgacgagacccugccaaccagcgacucgcgacccgagagccagaa
cacccggaaccaguggccugugcgggaccccacgccucaggacgcgggaaagccaucaggaccaggaagcauaaggaagaagc
gauuuguguccagccccguuauguggaaaccaugcucguagcugaccaguccauggccgacuuccacggcagcggucuaaa
gcauuaccuucuaacccuguucucgguggcagccagguuuuacaagcaucccagcauuaggaauucaauuagccugguggu
ggugaagaucuuggucauauacgaggagcagaagggaccagaaguuaccuccaaugcagcucucacccuucggaauuucugc
agcuggcagaaacaacacaacagccccagugaccgggauccagagcacuaugacacugcaauucuguucaccagacaggauuu
auguggcucccacacgugugacacucucggaauggcagauguuggaaccguaugugaccccagcaggagcugcucagucaua
gaagaugaugguuugcaagccgccuucaccacagcccaugaauugggccauguguuuaacaugccgcacgaugaugcuaagc
acugugccagcuugaauggugugaguggcgauucucaucugauggccucgaugcucuccagcuuagaccauagccagcccu
ggucaccuugcagugccuacauggucacguccuuccuagauaauggacacggggaauguuugauggacaagccccagaaucc
aaucaagcucccuucugaucuucccgguaccuuguacgaugccaaccgccagugucaguuuacauucggagaggaauccaag
cacugcccugaugcagccagcacauguacuacccugguggugcacuggcaccuccgguggcuuacuggugugccaaacaaaac
acuucccuugggcagauggcaccagcuguggagaagggaagugguguguggcaguggcaagugcgugaacaagacagacauga
agcauuuugcuacuccuguucauggaagcuggggaccauggggaccguggggagacugcucaagaaccugugguggugggag
uucaauacacaaugagagaaugugacaacccagucccaaagaacggagggaaguacugugaaggcaaacgaguccgcuacagg
uccuguaacaucgaggacuguccagacaauaacggaaaaacguucagagaggagcagugcgaggcgcacaaugaguuuucca
aagcuuccuuugggaaugagcccacuguagaguggacacccaaguacgccggcgucucgccaaaggacaggugcaagcucac
cugugaagccaaaggcauuggcuacuuuuucgucuuacagcccaagguuguagauggcacucccuguaguccagacucuacc
ucugucugugugcaagggcagugugugaaagcuggcugugaucgcaucauagacuccaaaaagaaguuugauaagugugc
guuuguggaggaaacgguuccacaugcaagaagaugucaggaauagucacuaguacaagaccugguaucaugacauuguca
caauuccugcuggagccaccaacauugaagugaaacaucggaaucaaagggggucccagaaacaauggcagcuuucuggcuau
uagagccgcugaugguaccuauauucugaauggaaacuucacucuguccacacuagagcaagaccucaccuacaaagguacu
gucuuaagguacagugguuccucggcugcgcuggaaagaauccgcagcuuuaguccacucaaagaacccuuaaccauccagg
uucuuaugguaggccaugcucuccgacccaaaauuaaauucaccuacuuuaugaagaagaagacagagucauucaacgccau
ucccacauuuucugagugggugauugaagagugggggagugcuccaagacaugcggcucagguuggcagagaagaguagu
gcagugcagagacauuaacggacacccugcuuccgaaugugcaaaggaagugaagccagccaguaccagaccuugugcagac
cuuccuugcccacacuggcaggugggggauuggucaccauguuccaaaacuugcgggaaggguuacaagaagagaaccuuga
aaugugugucccacgaugggggcguguuaucaaaugagagcugugauccuuugaagaagccaaagcauuacauugacuuuu
gcacacugacacagugcaguuaagaggcguuagaggacaagguagcgugggggaggggcugauacacugagugcaagaguac
uggagggauccagugagucaaaccaguaagcagugaggugugcaaggaggugugugguaggggauacauagcaaaggaggu
agaucaggacacuacccugccaguuacauucugauaagguaguuaaugaggcacaguagcaucugaaagaccauacagagca
cuaaggagccccaaagcacuauuaguaucucuuuucuuauaucuaucgcccaaauaauuuucagagucuggcagaagcccug
uugcacuguacuaacuagauacuucuuaucacaaagauugggaaaggcaaagcagaaagaugguaagacugggguuucaaaca
aggcuugguuucaaucacuggaggcaaggaggaggggacaaacaagaucauuauucgaagucgcugguugcugugguuuua
cggaagguugaugcaucauuccuaucaacagugaaaaguucagcuuguucaacgugacagaaaggcucaucuccgugaaaga
gcuccugauuucuucuuacaccaucucaguucuuaacuauaguucauguugagguagaaacaauucaucuauuuauaaaau
guacauuggaaaaaaaaagugaaguuuaugagguacacauaaaaacugaaggaaacaaugagcaacaugccuccugcuuugc
uuccuccugagguaaaccugccuggggauugagguuguuuaagauuauccauggcucacaagaggcagaaaauaauacau
guugugccagaguuagaaugggguauagagaucagggucccaugagauggggaacauggugaucacucaucucacaugga
ggcugcugcag

| SEQ ID No: | Access. # | Sequence |
|---|---|---|
| 18 | M61007 | ccgcgggcccgcguucaugcaccgccugcuggccugggacgcagcaugccucccgccgcc<br>gcccgccgccuuuagacccauggaaguggccaacuucuacuacgagcccgacugccuggc<br>cuacggggccaaggcggcccgcgccgcgccgcgcgcccccgccgccgagccggccauugg<br>cgagcacgagcgcgccaucgacuucagccccuaccuggagccgcucgcgcccgccgcgga<br>cuucgccgcgcccgcgcccgcgcaccacgacuuccucuccgaccucuucgccgacgacua<br>cggcgccaagccgagcaagaagccggccgacuacgguuacgugagccucggccgcgcggg<br>cgccaaggccgcgccgcccgccugcuuuccgccgccgccucccgccgcgcucaaggcgga<br>gccgggcuucgaacccgcggacugcaagcgcgcggacgacgcgcccgccauggcggccgg<br>uuucccguucgcccugcgcgccuaccugggcuaccaggcgacgccgagcggcagcagcgg<br>cagccuguccacgucgucgucguccagcccgcccggcacgccgagccccgccgacgccaa<br>ggccgcgcccgccgccugcuucgcggggccgccggccgcgcccgccaaggccaaggccaa<br>gaagacgguggacaagcugagcgacgaguacaagaugcggcgcgagcgcaacaacaucgc<br>ggugcgcaagagccgcgacaaggccaagaugcgcaaccuggagacgcagcacaaggugcu<br>ggagcugacggcggagaacgagcggcugcagaagaagguggagcagcugucgcgagagcu<br>cagcacccugcggaacuuguucaagcagcugcccgagccgcugcuggccucggcgggcca |

TABLE 3-continued

RNA transcripts up-regulated during HF stem cell activation.

| SEQ ID No: | Access. # | Sequence |
|---|---|---|
| | | cugcuagcgcggcgcgguggcgugggggcgccgcggccaccgugcgcccugccccgcgc<br>gcuccggccccgcgcgcgcgcccggaccaccgugcgugcccugcgcgcaccugcaccugc<br>accgaggggacaccgcgggcacaccgcgggcacgcgcggcgcacgcaccugcacagcgca<br>ccggguuucgggacuugaugcaauccggaucaaacguggcugagcgcguguggacacggg<br>acuacgcaacacacguguaacugucuagccgggcccugaguaaucaccuuaaagauguuc<br>cugcgggguuguugauguuuuugguuuuguuuuuguuuuuuguuuuguuuuguuuuuuu<br>uuuuggucuuauuauuuuuuuuguauuauauaaaaaaguucuauuucuaugagaaaagagg<br>cguauguauauuuugagaaccuuuuccguuucgagcauuaaagugaagacauuuuaauaa<br>acuuuuuuggagaauguuuaaaagccaaaaaaaaaa |
| 19 | C85523 | aaaauguagaaggcaagauuuaauaaggcagcaacaugaaagcacacagaccagagcucu<br>ggggucgaaauaaagcagcaacauggaagcacacagagcucuggggucgaaacucauaca<br>ccuuagcacaggguagaggagucucgacggucanccagaauuuuucacaggcuuauauag<br>uaaaacucaaagggggagaacugggcagggaaaguacaaguuuacaucacuagggaguuc<br>ugccaaaggacaangggguucunucagaggaaucuacguaacuaaggngucaugucc uauc<br>aaggnaucuacguaacuaaggagucauguccuaucauuuggcaauguacccgnucuuuu<br>gagguuguuccggagggncuuauucucaaaauguuuuucagauuggaagggguggguunc<br>cgguaaaaaguucuguuuucaaagaggcnguaauuuucuauucuucauuccccauucucc<br>uguaaguauucnnaucuuagaauuucagaaguccauauucncuaugugggggaauaacugg<br>cuuuaacccnaucuuuaaaaaugggggg |
| 20 | AW122030 | uuuuuuuuuuuuuuuuuaugaaacaguuuuguucagcccaugacuuugugcaugacuguc<br>guccguucuagucaccugugcucuccaucuacugccuuuuaaagcugcgucaugagaagg<br>aucuacacguuccaccaugacucucguuucuugccacaaguagaagaaaugguugauucu<br>uugcuuuucgguuaggccguuaaacaaaacucagucacaccccugccuuccacccucaaa<br>cugugaucacguggcuguucuuguaguunaaccagggcaacacuauauauuccaggucua<br>uacauugcugaggucuuuuucugguuguucauguaucaguguuucaaccucgugccg |
| 21 | U57524 | Sequence below. |

gcggccgcggcuccagaccccggccuugcgcacccucccccccaccuccagcccgcgccucccccccccccacgcauggcucacc
accccucggguuucccugucaucccucagguuccugcacuuggcaaucauccacgaagagaagccgcugaccauggaaguca
uuggucaggugaagggagaccuggccuuccucaacuuccagaacaaccugcagcaggugcgcugcuugcuugccccgcggu
gccccucuuugaccccuugguggagucagauguagcacggucgcccccaaagcguuucuaaauuaauagucacuuaguucu
uaucugccuuggcuuuuuugcauucaaaucagccaacgucuuagaaccagaagaaaaaucccuugguuuuagugaggucuu
uaugacccaccuagggccuccuguuugccugaucuccuaagagacaaaugggaggaucagauuccauagcgggaggugucu
gggguucaggaaacucaagacuauggguuugcuccauggcuuaucccuuucuguuuccucuuccauuuguagacuccacuc
cacuuggcugugaucaccaaccagccaggaauugcugaggcacuucugaaagcuggcugugauccugagcuccgagacuuuc
gaggaaauaccccucuacaucuugccugugagcagggcugccuggccaguguagcagucuugacgcagaccugcacacccca
gcaucuccacuccguccugcaggccaccaacuacaaugguaggucugccaguccauccaaggaugcagaggagggagagaga
uggggccacuugagucuuaaacuccgaacguauacaaaguucagacacugugaucuuuuuaaaaaguuucuccucgaugcc
uauaugauauucacucagaacccagauucugaguucuucaaaacugaugauguuugugguuguccucaagacaauagacau
gaguugugugaggauugaaacacguaguacaguuuuugucuuccuccuccaggccacacgugucugcaccuagccucuacu
cacggcuaccuggccaucguggagcacuuggugacuuugggugcugaugucaacgcucaggugaguacaucucccuuccac
cuaaucucuguugggcuggcucugauggugagcagguuuccagaugcagccguaaacuaacgccugauugcuuuugguuuc
aggagcccugcaauggccggacagcccuccaccuugcgguggaccugcagaauccugaccugguuucgcucuuguugaaaug
uggggcugaugucaacaggguaaccuaccaaggcuacucccccuaccagcuuaccuggggccgcccaaguacccggauacag
cagcagcugggccagcugacccuggaaaaucuccagaugcuacccgagagcgaggaugaggagagcuaugacacggagucag
aauucacagaggaugaggugaguguuccucccucagcacgcugacggcuguucuagggcugcuuuggaucagagggauuu
caguuguuuaacuucucagacucggcuugcaaagcaggaucccaagaauuugucucugguuuguuuuaagagcuuacccuu
uugguugaggaaugagggaauucuagaaauugaacccaggccuuagcacauggugauaagcacacguucaaccauuaagcuc
cacccccucaauagcuuagacuuuuuuuuuuuuuaaggaaagaauagguaagggaaacuccuacagccuggugcccuuguu
cuauuugggguuaaggagaaaaagagcccaagaauaggaguuauuucagcagcagcucuccccuuaucccaaugucuugguga
aguucuaggaauuuaauaugucuuuuuccccucucuuguuuuagcugcccuaugaugacuguguguuuggaggccagcgu
cugacauuauaaguggaaaguggcaaaaaagaauguggacuuguauauuuguacaaauagaguuuuauuuuucuaaaaaaa
aaaaaaaaaaaaaaaaaaaaaaaaaaaguauacuuagcaccacaccacacagcgccuagacccaggcauuuuacugggggugau
ucggcuguugucuuugugaaauccgggg

| SEQ ID No: | Access. # | Sequence |
|---|---|---|
| 22 | U05809 | cucucggucacugccggucgcuuccugagccgcugcuggcucugugucucuguccucagc<br>guucucuuccucguccucguccuaccacgccauggaagguuaccauaagccagaucagca<br>gaagcuccaggcccugaaggacacagccaaucgccugcgcaucagcuccauccaggccac<br>caccgcggcaggcucaggccaccccacaucaugcugcagcgcugccgagaucauggcugu<br>ccuguuuuuccauaccaugcgcuacaaggcccuggauccccgaaacccucacaaugaucg<br>cuuugugcucucuaagggccaugcagcucccauuuuauaugcagucugggcugaagcugg<br>cuuccugcccgaggccgagcugcugaaccugaggaagaucagcucugacuuggacgggca<br>uccugucccgaaacaagccuucaccgauguggccacuggcucccugggccagggccuggg<br>agcugcuugcgggauggcauacacaggcaaauacuuugacaaagccagcuaccgagucua<br>uugcaugcugggagacggggaggucuccgagggcuccgucugggaggccauggccuuugc<br>uggaauuuacaagcuggacaaccucguugccauuuuugacaucaaccgccugggccagag<br>cgacccagccccgcugcagcaccagguggacaucuaccagaagcgcugugaggccuuugg<br>cuggcacaccaucaucguggacggacacagcguggaggagcugugcaaggccuuugguca<br>ggccaagcaccaaccaacagccaucaucgccaagaccuucaagggccgagggaucacagg<br>gauugaagacaaggaggcguggcacgggaagccccuccccaaaaacauggccgagcagau<br>uauccaggagauuuacagccagguucagagcaaaaagaagauccuggccacgcccccuca<br>ggaggaugccccauccguggacauugcuaacauccgaaugccuacgccacccagcuacaa<br>aguggggggacaagauagccacccggaaggccuauggacuggcccucgcuaagcugggcca |

TABLE 3-continued

RNA transcripts up-regulated during HF stem cell activation.

| SEQ ID No: | Access. # | Sequence |
|---|---|---|
| | | cgccagugaccguaucauugcccuggauggagacaccaagaauuccaccuucucggagcu<br>cuucaaaaaggagcacccagaccgguucauugagugcuacauugccgagcaaaacauggu<br>gagcauugccgugggcugugccacacgugaccggacagugcccuucugcaguacuuucgc<br>ggccuucuucacacgggccuucgaccagauucgcauggccgccaucucugagagcaacau<br>caaccucuguggcucccacugugguguguccauuggggaagacgggcccucucagauggc<br>ccucgaagaccuggccauguuccggucaguccccauguccaccgucuuuuacccaagcga<br>uggaguugcaacagagaaggcaguggaguuagcagccaacacaaagggcauuugcuucau<br>ccggaccagccgcccagagaaugccauuauuuauagcaacaaugaggauuuccaggucgg<br>ccaagccaagguggucugaagagcaaggaugaccaagugacagugaucggggcuggugu<br>aacucugcaugaggccuuggcugcugcagagagucuaaagaaagauaagaucagcauccg<br>ggugcuggaucccuucacuaucaagccccuggacaggaaacucauccuagacucugcccg<br>agcaaccaaaggcaggauccucaccguggaggaccacuacuacgaagguggcauaggaga<br>ggcagugucugcugccguagugggugaaccuggagugacggucacucgccuggcugucag<br>ccaaguaccacgaaguggcaagccagcugagcuacugaagauguucgguauugacaagga<br>cgccauugugcaagcugugaaaggccuugucaccaagggcuagggagggcaugggaugcu<br>gggugggugaacuacacauuccagggagguucuggcagagguggcgaagguguacugagu<br>ggggagguaaauauauguuuug |
| 23 | AW212475 | uuaacggugucauaaauaaguaauauaacuuuauuaaaaugaaaagacaauauucaaaau<br>aaugcaacaaaaugaauaaauccuuuguccaauacuguacacacagugcggagaucagug<br>cauuuuucuaaagcauguuuuaaccuucauuuaguucauacuaaaguaagcuuuaaauag<br>cucaaauaaugucauucagcaguuuaaacugaacagcuuguugggacaug |
| 24 | V00835 | ugaguucucguaaacuccagagcagcgauaggccguaauaucggggaaagcacuauaggg<br>acaugauguuccacacgucacaugggucguccuauccgagccagucgugccaaaggggcg<br>gucccgcugugcacacuggcgcuccagggagcucugcacuccgcccgaaaagugcgcucg<br>gcucugccaggacgcggggcgcgugacuaugcguggggcuggagcaaccgccugcugggug<br>caaacccuuugcgcccggacucguccaacgacuauaaagagggcaggcuguccucuaagc<br>gucaccacgacuucaacguccugaguaccuucuccucacuuacuccguagcuccagcuuc<br>accagaucucggaauggaccccaacugcuccugcuccaccgguaagacucccgauccuug<br>gucuuuagaauaccaaguugggaccgcagagcggaaucccccgaguuguagaggcuuggcg<br>ggaauaggcaccuuuaguuggcgauucauuccgguucuuucuagaauccgcucuugcaaa<br>agccuucauuaguuacgaguauugucgaacggguccuuuggcgggguuggggcuaggauu<br>uagacgcgcaaauguccgguuccugaucacccaguuaguggggacaucugggguugagucc<br>caggcauuacuaaacuuacugugaauugcuugaauuaagaaagaggugaaggaccuuuau<br>gucuugggacucaaagacauaaucccugacuuaaccugugaggagaaaaguggggcuagg<br>cucccugcagcuccgaggaggacuuagugaacugagccgggacucgugguguuggccacu<br>gcuguaaugcugccucccucaugcugucuucuuucuccucccaggcggcuccugcacuug<br>caccagcuccugcgccugcaagaacugcaagugcaccuccugcaagaagagugaguuggg<br>acaccuuggguggcggcuaaggcuaggggcggggaacuccuacaaaacuggcucugagaa<br>auguccuuugcuucccggaggccauuguauugucucggggacagaacuauacagagaacu<br>auuuaaaaaaaccgaggucuucucuguuggggacaggaagcagaggucuucagccaggcu<br>gccucuuccuccuucuucuaggcugcugcuccugcugucccgugggcugcuccaaaugug<br>cccagggcugugucugcaaaggcgccgcggacaagugcacgugcugugccugaugugacg<br>aacagcgcugccaccacguguaaauaguaucggaccaacccagcgucuuccuauacaguu<br>ccacccuguuuacuaaacccccguuuucuaccgaguacguuaauaauaaaagccuguuug<br>agucuaacucugguuucuuggugugguuuggcaauaagaaacugggggugacuugauaguc<br>uggggaucugguuuuggacccccucgugccuuuaccuccgcccucuggcccucacagagg<br>gguaaugucuuuggguaaagccaagcuauaucccauaagcuuccucauggaaaacagcug |
| 25 | AV374868 | gcggcacgaugugucuucggguggcuuuuuuuuuuuuguuuugaauaauguuuacaauuu<br>cccucaaucacuuuuauagaaauccaccuccaggcccccccccuuuccccacuuaggccuu<br>cgaggcugucugaagaugcuugagaaacucaaccaaaucccaguucaauucagacuuugc<br>acauauauuuauauuuauaaucagaaaagaaacauuucaguaauuuauaauaaaagagca<br>cuauuuuuuaacg |
| 26 | M21285 | See above (same Accession Number). |
| 27 | U74683 | acugccaucgagugguguuccaguugaacuugcucucucugccaucugcuccgcgggcgc<br>cgucagcauggguccccuggacccacuccuugcgcgccguccugcugcuggugcuuuuggg<br>agucugcaccgugcgcuccgacacuccugccaacugcaccuacccugaucugcugggcac<br>cuggguguuccagguggggcccuagaaguucccgaagcgacauuaacugcucggugaugga<br>agcaacagaagaaaagguagugguacaccuuaagaaguuggauacugccuacgacgagcu<br>gggcaauuccgggcauuuuacccucauuuacaaccaaggcuucgagauuguguugaauga<br>cuacaaaugguuugcguuuuucaaguaugaagucagaggccacacagcuaucaguuacug<br>ccaugagaccaugacugggugggguccaugaugugcugggccggaacugggcuugcuuugu<br>uggcaagaagguggaaagucacauugagaagguuaauaugaaugcagcacaucuuggagg<br>ucuccaggaaagauauucugaaagacucuacacucacaaccacaacuuugugaaggccau<br>caauaccguucagaagucuuggacugcaacugcauauaaggaauaugagaaaaugagccu<br>gcgagaucugauaaggagaaguggccacagccaaaggaucccaaggcccaaaccugcccc<br>gaugacugaugaaauacagcaacaaauuuuaaauuugccagaaucuugggacuggagaaa<br>cguccaaggcgucaauuauguuagcccuguucgaaaccaagaaucuuguggaagcugcua<br>cucauuugccucuaugggguaugcuagaagcaagaauucguauauuaaccaacaauucuca<br>gacaccaauccugaguccucaggagguuguaucuugcagccccuaugcccaagguuguga<br>ugguggauucccauaccucauugcagggaaguaugcccaagauuuuggggugguggaaga |

TABLE 3-continued

RNA transcripts up-regulated during HF stem cell activation.

| SEQ ID No: | Access. # | Sequence |
|---|---|---|
| | | aagcugcuuucccuacacagccaaagauucuccaugcaaaccaagggagaauugccuccg<br>uuacuauucuucugacuacuacuaugugggugguuucuaugguggcugcaaugaagcccu<br>gaugaagcuugagcuggucaaacauggacccauggcaguugccuuugaaguccacgauga<br>cuuccuacacuaccacaguggaaucuaucaccacacugggcugagugacccuuucaaccc<br>cuucgagcugacaaaucaugcuguuuugcuugugggcuauggaagagauccaguuacugg<br>gauagaauacuggauuauaaagaacagcuggggcucuaacugggggagaguggcuacuu<br>ccguauccgcagaggaacugaugaaugugcaauugagaguauagccguggcggccauacc<br>gauuccuaaauuauaggacauagcucccaguguuacauacgggucuuuaucacucacaga<br>gugauuuagucacaugcugaagacuuuuucagagcaauaucagaagcuuaccacuaagca<br>ucuuuaaagaauuuugucuuugaacuuaaaaccauccuugauuuuuuucuuuuaauaucu<br>uccccaucaacuacugaacuacuuuucuuuuuaaaguacuugguuaaguaauacuuuuau<br>gagcagugguucaguuguccaauauuuuuugcaggucaucuacaaugcaaccagauguuu<br>caguucuaaaaaucuauguaaaaguacaagcucguuuuuaaauuauguaagucacaugaa<br>aacauggcaaaaaaauuaguuaaauuuuuuacaaagaguuuuaaauaaauguuuauguaa<br>ucaguaccauagucuuucuaugugugguuuacaagaauuuuugucaccuacuucuucccuu<br>agaagcauuuaugcuccauggacguacuucuuuauggagaaaaaaaaaa |
| 28 | X61800 | gagcucgaucccuguuccgccuuugcuaugucugaaggcguccugcuuugcgcgugucgg<br>ggccaaauccagauuuucauuucgcuccaggcuuggacggcuaaguagguccaaaccgca<br>caaacaggaaggagggaaggcaaggagugcgggcagagggcgggucguucccagcagcac<br>cccagucccuccccgcuccgucuccgacccacuggggccggggcgggcgugcgcgucagc<br>uggggcuagaaaaggcggcgguccggcccggcgaggugacagccaacuuggacgccaggu<br>ccggccgacgccgccaugagcgccgcgcuuuucagccuggacagcccggugcgcggcaca<br>cccuggcccacagaacccgcggccuucuacgagccaggcaggguggacaagcccggccga<br>gggcccgagccaggggaacuggggagcugggcuccacgacuccugccauguacgacgac<br>gagagcgccaucgacuucagcgccuacauugacuccauggccgccgugcccacccuagag<br>cugugccacgacgaacucuucgccgaccucuucaacagcaaccacaaagcggccggcgcg<br>ggcggccuggagcugcugcagggcggcccuacgcgaccccgggugugggguctgucgcu<br>agggggccgcucaagcgcgaacccgacuggggcgacggcgacgcgccgggcucccugcug<br>ccggcgcaaguggcggugugcgcgcagacagguggugagcuuggcggccgcggcucagccc<br>acuccacccacuucgccggagccuccucgaggcagcccggggccgagccucgcgcccggc<br>acaguccgagaaaagggcgcgggcaagaggggguccggaccgcggcagcccggaguaccgg<br>cagcggcgcgagcgcaacaacaucgcugugcgcaagagccgcgacaaggccaagcgccgc<br>aaccaggagaugcagcagaagcugguggaguugucggccgagaacgagaagcugcaucag<br>cgcguggagcagcucacccgggaccuggcuggccuccggcaguucuucaaaaaacugccc<br>agcccgccuuuccugccgcccaccggcgccgacugccgguaacgcgcggcgugggccuuu<br>gagacucugaacgaccuauaccucagaccccgacagcggggagcagacgccgcccgaauc<br>gcuaguuucuuugggaccugcgagcgacaggaagcugcagcuugggcacuggacugcgag<br>agaagcuauauuaaucuuuccccuuaaauuauuuuuuauaaugguagcauuuucuacguc<br>uuauuaccauugcagcuaagguacauuuguagaaaagacauuuccgacagacuuuuguag<br>auaagaggaagagacugcgcaugcuuuuuauauucauuuuuacaguauuuguaagaauaa<br>gaauaagaauaaagaagcauuuaaaucgcaaaaaaaaa |
| 29 | U20735 | Sequence below.<br>uugaggguggccaggccagcguaggaggccagcguaggauccugcugggagcggggaacugagggaagcgacgccgagaaa<br>gcaggcguaccacggagggagagaaaagcuccggaagcccagcagcgccuuuacgcacagcugccaacuggccgcugccgacc<br>gucuccagcucccgaggacgcgcgaccggacaccggguccugccacagccgaggacagcucgccgcucgccgcagcgagcccg<br>gggcggcccuucaggggaccuuucccagaucgcccaggccgcccggaugugcacgaaaauggaacagccuuucuaucacga<br>cgacucuuacgcagcggcgggauacggucggagcccuggcagccugucucuacacgacuacaaacuccugaaacccaccuug<br>gcgcucaaccuggcggaucccuaucgggggucucaaggguccuggggcgcgggguccaggcccggagggcaguggggcaggc<br>agcuacuuuucgggucagggaucagacacaggcgcaucucugaagcuagccuccacggaacuggagcgcuugaucgucccca<br>acagcaacggcgugaucacgacgacgcccacgccuccgggacaguacuuuuaccccgugggggguggcagcgguggagguac<br>agggggcggcgucaccgaggagcaggagggcuuugcggacgguuuugucaagcccuggacgaccugcacaagaugaaccac<br>gugacgcccccaacgugucccugggcgccagcggggucccccaggccggcccagggggcgucuaugcugguccggagccgc<br>cucccgucuacaccaaccucagcaguuacucuccagccucugcacccucuggaggcuccgggaccgccgugcggacugggag<br>cucauacccgacggccaccaucagcuaccucccacaugcaccacccuuugcgggcggccacccggcacagcugguuugaguc<br>guggcgcuuccgccuuuaaagaggaaccgcagaccguaccggaggcacgcagccgcgacgccacgccgccugugucccccauc<br>aacauggaagaccaggagcgcaucaaaguggagcgaaagcggcugcggaacaggcuggcggccaccaagugccggaagcgga<br>agcuggagcgcaucgcgcgccuggaggacaaggugaagacacucaaggcugagaacgcggggcugucgagugcugccgguc<br>uccuaagggagcaaguggcgcagcucaagcagaaggucaugacccaugucagcaacggcugccaguugcugcuaggggucaa<br>gggacacgccuucugagagccucccuugccccauacggacacccccagccuugaaggcugggcgccugcccccacuggggu<br>gagggggcaggcgaugggcacccgccaaaaggccuggggcgcagcucacacacuggacuccggcccgcccgccugcgccca<br>guccuuccaccucgagguuuacauggccccuuccagcguauuuuguauguuuuuuuuucugcaaagagacugaauucau<br>auugaauauaauauauuuguguauuuaacaggagggagaagggggcugucgcggcggagcuggccgccgcuugguacucag<br>cugcggggauacuagggagggaccuccgccccugcccucccccucugcauaguacuguggagaagaaacacgacuucgugu<br>cuaaagucuauuuuaagauguguuuguguguguguuugacuuuuuauugaaucuauuuaagua |
| 30 | U19118 | Sequence below<br>gaauucggcacgagcagcgagacgccgcgcacggugcuuccccaguggagccaaucggcuaacccgcgcuccggcagagucc<br>uuggcgcucgcccgccggcgggacagaccacccgccucuggccgcucucuggacccuggccgccccgagcgaagacuggagc<br>aaaaugaugcuucaacauccaggccaggucucugccucagaagucagugcgaccgccauuguccccugccucucaccuccug<br>ggucacugguauuugaggauuuugcuaaccugacacccuuugucaaggaagagcugagauucgccauccagaauaaacaccu<br>cugccaucggauguccucugcgcuggagucaguuaccgucaacaacagaccccuggagaugucagucaccaagucugaggcg<br>gccccugaagaagaugagaggaaaaggaggcggcgagaaagaaauaaaauugcugcugccaagugucgaaacaagaaaaagga<br>gaagacagagugccugcagaaagagucagagaaacuggagagugugaaugcugagcugaaggcccagauugaggagcugaag |

TABLE 3-continued

RNA transcripts up-regulated during HF stem cell activation.

| SEQ ID No: | Access. # | Sequence |
|---|---|---|
| | | aaugagaaacagcauuugauauacaugcucaaccugcaccggcccaccuguaucguccgggcucagaauggacggacaccgg<br>aagacgagaggaaccucuuuauccaacagauaaaagaaggaacauugcagagcuaagcagagguggcacggaggcaauuggg<br>gaguucuuacugaauccuccuuuuccaccccacacccugaagccauuggaaaacuggcuuccugugcacuucuagaauccca<br>gcagccaagagccguuggggcaggagggccugguggugaccuacugcauugacccacucugcccccgagugaaccguggagca<br>ggcaggagcauccuuugucucaccaauuccaggauuuaggccuuaucaucccggccagucucagaugaccuagcuggcccca<br>ggcugggguccuaugcaaagcaggaucccacuaaugggauucaggcagaagugucuaccuugauagguggggugggaccac<br>auccucuacuguggcugacaacgcccuuccaagggaauauggaaugagaacauucauuauugagguuguccaauggccaggg<br>uaugcuuucuagaaaauaugcuguucugucccagaaugacugugcauaggguauccguuucagagccugguguugugcuau<br>uuagauguuugucuugcacaacauuggcaugauuuuuccgggaguuucaucagaucugauuucugagagucuggggaucu<br>gccaugguggaaagugccccucaaaagcauuuguguggccacaugaacuggcuggcaccaggggagugaaacuggcugauga<br>ccagcugagccacuuugugccaacagaggauggacgacaccuuucccuguacccacugcagaggaagaacccugggcacagca<br>gcuuuguccuuggcuacaaacuguuacaacgucacacaaugaaggcacaaaguccaacuuucaaaggguguaggacuccaua<br>cucagugacagggcaggaagagccaaagauaaccacagccacagccuguggagaccaggguuggaagccaggugcagggcca<br>ggcaucugcauugugggauguuaauggcacuuuugucuuguagcuauuuugagaugugguccagagcauuucagcuggga<br>gaucucccucuggccaccaggacucuggcuacuguuaaaauccugauguuucuguggaauccucaguguuuaaucccacuca<br>auaguaucauuacaguuuucuguaagagaaaauauuacuuauuuaucccaguauuccuagccugucaacauaauaaauaucg<br>gaacaaaaccuggua |
| 31 | AW049031 | uuuuuuuuuuuuuuuuugcugauaagaauucuuuuuauguuauucgaauaaaaaauaca<br>uucauacagaaauauaacaaucucgcaaaaaacaauuucaaauaaaaucuuguaaaacaaa<br>auuuuacaaaaaucuuacaaagauucuuuagauaacagggugcuucaaaaaaaaagaaau<br>aaagaaauuucacuaauagaaauuuuuuuuuuuaauuucaagcaaaaguuccugcuugau<br>ugaggcucaguugucaccugaccagaauggacugcuuaguauuaaaguuacagcaucgac<br>acggacggcacccagccccagccagaccagcaacgucgcuguguuucauaagugagacgc<br>gccagcacaaguuuccucucucuucuguuuaccuucuuacuuaauggaauugcuauggau<br>aagcacacagcagggccaaaaaaggaguuuuccaaaauccagcaaaucaagug |
| 32 | M93275 | uagguggugaucuggaccgugcggacuugcucgucccucagcucuccuguuaggcgucucu<br>uuucuccaggaggaaaaaauggcagcagcaguaguggauccgcaacagagcguggugaug<br>agaguggccaaccugcccuuggugagcucuaccuacgaccuuguguccuccgcuuauguc<br>aguacaaaggaucaguacccguauuugagauccgugugugagauggccgagaagggcgug<br>aagaccgugaccucugcggccaugacaagugcccugcccaucauccagaagcuggagcca<br>caaauugcgguugccaauaccuaugccugcaaggggcuagacaggauggaggaaagacug<br>ccuauucugaaccagccaacguccgagauuguugccagugccagaggugccguaacuggg<br>gcgaaggauguggugacgacuaccauggcuggagccaaggauucuguagccagcacaguc<br>ucagggguggugggauaagaccaaaggagcagugacuggcagcguggaaaggaccaagucu<br>guggucaauggcagcaucaauacaguuuuggggauggugcaguucaugaacaguggagua<br>gauaaugccaucaccaagucggagaugcugguagaccaguacuucccucucacucaggag<br>gagcuggagauggaagcaaaaaagguggaaggauuugauaugguucagaagccgagcaac<br>uaugaacggcuggagucccugucuaccaagcucugcucucgggcuuaucaccaggcucuc<br>agcaggguuaaagaggccaaacaaaagagccaggagaccauuucucagcuccacuccacu<br>guccaccugauugaauucgccaggaagaauaugcacagugccaaccagaaaauucagggu<br>gcucaggauaagcucuaugucucgugggugggaguggaagagaagcaucggcuacgacgac<br>accgaugagucccacuguguugagcacaucgagucacguacucuggcuaucgcccgcaac<br>cugacccagcagcuccagacuacaugccagacuguccuggucaacgcccaaggguuacca<br>cagaacauucaagaucaggccaaacacuuggggggugauggcaggcgacaucuacuccgua<br>uuccgcaaugcugccuccuuuaaggaaguguccgauggcguccucacaucuagcaagggg<br>cagcugcagaaaaugaaggaauccuuagaugaaguuauggauuacuuuguuaacaacacg<br>ccucucaacuggcugguagguccuuuuauccucagucuaccgaggugaacaaggccagc<br>cugaagguccagcagucugaggucaaagcucaguaaaccccuccuugucaccagagcaug<br>auguugcuggccagaugaccccuuuugcuguauugaaauuaacuugguagauggcuuuag<br>cuuagaaaagcagcuucuuagaaccaagggccucauuauggucacucacagcucaguuau<br>ggucuugccccagcuggcccuggcacaggaguucucuuaccuggcuggugaguggccugu<br>guuagucuugugaggaccuggaggaaccuaaaagcucagaugcacuuacagucuugucug<br>uggccuuuguauuguuauuggcuguaaacgucugucuggaccgaauaaagauucacguga |
| 33 | AB000713 | ggcacgagggagcugcaguguucgcgcuugguagcuggugcaucggacucagcuggcuuu<br>gugucccugaggcucaccgaaaaacacuuucucagcccucugacuccagagagagagaga<br>gagagguacuuuuuguggucaccgacuuugaccccugcagaggcugagcgauggcgucua<br>ugggacuacagguccugggaaucuccuuggcaguccugggcuggcuggggaucauccuga<br>guugugcgcuccccauguggcgggugaccgccuucaucggcagcaacaucgucacggcac<br>agaccagcugggagggccucuggaugaacugcguggugcagagcacaggucagaugcagu<br>gcaagauguacgacucgaugcucgcccugccgcaggaccugcaggccgcccgagcccuua<br>uggucaucagcaucaucgugggugcucuggggaugcuucucucagugguagggggcaagu<br>gcaccaacugcauggaggacgagaccgucaaggccaagaucaugaucaccgccggagccg<br>uguucaucguggcaagcaugcugauuauggugcccguguccuggaccgcucacaacguca<br>uccgcgacuucuacaacccuaugguggcuuccgggcagaagagggaaaugggggccucgc<br>uuuacgucggcugggcggccuccgggcugcugcuccugggaggaggccuccucugcugca<br>guugcccaccucguagcaacgacaagcccuacucggccaaguacuccgccgcccgcucug<br>uccccgccagcaacuauguguaagguggccacucuguccacauugccuuuguuauuuuu<br>uuucggauugagcucauaacagccuguggccccucacauucuccaggaccugcccugcua<br>ugggccacuaacugcuugcuggggacaggcaaacccggacugugcaaaguuacuagcccg<br>uagcucuugggcugcuccacauggcuccuuacggccggcaagaauggauguaaaaauauc<br>uugcugcuuacauccaaauugcgguggauaugggcugaaggcagaagcagcugggaaggg<br>caguagaggcgcaagcuggguccugcuggccggggguagcucagcugugacuuuggacucg |

TABLE 3-continued

RNA transcripts up-regulated during HF stem cell activation.

| SEQ ID No: | Access. # | Sequence |
|---|---|---|
| | | gaguggauguccucauguuagcaaacguccacuguccuuucucuaucccccucacucagc<br>cuacacguuacuccagcgcuacucuugccauuacgccccguguuuccgagcacagcuggu<br>ccuaccccaagucauggugugcugagugacugaugaggggccauugagagccgguggggcu<br>cugccauggaacccuuccguugauuagcaaugacugugcuugacccacccaccuacccua<br>cuaaugaauuucuguagaguggauggacggguuugagggaagaaggguggagguggauu<br>aaacugguuuggggagggcuggggaccuagaagcagcccaguguguccccaccccuuuucc<br>gcacugucuugcuaauguucugaucacugugcgccccccuccccucuucagaaggacccugg<br>gccucuugaguuggccccucugaguucccucccuuugcccauuucaaggacaccggccag<br>ucugcggaaggaagguacgggggggggggggggggugauggcauuguaccagggaguc<br>uccuggacuccccugccuucucugugguuucuuguuuuguaauuaaggucuguucacagc<br>uguaauuauuauuauuuucuacaauaaauggcaccugcauacag |
| 34 | U20735 | See above (same Accession Number). |
| 35 | U83148 | augcagcugagaaaaaugcagaccaucaaaaaggagcccgcaccccuagauccuaccagc<br>agcucagacaagaugcugcugcugaacucugccuuagcugagguggccgaggaccuagcc<br>ucaggugaagauuugcuccugaacgaagggagcauggggaaaaacaaauccucggcgugu<br>cggagaaaacgggaauucauuccggacgagaagaaagacgccauguauugggagaaacgg<br>cggaaaaacaacgaagcugccaaaagaucucgggagaagcgccgccucaaugaccugguu<br>uuggagaacaagcugauugcccugggagaagaaaaugccacuuuaaagcugagcugcuc<br>ucccugaaauuaguuugguuuaauuagcuccacggcguaugcccaagaaauccagaaa<br>cucaguaauuccacagcugucuacuuucaggacuaccagacauccaaggcugccgugagc<br>ucuuuuguggacgagcaugagccugcgaugguagccggaaguugcaucucagucaucaag<br>cacucuccccagagcucgcucuccgaugugucagagguguccucgguggagcacacucag<br>gaaagccccgcacagggaggcugccggagcccugagaacaaguucccugugaucaagcag<br>gagcccguggaguuggagagcuuugccagggaggccagggaggagcggggcacguauucc<br>accuccaucuaccagagcuacaugggaagcucuuucuccacuuacucccacuccccaccc<br>cucuugcagguccauggguccacuagcaacuccccaagaaccucagaggccgaugagggu<br>guagugggcaagucuucugauggggaagacgaacaacaggucccuaagggccccauccau<br>ucuccaguggagcugcaacggguucacgccacgguggugaagguuccggaagugaacccu<br>ucugccuuaccgcacaagcuucggauuaaagccaaggccaugcaggucaaaguggaggcu<br>uuggacagcgaguuugaaggcaugcagaaacucucuucacccgccgaugcgaucgccaaa<br>agacauuuugaccuggagaaacauggaaccucggguauggcccauuccucccucccuccu<br>uucucagugcaggugacgaacauucaagauuggucccucaaaucggaacacuggcaucac<br>aaagaacugagcagcaaaacucagaguagcuucaaaacagguguggugggaagucaaagac<br>gguggcuauaagguuuccgaagcugagaauuuguauuugaagcagggaauagcaaacuua<br>ucugcagagguggucucgcucaagagauucauagccacacaaccgaucucggcuucggac<br>uccagguaa |
| 36 | L10244 | gcucccgggaaacgaaugaggaaccaccuccuccugcuguucaaguacaggggccuggug<br>cgcaaagggaagaaaagcaaaagacgaaaauggcuaaauuuaagauccguccagccacug<br>ccucugacugcagugacauccugcgacugaucaaggaacuggcuaaauaugaauacaugg<br>aagaucaagucauuuuaacugagaaagaucuccaagaggauggcuuuggagaacaccccu<br>ucuaccacugccugguugcagaagugccuaaagagcacuggaccccugaaggacauagca<br>uuguuggguucgccauguacuauuuuaccuaugacccauggauuggcaaguugcuguauc<br>uugaagacuucuucgugaugagugauuacagaggcuuugguauaggaucagaaauuuuga<br>agaaucuaagccagguugccaugaagugucgcugcagcaguaugcacuucuugguagcag<br>aauggaaugaaccaucuaucaacuucuacaaaagaagaggugcuucggaucuguccagug<br>aagagggauggaggcucuucaagauugacaaagaguacuugcuaaaaauggcagcagagg<br>agugaggcgugccgguguagacaaugacaaccuccauugugcuuuagaauaauucucagc<br>uucccuugcuuucuaucuuguguguagugaaauaauagagcgagcacccauuccaaagcu<br>uuauuaccagugacguuguugcauguuugaaauucggucuguuuaaaguggcagucaug<br>uaugugguuuggaggcagaauucuugaacaucuuuugaugaagaacaagguggua ugauc<br>uuacuauauaagaaaaacaaaacuucauucuugugagucauuuaaauguguacaauguaca<br>cacugguacuuagaguuucuguuuugauucuuuuuuuuuaaauaaacucgcucuuugau<br>uu |
| 37 | U88328 | cgcuggcuccgugcgccauggucacccacagcaaguuucccgccgccgggaugagccgcc<br>cccuggacaccagccugcgccucaagaccuucagcuccaaaagcgaguaccagcuggugg<br>ugaacgccgugcgcaagcugcaggagagcggauucuacuggagcgccgugaccggcggcg<br>aggcgaaccugcugcucagcgccgagcccgcgggcaccuuucuuauccgcgacagcucgg<br>accagcgccacuucuucacguugagcgucaagacccagucggggaccaagaaccuacgca<br>uccagugugagggggcagcuuuucgcugcagagugacccccgaagcacgcagccaguuc<br>cccgcuucgacuguguacucaagcuggugcaccacuacaugccgccuccagggacccccu<br>ccuuuucuuugccacccacggaacccucguccgaaguuccggagcagccaccugcccagg<br>cacuccccgggaguacccccaagagagcuuacuacaucuauucugggggcgagaagauuc<br>cgcugguacugagccgaccucucuccuccaacguggccacccuccagcaucuuugucgga<br>agacugucaacggccaccuggacuccuaugagaaagugacccagcugccuggacccauuc<br>gggaguuccuggaucaguaugaugcuccacuuuaaggagcaaaagggucagagggggggcc<br>ugggucggucggucgccucuccuccgaggcacauggcacaagcacaaaaauccagcccca<br>acggucgguagcucccagugagccaggggcagauuggcuucuuccucaggcccuccacuc<br>ccgcagaguagagcuggcaggaccuggaauucgucugaggggagggggagcugccaccug<br>cuuucccccucccccagcuccagcuucuuucaaguggagccagccggccuggccuggug<br>ggacaauaccuuugacaagcggacucuccccucccccuuccuccacacccccucugcuucc<br>caagggaggugggga caccuccaaguguugaacuuagaacugcaaggggaaucuucaaac |

TABLE 3-continued

RNA transcripts up-regulated during HF stem cell activation.

| SEQ ID No: | Access. # | Sequence |
|---|---|---|
| | | uuucccgcuggaacuuguuugcgcuuugauuugguuugaucaagagcaggcaccuggggg<br>aaggauggaagagaaaagggugugugaaggguuuuuaugcuggccaaagaaauaaccacu<br>cccacugcccaaccuaggugaggaguggguggcuccuggcucuggggagaguggcaagggg<br>ugaccugaagagagcuauacuggugccaggcuccucuccaugggggcagcuaaugaaaccu<br>cgcagaucccuugcaccccagaacccucccccguugugaagaggcaguagcauuuagaagg<br>gagacagaugaggcuggugagcuggccgccuuuuccaacaccgaagggaggcagaucaac<br>agaugagccaucuuggagcccagguuuccccuggagcagauggaggguucugcuuugucu<br>cuccuaugugggggcuaggagacucgccuuaaaugcccucugucccagggauggggauugg<br>cacacaaggagccaaacacagccaauaggcagagaguugagggauucacccagguggcua<br>caggccaggggaaguggcugcaggggagagacccagucacuccaggagacuccugaguua<br>acacugggaagacauuggccaguccuagucaucucucggucaguagguccgagagcuucc<br>aggcccugcacagcccuccuuucucaccugggggggaggcaggaggugauggagaagccuu<br>cccaugccgcucacaggggccucacgggaaugcagcagccaugcaauuaccuggaacugg<br>uccuguguuggggagaaacaaguuuucugaagucagguauggggcuggguggggcagcu<br>guguguuggggguggcuuuuuucucucuguuuugaauaauguuuacaauuugccucaauc<br>acuuuuauaaaaauccaccuccagcccgccccucuccccacucaggccuucgaggcugucu<br>gaagaugcuugaaaaacucaaccaaaucccaguucaacucagacuuugcacauauauuuau<br>auuuauacucagaaaagaaacauuucaguaauuuauaauaaaagagcacuauuuuuuaau<br>gaaaaaaaaaaaaaaaaaaaaaaaaa |
| 38 | X82786 | Sequence below. |
| | | aaggaaucuucaguacagaaacaagacccaaguguaaguuuaacuggcaggaggaaccaaccaaggacaguuaaggag<br>aaaacccaacccuuagaagaacucaccaguuuccaagaggaaacugccaaaagaauaucuuccaaaucuccacaaccgg<br>aagagaaggaaaccuuagcagguuuaaagaggcagcucagaauacaacuaaucaacgaugguguaaaagaagagccca<br>cagcacagagaaagcaaccauccagggaaaccaggaacacacucaaagagccuguaggugacaguauaaauguugaag<br>agguuaagaagucuacaaagcagaaaauugauccaguagcaagugugccugucagcaagaggccacggaggguaccc<br>aaggaaaaggcacaggcccuagaauuggcuggucucaaaggaccaauccaaacccuaggccacacugaugaaucagca<br>agugauaaaggacccacacagaugcccuguaauucucuacaaccagagcaaguugacagcuuccaaagcucaccaagg<br>cgacccaggacaagacgugggaaaguagaggcagaugaagagccuucagcaguaagaaagacaguaucaacaucaagg<br>caaacuaugcgaucccgcaagguccugaaauugguaacaaugguacccaaguuucaaaggccuccauaaagcagaca<br>uuagauacaguagccaaaguaacuggcagcaggaggcagcuaaggacacauaaaggaugggguucaacccucuugaa<br>guuguuaggugacuccaaagaaauaacccaaauaucagaucacucugagaaacuagcacaugacaccaguauccuuaa<br>gagcacucaacagcaaaagccagacucaguaaaaccucugagaacaugcagaagagugcugagggccucuaaagaggu<br>ccccaaggaaguguugguggacaccagagaccaugcaacauuacaaagcaaaagcaacccuuugcuguccccgaagag<br>gaagucugcaagagauggaagcauugugagaaccagggcuuugcgcucuuuagcaccaaagcaggaagcaacagaug<br>agaagccuguaccugagaaaaaaagggcugcuuccagcaagagguauguaucaccugagccugugaagaugaaacacc<br>ugaaaaucgugucaaacaaacuugaaucuguggaagagcagguuagcacuguuaugaaaacagaagaaauggaagcc<br>aaaagagaaaauccugucacuccagaucagaacucuagguaccgaaagaaaaccaauguaaaacagccaaggcccaagu<br>uugaugcaucugcagagaaugucgggauaaagaaaaacgagaagacuaugaagacugccucccaggagacagagcug<br>cagaauccagaugauggagccaagaaaucuacaucucggggccaagucagugggaaaagaacaugcuugaggucuag<br>aggaacgacugagaugccccagccuugugaagcagaagagaaaacaagcaaaccagcugcagaaaucuugauaaagcc<br>ucaggaagagaaaggagucucuggagagucugauguuagguguuugagguccagaaaaacuagagucgcuuuggac<br>agugaaccuaagccaaggguaacucguggaaccaagaaagaugcaaaaacucugaaggaggaugaagacauuguaugc<br>accaagaaguuaagaacaagaaguuaagaacaagaaguuaccagaaaagugaaacuauguagcaaagacauuuaagaa<br>ggaaaaguaaauuugacuuagugauaaguuccagugugguuuucaccuccaguguaaagaugaacuguaaauacuac<br>ugcuacugccugaguuuaaggaaggaagcuuugagcuuuccuggucauacucucuucagacgccaauggaggucau<br>gaggaagaucaccagggaucucagcgcaauuacaguuuaggggugagcaggcagaaauguggcccucuguccuaucc<br>aauaaagcucugaaauucgcugccaaaa |
| 39 | AW122523 | uuuuuuuuuuuuuuuuuuaaaucaaaaguuaugaugacuuuauuuuaaaucuuaauacacc<br>aaaaauauuuuucaauguugugagauaagcacuugaaaauaagaauuccaacacugcugu<br>gauuucgcugugaggcuugauagugaauuuucccucugaauaugggguuuagggccuagga<br>agcagaaugccagucauuuuccaaguagcagugagcuaagcccagcccggucaugcucag<br>acccacacuuaacugaaauauucacacuaggaggcggcaccaccaggcaacaccuugauc<br>aaccaggagaacaaaagucugaagugccaccaagcauuggggaaaugauauuguuuagau<br>gcuagugagucagguucuuucaaaugugccuaacuggguugcaaacauaguugcauccu<br>uau |
| 40 | AI642048 | gucuguaaaaaucuguuuaauaaauauacaucuuagaaguaccaaaauaauuaccaacaa<br>aauacaacauauacaacauuuacaagaaggcgacacagaccuuaguuggggggcgacuuuu<br>aagcacaugccacugaacaccuggcucuuacaugggaggacacacugggcucacuuacua<br>ggucuaugguggguucaaucaaaagcacaauaaauaaaacgugguccuuucauuagguucu<br>ggaaaaucaccucccccccccccaaaaaaaaucccacaaacaugaaccuuaagagacauu<br>uucuuugaauuucagugaucuguuuccccggauuucacaaagacaacagccgaaucaccc<br>caguaaaaugccugggucuaggcgcuguguggugugggugcuaaguauacccuuucucauu<br>uuuuuucuuuuucu |
| 41 | L07264 | cggccgccagaccuucaagggcuggaguggacgcgcggaccgacucugaacagacagacg<br>aaccgcggccgcaagguucccagacaggaucucacccagaggcaggcagcggacagugcc<br>uuaguggaaccucgcugucccuccaccgccuggccccggugcaggcguccaguggccgccg<br>cauccaaagugaucgcugccucccccgucuccgccagcucgggaccaugaagcugcugccg<br>ucggugaugcugaagcucuuucuggccgcaguguuguccgcguuggugaccggugagagu<br>cuggagcggcuucggagaggucuggcggcagcaaccagcaacccugacccucccacugga<br>uccacaaaccagcugcuacccacgggaggugaucgugcucagggggguccaggacuuggaa<br>gggacagaucugaaccuuuucaaaguugcuuucuccuccaagccacaaggccuggccacc |

TABLE 3-continued

RNA transcripts up-regulated during HF stem cell activation.

| SEQ ID No: | Access. # | Sequence |
|---|---|---|
| | | ccaagcaaagaaaggaaugggaaaaagaagaagaaaggaaagggguuagggaagaagaga<br>gacccaugccucaggaaauacaaggacuacugcauccacggggagugcagauaccugcag<br>gaguuccguacucccucuugcaaaugccucccugguuaccacggacacaggugucauggg<br>cugacucuaccaguggagaauccccuauacacauaugaccacacuacagucuuggcugug<br>guggcuguaguacugucguccgucugucuucuugucaucgugggacuucucauguuuag<br>guaccacaggagaggagguuaugacuuggaaagugaagagaaagugaaguugggcguggc<br>uagcucccacugaggaggaccugagcuauaggaaccuucagaggcuacuucugagacagug<br>guucguuacacguucuacauagaggagaaauauuucaccagcagccaugaaaacgucuuc<br>auucauuuccaguugcuacccugacugggccuccuguaau |
| 42 | M15668 | ucgaccucacggucuugccaaaaugucgcuuuccaacaagcugacuuuggacaagcugga<br>cgugaaggggaagcgggucgugaugaggguggacuucaacguuccuaugaagaacaacca<br>gauaacaaacaaccaaaggaucaaggcugcuguuccaagcaucaaauucugcuuggacaa<br>uggagccaacuccguuguccuuaugagccaccugggccggccugaugguguucccaugcc<br>ugacaaguacuccuuagagccaguugcugcugaacucaaaucucugcugggcaaggaugu<br>ucuguucuugaaggauugugugggcccagaagucgagaaugccugugccaacccagcggc<br>ugggacugucauccugcuggaaaaccuccgcuuucauguagaggaagaagggaagggaaa<br>agaugcuucugggaacaagguuaaagcugagccggccaaaauugaugcuuuccgagccuc<br>acuguccaaacuaggagaugucuaugucaaugaugcuuuugggacugcacaccgagccca<br>uagcuccaugguggguguaaucugccacagaaggcugguggauuuuugaugaagaagga<br>gcugaacuacuuugccaaggcuuuggagaguccugagcgacccuuccuggcuaucuuggg<br>aggcgcuaaaguugcagacaagauccagcugaucaauaauaugcuagacaaagucaauga<br>gaugaucauugguggugggaauggccuuuaccuuccuuaagguccucaacaacauggagau<br>uggcacaucucuguaugaugaagaaggagccaagauugucaaagaucucauguccaaagc<br>ugagaaaaauggugugaagauuaccuugccuguugacuuugucacugcugacaaauuuga<br>ugagaaugccaagacuggccaagcuacuguggccucugguauaccugcuggcuggauggg<br>cuuggacugugguacugagagcagcaagaaauaugccgaggcugugggucgagcuaagca<br>gauuguuuggaauggucuguuggggguauuugaaugggaagccuuugccaggggaaccaa<br>gucacucauggaugagguggugaaagccacuucuagggguugcaucacuaucauaggugg<br>uggagacacugccacuugcugugccaaauggaacacagaggauaaagucagccaugugag<br>cacugggggcggugccagucuagagcuccuggaagguaaaguccuuccugggguggaugc<br>ucucagcaauguuuaguauuucuuuccugccuuugguuccugugcuccuaagcuaaccu<br>gcuguuuuccacaucuccauuugguguuagcgcaagauucagcuaguggcugagaugugg<br>cacagaccuuaacagugcaagcaucucagcucgucuuacugcaucagaugcugguucuuc<br>aagaucccauuuaaauuccuuagugacuaaaaccauugugcauuguagagggcgucuauu<br>uauauucugccugagaaaggaagugagcuguaaaggcugagcucucucucugacguaugu<br>agccucugguuagcuucgucacucacuguucuugacucagcauggcaaucugaugaaauu<br>cccagcuguaagucugcagaaauuuccgaauuc |
| 43 | AI047508 | uuuuuuuuuuuuuuuuucauguuuaauaguuuauuucuuauuuuguugcuuauaucuuc<br>aauaaaucauuuugcagguuuuguuacagauuuuugauaagccaacucaaguacugauuu<br>uucauccucucugaaaguuuuaaaccaggaaaggaaaacguuccauggaauccaucuucca<br>cauggugaugagucacaugaacuccaacauucugaagccgcuugacauacaugaguccauc<br>aucucuuaggacaucauacuggcaagugaugauauaggucuuagguaaaugaugcaauau<br>auugucauuggccaacagagggcaugccuucacaucuaugaacccuggauacuuuugagc<br>cagcucagaacuaccaggagugggauuuuuguaaacgggacuuuucuuguaucucucagg<br>gagcaaggaacuccaauucacaaacuguaacaaguggcuagauuccaugguacauguug<br>guuga |
| 44 | AJ001418 | Sequence below. |

gagcacccgggacccugggaccacaacgcacuugcucccucucgaccgcgcuccugacccgcagcccucgccaacccuacgga
uccuaaccaccgccagccuagguggggcgucaggaugaaggcagcccgcuucgugaugcgcagcgccagcucgcugagcagcg
ccagccugguccccagggaggucgagcuguucucccgcuacagcccguccccgcuguccaugaagcagcugcuggacuuugg
uucagaaaaugccugugaaagaacguccuuugcuuuucugcggcaagagcugcccguccgccuggccaauauccugaaggag
auugacauccugccugaccgcuuagugaacacuccuucggugcagcuggugaagagcugguauauccagagccugauggau
uugguggaguuccaugagaagagcccagaagaccagaaagcccugucagaguuuguagacacgcuggucaaaguucgaaaca
gacaucauaaugugguccccuacaauggcucaaggcauccuggaguauaaagacaccugcacaguggaccccguuaccaaucaa
aaucuucaguauuuuuuagaccgguuuuacaugaaccgcauuucuacucggaugcucaugaaucagcacauccucauauuca
gugacucaaagacgggaaacccaagccacauuggaaguaucgacccaaacugugaugugguagcaguaguccaagaugccuu
ugagugugcaaagaugcucugcgaccaguauuaucuaacaucgccagaauuaaaccucacacaagucaauggaaaauuucca
ggccaaccaauccacauuguguacguuccuucacaccuucaccacaugcucuucgaacucuucaagaaugccaugagggccac
ggucgagcaucaagaaaaccguccuuccuugaccccaguagaggccacugucgucuugggaaaagaagaccuuacaaucaag
auuucugaccgaggaggcgguguuccucugaggauuacugaccgccucuuuaguuacacguacuccacugcuccaacaccug
ugauggacaauucccggaaugccccuuuggcugguuuugguuauggcuugccaauuucucgucucuacgccaaguauuuuc
aaggagaucugaaucucuacucuaugucagguuaugggacagacgcuaucaucuacuuaaaggcuuuaucuucugagucug
uagaaaagcucccagucuuuaacaagucagccuucaaacauuaucagaugagcuccgaagcugaugacugguguaucccaag
cagggaaccgaagaaccuggcgaaggagaagcuggcagugugaagcggaugacgccugacauuuuacgggaucaaagugggu
cuguggcauugcugcuucgugaauguguguggacucuaguuuccgcaaaacaacgcaacacaaaaccaagcaagcaaaacaca
aacacgaguacaaaccuugaccugaugagggacagagcuugguuggaugacccgggagaagucagggcagggcuccaggga
uaacaggugucccugcuucuccuuuggcaaugcaaaaugacuccugacuguuccaaauacugaaaagaagucugccucugagu
uacagcucuuucucaacaaguacagaguuugaggcuugcaguugcaacagcuggauguuuggugguucuugcugccagcca
aauaaauugguguuuagugaacauuuucaguguuucccccgccaugcaaagcuuggcgccuugggagaaaugugguguaaaug
uacauuguauagguauuagugugcucuagaaaggacaggauggaaggaaucaaagcacuuuaucgagcuuguggcugagca
uugcagccuaugugcaaacccagaggaaaaguaucucugucaagacagcuccaguaucaugcagcuuuuuauguuugcacuc
aaaaagccagugccuucuggcugguggugccgaggcuugggugaaauguuaaauaugcacugaccucagaaagucgaguucaaaa TABLE 3-continued RNA transcripts up-regulated during HF stem cell activation.

| SEQ ID No: | Access. # | Sequence |
|---|---|---|
| | | gggagauaaaauugccaaagugauccaaggauugugcauguugggaaacccauaugagagaaaggauucucauacuuagaac<br>uuuccuaugaagaaaugguggguaaacuuucucuaccuagaaguaguggaaauuucaaggucaucuuaaaaaagaugugcgu<br>uguauauuuuaacuacauucucuacacucuaacauuaacauaucuauucaaauuugucuaguugccaauugucuucagagu<br>gugaaaauuuaaauccuucuugaaguaucuuucgugagaguaguauggaaguaaaacguucucauaucaggaggaugucau<br>uugugaagcauggggacaucaugaacuagugaugugcgugaggcuugggaggcugaaggguaaggaucagcgggaggccau<br>ccauguaggagagagaauuaaaacgaggagcgagggaagcaauggagagagggaagcaagaaaggaaccagaaggcuggcau<br>cauccuauuucccacaggcuaacccaagggaugcucugugccuuuccuggggagggaagggggugaacugguagauuugaa<br>agcaguauggcuucuucuguggucucccucuuacuagacaaggugaaaugauaauucgugucaaauuaaugugaaauuuu<br>uuuccugcauuguaauauuaugaggccugagucgcaguugaguuugaaauuuguauuuaauuucacagugaccuagagcua<br>aggugcucccgguuguggcaauaggagccacaaguauuuucuuucuuucuuucguucuuucuuucuuucuuucuuucuuu<br>cuuucuuucuuucuuucuuuccuuccuuccuuccuuccuuccuuccuuccuuccuuccuuccuucuuccuuuccuuuucu<br>uuucucuucucuucuuuucuuuuuucuguuucuuuuucuuuuuuugcauuguagauguuguccuuaaaagaucagggca<br>gugacuuucacagcaggacuuugacucccacauugguugaucacacaaaacugucagcauuugguaaucugauguauagu<br>uguuuuguugcugauguuuccauugaaauuucagcucugaguuugugcacaugaauacuuacuuguguuuaccaaagguc<br>uaaggcauuugguuacuuaacccaaauauccugaacugugcguaaaguaauagagaaaagcuuuagggucucaauaguguca<br>ccuguguaaaucaaaucaaaauagccuucccuauuauuuaugaacccaugggagacuuuaaacucuuguagauagaugcuaa<br>augcccaggcccacuuaacuuauuaaugugugaauuacauuuauguuuuuaguuuauaugcaaagaauugugauaauuuua<br>uaauaaauauuuuuauuauaauagu |
| 45 | AI838080 | uuuucuuuuuuuuuuuucuucucuuuuuucugccaccaacagcacugugcaguuuauua<br>accauucauguacaguagccaucuggggagauugggacagaauugggaucgcaaagugga<br>uagauauucagcaucuaaugguuggcagaagccgccauauacucuucacaaauaucuucc<br>acagucaauacagaacuagccauuaucccagcacaccgauuugugc |
| 46 | AF072127 | agccaggagccucgccccgcagcugcacagagagcaaggguauaggcacuaacuuguuug<br>cagagaccccaucaccuucgggagcucaggugcgcaccuugcaaacuccacuuucugcau<br>cugccacugagcccgcgggagccucggaaagagccauggccaacgcggggcugcagcugc<br>uggguuucauccuggcuucucugggauggaucggcuccaucgucagcacugcccugcccc<br>aguggaagauuuacuccuaugcuggggacaacaucgugaccgcucaggccaucuacgagg<br>gacuguggauguccugcguuucgcaaagcaccgggcagauacagugcaaagucuucgacu<br>ccuugcugaaucugaacaguacuuugcaggcaacccgagccuugaugguaauuggcaucc<br>ugcuggggcugaucgcaaucuuuguguccaccauuggcaugaagugcaugaggugccugg<br>aagaugaugaggugcagaagauguggauggcugucauuggggcauaauauuuuuaauuu<br>caggucuggcgacauuaguggccacagcaugguauggaaacagaauuguucaagaauucu<br>augaccccuugacccccaucaaugccagguaugaauuuggccaggcccucuuuacuggcu<br>gggccgcugccucccucugccuucugggagguguccuacuuuccugcuccuguccccgga<br>aaacaaccucuuacccaacaccacggccuuaucccaagccaacaccuucuagugggaaag<br>acuaugugugacagaggcaaaggaagagaucuuccuggagcaaauacaaaauggacauug<br>aaccuaggauugacauuaacgccuuagacuguugaugaugguuaucggaacugugguaga<br>acagaaggaagcauauuuuuauacauccccauggcuaugcaggccuuggcug |
| 47 | X80417 | Sequence below. |
| | | cggcacgagcggccacugaccgagaagugcccccgccuggagucagccugggggcaggccagggucccaccagacccc<br>gggaugaccgcagccagucgggccaaccccuacagcaucguaucaucagaggaggacgggcugcaccugguuaccau<br>gucaggcgccaacgguuuuggcaauggcaaggugcauacacggcgccggugccgcaaccgcuucgucaagaagaacg<br>gucagugcaacauugaauucgccaacauggacgagaagucacaacgcuaccuggcugacauguuuaccacgugugug<br>gacauccgcuggcgcuacaugcugcucaucuucucucuggccuuucuugccuccugguuguuguuuggcaucaucu<br>ucugggucauugcugucgcccacggggaccuggagccagccgagggccguggccguacacccugugugcugcaggu<br>ccacggcuucauggcagccuuucucuucuccauugagacacagaccaccauuggcuacgggcuacgcugugugacug<br>aagagugcccgguggcugucuucaugguggugggcgcaguccauugugggcugcaucauugacuccuuaaugaaugg<br>ugccaucauggccaagauggcacggcccaagaagcgcgcacagacucugcuuuucagccauaaugccgugguggcuc<br>ugcgugacggcaagcucugccucauguggcgcgugggcaaccugcguaagagucacaucguggaggcccaugugcg<br>ggcccagcucaucaagcccagggucacagaggagggugaguacaucccacuggaccagauugacaucgaugucggcu<br>uugacaagggccuagaccguaucuuccugguaucacccaucaccaucuugcacgagauugaugaggccagcccacug<br>uuuggcauuagccgucaggaccuugagacagacgacuuugagauuguggucauccuggagggcaugguagaggcca<br>cagccaugaccacacaggcucgcaguuccuaccuggcuaacgagauccuguggggccaccgcuuugagccagugcuc<br>uucgaagagaagaaccaguacaagauugacuauucacacuuccacaagaccuacgaggugccaucuacaccccgcugc<br>agcgccaaggaccugguggagaacaaguuccuccugcccagcgccaacucuuucugcuaugagaacgagcuggccuu<br>ccugaucagagaugaggaggacgaggugucuaccgaccgggauguccgcaccccucagcccgagcaugacuuugaca<br>gacugcaggccagcagcgcugcccuugugcggcccuacagacgggagucggagauuugaaugcccuuggcuuagaug<br>cagcaccacccugaccacaauaggucccaugucccuuggggggccugcguuugagcagagcaggccgaaagccucggg<br>ucacagacucaguagcaucuuagucuuuuucauguuuuuucgcaguagcuugggaaaguuggcgggagcguggaug<br>gcccaaaugacuggcucacggccucggaggcugauguauacccaugggcaaggaggugacuucuuggggguaggguu<br>gcucaggaguuagggacucugcuggaggccuuaggugcaggucccaaccccggugggaggaggcuguguauguaca<br>cuucauugguuuuuaacuugggcaagacuguuuacaaaccaaaacaaacaaacaaacaauc<br>caaaaaaaaaaaaaaaaaaaaaaaaaaa |
| 48 | AI847051 | uuuuuuuuuuuuuuuguuccuuuuuuggaauucccaaagcugguuuuaauuucaaaaaau<br>uaugaggucucuucccacacuggggauaaugggaugggauagcccaaacuauuaucccagu<br>ucaaccccagccugguccaaacaccauuacugucacugggcccugucauuucacc |
| 49 | U09504 | uccucguccucgucuguuccaucuucuccaaauagcucuaacugugaugccaacggcaau<br>cccaagaacgcugauaucucuagcaucgaugguguucugaagagugaccgcacagauugu<br>ccugugaaaacaggcaaaaccagugcuccuggcaugacuaagagucacaguggaaugaca<br>aaauuuaguggcaugguucuacuguguaaagucuguggggauguggcaucaggauuccac |

TABLE 3-continued

RNA transcripts up-regulated during HF stem cell activation.

| SEQ ID No: | Access. # | Sequence |
| --- | --- | --- |
| | | uauggaguucaugcuugugaaggcuguaaggguuucuuucggaggagcauucagcaaaac<br>auccaguauaagaagugccugaagaaugagaacuguuccaucaugaggaugaacaggaac<br>cggugccagcagugccgcuuuaagaagugucugucugugggaugucacgagaugcuguu<br>cgauuuggccgaauuccuaagcgugaaaaacagagaaugcuaauugaaaugcaaagugca<br>augaagaccaugaugaacacccaguucaguggccaccugcagaaugacaccuuagcagaa<br>cagcaugaucagucagcacuaccagcucaggaacagcugcggcccaagucccagcuggag<br>caagaaaacaucaaaaacacuccuucugauuuugcaaaggaggaagugauugguauggug<br>accagagcccacaaggauaccuuucuguauaaucaggaacaucgagaaaacucaucugag<br>agcaugccaccucagagaggagaacggauucccaggaacauggagcaauauaauuuaaau<br>caagaccaucguggcaguggauucacaaccacuuccccuguagugagaggcagcaacau<br>cucaguggacaguacaaagggaggaacauaaugcauuacccaaacggccaugccguuugu<br>auugcaaauggacacuguaugaacuucuccagugcuuauacucaaagagucugugauaga<br>auuccaguagguggauguucucagacugagaacagaaauaguuaccugugcaacacugga<br>gggaggaugcaucugguguguccuaugagcaagucuccauauguggacccucagaagucu<br>ggacaugaaaucugggaagaauuuucaaugaguuuuaccccagcaguaaaagagguggug<br>gaauuugcaaagaggauuccuggcuuccgagaucugucucagcaugaucaggucaaucug<br>uuaaaagcugggacuuuugagguuuuaaugguacgauuugcuucauuauuugaugcaaag<br>gaacggaccgucaccuuucuaagugguaagaaguacaguguggaugaccugcacucaaug<br>ggagcaggggaucugcucagcucuauguuugaguucagugagaagcugaaugcccuccag<br>cucagugaugaggaaaugagcuuguucacagcaguuguucugguaucugcagaucgaucu<br>ggaauugaaaaugucaacucaguggaggcuuugcaggaaacacucauccgugcacuaagg<br>accuuaauaaugaaaaaccauccaaaugaggccuccauuuuuacaaaauuacuucuaaag<br>uugccagaucuucgaucuuuaaacaacaugcacucugaggaacucuuggccuuuaaaguu<br>cauccuuaa |
| 50 | U22033 | auggcguuacuggaucugugcggugccgcucgggggcagcggcccgagugggcugcccug<br>gaugcgggaagcgggggucgcucggacccgggacacuacaguuucuccgcgcaagcuccg<br>gagcucgcacuuccccggggaaugcagcccaccgcauuccugagguccuuugguggugac<br>caggaaaggaauguucaaauugagauggcccacggcacaaccacacucgccuucaaguuc<br>cagcauggcgucaucguggcuguggacuccagggccacugcagggaguuacauuagcucc<br>uuaaggaugaacaaagugaucgagauuaacccuuaccugcuuggcaccaugucugguugu<br>gcagccgacugccaguacugggagaggcuguuggccaaggagugcagguuguauuaucuu<br>cggaauggggaacgcaucuccgugucugcagcauccaagcugcuuuccaacaugaugcug<br>caguaccgggggaugggccucuccaugggcagcaugaucuguggcugggacaagaaggga<br>ccaggacuuuacuacguagaugacaaugggacucggcucucgggacagauguuuuccacu<br>ggcagcgggaacaccuaugccuacgggggugauggacagugguuaccggcaggaccucagu<br>ccugaagaggccuacgaccuuggccgcagagcuauugcuuaugcuacccacagagacaac<br>uauucuggaggagucgucaacauguaccacaugaaggaagacgguuggguggaaaguggag<br>aguuccgaugucagugaccugcuguacaaguaccgagaggccgcucuguga |
| 51 | AF033034 | Sequence below. |

auuccaggaguuccagcugcuggagaggacuguguagaagguaaccuaccccaucucucuuacuucgucucuagaugggag
cagacaaguacauauagccugcuuggagcgaggacuuugaaaggcugagacuugcguccacucugagggcaacuaguccaga
cucugacaggucagcauuuccugacugggugcacugaaugccaagcaccagaggucugucaccuuccgacauuggaccaaga
gagucccagagacccucaaagacacaggaacagagguguccuuugggugagagaccugugcccugccaagccucucagcccc
uagaaaggcggcagggcugaguagcugagugugugcaacuugggagcagccugauuucagugcuugucaccugugagggca
aaggcagcaugcuuaaugccaucaguccuacucuucucacccguggaacagacgcauaacugaccuuuuuucgugaccacua
uuagggugcauuuaaaaaucaaucucucucuuuucugcucccucuuucuccaccuucccucaugugugugucugugugugu
guguuucugugugugugugcgugcaccauacagguauaugugccaugacaugugugcaggucaguagacagccuugguug
ucagucccugccuucuacuuuguucaaggcagggucuauucuuuauuauugacugcuauccagguacaccaagacaguugg
ccugugagguuccagggagucuccugucucuggcccccaucuuauagcaggaguugugagauuucagaaaugugcacccac
aucuagcuuuauuuggcaucuuggcacccaaacuugggguucucaugcuuuccaagcaaggacuucacccacugaaccaucuc
accagcuccacuauggcgguuuucugaaacugaagggagugggggagaaggcgcugagugugaacgggucuggaaggcgggu
auaaccuuuaaggcuggcugguucugagagaggaaagccggcuugugucccauucaggugccaggugcagcaucaaaugug
gcuccacccaacggucaguaacuccgcagacagcaccgugguuaacugccucacagaggggcccagggaccuaguuccuua
aagcccacuuaguuugagagacgacauggaggggcaagcccagcccuguccagcugcauucacacgaggcccuucuccucc
gaggacccuaccuuuguguuuaguggcugaggcugugugcucugcuugaagcucuggcuaucaggaaggaccuggcccac
cggcuggcaggacaaacuggcccagugaaggcacuguccggucuccugguggaucacaaggaaaggggcguggcauguccag
auuugaacccuggaugccucuucccagguaggaagucuaagggucaacaugaauaggugaggguggugguggaaagaauc
ugcaugcaaaaucaggcacucaugucugacaucgucaaacacuauauuuauguagauuuauaugggggugaggcuuggga
gcacuuguauuuuugugugcaauugcaagagcuuccuccacauugcaguguuaaauaucauauggugcuggaccaaccauc
ucuggaacgagggugagguuugguacccgugacuaugguucucuguguaguagaaacggcuucuugggaagagagagga
agugcuuugaaaugcauccucucuuguuucauucugcaucauggccagguuucucugcacaaagaugcaauagacauucag
gaaaauaagcgcauugcaagaugucaaaagucaugaaaaaugaaaagcaaggucacugcagcuggggguaguguggcugua
gaagcacguuuaugauguacagguuccgggagagggaggaagagagagggagggaaggaggaauggaggaagagagggaga
gggagcaagagagggggggagggagggaggggagaagggagagagagagagaagaaagagagggagggaagaaggaauggag
gaagagagagaaagaggggaagaaagagagggagggaaggagggguggaggaagagagaggugugagggauggagggacag
agagggagggaaggagaaauggaggaagagagaaacagagagauggaggaagagagaaaagucaccaauuauuuuucucccc
agucgcccccugcccucacaccaagguaccccacuuuucuuucacucaugcacacacacuacacccaauguuagguaaca
cauguagggcaggcagagccuuugugaaugugcuugguaguuucugccuuacuucuaaauaaccaaucacacggaugcca
caggguuccuuuagacuguccagggcuccggggcucuuagacuguucccaauguggugucacaugcaaacaguaagcacc
uucuuguuugguggugcccaggaugcugcagguacuagaaauuccugcacagaccuuugcuacuucuacacagacuuacccu
uuaaaacauuuaauuauauguuuuuuucagcauaaagaucuauuuugauuauuuuuaguugcguguaugggugugugccu
gugugugauuguguaauugucuguaugggaguguaagugccuacagaggcaucggauccccuggagcugccguuacaagua
agggacugggacucagaccugagugguuuggaugagcagugaaugagcguggugagccaucccaccaugcccuauaaacacu TABLE 3-continued RNA transcripts up-regulated during HF stem cell activation.

| SEQ ID No: | Access. # | Sequence |
|---|---|---|
| | | uucaagaggacuuugcuggguauggucaaguuguccccugcgacagccaccccaacuugccauccucauuuacuguacugg<br>aagcagcaaccaccucugcaauuuugcacaagaaccugagagucugaaagacuuuuguuggcacuggccuguguuccacugg<br>gguggacacauuaaucuaaaagcuaagaagcucacuucagcuuugccaggcaaccagcacguuugagcacaacgguguagcc<br>aggaagggugugugggaauuuugaugcuaguuuuucuuuaauuagguugagagugaaaucauggucuguaugcauccaac<br>aacuuaauccaaaaaguugguugcacggcuccuggaagguuuaccggcaaggaaccugucccauuuuguaaguaggugggga<br>cuggagaguugccaagaagcccccucccugccccuuccuccuggcagauucugcuuaaaaugagugugguucacugcaga<br>auagugucaccugucuucagaugucuaaagacauaagaaaggccuagccagcuaagucagaaaaggggacuuuccggugga<br>augcauuuuccagucucuaggagaagucuuuauccaaauaaaauuagcauagugguggagucacugccagggcgcuggugc<br>ggaagcacagcccagagccgaggacguggccauccuccuuccucugaugcaaaguguucucuaucccccaguuaccaugagca<br>auaucaguagcaucgugaaccgggcccgugaugccuuuaacucaggcaagacucgaccgcugcaguuccggguugagcagcu<br>ggaggcguugcagcgcaugauc |
| 52 | AA960603 | uuuuuuuuuccaaaaaauuuuauuggggaaacuacaaaacauuuacaguacaauguuua<br>cagucacaauuuguagugaacugauuccccaaaauauauuacaacucaaguugacuuaau<br>cuuguuacauucaaaaaccuacuucugucaaaguaguccagagugcacacgcggugcucc<br>aacuguaccuacauacaaacuaaacaacugcucauuuaucugccauccaggaaagccgga<br>gacauuccugccucuuuacauugaaaaauaauaguacaaguuuuggacugucauugaac<br>aaggcauauucauguaccaccaacauuuc |
| 53 | U47737 | Sequence below.<br>ggugauccuccaggaccuaagguuucgguauuaucuucggggccucuucacccggaggugagucugcugagcccgaccuca<br>gguguucacucgucacgcgagggccuggccacggcggggaagcacugggagagagcgggaggccuugaccgcagcguguag<br>gaucugggguccccggcgcucugcucccgggugcagagugguuggagcaugcgaggcccucugcagcgugcucuguuccuac<br>caucaccccaccccccaccccaguccuuccugcacguuucuggagaggcaaaggccccugcugagccuucacugguaccccua<br>ucucgacuccacuugucugcuugggaucuccaaaggggauacacccucguaaacuagagcaggaggcuggggggugggggg<br>uaggguagggucugaccaguuagauugaggcuggacccuccccagagugaggagcgggaagcucuuugucuuauccagga<br>uuuugcauaucaaugcugagguucuggugauuaaguaggguccuggcuagcgggguaaccugaacaaccuuccuccgcu<br>ggccgcuagccaauagacaccuggcuuccgcggaugagcccuuugaguuuguggagguguuccucagguccccagggcccu<br>gccccguugccugcagaugugugacagacaaaacauuggacucguuuuccaaccacuucacccuuccuucgcuagucuc<br>cgguggacgaugggaugccucauugacuuguuuguggcugugcaugccagagcuuccuagcagacagcucagggcuccauc<br>guuccuaaaucccacuguguaacgaaaaaaaaaaaaaacaaaaacaacaacaacaacaacaacaaaaacaaaaccagaaaugagga<br>caggcccagcugggcuuggcacugaacuuggccaccuggagcuuuggcuacccacuacaagaugucagcaagucucaggaua<br>gaagaggccuaaggccaguccuggaagauaccaaaacuucaccuccucuauaccccguuccucuaggagaacuguaagccacc<br>uuugucucugggacgccccucucccacucaacagauggcaccagucaucuuccuccucaagaggccagugguauucaaaaua<br>ggauauugaaaccaagcaagcugguccucuccucuacccuaugccaaagacuucugcccaaagggcccagaaaagucccauag<br>ccaucuggcuggcuagugugcugacugcuacaggugucagugucccccagcgagcagguaguggaguggaggugucuucuu<br>guggaaauggguccugagccucuaccuuguacagaaaggaauuagugaagcccagaggccuccagcccgugucucugccaca<br>agagagaggggguggggguggggcuguauuugguucccagggcucagggaagguuuucgguucaugcaugcucauuuauc<br>ugaccacugucuuaaccccaggacaaccacuuaacuguccacuuccauaucagaguucuugguuccccuuuacuucgucuau<br>ggagccccugaguuugggaagggguauuaacugaaagguaccauuagaugaacuuggagaaagauuuguaggugccacggg<br>agauuucagguaaaagcucuuuuaauaauuggcuacaauagcagcaggaggaggccaggaauucugagguagagauuugau<br>uagcagcacguggagcaaaggagacuucugacuccuacagguuucagaaaguggggagaggcucucagaugaauggcuugg<br>acugugagguaaguguuaguguagcacgagacuagcuuaaggcuguacaaauuguccgucugauuggugcauugggccagg<br>uagacacuagauaagcaauugggccuuaacucgaguugucuuaauggcuaccccccagggcagcagggagucaauacugcucu<br>ccugucuggggccugaaugcugaaaccaucuacaaaggggacauaaggcauauuggggagguguagagugggccaggccca<br>gggucugcugguaucuaugccaggauccugagugguggugcguagccugucuuuuaaccaacugccucucucacaguagg<br>cuuacuuuggcuugcgaaccuucagcagaugucugccacuuccaacaugagagucuuccugccugugcuguuggcagcccuu<br>cugggcauggagcaagguauggagcucugagauaacccugcagccugguccuccuccugaucucucauucuuucuccugag<br>uagaugcccagggcuccuccugagccagcccuccuaggaacgucuggccuucccaccuccuacucucuagccaacugaccua<br>guuccccugaugcugugcuggcccagcuacaccuuugucaccucguguugacuuuagccacuccaguaccaaagucugaagu<br>caguugucauuggcuggcuuuuuucccugacccagggcugagcaugcuguugcuucuugucagugggguuggggaucaagg<br>gccccacuggaaagucaccuuacccuggaaggcuuccccaggcaauaggcaggugucaccuacagcauugucccuuuugcag<br>uucauucccugaugugcuucucauguaccgaucagaagaacaauauaaacugccuguggccaguuucaugccaggagaaaga<br>ccauuacuguaucacguuaucugccgcugcgggcuuuggugaguagcugccuguuucccuagccagggccagggaccugcg<br>gggcuuuccccauuuccugcucccugucugucuguccccucauccucacuuuccaugcagggaugucaaccuuggcuaca<br>cccugaacaagggcugcuccccgaucugccccagugaaaaugucaaucucaaucucgguguggcguccgugaacagcuacug<br>cugccaaagcuccuucugcaacuucagcgcagcuggccucggacuucgugccaguaucccacuacugggccuuggacuccug<br>cuuagcuuguuggcucugcugcagcugagccccugaccaucccccauguguucuccauaucccccccagcucaggaaaagccc<br>agcuccuuuuaggucccaggggacccuaggaaccuucagcuccuccugggugugucuaguucccccuccacacucucucaac<br>gucagggcuaaguaccaaacucacccauaccugcucuguugaagugguacuggcuacccuugcuuccagagccaauccuaua<br>accucccuuggggaaccagcgaaggggugaagaucuccuuggagucucaagaguaccagagucagcgccgaaucuuguggac<br>acacugacaaggaugucuaauccaaauagauguauaucugugugcucaguguaucccugugugaaugaagccacuuggauu<br>cugggguggggcaaagaagaccugaaaagauucuacagcagaaggccugugucgccaccaaaaccccucccccugguaucauu<br>guacccaccuuguacucuguucaggaggcugcccauggaggacugccaccccuccagaugaaggcucccacuacccgaugca<br>guugagucccauccugcccucucugcccacacuggcuuccugcugcuauucuagugccucaaauaaaccguucacacccuu |
| 54 | L00039 | cuuccucccucuacagaagaagagcaagaagaugaggaagaaauugaugugguguguucugug<br>gagaagaggcaaaccccugccaagaggucggagucgggcucaucuccauuccgaggccac<br>agcaagccuccgcacagcccacugguccucaagaggugccacgucuccacucaccagcac<br>aacuacgccgcacccccccuccacaaggaaggacuauccagcugccaagagggccaaguug<br>gacaguggcaggguccugaagcagaucagcaacaaccgcaagugcuccagccccagguccc<br>ucagacacggaggaaaacgacaagaggcggacacacaacgucuuggaacgucagaggagg<br>aacgagcugaagcgcagcuuuuuugcccugcgugaccagaucccugaauuggaaaacaac<br>gaaaaggcccccaagguagugauccucaaaaaagccaccgccuacauccuguccauucaa<br>gcagacgagcacaagcucaccucugaaaaggacuuauugaggaaacgacgagaacaguug |

TABLE 3-continued

RNA transcripts up-regulated during HF stem cell activation.

| SEQ ID No: | Access. # | Sequence |
|---|---|---|
| | | aaacacaaacucgaacagcuucgaaacucuggugcauaaacugaccuaacucgaggagga<br>gcuggaaucucucgugagagcuaaggagaacgguuccuucugacagaacugaugcgcugg<br>aauuaaaaugcaugccaaagccuaaccucacaaccuuggcuggggcuuugggacuguaag<br>cuucagccauaauuuuaacugcucaacuaaauaguauaaaagaacuuuuuuuuaugcuuc<br>ccacucuuuuuucuuuuuccuuuuaacagauuuguauuuaauuguuuuuuuaaaaaaucg<br>uuaaaaucuauccaauuuuccauguaaauagggccuugaaauguaaacaacuuuaauaaa<br>acguuuauaacaguuacaaaagauuuuaagacauguaccauaauuuuuuuu |
| 55 | D21099 | gugggacgggcccccucgaggucgacccacgcguccgggaguacccccgaccuuggcug<br>cgugcugacucgcuuccuucugccugcccaggcuugcacuccccggggaucugccucugc<br>aucucuugccuucgcuguuguuucccucucuguccagcucccccucccgcucucgcccugg<br>agaauggcucagaaggagaacgccuacccguggcccuacggcucaaagacgucucagucu<br>ggccugaacacguugucccagagaguccuacggaaggagccugccacgacaucugcgcuu<br>gcucucgugaacugguccaacagccaguccacagcugccccuggccagaaguuggcugag<br>aacaagagucagggcuccacugccucgcaaggaucccagaacaagcagccuuucacuauu<br>gacaacuuugagauugggcguccuuugggcaaaggcaaauuuggaaacguguacuuggcu<br>cgggagaagaagagccguuucaucguggcacucaagauccucuucaagucucagauugag<br>aaggagggguagagcaccagcuucgccgagagaucgaaauccaggcgcaccugaaacau<br>cccaacauccuucaacucuacaacuacuucuacgaccagcagaggaucuacuuaauccug<br>gaauacgccccucgcggggaacucuacaaggaacugcagaagagucggaccuucgaugag<br>cagcggacugccacgaucauggaggaacugucagaugcccugaccuacugccacaagaag<br>aagguaauucacagagacauaaagccggagaaccugcuguuaggucugcagggagaacug<br>aagauugcagacuuuggcuggucggugcaugccccaucccugaggaggaagaccaugugc<br>ggcacgcuggacuaucugcccccagagaugauugaggggcgcaugcauaaugaaauggua<br>gaucuauggugcaucgggugcucugcuaugaacugauggugggaacccccccuucgag<br>agcccuagccacagugagacguaucgucggauugucaagguggaccugaaguuccccucu<br>ucugugccuucgggcgcccaggaccucaucuccaagcugcucaaacauaaccccuggcaa<br>cggcugccccuggcggagguugcagcucacccuugggucccgggccaacucaaggaggguu<br>cugccucccucugcccuuuagccugcuccuugguuuuuuguccccugucauuuuucagugu<br>ucuuuguaugucuguguauguguucugagaagggguggggaacuggaaacuauuccuagc<br>uccaguucuaggggaucugaucucucuucugaccucuacaggcaaaauuaggcaccccugu<br>ggugcacauauaugcacgccaaacacaugaaguuacaaacaaacaacaaacacacagaua<br>gugcuggagagauggcucggcaguuaaaagcacuggcugcucuucccaggaaccuagaac<br>ucaauucuagcacuacauggugcucacggccacugucuguaacacccaguccuggggaau<br>cuggggccuucgagccucugcaggcacuaggcauggaugugguauacauguaugcaggca<br>aaacacccaugcacugacuuuuaagaaacccucuagucugauuccuuucaauuugucaaa<br>uguugaauguuauuuuuaaaauauuauaagccauuuaauacaauuuuucuuugaaacaug<br>guauagccuagucugucuuaaauucagaaaaauuaugaagaacaacauuuuauaauaaag<br>ucuuaaauguuucauguuuuug |
| 56 | AF026481 | Sequence below. |

uugccuaggaagggcgcgucgucucucugcucguccggcugugacggggaagggucccgcugcguuuuggucacugugag
uaccaaguuuggggauccccgagggacucucgagagcucauuuuagggaugcaggggcuacuccccgguggguagagagcu
uucuaguuggcaggagguuucguauguggaggaggccagcuuaggcagaaagcacauguucucagagaugaggacaagacu
aagaccgucuaaucccugaucuuuaccuuccggcccgcugaccugggccuggaugcuaaagcccucugcuuucgucuaaaca
gcgcuaaauaguaaacaguauugccuaagauaaaugcggauuauuacccgauucagugucgggaaaaggcagcuaggagaga
gcggcuggcacgugguaagcacacgguaaguuucgguuaaauuaaaacaaccauccguugagcaucucuuagcaagcuccuu
ccacccuucaaacaaucagugauagugcgucuguuucacugauuagggagcuaaggcuccaacagcagcaaaggaacuaauc
cgccucugaucaacauggcguuucuuacagggcauuccuuauacgcuuucccacgugcguaacaggaaucggguguucccg
gguuuuguuuuguuguuguuguuuuuguuuuguuuucuuagugaaagaggcaggguggggcuccaggccgcugaggauua
auaaagagauucuaugaggaggaaauaacaggcagguggguaugaucgaggcaaggcccugaggaaggcuuggguggggguga
guagaaccagagccggaaguccacucagcagccuggggcacuuaaagcuucugcuggggcaaaugguaaggcggcguaaggu
cacauuccuuucauuucuuccagacucaggaggagaccacaccuuccggagaaccaggccugaaccgagguacuauuuugua
gcucucagaagccaggacucugcaacacuguuugcugccuguggaucuucuauauucacagugucccaguugcuucugauc
uaccacuguuagauacuucugccacccauccuaagaguauaguuguucuuggaaaggagucucagcugcugucagcaggag
ucccucauucgacuccugugguugcccuuuccaccaugccaaagaauaaaggcaaaggaggcaaaaacaggcgcagagguaaa
aaugaaaaugaaucugagaaaagagaguugguguuuaaagaggaugggcaggaguaugcucaggugaucaaaaugcuggga
aauggacgguuggaagcaaugugcuuugacggugugaggaggcuggccauauaagagggaagcugagaaagaagguuugg
auaaauaccucggacauuauauugauuggucuacgagacuaucaagauaacaaagcugauguaaucuuaaaguauaaugcag
augaagcaagaagucugaaggccuauggagaacuuccagaacaugccaaaaucaaugaaacggacacauuugguccuggga
ugaugaugaaauccaauuugaugauauuggagaugaugaugaagacauugaugacaucuagccugaccuaagcaugcuacc
uuccaaguucucugaagauagcuccacacaguggcaucuugaccuucaucuguuaaguaaaacuucauggcauguguaugac
uuguuaaugcaagcuaaugaauuuuauuuuuugaaguacuauauuucuuugaaaaccaaagauguugaguuaucaucuuaa
gugacauguuaacacuuugugcuuuugaauauaauugaaccuagcgcacagcagugagcacuguuaagagacugccuuucc
auuuguagcuucauuucuggcacgggaguguuuugugucagcaguucugccagguggccaucgaugagcugaaguaaguc
cuaguccagcacaucugcuucaggccuuuguacucuagucaucuggcugcguucgagacuucucagcagaacuuauagaug
uguacggcugcacuuggagucagacaagauauggcuacuuuuguacuuauggagccaugccauuuuauacuuucacguugu
auacauucguuugacccuuuaaguuguugccacccauaaaaaggcaucuuacagugcaguuuuuaaauuacaugguagca
auuuugaguuuuaaaaauuagucauugcagaaauuaaauacuuagaggagauaauccauuaucuugauuuuaggaauauaa
uaguugacaauguuuauauaauuuuacuucucuaaggcauacccaaaaauagaaaaugaaaaagagcagugagucuguuc
ugaugcuugcauugcauagagaaguuuuccaacaaagcagcuguuaauaacacauaaaauauguuuuacuuugcaaaguagg
uuguguuaagucauuuucaaaaguuaccuacuauaucgaggcucuggauaauuacuauguguugauuaaaguuaguuaca
gaauuguacaagcuaagauuuuccuuaaacuaagcuuagguuaaagggagaggagccacagcucaaugaaaacacgguuccug
uuuucuaaauggaggcgcccagaaacacaauaaaacauguugguacaaaaaaaaaaaaaa TABLE 3-continued RNA transcripts up-regulated during HF stem cell activation.

| SEQ ID No: | Access. # | Sequence |
|---|---|---|
| 57 | J04596 | caugaucccagccacccgcucgcuucucugugcagcgcugcugcugcuggccaccagccg<br>ccuggccacaggggcgccuaucgccaaugagcugcgcugucagugccugcagaccauggc<br>ugggauucaccucaagaacauccagagcuugaagguguugcccucagggccccacugcac<br>ccaaaccgaagucauagccacacucaagaauggucgcgaggcuugccuugacccugaagc<br>ucccuugguucagaaaauuguccaaaagaugcuaaaaggugucccccaaguaacggagaaa<br>gaagacagacugcucugauggcaccgucuggugaacgcuggcuucugacaacacuauaca<br>auuucuuuugaggguccuauuuauuuauguauuuauuuauuccacaaagugugugguuu<br>uuauuuuacauuaauauuuaacaguguggauacauuucaucgaugguaguucaguucugc<br>uuguucaguuuaaagaugguaggcuuaaaauauuucauuaaaacuaauauuuauugggag<br>accacuaagugucaaccacugugcuaguagaaggguguugugcgaaaagaagugcagagag<br>auagaguuuaguauuauguuuuguauguauuagggugaggacaugugugggaggcugug<br>uuuguaugucuugaaaagaaugucaguuauuuauugaaagucgucuuucauauuguaug<br>gucaacacgcacguguugacgcuucccuuggacauuuugugucuaguugguagcccauaa<br>ugggcuuuuacauucuuuaacccuguuucuccuggucucgucucgcucgggacagagacg<br>uucaaaggacuguuacaaaugaaguaaaaauaaaaguuuuauuaag |
| 58 | X81580 | cgucucccgcauucgucugggccgugcaccugcccgcuagcucgcugcacuaccguugcc<br>cacaagccaacaugcugccgagauugggcggccccgcgcugccgcugcuccugccgucgu<br>ugcucuugcugcugcucuugggcgcgggcggcugcggccccggggugcgcgccgaggugc<br>uguuccgcugcccacccugcacgcccgaggcucuggccgcuugcgggcccccacccgacg<br>cgcccugcgccgagcuggugcgagagcccggcugcggcugcugcuccgugugcgcacggc<br>aggagggcgaagcaugcggcgucuacaucccgcgcugcgcccagacgcuacgcugcuauc<br>ccaacccgggcuccgagcugccccugaaggcgcuugucacaggcgcggguaccugugaaa<br>agagacgcgugggcaccaccccacagcagguugcagacagugaugacgaccacucugagg<br>gaggccugguggagaaccacguggaugggaccaugaacauguugggaggugguagcagug<br>cuggccggaagccccucaagucaggcaugaaggagcuggcuguguuccgggagaagguca<br>augaacagcaccggcagaugggcaagggugccaaacaccucagucuggaggagcccaaga<br>aguugcgcccgccucccgccaggaccccuugccagcaggaguuggaccagguccuggagc<br>ggaucuccaccaugcgccuuccggaugaucgggggccccccuggaacaucucuacucccugc<br>acaucccccaacugugacaagcauggccgguacaaccuuaagcagugcaagaugucucuga<br>acggacagcgcggggagugcuggugugugaaccccaauaccgggaagcccauccagggag<br>cucccaccauccggggagaccccgagugccaucucuucuacaacgagcagcaggagacug<br>gugggggcccaugcccaaagugugcaguaaaccccagccagucggugccuggcuuccccau<br>cccgaacaccagcagaaauggagggcgucagggugacggguguggaggaguucccaguuu<br>ugacacauguauuuauauuggaaagagaccaacacugagcucagaagcccccucugacc<br>cccccagcggcuguuaacugaaccucccuugcuucuguuagagaggggaagggugguau<br>ggagggcacuggguacaggccugggaauggggaaagaaauuuuuauuuuugaaucccugu<br>gucucuuuuacuuaagauuaaaggaaggaaaaauaaaaaaaaaaaaaaa |
| 59 | AI314958 | gaugugaaaaacguuuuuauuauaaucucuuaaacuuucaguguauauuuucauuacaau<br>cauugguacaauaaauauggaaaugcugagcagacaauuaucacaguggccuaugggcug<br>agggacagggacccaggaauacuguuacccuggauacuucccucagggccaaucaggaggu<br>cuucaaagaguauugagagggagagggauagaaauauuauuaagacugucagugcagcaa<br>cuuuuagaaugucuauuaaagccauggauacaggauuuacgauaacagaagauggauacu<br>aaaaaagaacagagacucaaguucuccuguaagaggcagaagaaacauugcagaagccag<br>ugccuuccucgggucccccaguguguggcccccauccacccacgcauuguguuggucaucuc<br>caccugcccugugcccagcccugugcccacccagguucuccuaggcacccaccuugcacc<br>ucgcacg |
| 60 | AF058798 | gaauucugcgcgguuuugcauuuuuugggucagauuggcuuuuuacaugauuacgaagc<br>uccaacgacuagaccacagggaccgucgccuuggcggccgagcagucguauccaacuugga<br>gacagccaguucgccgugugucugucuguccuucaucgcagucauggagagagccagucu<br>gauccagaaggccaaguuggcugaacaggccgaacgguaugaagacauggcagcuuucau<br>gaagagcgccguggaaaagggcgaggagcucuccugcgaggagcgaaaccugcuuuccgu<br>agccuacaagaacgugguggggcggccagagagcggccuggaggguccuguccagcaucga<br>gcagaagagcaacgaggagggggucagaagagaagggccccgaggugaaagaguaccggga<br>gaagguagagaccgagcucagaggugugugcgacaccguacucggccugcuggacucgca<br>ccucaucaaaggggcuggagaugcagagagccgcgucuucuaccugaagaugaaggguga<br>cuacuaccgcuaccuagccgagguggccacuggcgaugacaagaagcgcaucaucgauuc<br>ugcccggucagccuaccaggaggccauggacaucagcaagaaggagaugccgccuaccaa<br>ccccauccgccugggccuggcccugaacuuuucagucuuccacuacgagauagccaacag<br>ccccgaggaggccaucucgcuggccaagaccaccuucgacgaggccauggccgaccugca<br>cacccucagugaggacuccuacaaggacagcacccucaucaugcagcuccugagagacaa<br>ccugacgcuguggacagccgacagugcuggggaagaggguggugaggcuccggaugaccc<br>ccacaucugaagcagcggaaaaacaacccggguuggcuuggccuuccaguccccagccug<br>gcauagaggauuaaaagggagugggauuuugccuuucccaaacccugaauguucagcaac<br>accuugggaaggucuuucgaagggggcgcagccaagcugaagccaccagggcagggaauu<br>uaauuuuucguguagcuguuuggguggguguuucccaaaaccaucccaccccuguuuuuu<br>gaacccccucccccaauucuuccccccugagccucccucgggcaccuguugcuuuuggaucc<br>gaauaauccaggagguuccccacccuguggcugagaaauggacuguggcaagggcugugu<br>gugugugagagagagggaaacucugugugugugugugugagagagagagagagagagugaa<br>ugagagggaaaaaguuugcuggguguga ccaugguaccaaucaauaaaguugcccuguga<br>gacucaaaaaaaaaaaaaaaaaaaaaaaaaaaaaaaaaaaaaaaaaaaa |

TABLE 3-continued

RNA transcripts up-regulated during HF stem cell activation.

| SEQ ID No: | Access. # | Sequence |
|---|---|---|
| 61 | AW046627 | uuuuuuuuuuuuuuuuuuaaauaccaaaacauuuaauugaaauaccuguauaaaaaauaug<br>aucuucagacauuucacacuuuugaacuuauacaaccccaccccugaugcuuagucacac<br>cagggucacagaaacacagcugcuaaaauaaauuaagggcuugagacucuguccccaac<br>cccagcuuucagagccagcaagcagacuguacaaggucaauaauuuaaaccccuccccag<br>cgcagagugcucagggugacagggucuc |
| 62 | AI848050 | uuuuuuuuuuuuuuuuuaauguaacgaccggugugcuucaguuuguuuagcagaaccac<br>ucucuugaaucacauuaacuuuugagauuuaaaaaaaacaaaacaaaaaaaaaaaaaaaca<br>acaaaaaaaaaaccaacccuccauagcacagcugucuuuuaugcaagcaagagcacaccu<br>acuccagcaugauuugucaucuaaagacuugaaaacaaaacaacaacaacaaaaaguuac<br>uuauagucaauggauaagcagaguccgaauuuacacuaaucaagacagaccuucgagggg<br>ucacgauaaguccggaacuuucaaaccuugcuucguaugaauuguacuaucugaacauaa<br>acugcacuuuuauuuuc |
| 63 | AF065441 | augagacuccacagccucauccugcucuccuuccuucuccuggcuacucaggcguucuca<br>gaaaaggucagaaagagagccaagaacgcaccacacagcacagcggaggagggguagag<br>gguucagcucccucguuagggaaggcccagaauaagcagagaagcaggacaucuaaaucu<br>cugacgcauggcaaguuugucaccaaagaccaagccacaugcagaugggcugugacugag<br>gaggagcagggcaucagccugaagguccagugcacacaagccgaucaggaguuuucuugu<br>guuuuugcuggugacccaacugacugccuuaaacacgacaaagaccagaucuacuggaaa<br>cagguugcccgcacgcugcgcaaacagaaaaauaucugcaggaacgccaagagugucuug<br>aagaccagagugugcagaaagagauuuccagagucuaaccucaagcuggugaaccccaac<br>gcacguggaaacacgaagcccaggaaggagaaagcagaggucuccgcaagggagcacaac<br>aagguccaagaagcugucuccacggagccaaacagggucaaagaagacaucacacucaau<br>ccagcugcgacccagaccauggccauuagagauccagagugucuagaggauccagaugug<br>cucaaccagaggaagaccgcccuggaguucuguggggaaucuuggagcuccauuugcaca<br>uucuuccucaacauguuacaggcgacaucaugcuaa |
| 64 | AF022992 | Sequence below |

cgggucgacccacgcguccgcccacgcguccggcggagcuucuggguugcgggccgaaacggcaagcggauggagggcgcuc
gaacggccaggugucgugauuaaauuagucagcccucagagacaggcguccuaccucccuuuauccagaccucaaaagccccg
uugugcacccgugguggcuucuucaccuucccuguuucguccuccacuguauggcccagacaugagugguccccuagaagg
ggccgauggggggaggagaccccaggcccggagaaccuuuuuguccuggaggagucccauccccuggggccccgcagcaccgg
ccuuguccaggccccagccuggcugaugacacugaugcaaacagcaauggcucaaguggcaaugaguccaacggacccgagu
ccaggggcgcaucucagcggaguucucauaguuccucuucuggcaauggcaaggacucagcucugcuggagaccacugagag
cagcaagaguacaaacucacagagcccaucccacccagcagcuccauugccuacagccuccugagugcgagcucagagcagg
acaacccaucuaccaguggcugcagcagugaacagucagcucgagccaggacccagaaagaacucaugacugcacuucgggag
cucaaacuucgacugccaccagagcgucggggcaagggccgcucugggaccuuggccacacugcaguacgcucuggccugug
ucaagcagguucaggcuaaccaggaauauuaccagcaguggagucuggaggagggugagccuugugccauggacaugucua
cuuacacccuggaggaauuggagcauaucacauccgaauacacacuucgaaaccaggacaccuucucuguggcuguguccuu
ccugacaggccggauugucuauauuucggagcaggcaggugucccugcugcguugcaaacgggauguguuucgggggugcccg
cuucucagagcuccuggcuccccaggauguggugucuucuauggcucuacuacaccaucucgacugcccaccuggggcacu
ggcaccucugcagguucaggucucaaggacuucacccaggaaaagucugucuucugccgaaucagaggagguccugaccggg
auccagggccucgguaccagccauuccgccuaaccccauaugugaccaagauucgggucucagauggagccccugcacagcc
gugcugccuacucauugccgagcgcauccacucugguuaugaagcuccccggaucccuccugacaagaggaucuucaccacc
cgacacacaccaagcugccucuuccaggauguagaugaaagggcugccccacugcuggguuaccuuccccaggaucuccugg
gggcuccaguacuucucuuucuacauccugaggaccgaccccucaugcuggccauucauaagaagauacugcagcuggcagg
ccagcccuuugaccauuccccuauucgcuucugugcucggaacggggaauaugucaccauggacaccagcugggccgguuu
ugugcaccccuggagccgcaagguggcuuucguguugggucgccauaaagugcgcacggcaccccugaaugaggacgucuu
cacucccccagcccccagcccagcuccgucccuggacucugauauccaggagcucucagagcagauccaucgauugcugcugc
agccugugcacagcuccagccccacggggcucuguggaguuggcccucugaugucccccugguccucuacacagcccuggcuc
cuccagugauagcaauggggggacgcugaggggccugggccuccugcuccagugacuuuccagcagaucuguaaggaugu
gcaucugguaaagcaccagggacaacagcucuucauugaaucucgggccaagcccccaccccggccccgccuccuugcuacag
guacauucaaagccaaaguccuucccugccaguccccaaaccccgaacuggagguggccccaguuccugaccaagccucguua
gccuuggccccugaggagccagagaggaaagaaaccucuggcuguuccuaccagcagaucaacugccuggacagcauccuca
gguauuuggagagcugcaacauucccaguacaaccaagcguaaaugugccuccuccuccuccuacacugccucuucagccuc
ugaugaugacaagcagagggcagguccaguuccuguggggccaagaaagauccgucgucagcaaugcugucuggggaggg
ggcaacuccucggaaggagccagugguggaggcacccugagcccgcucgcccuggccaauaaggcagagagcgugguguccc
gucaccagucaguguagcuucagcuccaccaucguccaugugggagacaagaagcccccggagucggacaucaucaugaugg
aagaccugccuggccuggccccuggcccagcccccaguccggcccccagccccacaguagccccugacccaaccccagaugcu
uaucgcccaguggguc ugaccaaggccgugcugucccugcacacacagaaggaagagcaagccuuccucaaccgcuucagag
aucuuggcaggcuucguggacuugacaccucuucuguggcccccucagccccuggcugccaccauggccccauuccccccugg
ucgccgacaccacugccgaucuaaagcaaagcguucccgccaccaccaccaccagacccccggcccgaaacucccugcuaugu
cucccauccuucaccugugcccucuucuggacccuggccacccccaccagccacgaccccuucccagcaauggguccagcccu
acccacucccaguauucuccccucgaggaggaccccagccccuucccccugccccuacaucugugucccccugcuaccuucccu
ucucccuuagugaccccaaugguggccuuggugcucccuaacuaucuauucccuaccccaccuaguuauccauaugggggugu
cccaggccccuguugaggggccacccacgccugcuucccacucgcccucuccaucccugcccccaccaccucucagcccccccc
accgcccagacuccccacuguucaacucgagaugcagcuccccacuccagcucaaucugcugcagcuugaggaguccccccgc
acggagggggggcgcugcugcaggaggcccaggaagcagugcugggccccugccucccagugaggagacugcugagccagagg
ccagauugguggagguuacugagucguccaaucaggaugcacuuucaggcuccagcgaccugcuggagcuacugcuccaaga
agacucucgcucgggcacaggcuccgcagccucaggcucccugggcucuggccugggcucugggucugguucaggauccca
cgaagggggaagcaccucagccagcaucacccgcagcagucagagcagccauacaagcaaguacuuuggcagcaucgacucuu
ccgaggcugaagcuggggcugcucgggccaggacugagccuggggaccaggucauuaagugugugcuccaggaccccaucu
ggcugcucauggccaaugccgaccagcgugucaugaugacauaccaggugccguccagggaugcagccucugugcugaagca
agaccgggagaggcuccgggccaugcagaaacagcagccacgguucucagaggaccagaggcgggaacugggugcugugcac TABLE 3-continued RNA transcripts up-regulated during HF stem cell activation.

| SEQ ID No: | Access. # | Sequence |
|---|---|---|

uccugguccggaagggccagcugccucgggcccuugaugugauggcgugugugg acuguggcagcagcguucaagauccu
ggccacucugaugacccgcucuucucagaacuggauggauuggggcuggagcccauggaagaggguggaggcgagggguggu
gggugugguguuggcgguggugggggugaugguggugaggaggcccagacccaaauuggggcuaaggguucaagcucuca
ggacucugccauggaggaagaagagcaagguggggggcucauccagcccagcuuuaccugcagaagaaaacagcaccagcuag
auccauuuuggggccgcuuacagcagucuaaugagaggcuuccuuucgaccauguuggggguucuuauaacucaagauacag
cuggaccaaccaauaggaaacugccccagcuucucccaacauagggggcuggacccccauuaccagcccaggcacaggagcug
ccucuagcuucuuagcagaguggaaguucucagccccauuuggaggauuguccacgcccgucccacugaggagacgggcgg
gucuucgguuaagguugcugacaagcugcugaaguggucuguccaaaucccagcugagccugagucccagucgcaggguug
gggcugcacuuauuuauuugggagagacagcucacucucccaccucaccccaagaugggaggaggggaaccugggaucugu
guaggauccagguccgugaaccccuagcugcuccagggugggggagguugguggaccauggagucccuggugcugccccuc
aggugggacccagguguucucagcucuacccucuaccaaugacauuuguguuuugauauugugucuguuauuuuuuuu
uaauacaaaaugacaaaaugaaaaaccaaaaa 65 AF064088 Sequence below.
gacagcggagcgcgguggcgucgacgucuagugucucagugcucccgucuguggcuaacuaagcagccagcagccaggcagc
ucgcgaccugcggccaggcagccaaccaugcucaacuucggcgcuucucuccagcaagcuucggaggggaaaauggaacuaa
uuucugaaaagcccagagaggggaugcaucccugggacaaagcugagcagagugacuuugaagcgguggaagcgcucauguc
caugagcugcgacuggaagucucauuucaagaaauaccuugaaaacaggccugucacaccagugucugauaccuccgaggau
gacagcuugcuuccagggacgccugaccuucagacagucccagcauuuuguuuaacgccaccuuacagccccucugacuucg
aacccucccaaggucaaaucugacugcaucagcgccaucuacuggccacuucaaaucuuucuccgaugcugccaagccucca
ggcgccacuccuuucaaagaggaggaaaagaauccuuuagcugccccuccucuuccuaaggcucaagccaccagugucaucc
gucacacagcugaugcccaacugugcaaccaccaguccugccccgugaaagcagcuagcauccucaacuaucaggacaauucu
uuccggagaagaacccacggaaauguugaggcuacucgaaagaacauacccugugcugcagugucaccaaacagauccaagcc
ugagcccagcacaguguccgauggugaugagaaggcgggcgcugcacuauaugacuuugcugugccuuccucagagacagu
aauuuguaggucuagccagcuccuucguccccagugcagaagucaguacuggugucuucaccuacaguauccacuggggg
agugccaccccugccugucaucugccagaugguuccccuuccugccaacaacucucuuguuagcacaguuguccccagcacu
ccuccuagccagccaccagcugucugcucaccuguguuguucaugggcacucaggugccugagggcaccgucguguuugug
guaccccagcccguugugcagagcccaaggccuccaguggugagccccaguggcaccagacugucucccauugccccugcuc
cuggauucucuccuucagcagcaagggucacuccucagauugacucguccagaguaagaagucacaucuguagccacccagg
guguggcaagacuuacuuuaaaaguucccaucugaaggcccacgugaggacacacacaggggaaaaaccuuucagcugcagc
uggaaaggcugugaaaggagguuugcucgcuccgaugaacuguccagacaccggcggacacacacaggugagaagaaguuug
ccugucccaugugugaccgucgguuuaugaggagcgaccauuuaaccaagcaugcccgacgccaccuaucagccaagaagcu
gccaaacuggcaaauggaaguuagcaaguuaaaugacauugcucugccuccgaccccugcuuccgcacagugacggccagaa
gauggagacgcagaauaaacuuggucagagucaggagccagugauggugucaagugcuucugcaaggcuguggcccucca
aaagggccuaaaguagaagcccuggccugggggaggccccgccugggugaaaugacaagaagugcuucagccacaggcaggu
cacagaggacagggcucaguucuuaccacagagagagaggagaacccuuuuauuccucccuuauuuuagucuggaaaguuuc
ggcugaggugagcgcagcacagguuuugaaucacauacacauuggggacuuuguuuuugccauuuauacuugagaccagcu
uugcagugugauucuuucaaaggauugguuucaagaauauagaggcuggaaauuacgguacagaaauggagcuagaaaaug
aguuuguguuacacagagaugucaucuucucccagaguuaucuuguuucuuauuccuagucuuuccagucaaauccgugga
uguagcuaaguauaucuaaaacucauuuuuccacuauuguugguauuugaaguugaacagcuguacauugcuguggggggag
ccaaaggauuggaacccucauuaauuuaauugcuuggaaaugcagcuaaaauucuucuuuggcauuuuguuuugaaaguuu
aggcauuuuacucuacuuuagauuuuaguuugcuugcaguuuuuuguguagauuugaaaauuguauaccaauguguuuuc
uguaggcuuaaaaauacacugcacuuuguuuagaaaaaaaucuggagaugaaaauauguauuauaaagaagagagugucaagaa
uuugagauaaacucccuugagaaaguuggcuuuaugucaucagcaaaggacacuuaacgucaagcauacacugugguuuuuuu
guuuuuuuguuuuuuuuuuucaaauuagaaaguuuaaugaccguuacagauggacagugucuuuuuauuuauaggaguuu
uucaggaugucagaguagauagguaggaaaauuguuauuagaacauucgcuucuaccuugaaaaggauguuaaaugugguca
uguucuuagcaccacagugucugggcaucugggaaacuccgagacuuuuuuaaagugucaugaugugaucacaccugcagu
uuggggcaucgaauccagggccuugcaugucuucuguaagagcucucaucgcugaccuguauccccccgcaagagcaaugacu
uuugcuaacaguauuucuuuucuguuguaaaguggacagaugauacacuuggucgcaaagguaaauuauucaaaauccaca
gugaaaaccucaccacacuuucccauuuaaacuauuuccauaucucagagguuucugacaugcaaacuugaacccuugaaag
aagaguuuucuuaaaaaauuauaaaaaucacgaguuacaauuugcacaauauuuuuuguugaacuuuauaccuuguuuaca
auaaagacuuuucuuug 66 AI787713 uugucanuugcacgacagaaacugcaggaagaugagaugcgccgggcugcggaggagcgc
aggagggguaaaggcugaagaguuagcugccagacaaagggguucuagaaaaaaauugaaagg
gacaaagcagagagagccaagaaguaugguggguagugugggguucucggucauccccacca
gcaacagacccagguccuguuccuucuucucccagccaggagcccccuacuaagcgggag
uaugaccagugucguauacagguuaggcugccugaugggacuucacugacccagacuuuc
cgggcccgggaacagcuggcagcugugaggcucuacguggagcuucaccgugggggaggag
ccuggacaggaccaggacccugugcaguugcucaguggcuuccccagacgggcuuucuca
gaggcugauauggaacggccucugcaggaacugggacucgugccuucugcuguccucauu
guggccaagaagugucccagcugagggguucuccaucccaccaucuc 67 AI853531 uuuuuuuuuuuuuuuuucacaaauaaguaauauaacuuuauuaaaaugaaaagacaauau
ucaaaauaaugcaacaaaaugaauaaaauccuuugucccaauacuguacacacagugcggag
aucagugcauuuuucuaaagcauguuuuaaccuucauuuaguucauacuaaaguaagcuu
uaaauagcucaaauaaugucauucagcaguuuaaacugaacagcuuguugggacauggca
gcaguguccccugcuagcaagcaccuucucuuuguguuuaucugcacaagauaaacaauca
gaggauguaaaaacugaacacaaacugcgugucucacugaaucucagggcagugaagcag
ccagcgugagguuucaaagcaggaagaugcugaagugaccucuggcauuaagacguucug
ugcua 68 X14678 Sequence below.
uucauuggaaagcacauugcucuucucaguaauuucuuuaguaucuucaugaauuuuuuccuuuugcgucguuauuucag
caauucuaucugcagaucauaaagguaguauugacagaugugauucuuuuucuuaaacauuucauuuccaggguaaggaac TABLE 3-continued RNA transcripts up-regulated during HF stem cell activation.

| SEQ ID No: | Access. # | Sequence |
|---|---|---|
| | | ucaauggcuauguuuucucucccucuagugcauccuucuccuuuucuaccauuuucacucuauuuaacuucaucauguuc<br>agucuggccuuuggguuucaucauagcaaucuguucaacuucacccugcaagauuaaaaaucgauuauggucuaagucaau<br>gccauggcuucuaaggagauuuccaacaucuuuaaacgucuucuucuucccacuuaugugguagacagaagugcuaucucu<br>guaggcgguucuggauacauagaaguugcuguuaggaaggacuucguaaucaucuccuuccuuaucaauuaucuuuugaaa<br>augaacuucuacaguacaacucugaauauccuuguguucaucagaauuauguaucaguaccgauagcuuuuuagaccuuau<br>uuuuugugcucgauagccaaacacaaaaagcauggaaucaauaacauuggauuuuccacugccauuugguccaauaauacag<br>gaaaagcgcuuauggaaagguccccacaaguuucucuccagcauaggacuugaaguuuugguuuacaauaugaguuaucaug<br>agacgaggagcuccagcuucacuggccauggcuggaggugggggguggagggauacuauucaaaaucuccucuaaacuucug<br>uuauccagcuccucaccuggaggcuuugcgggugcagcgcucccccucaccuacuucgccuacugcaacucccaccaccuccu<br>cucgauacaagaccgagcucugucggaccuacucagaaagcgggcguugucgcuacggggccaagugccaguuugcucacgg<br>ccugggugaacuuucgccaagccaaucgccaccccaaguacaaaacggaacucugccacaaguucuaccuccagggccgcugcc<br>ccuauggcucucgaugccacuucauccacaaccccaccgaggaccuagcucucccuggccagccccaugugcugcgacaaagc<br>aucagcuucuccggcuugccucaggccgcagaagcucgccgccaccuccaggcuuuucuggcccuucccuguccucuuguuc<br>cuuuucgccuuccagcuccccaccgccccccuggggaucuuccacuuuccccuucugccuucucugcugccccugggaccccu<br>gugacucgaagagacccuaaccaggccuguugccccuccugccgaaggucuacuacccccagcaccaucugggggcccuugg<br>guggccuggcucggagcccaucugcccacucucugggauccgauccugaugacuacgccagcagcggcagcagccugggggg<br>gucagacucaccugucuuugaggcagggguguuugggccuccccagaccccugcacccccaaggcgucuccccaucuucaau<br>cguaucucugucucugagugacaagugccuaccuacccaguauggaucagcuagaucucaaagagagggcagggacugcuca<br>uugcuguggggaccuggggcacuccucuaaguuaauaagucccaucuucuggacauuccaagaugcaauaacccauuucccu<br>ggugcugggcuggggcaggucccuaguuugcaaauucaguguuggguggauccguuccuagguaccuaagauguuuga<br>gggagacaguugacaguuggucuuccaggccccaagucuucuguuguuuuugagauaggagcuuauuaugguaccccaggc<br>uggcuuugaacucaauauaauccugccuuagccuuuuccaaguucugggguuacagguaugcaccagccccucugcaacucu<br>ggucuccuggaaucuuaagugcugugaagagccggcucccacaauacuauccuaauuuuuacuagacccugaaguucagug<br>uccgguggucgaagccucuccugagaauccuggugcucaaauuucccuccuaaagcaaauagccaaagccauugccaaaucc<br>cuucucccccaaccagugggcccuuuauuuaugacgacuuuauuuauuguauuaagauuuuauaguauuuauauauauugg<br>gucgucuacuccguuuuucuuuuguaauguuaaaacugauacuguauuaaguauaugcuauaauauauuaauauauugcu |
| 69 | AI854358 | cggacgcugcagaccugaccgacgugcugugcgaguucgacgcggugcuggccgacuucg<br>cgucgcccuuccacgagcgcacuuccacuaugaggagcaccuagagcgcaugaagcggcg<br>cagcagcgccagcgucagcgacagcagcggcuucagcgacucggagagugcagacucagu<br>guacagggacagcuucaccuucagugaugagaagcugaauucuccaaccaacuccucucc<br>agcucuccugcccuccgcugucacuccucggaaagccaaauuaggugacacuaaagagcu<br>cgaagacuucauugccgaucuggacaggaccuuagcauguaugugaagcaaggaguuugg<br>gguc |
| 70 | X67668 | ccgggccgaggagaagucugcaaaacaagaggcuggggauugccuuagcgagaaaucagu<br>ucucuuaggagguuagggaaggaagucuuucucuggaggucugagggaagcgcucguguc<br>agaugccggguugucaugggguaagggugaccccaucaagccgcugggcaaaauguccucu<br>uacgccuuuuuugugcagaccugccgggaggagcacaagaagaagcaucccaauucgucg<br>gucaacuucgccgagaucuccaagaaaugcuccaagagauggaagaccaugucugcaaag<br>gaaaacucgaaguuugaagauuuggccaagagcgacaaagcuuguuauuacagggagaug<br>aagaacuauguuucucccaaaggugauaagaaaggaaagaaaaaagauccaaaugcuccg<br>aagagaccaccgucugccuucugccuguuuugcucugaaaaucgcccaaagaucaaaauu<br>gaauacccgggccugucuauuggagauacugcgaagaaacuggugagaugugucugag<br>cagucugccaaagagaaacaaccguaugagcagaaagcagcuaaacuaaaggagaaguau<br>gaaaaggauuuugcugcauaccgugucaagggcaaaagugaagcaggaaagaagguccu<br>gguaggccagcaggcucaaagaagaaugacucagaagaugaggaagaagaagaggaggaa<br>gaugaagagggggaagaagaggaugaagaauaaguggcuauccuaaagugugggaguauau<br>gugcucaggcaguuauuuugcuaagaauguaaauucaagcgcagcucaacauuagcucca<br>guaggaa |
| 71 | K02236 | aucacgcuccuagaacucuucaaaccgaucucucgucgaucuucaa<br>ccgccgccuccacucgccauggaccccaacugcuccugugccuccgguaaggggacugc<br>ugacgggauuucugggagagcuagacaggcuuuuggccccuccuuuaguaauuacuuua<br>aggguacgaccggcuaccccuuccgaaugaauucugaagcacuccugcuccuuuaaacua<br>guccuugagauaguggcucgccuacccgggugauuugccucaccuuccuaggagaacagc<br>guucagguacucccggguccccacucaaccgcgcucacugacugccuucuacuuuuagaug<br>gauccugcuccugcgcuggcgccugcaaaugcaaacaaugcaaauguacuuccugcaaga<br>aaaguaaguuggaucuucucugccauuuccccgucacucuccuggggucccuagcccgcc<br>gcgccgcgccuucccucccgggagcguucagguggugugccucugacaagguuucucgcu<br>cacguucaacucuucucuccccacaggcugcugcuccugcugccccgugggcugugcgaa<br>gugcucccagggcugcaucugcaaagaggcuuccgacaagugcagcugcugugccugaag<br>gggggcggagggguccccacaucuguguaaauagaccauguagaagccuagccuuuuuug<br>uacaacccugacucguucuccauaacuuuuucuauaaagcauguaacugacaauaaaagc<br>cguugacuugauu |
| 72 | X51829 | Sequence below. |
| | | gcucugaguuuguggaagauuacaugcgauaucccgcgcgaccccgcaucccuuugccggccgggacagccuuugcuacagc<br>cugugaaacauugcguccccgagccccacgccugagggcgacaugaacccgcuggcuucgcgagcaguccggacccacgauc<br>gcuuuuggcaaccagaaccggcgcuucagcccccggggugacgugcagcccgccgcccagacacauggccccgagcccaagac<br>cccagcauguccugcacuggagggacgcccacaacuucuaucuccuguccccacugaugggcuugcucagucgggccuggag<br>ccgccugaggggcccagaagucccagaggcauggcuggcaaaaacaguaacaggagcagaucagauagaagcugcggcucug<br>cugacaccuaccccugucucugguaaccuccucccucauggggagacugaagaaaguggaucuccugaacagagucaagcag<br>cccagaggcucugccuuguggaagcugaaaguuccccuccugaaacuuggggacuuucaaauguugaugaguacaaugcaaa<br>gccaggacaagaugaccuuagagagaaggaaauggaacgcacagcuggcaaggccacacuacagcccgcuggccugcaagggg |

TABLE 3-continued

RNA transcripts up-requlated during HF stem cell activation.

| SEQ ID No: | Access. # | Sequence |
|---|---|---|

cugauaagaggcuuggggagguggugggcuagagaagagggaguggcugagcccgcuuaucccacaucacagcuggagggug
guccagcugagaaugaagaggauggagaaacagugaagacuuaccaagcuucugcugcuuccauagcuccgggauacaaacc
cagcaccccugugccuuucuuggggggaggcagaacaucaagccacggaagaaaaaggaacagaaaacaaggcugacccccucca
acucuccuucuucaggcucccacuccagagccugggaguacuacucuagagagaagccuaagcaggagggagaagccaaggu
agaggcacacagggcagggcagggucacccuugucggaaugcugaggcugaggaaggaggaccugagacaacuuuugucug
uacuggaaaugccuuccugaaggccuggguguaucgcccaggagaggacacagaggaagaagacaacagcgauucggauuca
gcugaggaagacacagcucagaccggugccaccccccauacaagugccuuccugaaggccuggguguaucgcccaggagagg
acacagaggaagaagacagcgauucggauucagcugaggaagacacagcucagaccggugccaccccccauacaagugccuuc
cugaaggccuggguguaucgcccaggagaggacacagaggaagaaaacagcgauuuggauucagcugaggaagacacagcuc
agaccggugccaccccccauacaagugccuuccugaaggccuggguguaucgcccaggagaggacacagaggaagaaaacagc
gauuuggauucagcugaggaagacacagcucagaccggugccaccccacauacaagucccuuccugaaggccuggguguauc
gcccaggagaggacacagaagaugacacagaagaggaagaggacagugagaauguggccccaggugacucagaaacagcugac
ucaagccagagucccugccuucagccccagcguugucuaccaggagagaagaccaagggacguggggaagagcccccucucu
uccagguggccuucuauuuacccggagagaagccagaaucaccuugggcugcaccuaagcugccccuucgacugcagaggcg
gcucagauuguucaaagcccccacccgggaucaggaccccgagauuccucuaaaagcucggaagguacacuucgcugagaaa
gucacaguccauuuccuugcugucugggcaggaccagcccaagcugcccgucgagguccccugggagcaguuugcacgagauc
gaagccgcuuugcucgacgcauugcccaggcagaggagaagcugggucccuaccuuaccccugauuccagggccagagcaug
ggcacgccuuagaaacccaucucuuccacaguccgagccucgcucuuccucugaggccacucccuugacccaagaugugacca
cacccucuccccuucccagugaaaccccuucgcccagccuguacuugggagggaggcggggcuaagccugaguaguuuccua
uuauuuauuuauuuauuuauuugaauaagaaauaaagccuuuuaauuuguagugau 73 AW048937 uuuuuuuuuuuuuuuuuaaucaucgagaaguauuuauugagcaccagcuuuggggucgg
gugugaggacucgggacaaugcagggugcugucccuucucgugagacgcuuacaaucuga
guggagacagggagggagccacaauacauguucuuggggugcgggcuaaggguagacagu
ccagaccaggauguuacagaaacagggauguuuggggcuggagucagacccacuaagugcu
uugacacccacgguauucaacacugagaaaggaucagccauugcucaguguccugugagc
ucccuuagcccccaagacaccaucuuggccuggcuccuuguacaacugcuacuaa 74 AV139913 cccaaaacccauucagcaaaguucccaaccucgacgggcuagcaguauuuaaccagugau
ggguucacuguuguauuuggugaauacuguauuuuguuucaguucuuucucccagauaa
uuugaaaacguuccaggagaaggcagcuuccuauaugcagcgugugcuuucuuauucuuu
uuuuuaauauaugacaguuauuugagaacccauuucuacuuugaauucauuuucguugaa
agugauguuucuucaccuaccauuuuccuauuaaaguucuguauucaaau 75 M32490 Sequence below.
agaccgugagcgagagcgccccagagaagcgccugcaaucucugcgccuccuccgccagcaccucgagagaaggacacccgcc
gccucggcccucgccucaccgcacuccgggcgcauuugaucccgcugcucgccggcuuguugguucugugucgccgcgcuc
gccccgguuccuccugcgcgccacaaugagcuccagcaccuucaggacgcucgcugucgccgucacccuucuccacuugacca
gacuggcgcucuccaccugccccgccgccugccacugcccucuggaggcacccaagugcgccccgggagucggguuggucg
ggacggcugcggcugcuguaaggucugcgcuaaacaacucaacgaggacugcagcaaaacucagcccugcgaccacaccaagg
gguuggaaugcaauuucggcgccagcuccaccgcucugaaagggaucugcagagcucagucagaaggcagacccugugaaua
uaacuccagaaucuaccaaaacggggaaagcuuccagcccaacuguaaacaccagugcacauguauugauggcgccgugggc
ugcauuccucugugucccccaagaacugucucuccccaaucugggcugucccaacccccggcuggugaaagucagcgggcagu
gcugugaagagugggguuugugaugaagacagcauuaaggacucccuggacgaccaggaugaccuccucggacucgaugccu
cggagguggaguuaacgagaaacaaugaguuaaucgcaauuggaaaaggcagcucacugaagaggcuuccugucuuuggcac
cgaaccgcgaguucuuuucaacccucugcacgcccauggccagaaaugcaucguucagaccacgucuuggucccagugcucc
aagagcugcggaacuggcaucuccacacgaguuaccaaugacaacccagagugccgccuggugaaagagacccggaucugug
aagugcguccuuguggacaaccaguguacagcagccuaaaaaagggcaagaaaugcagcaagaccaagaaaucccccagaacca
gucagauuuacuuaugcaggaugcuccagugucaagaaauaccggcccaaauacugcggcuccugcguagauggccggugcu
gcacaccucugcagaccagaacugugaagaugcgguuccgaugcgaagauggagagauguuuuccaagaaugucaugaugau
ccaguccugcaaauguaacuacaacugcccgcaucccaacgaggcaucguuccgacuguacagccuauucaaugacauccaca
aguucagggacuaagugccuccaggguuccuagugugggcuggacagaggagaagcgcaagcaucauggagacguggggugg
gcggaggaugaauggugccuugcucauucuugaguagcauuaggguauuucaaaacugccaaggggcugauguggacggac
agcagcgcagccgcaguuggagaaugccaaggggcugauguggacggacagcagcgcagccgcaguuggagaagacuucgcu
ucauaguacuggagcgggcauuauugcuccauauuggagcauguuuacggaugacguucuguuuucuguuuguaaauuau
uugcuaaguguauuuuuuugcuccagacccccccccccuuucuugguucuacaauuguaauagagacaaaauaagauuagu
ugggccaagugaaagcccugcuuguccuuugacagaaguaaaugaaagcgccucucauuccuucccgagcggagggggacac
ucugugaguguccuuggggcagcuaccugcacucuaaaacugcaaacagaaaccagguguuuuaagauugaauguuuuuuu
auuuaucaaaguguagcuuuuggggagggaggggaaauguaauacuggaauaauuuguaaaugauuuuaauuuuauauca
gugaagagaauuuauuuauaaaauuaaucauuuaauaaagaaauauuuaccuaaa 76 AI121305 ccaauaccacagccgugaccacagccaagaccacagccaaaagccuggccauccgcacuc
ucggcagcccccuggcagugcccuccauauccugcuuguuuuucucauuaguaaacuccu
cuucuaaagaaaacuggggaagcagaucuccaaccuccaggucauccucccgagcucauu
ucaggccagugcuuaaacauacccgaaugaagguuuuauguccucaguccgcagcuccac
caccuuggaccacagaccugcaacacuagugcacuugagggauacaaaugcuugccugga
ucuuucagggcacaaauuccgcuucuuguaaauacuuaguccauccauccugcgugua 77 U35374 auggagaacgaguucacauacgaagauuaugagaccacugccaaguggcuucugcaacac
acugaauaucgaccucaaguggcagugaucugugguuccggcuuaggagggcugacugcu
cacuuaaaggaggcucagaucuuugacuacaaugagauacccaacuuuccccaaagcaca
gugcaaggucacgcaggccgacugguguuuggauugcugaauggcagaugcugugugaug
augcaaggccgguuccauauguaugaaggauacucacugucaaaggugacauucccagug
agaguuuuccaucuucuggguguggaaacuuuggugguucaccaaugcugcuggaggacuc
aaccccaauuuugaaguuggagauauuaugcugauccgugaucacaucaaccuaccuggu TABLE 3-continued RNA transcripts up-regulated during HF stem cell activation.

| SEQ ID No: | Access. # | Sequence |
|---|---|---|
| | | uucuguggccagaacccucuccggggccccaacgaugaaagguuuggaguucguuuuccu<br>gccaugucugaugcuuaugaccgggauaugaggcagaaggcuuucagugccuggaaacaa<br>augggggagcaacgaaagcuacaagaaggcaccuacgugauguuggcaggccccaacuuu<br>gagacuguggcagagagucgucugcuaaagaugcugggggcagaugcuguuggcaugagc<br>acagucccagaaguuaucgucgcaaggcacugugggcuccgugucuuugguuucucacuc<br>auuacgaacaagguugucauggauuaugagaacuuggagaaggccaaucacauggaaguu<br>cuggaugccgggaaagcagcugcacagacauuggaaagguuugucuccauucuuauggag<br>agcauuccacucccggaucguggcagcuga |
| 78 | X15643 | Sequence below. |

uuccaggacagcuggggcuccacgagagaaacccugccucccccccaaaaauggcccaaaguucacugacaaacucacauuug
ucugauauuuagcuauguaacagcacuuacgguagcaauagaauuugauucucacucaucacaaugaaaauggcuggcgcuc
ucucucucccucucuccccauuucaaaucugcaagcacaccccuuagagauggagagaauuugauccauuggagaaucgagc
uaaaaauaccaccauggaauugugggaaggauuaaaugcaauaaugcacaaaaggcacauagcagaaugugcccuaaauguca
gccauuguuaugguauuauguaaucuacaaaguauguuugcuuacuccgugugaaagacuuucagucuaucaaacauaaua
caugugaaaucaaaccuugaaaauuaauuuuuuucccaacagucaagacauuugccagcugcagagauuagcauuucaugaa
ucuuagucuugucugauuuuuuuaaugggaaggaacaacuauccucaacuauccuuuuuuuuuuucuguaguuuuaaaau
gaacuccacaaaacauguuuuuaauauagggaauuauaugaaauugugggugggcagcgagguuaaaggcagaaauagccc
aaugguggcacauucacugacacagccuaaaagauuagcaaauuacccagccaacacauacaauuaauacaauuaauauuuuu
auaguuaaaacagaguuacuaaagaaauuguuugaaaagaaaauuaugaagacuggaaagacggcucagugcuuaagagcuu
uggcuagucuuccagagaaccagggucauccagcacucacaaggcagcuugugagcugauacuaucuguauauucaguccua
gggaaucugaugcuuuguccugaccuccaaaacaggcacaaaugguggugcacaggcaaauguagagauaagacucccaugca
cagaacauaaauaacguaguuuaauuuuuuaaauuguaaaacugaaaaugguugcacuugcauuuuuauuuucagcacauc
cccagauauccgccauauaacaagaaaaugaugccacacucccaagaauuaagaauuacaccucccaacccuacccaaaugugu
auacucuaggucuaaagaaaugcaaaggaugaaguuacugccuugugcgguucucaaggagggaggaugccaaaaaaauauu
uuuucacaaagugugcugagaaacucuguagcuguuggagucaucuccugugcucuugccaaauaacugaaaggggauaca
cuggaugucugugaauggggugucacuuaugagugcuagaagcggguaccuggauguggacacggugucugagugguccg
cacuccaugucuccacaggagcgcuuauguguguuucuuuccuccugcuucuggguguuccugguuuguuuacagccacc
ucucuguuggaccaggagacagcugucgucuccagaaugagcgggcacgggugugucucgguggcuguggcugugguucg
gcauaagucugagcauguccuggucgucagggugcguuugugcugugugugcguguccgggugagcuugcucuuucuguu
ccuaaaagaaaaugcacccugcgcuaccggcguccagagacucucagcccgcagaggugaccugaacggacagguagcaccuc
cagacagcgccugguuggcggguugcacagcagccccagauuucucucucuggugccccagcuaggguagcuggaagggag
cgguggccuggccuccggggagccgcugggccccgccgggcuaacccaggaggaggccggcuaggcugggaggguuagccc
uuggugcccuacgccugcccgggccagucgcggccgccggccauuggcccaaagaauuguugcacgucacuggcaauucccc
uagaagucugugcacauaacgggcagggcgcacugcaaggcugcuucucccgcauuuaggcugcggcugcaggcaccgcgag
cccggagcacccacgagcuuagugugcaggacgcaccccagcacagccaccuacggccgcugaaugaagcuuccaggaguccg
cccccggccgucgccccgucggaggugcacccgcugagagcgccuggaccgaaaggccggugcgcucaccugcuaaccugcc
agccauggggccacacgggaacgacagcgacuucuugcuggcacccaacggaagccgagcgccacaccacgacgucacucagg
aacgggacgaagcgugguuguggcauggccauccucaugucgguuaucguccuggccaucguguuuggcaacgugcugg
ucaucacagccauugccaaguucgagcgacuacaaaccgucaccaacuacuucauaaucuccuuggcgugugcugaucuagu
caugggccuagcgguggugccguuuggggccgucacaccucuaugaaaauguggaauuuggcaacuucuggugcgaguu
cuggacuuccauugauguguugugcgucacagccagcaucgagacccugugcgugauugcaguggaucgcuauguugcuau
cacaucgcccuucaaguaccagagccugcugaccaagaauaaggcccgagugguca uccugaugguauggauuguaucuggc
cuuaccuccuuuuugccuauccagaugcacugguaccgugccacccacaagaaagcuaucgauuguuacaccgaggagacuu
gcugugacuucuucacgaaccaggccuacgccaucgcguccucgauugugucuuucuacgugccccuggugguga ugguc u
uugucuauucccgggucuuccagguggccaaaaggcagcugcagaagauagacaaaucugaaggaagauuccacgcccaaaa
ccucagccagguggagcaggaugggcggacgggccacggacuccgaagguccuccaaguucugcuugaaagagcacaaagcc
cucaagacuuuaggcaucaucaugggcacauucacccucugcuggcugcccuucuucauugucaauaucgugcacguuauca
gggacaaccucaucccuaaggaaguuuacauucuccuuaacugguugggcuacgucaacucugccuucaauccucuuaucua
cugucggaguccagauuucaggauugccuuucaagagcuucugugccuucgcaggucuuccuucgaaaccuaugggaacgg
cuacucuagcaauagcaacggcagaacggacuacacaggggagccaaacacuugucagcuggggcaggagagagaacaggaac
ugcugugugaggaucccccaggcauggaaggcuuugugaacugucaagguacugugccuagccuuagcguugacucccaag
gaaggaacuguaguacaaaugacucgccacuguaauacaggcuuucuacucucuaagacccuccuugacaggacacuaacca
gacuauuuaacuugaguguaauaacuuuagaauaaaauuguauagagauuugcagaagggggggcacauccuucucgccuu
uuuuuaauuuuuauuuuauuuuuuagcugcaaacaagagagagaacuguauuugagugcuuauuguucuuguauaguuca
guuccucuuguauggaacuuaaagguuucugucugaagaguguugguucugaggacugagucugucugucugucugucug
ucugucugucuggaugauguuucauguaucuaccucacuggucaaguauuaagaaugauauauugcugcuggaaaucc
auaucuaaaggagagaguuuucuuccuguacccuuggacuugaaauauccugugucuuggaccuuucugcugugacaaugg
gcccuuucucucucacuccacuuauuuacucaaauggauucgaggcagggauuugagggacaacacuaguuguuuuguuuu
uguuuuuguuuuuuuguuuguuugguucguuuuugguuuguuguuguuuuuuggggguuuguuuuuguuuuuguuuuu
uuggguuuuuuuuuuuugcugagaaaagucuaaaguuuacaguaaauaaauuguuuaaccaugacuucauugcacccguuu
cuucaaaaccucuugacucuggagugucuugucucucccacuggaaaccacagguaaacuaugugucgugaccgaugagug
gcuuaauguguaagaguaccagaauggcaugcuugcaugcaccgugccuagcccuuccgugugugucuucagagcuccaga
ugcaaaccugugccuucccuaacuucacucgugucccaaagcaguccugccuguucacagcauaacccaguauguccuacag
uugcucuucugugcugucacuccagaaacccugacucacggaaacagaguuauggacauauguuuuguccccauaugcuc
ugacaccaccuucagccuuacuugcuuaauaacuguguauauuuacaucacugcgucucuuacaguagugccuuuguacug
caucagggcuuggugugu ucaggaugaggaagauguucuguguaauagcuguucaagcaucuagaaauucugagggaaauc
aaaggccucggucagagagagagagagagagagcaaagcuuuaaaaaacauagcugguga augcuucacgcccuucagccucuc
cucgcuccgucugcugucccgugucuucuguucccaauucucugcacuucuguguaaaccaggcuucccaugucuggcauu
ccgugcauuauaugauauuuggcggcacgucuguaccaguaaauucugguagcacccccuaguuacaauaauugcagacacu
cagcgcguacgacccccuaguuacauaugcagacacu

| SEQ ID No: | Access. # | Sequence |
|---|---|---|
| 79 | AI849109 | uuuuuuuuuuuuuuuuuuaagcguccaggcuguacuuuauuuuacacaagugguggcccc<br>agaaccacagggacaugaccuggagaguaggcacagugccugaggcugcaagagccaaaua<br>cagggauucaugccuucuccuugguccccaugaccaaauuaaaaaaaaaaaaaaacaacaa |

TABLE 3-continued

RNA transcripts up-regulated during HF stem cell activation.

| SEQ ID No: | Access. # | Sequence |
|---|---|---|
| | | aucacacagcacacaucgccacacccaucccccuccuuccuuucagcaacagccaauucag<br>cuuucuagccaaagacaguggcuacaacugaauuuacagagaaccaugcagccaagaaac<br>cagagccacggaggggagaggcuugcguugacuucccacaugugcugucccauagcagcu<br>gagugaccccacca |
| 80 | U70132 | agaaagauaagggccagcaaggaaagaaugaggaugugggcgccgaggacccguccaaga<br>agaagcggcaacgccggcagaggacucauuucacuagccagcagcugcaggagcuggaag<br>ccacuuuccagagaaaccgcuacccagacauguccacucgcgaagaaaucgccgugugga<br>ccaaccuuacggaagcccgaguccggguuugguucaagaaucgccgggccaaauggagaa<br>agcgggaacgcaaccagcaggccgagcugugcaagaauggcuuugggccgcaguucaacg<br>ggcucaugcagcccuacgaugacauguaccccggcuauucguacaacaauugggcugcca<br>agggccucacgucagcgucucuguccaccaagagcuuccccuucuucaacuccaugaacg<br>ucaauccccuguccucucagaguauguuuccccgcccaacuccaucucaucuaugagua<br>ugucguccagcauggugcccuccgcggugaccggcgucccgggcuccagccucaauagcc<br>ugaauaacuugaacaaccugagcagcccgucgcugaauuccgcggugcccacgcccgccu<br>guccuuacgcgccgccgacuccuccguacguuuauagggacacauguaacucgagccugg<br>ccagccugagacugaaagcaaagcagcacuccagcuucggcuacgccagcgugcagaacc<br>cggccuccaaccugagugcuugccaguaugcagucgaccggccggugugaaccgcgccca<br>gggcgcggggauccgaggacugucggagugggcaacucugccccagaaagacugagaauu<br>gugcuagaaguucgugcgcacuaugggaaggaagagggggaaaaaagaucagaggaaaa<br>gaaaccacugaauucaaagagagagcgccuuugauuucaaaggaaugucccaagugucu<br>acgucuuucgcuaagaguauucccaacaguuggaggacgcguacgcccacaaauguuuga<br>cuggauaugacauuuuaacauuacuauaagcuuguuauuuuuuaaguuuagcauuguuaa<br>cauuaaaaugacugaaaggauguauauauaucgaaaugucaaauuaauuuuauaaaagca<br>guuguuaguacuaucacuacaguguuuuuaaaggcuaggcuuuaaaauaaagcauguuau<br>acagaaucaguuaggauuuuucgcuugcgagcaaaggaauguauauacuaaaugccacac<br>uguauguuucuaacauauuauuauu |
| 81 | M13805 | cugagaggccaggugggcggcgaaaucaacguggagauggaugccgcucccgguguggac<br>cugagccgcauccugucagagaugcgugaucaguacgagaagauggcggagaagaaccgc<br>aaggaugccgaagacugguucuucagcaagaccgaggagcugaaccgcgagguggccacc<br>aacagcgagcuggugcagagcggcaagagcgagaucuccgagcucaggcgcaccaugcag<br>gcccuggagauugagcugcagucccagcucagcaugaaagcaucucuggagggcagccug<br>gcagagacagagaaccgcuacugcgugcagcugucucagauccaggggcugaucggcagu<br>guggaggagcagcuggcucagcugcgcugcgagauggagcagcagaaccaggaguacaag<br>auccugcuggaugugaagacaaggcuggagcaggagaucgccaccuaccgccgucugcug<br>gagggagaggaugcccaccugacucaguacaagccaaaagaaccugugacccacccgccag<br>gugcgcaccauuguggaagaaguucaggauggcaaggucaucucaucccgggaacaggug<br>caccagaccacccguuaaggacucagcuccuuccgcccaguuccccgaggcugcagagag<br>gcagcuucccucuccgcuccggcauuacccuccugcuacagccucuccccagcauuccua<br>ugcuugagaccauuaaagcuugcugaccugaagugaacuguggccuuuguucugaacacu<br>gaaauaaaugaccauggugac |
| 82 | AV138783 | ccccaggggugaaaugaggauuccccacccugcggaacagugaaauguguauaauuaag<br>aggagggcgacgacccuugccgcgggacccgggacucgagcccgggacuucgcagcuaca<br>gcaaaucuauuuuuaauauugugcugagcaagacagaucgcuugcauauuuuuaaaaauu<br>uuuacuacagagacauuccaauaaauucguuaagcc |
| 83 | K02927 | Sequence below. |

cugacagucgucucugucccuucuucgccucggagcugcuaacuggucucgaaccucucagcacuucagcuucuagcggcga
ugcaugugaucaagcgagauggccgccaagagcgaguuauguuugacaaauuacaucacgaauccagaaacucuguuaugg
acucaacauggacuuuguugauccugcugcagaucaccaugaaaguaauccaaggccuauaguggggucaccacaguggaa
cuggacacccuggcugcugagacagccgcgaccuugaccacgaagcacccugacuaugccauccuggcagcaaggauagccg
ucucuaacuugcacaaagaaacaaagaaaguguucagugaugugauggaggaucucuacaacuacauaaauccgcacaacgg
cagacacucucccaugguggccagcucaacacucgacauuguuauggccaauaaggaucgccugaauucugccauuaucuau
gaccgagauuucucuuauaacuacuuuggcuuuaagacacuggaacggucauauuuguugaagaucaaugguaaaguggcu
gaaagaccacagcauauguugaugaggguuucuguggggauucacaaagaagauauugaugcugcaauugaaaccuacaacc
uacuuucugagaagugguucacucaugccccuccuacucucuucaaugcugggaccaaccgcccacagcugucuagcuguuu
ccucuugaguaugaaagaugacagcauugaaggaauuuaugauacucugaagcagugugccuugauuucuaaguccgcugg
gggaauugguguugcugugaguuguauucgggccacugguagcuacaucgcugggacuaauggcaauucuaauggccuug
ugccaaugcugagaguauauaacaacacagcucgcuauguggaucaagguggaaacaagcgcccaggcgcguuugcuauuua
ccuggagccuuggcacuuagacaucuuugaguuccuugacuugaagaagaacacaggcaaggaagaacagcgagcacgcgau
cucuucuuugcacuuuggaucccagaucucuucaugaagcgagugggagacuaaccaggacuggucauugaugugucccaau
gaguguccuggucuggacgaggucuggggagaggaguuugagaaguuauaugaaaguuacgagaagcagggucguguccga
aaaguuguaaaagcucagcagcuuugguaugccaucauugagucccagacggagaccgguaccccauacaugcucuacaaag
auuccuguaaccggaagagcaaccagcagaaccugggaaccaucaaaugcagcaaccuguguacagaaauaguagaguacacc
aguaaagaugagguugcaguuuguaacuuggcuucucuggcucugaauauguaugucacaccggaacauacguaugacuuu
gagaaacuggcagaagucacuaaagucauuguccgaaaucugaauaaaauaauugauauaaacuacuacccuauuccagagg
cacacuuaucaaacaaacgccaucggcccauuggaauugggguacaagguuuagcagaugcuuucauccugaugagauaccc
cuuugagagcccagaagcccaguuauuaaauaagcagaucuuugaaaccauuuacuauggagcccuggaagccagcugugaa
cuagccaaggaguauggccccuaugaaacguaugagggaucuccagucagcaaggguauucuucaguaugacauguggaau
guugcuccuacagaccugugggacuggaagccucucaaggagaagauugcaaaguaugguauaaggaacaguuuacuuauu
gccccaaugccuacugcuucaacugcccagauucuggggaauaaugaguccauugagccuuauaccaguaacaucuacacuc
gaagagucuugucaggggaauuucagauugugaauccucacuuacugaaagaucuuacugagcggggcuuguggaaugaga
gaugaaaaucagauuauugcaugcaauggcuccauucagagcauaccagaaauuccugaugaccugaagcaacucuauaag TABLE 3-continued RNA transcripts up-regulated during HF stem cell activation.

| SEQ ID No: | Access. # | Sequence |
|---|---|---|
| | | accgugugggaaaucucucagaagacuguucucaagauggcagccgagagaggugcuuucaucgaucagagccagucuuuaa acauccauauugcugagcccaacuauggcaaacucacuaguaugcacuucuacgguuggaagcaggguuuaaagacuggaau guauuacuuaaggacgaggccugccgcuaauccaauccaguucacucugaacaaggaaaaacugaaagauaaggaaaaggcac ugaaggaggaggaggagaaggagaggaacacagcagccauggugugcucuuuggagaacagagaggagugccugaugugug gauccugagaaaagcggggccugggagacgcagcgggcucuccugcccgagaggcagacgauuugagcauagauaggauagu ggguuugcuugguuaucagcagcucugcuuggacgugccugccaggacagggagccacgacuuacaguacuguuucuacac aguguaaauaucauuuuuaacaaacagaaaaccaaagccagcuuugauauuaggaaucaagguagaggcuuugggaauacua aagagccuuccugcaaauagugaggagacuuaggaagucucgucucuccagcuuucccugccuggccauucucaguuuggg caaagagauuuaguuugauuugacugauugccuagaaguaaaaucaagcaauuacucaucagcuaaagaccuuugucuagac aaacuucuauaagucauuuugaaauaaacauuucuaagugau |
| 84 | X07699 | Sequence below. |

uugccucagacgcuagcuguagcuggcaggcgguuguacgugcuccagagucgucgguacccgcuacugcagucgcuuucg
uguggcuuccgcugagcucuuccgagcugcucgcucuccacacgcgccgccgccguaauccgccaccauggugaagcucgca
aagguaagaggccuuggcgcgccgacgcggacgacuaggccccugcuuucggagggacgcgcgcgcgcccgcccguccgucg
cggaggggaggagggcuugcgcgcaaucccgggcgcguucgagggcgccaugcugggggggaaagucucgcgcgacuagcg
ggaggucucgcggugcuugcccucugacuuagggggaugagaagagcggaggcagguuuccgggagggcgauaucgaggg
uucggauguagcgggcgggaggggacggugugaggagagaucggaggagcugagagcggauaggggcacggcgugggaaga
gagggccaaccuuaggcggcgagcggucccggggccccgccuccccgcgcacgugcucuggugcgcgcccgccacgugcucu
gcggagccccgcacgugucgcgcgacccggggcaguggggggagugucuguaguaccccggaaaggggacggcagcguggg
gauggauggguggcccggcgaucugcugucucugccggugaccgggauggacacgugguggaccccugagguggcggcgu
ggugacuccacgugguggggcuggaagcgagagaaagugggaagcaguuggguuacguggugcugcuuuaagaggugauu
ucgagauaccccuuccccagcaaauaacuuaaagggaucccuuuaacuggguuuuuuuuuuuuuuuuuuuuuuuuuuu
uguggaagaugccagaaaauagauggccaggauuaggagacuuuauaaccuguggcuguuucuugguguagaguucuguc
ugcucaguuaucugugagaaggaaaaaaaaauuaugcgcgguucgcagaaaaaacugccaggagaaugccaugccuggccaa
gaagaagucuuuaugcuuguguccuuuaguaagaaaaagguggugcccaaaggcaaagugacugaaaaugcgugcaauuuu
ugugugcguuuguaggcuggcaaaacccacggugaggccaagaaaauggcuccuccuccaaaggagguggaagaggauagu
gaagaugaagaaaugucagaagaugaagaugacagcaguggagaagaggagguaagaagcuauuugcagcgaagaauuaaaccgg
uggaauugaaugcuggaagucuuagaaauacaggauauguaguaaugguugaauggcaagccccuuccucccucccuccc
ucccucccucccucccucccucccucccuuccuuccuuccuuccuuccuuccuuccuuccuucugcaagacagucggcaaaac
aggggacagaaacaggcagaauuuugaguuccaggcaagcagggaguagacauaugaaaccuugucucaagaccguuguu
auggucaugcucaaucagauuucuuagaaaagcucaggugcugaguccaguuuuuuuuuuuuuuaaaguauugaaagccaug
ucuccuuauuucaggguuuaauguuuaucuuugugugugcgcgcacccauuaagcaugcuugguacccucauacuagaaug
uacuuggauccccuggaacuggaguuaaagccacaugugaauguuacauguuacaagaguaacacaugugcuuaacuuuug
agucaucucuccaguucuugguuguuuguuuuuuuuuuuuuuuaagccuaucuaauguccauuuucuugugcucaaaguuag
ucucuuaauguagcauuggguauaaaggaaugcuuaugauuuguuugcuuucaagguugucaucccucagaaaaaaggcaa
aaaggcuaccacaaccccagcaagaagguggguuguuucacaaacaaaaaaggcugcaguucccacaccagcuaagaaagcag
cugugaccccaggcaaaaaggcaguagccacaccagcuaagaaaaacauuacaccagccaaagucauuccaacaccggguaaga
agggagcugcacaagcaaaagcguugguaccaacuccugguaaaaagggagcugccacuccagcuaagggggcuaagaacgg
uaagaaugccaagaaggaagacagugaugaggaugaagaugaagaggaugaagaugauagcgaugaggaugaagaugaugag
gaagaggaugaguuugagccaccaauaguaaaaggagugaagccagcaaaagcagcuccugcugcuccugccucagaggaug
aggaagaugaugaggaugaagaugaugaggaagaugaugaugaagaggaggaagaugguggaguuagaucuuaggauauuua
ggguacugcauguacauucccucacuguuucauuagauuaaaaacucauuuugugcucuuaguucuuuccauaacuuaaua
gguuuucauuugcuaaguaguuuuuguuuuuuuuaaguauuuguagcauuuaucuugucuggauugguagguagcaaau
acauuugccugauuugccaucuuucuuccagacucugaggaagaaguuauggagaucacaacagccaaaggaaagaaaacuc
cugcaaaaguuguuccuaugaaagccaagagugugggcugaggaggaggaugaugaggaagaggaugaagaugacgaggaug
aggaugaugaggaagaggaugacgaagaugaugaugaggaagaagaggaggaagguaaccauauuaacuuuuaaaguaugc
ugaccuaaguaaggcuuacuggcuaugcuaaagugucugcuuacucaugaauggcauuuuaaaacaucuagaaccuguuaaa
gcagcaccuggaaaacggaagaaggagaugaccaagcagaaagaagccccugaagccaagaaacagaaaguagaagguaagcc
ugcaaaacuggggaaacagaucagaguagcacuagcacaagugaugagugacaaagggacuuaauacugaaccaugggguug
aaaugaaauaugcugaugugcuuuauaguuuaugaugaaauuuguugugugcuuaagugggcugaaaguucauuuuuugu
gugugcaggcucagaaccaacuacaccuuucaaucuguucauuggaaaccuuaauccaaacaagucuguuaaugaauuaaaa
uuugccaucagugaacuuuuugcuaaaaaugaucuugcuguuguggaugucagaacugguacaaauagguaaguuuuaauu
gaauguuacauguguaucagcuagaauuuuuaguuuccaguuguauucuucccugccuuuaaacauggggcuauaucuaac
uauguuaguaaaagucaguugucuccucucguggccuuaaguacaguuaaggagcugcaguaagaaagacuauaguauuga
acuaaaugaucgagucauagggccugcaauuugaaguuccuguguuugacuugauaaagauaaaauaaaauuuaaagaagaa
aagauauuaaacacauaaaauuuugugcaguaucuacaacuauggaucugcauagucauaugcuuuuagcuaaaaguauucu
cuguacuuuuagcgggguccaugcuagcuacugcuguuaguuacaauauacugaaugaagaaaucgaggugaauuuguugu
aaugucuugguacauggacuuguuuuguuuuuuguuuuuuuuucuuuaagauuuguuuauguauaugagcacacuguag
cuguccagaugguuuugagccuucaugugguuguugggaauugaauuuuuaggaucucagcucgcucugcucucaguccu
ugcuugcucuggcccaaagauuuauuuguuguuauacauaaguacacuguagcugacuuaagaugcaucagaagagggcau
uaggucucauuaugggugguggugagccaccaugugguugcugggauuugaacucaggaccuucagaagagcagucaaugu
gcuuacccgcugagccaucucuccagccuuuggacuugguuuuauggaagauaagggugaucuaguuuuauuuuuguuag
ugcuguagaugcucugugugugugccacaugguauaagugcagaucaccuucucauaccuguaaucuuguuuuuuccaucu
ucaaggaaauuugguuauguggacuuugagucugcugaagaccuagaaaaggccuuggagcucacugguuuaaaaguguuu
ggcaaugaaauuaaacuagaaaaaccaaaaggaagagauaguaagaaagguauguaaggggguucugggugacuggauacuaa
cagacuuaggcagucuggugccucuuccuuaguuucauccucauugugaaccaaugagaugucauaggucaugugcuuguu
gacagguuugauuccugggauauauaaugucagggcugacaggaggaauagcuuagugaguaaagaugcuugcugcaaaau
guuugaucucuagaagccacaugaagagagaagaaccuuuaaucccagcauuugggagacagaggcaggcagauuucagagu
ucgaggccagccuggucuacagagugaguuccaggacauccagggcuacacagagaaacccugucucggaaaaaaaguuuua
gcuuauccucugaccacauguguaucgugacaugcuugaagcuuaccuaucucuuaaaugaauucuugaucccuauauuuu
gaguuucagaauuuggauuuuaaguguuuguuucuuaguugugcugaaaauugaacgugggcuuuucacaugcuaggcaa
auuuguuggguuuuuuuguuuguuuuuuucucaagacaggguuuuucuguguagcccuggcuguccuggagaccaagcua
gccuugaacucagaaaucugccugccucccaagugcugggauuaaaggcgugagucaccacugcccugcuaggcaaucacuc
uuaaaacugcuacauauccucuguccccuuuugcucauuuuacaagguugcugugugcucaaucugcagucuauguuauau TABLE 3-continued RNA transcripts up-regulated during HF stem cell activation.

| SEQ ID No: | Access. # | Sequence |
|---|---|---|

gcuuacuggaucuaggcuuuugauguagaaugaaccauaugagugaugagguaucuuagagauggaaacuaagucuaaaua
gacuuguuccauauacaacuuaauacauauggucuaaggaacaugauauacauguaaacaaguaggaaggagauaagucugg
uguccagggaagccaggagagccucaucugaaacuggacagggguuugugagucaucaggugacaauugaacauagguacu
cuucaugcaaugguuaguaaccauugagccaccucuccaucccuuuauaccauuuuuuuuuuagcauauauccuuguac
uuuauaggaauuauuugcuuuauucucuugugacuuguaaauugauguacuuaauuaaaucuuuuuccaacauaguucga
gcugcaagaacacuucuagccaaaaaccucucuuucaacaucacugaggaugaauuaaaggaaguguuugaagacgccaugg
agaucagauuagucagccaggaugggaaaaguaaaggguaguuuuguguuuugaguguuaaaguuuuauuaaguuuagu
gucuucuuccccucuccuuguccuugcagucucuagucugcugcuucaaacuuaacuucauaaccagaaaauugaauaucu
gguccucuggccucuaccucccaaguucugacauuaaaaaugcucaacugauggguuuugaaggugugaucaauuuucag
gcucaauccaaauuggcaucuuuugccacaaguacuauccuucccuauuuuaugagagaaaugugauucuaggcaguucag
ucuauuguguuggcucuuuuuccuccucaccaguuuaaaggaugaagaugagcuaauacauaguaaaagaacaguaaaagca
caugugacuaaguccuucaugucugaugcuugaguaauauuuucucuaacguaguaacugaauugucuuguacucuuucag
gauugcuuauauugaauuuaagucugaagcugaugcagagaaaaauuuggaagaaaagcagggggcagaaauugauggacg
aucuguuucacucuacuauacuggagagaaaggucaaaggcaagagagaacuggaaagaccagcacuuggagugguaaguua
aaggguuuauuguguagugggaacaggaaucauuuguaucuuuguauuuuaaguaauugguuaccuacaauuaguucacc
uuuguucauauagcugauguuuagucuucaugagugaaagcuauuugaaaucauuuccuuuggaguauaguaggcaaauaa
agcuuuuuguugguauguuuuguacuuuaaauggcuuaaacuauuuuagaaaauaguguaagacaacaaagaacaguuau
cuaauuagaaugaaaaugaaaggagcaaagaaggcauuacuguauauaauggauauacacugguggcuucuagaauuauggu
auaugguacaugguugaagugccauuguuucaguuaacauuccaguaaccuuguggauuagguuggagacaugcuuuauag
gugacccacuuacugaguguuuaaauauacacagacauacucuaacauaccuugcuaauguguuaucuuuguauuugcagg
ugaaucaaagacuuugguuuuaaguaaccuuuccuacagugcaacaaaagaaacucuugaggaaguauuugagaaagcaacu
uuuaucaaagugccccagaacccacauggcaaaccuaaaggguaaaauaauuuuuacguuagaugugggcuggacauacaua
cucuuacguauaagaguaagacuguccuguuagcuuaaaaaaaaacuaaaguuuuagcuauacaaagggcaguaaauauuga
uaguaaauuacaugcugaugccaaguguuucuaagcuuuauucugagaacugacuuucaaccuucagguaugcauuuauag
aauuugcuucauuugaagaugcuaaagaagcuuuaaauuccuguaauaaaauggaaauugagggcagaacaaucaggcugga
guugcaaggauccaauucgagaagucguaaguccuuugacaugauaugacuugguugggugauuuuuuuuuuauuuuua
ugugccuauaugcucauuuggggcugucuuuauguuguugcugagaaaaugacaacuggauaugaugacugauuaccuga
gaaauaauugaugaaaucucaagaaaauuccucuagauagucaaguucugauccagcuaugucaacucaaagcagcaaccuu
gauugcccucugaguacgcuuuuuuuuugauccaguguagucuuuuuuuuuuuaaccuuaauuucuuguguuaauugcuu
uuucugguaaaaggggaaaaaaagacauaacaaaaucaguguaagggaaggcucagugguugagcacugagaggaccuggg
uucaaaucccagcacucacauggcaccuaucgagacaggauuucucuguguaguccugccugucguggaacucacucuguag
accaggcuggccucaaacucagaaaucugccugccucugccuccuaggugcugggauuaaaggugugcgccaccacugccca
acccugucuguaacucuuaagaucugacauagauugcagacaaaacacuaaugcacauaaaaaaauuuuuuuuuuuaaaaaa
ggaaucuacuucagcugaauguggcaguauggcaguauucaccaagguucauagugaaacaggaauuuuucucuuccaga
accauccaaaacucuguuugucaaaggucugucugaggauaccacugaagagaccuuaaaagaaucauuugagggcucuguu
cgugcaagaauagucacugaucgggaaacugguucuuccaaaggguaagaaggcguaguaguguugcugcuuuuuagugaa
uucugcauggagaacuugggucugcaguaucuucucauugagcuccuuucuguccaucagugauagauuauggauucgcac
gagaagaagagagaauucacagaacuggcacuuaucuucuguuuuugcagaaguauauuuggcuguugugugagacauuau
gagauacuggcgauuuucucgaccugaagaguacuuuggucacucuacuuggugacuugguacuuauuguguuacuuua
aaauguguuuacuuaauggugugagguuuuuuguuuuucuuuucuguuuuagguuugguuuuguagacuuuaauaguga
ggaagaugccaaagcugccaaggaggccauggaagauggagaaauugacggaaacaaaguuaccuuggacugggccaaaccu
aagggugaagguggcuuuggugggucgagguggaggcagaggagguuucggaggcagagguggaggcagagguggaagagg
uggauuuggaggaagaggccggggaggcuuuggagguaaggaagggaaaggaacuggaaacggauuccuaaaccugugucc
uaaccaaccaccuuaauggaaggucaguccuaauuguaucacccuuugauguuuuuccuuccuauagguagaggaggcu
uccgaggcggcagaggaggagggggagacuucaagccacaaggaaagaagacgaaguuugaauag 85 X57800 Sequence below.

uuagacgguugcgcgcagaggguugguaguugucgcuguaggccuucgcugccgcuucugcaucgugaaucgggggac
cuuggcagccagaccucguuccucuuagaguagcucucaucuagucgccacaacuccgccaccauguuugaggcacgccuga
uccagggcuccauccugaagaaggugcuggaggcucucaaagaccucaucaaugaggccugcugggacgucagcucgggcgg
cgugaaccugcagagcauggacucgucucacgucuccuugguacagcuuacucugcgcuccgaaggcuucgacacauaccgc
ugcgaccgcaaccuagccaugggcgugaaccucaccaggugagcggguggcgggagcggggccccacucuucccgcuuccgc
ucuuggcggggcugugacucugcacgcucauuggcuggcuuggccauccgcgcuuucugauuggucuauggugucggggg
cagcccucaccaaagcgcgcgguuccgaaaagcccgcgcuggcaguggcgcccacucuguuuccgcgccaaagccacaaagcg
ggaguccgcgggaaaaugagugcuccggagcugugcucauuaaaugccugcagcuuugaguggcuggucuuagcgccuaau
aaacgagucuuagugcaaauguaaugucgacuuagagugacaauagaccuuuucuugacuuccagagucucacugcgcauca
uggauuugaggggaaaucugucaguuuuagcuuuuaacuuugcuacagcuaccuagguuagugccuccuguauacguguu
caaggacagugugugacuuauuuuaguacagauacauggauuagugccacuuguauacauuuugaaagauuuacgaaaagg
ccagacgugauggggcacauucuccaguacacuagaaaccaaggacaccccgcucaaaaagaugcuuucucgaauguuggcu
uuuagugcauuuuacuaagucgguuuuaagaaucacauauacccgguaauuugcuucaccccugagagaguuggguacc
cuuagccccuuuaacaguucuccaaccgugagugugaaaugguacaacuuguaauugcuuuuuaaaauauagauguggauu
acauguugauaaagccugucuuuuuuuuuugggggguagcauguccaaaauucuaaaaugugcugguaaugaagacauca
uuacauuaagggcugaagauaaugcagacaccuuagcacuaguauucgaagcaccaaguaaguuaaacaccuuuaaaacucg
gaguuacguguuguuucuguuucucaaaaccaaaaaaaauauuaacaauauuguaaauuccaucauagauaggaccgugug
gugugcuugguaacauuuuccuucuuuugguagaucaagagaaaguuucagacuaugaaaugaaguuaauggacuuagaug
uggagcaacuuggaaucccagugaguuaccuuguuucugauuguguguuacccugcugugauaccagcugaugcguguuc
ugaguggagugguggguauuggggaugaauggcacacugccauuucacuaaaccacagcagucuaaaguugauugaguuuua
aagaaaccagaagucuugcauucugaguucugguuaagaugcuaaaucuugagaacaugaagcugagccuuccccccuuuucu
agacugaccuuuaacuugugggguuuacaggaacaggaguacagcuguguaauaaagaugccgucgggugaauuugcacgua
uaugccgagaccuuagccacauuggagaugcuguugugauauccugugcaaagaaugggggugaaguuuucugcaagguggag
agcuuggcaaugggaacauuaaguugucacaaacaaguaauguggauaaagaagaggaggcggugaguaguaagggggcgu
ccaguuaggugucugaagcagggauggagccucggcuuuuguuuuuauuuauucauucauuuugagauggagucuugagu
agaccaagcuaucuuagagcucagagacgacuccauaagcuuuuacagguagcauuuggaaagcuaaguguacagccuuuug
cuuccuggaaauacucuuggcaaauaagugagggguuggcaagugagcaaaagaaaaugguugggggguauguagcuuuau
guguugcagguucaagaguauuugcagucccaagggaaauaagaaagacuucacaaaauguggaaagaguuguauuaaaugc TABLE 3-continued RNA transcripts up-regulated during HF stem cell activation.

SEQ ID No: | Access. # | Sequence ucuugacaguuacauccauagagaaagcugggcaugaugucucaaacccacaacugauguacucaaagcuacagcaggaaga
uucucagcuuaaagucaaccuggcagaaaaucuagcucaaaaagaaugaggaagaaauugggaaggcaaaggaagauguucu
ccgaguccuccucauucaaguagaacauacuaggccucuuuaauuucuaaguaucccugaaucgaggcuuuuucucaggaau
ccaauguauauuucauggcuacacuuuuuuuuuucuuuuuuaaguuuugcuagcuagccugagcaucagaauuacacacag
aagucugaacuaaauaggauuuuuaggguuuaguauagugaaauucagagugcuucugcaaguauuuaagguaaauauaag
guguuacuuggccucugcaugaauuuaaaguaaaugaaaguguaagaauucgaacauagauaaacacacaacccaagaacua
guucuuaaccuuaaucugcugaauuauuucuacuuccauaucaacuucagcuccucaguucucaaauacugacauguaauuc
aucaguauuugucugaugugcaagcauuuccacaacaaaagaaauuaaggaauuuuucaguauccacauguucaaggauugg
gaauugaauaaaauugauaaucauacaaugaagacugguuuacugucccuuagcuugcauucagcuguugguucuuguuuu
uggaagugguuauguguuaucuucccucucuucaugcauucuuugcaagagaaguauguacaaucugaauaggaacaacuuu
cuccuuuguuuugauugcuuggggugugcucuacaggaugggcaagcuagacuuuuuucuucuuuagucaagguuuuca
ucaacccuuccaaaaugauaacuauuuguuuugcuuugugguauaauaccgugaucuaauagugugaguuucugaugucua
cagugagccuguuuucuccucuagguaaccauagagaugaaugagccuguucaccuaacguuugcucugagguaccugaac
uuuuucacaaaagccacuccacugucuccuacaguaacacucaguaugucugcagaugugccccuugguaagaugauaaguu
ugaacauuguuuuguaaugugguauuuauaguauucggugguuuaauuuuuccugucuuucaguuguagaguauaaaauu
gcugacaugggacacuuaaaguauuauuuggcucccaagauugaagaugaggaagcaucuuaggcauugcuagaaauugag
aaaacuaaaccuuugaagauugcuccugagaugccagcguguccugaggucuuuucugucaccaaguuuguaccugaguau
ucuuaaauauuaaaauaaaauauguagauaucuucuguaaauaaccuacuucuuuucucuccauucuccauaauuugcuu
aaagaauaagcuccaaaguaaaaacuaguuuuguuaacaugaauguuucugcuuuacaaauacuggugauuuuccaucaaug
aucuugacgcuaaaugcaguuuuaagaaauauuguucaauuuaaauaaaguuaacaauuugaaaaguca 86 M35247 Sequence below.
ggugcaggauguaggccugcagaauugucagacccaguggcggcuuuugccacuggaagaauuuccaacauaaaacaga
ugaucaguuugggacaaucgauucugcgaccagagguagugucauuugguuacuuuuaaaauucagauugucuggugu
uuuccaaucacucgcgacuguaauuugaaguuggguucugagauaauacaaucgcugucgcucuaguuuauaaagcugu
ccaagaucugcccagucccagauguccuggguccucagggccgcugugguc ugccaacuucugcagcuggaugccagacc
auccuggacucggaucccuuuggguauuucuacaccgcugugucccggccuggccuuggggagcccugguucauaaucg
ucggcuauguggacgacaugcagguccugcgcuucagcagcaaggaggagacuccgaggauggcacccuggcuggagca
ggaggaagcaggugacugggagcagcagacucguauagucacaauucaaggacagcugucugaaaggaaucugaugaccc
ugguucauuuuuacaacaagagcauggacgacucucacacacuacaguggcugcaaggcugcgauguggagccagaucg
gcaccugugucucugguacaaccagcucgccuaugauagcgaggaucuccccacccugaacgaaaacccaaguuccugua
cagugggaaacagcacuguaccucacaucucucaggaccugaagagccacugcucagaucugcugcagaaauaccuggaa
aaagggaaggagaggcugcugcguucagacccuccaaaggcacaugugacccgucaccccagaccugaaggugaugucac
ccugagguguugggcccugggcuucuacccugcugacaucacccugaccuggcaguugaauggggaggagcugacccag
gacauggagcuuguggagaccaggccugcaggggauggaaccuuccagaagugggcagcugugguggugccucuuggga
aagagcagaguuacacaugccauguguaccaugaggggcugccugagccccucauccugagaugggagccugcauggua
ccaaaagccuuggauuuggauuguugccaugguuuucauuuuguucaucauuugucucugugugguuugcauaugcau
gaagaagaaugcagguggg agaggaaggcgugacacccaagaagcaggcagagacaguccccaagacucuagcaagacug
uuguggaugaugaggagauggggguuugcuuuuggaagauuaaguccuguaaaacuugucuaggccacuccccaggaac
uucaguuggcgagucuuuacugucaccuugacuggauuuaggaucaucugggagaugccccuuugaguggcugggcug
ugaggacagcaggccaguucuugccacccuggacagaaacacaucucaccuuucuggcucaaggaucugaacaccugucu
cuugccuacucggcuucuagucaggcauuuugucaccuugucaagggucccagggacacaaagcucccuccucucaccca
cagcacucuggguccuacccucagugcuucagggacauuuaaucaggucaaauugggaucaauggcuuugaugcagaaa
agaacuguggacuaauagagauaggguuuaauuaaaaaauauaucuuuuuaauuuu 87 AI553024 cuggcacggacauggcugucuucugucugcugugugggaaacgcuuucaggcacaaagcg
cacuccagcagcacauggagguccacgcaggcgugcgcagcuauauuugcagugagugca
accgcaccuuccccagccacacggcucucaagcgccaccuucgcucacauacagguuuuu
uucuccaugugucaccaagugaaguuugugccuucuauagcaaagagaauauuuuuuaca
uccuacuaacaguagauuuuuuuguagugaacauuuuuuguauuuuuauuuauaagucuc
auaagaaaaauagcgauguucaguuguauaccuugaaucugcaguuagaagagaauaaag
uuaacuc 88 X16995 Sequence below.
ggagccccagugcaggaggcugcgaaaguuggggagugugcuagaaggacugcggagcggagcgcacgcgggaccaggcu
gcgacuggg ucgcugguccc ggccacagggagugggagccggcugggguagguaccccgcagggagcguguuucuguuucua
gggacagugcaugaaagagaugggguguacgcgcgggcgaaaaggaaggguguuuucgggucggcuuacgaggaggggug
uguagggugcauuuuugguauuaaaggauagcucuuggaguagggugagccagggcuugaaguuuaggaagcgggcgaag
ggucugcaaggugcuugguuuugguagguagugggcgcuuguuuaggagguuuccccgcuaggaucuccagugugaggca
cucuguacucuggguuuggguguugauugccggguagggg guugucugagcauggacugggaaaagguacucagagcuuc
ggcguugcuggggauccauccaaguacaaguaagauuggauuuccacgggucuccuucccggcucucagccccuuucccag
uguuuacuuaauacuucauaggcuguacuuagauuuucugauucccuuaccgaacuuucuuucugaaccgugcuggaagac
cugggg guugcugaaggaaauggccagcuagguuggcuggguaaugguuguguuagacuaaguugucagaguaucuagaa
accuaggagcuguagccuggugcagcuacugaaagccgcacguggagccuggguggaaguugcucacgauagagucucgau
guaguacugacuagggggg agaccccuucugucaucagacagacuuguauaccccagugg ucuuuugaaucuguuagguag
ggugcagccugcgggcuuggucaccuaacagguguugccaggaccugccccaagccggauucucccacucccucuuucaacc
ccgccucuuccuccuccuugagacacccccacccccucaggaggcuagaugcagaucuguaucuuguguugcugacuaucgg
ccugaagcugggua gauugguggggguugauccggauguaggauguccaaguggagaaacaggauuugaauggagcuggaa
caaacgcccaguccugacugcugccacccuucuuccuccacccccaacccaucccuucccaggcuucuugcaaacagaggcag
aaguggccauauuucuuucuuucucccaggugcuguaugcccuagggacuugacacggggcaggcgggguggg aacugguu
ggggggggacgugcuguuuuaugggaagucguaugccuagccagcgguggagcuguccuggcuaggcacccagggguggu
guggggaaugggagaaauacugggacuagagggucucaagggccagcagguggugauagucuuuuucuccaccccacccuc
ugcuccaccaccccucugccucagcaccccucugcccucagcaccccucugccucagcacccucugccuccagccacccucug
ccucagcacccucugccucagcacccucugccucagcacccucugccucagcacccucugccucaguguuccugugugaccu
gucuuuucaacuagaaagucuagaacuguacagaccccagaguuggagguggaaagggacacuagguccuggagccuccucu TABLE 3-continued RNA transcripts up-regulated during HF stem cell activation.

| SEQ ID No: | Access. # | Sequence |
|---|---|---|
| | | gugggcuuuuuugaccagaugagaacguaagggccuccuccagcuaucccuggucauucaggugcuucagguuugugaccu<br>uugcugagacccuggaugcugcagcaaacagacaucugcuuuagcagagggacagcuugucucugugcauccgcugguagg<br>auccuccacucuguccaauuagcuugcgcugcugcuggguucugaguguucucuuacaaaaugacaagguuagggggcugg<br>agagauggcucaggggcuaagagcacccauguggcaguuugcaacugucuguaacuccuguuccagggggggaucugacacc<br>cucacacggacaaacaugcaggcaaaacaccuauuggcauggaaaaugaaaauaaaugaccggguuagcugagaaauuccuuu<br>ugagaguugucuuuucuccaguccaggacugcucucuggaucuuccugcucaguuccucgccucccuuccauauaugguau<br>uuaagguuuuacuuuuuuuugcguuuucaauuguuuuuaauuguauuuauaugugucucugugugugcacaugagcaug<br>ggugucuacaaggcuagagacaucagauguccuggagcuagaguuacagaugguugugagccaccugauguaguugcugg<br>gaacuggauuuaguuccuguggaagagcagugcaugcucuuaaccacugagcaacuucuccacgcggcccccccccaguaua<br>cgguauuuaaaacucuauagcaaugcuacccaacccauuguggagcuggggauggugagguggccuaguuccccccaacucc<br>uggaaacaugucagaaaguacagaguggugccugugggaucagcaugcggggguggugguggugaggugugggcugc<br>uuucucccgaggcuaccgugauagacaguuguaccuugcuggcagccucuaccccauuuccaggaugucagucucugcagac<br>guauggggacggugggaagggguauacagagccauggugugccugggaauguacucccaggaagugacugguugaaaa<br>gucagcagaucuccuggggauagaggggugggcugaagcucugugggguugccucucucagcccugaccugugaacaggga<br>ggcugggguuggaggaacacagcuuccccuguuccugggggacaugcuggacagccuuuccuagcucccccggcccac<br>uggggugguggcuggucgucggacugagcucuuuuggaccuggucucugccugugagcuuugugacucguugagauagcau<br>uugggcugagggauugggagucuucuguucuuugguccugacacccgcuuccuugucuaggccugccaccuggcuccccccc<br>acccccuccccggccuaccaaguuucuugcuucccuuacugaccccucuccucccuccuuugugucuccucccucuccag<br>agaugcccuguauucaagcucaauauggaacaccagcaacgagcccaggaccgcgugaccaccugaccggugaucccccuggcc<br>cuugaguucggcaagccuaccauggaccuggccagccccgagacagcaccugccgcaccugcuacacugcccagcuucagcac<br>cuucauggacggguacaccggagaguuugacaccuuccucuaccagcugccggggacgacccagccgugcuccucagcuugu<br>uccucugccuccuccacgucuucuuccucauccucggccaccucccccgcuucggcguccuucaaguuugaggacuuccagg<br>uguacggcugcuacccgggcacccugagcggcccauuagaugagacccuauccuccagcggcucugaguacuauggcagucc<br>cugcucagcccccucgccaucuacacccaacuuccagccgucccagcuuucucccugggacggcucauuggccacuucuccc<br>cgagccagacuuaugaaggccucugggcauggacagagcaguugccuaaggcuucuucagggccuccgccaccuccaaccuu<br>cuucuccuucaguccucccacuggccccagccccagccuggcccagaguucucugaaauuguucccaccaccagccacccacc<br>agcuuggggagggggagagcuauuccaugccagcagcuuuccccggcuuggcacccaccucuccgaaccgugacacuuccgg<br>cauucuggacgcacccgugaccuccaccaagucccggagcggggcuucagguggcagcgagggccgcugugcagucugugg<br>ugacaaugcuucgugucagcacuaugggguccgcaccugugagggcugcaagggcuucuucaagguauuuuguugguucu<br>gggggacgaugauaucauguuggagguggggguggagugggucauccguugggaucuguagugaccucuccugagguuuc<br>uucccagcugguucuguccugcaggacgagggacaggugugugccaucuuagaggcugggacuuuuuauucagcagggcac<br>acaucucucuagggcugcagaaagcuggggaagggggcagaaggugugugugugugugggccugcaguggugcucagaaaca<br>gaaaaccuagugggcagccucugguucuccacagaacuuguguuucuggcacuggaugaaaggacacaggcagaggguuug<br>guucuugcugggggguggacuugggaacaggcuguguguuuguccccagugcugggugccugcuuggcnnnncccaccucca<br>nccccuuaguccucuccucugcgccaggaaaagggcagguggacacaugcagacaccuguuagaacaggugucuggacggcc<br>gugggaguuccuagacccuggucuuggguucugggaucuucccugugagguugaaaccuucuccaguaucucccagacucc<br>ucucugcgcucuggcccuccguuucucccucccccuacauccaaauguuaggaaaauagcuaugaacagagggcgcuuuugu<br>cugcgucggccacaggaucuggacggucccccuccccugggcucuccacccccccccaaaccccaugcucugacagccuguuc<br>cgugucccccuuccuccagcgcacaguacagaaaagcgccaaguacaucugccuggcaaacaaggauugcccuguggacaag<br>aggcggcggaaccgcugccaguucugccgcuuccagaagugccuggcugugggcauggugaaggaagguggguggcaagau<br>ggugcccucggcauaggcgaccugaugggguggggacagccgggcucaccaggaucugcaccuaauucccacucccacuucua<br>gauuccagccccuaaaugcagguguagcuuccaccugcuuucuggaaagggugggugaggagggccuugugggguccccca<br>ucauggucugaguucucugucucugacuucucagaagugggguguauagugugcccugaagacccuccuucuccaggucuc<br>cuuucucaauacugcccgucucucugcaguuguacggacagacagccuaaaagggcggcggggccggcuaccuucaaaaccc<br>aagcagccuccagaugccuccccuaccaaucuucucacuucccucauccgggcacacuuggacuccgggccuagcacugccaa<br>auuggacuauuccaaggugaggucuugcccgcccaucugcccugcccugagaacauaugcaaugccuuugugccuguuagg<br>aaaggcucucccuccagggcaacaucaggaaacaagcauccucuauguacuggcuaguuggagaaaugcauugggaugggug<br>ugggggucggggagccaguuacaaacagcugccguagcccuguuuuccugugggaauugacaagcacaugggcccagaauag<br>ggcucuuuugcacgccuggaucugguguccccagugcaugagagcucuguaaugcagcuuguguaggcuuugcuguggaccc<br>aaugcaggacacagcugugugaugcaggccuugcuguggagccagugcgugacacagcugugugguggcaggcccucaugug<br>gaacuuaccugcguuccuuucaguuccaggaacuggugcugccccgcuucgggaaggaagaugccggugacgugcaacaau<br>uuuaugacuugcucucugguucccuggacguuauccgaaagugggcagaaaaaaucccuggcuucauugagcuuugcccag<br>gagaccaagaccuguugcuagagucugccuuccuggaacucuucauccuccgccuggcauaccgguaagcugcccaccaucc<br>uccuagcccuggccccagcccugcggccccggccugccuggacccugaguccugacuguucucugccuucugccagaucuaa<br>acccggugaggggaagcucaucuucugcucaggccugguacuacaccagcugcagugugcccguggcuuuggugauuggau<br>ugacaacauccuggccuucucacgguccccugcacagcuuggguguugauguucccgccuuugccugccuguccgcucuggu<br>ccucaucacuggugaguggcagaaacuagacugggcccaaggguugcaggaccauugguagguagcaucuaacacuuugg<br>ggacccccuagagugccugcaacauugggauguuaggaccugcaaagggacuuagcucuauucgccccuaaagcuuaaaucag<br>ccuccgaaugaccccggacuccucagguacgacuguaggcgcugggcaucuagcuuagggauucuguuuguuuaaaaaccu<br>agcugucaaccucacaagacacaggaacgugcacacaugaauuuuucacauucugcgcuuggauagcuaucgccaugguccca<br>gaaacaggaccuacuucagcucuguugggcucccucccuuauugucucuguaagagguaaccacucugccagccucaguggca<br>uuccugucauggauuuuacugugcguaucacaggguauggacucuaguguuaaauguagagguuucuggguccccuucucg<br>uuccgcucccauuuccacuuaaauuucuuaggggauccuccugaguagaucaagaccaggagcuggaucuugaaagguag<br>ggagugauaucuacacccagcucaguccuuagucuguccugcgagacuccaggauuuuagaacaguguggagccuggaccuc<br>cagaaaaccuggauuaggcuuuugccuuggccagccauucagugguuucaaauauugaccagucuggacagugggcucccug<br>ugggacgugcuagagggcuggggaagcuugucagggagaaggcgucaacugagcggggcugacucuaccuucccugcugca<br>gaucgacacgggcuccaggacccucgucggguggaagagcugcagaaucgcauugcuagcugucugaaggagcacauggcua<br>ccguggcaggagacccacagccggccagcugccugucacgucugcugggcaaacugccugagcuucggacccugugcacuca<br>aggccugcagcgcaucuuuugccucaaguuggaggacuugguaccccccuccaccuauuguggacaagaucuuuauggacaca<br>uugucuuucugaccccugcccugaacaugugugcgcacacgugcgugcucuucugucacccaugugccuuuaagccuauag<br>cccacggacccccagaccacccuacccccagccugguuuugagcuaagacugacguaccuccucacuccagaagauggacaga<br>gaacucaagaccuggggggagggugugugauucacgggggugaccccacuauuugucuuaucccuccagcucaguccuggccu<br>ucguguguuuuuguaagauaaaccauuuuuaacacauaccacucuguuguaaauaagcugacgcuacuguaaauacagaaag |

TABLE 3-continued

| RNA transcripts up-regulated during HF stem cell activation. | | |
|---|---|---|
| SEQ ID No: | Access. # | Sequence |
| | | gaagagguugagauggggguugggaggaaggggugggcucccaccagcugggcgagccuccaacucgagaucucuuccgc<br>ucuccuuccauguguacauaacugucacucaagaaggugauugacagauucugauuuauauuuguguauuuuccuggauuu<br>auaggaugugacuuuucugauuaauauauuuaauauauugaauaaaaaauagacauguaguugaaa |
| 89 | AF038562 | ggcacgaggcugugcccgccaugucugcuacccaucacaagaccucccugccucagggcg<br>uccgcgugggcacugucaugagaauucgaggcuugguccugaccaggcuggcagguucc<br>auguaaaccugcuaugcggugaggagcaaggagcagaugccgccuugcacuuuaacccga<br>ggcuggacacuuccgagguugucuucaacaccaaacaacaaggcaaaugggccgugagg<br>agcgaggcaccggcauccccuuccagcgugggcagcccuuugaagugcuccucaucgcca<br>cagaggaaggcuucaaggcugugguccggggaugacgaauaucuccacuuccaccaccggc<br>ugccgcccgcccgcguucgcuugguggaagugggcggagacgugcagcugcauucauuga<br>auaucuucuaagcaaaggacccaagggccuuugcccgguuacggguugggggguuuuuuga<br>ucccacaagaaagguuuuggaucggccaauaacauuuuucuguuguucugaaaaauuaaa<br>aaaaaaaaaaaaaaaaaaaaaaaaaaaaaaaaaaaaaaaaaaaaa |
| 90 | Y11666 | gccacauuguugcaccaacuccagugcuggagucucaggacaccaca<br>ggcuacccggaguuguucugcuuuggagauccgagggcaggagcaucacgccagugacuc<br>ugauaggugcgaucgccggauuggaacagaacugucauuuuuuuccgaaguugagccuua<br>gugacccagugagugaaguuagcgacgggacgcuaagcagcuagaccggucggcaggagu<br>gagacuuaggguaccuucuaguaguugugauuaaaaaaauugaaaaaaagaaaaaaaaaa<br>acccuguuucuggaaacuugaggcccucagcuggugagccaucgugguuaagcuucuuug<br>uguggcuccuggagucuucgaucccagccggacacccgggccugguuucaaagcggucgg<br>acagcgcugccugcuccaucgguagcgcucgagccucgguuucucuauuuggccccgacu<br>cgccgcaacaagaugaucgccucgcauaugaucgccugcuuauucacggagcucaaccaa<br>aaccaagugcaga |
| 91 | U40930 | Sequence below. |
| | | cccagcuguuucguccguaccuagaccgcgguuauggcgucguucacggugaaggccuaucuucugggcaaggaggagg<br>cgacccgcgagauccgccgcuucagcuucugcuucagcccggagccggaggcggaagcccaagccgcggccggcccgggg<br>cccugcgagaggcugcugagccgaguggcugugcuguuccccacgcugaggccuggcggcuuccaggcgcacuaccgcg<br>augaggauggggacuugguugccuuuuccagugaugaggagcugacaauggcuauguccuaugugaaagaugacaucu<br>uccgcaucuacauuaaagagaagaaggagugccggcgggaacaucgcccaccaugugcucaggaggcaccccgaaacaug<br>gugcaccccaaugugaucugugaugguugcaacgggccugugguggggaacucgcuauaagugcagugugugcccagacu<br>acgaccugugcagcgugugcgaggggaagggccugcacagggaacacagcaagcucaucuuucccaaccccuuuggccac<br>cucucugauagcuucucucauagccgcuggcuucggaagcugaaacauggacacuuuggcuggccuggcugggagaugg<br>gcccaccggggaacuggagcccacguccucccucgugcaggggauggccgcccuugcccuacagcugagucagcuucugcu<br>ccaccagaagaucccaaugucaauuuccugaagaaugugggggagagugugggcagcugcccucagcccucuaggcauuga<br>gguugacauugauguggaacauggagggaagagaagccgccugacacccacuaccccagaaaguuccagcacaggcacag<br>aagacaagaguaacacucagccaagcagcugcucuucggaagucagcaaaccugacggggcuggggagggcccugcucag<br>ucucugacagagcaaaugaaaaagauagccuuggagucggugggacagccagaggaacagauggagucgggaaacugcuc<br>aggaggagacgaugacuggacacauuugucuucaaaagaaguggacccaucuacaggugaacuccagucucuacagaugc<br>cagaaucggaagggccaagcucucuagaccccucacaggaaggacccacagggcugaaggaagcugcccuauacccacauc<br>ucccaccagaggcugauccccggcugauugagcccucucccagaugcuguccauggguuucucggaugaaggcggcug<br>gcucaccaggcuccuacagaccaagaauuacgacaucggggcugcucuggacacgauccaguauucgaagcacccuccacc<br>auugugauagugcuguggccaagccccacccccuuugucuuguaguugcaucacguagagcagcagggcuucuauagau<br>aggcccagugucuuggcauucuuguagaaucuucagguggggaaugugugaugccuuuucaggcaauaggaaagugcau<br>gaggagaguuuugaaugugcauaugcugacgccugagaacagacccagguacccguggcugagcugagcuuccucugcu<br>uccccuaggccuggccucugcagggaacugcagcacacacugcacucccaccugcucuugccgccagcauugcaccagca<br>guccagaauuccugccugacaacccguguuuccuuuauuaaaagugauuaguacaacugcuaguuauuuucaacaaaua<br>aagccauuauguuaagaggggacuguccauagugagugaaagguggcaggcaggggccuacagcuccuagggaauggag<br>aauucaugugaagccgaaugaaggaucuuaucuuauacuguccccccuuucuaauggccacucuuuaguguuugugucua<br>auguuaaugcuuaaagcacaggaccccccauguagcuuccucugacuugguuuguaaguaaccuguaauaaaaugccaua<br>ugcacuuuaacca |
| 92 | D26090 | Sequence below. |
| | | gagggaauugcgggaccccgucuggggaagcucccgccgccccgggugcucagcucucugucucccuugacccaggua<br>cagucaugucgggcuucgacgacccgggcauuuucuacagcgacagcuucgguggcgaccccggugcggaagagggcca<br>ggcccgcaagucgcaacugcagaggcgauucaaggaguuccugagacaguaccgagugggcaccgaucgcacgggcuuca<br>ccuucaaguacagagaugaacucaagcggcauuacaaccuggguggaauacuggaucgagguggagauggaggaccuggcc<br>aguuuugacgaggaacuggcugaccacuugcauaaacagccggccgagcacuuacagcugcuugaggaagcugccaagga<br>gguggcagaugaggugacccggccccggccagcuggagaugagcugcuccaagacauccaggucaugcucaagucagaug<br>ccagcccgucgagcauucggauucugaagucagacaugaugucacaccuggugaagaucccuggcaucaucauuucagcc<br>ucugcaguccgugccaaggcuacucguaucuccauucagugccgcagcugccacaacacccucaccaauaucgccaugcc<br>caggccuagagggcuaugccuucccaggaagugcaauauggaucaggcugggcgcccaaagugcccacuggauccauacu<br>ucaucaugccugacaagugcaagugugguggacuuccagacucugaaacugcaggagcugccugaugcagucccucaugg<br>ugagaugcccaggcacaugcagcuuuauugugacagguaccugugugacaagguuguuccugggaacagggucaccauc<br>augggcauuuauuccaucaagaaguuggcuugaaccccagcaagggccgggacaggguaggugugggcauccggagcu<br>cguacauccgagugcugggcauccagguggacacagauggcucuggccgaagcuuugcugggucugucagcccacagga<br>agaggaggaauuucgucgccuggcugcccuccccaacauauaugagcucaucuccaagagcauuuccccccuccaucuuug<br>ggggcauggauaugaagaaggccauugccugccugcuuuuuggggguucccggaagaggcucccagauggacucacucg<br>ccgaggugauaucaacuugcugauguugggagacccugguacagccaagucucagcuucugaaguuuguggagaagugc<br>ucucccauugggguguacacaucugggaaagguagcagugcugcaggcuugacugccucagugauacgggaccccucau<br>cucgaaacuucaucauggaagguggagccaugguucuggccgauggugggguugucuguauugaugaguuugacaaga<br>ugcgggaagaugaccguguugcaauccaugaggcuauggagcagcagaccaucuccauugcuaaagcugggaucacuacc<br>accuugaacucucgcugcucuguucuggcugcagccaacucaguguuuggccgaugggaugagacaaaggggaggaca |

TABLE 3-continued

RNA transcripts up-regulated during HF stem cell activation.

| SEQ ID No: | Access. # | Sequence |
|---|---|---|

auauugacuucaugccuaccaucuugucccgauuugauaugaucuucaucgucaaagaugagcacaaugaggagaggga
caugaugcuagccaaacaugugaugacucugcaugugagugcacugacacagacacaggcuguggagggugagaucgac
cuggccaagaugaagaaguucauugccuacugccgagcgagguguggaccucggcuaucagcagaggcagcagagaagcu
gaagaaccgcuacaucaucaugcggaguggggcucgucagcaugagagggacagugaccggcguuccagcauccccauca
cugugcggcagcuggaggcuauugugcgcauugcugaggcccucaguaagaugaaacugcagcccuuugccacugaggc
ugauguagaggaggcauugagacuguuccagguguccacacuggaugcugcuuugucuggcaaucugucgggggugga
gggcuucacuacccaggaggaccaggagaugcugagccgcauugagaagcaacucaagcgccguuuugccauuggcucuc
aggugucugaacacagcauuguccaggacuucaccaaacagaaauauccagagcacgcuauccgaaaggugcugcagcuc
augcuacgcaggggugagauccaacaccguaugcagcgcaaggugcucuaucgccucaagugagcccauugcccaucaac
ccucaagccugaaaugcugccaccacccuaucucccagucagugcuccaaaccuccuuuugcccugccucuccaccucaga
cugcugucugcagcacaucugcagccccuggaaauguacuuuggucuguuggcucauacuguguuugagugucugagg
acucucugcucuggguguciuaucccugucaugccuucucaacaagaugagucuggagcaggaacaggcccuggaaugu
agaugggucuguauauuggcucccgggccacucacugccaagcuucuuuguauguacagagguaauaaagcaauugagu
cccuggcugcuaaggucaguggacccagu 93 AI787627 ggaugcagccggaagugcagcgugcgugcgguuuggugggucgcugugugcgcuccgcgu
gugcagccgcgugggccaugggcggcgggcgcggggccggcgguuccagcagccgccgc
agccugagggcgaggaagacgccagcgacggcggcagaaagcgaggccaggcgggcuggg
aagguggcuaucccgagaucguaaaggagaacaagcucuucgagcacuacuaucaggaac
ucaagaucgugccagagggagaaugggaccaauucauggagucacuccgagaaccucucc
cagccacacugagaaucacugguacaaaagccaugccaaagagauucuccauugcuuga
agaacaaguacuuuaaggaguuggagganccugaaguagauggacagaaaguugaguucc
acaaccacuaagcugguacccugaagaacu 94 M33988 gagcucaaauucuggcuuucuauuggguacgauauauuaaccaaugggagaaacacaaac
agaauaccuccaguuaguauaaaugcuugcuguucaguugcagaauuuacuauauauucu
uuuccuuucucugcuuugccuuuacugauacuuaaacgcauacaugucuggacgcggaaa
gcaagggugcaaggcccgcgcuaaggccaagacccgcuccucccgggccggccugcaguu
ccccgugggccgcgugcaccggcugcuccgcaagggcaacuacucggagcgcgugggcgc
cggcgccccgguguaccuggcggcugugcuggaguaccugacggccgagauccuggagcu
ggcgggcaaugcggcccgcgacaacaagaagacgcgcaucaucccgcgccaccugcagcu
ggccauccgcaacgacgaggagcucaacaagcugcugggccgcgugaccaucgcgcaggg
cggcguccugcccaacauccaggccgugcugcugcccaagaagaccgagagccaccacaa
ggccaaggggaaguaaucuggcgauugucuguacugcccaguugaaaguuaaccaaaaca
aaggcucuuuucagagccacccacaucuuuccauaaaaugagcugccaccucgugaaacg
uucuuccacuacaguuuuuauacuacauaugaaaaaguuacgaaguagcuuucaaucuua
guaaauugauuuuaauacuguuagucccugcgauaaaucuuacgaccuuccuuaguuuga
gucaaaaguguguaagagaugaaaccuuuagaacauacuauaaauuuuuaguagaaauuu
ggcacccagguuugucauucacgucacgauugucuagagcauaaugguaguaagggcuaa
gggccauuaaaucccacuuccauaguuuc 95 AI845182 uuuuuuuuuuuuuuuuuggaaaugaagguaauuuauugaaacugguuuugggacaggcga
guggacaacuguugaaaggagcuagcgcacagccgggugggagcgggugcuuagccacag
auccuaucugaggcccaacuuuuucuuuuccuucugcuucuuacggaccacauccagguu
ccgguccuuccacaugcuuuugcgaagcuugauggggcgugagcccacauacuucccauu
caucucucgcauggcgcgcacauagucacuggggucuuugaagcugacaaagccauagcc
cuugguuuugccugugcgcuuguca 96 AA619207 uucggauccuugccaauauauguaucccauuuggaauggugaucuuaaaaugugagugca
ugcauacuaucuuauuuaagauacuugcaccccacccacucccaucucccgaagcuggaa
cacugccaacuagguccuuaagaaucacgcaauuaacacaagguugggugcugcuaauuc
uucaugaaaauccaaacacguuaagggaccagggagaugccacugcccccugaauuuuc
aucaaaaauagacacguuuauguaaacagaacuauuuuccauauucauagugacuuuuua
aguauuugagccuaaagauuuugaucuccauuuuuauaacuauuuaaauuguucacaauu
auuacau 97 AW125783 cggccgccgccgcccccacacugccccgcguugacgagcgccgcgacggcaaggacagcg
ccucgcuuuucgugguggcucggauccuagcggaccucaaccagcaggcgccggcgcccg
cccccgcggaacgcagagaaggggccgcugcgcgcaaggcgaggaccccugccgccugc
cgccugcgcccccugcgccgccacccggcccagagcccgccuccccgggacaagcaggcg
cgccggccgcgcccccagccccgcguggagcgagccggaggcggcauuggagcaggagc
ccggccccgcggggagcggcgagccuggccucagacaaagggggucggggaggccggagcc
gcgcggaccucgaguccccgcagaggaagcacaagugccacuacgcgggcugcgagaa 98 J04103 Sequence below.
cgucaguccccgccaccuccccggccccgcgcgcccggaucggcccuacggccucgucucgcccggccuugcgcgccgggacc
gccgcgaucuccucuccccgccgcccuccggcuggcccugccugcugcggcgcgaugaaugacuuuggaaucaagaacaugg
accaaguggccccugucgccaacaguuuucguggggacacucaagcgccagccagccuuugacaccuucgauggcucucuguu
ugcugugcucccuucucucagugaagaucagacacuccaagaagugcccacgggccuggauucugucucccaugacucggcc
agcugcgagcugccuuugcucacucccugcagcaaggcagugaugagccaagccuuaaaagccaccuucaguggcuuccaaa
aggagcaacgacgucuuggcauccccaaaaaccccuggcuguggagcgagcagcaggugugccaguggcuucucugggccac
caacgaguucagccuggugaaugugaaccugcaccaguuuggcaugaacggccagaugcuguguaaccucggcaaggagcgc
uuccuggagcuggcgccugacuuugugggugacaucccucugggaacaucuagagcagaugaucaaagagaaccaagaaaaga
cagaagaccaauaugaggaaaacucucaccucaacgcgguucccucauuggaucaacagcaauacauuaggcuucagcaugg aa
caggcuccauauggaaugcaggcaccaaacuaccccaaagacaaucuccuggacagcaugugcccgccaucggccacgccugc TABLE 3-continued RNA transcripts up-regulated during HF stem cell activation.

| SEQ ID No: | Access. # | Sequence |
|---|---|---|

agcucugggcucugagcuccagauguugcccaagucucggcucaacaccgucaaugucaauuacuguuccaucagccaggac
uuccccagcagcaacgugaauuugcucaacaacaauucuggaaaacccaaggaccacgacucuccagagaacgguggggacag
cuucgagagcuccgacucgcugcugagguccuggaacagccagucgucccuacuggauguacagcgggguaccuuccuucgag
agcuuugaggaggacuguagccagucucugugccucaguaagcugaccauguccuucaaggacuacauccaagagaggagcg
acccagucgagcaaggcaaaccaguuauuccugcagcaguacuggcuggcuucacuggaagcggaccaauccaguuguggca
guuucuucuggagcuacucucugacaagucuguccaaucuuucaucagcuggacgggggauggaugggaguucaagcuugc
ugaccccgaugagguugcccgccggugggggaagaggaaaaauaaaccaaagaugaacuacgagaagcugagccggggcuua
cguuacuacuacgacaagaacaucauccacaagacuucgggcaagcgcuacguguaccguuucguaugugaccugcagaacu
ugcugggcuucacuccggaggaacugcaugccauccugggcguccagccugauacagaagacugagggccuca 99 D90146 Sequence below.
auggcucuaacaacgcugcucuugguggugggcggccgcccugacccugaucgagacccgcgcgggugagugcggggucggg
agggaaacagccccugugccgcguccccgcuucgcccaccggaccuccgccccuucucccacccgagccccgagcccugcucca
cucccggcccgcguacccgaccgggguucccgggaggaggucggggucucaccgcgcgccgcccccaggcccacacucgcugc
gguauuuccacaccgcuguguccccggcccggacucggggagcccccgguucaucaucgucggcuacguggacgacacgcaguu
cgugcgcuucgacagagacgcggaaaauccgaggauggagccgcgggcgcgguggauggagcaggagggcgccggaguauug
ggagcgggagacacagaucgccaagggccaugagcagaguuuccaagggagccugaggacugcacagagcuacuacaaccag
agcaagggcggugagugaccccgggucggaggucacuaccucuccacgucccgaaacagaggccggugaggucccgggugca
aaguccgagguucaggagcagaacugacccaggacuggauucccuuucaguuuggaggaguccgcggugggggggguggggg
gggggcggaggagggacugaccacugggucccgcaggcucucacacacuccaguggauguauggcugugacauggggguccg
acgggcgccuccuccgcggguaccugcaguucgcuccuaugaaggccgcgauuacaucgcccugaacgaagaccugaaaacgug
gacggcggcggacauggaggcacagaucacccgacgcaagugggagcaggcugguauugcagagagagaccgggccuaccug
gaggucgcgugaggcuccgcagauaccugcagcucgggaaggagacgcugcugcgcacaggugcaggggccgcgggcagcuc
cuccccucugcccucaggcuggggcucaguccuggggaagaagaaacccucagcugggggugguggccccuggcucagaggga
gagagugacccugggucuccugauccucaucacagugacugcacugacucucccagggcucagccuucucccuggacagug
cccaggcugucucaggagggaaggagagaauuucccugagguaacaacagcugcuccccuucaguuccccuguagccucuguc
agccauggccucucccaggccaggguucucagccuacacccacugucuguagacacugacuccuguccugcugagugugucca
gcccuuacaccucaugaccugaagucuccuuuacccgaugggagacauggacaucuacacuaggcugguuccccccaguuucu
agaacuuuccaaagaauacagucuaccagauccuucccugucuguggggguuugcauccuuugacacccaauucuaucuauuc
cugcaaugggugaauagucacaugagccauuaugguuacccuaaacaaauacuuuucuuguguuuuccccucucguuuuc
uuuuuaucuuuacuuuuuuuuuaaggguauuauguugcuuauaaucgguuuuucuucggcacuggaaugauauugcucuc
ucuccccaccauaccccccaccccgccuauaucauuuguaucaguagcccuggcugucguggaacucacucuguagaccagg
cuggccuugaacucagaaaucagccugccucugucucugccucugccucccaagugcugggauuaaaggcuugggccaccac
cacugggcagaagaaagguuccugugagcuuaaaauguuuucuggcagaauuaaccauccagaucacacuccugauaucccugu
gccccaccaaguuacagugcucccccugugugaaucagaacuuggacucugagagacagggucuucugcaauccaggccugag
ugagagggaagaccacacacccugugagcccacuguguuccagugagugcugcacuggggguccacagcacauuccagggauc
cugugugacacaucuguaccuugucccccagagucaggggcugggagucauuuucucuggcugagugucagagguucacca
cauuucugcuacacacucccugauggcuguuuacuuggacugacaguuaauguuggucagcaagaugaccacagugguuua
gucucaauggugucacucuuccaguagcauauggucucugauuucuaauuuagauacgaacucaaacacauaugaaauuucu
uauuuuccauuccaucuuccauuauauagcuaccuaucucgugcuauugaacaucacauaaggaugaccauguugacccacu
ggcucaugugauucccucuuagcuucugagucccccucaggaaaaugugcaguccugugcugagggggccagcucugccug
caggucacuagugccaugacaguuaaaguguucauacagacacauaguucauuguaauuacugauuuagcguugucuuggc
aguuuucaguuugcaugcauuuauuuauuuauuuauuuauuuauuuauuuauuuauuuaaugcauggaaguacacuguugcugu
acugaugguuguuugccuuuguguggugguuguuggggaauugaauuuuuuuuuuuaggaccucucuuugcucuggucgaccc
ugcucacuccggucaacuccuaugggucaacucugcucauucagucccugcuuguucuggcccaaagauuuauuuauuauu
uauuauacauaaauacacuguagcugacuucagaugcaccagaagagggcgucagaucucauuacagagguugugagccac
caugugguuguuggaguuugaacucaggaccuucaaaagagcagucagugcucuuacccucugagccaucuccccaguccuc
aguuugucuucuuaauugugcgauuucuugaaucuucaaacagauccccaaagacacaugugacccaucaccccauaucu
uaugaugcugucacccugaggugcugggcccugggcuucuacccuguugacaucacccugacuuggcaguugaaugggggag
gagcugacccaggacacggagcuuguggagaccaggccugcaggggauggaaccuuccagaaguggggcagcugugauggug
ccuuuuggggaggagcagaauuacacaugccaugugcaccaugaggggcugccugagccccucacccugagaugggguaagg
aggggugugggugcagagcugugggucagggaaagcuggagcauucugcagacucugagcuggucagggcugagagcuggga
ucaugacccucaccuucauuuccuguaccugucuucccagagccuccuccauacacugucuccaacauggcgaccauugcu
auugugguugaccuuggagcugugggccaucauuggagcuguguggcuuuugugaugaauaggaggugaaacacagguag
gaaagggcagggucugaguucucucucagucuccuuuagaagugugcucuaaucauuaaugggaaacccaucuacaccccac
auugcuaccuucuccaacugggucccucugucaguucugggaacuuccaagaucuuccuugaacucucacagcuuuccuucu
cacagguggacaaggaggggacugugcuccagcuccagguuagugugggggacaggauugucccuguggacauugcagugaag
cuggagauguuggggagcucugggaacccauaguaacucuuccagagaaaucuuccagggccgcaguugucccaauaugaaua
cauauauguacauaugcauauacauuuuuuacccuuggcagggacagcuccuagagcucugauagaucucucccagguggu
aaaggugacacucugggaccugauuggggagggggcaauguggauaugauuggguuucagggacuccacgaaucccccucuga
gugagugguggguuguuggaaguugucuucacagugaugggucgugucccuc 100 AI563854 uuaaaucuggagggauuuuucacacagccuaucuuuuuaggugugccuuucccauauuuu
auuaaacucgaguuguuguuuuaaaaaaacagcagcauuaucaaagacacaucuguacaa
acauuuuacaaaagagaacucucuaggaucagcuacaucaaggacaagcagaaaaauaga
ugcaguccaacaaagacauugaaaaugacuu 101 AF017128 Sequence below.
ggucgcuuucugucuguagaggcggcuugccacccgagcagagggucgugaaguuccgaccggaccgguccacagaggu
ucaucuggagagguggguccccuccgaggugaaaggcgccgcugagaaacgcccccacccccgugguucaaguggguuca
gcccaagaacuuuucauucauaaaaaaagaccagacuccgagaggcgcgagugagucagaaccgcagccgccaacgcggacc
cuaccgaacauccagcccagggcauguaccgagacuacggggaaccgggaccgagcuccggggcuggcagcccguacggu
cgccccgcgcagccccccgcaagcucaggcacagaccgcccagcagcaggugagacuggccgaaucgucggggggggggggg
accugaguuuggacagcaucagggaugcugggauuagucuaguuugcuccgggauuuggacuggggccccgagcagcau
cugacucugguggucgcgaccgaggauccugcacguucugugugguucggggaaccuauguacccgguggccaaggggac TABLE 3-continued RNA transcripts up-regulated during HF stem cell activation.

| SEQ ID No: | Access. # | Sequence |
|---|---|---|

gagcgcagcgggaagcgcgaauaucugcgaauuccccuucucgcucgcccguaucucccuagcugacugucuuucugccc
cuccgucuccguuacggucuuacauuuccuccuaucugccccuaauacgcugucccucuaaauaccugccccaucccugc
cuggacaggaucagagguguucuccaucuccaguuaauaacugggaccuggggucugggcacauagagacgggguccau
cagaacucagccgggacagagaauucuuagcagccuguccgaggcuguccguguguugcucugguuguccgugucccuu
uauccggucaaguccucaucucuuugugcgcaguauagagcccaugggccccaggcagugguuccgagggguuccugga
gaccacgaaguguugggaugugcgcgggucaccugcccggccacacucgcgcuccacauucucggcacccgacgucucu
cacugcuggauaggggcacuugagagguugcagguguccauuuccugucgaggggccgcgagcacgugucgccagggga
gggaaggagcugcguccguuucgccgagucacagcgggccgagucacugaggcugagucacccugggugccccucccuu
ccuggccccaaacggccccuaaggaccgacgaccugggagcgagagaugccccuggcagugcuucuagcccagaacgggg
gucacugagaugcugggucccccaguauugggcuggggacauagcuguccagacuugccuaagcaugugaggugcuucc
uggacuggagggcccccacauccuuagcucacagagcuugaacccaguuucucucccagaacgcugagcccccaccccca
ccgacacucaaucccaacacaugccucagauuucugcaagaaaaggaaggaaaggaugccagacccuuauaggaggcuuu
uacucucuucacuuuauuucauggacuuaaaaaaccccaucaauuugaacuuucaaguuuuuaagucgacagcuaggca
ugcauuuaaucccagcauucaggaggcagaggcaggcagaucucugggaguuugaagccaauuuggucuacaaagugac
uuccaggucagcuagagcuacauaauagagauccugucucaaaacuuaaaaaauaaaaaacaaaaacaaaagccgauuaaa
acucugauuucugagcuaugagagcuggcuucucaacagcaauggaacguugaaugauguuaauaacagggaaacugag
acuaaauaacaugccccagucucaaagcccaucaauggccaagcuccaagcugaugcuggacucccaagcucuggugcuac
augucuauagucuuggugccugggagguagaggcagaggaaucgugaguuuaggucuagccugagcuaugugagaucc
ugcccaccccacccccggcccccaaacaacaaauucucauccugauucucagaauugccuugggagcuagaagcugaaagu
augcccaucugugaggacugggucucaaaucuuaguuucuacuuacuagcugugggucuaugggcaacugcucuccugu
cugaaaacaggauuauggcagcugugugagucacuauuuguuaaauaguuggaacaguguuacgcaguccauacuugau
uuaaaacaaaaaaccaaacuaucucuggugggggaaacagacagacgaagagagacauuuugugaccugcccaaaaucacac
agcuccugaacaaguaaguuucugguugccaaauguugcuccuuguggucucccaaaacugguaucuacacugagguga
agggagacagaaguccagccucuguccccgggaagccccucaguccacacagaccuuaucauuucccuucuuaucucuca
gaaguuccaccuugugccaagcaucgacagcagcagccaggaacugcacuggauggugcagccucauuuccugggaccca
cuggcuauccccgaccucuggccuauccccaguacagucccccucagccccggccaggagucauacgagcccuagggccac
cuccgggggugcgucgcaggcccugcgagcagguaagaaacagcgauguuucacuuuccauagcccguagggguccuac
uagacagggacaggaucuugcuacgagggaauuucuuauucagcauugaaguuccugagaggccaagaaggagguaaaa
ggucaccuuugagucaaggaaggcuuccuggagaaggcuacacguuaaccuaaaccacggauaggauuugcguauggaa
gcugaaaagaaucuucugggaggagguuggaggcacagaauugaggugaaggggacagaguguuaagugagcaugucu
ccacugucugacgugcacaggguggaaggaagccugaugcuggcuuuguaccucgggguгacucuucuuuucaacaguc
acggaaucucagccuauuucuuuuaauuaucacaaaaagugagugggcagugguggcucacaccuuaaauuucagcacug
gggaggcagaggcagguggaucucuggguucaaggccagccugguuuacagagugaguuccaggacagccaaggcuaca
gagaaacccugucucaagaaagggaaaaaaaagugaaugggaaauguauuucaauuuuuccaucuuccaucagaggaag
ugaagcauagagggguacucacuuguccagauucauacaaaugugaguaaugagacaggacugguccuggccugagguc
uacucaacucccaaagucagagcuuaaugagccacugucucaaugggagcucacagaagccugcagagggagugagcuga
gaacuuuugccucccugaaugccuuucuaaaauaaagaagggugugguuugguugguuuguagaggugggucuugag
agccuccugccuucccaagugcuaggaguauagguguaugcuagauacccgacagggaugacggaucuuuuaggccaua
gcacuuucuuuccucucccugaaguacugagacugagucuagugcagggaggccuccauacuaaaaagcuggguguaccc
guaaucccagaacucggaaaaucaagacaggaggagccauucaagucacgcucagaaacauggagaguuuaaggucagcc
ugggauauauaaacccuaucuccgauaaccaaacaacaaucaaagcaaaccugacuuaaguguuaaguaggaaagaauaug
cuguaagucaucagccuggcuggggggacugaccgccucugagggacugaagaaccugcuucaagcccggagcccugcacu
caaccccuaguggaugcacacacagauccuugccaugauggcucgaagagggauggcaagacccugggagauaugugaga
uuggccagagaagagccagcaacaggcuucccagcaagggaacagcuuaccucugugaucagcuggggcgugagcaagag
gcaagcccagggugaauccuuccuuuagcccuguccugaggagacaccuuuugaccacggguacuagugggguuggagcu
gugagcugugggguaggugguuccccucgguugugcucuggaacuugaacaaaucacucauccuuccugagcuuccucac
augugagugugcagagaucuggaugggugacucagcagcggcucuggcugcuccuuagaggauccggguuccaaucuca
gcacccacguggcaacucacuguccacaacgucccccaaagguucugaugcccucuucuggccuccaccagcacugaaugc
acaaggugcucauacaaacacacaggcaaaauacucagagguaaauuuguucuuuuuuuucuuuugagacaggguuucu
cuguauagcccuggcuguccuagaacucacucuacagaccaggcuggccucaaacucacagaggcaucugccugccuccc
aaguguugggaccaaagauguaugccaucacuauaagccuuuuuuuuuuuuguaaauuuuauuuaugaaugagugcuuc
cauguauaccuucaugccaggagagggcaucagauccuauuauagguggugugugagccaccgugugugggcugggauuug
aacucaggaccucugaaagaggagcucuuaacugcuaaaacaucucucuagccccagucuacauauuuaaaucuuuuuu
uaagauugauuuauuuauuauacauaaguacauuguagcugucuucagacacuccagaagagggcgucagaucuuguua
uggaugauugugagccaccaugugguugcugggauuugaacucaggaccuuuggaagaguagucaaugcucuuacccgc
ugagccaucucaccagccccuuuuuuaaucuuuaaaaaaaaaagggggggggccuggagagauggcucagccguuaagag
cacugaaugcuuuuccagagguccugaguucaauucccaacaaccacaugguagcucacaaccaucuguaaugggaucca
augcccucuucugguguaucugaagacagcaagggucuacucacauauguuaaauaaauaaauaaaaauuuaaaagccag
gugguguugguucagacagcagaucucuguuuaaggccagccuggucugaucuacaaaccaaguuccaggacagccagg
gcuacacagagaaacccucuaaaaaaccaaucuauguaggggggugcuggugaaauggcuccgugguaaagguacuugcu
gcgaaauuaaugaccugaguucaauccuugaaauccacacaguagaaggagagaaccaaccuccaagggugcuaugacaca
cacacacacacacacacacacacacacacacacacacacacacgacuauauauaugaauauaugacucuagccaggca
uaguguggcacaugccuuuaaucacaguacuugggaggcagaggcaggugaaguuugaggccagccuacagagugaauu
ccaugacagcuagaacuaugaagaugaacccugucuuuaaaaacaacagcaacauaaagaaucuauguagggaagcuggaa
gggaugcugauacagucugcaauccuauuacucuagagguggaagccaaagaaucagggguuucaggccggucuugccu
auacacugagcuaaaggccagccugggacacaugagacuuugucucuuuuaaaaagacaaaacaaggggguugguuagau
ggcucagugggguaagagcacccaacugcucuucugcagguccgaaguucaaaucccagcaaccacauggugguccacaac
caucuguaacgaaaucugagucccucuucuggagugucugaaaacaacuacaguguacuuacauauaauaaaaauaaaua
aaucuuaaaaaaaaaaaaaaaaagacaaaacaagccagaugaggucugugaguuccaggccagccuggucuauaaaucaagu
ucaaggccaggcagggcuacucagagauucugucuaaaauacaaagaaacaaaacuacaaaaagcagaaaaaggaaucuac
gaaagggcuggugaagggguguaacucagugguagagcauuugccgagcuagcauguaccaagccaugguuugauccc
uagcacuaagcaaaagaaaaguccuacaaagggcuuuguuggcauaguagauugauucccaguagcuuuuggcacucaag
agcaccuucuacaauucacagcuccuggggggaagaaaucccaucuuccacagaugaggaggcugagaguccugugaaaag
agauaaucaugucucauacacucaggagagaaggcuacuucugccugagaaaugaaaaggcuuccuggggucccaacauc
uuaguccaguccuaagaugcggaagggaggaagaucaaaguuuacagagagggaaagcauuucaggaaagaaaccagcag TABLE 3-continued RNA transcripts up-regulated during HF stem cell activation.

| SEQ ID No: | Access. # | Sequence |
|---|---|---|
| | | uaaagcuaggugugugugagcuggaaaugucaccaaugagaugacaagcguccgguacagagaagcaacuguggagugu<br>ugggugguggcaccuagacuacagacugaaggaaagcuggaugaccagcucagggcagcugguggcucagagucagccu<br>cauugucucccuucuucuaucccaaccuagaucagcccagaggaggaagagcgccgcagggugagacgcgagcggaacaa<br>gcuagcagcugcuaagugcagaaaccgaagaaaggagcugacagacuuccugcaggcggugagcaucauccccaggcccg<br>gacccacagagccccaagaggggucucggcucccaagaacacaaaagacccaaaauuacuccucaggacucugucauccuc<br>ccugccuguggggaaguccuggaaaaggauaagggaaaguggcuuaaauauuguuugucgggcuucgaggcagagucg<br>aagaugguaggcagcaauucuccuaagaugcccccgucugaugggagucauggccauuuucucccagaggcucacggga<br>gggaguugcaguccagacuuguuggggaugacaggcacagucccuacuccagccugaggcuuggggaucuuuagccuuc<br>auuuuccuaucuuucugcuaauccuguaaaggagaccgacaaauuggaggaugagaaaucggggcugcagcgagagauu<br>gaagagcugcagaagcagaaggaacgccuugagcuggugcuggaagcccaucgccccaucugcaaaaucccagaaggaga<br>caagaaggacccagguggguucuggcagcaccagcggugcuagcagcccaccagcccccggccgcccagugccuugcaucu<br>cccuuucuccaggacccguacuugaaccggaagcacugcauaccccccacgcucaugaccacacccucucugacuccuuuua<br>cuccgagucugguuuucaccuauccuagcacaccagaaccuugcuccuccgcucaccgaaagaguagcagcagcaguggc<br>gaccccuccuccgaccccugggcucuccuacacuccuggcuuugugaggcacccagccacaucccuugcuggugcuacu<br>ccaagccaucccccuuucucccauugauccagcaggccuggaccauacccuugccccaaaccagcagaucuuuuaucucuuc<br>cgacuagaacaaacacauuaugcuuugauguagagccagcuuggaggggaucccccaaagcugcucacuguuuuucuagag<br>cuggccuaucauaauuugcacaaaauuagaggaaaauauguucccucugccagagaacgccuggcagcccagacuuugua<br>gaucccccaggggguccuuugacacccuuaccccuugcagaccacuuucccacaccacgucacuuucuucauguuauccagc<br>cuacucuacaccuagacagaaggugcccuuugacuagccuagaacacuaacucacacagcaucaacagccagcagcaccgg<br>acauccugcaggcuccuccugaauggcacaacgcaggaggcgccaggggcuucugugaggagcggagcugcacucccuag<br>cucugagaagcgcuuagcuucaggguauccgagccuccaccgcaagggcagcugcuauuuauuuuccuaaagagacuauuuuuaua<br>caaaccuuccaaaauggaauaaaaggcuug |
| 102 | X67644 | Sequence below.<br>ccgugggguuccuaauggugcuauugacgacgggcacaaagucucauaauuuuagaaacuucacuuauuuugugacccaccu<br>aguauggggcaaaggcaggagcuucggacuuccugucuucccucuaucccuuugaauagcgucucgggaguguccuaagu<br>aaccauugcaguuuuguguccgugugcucuguugaaaucucugugaugugugugguuuucacgugaacggaggcaggc<br>agagcccggucugugggguucuaguguguucuuuaucuucuuggaaguuugugcaaugacuucccuccuguuuccugcgca<br>uaccuccaaguaaguacgugaauguguuuucuguggucccuugaucuugcuggacuucacuaaggagggguggcuggaccau<br>cugcuacgugucugagagccccucucuagcuaccucauguccggacgugagcuuacucccaauguuuuuacccacaagcauu<br>cacuacucccaggaaagaacgugcacuggggcaccuagagaauaaccaaucaacgcuccgccuacauuuugcuuccuccuug<br>gaauuuccagccccuugcagccaacugcuccccagcugcgaagggcggaguucccccggcccggccccuucuuuggcucua<br>uaaguagcucugcuuugcgggggauuugcacuccucuacacucucugcacaacgucuaaauuaugugccacucgcgcaacca<br>ucuccacaccaugacuggccugagggccccuucuccagcucccuccaccggcccggaacuccggcggggcucuggucccgaa<br>auuuucaccuucgacccucucccggagcgggccgugguguccaccgcgcguuugaacacuucucgcgggcaccgaaaacgca<br>gccgaagggugcucuacccucgagugguggaguaucgcccgagugggcaucaggaggucgcgucgcccuggaacuuguaggu<br>aacaacuaggagcagggaccuucgaucugacguuucccucuuuuaucugcucagguccggcgccagcuaccaaccgaggaac<br>ccaacauugccaagaggguccucuuucuccuguucgccagcaucuucugccagauuuugauggcugaagaggguguguucgc<br>agccccuggcuccggaggaugcuaccagcgccgugacaccugagcccauuucugcgcccauuacugcgcccccgguccucga<br>gccuuugaaccugaccucggaguccucggacuaugcgcuggaucuuaaagcuuuucucuagcaacauccggcggccuucuaa<br>acgcgauggggucacaguccgaagaaacaaaggcaccauggaugggguaccuggugcgagagaacguaucccaaacugggauuu<br>cuaaggcaacgcuaacucagaacacuaccgccaagagacaccgcggguccuggcuaggcccacuggggacggacagagacuuu<br>cuccgugucuaauuaauauuuauguauuuauguauauccuccuagguggaaggaggggguguauguaauauuuauucuaacu<br>uaugcaggggugcgagauaugccucccugcuguaacacagauauuuauuacgauuuauagggucgguaagacagaguugug<br>ggagggaggacccggguggguaggacucccagcuuggggauuagucugggggggguguaauaagauuagggguaacacuccg<br>ucuuccagcacuucaacucuguagucuguuguaaggcuuuggaagacccuugggaauccggccuuugaugucuucugguug<br>cuucucaggggcagcugcaggagucuugggguccauggauugucagagggcggcugucuggggucgccuaguauguauguu<br>cugugaacacgaauaaacuugauuugccugucauuauuaucugcaguucucgaaguguaucauucag |
| 103 | AF064088 | See above (same Accession Number). |
| 104 | AI843085 | uuuuuuuuuuuuuuuuuuaaauugccgaauuaaguucuuuuaauagauugcauauauagau<br>guuuagccauacucuagaucaacucuuuaagaguagaauuuuauauccaauuuacaugcu<br>ucagauaucaccucuguuuguuacauaaggucuuguauccaaauguccacuuguacacug<br>agagcuuuaggaacaaaaaaggacacagagagaguugccauuuuuagcagcaaugaaaca<br>ucacuaaccccuuuuuacauaccgaauucaagucacuac |
| 105 | AW124932 | cggccgccgguauuuuuuugcaaguauugagaguucuguauguuuugaaaagaguaauuu<br>uaacguuugggugccaagaagugggguuuucucagaguccauugccggcaaugggcaagcc<br>uggcgguacucccucgugccgaau |
| 106 | X58609 | augg<br>cgcugggaacgcugcuccugcugcuggcggccgcccuggcccggacccagaaccgagccg<br>gugagugcagggucgggagggaaacagaacuuuccaaacagucugcggggaggggcgggu<br>gcggcaccggggaagccgcgugcccgcgucgcccaccagacccuccgucucuuuacccgc<br>gucccuagccccgcgcccugcuccccuccugucccgcgcauccgcccggggucccgggag<br>aaggucggggucucaccgcgcgccgcccccaggcucacacucgaugcgguauuucgagac<br>cgucguguccccggccgggccucggggagccccgguacgucucugucggcuacguggacga<br>cacggaguucgugcgcuucgacagcgacgcggagaaaccgagguaugagccgcgggcgcg<br>guggauggagcaggaggggccggaguauugggagcggaucacgcagaucgccaagggcca<br>ugagcagugguuccgagugagccugaggaaacugcuaggcuacuacaaccagagcgcggg<br>cggugagugaccccgggucggaggucaggccccuccacuucccgacacagggacgcugac<br>guccugguucccaagucugagguucgggaacagaacggacccgggaccgguuucccuuuc<br>aguuuggaggaguccgcggguggggcggggcugaccgcggggucccgcagguucucacaca<br>cuccaggagauguauggcugugauguggggaucggacgggcgccuccuccgcggguaccgg |

TABLE 3-continued

RNA transcripts up-regulated during HF stem cell activation.

| SEQ ID No: | Access. # | Sequence |
|---|---|---|
| | | caguccgccuaugauggcugcgauuacauugcccugaacgaagaccugaaaaccuggacu gcgaaggauguggcagcgcugaucaccagacgcaaguggggagcaggaugguggcugcagag uauuacaaggcuuacauggagggcgagugcgugcagucgcuccgcagauaccuggagcuc gggaaggagacgcugcugcgcacag |
| 107 | M18837 | Sequence below. |

auggcgucaacaaugcugcuucugcugguggcagucgcccagacccugaucgagauccgcgcgggugaguaccgggucgg
agggaaauggccucugaggaaagggggaggggcggcacgggggaagccgcgucccggcgucgcccaccugacccuccgcccc
uucuccacccuagccccgcgcccugcuccccucccggcccgcucacccgcgggggucccggaaggaguucggggucucaccg
cgcccugccuccaggcccacacuugcugaguuauuucuacaccuccgugucccggccgggccuuggggagccccgguucauc
ucugucgguuacguggacaacacggaguucgugcgcuucgacagcgacgcggagaauccgagauaugagccgcgggcaccgu
ggauggagcaggaggggccggaguauugggagcgggaaacacagaaagccaagggcaaugagcagauuuuccgagugaaccu
gaggacccugcucagcuacuacaaccagagcgcgggcggugagugacccggaucggaggucacgaccccuccacgucccaaa
acaggggcccgagacgucccgggccccaaguucgagguucugagcagaacggacgcgggacugguuucccuuucaguuugg
aggagccgcggguggggcggggccggggcgugugggcggggcugaccgcgggguccccgcaggcucucacacuauucagguga
ucucuggcugugaagugggguccgacgggcgccuccuccgcggguaccagcaguucgccuacgacggccgcgauuacaucgc
ccugaacgaagaccugaaaacguggacggcggcggacauggcggcacagaucacccgacgcaaguggggagcaggcuggugcu
acagagaaaagcaaggccuaccuggagggcgcgugcgugcagucccuccgcagauaccuggagcucgggaaggagacgcugc
ugcgcacaggugcaggggccgcgggcagcuccucccucugcccucgggcuggggcucaguccuggggaagaagaaacccuca
gcugggggugaugccccugucucagagggagagagugacccuggucucccugaucccucaucacagugacugcacugacucucc
cagggcucagccuucucccuggacagugcccaggcugucucaggagggaaggagagaauuucccugagguaacaacagcugc
ucccuucaguuccccuguagccucugucagccauggccucucccaggccggguucucagcccacugucuguagacacugacu
ccuguccugcugagugugucagcccuuacaccucaggaccagaagucgcccuuuaacugaucggagacauggacuacccuaca
cuaggcugauugccucaguuuccugaauuuucaaaagaauacauucucccagaucccucccugucugugggguuuccacccc
uucgacaaccuaauucucucuauucccuauaguggugucacaucagcccuuauggggguacccuggaggaauaucaauagug
gaauuucuucuucuucuucuucuucuucuucuucuucuucuucuucuucuucuucuucuucuucuucuucuucuucuucuucu
ucuucuucuucuucuuccuucucucucucucucucucucucucucucucucucucucucucucucucucucucucucucuc
ucuucuucaguuuuugagauaggguuucucuguaugcccuggcuguccuggaacucacuuguagaccaggauggccucgac
cucagaaauccgccugccucugccucccagugcugggauuaaaggcgugguggccaccuugcccagccuuucuuauuuucuu
uacuuuuuuuuuuuuuuuuggagggggguaauuuuguuucuagucaucuuuugucuuuugucugcacuggagugauccug
uuucucccugcccuuauauuaucauguguaucagucucccacaggugccagggaaguuaagacaaguuaaaucaggguucuc
uuuaaaggagagauuccugugaacuuagacuguuuccugucagaacuaaacauccagaagccuccugcucuucccugucccc
acaaguuacagugcucccccccccccccccagugaaucuggacuuggacucugagagacagggucuucugcaauccagggcug
gagugagagggaagaccacacacccugugagcccacuguguugcagugagugcugcacuggggucccacagcauacuccaggg
auccuguguggacacaccuguaccuugcccccagagucaggggcuggaagucauuuucucuggcugagugucagagguuga
caccauuucugcuacacacucugugauggcugcucacuuggacuggcgguuaugcuaguuagcaagaugaacacagugguu
uacgucucaguugucacacccuuccaguggcauauggcucuaauuucuacuuugauacgaacucaaacacuuauuaaauua
guuaguuuccauuccaucuuccauucuaguccauucaugcuaaagaacaucacauaaggacugccaggaugacccacuggcu
cauguggauucccucuuagcuucugagucccccagaaaaaugugcagcugaggaaaccagcucugccugcaggucaccagug
ccaugacaguugaagugucaaacagacacauuguucagugucaucagugauuuaacugugccuuguguagauuucagaggg
ucuuguuaauuguggaucuuuuuuuuguuuuuuguuuuuuuuuuuuuuguuuuguuuucaagacaggauuuuucugu
auagcccuggcuguccuggaacucacauuguggaccaggcugaccacgaacucagaaaucugccugccucugccuccccgagu
gcugggauuaaaggcgugugccaccaccaaccagcuaaucgugagauuucuuucuuuuuucuuuucuuuucuucuuuuuu
uuuuuuuuuuguuguuguuuguuuuuguuuuugagacaggguucucuguguaucccuggcuguccuugaacucacuuug
uagaccaggcuggccuugaacuuagaaauuugccugccucugcucccggagugcugggauuaaaggcaugugccacuaccaac
cagcuaauuguggauuucuuaaaucuuccacacagauccuccaaaggcacaugugacaugucaccacagaucugacgguga
ugucacccugaggugcugggcccugggcuucuacccugcuaacaucauccugaccuggcaguugaauggggaggagcugac
ccaggacauggagcuuguggagaccaggccuucaggggauggaaccuuccagaaguggcgcaucugugguggugccucuugg
gaaggagcagaauuacacaugccaugugcaccaugaggggcugccugagccccucacccugagaugggguaaggagggugug
ggugcagagcuggggucagggaaagcuggagccuuuugcagacccugagcugcucagggcugagagcuggggucaugaccu
caccuucauuuccuguaccuguccuucccagagccuccuccauccacugucuccaacauggcgaacguagcuguucugguug
uccuuggagcuuggccaucauugcagcugugguggcuuuugugaugaagagaaggagacacacagguaggaaagggcagag
ucugaguuucucucagccuccuuuagagugugcucugcucaucaaugggggaacacaggcacaccccacauugcuacugucu
guaacugugucugcucucaguucugggaacuuccuagugucaagcucuucccuugaacucucacagcuuucccuucucacagg
uggacaaggaggggacuaugcucuggcuccagguuagugugggggacagaguugucccugaggucauuggagugaagcugg
aguguugggugcucugggaacccauaauagcuucucuguuguaaucccucugguggccugugucagaucuugcuauagau
auaucuuuguauauauuuuucccuaggcagggacagcucccagagcucugauauguuucucucaagauuguaaaggugaca
uucuauggccugauugcagaggggcacuguggacaugguuguuuucagggacucccacaaucccugugaguggugggu
uguugggauauugucuucauuguggugguuccugacccucauucucuaucaugaagacagcugccuggaguggacuuagu
gacagccagugugaccuugggucuucauuuuucuuuagagaacagcgccugauguucccugugagccuaugggcucaaugu
gaagaauuguggagcccagccuucgccuacacaccaggaccugucucuugcauugcccuguguucccuuccaccgccaaccu
uccgggucugcag

| SEQ ID No: | Access. # | Sequence |
|---|---|---|
| 108 | AW124268 | uuuuuuuuuuuuuuuuucagaauaaaugcagacaaauuccauuuauuuucuaaaaaccu cauuaucuaaaauuuauacagccucacauuccuaaaccaccucuggcacuuuucuugaau uaagucaaggcguacacagcuccgaaagaaaaauagagauccgguuccaggaagauggcc augaggacucgcagauaugucucccuccggaccuggaagcgugucagccaugggauccacua auccaccauccgguacacagggucacccacucucaggcucccaagcuucuccaccgagaa auacaucccaaaaaguggagaugacugguauauacucuucacagaaggaucacacaggcg auagcucuucagggucuccaguggc |
| 109 | AF090738 | Sequence below. |

cucuagaugaauacacucucaugagggccaccuucucugguaguucaggucgccucugcccauccuucccugcguccucucc
caaaguggccuacaacccuuacccagaggacuauggagacauugagauugguucucacaagaguuccagcaguaaccugggg
gcagaugauggcuacaugcccaugaccccuggggcagcccuuaggagugguggucccaauagcugcaagagcgaugacuaca TABLE 3-continued RNA transcripts up-regulated during HF stem cell activation.

| SEQ ID No: | Access. # | Sequence |
|---|---|---|
| | | ugcccaugagccccacaagcgugucugcucccaagcagauccugcagccacgcuuggcagcggccuugccccccuuccggagc<br>agccgugccagcaccccccuucaggggugggcaggaccuucccaguaaacggagguggcuacaaagccagcuccccagcggag<br>agcuccccagaagacagugguacaugcgaaugguguggcuccaagcugucuauggagaacccagacccuaagcuacucc<br>ccaacggggacuaccucaacaugucccccagcgaggcaggcacugcagggaccccaccugacuucucagcagcuuugcgugg<br>aggcagugaaggccucaaaggcaucccgggccacugcuacagcucuuugccccgcucuuauaaggcucccuguuccugcagc<br>ggagacaaugaccaguaugugcucaugagcuccccugugggccggaucuuggaagaggagagacuggagccccaggccaccc<br>caggggcuggcaccuuuggggcagcugguggguagucauacccagccucaucacucagcagugccuuccuccaugaggccgag<br>ugccaucgguggccgcccugagggcuuccugggccagcgaugucgggcagugcggccuacacgccuaucgcuagagggacu<br>gcagacccuucccagcaugcaagaguacccucuacccacagagcccaagagcccuggcgaguacaucaacauugacuuuggug<br>aggcagguacccgucugucuccgccugcccccccacuacuggcauccgcggccucaucuucuucacugcucucagcuaguag<br>uccugcuucaucccugguucaggaaccccaggcaccagcagcgacagccggcagcgcucuccacucucugacuauaugaacc<br>uggacuucaguucucccaaguccccccaagccuagcacccgcaguggggacacaguaggcuccauggauggccuucucucucc<br>agaggcuucaucccccauacccaccacugcccccacguccuuccacuucccccuuccuccuuacagcagccucugccaccugccc<br>cgggagaccuauaccgccugccuccagcaucagcugccacuucccagggucccacugcuggcuccucaauguccuccgagcc<br>uggggauaauggugacuauaccgagauggccuuugguguggcugcaaccccgccacaaccuaucguggcaccuccaaagcca<br>gaaggugcccgaguggccagucccacaucgggcuugaagcggcuaagucucauggaucagguaucugggguggaggcuuuc<br>cuucaagucagccagccccccugaccccccaccggggugcuaaggucauccgugcagacccacagggggggacgucgucgccacag<br>uucagagaccuuuuccucuaccaccaccgucaccccagugucccccauccuuugcccacaauuccaagcgccacaauucggccu<br>cuguggaaaaugucucacucaggaaaagcagugaaggcagcaguacccugggaggaggugaugagccgcccacauccccagg<br>acaggcacagcccuugguggcugugcccccagugccacaggcuaggccguggaaccccggucagcccggagcuuugauuggc<br>uguccuggaggcagcaguucucccaugcgcagagagaccuccgugggguuuccagaacggccucaacuauaucgccaucgaug<br>ugagaggcgagcagggguccuuggcgcagucucagccgcagccaggagacaagaacuccuggagccggacccguagccuugg<br>ggggcuccucggcaccgucggaggcucuggcgccagcggagugugugggggguccaggcacuggagcuuugcccucugccag<br>caccuaugcaagcaucgacuuccugucccaucacuugaaggaagccacagucgugaaaggugaggcccuuugaccuugagga<br>ugggggagggagaguggaguauuggguggcu |
| 110 | AI834950 | uuuuuuuuuuuuuuuuuucagcugugaacuauuggauuugagacaggaacagaacaaaucg<br>acgggccagaggaggguggagagagcacgagugguuuaaauaggggaggaugggagcaug<br>gcgguggggggugggggaagaguuauuuacaagaaggcucagggggccagaggcucaucuu<br>ggaauauuuuauaacaauauauauaagauucugguuugcuuuuccuuuucgucucguaaa<br>ggagagagaauugcauaguucgauucuguccaagggggcagcugcauauggucggccggg<br>cgggucacuggucgu |
| 111 | AI851365 | uuuuuuuuuuuuuuuuuuaagugucaccacuugugacagucagcauguuacuaucagcucc<br>agccgcagcguuuuuaaggcguuauagauuaggcaggcaauacaaggaacacgauuaaga<br>aacugacacguaccacacgagcaauuuccagaggcuccucuucugcggugcacacguaac<br>agugcucuuguugacauucagacaguucugagggccacucugagaggcgccuuccuguuc<br>ucaccugacaaggauauuguuugguuugguuugguuugguuuugccuuacuauggcuuuu<br>cuuucaacuacauuuugugucaugcuuguuagcuaacucaaauuuugucuuuguauauuu<br>acuacuguaaaauuagaauaauuuacuguucaucucauccucugucacugauggaaccua<br>gagacgccacaagagccacugccgugacauaccucacaagcuacaucccuguccucaaaau |
| 112 | AW047339 | cggccgcggccaccggccugcgccaagcugcugcugcggcagccaguaccucggugaagc<br>ccauuuucagucgcgaccugaacgaggccaagcggagggugcgcgagcucuaccgcgcuu<br>gguaucgggagcgugccgaacaccgugcacuuaaugcagcuggauaucacggugaaacaa<br>ggacgggauaaaguccgagaaauguucaugaagaaugcccaugucacagaccccagagug<br>guugaucugcuggucauuaagggaaagauggagcuccaggaaaccaucaaaguauggaag<br>cagcggacacacguuaugcgguuuuuccaugaaacagaaacaccaaggccaaaggauuuc<br>uuauccaaguucuauaugg |
| 113 | U06834 | Sequence below. |
| | | gcaccugagcgcgggugccuggcgcgcccgaugggaucguugagaggcccucgacggaaagucccaaacucggaucgcauuc<br>agccaaagugaggcggcgccauggagcuccgagcgcugcugugcugggcuucccucgccacugcuuuagaagagacccugu<br>ugaacacaaaacuggaaacggcggaucugaaauggggugacuuacccucaggcagagggccagugggaggagcuaagcggccu<br>ggaugaggaacagcacagcguccgcaccuaugaggugugcgacaugaagcgucca<br>gggggccaggcucacuggcugcgcacuggcugggucccaaggcgaggugcuguccacguguaugccacgauacgcuucacca<br>ugauggaaugccugucccugccgagggccagucgcuccugcaaggagacauucacugucuucuauuacgagacgaacguga<br>uacggccacggcccauacgcccgccuggauggagaaccccuacaucaagguggacacaguggccgcagaacaucugacucgga<br>agcgcccuggagcugaagccacagggaaaguuaauaucaagacgcugcgccug<br>gguccucucagcaaagcuggcuucuaccuggcuuuccaggaccaaggagccugcauggcucugcucucccugcaucucuuu<br>uacaagaagugcuccuggcugaucacgaacuugaccuacuuccccgagacggugccucgggagcucgguggugccgguggca<br>gguagcugcguggccaacgcggucccuaccgccaaccccagccccagccucuacugccgggaagauggucaaugggcugagc<br>agcaggucacgggcugcagcugcgcgccagguacgaggcugcggaaagcaacaaa<br>guaugcagagccuguggccagggaaccuucaagccccaaauaggagacgaguccugccgccgugcccagccaacagccacuc<br>gaauaacauugggucuccugucugccugugucgaauugguauuaccgggcccgcucagaccccggaguucaccuugcac<br>uaccccacccucugcuccaagaagcgugguucaccauuugaaugguuccacccugcgccuggaguggagugcuccccuugag<br>uccggaaggccgagagaccucacuuaugcuguucgcugccgagagugccguccugggggguuccugcuugcccugugggggc<br>gacaugaccuucgaccccgguccucgagaccugguugagcgcuggguggcaauccgagggcugcguccugaugucaccuau<br>accuuugagguugcugcuuugaaugguguguucuaccuuagccacuggaccaccuccuuuugagccugucaaugucaccacu<br>gaccgugaggugccuccugcagugucugacauccgagugacucggucgucacccagcagcuugauccugucaugggcuauc<br>cccagagcacccaguggggccgugcuggacuacgaggucaaguaucaugagaagggcgcagagggccccagcaguguucguu<br>uccugaagacaucagaaaaccgagcugagcuccgggggcugaagcggggagccagcuaucugguccagguacgcgcacgguc<br>cgaggcuggcuacggucccuucggccaggagcaucacagucagacucaacuggaugagagcgagagcuggcgggagcagcug<br>gcccugauugcaggcacugcgguuguggguguggucugguccugguggucgucaucauugcaguucucugccucaggaa<br>gcagagcaaugggagggaaguugaguacucggauaagcaugggcaguaucucaucgggcacgguaccaaggucuacauuga |

TABLE 3-continued

RNA transcripts up-regulated during HF stem cell activation.

| SEQ ID No: | Access. # | Sequence |
|---|---|---|
| | | uccuuuuacuuacgaagacccuaaugaggcagugagggaauuugccaaagagaucgaugucuccuaugucaagauugaaga<br>gguaauuggugcaggugaguucggcgaggugugccggggucggcugaaggcaccagggaaaaaggagagcuguguggccau<br>caagacucugaaggguggcuacaccgagcgccagagggcugaguuccugagcgaggccuccaucaugggccaguucgagcau<br>cccaacaucauccgccucgagggcguggucaccaacagugugccgguuaugauccucacggaauucauggagaacggagccc<br>uggacuccuuccugcggcugaacgacgggcaguucacagucauccagcugguggggcaugcugagggcaucgccucgggca<br>ugcgguaccuggcugaaaugagcuauguccaccgagaccuggcugcucggaacaucuuggucaacaguaaccuggucugcaa<br>gguguccgacuuuggccucuccagauucuuggaggagaacuccucugaucccaccuacacaaguucccugggaggcaagauu<br>cccauccgauggaccgccccugaagccauugccuucaggaaguucaccucugccagugaugccuggcgcuaugggaucguca<br>ugugggaggucaugucuuuuggggaacggccauacugggacaugagcaaccaggaugugaucaaugccauugaacaggacu<br>accggcugccuccuccuccagacugccccaccucccuccaccagcucaugcuggacuguuggcagaaggaccggaaugcccgg<br>ccccgcuuuccccaggugguc agcgcucuggacaagaugauccggaaucccgcuagccucaaaaucguggccagggagaaug<br>gcggggccucacauccacucuuggaccaacggcagccucacuacucugcuuucgguucugguggucgaguggcuucgagcca<br>ucaagaugggaagauacgaggaaaguuuugcagcggcuggauucggcuccuuugagauggucagucagaucucugccgagg<br>accuucuccgaauuggagucacucuggcaggacaccagaagaaaaucuuggccagugugcagcauaugaagugggaagcuaa<br>gccaggagccccugguggggacagggggaccagcccagcaguucugaccuccaaggacucaccaccguggcagauucuucuuu<br>ccgggaggcagaguuggguggggacucacaagaugagccccucccccucgucacagccuucccauuggauugcacuuugaac<br>agaggggggucggagacacagauuuggggaaccgugccauaugggaucauacaugugcccuccaggcggggaaccccaaacuc<br>agagugagucuuucccucaagacugggcaaagaaacaucccuacgucucuaaccucccaucuucccagaggcucucuccccaa<br>gcgccuuccaccucaacgggcaugucccugcagaccaaagagaaaggggugaccagccugccaacuugggaguggaaaaugcc<br>gucccaggaggcaggaaggggcugucaggacccggugauguaaucauugguuuugauguccugacuugcugucaccacca<br>aaggcaaucauuuuucccuuguaaaugccccucccccucaucugccuucauauugaagguucugaaguuuuacuguuuuuua<br>uuuuguuaauuuuuuccuccuucccccucccucccccuucuuguccagauuuuguguguuaaagggcaccugguuccacua<br>ucuccuguugggaacaaggacccaucgauauguucuagaacagugccuuggaaaugcca |
| 114 | AA980204 | ggcagcgagacgagcucacggucgaggauacgggugaagcgggacaggagcaggagccgg<br>agccgggccaaagcagaaggugcaggucggcgccggcgguugggcangacccagucaagc<br>cggacagugaggagcggaugcagacggcacgaccauggccacgauggugcuuccucgaga<br>ggagaagcugagucaggacgagauagugcugggcaccaaggcggugauccaggguuuaga<br>gacccugagaggggagcaucgugcccugcuagcuccccuagcuucucaugaagcaggcga<br>ggcugagcgggcucacaggagcgcugccuccuccugcgccgcucccuggaggccaucgag<br>cuggggcuuggggaggcucaggugauccuggcauuaucaagccaucugggggcuguggag<br>ucagagaagcagaagcugcgggcucaggugcggcccugguacaagagaacagugguugcg<br>ugaggagcuggcagggacacagcagaagcucagcgcagugaacaggcgguggcucagcug<br>gagaagagagcagcacaucu |
| 115 | AI843232 | ggcagcgagacgagcucacggucgaggauacgggugaagcgggacaggagcaggagccgg<br>agccgggccaaagcagaaggugcaggucggcgccggcgguugggcangacccagucaagc<br>cggacagugaggagcggaugcagacggcacgaccauggccacgauggugcuuccucgaga<br>ggagaagcugagucaggacgagauagugcugggcaccaaggcggugauccaggguuuaga<br>gacccugagaggggagcaucgugcccugcuagcuccccuagcuucucaugaagcaggcga<br>ggcugagcgggcucacaggagcgcugccuccuccugcgccgcucccuggaggccaucgag<br>cuggggcuuggggaggcucaggugauccuggcauuaucaagccaucugggggcuguggag<br>ucagagaagcagaagcugcgggcucaggugcggcccugguacaagagaacagugguugcg<br>ugaggagcuggcagggacacagcagaagcucagcgcagugaacaggcgguggcucagcug<br>gagaagagagcagcacaucu |
| 116 | U59807 | Sequence below. |
| | | augaugugugggcgcgccaucugccacaaugccagccacggccgagacgcaggaggucgccgaccaggugaggcugggcccag<br>gucaggccagucugagccaggccugcggagacccggcggccucagggaccggccugcccagacuggucagguccugcagcgg<br>guuuccggggcggccacaagugugacugggagcugggggcucuggaucugguuggaagauucagggccgggaacuggggc<br>gagucuucugccgcuugcauacaagagggccacucaccuauuagggaacuagccccgggaucgguggagggauccggugu<br>cccagagaauucaggaaggcaguguuagaaccuagacggcaccuuuuugacuuacacccaggccuaaacaagagaaagccaga<br>cugggcuacugugcuugucucccucaaaagaaagagcuaggacuguuuagcucaguggcaggaauucaacugauaccaccacc<br>accaucaccaacaccgccccucagggaaaaaaaaaaggaucaaaaccagaaguuguagaacuugcuugugccuagucugaaac<br>gagggggguggaccuugggccugggcugcccuuccugugacuguuagcagagcagagauucaguacaagguaggggggagguu<br>caggguauuagcaagagaagaaaaguuaaacaaauccucucuucagcucuccugccacgccccaagcccaggacccuguccac<br>uaagccuagcugaucuugggagguguuugcucugaacugaaguggccaagaaggaagugagucagcuccaugagacccuag<br>aaaugaggaaauguuacagacacacuggccaggcaagggaaccuuggccacgugccacaucagcacucaggaggcagagacag<br>gcgagucucucugaauuugaagccagcccaguuugcuuaguuccaugccagccauagcuacauagugagacccugucccccc<br>cccccccaaaaaaaaggagcuguguuguucuuuaucaguggggccaacaguuuaccaugucccccggaaugaggaguauuga<br>aggcuggcagugugugugugugggggcaccugugcaugaaucuaaguccuuccuucucacccaccauccaggugaagucccc<br>agcuugaaucgaaagaaaaucagaaguuugaugucuuuaaagccauauccuucaagagacagauaguggcuggcaccaaccu<br>cuucaucaagggugguacugauaguagcuugccaugaacuggggacauagucucagaguagagcagaguguccugcaacuu<br>ccugcagagaaccccuuaaggggacauguacauguucugagaggaugaauuuggggguguuaggguucccggccuuaaagga<br>ggagacaaggguuaucacuggcuaaguuaguggcugguggccuguucuggcucaguuucuaaggcuggguuaagccugga<br>acuggaaccuuaccuuucacucacaugucugucugucugucuuccuccagguugauguugguggagauaaaugcgugcacu<br>ugaggguguuucaaccccucccccaugaaaacaagccuuugacccugucuuccuaucagaccaacaaagaaaggcacgaugag<br>cucuccuacuucuga |
| 117 | AI152659 | gaaaauguuaagagccaucaaauuucuggauauuuugcuaggaaaaugaaauucuacacu<br>uauuuuuuguagacuuuuuuuaaaugcuguuuacaugaauuguauuuuggaaaaaauauu<br>auacugugcacccugugaugcaugaagugauuuuauguauggucugcuaugugggcagag<br>gucaccuuauuccuaugaucuggaauuguuuacuuucuacaaaguaagcuuugugggau<br>uuugcuuucauuuucuuuguagcugauguuauuuuaccaggugugcagcaggaauuacac<br>cacuguguggaauuauaaauacaucccaugugca |

TABLE 3-continued

RNA transcripts up-regulated during HF stem cell activation.

| SEQ ID No: | Access. # | Sequence |
|---|---|---|
| 118 | AI850090 | uuuuuuuuuuuuuuuuuccuggugaauauuuuuauuagaggugacaguuucccaggugac<br>aguuuuucccaaggaagcaaaucucugcgucuauaagggaagaccacagaaccuucacuu<br>uguaauuuaccuguguaauuuauccaagaacacagcacagcaauugcuuuaugugguacu<br>cugaccuuaaguaacaaguuguuaacagaaaacacaucaaacaaaaggauaauucucuaa<br>uuaucaagucagccaucagcuuuucuuaggagagagagagagagagugugugugugugug<br>ugugugugugugugugucugucugucugucugucuggguaucccacuuagggccaugu<br>gcauguuagguaaaugcuccaccacugagcuguuucuuagccgcacuuuucucagauuuc<br>agguuuguuuguuuguuuguuuguuuuuuaacuaggcaugaaaauaaacuucacuucaaau |
| 119 | AF064635 | See above sequence (AI850090). |
| 120 | AI843106 | uuuuuuuuuuuuuuuuuguggaaauuacucuuuauugaaaaauaccaguaauacugacag<br>acuucaaaaucaauuuacgguuccagaauacaaaguacuuaauacauuuuuuuccaaacc<br>uguuuguaucucaaaguuagcauuuuuguaaaucaagauacaaauaugauaacuucacua<br>aaauauuuuccagcuuuauucuuuaaggagcuguauaaccuucaaagucaggucccgag<br>gucagcagggcauggggcagaaugcaccuggcacucccugugcagcagacugcaaccaca<br>uu |
| 121 | AF033186 | auggccagcuuucccccgagggguuaacgagaaagagaucgugagaucacguacuauaggg<br>gaacucuuggcuccagcagcuccuuuugacaagaaauguggugugagaacuggacgguu<br>gcuuuugcuccugaugguuccuacuuugcguggucacaaggauaucgcauagugaagcuu<br>gucccguggucccagugccguaagaacuuucuuuugcaugguuccaaaaauguuaccaau<br>ucaagcugucuaaaauuggcaagacaaaacaguaaugguggucagaaaaacaagccuccu<br>gagcacguuauagacuguggagacauagucuggagucuugcuuuugggucuucaguucca<br>gaaaaacagagucguugcguuaauauagaauggcaucgguuccgauuuggacaggaucag<br>cuacuccuugccacaggauuaaacaauggucgcaucaaaaucugggauguauauacagga<br>aaacuccuccuuaauuugguagaccacauugaaaugguuagagauuuaacuuuugcucca<br>gaugggagcuuacuccuuguaucagcuucaagagacaaaacucuaagagugugggaccug<br>aaagaugauggaaacauggugaaaguauugcgggcacaucagaauuggguguacaguugu<br>gcauucucucccgacuguucuaugcuguguucaguuggcgccaguaaagcaguuuuccuu<br>uggaauauggauaaauacaccaugauuaggaagcuggaaggucaucaccaugauguugua<br>gcuugugacuuuucuccugauggagcauugcuagcuacugcauccuaugacacucgugug<br>uaugucugggauccacacaauggagaccuucugauggaguuugggcaccuguuucccucg<br>cccacuccaauauuugcuggaggagcaaaugaccgaugggugagagcugugucuuucagu<br>caugauggacugcauguugccagccuugcugaugauaaaauggugagguucuggagaauc<br>gaugaggauuguccgguacaaguugcaccuuugagcaauggucuuugcugugccuuuucu<br>acugauggcaguguuuuagcugcugggacacaugauggaaguguguauuuuugggccacu<br>ccaaggcaagucccuagccuucaacauauaugucgcaugucaauccgaagagugaugucc<br>acccaagaaguccaaaaacugccuguuccuuccaaaauauuggcguuucucuccuaccgc<br>gguuag |
| 122 | Z50159 | auggccagcuuucccccgagggguuaacgagaaagagaucgugagaucacguacuauaggg<br>gaacucuuggcuccagcagcuccuuuugacaagaaauguggugugagaacuggacgguu<br>gcuuuugcuccugaugguuccuacuuugcguggucacaaggauaucgcauagugaagcuu<br>gucccguggucccagugccguaagaacuuucuuuugcaugguuccaaaaauguuaccaau<br>ucaagcugucuaaaauuggcaagacaaaacaguaaugguggucagaaaaacaagccuccu<br>gagcacguuauagacuguggagacauagucuggagucuugcuuuugggucuucaguucca<br>gaaaaacagagucguugcguuaauauagaauggcaucgguuccgauuuggacaggaucag<br>cuacuccuugccacaggauuaaacaauggucgcaucaaaaucugggauguauauacagga<br>aaacuccuccuuaauuugguagaccacauugaaaugguuagagauuuaacuuuugcucca<br>gaugggagcuuacuccuuguaucagcuucaagagacaaaacucuaagagugugggaccug<br>aaagaugauggaaacauggugaaaguauugcgggcacaucagaauuggguguacaguugu<br>gcauucucucccgacuguucuaugcuguguucaguuggcgccaguaaagcaguuuuccuu<br>uggaauauggauaaauacaccaugauuaggaagcuggaaggucaucaccaugauguugua<br>gcuugugacuuuucuccugauggagcauugcuagcuacugcauccuaugacacucgugug<br>uaugucugggauccacacaauggagaccuucugauggaguuugggcaccuguuucccucg<br>cccacuccaauauuugcuggaggagcaaaugaccgaugggugagagcugugucuuucagu<br>caugauggacugcauguugccagccuugcugaugauaaaauggugagguucuggagaauc<br>gaugaggauuguccgguacaaguugcaccuuugagcaauggucuuugcugugccuuuucu<br>acugauggcaguguuuuagcugcugggacacaugauggaaguguguauuuuugggccacu<br>ccaaggcaagucccuagccuucaacauauaugucgcaugucaauccgaagagugaugucc<br>acccaagaaguccaaaaacugccuguuccuuccaaaauauuggcguuucucuccuaccgc<br>gguuag |
| 123 | X78683 | Sequence below. |

gaauuccgugugcaaggcgaggucuguaagcuggagcggggcagaggcuggcgggcaccccuuccugaccgcuggugccgc
cgccgccgccuucgggaggaucagacauggcccagaacuugaaggacuuagcuggacgccugcccgccgggccucggggcau
gggcacggcgcugaagcugcugcugggggccggggcgguggccuacggcguccgcgaauccguguucaccguggaaggcgg
ucauagagccaucuuuuuuaaucguauugguggcgugcagcaggacacgauccuggccgaauuucacuucaggauccccug
guuccaguaccccaucaucuaugacauucgggccagaccucggaaaaucuccucccccacaggcuccaaagaccugcagaugg
ugaacaucucccugcgugugcugucccgacccaaugcccaggagcuccccagcauguaccagcgucuagggcuggacuauga
ggagcgagugcugccguccauuguuaaugaggugcucaagagugugguggccaaguucaaugccucgcagcugaucaccca
gcgggcucagguguccuguugauccgaagagagcugacagagcgcgccaaggacuucagccucauccuggaugauguagc
uaucacagagcugagcuucagccgagaguacacagcugcuguagaagccaagcaaguggcccagcaggaagcccagcgggccc TABLE 3-continued RNA transcripts up-regulated during HF stem cell activation.

| SEQ ID No: | Access. # | Sequence |
| --- | --- | --- |
| | | aguuuuugguggagaaagcgaagcaggaacagcgacagaagauugugcaggcugagggggaggcggaggcugccaagaugc uuggagaagcacugagcaagaauccuggcuauaucaagcuccgaaagauccgggccgcccagaacaucucuaaaacgaucgcc acaucacagaaccgaaucuaucucacagcugacaaccuugugcugaaucuacaggaugaaaguuuuacucggggaagugaca gccucauuaaggguaagaaaugaguguggacaucaagaaccccaccaccagagaaguuggcacacuuguccagcuuggagga gccagcucgggggucaagcacagcccacccugccccaggcaucaugugauggacuuuucuguaucugcccucuuggauuaagg aagacugagaccagcccuuucagaggcuuuccuccuuccuguguuggcugggaagcgggguggacaaugugauuucuccgu gauuuccuacagccuugagccucucccagagugggggagauaaccaccaugccaggaauuc |
| 124 | X68193 | acccaccggcuuucggaccauggccaaccucgagcguaccuucauugccaucaagccaga uggcgugcagcgcggccugguggggcgagaucaucaaacgguucgagcagaagggguuccg ccugguggccaugaaguuccuucgggccucugaagaacaccugaagcagcauuacaucga ccugaaagaccguccuuucuucccggggcuggugaaguacaugaacucggggcccguggu ggccauggucugggaggggcucaauguggugaaaacgggccgagugaugcugggggagac caauccagcugauucaaaaccaggcaccauccguggggauuucugcauucaaguuggcag gaacaucauucauggcagugauucaguggagagugcugagaaagagauccaucugugguu uaagcccgaagaacugaucgacuacaagucuugugcccaugacuggguguacgaguagac augaagaaaccagaauccuuuucagcacuacugaugggguuucuggacagagcucuucauc ccacugacaggauggaucaucuuuucuaaaacaauaaagacuuuggaacugaaaaaaaaa aaaaaaaaaaaa |
| 125 | AA062013 | uuuugcuuucaacaugacagaugccgcugugucuucgccaaggacuucuuggccggugg aguggccgcagcaucuccaagacagcggucacaccaucgagagggucaagcugcugcugc aggugcacaugccagcaagcaaaucacggcagauaagcaauacaagggcaucauagacug cgugguucguaucccccaaggaacagggagugcucugguccuuugggcgugggaaccgggc caaugucaucagauacuuccccaccaaggcucucaacuuggccuucaaaguuaauuccaa gcagaucuuucuggguggguguugacaagaggacccaguucuggcgcuacuuuugcaggga accuggcaucagguggguugccgcuggggcuacauccuugggcuuuguguacccucuugau uuuugccgguaccgucuagcagcugaugugggcaagcuggagcuaaagggaauucaaggg ccuugggacugccugguaagacuucaaucugaugggauaagggcuguac |
| 126 | AI465965 | auccgggacccccacggccccuuugcagcuugccacaagguucugagccccuuggaauac uuccgccaaugugugugaugacaugugugcccauaagggugacaaagccuaucucugccgu agccuggcugcuuauacugcagccugucaggcagcugggggcagcagugaagcccuggagg acagacagcgucugcccucuccaguguccugcccacagccacuacuccaucugcacccgc uccugccagggcuuccugugcugcucucucuggccucacuggcugcaccac |
| 127 | U50413 | Sequence below. |

ggcacgagccgaguuggaggaagcagcggcagcggcagcggcagcgguagcggugaggacggcugugcagccaaggaaccgg
gacagcgaagcgacggcaggucgcagcuggaucgcaggagccugggagcugggagcuucagaggccgcugaagcccaggcug
ggcagaggaaggaagcgagccgacccggaggugaagcugagaguggagcguggcaguaaaaucagacgacagauggacagug
ugacaggaacgucagagaggauugggccucgcugcgagagucagccuggagucaagguguugacaaguugcugagaaggac
acgugggaggacgguggcgcgcggagggagagcccugucuucagucaccccguugauggaggacagauggacagcagccgg
acggccagucaccucucuuaaaccuuuggauagugguccuuugugcucugcuggacaccuguuggggauuuuagcccauuc
ucugaacucacuuucucuuaaaacguaaacucggacggcagugugcgagccagcuccucuguggcagggcacuagagcugca
gacaugagugcagagggcuaccaguacagagcacuguacgacuacaagaaggagcgagaggaagacauugaccuacaccugg
gggacauacugacugugaauaaaggcuccuuaguggcacuuggauucagugauggccaggaagcccggccugaagauauug
gcugguuaaauggcuacaaugaaaccacuggggagaggggagacuuuccaggaacuuacguugaauacauuggaaggaaaag
aauuucacccccuacucccaagccucggcccccucgaccgcuuccuguugcuccggguucuucaaaacugaagcugacacg
gagcagcaagcguugccccuuccugaccuggccgagcaguuugccccuccugauguugccccgccucuccuuauaaagcucc
uggaagccauugagaagaaaggacuggaauguucgacucuauacagaacacaaagcuccagcaacccugcagaauuacgacag
cuucuugauugugaugccgcgucaguggacuuggagaugaucgacguacacgucuuagcagaugcuuucaaacgcuaucuc
gccgacuuaccaaauccugucauuccuguagcuguuuacaaugagaugaugucuuuagcccaagaacuacagagcccugaag
acugcauccagcuguugaagaagcucauuagauugccuaauauaccucaucaguguuggcuuacgcuucaguauuugcuca
agcauuuuuucaagcucucucaagccuccagcaaaaaccuuuugaaugcaagaguccucucugagauuuucagccccgugcu
uuucagauuuccagccgccagcucugauaauacugaacaccucauaaaagcgauagagauuuuaaucucaacggaauggaau
gagagacagccagcaccagcacugcccccccaaaccacccaagcccacuacuguagccaacaacagcaugaacaacaauauguccc
uugcaggaugcugaaugguacuggggagacaucucaagggaagaagugaaugaaaaacuccgagacacugcugaugggaccu
uuuugguacgagacgcaucuacuaaaaugcacggcgauuacacucuuacaccuaggaaaggaggaaauaacaaauuaaucaa
aaucuuucaccgugauggaaaauauggcuucucugauccauuaaccuucaacucugugguugaguuaauaaaccacuaccgg
aaugagucuuuagcucaguacaaccccaagcuggaugugaaguugcucuacccaguguccaaauaccagcaggaucaaguug
ucaaagaagauaauauugaagcuguagggaaaaaauuacaugaauauaauacucaauuucaagaaaaaagucgggaauauga
uagauuauaugaggaguacacccguacuucccaggaaauccaaaugaaaagaacggcuaucgaagcauuuaaugaaaccauaa
aaauauuugaagaacaaugccaaacccaggagcgguacagcaaagaauacauagagaaguuuaaacgcgaaggcaacgagaaa
gaaauucaaaggauuaugcauaaccaugauaagcugaagucgcguaucagugagaucauugacaguaggaggagguuggaa
gaagacuugaagaagcaggcagcugaguaccgagagaucgacaaacgcaugaacaguauuaagccggaccucauccaguuga
gaaagacaagagaccaauacuugauguggcugacgcagaaaggugugcggcagaagaagcugaacgaguggcuggggaauga
aaauaccgaagaucaauacucccugguagaagaugaugaggauuugccccaccaugacgagaagacguggaaugucgggagc
agcaaccgaaacaaagcggagaaccuauugcgagggaagcgagacggcacuuuccuuguccgggagagcaguaagcagggcu
gcuaugccugcuccguagugguagacggcgaagucaagcauugcgucauuaacaagacugccaccggcuauggcuuugccga
gcccuacaaccuguacagcucccugaaggagcuggugcuacauuaucaacacaccucccucgugcagcacaaugacucccuca
augucacacuagcauacccaguauaugcacaacagaggcgaugaagcgcugcccucggauccaguuccucaccuucaagccac
ccaaggccucugagaagcaaagggcuccucuccagcccgaccugugaacugagcugcagaaaugaagccggcugucugcaca
ugggacuagagcuuucuuggacaaaaagaagucggggaagacacgcagccucggacuguuggaugaccagacguuucuaacc
uuauccucuuucuuucuuucuuucuuucuuucuuucuuucuuucuuucuuucuuucuuucuuucuuucuuucuaauuua
aagccacaacacacaaccaacacacagagagaaagaaaugcaaaaucucuccgugcagggacaaagaggccuuuaaccauggu TABLE 3-continued RNA transcripts up-regulated during HF stem cell activation.

| SEQ ID No: | Access. # | Sequence |
|---|---|---|

gcuuguuaacgcuuucugaagcuuuaccagcuacaaguugggacuuuggagaccagaagguagacagggccgaagagccug
cgccuggggccgcuuggaccagccuggguguagccuggguguCguCuggguguggugaacccagacacaucacacugugganu
auuuccuuuuuaaaagagcgaaugauauguaucagagagccgcgucugcucacgcaggacacuuugagagaacauugaugca
gucuguucggaggaaaaaugaaacaccagaaaacguuuuuguuuaaacuuaucaagucagcaaccaacaacccaccaacagaa
aaaaaaaaaaa 128  AW120502   uuuuuuuuuuuuguuuuaauuuggcuccaaugaucgcauucucaaacuccuuugggaggg
             cauuagaugacccaguauccgacgacuuagauucacgugguuuucccucucugagcucu
             uuucuccaggcucacngucuuuguuuuucaagcuuucuugggccuuugaacaauuuucuu
             ccuuugaagauucuccugg 129  X62940    Sequence below.
agccgaguaggaccgagcugcugcagacgcgccgggucacucgagccagcaccaccguucucacgcccugagcugcagacagc
uaggcgguuuuaucuaguuugaaccaggcugcuggagcuugcucccucccgcccucucuuuuuuuuccacgggggcuguu
uuuuaauuuggcugcaauugcaugaaaucccaaggguguagaccaguggcgauggaucuaggaguuuaccaacugagaca
uuuuuccauuucuuucuugucgucuuugcugggaaccgaaaacgcuuccgugagacuuagacaauagcucugguugcaagugu
gguagcuaucgacaacaaaauagagcaagcuaugaucuggugaaaagccauuuugauguaugcggugaggaggaagugga
aguucugaaggagcagaucaaagaacuaauagagaaaaacucccagcuggagcaggagaacaauucugcugaagacgcuggcca
guccggagcagcucgcccaguuucaggcccagcugcagacuggcuccccuccggccaccacgcagccacaggggaccacacag
cccccugcacagccagcauccagggcucaggaucaaccgcauagccucuaggccccaacagaacuggcugcugcugcugcu
gucugaacugaacagaccgaagagaugugcuagagagaagccgccuccacagucacccauuucauugcugucuacgaaagag
acgugagacucacacgcuguucucgcuuucucccaguauuaagcacucauaagcuuuuggcuugaagaaaugauacuaguu
gagugaauuaaagguuaaucagagagugagcagggaugugcccugugcaacgguggcagaugucugaggaauggguuuaauug
accccgaggagcucugugccuuuucaaccccuccccagccgcccaccugcuucugagagcucgggcggcucgccuucguggg
gcucgccugcgugggguucgaaagugggcugcuccuggauucugccucucuuuccuucccuucaaagaacucggagagg
ccagaaacaagacugcaaugggggggcggggggagggaugaugcagucuuauacaaaaccgacaacugucaccaaagcuuau
aaaacacgauaguacugucccucuuuucugaaccaucagaagacacaaaacuguuagugacacaacggugacagguagcugg
gaccuaggcuaucuaauuaugaaggungauuugcuuguugauauuuuguauguaguguuaacgaauuguuaccauuagag
gacuguccguaacuacguuuuagcuuucuacacauugaaaauguagauguucaucuggcucugaaaagguguggcuuguucc
uuccuagagagaucuacuuaaaaaacugcuuuuguggcaaaaaccacaccugaagaaauuuuuaagaauuuuggcccaguuaguca
cucuguguaaucccggaaucuagcugcugaagucuugcgaaguaaaacuccccgugaccgauguccaguuaagcuggugauac
cuggagaaguggucaguugcuaaggaaguggauuucccaguaggggguuucugcaccucaccuguauagucguucugcgcau
guccccccacacagucccccaccuguauuuaccuguucuacuugucaccuuucaauaaagcauaucaaauguugau 130  U60020    Sequence below.
auggcugcgcacgucuggcuggcggccgcccugcuccuucgguggacuggcugcugcugcggcccaugcucccgggaauc
uucucccuguuggcuuccagaggcgcgugcuccgaggugugugugccccgagucgcuggcgagggacuagg
ggucegcggggcgugcucggggucaccgcaggagcccauggcuggcuggcugcuuugcagccgcuggcggccgcacugaguuu
ggccucgccuggacuugccuuguuccgagagcuggccgccuggggaacacucccggagggggugacagcgcuggauuacugua
cuggaacaagucguccagaugccuucgcuaucaguuauggcagcauugcccgcagccgcccuguggcacaaguugggagag
cucuggggcgcccagcggcaacagggacgcuggagacaucgcuggugcucggaaugacacgcuccuaagaagagacg
ucucuaccggguucuggnucucuugaucucuuguggcuuggggaaauggccauuccccuucuucacggggccgcaucacuga
cuggauucuucaggauaagacaguccugcuucaccgcaacauauggcucauguccauucucaccauagccagcacagcg
cuggaguuuucaagugauggaaaucuacaacaucaccauggcauggaacacaugcacggccgugugcacagagagugguuucgggcc
guccucgccaggagacagggguuuuccugaaggaaaccagacuggcagagggggacacggggaccacagccacg
ugugcgagccauuaguagaaacgcugagccgcugcuguguggaccuggggcgagcccugugucucuuggguguucauguuu
uggggggcuccaccguaccucacucuggucaccuccugaucaaucgccccugcuuuuucuuugccugaagaagcugggaaaagug
caccagucacuggcagugaaggugcaggagucucuagcaaagcccacgcagguggcccuugaggccuuauccggcgaugccua
ccgugcggagcuuuugccaacgaggaggugaggcccagaaguucaggcagaaguggaagaaaugaagacgcuaaacaagaa
ggaggccuuggcuuacgucgcugaaguccuggaccacgaguguccugggaugcugcugaaggugggaauucuguaccuggg
cgggcagcuggugaucagagggacucucagcagcggcaaccuugucucauucguucucuaccagcuucaguucacccaggcu
guucaggucucugucucucccucuaccccuccaugcagaaggcgugugggcucucagagaaaaauauucgaauacuuggaccgga
cuccuugcucuccacucaguggcucguuggcacccucaaacaugaaaggccuuguggaguucaagaugucucuuuugccu
accccaaaccagccaaaguccagggcuuucaggggcugaguucaccucuggaaccucccugcagcggguugguggagcc
caauggaucaggaagagcaccguggcugcccugcugcagaaccuguaccagccaccgggggccagcugcugcuggauggc
cagcgccuggucaguaugaucaccauuaccugcacacucaggugcccgcagugggacaagagccgcugcuauuuggaagaa
guuucgagaaauauugcguauggccugaaccggacuccaaccauggaggaaaucacagcuguggccguggagucuggag
cccacgauuucaucucugguuccccucagggcuaugacaggaggugagacgugggaaccagcgucagggaggucagc
gacaggcagugggccuuggcccgagccuugaucccggaagccacuccugcuuauguuggaugaggccaccagugcccuggaugc
uggcaaccagcuacggguccagcggcuccuguaugagagcccaagcgggcuuucucggacgguucuucuuaucacccagcag
cucagccuggcagagcaggccaccacauccucuuuucagagaaggcucugucggcgagcagggcaccaccugcagcuca
ugaagagaggagggugcuaccgggccaugguagaggcucuucgcggccucugcagacuga 131  L32752    gaauuccggggccgcucucuccggcaggaucgccgcgauggccgcccagggagagccgca
             gguccaguucaaggucguccuggugggcgacggcggcaccggaaagacgacauucaugaa
             gcgccacuugaccgagaguuugagaggaguaugaugcgcccugggcguggagggca
             cacauuagucuuccauaccaacagaggaccuaucaaguucaaugugugggacacagccgg
             ucaggagaaguucgggggggcucgcgaugcuacuacaucaagcccagugugccauuau
             aauguuugacgacaucagagauucauuacaagaauugccuagcuggcauaagaucu
             agucgugugugugaaaacauccccauuguaaaguguguuaaaga
             caugaaagugaaggcaaaaccuauucucuuccaccgaaagaagaauacucaguacuauga
             cauuucugccagaagucacuacaacuuugaaaagccuuucucuggcuugccagaaagcu
             cauuggagaucacuaccuggaguucguugccaugccucucuugcccaccugagguagu
             cauggacccagcuuuggcagcacaguacgagcaugauuuagagguugcucagacgacugc
             ucucccagaugaggaagaugaccugugagaaagugaagcuggagcccugcgucagaaguc TABLE 3-continued RNA transcripts up-regulated during HF stem cell activation.

| SEQ ID No: | Access. # | Sequence |
|---|---|---|
| | | uauuuuaggcaacuguccugugaugccagccagcggugcagugugugugccaccuuauuu<br>agcuaaaggagaucgugcaauucauugggaugcugaaggagaugaaugggcuucggagug<br>aauguggcaguuaaaauacaccuucauuuuuuuggacuugcguauuuagccccuggaac<br>agaguuguucuggauuucaaagauaagacugcuaccguagcaucacaauagucaguggug<br>accggaauuc |
| 132 | AI840013 | uuuuuuuuuuuuuuuuugauuuaugaaaaguuuuauuuaucaguacugugaagaauucuc<br>aucauaauugcuacguuaaucaaggaaaaggcacagagaagcaugugucguuugagucccu<br>cgauacuggaccucccagcccaugcucccuaugaggagucuagcugcugugguggucuuc<br>acagcuuugguuuucuggagacgaagcucaugauugcguucaugcacuccucugacagcc<br>accuugcuugcagaguagugcacucuucagcguugacugcguagagcuuuucuuucucau<br>uuuuucugauuaacucuuuggaaauucucauuggguuuggcgggagcuucgcauau |
| 133 | AB020424 | ucgggaaucgauugagagaccgcgaaccuguaaacggaugauaccgagucgggcaggcgu<br>uaugccagcccaacucgggaccucgcaucauguccgcggcuaccuuagaguguuucggga<br>augauuugcgguggaugaacgaaaccccgguacguccugugccaaggagcauaugucagg<br>acggacgcucguuaaugccucagugguggggcaacguucgcucucuaucuauacgacucu<br>cgacaauggauaucucggcucucgcaucgaugaagaacguagcgaaaugcgauacuuggu<br>gugaauugcagaauccugugaaccaucgagucuuugaacgcaaguugcgcccgaggccuu<br>ucgguugagggcacgccugccugggcgucacgccuuguuuugcucugugcccgugcucuu<br>ucgggggcggucauggaugcggagauuggcccuccgugccucgugugcggcgggcuuaag<br>cgcggggugucggcgucgggaagggcacgacgagugguggacggagcaccagcaggaugu<br>uguggucccccgucaccuuaaggggcucaagagacccggacuaggcgagccgcgcuucgu<br>aagaggagggcgagcugucucgcaau |
| 134 | AI848453 | uuuuuuuuuuuuuuuuugaaguugcugccccuuuauuggugacccgggcaaguuuaagga<br>gaacaacauuaaagcacacaaaguguauccaugucaccagcucaaccaggaggagugagg<br>gucacggcaggguucucccaugguguaagaaaucaacgcaauuucaucacaccccguuac<br>uuuccaaguuaacgaaccgauaagaaaagauucucccuuaaacugacaaguacaauguac<br>auguacaugauuuuggaauaauuuaauacuuuaaccucaagauacaacuauauucuaaga<br>ccauuauuuuaaaggaacggauccuuacaaaccaaaauaacccauauagcacgagguug<br>guuuagccuuucuucuucuuucaacaaacgugcaccacauguuucaguagcaaggccgau<br>gccauggauaugagagcugugauuugcagggaccaaccacaucuagaaccggggaggcca<br>aucanacgguggguu |
| 135 | AU040563 | cccuuggaggauaguuuuauugacaagucgaguuagguuuuagaguaaacuuuuaucacc<br>ccagucaggccccuucccaggggaggcucgcugguagcucagauggccuugguggugggc<br>agauuguuguaguugucuuccuggcccuccagcaggcuucgggagguggcuaucuccugc<br>uccagccuggacuugauguccaguagcugcuuauacuccggguucuggcgcucuaugugc<br>ggcacgcaggugcngcg |
| 136 | X89749 | Sequence below. |

ggacugacuccuugggcagauugccucuccuccuucucaugccagaggcugcugaugaggaaagguccaggggacugucca
ugcugucuucauccucagagucacugccugaugcugcaacaagacccuucuuguuuagcaauagugguuggaacacucucu
uguaaguuaccggagcacuaguauaggaggaggaucaucgacuacccucccgccacuccacggcugcuggcuccuagaaacc
ccagcuucaccucucacugggacucgaguuccagaaugaaaagcaagaagggucuuguugcagcaucaggcagugacucuga
ggaugaagacagcauggacaguccccuggaccuuuccucaucagcagccucuggcaugagaaggaggagaggcaaucugccc
aaggagucaguccagauucugcgagacuggcuguaugaacacagauacaacgccuaucccucagagcaagagaaagcacugc
ugucccagcagacacaccuguccacacuacaggucuguaacugguucaucaacgcccgccgcaggcuccuuccugacaugcu
gagaaaggauggcaaagauccaaaucaguucacgauuucccgccguggggccaagauuucagaagcuagcucuauugaagcu
gcaaugggguaucaaaaacuucaugccaacucuagaagagagcccauuucauuccugcguaguuggacccaacccaacccuag
ggagaccagugucucccaaaccucccuccccaggauccauuuuggcucgcccgucagugaucugccauaccacugugacugc
auugaaggaugggccuuucucucucugucagccgauuggugugggacagaguacagauguaccgcaaauagcacccagcaac
uuuacagacaccucucucguguacccagaggacacuugcaaaucuggacccaguccaaacccucagagugguguuuucaaca
cucucccccuacuccaccagaccucaaccaggauuuuaguggauuccagcuucuaguggauguugcacucaaacgagcggc
agagauggagcuucaggccaaacucacagcuuaaccguuuuuucaaacaaaacaguucuccaaaauacgguccugauugccg
ggggugauggcaagagaugcauuauuuuauauauuuuuuc

| SEQ ID No: | Access. # | Sequence |
|---|---|---|
| 137 | AW125390 | uuuuuuuuuuuuuuuuugguggguuaucaagugcacuuuauugaauccacuguggauagau<br>aaaugaguguuacaccugcguguagggaggggcaaggagggacgcagcugcggaggguga<br>agcacuucaggaccggaagucggaauccucuauuaagugugaagguuuugagcguuaaga<br>acaaugaugaugacacuaacaauggugauaacaaccaucaggaugcugaggaccaaggug<br>cugauguucaggcacuuagcaguggaggcguaggccugggcuccagucacaucacccacc<br>aucuuccgaucccuagacuucacggaguaggcauaggcuaugaagcccaggcagcagaag<br>uucaugaagaguguauugaacagggaccagaccacauggucaggcaccgacaccucucug<br>ggcauguugaucacaguaguucugacagaagccga |
| 138 | X05862 | Sequence below. |

aagcuucaggauacagugcacacucguaaauaaaaacuacaggcugcugcgaauuauauuucaacugaccggagaggcaaag
ccugacuguccauuaacccuuaacuuccaaacgcaaacugcuuacugcaucuuuggcauuuuaccuuaugccuuguuagg
uccaaggcaagagaagcgucaucaauaaccacgcaugugcaacagcuuuuccagaggaaaggugugggugggcucuuaaaaga
gccuuugaguuaggagugugaguuaaacgagcucacuuggagcugguguacuuggugacugccuuggugcccuccgacacc
gcgugcuuggccagcuccccgggcagcagcaggcgcacggccgucuggaucucccgggacgugauggucgagcgcuuguug
uaaugcgccaggcgggaagccucgcucgcgaugcgcucgaagaugucguucacgaacgaguucaugaugcccauggccuug
gaggagaugccggugucggggugcacuugcuucagcaccuuguacacguacaccgaguagcucuccuugcggcugcgcuug TABLE 3-continued RNA transcripts up-regulated during HF stem cell activation.

| SEQ ID No: | Access. # | Sequence |
| --- | --- | --- |
| | | cgcuucuugccgucuucuucugggccuuggugacggccuucuuggagcccuucuucggggcgggagcggacuuggcggg<br>cucaggcauacugagaggaugaagugaacuaaguugaaaaaggauaaacuaaaaguuaaugacuguucuggcugcaauuuuaa<br>acaaacuuacggcuauggcaaccugaaucaccauacgucauguacuaacaguccaaucaaaacaagggauuuucaaaccaggg<br>cgccauugguaaccaauguguaaccaaugaaaucucuccguuuucgcguccagccuugacuauauauacuaugcguauacgu<br>uuuugcuucuuacugcgguggguuaucuacagcugaguuaugucuggacguggcaagcaaggacguggcaagcaaggaggca<br>aggcccgcgccaaggccaagacgcgcuccucccgggccggccugcaguucccguggccgcgugcaccggcugcuccgcaa<br>gggcaacuacucggagcgcgugggcgccggcgccccgguguaccuggcggccgugcuggaguaccugacggccgagauccu<br>ggagcuggcgggcaacgcggcccgcgacaacaagaagacgcgcaucaucccgcgccaccugcagcuggccauccgcaacgacg<br>aggagcucaacaagcugcugggccgcgugaccaucgcgcagggcggcguccugcccaacauccaggccgugcugcugcccaa<br>gaagaccgagagccaccacaaggccaaggggaagugaaaccaaacauuacgaaucaccaaggcucuuuucagagccacucacu<br>uucucaaagagaccuaacacuacugggauagugcauuguggggaaaaucgugugauuaaccuucuccucuauuuucccugcuug<br>ugguuaguucaaccccuaagccuuaggcuaagaguauauugguuuuuggaaggcaggcacccaaccucggaccuaguacaua<br>aaacagacacaucuugaacuccaggccagccuacucugcaggacgaguuccaggacagaccggacugcacaaagaauugucuu<br>gaaauguuccuuuaucagcacauaugcugauaaacaacuaaucacuguacaaucaauccucacuugaauccuguuuaugugg<br>caugauugacaaguccugccauuuggcaaagucaaaaucagcaaaggauguuaaagcauuugguguaucacagcuaaaac |
| 139 | AW046181 | uuuuuuuuuuuuuuuuaugcaaauaguuuucaagauuuuauugcaaaccaaaauugguuua<br>ucgcacacaaaaaaaguuguguguuaaggaggaggaauuguacaggauuauaacccaugu<br>uaauuacaguacauuaaaaugaugguuuacaaauaagccuguaaguuuaaaauaucuagug<br>uuauaacccaauguacagacuuccuuuacacgauacauacaauaaucaggaaugcaaaag<br>aauaugaacaaagggaaaaaaacauaaauaaugcccguuuuauaggugacauuuuaaac<br>aauugaaaacaccaaccggcuuugacugacaacuggggcauugguccauaaaaacccuuu<br>cuaaaaaauagaaauau |
| 140 | U10118 | Sequence below. |
| | | gaggcugcucaagagcugcgguugggucaccgcuucauguuucucugccgauucuggggaaagauggcaacgaaugaugcu<br>guucugaagaggcuggagcagaaggggugcagaggcggaucagaucaucgaauaucucaagcagcagguugcucuucuuaag<br>gagaaagcaauuuugcaggcaacaaugagagaagaaaagaaacuucgaguugaaaaugcuaaacugaaaaaagaaauagaaga<br>gcuaaagcaagagcugauucuggcagaaauucauaacggaguggagcaagugcguguucgauugaguacuccacugcagacg<br>aacuguacugcuucugaaagugugggugcagucucccaucaguagcaaccaccgccucuccugcuacaaaagagcagaucaaag<br>cgggagaagaaaagaaggugaaagagaagacugaaaagaaaggagagaaaaaggagaagcagcagucggcagcagcaaguacu<br>gacuccaagccuaucgacgcaucgcgucuggaucuucgaauugguuguauuguuacugccaagaagcacccugaugcagau<br>ucacuguauguggaggaaguagaugugggagaagcagccccgcgcacggucgucagcgggcuggugaaucauguuccucua<br>gaacagaugcaaaaucguauggugguuuuacucuguaaucugaagccugcaaagaugcggggaguucugucucaagccaug<br>gugaugugugccaguucaccagagaaaguggagauucuggccccucccaacgggucc guuccuggggacagaauuacuuuu<br>gaugcuuuuccuggagagccugacaaggagcuaaacccuaagaagaagaucugggagcagauccagccugaccugcacacca<br>augcugagugugugccacauacaaaggagcucccuuugaggugaaggggaagggaguuugcagagcccaaaccauggccaa<br>uaguggaauuaaauaagugcucuguaacugaaagacauuggcgaaaacuuaauaacaauaaagagaagugugguuuaucacuu<br>acauau |
| 141 | AW212775 | ggccuuguuuuugguuugcaauaaagaguauuucuuuaaaaggcacauuuuguuaaauag<br>gcaguuccccuccugccucuuccuuuguagcaguguacugcauccuagaaacauuuagca<br>aagcagcccuuagccuccccgacccccuuucccucccucccagca |
| 142 | AI846302 | uuuuuuuuuuuuuuuuuaaacaaugacgccguuuauuuaaaauguuuacucccagaaaua<br>uagauauaaaaaaaaaaauaagacaauuaacagcacuaaaccaggcaccuucaaccgaau<br>cccaccauccucguuaacucccuuccuguuacccuuuguagaugaccagaagauuucagg<br>agccccuggacagccagagugguuccugcccagggcuucccgccuuccuccuguccuaga<br>gcuucccguggggaaagcuuggguggagaauuuuagccuaaagggagggggcuguggccggg<br>cacuuugcgcucauccacugcagg |
| 143 | M22998 | Sequence below. |
| | | acaggguacaguugugcgucagggcguggaggucuggcgggagacgcauaguuacagcgcguccguucuccgucucgcagc<br>cggcacagcuagagcuucgagcgcagcgcggccauggaucccagcagcaagaaggugacgggccgccucauguuggcugugg<br>gaggagcagugcucggaucacugcaguucggcuauaacacugguguccaucaacgcccccagaagguuauugaggaguucua<br>caaucaaacauggaaccaccgcuacggagagcccaucccauccaccacacucaccacgcuuuggucucucuccguggccaucu<br>ucucugucgggggcaugauugguuccuucucugucggccucuuuguuaaucgcuuuggcaggcggaacuccaugcugaug<br>augaaccuguuggccuuuguggcugcugugcuuaugggcuucuccaaacugggcaaguccuuugagaugcugauccuggg<br>ccgcuucaucaucgguguguacugcggccugacuacuggcuuugugcccauguaugugggagaggugucaccuacagcucu<br>acguggagcccuaggcacacugcaccagcugggaaucgucguuggcauccuuauugcccagguguuuggcuuagacuccau<br>caugggcaaugcagacuuguggccucugcugcucagugucaucuucaucccagcccugcuacaguguauccuguugcccuu<br>cugccccgagagcccccgcuuccugcucaucaaucguaacgaggagaaccgggccaagagugugcugaagaagcuucgaggg<br>acagccgaugugacccgagaccugcaggagaugaaagaagggucggcagaugaugcgggagaagaaggucaccaucuugg<br>agcuguuccgcucacccgccuaccgccagcccauccucaucgcuguggugcugcagcugucccagcagcugucggguaucaa<br>ugcuguguucuacuacucaacgagcaucuucgagaaggcaggugugcagcagccuguguacgccaccaucggcuccgguauc<br>gucaacacggccuucacugugguguucgcuguuuguuguagagcgagcuggacgacggacccugcaccucauuggccuggcu<br>ggcauggcaggcugugcugugcucaugaccaucgcccuggcccuugcuggaacggcugccuuggauguccuaucugagcauc<br>guggccaucuuuggcuuuguggccuucuuugaaguaggcccugguccuauuccaugguucauuguggccgagcuguucag<br>ccagggggcccguccugcugcuauugcuguggcuggcuucuccaacuggaccucaaacuucauuguggggcaugugcuucca<br>guauguggagcaacugugcggccccuacgucuucaucaucuucacggugcuccucgugcucuucuucaucuucaccuacuu<br>caaaguccccugagaccaaaggccgaaccuucgaugagaucgcuuccggcuuccggcagggggggugccagccaaagugacaag<br>acacccgaggagcucuuccacccucugggggcggacucccaagugugaggagccccacacccagcccggccugcucccugcag<br>cccaaggaucucucuggagcacaggcagcuagaugagaccucuuccgaaccgacagaucucgggcaagccgggccugggcgc<br>cuuuccucagccagcagugaaguccaggaggauauucaggacuuugauggcuccagaauuuuuaaugaaagcaagacugcu<br>gcucagaucuauucagauaagcagcagguuuuauaauuuuuuuauuacugauuuuguuauuuuuuuuuuuaucagccac |

TABLE 3-continued

RNA transcripts up-requlated during HF stem cell activation.

SEQ ID No: | Access. # | Sequence ucuccuaucuccacacuguagucuucaccuugauuggcccagugccugagggugggggaccacgcccuguccagacacuugcc
uucuuugccaagcuaaucuguagggcuggaccuauggccaaggacacacuaauaccgaacucugagcuaggaggcuuuacgc
uggaggcgguagcugccacccacuuccgcaggccuggaccucggcaccauaggguccggacuccauuuuaggauucgccca
uuccugucucuuccuacccaaccacucaauuaucuuuccuugccugagaccaguuggaagcacuggagugcagggaggaga
gggaagggccaggcugggcugccagguucuagucuccugugcacugagggccacacaaacaccaugagaaggaccucggagg
cugagaacuuaacugcugaagacacggacacuccugcccugcuguguauagauggaagauauuuauauauuuuuugguugu
caauauuaaauacagacacuaaguuauaguauaucuggacaaacccacuuguaaauacaccaacaaacuccuguaacuuuacc
uaagcagauauaaau
ggcugguuuuuag 144 X64837 Sequence below.
gcuuucuaaacuagcaagcaucgugugggguccuucaggagugggagugcagacagaccugacagcguccgcuaagcgacacu
gacuguacuuccacuccugaaggacccacacgaugcuuucuaaacuagcaagucugcagaccauugcugcucugcgccgagg
aguccacaccucagucgccucugccacgucuguugccacaaagaagacagagcaaggcccaccauccuccgaguacauuuuug
aacgggaaucuaaauauggugcacacaauuaccauccuuugccuguagcccuggagagaggaaaaggcauuuauauguggga
uguggaaggcaggcaguacuucgauuuccugagugcuuauggugcugucagccaaggacacugccacccaaagaucauagau
gccaugaagagucagguggacaagcugacauuaacaucucgggcuuucuauaacaauguccuuggugaauacgaggaguaca
ucaccaagcuuuucaacuacaacaaaguucucccuaugaauacaggaguggaggcuggagagacugcauguaagcucgcucg
ucguuggggcuacaccgugaaaggcauccagaaauacaaagcaaagauuguuuuugcugaugggaacuuuuggggucgaac
acuaucugcaaucuccaguuccacagauccgaccaguuaugauggcuuuggacccuucaugccaggcuuugaaaccauccca
uauaacgaucugcccgcacuggagcgugcucuucaggauccaaauguugcugccuucaugguggagcccauccagggugaa
gcaggcguuaucguuccggauccaggauaccugacaggaguucgggaacucugcaccaggcaccagguccuguuuauugcu
gaugaaauacagacaggauuggccagaacugguagauggcuggcuguggaucaugagaaugucagaccugauaugguucuu
cuugggaaggcccuuucuggcgguuuauacccugugucugcagugcugugugacgaugagauaaugcugaccauuaaacca
ggcgagcacggcuccacauacggcggaaacccacuaggcugccgaauugccauugcggcucuugagguuuagaagaggaga
aucuugcugagaaugcagacaagaugggcgcuauccugaggaaggagcucaugaagcugcccucugacguugugaccucag
ugagagggaaaggguugcuaaaugccauugucaucagagaaaccaaagacugugaugcuuggaaggugugccugcgacuuc
gagauaacgggcuucuggccaagccaacccacggugauaucaucaggcuugcccucccccuugugaucaaggaggaugagau
ccgggaguccguggagaucaucaacaagacuaucuuguccuucugagaguaggaacucuggggagccaucuucagacagggc
ucuugugaaacucugcuugcaguggccagagccugucuccugaaaggcauauauuucaguugaugcauaauagagugacac
cuaggaaccugcagguggcugcgugacagaaaagugagagcgagaggcgaggcgucucuuuguugagguuugacugugugg
gaacuuucuaaggagaaacggacccaucugcguacagccugcagauggaggccugcagucauuuacgugcgucuuuacaguu
uccuugcugaugugaaugguuuguauuuagaaguuauuucugagauacuacagaacaguuaaaucauuauaaucaaugaau
guuaaguugauugaagguuaagcauauguaaaauacuaguuuaaaguaaacuuuucauuggccaacaccagaauguauuau
auagauucugagaauucauuacuaaauuacacuuugcuugauugcaauuuguaaaacauuuauuuucaguauuucuuugaa
uaaagcuuaauguuucuuuuuacgccaacagaguauuuuguauuuccauuuugguaauaaucaguguauuauuucauccu
gaugacuggcauuucaucaccuauugagaucacugggugugguuucaggccuuuuauucuaaauaaagcuaugaccaguuuc
ugucugu 145 AI843119 uuuuuuuuuuuucuuuuccgacgcccacaagaggaauaagagauuuaaugauggaaagua
uggggaaaucacaguuuucagacaugaguaaucaaaaacuugacauuuuucuugauaucc
aaaucuagaugucuguaucaaaccagaggugauggccuuggggauggcagugaagacugu
uaggaccauuagaucagau 146 AI837786 uuuuuuuuuuuuuuuuuacaguuuaaaacaauacacagcuuucucgggcugaagcaauu
gcaagaacguauugguauugguauauuacagcuacauacaagguuuaugaauagcaaugg
agaaaaauaaguuauuuaaauauugacuucauaaagagaaagugcaauguuguuaguugu
cauaucacuugcuugacaguuuguggggguuucuucccuaucaauuuuaacaaucaagaua
acauggacucaagacagaauuuuucgggaaccucacucaguccucacacagcagugacuu
gggaaucuacguguguuccaccgcaguugugaaacacacuacuccguguccaggacucau
uucucagagaagaaucaauucgaguuccauccacaccuggggucgggacaca 147 U41465 Sequence below.
ccgggcucgaauucucuagacucgaguuuagagaauucgagcucucccaguuuaaagcaaaauuuggacugugaagcaa
ggcacugggcaaacacaacauggccuccccggcugacagcuguauccaguuuacccggcacgcuagugauguucuucucaac
cuuaaucgccuccggagucgggacaucuugacggacguugucaucguggugagccgugagcaguuuagagcccauaagaca
gugcucauggccugcagcggccuguucuacaguaucuucacugaccaguugaaaugcaaccuuaguguaaucaaucuagauc
cugaaaucagcccugagggguuuugcauccuccuggacuucauguacacaucuaggcucaaccugagggaaggcaauaucau
ggcggugaugaccacagccauguaccugcagauggagcauguugucgacacaugcaggaaguucaucaaggccagugaagca
gaaauggccccugcacuuaaaccuccccgugaagaguuccugaacagccggaugcugaugccccaugacaucauggccuacc
gaggucgugaggucguggagaacaauaugccacugagaaauacucccgggugugagagcagagcuuuugcuccuccucugu
acaguggccugucaacaccaccagccucuuaucccauguacagccaucucccgcucagcaccuuccucuucucugaugagga
gcuccgagaugccccccgaaugccuguggccaacccuuuucccaaggagcgugcccucccccugcgacagugccaggcaaguc
ccuaaugaguauagcaggccagccauggagguguccccccaguuugugucacagcaacaucuacucgcccaaggaggcagucc
cagaggaggcucggagugacauacacuacagugugccugagggccccaagccugcugucccuucugcucggaaugcuccaua
cuuccccugugacaaagccagcaaagaagaagagagaccuucuucggaggaugagauugcccugcauuucgagccccccaau
gcacccuugaaccggaagggucugguuaguccccagaguccccagaaauccgacugccagcccaacucacccacagaguccug
cagcagcaagaacgccugcauccuucaggccucuggcucuccgccagccaagagccccacugacccgaaagccugcaacugga
agaaguauaaguucaucguucucaacagccucaaucagaaugccaaacccgagggcucugagcaggcagagcuggucgccu
cucccucgagccuacccugcaccgcccgcuugccagccgccuauggagcccgcgaaccuugaucuccaguccccgaccaagc
ucagugccagugggggaggacucuaccaucccccaagccagccggcucaauaaucucgugaacaggucccugggaggcucccc
ccgaagcagcagugagagucacucaccacucuacaugcacccccccaaagugcacauccugcggcucucaguccccacagcaua
cagagaugugccuccauacugcugggcccacguucccggaggagaugggggaaacccagucagaguauucggauucuagcu
gugagaaugggaccuucuucugcaacgaaugugacugccguuucucugaggaggccucgcucaagaggcacacgcugcagac
gcacagugacaaaccauacaaaugugaucgcugccaggccuccuuccgcuacaagggcaaccucgccagccacaagacugucc TABLE 3-continued RNA transcripts up-regulated during HF stem cell activation.

| SEQ ID No: | Access. # | Sequence |
| --- | --- | --- |

acacgggugagaaacccuaucgcuguaacauuuguggagcgcaguucaaucggccagccaaccugaagacccacacucgaau
ucacucuggagaaaagcccuacaaaugugaaaccugugggggccagguuuguucagguggcccaccuccgugcccacgugcuc
auccacacuggagagaagccguaccccugugaaaucuguggcacucgcuuccggcaccuucagacucugaagagccaucugc
gcauccacacaggagagaaaccuuaccauugugagaaguguaaccugcacuuucgucacaaaagccaacugcgacuucauuu
gcgccagaagcacggcgccaucaccaacaccaaggugcaauaccgcgugucggccgcugaccugccuccggagcuccccaaag
ccugcugaaugaagcauggaguguuccucgcccuuuccucuccagccccuucucagaaucuacccaaaggaugcuguaacac
uuuauacaaaggucaucccaugauguagugccucucucauccacuagugcaaaucauaguuggggugggggguggg 148 U70494 ucgcgguccgacggaggagugggcgcugggaucucgcugagcguccgccuggccucgucu
cuuccucgcucgucggagcuucagcacgguccgagauggcuggcgguaaggcuggaaagg
acuccggaaaggccaagacaaaggcgguuucccgcucgcagcgagccggcuugcaguucc
cugugggccguauucaucgacaccugaaaucuaggacaaccagccacggacgugugggcg
cgaccgccgcuguguacagcgcagccauccuggaguaccucaccgcagagguacuugagu
uggcaggaaaugcgucaaaagacuuaaagguaaagcguaucaccccucgucacuugcagc
uugcuauacguggagaugaagaauuggauucucugaucaaagcuaccauugcuggugug
gugucaucccacacauccacaaaucgcugaucgggaagaaaggacaacagaagacuguuu
aaggaugccuggauuccuuauuaucucaggacucuaaauauuccuaacagcuguccagug
uuggugauuccaguggacuguaucucugugaaaaacacaauuuugccuuuuuguaauucu
auuugagcaaguuggaggcuuaauuagccuuccaaccaaccaaauuucugcauucgaguc
uuaaccauauuuaaguguuacuguggcuucaaagaagcuauugauucugaaguagugggu
uuugauugaguugacuguuuuuaaaaaacuguuuggauuuuaauugugaugcagaaguua
uaguaacaagcauuugguuuuguacagacauuguuuccacucugguggauaagcucaaua
aaggucauaucccaaacuagcuuuaaacuugcuuaauaaucgggucuuaccuuagaucuc
acucagcaacaaguacauucucugcuuacuaauuaaacagugcaucuguagucauaaaaa
aaaaaaaaaaaaaaaaaaaaaaaaaaaaa 149 D17666 Sequence below.
caccaccgugcacgcagcuccgggcccgugggguguugguucuugcccucguaaccccucuguccagccaccaugauaagc
gccagcagagccgcggccgcgcgucucgugggcaccgcugcgucccggagccccgcagccgcccguccccaggugagaagcu
gccaugccuuccggugggggcuccaggcccggacucgagugaggcaggccuugccuucgggucagacucuaggaaaaauccg
gagcgaagggauguaacggaccuucugugggcauuguuggccuucuugcagggcuuuagcuucgaacugugcugagucaca
auccuuggcguuccuaagucuuuaccccgcuaauugagacgucugucccccucuaaccugugcgcuuugaaugugccugg
acuuaggcaguggacguaguuuacuggaaannnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnuuuuacauacuaaggacuaaagcuug
cauguguuccucagaauaugaaaagcccaaguucuuguguaguugauggcugaugcaacuuuuuucccccaggauggcug
gaauggccuuagccaugaggcuuuuagauuuguuucaagaagagauuaugcguaaguacaaccucaguuucucugagaaaa
aaaaaaaacacuuauugaaccucaaagcuuggauggguugggugcguuauacauuuguacuuguaguuuauucaauaugcc
acugguaacaccaacauaaaacacaguucuucguauuggagaccacuguucagaugaccauggaauuucauuucuuacagau
cagaagcaaucaagggugcagugguugguauugauuuggguacuacuaacuccugugugcuguuauggagggcaaacaag
caaaggugagcaugauuggaaaccugaggucacuuagauacccagucuggcauuaaguacauaggaaugcugagucggagcc
cagguuagugguggggcacuuuaauccuaguaaaggcagagggaucucugaguucaggaccagccuagaguacaaagugagn
nnnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnacuuuaaucagugucuuugggaauuuagguccuggagaaugcugaaggugccaga
acuaccccuucugugguugccuuuacagcagauggagaacgacuuguugguaugccagcaaaacggcaagcugucaccaauc
caaacaauaccuucuaugcuacuaagcgucuuauuggacgacgauaugaugacccugaaguacagaaagacacgugaguaau
aggaaaaucaguccagaagacuggugcuuugaucaaaguucuguggauaccuugaguucuguggaucaccuuggaucacuu
uuucauuauuucugcuugggaagaaaucacaccaccaucagaggcauauagguuuuuuuuuuguuauuucuuuguuguug
uuguuuuccuauuuauuuguuuguuuguuuggggggggguuucuuuguguauuuuccuggaacucauucuguagaccag
gcuggnnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnucaugugauauaugaugaacuuagagugguuaaguuucacagggauaguu
uacuuacauaaucuuucugucuuuaaguaagaauguuccuuuuaaaauuguccgugccuccaauggugaugcuugguuga
ggcucauggaaaacucuauucuccaagucagauuggagcauuuguguugaugaagaugaaagagacugcagguaagugau
uuauuucacauuuaggaaauuggaaugugcuguuuauuucucugcauuaauacugauuaacuucauauucuguagauaau
ggagucugaagcuunnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnngaauucaugcuccuccugcugccuccugggugcuaaguugca
aggugauagcucagguacucacucuagugucuuucuugggggugcucuuuuccaaggccucucuacauauuaagccacaaag
gagucuguugccccucaagaggaugagauguggaauauuaggcuacaguuuuguugccuuuuuuuuauuuuccuaacaug
guaccacaauugaauuuuauucuuuguuucccagaaaauuacuugggccacacagcaaaaaaugcugugaucacagucccug
cuuauuucaaugauucacagcgacagguaaaauuagaucucuuguuugcugggaguggaggugggguaccugaguuaaagg
auggaaagauagauuuauuucuacuuucucuaggccacuaaggaugcuggccagauaucugggcuaaaugugcuucgagug
aucaaugagccuacagcugcugcucuagcuuacggucuggacaaaucugaagauaaaguguaaguuggucagaugacguagc
auuaccugcauuuacagggguuguguguguguguguguguguaauuuuacuacaauuugugugggucc gugu guugu
gguacauuuguacauuuguacauggcauggauauggaugucaaagauunnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnnnnnnnaaaccagu
aguuggugug uuacuaauuuuacuuguuucuguaugacaugcuuauaugauacguuaacaggcaugccacuuagguugau
aacuacauucaguuauuaaguauuucaggaaauaucauaguuaauaauuaaacuuuuggucuuuuaauucguuccuuuguu
uuguuccuuggaacuuaacuuacuuauuuauuuuuuagcauugcuguguaugauuuaggugguggaaccuuugacauuuc
uauccuggaaauucagaaaggaguguuugaggugaaaucuaccaaugggacacuuucuuaggaggggaagacuuugacca
agcuuuguugcggcacauugucaaggaguucaagagagagguuaguuaccacugcuuagucaccacugguuaagguguagg
cguugguuguugagaauuuuuguuuguuugcauugcuuuuagcuuuguuaauagcuuuuuuauacuaagguaacuaac
uauacuucagauucaugguaaacuaaaccaguuuaguuauauaaucuuagauugggaacaaaagaccaagugacaguguua
uaguagggagaagnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnacuacucucucgcagucuauauaugucuccuaauccuauuuau
agacagggguugauuugaccaaagacaacauggcgcuucagaggguucgggaagcugcugagaaggcuaaaugugaacuuu
ccucaucugugcaggugagggauggaaaaaucccaguacugagcauauuugaauaguguauucuaauuuaccuaaugucag TABLE 3-continued RNA transcripts up-regulated during HF stem cell activation.

| SEQ ID No: | Access. # | Sequence |
|---|---|---|

uguagcucuuuacaguuuucuguuggcugaaaacuuggggcaugagcaaaggaacaacuugaugaucaguucuuuucauuu
gaaugaaugaaguagauuuauggaugugugguaucuuuugccugcaugugugucuguacuacauuugugcuugguuucugu
ggcggccagaagaggguaucagaacugacaugucaguguuggggannnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnnnnnncacacugaguc
uaaauucugaucaugucuuucagucguguuauguuacuuugagugaguaucaaagaucacgucucccaucugacgugugu
ccugugcagacugacaucaacuugccauaccuuaccauggaugcuucuggaccaaagcauuugaauaugaagcugacucgag
cucaguuugaaggcauugucacagaucuaaucaagagaacuauugcuccgugucagaaagcuaugcaggaugcagaagucag
caagagugacauaggagaagugauucugguugguggcaugacaaggaugcccaagguauggacucaugguauuucuccuag
aggaaaaaaauaacaaugcauucuugaggcaaauggcuuguguuguguguggaaacaaaugugauccauucuucuaguguu
cuuuaaagagugguggagaccagacucaccaaaaagugcuuuuagucgccugugauggcucauguaggaggauggccuugag
uucugguaagaugcagcuacagaauucuaccuugcacacacacuuaaacccagucugguaaagagaaguuguuaagcuunn
nnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnnnnncagauguaaaauugauaauacuucuuccuaagauugggcgauuguguagaauaugaga
acuguauuuuauaaccccuugucaugugccuucuauuucaaaugauauccucugggaagcuagauaauuaaauucuucucu
cauuuaaguggacaguggaugagaugcucugaaguugucaaauacaaacaagucugcagucuuggauaugaaucucucuga
cuugcugucuggcaggcguauucuguuuggcuccaucagucgcccuggguguuggcuaacagguucuuucucccugaugc
uuagguucagcagacuguacaagaucuuuuuggcagagccccgaguaaagcuguuaauccugaugaggcuguagccaucgg
agcugccauccagggaggugugguuggcuggugacguuacagacgugcugcuccuggaugucacuccccucucucuggguau
ugagacucugggaggcgucuuuaccaaacuuauuaauaggaacaccacuauuccaaccaaaaagagccagguaagagccauu
cuuuuuuccugccuauuaacagucccaaguuguacaagugcuguuuacaaucacuuuaugaacucuuuaaaacuuuguuuc
uaagacuauacuaacuggacugggugnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnccuagguguuucuacugcugcugauggac
aaacucaaguagagauuaaagugugucaggggaacgagagauggcuggagacaacaaacuucuaggacaguucacuuuggu
aaguguuuugagucugaguaucaugcuuuggggucuauagcuugcaaagcuccaaacugcugacauuacaggcauauug
uguuauuuuuuaaaagaacguuauguacaugaguuaugaaacccaugauuuuaguuuuuuaccuaaagugcuuuguguu
uucagaauuugaaauuuucaaagccugggaaauguucagacucagaagcaaugcuaacucagaaguuaguuuuauccugau
uacucauuuuaaaaaacuuaauagcuacugguucuggucagcauugcuacaguagagaaguuuauuugcuguaaauucugg
gcacauauaaccaucaugguuauuaacuucuugaagcccagugauuucagaaagcacuaaaacuaccaccaucacuuaaaauc
ucaagguuuugaacauucagugaagauacuuguuuuaggaaacaagugguuaguuggccugauuuggaaaugagaauacau
gggccuuucaaaggagcucacucuggauauuuauuuuagauuggaauuccccagccccucguggagugccccagauugaa
guuacauuugacauugaugccaaugggauugugcacguuucugccaaagauaaaggcacuggucgugagcaacaga 150 X14897 Sequence below.

auaaauucuuauuuugacacucaccaaaauagucaccuggaaaacccgcuuuuugugacaaaguacagaaggcuuggucaca
uuuaaaucacugagaacuagagagaaauacuaucgcaaacuguaauagacauuacauccauaaaaguuuccccaguccuuau
uguaauauugcacagugcaauugcuacauggcaaacuaguguagcauagaagucaaagcaaaaacaaaccaaagaaaggagcc
acaagaguaaaacuguucaacaguuaauaguucaaacuaagccauugaaucuaucauugggaucguuaaaaugaaucuuccu
acaccuugcaguguaugauuuaacuuuuacagaacacaagccaaguuuaaaaucagcaguagagauauuaaaaugaaaaggu
uugcuaauagaguaacauuaaauacccugaaggaaaaaaaaccuaaauaucaaaauaacugauuaaaauucacuugcaaauua
gcacacgaauaugcaacuuggaaaucaugcaguguuuuauuuaagaaaacauaaaacaaaacuauuaaaauaguuuuagagg
ggguaaaauccagguccucugccaggaugcuaaaauuagacuucaggggaauuuugaagucuucaauuuugaaaccuauua
aaaagcccaugauuacaguuaauuaagagcagugcacgcaacagugacacgccuuuagagagcauuacuguguaugaacaug
uuggcugcuaccagccacagucaauuuaacaaggcugcucagucaugaacuuaauacagagagagcacgccuaggcagcaag
cacagcuugcugggccacuuuccucccugucgugacacaaucaauccguguacuugguguaucugaagcgcacgcugcaccg
cggcacugcccggcggguuucugggcggggagcgauccccgcgucgcccccgugaaaccgacagagccuggacuuucagga
gguacagcggcggucugaaggggaucugggaucuugcagagggaacuugcaucgaaacuugggcaguucuccgaaccggag
acuaagcuuccccgagcagcgcacuuuggagacguguccggucuacuccggacucgcaucucauuccacucggccauagccu
uggcuucccggcgaccucagcguggucacaggggccccccugugcccagggaaauguuucaagcuuucccggagacuacga
cuccggcucccgguguagcucaucacccuccgccgagucucaguaccugucuucgguggacuccuucggcaguccacccacc
gccgccgccucccaggagugcgccggucucggggaaaugcccggcuccuucgugccaacggucaccgcaaucacaaccagcca
ggaucuucaguggcucgugcaacccacccucaucucuuccauggcccagucccaggggcagccacuggccucccagccucca
gcuguugacccuuaugacaugccaggaaccagcuacucaaccccaggccugagugccuacagcacuggcggggcaagcggaa
gugguggccuucaaccagcacaaccaccaguggaccugugucugcccguccagccagagccaggccuagaagaccccgagaa
gagacacuuaccccagaagaagaagaaaagcgaaggguucgcagagagcggaacaagcuggcugcagcuaagugcaggaaccg
ucggagggagcugacagaucgacuucaggcggaaacugaucagcuugaagaggaaaaggcagagcuggagucggagaucgcc
gagcugcaaaaagagaaggaacgccuggaguuuguccugguggcccacaaaccgggcugcaagauccccuacgaagaggggc
cggggccaggcccgcuggccgaggugagagauuugccagggucaacauccgcuaaggaagacggcuucggcuggcugcugc
cgcccccuccaccaccccccccugcccuuccagagcagccgagacgcacccccccaaccugacggcuucucucuuuacacacagug
aaguucaaguccucggcgaccccuuccccguuguuagcccuucguacacuuccucguuuguccucaccugcccggaggucuc
cgcguucgccggcgcccaacgcaccagcggcagcgagcagccguccgacccgcugaacucgcccucccuucuugcucuguaaa
cucuuuagacaacaaaacaaacaaacccgcaaggaacaaggaggaggaagaugaggaggagaggggaggaagcaguccgggg
gugugugugugggacccuuugacucuucugucugaccaccugccgccucugccaucggacaugacggaaggaccuccuuugu
guuuugugcuccgucucugguuuucugugccccggcgagaccggagagcuggugacuuuggggacagggggugggggcggg
gauggacaccccuccugcauaucuuuguccuguuacuucaacccaacuucuggggauagauggcuggcuggguggguaggg
ugggggugcaacgcccaccuuuggcgucuugcgugaggcuggaggggaaaggguguc ugagugugggggugcagggugggguug
aggucgagcuggcaugcaccuccagagagacccaacgaggaaaugacagcaccguccuguccuucuuuccccccacccacccca
uccacccucaagggugcagggugaccaagauagcucuguuuugcucccucgggccuuagcugauuaacuuaacauuuccaag
agguuacaaccuccuccuggacgaauugagcccccgacugagggaagucgaugccccccuuugggagucugcuaaccccacuu
cccgcugauuccaaaaugugaaccccuaucugacugcucagucuuucccuccugggaaaacuggcucagguuggauuuuuu
uccucgucugcuacagagcccccucccaacucaggcccgcucccaccccugugcaguauuaugcuaugucccucucacccuca
cccccaccccaggcgcccuuggccguccucguugggccuuacugguuuugggcagcagggggcgcugcgacgcccaucuug
cuggagcgcuuuauacugugaaugagugggucggauugcugggugcgccggaugggauugaccccccagcccuccaaaacuuu
cccugggccuccccuucuuccacuugcuucccucccucccccuugacagggaguuagacucgaaaggaugaccacgacgcaucc
cgguggccuucuugcucaggccccagacuuuuucucuuuaaguccuucgccuuccccagccuaggacgccaacuucucccca
cccugggagccccgcauccucucacagaggucgaggcaauuuucagagaaguuucagggcugaggcuuuggcuccccuauc TABLE 3-continued RNA transcripts up-regulated during HF stem cell activation.

| SEQ ID No: | Access. # | Sequence |
| --- | --- | --- |

cucgauauuugaauccccaaauauuuuggacuagcauacuuaagagggggcugaguucccacuaucccacuccauccaauu
ccuucagucccaaagacgaguucugucccuucccuccagcuuucaccucgugaaucccacgagucagauuucuauuuuuu
aauauuggggagaugggcccuaccgcccguccccgugcugcauggaacauuccauacccuguccugggcccuagguuccaa
accuaaucccaaaccccacccccagcuauuuaucccuuuccugguucccaaaaagcacuuauaucuauuauguauaaauaaau
auauuauauaugagugugcgugugugugcgugugcgugcgugcgugcgugcgugcgagcuuccuuguuuucaagugugc
uguggaguucaaaaucgcuucuggggauuugagucagacuuucuggcugucccuuuuugucaccuuuuuguuguugucuc
ggcuccucuggcuguuggagacagucccggccucucccuuuauccuuucucaagucugucucgcucagaccacuuccaacau
gucuccacucucaaugacucugaucuccggunugucuguuaauucuggauuugucggggacaugcaauuuuacuucuguaa
guaagugugacuggguggu agauuuuuuacaaucuauaucguugagaauuc 151 AJ006289 Sequence below.
caccugauucccggaggcccgagcccuuagucugggcgggguggcgcgggccggaaggacgccaucccggccugggccaugg
aggcucccgcaccgucccucacggaggaggauuugacugaagugaagaaggacgcuuuagagaauuuacguguuuaccugu
gugagaaaaucauagcugagagacauuuugaucaucuacgugcaaaaaaaauacuaaguagagaagacacugaagaaauuuc
uugccgaacuucaaguagaaaacgggcugggaaguuguuagacuacuuacaggagaaccccaggggccuggacacccuggug
gaauccauccgcagggagaaaacacagagcuuccugauucagaagauaacggaugaggugcuaaagcuucggaauauaaaac
uggagcaccucaaaggccugaagugcagcagcugugagcccuuugcagccggagccaccaacaaccucucuaggugcaauuc
cgaugagagcaaucucucugagaaacagagagcauccacugucauguaccacccggagggagaguccagcacggcucccuuc
uucucuauggcgucgucccugaacuugccaguccuggaaguuggcaggacugaaaacagcagcuucucuucagccacucuuc
cucgaccuggggacccuggggcucccccuuugcccccagaccuucgguuggaagagggggaaguuguggaaacucaagug
agauguuucuccccuuacggucacgggcucuuucacgccaaugauacaucaccgccuaguuguuuuacuagugaugcaaaau
gcugugaaggaggccaucuuucuauacaaaccacggugacaggucacucacauucgaugcgugccuuuaaaaucaguguaca
cauucucuguaaauaggauuuguuaggguaaagaagcgcucuggggcggcgugguguaaucaugguggucgugacuuuuc
cauaauguccuuucuuuuuuauuauuuuuagguguuugcguauuuugaacuuuucauaagauuaauuuuaucggaauauu
ucucaauuugagaaaacaacuuguggauugggaauaauguuuuagcacauuuaugcuacaaauuuucagucugauuguuu
uucccacugaucuggcaguauauuuuagcaguaagcuguugugugucaggaaagcuggacacgggaaagcugccgacacac
ucagcagugucccacuccuuaguucugagaagccgucggguucugaggagacaccugguggcacugagccuggugaccuca
gugggccaaaauuuguuuuauacucacccugccagcgugagugucuuacuuucacaggccuuguguccucagucuuaucuu
aaaggauguuaucuuggcagggcaucacuuguaauuaauggaugauacuuguaauugacuaaaguccucgcucugagccgu
uuguucuggcuccgagagcgcugacaugugaagcauggugagcagcgagggaacugacaggauguggccguggccagugug
gcuuuaguguuugcaucaggcagccaccagcuccauccguguucuuacugcuuuacaaaguuugacuaacuuuacacauuu
uaaaaaugcugauugucuucguuuaaauuauaauuuuaccuauuucuugacaucuaacuccuauuuauuucuauuauuuaa
aaauuaagaaaugaaaauuugcuauuaacaauaaaguuuuuuuaaugu 152 X12944 Sequence below.
ggggggggggggucagcgccgacguccccugccgccaccaugcccaaaagaaaggcugaaggggaugcuaaaggagacaaaa
ccaaggugaaggacgagccacagagaagaucugcaagguugucugcuaaaccugcuccuccaaagccagagcccaaaccuaaa
aaggccccugcgaagaagggagagaagguacccaaggggaagaaggggaaagcugacgccgggaaggaugcgaauaauccug
cagaaaauggagaugccaaaacagaccaggcacagaaagcugaaggugcuggagaugccaagugaugugugugcauuuuuga
uaacuguguacuucuggugacuguacaguuugaaauacuauuuuuuaucaaguuuuauaaaaaaugcagaauuucguuuuac
uuuuuuuuuuuuuuuaagcuauauuguuagcacacagaacacuucauuacuggguggggga aggaucaugugucaguaac
aaaaucucucccaagcuggauugaggacagaaaaccucuuucccugauaauuuuggaaggcuccuguuggcucccaggagag
agauccuggucuugaccuagguggccaccaaggcacaacaaugccuuguggucugggaaaacuauaaauucacuuuuauauc
cucuuccccuguacuaucaacauagacuuaauucccuuaaaaaccagagaccuguuggaaccuggcccccaaaauugguuu
cccaguccauugagugauggggacuuugcagugacuucauugaguguucucaaaagagcacugguuccuuuuauaaaagau
uguggaucuucagauugauaauucugccuaaaagucagggucggcuugugaaaaguuguuaaaacaacauccuuaaugaga
aaugucaacccucacucuaagcuacuuccccccuuuucaaagcauugaaugaagacuucauuggguuuuauaguggcuuucu
gauuuugguagucauaucagaagggaauuuggaaguucuuguauauuguugcauugucugcccauguccugccugaauacc
augauuguuuaugaaagaaucuuaauaaagcugguuacaguuaggcuggaaaa 153 AW061302 uuuuuuuuuuuuuuuuuggaaguccauaaguaguuuauugucuucaagacuacagugugg
auucccucucccagagaagggucuuucagaggcaggggacugucacccaggugcaggccgu
cuacuugucauuuucauacauggcuggauucuuccuuuucgacugcucaaacuccugguu
gccccauguguagaucagguagaccacuacaaacggcggcgccacgcgcaggaugcgcuc
gcgagugcggcgcaacacguuggggaugccuuugcugaaauagcuugggaaggcgcgcug
cucaaagggcgacaagcugua 154 U67328 Sequence below.
caugaagccagagauguggaagaugugucuagacugcaucaaugaacugauggauacguuggaugcacauuccaacaucucu
gucggagagaacauuuuggcagagagugagaacuuacacaacuuugaucaguucacuccguguacgacgcugcauccuaacu
uugguggagcgaauggaugaagaauuuaccaaaauaaugcaaaauacugauccucacucccaagaguauguggagcaccuga
aggaugaggcacaagugugugcaucauugagcgagugcagcgcuaccuggaggagaaagguaccacugaggagaucugccag
aucuacuuaaggcgcauccugcacacguacuacaaguuugacuacaaggcccaucagcggcacguuacuccuccugaaggau
ccucaaagucugagcaagaccaggcagaaaaugagggugaggacucagcugugcuaauggaaagacugugcaaguacaucua
ugccaaggaccguacagaccggauccguaccugugccauccucugccauaucuaccaucaugcgcuccacucccgcugguau
caggcccgugaccucaugcucaugagccaccuacaggacaacauucagcacgcagacccgccggugcagauccuguauaaccg
uacuauggugcaacugggcaucugugcuuuccgccaaggccugacaaaggaugcacacaauggcacuucuggauauucaguc
aagugguggugccaaggagcuucuaggucaggguuugcugcugcgcgcuugcaggagcgaaaucaggaacaggaaaaggua
gagcgacgccggcaggugcccuuucaccugcacaucaaccuggagcugcuggagugugucuaucuggugucagcuaugcuc
cuggagauccccuacauggcugcccaugagagcgaugcccgccgacgcaunaucagcaagcaguuccaccaccaacugcggg
ugggcgagcggcacgcccugcuagguccucccgagucaaugagggagcaugguggucgcugccuccaaggccaugaagaugg
gcgacuggaagaccugccacaguuucaucauuaaugaaaagaugaaugggaaagugugggaccuuuucccugaggcugacaa
aguucgcaccaugcuaguucggaagauccaggaagagucucugaggaccuaccuuuuuaccuacagcagugucuaugacuca
aucaguauggagacacuaucagauauguuugagcuggaucuacccacuguucacuccaucaucagcaagaugaucauuaacg
aagaauugauggcuucccuggaccagccgacacagacugguggugaugcaccguacugagcccucugcccagcaagaaacuug TABLE 3-continued RNA transcripts up-regulated during HF stem cell activation.

| SEQ ID No: | Access. # | Sequence |
|---|---|---|
| | | gcucugcaagcuggcugagaaaacuuggcacccuaguggagaauaauggacggguguuugaccaaaaacagggaaccuaugg<br>uggcuauuuccgagaccccaaggguggcuaccggaaaaauggaggcuaaaugccccgugguggcuacccccagcaacagucu<br>cagacaaccuccugaguuccccacuucagucacccuguggacagaccaucuaaccuuuuucuccuaacucaccccaaucauua<br>aagaucuuuugaggaauuaaaaaaaaagaaagaaaaaaaaaaaaaaaaaaaaaaaaaaaaaaaaaaaaaaaaaaaaaaaaaa |
| 155 | AI604314 | uuauuaauuaaaaaacaauuuauugaaaaagaguagugcuuuguacaaauucccauugca<br>gcccccagauaucaacugaucucuuuccagcuuugguaguaggguauaaaaauaucaaaa<br>cuagguaaguucugauguaagauuucuaugggauuauuuuagaauauauagauuugugua<br>guuuggcaaguaucauuucuaugcauuuacauuacauauuaagcacagauucuguggcaa<br>aacaucuuugcaugauuacuuuacacacacaaauauaguaaaacuuacauaguacaaauu<br>cacauaagacuccauucugucuauaacuucauccaugugguuuuaccaugaauuauaauu<br>cuuaaccucuccuauaacugucagcuuccauuuaauuuugaaaguaucacuucacaaaga<br>gcacuucauuugcuuuuagaguauacauagacu |
| 156 | AI845121 | cggccgccaagaaguauaacaugcgaguggaagacuacgagccauaccccgaugauggca<br>uggggguauggcgacuacccgaugcuccccaaccgaucacagcaugagagggauccguggu<br>aucagugggaccacucagaacucaggaugaacuggggugaaccgauacacugggaccuag<br>acauguacaucaggaaucguguggacacgucaccuaccccuguguccugngaugucaugu<br>guaaacaucucuucggcuuuguggcuuucaugguuuucauguucuggguagggcacgugu<br>ucccuuccuaccagccuguggguccgaagcaguacccuuacaaaaaucuguaccuggagcg |
| 157 | AW047756 | uuuuuuuuuuuuuuuuugaugcaaaugucuuuauuuuccacuuaaacaaguucccuuuu<br>gcacuggccuguggcacaaaacagauggcuggguggugacauuaacugucaaguuaguga<br>gaugcagagauggugagacacugcauuugagugcauaauacuuuuauuccagaggaacgc<br>caugcagcccaguuacaccuuuaggucagaaaggcugaugcgugaccagccucuauugcc<br>ucccuugguaagaaggacccacaagugcagaguccaacagaugcuggcucugagcugaac<br>ucagggcauuccaauuaccacuuucuucuucaccuacacagggccugcucagauguccuu<br>uuuacaacuccauaagcccuuuggccaaagucccugcaguguuuggggaggaccuuccca<br>cccuucaccagucagugucugaucugguggag |
| 158 | AI838021 | uuuuuuuuuuuuuuuuuaauaucuguaauaguuuauuucaaagauuugacauuuacaagu<br>agaggcaccacaugcuaucugacaguaaaauacugcagggacugaaggccaaggagagag<br>auccacagaagacaggccuguagugcaggcauugcaucgaccuugcccacagugcuuugu<br>ucccaacucaggacaguacuuuagugcuugcuucauuuacuggaaaaguucacuggacau<br>aguuuccacuucuuccccccacagcuuccagcucagcaaacuuaagcuacuacuccucgau<br>gcucucauagaggcucuugauuugugucuggaagaacuuggcaagcucuacucguuuggc<br>uuucagugucggugucagaaguccguuuucaa |
| 159 | AW122893 | uuuuuuuuuuuuuuuuucugagguauuaaaauaucuagacugaauuuugccaaauguaag<br>agggagaaaguuccugaagacucugacuacuugcuuauuuuugauugaccuucuaugcuu<br>augucauuacugccucacaacguguuugauguccuuuaaugauacaaagugagccugugc<br>cuucauuuucuugcccauuuugguaccccucgugccg |
| 160 | M59821 | Sequence below. |
| | | gcgcccgaacgucuagcagaguaccugcugcuguaagcuugucgucugggcugcaccgcccgucuuaacccauucucgacuu<br>aacuacucucgucgaacaagcauggaaguacagaaagaagcgcagcgcaucaugacucugucgguauggaagauguaccacu<br>cucgcaugcagcgagguggcuugcgacuccaccggagucugcagcuaucccucguuaugcgcagcgcucgagagcucuaccu<br>cucagccaagguagaagcccaccagcccgaguucccgccaucccgcagggcucuugacccucgccugcacccgccgcgggaag<br>ccgaaguugcaguggaaguagcgucccccgaagccgugcagccuccggagcccauggauacgcaagaggaagugcugcgagu<br>ccaggagaccccugcgcucugugacccgcccccccgcuagagucagccgcaagcgccggagcagcagcgauuugagcgacagua<br>gugaugccggacugguaccaagcaagaaggcccgucuagaagagguggagggggaggcgacgucggagguucccgaucgcc<br>ugcagcuuccuccggcacaaagcgaaggugccuucccuaaccucgcccgcguccuccaaaggcgcuucuccagucuccugaac<br>uguggacccgccgugccccgccgacgcccccacgugcgaggccaagccagccugccgcccggccgacaauaugcucaacgu<br>gcuggugcgagcugugguggccuucugagagcucugguggcuucuuucgagcggcgccaccggagcggagaacgcacaccc<br>gaggcgaaggccggcgggggccgugaagaagagccgcggcccgagcugccgagaggccagggcaaggacugaggagcgaggg<br>gcgcgggcgccuucucccagacgugcguccauaggugcuauuaaaggacugucccuuccuuggcuuggagaagggacaccu<br>agaucuugaaucucagggucgaacucucuaggggccaggcugcccuuucaaggccguuucacuaccauucgcguuucggcc<br>ccuacaagugggcacgcuugugcaagcggucagaguugcgucaugggacagacgcgggugcuuccuguugccuugcguggg<br>ugugggggccugggaggaggccaggguguggacccgcccuagggacugggaagugacuugagucaccucgcccccacaggcu<br>gcugugggugagccugaacugaaccaaucaaaucugcgcagaguugaaguggcuggagaccccgggacuggucaaccuagau<br>gaucgccuggcguggaccaccgcgggacggugggccgcuggucguaguugcugccguagacacagcuucuucgggcagga<br>aagaaaauuuuuuuuuaccagcguguuuaagaaagucuguuuacuuuucccacgguggguuguuuaauuagcaacuaccu<br>ggaguuuuacaaugucagcuaggaaaauaaagaccaucggugu |
| 161 | M13805 | See above (same Accession Number). |
| 162 | AI845886 | uuuuuuuuuuuuuuuuuugguuccacuuaaguugcauguuuuauuucucccaaucccagca<br>auagcacagaagcccaucauguccaucccagacugguuucuaguaggcugagaugacagg<br>gagccucaguaacgcuaauggcacagagggcucccaaaugccaggcacaacugugccucc<br>acacuggugacugcccagagugcccuggccccagugugcuuggcacucagucugacuuuac<br>aacgcaaccugcaccuuugaaagggacagucugggaguggggagugugagggagugaagc<br>ucaaacugccuccugucagcucacccuuucaacauuaaacagagaccaagagagaaacag<br>uuccaauauuucacauauauuucuucuugugcagucuaagccgagaaugccauguaaaug<br>ggucacugcgaaaugcagcaauuuagu |

TABLE 3-continued

RNA transcripts up-regulated during HF stem cell activation.

| SEQ ID No: | Access. # | Sequence |
|---|---|---|
| 163 | X53157 | gucucgggcgagauggcuucaagguuacuucgcggagugggcgcuuuggcggcgcaggcc<br>cugaggcgcacggcccguggcgcggccgugacccgcuccauggcuucuggagguggug uc<br>cccacugaugaggagcaggcuacugggcuggagagggagaucaugauagcagcacagaag<br>ggacuggacccauacaauaugcuaccuccaaaggcagcuucaggcaccaaggaagacccu<br>aaucuagucccguccaucagcaacaagagaauagugggcugcaucugugaagaggacaac<br>uguacugucaucugguuuuggcugcacaaaggcgagagucagcgaugccccaacugugga<br>acccauuacaagcuggugccccaccaaauggcccacugagccccuguguuaucuuuucag<br>aauguaaagaaaaacuucucucuaauaaagacuagccauugcaccugcuccuccc |
| 164 | U19118 | See above (same Accession Number). |
| 165 | AF062071 | Sequence below.<br>gcgcaccgccygyguygcgcgscagcgucgucuaggugcaucgcgggcccccgcagrwagaaaaauauggcucaggagacua<br>accagaccccagggcccaugcuguguaguacaggauguggcuuuuaugggaauccuaggacaaauggaauguguucuguuu<br>gcuacaaagaacaucuucagagacagcagaauaguggcagaaugagcccaauggggacagcuagugguuccaacaguccuac<br>cucagauucugcaucuguacagagagcagaugcugguuuaaacaacugugaaggugcugcuggcagcacaucugaaaauca<br>agaaaugugccuguggcugccuugccuguaacucaacaaaugacagaaaugagcauuucaagagaggacaaaauaacuacccc<br>gaaaacagaggugucagagccaguugucacucagcccaguccaucaguuucucagcccaguucuucucaaagugaagaaaaa<br>gcuccugaguugcccaaaccaaagaagaacagauguuuuauguguagaaagaaaguuggccuuacaggguuugacugccgau<br>guggaaauuuguuuuguggacuucaccguuacucugacaagcacaacuguccauaugauuacaaagcagaagcugcagcaaa<br>aaucagaaaagaaaauccaguuguuguggcugaaaaaauccagagaauauaaaauuacuacaugugaagagacugaaacuuu<br>guuuuuauuuuaauauaucguaggaaaacauuaaagagcagaugcauggccauuuuccuuugauguucuccagaguuuugc<br>uuuauacuugucugucauauaauugaucuuuuaggauguuuggguguuuguuacaggcagaauuggauagauacagcccu<br>acaaauguauaugcccucccccucaguaaaauuggacaaaaauaugcacaacaaauugaaauacacauauacuaggaacaaaau<br>uuaguuccacgugccaaacuaaaggaaugaaaucucugcauguuugcagcauaucugccuuuugggaauguaaucaaggua<br>uaaucuuuggcuaguguuaugugccuguacuuaaaaaaaaaaaaaaugguacaccagaaaaggacuggcagucuacuaccaua<br>gucaaacuucaccuuaauuucgacaugacuuuuggaagcaggaagaaagcuacaaaacugguauuugguaccaugugugagc<br>cugguuaaauuggucuucuaaaagcugucaauuaggacauucugcgaaagguaacaucacaacugguucuaagucaaaccau<br>caagucaacagcagggugccugagauaaucuuggaagcuuauugugcuggccugcaccagaagauaucugcauucucauuac<br>uaaaauuguagcacagaacugcacuaggauuuguuuacaaggagaaauuaaacucuguuugguuuucacauauagcagcuc<br>uguuaaauaacaugcaucugaauuuuaaguugcaaagguaucugaacaguuaauuuuucaugugcaucuuuuguugaaugu<br>uuugguucaagaaagaauguuuaaagcuuuuuaaagacuucaguucuuaauguaacuguacccuucugcauggaaaaucau<br>aaccaacauggcugcaguagacuucuuuagugguauccagcaccacuugcagagggcugcuuuaucauauuguacuugggu<br>guaggacucuaguguucuuggguguauugcaugggcugcauuaucuacagcauuguacaauaacaacuagaaaaggcggua<br>uacuucacugaugcuugucugguaauaucacuucuguguuaaaauggaagguuuuuugugauguaugaaacuuguguuuu<br>uuauauauaaaugaguauaguuagauuaguguugugguaaugccuguuuucaucuguaaauaguuaaguauguacacaaca<br>aggcacuacuucugauuuuugcaguguucaguccuaguuuucuuuauuaaaacauugaguuuugcuucaauuuuaugua<br>ccuuaguucuaaguuagauuugcagauguguacagauaguucauauuuauguauugcacauaaucaugcuauucagcauug<br>augcuauauuguauuauguaaauaauaaaagcaguguacagagggaaaa |
| 166 | U10404 | augacagaugccgcuguguccuucgccaaggacuucuuggccgguggaguggccgcagcc<br>aucuccaagacagcgguagcacccaucgagagggucaagcugcugcugcaggugcagcau<br>gccagcaagcaaaucacggcagauaagcaauacaagggcaucauagacugcgugguucgu<br>auccccaaggaacagggaguccuguccuucuggcguggaaccuggccaaugucaucaga<br>uacuuccccacccaggcucucaacuuugccuucaaagauaaauacaagcagaucuuucug<br>gguggugugg acaagaggacccaguucuggcgcuacuuugcagggaaccuggcaucaggu<br>ggugccgcuggggcuacauccuugugcuuuguguacccucuugauuuugcccguacccgu<br>cuagcagcugaugugggcaaagcuggagcugaaagggaauucaaaggccuuggugacugc<br>cugguuaagaucuacaaaucugaugggauuaagggccuguaccaaggcuuuaaugugu ca<br>guacagggcauuaucaucuaccgagcugccuacuuugguaucuaugacacugcaaaggga<br>augcucccagaucccaagaauacucacaucuucaucagcuggaugauugcacagucuguc<br>acugcugucgcuggccugacuuccuauccuuuugacacgguucgccgucguaugaugaug<br>cagucuggacgcaaaggaacugauaucauguacacaggcacgcuugacugcuggcggaag<br>aucgcgcgcgaugaagggagcaaggcuuuuuucaagggcgcaugguccaacguucucaga<br>ggcauggguggcgccuuugugcuugucuuguaugaugagaucaagaaauacacauaa |
| 167 | U07634 | Sequence below.<br>cguagaaguugucucugucggcgggcgggcgggcaggauuggggcaccgagaccggcgugcggacagcagggaucgcgggg<br>agcgaggggugcggcauggagcuccgggcagucgguuucugccuggcgcugcugugggguugcgcgcuggcggccgcggc<br>ggcacagggaaaggaaguuguuuuguuggacuucgcagcaaugaagggagagcucggcuggcucacgcaccccuauggcaaa<br>gggugggaccugaugcagaacaucauggacgacaugccuaucuacauguacucggugugcaacgugguauccggcgaccag<br>gacaacuggcuccgcaccaacuggguguaccgggaggaggccgagcgcaucuuuauugagcucaaguucacggugcgagacu<br>guaacagcuucccggguggcgcccaugccugcaaagagaccuucaaccucuacuaugcagagucagauguggacuauggcac<br>caacuuccagaagcgccaguucaccaagauugacaccaucgccccugacgagaucacggucagcagugacuucgaggcucgca<br>acgucaagcugaacguagaggagcgcauggugggggccccuuacccggaagggcuucuaccuggccuuccaggacaucggcgc<br>cugcgugcggcugcucuccguucgcgucuacuacaagaaguguccc gagaugcugcagagcuuggccugcuuccccgagacc<br>auugcugucgcuguuuccgauacacaaccccuggccacgguggccgguaccugcguggaccaugccguggugccuuauggg<br>ggcgagggggcucucaugcacugcacgguggauggcgaguggcuggugccauccgagugccugugccaggaaggcuacgag<br>aaggucgaggaugccugccgagccuguucuccaggauucuucaagucugaggcaucugagagcccuucccuggagugucca<br>gagcauacccugccauccacagagggugccaccuccugccagugugaagaaggcuauuucagggcaccugaggacccacugu<br>ccaugucuugcacacguccacccucugccccuaacuaccucacggcaugcauggg ugccaaaguagaacugcguuggacagc<br>ucccaaggacacugguggccgccaggacauugucuacagugucacuugugaacagugcugcgcagagucuggcgagugugg<br>gcccugugaggccacggugcgcuauucagaaccuccucacgcccugacccgcacgagugugacagucagugaccuggagccc<br>cacaugaacuauaccuucgcugucgaagcacgcaauggcgucucaggccuggugacuagccgaagcuuccggacugccagcg<br>ucaguauuaaccaaacagagcccccaaagugaggcuggaggaccgaagcaccaccucccugagugucaccaggagcaucccg |

TABLE 3-continued

RNA transcripts up-regulated during HF stem cell activation.

| SEQ ID No: | Access. # | Sequence |
|---|---|---|

gugucacagcagagccguguguggaaguacgaagucaccuaccgcaagaaggggaugccaacagcuauaauggccgccgca
cggaaggcuucuccgugacccuggaugaccuugcuccggauaccacguaccuggugcaggugcaggcauggacgcaggagg
gccaaggagccggcagcaaagugcacgaguuccagacgcuguccacggaaggaucucgcaacauggcggugaucggcggugu
ggcuguagguguuguuuugcuucugguacuggcaggaguuggccucuucauccaucgaaggaggaggaaccugcgggcuc
gccaguccucugaggauguccguuuuuccaagucagaacaacuaaagccccugaagaccuauguggauccucacacuuacga
agaccccaaccaggcuguacucaaguuuaccaccgagauccacccauccuguguggcaaggcagaaggucauuggagcagga
gaguuuggagaggucuauaaagggacgcugaaggcauccucggggaagaaggagauaccgguggccaucaagacacugaaag
cgggcuacacugagaagcagcggguggacuuccugagcgaggccagcaucaugggccaguuuagccaccacaauaucauccg
ccuggaggcggugguccucuaaauacaaacccaugaugauuaucacagaguacauggagaauggagcgcuagacaaguuccuu
agggagaaggauggugaguucagcguacuucaguuggugggcaugcugagggguaucgcauccggcaugaaguaccuggcc
aacaugaacuacgugcacagagaccuggcugcccgcaacauccucgucaacagcaaccuggugugcaagguguccgauuuug
gccugucgcgugugcuggaggaugaccccgaggccaccuacaccacaaguggcggcaagaucccuauucgauggacagcccc
agaggccauuuccuaccgcaaguucaccucagccagcgauguguggagcuacggcauugucaugugggaagugaugacuua
uggcgaacggcccuuacuggaacugucaaaccacgaggucaugaaagccaucaacgacggcuuccggcuccccacgcccaugg
acugcccuucagccauuuaccagcucaugaugcagugcuggcagcaagagcgcucccgccggcccaaguuugccgacaucgu
uagcauccuggacaagcucauccgacgccccgacucccucaagacgcuggcugacuucgauccccgaguguccauccggcug
cccagcaccagcggcucggagggagucccuuccguacgguguccgaguggcuggagagcaucaagaucgaacaguacacgg
aacacuucaugguggcuggcuacacggccaucgagaagggugguacagauguccaacgaagacaucaaaaggaucggagugcg
ucuuccuggccaccagaagcgcauugccuacagccugcugggacucaaggaccaggucaacacagugggggauuccuaucuga
guccauuggggcugucacacaauacuugaagagccacagugguucucccugccgaucuggugcuggcccacuggaacuuuau
uuauuucuguuuccucgucuaugccucccuaggacucugcaggggcuuuuugaaugacaccugccugagccugggaaacuu
ggauugcuggucagggcucucuuuccccugaaaaggacccagcuaagaacuuagcaguuugccauggccuucccagcauccc
cugaggcuaaaguuccaccaagagucgauaucgacgagggacauuuccaaacggaccuccccaucuucauuuggccuccuga
gaagccacucuggagcugaggcuaagcacuaagcccaggaccauaugacuagcacuguaccgcccgccccuaguuagagggu
agguuuuggacuuggcuggguuguggucacaagcaaucucccagugccuuuuacagaccccagucugcccucccgucgagg
gccagcuucuugcuuuccuagggcccucucaggaugcuuggcugugcugagguuuuuauuaaauauauauuuuauacuug
cggaaagaaugagugugugggcagggacuugccagggcuggagacagaggauccccugcaacaagacauucccgggcugggg
gcuggcggaccugcaggagacuuuccgccaccaccccgucuccagccccuuuggacaaaugucgcugucaguguuacagauu
ucuuuuauuggguuguuuuuuuguuguauuuuuuugaaccuuaacuuauuauuuuuuuuauauuuauuguuagaaaaug
acuuauuucugcucuggaauaaaguugcagaugguuca 168 X04663 Sequence below.
ccaaaaaccuuaauuuucuuucuuguucgguaccuacauuggaaccaccaaaaacaauuauuucaguaaaccguagccauga
gggaaaucgugcacauccaggccggacaguguggcaaccagaucggugcuaaguucugggaggucauaagcgaugaacaugg
caucgaccccaccgguaccuaccacggugacagcgaccugcagcuggaccgaaucucuguguacuauaaugaagccacaggu
ggcaaguaugucccucgagcuaucuugguggaucuagaaccugggacuauggacuccguucgcucagguccuuuuggccag
aucuucagaccagacaacuucguuuucggucagucuggggcaggcaacaacugggcuaaaggccacuacacagagggagcug
aguugguugacucugucuuggauguggugcggaaggaggcggagagcugugauugccugcaaggcuuucagcugacccac
ucacuggguggaggcacuggcucuggcaugggcacccugcucaucagcaagauccgggaagaauauccugaccguaucauga
auaccuucagugugguggcccucgcccaaagucucugauaccguggucgagcccuacaaugccacccugucuguccaucaguu
gguugagaacacggaugagaccuacugcaucgacaacgaggcccucuacgacaucugcuuccguacccucaagcucaccacgc
caaccuacggagaccugaaccaucucgucucggccaccaugagcggcgucaccaccugccuccguuucccgggccagcuuaau
gcugaccuucgaaagcuggcugucaacauggugccauucccacgucuccacuucuucaugccuggcuuugccccucucacca
gccguggaagccagcaguaccgggcccucacugugccugaacuuacccagcaggucuucgaugccaagaacaugauggccgc
cugcgacccgcgccacggccgguaccucacaguugccgccgucuuccguggacggauguccaugaaggagguggaugagcag
augcucaacgugcagaacaagaauagcagcuacuucguggaauggaucccaacaaugucaagacagcugucugugacaucc
caccgcguggccucaagauggcagucaccuucauuggaaacagcacagccauccaggagcuguucaagcgcaucucugagca
guuuacggcuauguuccgccggaaggcuuuccuccacugguacacgggugagggcauggacgagauggaguucaccgaggc
ugagagcaacaugaacgaccuggugucugaguaccagcaguaccaggaugccaccgcggaagaggaagaggauuucggagag
gaggcagaagaggaggccuaacggcagagagcccugcaucagcucaggcugcuuagaucccucagccuuucuccaacugccc
uuuguccuccaguuucuuucugcugccucugucuuguauuuguuuugcuucuguuuucucauuggggguaaauggugcc
uggcacauggcaggcacucaauaaauauuuguuugugg 169 X61232 Sequence below.
ggcagacaaaagaggccggcagugcagcucgcgggacgcauggccgggcgcggaggacgggugcugcuggcgcugugugcc
gcgcugguggccggcggguggcugcugacgcgugaagcccaggagcccggggcgccagcggcuggcaugaggcgccgccgg
cggcuccagcaagaggacggcaucuccuucgaguaccaccgcuauccagagcugcgcgaggcgcuggugucgguauggcugc
agugcaccgccaucagcagaaucuacacagugggcgccagcuucgagggccgggagcuccuggucaucgagcugucugacaa
ccccggggucagugagccgggugaaccugaauuuaaauacaucgggaacaugcauggcaaugaggcgguuggacgggaauu
gcucauuuucuuggcccaguaccuguguaacgaguaccagaaaggcaaugagacaauugucaaccugauccacagcacccga
auucauaucaugcccuccuugaaccccgacggcuuugagaaagccgcauggcagcccgggcagcugaaggacugguuugugg
gccgcagcaacgcccagggaauagaucugaaccguaacuucccagaccuggacaggaucguauauguuaaugagaaagaagg
cggucccaacaaccaccugcugaagaaucugaagaaaauuguggaccaaaauucaaagcuugcccccgagaccaaggcuguca
uucacuggaucauggacauucccauuugugcuuucugccaaucugcacggaggagaccuuguggcuaauuacccauaugaug
agacacggagcgguacugcucacgaauacaguuccugcccugaugacgcaauuuuccaaagcuuggcucgcgcguacucuuc
uuucaacccagucaugucugaccccaaucgaccucccugcugcaagaaugacgaugacagcagcuuugaugauggaacgacc
aaugguggugcaugguacagcguccccgguggaaugcaagacuucaauuaccugagcagcagcaacugcuuugagaucacug
uggagcuuacgugugagaaguucccaccugaagagacucucaaaagcuacugggaagauaacaaaaacucccucaucaacuac
cuggagcagauacaccgagguguuaaaggguuuguccgugaccuucaggguaacccgaaugccaacgcaaccaucucugugg
augggauagaccaugaugucaccucggcuaaggaugggg auuacuggcgauugcuugcuccuggaaacuauaaacuuacag
ccuccgauccuggcuaccuggcaaucacaaagaaaguggcaguuccuuuuagcccugcuguuggggugg acuuugagcuug
agucuuucucugaaaggaaggaggaggagaaggaagaauugauggagugguggaaaaugaugucagaaacuuugaauuuuu
aagaaaggcuucuaacuaauugcuuucaucuaucuauagacuguaguaagaugcaaugugg cucuuuucuuuuagguugug
ugcaguugauauuuaacauugauuuauuuuugaucauuaaguaauaguuacuaaucacguaaauacacccggacagaaaua
uaaugcuggacaucuucauucuacaucaacauucgcuuaaaucauucgaagccucuuuuaacguaaugggugacaaugucac TABLE 3-continued RNA transcripts up-regulated during HF stem cell activation.

| SEQ ID No: | Access. # | Sequence |
|---|---|---|

uugacagaugcaugagagucacgauauagcugacugugacccugcacugcaaucacauaguuccauauaaguuguccuuagu
cucuugugcugauucacuguauaagcaugauccugguaaugcacuuuggaugggaagaaaauguacgugcuuuucagaggg
gcucugaacagaaugaaaaccuaguucuugcguguacuuugaagaauggaauuguauuagucagcuguuaaugccacuuca
gaaguuuggggguuuugucuugauuguagauugg 170 X14309 Sequence below.
gccacggacgccucucugaacggggauccaggcaggauuagagcugccucacugacuacaggccgugucgugucaccguuuc
ugcaggcaccaugagccaggacaccgaaguggacaugaaagauguggagcugaacgagcuagaaccggagaagcagcccaug
aaugcagcggacggggcggcggccggggagaagaacggucuggugaagaucaagguggcggaggacgagacggaggccggg
gucaaguucaccggcuuauccaaggaggagcuacugaagguagcgggcagcccuggcugggugcgcacccgcugggcgcug
cugcugcucuucuggcucgguuggcugggcaugcuggcgggcgccgugguuaucaucguucgggcgccgcgcugccguga
gcugccuguacagagguggugcacaagggcgcccucuaccgcaucggcgaccuucaggccuuuguaggccgggaugcggg
aggcauagcuggucugaagagccaucuggaguacuugagcacccugaaggugaagggccugguguuaggcccaauucacaa
gaaccagaaggaugaaaucaaugaaaccgaccugaaacagauuaaucccacuuugggcucccaggaagauuuuaagaccuuc
uacaaagugccaagaaaaagagcauucacaucauuuuggaccucacucccaacuaccagggccagaaugcgugguuccucccu
gcucaggcugacauuguagccaccaaaaugaaggaagcucugaguucuuggcugcaggacgguguggaugguuuccaauuc
cgggauguggggaaagcugaugaaugcacccuuguacuuggcugaguggcagaauaucaccaagaacuuaagugaggacagg
cuuuugauugcagggacugaguccucugaccugcagcaaauugucaacauacuugaauccaccagcgaccugcuguugacca
gcuccuaccugucaaauuccacuuucacuggggagcguacugaaucccuagucacuagguuuuugaaugccacuggcagcca
augguggcagcuggagugugucgcaagcaggacuccucgcagacuuuauaccggaccaucuucuccgacucuaccagcugcug
cucuucacucugccagggacuccuguuuuuagcuacggggaugagcuuggccuucagggugcccuuccuggacagccugcg
aaggccccacucaugccguggaaugaguccagcaucuuucacaucccaagaccuguaagccucaacaugacagugaagggcca
gaaugaagacccuggcucccuccuuacccaguuccggcggcugagugaccuucgggguaaggagcgcucucuguugcacgg
ugacuuccaugcacugucuuccucaccugaccucuucuccuacauacgacacugggaccagaaugagcguuaccugguggug
cucaacuuccgagauucgggccggucagccaggcuaggggccuccaaccucccugcuggcauaagccugccagccagcgcua
aacuuuugcuuaguaccgacagugcccggcaaagccgugaggaggacaccucccugaagcuggaaaaccugagccugaaucc
uuaugagggcuugcuguuacaguuccccuuuguggccugauccuuccuaugcagaaccuaccacccuccuuuguucucccc
aggccuuuuggauucuagucuuccucuccuuguuuuuaaacuuuugcagauuacauacgaauucuuauacuggguguuuu
ugucuucaaauaaaaacaucaccccugccucaug 171 U42386 Sequence below.
gncuuaagccncguuuauuuugaugnccuguuggcucagunaugnccaagaugccnauuguuuuugcccnaaauaaauuu
acugaacuugggcuaaaaccaaaccuuggcacacaggugugauacaacuuaacaggaaucaucgauucauccauaaauaauau
aaggaaaaacucaagugguagccugucuuaaggcuuuugauacuugcagauuggggaaaaacaaacaacaaacgucuugaag
cauauuaauggaauuaguuucuaauguggcaaacuguauuaaguuaaaaguucugauuugcucacucuauccuggauaggu
auuuagaaccugauaauagucuuuaaacaagccauuccagucaugaugaggugauguauggauacaugcauacauucaaagc
acuguucucaaaguuaaugcaaguaaauacagcaauuccucuuucaauguuuaggcagaucguuaacuaugagcuagccaaa
uguggggcauguuauuacagggaaaguuuaaaggucugauaacuugaaauagguuuaggagaauucaucuacuuagacuuuu
uaaaugccugccauaaaaaauugaaaugguagaauggcugaccacagcaaugaccagcccucaccuagggcucuggaugauu
uuuggucuaauaacgcaugcuaguguugauguuuuuggucaagaugggaaugaacaggaagaauuaugcagcaggcuuua
uuuuaaaugccgauucacauuacucuguucaagcugcguugagauguuaaacuggcuuacuauagacuuuguaaaaaaaa
aaaaaccaaacaaauggcuccagaagaguaacaaacugaaaucugagaucacacagguuggaaauauguacauaacugaacaa
ggugucaauucugcucuacagugcaguuuagucaguuuuaguugcauagguuuccauuguuuuuauagucuguuuaugcu
aaaucuggccaaagaugagcauuguccaccacuaaaaugccuaugccacugggaauucuggguuaauuuugugaccagaaug
cagugaucaaaauguucaaucuuuuuacaguggcauaggaagauggcaaaaauuuccuaaagugcaauagauuuucaagug
uauugugccuuguucuaaaacuuuuauuaaguaggugcacuugacaguauugaggucauuuguuauggugcuauuucaau
uagucuagguuuaggcccuuguacauuuggcccauaacuuuuuacaaaguacuucuuuuauugcacauucagagaauuuua
uauauaugucuugugugcguguccuuaaacuuccaaucuuauuuugucucuuggagauuguugaacgcagcuugucuagg
aaagggaugggacuagauucuaaaauuuauuugggaccaugggaaugauaguugggaagaaacuuugcacacgacagauuu
cuagauacuuuuugcugcuaguuuuauguaauauuuauugaacauuuugacaaauauuuauuuuuguaagccuaaaagug
auucuuugaaaguuuaaagaaacuugaccaaaagacaguacaaaaacacuggcacuugaauguugaaugucaccguaugcgu
gaaauuauauauuucgggguagugugagcuuuuaauguuaagucauaauaaacucuuaagucaaauuaagcagacccggca
uuggcguguagccauaacuuucugauguuaguaaaaacaaaauuggcgacuugaaacuaaaucaugccaagguuugauacac
uugucuugagauauuaacgaaacacuuccaaacacugauacaaaguguccagauucucagauguuguugugugaguuuug
uuuaguuguauuuuuuuucagugaaugucuggcacauugcaauccucaaacaugugguuaucuuuguuguauuggcaua
uucagugacuuguacauucagcaauagcauuugagcaaguuuuaucagcaagcaauauuucaguuauguuuccaaauuaa
gaaugguuuaaacuugcugaauguaaagauugacccucaagucacuguagcuuuaguaguugcuuauuguauuaguuua
gaugcuagcacugcaugugcugugcauauucugguuuuauuaaaauaaaaaguugaacugcacagucuccuuuguuguugu
caauugugguuuacuuuuagaggugaaaauaaaguugugcucuugccucgugccaauauguacauaacugnacaaggugu c
aauncugcucuacagngnaguuuagncaguuuuagungnauagguucccaunguuuuuaungncuguuuaugcuaaaucu
ggccaaagaugagcauugcccaccacuaaaaugccuaugccacugggaauccuggguuanuuuggngaccagaaugaaguga
ncaaaauguccanucuuuuuacaguggnauaggaagauggnaaaaauunccuaaagugnaauagauuuccaaguguuungu
gccugguncuaaaacuuuunuuaaguagggugcacunganaguauugaggncauugguuauggugcuauuuccanuuagu
cuagguuuaggcccu 172 U51126 Sequence below.
cucggucuccaagaugguggcuaacaaaacgugaggccuagagguugauccuaggucacuggaagcauguccuugaagagg
acuaugggcaucugguucuuccucuucuacuuggccacgagguaaccggcuucuuguaccacgugugcucaccucuacaa
ucugugcggauucagacuccaagcaacuaggcuacccagugacaggcuaaaaacuacagcucuaacgucuuggaaggcgauu
ccauggaccaggauguggaaagcccaguggccauucaccagccaaaguugccuaagcaggccagggacgaccugccgagacac
aucagccgagacaggaccaaaaggaaaauccagagguacgugaggaaggaugggaagugcaacguucaccacggcaaugugc
gggagacguaccgauaccugacggacaucuucaccacccugguggaccugaaguggagauucaaccuguugaucuuugucau
ggucuacacagugacguggcuuuucuuugggaugaucugguggcugauugcguacauccggggagauauggaccacauaga
ggaccccucguggacuccuugugucaccaaccucaacggguuugucucugcuuuuuuauucuccauagagacagaaaccacc
aucgguuauggcuaccgggucaucacggacaagugcccugaggggauuauucuccucuuaauccaguccguguuggggucc TABLE 3-continued RNA transcripts up-regulated during HF stem cell activation.

| SEQ ID No: | Access. # | Sequence |
|---|---|---|

auugucaacgccuucaugguaggauguauguuugugaaaauaucccaacccaagaagagggcagagacccuggucuuuucca
cccacgcggugaucuccaugcgggaugggaaacugugcuugauguuccggguggggacuugaggaauucucacauugugg
aggcauccaucagagccaaguugaucaaguccaaacagacuucagaggggaguuuauuccccucaaccagacugauaucaac
guggguacuacacaggggacgaccggcucuuucuggugucaccauugauuauuagccaugaaauuaaccaacagaguccu
ucugggagaucuccaaagcgcagcugccuaaagaggaacuggagauuguggucauccuggagggaaugguggaagccacag
ggcaguucugaaaucgaaaucaagcagaggucuauaagaacacccuggagaccccaugcugcuggaucuugguccaugaa
cugcuuuuauuugcugcaaucaaaaaugcuagucgcugaucugauaggagaggaaacgagacucagagccugaaggauaaca
cgcugagggcugauuucauacacucuucccggcuggaucaucccagcccccacagcguccaggcuuaguuucuuccuuugu
uuuaacaaucuauacuuccuccagccugggcgagcuaguauacccagaguuugguuuuguuucuuuucagagcuguaagcc
cagugcccagugaccucaucugggaggagaguuaagcaauaagaccugaaugcuaacucugggguagaaaaccucugcag
agacagcgucucugggaagucucuacagagacagaguagggaagucucacgaaggucagagucuuacuuccauaccuggaga
aauccgcccguccguucagugccgguuucaacuccucugccaaagacuucuuuccaagacacugguaucagcuaucccagca
guaacuuuggcaguauauaaaucaauggcacugccccauaaaaccccguugaguaaaaccuauggucuucaacagcuggga
gccuguagcccagcuccugugugaggcuaaggcuguggagaccaugccugcucaccuccucguugaaaagcaaaacacugua
agaaaccuaacaugacuuuuuccaacauuucucaggcuggggagaagacuugguccacaaagagcuugaggucuugaucug
gaucccuagcauccauggaagaaggugggcaugaucacccacacuccucaucccauagcucugaaugagguaggcagauucc
uggggcucaccagcucauccuaacagccaggucccaaugagggacugucuacaaaagaacaagagguggauccugagaagcg
acacccaagcuugaccucuagccccuguacacaccuguuaagcaccugggcaucgggacacacacucgcaauuugcaaacaag
gcaaauucucacacuucagaaggcacugagagaaucccauaagcucaaaaaguuaggagccaagauugaccauuaaugacuu
ggguugaaaagacuaaaccacuggauagaauguuucauuacuaaaacaccuuaccugaaaguauuacugcucuucuuucug
caacuggaccaugcagagauccacaaagagaugcccagagauuauuagugauggucauaugauauacacaaugugacucua
agccaaggccccaucaacucagauccagaggcugacagugugcuuaucuuagagauaccacaguggcugccuaaucaccacg
uccuuaagucaggggaguuugauuauuuccuaugaacaccgaguggggacagcggauuaccaaugaagcaauccaaccugac
aauccuaaccacccagaagaggaucgcuggggggaaagcaugaauuauuuacgugucaacaugugcacacuccggccacgcag
cucaacagccaggagugcuucuccacuuagcccugcccuggcauccauuuaugaucucgucuguuguguuaauuacccagcu
agcuuuuuucucaaaaauaauaucucccagccauagaccuacucaucugugucccucuuuaauuucaacccacaguuacauca
uucacuggcuugcucaguuucuucaacucugaaaugggaaugaugaugaugaugccucuuccccccaagccaccauccucccc
cgugaccuuccuagguacagacucaaaccagggaagauuauuuccuucucauaggccacagggugaaaugcaauaaagaaca
aagccuuguagggaggcagagggaaagaccaguccucacaagaggcuccauuguuuccagggacuuugaagcuuggacagaa
ugucagaugaucccuuugaaggugcuccaaagagucaaugugaaaaauauugacugaugugugcccuccacaagccaagg
ugccucugcccuggucaccuaccaugaauuauaaacugaugauauuugaaauaauaaggaacacuggagccggccagaaagg
auucugcagucccauaaauagcaacauucaucacuacaaugccugccaacgguggccgugaauguagauuacccccggcucu
ucugaggccacugaggacagggcaaacuaccucugagaauggaggcucacuguucugcaucccacuucuaaauguuccauga
auuuuuugagacaucucccauaucccuguuagaaagauucaaccuugugcuauuaaccaaaucauuuugaauuccauaaacc
ucuacucuaaaguauacacuuaauucuacaauacagacaacaaauaugacuuuuuccuaugaaagagugauaaagauacugu
aucagucugcuuugacucaaaaaaaaaaaaaaaaaaaaaaaaaaaaaaaaaaa 173 AF093853 Sequence below.

uggaauggggugcuaggugaaggcuuuguugaaucaggaugcugagcugguguuuuuacagguccagauaugaugagcugg
aguuuugguaggcccagguaccuccuccaaaauugaccacauaauuggucacaaaucaggccuccacagauacaaaaauauu
gaaauuaucccaugcauccugucugaucaccacagacuaaggcugaucuucaauaacaacauaaaaauagaaagccagguuca
cugcugcggcugcgccuccuuguucucagcgucaccacugccgccaugcccggaggguugcuucucggggacgaagcccca
acuuugaggccaauaccaccaucggccgcauccgcuuccacgauuuccugggagauucauggggcauucucuuuucccaccc
acgggacuuuaccccagugugcaccacagaacuuggcagagcugcaaagcuggcgccagaguucgccaagaggaauguuaag
uugauugcucuuucaauagacaguguugaggaucaucuugccuggagcaaggacaucaaugcuuacaauggugaaacaccca
cggaaaaguugccauuucccaucauugaugauaagggcagggaccuugccauccuuuugggcauguuggauccagucgaga
aggacgauaacaacaugccugugacggcccgugugguguucauuuuuggcccugacaagaaacugaagcugucuauccucu
acccugccaccacgagcaggaacuuugaugagauucucagagugguugacucucuccagcugacaggcacaaagccgguugc
caccccaguugacuggaagaagggagagagcgugaugguaguccccacccucuccgaagaggaagccaaacaauguuucccu
aaaggagucuucaccaaagagcucccgucuggcaaaaaauaccuccguuauacaccccagccuuaagucuuugcggaaauug
gggcugcaucugcacguccagcacuggggccugaggacgucagccggcagccgugggguccuugcagcagguccguagaaaga
ucguggcaugaucacagccggccuguagaucgcucgcuauacuacugggucauuaaauggaaauggcaccaaaaccuucuc
gggauucuuuacucugugccuucgccagcauucugccccucugccugucacagugcccuacugacuggcucucuuugaaac
gaauuauguauugaagauuccuuaggucucugcagggucuuugaucagcaagcaagguagucagugugggcucugugc
uagaaugaugaaacaccuuuuguagcuuuccgaacggaaucuucuguuacccauuuuggagagcacugacauggggagaag
cuuucaauucuguauuuuuaguaaauaaaguggggacagccgggagaauucuuacagggaaucuauuguaaguuucuaucg
aagugggcucagaaagccuuucgccucccaagagugcgcauguaccuccuagaguuuccacaucugcucucuggugauguc
ugccugugaacgcaccuuauaaaagacgggcggugacaguguuuuaccacucaguguccuaguaguggguggccauuucug
aauucugcuuuuugagguucaacaaauaaaauccugaucagaaaaaaaaaaaaauagaaagccaacauucauguggaaacuga
acaacacuacucaaugauuccuuggucagagaugaaauaaagaaagaaauuaaagacuuuuuagaguuuaaugaaaaugaag
ccacaacauacccaaacuuaugggacacaaugaaggcauuucuaagaggaaaacucauagcccugagugcauccaaaggaaaa
aaaaaaaaaccuagagagaguguacacuagcagccugacugcacacuuagaagcucugcaaaaaaaggaaucaaauucaccca
agaggaauagacagcaggaaauaaucaaacuuagggcugaaaucaaccaaauggaaacaaaaagaacuauucaaagagugggc
caaaccaggagcuaguucuuugagaaaaucaacaagauagauaaacccuuagccagacucacuagagggcacagggacagcau
ccuaauuaacaaaaucagaacugaaaagggagacauaacaacagauccugaagaaauccaaaacaccaccagauccucuacaaa
aggcuauacucaacaaaacuggaaaaccuggaugaaaggaaaagcuucuagacaga 174 Z19521 Sequence below.

augagcaccgcggaucugaugcgucgcugggucaucgcccugcuccuugcugcugccggaguugcaguagaagacucaggc
agcaggaacgaguuccaguguagagacggaaaaugcaucgcuagcaaguggguguggcgauggcagccccgagugcccggaug
gcuccgaugaguccccaaagacaugcaugucugucaccugucaguccaaucaauucagcuguggaggccgugucagccgaug
cauuccugacuccuggagaugugauggacagguagacugugaaaaugacucagacgaacaaggcuguccccccaagacgugc
ucccaggaugacuuccgaugccaggauggcaagugcaucuccccgcaguuugugugugauggagaccgagauugccuagau
ggcucugaugaggcccacugcccagccaccacuuguggccccgcccacuuccgcugcaaaucauccauaugcauccccagucu
uugggccugcgacggggaugucgacuguguugacggcucccaugaguggccacagaacugccaggccgaagacacggccucc TABLE 3-continued RNA transcripts up-regulated during HF stem cell activation.

| SEQ ID No: | Access. # | Sequence |
|---|---|---|

aaaggcguuagcagccccugcuccucccuggaguuccacugugguagcagugaguguauccaucgcagcugggucugugac
ggcgaggcagacugcaaggacaagucagaugaggagcacugcgcgguggccaccugccgaccugaugaauuccagugugcag
auggcuccugcauucacgguagccgccagugugaccgugaacaugacugcaaggacaugagcgacgagcucggcugcgucaa
ugugacacagugugauggccccaacaaguucaagugucacaguggggagugcaucagcuuggacaaggugugcgacuccgc
ccgcgacugccaggacuggucggaugagcccaucaaggagugcaagaccaacgaguguuuggacaacaaugguggcuguucc
cacaucugcaaggaccucaagauuggcucugagugccugugucccagcggcuuccgguugguggaccuccacaggugugaa
gauauugacgagugucaggagccagacaccugcagccagcucugugugaaccuggaaggcagcuacaagugugagugccagg
ccggcuuccacauggacccacacaccagggucugcaaggcugugggcuccauaggcuaucugcucuucaccaaccgccacga
gguccggaagaugacccuggaccgcagcgaguacaccagucugcuccccaaccugaagaauggugguggcucucgacacggag
gugaccaacaauagaaucuacugguccgaccugucccaaaaaaagaucuacagcgcccugauggaccaggccccuaacuuguc
cuacgacaccaucaucagugaggaccugcaugccccugacgggcuggcgguagacuggauccaccgcaacaucuacuggaca
gauucagucccaggcagcguaucuguggcugacaccaagggcguaaagaggaggacacuguuccaagaggcaggguccagac
ccagagccaucguaguggacccugugcauggcuucauguacuggacagauuggggaacacccgccaagaucaagaaagggg
uuugaauggugugggacauccacucacuggugaccgaaaacauccaguggccaaauggcaucacacuagaucuuuccagugge
cgucucuauugggguugauuccaaacuccacucuaucuccagcaucgaugucaaugggggcaaucggaaaaccauuuuggag
gaugagaaccggcuggcccaccccuucuccuuggccaucuaugaggacaaaguguauuggacagaugucauaaacgaagcca
uuuucagugccaaucgacucacggguucagaugugaauuuggugggcugaaaaccucuuguccccggaggacauuguccugu
uccacaaggucacacagccuagaggggugaacuggugugagacaacagcccuccuccccaauggugguugccaguaccugug
ccugcccgccccacagaucggucccccacucgcccaaauucaccugcgccugcccugauggcaugcugcuggccaaggacaugc
ggagcugccucacagaagucgacacuguacugaccacccaggggacauccgccguccggccuguggucaccgcaucagcuac
caggccaccgaagcacagugaggaucucucagcucccaguacuccuaggcagccuguggacaccccagggcucagcacagugg
cgucagugacaguguccccaccaaguccaggggugacauggcuggcagagggaaugaggagcagccacaugguaugagguuccu
guccaucuucuucccuauugcacugguugcccuccuuguccuuggggccguccugcuguggaggaacuggcggcugaagaa
caucacaaucaacagcauaaacuuugacaacccagucuaccagaagaccacagaggacgagcuccacauuugccgaagccagg
auggcuauaccuaccccucaagacagauggucagccuggaggacgauguggcaugagcagccgggagagccgucucuuuccg
ggauccauugccaagcuuaggcagaaaagacacucucuccagaccucccccauccagcacugguccugccaccucccugggucu
guguugcucaaagcaagauagagcaaagcugggcugggggccaagcucagcuuccugucugccccagguucuguuuuaua
uauuuauugucugggacagaaaaggcuacuggcugugcuugaaauucga 175 U04354 Sequence below.
accggucaucgggcucuuccuugggcucagggcacggaucaaguccucggcucgcucggccagcaccgcggcaccauggcgc
aggagcugcagcaccccgaguucgcgcgcgcaggccagcaggcugggcugcagguguggagggucgagaagcuggaacugg
uaccggugccccagggugccuauggugacuuuuacgucggagagcccuaccuggugcugcacaccaccaaguccagcagggg
cuucuccuaccgccugcauuucuggcugggaaaggaguguucccaggaugagagcacagcggcugccaucuuuacgguccca
gauggacgacuauuugggguggcaagccaguccagagcagagagcuucaaggcuaugagucgacugauuuuguggggcuauuu
caaaggcggucugaaguacaaggcuggaggugguggcuucuggacuaaaccauguccucaccaaugaucugacugcgaaaaga
cuucugcacgugaagggucggagagugggucagagccacugaaguuccccucagcugggagagcuucaacaagggcgacugcu
ucaucauugaccuuggcaccgaaauuuaccagugguguggguuccuccugcaacaaauaugagcgucugaaagcaagccaggu
ggccauuggcauccgggacaaugagaggaaaggaagaucucaacucauugugguggaagaaggaagugaaccaucagagcuc
augaagguuuuagggagaaagccugagcuuccagauggggacaaugaugacgaugucguagcagacauaaguaacaggaaga
uggcgaagcucuacaugguuucagaugcaagugggguccaugaaaguaacacugguggcugaagaaaacccguucuccaugg
gaauguugcuuucugaagaaugcuucauuuuggaccauggugcugcaaaacaaauuuuuguauggaaagguaaaaaugcua
acccacaggagaggaagacugccaugaagacagcugaggaguuuuuacagaaaaugaaguauucuacuaauacucaaauuca
gguucuuccggaaggcggugaaacaccaauuucaaacaguucuuuaaggacuggaaggauaaagaccagagugauggcuu
ugggaagguguacaucacggagaaaguggcucagauaaagcagauuccguuugaugccucaaaacugcacaguucuccgcag
auggcagcccagcacaacaugguggacgauggcucuggcgggguggagaucuggcguguagagaacagugguagaguccag
auugacccaagcuccuauggcgaguucuauggcggugacugcuacauuauccucuacacuuaucccagaggacagaucaucu
acacauggcaaggagcaaaugcuaccagagaugaacugaccauguccgcguuucugacuguccaguuggaccggucccuugg
agggcaggcugugcagguccgugucucucaaggcaaagagccugcucaccugcugaguuuguucaaagacaaaccacucauu
auuuauaagaaugggacauccaagaaagaagggcaggcaccggcucccccuacacgccuuuuucaaguccggaggaaccugg
caucuaucaccagaauuguggagguugacguugaugcaaauucauuaaauucuaaugacacuuuuguccuaaaacugccacg
aaacaauggcuucaucuggauaggaaaaggugcuagccaggaggaggagaaaggagcagaguauguggcugauguccucaag
ugcaaagcuucaagaauucaagaaggcaaggaaccagaggaauucuggaacucucuuggagggaggggagacuaccagacuu
caccauugcuagaaacucgggcugaagaccauccaccucggcuuuaugguugcuccaacaaaacuggaagauucauuauuga
agaaguuccgggagaguucacccaggaugaccuggcagaagaugaugucaugcuacuugaugcgugggaacagaucuuuau
uuggauuggcaaagaugccaaugaaguugagaaaaaggaaucagugaagucugccaaaauguaccuggagacagacccuucu
ggaagagacaagaggacaccgauugucaucaucaagcaagggcacgagcccccacauucacaggcugguuucugggcuggg
acuccagcagguggaaaaccagcaacuauccuggcugcauuggggcagcugccacuuuguuguuggggaauuguuuacuu
uuuguuauuggcuuuugaagauaaacuccugccaaauggauauauaucuauaucuauaucuauaucuauaucuauaucuau
aucuauaucuauaucuauaucuaucuauaucuaaucuauaucuaucuaucuaucuaucuaucuaucuaucuaucuaucuau
cuaucuauaugcuccucuuuuccuucucuuucaaagggaauugcuguauguuacuauacugaaauaaccuaaagcaaccauu
uguuuucgagcaauuuugcaaucuggggaccucugaggaaguaauuuugucauucagccacugcuagccaaacuugucuuu
ucccauagagaggaaggagagccacagugcuucuaagcauuuccccgucugcuacucuguuugcagugagcuuuacuuuau
guauggcuuuaacaaugccuugcuguuucccaucucaagucaaugccacuuggaugccauucacucccaaguguccuuacau
aggaugaacuucuuuagcuuuuuuagaaaacuaaaaucaugucuuuuaugauaaaacacauuuuauuucuauaaguuuaac
uuuauauauuugauagcacaugcucaauagcauaaagaauaugcauugaaugauguuuuucauaauuaaaauauauccuuu
ugg 176 M35244 Sequence below.
caggguugagagcaagaaggugcaggauguaggccagcagaauuaucagacccaguggcggcuucugccacuggaagaauuu
ccaacauaaaacagaugaucaguuugggacaaucgauucugcgaccagagguagugucaucugguuacuuuuaaaauucaga
uugucugguguuuuccaaucacucgcgacuguaauuugaaguuggauucugagauaauacaaucgcugucgcucuaguuua
uaaagcuguccaagaucugcccagucccagauguccuggguccucagggcggcugugggucugcgcccuucuccugcagcug
gaugccagaccauccuggacucggaucccuuuggguucacacucgcuuagguauuucuacaccgcugugucccggccuggc
cuuggggagcccugguucauaaucgucggcuauguggacgacaugcagguccugcgcuucagcagcaaggaggagacuccg TABLE 3-continued RNA transcripts up-regulated during HF stem cell activation.

| SEQ ID No: | Access. # | Sequence |
|---|---|---|

aggauggcacccuggcuggagcaggaggaagcagaugacugggaacagcagacucauauagucacaauucaaggacagcugu
cugaaaggaaucugaugacccugguucauuuuuacaacaagagcauggacgacucucacacacuacaguggcugcaggacug
cgauguggagccagaucggcaccugugucucugguacaaccagcucgccuaugauagcgaggaucuccccacccugagcgaa
aacccaaguuccuguacagugggaaacagcacuguaccucagaucucucagcaccuggagggccacugcucagaugugcugc
agaaauaccuggaaaaagggaaggagaggcugcugcguucagacccccccaaaggcacaugugacccgucaccccagaccugaa
ggugaugucacccugaggugcugggcccugggguuucuacccugcugacaucacccugaccuggcagaaggaugggggaggag
cugacccaagauguggaguuuguggagaccaggccugcaggggauggaaccuuccagaagugggcagcugugguggugccu
cuuggaaaggugcagaguuacacgugccauguggaccaugaggggcugccugagccccucacccugagaugggagccugcau
gguaccaaaagccuuggauuuggauuguugccacgguuuuuuccauuuugcucauuugucucugugugguggcucgcagaccca
ugaagaagaaugcaggugggagaggaaggcgugacacccaagaagcaggcagagacaguccccaagacucuagcaagacugu
uguggaugaugaggagaugggguuugcuuuuggaagauuaaguccuguaaaacuugucuaggccacuccccaggaacuuc
aggaucaucugggagaugccccuuugaguggcugggcugugaggacagcaggccaguucuugccacccuggacagaaacaca
ucucaccuuucuggcucgaggaucugaacaccugucucuugccuacucggcuucuagucaggcauuuugucaccuugucaa
gggucccagggacacaaagcucccuccucucacccacagcacucuggguccuacccccaaugcuucagggacauuuaaucagg
ucaaauugggaucaauggcuuugaugcagaaaagaacuguggacuaauagagauaggguuuaauaaaaaaaauaucuuuuu 177 AW121930 uuuuuuuuuuuuuuuuucaacuuuaaagacuggauuugagguucagucugggucucuggg
ggggaccucugucaucacgccuauaaucaucccgagaguagucaucccuggagcuccacg
accgaucaucccgucugucauagcggucuucauagcgguccccaccuccucuguagucau
caucucuccgguacccacuuccaaaugcccuucugccacugccuauccuggagucauagc
cucggucauagucucugcugccucggucaucauagcgaucccggcccccauagcggucca
ugucucugcgugggccgucccgauauccgucccuauacccaucccgauaccggucugaau
cguaacgaucucgauacuugucuccaaagcuaucaucgccucuucuaggugggguagucau
cacaacugucugugguggggacgggcccuccagucugugucuguuuug 178 AI852632 uuuuuuuuuuuuuuuuuggcccccaggcucugucucaaggaugggaauagaucaagccaa
acagugaaaaauaaggcaaaucguggcuucgggguuugagacuggcaccaauggcaaauc
agcagaggagaugcaaaugggguaacaaucacaguuaguggggguaacaugagcaggcagg
aaacccuugagacaacacccaagguccacgucuucgcaugugcagggcacaacuccagca
gcaguuucugggcuuggaggcuuguuacucuuccuaccuuucccaccccuaaaagacac
caagauggagcccacgaagagauuacaucaagcucuucuggcuggg 179 U70475 Sequence below.
ucuaggacagccagggcuacacagagaaacccugucucaacuaaaacaaagcaaacccccccgaauauuguuuuuauuugcg
gaugucuguuuauugagacgggguucauggcagacaugagugucucagugcauuugcuauccucucuucuaaaggggcgg
gggggggggugcgcuggagagguggcucagcaguuaagagcacugacuucucuuccagagguccugaguucaauucccagc
aaccacaugguggcuuauaaccaucuauagugagaucugaugccuucuucuugccuguaggcagaccacuguauacauaaua
aauaaaucuuaaaaggggggggaagguguggagcuaaaaguauggcaauaugcauaaguuuagcuauuucuguuguuuugc
agucaucagugagccaaacuaauucgaaugggguagcuagaucuuguugcuuuuagcgaauauauauugagugaauggaauu
gacagucuucuguauucucauucaguuuguuuguguucuuccccaucagugauaacauguagugaacuaacccgugugggac
caucuuaaccauggcuucuccuuccuuuucuguuuuaaacauaggacauggauuugauugacauccuuuggaggcaagaca
uagaucuuggaguaagucgagaaguguuugacuuuagucagcgacagaaggacuaugagcuggaaaaacagaaaaaacucga
aaaggaaagacaagagcaacuccagaaggaacaggagaaggccuuuuucgcucaguuucaacuggaugaagaaacaggagaa
uuccucccaauucagccggcccagcauauccagacagacaccaguggauccgccagcuacucccagguacacucgucguggug
ggagcuaaggaaaacucuagugagaaagcagacucucuggaguugaguucuuggucugccauuuacugugucuuuugugag
gaggagaaguucucaaacuucgcuucuugauaaucaggacacagaucacagggaggacuuugugaguucagaaacauccucu
guggugaugaaacagcggcagaaauacuguugggaguaaaagaaguaggcauugcucauugugguaggcagggcccugauu
guaugggguaacugacuuaacuguguuaaguaugauucccauuuuauauucccaugucuaaacaacuaaagcauuugcccag
aacacucagaaagaaaugaagggagguuauugccuagcacagagcccugguucaguccccccacgcuguucguuaaaggggag
ggacuaauaauuugaacacaaucugguuugaaucuaugcaaaucgauuucugaaaugagaccauagguuauuuuaugaaca
agucuuauugcucguugugacccugugcuuagaacauuucauaaaugaugcucucugugccuuuccccuuccuccagguug
cccacauucccaaacaagaugccuuguacuuugaagacuguaugcagcuuuuggcagagacauucccauuuguagaugacca
ugagguauaaaaauguuuguuuaacagcaaaacucccuuaucugauauuaguuccuuucaugugucuccaauuaagagaag
aaaagaaaauuuuagaaggaaaaaauugaucaaagaaauugucaaguaaacuguaugagagcuauauaaugcuuaaaaauaa
gaccuguaugggcuggugagauggcucaguugguaagaguacccgacugcucuuccgaagguccagaguucaaaucccagc
aaccacaagguggcucacaacauccauaacaagaucugacucccucuucuggagugucugaagacagcuacaguguacuuac
auauaauaaauaaauaaaucuuuaaaaaaaaaaaaauaaggccuguaaacuacaaguccauuuuacuguauagcuggaaacagg
aaucagaauaauuuucccuggaaacuggauauagauauaaaauauuugacuaguaaagaacaacuauuaaucagcauuu
ggauuaaaaaaucuuaaucuguuguuugaagcauucugcuagauauuaugggguacagauuaaguccuaaugaauguuuuua
uccauuuugaagucugccuuuaaauacauggagugaaauaaccuaggaguguauuaauauggagucacugggaggaggaaa
uguuucauuuuauaaaagcagccugagagcuguaggcccugcugcugucuguucuucaugccuuggcucucacucacauga
aucaaugucacgucaaucuuggcuuucuucacuugcauuucagucgcuugcccuggauaucccccagccacgcugaaaguuca
gucuucacugccccucaucaggcccagucccucaauagcucucuggaggcagccaugacugauuuaagcagcauagagcagg
acauggagcaaguuuggcaggagcuauuuuccauucccgaauuacagguaagagagcucuaggagugugcuguuuucugcg
ggcccuuuuaaauuagucauccuaguuauuuauuauuuacaugcuaccuccucaaaggaagaaauugaugguguauuuaaa
uuacucaugagagcuucccagacucacuuaacacacauaguuuuuagguaaucagacugaauauuucuggauaaaauucauuc
aaagacugaaagcuaauuuagaguucugacaaagauaaaauacuuaucuauugaaaaaugggaguugaaggaauuauugaaa
agaacaccuuggauuuggggguagggaauugaucuaaaaugcacuuagccucugcucauacaaugugaccuucuuuccuag
ugucuuaauaccgaaaacaagcagcuggcugauacuaccgcuguucccagcccagaagccacacugacagaaauggacagcaa
uuaccauuuuuacucaucgaucuccucgcuggaaaaagaagugggcaacuguggucccacauuuccuucaugguuuugagga
uucuuucagcagcauccucuccacugaugaugccagccagcugaccuccuuagacucaaaucccaccuuaaacacagauuuu
ggcgaugaauuuuauucugcuuucauagcagagcccagugacgguggcagcaugccuuccuccgcugccaucagucaguca
cucucugaacuccuggacgggacuauugaaggcugugaccugucacuguguaaagcuuucaacccgaagcacgcugaaggca
caauggaauucaaugacucugacucuggcauuucacugaacacaagucccagccgagcguccccagagcacuccguggaguc
uuccauuuacggagacccaccgccugggguucagugacucggaaauggaggagcuagauagugccccuggaagugucaaacag TABLE 3-continued RNA transcripts up-regulated during HF stem cell activation.

| SEQ ID No: | Access. # | Sequence |
|---|---|---|

aacggcccuaaagcacagccagcacauucuccuggagacacaguacagccucugucaccagcucaagggcacagugcuccuau
gcgugaaucccaaugugaaaauacaacaaaaaaagaaguucccgugaguccuggucaucaaaagccccauucacaaaagaca
aacauucaagccgcuuagaggcucaucucacacgagaugagcuuagggcaaaagcucuccauauuccauucccugucgaaaa
aaucauuaaccucccuguugaugacuucaaugaaaugauguccaaggagcaauucaaugaagcucagcucgcauugauccga
gauauacgcaggagagguaagaauaaagucgccgcccagaacuguaggaaaggaagcuggagaacauugucgagcuggagc
aagacuugggccacuuaaaagacgagagagaaaaacuacucagagaaaagggagaaaacgacagaaaccuccaucuacugaaa
aggcggcucagcaccuuguaucuugaagucuucagcauguuacgugaugaggauggaaagccuuacucucccagugaauac
ucucugcagcaaaccagagauggcaauguguuccuuguucccaaaagcaagaagccagauacaaagaaaaacuagguucggg
aggauggagccuuuucugagcuaguguuuguuuuguacugcuaaaacuuccuacugugaugugaaaugcagaaacacuuua
uaaguaacuaugcagaauuauagccaaagcuaguauagcaauaauaugaaacuuuacaaagcauuaaagucucaauguugaa
ucaguuucauuuuaacucucaaguuaauuucuuaggcaccauuugggagaguuucuguuuaaguguaaauacuacagaacu
uauuuauacuauucucacuuguuacagucauagacuuauaugacaucuggcuaaaagcaaacuauugaaaacuaaccagacc
acuauacuuuuuuauauacuguaugaacaggaaaugacauuuuuauauuaaauuguuuagcucauaaaaauuaaaaggagc
uagcacuaauaaaagaauaucaugacuuaaacuacuuuggacuuuuugaauuuauucacacuauuuuccauaggacaaucac
ucauuuaccacauuugguuauuuuacauuuucaaaauggguuugaaaauacagaggcauuuuauagccaugugugcaguc
caugauuuuuuauucccgacauucaggaggcagaagcaggcagaucccugggcuccaggacggccaaggcuacaugagagcc
ugucucaagaaagacaaacccuuucuauacuaaacguuagcuaggauugucaaggagaugguauauauccacaaugguaugc
cugcuguacaguacuguggcacagagaacaaaaccuguaaccuccuguguucuuagaaguggcauucuaagaagggcuagga
aga 180 U09659 ggccagcaggacucuccuugcagcagcggcccgaguucagaguccggagcugcggugg
gcggcgaaggcgagagucauggcuggacaagcuuuuaggaaguuucuuccgcucuuugac
agaguauugguugaaaggagugccgccgaaacuguaaccaaagguggcauuaugcuucca
gaaaagucucaaggaaaaguguugcaagcaacggucguggcuguggggucaggagggaaa
ggaaagaguggagagauugaaccugucagugugaaaguuggagauaaaguucuucuccca
gaauauggaggcaccaaaguaguucuagaugacaaggauuauuucuuauuuagagauagu
gacauucuuggaaaguaugucgacugaaaucacuguugaaauggugucacgugaagcugc
cauuccacugaugucugaacuauuucaucauguaaauaauuu 181 AW124785 uuuuuuuuuuuuuuuuucaggucucauuuucguuuauuugaaauucggugcucguguaag
uuuuuucucuuccccucaaauuuuauuucaguaaaaggagacuugggcgagguggauacc
ccacagccggauucuucccccccugcccccccaggguggcuaaugcuaucuggggaagucg
ucauagggaagagaacuauggugggcuccugccugaggccuccaaucucagcccagugg
acauaucacaggcagcuuaaaaaaaaaacccuaaaaaaaaacaccccaaaacacacauuua
aauagguauucaagacagcuuuaaaaaaugcacccacucacacccccccucccuuuucuuu
uuggaaaaaaaaauaggaaaaaaaaaaaaaaccaaaccgaauucucgcuuggccucua 182 AF071315 Sequence below.
auuuggcuccgaggccaagaauucggauccaaggcgggcgcggggaaaauggcggcggcagcugcggcgggggcgaauggg
agcggaggcagcagcggcauggaaguggaugcagcaguccccagcgugauggccuccggagugacugggaguguuuccguc
gcucuucaucccuugucauccuuaacaucucagaccauuggauccgcaugcgcucccaggaggggcggccuaugcaggug a
uuggggcucugaucgggaagcaggaggggcgaaauaucgaagugaugaacuccuuugagcugcugucccacaccguggaag
agaagauuaucauugacaaagaauauuauuacaccaaggaggagcaguuuaaacagguuuucaaggagcuggaguuucugg
guugguauaccacagggggccaccugaccccucagacauccacguccauaagcaggugugugagauaauugagaguccgcu
cuuucugaaguugaacccuaugaccaagcacacagaucuuccugucagcguuuugagucugucaucgauauaaucaaugga
gaggccacaaugcuguuugcugagcucacuuacacucuggccacugaggaagcugaacggaucgguguagaccacguggccc
ggaugacagcaacaggcaguggggagaacuccacuguggcugaacaccugauagcucagcauagugccaucaagaugcugca
cagccgugugaagcucauuuuagaauaugucaaggccucugaagcaggagagguucccuucaaccaugagauccugcgggag
gccuaugcccuaugucacugucucccaguucucagcacugacaaguucaagacagacuuuuaugaucaaugcaaugacgugg
ggcucauggccuaccucggcaccaucaccaaaacgugcaacacaaugaaccaguuugugaacaaguucaacguccucuacgac
cgacaaggcauuggccggcgaaugcggggacuguuuuucugaugaugguucuggaagggaugguguguggggcucagaca
gcuguuccauggaccugaguaccacauucccuuuagagaaacucauuaauaaaagagcagccccuuaaaaaaaaaaaaaaaaa
aaaaaaaaaaaaaaaa 183 D49733 Sequence below.
aaaacccaauguuugguuuuaaagccaaaaauauaagggaagugcauagguuuggguuuuguuuuuuguuuuuucccgag
guccuugaucuuugcccccaaauuugagggcauaaaguaaucccucaguuaccuaaaaacacagccauuccuuugccauucc
acucuccuggauuggccgcuucugugcgcgggggagaggugacucacuauuacuacugaggaaaggggagccaguggugga
aguggggugagucacugaugggcagcagcuucagcccucccccccaacuuccuuggcucucuggggaugccugauccucuccc
ucacuuugcaccuacuuccccugguccccucaccacuacccuuugcccacccacucaaauucuuuggcucugcucuuuacucc
agaaggccaaaggcaagcuuagaguugaguaggcaggaaccaacauugugaagccccaggccagaaagggguguucugcaga
gugaggguuggcaugcuggcuccuccucaccauaccugcccccgccccuuuggguacaggauggcuccuuuaagagcagug
gauccaccccccuguagaggagggccuauuagagccucugccuggcugucagugacucaguguucgcgggaacgcugccuca
gccucaacaccagccaacccagaucccgaggugcgccagcgcccagcccagaucuccacgccugccaggagcgagcuucgccg
gcucgcuguccccccugagcagccucuguccuucuguccaagucccgcgcccuucucgggaccccugcccagcgggcagcacu
gucacccugccggccauggagaccccgucacagcggcgcgccacccgcagugggggcgcaggccagcucuaccccacugucgcc
cacucggaucacccggcugcaggagaaggaggaccugcaggagcucaaugaccgccuggccguguacaucgaucgcgugcgu
ucccuggagaccgagaacgcggggcugcgccuucgcaucacugagucugaagagguggucagccgagagguguccggcauca
aggcggccuacgaggccgagcugggggaugcccgcaagacccuugauucuguggccaaggagcgcgcccgccuccagcuaga
gcugagcaaagugcgugaggaguucaaggagcugaaggcucggugagugaggcccggccggccggcaccagggaggcagca
gucgccuguaacuggccaucuagucccucccuccccggaacugccucccgcggugacuggcagugccaannnnnnnnnnnn
nnnnnnnnnnnnnnnnnnnnnnnnnnnnnnnnnnnnnnnnnnnnnnnnnnnnnnnnnnnnnnnnnnnnnnnnnnnn
nnnnnnnnnnnnnngcuaggccagauauagaaagcuuucuguauuuaauacacaguacaugcaucauucaugucuacauaa
uuaagauaaaggaagcugcauuguuaaugggaaaaaaaauagggucugggaauguagugugccuagcauuuacgaacuucg
ggguuuggguuugaucccagcaucucacaaaccacguguaaucccagcacuuggaagguagaggccggaggauccgaaguu TABLE 3-continued RNA transcripts up-regulated during HF stem cell activation.

| SEQ ID No: | Access. # | Sequence |
|---|---|---|

uaaggucauucuugacuacuuagcaaauucggggcacccuaggauaccugagacccugucaugaauaaaaauaaauaauaaa
uaaaccaauaugggucuagguugagcagcagcuugggcaggguagggccggaaguuagccagguagagguugcaguccca
ggaggacccuggcugggagcagcaccucaguccccugcccaaccacaggggccaccgggucuuuccggaacuccugagggc
gcaaggccuugcucucucuggcccagccauggggaacgcggagggccggugaggcaggcggcaggcgggcgggcggggcgc
gggccgucauccccuccugcuccuuauuuuagcccaguguagagucugggccgccugucccucccccaggacaggggag
gaaauunnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnngaugccaacaauccuaauguaaugaugcccucuucugacagcugcggggac
cgcagagaggucccaucccagaugcacuccugaaaccugcuuuucuuuuucuagcaacaccaagaaggaggggacuuguug
gcugcgcaggcccggcucaaggaccucgaggcucuucucaacuccaaggaagcugcccugagcacugcucucagugagaagc
gcacauuggagggcgagcuccaugaccugcgggggcagguagccaagguaggccgcuguccugugaccccagugaccccacc
ugguccgacauaucauucggucccauuugccugcucaccuucacuucuccagucuagannnnnnnnnnnnnnnnnnnnnn
nnnnnnnnnnnnnnnnnnnnnnnnnnnnnnnnnnnnnnnnnnnnnnnnnnnnnnnnnnnnnnnnnnnnnnnnnnnn
nnucuagauggggacagccaucaccucuccuuuggcauuuccugaaccccucccaccucuccaugaacuuggcuuucuccc
ucucagcuugaggcggcccugggagaggcuaagaagcagcuucaggaugagaugcugaggcgaguggaugcugagaacagg
cuacagacgcugaaggaggagcuugacuuccagaagaacauuuacagcgagguaagcgucccgcuguacaggucuuucuuac
uguggacagcugggaggggucaccuaauaaugccaggcuaagcgagggcugcccgugccuggccgguggaguuacgacuuc
uggucucagcuucuaaggaaccauugcgauguucuaaucuaagugucuccccuuaaccuuucaggaacugcgugagaccaag
cgccggcaugagacgcggcuuguggagaucgauaacgggaagcagcgagaguuugagagccggcuggcagaugcccugcag
gagcugcgggcucagcaugaggaccagguggaacaguauaagaaggagcuagaaaagacauacuccgccaaggugcuggccu
cauccuguccucucccuggugcugcccuggggacgggugggugguggcagggggccagggaugccuuccucaggcccccag
cuccagguuccugcucucauaacugugugcucccugcagcuggauaaugccaggcagucugcugagaggaacagcaaccucg
ugggggcugcccaugaggaacugcagcagucucgaauccgcauugacagccucucggcccagcucagccagcuccaaaagca
ggugacccucaguuuaccccucccaccuuggcucuggucuaagcagauacugcagaagcccacugagaagggguggggag
ggacuccaggaccacaugcuaugguucugaaucugaugccugucuggcuuuccagggcucuccuuuagcuagcccugaucc
ucagagccucuauuuuacugugcaugaaggguuuuucauguuucuucugugccugccggagacugaaccagaggccucuug
cuugguagauaggugcuuucucacugaguuacaaacccagccgcauucccuacuuggagauagagcuucccuuggacugga
cauguagcucaguugguacagugcuugcuuauuauacacgauggccuggcuucuauccccaggaccnnnnnnnnnnnnnn
nnnnnnnnnnnnnnnnnnnnnnnnnnnnnnnnnnnnnnnnnnnnnnnnnnnnnnnnnnnnnnnnnnnnnnnnnnnnn
nnnnnnnnnnucuagagagagccuacagauccugagugucccucugccugccccugugccccucccucuucaucgacauca
gcccuugggagcucaucagacccuuugucuuccccgccccaguuggcagccaaggaggcaaagcugcgugaccuggaggacu
cgcuggcccgugagcgcgauaccagccggcgccugcuggcugagaaagagcgagagauggcggagaugcgggcgaggaugca
gcagcagcuggacgaguaccaggagcugcuggacaucaagcuggcccuggacauggagauccaugccuaucgaaagcugcug
gagggcgaggaggagaggugaacuaggaggggucuacagaacuugucaggggccucuggccgcaacuaccaugacuaacccc
gcaccgugucuccaccuuccccaggcugcgccugucccccagcccuaccucgcagcgcagccguggccgcgccucccucccacu
caucccagucucaggguggaggcagcgucaccaaaaagcgcaagcuggagucuuccgagagccggagcagcuucucgcagca
ugcucgcacuagcgggcguguggcgguagaggaagucgaugaagagggaaaguucgugcggcugcgcaacaaguccaacga
gguggccugugaaccaggguggucuuuucaguggcugggaguucuugguucucguggagcaucugucucccuaucugag
aauuuggagugugugguaguccugucaucuuuaaauuguugggaagaugcaugauauagggaugggugacccuugagcca
auagucuagguuugaugccagagguaguggugugaagccugucuuucuuuucuuuuucuuuuucuuuucuuuuucuuuu
ucucuuucuucucucuuuuuuuuuuuuccgauggggucuugcccagguuggcuuugaucucccuaguuaagcuguucccc
ugccucagccuccauaguagcuggaacugcaggngcacacuggcgnccagccuaccuaagcuccugagugagauaauccaag
agucgguugaacucccuguccuccuuccuccuuccuccuuccuccacccuacuucaggaccaguccaugggcaacuggcaga
ucaggcgucagaauggugacgauccuuugaugaccuaucgcuucccaccgaaguucacccuaaaggcugggcagguggugac
ggugaguggaagggcacuugggacucuggcuggaguggagaaguuggccucaggacaggagcauuaaaaauaagcacaucu
cuuaaaccaucuuuucccagaucugggcuucaggagcuggggccacccauagcccccuacugacuuggugugggaaggcgca
gaacaccuggggcugugggagcagccuucgcaccgcucucaucaacuccacuggagaagugaguauguugcagccgguagcu
ugcuggacaaggcucccccgggugaccauaaugggaacuagcuaccuccaacccaagggaaccugccuuggguuuaggaucg
cuuuccugagcccaagucccacccaguaagcaagccagaagucucccccaguagaauaaugggguggaagucagccagugagug
uuaauagcagacuccagcuuacagagcaccgagcucucaguuguguccuuuuugcgcgugcgugcgcgcgugugcacaugu
gcauguguuuauccuuaguccccagcaucagagguuggacaagguuguauaaaggcccgggacaguucuaagugguuacua
ugguagacaggcugcacagcccucaccccugacucuugggccugggcuuaugucccacaggaaguggccaugcgcaagc
uggugcgcucacugaccaugguugaggacaaugaggaugacgacgaggauggagaagagcuccuccaucaccaccgugugag
uggcagccgccgcugaggcccagcccacaagguagcccugccagccuagggcagcucucccaccuccaugccaaagucuuu
ucauuaaagaauguuuuggaaugccacuugcugcccuggccuuucuucucucuccucccucuaccuugaacagggaacccag
gugucugguaaggaagggaguggggacuugcugaugccauggauacuccacgguggcaguggacaggguucuggauuugu
guccugggaaggggcugggaggacagagguggccccagcccugccucucuuccucacucccauugcaugcacacuucucucc
ucucuccuuccacccuauugcaugcuucuccucagauuucccugcaacaauguucucuuuccuuccugucccucacaaauu
aagucucuccaucuuugcucuuccucuugauugccccauaagugucuaagauucaggagagaguuaaagccacagcucuuu
auuucgaaggcuuccuggcuauuuccccaucaugcccuuccucccagccacaggucucccaaguccccaucacuugguugu
cuggguacagacagaggucaccuuccugcccaauggccaggaagcuccaagagcccacagccuaggugccgguccuaagaag
ucagucccaaacucgcugucccuccugagccuugucucccuucccaggguucccacugcagcggcucggggaccccgcuga
guacaaccugcgcucacgcaccgugcugugcgggacgugugggcagccugcugacaaggcugccgguggagcgggagccca
gguggcggauccaucuccucuggcucuucugccuccagugucacagucacucgaagcuuccgcagugugggggcagugg
ggguggcagcuucggggacaaccuagucacccgcuccuaccuccugggcaacuccaguccccggagccaggugagucaucuc
ugcccuacagcaggacacugcucacugagcagcagggcagggcagcccaagggagugggguccccuccuugcagucccucu
ugcauccugccccuccugucugaaccccagacucgaggucagggcaaggcccagagugugagguuggggagacaaccccuu
uggggucagggagggagaggaagggccagccacugcugcucacaccucugccuucucuucucucuuagagcucccagaacug
cagcaucauguaaucugggaccugccaggcagggcugggggcagaggccaccugcucccccccucaccacaugccaccuccug
ucugcuccuuaggagagcaggccugaagccaaagaaaaauuuauccccugccuuugguuuuuuuuuucuucuauuuuuuu
uucuuuuucuaagagaaguuauuuucuacagugguuuuauacugaaggaaaaacucaagcaaaaaaaaaaaucuuuaucuca
auccuaaguccuuccccuuucuuuccuuguaucugccuuaaaaccaaagggcuucucuaggagcccagggaaaggacugcuu
uuuauagagucuagauuuuuguccugcugccuuggcuuuacccucaucccaggacccugugacaauggugccugagaggca
ggcauggaguucucuucaccagccuccuccaacagcuggcccacugccacgccagcugcagagaaauggggcgcagagagga
ugacugagaaggucaagccccuccccggcacuacacgaggccgaggcuccucugccugccuuaccuucuuccugcccuuccc
uagccuggggcgaguggauucccagaggcaaaucugccgugcuugcuuuuucuauauuuuauuuagacaagagaugggaau TABLE 3-continued RNA transcripts up-regulated during HF stem cell activation.

| SEQ ID No: | Access. # | Sequence |
|---|---|---|
| | | gacggggaaggagaagggaagaucaguuugagccuaccuuuucccagcuucugagccugguggcucugucucaaugaugg |
| | | agggcaaugucaaguggauacagggaagaguggggacgaaggcucccagagaugggagaaccugcugggcuggugag |
| | | aagucuagaggugcggcgauugguggcuacagcaaacacuaaggaacccuucaccccauuucccaucugcaccucugcucuc |
| | | cccuccaaaucaauacacuaguuguuuccaucccagaugcugugguguccuuuguugggugugaugugguuuucaggg |
| | | gcagacacaugcacacagaggugccacacauucacuauauauucacuacccagcuauaaaggugugguaugagggagacuucu |
| | | agaaaggucagcauaugugggugagcgaggggugucccuuccuaucccucauccauccagcaccuuuuaaaaggggccagca |
| | | auccacaugugcaucagacacaggagcacagagagacggaggguagaguagggcagaguagcagagcuuccuugcugcccug |
| | | uagucgcaggcucuugaucgugugaucgcu |
| 184 | X80899 | Sequence below. |
| | | gcggugcgaagcgggccuccgccaacauguacuacaaguuuagcaguuucacgcagaaguuggcuggagcuugggcuucgg |
| | | aagccuacaccccgcagggguuaaagccaguuuccacagaagcaccaccuaucauauuugccacaccaaccaaacugaccucc |
| | | agugugacagcaugauuauucugggaagaacaaaguuccagagcugcagaaguuuuuccagaaggcugaugguuuccac |
| | | cugaaacgaggccuuccagaccaaaugcuuuaccggaccaccauggcucugacacugggagggaccaucuacugccugaucg |
| | | cccucuacauggccucgcagcccagaaacaaaugagcuugccuguggaggacugguucacuuuguggcacaaacccuuugaa |
| | | uccucacguuucauguuuccacuuggauagucuacuuaacauuuugcaaacaaaggaaaagauaagaauacauuguuuug |
| | | auuuguuuaugguguggcagauggccugucagaugucagagcugguuugacaguuaaaacuauuguuuaaggaaaugucac |
| | | ugagccaucacugagcugugcuucugcuccugauuucccuggaguucugcaggaaaguugcucuccagcucauucguggcc |
| | | agccgugcucagggccucgggacucaggcggugucugagcgggaagcgaacgcggaagccuuuuggaguguaggugugauu |
| | | gaggaaggaaaacaaaagccagcggacagguggugaagugagggcugaguuagccacccuagggauucguccgccuugcaga |
| | | aaacauugagaggaaugauagcaaccugccucuauuuguggcaguugguuucaaaggguugugugucucgcccagaaccu |
| | | agggaaaugggguuuguuccaucgugggaggagcaccugucagugcugcacauuagacagcugugucaggacuucuccuu |
| | | uaauaaugcuguggcuuuacguuaugauugaccggacugcggaauaaacacuggaaucaaaaaaaaaaaaaaaaaaaa |
| 185 | D83203 | Sequence below. |
| | | cugagacagaacgaaacguccgcagauaacuacccguucuggcucuuguuaguucuauguguauggauaaugucuugggag |
| | | guuuugaaaugccacaagccuugcuggcccagggugcagcugccucugccguucagaccucagauuauaaggacagaacaca |
| | | gcacggaaguggggggaucagaaccaugggagauccaggacgaaggguccugugcgcaggugcggcaccgaauccuauauu |
| | | ugacauugaagcugucgucagcccaacuaguguguuauuaacauggaagcacaaugacucaggcgcuucagaauguagaaua |
| | | gagaauaagauggagagcaaucugacguuuccuguuaaaaaccagacaucauguaacauuacaggcuuaagcccagguacuu |
| | | cguauacauucuccaucaucucuguaacaaccaaugagaccuugaacaaaacuaucacaacagagcccuggccagugucugau |
| | | cuccaugucaccucuguggugugacacaggcucgucucaccuggagcaaugcaaauggcacugccuccuaccggaugcuga |
| | | uugaagaguugaccacacauuccucagucaauauuucaggucugaagccggggaccaauaauacguucgcuuucccagaauc |
| | | aaaugagacacaggcugacuuugcaguugcagaggagguccggaugccaaugguaccaagagaaucccagugaccaaccua |
| | | ucccaaccacacaagaauucucuugccucuguggacccacccucuggccaggaucccucccucacagagaucuugcuuacuga |
| | | ccuaaagccugauacucaguacaaugccaccaucuauucucaagcagcaaauggcacugaaggacagcccaggaacaaagugu |
| | | uuaaaacaaauuccacccagguuucugacguccgagcuaugaacaucagugccucaagcaugacccugaccuggaaaagcaau |
| | | uacgauggguccccguacuucaauugucuacaaaauacacguggcuggggggaccacuccgucaaccaaacugucaauaaga |
| | | cugaggccaucauccucggacucagcuccagcaccuuguacaacaucacaguucauccuuuccuggucagacggagggcac |
| | | accaggcuuccuccaaguguacacuuccccgaucaggucucugacuuccgagugacaaaugucagcacaagggcaauuggu |
| | | uuggcuuggaggagcaaugacuccaaguccuucgagauuuucaucaagcaggacggaggugagaagcaucgaaaugcuucg |
| | | acgggaaaccagagcuauaugguugaagauuuaaagccuggaaccaguuaccauuuugagauaauuccacgaggaccagacg |
| | | ggacagaagggcuguccaguacagugaaugggagcacugaccccagugccgugacugacauccggguggucaacauuagcac |
| | | cacugaaaugcaguuggaguggcagaauacggacgaugccucuggauacacuuaccauuuaguucuagagucuaaaaguggc |
| | | uccaucaucaggaccaacaguucucagaaguggaucacaguagggagccucaccccaggcaccuuauacaaugucacaaucuu |
| | | uccagaaguggaccagauccagggaaucuccaacuccauuacccaguacacacggcccagcagugugucccacauugaaguaa |
| | | acaccaccaccaccacggcagccauccgauggaagaacgaggacacagccucugcuuccuaugccuacuccguccuuaucuug |
| | | aagacuggagauggcagcaauguaaccagcaacuucacaaaagacccuucuauucuaaucccugaguuaaucccuggcgucu |
| | | cuuacacagugaagauccuuacacaaguuggggaugguacaacaucacugguaccugguuggaagcuguucuguacggaacc |
| | | ugaaucagugaccuccuuccacugugaaguggucccuaaggagccagcauugguucucaagugggccugccccuuuggcau |
| | | guacacaggcuucgagcugggggucaggagugauuccugggacaauaugacacgccuagagaacugcacaucggaugaugac |
| | | acagagugcaggacggaagucgccuauuugaauuuuucuaccucguacaacaucagcaucgccaccuugucaugugggaaga |
| | | uggcgcuucccgcccagaacaucugcaccacuggcaucacagacccaccuacuccggauggauccccuaauauuacaucgguc |
| | | agucacaauucaguaaagguuaaguucagcggguuugaagccagccacggaccuaucaaagccuaugcugucauccucacca |
| | | ccggggaagcugcccaaccuucugcagauguuuugaaguacacguaugaggauuucaaaaggggagccucggauacuuaug |
| | | ucacauaccucauaagaauagaagagaagggacagucucagggcuugucugaagucuugaacuaugaaauugauguggggaa |
| | | ccaauccacuacccucggcuacuacaacgggaggcuggagccucugggcuccuaccgggauuguguugcuggcuuuaccaau |
| | | auuaccuacaaccuucagaaugacggccucaucaauggggaugagagcuaugugucuuucaguccauauucagaggccgug |
| | | uucuugccccaggauccaggugucaucugcggagcaguguuggauguaucuuuggugcccuggccaucacagcuguggga |
| | | ggcuucaucuucuggagaaagaaaaggacagaugccaagaauaaugaaguguccuuuucucaaauuaaaccuaaaaaaucca |
| | | aguuaauccgaguggagaauuuugaggccuacuuuaagaaacagcaagcugacucuaacugugggguuugcagaggaauaug |
| | | aggaccugaagcugauugggauaaguuuaccuaaauacacagcugagauagccgagaacagagggaagaaccgcuacaacaa |
| | | uguucugcccuaugauauuucucgagucaaacuuucaguccagacccauucgacagaugacuacaucaaugccaacuauaug |
| | | ccuggcuaccauuccaagaaagauuucauugccacacaaggaccuuuacccaacacuuugaaagauuucuggcguaugguuu |
| | | gggagaaaaacguauaugccauuguuauguugaccaaaugcguggagcagggaaggaccaaaugugaggaguacuggccuu |
| | | ccaagcaggcucaggacuacggggacauaacuguggcgaugacaucagaagucguucuuccagaauggaccaucagagauuu |
| | | uguggugaaaaauaugcagaauagcgagagccauccucugcggcaguuccauuucaccuccuggccugaccacgguguuccu |
| | | gacaccacugaccugcucaucaacuuucgguaccugguccgggauuacaugaagcagauacccccgagucaccaauucugg |
| | | ugcauugcagugcugggguuggaaggacgggcacuuucaucgccaucgaucgccugaucuaucagauagagaaugagaaca |
| | | ccguggacguguaugggauugucuaugaccuucggaugcacaggccucugauggugcagacagaggaccaguauguuuucc |
| | | ucaaucaguguguuuuggauauuaucagagcccagaaagacucaaaaguugaucucaucuaucagaacacaacggcaaugac |
| | | aaucuaugaaaaccucgagccaaguuccuugaaugugacuauguugcuucauccacagcugaacgauuuuggauguugggu |
| | | ucuagguccuggcuguugcuggucugcuaggauccagggccuuguugacaucugggaagauguaaauugucccgcugaagg |
| | | ccgcaguuuuagauguggccacuagauggagccagagcacugguaugaaggagcaccagggccguguaaggcaaaagaggac |

TABLE 3-continued

RNA transcripts up-regulated during HF stem cell activation.

| SEQ ID No: | Access. # | Sequence |
|---|---|---|
| | | ccagaaaaagaaacuuaacuuguucacuccugagaaaccugcaagucaacaagccaaggaagugccuuugcaugcauuuggu<br>agccuuuccaaucccgcuuauuacauaauauguucauguucauggcaaaaaaaaaaaaaauaaaauaaaauaaauaaaaaagg<br>aaaacaaaauaaaaaaaaucuuagaacauu |
| 186 | Z20410 | gcccccucaagggcauccugggcuacacugagcaccagguggucuccucugacuucaaca<br>gcgacacccacuccuccaccugacgcuggggcuggcauugcccucaacgaccacuuuguc<br>aagcucauuuccugguaugacaacgaauuugcuacagcaacagggugugggaccucaugg<br>cccacauggccuccaagguaagccccuggaccaccagccccagcaaggcacaagaggaagg<br>agagacccu |
| 187 | AI839906 | uuuuuuuuuuuuuuuuucauauuaaacuuguaguuuuauucagguuugauuuuuaaca<br>aaugugucagggagagagcccacaggaaaggguaaagcccguggggcaaggccuuccca<br>gaugccugaggagggaucgugucccccucccccccuccucuucucaccaccccuacagggg<br>uuugggaagagacacaggcagggaaggggcugguccccagucuguacagugggugcuugg<br>gggugaaggacuauggagaacaggggaccagaucggggaugaguaggauaaagggcaca<br>agaccauuuaccagaauccagcuuucugauuccaaauugaauuaaaaagaaaaaaaggag<br>aggggaaccuaaaccacaagcaguacccaacucccuuucccccaucagggcugc |
| 188 | AI843448 | uuuuuuuuuuuuuuuuuagggaagaggcugaugccagauaaguuuuuauuauauuaaa<br>aaaaaaaaaaaaaccagugcaacuggaaaucagggugagucgcuggaggugagugagagu<br>cggaaggcccuccacaccucaguggugggcaggaucuggacccguagccuaagccuggucu<br>gauccagccgagaugcuggaaagcagagcacacggugggugcccaucagggcaaagagggc<br>aagagagcccacggcuccuccauaccgcuugcuagggucuccuguguaguagccauaugc<br>guaaaggacucgcccaauaauccaggccaggcccaggccagaagcuaugcgcggguggua<br>aacaccucccaccguuaggaaaaa |
| 189 | AW125336 | cggccgcgugaguuuugacugagcuucugcangaaguucanaugcaacuccauacauca<br>guucauuuucuagcauuaccacuggguuauuaucacgaauggccgauuuaauaagucccu<br>uuugcauccucggaauuccaggggcugaccacuuuuaaaccugggcagugcccauacca<br>ugcagcaaagcauugcgagugcugagcagcuacaccugcugaggcgccauugggcccccu<br>gaauacuaugggcaca |
| 190 | AW123802 | uuuuuuuuuuuuuuuuugaagggccauuggaguuuauuuacagacaaccuuaggugag<br>gccuuuuccucuaggaucuacaugcuuuugaaguuacuugguuucaggcuucuugucu<br>ccagcuucgagcuugagacucucaggaggcuggcgauaggcagggaaagccucccaggg<br>gcuguucaggucaaacuugcggaauucuugugccagcuccacugguucagccacuaccc<br>gcuuuaccucaucgucguaacgaagcucaacauagccagugaggggaaagucuuuccgga<br>aaggaugucccucgaagccauaaucugucaggauccuucuuaaaucaggugguuaaaa<br>aaaaaaaaaaaaaaaaa |
| 191 | AI835771 | uuuuuuuuuuuuuuuuugggggcagcgaacuuuauugaugguauucaaaaaaauagg<br>gagggcucccuaggcccccccuguuauuauggggucugggauggaaauuuugagggaa<br>augcucaauuuuggggggcccauuugggaaaaggcccccccuugcccaauguccuugcugg<br>ggugggugguccaagguuucuuacuccuuggaggccauuuuggccaagagguccaccac<br>ccuguugcuguagccguauucauugucaaaccaagaaaugagcuugacaaauuugucau<br>ugaaaaaaaugccaaccccggaaucaaagg |
| 192 | X53584 | Sequence below. |

gcuccucaucucacucgggccuaugccaaagauguaaaauuuggugcggaugcucgagccuuaaugcuucaagguguagac
cuuuuagccgaugcuguagcuguuacaauggggccaaagggaagaacagugauuauugaacagaguuggggaagucccaaa
guaacaaaagauggggucacuguugcaaagucaauugauuuaaaggauaaauacaaaaauaucggagcuaagcuuguucagg
auguugccaauaacacaaaugaagaggcuggggauggcaccaccacugccacuguucuggcacggucuauugccaaggaggg
cuuugagaagaucagcaaaggggcuaauccaguggaaauccggagaggugugauguuggcuguggaugcuguaauugcuga
acuuaagaaacagucuaaaccugugacaaccccugaagaaauugcucagguugcuacaauuucugcaaacggagacaaagaca
uugggaacaucauuucugaugcaaugaagaagguuggaagaaagggugucaucacagugaaggauggaaaaacccugaauga
ugagcuagaaauuauugaaggcaugaaguuugauagaggauauauuuccccauauuuuauuaacacaucaaaaggucaaaaa
ugugaauuccaagaugccuauguuuuguugagugaaaagaaauuuuccaguguucaguccauugucccugcucuugaaauu
gcuaaugcucaucggaagccauuggucauaaucgccgaagauguugacggagaagcucuaagcacgcugguuuugaacaggc
uaaaaguuggucuucagguuguagcagucaaagcuccagguuuggggacaacaggaagaaccagcuuaaagauauggcua
ucgcuacugguggugcgguguuuggagaagagguuugaaucuaaaucuugaagauguucaagcucaugauuuagggaaa
guuggagaggucaucgucaccaaagaugaugccaugcuuuugaaaggaaaaggugacaaagcucacauugaaaaacguauuc
aagaaaucacugagcagcuagacaucacaacuagugaauaugaaaaagaaaagcugaacgagcgacuugcuaaacuuucagau
ggaguagcuguguugaagguuggaggaacaagugauguugaagugaaugagaagaaagacagaguuacugaugcucucaau
gcuacaagagcagcuguugaagaaggcauuguucuaggaggggcugcgcucugcuucggugcaucccagccuuggauuca
uuaaagccugcuaaugaagaccagaaaauagguauagaaauuauuaaaagagcacuuaaaauuccugcaaugacgauugcua
agaaugcagguguugaaggaucuuugauaguugagaaaauucugcagaguuccucagaaguugguuaugacgccaugcuug
gagauuuugugaacauggugggaaaaagggaucauugauccaacaaagguugugagaacugccuuacuggaugcugcugggg
uggccuccuugcuaacuacagccgaagcuguagugacagaaauuccuaaagaagagaaggacccuggaaugggugcaauggg
uggcaugggagggggguaugggaggcggcauguucuaacuccuagaguagugcuuugcccuuaucaaugaacugugacagga
agcucaaggcagguuccucaccaauaacuucagagaagucaccuggagaaaaugacugaagagaaggcuggcugaccacugu
aaucaucaguuacugguuuccuuugacgauauauaaugguuuacugcugucauuguccaugccuacagauaauuuauuuug
uauuuuugaauaaagaacauuuguacauuccugaugcugguugcaagagccauauaccaguguccugcuuucaacuuaaau
cacugaggcaucucuacucuucugugagucaucaggacuguagcgcugugucaacaaaacauagagaguucagaagacagcc
uuucuguggaaggguggggaaugauuguguacaaaguagagaaguauccaauuaugugacaaccuuuguguaa TABLE 3-continued RNA transcripts up-regulated during HF stem cell activation.

| SEQ ID No: | Access. # | Sequence |
|---|---|---|
| 193 | M32599 | |

acagccgcaucuucuugugcagugccagccucgucccguagacaaaauggugaaggucggugugaacggauuuggccguau
ugggcgccuggucaccagggcugccauuugcaguggcaaaguggagauuguugccaucaacgaccccuucauugaccucaac
uacaugguccuacauguuccaguaugacuccacucacggcaaauucaacggcacagucaaggccgagaaugggaagcuuguca
ucaacgggaagcccaucaccaucuuccaggagcgagaccccacuaacaucaaaugggggugaggccggugcugaguaugucgu
ggagucuacugggugucuucaccaccauggagaaggccggggcccacuugaagggguggagccaaacgggucaucaucuccgcc
ccuucugccgaugcccccauguuugugaugggugugaaccacgagaaauaugacaacucacucaagauugucagcaaugcau
ccugcaccaccaacugcuuagccccccuggccaaggucauccaugacaacuuuggcauuguggaagggcucaugaccacagu
ccaugccaucacugccacccagaagacuguggauggccccucuggaaagcuguggcgugauggccguggggcugcccagaac
aucaucccugcaucccacuggugcugccaaggcugugggcaaggucaucccagagcugaacgggaagcucacuggcauggccu
uccguguuccuacccccaaugugucccgucguggaucugacgugccgccuggagaaaccugccaaguaugaugacaucaagaa
gguggugaagcaggcaucugagggcccacugaagggcaucuugggcuacacugaggaccagguuguuucuccugcgacuucaa
cagcaacucccacucuuccaccuucgaugccggggcuggcauugcucucaaugacaacuuugucaagcucauuuccugguau
gacaaugaauacggcuacagcaacaggguggguggacccucauggccuacauggccuccaaggaguaagaaacccuggaccaccc
accccagcaaggacacugagcaagagaggcccuaucccaacucggcccccaacacugagcaucucccucacaauuuccauccca
gacccccauaauaacaggaggggccuagggagcccucccuacucucuugaauaccaucaauaaaguucgcuugcacccac

| SEQ ID No: | Access. # | Sequence |
|---|---|---|
| 194 | AF035644 | agaagcuuccuaaggaacaagcaaguugaauagagaaaauagugaucaauaauaggcauu uuaguggucuuuuuaauguuuucugcugcggaacauuucaagauuuauugauuucccucc ucccccccauuuuuuucccaccacacucacacacgcacgcucacacacuuuuuauuugccauaa ugaaccguccagccccuguggagaucucuuaugagaacaugcguuuucugauaacucaca accccaccaaugcgacucucaacaaguucacagaggaacuuaagaaguacggagugacaa cuuugguucgaguuugugaugcuacauaugauaaagcuccaguugaaaaagaaggaaucc acguucuagauuggccguuugaugauggagcuccaccccccuaaucagauaguagaugauu ggcuaaaccuguuaaaaaccaaauuucgugaagagccaggcuguuguguugcagugcauu guguugcaggauugggaagggcuccugugcuaguugcgcuugcauugauugaaugcggaa ugaaguaugaagaugcuguucaauuuauaagacaaaaaagaagaggagcauucaauucca aacagcugcuuuacuuggagaaguaccgaccuaagaugcgguuacgcuucagagauacca augggcacugcuguguucaguagaaguagaagcaggcuggcuggaucguggcauuagagg gaa |
| 195 | Y00629 | Sequence below. |

auucagguuccucacagacccagggggugaggauguugcuuuuugcccacuugcuucagcugcuggucagcgccacagucc
cgacccagaguaguaagugagggggagggggugaggggaggggguugggagcgaaaaagacucugugaggaaaagcgggagggu
gguggugggcggaggugcagcaccccaaguuccgcccgcccugucc uagucccucccccgccuuuaccugggaccuugagccug
ggggaggucgggucucaccgcgcgccgcccccaggcccacacucgcugcgguauuucaccaccgccguguccccggcccggc
cucggggagccccgguucaucauugucggcuacguggacgacacgcaguucgugcgcuucgacagcgacgcggaaaauccga
ggauggagccucgggcgcgguggauugagcaggaggggccggaguauugggagcgggagacuuggaaagccagggacaugg
ggaggaacuucagaguaaaccugaggacccugcucggcuacuacaaucagaguaacgacggugagugcggcugggaucacag
cuaugaucacuccaugucccugagacgggccugggucaucuugacccgcugagacaaaguuucauccaaacgccuacccag
aaccucagacaaaaaagccccgcagaguucugcuuagguuugggguuguacuuuuguuucucuuuuguuuugagauaucu
acuaacauugggcaaaguggccacagguggcgcucaucagcguaucccuuccagaaucucacacgcugcaguggauguacgg
cugcgacguggggcccgaugggcgccugcucccgcggguauugucaggaggccuacgauggccaggauuacaucucccugaa
cgaggaccugcguuccuggaccgcgaaugacauagcucacagaucucuaagcacaagucagaggcagucgaugaggcccac
caacagagggcauaccugcaagguccuugcgugggaguggcuccauagauaccuacggcugggaaaugagacacugcagcgcu
caggugcccuggagagcucuccucacuuuucccucugcgguuuggggggaaauccuugagguauaaccucaggggcagaacgc
uguucagcgggcacagcgcggaggaggagggagagggacucccaaaacugcuuuuccccuguagggauucuaauccuuaaca
aaagcagaucaggcucgacaauggcccuggacccaugggggggaggggcucuuucucaggcccucccuccuugcccuacucag
ugucucuauagucagacuccagcuuuucucaaucucuuggcccucauccagcucaggaccagaagcccuucccaugagucug
cagagaccuggagccuccuguccauguuguccugcucacauccuaaggcaucccuaagagcagauccuccccaggugcaggug
cucuagcuggugucuagaugauggacaccauaaucccaccgcaguccuccugucccacccaggacggucacaugaacacugc
ugaguccccagaagaaagcaagaugccucaucccuuucaacucucucccucagacccuccaaaggcacaugugacccaucaccc
uagaucugaagaugaagucacccugaggugcugggcccugggcuucuacccugcugacaucacccugaccuggcaguugaau
ggggaggagcugacccaggacauggagcuuguggagaccaggccugcaggggauggaaccuuccagaagugggcagcuguc
guggugccucuugggaaggagcaguauuacacaugccauguguaccaugaggggcugccugagccccucacccugagaugg
gguaaggagggugugggugcugaacuggggucagggaaagcuggagccuucugcagacccugaguuggucauggcucagag
cugggaucauaacccucaccuucauuuccuguaccugucccuucccagagccuccuccauccacugucuccaacaugguaauc
auagcuguucugguugucccuuggagcugugaucauccuuggagcugugguggcuuuugugaugaagaggaggagagacacau
agguaggaaagggcagggucugaguuuucucucagccuccuuuugcagugugcucugcuccuuaaugggaaacauagccac
acccacauugcugcaguccccaacugggucagcugucaguuccgggaacucccuagggcugguguuucucuggucucucau
ggcuuuucuucucacagguguaaaaggaugcuaugcucauguucuagguaagugcgagagaggggcaggggacacccuugu
cccugaggcucucaggauggagcugggauuuguuccagccccauaaaucuccucuugccacauccucucugucuccucugugu
gccuuguuaucucuucuacugcaggcagcaagagcuuccagaccucugacuggccucagaaggcaugaaaaucccuggggggg
gcuggugagagauggcucaguggguaagagcacugacugcucuucugaagguccagaguucaaaucccagcaaccacauggug
gcucacaaccauccguaacgagaucugacucccucuucuggagugucugaagacagcuacaaguacuuacauauaauaaa

| SEQ ID No: | Access. # | Sequence |
|---|---|---|
| 196 | AW125380 | uuuuuuuuuuuguucccuugaaagccagauguuccaaaaaguagccugcuccauuguucu ucucagucucauagcgacugccagcgucaauccacacucccaccgugcagguagcaugcg aggacugcuccgaggccacacgcagcccguuguccaagaugcugaccugggucuccggca cgcucuggagggccugggcgaagguugcgguaccccgcaaggcagguaaccucagcaggg ccggcgagcggcgggugcgccucgugccg |
| 197 | U68564 | Sequence below. |

ggugcuuaauguuuugaccuguagagguccucacuuuucgucauggcgcugaagguggcgauagcugcuggcggugcugc
aaaggcaaugcucaagccaacucucccucugccguccuugggagguucuggcugcccauguggcccccgaaggagcauuucc TABLE 3-continued RNA transcripts up-regulated during HF stem cell activation.

| SEQ ID No: | Access. # | Sequence |
|---|---|---|

ucacaacaaacaauuccuccaucugcuaaguaugguggcggcauacagugacuaugaucccaggggauggcaucggcccag
agcucauguugcauguuaagucuguauucaggcaugcaugugugccgguggacuuugaagaggugcauguaagcuccaacg
cugaugaggaggacauccgcaaugccaucauggccauccgccggaaccguguggcccugaagggcaacauugaaacaaauca
uaaccugccaccaucccacaaaucucgaaacaacauccuucgcaccagccuagaccucuaugccaacgucauccacuguaaga
gccugccaggaguggugacccggcacaaggacauagacauccucauuguacgggaaaacacagaaggcgaguacagcagccu
ggagcaugagagcguagcaggagugguggagagcuugaagauuaucaccaaagccaagucccugcgcauugcugaauaugc
uuucaagcuggcccaggagagugggcguaagaaagugacggcugugcacaaggccaacaucaugaaacuggguggauggacuc
uuccuccagugcugcagggaaguagcagcccacuacccucagaucaccuuugacagcaugauuguagacaacacaacaaugca
gcugguaucccggccucagcaguuugaugucauggugaugccuaaucucuaugguaacauugucaacaacgucugugcagg
gcuaguuggaggcccaggccuuguggcuggggccaacuauggccauguguaugcaguauucgagacagcuacaaggaacac
aggcaaaaguauugccaauaagaacauugcuaacccgacugccacacugcuagcaagcugcaugaugcuagaccaccucaagc
uccacuccuaugccacuuccauccgcaaagcugucuuagcauccauggacaaugaaaauaugcauaccccagauauuggagg
ccagggcaccacaucccaagccauccaggacaucauucgucauauccgcaucauuaauggacgggcuguggaggcuuagcua
ucccuacaguuuugcucagcuugucuguaggacucucuucucacuuuagcacuccagcuagcuuggggacaggacccaga
auaaagccacuucuguuccagaaaaaa 198 AW125346 uuuuuuuuuuuuuuuuuguucuuaauagaaaacuuuauuuucacugauaaugucacugua
acauaauuucauagcagaccugugcaaaagaucccacaucaccaaugucuccaagagauu
ucacacacuucugggcaggacgcacagcucugccccacccccguguugacagucaacau
uuuaccccgcuaugaguacagaaaggcgaggcaucauaacgaagccgccugaaggcagc
gugagcugaagucggacgcuugccaccucugaaugaauggucaccacagcaacagcacau
gguugccucagugugcucagggugggucuuugaaaaaacgucccacuauguaaauaugcu
gcacuuaucccuucaacauugu 199 X61232 See above (same Accession Number).

200 D20333 gauccuguauaugugguuuuggggagcuaugauaaguuuuauggcaaacgguugguau
uguuaacuuuuuauugucaucaaaaguucauaaaaguccuauuaaucccccauauucunnn
ncugcccuuaacucugguauacaccaaaaagaaaucuuuacuuuccuuguuuuaucauua
uaaaaauaaaguauuuugcuaguauggaaa 201 AB025218 aguccgcgucccggcgucggcccgucccgcaccauggugacgcucgccgagcugcuggcg
cugcuggccgcgcugcuggccacggccucgggcuacuuugucagcaucgacgcgcacgcc
gaggagugcuucuucgagcgggucaccuccggcaccaagaugggccucaucuucgaggug
gcggagggcggcuuccuggacaucgacguggagaucacaggaccagauaauaaaggaauc
uauaaaggagaccgggaguccagcgggaaguacacauuugcagcccacauggaugggaca
uacaaguucugcuuuagcaauaggauguccacuaugacuccaaagauaguaauguucacc
auugacauuggggaggcucccaaaggacaagacauggagacagaagcucaucagaacaag
cuagaagaaaugauuaaugagcuggcaguggcaaugacagccguaaagcacgaacaggag
uacauggaaguccgggagagaauacacagagccaucaaugacaacacaaacagcagagug
guccuuugguccuucuucgaagcucuuguucuaguugccaugacauugggacagaucuac
uaccugaagagauuuuuugaaguccggaggguuguuuaaaaggccuuuuccuguugaucc
caaauucaugauuuacu 202 U84411 Sequence below.

gcauuggcucugggcugcggccggcucggcgacgcuccucgggcagcucacugcauggucgucuggugccccgccgccug
cauccccgccgccgccccgcgacgcccaccgccgccugcccugccgccgccugcgccgccucgggaccggcuguaugauu
aggccacaaucuucaaugaguagacauauuccucaguucugugguguucucggucacacauuuauggaguuucugaagggc
aguggagauuacugccaggcacagcacgaccucuaugcagacaagugaacuguagaaauucauuacuacuccaccaagaaacc
cccauaagaguggauaaccuggacacaggcguguugaauugaaaucugcacagcauuugagaagagcucagaccuggauggg
guaaaccucagugccacuuccuuuguauugccucuaguauuacugggauugaagagucacugcuucuuguuuaggagguuc
auuucauuggcccguuucucccaauuucauacucaagcacugagaauuucaaguggaguauaucgaauaucgaaguagacu
ucagguuguuuuuugguuuuguuuuguuuuuuuuuguuuugguuuuuuuuuuuuuucuguuuugguuuaaaucau
uucuguauucaauuuuuuaauucuuucauaacccuauugggguguuuuuuaaacuaaauuaacauggcucgaaugaaccgc
ccugcuccuguggaagucacauacaagaacaugcgauuucuuauuacacacaauccaaccaaugcgaccuuaaacaaauuuau
agaggaacuuaagaaguauggaguuaccacaauaguaagaguaugugaagcaacuuacgacacuacucuuguggagaaagaa
ggcauucauguucuugacuggccuuuugaugauggugcaccaccauccaaccagauugucgaugacuggcuaagucuugug
aagauuaaguuucgugaagaaccugguugcuguauugcuguccauugugucgcaggccuuggcagagcuccggugcuugu
ugcccuagcauuaauugaagguggaaugaaauaugaagaugcaguacaauucauaagacaaaagcggcguggagcuuuuaac
agcaagcaacuuuuguaucuggagaaguaccguccgaaaaugcggcuccgcuucaaggauuccaauggucauagaaacaacu
guuguauucaauaaaacuggggugccugaugccauugccuuggaaguggaacuucagaugggaccugauuugucaugcaua
uuacccaaugugucggcuuacugaauaagucuacugcagcuccacaggaauacugaaaaccagucuuaccaggccacaagu
uugacagaauugcaaccucuauauuugggcuaugaucaacauguuuggacacuuagcaaaagauuuuugcuguucagcauu
uaaaaugugcuuauuauuuguaccaauugaccuuuccuaaaauaagguauugaguuaugucauuaaauguacuccugugcc
agaauauuauuagucuauaaggaauuuagaaggauuaggugccaaaauacccagcacaauacuuguauauuuuuagcaucau
acagaaccaaaauugcaggaacugagaacucucagaccauccaugguguauuccuucagucauuucaaacacugcagggcuc
cucucguuaucugccugcucacucuguuuacaucucccacacuuaugccagaauacgucagguuugcuuagccauccuuua
uuuuuuuuauuuuuuuuuuuaacuaagucuugcgcugauuauuuaauaugucugucucauuuuguuuuguuuugggaaa
ccucugucugaaaaaucaacuuuguuacagaagcacauaucuucaacaaugucuccagacaaaaagccuuauaguuaauuua
auguuugcacucagaagugcaaccuaacagggagggccugaaaaagaaacgagaggaggcuauuaaauauuuuuaguaauau
guugccuuugucaugugcagaacauguagaguaugcucuuaauuuaguaaauauuuuuaagacauagagauacauguguag
cuaacccauucuuauucaaaauucuggaauuuuguguuuuccnauaccuaucaggaaguuuccagcuuguuugaauuaugg
cuuuccucuucccaaucucuugcaaaaaagacaaagugggaugaaucugcuagugaacugagcagaaauguuuuauaacgcc
uuuugagcuauguaacuuaauaauuggauacuugaucauuuguuuuauuauguaaucggauaaaauggugauguguauua
aaguuaguucaaccauauauuuauacugucugggaaugugugguuauaguucugugggagaaauaguuugucaguguuca TABLE 3-continued RNA transcripts up-regulated during HF stem cell activation.

SEQ ID No: Access. # Sequence ccagcuuguaaaaacuuaguaugagagcuucaacauuuaaauaaaugaugaaccgcauucgucacugaggacacuuuugccu
aaaauuaacuuaauuuguagaaaacaauggauucaguuaauaucauuucaauuuauggaaaaaauuguuagguugccaag
ugcuuuuuauuaaaaguuucucuuuaaaggucuagauaauugugaaucaguugaauguugggcaccgaggggaaacaguuu
guaauagaugaucuagauuuuucaguucaguuccaucagucacuuguagcucugcaauuuccagaccaguuucucauuuu
uaaguucauuacaugccuguauauauuuugaaauuaacuugaaccugaguauuuggcacaugauggcuuaauaaauuuuaa
cuuuc 203 M62362 Sequence below.
acgcuccccaaccuccaccuccccucgcucggccucuauaugcucccgggcucccuaguguuggcuggaagugggugacuua
gaggcuuaaaggaggggcgccuaaccacggaccacgugugugcgggggcgacagcgccgccgggguggggcugagcgcugc
aagccggguucgccuugcagcgcaggagucagugggcguugcgccacgaucucucuccacuagcacuaugcucccgccccac
ucaccgccuuggaaagucacaggagaaggcgggcucuaagacccagcaggcaccauccuacuggcgccuucgauccgagaccc
guuuggacaccaggggcgaugccgacccucuauaaaagcgguccccgcgcgggccuggccauucgcgacccgaagcugcgc
gggcgcgagccaguuggggcacuggguggcggcggcgacagcggcgccacgcgcaggcuggaggccgccgaggcucgcca
ugccgggagaacucuaacucccccauggagucggccgacuucuacgagguggagccgcggcccccgaugagcagucaccucc
agagcccccgcacgcgcccagcaacgcccgccuuuggcuuuccccggggcgcgggccccgcgccgcccccagccccaccugc
cgccccggagccgcugggcggaucugcgagcacgagacgucuauagacaucagcgccuacaucgacccggccgccuucaacga
cgaguuccuggccgaccucuuccagcacagccgacagcaggagaaggccaaggcggcggcgggccccgcggguggcggcggu
gacuuugacuacccgggagccccggcgggcccccggcggcgcggucauguccgcgggggcgcacgggcccccucccggcuacg
gcugugcggcggccggcuaccuggacggcaggcuggagccccuguacgagcgcgucggggcgcccgcgcuacggccgcugg
ugaucaaacaagagccccgcgaggaggacgaggcgaagcagcuggcgcuggccggccucuucccccuaccagccaccgccgcca
ccgccaccgccgcacccgcacgcgucucccgcgcaccuggccgcccccacuugcaguuccagaucgcgcacugcggccagac
caccaugcaccuacagccuggccaccccacaccgccgcccacgcccgugcccagcccgcacgcugcgcccgccuugggugcug
cgggccugccuggccccgggagcgcgcucaagggcuuggccggugcgcaccccgaccuccgcacgggaggcggcggcggugg
cagcggugccggugcgggcaaagccaagaagucgguggacaagaacagcaacgaguaccggguacggcgggaacgcaacaaca
ucgcggugcgcaagagccgagauaaagccaaacaacgcaacguggagacgcaacagaaggugcuggaguugaccagugacaa
ugaccgccugcgcaagcggguggaacagcugagccgugaacuggacacgcugcggggcaucuuccgccagcugccugagagc
ucccuuggucaaggccauggcaacugcgcgugaggcgcgcggcugcgggaccgccuugggccggccccuggcuggagaccca
gaggaugguuucgggucgcuggaucucuaggcugcccgggccgcgcaagccaggacuaggagauuccgguguggccugaaa
gccuggccugcuccgcguguccccucccuuccucugagccggacucggugcgucuaagaugagggagucaggccguggugg
uuucuccuugagaccgagagacuuuuccgcggagcugagcugggggcccggcaguacuaguauuaaggaaguaaccuugug
ccuuggauacucaaaacucgcuccuuuuccuaccgaguaggggagcaaaaaugugccuugauauuuuauuuggaggauuc
cugcuuccucucgggccucagcuggcccccgugagaaaaaugaagggugcaggcccagggcaggaggaagauacaggaagcu
gagaucccggcagugcccugagcugccccucagucccugucuuuagaggggagggacuuagguguuggggauuugagucug
uguccucacccccagcuacagggagguggagggcuccuaaucccuugcuuuuugcaccuccaccuacauccccccccccccac
ucagcuuacaacaggccagguuuccugggugaguucauggagaaugggggcaccacccccagucagacagaaagcugaguug
ugaguuagccaugugguaggagacagagaccuagguuucugggcuuuguggggugggggauaggaggacacggggaccau
uagccuuguguguacuguaugucgccagccgcuguugcugaaggaacuugaagcacaaucgauccaucccagagggacugg
aguuaugacaagcuucccaaauauuuugcuuuaucauccgauaucaacacuuguaucuggucucugugucccagcggugcc
uugugcaauggcagugugcacgucuaugcuaaaccaccauuuuauuuggucuuuuguuuuguuuugguuuugcucugauu
cuugccaaacugagacucuucacuaacggcugggggaaggagcugagugaggcucucauucuuuuugguuuagggauguu
uggguuuuuucgucugccucccagaggaccaaugaaaugaagugggcuucccccucuccccuaguuguccaaggguguaug
uaguagugggucuuagcuuccuccggcuaagacuuaggcuuccccacccacccaaccccauccccaacggcccuggcucugg
gucuggaaagaaggccaccuccagccaguucauacacacaccccuguggcugggagcagggcuggaccgcuuccuucucuuc
uuuuuuggggggggggacacaaaguuucaugcuagaugucguauguauuauaucuauaauauaaacauaucaaacucaa 204 AA032310 gaagcucagugucgugaaauggaaaccaaaccuuggagccaucgcugaguauaaaaaaa
ggaagauuuauauucngcaaagaguagccgaacuggacaaaauuacuucugaaagagaua
auuuuagacaagcauaugaagaucuucgaaaacaaaggcugaaugaauuuauggcugguu
uuuacguaauaacaaauaaacuaaaagaaaacuaccagaugcucacauugggaggagaug
cugaacuggagcuuguggacaguuuagauccuuuuucugaaggaaucauguucaguguuc
ggccaccuaagaaaaguuggaagaagaucuuuaaccucucaggaggcgagaaaacccuua
guuccuggccuuaguguuug 205 M94087 Sequence below.
gccgguuugaguugugcgcucgggugucccuuuccucuuccccucccgcagggcuugcggccaccauggcguauuagaggc
agcagugccugcggcagcguuggccuuugcagcggcagcagcaccaggcucugcagcggcaacccccaccggccuaagc
cauggcgcucuucacgaaauccagcagcaguguugcuguaacggacaaagauaccuucgaguuaagcacauuccuggaaucc
agcaaagccccacaacaugaccgagaugagcuuccugaacagcgaaguguuggcgggggacuugaugucccccuucgaccag
ucggguuuggggggcugaagaaagccuaggucucuuagaugacuaucuggagguggccaagcacuugaaaccucaugggguuc
uccagcgacaaggcgggcuccucggaauggccggcuauggaugauggcuuggccagugccucagacaccggcaaggaggaug
ccuuuuccgggacagauuggauguuggagaaaauggaucugaaagaguuugacuucgaugcucuguuucgaauggaugacc
uggaaaccaugccagaugagcucuugaccacguuggaugacacaugugaucuuuuugccccucuaguccaagagacuaauaa
ggagcccccucagacagugaacccaauuggccaucucccagaaaguuuaauaaaagucgaccagguugccccuuuacauuc
uugcagccuuuccccuguuccccagggguucugucuuccacuccagagcauuccuuuaguuuagagcuaggcagugaaguu
gauaucucugaaggagacaggaagccugacucugcugcuuacauuacucuaaucccuccauguguaaaggaggaagacacuc
ccucugacaaugacaguggcaucuguaugagcccggaguccuaccugggcucuccccagcauagccccuccaccuccagggc
cccaccagacaaucugccuucuccagguggguucccgugggucuccucggcccaaaccuuaugacccaccuggaguuaguuug
acagcuaaagugaagacugagaaauuggauaagaagcugaaaaagauggagcaaaacaagacagcagccacuagguaccgcca
gaagaagcgggcugagcaggaggcccucacuggcgaguguaaggagcuagaaaaaaagaaugaggcucugaaagagaaggca
gauucucuggccaaggagauccaguaucugaaagaccugauagaagagguccguaaggcaagggggaagaagagaguuccgu
aauaggguagucaggugcuuugugcuuguacauagucuuguguugcuguguuugcuguaauaaauuauuuuguagugaaa
gu TABLE 3-continued RNA transcripts up-regulated during HF stem cell activation.

| SEQ ID No: | Access. # | Sequence |
|---|---|---|
| 206 | AI847609 | uuuuuuuuuuuuuuuauguagggaaguucauauuuuauuuguccagugacauuuuuuac<br>aguugaauacaaguuaaaggccugcuugcacaccaaagccagguccuuuggguggguucag<br>ucaaagaaguaaggccuccagcuggcucacaacagaagcggccacuccuuggcccugguuu<br>gggaacuuuuccagcuuugaguucaucaauaaucucuucaauauccuugggugucagauc<br>cucauaguaguugucauuuauuugaaccaucggugcauuuacacaggccccuaaacauuc<br>cacuucuauaagagugaaaaguuugucagguguagucucuccaaccuuuauuccaa |
| 207 | AI853294 | uuuuuuuuuuuuuuuuugggggugaauauagccaaguauuccauuuauuaacaaaauagu<br>cuuagcaagggagagcucuguucaccccacaagaggccccgcagccgaggccggcccgaag<br>ccccagcgcugcugcguaagaccgggagggagggaagguguuggggagaagacuuguauu<br>aagucuuuaauccuagccaccgcaggaacccacggaaaccuaaugccagcuuuggcgauu<br>gcuggcucaggucugggacauggcgaagggagugcucugauccuagggcucccugagucc<br>ccagccugccccaacagagcuccuaaaguugucuggucugcugacuugaggacugguaa<br>gcuuuggagggauccaucaaggauuccccgaccccaccccuaucgccagggga |
| 208 | M33934 | Sequence below.<br>ccucugcggcgcgguccucggagcggcgcgguucucggagccacgcgucugucuuccuccguggucauggcggacuaccug<br>auuagcggaggcaccucuuacgugccggacgacgggcucacagcgcagcagcucuucaacugcggggacggccucaccuaca<br>augauuuucucauucuuccuggguauaucgacuucacugcagaucagguggacuugacgucugcucuaacuaagaagauua<br>cacuaaagaccccauugguuuccucacccauggacacugucacagaggcuggaauggccaucgcgauggcgcuuacaggagg<br>uauugguuucauccaccacaacugcacaccugaauuccaggccaaugaaguucggaaagugaagaaauacgaacagggauuc<br>aucacugaccccgugguccuuagccccaaggaucguguacgcgauguuuuugaggccaaagccaggcauggcuucugugguu<br>auccccaucacagauacaggccggauggggagucgauuggugggcaucaucuccucaagggacauugauuuccucaaggagg<br>aagagcaugaccgguucuuggaagagaucaugacuaagagggaagauuuggugggucgccccugccggcgucacucugaaag<br>aggcaaaugagauucugcagcgaaguaaaaagggaaaguugcccauugugaaugaaaaugaugagcugguagccaucauugc<br>ccggacagaccuaaagaagaaucgugauuaccccuggccuccaaagaugccaagaagcaacugcugugugggggcagccauu<br>ggcacucaugaggaugacaaguauaggcuggacuuacuggcccuugcugguguggauguagugguuuuggacucuucccag<br>ggaaacuccaucuuccaaaucaauaugaucaaauacaucaaggagaaguaucccagucuacaggucauuggaggcaauguag<br>ucacugcugcgcaagccaagaaccucauagaugcagguguagaugcuuugcgagucggcaugggaaguggguuccaucugca<br>ucacccaggaaguguuggccugugggcggccccaagccacagcaguguacaaggucucugaguaugcccgucgcuuuggug<br>uuccuguuauugcugauggaggaauccaaaaugugggucauauugccaaagcuuuggcucuuggggcuuccacagucauga<br>ugggcucccuccuggcugccaccacugaggccccuggcgaguacuucuucucagaugggauccggcugaagaaauaccgagg<br>uauggguucucuugaugccauggacaaacaucucagcagccagaaccgauacuucagugaagcugacaaaaucaaaguggcc<br>caaggaguuucaggggcagugcaggacaaggggucuauccacaaguucguuccuuaccugauugcuggcauccagcauucc<br>ugucaagacauuggugccaagaguuuaacccaagucagagccaugacguacucgggggagcuuaaauuugagaagaggacau<br>ccucugcucagguggaagguggcguccacagccuccauucguacgagaaacggcuuuucugaaaacagauccaguauaugcc<br>uugaauuuuucaauaaaaguuugggaaaaaaaaagugaaaaaaaaaaaaaaaaaaaaaaaaaaaaaaaaaaaaaa |
| 209 | X16202 | gugugggugcagagcugggggucagggaaagcuggagccuuuugcagacccugagcugcuc<br>acggcugagagcugggggucauuacccucaccuucauuuccuguaccuguccuucccagag<br>ccuccuccauccacugucuccaacauggcgaacguagcuguucugguuguccuuggagcu<br>uggccaucauugcagcugugguggcuuuugugaugaagagaaggagacacacagguagga<br>aagggcagagucugaguuuuu |
| 210 | AI661431 | acaggaggggaaggccaaagcaagaaugaaagucccccgccccguaucaccacgggcacu<br>cggggucacccucaggaacaugcagucucugcacgugaggaaagaaacacgcagagaugg<br>acgagcacuuuuacacccuaauaaaauuagaugcacuaaccacagaccccccu |
| 211 | AI839109 | uuuuuuuuuuuuuuuuuuaaaaaaaaaaauggcaucuuuuauucaucaaucccuguuacac<br>acugaaauacaugcaucuuucuuauguuacuuagcaacguccuuucuauccuuucaccca<br>uaaaucagucugaugaauucaucuuuaaauucaagaaguuuuucuuuuugaaacgcuacu<br>uacauuuuauugucucaauaucaaagccaaucuagagauuuauucuuccuacaggugaaa<br>uagauguuaauacgggaacagucaguacauguucaagaugacaucaaaguuaugcccuaa<br>gcagauauuucaaggcaauaucaugccacuagcucugagacucuaaguaucacugauagu<br>acuaaaagguagaagucagcuucaaaaacacacucuugcaauggacacugcucaugaugu<br>cuaagauuguucacucccacagucaugauuucagaugcacaguuuuuuuugcuuuccuga<br>gcauucgguuugac |
| 212 | AI849135 | uuuuuuuuuuuuuuuuuuaagagugucaccaaagcuuuauuuacaugcgucaucaucucuu<br>uuacaaacuagauuaugguuuuaaauggaauacacaggcaauaucuacaaacgccacggg<br>aaguacgcaccuccauuccaccgggaaggggcagauucccaaaucaaacugguuuugauc<br>cuugagaagaaaggcggcagagcuaacucacggcagcguaugguuagacaagguccucag<br>uacccagaaugcagcaggauugcgucugccucaaaccagacgaccaacugcugcaggugu<br>uuaaacauggccacgcgccacacgaaauucuaguuuguguggguagaagcaagaaaaaa<br>aaaaaaccauggcgccucgugccg |
| 213 | M32459 | gguccggauaguaaacugcucccuuacaucuccuuaaauauaaaguaaggaaaaagaaaa<br>aacucaguucggguaaccaaguucaacaaguaauccuuggggccgcugugguaucgccaa<br>aaucuacauaguaucucuuauuaaaauguuuugacgaaaauguaacaauuacgguacuua<br>augguaacaauguggcugaggaagcaauaguuaacaaagaggagcuaagcuaugcaacaa<br>accagauuucuauuggucacaaauuugaaguugagaccuguuauccaauuaccaaguacu<br>uccgcauacaucaucauaggcauuugaagauuucaaccaaucaggagcauguuccuucua<br>uaaaggaacccagaaccuaaccucugcauuuccuauuucuuuguagaaauggcucguacg<br>aagcagaccgcucgcaaguccacuggcggcaaggccccgcgcaagcagcuggccaccaag |

TABLE 3-continued

RNA transcripts up-regulated during HF stem cell activation.

| SEQ ID No: | Access. # | Sequence |
|---|---|---|
| | | gccgcccgcaagagcgccccggccaccggcggcgugaagaaaccucaccgcuaccguccc<br>ggcaccguggcgcugcgcgagauccggcgcuaccagaagucgaccgagcugcugauccgc<br>aagcugccguuccagcgccuggugcgcgagaucgcgcaggacuucaagaccgaccugcgc<br>uuccagagcucggccgucauggcucugcaggaggcgagcgaggccuaccuugugggucug<br>uuugaggacaccaaccugugcgccauccacgccaagcgugucaccaucaugcccaaggac<br>auccagcuggcccgccguauccgcggcgagcgggcuuaauaggcacgcuuucuacacugg<br>cacguaaaccaaaacggcucuuuuaagagccaccuccauuauccaccaaagaugcuugaa<br>guacaaguugugagaguuuucuaggguuuccuauuauagccuuucuugacaaugugagca<br>ccacccgacgaagcagucugag |
| 214 | AI841389 | uuuuuuuuuuuuuuuuuggacuucugcggcuuuuauuuuugcauguaaaccacuggggg<br>agggggaucuugaugguggcacccuagagauuacacuggaguuccgagggcuccagaca<br>cuagcugggaagucaggugacagaaacaaugauucagaccaaucacaugauugcaaaacu<br>gggucuccagcagggauucugguggucaggugugggaugccuaaggaagcagugacauggg<br>aggggcacgcacugggcuggccuugagcugcugggaugacaucagggauagaggaccuag<br>cagcugguggcuccagggaucuccgguccaugcuuuauuuggccaggggguuccugaagg<br>accugccagcaaacuuggcuuugcugcccagcucuuccucaauucugaggaucugauugu<br>acuu |
| 215 | X03039 | Sequence below. |

auucuaaggaucaugucugcgagucaggauucucgauccagagacaauggccccgacgggauggagccggaaggcgucaucg
agaguaacuggaacgagauuguggauagcuuugaugacaugaaucucucagagucccuccuccgugguauuuaugccuaug
guuuugagaagcccucugccauccagcagcgagcuauucuuccuuguaucaaggguuaugaugugauugcucaagcccagu
cugggacugggaaaacagcuacauuugccauaucaauucugcagcagauugaauuagaucuaaaggccacucaggcuuuggu
ucuggcacccacacgugaauuggcucagcagauacaaaagguggguuauggcauuaggagacuacaugggugccucuuguca
ugccugcauuggggggcaccaaugugcgugcugaggugcagaagcugcagauggaagcuccccauaucaucgugggguacccc
uggccggguguuugacaugcuuaaccggagauaccugucccccaaauacaucaagauguucguacuggaugaagcagaugaa
auguuaagccgaggguucaaggaucagaucuaugacauauuccagaagcucaacagcaacacacagguaguuuuguugucug
cuacaaugccuucugauguccuugaggugaccaagaaauuuaugagagacccuauucggauucuugucaagaaggaagaau
ugacccuggaggguauccgccaauucuacaucaauguggaacgagaggaguggaagcuugacacauugugugacuuguaug
agacgcugaccaucacccaggcagucaucuuuaucaacaccagaaggaagguggacuggcucaccgagaagaugcaugcccga
gauuucacuguuucugccaugcacggagauauggaccaaaaggaacgagaugugaucaugagggaguuccggucuggcucu
agcagaguauuaauuaccacugaccuguuggccagaggcauugaugugcagcaggucuccuuagucaucaacuaugaccuuc
ccaccaacagggaaaacuacauccacagaaucggucgagguggucgguuuggucguaaggguguggcuauuaacaugguga
ccgaagaagacaagaggacucuucgagacauugagacuuucuacaacaccuccauugaagagaugccccucaacguugcugac
cucauuugaggggcuguccugcgaccuggcccuagcccaggguucaguccuggggugggggcuaaggaagagcuggaggggg
gaggggagggagccaagggauggacaucuuguuuuuguuuuggcuuuuuuuuuuuuuuguuucaguuuuuuuucucuau
gaauaaaugucacuuuuugaggc

| SEQ ID No: | Access. # | Sequence |
|---|---|---|
| 216 | AW049795 | uuuuuuuuuuuuuuuuuugccaggauauauuuauuacugaaaguacaagcaacugagguuu<br>acccugggaacacccacaaugaaacguguaucuucccuguuucucagaugcugccuccuu<br>ccacagagugaguuuucguuuaaaacucauaaugaggagaaggcagggggcuccaccccu<br>uuccuguucaaucugaagacugaauugggcuacacugggauggagauuucaggugcugca<br>ggucagugucaaccaaggguucgugugucaggaacucuggcugguaagaugacacaaagg<br>cuucaugcugaagcucagggagguccagggagccuggcagaauggaaucaucauggucau<br>caucaaacgucugugucuggaaggcuucaaggcucauaauugcaucauucucuggcaguu<br>ccugagagagcugccccuuccugguuugcacgcaucaaauuucacccacugguaauuga<br>cacaguuuugagcuucgggacaacucuuaaucagguuguggaugguuggaugagaaaacc<br>caaagaagucggcaccgcauga |
| 217 | D87691 | Sequence below. |

auuguaacagaagaaggaaaggaaaagaaaguuaacauugacuuugaaccuuucaaaccaauuaauacaucauuguauuugu
gcgacaauaaguuucauacagaggcucuuacagcguuacuuucagaugacagcaaguugguuuuauuguaauagacggaa
guggugcucuuuuuggcacgcuccaaggaaacaccagagaaguccugcacaaauucacuguggaucucccaaagaaacacgg
cagaggaggucaaucagccuugcguuuugcccguuuaagaauggaaaagagacauaacuauguucggaaaguagccgagacu
gcugugcagcuguuuauuucuggagaccaagugaauguggcugguuugguuuuagcuggaucagcugacuuuaaaacuga
acuaagucaaucugacauguuugaccagagguugcaaucuaaaguuuuaaaauuaguugauauauccuaugguggugaaaa
uggauucaaccaagcuauugaauuaucuacugaaguucucuccaacgugaaguucauucaagagaagaaauuaauaggacga
uauuuugaugaaauuagccaggacacaggcaaguacuguuuuggaguugaagauacacuaaaggcuuuggaaaugggagcu
guacaaauucuaauagucuaugaaaaucuggauauaaugagauacguucuucauugccaaggcacagaagaggagaaaauuc
ucuauuuaacuccagaacaagagaaggauaaaucucacuucacagacaaagagacuggacaggaacacgaacugauagaaagc
augccucucuuggaaugguuugcuaacaacuauaaaaaaauuuggagcuacacuagaaauugucacagauaagucacaagaag
gaucacaguuugugaaaggauuugguggaauuggagguaucuugcgguaccgaguagauuuccagggaauggaguaccaag
gaggagaugaugaauuuuuugaccuugaugacuacuagguagucgacauggguccggcaaccgugccucacccuccagcau
ucaacccaaggagcauacccgugguggaguccaacagaucccugccuuacaauuggagcauuuccagaacuuaauccgugag
cauuggauacugaaaagaaaagugaaacaaaaccagacccaacccuacacuugguuugucguggugucagcgcagcagccg
acaacuaagucucu

| SEQ ID No: | Access. # | Sequence |
|---|---|---|
| 218 | AI117211 | cagaggagucauuguugcugugguggcuuuugugaugaagaggaggagaaacacagcgua<br>agccagcugccuggaguggacuaagugacagacaaugucuucacacaucuccugugacau<br>ccagagcccucaguuuucuuuagucaaguaucugauguucccugugagccuaugggucaa<br>agugaagaacugugcagcccagccugcccugcacacagaacccugucccugcacugcccu<br>ggguucccuuccacagccaaccuugcugcuccagccaaacacugggcgacaucugcaucc |

TABLE 3-continued

RNA transcripts up-regulated during HF stem cell activation.

| SEQ ID No: | Access. # | Sequence |
|---|---|---|
| | | ugccagcuccaugcugcccugagcugcagcuccucacuuccacacugagaguaagaaucu<br>gaaugggaccuugauucuuaacauccugaccgaggguugauuucuuguuaauuucaugga<br>uugagaauacuuagaguuuugguuugucuugauuuuuuuucaag |
| 219 | Y00520 | ugaauaaaaacgaggagccgaagauucuaggggcuacagcugcgcuuuugcagcacuga<br>acaugguuccggguacucaagauauugcguuuguguuuggagagguguagauuguagauu<br>ccagccgagaagaccaggaaaagauaaggauaaagaaugucauauaucucaggagcuaga<br>ucacuucccgaugaacaaguaagaauugccucaacaaaaauggauggaauuggaccgaaa<br>aaagccauucagcuucguuaucgauuagguaucagugggaacaucaagaugaaugaguua<br>acuaaguaucagaucgaccaaauugaacaaaugauagcucaagaucauguuguucauugg<br>gaauugaagaggggagaacgagcagacaucgaacgauuaauuucuauuucucguuaucgu<br>ggaauucgucaucaagauggaucgcccuuacgcggucaacgaacucauacuaaugcaagg<br>acugcucgcaagcaaauucggaaaugaaagaaggcuaccgaaagaacaagcaacggauuu<br>cgcgcucaucccuugcuaaagcgcauacguuuucuugcuccuugguacuugucugaucaa<br>ucacacuguucauuaguucacuugauuuuucguucgaugucuugaaccgcuuacuaauca<br>cguauacguauaguaggccccccuucgccacuccacgucuggcccgucuuggucucgcuca<br>cuucgcccgccuaucguaucggcucggcuucguccgucaagcgacagcuucugccucuga<br>cggcuucacuaucgcucaugacugguaguacucuauguaguagucggccuuuguuaagcuu |
| 220 | AA638002 | uauaaccauguuagaagcggaaguuggccugaaaaccugaggcuuaggcuucauagcugg<br>gcuguagauuggauuuaaacccaguuggagugcaaagucauggugugcucaaggugauga<br>cagugaacagaguaug |
| 221 | Z22661 | caugggccuccugagaga<br>uccuuagauccagguuagugcauaggaaagugucccccacuaccuacagcuaagggauu<br>gggguggugggaucaugguggagggccguggugaauacuagcgaugucccccgcuacccg<br>ugcgucugccuccagggugccccuccaaccaggaugaggcucuucaucgcucuuccuguc<br>cugauuguggucguagccaugaccuuggaagguaagaaagagccuuggaagguaagaaag<br>augcuuggaagugugaaguuggccuugugccugcggcccaggcuuagaagacccucgagg<br>agggcucugaggucccuuucugugucaucauuccacuaccgcccucccaucguccccccau<br>cccaccugccaggugccuuauuuuugugucaaagugggugcugaaggaggcaacucuguc<br>cagaaaagacgcaguaaccaaugaccuaggauaccacccuuuggaauuggcuaaucuucc<br>uagaaggggcggacgguaaaaacaaggaggugagaggugcaguaaaaucaaguguccaau<br>acccucccccaugcuaaugaguuugcucgcaacccucucgcggcaggcccagcccccgcc<br>caggcggccccggauuuguccggaacauuggagagcauaccggauaaacugaaggaguuu<br>gggaacacuuuggaagacaaggcccgggcagccauugaacauaucaaacagaaggaaauu<br>uugaccaagacccg |
| 222 | X99644 | Sequence below. |

cagcgccuggggcgcggcgggcgucggcccaggagacgcguggcggcgcucggccucgcggcaucggcggcugccuggccg
uuggcggcgagcgcacuugcgccugcgcagcgggguccgugccccuccuccccugggcggcccccccacccccccggcggcg
ugugaauggcggccucggcggcagcgacugcagcggccucggccgcgacggccgccucggcggccucugguagcccagggguc
gggcgagggcucggcgggcggugagaagcguccggcugcuuccucagccgcggcggccucugcagccgcgucguccccugc
ggggggcgguggcgaggcgcaggagcuucuggagcacugcggcgugugucgcgagcgccugcggcccgagcgggauccucg
gcugcugcccugucuacauucggccugcagugccugccugggccccgcuacacccgccgcagcgaauaauucgggggauggc
ggcucggcgggcgacggcgcuaugguggauuguccagugugcaaacagcagugcuacuccaaagacaucguggagaauuau
uuuaugcgugauaguggcaguaaggccucuucugauucccaggaugcuaaccagugcugcacuagcugugaagauaaugcc
ccagccacuagcuauuguguggagugcucugaaccacuuugugagaccuguguggaggcucaccagcgggugaaauacacca
aggaccacacugugcgcuccacaggaccugcuaagacucgagauggagagcgaacagucuacuguaaugugcacaagcauga
gccccucgugcuguucugugagagcugugacacacucaccugccgcgacugccagcucaacgcucacaaggaccaucaguac
caguuuuuggaagaugcagugaggaaccaacguaaacucuuggcuucacuggugaaacgucuuggggacaaacaugccacac
uucagaaaaacaccaaggagguucgaagcucgauccgccaggugucugaugugcagaagcgagugcagguugaugucaagau
ggccauucugcagaucaugaaggagcugaauaagcgggggucgaguucuggucaaugaugcccagaaggugaccgaggguca
gcaggaacgucuggagcgccagcacuggaccaugaccaaaauucagaagcaccaggaacacauuuugcguuuugccucuugg
gcucuggagagugauaacaauacagcucucuugcucucuaagaagcugaucuauuuccagcugcaucgggcccucaaaauga
uuguggauccuguggagccucauggugagaugaaguuucagugggaucucaaugccuggaccaagagugcugaagccuuug
gcaagauuguggcugagcguccugguacgaacuccacagguccugggcccauggcuccuccaagagccccaggcccucuaag
caagcaagguucuggcaguagccagcccauggaaguacaagagggauauggcuuuggucagaugaucccuauucaagugca
gagccgcauguaucaggcaugaagcggucccgcucuggugagggagagguaaguggccucuuaaggaaggugccacgugug
agccuugaacgccuggaucuggaccucaccucugacagccagccaccagucuucaaggucuuuccuggaagcacuacugagg
acuacaaucugauuguuauugagcguggugcugcugcagcagcugcuggucaggcugggacugugccaccaggagccccug
gugccccaccccuuccuggcauggccauugucaaggaagaagagacagaagcugcuauuggagcucccccggcugcccccga
ggguccugaaaccaagccuguguugaugccucugacugaagguccuggugccgagggaccucgucuagcuucaccuagugg
caguaccagcucaggcuuggagguggugguccucugagguuacuucagccccaguaagugggccagguauccuggaugacag
ugccacuaucugccgagucugccagaaaccaggugaccuggucauguguaaccagugcgaauuuugcuuccaccuggauug
ccaccucccugcccugcaggauguuccaggggaggaauggaguugcucacucugccacgugcucccugaccuaaaggaggaa
gauggaagccucagccuggauggagcagauagcacuggugugguagcuaaacucucaccagccaaccagcggaaaugugagc
guguucuccuggcccuguucugccaugaaccaugccgucccuugcaucagcuggcuaccgacucuacauucuccauggagca
gccugguggguacccuagaccugaccuugauucgugcucgccuccaagagaagcugucaccuccuuauagcucccccccaggag
uuugcucaagauguggggccgcauguucaaacaguucaacaagcugacugaggacaaggcagauguucaguccaucaucggcu
ugcagcgcuucuuugagacacgcaugaaugaugccuuuggugacaccaaguuuucugcugugcugguagaaccaccaccau
ugaaccuucccagugcuggccuaaguucucaggagcucucuggcccuggugauggccccugaagcuggggcucuuguggguc
agcccaguccagcucuggucucuguauuucaccccauacccuguccuuugguggccugacuccuguucuugcuggcccca
ucguccccucagucccucuucacaaaaugguuuuuacuucuguggauuuaauaaaaacuucacugagucaguuaaaaaaaaa
aaa TABLE 3-continued RNA transcripts up-regulated during HF stem cell activation.

| SEQ ID No: | Access. # | Sequence |
|---|---|---|
| 223 | AI843895 | uuuuuuuuuuuuuuuuuaaaaauaauuucauuuuuuaauauucuguacaaaauuucucaa<br>ccuaugaaaauaaaguuugcaaaagucaaaguaguacaugggccugcccuggagccaggc<br>ccagccggaucuacacuauguacaggucucccagggugagccucagcuagggaaaagcca<br>cuaaggugccuacagagcaagagggugccaucgggccagugcagccucugcaauuuccag<br>aucugccacuagaggucggcauggucccugauugcuugucaggcucacccucuggaagacc<br>acagccaaugacaaagguccucaagggaaagcuuuggggucuagcuggaagugacggugg<br>guccgccgcccaggcgcaggagcaucugcuggcaguccagcaguaaccggugaucgccaa |
| 224 | M38724 | uccgucguaaccuguugaguaacuauggaagacuauaucaaaauagagaaaauuggagaa<br>gguacuuacggugugguguauaaggguagacacagagucacuggccagauaguggccaug<br>aagaagaucagacuugaaagcgaggaagaaggagugcccaguacugcaauucgggaaauc<br>ucucuauuaaaagaacuucgacauccaaauauagucagccugcaggaugugcucaugcag<br>gacuccaggcuguaucucaucuuugaguuccuguccauggaccucaagaaguaccuggac<br>uccaucccuccugggcaguucauggauucuucacucguuaagaguuacuuacaccaaauc<br>cuccagggaauuguguuuugccacucccggcgaguucuucacagagacuugaaaccucaa<br>aaucuauugauugaugacaaaggaacaaucaaacuggcugauuucggccuugccagagcg<br>uuuggaauaccgauacgaguguacacacacgagguagugacgcugugguaccgaucucca<br>gaaguguugcugggcucggcucguuacuccacuccgguugacaucuggaguauagggacc<br>auauuugcagaacuggccaccaagaagccgcuuuuccacggcgacucagagauugaccag<br>cucuucaggaucuucagagcucugggcacuccuaacaacgaaguguggccagaagucgag<br>ucccugcaggacuacaagaacaccuuucccaaguggaagccggggagccucgcaucccac<br>gucaagaaccuggacgagaacggcuuggauuugcucucaaaaaugcuagucuaugauccu<br>gccaaacgaaucucuggcaaaauggcccugaagcacccguacuuugaugacuuggacaau<br>cagauuaagaagauguagcccucuggauggaugucccugucugcuggucguaggggaaga<br>ucg |
| 225 | AW122989 | uuuuuuuuuuuuuuuuuacuaggcaaagaauuuuauuaacccuuuccaaacuuuauuccc<br>aggcuucuucagcuuuauuugccgcaaagaaugaauuagguauagcgaaaacugaaaaga<br>gcugcaguguccgggggcuugggcuuaaaaauauuagagaucuagauuuuaucagaucca<br>uaauaaacaaaaaaauuuuaaaaagcagucaugauauaaaauagcagcuccuguaauuuc<br>ugcaaguaucaccuucuucagaaguugcuucaauucaguuugccucauucuuagaagccu<br>caucaaaauucuccaccagaucuggaacuucaucaucaucauccucuccaguagcaaggg<br>gugcuuuuccauccacagauuguuugggcagagcuucagccagucuccuuaaacuaguca<br>ggcugucugcaccaagcugguugaggaugcugggaagcauuucugucagcugcuuuguc |
| 226 | AI844810 | uuuuuuuuuuuuuuuuuauucaugcuugccuagggauggggaauagaucauucaauaaaa<br>acauacaguaaaaacagggggugggggagggggaaggcuuaucauguacaauguuuaaacu<br>acaauagugauguaccuuaauuacuuccaugcacacaagucuaacauuacaaguuuuuaa<br>aaaauaaacaccauuaagacuucuaggagcauuuuauaauaaauuccuaauuuuuucuuu<br>guagauagaucaagcaccuccaaaauacagauuccuauacacagugagcacuuuacuuaa<br>cguacauggacagccucaggacgagcugacgucucggaucagcucggcaggcaacaaacc<br>auagugccaaauggaaagaagggcaguugcaaauaaacuuaaaacuaaguuaacuuuuau<br>aauuaaauacagaaaauauacugauuugcuaaaaauaaauaagaugugauguauuuaaca<br>cuucacuauaaagaaugaacaccaugacauccucgugccg |
| 227 | AA940430 | agaagaaggaggagugggaccgcaagcaugaggaugcuaguagggaguaugagaaaggca<br>ugaaagaguaugaaggaggaagaggggacucaucuaaaagggacaagucuaagaagaaaa<br>agaaaguaaaagcaaagauggaaaaaaaguccacuccuucccggggcucgucauccaagu<br>cuucauccaggcaguugagugacagcuucaagagcaaagaguuuguguccagugaugaga<br>gcucuucaggcgagaacaagagcaaaaagaagaggaggcggacgaggacucugaagagga<br>gcuagccaguaccccuccaagcucagaggacucugccucgggaucugaugaauaaaggag<br>ggaauucccaccccgucacagcuccagucucucacauaguccuuggauucugugccaucu<br>gaguaacugcucuugguggcuuccacugcccugaggcuuugagggaag |
| 228 | M38381 | Sequence below. |

aucgucguaaucguuugcagacuucucgccgucgccuuguaagcuuugucuucgccuugcaagcuuugucuucaggguug
gaaagaugagacauucaaagagaacuuacuguccugacugggaugaaagagacugggauuauggaacauggagaagcagcag
cagucacaaaagaaagaagagaucacauagcagcgcccgugagcaaaagcgcugcagguacgaucacuccaaaacgacagaca
gcuauuaucuggaaagcagauccauaaaugagaaagcuuaucauagucgacgcuauguugaugaauacaggaaugacuacau
gggcuacgagccagggcaucccuauggagaaccuggaagcagauaccagaugcauaguagcaaguccucugguaggagugga
agaagcaguuacaaaaguaaacacaggagucgccaccacacaucgcagcaccauucacacgggaagagucaccgaaggaaaaga
ucgaggaguguagaggaugaugaggaggucaccugaucugucagaguggagacguacuaagugcaagauaugaaauuguu
gauacuuuaggugaaggugcuuucggaaaaguggugaaugcaucgaucauaaagugggagguagacguguagcaguaaaa
auaguuaaaaauguggauagauacugugaagcugcucaaucggaaauacaaguuuggaacacuugaauacaacagacccccc
auaguacuuuccguuguguccagauguuggagugguuugagcaucgaggucacauuugcauuguguuugaacuucugggg
cuuaguacuuaugauuucauuaaggaaaacaguuuucugccguuucgaauggaucauaucaggaagauggcauaucaaaua
ugcaaaucuguaaacuuuuugcauaguaauaaauugacucauacagacuugaagccugaaaacaucuuauuugugaagucu
gacuacacagaggcuuauaaucccaaaaugaaacgugaugaacguacuauaguaaauccagauauuaaagugguggacuuug
gaagugcaacauaugaugaugaacaccacagcacauugguaucuacaagacauuauagagcaccggaaguuauuuuagcccu
cggguggucacagccaugugaugucuggagcauaggauguauucuuaucgaguauuaucuuggauuuacaguuuuuucga
cucaugauagcagggaacauuuagcaaugauggaaaggauucuuggaccacuaccaaagcacaugauacagaaaaccaggaaa
cgcagauauuuccaucaugaucgauuagauugggaugaacacaguucugcuggcagauauguuucucggcgcuguaaaccu
cugaaggaguuuaugcuaucucaggaugccgaacaugagcuucucuuugaccucauugggaaaauguuggaguaugauccc
gccaaaagaauuacucucaaagaagcccuaaagcauccuuucuuuuacccacuuaaaaagcauacgugauuuauaaacacagu TABLE 3-continued RNA transcripts up-regulated during HF stem cell activation.

| SEQ ID No: | Access. # | Sequence |
|---|---|---|
| | | gcucugaaaggaaucuuacagacuguaucagucuagcuuuuaauuaaguuauuuuguauagcuuaauuuguaaaacauuuu auguuuuuuagaugcuuuauuaaauacauggccaaaccaaauaacaucuuucaguaauuauagaaugauuuauuuggaaua aaauuugugcuuaugaauguaaaaaaa |
| 229 | AF014371 | ggacucgcgacaagcguccucagcgcgaagaggcggacucggaguccucgccuugagccu ugcaucugagaaguuccagguacuuuguacaacugcaucccagaaccuguguguuuucag caccuuuauaagugauggcugccaucaggaagaaacuggugauuguuggugauggagcuu gugguaagacaugcuugcucauagucuucagcaaggaccaguucccagaggucuaugugc ccacgguguuugaaaacuauguggcggauaucgagguggaugggaagcagguagaguugg cuuuaugggacacagcuggacaggaagauuaugacugccugaggccucucucuuauccag acaccgauguuauauugauguguuuuuccauugacagcccugauaguuuagaaaacaucc cagaaaaauggacuccagaagucaagcauuucuguccaaaugugcccaucauccugguug ggaacaagaaggaccuucggaaugacgagcacacgagacgggaguuggccaaaaugaagc aggagccgguaaaaccugaagaaggcagagauauggcaaacaggauuggcgcuuuugggu acauggaguguucagcaaagaccaaagauggagugagagagguuuuugagauggccacga gagcugcucugcaagcuagacgugggaagaaaaagucugggugccucaucuugugaagcc uugugaacgcagccucaugcgguuaauuugaagugcuguuuauuaaucuuaguguaugau uacuggccuuucauuuaucuauaauuuaccuaaga |
| 230 | Z30939 | uucaagaccgaccugcgcuuccagagcucggccgucauggcucugcaggaggcgagcgag gccuaccucgugggucuguuugaggacaccaaccugugcgccauccacgccaagcguguc accaucaugcccaaggacauccagcuggcccgucgcauucguggggagagggcguaaauu aggguagugagugaauuuggaccccaaaggcucuuuucagagccacccacauuuucuaua aaaggcuguauaucgauaagcuuuuauaaaccccacucagcaacucc |
| 231 | U28208 | uuaugugauaaaaaaauucaacuugguauuaacuuaacuaagggccuuggugcuggugcu uugccugauguugguaaaggugcagcagaagaaucaauugaugaaauuauggagcauaua aaagauagccauaugcucuuuaucacagcagggaugggugguguacuggaacaggugcu gcaccgguaauugcaaaagcagccagagaagcaagagcgguaguuaaagauaaaggagca aaagaaaaaaagauacugacuguuggaguuguaacuaagccguucgguuuugaaggugug cgacguaugcgcauugcagagcuuggacuugaagaguugcaaaaauacguagauacacuu auugucauucccaaucaaaauuuauuuagaauugcuaacgagaaaacuacauuugcugac gcauuucaacucgccgauaauguucugcauauuggcauaagaggaguaacugauuugaug aucaugccaggacugauuaaucuugauuuugcugauauagaaacaguaaugagugagaug gguaaggcaaugauugguacuggagaagcagaaggagaagauagggcaauuagugcugca gaggcugcgauaucuaauccauugcuugacaauguaucaaugaaaggugcgcaaggaaua uugauuaauauuacugguguggagacaugacucuauuugaaguugauucugcagccaau agagugcgugaagaaguggaugaaaaugcaaauauaauauuuggugccacuuuugaucag gcgauggagggaagaguuagaguuucuguucuugcaacuggcauugauagcuguaacgac aauucaucuguuaaucaaaacaagaucccagcagaggaaaaaaauuuuaaauggccuuau aaucaaauuccaacauuagaaacaaaagaauaugcuucaacugag |
| 232 | AV218217 | ugaucaggucacauuccggugccuuccacccccuauggcacgggcgccccgccuugccau accacagcucccuccaggcuuagaccuggcuucaccgcauuucaggugcuauaccccccc cugcuuuucccccauugcccuuaaaugccccucggccccuccaucccccggaacaggg uggcacuugccacucucaggaccaccuugccaaggagaauaaaccgaauccuguugcu |

Thus, the transcripts identified in this Example, the proteins they encode, and the pathways in which the proteins participate contribute significantly to HF stem cell activation. Accordingly, anagen can be induced by activation of these transcripts, proteins, and pathways.

Example 9

Molecular Pathways Activated During Induction of Epidermal Cells to Differentiate into HF Stem Cells The gene expression pattern of HF stem cells was analyzed as described in Example 8 and compared to non-bulge basal keratinocytes. 157 genes were differentially expressed in the HF stem cells, as assessed by microarray analysis and quantitative polymerase chain reaction (qPCR). A group of selected genes with increased expression in HF stem cells is depicted in Table 4. A group of selected genes with decreased expression in HF stem cells is depicted in Table 5.

TABLE 4

Genes up-regulated in HF stem cells. Numbers in parentheses are the fold increase as determined by quantitative real time PCR.

| Gene Name/ Protein name/ GenBk Acces #. | Fold Incr. | Sequence | SEQ ID No. |
|---|---|---|---|
| | | Cell surface proteins | |
| Cd34/Cd 34 antigen AI847784, AI173145 | 43 (189) | uuuuuuuuuuuuuuuuucacucaucacguuuauucagaagagaauacac<br>ccaauccucucaucucuggaaaguuuuguuccuagccaucauuaagauc<br>aggaccccuguucuccccuuaaccccaggagaggaagcuuauagucuuu<br>guagauauucugaaccucugaucacaaaggguuauaaaaauagugaaggg<br>guuuggacuaggaaaggcacagacugaaaggaaucugccaggggacuga<br>ggccacagcucccccaggagucagaggaagggggaagucacguauuuua<br>uagaaggccaagggccucagagcaagaguauuccuuugaagagcuca | 233 |
| | | Calcium-related | |
| S100a4/ S100A4 (mts) X15986 | 35 (144) | ugguggagcaggucucaggaaucucuucgcuucagcuucaaucauggcc<br>uguggucuggucgccagcaaccugaaucucaaaccuggggaaugucuca<br>aaguucggggagagguggccucggacgccaagagcuuugugcugaaccu<br>gggaaaagacagcaacaaccugugccuacacuucaauccucgcuucaaug<br>cccauggagacgccaacaccauuguguguaacaccaaggaagaugggacc<br>uggggaaccgaacaccgggaaccugccuuccccuuccagcccgggagcau<br>cacagaggugugcaucaccuuugaccaggcugaccugaccaucaagcugc<br>cagacggacaugaauucaaguuccccaaccgccucaacauggaggccauc<br>aacuacauggcggcggauggagacuucaagauuaagugcguggccuuug<br>agugaagccagccagccuguagcccucaauaaaggcagcugccucugcu | 234 |
| | | Transcription Factors and related genes | |
| Id2 helix-loop-helix protein AF077861 | 11 (25) | gugguucuucggcgccagguucgcccgcuucugcccuuagguaacauuc<br>ucuaaacugcguuucucucccaaucuuuugcaggcauuuggggacuuuu<br>ucuuuucuuuuuacuuucucuuuuucuuuugcacaagaagaagucuaca<br>agaucuuuuaagacuuuuguuaucagccauuucaccaggagaacacguu<br>gaauggaccuuuuuaaaaagaaagcggaaggaaaacuaaggaugaucguc<br>uugcccaggugucuuguucuccggccuggacugugauaccguuauuuau<br>gagagacuuucagugcccuuucuacaguuggaagguuuucuuuauauac<br>uauucccaccauggggagcgaaaagguuaaaaaaaagaaaaaaaucacaa<br>ggaauugcccaauguaagcagacuuugccuuuucacaaagguggagcgu<br>gaauuccaggaggacccaguauucgguuacuuaaaugaagucuucgguc<br>agaaauggccuuuuugacacgagccuacugaaugcuguguauauauuua<br>uauauaaauauauauauauugagugaaccuuguggacucuuuaauuaga<br>guuuucuuguauaguggcagaaauaaccuauuucugcauuaaaauguaa<br>ugacguacuuaugcuaaacuuuuuauaaaaguuuaguuguaaacuuaac<br>ccuuuuauacaaaauaaaucaagugugguuuauugaauguugauugcuug<br>cuuuauuucagacaaccagugcuuugauuuuuuuuuaugcuauguuau<br>aacugaacccaaauaaauaccaguucaaauuuauguagacuguauuaaga<br>uuauaauaaaaugugucugacaucaa | 235 |
| Id4 AJ001972 | 4 (12) | cgaugaaggcggugagcccggugcgccccucgggccgcaaggcgccguc<br>gggcugcggcggcggggagcuggcgcuacgcugccuggcggagcacggc<br>cacagccuggguggcucggcagccgccgccgccgcugcggcggccgcgcg<br>cugcaaggcggccgaggcggcggccgaugagccggcgcugugccugcag<br>ugcgauaugaacgacugcuacagucgccugcggaggcucgugccuacca<br>ucccgcccaacaagaaagucagcaaaguggagauccugcagcacguuauc<br>gacuacauccuggaccugcagcuggcgcuggagacucacccugcuuugc<br>ugagacagccgccaccgcccgcgccaccucuccacccggccggggcuugu<br>ccggucgcgccgccgcggaccccacucaccgcgcucaacacugacccggu<br>gagaagccuuggcgggcacccugggcaucgcgggaaagguggcggggcg<br>gcgagauacggguggucuugcuccucucagggaaugacagccgcuucuc<br>ccgucuccaccgagagccgccugcugggcuuggugauccacugguccccu<br>gagccgagggcgguugggcuuggagcccugcgucuccggagugucccuu<br>gcaucacaggaggcuuccccagcuucgggcucgggugggggacucugcuc<br>accugccuaguuuuccaggacgucuccuggguggugggcgacacugugau<br>augcgcacucuaaccgcuuuuccccuugguguuggguugcuguuccagg<br>ccggcgccgugaacaagcagggugacagcauucucugccgcu | 236 |
| Peg3/ Paternally expressed gene 3 zinc finger protein AF038939 | 12 | Sequence below. | 237 |

acuagucucgaccauguaccaucacggagacgacaccaacagugacaugaacagugacgacgacaugagccgaagugggagag
aaaccccacccccucgaccaucucaugcuuuuggcagugagcgagaccuggagcgcaggggcagaagcagagauguggagcc TABLE 4-continued Genes up-regulated in HF stem cells. Numbers in parentheses are the fold increase as determined by quantitative real time PCR.

| Gene Name/ Protein name/ GenBk Acces #. | Fold Incr. | Sequence | SEQ ID No. |
|---|---|---|---|

ucgagaccgcuggccauacaccaggaaucccagaagcaggcugccucaacgggaucuuucucuuccugugaugucaagacca
cauuuuggacuggacagagaugaugacagacguuccauggauuaugagucucgaucccaggaugccgagucauaccagaaug
uuguggaacucaaagaggacaagaagccucagaauccaauucaggacaaccuggagaacuacagaaagcugcucucgcuggg
aguccagcuugccgaagaugaccgacacucucacaugacacaaggccacucaucgagguccaagagagcugccuacccaagca
ccagccgaggucucaaacccaugccugaggccaaaaagccaucccacaggcgugggaucugugaggacgagucuucucaugg
agugauaauggaaaaauucaucaaggauguggcucgcaaccccaaauccggaagagcaagggagcugaacgagcguccuccu
ccaagguuccccaggccuaaugauaacuggaaggacaguuccuccagcagaagagagucagugauccaggagaggggguuaug
aagggagcgcauuuaggggcggcuuccgguucaacgcagaccuggcuuccagaagcagagcucuagaaaggaagaggcguua
ccacuuugauucugaugagcgggguucgggccaugagcauaaaagcugugugaggaagaagccuuuugaguguggugcuga
gaugagacaggcuaugagcaugggcaaccugaacagcccuuccuucucugagucgcagucaaucgauuuuggggccaaccca
uacgugugugaugagugcgggaggcaguucagugucaucucugaguuuguugagcaccagaucaugcacacuagggagaac
cucuaugaauauggagaguccuuuauucauagcguggcugucaaugaggugcaaagaagucagggugggggaaacgcuuu
gaguguaaggaauguggagaaaccuucaguaggagugcugcccuggcagagcaccgccaaauccaugcuagagaauaucuug
cagaauguagagaucaggaggaugaggagaccaucaugccuagcccgaccuuuagugagcugcagaagauguauggcaaaga
uaaguucuaugagugcaaggugugcaaggagaccuuucugcacaguuccgcccugauugagcaccagaaaauccaugguaga
ggcaacucagaugacagagauaaugagcgugaacgcgaacgugaucgucuacgugcacgugcacgagagcagcgugagcgcg
aacgugaacgggagcgugagcgugagcuuggggaacccuuucugaccuguccaaacuucaaugaguuucggaagauguaca
ggaaagacaaaaucuaugagugcaaagugugugggagagcuuucuucaucucucaucccugagggagcaucagaaaaucca
uacuagaggaaacccauuugaaaauaagagcaggaugugcgaggagaccuuugucccuagucagucucuccgacggcgccag
aaaacuuacagagagaagcuguucgacuuuaacaaugccagggaugcacugaugggaaacucagacuccagcgagcaucaga
aaaaccguucccgaaggaacuucuuugagggcagaggauuugagaaacccuucguugaaucucagaagagucauacuauaac
aagaccaccugaaaacaaagacgaugacaagccguucacaaucagugucaacccuaaugacaagcugaaacuccccaucaugg
aaaauggcucccagggcaaauccugugagaggucuguuauucauagcuugggcuccgcagaagcucagaagagucauggug
gacugggguucaguaaaccaagaccaguggcagagucuagcacccagagcucaagcagcauuuacuaccccagagcacacucu
ggaggcaacaccuaugaaggaaaagaauacaaggacucuaucauccauagcuugccagcuccucgaccucugaaacgucauag
agcaaaugaccauauucaaugugaugagggggagaauccuccauuuauaucccagauauuauuaauaagggaaggaagauu
ccugccagagaagaugcuuaugaaggaaguagcagcagcaacuaccacacaccaaauguaucccgugcugagccuccaagucu
uucuggagagucccaugacucuaagcaggaugucacguuucaguucccagcucaaguguucgugaacaccagaaagcucgu
gccaaaaagaaguacauugagcccaggaacaacgagaccucuguuauccacucccuaccuuuuggugaguugcuugcagguc
accguagggcaaaguucuuugagugucaggaaugcggggaggccuuugcucguaggucugagcucauugagcaccagaaga
uucaugauagagaaagaccuucuggaagccgacauuaugagcgcucugucauccgcagccuugcgcccagugacccucagac
caguuaugcccaagaacguuucauccaagaacaagugcguaaauucagagcguuggacaacgcucaacuaccagcaacaacc
ucaguguacagaaaaucuaugcccaagagacauuuaaugccgaggagccccaugauaaagaaacucauggucaaaaaauucau
gacaaagagccauaugguaaggagcccaguggcaaggagccccauggugaugagccccaggacaaagaaccccuuguucagg
agaugcgcagugaagagccccaugaugauaagccccauggccaggagccccaugaugauaagccccauggccaggagccccau
gaugauaagccccauggccaggagccccacggugaugagccccauggccaggagccccacggugaugagccccaugacaagga
acccauugaucaggagaugcgcagugaagagccccacagugaagagucucauggugaugagccccauggugaagagucccau
ggccaggagaaaguugaagaugcuaccauucaggccucaguuucugaagagcaucagaaagaugacgcuggugaugcaaucu
augaaugccaggacugugggcugggcuuuacugaucucaaugaccucacaagccaccaggacacccauagcagaaaggcucu
gguugacagucgugaauaugcacauucugaaguucaugcccacuccgucagcgaauuugagaaaaaaugcucuggagagaaa
cuauaugaauguccaaaauguggggagucuuucauucacagcucguuacuuuucgagcaccagagaguucacgaacaagacc
agcuguauuccguaaaggccuguuaugacgcuuucaucgcucuguugcccguuagaccaaggagaaauugcacuguugaaa
ggaauccugccguuucugggucagccauucgaugccgucaguguggacaaggcuucauucacaguucugcccuaaaugagc
acaugagacagcacagagauaaugaaauaauggaacagagugagcuuucagaugagauuuucauucaaggccuagcccucac
ugaguaucaggggagugaaacagaagagaagcuuuucgagugcacaaucuguggggaaugcuucuucacugccaaacagcuc
ggggaccaccacaccaaaguucacaaggaugagcccuaugaguaugggcccuccuacacccaugccuccuuucucaccgagcc
ccucaggaagcacaucccacuguacgaaugcaaagauugcggccaguccuuccuagacgacacugucaucgcugagcgcaug
guguuucauccugagcgagaaggugggucagaaauaguagcugccacugcccaagaggucgaagccaauguccucaucccac
aagaaguacugcgaauccaggggucaaaugcagaagcugcugagcccgaaguggaggcugcagagcccgagguggaggcugc
agagccugagguggaggcugcagagccuauuggagaggcugaagggccagauggagaagcugcugagccugauggcgaggc
ugagcagcccaauggagaggcugaacagccaaacggugaugcugacgagccagacggagccgggaucgaagacccagaagaga
gagcugacgagccugaggaagacgucgaagagccagagggagaugcagaugagcccgauggugcagacauugaagacccaga
agaggaaggagaagaucaagagauugagguugaagaaccauacuacaacugucaugaaugcgcagaaacguucgcuuccagc
ucagccuuuggcgagcaucugaaaagucacgccagugugaucaucuucgagccggccaaugcuccuggagagugcucuggc
uacauugaacgggccagcaccagugcagguggugcggagcaggcagacgacaaguacuucaaaugugaugugugcgggcaac
ucuucaacgaccgccucucccuugccagacaccagaauucucacacugguugaguaaccaggcugaagaaaagaagagcaaag
ccaaaccuucuucccagaaccagacccuuaauaaaucacaaagagagccuaaaccaacccauaaugucuauaagaaauucaccu
uccuguauacauaccggacuucacaucaaagacuuucacucucaucacagacugaaaaaagaaaagacauugaacgcagggac
ucuuucaguuuuagcuguucccuauggaacaucaguguauauuugggaaagcuagagugaacaucuacaucuuccauuuca
ucuaaguaacuagauugagggaaaccuagugacaauuccagaccacagagguugccccagucgacuguaaaugauaccccuu
ucauacccuauacauaaugauuccugccauguauauaaaugagcaaaucagugauacauauauuuggauuuagugugcuau
agaauuuacaguuuacucuacagagcuaccuagccugguacucugauuuuuucccugaggaggaagagagcaacaauuuagc
auauauuuguaaguauuguccaugcagaagcuuuucugugcaucauuugaaccccauuaguauccuuuccaguaauggagu
guucuguccccuaccucuuagauaguccugugaagguguggugugaaagaucgugugucuuugaauccuggcugugugg
aaacaggcauuuuagcuucuacagccauuuggugugcacccagaccccuugagacugauuguguaacccuuuacaauauaug
gauuugucucugugacccaaaucaacccaucccuacauuuauauaccuuacagugguuuucuugc TABLE 4-continued Genes up-regulated in HF stem cells. Numbers in parentheses are the fold increase as determined by quantitative real time PCR.

| Gene Name/ Protein name/ GenBk Acces #. | Fold Incr. | Sequence | SEQ ID No. |
|---|---|---|---|
| **Growth Factors, Receptors and Related genes** | | | |
| Fz2/ Frizzled 2 AW123618 | 9 (17) | uuuuuuuuuuuuuuuuuuaccguucuuuauuuaaaaaaauaaaauagga guccguagggugcacccucccccccuccugagugaaggagggcacggugc aguccggaccugggagaggggaaagcccggcaggcaggcgagaccgcuuc acacaguggucucgccaugccggcuguuggugagacgaguguagaacuu ccuccacgagugcagugucuugccggaccagauccagaagcccgacguga ugcccacgaugagcgucaugagguauuugaucauguagacugugaaguc gggcgacaugcggggcguguagugggccgggcaggggauggcuaggcuc uugcagugcuggcuuacccaggagcgcucccagugcucgcggaaggccu gcucauagaaguagcaggcgaug | 238 |
| Dkk3/ Dickkopf 3 AJ243964 | 6 (22) | Sequence below. | 239 |

ggccgcgucgacgccucuccagcugcucuguggcagcccagcuaccggucgugaccagauccagcuugcagcucagcuuugu
ucauucgaauugggcggcggccagcgcggaacaaacaugcagcggcucgggguauuuugcuguguacacugcuggcggcg
gcggucccccacugcuccugcuccuuccccgacggucacuuggacuccggcggagccgggcccagcucucaacuacccucagg
aggaagcuacgcucaaugagauguuucgagagguggaggagcugauggaagacacucagcacaaacugcgcagugccgugga
ggagauggaggcggaagaagcagcugcuaaaacguccucugaggugaaccuggcaagcuuaccucccaacuaucacaaugag
accagcacggagaccagggugggaaauaacacaguccaugugcaccaggaaguucacaagauaaccaacaaccagaguggaca
ggugguguuuucugagacagucauuacaucuguaggggaugaagaaggcaagaggagccaugaauguaucauugaugaaga
cugugggcccaccagguacugccaguucuccagcuucaaguacaccugccagccaugccgggaccagcagaugcuaugcacc
cgagacagugagugcuguggagaccagcugugugccuggggucacugcacccaaaaggccaccaaagguggcaaugggacca
ucugugacaaccagagggauugccagccuggccuguguugugccuuccaaagaggccugcuguuccccgugugcacaccccu
gcccguggagggagagcucugccaugaccccaccagccagcugcuggaucucaucaccugggaacuggagccugaaggagcu
uuggaccgaugccccugcgccaguggccuccuaugccagccacacagccacagucugguguacaugugcaagccagccuucg
ugggcagccaugaccacagugaggagagccagcugcccagggaggccccggaugaguacgaagauguuggcuucauagggga
agugcgccaggagcuggaagaccuggagcggagccuagcccaggagauggcauuugaggggccugccccuguggagucacu
aggcggagaggaggagauuuaggcccagacccagcugagucacugguagaugugcaauagaaauggcuaauuuauuuuccc
aggagugucccccaagugugggaauggccgcagcuccuucccaguagcuuuuccucuggcuugacaagguacagugcaguaca
uuucuuccagccgcccugcuucucuggcuugggaaagacaggcauggcggguaagggcagcggugagucgucccucgcugu
ugcuagaaacgcugucuuguucuucauggauggaagauuuguuugaagggagaggaugggaaggggugaagucugcucau
gauggauuuggggauacagggaggaggaugccugccuugcagacguggacuuggcaaaauguaaccuuugcuuuugucu
ugcgccgcucccaugggcugaggcaguggcuacacaagagcuaugcugcucuguggccucccacauauucaucccuguguu
ucagcuccuaccucacugucagcacagcccuucauagccacgccccucuugcucaccacagccuaggaggggaccagagggg
acuucucucagagccccaugcucucucucucaaccccauaccagccucugugccagcgacagcccuuccaaauggagggagu
gaaauccuuugguuuuauuauuuucuccuucaaggcacgccugccacuaaggucaggcugacuugcaugucccucuaacgu
ucguagcagugugguggacacugucuuccaccgacugcuucaauaccucugaaagccagugcucggagugcaguucgugua
aauuaauuugcaggaaguauacuuggcuaauuguagggcuaggauugugaaugaaauuugcaaagucgcuuagcaacaaug
gaaagccuuucucagucacaccgagaagucacaaccaagccagguuguguagaguacagcugugacauacagacagaagaag
gcugggcuggaugucaggccucagaugacgguuucaggugccaggaacuauuaccauucuguaucuauccagaguuauuaa
aauugaaaguugcacacauuuguauaagcaugccuuucuccugaguuuuaaauuauauguauacacaaacauguggcccuca
aagaucaugcacaaaccacuacucuuugcuaauucuuggacuuuucucuuugauuuucaauaaauacaaaucccccuucaugc
aaaaaaaaaaaaaaa

| Gene Name/ Protein name/ GenBk Acces #. | Fold Incr. | Sequence | SEQ ID No. |
|---|---|---|---|
| Sfrp1/ Secreted frizzled-related protein 1 U88566 | 6 | Sequence below. | 240 |

gcacgagcagcccgcagcccgccgcgccugugcgagccgggacagcacucggccccgcgcgcuccccgccccgcgccagcccc
gccgcggcgaccugcugcagcggaggaccccaucgaucggagacccggggagcagcgcgcagcccgcgagccgacgggcccc
gacugcgucuuuguccccggaggcuccgggaaguuugcagcgggacgcgcgcgugaaggcagcgugggcagccccgacguc
gccgagcaacaugggcgucgggcgcagcgcgcggggucgcggcggggccgccucgggagugcugcuggcguuggccgccgc
ucugcuggccgcggguucggccagcgaguacgacuacgugagcuuccaguccgacaucggcucguaucagagcgggcgcuu
cuacaccaagccccccgcagugcguggacaucccgguggaccugaggcugugccacaacgugggcuacaagaagauggugcug
cccaaccugcuggagcacgagaccauggcagaggugaagcagcaggccagcagcugggugccgcugcucaacaagaacugcca
caugggcacccaggucuuccucuguucgcucuucgcgcccgucugucuggaccggcccaucuacccgugucgcuggcucug
cgaggccgugcgcgacucgugcgagccggucaugcaguucuucggcuucuacuggcccgagaugcucaaaugugacaaguu
ccccgagggcgacgucugcaucgccaugaccccgcccaauaccacggaagccucuaagccccaagguacaaccgugugucc uc
caugcgacaacgaguugaagucagaggccaucauugaacaucucugugcaagcgaguuugcacugaggaugaaaaucaaaga
agugaagaaggaaaacggugacaagaagauuguccccaagaagaagaaacccuugaagcuggggcccaucaagaagaaggagc
ugaaggcgcuugugcuguuccugaagaacggugccgacugucccugccaccagcuggacaaccucagccacaacuuucucau
caugggccgcaaggugaagagccaguaccugcugacagccauucacaagugggacaagaaaaacaaggaguucaaaaacuuca
ugaagagaaugaaaaaccacgagugucccaccuuccagucuguuuuuaagugauacuggggcggacuggggaaggggagug
uggcuuggggugaggguggggcgcguggaugacccuggcucuungggcucacauauugcucucacccauacaguugug
gcuuuugcauugcaccuggcucuguuccuacagcgaacccucucccuunccuccauagccacauccagcuaaggccacggcc
uuuagauuaggaaggcuuuuuuuuuuuuaagggcugcagcagggccagcagcgacgugcaaaaggagaggcagaauccuuu TABLE 4-continued Genes up-regulated in HF stem cells. Numbers in parentheses are the fold increase as determined by quantitative real time PCR.

| Gene Name/ Protein name/ GenBk Acces #. | Fold Incr. | Sequence | SEQ ID No. |
|---|---|---|---|

cacugagccuggggcacaaaaaacagaaaauguunnccgguuuggaaaaacaaaacaaaacggauuguaaagaacugcagacg
gacagcugcucagcucaacguuguucgggacaucauuaccaauugcuuguggagucuaagccucuacagguagaagagucu
gaucauugccaagccaggcugcuuucaguuuauuauuaaucccccucuuucugccuuagauagaccaucgccaccuucaaaa
cacacacacacacacacacacacacacacacacacacacacacacacacacacacacuucugaaaguagccaggguaucccaguaua
gaacgggauagcuaagguuuggguggaggccacugcuacucuaccuucagcuuugaacuggccaccuuugauaggaaa
cugaggucucagauggacacuucuaccaguccaucgggauacaaggaugccaggcaagggucugcuuuugucugaaggagg
uacgugggcaugaagagacaugaggcauuucaggcugagaagcaacagcuacuaguuucaacaauagaguggaagaaauga
gcaaagguagaaaugucaagcaggucacaagucagggugauuggggaauccugugccaacagccucacuuuguaauuccau
cugucacuuucaaaagaacagcagcauaagacagggauaaaagcccacauacccuccaaggcuugaguaaaaguccacacuca
gcauuucaaagacuaacgucguugacugcccaaggcugcccucuuaauacaccgccuaugcaugugcuguggaaggcaacuc
ugugcaugugcuguggaggagaugggccucauggcugugcuggcugcccggaaucaguauagcguggaaggagacaguauc
cauagacucugcuuuucugcaaggaaagcccuuuuccuuauacaugauugccuauaauucagacaaauuuaaaaucgcugcc
ugccugagcccuccaccuuuacuuuugcauucuccggucauauucuuuugaggcuaaagugcccuauccgaggagaugguu
ucaaaggcuaacuaaucugcagcuuucccaagugcccagagguauuucucaaaguugguaugcuuaauaagugauguaaaua
uuccaguucucuuaggcagccuuacuccuguugucccug Dab2/ 15 Sequence below. 241
Disabled
homolog 2
U18869
aauuccgaguggccgcgcggcuauuuaaguggcguuacuccgcguccucggcgcugcagccuugaggcuucgggcgcgggg
gaagucaugcuggcuccacagaagcacuagcuaguccguguacuuugugguucuguccuuuugagaccugcccgccgggg
auuggcugguaucagugacugucuacugcuggauuuucugcuugccuucccgucaugucuaacgaaguagaaacaagcaca
accaauggccagccugaccaacaggcugccccgaaagcgccaucaaagaaggagaagaagaaagguucugaaaagacagacga
guacuuguuggccagguucaaaggugaugguguuaaauacaaggccaagcuaaucgguauugaugaugugccugaugcucg
aggagacaaaaugagucaggauucuaugaugaaacucaagggaauggcagcagcuggucgcucucagggacaacacaagcaa
agaaucugggucaacauuuccuugucuggcauaaaaaucauugaugagaaaacugggguaauugaacaugaacauccaguaa
auaagauuuccuucauugcucgugaugugacagacaacagagcauuugguuauguguguggaggugaaggccagcaucaau
uuuuugcuauaaaaacagggcaacaggcugagccauuagucgucgaucuuaaagaccuuuuucaaguuaucuauaauguaa
agaaaaaggaagaagauaagaaaaagguugaagaagccaacaaagcagaagagaauggaagugaggcccuaaugacccuugau
gaucaagcuaacaaauugaagcuggguguugaccagauggauuuguuggggacaugucuacaccuccugaccuaaauagu
ccaacagaaagcaaagauauccuguuaguggaucuaaacucugaaaucgacaccaaucagaacucuuuaagagaaaauccauu
cuuaacaaauggagucaccuccuguucucucccucgaccaaagccucaggcauccuucuugccugagaacgccuuuucugcc
aaucucaacuucuuucccaccccuaacccugauccuuuccgugaugaucccuuugcacagccagaccaaucggcacccucuuc
guucgauucucucacaucuccagaucagaagaaagcgagucugaguagcucgucuacuccacagaguaaagggccccugaac
gucgauacugauuacuuuggucagcaauuugaccagcucucuaaccggacuggcaaaccggaagcucagggaggcccguggc
ccuacccaaguucgcagacccagcaagcagugagaacucaaaaugggguaucugaaagagaacagaacggcuuccauaucaaa
ucuuccccgaacccuuuugugggaagcccucccaaaggacuaucgguaccgaauggcguaaagcaggacuuggaaaguucug
uccaguccucagcacaugacuccauagccauuaucccaccuccacaaaguaccaaaccaggaagaggcagaaggacugcuaag
ucuucagcaaacgacuugccugcuucagacaucuuugccucagaaccuccaggccagaugucccccacaggacaaccugcagu
cccgcagucgaacuuccuggaucucuucaaaggcaaugcucccccccaguggggcccccuuguaggucuagguacggucccca
guaacacccccccaagcaggacccuggacgccuguugucuacaguccuucgacaacugugguccccaggagccauaauaagug
gccagccucccaguuucgccagccacucguuuuugguacaaccccagcaguacaagucuggaaucagucuccaucauuugc
aaccccagcuuccccuccacccccccacaguuugguguccuaccacaucuguggcgcccaacgcuuggucauccacaagcccuc
uggggaauccuuuucagaguaauaauaucuuuccaccucccaccauguccacucaguccucuccucagccuaugauguccuc
uguucuggccacaccgccucaaccaccuccccgaaauggcccacuaaaggacauucccagugacgcuuucacuggcuuagacc
cccuuggggauaaagaggucaaggaagugaaagaaauguuuaaggacuuccagcugcggcagccaccucuuguucccucaag
gaagggggagacgccucccucugggacuucaagcgccuucuccaguuacuucaacaauaaaguuggcauuccucaggagcau
guagaccaugaugauuuugaugccaaucaacuguugaacaagauuaaugaaccaccaaagccagccccgagacaagguguccc
ucuuggguaccaagucugcugacaauucacucgagaacccuuucuccaaaggguucagcucaucaaaccccucugugguuuc
ucagccugcaucuucugauccccacaggagcccuuucggaaauccuuuugccuagcuucugaaguuguaaugaugacuaucc
agaugagcaaaagacuggcuuuggucaagaaugaagcagacagccagaaacauguugaccucuguccucgcuccagcuuuga
cguauuaucuguuacccuauuuguuuuggccucuuguacuuguaaaaugccuuucauuuuccugucuaggcuaaagcuaaa
cuuaaacuauggcuuuacguaaauuaagcuccuaaacucucuagcuccaauauaaaugaaguagcuucccuaucaaaucccu
gucuguugugccccccuugaaacuuccagaauauucuccauucuacccuccauuugggaggagcggcuaccuuuacccuuaa
uaucacacugccuugagucaauguccaaauacucauagcucucaaagucauugggguuccuggugugcggccuaaaccuaa
agcauccuauuaauagggaaguaagacaccuugcuuccuauguccacucagggagaauuuuauuuaauaaaaugaaagcaag
acuaacuucucaaauccacccaaggaccauuuugagauggucguuucucagcuaacugcaccauuuaccaauccugccccaag
uggugcuuacauuugacuugaagaagagaaagagcuaacucaaaacacaaggcauuauucaaagcuaauaaaacaauuucuc
ccuggggccccacauuguuuucauuccagauacguugcagcuguuugacccugaugacauuaugcccuacauuuuccuuga
agauccugauuuuauuucaugugauuuuuguuucucaauaaagaugauuauugugugcacggaauuc Cktsf1b1/ 12 (12) Augaaucgcaccgcauacacugugggagcguugcuucuccuccugggga 242
Gremlin, cccuacugccaacagcugaggggaaaaagaaagguucccaaggagccauu
Cysteine ccgccuccugacaaggcucagcacaaugacucugagcagacccagucccc
knot accacaaccuggcuccaggacccgggggcggggccaggggcggggcaccg
superfamily ccaugccuggagaggaggugcuugaguccagccaagaggcccugcacgu
1, BMP gacagagcgcaaguaucugaagcgagauuggugcaaaacucagccccuga TABLE 4-continued Genes up-regulated in HF stem cells. Numbers in parentheses are the fold increase as determined by quantitative real time PCR.

| Gene Name/ Protein name/ GenBk Acces #. | Fold Incr. | Sequence | SEQ ID No. |
|---|---|---|---|
| antagonist 1<br>AF045801 | | agcagaccauccacgaggagggcugcaacagccgcacuaucaucaaccgc<br>uucuguuauggccagugcaacuccuucuacauccccaggcacauccgaaa<br>ggaggaaggguccuuucagucuugcuccuucugcaagcccaagaaguuc<br>accaccaugauggucacacucaacuguccugagcuacagccacccaccaa<br>gaagaaaagggucacacgcgugaagcagugccguugcauauccaucgacu<br>uggauuaa | |
| Fgfr1/<br>Fibroblast<br>growth<br>factor<br>receptor 1<br>U22324 | 10 | Sequence below. | 243 |

guggaauauccauggagguacggagccuuguuaccaaccuuuaaccgcagaacugggaugugggcuggaagugccuccuc
uucugggcugugcuggucacagccacucucugcacugccaggccagccccaaccuugcccgaacaagcucagcccuggggag
ucccuguggaaguggagucucuccugguccacccuggcgaccugcuacagcuucgcugucggcuucgcgaugaugugcaga
gcaucaacuggcugcgggaugggggugcagcugguggagagcaaccguacccgcaucacaggggaggagguggaggugcggg
acuccauccccgcugacucuggccucuacgcuugcgugaccagcagccccucuggcagcgauaccaccuacuucuccgucaa
ugucucagaugcacucccauccucggaagaugaugacgacgacgaugacuccuccucggaggagaaagagacggacaacacca
aaccaaaccguaggccuguagcucccuacuggacauccccagagaaaauggagaagaaacugcaugcggugcccgcugccaag
acggugaaguucaagugcccgucgaguggggacacccaaccccacucugcgcugguugaaaaauggcaaagaguuuaagccug
accaccgaauuggaggcuacaagguucgcuaugccaccuggagcaucauaauggauucugguggugccuucugacaagggcaa
cuacaccugcaucguggagaaugaguaugggagcaucaaccacaccuaccagcuugacgucguggaacgaucuccgcaccga
cccauccuucaggcagggcugccugccaacgagacaguggcccugggcagcaauguggaguucauguguaagguguacagcg
auccgcagccucacauucaguggcugaagcacaucgaggugaacgggaguaagaucgggccagacaacuugccguaugucca
gauccugaagacugcuggaguuaauaccaccgacaaggaaauggaggugcuucaucuacggaaugucuccuuugaggaugc
gggggaguauacgugcuuggcggguaacucuaucggacucucccaucacucugcaugguugaccguucuggaagcccugga
agagagaccagcugugaugaccucaccgcucuaccuggagaucauuaucuacugcaccggggccuuccugaucuccugcaug
uugggcucugucaucaucuauaagaugaagagcggcaccaagaagagcgacuuccauagccagauggcugugcacaagcugg
ccaagagcaucccucugcgcagacagguaacagugucagcugacuccagugcauccaugaacucugggguucuccugguucg
gcccucacggcucuccuccagcgggaccccaugccggcuggagucuccgaauaugagcucccugaggauccccgcugggag
cugccacgagacagacuggucuuaggcaaaccacuuggcgagggcugcuucgggcagguggguguuggcugaggccaucggg
cuggauaaggacaaacccaaccgugugaccaaaguggccgugaagauguugaaguccgacgcaacggagaaggaccugucgg
aucugaucucggagauggagaugaugaaaaugauugggaagcacaagaauaucaucaaccuucugggagcgugcacacagga
ugguccucuuuaugucauuguggaguacgccuccaaaggcaaccucccgggaguaucuacaggcccggaggccuccugggcu
ggaguacugcuauaaccccagccacaaccccgaggaacagcugucuuccaaagaucugguauccugugccuaucagguggcu
cggggcauggaguaucuugccucuaagaaguguauacaccgagaccuggcugcuaggaacguccuggugaccgaggauaac
guaaugaagaucgcagacuuuggcuuagcucgagacauucaucauaucgacuacuacaagaaaaccaccaacggccggcugcc
ugugaaguggauggccccugaggcguuguuugaccggaucuacacacaccagagcgaugugugguucuuuuggagugcucuu
gugggagaucuucacucuggguggcuccccauaccccggugugccuguggaggaacuuuucaagcugcugaaggaggguca
ucgaauggacaagcccaguaacuguaccaaugagcuguacaugaugaugcgggacugcuggcaugcagugcccucucagaga
ccuacguucaagcaguugguggaagaccuggaccgcauuguggccuugaccuccagccaggaguaucuggaccuguccauac
cgcuggaccaguacucacccagcuuucccgacacacggagcuccaccugcuccucaggggaggacucugucuucucucauga
gccguuaccugaggagcccugucugccucgacaccccacccagcuugccaacaguggacucaaacggcgcuga

| | | | |
|---|---|---|---|
| Fgf1/<br>Fibroblast<br>growth<br>factor 1<br>M30641 | 10 | auggcugaaggggagaucacaaccuucgcagcccugaccgagagguucaa<br>ccugccucuaggaaacuacaaaaagcccaaacugcucuacugcagcaacg<br>ggggccacuucuugaggauccuuccugauggcaccguggaugggacaag<br>ggacaggagcgaccagcacauucagcugcagcucagugcggaaagugcgg<br>gcgaaguguauauaaaggguacggagaccggccaguacuuggccaugga<br>caccgaagggcuuuuauacggcucgcagacaccaaaugaggaaugucugu<br>uccuggaaaggcuggaagaaaaccauuauaacacuuacaccuccaagaag<br>caugcggagaagaacugguuugugggccucaagaagaacgggagcugua<br>agcgcgguccucggacucacuauggccagaaagccaucuuguuucugcc<br>ccucccggugucuucugacuag | 244 |
| Gpr49/<br>G protein-<br>coupled<br>receptor 49<br>FEX<br>AF110818 | 64 (377) | Sequence below. | 245 |

auggacaccuccugcguccacaugcuccuguccuugcuggcgcugcugcaguugguggccgccggcagcucaccgggaccag
augcgauaccgcggggcugcccaucacacugucacugugagcuggauggcaggaugcugcucaggguggacugcucggacc
uggggcucucggagcugcccuccaaccucagcgucuucaccuccuaccuggaccucaguaugaacaacaucagucagcuacc
cgccagucuccuacaucgccucugcuuccuagaagaguuacgucuugcuggaaaugcuuugacacacauucccaagggagcg
uucacgggccuucacagccucaaagugcuuaugcugcagaacaaccagcugagaaagguuccggaggaagcgcuacagaauu
ugagaagccuucaaucccugcgccuagaugccaaccacaucagcuacgugccacccagcuguuucagcggccugcacucccug
aggcaccuguggcuagaugacaaugcucucacagacgucccuguccaggcuuucagaaguuuaucagcccugcaagccauga
ccuuggcccugaacaaaauacaccacauagcagacuacgccuuuggaaaccucuccagccucgugguucugcaucuccauaau
aauagaauccacucccugggaaagaaaugcuuugauggacuccacagccuggagacuuuagauuuaaauuauaauaaccuug TABLE 4-continued Genes up-regulated in HF stem cells. Numbers in parentheses are the fold increase as determined by quantitative real time PCR.

| Gene Name/ Protein name/ GenBk Acces #. | Fold Incr. | Sequence | SEQ ID No. |
|---|---|---|---|

augaauuccccacugcaaucaagacacucuccaaccuuaaggaacuaggauuccacagcaacaacaucaggucaauaccggag
cgagcguucguaggcaacccuucucuuaucacaauacacuucuaugacaaccccauccaauuuguuggaguaucugcuuuuc
agcauuugccugaacuaagaacacugacuuugaauggugccucgcacauuacugaauuuccucacuugacaggaacugccac
ccuggagagucugacuuuaacuggagcaaagaucucaucucuuccccaggccgucugugaucaguuaccuaaucuccaagug
cuagauuugucuuacaaccuacucgaagacuuacccaguuugucaggcugccaaaaacuucagaaaauugaccugaggcaua
acgagaucuaugaaauuaagggcagcacuuuucagcaguuguuuaaccuccgaucucugaacuuagcauggaauaaaauugc
uaucauucaccccaaugcguuuucuacguugccgucucuaauaaaguuggaccuaucauccaaucuccugucguccuucccu
gugacugguuacaugguuuaacucacuuaaaauuaacagggaaccgagccuuacagagccugauaccaucugcaaacuucc
cagagcucaagauuauagaaaugccaucugcuuaccaguguugugcauugggggugugagaaugucuauaaaauuucua
accaauggaauaaagacgacggcaacaguguggacgaccuucauaagaaagacgcugguuauuucaaguucaagaugagcg
ggaccuugaagauuuccuacuugacuuugaggaagaccugaaugcccuucacucggugcagugcucgccuuccccaggucc c
uucaagcccugugagcaccuauuugguagcuggcugauccgaaucggggugugggaccacggcaguacugacgcuuuccugc
aaugccuugguggcuuugaccguguucagaacuccccuguacaucucuuccauaaagcugcuaauuggguaaucgcggua
guggacauucucauggggucuccagugcugugcuggcugccguggaugcauucacuuuuggccguuuugcucagcacgg
ugcgugguggaagacggaaucggcugccaaaucguuggcuuccuguccauuuuugcuuccgaaucgucgaucuuccugcu
cacucuggcagcgcuggaacgagguuuuucugucaagugcucuucgaaguuugaagugaaagcuccccuuuuuagccugag
agcgaucguuuugcuauguguccuguuggcccugaccauugccacaauccccuugcuaggaggcaguaaguacaaugccuc
uccccucugccugcccuugcccuuuggggagcccagcaccacgggcuacauggugg cucucguguugcucaacucucucug
uuuccucauaaugaccauugccuacacaaagcucuacugcaguuuggagaaaggagagcuggagaaucuuugggauuguuc
gauggugaagcacauugcucuguugcucuucgccaacugcauccuuuacugccccguggcuuucuuauccuucuccucuuu
gcuaaaccucaccuuuaucaguccugacgucauuaaauuuauacuucucgugaucgucccacuuccuuccugucucaaccca
cuucucuacauugucuucaauccccauuuuaaggaggauaugggcagccugggaaagcauacccguuucuggaugagauca
aaacacgcgagucugcuguccauuaacucggacgauguugagaaacgguccugugagucaacccaagccuuaguauccuuua
cccacgccagcauagccuaugacuugccuuccacuuccggggcaucaccagcuuaccccaugacugaaagcugucaucucuc
uucaguugcauuugucccaugucucuagugacuaugagagaggaacguuuuuaagaguuggaaaccugaaaagugauuucu
aucagagcaguagcuaagaaaagcugagcuaaaaaccuaccuuaaaacccaagcaaacaucucuaaauugguguggaaacagu
ggugccuuagagcaggagagcaucauuaaacaccgcuuguaucauuuguucagcuaagaaggaaagccaucaagucacuuag
gugaacccagaugagaaaagcagccugaaaugcucuucgcauuguagucucuucugacucaccagcauagucucccauagug
agaagacucguuggaugacucaauggguguauuuaaauccacaaauuccuuguuuaaagguuagaguuuuaagaaaaaaaa
aaaaaaaaa

| Gene Name/ Protein name/ GenBk Acces #. | Fold Incr. | Sequence | SEQ ID No. |
|---|---|---|---|
| Igfbp5/ insulin-like growth factor binding protein 5 L12447 | 37 | Sequence below. | 246 |

uuuuuuuucuucaccuccucccuuuucaaggccuccaagcuaauuauuucuguugcuuuggagugagcaauucugugguu
cucuccaccaccaccccaauucugacccgaucccgccugggguuucuacggucuccgcucacucugcgugcaccuggcgc
gccucuuuuuuucacccccaaccuguugcaagucuuuaauccucgcaauugggacuugcgugcaggcaccugaauccuccu
ugccucauauuuugcaaguguuuggggagagcaccugcucuaccugcaagagauuuaaaaggaaaaaaaucuccaggcucc
cucuuucuccacacacucucgcucuccugccccgccccgagguaaagccagacuccgagaaaauggugaucagcgugguccu
ccugcugcuggccgccuaugccguaccggcucaaggccugggguucuuucgugcauugugaacccugcgacgagaaagcucu
guccauguguccccccagcccucugggcugugagcuggucaaagagcccggcuguggcugcugcaugacuugcgcccuggc
ggagggacagucgugugguguucuacacagagcgcugcgcccaggguuugcgcugccucccccggcaggaugaggagaagcc
gcugcacgcccugcugcacggccgcgggguuugccucaacgaaaagagcuacggcgagcaaaccaagauagagagagacucu
cgggaacacgaggaacccaccaccuccgagauggcugaagagaccuacucccccaaggucuuccggcccaagcacacucgcau
uuccgagcugaaggcugaggcugugaagaaggaccgcagaaagaagcugacccaguccaaguuuguggggggugcagagaac
acugcccaccccagagucaucccugcaccugagaugagacaggaauccgaacaaggccccugccgcagacacauggaagcuuc
ccuccaggaguucaaagccagcccacgcauggugccccgugcuguguaccugcccaacugugaccgcaaaggauucuacaag
agaaagcaguguaagcccucccguggccgcaaacguggcaucugcuggugugugg acaaguacggaaugaagcugccgggca
uggaguacguggauggggacuuucagugccacgccuucgacagcaguaacguugagugacgcgucccc ucccuuccucccccc
uauccuacccccccagccccaacuccagccagcgccucccuccaccccaggacgucacucauuucaucucauuuagggaaau
auauauacauauauauuugaggaaacugaggaccucggaaucucuagcaagggcuaaggagacacuccccaccaugaccccg
gaaauguauuccuuuuugaagcaaguugaacggacagagaagggaaggagagaagaagcaagagggagcgagagauggaaag
aaagcaaagcguuggaauagaggaaaagagggaaggacagauaggauuagagagagaagagagaaacagcaaggcagaaagga
cuccacaaccaaggcugaaucugcccuuuugcuuucagcucuagccuggggucagaaaaguguggcauucagugacaccca
guuuagauuggucaaggggagaaaagaaacaaggugugucagugccucucgggucuguccccuccugcagccagcagugug
gauggcuagaccccucacccuccucuccucuuacccaagugcagggugauuucauccccaaauuuacaaagacuaaaaugcau
uccaucccucugaaaauaaacaaaagugagugauugaagauagguuuucccccagcagacaagugaacucagaaugugugca
aauuuuacucuuguuaaagauuuuuuuaagaagucaguacgcacccccaacacuggaaagacuugauucuccaggugacaa
gcaauucagaagcgcguggcuucggcccuugauuucacuagacucaaagcuggcccggcagccucuguggaggaggaugag
agguggagaaaaccaaggggcuuguacucacccacaagacuccauguagacuuuauaggcauauaaaucuauuuucuuuacc
uuuuuuucccuuucccuuucuuucgaaguuuugcauuaccucuuuaaaguaguuuuuuuuaggacacugaagaucuuccu
cauucugggaaaaauccauauuucacaaauacaacccagaacgccagcuuggccugcguccaggcagccuuucucgugagcu
acaagugugg cucuuuugugggg caccgauuuggaucuucucaugauuccaaacgugu guugaagugaauccaccaagcca
gguaacugccagcacccaagggugcaucaagugcauagcccaggucaccccauuucagccuuccaacccgcagaaaguaacug
ucucacaccacaccacauaaaccugccagauccaucuguaacccacuggccugcccagaccuuuuuuucccaucugcauuuuu
uuuuuugaacugcauuuugaaagccucccucagaugccaggcugacagaucagagagaaacuaacaugagagaugacagagg
aggaggaaguggagggugggggcagagacuuccacagagagacauagaagauggagcagaggucuggggguggggaggaca TABLE 4-continued Genes up-regulated in HF stem cells. Numbers in parentheses are the fold increase as determined by quantitative real time PCR.

| Gene Name/ Protein name/ GenBk Acces #. | Fold Incr. | Sequence | SEQ ID No. |
|---|---|---|---|
| | | agaaagagacagagagaggaaaauaccaauagaauuuuccuuggugucucccaucuaaucaacucucugagauuugagagga aaaagaaggcaggggaagaacuugagguagaaaugaggucaguucaagucacagggcccagaugguggguaacugaggcagg auccagacuugagacacacgguuggaaacaaggcugguuagccugacugggguauugaagggugaagaggaugccuuggaaa gacagcacaacuucaguucaacuucaggccccaaggaggaacugaggccaaagaauccuucaagugcuucaugagucuccuc ugcccgacucaaacauccuucccugugauggaggaugguagaaagcccaggacaacucaggcccggaucuucacgacuguug ucauuugccagccugauuuugauccaagagaagcaucucauugcccacuggcuucuucaacaaagaggugcuuaacaaaagg cucaggacuaucuuugaagacugaagauaaccuuccaggagaggagacucggacauugguacaggaggccccuuuuggcgg gggacacagcucuuugcgcucucuugauggcauggcauaguagaggcccccuccaacccggaacauggagcaacacaaaggg agagcaaagaaacugacgugcgucgacucauaggacaugggugugcugcgggcacagaaagggaugccuccuguugccuggac aggacaguuggcugggaaggaaagagaaaauugaucuucauaagacaaagggccugaugggauggcaauagaaggacuuacc agaccugcagggucaguauacccaucaccccgcacaacauccccagcccccaacucaaacuucaauauaucuuaggccaguau ccuagaccuaagucucucccuuucugccauuauuucuccgcaucuugagcagucaucugacugagauuugccaaguggauac uggggguaccacugcccccaagaaaagacugagccaggaacugccuacucgcucccccucccgagccuggagcuaacuccugu gaggggugcucucuucaccccacaacuuacuagaccuugagugagccucugucccuuaugugggcucuucgcgugugagcca cagauggaggucauuguauagacaguuagccuuccccaggucagccuaccuccccccaaacuugugagucuccccgcugcuca uauggagaggcaugucuaagacagcaagucuucuagaggaagcuugccuuuaacagacagauggaacuaaaccuuccaaaug ggagaucuggcugaacccaggauacagagaccauggacauggaugggggucaucaagagaagagggaugccuucuccagguu agggagagagagaaggcaaguuugcaacgaucccaucaugcccugagcaagaagcuuuuggcccaggcuagccuuuaacuccau uagaggccucucuguuggguuuauccacagcaguaggcccaaguauggccuguccccaccucuacuaucccguggaagguu ucuucccaccccuuuuugacaaaugccucacucgagcaguggaaagauagcucucuucccccucuucugccagguaacaaag agaccuaaccaggaccuauucucuccaccccagccagucuugaccagccagaacaaagcagggaaccuggagaauaaaagacucu acguuccucugacaaagacucuacguuucucugacggccaggccuaaacagacaaggcuugggaacaucugccccacaggau acggaggaggucagcugugcucacuccucuucuccuuccaagacccucuuccgaccaugacuuaucuccaugguaacauccu caccaucauucucccacuaccaaggguugccauggcaaccucccaaccaccugcccaucccaggcaggcagcuguccuucugc ucagaacccuagaggacucuaggugaaauuuuacagcuuaagagaggagugagccaaggagaagagacccuguaguccucug gcuuucaagagaaagaaggcuaugauuuaaaacacaguagaagggaaagaggucucgucgaggucgaccucucccggggagc uuaggggguuguacugucuuuauuuuuuaaaccacuaaagugcaaunuuuccugcacucuuguuaccccgccucucuucccu guuagguuuucauuuccuugagcagacuuucuugguuuuuuaauggaguauagacuuucaccacuucacagacucuggccu ccucuccaagucucucuggaugggaaaaggaagguagagggucagaggggaaggggucccucgucaccccgcauccauuca cccccacuucucuggucccuagucaccggcuucaccccnaucuccgacaccaucacugucacacaguagccugucacacggau aguacaguucagacaagacuccuucagauuccgagacgccuaccgguuguuuuugguuuuguuuuguuuucuuuuguuu guuuguuuguuuguuuuuacaacagcaauaaccacaucacauauuacuguagcucucuauaguguuacguucagacaccg uagcucuguccucucuuauuuuguugguuuugacuuaaaaaaaaaauacuuaugcuuuuuacuggugaaacagauugaaaaa aaaauugaacaacaaaccaguuugugaaaaaaaaaaaaaaaugugaaaaaaaaaucaccccgauguggaagagcucggcuccucu uuagcauuuuguacuuaaggaaauaaaaaagaaaaaccuggaagaucucacauuuuauuacaaagugaaaaaaaaa | |
| Myoc/ trabecular meshwork induced gluco- corticoid protein AF041335 | 111 | Sequence below. | 247 |
| | | guccagucugcagucuguauucggaagacauagauacuaaaauacauggcaacucuuuuuuuuguuuguuuuaauucaucag gauguggagcgcuagucuggguaggagagccagucacccugaggacagcugaaacaaucgcuggcaaguauggagugugga ugagagaccccaagcccacccaccccuacacccaggaaagcacauggaggauugacacgguuggcacagagauccgccaggug uuugaguacagucagauaagccaguucgagcagggcuauccuuccaagguccaugugcucccucgggcacuggagagcacgg gugcuguggguguaugcggggagccucuauuuccaggggcugaguccagaacuguggucagguaugagcuagacacggaga ccgugaaggcagagaaggaaauuccuggagcuggcuaccacggacacuucccguacgcguggggguggcuacacagacauuga cuuagcuguggaugagagcggccucugggucaucuacagcacggaggaagccaagggggccauaguccucuccaaauugaac ccagcgaaccuggaacuugagcguaccugggagacuaacauccguaagcagucuguggccaaugccuuuguuaucuguggca ucuuguacacggugagcagcuacucuucagcccaugcaaccgucaacuucgccuacgacacuaaaacggggaccaguaagacc cugaccaucccauucacgaaucgcuacaaguacagcaguaugauugacuacaacccccuggagaggaagcuguuugccuggg acaacuucaacauggucaccuaugauaucaagcucuuggagaugugaggagccucuaugccuaccagcaaaggccagaaaag gugaaguuccgggcucccgggugaagcagcugucagcagaggcagccagaugcauggaguuucuccuccugcuaaagauuu uguuuauccgggucaauguacagcuagcuccccucugacugacacguccuccaggcuuguauagucgcauagacucuguuc ucuucugucagcuuucaaagggcuguucccucuuuuaaaaaucacauagug | |
| Itm2a/E25 putative Integral membrane protein 2A L38971 | 30 | Sequence below. | 248 |
| | | gggagaccugagcucgcugcugccuguggaagacugggagaggagacacuaagugcugcucaagcaagcgcgauccucuccu cuuucaaccugcagcccaagauacugauucgagccgcgccuuaccgcgcagcccgaagauucaccauggugaagaucgccuu caacaccccuacggcggugcaaaaggaggaggcgcggcaagauauagaggcgcucgucagucgcacuguccgagcucaaauc cugacuggcaaggagcucagaguugucccgcaggagaaagauggcucaucugggagaugcaugcuuacucuccuaggccuc ucauucaucuuggcaggacugauuguuggugggagccugcauuuacaaguacuucaugcccaagagcaccauuuaccauggu gagaugugcuucuuugauucugaggauccugucaauuccauuccuggaggagagccauacuuucugccugugacugaggag | |

TABLE 4-continued

Genes up-regulated in HF stem cells. Numbers in parentheses are the fold increase as determined by quantitative real time PCR.

| Gene Name/ Protein name/ GenBk Acces #. | Fold Incr. | Sequence | SEQ ID No. |
|---|---|---|---|

gcugauauccgugaggaugacaacauugccaucauugaugugccugugcccaguuucucugauagcgauccggcggcaauu
auucacgacuuugagaagggaaugacugcuuaccuggacuugcuuuugggaaacuguuaucugaugccccucaauacuucc
auuguuaugacuccaaagaaucugguggaacuuuuuggaaaacuggcaaguggcaaguauuugccucauacuuaugugguu
cgugaagaccugguugcuguggaagaaauucgugauguuaguaaccuugguauuuuuauuuaccaacuuugcaacaaccga
aaauccuuccgccuuagacgcagagaccuucugcuggguuucaacaagcgugccauugacaaaugcuggaagauuagacacu
uccccaaugaauuuaucguugaaaccaagaucugucaggagugaaaugugacagauaaagaguauccuugauaauaagaagu
caggaacuuaccgucugacuuggaaaauugaaauugaugggauacucaugcuauuuacucauacauuuacucuauugcuua
uacuggaaaaggaaagggaaagggggagaaaacuacuaaccacugcaagcgauuguccaauucuacuuuaauugacauugc
uugcuguuuucaacaagucaaaugauuaucuuuucucuugaauuuauaggguuuagauuucugaaagcagcaugaaugug
ucaucuuaccauccugacaauaaagcccauccucugguuuuauuuaaagcaagcucuuuccaacaucacuuggcuagagcau
gcuuuaaauuuaaaauauuugaaauuuguuuuugacauuuuuuugugugaaacaugucaaaucucuuaccauucuuuggu
uuucuucuuuauuauguucaacucuccugauuucagaaguuacauuuuugcauuucuaucaggugcuguguaacgaaucu
gacugauaugugaacaaucuucaugaggaagcaauuuuuuacucauguaaugauucuuucucacugauaucuguauuguga
aauccacagaacuguacaggugcugaaugcuguaaggaguucugguuguaugaauucuacaacccuauaauaaaguuuaccg
uauucaauca

| | | | |
|---|---|---|---|
| Eps8/ epidermal growth factor receptor pathway substrate 8 L21671 | 15 | Sequence below. | 249 |

ggccauuaccaaucgcgacccgcgcacacacggcccgggcggcgggcgaagcgggcucccggggcgcugggcgcagggcgcg
gggcaagccccagcagcgugucugcaacggggcgcggcgggcgcuccagcuccgggaucuuucucccucggucaccucccuc
gcgucuagggaggucguggcacucccugaggagcgcggcugcucggagggcggauccuagaacagaggcgugagagccggc
augaauggucauaugucuaaccgcuccagugguauggagucuacccuucucaacugaaugguuacggaucuucaccacccu
auucccagauggacagagaacacagcucaagaacaagugcaaaggcccuuuaugaacaaaggaagaacuaugcccgagacagu
gucagcagugugucggacgugucccaguaccgcguggaacacuugaccaccuucgugcuggaucggaaagaugcaaugauca
cugucgaggacggaauaagaaagcugaaguugcuggaugccaagggcaaaguguggacucaagauaugauucuccaagugg
augaccgagcugugagccugauugacuuagagucaaagaaugaauuggagaauuuccucuaaacacaaucucgcauuguca
agcaguggugcaugcaugcagcuaugacuccauucucgccuugguaugcaaagagccaacgcagagcaagccagaccuucac
cuuuuccagugugaugagguuaaggcaaaccuaauuagugaagauaucgaaagugcaaucagugacaguaaaggugggaaac
agaagaggcggccggaggcccugaggaugauugccaaagcagauccuggcaucccuccucccucccagagcuccugccccugu
gccaccggggacugucacacagguggacguuaggagucgcguagcagccuggucugccugggcagcugaccagggugacuu
cgagaagccccggcaguaccacgagcaagaagagacgcccgagaugauggcagcccggaucgacagggaugugcaaaucuuaa
accauauuuggaugacauugaauuuuuuaucaccaaacuccaaaaagccgccgaagcguuuucugagcuuucuaaaaggaa
gaaaaguaagaaaaguaaaaggaaaggaccuggagagggcguuuuaacacugagggcaaaaccgccaccuccugacgaguuu
guugacuguuuccagaaguuuaaacauggauucaaccuucuggccaaguugaagucccauauccagaacccgagugcuucag
aucugguucauuuuuuguuuacuccacuaaauauggugguccaggcaacagguggcccugaacuggccaguucgguacuca
gcccacuguugacaaaagacacaguugauuucuuaaacuacacagccacugcggaggaacggaagcuguggaugucacuggg
agauaguugggugaaagugagagcagaguggccgaaagaacaguucaucccaccuuacgucccgagguuccgcaacggcugg
gagcccccgaugcugaacuucaugggcgcgcccacagagcaagacauguaucaacuggccgaguccguggccaacgcagaaca
ccagcgcaaacaggacagcaagaggcuguccacagagcauuccaauguguccgacuauccuccagccgacggauaugcguaca
guagcagcauguaccacagaggaccacaugcagaccacggggaggcugccaugccuuucaagucaacuccuaaucaccaagua
gauaggaauuaugacgcagucaaaacacaacccaagaaauacgccaaauccaaguacgacuuuguggcgaggaacagcagcga
gcucucgguuaugaaagaugaugucuuagagauacucgacgaucgaaggcagugguggaaaguccggaaugccaguggaga
cucugggguuugugccaaauaacauucuggauaucaugagaacuccagaaucuggaguggggcgcgcugacccccccauacaca
cauaccauacagaaacaaaggacggaauacggccugagaucagcugacacuccuucugccccaucacccccuccaacgccagca
cccguuccgguccccccuuccaccuucuguaccagcacccguuucugugcccaagguuccagcagaugucacccgccagaaca
gcagcuccagugacaguggggcagcauugugcgggacagccagagauacaaacaacucccaguggaccgaaggaaguccca
gauggaagagguucaggaugagcucuuccagaggcugaccaucgggcgcagugcugcgcagaggaaguuccacgugccacg
gcagaacguuccagugaucaauaucacuuaugacuccucaccggaagaaguaaagacuuggcugcagucaaagggauucaau
cccgugacugucaauagccucgggguguugaacggagcacaacucuuuucucucaacaaagacgaacugaggucugucugcc
cggaaggugccagagucuuuaaccaaaucacuguucagaaagcugcuuuggaggacaguaauggaagcuccgaguuacaaga
gaucaugcggagacggcaggagaagaucagcgccgcugcgagcgacucgggaguggagucuuuugaugaagggagcagcca
cugaguccaugaacuuccuuauucuugguguggucguugaacagugauggacaugcuuuguuuuaagaagccuugaaggg
aaugucaaagcugucgucuugguauauguaauuuaucgccauauaaggaaacaguauaugccugaguaagcagaggacccgc
ugcuucugugcacauuaguuugauuaaaacugagaagcggguaggugagauggcucagcaaguaaaggugcuugcugccaa
gcccaaugacccaaguucgagucccuggguccuacaugguaggagagagcuggcuucugcaaguuguccucugaccaccacac
auaaauaaauaacaaauguaauuuacaaacuuuuaaaagaaaauguaauuuaaaaaaccagacguucuagacuguucugggc
uugggaaauauuuuuuucacuuuccuaagguguacuuuccuuugcuacauuaauuauugcagccuuguucgaugaucuaa
guggggauauuugacaauggcagauuuauucauugcaacaaggaaagacacagccauugaugaaaaaaaaaagaaagucuca
gcuuucagugacugggauaccugcuguccagggaggaggcucaguuagacuacccucugcuuacuugaggucugacaugcc
caaugagaguguauuuagcuuuauuuaaaguucuuaaugccaacaguuuuaaaaaucacauuuaaaugaacuguacaaggu
agccagaccuugaauguaugaauagacuauauaauaugucccgagaaacuuuguuacucucagcucuguugauugcgaaauc
uugcauagauuaugcuuugauuuaguuucu TABLE 4-continued Genes up-regulated in HF stem cells. Numbers in parentheses are the fold increase as determined by quantitative real time PCR.

| Gene Name/ Protein name/ GenBk Acces #. | Fold Incr. | Sequence | SEQ ID No. |
|---|---|---|---|
| Fyn/Fyn proto-oncogene M27266 | 10 | Sequence below. | 250 |

ccugggccccgccgcggacgcgcggagccgccugggccgcgccggaggagggcggggagaggaccaugugaaugugcuccg
gagcugagcgccaagccaagcaguguuugaaaggaacaggaugcugaucuaaucguggcaaaaagucaguccgaccgcuggu
uucgaagacaugugguguauauaaaguuugugauaguuggugg aaauugggagcuuggauaaugggcugugugcaaugu
aaggauaaagaagcagcgaaacugacagaggagagggacggcagccugaaccagagcucugg uaccgcuauggcacagaccc
caccccucagcacuaccccagcuucggcgugaccuccaucccgaacuacaacaacuuccacgcagcuggggccagggacuca
ccgucuuuggggugugaacuccuccucucacacugggacccuacgcacgagaggagggacaggagugacacuguuugugg
cgcuuuaugacuaugaagcacggacggaagaugaccugaguuucacaaaggagaaaaauuucaaauauugaacagcucgga
aggagauuggugggaagcccgcuccuugacaaccggggaaacugguuacauucccagcaauuacguggcuccaguugacucc
auccaggcagaagagugguacuuuggaaaacuuggccgcaaagaugcugagagacagcuccuguccuuggaaacccaagag
guaccuuucuuauccgcgagagccaaaccaccaaaggugccuacucacuuuccauccgugauugggaugauaugaaaggga
ccacgucaaacauuauaaaauccgcaagcuugacaaugguggauacuauaucacaacgcgggcccaguuugaaacacuucagc
aacugguacagcauuacucagagaaagcugaugguuuguguuuaacuuaacugugguuucaucaaguuguaccccacaaa
cuucuggauuggcuaaagaugcuugggaaguugcacgugacucguuguuucuggagaagaagcuggggcagggguguuuc
gcugaagugugg cuugguaccuggaauggaaauacaaaguagccauaaagacccuuaagccaggcaccaugucuccggagu
ccuuccuggaggaggcgcagaucaugaagaagcugaagcaugacaagcuggugcagcucuacgcggucgugucugaggagcc
cauuuacaucgucacggaguacaugagcaaggaaguuugcuugacuucuuaaaagauggugaaggaagagcucugaaguu
gccaaaccuuguggacauggcggcacagguugcugcaggaauggcuuacaucgagcgcaugaauuauauccacagagaucug
cgaucagcaaacauucuaguggggaauggacuaauuugcaagauugcugacuuuggauuggcucgguugauugaagacaau
gaauacacagcaagacaaggugcgaaguuucccauuaaguggacagcccccgaagcggcccuguauggaagguucacaauca
agucugacguauggucuuuuggaaucuuacucacagagcuggucaccaaaggaagagugccauacccaggcaugaacaaccg
ggaggugcuggagcagguggagagaggcuauaggaugcccugcccacaggacugcccgaucucccugcacgagcucaugauc
cacugcuggaaaaaggauccggaagagcgcccgaccuucgaguacuugcagggcuuccuggaggacuacuuuacggccacag
agccccaguaucagcccggugaaaaccugugagagccugcgcuucagacgccucuucccgaggccucccuaccccuccccauu
agcuuccaauucuguagccagcugccccagagcaggagaaccguccaggaucagauugcaugugacucuugaagcugaacuu
ccacggcccucauuaaugacacuuguccccaguccgaaccuccucugugaaccaucugagacagaagcguguuauuucuca
gacuuggaaaugcauuguaucgauguuaugucaaaggccaaaccucuguucaguguaaauagcugcuccugugccaacaauc
ccagugcuuuccuuuuuuaaaaaagaaaaagcaaauccuaugugauuuuaacucugauuucaccugauucaacuaaaaaaaa
aaaaguauuauuuuccaaaaguggccucuuugucuaaaacaauaaaauuuuuuuucauguuuuaacaaaaaaaaaaaaaaaa
aaaaaaaa Structurally-related

| Gene Name/ Protein name/ GenBk Acces #. | Fold Incr. | Sequence | SEQ ID No. |
|---|---|---|---|
| Col6a1/ Procol-lagen, type VI, alpha 1 X66405 | 36 | Sequence below. | 251 |

cccucccuggcucucucccucagcucugggcucugacugcagcaagcagagacaaccucucacucugccuuucccagcgcccac
ccugacccuggcccacauuugacggugacucgcaggccagccagaaacaugaggcuggcccacgcucugcugccccugcugc
uacaagccugcuggguggccacacaggacauccagggcuccaaagcgauugccuuccaagacugcccuguggaucuauucuu
cgugcucgacaccucggagaguguggccuugaggcugaaaccuuauggggccuugguggacaaggugaaguccuucacuaa
gcgcuucauugacaaccugagagacagguacuaccggugugaccgcaaccugguuuggaaugcgggugcgcugcacuacag
ugacgagguggagaucauccgagggcucacgcgcaugcccaguggccgcgaugagcucaaggccagcguggaugcggucaag
uacuucgggaaaggcaccuacaccgacugcgccauuaagaaggggcuggaggagcugcucauagggggcucccaccugaagg
agaacaaguacuugaucguggugaccgacgggcauccucuagagggcuacaaggaaccaugcggggg ucuggaagaugcagu
aaaugaggccaaacaccugggcaucaaggucuuuucuguggccaucacaccugaccaccuggagccacgucuaaguaucauu
gccacagaccacacauaccggcgcaauuucacggcagcugacuggggg cauagccgcgaugcagaagaggucaucagccagac
cauugacaccauuguggacaugauuaaaaauaacguggaacaaguguguuguucuuuugagugccaggcugccagaggacc
uccagggccccgaggcgacccugguaugagggggagcgaggaaagccaggucuuccgggagagaagggagaagcuggagac
ccuggacgaccuggggaucuuggaccagucggguaccaggguaugaagggagaaaggggagccguggagagaaggguucc
agaggaccgaaagguuacaagggcgagaaaggcaagcgcggaaucgacgggg ucgacggcaugaagggagagacgggguacc
caggacuaccgggcugcaagggcuccccaggauuugauggcauucaaggacccccggguccca agggugaugcuggugccuu
ugggaugaagggagaaaggg ugaagcuggagcagacggugaggcugggagaccagggaacucagggucaccuggagauga
gggugauccuggagagccugguccccccggagaaaaggagaggccggugaugaaggaaaugcuggcccagacggugcccu
ggagagagggguggcccuggugaaagaggaccucggggaccccuggugugagaggaccaaggggagacccgggugaagcu
ggaccacagggugaccaaggaagagaggggcccgucggcaucccuggagacucgggugaggcuggccccauuggaccuaaag
gauaccgaggugaugagggucccccagguccugagggccucagaggagccccaggaccuguugguccuccuggagaccccgg
acugaugggugagagaggugaggauggaccaccaggaaacggcacggaagguuuccccggcuucccugggu auccaggcaac
agaggcccuccugggcuaaauggcacaaaaggcuacccuggccucaaggggg augagggugaagugggagacccaggagagg
auaacaacgacauuucaccccgugggg ucaaaggggcaaaggg auaccgaggcccagaaggaccccaggaccuccaggacau
gugggaccaccugggccagaugagugugagauccuggauaucaucaugaaaaugugcuccugcugugagugcacaugugga
cccauugacauccucuucgugcuggacagcucggagagcauuggccuacagaacuuugagauugccaaggacuucaucauca
aggucauugaccgguugagcaaggaugagcuggucaaauuugagccagggcagucucacgcgggcgugguacaguacagcc
acaaccagaugcaagagcacguggacaugcggagccccaacguccgcaacgcccaggacuucaaagaagcugucaagaagcua
caauggauggcugguggcacauucaccggagaagcgcugcaguacacccgggaccggcuacucccacccacacagaacaaccg
aauugcccuggucauuacggauggacguucugacacucaacgggacacgacaccucucagugugcucugguggugcagacauu TABLE 4-continued Genes up-regulated in HF stem cells. Numbers in parentheses are the fold increase as determined by quantitative real time PCR.

| Gene Name/ Protein name/ GenBk Acces #. | Fold Incr. | Sequence | SEQ ID No. |
|---|---|---|---|
| | | cagguaguuucugugggaaucaaggauguguuuggcuuuguggcgggcuccgaccagcucaaugucauuuccugccaaggc<br>uuaucgcaaggucguccagguaucucccuggugaaggagaacuaugcagagcuucucgaugacggcuuucugaagaacauaa<br>cagcccagaucuguauagauaagaaguguccggauuauaccuguccaaucacauucuccuccccggcugacaucaccauccu<br>gcuagacagcucagccagugucggcagccacaacuucgaaaccaccaaggucuucgccaagcgccuagcugagcgauuccug<br>ucagcaggcagggcggauccuucccaggaugugcggguggccgugguacaguauaguggccaggggcagcaacagccaggu<br>cgggcggcucuucaguucuuacagaauuacacagugcuggccagcucuguggacagcauggauuucaucaacgacgccacag<br>acgucaacgaugcucugagcuacgugacucguuucuaccgggaagccucgucaggugccaccaagaagagagugcuguugu<br>uuucagacggcaacucucagggggccacagcagaggccauugagaaggcugugcaggaggcccagcgugcaggcauugagau<br>cuuugugguggugguggaccccaggugaacgagccccacauccgugugcuugucacuggcaagacugcagaguacgacgu<br>ggccuuuggcgagcgccaccuauuccguguaccaaacuaccaggcccugcuacguggcguacucuaccagacagucuccagg<br>aagguggcacugggcuagagggccacacacguggcuggacacacauggcauggagacacauuucaacaggccuucccgcccu<br>ucccacugacaaaacaggaauaggaaaugugacccaacuggucaacucaacugucuuaaagggaacgcugagaugcacacucu<br>uugcuuuguguaaugucccccuguggcucaccugagcuccuaucuagaucccgcccuugguuuguacaucaugguggccauc<br>uugcugaccccucccccaucugggacuggauccagccaucucgucuuccuccucacugccccuaaccuauccguggugucuu<br>cacaccaucacugcaguuuccgucuguguucugucuuccaugcucaacaugaagcagaccuucucaugaguucagcuugcug<br>gauuauggcuuuuaggaaauugaacacaggaggaguuccaaacacaaacuuggaggagacccccuccucuucaucaggugcuu<br>gucagugaccuacaugcaucuuggucugguccuuaguggcuaguccuuccacucugaaagcaaaggugcuaucuaucugua<br>agggcucucucuacacacccagaggcuuagcuuggacaguucacacucaagugucccugucagaaucaauccagagcuuucuc<br>ccucaaaauagugacuugucuccccccugguccccaaaggcuccccuuuaguuaguuucuucauggcucccccacauuccccg<br>uaaucugauccaagccagcuaucucugcuaauaaagguuuccauuuuucaaaaaaaaaaaaaa | |
| Tnc/<br>Tenascin C<br>AV230686<br>X56304 | 17 | accccaugccccacccccaccuucgauguuuugaacauuucuaacaacug<br>aagccaguaaagucauauucuuuaaauuuccaggacauucauauuauuc<br>acauaaucauggucauggugaugauggaaacugaggacuuuaaaagaga<br>uuuucccuucccaaacguuucuggacaguaccugauuguauuuuuuuug<br>uuuuguuuuguuuuuuaauaaaagcacaguacuuuucc | 252 |
| Krt2-6a/<br>Keratin<br>complex 2,<br>basic, gene<br>6a (keratin<br>6a)<br>K02108 | 10 | Sequence below. | 253 |
| | | gucugcccugccguuucucuacuucccagccuucucaucuccaggaaccaugucuaccaaaaccaccaucaaaagucaaacca<br>gccaccguggcuacagugccagcucagccagagugcuuggacucaaccgcucgggcuucagcaguguguccgugugccgcuc<br>ccggggcagcgguggcuccagugcaauguguggaggagcuggcuuuggcagcaggagccucuaugguguggggagcuccaa<br>gaggaucuccaucggagggggcagcuguggcauuggaggaggcuauggcagccgauucggaggaagcuucggcauuggugg<br>uggagcugguaguggcuuuggcuucgguggugggagcuggcuuugguggugggcuauggggggagcuggcuucccggugugc<br>ccacuuggaggcauccaagaggucaccaucaaccagagccuccucacaccccugaaccugcaaauugaccccaccauccagcg<br>ggucaggacugaggagagggagcagaucaagacccucaauaacaaguuugccuccuucaucgacaaggugcgguucauggag<br>cagcagaacaaggucauggacaccaagugggcccugcugcaagagcaggacaccaagaccgugaggcagaacauggagcccau<br>guuugagcaguacaucagcaaccuccgcagacagcuggacagcaucauuggagagagggggucgcaugaacucagagcugagg<br>aacaugcaggaacucguagaagaacuacggaacaaauaugaagaugaaaucaacaagcgcacagacgcagagaaugaauucgu<br>gacccugaagaaggauguagaugcugccuacaugaacaaaguugaacugcaagccaaggcagacagucuaacagaugauauc<br>aacuucuugagagcucucuaugaagcagaacugucucagaugcaaacucacaucucagacacaucuguggucccucuccaugg<br>ucaacaaccguagccucguccuagacagcaucaucgcugaggucaaggcccaguuugaggucauagcucagagaagucgggc<br>ugaagcugagucauuguaccagacuaaauaugaggagcugcaggucacagcuggcagacauggggacgaccugcgcaacacc<br>aagcaggagauugcugagaucaaccgcaugauccagaggcugagaucugagaucgaccacguuaagaagcagugugccaacc<br>ugcaagcugcuauugcugaugcugagcaacguggggagauggcccugaaggaugcaaggggcaagcuggaagggcuggagg<br>augcccugcagaaggccaaacaggacauggccaugcugcugaaggaguaccaugaacucaugaaugucaagcuggcccuuga<br>uguggaaauugccaccuacaggaagcugcuggaaggagaggagugcagguugaauggugaagguguuggaccagucaacau<br>cucugguggugcaguccaccguguccagcggcuauggcagugccgggggugccagcagcagcuuaggcaugggugggaggcag<br>cagcuacuccuauagcagcagccauggccuuggagguggcuucagugcuggcaguggcagagccaucggagguggccucag<br>cucuucugguggccucagcucuucuaccaucaaauacaccaccaccuccuccagcaagaagagcuacaggcagugaauucug<br>ucaccaagagcuugucucugguccccagaugucauggcugcagcugaaccacaugcuuugguucccggaagggaacgaaucccc<br>aaccucuggccuccccauggcucaguucuacauuuguguugcacgucagcaccuauacauguucuuuggugacccagacccc<br>aaaauguugcagaauguagaccuccaagacgaaaccccaaacccuacccagaauacccaccuaaauucugucaugguucugac<br>uuccuccagagucuguaaaauaaaaugccccccacaacaaac | |

Channel-related

| | | | |
|---|---|---|---|
| Potassium<br>channel,<br>subfamily<br>K, member 2<br>AI849601 | 14 | uuuuuuuuuuuuuuuuuugauuuuaauuacaaacuuuauuuguccuc<br>caguucacaguuuauacgugguacaucccaccaugucagcuuccagaa<br>cggcuauucaggagauggguggagcuuucuuuguaaaggaacccgac<br>auuuuaaaauuuugguuagaaucuucauagguuuauaaaaguacucu<br>cugcaagcgaacuggauauauuuacauuuauagcuuaaauucaaauu<br>uuggaaaauaggaaucuuuuuguguuuuuaaacauccugguuuau<br>gucuuaagacuuuacucugaaugccacaugaucacguaagcccaagcc<br>ucccccagaagggaaaaaucaguuuugc | 254 |

TABLE 4-continued

Genes up-regulated in HF stem cells. Numbers in parentheses are the fold increase as determined by quantitative real time PCR.

| Gene Name/ Protein name/ GenBk Acces #. | Fold Incr. | Sequence | SEQ ID No. |
|---|---|---|---|
| Skd3/ Suppressor of K+ transport defect 3 AI837887 | 4 | uuuuuuuuuuuuuuuuuugggugccaugccacagcaaggggccuuua<br>uuagauguucagggcacagacagguggaugcuagaugguguagcaca<br>ccuucucaggguggaguggugccuggauguccaguuugcgggucuu<br>gcuguccuuaucaaugaucuccagucgcaauguagguggacgcuucu<br>cagccuggggugagggcagcucacggcucuugaggaggugcuugucc<br>gaauccuccacagugauacccagggugcaaccccccugg | 255 |
| Clic4/ Chloride intracellular channel 4 (mito-chondrial) AI845237 | 3 | uuuuuuuuuuuuuuucugacacaguaguaauccuuccagacuccuua<br>cacaauauuacaacucccccaguacauaaauguuccuauaccaugcaca<br>cagcaacauggggucccacugaugucgcaggcgacuuuucuaauggug<br>gaacauagcaccucaaguucugccaucuacacagugaagggacgugau<br>ggucggggcuccagagugacagcaaacugccucuugggugacacgcu<br>uguggcgaagugccucc | 256 |
| Col18a1/ Endostatin (alpha 1(XVIII) collagen) L22545 | 5 | Sequence below. | 257 |

gagaauguugcugaggaggugggcugcugcagcuccuuggagacccccuaccugagaagaucucacaaaucgaugacccuc
acgucgggccggccuacaucuuuggaccagacuccaacaguggccagguggcccaguaucauuucccaaaacucuucuuccg
ggacuuuucgcugcuguuucauguccggccagccacagaggcagcaggggugcuauuugccaucacagaugcugcccaggu
gguagucucacugggcgugaagcucucagagguccgagauggacagcaaaacaucucauugcucuacacggagccuggggcc
agccagacccagacgggagccagcuuccgccuaccugcauuuguugggcaguggacacacuucgcgcucagcgucgacggag
gcucuguggcucucuacguagacugugaagaauuccagagggugccauuugcucgggccucgcagggacuggagcuagagc
guggcgcuggccucuuuguggucaggcuggaacagcagacccugacaaguuccaggggaugaucucagagcugaagguac
gcaaaacccccgggugagcccugugcacugucuggaugaagaagaugaugaugaagaccgggcaucuggagauuuuggaag
uggcuuugaagaaagcagcaagucacacaaggaggauacaucucuacuaccugggcucccucagccaccuccugucacuucc
ccaccccuggcuggaggcagcaccacagaagauccuagaacagaagaaacggaggaagacgccgcgguagauucuauaggagc
ugagacccuuccuggcacagguucaagcggugcaugggaugaggcuauccagaaccccggaaggggcuugauaaagggagg
uaugaaaggacaaaagggagaaccaggugcccagggcccaccuggcccagcuggcccccaggguccugccgguccagugguc
cagagccccaacucacaaccugucccuggagcacaaggacccccgggaccucaggggccaccagggaaggauggcacuccagg
aagggaugguggaaccgggugacccuggugaagaugggagaccgggugacacuggaccucaaggcuuuccagggaccccagga
gaugugggcccuaagggcgagaagggagauccugguauugggccccgaggaccuccagggccuccagggccaccaggacccu
ccuucagacaagacaagcugaccuucauugacauggagggauccgguuucagcggagacauagagagccuuagaggcccacg
aggcuucccuggcccccggggcccccuggugucccaggacuuccuggugagccaggacgcuuugggaucaaugguuccua
ugcaccaggaccugcaggccuuccugguguaccugggaaggaaggacccccgguuuuccaggucccccgggaccuccaggu
ccuccaggcaaagagggcccaccaggaguggccggccagaaaggcaguguuggugaugugggcaucccaggacccaaggga
gcaaaggagaccuugggcccaucgguaugccuggcaagucuggcuuggcuggauccccugggccaguuggacccccaggacc
uccagggccuccagggccaccaggaccaggauuugcugcuggauucgaugauauggaaggcucuggaauaccccucuggaca
acagcccgaagcucugaugggcugcagggaccucccgggucgccgggacucaagggggauccuggaguggcaggccuaccug
gagccaagggagaaguuggagcagauggagcccagggcaucccugguccccaggaagagaaggugcagcuggaucuccggg
gccaaaaggagagaaggggaugccgggagaaaagggaaacccaggaaaagauggaguggccggccgggccucccugggccu
ccaggaccuccagggcuggugaucuaugugucaagugaggauaaagcaauagugagcacgccaggaccugagggcaagccag
gguacgcaggcuuuccuggaccugcuggaccgaagggugaccugggguuccaaaggcgagcagggucuuccgggguuuaagg
gugagaagggagagccaggcacuaucuuuaguccugauggcagacgucugggccauccccagaagggagccaagggagagcc
aggcuuucgaggaccccggguccuuauggacgaccugggcacaagggugaaauuggcuucccuggacggccgggucgacc
uggaacgaauggcuuaaagggagagaagggagagccuggagaugccagccuuggguucagcaugaggggauugccuggccc
cccugggccuccaggacccccagguccuccugggaugcccaucuaugacagcaaugcauuuguggagucuggccgaccugga
cuaccaggacagcaggguguggcaggggccuucaggaccaaaggugacaaaggagagguggggccaccuggggccaccagggc
aauuccccauugaccucuuccaccuggaagcggaaaugaaggggacaagggagaccgaggggaugcuggacagaaaggaga
gaggggagaaccuggggcuccugguggugaguucuucagcucaagguaccuggcccacccggcccaccuggauacccugga
auuccggguccaaagggagagagcauccgggggccaccuggcccuccuggcccgcagggaccuccuggcauuggcuaugagg
gucgccaggguccccccaggaccuccaggaccuccaggaccucccuccuucccuggcccucacagacagacugucaguguuccu
gguccuccgggcccaccugguccuccagguccccaggagccaugggugccucugcugggcaggugaggaucugggccacau
accagaccaugcuggacaagauccgggaggugccggagggcuggcucaucuuuguggccgagagggaagagcucuauguac
gcguuagaaauggcuuccggaaggugcugcuggaggcccggacagcccuccugagaggcacgggcaaugagguggcugcuu
uccagcccccauugguccagcuucaugagggcaguccauacacccggagggaguacuccuauuccacggcacgacccuggcg
agcagaugacauccuggccaacccaccgcgccugccagaccgccagccuuacccuggaguuccacaucaccacaguuccuaug
ugcaccugccgccagcccgccccacccucucacuugcucauacucaucaggacuuucagccagugcuccaccugguggcacu
gaacacccccugucuggaggcaugcgugguauccguggagcagauuuccagugcuuccagcaagcccgagccguggggcug
ucgggcaccuuccgggcuuuccuguccucuaggcugcaggaucucuauagcaucgugcgccgugcugaccgggggucugug
cccaucgucaaccugaaggacgaggugcuaucucccagcugggacucccuguuuucuggcucccagggucaagugcaacccg
gggcccgcaucuuuucuuuugacggcagagauguccugagacacccagccuggccgcagaagagcguauggcacggcucgga
ccccagugggcggaggcugauggagaguuacugugagacauggcgaacugaaacuacuggggcuacaggucaggccuccucc
cugcugucaggcaggcuccuggaacagaaagcugcgagcugccacaacagcuacaucguccugugcauugagaauagcuuca TABLE 4-continued Genes up-regulated in HF stem cells. Numbers in parentheses are the fold increase as determined by quantitative real time PCR.

| Gene Name/ Protein name/ GenBk Acces #. | Fold Incr. | Sequence | SEQ ID No. |
|---|---|---|---|
| ugaccucuuucuccaaauaggccucugccagcuaggguggcagacagaggccaugcagaacuuugacacagcgcagggagca<br>uucagucagcacccagggcucuggcugggauacaacuccuguauaguucccauuuuuauguaauccucaagaaauaaaagga<br>agccaaagaguaaaaaaaaa | | | |

TABLE 5

Genes down-regulated in HF stem cells.

| Gene Name/protein | Fold Decr | Sequence | SEQ ID No. |
|---|---|---|---|
| Growth Factors, Receptors and Downstream genes | | | |
| GNA-14 Mouse G protein alpha subunit (GNA-14) M80631 | 32 | Sequence below. | 258 |
| aacugccuucgagaagcguuagccuagagauccgagccucuucuccauaccauaguugguucagguggguuuccucuucaaac<br>cuugcgucugcggauaauccgcgcggccgggcguuaagcuccaggucccugucgcuccgucgagguggcaagccauggccg<br>gcugcugcuguuugucugcggaggagaaagagucucagcgcaucagcgcggagaucgagcggcacguucgccgcgacaagaa<br>ggacgcgcgccgggagcucaagcugcuguugcugggaaccggugagagugggaaaagcaccuuuaucaagcagaugaggau<br>aauccaugggucuggcuacagugaugaagauagaaagggcuucacgaagcugguuuaccaaaacauauucacggccaugcaa<br>gccaugaucagagcaauggauacccugaggauacaauacaugugugagcagaauaaggaaaaugcccagaucaucagggaag<br>uggaaguagacaaggucacugcacucucuagagaccagguggcagccaucaagcagcuguggcuggaucccggaauccagga<br>guguuacgacaggaggagggaguaccagcugucagacucugccaaauauuaccugacggacauugagcguaucgccaugccc<br>ucuuucgugccaacacaacaggaugugcuucguguuagagugcccaccacuggcaucauagaauauccauucgaccuggaaa<br>acaucaucuuccgaaugguggauguugguggccagcgaucugaacgacggaaauggauucacugcuuugagagugucaccu<br>ccaucauuuucuugguugcucugagugaauaugaccagguucuggcugagugugacaaugagaaccgcauggaggagagca<br>aagcccuguuuagaaccaucaucaccuaccccugguuucugaacuccuccgugauucuguucuuaaacaagaaggaucuucu<br>agaggagaaaaucauguacucucaucuaauuagcuacuucccagaguacacaggaccaaagcaagaugucaaagcggccaggg<br>acuuuauccugaagcuguaucaagaccagaauccugacaaagagaagguuaucuauucucacuucacuugugcuacagacac<br>cgagaauauccgcuuuguguuugcugcugucaaagacacaauccuacagcuaaaccuacgggaguucaacuugguguaaaug<br>gagggccuacuccuccgagacagagggugaucugagcccuuccugccugaucuacaagugcuucuggaccaggaccuaagga<br>cauuauguagcccacaggacagagaugggguagugcaaugugaaaaauacuucaccaacccuuuuaagugucuuuaauucuuc<br>acugucuaacucuuuucucgccuuuugguugaacgauuagguaucauuuuugagugguuccccucuccuauuuuuuuaa<br>acuaguguucaacaguuauuaaaaaaucaugc | | | |
| Ly6/Lymphocyte antigen 6 complex X04653 | 12 | gaauucccugcaaccuugucugagaggaagcaaggacuggugugagg<br>agggagcugugagguuuuaucugugcagcccuucucugaggaugga<br>cacuucucacacuacaaaguccuguuugcugauucuucuuguggccc<br>uacugugugcagaaagagcucagggacuggaguguuaccagugcua<br>uggagucccauuugagacuucuugcccaucaauuaccugccccuacc<br>cugauggagucuguguuacucaggaggcagcaguuauugugguuc<br>ucaaacaaggaaaguaaagaacaaucuuugcuuacccaucugcccucc<br>uaauauugaaaguauggagauccugguacuaaggucaaugugaaga<br>cuuccuguugccaggaagaccucugcaaugcagcaguucccaaugga<br>ggcagcaccuggaccauggcaggggugcuucuguucagccugagcuc<br>aguccuccugcagaccuugcucugaugguccucccaaugaccuccac<br>ccuuguccuuuuauccucaugugcaacaauucuuccuggagcccucu<br>agugaugaauuaugaguuauagaagcuccaagguggaguagugug<br>ugaaauaccauguuuugccuuuauagcccugcugguagguaggug<br>cucuaauccucucuagggcuuucaagucuguacuuccuagaauguca<br>uuuuguuguggauugcugcucaugacccuggaggcacacagccagca<br>cagugaagaggcagaauuccaagguauuaugcuaucaccauccacac<br>auaaguaucugggguccugcaauguucccacauguauccugaauguc<br>ccccuguugaguccaauaaacccuuuguucuccc | 259 |
| Bmp4/Bone morphogenetic protein 4 L47480 | 11 | Sequence below. | 260 |
| ggaagaaagagagggagggaaaagagaaggaaggaguagaugugagaggguggugcugaggguggggaaggcaagagcgcga<br>ggccuggcccggaagcuaggugaguucggcauccgagcugagagaccccagccuaagacgccugcgcugcaacccagccuga<br>guaucuggucuccgucccugaugggauucucgucuaaaccgucuuggagccugcagcgauccagucucuggcccucgacca<br>gguucauugcagcuuucuagagguccccagaagcagcugcuggcgagcccgcuucugcaggaaccaauggugagcagggcaa<br>ccuggagaggggcgcuauucugaggauucgaggugcacccguaguagaagcuggggauggggcucaggcuguaaccgaggc | | | |

TABLE 5-continued

Genes down-regulated in HF stem cells.

| Gene Name/protein | Fold Decr | Sequence | SEQ ID No. |
|---|---|---|---|

aaaaguuggccuauuccuccuuccuucuccaacaguguuggaggugggaugauggaggcuaaaaggcaccuccauauaugu
uacugcgucuaucaaccuacuuuagggaggugcgggccaggagaggcgggaaggagagaaggccuuggaagagaggucauu
gggaagaacugugggguuugguggguuugcuuccacuuagacuauaagagugggagaggagggagucaacucuaaguuuc
aacaccaguggggg acugaggacugcuucauuaggagagagaaccuagccagagcuagcuuugcaaaagaggcuguaguccu
gcuuugcucuaaagcgcgacccgggauagagaggcuucccuugagcggggugucaccuaaucuuguccccaacgcaccccc uc
ccagccccugagagcuagcgaacuguagguacacaacucgcucccaucuccaggagcuauuuucuuagacaugggcacccau
gauucugccuucugguacucuccccucccugggaaaggggguguaagguuccgacggaaccguggccaggaugccgaaaggc
uaccugugcgggucuucugccaugcugugucugugcggacaugccagcagggcuaaugaggagcuugcgauacuccaaagg
guucgggaauugcggggucccuuacacgcaguggaguugggcccccuuuuacucagaagguuuccgccacggcuuugguugau
aguuuuuuuaguauccugguuuaugaacugaagguuuugugagauguugaaucacuagcagggucauauuggcaaaccg
aggcuacuauuaaauuugguuuuagaagagauucuggggagaaagugaaggguaacugccuccaggagcuguaucaacc
ccauuaagaaaaaaaaaaaauaccaggagaugaaaauuuacuuugaucuguauuuuuuaauuaaaaaaaaucagggaagaaag
gagugauuagaaagggauccugagcgucggcgguuccacggugcccucgcuccgcgugcgccagucgcuagcauaucgcca
ucucuuucccccuuaaaagcaaauaaacaaaucaacaauaagcccuuugcccuuuccagcgcuuucccaguuauucccagcgg
cgacgcgugucggggaauagagaaaucgucucagaaagcugcgcugaugguggugagagcggacugucgcucaggggcgcc
cgcggucucugcacccagggcagcagugugggauggcgcugggcagccaccgccgccaggaaggacgugacucuccauccuu
uacacuucuuucucaaagguuucccgaaagugcccccgccucgaaaacuggggccggugcgggggggggagagguuagg
uugaaaaccagcuggacacgucgaguuccuaagugaggcaaagaggcggggugggagcgggcucuggagcggggagucccug
ggacucgguccucggauggaccccgugcaaagaccuguuggaacaagaguugcgcuuccgagguuagaacaggccaggcauc
uuaggauagucaggucaccccccccccaaccccacccgaguuguguuggugaauuucuuggaggaaucuuagccgcgauuc
uguagcugggugcaaaggaggaaaggggugggggaaggaaguggcngngcgggggugcgguggggguggagugguuua
aaaaguaagccaagccagagggagaggucgagugcaggccgaaagcuguucucggguuuguagacgcuugggaucgcgcuu
ggggucuccuuucgugccggguaggaguuguaaagccuuugcaacucugagaucguaaaaaaaaugugaugcgcucuuucu
uuggcgacgccuguuuuggaaucuguccggaguuagaagcucagacguccacccccacccccgcccacccccucugccuu
gaauggcaccgccgaccgguuucugaaggaucugcuuggcuggagcggacgcugagguuggcagacacgguguggggacuc
uggcggggcuacuagacaguacuucagaagccgcuccuucuaacuuucccacaccgcucaaaccccgacacccccgcggcgga
cugaguuggcgacggggucagagucuucuggcugaaaguuagauccgcuagggg ucggcugccugucgcuagaagcauuau
uuggccucucggagacccguguggaggaagugcuggagugugcgagugug uuugcgugugugugugugugugugugu
gugugugugugugugugugugcgcgcgcccuuggaggg ucccuaugcgcuuuccuuuucauggaacgcugucgugaggcu
uugguaaacugucuuuucgguuccucucucggcugcacuuaagcuuugucggcgcuguaaagagacgcgucuucaagugca
cccugauccucaggcuucagauaacccguccccgaaccuggccagaugcauugcacugcgcgccgcagguagagacgugccc
cacguccccugcgugcagcgacuacgaccgagagccgcgccaguguggugucccgccgagaguuccucagagcaggcgggga
caacucccagacggcuggggcuccagcugcgggcgcggagguuggccucgcucgcaggggcuggacccagccgggguggga
ggauggaggaggggcgggcgggcucuucggugagugggg cggggccucuggguccacgugacuccuaggggcuggaagaa
aaacagagccugucugcuccagagucucauuauaucaaauaucauuuuaggagccauuccguagugccauucggagcgacgc
acugccgcagcuucucugagccuuuccagcaaguuuguucaagauuggcucccaagaaucauggacuguuauuaugccuug
uuuucugucagugaguagacaccucuucuuucccuucuugggauuucacucuguccucccaucccugaccacugucugucc
cucccgucggacuuccauuucagugccccgcgcccuacucucaggcagcgcuaugguucucuuucuggucccugcaaggcca
gacacucgaaauguacgggcuccuuuuaaagcgcucccacuguuuucucugauccgcugcguugcaagaaagagggagcgcg
agggaccaaauagaugaaagguccucagguuggggcugucccuugaagggcuaaccacucccuuaccagucccgauauaucc
acuagccugggaaggccaguuccuugccucauaaaaaaaaaaaaaaaacaaaaaacaaacagucguuugggaacaagacucu
uuagugagcauuuucaacgcagcgaccacaaugaaauaaaucacaaagucacuggggcagccccuugacuccuuuucccagu
cacuggaccuugcugcccgguccaagcccugccggcacagcucuguucuccccuccuccuguucuuaaccagcuggaaguug
uggaaauugggcuggagggcggaggaagggcggggguggggggguggagaagguggggggggggaggcugaagguccga
agugaagagcgauggcauuuuaauucucccuccnccuccccccuuuaccuccucaauguuaacuguuuauccuugaagaagc
cacgcugagaucauggcucagauagccguugggacaggauggaggcuaucunauuugggguuauuugaguguaaacaaguu
agaccaaguaauuacagggcgauucuuacuuucgggccgugcauggcugcagcuggugugugugugugu agggugugagg
gagaaaacacaaacuugaucuuucggaccuguuuuacaucuugaccgucgguugcuaccccuauaugcauaugcagagacau
cucuauuucucgcuauugaucgguguuuauuuauucuuuaaccuuccaccccaaccccucccccagagacaccaugauuccu
gguaaccgaaugcugauggucguuuuauuaugccaaguccugcuaggaggcgcgagccaugcuaguuugauaccugagacc
gggaagaaaaaagucgccgagauucagggccacgcgggaggacgccgcucagggcagagccaugagcuccugcgggacuucg
aggcgacacuucuacagauguuugggcugcgccgccguccgcagccuagcaagagcgccgucauuccggauuacaugaggga
ucuuuaccggcuccagucuggggaggaggaggaggaagagcagagccagggaaccgggcuugaguacccggagcgucccgcc
agccgagccaacacugugaggaguuuccaucacgaaggucaguuucugcucuuaguccuggcgguguaggguggg guagag
crccggggcagagggugggggguggg cagcuggcagggcaagcugaaggg guuguggaagccccccggggaagaagaguuca
uguuacaucaaagcuccgaguccuggagacuguggaacagggccucuuaccuucaacuuuccagagcugccucugaggguac
uuucuggagaccaaguaguggugguggaugggg gagggggu uacuuugggagaagcggacugacaccacucagacuncugcu
accncccagngggugu ucuuuagcuauaccaaagncagggauucugcccguuuuguuccaaagcaccuacugaauuuaaua
uuacancuguguguuugucagguuuaucaauaggggccuuguaauacgaucugaauguuuccuagcggauguuucuuuuc
caaaguaaaucugaguuauuaauccuccagcaucauuacuguguuggaauuuauuuucccuucuguaacaugaucaacaag
gcgugcucuguguuucuaggaucgcuggggaaauguuugguaacauacucaaaaguggagagggagagagggguggccccuc
uuuuucuuuacaaccacuuguaaagaaaacuguacacaaagccaagaggggg cuuuaaaaggggaguccaaggguggug gag
uaaaagaguugacacauggaaauuauuaggcauauaaaggagguugggagauacuuucugucuuugguguuugacaaaugu
gagcuaaguuuugcugguuugcuagcugcuccacaacucugcuccuucaaauuaaaaggcacaguaauuuccuccccuuagg
uuucuacuauauaagcagaauucaaccaauucugcuauuuuuuguuuuuguuucuuguuuuuguuuuguuugguuuuuu
uuuuuuuuuuuuuuuuuugucucagaaaagcucaugggccuuuucuuuuccccuuucaacugugccuagaacaucugga
gaacaucccagggaccagugagagcucugcuuuucguuuccucuucaaccucagcagcaucccagaaaaugaggugaucucc
ucggcagagcuccggcucuuucgggagcagguggaccagggcccugacugggaacagggcuuccaccguauaaacauuuau
gagguuaugaagcccccagcagaaaugguuccuggacaccucaucacacgacuacuggacaccagacuaguccaucacaaugu
gacacggugggaaacuuucgaugugagcccugcaguccuucgcuggacccgggaaaagcaacccaauuaugggcuggccauu
gaggugacucaccuccaccagacacggacccaccagggccagcaugucagaaucagccgaucguuaccucaagggaguggaga
uugggcccaacuccgcccccuccuggucacuuuuggccaugauggccggggccauaccuugacccgcaggagggccaaacgu
agucccaagcaucacccacagcgguccaggaagaagaauaagaacugccgucgccauucacuauacguggacuucagugacgu
gggcuggaaugauuggauuguggccccacccggcuaccaggccuucuacugccauggggacugucccuuuccacuggcuga
ucaccucaacucaaccaaccaugccauugugcagacccuagucaacucuguuaauucuaguaucccuaaggccuguuguguc TABLE 5-continued Genes down-regulated in HF stem cells.

| Gene Name/protein | Fold Decr | Sequence | SEQ ID No. |
|---|---|---|---|

cccacugaacugagugccauuuccauguuguaccuggaugaguaugacaagguggguguugaaaaauuaucaggagauggug
guagaggggugguggaugccgcugagaucagacaguccggagggcggacacacacacacacacacacacacacacacacacaca
cacacacacguucccauucaaccaccuacacauaccacacaaacugcuucccuauagcuggacuuuuaucuuaaaaaaaaaaaa
aagaaagaaagaaagaaagaaagaaaaaaaaugaaagacagaaaagaaaaaaaaaacccuaaacaacucaccuugaccuuauuu
augacuuuacgugcaaauguuuugaccauauugaucauauuuugacaaauauauuuauaacuacauauuaaaagaaaauaaa
augag

| Gene Name/protein | Fold Decr | Sequence | SEQ ID No. |
|---|---|---|---|
| IL1r2/Interleukin 1 receptor, type II<br>AV223216<br>X59769 | 11 | gaaucccacuuacaugcgagcaucucuauauacauccucaaucuauc<br>cccucgaauccacggacuuaucagucaaucaauacuacagucaaagaa<br>uuuuuuucuacguuauccuggagcauugcgcuggcaccucuuuuuc<br>uaaucaucuugguuguggggccaauauggaugcgcagacgguguaa<br>acgcagggcuggaaagacauauggacugaccaagcuacggacugaca<br>accaggacuucccuuccagcccaaacuaaauaaaggaaaugaa | 261 |
| Wnt3a/wingless-related MMTV integration site 3A<br>X56842 | 4 | Sequence below. | 262 |

gaauucaugucuuacggucaaggcagagggcccagcgccacugcagccgcgccaccucccagggccgggccagcccaggcgu
ccgcgcucucgggguggacucccccgcugcgcgcucaagccggcgauggcuccucucggauaccucuuagugcucugcagc
cugaagcaggcucugggcagcuacccgaucugguggucuuggcugugggaccccaguacuccucucugagcacucagccca
uucucugugccagcaucccaggccugguaccgaagcagcugcgcuucugcaggaacuacguggagaucaugcccagcguggc
ugagggugucaaagcgggcauccaggagugccagcaccaguuccgaggccggcguuggaacugcaccaccgucagcaacagc
cuggccaucuuuggcccuguucuggacaaagccacccgggagucagccuuuguccaugccaucgccuccgcuggaguagcuu
ucgcagugacacgcuccugugcagagggaucagcugcuaucugugggugcagcagccgccuccagggcuccccaggcgaggg
cuggaagugggcggcuguagugaggacauugaauuuggaggaauggucucucgggaguuugccgaugccagggagaaccg
gccggaugcccgcucugccaugaaccgucacaacaaugaggcugggcgccaggccaucgccagucacaugcaccucaagugca
aaugccacgggcuaucuggcagcugugaagugaagaccugcugguggucgcagccggacuuccgcaccaucggggauuucc
ucaaggacaaguaugacagugccucggagauggugguagagaaacaccgagagucucguggcuggguggagacccugaggc
cacguuacacguacuucaaggugccgacagaacgcgaccuggucuacuacgaggccucacccaacuucugcgaaccuaacccc
gaaaccggcuccuucgggacgcgugaccgcaccugcaaugugagcucgcauggcauagaugggugcgaccuguugugcugc
gggcgcgggcauaacgcgcgcacugagcgacggagggagaaaugccacuguguuuuccauuggugcugcuacgucagcugc
caggagugcacacgugucuaugacgugcacaccugcaaguaggagagcuccuaacacgggagcaggguucauuccgaggggc
aagguuccuaccuggggggcgggguuccuacuuggaggggucucuuacuuggggacucgguucuuacuugagggcggagau
ccuaccugugagggucucauaccuaaggacccgguuucugccuucagccugggcuccuauuugggaucugguuccuuuuu
aggggagaagcuccugucugggauacggguuucugcccgaggguggggcuccacuuggggauggaauuccaauuugggccg
gaaguccuaccucaauggcuuggacucccucucuugacccgacagggcucaaauggagacagguaagcuacucccucaacuag
guggggguucgugcggauggguggggagggggagagauuaggguccccuccucccagaggcacugcucuaucuagauacaugaga
gggugcuucagggugggcccuauuugggcuugaggaucccgugggggcggggcuucaccccgacuggguggaacuuuugg
agaccccccuuccacuggggcaaggcuucacugaagacucaugggauggagcuccacggaaggaggaguuccugagcgagccu
gggcucugagcaggccauccagcucccaucuggccccuuuccaguccugguguaagguucaaccugcaagccucaucugcgc
agagcaggaucuccuggcagaaugaggcauggagaagaacucagggggugauaccaagaccuaacaaaccccgugccuggua
ccucuuuuaaagcucugcaccccuucuucaagggcuuuccuagucuccuuggcagagcuuuccugaggaagauuugcaguc
ccccagaguucaagugaacacccauagaacagaacagacucuauccugaguagagaggguucucuaggaaucucuaugggga
cugcuaggaaggauccugggcaugacagccucguaugauagccugcauccgcucugacacuuaauacucagaucucccggga
aacccagcucauccgguccgugauguccaugccccaaaugccucagagauguugccucacuuugaguuguaugaacuucgga
gacauggggacacagucaagccgcagagccaggguuguuucaggacccaucugauuccccagagccugcuguugaggcaaug
gucaccagauccguuggccaccacccugucccgagcuucucuagugucugucuggcccuggaagugaggugcuacauacagcc
caucugccacaagagcuuccugauugguaccacugugaaccgucccucccccuccagacaggggaggggauguggccauaca
ggagugugcccggagagcgcggaaagaggaagagaggcugcacacgcguggugacugacugucuucugccuggaacuuugc
guucgcgcuuguaacuuuauuuucaaugcugcuauauccacccaccacuggauuuagacaaaagugauuuucuuuuuuuu
uuuucuuuucuuucuaugaaagaaauuauuuuaguuuauaguauguuuguuucaaauaauggggaaaguaaaaagagagaa
aaaaaaaaaaaaaaaaaaaaaaaaaaaaaaaaaaa

| Gene Name/protein | Fold Decr | Sequence | SEQ ID No. |
|---|---|---|---|
| Il12rb2/Interleukin 12 receptor, beta 2<br>U64199 | 3 | Sequence below. | 263 |

cgcaccggagguccacacugccgcguggacuccagcgauggcgcugcgcuaggcuagcgggugccaggaucccucucugcgu
ccugugcgcgggaagagcucuggagaaccagaguugcauucuggaguugaagacucauggcacagacuguuagagaaugcu
cauuggcacuucuuuuuuguucauguggcugcugauuaaagcaaauauagaugugugcaagcuuggcacugugaccgucc
agccugccccugugauuccucuugggucagcugccaauauuuccugcuccuugaaucccaagcaaggcuguucacauuaucc
caguucuaacgaauuaauccucuuaaaguuugucaaugauguccuuguugaaaaucuccauggcaagaaaguccaugaccac
acuggucacuccuccacuuuucaagucaccaaccugucccuugguaugaccuuguuugucugcaagcuaaacuguagcaacu
cucaaaagaagccaccagucccaguaugugggguggagaucucaguugguguugcuccagagccaccucaaaacauaucaug
uguccaggaaggagaaaauggaacuguggccuguuccuggaacucuggaaaaguuacuuaucugaaaaccaauuacacuuua
caguuaaguggaccaaacaaucugaccugucagaaacaauguuuuucugacaaucgucagaauugcaaucgccuggaucuug
ggaucaaucuaagcccugauuuagcugaauccagguucauaguccguguuacugccaucaacgaucuuggaaauucuucuu
cacuuccgcauacguucacguucuuggacauagugaucccucuuccuccgugggacaucagaaucaacuuucuaaaugcuuc
ugggagcagagguacacugcagugggaagaugaggggcaagugguacucaaucaacucagauaucagccucuuaacagcacg
uccuggaacauggucaaugcuacaaaugccaaaggaaaauaugaccugcgagaucugagaccguuuacagaauaugaauuuc
aaaucuccucuaagcuacaucucucuggaggaaguuggaguaauuggagugagucacugagaacacgaacaccagaggaaga
gccuguugggauauuagacaucugguacaugaaacaagacaucgacuaugacagacagcagaucucucuuuucuggaagagu TABLE 5-continued Genes down-regulated in HF stem cells.

| Gene Name/protein | Fold Decr | Sequence | SEQ ID No. |
|---|---|---|---|

cugaauccaucagaggcaaggggaagauccuccacuaucaggugacguuacaagaggugacaaagaaaacaacacugcagaa
uacuacaagacacaccuccuggaccagggucauccccgaacuggggcuuggacggcaucagugucugcagccaacucaaaag
gcgcuucugcacccacucacauuaacauaguggaccuauguggcacuggguugcuggcuccucaccaggucucugcaaaguc
ggagaacauggacaacauucuagugaccuggcagccuccuaagaaagcugauucugcuguucgggaguacauaguggaaug
gagagcucuccaaccagggagcaucacgaaguuuccccacacuggcugcggaucccccggacaacaugucugcucugauu
ucagagaacauaaagcccuauaucuguuaugaaaucagggugcaugcacugucagagagccaaggagggugcagcuccaucc
ggggugacuccaagcacaaagcaccagugaguggcccucacauuacugccaucacagagaaaaaggaacgccuuuucauuucc
uggacccacauuccauucccggagcaaaggggcugcauccuccauuacagaauauacuggaaagaacgagacucgacagcaca
accugagcucugcgaaauucaguaccgacgcucucaaaacucacauccaauaagcagccuacagcccagggugacauaugucc
uauggaugacagcugugacagcugcuggugaaagucccaaggaaaugaaagggaauuuuguccacagggcaaagccaacug
gaaagcauucgugauaucaagcauuugcaucgcuaucaucacggugggcacguucucaauucguuacuuccggcaaaaggca
uuuacucuccugucuacucucaaaccucaaugguauagcagaaccauuccagauccagcaaacagcacuuggguaaagaagu
aucccauucuggaggagaagauccagcuaccuacggauaaucuccugauggcauggcccacuccugaagagccugagccccu
gaucauccaugaaguccucuaccacaugaucccaguugucagacaaccauauuacuucaaaagaggccaaggauuccaaggcu
acucuaccuccaagcaagaugcaauguauauugccaauccacaagcuacaggaacucucacagcugagaccagacaacuagug
aaccuauacaaggugcuagaaagcagagacccugacucaaaacuggccaaccugaccagccccuugacagucaccccagugaa
cuaccuuccuagccaugaaggcuauuuacccuccaacauagaagaucugucaccacaugaggcugacccaacugauucuuuu
gaccuggagcaucaacauauuucucuuuccauuuuugcaucaaguucucuccgcccacucaucuucgguggugagcggcug
acucuagaucgguuaaagaugggcuaugacucccucaugaguaaugaggcuugauacuagaaagccaacguaccucauuuua
ucugcccaguuccuacuccaaaggucugugacagugaagacaagccagcugucucuggauaaaguuagcuucaccauaggua
cuuaagucuuauggauaagguggcaauacaccaacacugauaucauauagaaaggaccccaagauagucaugcuc

| Gene Name/protein | Fold Decr | Sequence | SEQ ID No. |
|---|---|---|---|
| Wnt10a/Wing-less-related MMTV integration site 10a U61969 | 3 | Sequence below. | 264 |

ggcacgaguucacccucugcaugcguuccccuccccccucuccagcaaacacggcgcgccaguccaaagcggacucaguggcc
ucggggacgggagcaugccaccuccugguggugacgucacuuggguagaacccuuagacacuacauggggggggggguac
agaacucccgagccaggacagucacucacucuucaggcgguggggcugggccagacaguaccgcccccaccgcgcccgccucg
cacacccucggaagcgcaggcucgcagcgcggcgcugggguggggguugcgccccagaacuucggccuccaguccccagcc
cgcugcaccuccuuacccucuagaggccccucccccuuacccucuagaggcaccaggaguugucgcaaggggcccuuggga
aauucccuggaccccugugccaggaggugcccgguucgcccgcuccccauccacccccccgagggcggugcccgggggcgcu
gccccauggagcggggaggcgggcgccgucugcugcgggagcugugaccugaguaggagcugugugucgcagccgccccac
cccugccgaucaugcgccggcgacccugguucgccagucccacugggcugugagcccccacuccuggccugucacggcccg
cgcgccaugggcagcgcccacccucgccccuggcugcggcucccacaagggccccagccgcggccugaguucugggcgcucc
uguucuuccuacugcugcuggcugccgcugugcccaggucagcacccaacgacauccugggccuccgccuaccccagagcc
cgugcucaacgccaacacagugugccugacauugcccggccugagccggcggcagauggaggugugugugcgucacccugac
guggccgccucugcuauccagggcauccagaucgccauccaugagugccagcaucaguuccgggaccagcgcuggaacugcu
ccagccuggagacucggaacaaagucccuacgagagccccaucuucagccgagguuuucgagagagugcuuucgccuacgc
cauagcagcugccggggugguggcacgcaguguccaacgcgugcgcucuggguaaacugaaggcuugcgguugcgacgccuc
cagacguggggacgaagaagcuuuccgucggaagcugcaccgcuugcagcuggacgcgcugcagcgcggaaagggcuugagc
cacgggguccugaacacccggccauacuuccugccagcccaggucugcaggacuccugggaguggggguggcugcaguccgg
augugggcuucggagaacgcuucucuaaggacuuucuggacucccgagagccucacagagacauccaugcucgaaugagacu
ccacaacaaccguguggccggcaggcggugauggagaacaugcggcguaagugcaaaugccacggcaccucaggcagcugc
cagcucaagaccugcuggcaggugacgccugaguuccgcacaguaggggcgcugcugcgcaaccgcuuccaccgcgccacgc
ucauccggccgcacaaccgcaacgguggccagcuggagcccggccccgcgggagcacccucgccagcaccgggcacuccaggg
cugcgccgcagggccagccacuccgaccuggucuacuuugagaaaucucccgacuucugugagcgcgagccgcgccuggacu
cggcaggcacuguggccgccugugcaauaagagcagcacgggucccgauggcugcggcagcaugugcuguggccgcggcc
acaacauucugcgccagacgcgcagcgagcgcugccacugccgguuccacuggugcugcuucgugguucugcgaagaaugccg
caucaccgagugggucagcgucugcaagugagcagacccaagcuccucugggucucaagaaugguuguccucuuggugccu
ggcuucugccgcuagcggaucugagccaggcagcaagcagcagccuuggcuccugagagagagguggguuggcucuuacagcccc
gagggucuacaaucaccagacaguccagaucugauugacauuccuccgcucaccucuguagguuccccucuuucuguuccua
gcucagacagcugggggugauaguggagacuguuccacacccuaggacaggucaccaaagcagcccagccuggcaugccuac
cuccugucaucucuucuucccuuccccaggagugauaggcaaugcacugaagcugaugggcaccggggaagaaaacuaaaag
gcagaaauggccgucaucgggcugaagugacucuaagggcuccagaccucugcuccugucuuucacuuaacagauauuuau
uuuugcgcucucuuugagacacucucuggggaaaaagaagcuccggagucuacaggcugauuaagggacauggacaauaaac
caguaaacacacaaaaaaaaaaaaaaaaa

| Gene Name/protein | Fold Decr | Sequence | SEQ ID No. |
|---|---|---|---|
| Ifngr2/Interferon-gamma receptor precursor M28233 | 3 | Sequence below. | 265 |

gaauuccgggccgcuugcacuuggcgacuagucugcggcggacgugacgccaaggccacgggcagcgcggguccccugucag
aggugucccucgcgcaggaaugggcccgcaggcggcagcuggcaggaugauucugcugguggccugaugcugucugcgaa
ggucgggaguggagcuuugacgagcaccgaggauccugagccucccucggugccuguaccgacgaauguucuaauuaaguc
uuauaacuugaacccugucguaugcugggaauaccagaacaugucacagacuccuauuuuuacuguacagguaaaggugua
uucggguuccuggacugauuccugcaccaacauuucugaucauuguuguaauaucuaugaacaaauuauguauccugaugu
aucugccugggccagaguuaaagcuaagguuggacaaaaagaaucugacuaugcacggucaaaagaguuccuuaugugccua
aagggaaaggucgggccccuggccuggagaucaggaggaagaaggaagaacagcucuccguccucguauuucacccugaag
ucguugugaauggagagagccagggaaccauguuuggugacgggagcaccuguuacacauucgacuauacuguguaugugg
agcauaaccggaguggggagauccuacauacgaaacauacggucgaaaaagaagaguguaaugagacucugugugaguuaaa
caucucaguauccacacuggauuccagauauuguauuucaguagacggaaucucaucuuucuggcaaguuagaacagaaaaa TABLE 5-continued Genes down-regulated in HF stem cells.

| Gene Name/protein | Fold Decr | Sequence | SEQ ID No. |
|---|---|---|---|

ucgaaagacgucuguaucccuccuuuccaugaugacagaaaggauucaauuuggauucugguguugcuccucuuaccguc
uuuacaguaguuauccugguauuugcguauugguauacuaagaagaauucauucaagagaaaaagcauaauguuaccuaag
uccuugcucucugugguaaaaagugccacguuagagacaaaaccugaaucgaaguauucacuugucacaccgcaccagccag
cuguccuagagagugagacggugaucugugaagagccccuguccacagugacagcuccagacagccccgaagcagcagaaca
ggaagaacuuucaaaagaaacaaaggcucuggaggcuggaggaagcacgucugccaugaccccagacagcccuccaacuccga
cacaaagacgcagcuuucccuguuaaguaguaaccagucaggcccuuguagccucaccgccuaucacucccgaaacggcuc
ugacaguggccucgugggaucgggcagcuccauaucggacuuggaaucucucccaaacaacaacucagaaacaaagauggca
gagcacgacccuccacccgugagaaaggccccauggccuccgguuaugacaaaccgcacauguuggugggacgugcuugugg
auguugggggggaaggagucucucaugggguauagacucacaggagaggcccaggagcuguccuaaggucucccgaggccug
cugguggguaaagaaacugaccuuuuaggcaguuuuucugcauugauuucaugaaagaagcuauacauuagcuaaauacuaac
cacauagaauaucagacuuagauacgugaauaaggauccugugggcacugcuggguccacucugcaaaugccaagacuauca
aaggaacguauugucgcuucuggcuccuucccaggugggcuagcaucugugaguuugccucggcuagccuugcuuccuaca
gccgccacugcuccuccacccugaucaucucacaggacagggugggaccggguuuuuuuuuuuuuucacacaccuuuguau
auguaaguucauguauauaauauguuuacauguuucacuuugaacugaaagcuacucaaagccagccguaagucuauggua
gaaugugauggaacauguuggugggaagcuuguacaauagaacacauuggugggagcuuguacauacuuuuuuauggagcau
uacuuacgauuuuuuaaguaaaaauguuugaaaccaaaaaaaaaaaaaaggaauuc

| Gene Name/protein | Fold Decr | Sequence | SEQ ID No. |
|---|---|---|---|
| Fgfbp1/ Fibroblast growth factor binding protein 1 AF065441 | 3 | augagacuccacagccucauccugcucuccuucccuucuccuggcuac ucaggcguucucagaaaaggucagaaagagagccaagaacgcaccaca cagcacagcggaggaggggguagaggguucagcucccucguuaggga aggcccagaauaagcagagaagcaggacaucuaaaucucugacgcaug gcaaguuugucaccaaagaccaagccacaugcagaugggcugugacu gaggaggagcagggcaucagccugaagguccagugcacacaagccga ucaggaguuuucuuguguuuuugcuggugacccaacugacugccuu aaacacgacaaagaccagaucuacuggaaacagguugcccgcacgcug cgcaaacagaaaaauaucugcaggaacgccaagagugucuugaagacc agagugugcagaaagagauuuccagagucuaaccucaagcuggugaa ccccaacgcacguggaaacacgaagcccaggaaggagaaagcagaggu cuccgcaagggagcacaacaagguccaagaagcugucuccacggagcc aaacagggucaaagaagacaucacacucaauccagcugcgacccagac cauggccauuagagauccagagugucuagaggauccagaugugcuca accagaggaagaccgcccuggaguucugugggggaaucuuggagcucc auuugcacauucuuccucaacauguuacaggcgacaucaugcuaa | 266 |

Transcription Factors and Related Genes

| Gene Name/protein | Fold Decr | Sequence | SEQ ID No. |
|---|---|---|---|
| Klf5/Kruppel-like factor 5 AA611766 | 5 | aauucgucgacaugcgccguuccagugcauggugugccaacgcagcu ucucccgcuccgaccaccucgcgcugcacaugaagcgccaccagaacu gagcgagcgagcgcugccccacccgccugacgccuugcaguccgcuc ugccauccuuuaaaccgcagaccuaacuucauaaaaaga | 267 |
| Gata3/GATA binding protein 3 X55123 | 4 | Sequence below. | 268 |

gcuaaacuaucccgcaaagauuuuucuuucccucccuaaacccuccuuuuugcucuccuuuucuauacccuuaacugcaaaca
aaccauuaaacgacccucuccugggcucccgacggcaggaguccgcggaccuccaggccgacagcccucccucuacccgcg
agguuccgggccgggcgagagggcgcgagcacagccgaggacauggaggugacugcggaccagccgcgcugggugagccacc
aucaccccgcgguccucaacggucagcacccagacacgcaccacccgggccucggccauucguacauggaagcucaguauccg
cugacggaagagguggacguacuuuuuaacaucgaugguccaaggcaaccacgucccguccuacuacggaaacuccgucaggg
cuacggugcagagguauccuccgacccaccacgggagccagguaugccgcccgccucugcugcacggaucucugcccuggcu
ggauggcggcaaagcccugagcagccaccacaccgccucgcccuggaaccucagccccuucuccaagacguccauccaccacg
gcucuccggggccucuguccguuuacccuccggcuucauccucuucucuggcggccggccacuccaguccucaucucuucac
cuuccccgcccaccccgccgaaagacgucuccccagacccgucgcuguccaccccgggauccgccgggucggccaggcaagaug
agaaagagugccucaaguaucaggugcagcugccagauagcaugaagcuggagacgucucacucucgaggcagcaugaccac
ccugggugggggccucaucccucagcccaccacccccauuaccaccuaucgcccuaugugcccgaguacagcucuggacucuuc
ccacccagcagccugcugggaggauccccuaccggguucggauguaagucgaggcccaaggcacgauccagcacagaaggca
gggagugugugaacugcggggcaaccucuaccccacugugggcggcgagaugguaccgggcacuaccuuugcaaugccugcg
gacucuaccauaaaaugaaugggcagaaccggccccuuaucaagcccaagcgaaggcugucggcagcaaggagagcagggaca
uccugcgcgaacugucagaccaccaccaccacccucuggaggaggaacgcuaaugggggacccggucugcaaugccugugggc
uguacuacaagcuucauaauauuaacagaccccugacuaugaagaaagaaggcauccagacccgaaaccggaagaugucuagc
aaaucgaaaaagugcaaaaaggugcaugacgcgcuggaggacuuccccaagagcagcuccuucaacccggccgcucucuccag
acacaugucaucccugagccacaucucucccuucagccacuccagccacaugcugaccacaccgacgcccaugcauccgcccu
ccggccucuccuucggaccucaccacccuuccagcaugguacaccgccauggguuagagaggcagagcccugcuccacaugcg
ugaggagucuccaagugugcgaagaguuccuccgacccccuucuacuugcguuuuucgcaggagcaguaucaugaagcccgaa
agcgacagaucuguguuuuugaaggcagaaagcaaaauguuugcuucuuuuuucaaaggagcucgagguggugucugcauu
ccaaccacugaauccggaucccauuugugaauaagccauucagacucauauucccuauuuaacagggucucuagugcuguga
aaaaaauauugcugaacauugcauaaacuuauauuguaagaaauacuguacauuugaggaagacuuuauuguaccuggau
agcuguaagaaaggcaugaaggacgccaagaguuuuaaggaauauaggggnnuuaaaguauggagauacagaagaaaccacu
aagucugauguccaaaugggcacacugucaguuuuguuucccuucaguuguuugaugcauuuaaaaaaaaaaaaaaagaaagaa TABLE 5-continued Genes down-regulated in HF stem cells.

| Gene Name/protein | Fold Decr | Sequence | SEQ ID No. |
|---|---|---|---|
| Stimulated by retinoic acid 14, basic-helix-loop-helix protein Y07836 | 3 | Sequence below. | 269 |

caaccaccuccuaccugccugcccaaagcuccagggcuggagcacggagaccugucagggauggauuuugcccacauguacc
aaguguacaaguccaggcggggaauaaaacggagcgaagacagcaaggaaacuuacaaacugccgcaccggcugauugagaaa
aagagacgugaccggauuaacgagugcauugcccagcugaaggaucuccuacccgaacaucucaaacuuacuacuuugggucc
acuuggaaaaagcagugguucuggagcuuacguugaagcacgugaaagcauugacaaaucuaauugaucagcagcagcagaa
aaucauugcccugcagagcgguuuacaagcuggugauuugucgggaagaaaucucgaggcagggcaagaaauguucugcuc
agguuuccagacuugugcccgugagguacuucaguaccuggcgaagcaugagaacacucgggaccugaaaucuucccagcuc
gucacucaucuccaucgugugguc ucggagcugcugcaggguggugcuuccaggaaaccauuggacucggcucccaaagcc
gucgacuugaaagagaagcccagcuuccuagccaagggaucagaaggcccagggaaaaacugugugccagucauccagcgga
cuuuugcucccucgggugggggagcagagcggcagugacacggacacagacaguggcuauggaggugaauuggagaaagggg
acuugcgcagugaacagccguacuucaaaagcgaccauggacgcagguucgccgugggagaacgugucagcacaauuaagca
agaauccgaagagcccccaccacaaagagccgaaugcagcucucagaagaggaaggccacuucgcgggcagugaucugaugg
guuccccauuucuugggccacacccacaucagccucccuuuuugccuucccuucuaucucaucccaccaucggccacugccua
ccugccuaugcuggagaaaugcugguaccccaccucugugccaguguuauacccaggccucaacaccucagcugcagcccuc
uccagcuucaugaacccagacaagauaccgacucccuugcuucugccccagagacucccuucuccuuuggcacauucguccc
uugacucuucggccuugcuccaggcuuugaagcagaucccuccuuuaaacuuagaaaccaaagacuaaacucuggagggauc
uccugcugccuugcuuucuuuccucccuaauuccaaaaaccacgaagguuucccugagugcagagagaucagcccacccugc
agacccacagagaagauucagagugugugugagagugagugagugugcgugcgugcgugcuuguauguauguuuguauau
guaggacaauaaguuccuucugacacaagggagacacgagaaggauagccugacaucagaugacagacuggaggacuguagc
acaucucugggcguuucccuacccagagaagagcc Cell Cycle Related

| Gene Name/protein | Fold Decr | Sequence | SEQ ID No. |
|---|---|---|---|
| Mki67/antigen identified by monoclonal antibody Ki67 X82786 | 4 | Sequence below. | 270 |

agucaccgacguuguauaacgacggccagugaauuguaauacgacucacuauagggcgaauuggguaccggcccccccucg
aggucgacgguaucgauaagcuugauaucgaauucucgnccgcgugcgggucuggucggggcggagcgaaggccgcgggug
gccguggucgguccuccgcggcuaaggagccgagggcuccgacgcgggcugcgcccggugagcggcggccagagcuaacuu
gcgcugacuggaccagcugaggagcggcccggcggggcgacugcgagcuucaccgagaggcuucuccgcccugguccgcagu
cccgacggccgggcggaccauggcguccucggcucaccuggucaccaucaagcggagcggcgaugacggcgcacacuucccg
cugagccucagcuccugccuguuuggaaggaguauugaaugugacauucguauccagcugccuguagugucucaaagacau
ugcccaauuguaguccaagagcaagaggcgauauuauauaauuucaguucuaccaauccaacucaaguaaacgggguuacua
uagaugagccugugaggcugagacauggagacauaauaaccaucauugaccgcucccuuuagguaugaagauggaaaucauga
ggauggaagcaaaccaacagaauuuccaggaaagucccuuggaaaggaaccaucaaggcgagccucaagagauagcuucugu
gcugacccugauggggaaggucaagauaccaaagcuucaaaaaugacugcuucaagaagaucuuuuguguaugccaagggcc
uuucugcagauagcccugccucagauggcucaaagaacaguguuagccaagacucaucagggcauguagaacagcacacugg
cagaaacauaguagagcccacuucuggggggaucucuuuuaagaaguccaggucuacagggagcaguuacagggaaccgaagu
cuucuuccauacacagagccuuagcaauagcaacgaaaaggaaucucccuuugagaaacuuuaucaaucaaugaaggaagagu
uggauguaaaaucccagaaaucuuguaggaaaucagaaccccaaccugaccgugcagcagaggaaucgcgggagacacagcua
uuggugucaggcagggcaagagcaaagucuaguggaagcaccccuguuacugcagccucuucacccaaaguaggaaagaucu
ggacugagagauggcgcgguggaauggugccuguccagacuuccacagagacagcuaaaaugaagaccccugugcggcauuc
acagcaacuuaaggaugaagacucucguguuacuggcagacgacauucugugaaucuggaugaagguggaagugcccaggca
guccauaaaacagucacuccugggaaacuggcgacuagaaaccaaacuccgguggaggcuggggauguuggcagccccgcug
auacaccagaacauuccucuucccccagagaaguauuccugcaaagguagaggcuccaucugcagagacacaaaaucggcuc
ucuuuaacucagcgccuuguuccaggugaaaagaaaacucccaaggguuccuucagcaagccugagaaacuggccacagccg
ccgaacagacuugcucuggccuaccuggucuuaguuccguugauaucagcaacuuuggugauuccauuaacaagagugagg
gaaugccuaugaagagaagacguguauccuuugguggacaucuaagaccugaauuauuugaugaaaacuugccuccuaauac
accacugaaaagaggagaaacgccaaccaagaggaagucucuuggcacucacagcccagcuguccucaagacaaucaucaagg
aacggccccagucuccagggaaacaagagucuccugggauaacgccaccgaggacaaaugaucaaagacgcagaucaggcagg
acuuccaguggaagcaauuucuuaugugagacagacauucccaagaaagcaggcaggaagagcgguaaccugccugcgaaga
gagcauccaucagccggagucagcauggcauucuacagaugauuugcuccaaaaggcgaaguggagcuucugaagccaacuu
gauuguugcaaaaucaugggcugauguuguaaaacuuggcgugaaacaaacacaaacgaaaguugcgaaacaugucccucca
aagcagacgagcaagagacaaagaagacccagcacuccaaagaaacccacaagcaaucuucacaaucaauuuacuacaggccau
gcaaacucucccuguaccauuguaguagguagagcgcagauugaaaaaguaagugugccugcccgacccuacaaaaugcuga
auaacuugaugcuaaaccgaaaaguggacuucagugaagaucugucaggacuaacugaaauguucaagacuccagugaagga
gaagcagcagcagaugagugauacaggcuccguacuuuccaauucagcgaauuugucugaaagacaauugcaaguaacuaau
ucaggagacauaccugagcccaucaccacagagauuuugggagaaaaagugcuauccaguacucggaaugcagcaaagcagca
gucugauagauauucugcaaguccuaccuuaagacggcggagcaucaaacaugaaaacacagugcaaacuccuaagaauguc
cauaacauuacugaccuugagaagaagacuccggucucugagacagagccccugaagacugcaucgagugugagcaaguuaa
gaagaucuagagagcucagacauacccuuguggaaacuaugaaugaaaaaacagaagcaguccuugcugagaacaccacagca
agacauuuaaggggggacauuucgagaacaaaaaguagaucaacaggugcaggacaaugaaaacgcuccucaaagaugcaagga
aagugggugaauuaagugaagguucagaaaagacaucagcuaggagaucaagugccaggaagcagaagccgacaaaagacuua
cuaggaagucagauggucacccaaacagcagacuaugcugaggaacuacuuagucaaggacaaggaaccauacaaaaccuaga
ggaauccaugcacaugcaaaacacaucaauaagugaggaucaaggaauuacagaaaagaaagugaacauaauaguauaugcaa
ccaaagagaagcacucgccaaagaccccuggcaaaaaggcacaaccucuagaagggccagcuggucucaaggaacacuuugaa
acaccaaaccccaaagauaaaccuauaacggaagacagaacuagaguccuuugcaaaucaccacaagucacaacagagaauauc TABLE 5-continued Genes down-regulated in HF stem cells.

| Gene Name/protein | Fold Decr | Sequence | SEQ ID No. |
|---|---|---|---|

acaacaaacacaaagccacagacuagcacaucugggaagaaaguagacaugaaggaagaaagcucugccuugacaaaacguau
acauaugccaggggaauccaggcauaaucccaaaauuuuaaaacuugagugugaggauaucaaagcuuugaagcaaucugaa
aaugaaaugcugaccucaacaguaaauggaagcaagaggacuuuaggaaaaucuaaaaaaaaggcucagccccuggaagaccu
gacuuguuuccaggaacucuuuauaucaccaguuccuacuaacauaaucaaaaaaauucccagcaaaucuccacacacacaac
cagucagaaccccagcgagcacaaagagacucuccaagacaggucucaguaaaguggaugugagacaagaaccuucaacacuu
gggaaaagaacgaagucaccaggcagagccccaggcacaccagcaccagugcaggaagaaaaugacugcacagccuacaugga
aacuccaaagcagaaacuggagucuauagaaaauuuaacagggcuuaggaaacaguccagaacaccuaaagacaucacugguu
uccaggauaguuuccaaauaccagaucaugcuaauggcccauuagugguugucaaaaccaaaaaaauguucuuuaauucucc
acaaccagaaagugccauaacccgaaagagcagagagagacagucuagggcaaguauaaguaaaauagauguuaaagaagaac
uuuuagaaucagaggaacaccuacaauuaggagaagguguagacacauuucagguauccaccaacaaagucauuagaucauc
uaggaaaccugcaaagcguaaacuggauucaacagcugguaugccuaacagcaagaggaugcgcuguucuucaaaggauaac
acaccaugccuagaagaccugaauggcuuccaagagcucuuccaaaugccaggcuaugcuaaugacucuuugaccacuggaa
ucucaacaaugcuugcuagaucaccacaauuaggaccaguuagaacccaaaucaacaaaaagagucugcccaagaucaucuug
agaaaaauggaugugacagaagaaauuucaggucucuggaagcagucacugggcagaguccacaccacacaagagcaggagg
auaaugcaaucaaagcaauuauggagauuccaaaggaaacacugcagacugcagcagauggaacuaggcuuaccagacagcca
caaacaccuaaggaaaaaguucaaccgcuggaagaucacagugucuuccaagaacucuuccaaacaucacgcuacuguucuga
uccauuaauugguaacaaacaaacaagaauguccuugagaucuccacaaccaggauuuguuagaacuccacgaaccucaaaga
gacuggcuaagacaaguguugggaauauugcugugagagaaaagaucucuccagugagucugccacagugugcuacagggg
agguuguacacauacccauagggccagaagaugacacagagaacaaaggugugaaggaauccacaccucagacacuggacuca
ucagcaagucgaacugucagcaagaggcagcaaggggcacaugaggaaaggccucaguucucaggagacuuauuucaucccc
aagagcucuuucaaacaccagccaguggcaaagacccaguaacuguugaugaaacuacaaaaauagcucugcagucuccacaa
ccaggacauaucauaaacccagcaagcaugaagagacaguccaacaugagucucaggaaagacaugagagaauuuuccauacu
ugaaaaacaaacacagucacgaggcagagacgcaggcacaccagcaccaaugcaggaagaaaauggcaccacagccauuaugga
aacaccaaagcagaaacuggauuucauaggaaauucaacaggacauaagaggaggccucggacacccaaaaacagggcucagc
cccuagaagaccuggauggcuuccaagaacucuuucaaacaccagcuggugccagugacccugugaguguugaagaaagugc
aaagauaucuuuggcaucuucacaagcagaaccagucagaaccccagcaaguacaaagagacgcuccaagacaggucucagua
aaguggaugugagacaagaaccuucaacacuugggaaaagaaugaagucacuaggcagagccccaggcacaccagcaccagug
caggaagaaaaugacagcacagccuucauggaaacuccaaagcagaaacuggauuucacaggaaauucaucaggacauaagag
gaggccacagacaccuaagaucagggcucagccccuagaagaccuggauggcuuccaagaacucuuccaaacaccagcuggug
ccaaugacucagugacuguugaggaaaguguaaagaugucuuuggaaucuucacaagcagaaccagucaaaaccccggcaag
cacaaagagacucuccaagacaggucucaguaagguggaugugagagaagacccuucaauacuugagaaaaaaacaaagucac
caggcacaccagcaccagugcaggaagaaaaugacugcacagccuucauggaaacuccaaagcagaaacuggauuucacagga
aauucaucaggacauaagaggaggccacggacaccuaagaucagagcucagccccuagaagaccuggauggcuuccaagaacu
cuuccaaacaccagcuggugcuagugacucagugacuguugaggaaagugcaaagaugucuuuggaaucuucacaagcaaaa
ccagucaaaaccccggcaagcacaaagagacucuccaagacaggucucaguaagguggaugugagagaagacccuucaacacu
ugggaaaaaaacaaagucaccaggcagagccccaggcacaccagcaccagugcaggaagaaaaugacagcacagccuucaugg
aaacuccaaagcagaaacuggauuuugcagagaauucaucagggaguaagagaaggucacgaacaucuaagaacaggucuca
gccccuagaagaccuggauggcuuccaagaacucuuccaaacaccagcuggugccaguaacccugugaguguugaagaaagu
gcaaagauaucuuuggaaucuucacaagcagaaccagucagaacccgggcaagcacaaagagacuuuccaagacaggucucaa
uaagauggaugugagagaagggcacucucccgcucaguaagucaagcugugcaucacagaaagucaugcaaacccucacacuu
ggagaagaucauggcagagagaccaaagaugggaagguauuguuagcucagaaauuggaaccagcaauauauguuacucgug
gcaagaggcagcaaaggucauguaagaaaagguccc agucccc agaagaccucucugguguucaggaggucuuccaaacauc
aggccauaacaaggauucagugacaguggacaaucuugcaaaacugcccagcucgucuccaccacuagagccaacagacacuu
caguaaccucacggagacaggccagaacuggucugaggaaaguucacgugaaaaaugaacuuucaggaggcauaaugcaucc
acaaauaucaggggaaauuguggacuuaccuagagaaccagaaggugaaggcaaagucauuaaaacaaggaagcaaucugua
aaacggaaauuggacacagaagucaaugugccucgcaguaagaggcaaagaauuacaagagcagaaaagacccuagaggaucu
gccuggcuuccaagagcucugccaagcuccaagcuugguaauggacucaguuauuguugagaaaaccccaaagaugcccgac
aaaucuccagaaccugugg auacaacuucagagacacaggcaagaagaagacucaggagacugguuguuacugaagagccca
uaccacaaagaaagacuacaagaguuguaaggcaaaccagaaacacacagaaagagcccauaagugacaaucaagguauggaa
gaguuuaaggaaucuucaguacagaaacaagacccaaguguaaguuuaacuggcaggaggaaccaaccaaggacaguuaagg
agaaaacccaacccuuagaagaacucaccaguuuccaagaggaaacugccaaaagaaauaucuuccaaaucuccacaaccggaag
agaaggaaaccuuagcagguuuaaagaggcagcucagaauacaacuaaucaacgaugguguaaaagaagagcccacagcacag
agaaagcaaccauccagggaaaccaggaacacacucaaagagccuguaggugacaguauaaauguugaagagguuaagaaguc
uacaaagcagaaaauugauccaguagcaagugugccugucagcaagaggccacggaggguacccaaggaaaaggcacaggccc
uagaauuggcuggucucaaaggaccaauccaaacccuaggccacacugaugaaucagcaagugauaaaggacccacacagaug
cccuguaauucucuacaaccagagcaaguugacagcuuccaaagcucaccaaggcgacccaggacaagacgugggaaaguaga
ggcagaugaagagccuucagcaguaagaaagacaguaucaacaucaaggcaaacuaugcgaucccgcaagguccc ugaaauug
guaacaaugguacccaaguuucaaaggccuccauaaagcagacauuagauacaguagccaaaguaacuggcagcaggaggcag
cuaaggacacauaaaggaugggguucaacccucuugaaguuguuaggugacuccaaagaaauaacccaaauaucagaucacu
cugagaaacuagcacaugacaccaguauccuuaagagcacucaacagcaaaagccagacucaguaaaaccucugagaacaugc
agaagagugcugagggccucuaaagaggucccc aaggaagu guugguggacaccagagaccaugcaacauuacaaagcaaaa
gcaacccuuugcuguccccgaagaggaagucugcaagagauggaagcauugugagaaccagggcuuugcgcucuuuagcacc
aaagcaggaagcaacagaugagaagccuguaccugagaaaaaaagggcugcuuccagcaagagguauguaucaccugagccu
gugaagaugaaacaccugaaaaucgugucaaacaaacuugaaucuguggaagagcagguuagcacuguuaugaaaacagaag
aaauggaagccaaaagagaaaauccugucacuccagaucagaacucuagguaccgaaagaaaaccaauguaaaacagccaagg
cccaaguuugaugcaucugcagagaaugucgggauaaagaaaaacgagaagacuaugaagacugccucccaggagacagagc
ugcagaauccagaugauggagccaagaaaucuacaucucggggccaagucaguggaaaagaacaugcuugaggucuagagg
aacgacugagaugccccagccuugugaagcagaagagaaaacaagcaaaccagcugcagaaaucuugauaaagccucaggaag
agaaaggagucucuggagagucugauguuagguguuugagguccagaaaaacuagagucgcuuuggacagugaaccuaagc
caaggguaacucguggaaccaagaaagaugcaaaaacucugaaggaggaugaagacauuguaugcaccaagaaguuaagaaca
agaaguuaagaacaagaaguuaccagaaaagugaaacuauguagcaaagacauuuaagaaggaaaaguaaauuugacuuagu
gauaaguuccagugugguuuucaccuccaguguaaagaugaacuguaaauacuacugcuacugccugaguuuaaggaagga
agcuuugagcuuuccuggucauacucucuucagacgccaauggaggucaugaggaagaucaccagggaucucagcgcaauua
caguuuaggggugagcaggcagaaauguggcccucuguccuauccaauaaagcucugaaauucgcugccaaaa TABLE 5-continued

| Gene Name/protein | Fold Decr | Sequence | SEQ ID No. |
|---|---|---|---|
| Genes down-regulated in HF stem cells. | | | |
| Cks2/CDC28 protein kinase regulatory subunit 2, sim to cdk regulatory subunit 2 AA681998 | 4 | gacguagagccccuugcgcccgguuuccugaucccgcuuacuc<br>cucugcgcgccggcaggauggcccacaagcagaucuacuacuca<br>gacaaguacuucgaugagcacuacgaguaccggcaugucaugu<br>uacccagagaacucucuaaacaaguacccaaaacucaucugaug<br>uccgaagaggaguggaggagacuuggugccaacagagucuag<br>gaugguucauuacaugauucaugagccagaaccgcauauucu<br>ucucuuuagacgaccucuuccaaaagaacaacaaaaaugaagug<br>cagcugggaucaucuaaucuuuuucaaauuuaauguauaugu<br>guauauaagguaguauucagugaauacuugaaaaguguacaaa<br>ccuuucauccauaccugugcaugcgcuguauucuucacagcaa<br>cagagcucagucaaaugcaacugcaaguagg | 271 |
| Ccng2/ Cyclin G2 U95826 | 3 | Sequence below. | 272 |
| | | cuacccuagacaaucacggcuuagccggcgcgcggagucgaucgucucggucgcuagagcuguccugagcucgaacgguccg<br>acgcccccgccgcgccgguccgugacgccggggccgacacgaugaaggauuuggggccaagcacuuggcagguggcgaagg<br>gguucagcuuuucggauuguugaacuucuaccuggaacaagaacagagauaccaaccucgggaaaaagggcugaucuugaug<br>gaggcuaccccggagaaugauaacacuuuguguucaagacugagaaaugccaaaguggaagauuuaagaaguuuaacuaacu<br>ucuuuggaucuggcacugaaacuuucguucuggcugucaauauuuggauagauucuuggcccuuaugaaggugaaaccga<br>aacaccuguccugcauuggcgucugcugcuuuuugcuggccgccaggcuggcggaagaagaaggugacguucccccacgca<br>cgacgugauccgcaucagucaguguaaaugcacagcgucugacauuaaacgcauggagaaaaucaucucagagaaacugcac<br>uaugagcuggaagcuaccacugccuuaaacuuuuugcacuuguaccacgcgauuguauuuugucacacuucagaaaggaag<br>gagauucucagccucgauaaacucgaagcgcagcugaaagcuugcaacugccgaguugucuucuccaaagcaagaccaucug<br>uauuagcucugugccuucucaauuuggaaauagaaacgauaaaauccguggaacugcuggaaauucucuugcuuguuaaaa<br>aacauuugaagcucagcgacacugaauucuuuuacuggagggaacugguuucuaaaugucuagcagaguauucuucgccuc<br>gcugcugcaagccugaucugaagaagcugguauggauuguuucgcgacgcacugcgcagaaccuccacagcagcuacuacag<br>uguuccugagcugcccacuaucccagagggggguugcuuugacggaagugaaagugaggacucuggugaagacaugaguug<br>uggagaggagagucucagcagcuccccacccagcgaucaggagugcaccuucuucuuugacuuccaaguggcucagacacug<br>ugcuuuccaccauagaggaaucugacauuguucugugucagggaauuuauaagugugguaccuagguuucaaagcaauaa<br>acuugggguugaauagggguaguuuuccuagguuuccagcccccgucuagucagg | |
| Prc1/Protein regulator of cytokinesis 1 DNA segment, Chr 7 AA856349 | 3 | aacuaccuugggcagguucuauuaacugcaccuaacucagacg<br>ugaguaggacagaaggaagcugucccgggcgaacugaggucac<br>aaagacuugcuuuugauucaagagagaccuuaaaggcuaguua<br>ugauaguuaaguacaaguuuuaacaucugguagcuaacuuuu<br>uuucucuaccccguaauucuacuaugacugcucuucuagaggu<br>ccugaguucaaaucccagcaaccacaugguggcucacaaccauc<br>uauaaugggaucugaugcccucuucuggugugc | 273 |

Thus, the transcripts identified in this Example, the proteins they encode, and the pathways in which the proteins participate, contribute significantly to induction of epidermal cells to differentiate into HF stem cells. Activation of the transcripts, proteins, and pathways depicted in Table 4 is thus a method for enhancing EDIHN. In addition, inhibition of the transcripts, proteins, and pathways depicted in Table 4 is thus a method for preventing EDIHN and eliminating hair follicles. In addition, inhibition of the transcripts, proteins, and pathways depicted in Table 5 is a method for enhancing EDIHN. In addition, activation of the transcripts, proteins, and pathways depicted in Table 5 is thus a method for enhancing EDIHN.

Example 10

Expression of Wnt-1 Inhibitors During the First Nine Days After Wounding Causes Pigmentation of New HF

Materials and Experimental Methods

In this Example, doubly transgenic mice expressing both tetO-Dkk1 and K5-rtTA were utilized. When these mice are fed chow formulated with 1 g/kg doxycycline (BioServ, Laurel, Md.), they express Dkk1, under the control of the K5 promoter, in the basal epidermis. The control mice also received doxycycline, but they were K5-rtTA negative and thus did not express Dkk1.

Results

Figure 23A:
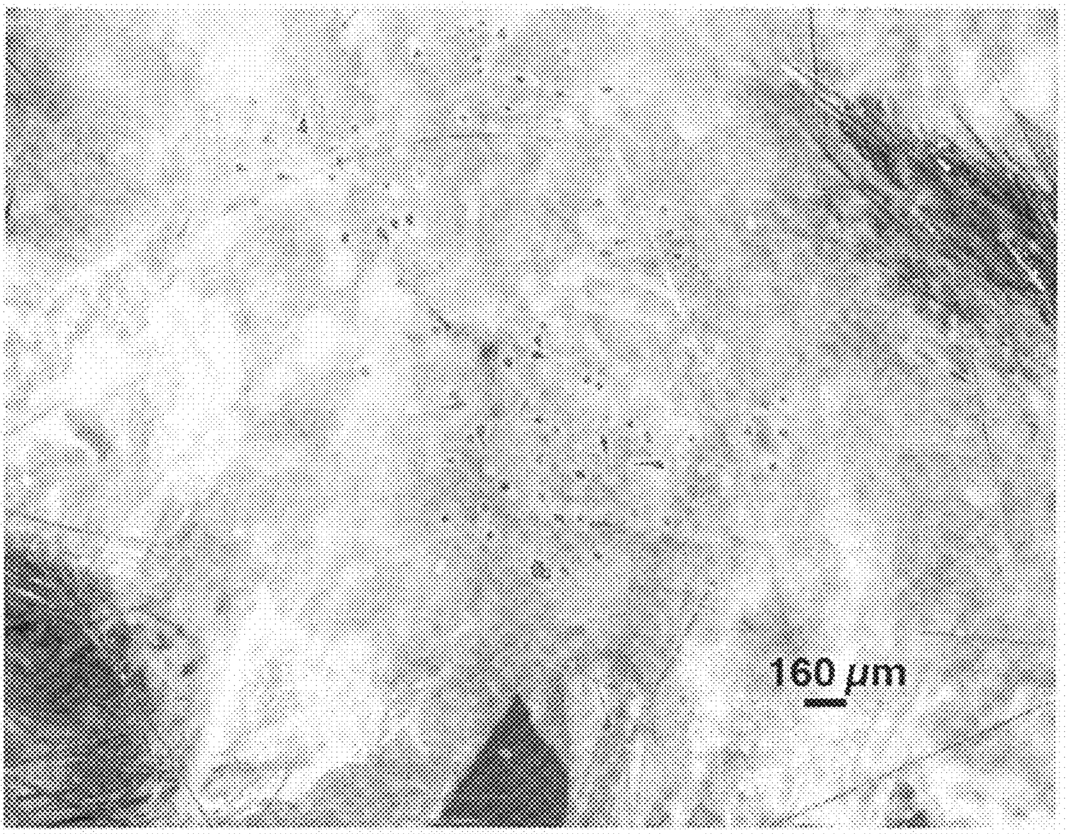
FIG. 23. Pigmented hair follicle neogenesis observed in the skin of Dkk1-expressing mice following EDIHN A. 3.2× magnification. B. 8× magnification.
Figure 23B:
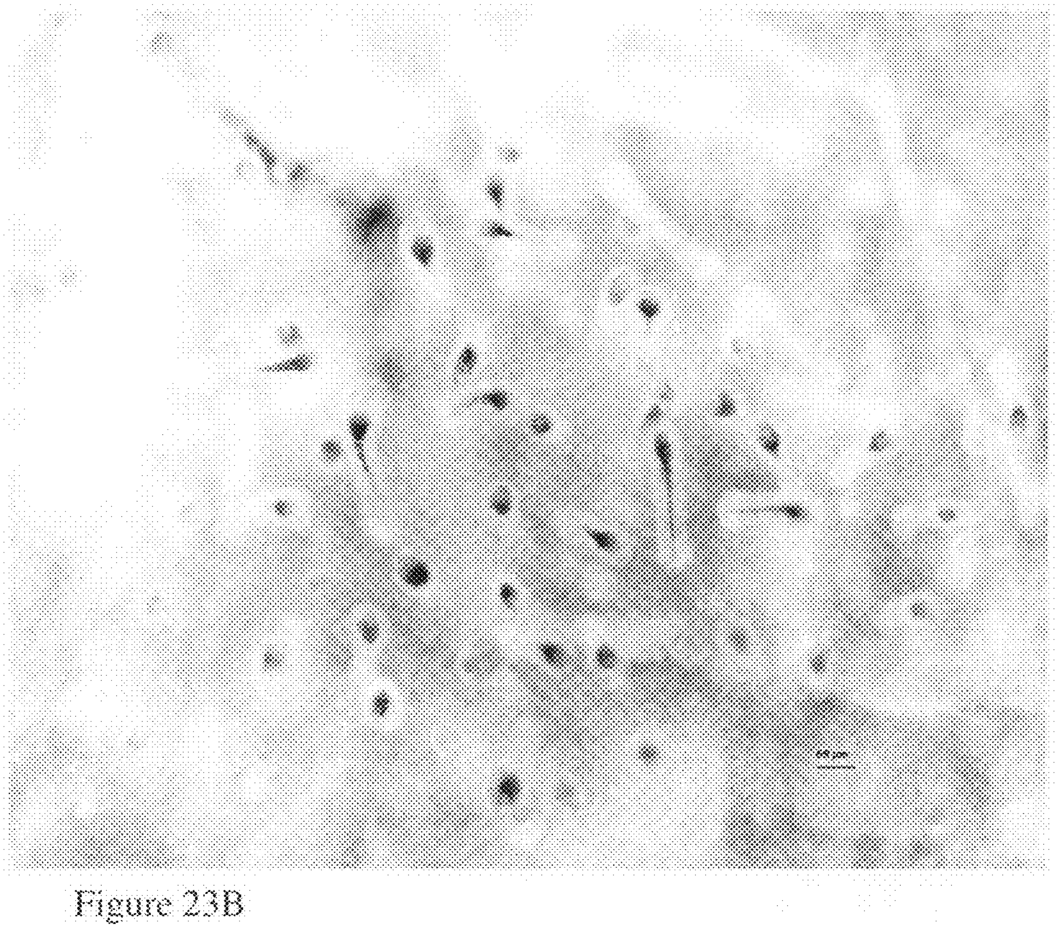
Figure 24:
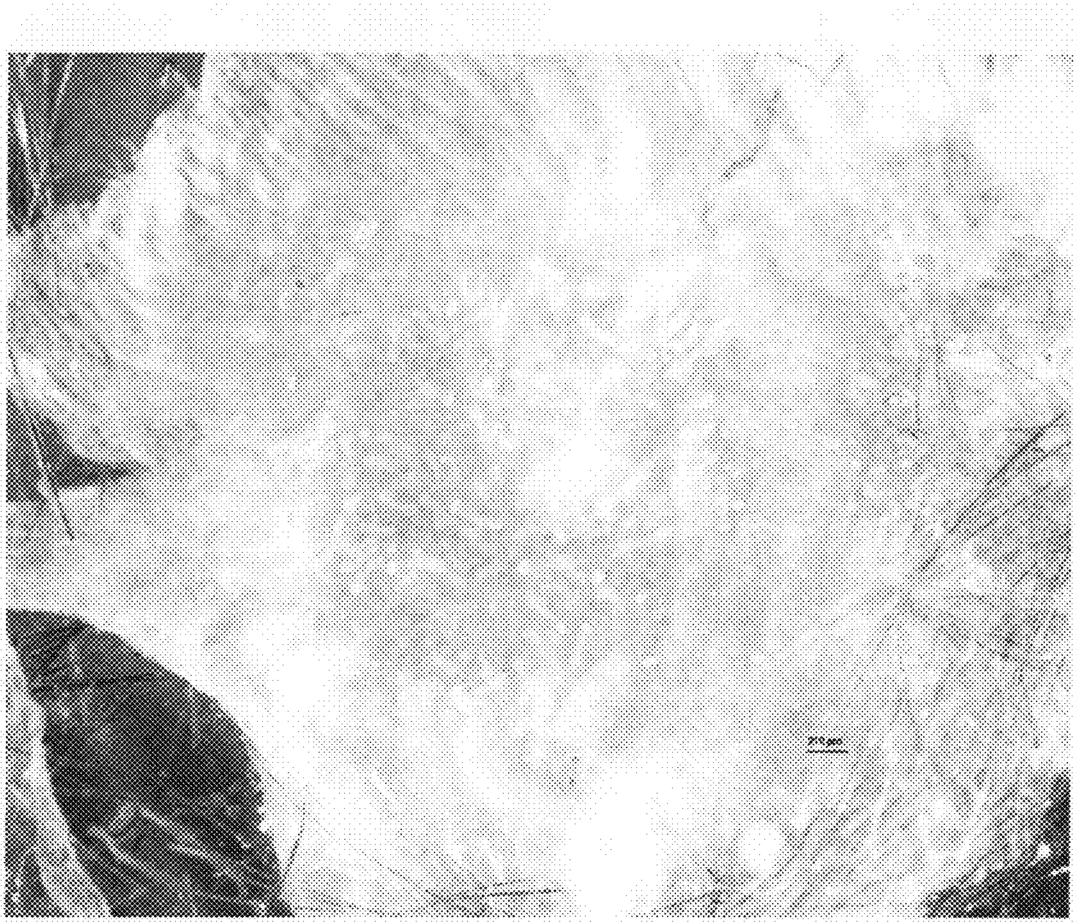
FIG. 24. Control mice lacked pigmented HF.
Figure 25A:
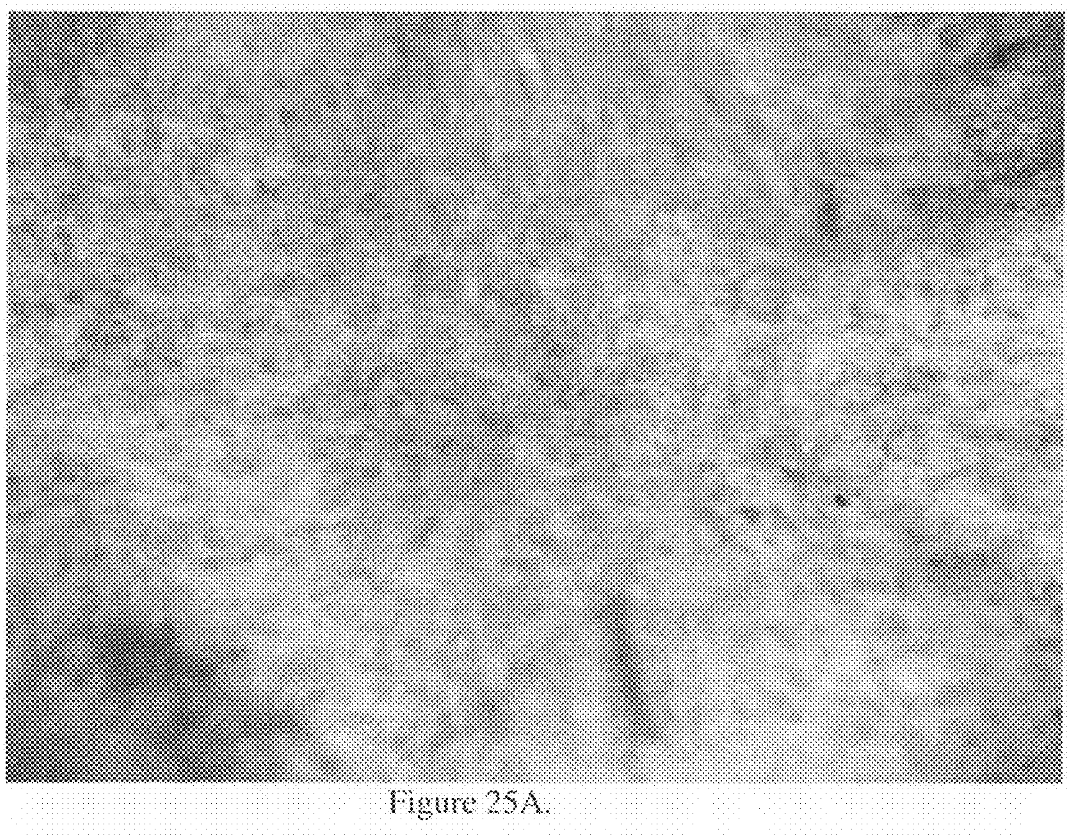
FIG. 25. EGF inhibits HF formation by EDIHN. A. K17 staining of wounded skin of representative mouse treated with EGF. Magnification is 4×. B. High magnification view (10×) of skin depicted in (A). C. K17 staining of wounded skin of representative control mouse that received no EGF after wounding. Magnification is 4×. D. Higher magnification view (10×) of skin depicted in (D).
Figure 25B:
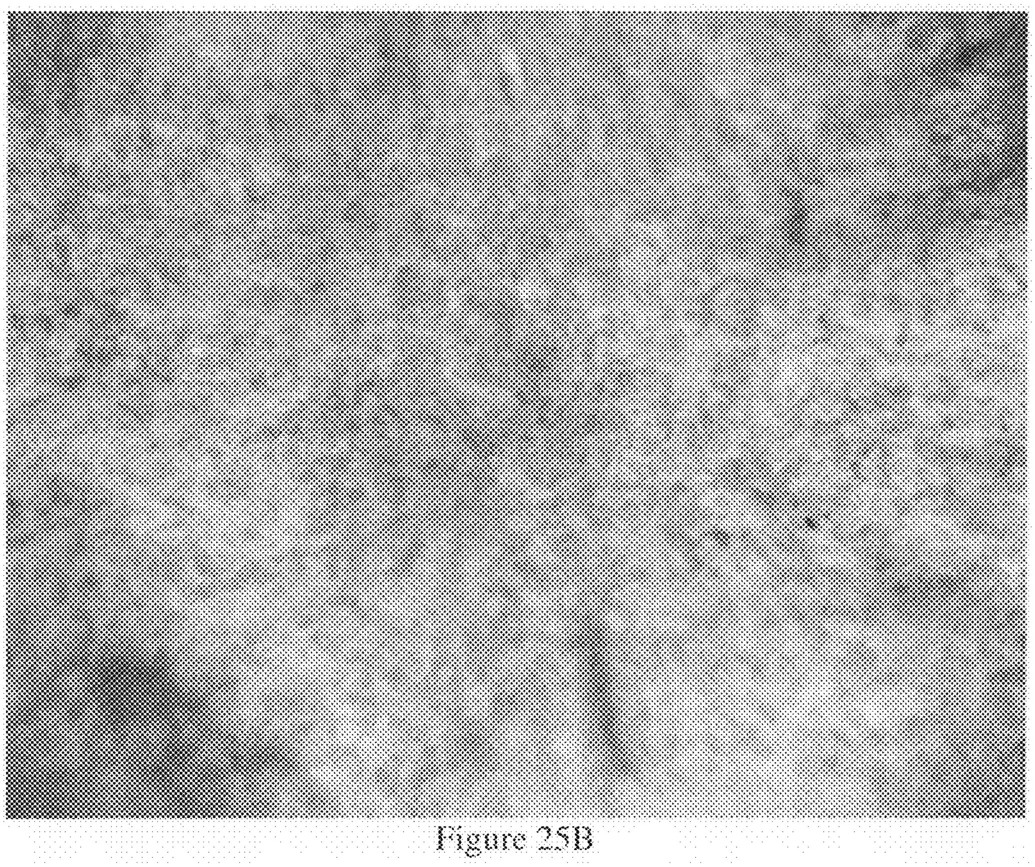
Figure 25C:
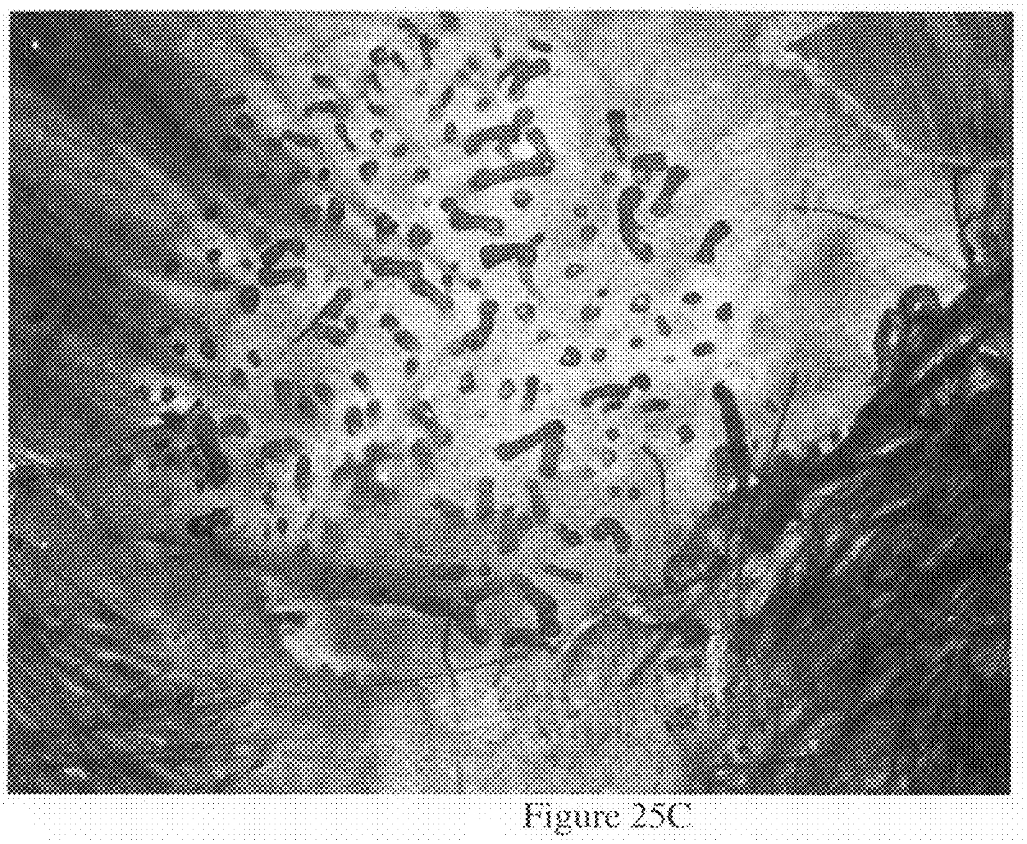
Figure 25D:
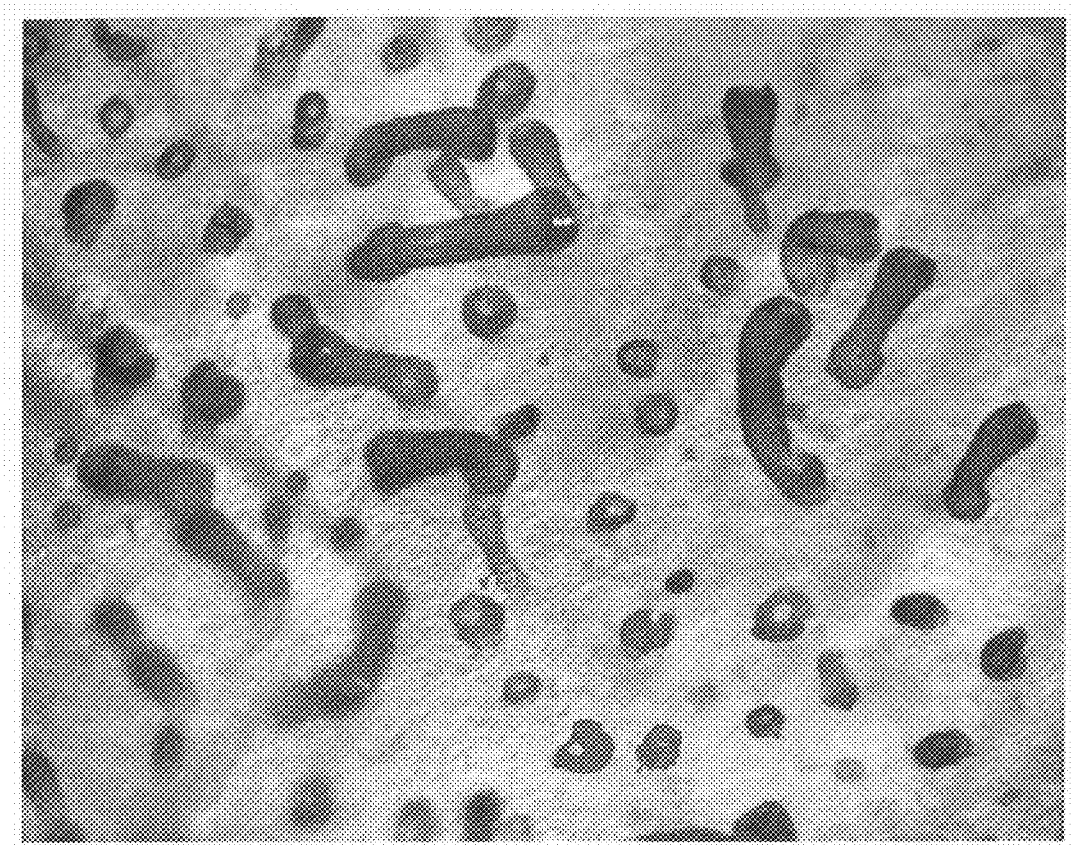

A 1 $cm^2$ wound was induced on the lower back of the doubly transgenic mice at 21 days or 50 days old. Mice were placed on doxycycline-containing chow immediately after wounding to induce Dkk1 expression, and then doxycycline was discontinued after completion of the re-epithelialization at 9 days after wounding. Dkk1 expression inhibits Wnt activity, which in turn induces follicle pigmentation. At 22 days after wounding, pigmented HF were observed in the excised skin after preparing the epidermal sheet (FIG. 23A-B). Control mice lacked pigmented HF (FIG. 24).

In other experiments, continued expression of Dkk1 after the 9-day period inhibited formation of new HF.

The findings of this Example show that pigmented HF can be produced by suppressing expression of Wnt1 or by inducing expression of Dkk1 during the period of re-epithelialization, then inducing expression of Wnt1. In addition, the findings of this Example show that factors that inhibit neonatal hair follicle formation (e.g. Dkk1) also inhibit EDIHN, thus further supporting the notion that hair follicles formed by EDIHN are similar to normal hair follicles.

Example 11

Inhibition of EDIHN by Epidermal Growth Factor Injection 21 day-old mice were wounded as described in previous Examples. Starting from day 11 after wounding, a time point corresponding to the point at which the wound had recently reepithelialized, 10 μl, of 1 μg/ml EGF was injected into the wound bed. EGF was injected once per day after this point for a total of 5 days. Three days later, the skin was collected, and whole-mount EDIHN assays were performed. EGF prevented HF formation as assessed by gross morphology. In addition, whole mounts of control and treated skin were analyzed with anti-K17 antibody immunostaining. All mice injected with EGF (n=4) exhibited no new HF formation (FIGS. 25 A-B), while control mice (n=2) had many new HF, as expected. (FIGS. 25 C-D).

In an additional experiment, recombinant EGF (1 microgram (mcg)/microliter (mcl)) was injected at days 11, 13 and 15 after wounding. Skin was collected at 18 days after wounding and stained for K17 and alkaline phosphotase. Once again, administration of EGF inhibited EDIHN.

The findings of this Example show that EGF inhibits HF formation. Thus, inhibiting EGF, EGFR, or one of the pathways in which they participate increases EDIHN-induced HF formation.

Example 12

Enhancement of EDIHN by Inhibition of EGF Receptor

Figure 26A:
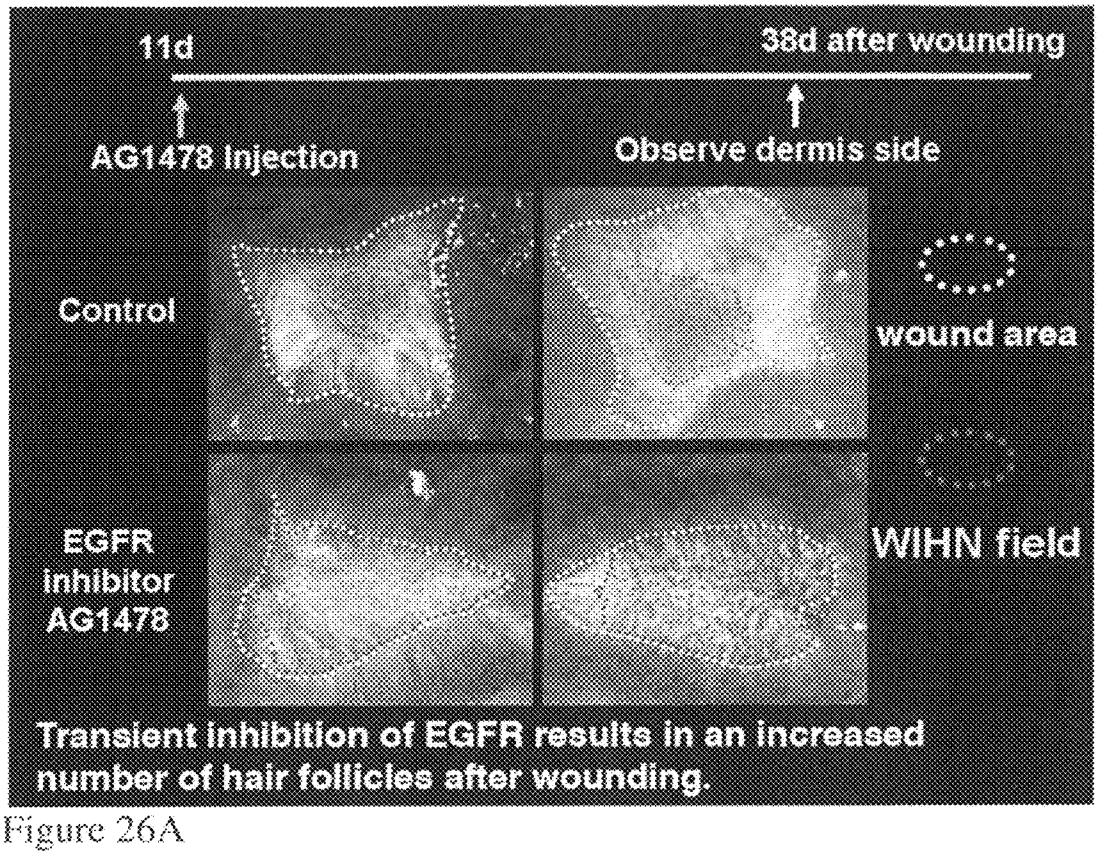
FIG. 26. Administration of an EGF receptor inhibitor (AG1478) leads to generation of more and larger HF compared with controls. A. Top: skin of 2 control mice. Outer dashed line indicates the extent of the wounded area after contraction and healing; inner dashed line indicates the area of neogenesis. Bottom: skin of 2 treated mice, in which the wounded area and area of neogenesis largely coincide, with the exception of a small area on the left side of the encircled area in each panel. B. Large hair follicles developed in the wounded area in the AG1478-injected mice. Left panel: epidermis stained for K17, with three large hair follicles next to each other. Right panel: dermis stained for AP with large coalescing DP areas. Scale Bars: 200 μm.
Figure 26B:
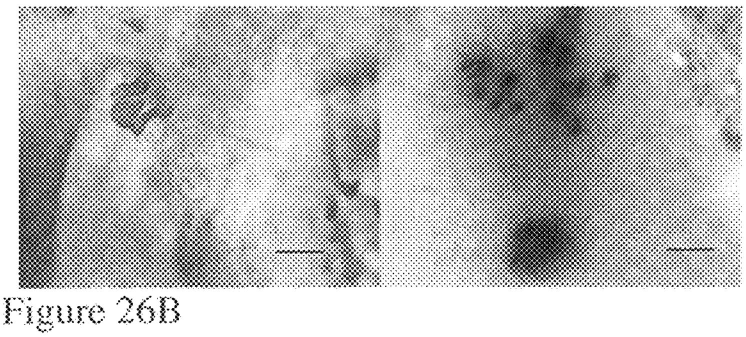

To determine the effect of administration of EGF receptor inhibitors on DIHN, the inhibitor AG1478 (150 μM in 10 μL volume) was administered as a single injection 11 days after incisional wounding (1 $cm^2$) to the middle of the wound near the skin surface. EGF receptor inhibitor administration led to generation of more and larger hair follicles compared with control mice that were wounded only (FIG. 26A). As shown in FIG. 26B, large hair follicles developed in the wounded area in the AG1478-injected mice. Left panel: epidermis stained for K17, with three large hair follicles next to each other. Right panel: dermis stained for AP with large coalescing dermal papilla areas.

The findings of this Example confirm the results of the previous Example, and show that more and larger HF can be generated when EDIHN comprises, or is followed by, administration of EGFR inhibitors, or with compounds with a similar mechanism of action; e.g. Hedgehog protein and androgen antagonists.

Example 13

Enhancement of EDIHN by Expression of a β-Catenin Activator

Figure 27A:
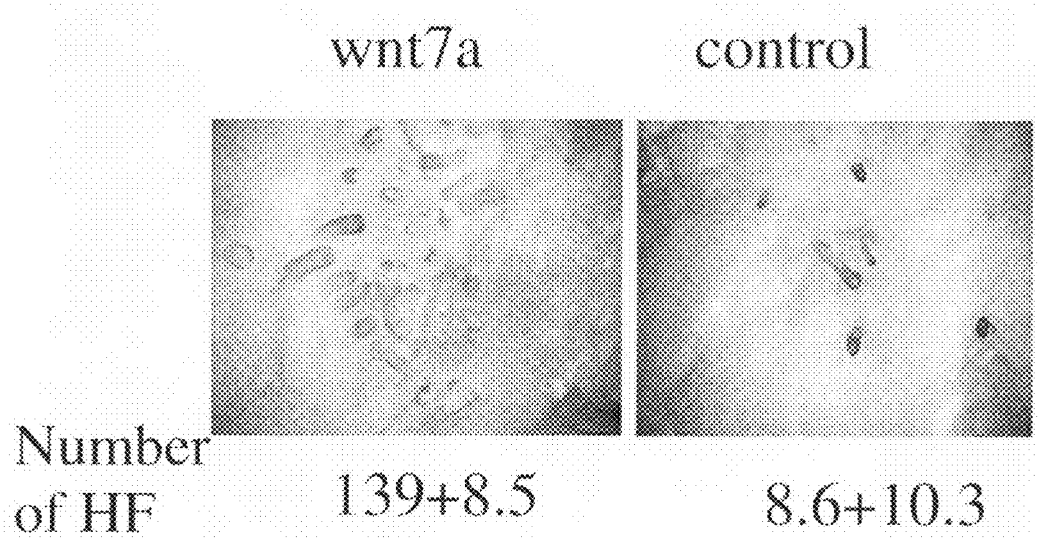
FIG. 27. A. Increased hair follicle formation in K14-Wnt7a mice. Left panel: Wnt7a transgenic mice. Right panel: control (wild-type) mice. B. Quantiation of experiment with 4 week old mice. C. Quantiation of experiment with 3 week old mice
Figure 27B:
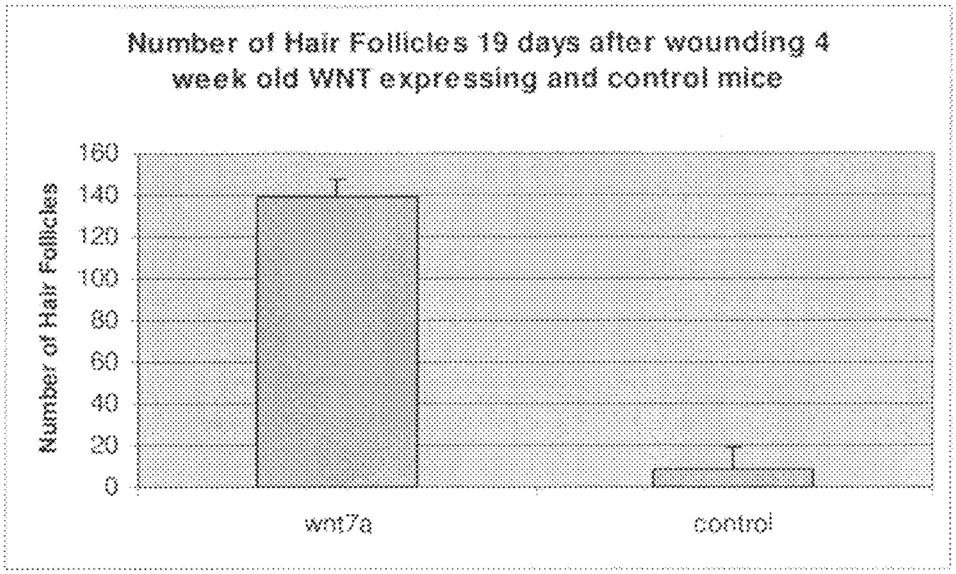
Figure 27C:
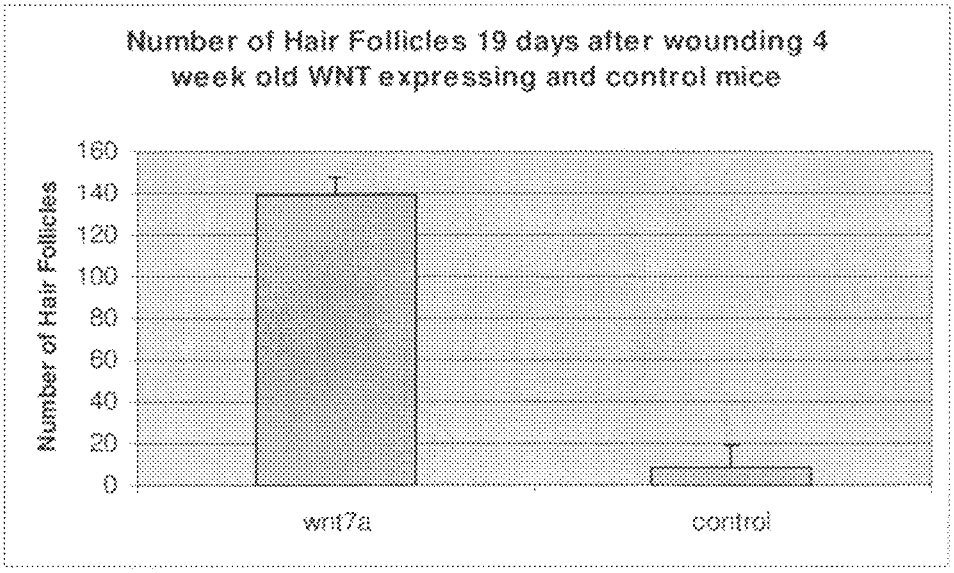

To determine the effect of administration of β-catenin activators on EDIHN, K14-Wnt7 transgenic mice, which overexpress the β-catenin pathway activator, Wnt7, in the epidermis, were subjected to EDIHN, then HF formation was measured 19 days after wounding. In each of 2 separate experiments, with 4 week old and 3 week old mice, the transgenic mice developed significantly larger numbers of HF compared to control, non-transgenic littermate mice (FIG. 27 A-C).

Thus, administration of β-catenin activators leads to an increase in EDIHN. The findings of Examples 11-13 show that new HF can be generated by (a) disrupting the epidermis; and (b) administering a factor that promotes a differentiation of an uncommitted epidermal cell into a HF cell.

Example 14

Enhancement of EDIHN by Administration of FGF

To determine the effect of fibroblast growth factor (FGF) on EDIHN, recombinant FGF is administered 11 days after incisional wounding, as described in Example 11. FGF administration enhances HF formation, showing that new HF can be generated by (a) disrupting the epidermis, and (b) administering FGF, a nucleotide encoding FGF, or a factor that increases signaling by FGF.

Example 15

Enhancement of EDIHN by Administration of Edar

To determine the effect of fibroblast growth factor (FGF) on EDIHN, K14-Eda-A1 transgenic mice, which overexpress (ectodysplasin-A1) Eda-A1 in the epidermis, are subjected to EDIHN, then HF formation is measured 19 days after wounding as described in Example 13. The transgenic mice develop significantly larger numbers of HF compared to control, non-transgenic littermate mice, showing that new HF can be generated by (a) disrupting the epidermis; and (b) administering a factor that enhances signaling by ectodysplasin.

Example 16

Enhancement of EDIHN by Administration of Minoxidil

To determine the effect of minoxidil on EDIHN, recombinant FGF is administered 11 days after incisional wounding, as described in Example 11. Minoxidil administration enhances HF formation, showing that new HF can be generated by (a) disrupting the epidermis; and (b) administering a minoxidil.

Example 17

Removal of HF by Abrasion and Administration of EGF

Hair-bearing regions of the epidermis of mice is abraded, as described in Example 1, then administering recombinant EGF, as described in Example 1. This method prevents hair re-growth in the abraded areas, showing that hair can be removed by (a) disrupting the epidermal layer; and (b) administering EGF, a nucleotide encoding EGF, or a factor that increases signaling by EGF.

What is claimed is:

1. A method for enhancing hair follicle neogenesis in a subject, said method comprising:

(i) disrupting the basal and suprabasal epidermal layers of the scalp of said subject; and (ii) contacting the disrupted area of the scalp of said subject with a compound comprising minoxidil, thereby enhancing hair follicle neogenesis in said subject.

2. The method of claim 1, wherein said disrupting is performed using a light-based method.

3. The method of claim 1, wherein said disrupting is performed using a laser.

4. The method of claim 3, wherein said laser is a CO2 laser, a fractional laser, or an excimer laser.

5. The method of claim 3, wherein said laser induces transepithelial injury.

6. The method of claim 1, wherein said disrupting is performed by abrading.

7. The method of claim 6, wherein said abrading comprises wearing away said epidermis or dermis by friction.

8. The method of claim 1, wherein said disrupting is performed using a mechanical method.

9. The method of claim 8, wherein said mechanical method comprises use of a tool that comprises sandpaper or a rotating felt wheel.

10. The method of claim 1, wherein said disrupting is performed by perforating.

11. The method of claim 10, wherein said perforating comprises use of a surgical tool.

12. The method of claim 11, wherein said surgical tool induces punch wounds.

13. The method of claim 1, wherein said disrupting is performed by freezing or cryoinjury.

14. The method of claim 1, wherein the step of contacting is performed 3-12 days after the step of disrupting.

15. The method of claim 1, wherein said compound is contacted to stimulate hair growth on the scalp.

16. The method of claim 1, wherein said subject is a human.

17. The method of claim 1, further comprising administering a lithium compound in an amount effective to stimulate hair growth.

* * * * *

UNITED STATES PATENT AND TRADEMARK OFFICE

CERTIFICATE OF CORRECTION

PATENT NO. : 9,700,502 B2
APPLICATION NO. : 12/904822
DATED : July 11, 2017
INVENTOR(S) : George Cotsarelis et al.

It is certified that error appears in the above-identified patent and that said Letters Patent is hereby corrected as shown below:

In the Specification

After Line 16, in Column 1, please insert the following:
--GOVERNMENT INTEREST STATEMENT
This invention was made with government support under grant numbers AR046837 and AR055309 awarded by the National Institutes of Health. The government has certain rights in the invention.--

Signed and Sealed this
Second Day of November, 2021

Drew Hirshfeld
*Performing the Functions and Duties of the*
*Under Secretary of Commerce for Intellectual Property and*
*Director of the United States Patent and Trademark Office*